United States Patent
Bindman et al.

(10) Patent No.: US 12,036,286 B2
(45) Date of Patent: *Jul. 16, 2024

(54) SELECTIVE DRUG RELEASE FROM INTERNALIZED CONJUGATES OF BIOLOGICALLY ACTIVE COMPOUNDS

(71) Applicant: Seagen Inc., Bothell, WA (US)

(72) Inventors: Noah Bindman, Bothell, WA (US); Nicole Okeley, Bothell, WA (US); Peter Senter, Bothell, WA (US); Divya Awasthi, Bothell, WA (US); Vivian Trang, Bothell, WA (US)

(73) Assignee: Seagen Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/697,844

(22) Filed: Mar. 17, 2022

(65) Prior Publication Data

US 2023/0091653 A1    Mar. 23, 2023

Related U.S. Application Data

(60) Provisional application No. 63/221,295, filed on Jul. 13, 2021, provisional application No. 63/162,773, (Continued)

(51) Int. Cl.
*A61K 47/68*    (2017.01)
*A61K 39/00*    (2006.01)

(52) U.S. Cl.
CPC ...... *A61K 47/6803* (2017.08); *A61K 47/6849* (2017.08); *A61K 47/6889* (2017.08); *A61K 2039/505* (2013.01); *C07K 2317/73* (2013.01)

(58) Field of Classification Search
CPC combination set(s) only.
See application file for complete search history.

(56) References Cited

U.S. PATENT DOCUMENTS 4,179,337 A    12/1979 Davis
4,301,144 A    11/1981 Iwashita
(Continued)

FOREIGN PATENT DOCUMENTS

BR    102016016339 A2    2/2018
CA    1182110 A    2/1985
(Continued)

OTHER PUBLICATIONS

Abdiche, Y. N. et al. (Aug. 31, 2012, epub. May 17, 2012). "Label-Free Epitope Binning Assays of Monoclonal Antibodies Enable the Identification of Antigen Heterogeneity," Journal of Immunological Methods 382(1-2):101-116.
(Continued)

*Primary Examiner* — Adam Weidner
*Assistant Examiner* — Laura Ann Essex
(74) *Attorney, Agent, or Firm* — MORRISON & FOERSTER LLP

(57) ABSTRACT

The invention relates to conjugates of biologically active compounds, wherein such a conjugate is comprised of a sequence of amino acids containing a tripeptide that confers selective cleavage by tumor tissue homogenate for release of free drug and/or improves biodistribution into the tumor tissue in comparison to normal tissue homogenate from the same species, wherein the normal tissue is the site of an adverse event associated with administration to a human subject in need thereof of a therapeutically effective amount of a comparator conjugate whose amino acid sequence is a dipeptide known to be selectively cleavable by Cathepsin B.

12 Claims, 60 Drawing Sheets

Specification includes a Sequence Listing.

Related U.S. Application Data filed on Mar. 18, 2021, provisional application No. 63/162,781, filed on Mar. 18, 2021, provisional application No. 63/162,776, filed on Mar. 18, 2021, provisional application No. 63/162,653, filed on Mar. 18, 2021, provisional application No. 63/163,017, filed on Mar. 18, 2021, provisional application No. 63/162,786, filed on Mar. 18, 2021, provisional application No. 63/163,012, filed on Mar. 18, 2021, provisional application No. 63/162,660, filed on Mar. 18, 2021.

(56) References Cited

U.S. PATENT DOCUMENTS

| | | |
|---|---|---|
| 4,496,689 A | 1/1985 | Mitra |
| 4,640,835 A | 2/1987 | Shimizu |
| 4,670,417 A | 6/1987 | Iwasaki |
| 4,791,192 A | 12/1988 | Nakagawa |
| 4,810,625 A | 3/1989 | Wagner et al. |
| 4,816,397 A | 3/1989 | Boss |
| 4,816,567 A | 3/1989 | Cabilly |
| 4,880,935 A | 11/1989 | Thorpe |
| 4,952,562 A | 8/1990 | Klein et al. |
| 5,122,368 A | 6/1992 | Greenfield |
| 5,223,486 A | 6/1993 | Gordon et al. |
| 5,225,539 A | 7/1993 | Winter |
| 5,332,726 A | 7/1994 | Klein et al. |
| 5,492,894 A | 2/1996 | Bascom et al. |
| 5,500,362 A | 3/1996 | Robinson |
| 5,585,089 A | 12/1996 | Queen et al. |
| 5,622,929 A | 4/1997 | Willner |
| 5,650,508 A | 7/1997 | Powers |
| 5,672,662 A | 9/1997 | Harris |
| 5,728,813 A | 3/1998 | Lyman et al. |
| 5,757,078 A | 5/1998 | Matsuda |
| 5,821,337 A | 10/1998 | Carter |
| 5,824,805 A | 10/1998 | King |
| 5,969,110 A | 10/1999 | Beckmann et al. |
| 5,981,245 A | 11/1999 | Fox et al. |
| 6,057,124 A | 5/2000 | Bartley et al. |
| 6,077,939 A | 6/2000 | Wei |
| 6,120,768 A | 9/2000 | Griffiths et al. |
| 6,130,237 A | 10/2000 | Denny |
| 6,194,551 B1 | 2/2001 | Idusogle |
| 6,232,447 B1 | 5/2001 | Cerretti |
| 6,235,929 B1 | 5/2001 | Powers |
| 6,413,932 B1 | 7/2002 | Cerretti et al. |
| 6,521,424 B2 | 2/2003 | Cerretti et al. |
| 6,596,852 B2 | 7/2003 | Cerretti et al. |
| 6,727,225 B2 | 4/2004 | Wiley |
| 6,737,056 B1 | 5/2004 | Presta |
| 7,232,559 B1 | 6/2007 | Kohno et al. |
| 7,498,298 B2 | 3/2009 | Doronina |
| 7,521,416 B2 | 4/2009 | Mcbride et al. |
| 7,612,181 B2 | 11/2009 | Wu |
| 7,659,241 B2 | 2/2010 | Senter |
| 7,923,538 B2 | 4/2011 | Shitara |
| 7,968,687 B2 | 6/2011 | Mcdonagh |
| 7,994,290 B2 | 8/2011 | Shitara |
| 8,039,273 B2 | 10/2011 | Jeffrey |
| 8,067,546 B2 | 11/2011 | Mcdonagh et al. |
| 8,163,551 B2 | 4/2012 | Alley |
| 8,258,268 B2 | 9/2012 | Wu et al. |
| 8,293,714 B2 | 10/2012 | Doppalapudi et al. |
| 8,343,928 B2 | 1/2013 | Doronina |
| 8,568,728 B2 | 10/2013 | Jeffrey |
| 8,574,907 B2 | 11/2013 | Alley |
| 8,586,714 B2 | 11/2013 | Ghayur et al. |
| 8,664,407 B2 | 3/2014 | Chen et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,822,645 B2 | 9/2014 | Ghayur et al. |
| RE45,272 E | 12/2014 | Jeffrey |
| 8,937,048 B2 | 1/2015 | Doppalapudi et al. |
| 8,940,501 B2 | 1/2015 | Ploegh et al. |
| 8,993,326 B2 | 3/2015 | Alley |
| 9,150,658 B2 | 10/2015 | Verploegen |
| 9,228,026 B2 | 1/2016 | Smith |
| 9,504,702 B2 | 11/2016 | Senter |
| 9,650,414 B1 | 5/2017 | Young et al. |
| 9,713,648 B2 | 7/2017 | Sievers |
| 9,731,030 B2 | 8/2017 | Jeffrey |
| 9,783,608 B2 | 10/2017 | Smith |
| 9,796,764 B2 | 10/2017 | Poth et al. |
| 9,816,069 B2 | 11/2017 | Alley |
| 9,982,254 B2 | 5/2018 | Nemoto et al. |
| 10,010,547 B2 | 7/2018 | Boyle |
| 10,098,963 B2 | 10/2018 | Sievers |
| 10,155,821 B2 | 12/2018 | Naito et al. |
| 10,195,288 B2 | 2/2019 | Masuda et al. |
| 10,201,615 B2 * | 2/2019 | Lewis ................ A61K 31/519 |
| 10,342,811 B2 | 7/2019 | Senter |
| 10,443,035 B2 | 10/2019 | Alley |
| 10,933,112 B2 | 3/2021 | Doronina et al. |
| RE48,959 E | 3/2022 | Smith et al. |
| 11,311,626 B2 | 4/2022 | Matsumura et al. |
| 11,510,959 B2 | 11/2022 | Doronina et al. |
| 2002/0042368 A1 | 4/2002 | Fanslow |
| 2003/0083263 A1 | 5/2003 | Doronina |
| 2003/0162712 A1 | 8/2003 | Cerretti et al. |
| 2004/0077620 A1 | 4/2004 | Kojima et al. |
| 2005/0009751 A1 | 1/2005 | Senter |
| 2005/0238649 A1 | 10/2005 | Doronina |
| 2006/0018923 A1 | 1/2006 | Yuen et al. |
| 2006/0074008 A1 | 4/2006 | Senter |
| 2008/0241128 A1 | 10/2008 | Jeffrey |
| 2008/0311681 A1 | 12/2008 | Johannsen et al. |
| 2009/0018086 A1 | 1/2009 | Doronina |
| 2009/0111756 A1 | 4/2009 | Doronina |
| 2009/0136526 A1 | 5/2009 | Mcdonagh |
| 2009/0148942 A1 | 6/2009 | Mcdonagh |
| 2009/0317869 A1 | 12/2009 | Alley |
| 2010/0143890 A1 | 6/2010 | Hong et al. |
| 2010/0239571 A1 | 9/2010 | Mcdonagh |
| 2010/0331274 A1 | 12/2010 | Gupta et al. |
| 2011/0020343 A1 | 1/2011 | Senter et al. |
| 2011/0293513 A1 | 12/2011 | Govindan et al. |
| 2012/0082617 A1 | 4/2012 | Govindan et al. |
| 2012/0107332 A1 | 5/2012 | Jeffrey |
| 2012/0141509 A1 | 6/2012 | Doronina |
| 2012/0183997 A1 | 7/2012 | Alley |
| 2013/0129784 A1 | 5/2013 | Senter |
| 2013/0259860 A1 | 10/2013 | Smith |
| 2013/0309223 A1 | 11/2013 | Sutherland |
| 2014/0031535 A1 | 1/2014 | Jeffrey |
| 2014/0031536 A1 | 1/2014 | Alley |
| 2014/0093473 A1 | 4/2014 | Hauser et al. |
| 2014/0107316 A1 | 4/2014 | Vlahov et al. |
| 2015/0072161 A1 | 3/2015 | Mayo et al. |
| 2015/0118184 A1 | 4/2015 | Kawai |
| 2015/0148285 A1 | 5/2015 | Cheng et al. |
| 2015/0337259 A1 | 11/2015 | Alley |
| 2015/0364824 A1 | 12/2015 | Song et al. |
| 2016/0060198 A1 | 3/2016 | Takahashi |
| 2016/0129130 A1 | 5/2016 | Sievers |
| 2016/0185858 A1 | 6/2016 | Smith |
| 2016/0310612 A1 | 10/2016 | Lyon |
| 2016/0361424 A1 | 12/2016 | Jeffrey |
| 2017/0014468 A1 | 1/2017 | Dominy et al. |
| 2017/0022147 A1 | 1/2017 | Nguyen |
| 2017/0022149 A1 | 1/2017 | Nguyen |
| 2017/0035790 A1 | 2/2017 | Senter |
| 2017/0189542 A1 | 7/2017 | Jeffrey |
| 2017/0216391 A1 | 8/2017 | Doronina |
| 2017/0247412 A1 | 8/2017 | Burke |
| 2017/0281794 A1 | 10/2017 | Sievers |
| 2017/0360950 A1 | 12/2017 | Vlahov et al. |
| 2018/0079810 A1 | 3/2018 | Smith |
| 2018/0110871 A1 | 4/2018 | Vlahov et al. |
| 2018/0125992 A1 | 5/2018 | Vlahov et al. |
| 2018/0155677 A1 | 6/2018 | Alley |
| 2018/0228909 A1 | 8/2018 | Parham et al. |

(56) References Cited

U.S. PATENT DOCUMENTS

| | | | |
|---|---|---|---|
| 2018/0280528 A1 | 10/2018 | Vlahov et al. | |
| 2018/0353524 A1 | 12/2018 | Gardai | |
| 2019/0015517 A1 | 1/2019 | Burke | |
| 2019/0016754 A1 | 1/2019 | Patwari | |
| 2019/0085091 A1 | 3/2019 | Sussman | |
| 2019/0151465 A1* | 5/2019 | Kim | A61K 47/6855 |
| 2019/0167805 A1 | 6/2019 | Govindan et al. | |
| 2019/0276796 A1 | 9/2019 | Alley | |
| 2019/0290775 A1 | 9/2019 | Cao | |
| 2019/0300571 A1 | 10/2019 | Cudic et al. | |
| 2019/0343828 A1 | 11/2019 | Jeffrey | |
| 2019/0388546 A1 | 12/2019 | Mao | |
| 2020/0061091 A1 | 2/2020 | Senter | |
| 2020/0149082 A1 | 5/2020 | Okeley | |
| 2020/0165335 A1 | 5/2020 | Smith | |
| 2020/0222553 A1 | 7/2020 | Mao | |
| 2020/0239585 A1 | 7/2020 | Heiser | |
| 2020/0246479 A1 | 8/2020 | Sandall | |
| 2020/0283540 A1 | 9/2020 | Kennedy | |
| 2020/0297864 A1 | 9/2020 | Wu | |
| 2020/0345845 A1* | 11/2020 | Kahvejian | A61K 47/6811 |
| 2020/0352839 A1 | 11/2020 | Kim et al. | |
| 2020/0360532 A1 | 11/2020 | Blanchard | |
| 2021/0008099 A1 | 1/2021 | Doronina | |
| 2021/0015939 A1 | 1/2021 | Rangwala | |
| 2021/0030885 A1 | 2/2021 | Stevens | |
| 2021/0030888 A1 | 2/2021 | Rangwala | |
| 2021/0107980 A1 | 4/2021 | Rangwala et al. | |
| 2021/0138077 A1 | 5/2021 | Bindman et al. | |
| 2021/0177987 A1 | 6/2021 | Rangwala et al. | |
| 2021/0221897 A1 | 7/2021 | Gardai et al. | |
| 2021/0283210 A1 | 9/2021 | Doronina et al. | |
| 2022/0119392 A1 | 4/2022 | Elgersma et al. | |
| 2022/0143209 A1 | 5/2022 | Jeffrey | |
| 2022/0193069 A1 | 6/2022 | Jeffrey et al. | |
| 2023/0036256 A1 | 2/2023 | Jeffrey et al. | |
| 2023/0132738 A1 | 5/2023 | Doronina et al. | |
| 2023/0381321 A1 | 11/2023 | Lyski et al. | |

FOREIGN PATENT DOCUMENTS

| | | | |
|---|---|---|---|
| CN | 1613862 A | 5/2005 |
| CN | 102177917 A | 9/2011 |
| CN | 104672025 A | 6/2015 |
| CN | 104892627 A | 9/2015 |
| CN | 104927395 A | 9/2015 |
| CN | 107540726 A | 1/2018 |
| CN | 110152013 A | 8/2019 |
| DE | 3320175 A1 | 12/1984 |
| DE | 252827 A1 | 12/1987 |
| DE | 3829594 A1 | 3/1990 |
| DE | 4016994 A1 | 11/1991 |
| DE | 4321502 A1 | 1/1995 |
| DE | 4433564 A1 | 4/1996 |
| EP | 0124081 A2 | 11/1984 |
| EP | 0171496 A2 | 2/1986 |
| EP | 0173494 A2 | 3/1986 |
| EP | 0174866 A2 | 3/1986 |
| EP | 0184187 A2 | 6/1986 |
| EP | 0272583 A2 | 6/1988 |
| EP | 0308917 A2 | 3/1989 |
| EP | 0326799 A2 | 8/1989 |
| EP | 0331988 A1 | 9/1989 |
| EP | 0349402 A2 | 1/1990 |
| EP | 0401384 A1 | 12/1990 |
| EP | 0421367 A1 | 4/1991 |
| EP | 0457195 A2 | 11/1991 |
| EP | 0472077 A2 | 2/1992 |
| EP | 0472078 A2 | 2/1992 |
| EP | 0501280 A2 | 9/1992 |
| EP | 0514268 A1 | 11/1992 |
| EP | 0520573 A1 | 12/1992 |
| EP | 0629240 A1 | 12/1994 |
| EP | 0785583 A2 | 7/1997 |
| EP | 0966975 A2 | 12/1999 |
| EP | 1381396 B1 | 4/2009 |
| EP | 2085120 A1 | 8/2009 |
| EP | 2107067 A1 | 10/2009 |
| EP | 2832856 A1 | 2/2015 |
| EP | 2418217 B1 | 1/2016 |
| EP | 3620471 A1 | 3/2020 |
| FR | 2977585 A1 | 1/2013 |
| GB | 2505448 A | 3/2014 |
| JP | H04139113 A | 5/1992 |
| JP | H04139115 A | 5/1992 |
| JP | H06321761 A | 11/1994 |
| JP | H0762399 A | 3/1995 |
| JP | H0762400 A | 3/1995 |
| JP | H1087629 A | 7/1998 |
| JP | 2005245429 A | 9/2005 |
| KR | 20120058866 A | 6/2012 |
| KR | 20180011423 A | 2/2018 |
| WO | 198601533 A1 | 3/1986 |
| WO | 198702671 A1 | 5/1987 |
| WO | 198704622 A1 | 8/1987 |
| WO | 198905818 A1 | 6/1989 |
| WO | 198910931 A1 | 11/1989 |
| WO | 199012565 A1 | 11/1990 |
| WO | 199012874 A2 | 11/1990 |
| WO | 199101976 A1 | 2/1991 |
| WO | 199214751 A1 | 9/1992 |
| WO | 199217196 A1 | 10/1992 |
| WO | 199222653 A1 | 12/1992 |
| WO | 199306128 A1 | 4/1993 |
| WO | 199317105 A1 | 9/1993 |
| WO | 199318141 A1 | 9/1993 |
| WO | 199414817 A1 | 7/1994 |
| WO | 199427627 A1 | 12/1994 |
| WO | 1995006654 A1 | 3/1995 |
| WO | 1995006655 A1 | 3/1995 |
| WO | 199514666 A1 | 6/1995 |
| WO | 199515742 A1 | 6/1995 |
| WO | 199517204 A1 | 6/1995 |
| WO | 199640750 A1 | 12/1996 |
| WO | 1997003091 A1 | 1/1997 |
| WO | 199707097 A1 | 2/1997 |
| WO | 199734631 A1 | 9/1997 |
| WO | 199808919 A2 | 3/1998 |
| WO | 199819705 A1 | 5/1998 |
| WO | 199831359 A1 | 7/1998 |
| WO | 199858967 A1 | 12/1998 |
| WO | 199951642 A1 | 10/1999 |
| WO | 199964495 A1 | 12/1999 |
| WO | 200142281 A1 | 6/2001 |
| WO | 200162300 A2 | 8/2001 |
| WO | 200162300 A3 | 4/2002 |
| WO | 2002043661 A2 | 6/2002 |
| WO | 2002066512 A1 | 8/2002 |
| WO | 2002088172 A2 | 11/2002 |
| WO | 2002094855 A2 | 11/2002 |
| WO | 2002094857 A1 | 11/2002 |
| WO | 2002100353 A2 | 12/2002 |
| WO | 2002043661 A3 | 1/2003 |
| WO | 2002088172 A3 | 2/2003 |
| WO | 2002100353 A3 | 5/2003 |
| WO | 2003048731 A2 | 6/2003 |
| WO | 2003062234 A1 | 7/2003 |
| WO | 2003089652 A2 | 10/2003 |
| WO | 2003048731 A3 | 1/2004 |
| WO | 2004010957 A2 | 2/2004 |
| WO | 2004018644 A2 | 3/2004 |
| WO | 2004010957 A3 | 6/2004 |
| WO | 2004048400 A1 | 6/2004 |
| WO | 2004092219 A2 | 10/2004 |
| WO | 2004092219 A3 | 2/2005 |
| WO | 2005014032 A2 | 2/2005 |
| WO | 2005082023 A2 | 9/2005 |
| WO | 2005082023 A3 | 12/2005 |
| WO | 2006000034 A1 | 1/2006 |
| WO | 2006017295 A2 | 2/2006 |
| WO | 2006020951 A1 | 2/2006 |
| WO | 2006023465 A1 | 3/2006 |
| WO | 2006034056 A2 | 3/2006 |
| WO | 2006045313 A2 | 5/2006 |

(56) References Cited

FOREIGN PATENT DOCUMENTS

| | | |
|---|---|---|
| WO | 2006045314 A2 | 5/2006 |
| WO | 2006045319 A2 | 5/2006 |
| WO | 2006058539 A2 | 6/2006 |
| WO | 2006113909 A2 | 10/2006 |
| WO | 2006137792 A1 | 12/2006 |
| WO | 2006137793 A1 | 12/2006 |
| WO | 2007005249 A2 | 1/2007 |
| WO | 2007007060 A2 | 1/2007 |
| WO | 2007011968 A2 | 1/2007 |
| WO | 2007014432 A1 | 2/2007 |
| WO | 2007042816 A1 | 4/2007 |
| WO | 2007044932 A2 | 4/2007 |
| WO | 2007051987 A1 | 5/2007 |
| WO | 2007059257 A2 | 5/2007 |
| WO | 2007066617 A1 | 6/2007 |
| WO | 2007080194 A2 | 7/2007 |
| WO | 2007082890 A1 | 7/2007 |
| WO | 2007085930 A1 | 8/2007 |
| WO | 2007086083 A1 | 8/2007 |
| WO | 2007087548 A2 | 8/2007 |
| WO | 2007087549 A2 | 8/2007 |
| WO | 2007088099 A2 | 8/2007 |
| WO | 2007011968 A3 | 10/2007 |
| WO | 2007120614 A2 | 10/2007 |
| WO | 2007135296 A1 | 11/2007 |
| WO | 2007135297 A2 | 11/2007 |
| WO | 2008003836 A1 | 1/2008 |
| WO | 2008024196 A1 | 2/2008 |
| WO | 2008083312 A2 | 7/2008 |
| WO | 2008101693 A2 | 8/2008 |
| WO | 2008116648 A2 | 10/2008 |
| WO | 2009000296 A2 | 12/2008 |
| WO | 2009000297 A1 | 12/2008 |
| WO | 2009052431 A2 | 4/2009 |
| WO | 2009067530 A1 | 5/2009 |
| WO | 2009099741 A1 | 8/2009 |
| WO | 2009117531 A1 | 9/2009 |
| WO | 2009135181 A2 | 11/2009 |
| WO | 2010004018 A2 | 1/2010 |
| WO | 2010009124 A2 | 1/2010 |
| WO | 2010010380 A1 | 1/2010 |
| WO | 2009135181 A3 | 2/2010 |
| WO | 2010043000 A1 | 4/2010 |
| WO | 2010057961 A1 | 5/2010 |
| WO | 2010066803 A2 | 6/2010 |
| WO | 2010091150 A1 | 8/2010 |
| WO | 2010104307 A2 | 9/2010 |
| WO | 2010133000 A1 | 11/2010 |
| WO | 2010150927 A1 | 12/2010 |
| WO | 2011023883 A1 | 3/2011 |
| WO | 2011071497 A1 | 6/2011 |
| WO | 2011071747 A1 | 6/2011 |
| WO | 2011094426 A1 | 8/2011 |
| WO | 2011119484 A1 | 9/2011 |
| WO | 2011130707 A2 | 10/2011 |
| WO | 2012019165 A2 | 2/2012 |
| WO | 2012020220 A1 | 2/2012 |
| WO | 2012020747 A1 | 2/2012 |
| WO | 2012047724 A1 | 4/2012 |
| WO | 2012054527 A2 | 4/2012 |
| WO | 2012078668 A1 | 6/2012 |
| WO | 2012078688 A2 | 6/2012 |
| WO | 2012092367 A1 | 7/2012 |
| WO | 2012078688 A3 | 8/2012 |
| WO | 2012112708 A1 | 8/2012 |
| WO | 2012118780 A2 | 9/2012 |
| WO | 2012161997 A1 | 11/2012 |
| WO | 2012177337 A1 | 12/2012 |
| WO | 2012177837 A2 | 12/2012 |
| WO | 2013033396 A2 | 3/2013 |
| WO | 2013065832 A1 | 5/2013 |
| WO | 2013106819 A2 | 7/2013 |
| WO | 2013109675 A2 | 7/2013 |
| WO | 2012019165 A3 | 8/2013 |
| WO | 2013122751 A1 | 8/2013 |
| WO | 2013123152 A2 | 8/2013 |
| WO | 2013130625 A1 | 9/2013 |
| WO | 2013139719 A1 | 9/2013 |
| WO | 2013147153 A1 | 10/2013 |
| WO | 2013163229 A1 | 10/2013 |
| WO | 2013173337 A2 | 11/2013 |
| WO | 2013173496 A2 | 11/2013 |
| WO | 2014017928 A1 | 1/2014 |
| WO | 2014033446 A1 | 3/2014 |
| WO | 2014036213 A1 | 3/2014 |
| WO | 2014047569 A2 | 3/2014 |
| WO | 2014067746 A1 | 5/2014 |
| WO | 2014074789 A1 | 5/2014 |
| WO | 2014127316 A2 | 8/2014 |
| WO | 2014145090 A1 | 9/2014 |
| WO | 2014184596 A2 | 11/2014 |
| WO | 2014200910 A2 | 12/2014 |
| WO | 2014201854 A1 | 12/2014 |
| WO | 2015011633 A1 | 1/2015 |
| WO | 2014200910 A3 | 2/2015 |
| WO | 2015032621 A1 | 3/2015 |
| WO | 2015057699 A2 | 4/2015 |
| WO | 2015080671 A1 | 6/2015 |
| WO | 2015123679 A1 | 8/2015 |
| WO | 2015057699 A3 | 9/2015 |
| WO | 2015134973 A1 | 9/2015 |
| WO | 2015162291 A1 | 10/2015 |
| WO | 2015162293 A1 | 10/2015 |
| WO | 2015189641 A1 | 12/2015 |
| WO | 2015195904 A1 | 12/2015 |
| WO | 2015196089 A1 | 12/2015 |
| WO | 2015196167 A1 | 12/2015 |
| WO | 2016007091 A1 | 1/2016 |
| WO | 2016040684 A1 | 3/2016 |
| WO | 2016080626 A2 | 5/2016 |
| WO | 2016094505 A1 | 6/2016 |
| WO | 2016080626 A3 | 8/2016 |
| WO | 2016149535 A1 | 9/2016 |
| WO | 2016201065 A1 | 12/2016 |
| WO | 2016210141 A1 | 12/2016 |
| WO | 2017004330 A1 | 1/2017 |
| WO | 2017011466 A1 | 1/2017 |
| WO | 2017059158 A1 | 4/2017 |
| WO | 2017059160 A1 | 4/2017 |
| WO | 2017072196 A1 | 5/2017 |
| WO | 2017083582 A1 | 5/2017 |
| WO | 2017093719 A1 | 6/2017 |
| WO | 2017096274 A1 | 6/2017 |
| WO | 2017096311 A1 | 6/2017 |
| WO | 2017112624 A1 | 6/2017 |
| WO | 2017143069 A1 | 8/2017 |
| WO | 2017147146 A1 | 8/2017 |
| WO | 2017151886 A1 | 9/2017 |
| WO | 2017161007 A1 | 9/2017 |
| WO | 2017165851 A1 | 9/2017 |
| WO | 2017201204 A1 | 11/2017 |
| WO | 2017201433 A1 | 11/2017 |
| WO | 2017216177 A1 | 12/2017 |
| WO | 2018039896 A1 | 3/2018 |
| WO | 2018049241 A1 | 3/2018 |
| WO | 2018075842 A1 | 4/2018 |
| WO | 2018107167 A1 | 6/2018 |
| WO | 2018111989 A1 | 6/2018 |
| WO | 2018164019 A1 | 9/2018 |
| WO | 2018175994 A1 | 9/2018 |
| WO | 2018203517 A1 | 11/2018 |
| WO | 2018218004 A1 | 11/2018 |
| WO | 2018222572 A1 | 12/2018 |
| WO | 2018226701 A1 | 12/2018 |
| WO | 2018232088 A1 | 12/2018 |
| WO | 2019031615 A1 | 2/2019 |
| WO | 2019036725 A2 | 2/2019 |
| WO | 2019040780 A1 | 2/2019 |
| WO | 2019051322 A1 | 3/2019 |
| WO | 2019075188 A1 | 4/2019 |
| WO | 2019089973 A1 | 5/2019 |
| WO | 2019091384 A1 | 5/2019 |
| WO | 2019108047 A2 | 6/2019 |
| WO | 2019108797 A1 | 6/2019 |

(56) References Cited

FOREIGN PATENT DOCUMENTS

| | | |
|---|---|---|
| WO | 2019109007 A1 | 6/2019 |
| WO | 2019113248 A1 | 6/2019 |
| WO | 2019108047 A3 | 7/2019 |
| WO | 2019161174 A1 | 8/2019 |
| WO | 2019164987 A1 | 8/2019 |
| WO | 2019173523 A1 | 9/2019 |
| WO | 2019183253 A1 | 9/2019 |
| WO | 2019183438 A1 | 9/2019 |
| WO | 2019195665 A1 | 10/2019 |
| WO | 2019206820 A1 | 10/2019 |
| WO | 2019217457 A1 | 11/2019 |
| WO | 2019217591 A1 | 11/2019 |
| WO | 2019236954 A1 | 12/2019 |
| WO | 2020037009 A1 | 2/2020 |
| WO | 2020037024 A1 | 2/2020 |
| WO | 2020041541 A2 | 2/2020 |
| WO | 2020051503 A1 | 3/2020 |
| WO | 2020092210 A1 | 5/2020 |
| WO | 2020159822 A1 | 8/2020 |
| WO | 2020163225 A1 | 8/2020 |
| WO | 2021055865 A1 | 3/2021 |
| WO | 2021067776 A2 | 4/2021 |
| WO | 2021067820 A1 | 4/2021 |
| WO | 2021067861 A1 | 4/2021 |
| WO | 2021113697 A1 | 6/2021 |
| WO | 2021198965 A1 | 10/2021 |
| WO | 2021198966 A1 | 10/2021 |
| WO | 2021262910 A2 | 12/2021 |
| WO | 2022008419 A1 | 1/2022 |
| WO | 2022150637 A1 | 7/2022 |
| WO | 2022197890 A1 | 9/2022 |
| WO | 2022198232 A1 | 9/2022 |
| WO | 2022246576 A1 | 12/2022 |
| WO | 2023020605 A1 | 2/2023 |
| WO | 2023078273 A1 | 5/2023 |
| WO | 2023131219 A1 | 7/2023 |
| WO | 2023137026 A1 | 7/2023 |

OTHER PUBLICATIONS

Abdiche, Y. N. et al. (Mar. 20, 2014). "High-throughput Epitope Binning Assays on Label-free Array-based Biosensors can Yield Exquisite Epitope Discrimination that Facilitates the Selection of Monoclonal Antibodies with Functional Activity," PloS one, 9(3), e92451.

Abdiche, Y.N. et al. (Mar. 15, 2009, e-pub. Dec. 7, 2008). "Exploring Blocking Assays Using Octet, ProteOn, and Biacore Biosensors," Analytical Biochem 386(2):172-180.

Akewanlop, C. et al. (May 15, 2001). "Phagocytosis of Breast Cancer Cells Mediated by Anti-MUC-1 Monoclonal Antibody, DF3, and Its Bispecific Antibody," Cancer Res. 61:4061-4065.

Al-Lazikani, B. et al. (1997). "Standard Conformations for the Canonical Structures of Immunoglobulins," J. Mol. Biol. 273:927-948.

Alley, S.C. et al. (Aug. 2010, e-pub. Jul. 17, 2010). "Antibody-Drug Conjugates: Targeted Drug Delivery For Cancer," Current Opinion in Chemical Biology 14(4):1-9.

Amsberry, K.L. et al. (1990) "The Lactonizatin of 2'-Hydroxyhydrocinnamic Acid Amides: A Potential Prodrug For Amines," J. Org. Chem. 55(23):5867-5877.

Anami, Y. et al. (2018). Glutamic Acid-Valine-Citrulline Linkers Ensure Stability and Efficacy of Antibody-Drug Conjugates in Mice. Nature Communications, 9(1), 2512. 1-9.

Ausubel, F. et al. (1987). Current Protocols in Molecular Biology, Greene Publishing and Wiley Interscience, New York, TOC, 7 pages.

Baeuerle, P.A. et al. (Jun. 15, 2009, e-pub. Jun. 9, 2009). "Review—Bispecific T-Cell Engaging Antibodies for Cancer Therapy," Cancer Res. 69(12):4941-4944.

Bargh, J.D. et al. (Aug. 12, 2019). "Cleavable Linkers in Antibody-Drug Conjugates," Chemical Society Reviews 48(16):4361-4374.

Behrens, C.R. et al. (2014, e-pub. Sep. 27, 2013). "Methods For Site-Specific Drug Conjugation To Antibodies," mAB 6(1):46-53.

Beidler, C.B. et al. (Dec. 1, 1988). "Cloning and High Level Expression Of A Chimeric Antibody With Specificity For Human Carcinoembryonic Antigen," J. Immunol. 141(11):4053-4060.

Benoiton, N. L. (2005). "Solid-Phase Synthesis," Chapter 5 in Chemistry Of Peptide Synthesis, Taylor & Francis Group LLC, Boca Raton, FL:125-154.

Berter, M. et al. (May 20, 1988). "*Escherichia coli* Secretion of an Active Chimeric Antibody Fragment," Science 240:1041-1043.

Binz, H.K. et al. (Oct. 2005, E-Pub. Oct. 6, 2005). "Engineering Novel Binding Proteins From Nonimmunoglobulin Domains," Nat. Biotechnol. 23(10):1257-1268.

Bird, R.E. et al. (Oct. 21, 1988). "Single-chain antigen-binding proteins," Science 242(4877):423-426.

Borrebaeck, C.A.K. (1995), "Strategies for Humanizing Antibodies," in Antibody Engineering 2nd Ed. pp. 179-181.

Brennan, M. et al. (Jul. 5, 1985). "Preparation of Bispecific Antibodies by Chemical Recombination of Monoclonal Immunoglobulin G1 Fragments," Science 229:81-83.

Burke, P.J. et al. (Jun. 2009). "Design, Synthesis, and Biological Evaluation Of Antibody-Drug Conjugates Comprised Of Potent Camptothecin Analogues," Bioconj. Chem. 20(6):1242-1250.

Capel, P.J.A. et al. (1994). "Heterogeneity of Human IgG Fc Receptors," Immunomethods 4:25-34.

Carter, P.J. et al. (May/Jun. 2008). "Antibody-Drug Conjugates for Cancer Therapy," The Cancer Journal 14(3):154-169.

Chari, R.V.J. et al. (Jan. 1, 1992). "Immunoconjugates Containing Novel Maytansinoids: Promising Anticancer Drugs," Cancer Res. 52:127-131.

Cheung, R.C. et al. (Jun. 1990). "Epitope-Specific Antibody Response To The Surface Antigen Of Duck Hepatitis B Virus In Infected Ducks," Virology 176(2):546-552.

Chothia, C. et al. (1987). "Canonical Structures for the Hypervariable Regions of Immunoglobulins," J. Mol. Biol. 196:901-917.

Chu, G. et al. (Mar. 1981) SV40 DNA Transfection of Cells in Suspension: Analysis of the Efficiency of Transcription and Translation of T-Antigen, Gene 13(2):197-202.

Chung, S.-W. et al. (Feb. 1, 2019, e-pub. Nov. 12, 2018). "Highly Potent Monomethyl Auristatin E Prodrug Activated by Caspase-3 for the Chemoradiotherapy of Triple-Negative Breast Cancer," Biomaterials 192:109-117.

Clarkson, T. et al. (Aug. 15, 1991), "Making Antibody Fragments Using Phage Display Libraries," Nature 352(6336):624-628.

Clynes, R. et al. (Jan. 1998). "Fc Receptors are Required in Passive and Active Immunity to Melanoma," Proc. Natl. Acad. Sci. U.S.A. 95:652-656.

Daeron, M. (1997). "Fc Receptor Biology," Annu. Rev. Immunol. 15:203-234.

De Haas, M. et al. (1995). "Fcγ Receptor of Phagocytes," J. Lab. Clin. Med. 126(4):330-341.

Digiammarino, E. et al. (2012). "Design and Generation Of DVD-IgTM Molecules For Dual-Specific Targeting," Meth. Mo. Biol. 889:145-156.

Doronina, S.O. et al. (Oct. 2008, e-pub. Sep. 20, 2008). "Novel Peptide Linkers for Highly Potent Antibody—Auristain Conjugate," Bioconguate Chem. 19:1960-1963.

Dubowchik, G.M. et al. (Aug. 1999). "Receptor-Mediated and Enzyme-Dependent Targeting of Cytotoxic Anticancer Drugs," Pharm. Therapeutics 83(2):67-123.

Ducry, L. et al. (2010), "Antibody—Drug Conjugates: Linking Cytotoxic Payloads to Monoclonal Antibodies," Bioconjugate Chem. 21(1): 5-13.

Eisenhauer, E.A. et al. (2009) "New Response Evaluation Criteria in Solid Tumors: Revised RECIST Guideline (version 1.1)," Eur. J. Cancer 45:228-247.

Endo, Y. et al. (2003). "High-Throughput, Genome-Scale Protein Production Method Based On The Wheat Germ Cell-Free Expression System," Biotechnol. Adv. 21:695-713.

Finch, P.W. et al. (Dec. 1997). "Altered Expression Of Keratinocyte Growth Factor And Its Receptor In Psoriasis," The American Journal Of Pathology 151(6):1619, 10 pages.

(56) References Cited

OTHER PUBLICATIONS

Freshney, R. I., (1987) "Culture of Specific Cell Types" Chapter 20 in Culture of Animal Cells: A Manual of Basic Techniques, Alan R. Liss & Co., New York; pp. 257-260, 270-273.

Fridkin, M. et al. (1974). "Peptide Synthesis," Ann. Rev. Biochem. 43:419-443.

Garber, K. (2014). "Bispecific Antibodies Rise Again," Nature Reviews. Drug Discovery 13(11):799-801.

Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.

Gebauer, M. et al. (2009). "Engineered Protein Scaffolds as Next-Generation Antibody Therapeutics," Curr. Opinion in Chem. Biol. 13:245-255.

Genbank (Oct. 11, 2000). "Integrin Beta-Subunit [*Homo sapiens*]," Genbank Accession No. AAA36122.2, 2 pages.

Ghetie, V. et al. (1997). "Increasing the Serum Persistence of an IgG Fragment by Random Mutagenesis," Nat Biotech 15:637-640.

Ghetie, V. et al. (Dec. 1997). "FcRn: the MHC Class I-related Receptor That Is More Than An IgG Transporter," Immunol. Today 18(12):592-598.

Graham, F.L. et al. (1977). "Characteristics Of A Human Cell Line Transformed By DNA From Human Adenovirus Type 5," Journal General Virology 36(1):59-74.

Graham, F.L. et al.(1973) "A New Technique for the Assay of Infectivity of Human Adenovirus 5 DNA," Virology 52:456-467.

Greene, T.W. et al. (1999). Protective Groups in Organic Synthesis, 3rd edition, Wiley.

Gruber, M. et al. (1994). "Efficient Tumor Cell Lysis Mediated by a Bispecific Single Chain Antibody Expressed in *Escherichia coli*," J. Immunol. 152:5368-5374.

Guyer, R.L. et al. (Aug. 1976). "Immunoglobulin Binding By Mouse Intestinal Epithelial Cell Receptors," J. Immunol. 117(2):587-593.

Hamers-Casterman, C. et al. (Jun. 3, 1993). "Naturally Occurring Antibodies Devoid of Light Chains," Nature 363:446-448.

Hamilton, J. Z. et al. (Apr. 8, 2021). "Improving Antibody-Tubulysin Conjugates through Linker Chemistry and Site-Specific Conjugation," ChemMedChem 16(7):1077-1081.

Han, S.-Y. et al. (2004). "Recent Development Of Peptide Coupling Agents In Organic Synthesis," Tet. 60:2447-2476.

Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," Bioorganic & Medicinal Chemistry Letters 9(15):2237-2242.

Hilpert, K. et al. (May 24, 2007). "Peptide Arrays On Cellulose Support: Spot Synthesis, A Time And Cost Efficient Method For Synthesis Of Large Numbers Of Peptides In A Parallel And Addressable Fashion," Nature Protocols. 2(6):1333-1349.

Hinton, P.R. et al. (Feb. 20, 2004). "Engineered Human IgG Antibodies with Longer Serum Half-lives in Primates," J. Biol. Chem. 279(8):6213-6216.

Hollinger, P. et al. (Jul. 1993), "Diabodies: Small Bivalent And Bispecific Antibody Fragments," Proc. Natl. Acad. Sci. USA 90:6444-6448.

Honegger, A. et al. (Jun. 8, 2001). "Yet Another Numbering Scheme For Immunoglobulin Variable Domains: An Automatic Modeling And Analysis Tool," J. Mol. Biol. 309:657-670.

Hunter, D.D. et al. (Dec. 1991). "An LRE (Leucine-Arginine-Glutamate)-Dependent Mechanism for Adhesion of Neurons to S-Laminin," The Journal of Neuroscience 11(12):3960-3971.

Huston, J.R. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.

Huston, J.S. et al. (1993). "Antigen Recognition and Targeted Delivery by the Single-Chain Fw," Cell Biophysics 22:189-224.

Idusogie, E.E. et al. (2000). "Mapping of the C1q Binding Site on Rituxan, a Chimeric Antibody With a Human IgG1 Fc," J. Immunol. 164:4178-4184.

International Preliminary Report on Patentability, issued Mar. 15, 2022, for PCT Application No. PCT/US2020/051648, filed on Sep. 18, 2020, 9 pages.

International Search Report and Written Opinion of the International Searching Authority mailed on Nov. 30, 2020, for PCT Application No. PCT/US2020/051648, filed on Sep. 18, 2020, 10 pages.

International Union of Pure and Applied Chemistry (Nov. 5, 1960). "Definitive Rules for Nomenclature of Organic Chemistry," J. Am. Chem. Soc. 82:5545-5473, 30 pages.

Jakob, C.G. et al. (May 1, 2013, e-pub. Apr. 2, 2013). "Structure Reveals Function of the Dual Variable Domain Immunoglobulin (DVD-Ig™) Molecule," MAbs. 5(3):358-363.

Jeffrey, S.C. et al. (2006, e-pub. Nov. 3, 2005). "Dipeptide-based Highly Potent Doxorubicin Antibody Conjugates," Bioorganic Medicinal Chemistry Letters 16:358-362.

Johnson, D.A. et al. (Jul.-Aug. 1995). "Anti-Tumor Activity of CC49-Doxorubicin Immunoconjugates," Anticancer Res. 15(4):1387-1393.

Johnson, G. et al. (2003). "The Kabat Database and a Bioinformatics Example," Methods in Molecular Biology 248:11-25, 15 pages.

Jones, P. et al. (May 29, 1986). "Replacing The Complementarity-Determining Regions In A Human Antibody With Those From A Mouse," Nature 321:522-525.

Kabat, E.A. et al. (1991). Sequences of Proteins of Immunological Interest, 5th Ed. Public Health Service, National Institutes of Health, Bethesda MD., Table of Contents, 21 pages.

Kabat, E.A. et al. (Sep. 1980). "Origins of Antibody Complementarity and Specificity-Hypervariable Regions and the Minigene Hypothesis," J Immunology 125(3):961-969.

Kim, J-K. et al. (1994). "Localization of the Site of the Murine IgGl Molecule That is Involved in Binding to the Murine Intestinal Fc Receptor," Eur. J. Immunol. 24:2429-2434.

Kingsbury, W.D. et al. (Nov. 1984). "A Novel Peptide Delivery System Involving Peptidase Activated Prodrugs as Antimicrobial Agents. Synthesis and Biological Activity of Peptidyl Derivatives of 5-Fluorouracil," Journal of Medicinal Chemistry 27(11):1447-1451.

Kirkland, T.N. et al. (Dec. 1, 1986). "Analysis Of The Fine Specificity and Cross-Reactivity Of Monoclonal Anti-Lipid A Antibodies," J Immunol 137(11):3614-3619.

Kozbor, D. et al. (1983). "The Production of Monoclonal Antibodies From Human Lymphocytes," Immunology Today 4(3):72-79.

Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3):548-555.

Lau, A. et al. (Oct. 1995). "Conjugation of Doxorubicin to Monoclonal Anti-Carcinoembryonic Antigen Antibody Via Novel Thiol-Directed Cross-Linking Reagents," Bioorganic & Medicinal Chemistry 3(10):1299-1304.

Lau, A. et al. (Oct. 1995). "Novel Doxorubicin-Monoclonal Anti-Carcinoembryonic Antigen Antibody Immunoconjugate Activity in vitro," Bioorganic & Medicinal Chemistry 3(10):1305-1312.

Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.

Liu, A.Y. et al. (May 1987). "Chimeric Mouse-Human IGG1 Antibody That Can Mediate Lysis of Cancer Cells," Proc Natl Acad Sci 84(1):3439-3443.

Liu, A.Y. et al. (Nov. 15, 1987). "Production of a Mouse-Human Chimeric Monoclonal Antibody to CD20 With Potent Fc-Dependent Biologic Activity," J Immunol. 139(10):3521-3526.

MacCallum, R.M. et al. (Oct. 1996). "Antibody-Antigen Interactions: Contact Analysis and Binding Site Topography," J. Mol. Biol. 262(5):732-745.

Maderna, A. et al. (Jun. 1, 2015, e-pub. Mar. 5, 2015). "Recent Advances in the Development of New Auristatins: Structural Modifications and Application in Antibody Drug Conjugates," Molecular Pharmaceutics 12(6):1798-1812.

(56) References Cited

OTHER PUBLICATIONS

Manning, D.L. et al. (1994). "Oestrogen-regulated Genes in Breast Cancer: Association of pLIV1 With Lymph Node Involvement," European Journal of Cancer 30A(5):675-678.

Mather, J.P. (1980). "Establishment and Characterization of Two Distinct Mouse Testicular Epithelial Cell Lines," Biology of Reproduction 23:243-252.

Mather, J.P. et al. (1982). "Culture of Testicular Cells in Hormone-Supplemented Serum-Free Medium," Annals N.Y. Acad. Sci. 383:44-68.

McCafferty, J. et al. (Dec. 6, 1990). "Phage Antibodies: Filamentous Phage Displaying Antibody Variable Domains," Nature 348:552-554.

McClelland, R.A. et al. (1998). "Oestrogen-Regulated Genes in Breast Cancer: Association of pLIVI with Response to Endocrine Therapy," Br. J. Cancer 77(10):1653-1656.

Mendoza, N. et al. (Oct. 1, 2002). "Inhibition of Ligand-Mediated HER2 Activation In Androgen-Independent Prostate Cancer," Cancer Res. 62(19):5485-5488.

Milstein, C. et al. (Oct. 1983). "Hybrid hybridomas and their use in immunohistochemistry," Nature 305:537-539.

Minotti, G. et al. (2004). "Anthracyclines: Molecular Advances and Pharmacologic Developments in Antitumor Activity and Cardiotoxicity," Pharmacol. Rev. 56(2):185-229.

Moldenhauer, G. et al. (Aug. 1990). "Identity of HML-1 Antigen On Intestinal Intraepithelial T Cells and of B-ly7 Antigen On Hairy Cell Leukaemia," Scand J Immunol 32(2):77-82.

Morel, G.A. et al. (Jan. 1988). "Monoclonal Antibodies To Bovine Serum Albumin: Affinity and Specificity Determinations," Mol Immunol 25(1):7-15.

Morris, G.E. (1996). "Epitope Mapping Protocols," Methods in Molecular Biology 66:1-12.

Morrison, S.L. (Sep. 1985). "Transfectomas Provide Novel Chimeric Antibodies," Science 229 (4719):1202-1207.

Neville, D.M. et al. (Sep. 5, 1989). "Enhancement of Immunotoxin Efficacy by Acid-cleavable Crosslinking Agents Utilizing Diphtheria Toxin and Toxin Mutants," The Journal of Biological Chemistry 264(25):14653-14661.

Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4):999-1005.

Nogusa, H. et al. (2000). "Structure-Activity Relationships of Carboxymethylpullulan-Peptide-Doxorubicin Conjugates-Systematic Modification of Peptide Spacers," Bioorganic & Medicinal Chemistry Letters 10:227-230.

Oi, V.T. et al. (1986). "Chimeric Antibodies," Bio Techniques 4(3):214-219.

Olsson, L. et al. (1983), "Human-Human Monoclonal Antibody-Producing Hybridomas: Technical Aspects," Meth Enzymol. 92:3-16.

Pabst, M. et al. (2017, e-pub. Mar. 1, 2017). "Modulation of Drug-Linker Design to Enhance in vivo Potency of Homogeneous Antibody-Drug Conjugates," Journal of Controlled Release 253:160-164.

Pluckthun, A. et al. (1989). "Expression of Functional Antibody Fv and Fab Fragments in *Escherichia Coli*," Methods in Enzymology, 178:497-515.

Portolano, S. et al. (Feb. 1, 1993). "Lack of Promiscuity in Autoantigen-Specific H and L Chain Combinations as Revealed by Human H And L Chain 'Roulette'," The Journal of Immunology 150(3):880-887.

Ravetch, J.V. et al. (1991). "Fc Receptors," Annu, Rev. Immunol. 9:457-492.

Rodrigues, M.L. et al. (Apr. 1995). "Synthesis and β-Lactamase-Mediated Activation Of A Cephalosporine-Taxol Prodrug," Chem. Biol. 2:223-227.

Salomon, P.L. et al. (2019). "Optimizing Lysosomal Activiation of Antibody-Drug Conjugates (ADCs) By Incorporation of Novel Cleavable Dipeptide Linkers," Molecular Pharmaceutics 16:4817-4825.

Sela-Culang, I. et al. (Oct. 8, 2013). "The Structural Basis of Antibody-Antigen Recognition," Frontiers in Immunology 4(Article 302):1-13.

Shaw, D.R. et al. (Dec. 7, 1988). "Mouse/Human Chimeric Antibodies To A Tumor-Associated Antigen: Biologic Activity Of The Four Human IgG Subclasses," J. Natl. Cancer Inst. 80(19):1553-1559.

Sheriff, S. et al. (Sep. 1996). "Redefining the Minimal Antigen-Binding Fragment," Nature Struct. Biol. 3(9):733-736.

Shiose, Y. et al. (2009, e-pub. Dec. 18, 2008). "Systematic Research of Peptide Spacers Controlling Drug Release From Macromolecular Prodrug System, Carboxymethyldextran Polyalcohol-Peptide-Drug Conjugates," Bioconjugate Chem. 20:60-70.

Sitaraman, K. et al. (2009). "High-Throughput Protein Expression Using Cell-Free System," Methods Mol. Biol. 498:229-244.

Spirin, A.S. (Oct. 2004). "High-Throughput Cell-Free Systems For Synthesis Of Functionally Active Proteins," Trends Biotechnol. 22(10):538-545.

Storm, D.R. et al. (Aug. 9, 1972). "Effect of Small Changes in Orientation on Reaction Rate," Journal of the American Chemical Society 94(16):5815-5825.

Stähli, C. et al. (1983). "Distinction of Epitopes by Monoclonal Antibodies," Methods in Enzymology 92:242-253.

Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.

Taylor, K.M. et al. (Apr. 1, 2003). "The LZT Proteins; the LIV-1 Subfamily of Zinc Transporters," Biochimica et Biophysica Acta 1611(1-2):16-30.

Teng, N.N.H. et al. (Dec. 1983). "Construction and Testing of Mouse-Human Heteromyelomas For Human Monoclonal Antibody Production," Proc. Natl. Acad. Sci. USA. 80:7308-7312.

Thorpe, P.E. et al. (Nov. 15, 1987). "New Coupling Agents for the Synthesis of Immunotoxins Containing a Hindered Disulfide Bond with Improved Stability in Vivo," Cancer Research 47:5924-5931.

Tsuchikama, K. (2019). "Novel Chemical Linkers for Next-Generation Antibody-Drug Conjugates (ADCs)," The Pharmaceutical Society of Japan 139:209-219. English Abstract.

U.S. Appl. No. 14/766,208, Jeffrey et al., filed Apr. 1, 2022. (not submitted herewith pursuant to the waiver of 37 C.F.R. § 1.98(a)(2)(iii) issued by the Office on Sep. 21, 2004.).

U.S. Appl. No. 16/972,469, Jeffrey et al., filed Nov. 9, 2020. (not submitted herewith pursuant to the waiver of 37 C.F.R. § 1.98(a)(2)(iii) issued by the Office on Sep. 21, 2004.).

U.S. Appl. No. 17/083,107, Jeffrey Scott, filed Oct. 28, 2020. (not submitted herewith pursuant to the waiver of 37 C.F.R. § 1.98(a)(2)(iii) issued by the Office on Sep. 21, 2004.).

U.S. Appl. No. 17/452,516, Jeffrey et al., filed Oct. 27, 2021. (not submitted herewith pursuant to the waiver of 37 C.F.R. § 1.98(a)(2)(iii) issued by the Office on Sep. 21, 2004.).

Uchida, J. et al. (Jun. 21, 2004). "The Innate Mononuclear Phagocyte Network Depletes B Lymphocytes Through Fc Receptor-Dependent Mechanisms During Anti-CD20 Antibody Immunotherapy," J. Exp. Med. 199(12):1659-1669.

Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.

Verhoeyan, M. et al. (Mar. 25, 1988). "Reshaping Human Antibodies: Grafting an Antilysozyme Activity," Science 239:1534-1536.

Watanabe, M. et al. (Feb. 1999). "Antibody Dependent Cellular Phagocytosis (ADCP) and Antibody Dependent Cellular Cytotoxicity (ADCC) of Breast Cancer Cells Mediated By Bispecific Antibody, MDX-210," Breast Cancer Res. Treat. 53(3):199-207.

Wawrzynczak, E.J. et al. (1987). "Chapter 3—Methods for Preparing Immunotoxins: Effect of the Linkage on Activity and Stability," in Immunoconjugates: Antibody Conjugates in Radioimagery and Therapy of Cancer pp. 28-55.

Weber, W.A. (2009). "Assessing Tumor Response to Therapy," J. Nucl. Med. 50:1S-10S.

Wood, C.R. et al. (Apr. 4, 1985). "The Synthesis and in vivo Assembly of Functional Antibodies In Yeast," Nature 314(6010):446-449.

(56) References Cited

OTHER PUBLICATIONS

Xu. J.L. et al. (Jul. 2000). "Diversity in the CDR3 Region of VH Is Sufficient for Most Antibody Specificities," Immunity 13:37-45.
Yu, X. et al. (Jun. 12, 2017). "Beyond Antibodies as Binding Partners: The Role of Antibody Mimetics in Bloanalysis," Annual Review of Analytical Chemistry (Palo Alto, Calif.) 10(1):293-320.
Better, M. et al. (May 20, 1988). "*Escherichia coli* Secretion of An Active Chimerica Antibody Fragment," Science 240:1041-1043, 4 pages.
Doronina, S.O. et al. (Jul. 2003). "Development of Potent Monoclonal Antibody Auristatin Conjugates for Cancer Therapy," Nat. Biotechnol. 21(7):778-784.
Doronina, S.O. et al. (Jan. 2006). "Enhanced Activity Of Monomethylauristatin F Through Monoclonal Antibody Delivery: Effects Of Linker Technology On Efficacy And Toxicity," Bioconjug. Chem. 17(1):114-124.
Extended European Search Report, mailed Oct. 2, 2017, for European Patent Application No. 15748980.8, 9 pages.
Extended European Search Report, mailed Sep. 30, 2021, for European Patent Application No. 21168364.4, 12 pages.
Hamblett, K.J. et al. (Oct. 15, 2004). "Effects of Drug Loading on the Antitumor Activity of a Monoclonal Antibody Drug Conjugate," Clin. Cancer Res. 10:7063-7070.
Harada, M. et al. (Dec. 31, 2000). "Determinants for the Drug Release From T-0128, Camptothecin Analogue-Carboxymethyl Dextran Conjugate," Journal of Controlled Release 69:399-412.
International Preliminary Report on Patentability, issued Aug. 23, 2016, for PCT Application No. PCT/US2015/16185, filed Feb. 17, 2015, 5 pages.
International Search Report and Written Opinion of the International Searching Authority mailed on Jul. 15, 2022, for PCT Application No. PCT/US2022/071211, filed on Mar. 17, 2022, 12 pages.
International Search Report and Written Opinion of the International Searching Authority mailed on Sep. 13, 2022, for PCT Application No. PCT/US2022/071210, filed on Mar. 17, 2022, 25 pages.
International Search Report and Written Opinion, dated May 1, 2015, for PCT Application No. PCT/US2015/16185, filed Feb. 17, 2015, 11 pages.
Invitation To Pay Additional Fees dated Jul. 21, 2022, for PCT Application No. PCT/US2022/071210, filed Mar. 17, 2022, 19 pages.
Klussman, K. et al. (2004, e-pub. Jun. 18, 2004). "Secondary mAb—vcMMAE Conjugates are Highly Sensitive Reporters of Antibody Internalization Via the Lysosome Pathway," Bioconjugate Chemistry 15(4):765-773.
Law, C-L. et al. (Feb. 15, 2006). "Lymphocyte Activation Antigen CD70 Expressed by Renal Cell Carcinoma Is a Potential Therapeutic Target for Anti-CD70 Antibody-Drug Conjugates," Cancer Res. 66(4):2328-2337.
Li, W. et al. (Sep. 6, 2019). "Synthesis and Evaluation of Camptothecin Antibody-Drug Conjugates," ACS Medicinal Chemistry Letters 10(10):1386-1392.
Lyski, R.D. et al. (Feb. 2021, e-pub. Dec. 3, 2020). "Development of Novel Antibody-Camptothecin Conjugates," Molecular Cancer Therapeutics 20(2):329-339.
Page, B. et al. (Sep. 1993). "A New Fluorometric Assay For Cytotoxicity Measurements In-Vitro," Intl. J. of Oncology 3(3):473-476.
Skehan, P. et al. (Jul. 4, 1990). "New Colorimetric Cytotoxicity Assay for Anticancer-Drug Screening," J. Nat'l Cancer Inst. 82(13):1107-1112.
Stark, M. et al. (Apr. 30, 2009). "Aberrant Splicing Of Folylpolyglutamate Synthetase as a Novel Mechanism Of Antifolate Resistance In Leukemia," Blood 113(18):4362-4369.
U.S. Appl. No. 18/185,341, Ryan Lyski, filed Mar. 16, 2023. (not submitted herewith pursuant to the waiver of 37 C.F.R. § 1.98(a)(2)(iii) issued by the Office on Sep. 21, 2004.).

Conilh, L. et al. (Mar. 9, 2021). "Exatecan Antibody Drug Conjugates Based on a Hydrophilic Polysarcosine Drug-Linker Platform," Pharmaceuticals 14(3):247, 17 pages.
Final Office Action, mailed Sep. 26, 2023, for U.S. Appl. No. 17/026,048, filed Sep. 18, 2020, 13 pages.
Gaertner, H.F. et al. (Mar. 11, 1994). "Chemo-Enzymic Backbone Engineering of Proteins," J. Biol. Chem. 269(10):7224-7230.
Goodson, R.J. et al. (Apr. 1990). "Site-Directed Pegylation of Recombinant Interleukin-2 At Its Glycosylation Site," Bio/Technology 8:343-346, 4 pages.
International Preliminary Report on Patentability, issued Sep. 12, 2023, for PCT Application No. PCT/US2022/071210, filed on Mar. 17, 2022, 13 pages.
International Preliminary Report on Patentability, issued Sep. 12, 2023, for PCT Application No. PCT/US2022/071211, filed on Mar. 17, 2022, 8 pages.
International Search Report and Written Opinion, mailed Nov. 14, 2023, for PCT Application No. PCT/US2023/064600, filed Mar. 16, 2023, 32 pages.
Invitation to Pay Additional Fees, mailing dated Jul. 4, 2023, for PCT Application No. PCT/US2023/064600, filed Mar. 16, 2023, 16 pages.
Jeffrey, S.C. et al. (May-Jun. 2006, e-pub. May 3, 2006). "Development and Properties of β-Glucuronide Linkers for Monoclonal Antibody-Drug Conjugates," American Chemical Society 17(3):831-840.
Kaneko, T. et al. (May-Jun. 1991). "New Hydrazone Derivatives Of Adriamycin and Their Immunoconjugates—A Correlation Between Acid Stability and Cytotoxicity," Bioconjugate Chem. 2(3):133-141.
Lau, U.Y. et al. (Aug. 1, 2018). "Lactone Stabilization is Not a Necessary Feature for Antibody Conjugates of Camptothecins," Molecular Pharmaceutics 15(9):4063-4072.
Lewis, T.S. et al. (Oct. 1, 2014). "Abstract 688: Characterization and Circumvention of Drug Resistance Mechanisms in SGN-35-Resistant HL and ALCL Clonal Cell Lines," Cancer Res. 74(19_Suppl.):388, 4 pages.
Malik, F. et al. (Sep. 1992). "Polyethylene glycol (PEG)-Modified Granulocyte-Macrophage Colony-Stimulating Factor (GM-CSF) With Conserved Biological Activity," Exp. Hematol. 20(8):1028-1035, 10 pages.
Rose, K. et al. (May-Jun. 1991). "Preparation Of Well-Defined Protein Conjugates Using Enzyme-Assisted Reverse Proteolysis," Bioconjugate Chem. 2(3):154-159.
Schmidt, M.M. et al. (Oct. 2009). "A Modeling Analysis of the Effects of Molecular Size and Binding Affinity on Tumor Targeting," Mol. Cancer Ther. 8(10):2861-2871.
Schwarz, A. et al. (1990). "Enzymatic C-Terminal Biotinylation Of Proteins," Methods Enzymol. 184:160-162.
Spicer, C.D. et al. (Feb. 11, 2020). "Synthesis of Phospho-Amino Acid Analogues as Tissue Adhesive Cement Additives," ACS Cent.. Sci. 6:226-231.
Toki, B.E. et al. (2002, e-pub. Feb. 12, 2002). "Protease-Mediated Fragmentation of p-Amidobenzyl Ethers: A New Strategy for the Activation of Anticancer Prodrugs," J. Org. Chem. 67(6):1866-1872.
U.S. Appl. No. 18/467,633, filed Sep. 14, 2023, Jeffrey et al. (not submitted herewith pursuant to the waiver of 37 C.F.R. § 1.98(a)(2)(iii) issued by the Office on Sep. 21, 2004).
U.S. Appl. No. 18/282,322, Rincon, A. et al., filed Sep. 15, 2023. (not submitted herewith pursuant to the waiver of 37 C.F.R. § 1.98(a)(2)(iii) issued by the Office on Sep. 21, 2004.).
Verma. R.P. et al. (2009, e-pub. Dec. 19, 2008). "Captothecins: A SAR/QSAR Study," American Chemical Society 109:213-235.
Veronese, F.M. (2001). "Peptide and Protein PEGylation: A Review Of Problems and Solutions," Biomaterials 22:405-417.
Veronese, F.M. et al. (Apr. 1985). "Surface Modification Of Proteins: Activation Of Monomethoxy-Polyethylene Glycols By Phenylchloroformates and Modification Of Ribonuclease and Superoxide Dismutase," Appl. Biochem. Bioechnol 11(2):141-152.

(56) References Cited

OTHER PUBLICATIONS

Walker, M.A. et al. (Jan. 21, 2002). "Synthesis of an Immunoconjugate of Camptothecin," Bioorganic & Medicinal Chemistry Letters 12(2):217-219.

* cited by examiner

Histology of bone by non-targeted tripeptide ADCs after administration in rats at 20 mg/kg

| | | h00-5 | | | | | | | | h00-7 | | | | | | |
|---|---|---|---|---|---|---|---|---|---|---|---|---|---|---|---|---|
| Day post dose | 5 | 5 | 5 | 8 | 8 | 8 | 8 | 5 | 5 | 5 | 5 | 8 | 8 | 8 | 8 |
| TISSUE | Animal # | 1 | 2 | 3 | 4 | 5 | 6 | 7 | 8 | 9 | 10 | 11 | 12 |
| BONE MARROW, FEMUR Depletion | 3 | 3 | 3 | 1 | 2 | - | 4 | 4 | 4 | 3 | 2 | 1 |
| BONE MARROW, STERNUM Depletion | 3 | 3 | 3 | - | 2 | 2 | NE | 4 | 4 | 4 | 3 | 2 | - |

FIG. 18

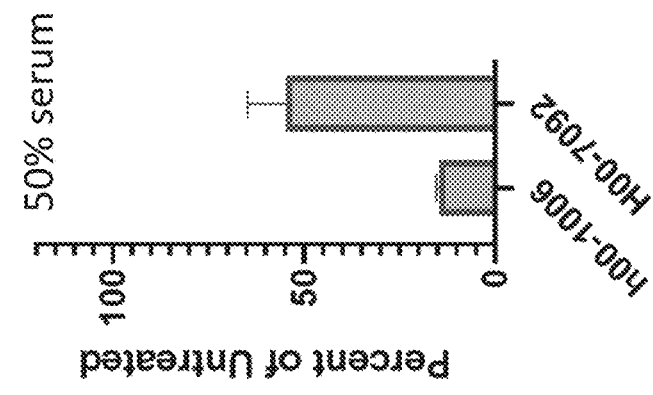
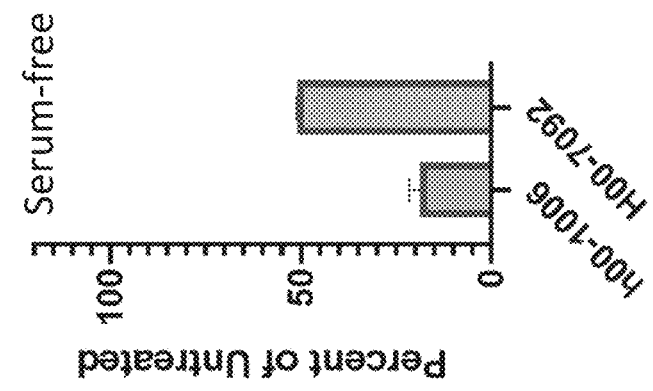
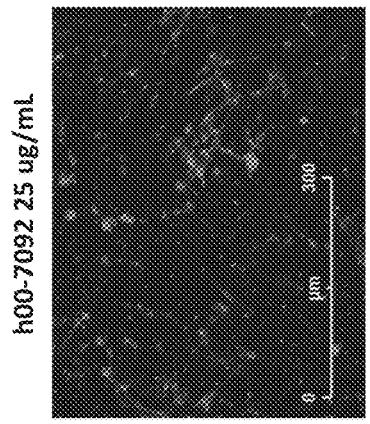
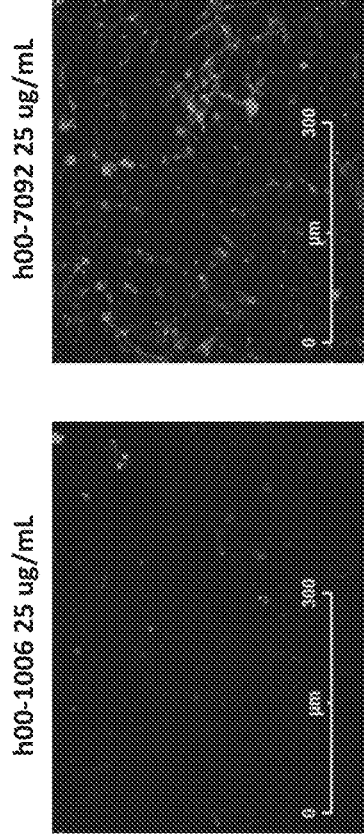

SEQUENCE LISTING

<160> NUMBER OF SEQ ID NOS: 953

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asp Tyr Tyr Ile Thr
1               5

<210> SEQ ID NO 2
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 2

Trp Ile Tyr Pro Gly Ser Gly Asn Thr Lys Tyr Asn Glu Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Tyr Gly Asn Tyr Trp Phe Ala Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Lys Ala Ser Gln Ser Val Asp Phe Asp Gly Asp Ser Tyr Met Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Ser Asn Glu Asp Pro Trp Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Synthetic Construct

<400> SEQUENCE: 7

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
```

```
            35                  40                  45
Gly Trp Ile Tyr Pro Gly Ser Gly Asn Thr Lys Tyr Asn Glu Lys Phe
         50                  55                  60

Lys Gly Lys Ala Thr Leu Thr Val Asp Thr Ser Ser Thr Ala Phe
 65                  70                  75                  80

Met Gln Leu Ser Ser Leu Thr Ser Glu Asp Thr Ala Val Tyr Phe Cys
                 85                  90                  95

Ala Asn Tyr Gly Asn Tyr Trp Phe Ala Tyr Trp Gly Gln Gly Thr Gln
                100                 105                 110

Val Thr Val Ser Ala
            115

<210> SEQ ID NO 8
<211> LENGTH: 111
<212> TYPE: PRT
<213> ORGANISM: Artificial Sequence
<220> FEATURE:
<223> OTHER INFORMATION: Synthetic Construct

<400> SEQUENCE: 8

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Phe Asp
                 20                  25                  30

Gly Asp Ser Tyr Met Asn Trp Tyr Gln Gln Lys Pro Gly Gln Pro Pro
             35                  40                  45

Lys Val Leu Ile Tyr Ala Ala Ser Asn Leu Glu Ser Gly Ile Pro Ala
         50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Trp Thr Phe Gly Gly Gly Thr Lys Leu Glu Ile Lys
                100                 105                 110

<210> SEQ ID NO 9
<211> LENGTH: 447
<212> TYPE: PRT
<213> ORGANISM: Artificial Sequence
<220> FEATURE:
<223> OTHER INFORMATION: Synthetic Construct

<400> SEQUENCE: 9

Gln Ile Gln Leu Gln Gln Ser Gly Pro Glu Val Val Lys Pro Gly Ala
 1               5                  10                  15

Ser Val Lys Ile Ser Cys Lys Ala Ser Gly Tyr Thr Phe Thr Asp Tyr
                 20                  25                  30

Tyr Ile Thr Trp Val Lys Gln Lys Pro Gly Gln Gly Leu Glu Trp Ile
             35                  40                  45

Gly Trp Ile Tyr Pro Gly Ser Gly Asn Thr Lys Tyr Asn Glu Lys Phe
         50                  55                  60

Lys Gly Lys Ala Thr Leu Thr Val Asp Thr Ser Ser Thr Ala Phe
 65                  70                  75                  80

Met Gln Leu Ser Ser Leu Thr Ser Glu Asp Thr Ala Val Tyr Phe Cys
                 85                  90                  95

Ala Asn Tyr Gly Asn Tyr Trp Phe Ala Tyr Trp Gly Gln Gly Thr Gln
                100                 105                 110
```

Val Thr Val Ser Ala Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 10
<211> LENGTH: 446
<212> TYPE: PRT
<213> ORGANISM: Artificial Sequence
<220> FEATURE:
<223> OTHER INFORMATION: Synthetic Construct

<400> SEQUENCE: 10

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

-continued

```
Tyr Ile Thr Trp Val Lys Gln Lys Pro Gly Gln Gly Leu Glu Trp Ile
         35                  40                  45
Gly Trp Ile Tyr Pro Gly Ser Gly Asn Thr Lys Tyr Asn Glu Lys Phe
 50                  55                  60
Lys Gly Lys Ala Thr Leu Thr Val Asp Thr Ser Ser Ser Thr Ala Phe
 65                  70                  75                  80
Met Gln Leu Ser Ser Leu Thr Ser Glu Asp Thr Ala Val Tyr Phe Cys
                 85                  90                  95
Ala Asn Tyr Gly Asn Tyr Trp Phe Ala Tyr Trp Gly Gln Gly Thr Gln
                100                 105                 110
Val Thr Val Ser Ala Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
        210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Asp Val Ser His Glu Asp Pro Glu
                260                 265                 270
Val Lys Phe Asn Trp Tyr Val Asp Gly Val Glu Val His Asn Ala Lys
                275                 280                 285
Thr Lys Pro Arg Glu Glu Gln Tyr Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly
            435                 440                 445
```

```
<210> SEQ ID NO 11
<211> LENGTH: 218
<212> TYPE: PRT
<213> ORGANISM: Artificial Sequence
<220> FEATURE:
<223> OTHER INFORMATION: Synthetic Construct

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 12
<211> LENGTH: 118
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Asp Tyr Gly Asp Tyr Gly Met Asp Tyr Trp Gly Gln Gly Thr
                100                 105                 110

Thr Val Thr Val Ser Ser
        115

<210> SEQ ID NO 13
<211> LENGTH: 111
<212> TYPE: PRT
<213> ORGANISM: Artificial Sequence
<220> FEATURE:
<223> OTHER INFORMATION: Synthetic Construct

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys
            100                 105                 110

<210> SEQ ID NO 14
<211> LENGTH: 448
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
                100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 15
<211> LENGTH: 218
<212> TYPE: PRT
<213> ORGANISM: Artificial Sequence
<220> FEATURE:
<223> OTHER INFORMATION: Synthetic Construct

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
            85                  90                  95
```

```
Glu Val Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Asn Tyr Gly Met Asn
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Trp Ile Asn Thr Tyr Thr Gly Glu Pro Thr Tyr Thr Asp Asp Phe Lys
1               5                   10                  15

Gly

<210> SEQ ID NO 18
<211> LENGTH: 12
<212> TYPE: PRT
<213> ORGANISM: Artificial Sequence
<220> FEATURE:
<223> OTHER INFORMATION: Synthetic Construct

<400> SEQUENCE: 18

Gly Gly Phe Gly Ser Ser Tyr Trp Tyr Phe Asp Val
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Lys Ala Ser Gln Asp Val Ser Ile Ala Val Ala
1               5                   10
```

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Ser Ala Ser Tyr Arg Tyr Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gln Gln His Tyr Ile Thr Pro Leu Thr
1               5

<210> SEQ ID NO 22
<211> LENGTH: 121
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Tyr Thr Gly Glu Pro Thr Tyr Thr Asp Asp Phe
        50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
                100                 105                 110

Gln Gly Ser Leu Val Thr Val Ser Ser
            115                 120

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
                20                  25                  30

Val Ala Trp Tyr Gln Gln Lys Pro Gly Lys Ala Pro Lys Leu Leu Ile
            35                  40                  45

```
Tyr Ser Ala Ser Tyr Arg Tyr Thr Gly Val Pro Asp Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln His Tyr Ile Thr Pro Leu
                 85                  90                  95

Thr Phe Gly Ala Gly Thr Lys Val Glu Ile Lys
            100                 105

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct

<400> SEQUENCE: 24

Thr Ala Gly Met Gln
1               5

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Trp Ile Asn Thr His Ser Gly Val Pro Lys Tyr Ala Glu Asp Phe Lys
1               5                   10                  15

Gly

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Ser Gly Phe Gly Ser Ser Tyr Trp Tyr Phe Asp Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Lys Ala Ser Gln Asp Val Ser Thr Ala Val Ala
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Ser Ala Ser Tyr Arg Tyr Thr
1               5
```

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Gln Gln His Tyr Ile Thr Pro Leu Thr
1               5

<210> SEQ ID NO 30
<211> LENGTH: 121
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
        35                  40                  45

Gly Trp Ile Asn Thr His Ser Gly Val Pro Lys Tyr Ala Glu Asp Phe
    50                  55                  60

Lys Gly Arg Val Thr Ile Ser Ala Asp Thr Ser Thr Ser Thr Ala Tyr
65                  70                  75                  80

Leu Gln Leu Ser Ser Leu Lys Ser Glu Asp Thr Ala Val Tyr Tyr Cys
                85                  90                  95

Ala Arg Ser Gly Phe Gly Ser Ser Tyr Trp Tyr Phe Asp Val Trp Gly
            100                 105                 110

Gln Gly Thr Leu Val Thr Val Ser Ser
        115                 120

<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Gln Gly Thr Lys Leu Glu Ile Lys
            100                 105

```
<210> SEQ ID NO 32
<211> LENGTH: 5
<212> TYPE: PRT
<213> ORGANISM: Artificial Sequence
<220> FEATURE:
<223> OTHER INFORMATION: Synthetic Construct

<400> SEQUENCE: 32

Ser Gln Asn Ile Tyr
1               5

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct

<400> SEQUENCE: 33

Tyr Ile Glu Pro Tyr Asn Val Val Pro Met Tyr Asn Pro Lys Phe Lys
1               5                   10                  15

Gly

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Ser Gly Ser Ser Asn Phe Asp Tyr
1               5

<210> SEQ ID NO 35
<211> LENGTH: 12
<212> TYPE: PRT
<213> ORGANISM: Artificial Sequence
<220> FEATURE:
<223> OTHER INFORMATION: Synthetic Construct

<400> SEQUENCE: 35

Ser Ala Ser Ser Ser Ile Ser Ser His Tyr Leu His
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Arg Thr Ser Asn Leu Ala Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

Gln Gln Gly Ser Ser Leu Pro Leu Thr
1               5
```

<210> SEQ ID NO 38
<211> LENGTH: 117
<212> TYPE: PRT
<213> ORGANISM: Artificial Sequence
<220> FEATURE:
<223> OTHER INFORMATION: Synthetic Construct

<400> SEQUENCE: 38

Glu Ile Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Gln
                20                  25                  30

Asn Ile Tyr Trp Val Arg Gln Ala Pro Gly Gln Gly Leu Glu Trp Ile
            35                  40                  45

Gly Tyr Ile Glu Pro Tyr Asn Val Val Pro Met Tyr Asn Pro Lys Phe
50                  55                  60

Lys Gly Arg Ala Thr Leu Thr Val Asp Lys Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Ser Gly Ser Ser Asn Phe Asp Tyr Trp Gly Gln Gly Thr Leu
            100                 105                 110

Val Thr Val Ser Ser
        115

<210> SEQ ID NO 39
<211> LENGTH: 108
<212> TYPE: PRT
<213> ORGANISM: Artificial Sequence
<220> FEATURE:
<223> OTHER INFORMATION: Synthetic Construct

<400> SEQUENCE: 39

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Ile Ser Ser His
                20                  25                  30

Tyr Leu His Trp Tyr Gln Gln Lys Pro Gly Lys Ser Pro Lys Leu Leu
            35                  40                  45

Ile Tyr Arg Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Ser Ser Leu Pro
                85                  90                  95

Leu Thr Phe Gly Gln Gly Thr Lys Val Glu Ile Lys
            100                 105

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct

<400> SEQUENCE: 40

Asn Tyr Ala Met His
1               5

```
<210> SEQ ID NO 41
<211> LENGTH: 17
<212> TYPE: PRT
<213> ORGANISM: Artificial Sequence
<220> FEATURE:
<223> OTHER INFORMATION: Synthetic Construct

<400> SEQUENCE: 41

Leu Ile Trp Tyr Asp Gly Ser Asn Lys Phe Tyr Gly Asp Ser Val Lys
1               5                   10                  15
Gly

<210> SEQ ID NO 42
<211> LENGTH: 6
<212> TYPE: PRT
<213> ORGANISM: Artificial Sequence
<220> FEATURE:
<223> OTHER INFORMATION: Synthetic Construct

<400> SEQUENCE: 42

Glu Gly Ser Gly His Tyr
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43

Arg Ala Ser Gln Gly Ile Ser Ser Ala Leu Ala
1               5                   10

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct

<400> SEQUENCE: 44

Asp Ala Ser Ser Leu Glu Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Gln Gln Phe Asn Ser Tyr Pro Ile Thr
1               5

<210> SEQ ID NO 46
<211> LENGTH: 115
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Asn Tyr
            20                  25                  30

Ala Met His Trp Val Arg Gln Ala Pro Gly Glu Gly Leu Glu Trp Val
        35                  40                  45

Ala Leu Ile Trp Tyr Asp Gly Ser Asn Lys Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Val Tyr Tyr Cys
                85                  90                  95

Ala Arg Glu Gly Ser Gly His Tyr Trp Gly Gln Gly Thr Leu Val Thr
            100                 105                 110

Val Ser Ser
        115

<210> SEQ ID NO 47
<211> LENGTH: 107
<212> TYPE: PRT
<213> ORGANISM: Artificial Sequence
<220> FEATURE:
<223> OTHER INFORMATION: Synthetic Construct

<400> SEQUENCE: 47

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Val Pro Lys Ser Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
            100                 105

<210> SEQ ID NO 48
<211> LENGTH: 5
<212> TYPE: PRT
<213> ORGANISM: Artificial Sequence
<220> FEATURE:
<223> OTHER INFORMATION: Synthetic Construct

<400> SEQUENCE: 48

Asn Tyr Ala Met Ser
1               5

<210> SEQ ID NO 49
<211> LENGTH: 17
<212> TYPE: PRT
<213> ORGANISM: Artificial Sequence
<220> FEATURE:
<223> OTHER INFORMATION: Synthetic Construct

<400> SEQUENCE: 49

Tyr Ile Ser Pro Gly Gly Asp Tyr Ile Tyr Tyr Ala Asp Ser Val Lys
1               5                   10                  15

Gly
```

<210> SEQ ID NO 50
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Asp Arg Arg His Tyr Gly Ser Tyr Ala Met Asp Tyr
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Synthetic Construct

<400> SEQUENCE: 51

Arg Ser Ser Lys Ser Leu Leu His Ser Asn Leu Asn Thr Tyr Leu Tyr
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Arg Met Ser Asn Leu Ala Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Met Gln His Leu Glu Tyr Pro Phe Thr
1               5

<210> SEQ ID NO 54
<211> LENGTH: 121
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Ile Arg Gln Ala Pro Gly Lys Gly Leu Glu Trp Val
        35                  40                  45

Ser Tyr Ile Ser Pro Gly Gly Asp Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                        85                  90                  95
Thr Thr Asp Arg Arg His Tyr Gly Ser Tyr Ala Met Asp Tyr Trp Gly
            100                 105                 110

Gln Gly Thr Leu Val Thr Val Ser Ser
        115                 120
```

<210> SEQ ID NO 55
<211> LENGTH: 112
<212> TYPE: PRT
<213> ORGANISM: Artificial Sequence
<220> FEATURE:
<223> OTHER INFORMATION: Synthetic Construct

<400> SEQUENCE: 55

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Leu Asn Thr Tyr Leu Tyr Trp Phe Leu Gln Lys Pro Gly Gln Ser
        35                  40                  45

Pro Gln Ile Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Pro Gly Thr Lys Leu Glu Ile Lys
            100                 105                 110
```

<210> SEQ ID NO 56
<211> LENGTH: 5
<212> TYPE: PRT
<213> ORGANISM: Artificial Sequence
<220> FEATURE:
<223> OTHER INFORMATION: Synthetic Construct

<400> SEQUENCE: 56

```
Thr Tyr Ala Phe His
1               5
```

<210> SEQ ID NO 57
<211> LENGTH: 17
<212> TYPE: PRT
<213> ORGANISM: Artificial Sequence
<220> FEATURE:
<223> OTHER INFORMATION: Synthetic Construct

<400> SEQUENCE: 57

```
Gly Ile Val Pro Ile Phe Gly Thr Leu Lys Tyr Ala Gln Lys Phe Gln
1               5                   10                  15

Asp
```

<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

```
Ala Ile Gln Leu Glu Gly Arg Pro Phe Asp His
1               5                   10
```

<210> SEQ ID NO 59
<211> LENGTH: 11
<212> TYPE: PRT
<213> ORGANISM: Artificial Sequence
<220> FEATURE:
<223> OTHER INFORMATION: Synthetic Construct

<400> SEQUENCE: 59

Arg Ala Ser Gln Gly Ile Thr Ser Tyr Leu Ala
1               5                   10

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct

<400> SEQUENCE: 60

Ala Ala Ser Ala Leu Gln Ser
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Gln Gln Val Asn Arg Gly Ala Ala Ile Thr
1               5                   10

<210> SEQ ID NO 62
<211> LENGTH: 120
<212> TYPE: PRT
<213> ORGANISM: Artificial Sequence
<220> FEATURE:
<223> OTHER INFORMATION: Synthetic Construct

<400> SEQUENCE: 62

Gln Val Gln Leu Val Gln Ser Gly Ala Glu Val Lys Lys Pro Gly Ser
1               5                   10                  15

Ser Val Arg Val Ser Cys Arg Ala Ser Gly Gly Ser Thr Thr Tyr
            20                  25                  30

Ala Phe His Trp Val Arg Gln Ala Pro Gly Gln Gly Leu Glu Trp Met
        35                  40                  45

Gly Gly Ile Val Pro Ile Phe Gly Thr Leu Lys Tyr Ala Gln Lys Phe
    50                  55                  60

Gln Asp Arg Val Thr Leu Thr Ala Asp Lys Ser Thr Gly Thr Ala Tyr
65                  70                  75                  80

Met Glu Leu Asn Ser Leu Arg Leu Asp Asp Thr Ala Val Tyr Tyr Cys
                85                  90                  95

Ala Arg Ala Ile Gln Leu Glu Gly Arg Pro Phe Asp His Trp Gly Gln
            100                 105                 110

Gly Thr Gln Val Thr Val Ser Ala
        115                 120

<210> SEQ ID NO 63
<211> LENGTH: 108
<212> TYPE: PRT
<213> ORGANISM: Artificial Sequence

```
<220> FEATURE:
<223> OTHER INFORMATION: Synthetic Construct

<400> SEQUENCE: 63

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Thr Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
    50                  55                  60

Arg Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Val Asn Arg Gly Ala Ala
                85                  90                  95

Ile Thr Phe Gly His Gly Thr Arg Leu Asp Ile Lys
            100                 105

<210> SEQ ID NO 64
<211> LENGTH: 5
<212> TYPE: PRT
<213> ORGANISM: Artificial Sequence
<220> FEATURE:
<223> OTHER INFORMATION: Synthetic Construct

<400> SEQUENCE: 64

Thr Tyr Ala Phe His
1               5

<210> SEQ ID NO 65
<211> LENGTH: 17
<212> TYPE: PRT
<213> ORGANISM: Artificial Sequence
<220> FEATURE:
<223> OTHER INFORMATION: Synthetic Construct

<400> SEQUENCE: 65

Gly Ile Val Pro Ile Phe Gly Thr Leu Lys Tyr Ala Gln Lys Phe Gln
1               5                   10                  15

Asp

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

<400> SEQUENCE: 66

Ala Ile Gln Leu Glu Gly Arg Pro Phe Asp His
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic Construct

<400> SEQUENCE: 67

Arg Ala Ser Gln Gly Ile Thr Ser Tyr Leu Ala
1               5                   10
```

<210> SEQ ID NO 68
<211> LENGTH: 7
<212> TYPE: PRT
<213> ORGANISM: Artificial Sequence
<220> FEATURE:
<223> OTHER INFORMATION: Synthetic Construct

<400> SEQUENCE: 68

Ala Ala Ser Ala Leu Gln Ser
1               5

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Gln Gln Val Asn Arg Gly Ala Ala Ile Thr
1               5                   10

<210> SEQ ID NO 70
<211> LENGTH: 120
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Val Gln Ser Gly Ala Glu Val Lys Lys Pro Gly Ser
1               5                   10                  15

Ser Val Arg Val Ser Cys Arg Ala Ser Gly Gly Ser Thr Thr Tyr
            20                  25                  30

Ala Phe His Trp Val Arg Gln Ala Pro Gly Gln Gly Leu Glu Trp Met
        35                  40                  45

Gly Gly Ile Val Pro Ile Phe Gly Thr Leu Lys Tyr Ala Gln Lys Phe
    50                  55                  60

Gln Asp Arg Val Thr Leu Thr Ala Asp Lys Ser Thr Gly Thr Ala Tyr
65                  70                  75                  80

Met Glu Leu Asn Ser Leu Arg Leu Asp Asp Thr Ala Val Tyr Tyr Cys
                85                  90                  95

Ala Arg Ala Ile Gln Leu Glu Gly Arg Pro Phe Asp His Trp Gly Gln
            100                 105                 110

Gly Thr Gln Val Thr Val Ser Ala
        115                 120

<210> SEQ ID NO 71
<211> LENGTH: 108
<212> TYPE: PRT
<213> ORGANISM: Artificial Sequence
<220> FEATURE:
<223> OTHER INFORMATION: Synthetic Construct

<400> SEQUENCE: 71

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Thr Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
            50                  55                  60

Arg Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Val Asn Arg Gly Ala Ala
                 85                  90                  95

Ile Thr Phe Gly His Gly Thr Arg Leu Asp Ile Lys
            100                 105

<210> SEQ ID NO 72
<211> LENGTH: 5
<212> TYPE: PRT
<213> ORGANISM: Artificial Sequence
<220> FEATURE:
<223> OTHER INFORMATION: Synthetic Construct

<400> SEQUENCE: 72

Arg Tyr Thr Met His
1               5

<210> SEQ ID NO 73
<211> LENGTH: 17
<212> TYPE: PRT
<213> ORGANISM: Artificial Sequence
<220> FEATURE:
<223> OTHER INFORMATION: Synthetic Construct

<400> SEQUENCE: 73

Val Ile Ser Phe Asp Gly Ser Asn Lys Tyr Tyr Val Asp Ser Val Lys
1               5                   10                  15

Gly

<210> SEQ ID NO 74
<211> LENGTH: 10
<212> TYPE: PRT
<213> ORGANISM: Artificial Sequence
<220> FEATURE:
<223> OTHER INFORMATION: Synthetic Construct

<400> SEQUENCE: 74

Glu Ala Arg Gly Ser Tyr Ala Phe Asp Ile
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Arg Ala Ser Gln Ser Val Ser Ser Tyr Leu Ala
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Synthetic Construct

<400> SEQUENCE: 76

Asp Ala Ser Asn Arg Ala Thr
1               5

-continued

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Gln Gln Arg Ser Asn Trp Pro Pro Phe Thr
1               5                   10

<210> SEQ ID NO 78
<211> LENGTH: 119
<212> TYPE: PRT
<213> ORGANISM: Artificial Sequence
<220> FEATURE:
<223> OTHER INFORMATION: Synthetic Construct

<400> SEQUENCE: 78

Gln Val Gln Leu Val Glu Ser Gly Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
        115

<210> SEQ ID NO 79
<211> LENGTH: 108
<212> TYPE: PRT
<213> ORGANISM: Artificial Sequence
<220> FEATURE:
<223> OTHER INFORMATION: Synthetic Construct

<400> SEQUENCE: 79

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

```
<210> SEQ ID NO 80
<211> LENGTH: 5
<212> TYPE: PRT
<213> ORGANISM: Artificial Sequence
<220> FEATURE:
<223> OTHER INFORMATION: Synthetic Construct

<400> SEQUENCE: 80

Ser Phe Trp Met His
1               5

<210> SEQ ID NO 81
<211> LENGTH: 17
<212> TYPE: PRT
<213> ORGANISM: Artificial Sequence
<220> FEATURE:
<223> OTHER INFORMATION: Synthetic Construct

<400> SEQUENCE: 81

Tyr Ile Asn Pro Arg Ser Gly Tyr Thr Glu Tyr Asn Glu Ile Phe Arg
1               5                   10                  15

Asp

<210> SEQ ID NO 82
<211> LENGTH: 9
<212> TYPE: PRT
<213> ORGANISM: Artificial Sequence
<220> FEATURE:
<223> OTHER INFORMATION: Synthetic Construct

<400> SEQUENCE: 82

Phe Leu Gly Arg Gly Ala Met Asp Tyr
1               5

<210> SEQ ID NO 83
<211> LENGTH: 11
<212> TYPE: PRT
<213> ORGANISM: Artificial Sequence
<220> FEATURE:
<223> OTHER INFORMATION: Synthetic Construct

<400> SEQUENCE: 83

Arg Ala Ser Gln Asp Ile Ser Asn Tyr Leu Ala
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct

<400> SEQUENCE: 84

Tyr Thr Ser Lys Ile His Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct

<400> SEQUENCE: 85

Gln Gln Gly Asn Thr Phe Pro Tyr Thr
1               5
```

<210> SEQ ID NO 86
<211> LENGTH: 118
<212> TYPE: PRT
<213> ORGANISM: Artificial Sequence
<220> FEATURE:
<223> OTHER INFORMATION: Synthetic Construct

<400> SEQUENCE: 86

```
Gln Val Gln Leu Gln Gln Ser Gly Gly Glu Leu Ala Lys Pro Gly Ala
1               5                  10                  15

Ser Val Lys Val Ser Cys Lys Ala Ser Gly Tyr Thr Phe Ser Ser Phe
            20                  25                  30

Trp Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Glu Ile Phe
    50                  55                  60

Arg Asp Lys Ala Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Leu Gly Arg Gly Ala Met Asp Tyr Trp Gly Gln Gly Thr
            100                 105                 110

Thr Val Thr Val Ser Ser
        115
```

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Lys Ile His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Phe Pro Tyr
                85                  90                  95

Thr Phe Gly Gln Gly Thr Lys Val Glu Ile Lys
            100                 105
```

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct

<400> SEQUENCE: 88

```
Thr Ser Ser Tyr Tyr Trp Gly
1               5
```

<210> SEQ ID NO 89
<211> LENGTH: 16
<212> TYPE: PRT
<213> ORGANISM: Artificial Sequence
<220> FEATURE:
<223> OTHER INFORMATION: Synthetic Construct

<400> SEQUENCE: 89

Thr Ile Tyr Tyr Asn Gly Ser Thr Tyr Tyr Ser Pro Ser Leu Lys Ser
1               5                   10                  15

<210> SEQ ID NO 90
<211> LENGTH: 11
<212> TYPE: PRT
<213> ORGANISM: Artificial Sequence
<220> FEATURE:
<223> OTHER INFORMATION: Synthetic Construct

<400> SEQUENCE: 90

Gln Gly Tyr Asp Ile Lys Ile Asn Ile Asp Val
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthetic Construct

<400> SEQUENCE: 91

Arg Ala Ser Gln Ser Val Ser Ser Tyr Leu Ala
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Synthetic Construct

<400> SEQUENCE: 92

Val Ala Ser Asn Arg Ala Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Construct

<400> SEQUENCE: 93

Gln Gln Arg Ser Asn Trp Pro Leu Thr
1               5

<210> SEQ ID NO 94
<211> LENGTH: 121
<212> TYPE: PRT
<213> ORGANISM: Artificial Sequence
<220> FEATURE:
<223> OTHER INFORMATION: Synthetic Construct

<400> SEQUENCE: 94

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Ser

-continued

```
                 20                  25                  30
Ser Tyr Tyr Trp Gly Trp Ile Arg Gln Pro Pro Gly Lys Gly Leu Glu
             35                  40                  45

Trp Ile Gly Thr Ile Tyr Tyr Asn Gly Ser Thr Tyr Tyr Ser Pro Ser
         50                  55                  60

Leu Lys Ser Arg Val Ser Ile Ser Val Asp Thr Ser Lys Asn Gln Phe
65                  70                  75                  80

Ser Leu Lys Leu Ser Ser Val Thr Ala Ala Asp Thr Ser Val Tyr Tyr
                 85                  90                  95

Cys Ala Arg Gln Gly Tyr Asp Ile Lys Ile Asn Ile Asp Val Trp Gly
            100                 105                 110

Gln Gly Thr Thr Val Thr Val Ser Ser
            115                 120
```

<210> SEQ ID NO 95
<211> LENGTH: 107
<212> TYPE: PRT
<213> ORGANISM: Artificial Sequence
<220> FEATURE:
<223> OTHER INFORMATION: Synthetic Construct

<400> SEQUENCE: 95

```
Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Val Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                 85                  90                  95

Thr Phe Gly Gly Gly Thr Lys Val Glu Ile Lys
            100                 105
```

<210> SEQ ID NO 96
<211> LENGTH: 5
<212> TYPE: PRT
<213> ORGANISM: Artificial Sequence
<220> FEATURE:
<223> OTHER INFORMATION: Synthetic Construct

<400> SEQUENCE: 96

```
Ser Ser Trp Met Asn
1               5
```

<210> SEQ ID NO 97
<211> LENGTH: 17
<212> TYPE: PRT
<213> ORGANISM: Artificial Sequence
<220> FEATURE:
<223> OTHER INFORMATION: Synthetic Construct

<400> SEQUENCE: 97

```
Arg Ile Tyr Pro Gly Asp Gly Asn Thr His Tyr Ala Gln Lys Phe Gln
1               5                  10                  15

Gly
```

-continued

<210> SEQ ID NO 98
<211> LENGTH: 8
<212> TYPE: PRT
<213> ORGANISM: Artificial Sequence
<220> FEATURE:
<223> OTHER INFORMATION: Synthetic Construct

<400> SEQUENCE: 98

Gly Tyr Leu Asp Pro Met Asp Tyr
1               5

<210> SEQ ID NO 99
<211> LENGTH: 11
<212> TYPE: PRT
<213> ORGANISM: Artificial Sequence
<220> FEATURE:
<223> OTHER INFORMATION: Synthetic Construct

<400> SEQUENCE: 99

Gln Ala Ser Gln Gly Ile Asn Asn Tyr Leu Asn
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 100

Tyr Thr Ser Gly Leu His Ala
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct

<400> SEQUENCE: 101

Gln Gln Tyr Ser Ile Leu Pro Trp Thr
1               5

<210> SEQ ID NO 102
<211> LENGTH: 117
<212> TYPE: PRT
<213> ORGANISM: Artificial Sequence
<220> FEATURE:
<223> OTHER INFORMATION: Synthetic Construct

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Thr Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asn Thr His Tyr Ala Gln Lys Phe
        50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Gly Glu Gly Tyr Leu Asp Pro Met Asp Tyr Trp Gly Gln Gly Thr Leu
            100                 105                 110

Val Thr Val Ser Ser
        115

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Asn Asn Tyr
            20                  25                  30

Leu Asn Trp Tyr Gln Gln Lys Pro Gly Lys Ala Pro Lys Leu Leu Ile
        35                  40                  45

His Tyr Thr Ser Gly Leu His Ala Gly Val Pro Ser Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Val Ala Thr Tyr Tyr Cys Gln Gln Tyr Ser Ile Leu Pro Trp
                85                  90                  95

Thr Phe Gly Gly Gly Thr Lys Val Glu Ile Lys
            100                 105

<210> SEQ ID NO 104
<211> LENGTH: 5
<212> TYPE: PRT
<213> ORGANISM: Artificial Sequence
<220> FEATURE:
<223> OTHER INFORMATION: Synthetic Construct

<400> SEQUENCE: 104

Ser Tyr Gly Met His
1               5

<210> SEQ ID NO 105
<211> LENGTH: 17
<212> TYPE: PRT
<213> ORGANISM: Artificial Sequence
<220> FEATURE:
<223> OTHER INFORMATION: Synthetic Construct

<400> SEQUENCE: 105

Val Ile Ser Tyr Asp Gly Ser Asn Lys Tyr Tyr Ala Asp Ser Val Lys
1               5                   10                  15

Gly

<210> SEQ ID NO 106
<211> LENGTH: 3
<212> TYPE: PRT
<213> ORGANISM: Artificial Sequence
<220> FEATURE:
<223> OTHER INFORMATION: Synthetic Construct

<400> SEQUENCE: 106

Asp Met Gly
1

<210> SEQ ID NO 107
<211> LENGTH: 11
<212> TYPE: PRT
<213> ORGANISM: Artificial Sequence
<220> FEATURE:
<223> OTHER INFORMATION: Synthetic Construct

<400> SEQUENCE: 107

Arg Thr Ser Gln Ser Ile Ser Ser Tyr Leu Asn
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 108

Trp Ala Ser Thr Arg Glu Ser
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Construct

<400> SEQUENCE: 109

Gln Gln Ser Tyr Asp Ile Pro Tyr Thr
1               5

<210> SEQ ID NO 110
<211> LENGTH: 127
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Leu Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Gly Trp Gly Ser Gly Trp Arg Pro Tyr Tyr Tyr Tyr
            100                 105                 110

Gly Met Asp Val Trp Gly Gln Gly Thr Thr Val Thr Val Ser Ser
        115                 120                 125

<210> SEQ ID NO 111
<211> LENGTH: 107
<212> TYPE: PRT
<213> ORGANISM: Artificial Sequence
<220> FEATURE:

<223> OTHER INFORMATION: Synthetic Construct

<400> SEQUENCE: 111

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 112
<211> LENGTH: 5
<212> TYPE: PRT
<213> ORGANISM: Artificial Sequence
<220> FEATURE:
<223> OTHER INFORMATION: Synthetic Construct

<400> SEQUENCE: 112

Asn Tyr Trp Met Ser
1               5

<210> SEQ ID NO 113
<211> LENGTH: 17
<212> TYPE: PRT
<213> ORGANISM: Artificial Sequence
<220> FEATURE:
<223> OTHER INFORMATION: Synthetic Construct

<400> SEQUENCE: 113

Asn Ile Lys Gln Asp Gly Ser Glu Lys Phe Tyr Ala Asp Ser Val Lys
1               5                   10                  15

Gly

<210> SEQ ID NO 114
<211> LENGTH: 9
<212> TYPE: PRT
<213> ORGANISM: Artificial Sequence
<220> FEATURE:
<223> OTHER INFORMATION: Synthetic Construct

<400> SEQUENCE: 114

Val Gly Pro Ser Trp Glu Gln Asp Tyr
1               5

<210> SEQ ID NO 115
<211> LENGTH: 14
<212> TYPE: PRT
<213> ORGANISM: Artificial Sequence
<220> FEATURE:
<223> OTHER INFORMATION: Synthetic Construct

<400> SEQUENCE: 115

Thr Gly Ser Ser Ser Asn Ile Gly Ser Tyr Tyr Gly Val His
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Synthetic Construct

<400> SEQUENCE: 116

Ser Asp Thr Asn Arg Pro Ser
1               5

<210> SEQ ID NO 117
<211> LENGTH: 11
<212> TYPE: PRT
<213> ORGANISM: Artificial Sequence
<220> FEATURE:
<223> OTHER INFORMATION: Synthetic Construct

<400> SEQUENCE: 117

Gln Ser Tyr Asp Lys Gly Phe Gly His Arg Val
1               5                   10

<210> SEQ ID NO 118
<211> LENGTH: 118
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Pro Ser Trp Glu Gln Asp Tyr Trp Gly Gln Gly Thr
            100                 105                 110

Leu Val Thr Val Ser Ala
        115

<210> SEQ ID NO 119
<211> LENGTH: 94
<212> TYPE: PRT
<213> ORGANISM: Artificial Sequence
<220> FEATURE:
<223> OTHER INFORMATION: Synthetic Construct

<400> SEQUENCE: 119

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Tyr
            20                  25                  30

Tyr Gly Val His Trp Tyr Gln Gln Leu Pro Gly Thr Ala Pro Lys Leu
        35                  40                  45

```
Leu Ile Tyr Ser Asp Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp
                85                  90

<210> SEQ ID NO 120
<211> LENGTH: 5
<212> TYPE: PRT
<213> ORGANISM: Artificial Sequence
<220> FEATURE:
<223> OTHER INFORMATION: Synthetic Construct

<400> SEQUENCE: 120

Ser Tyr Ala Ile Ser
1               5

<210> SEQ ID NO 121
<211> LENGTH: 17
<212> TYPE: PRT
<213> ORGANISM: Artificial Sequence
<220> FEATURE:
<223> OTHER INFORMATION: Synthetic Construct

<400> SEQUENCE: 121

Gly Ile Ile Pro Ile Phe Gly Thr Ala Asn Tyr Ala Gln Lys Phe Gln
1               5                   10                  15

Gly

<210> SEQ ID NO 122
<211> LENGTH: 6
<212> TYPE: PRT
<213> ORGANISM: Artificial Sequence
<220> FEATURE:
<223> OTHER INFORMATION: Synthetic Construct

<400> SEQUENCE: 122

Gly Leu Leu Trp Asn Tyr
1               5

<210> SEQ ID NO 123
<211> LENGTH: 11
<212> TYPE: PRT
<213> ORGANISM: Artificial Sequence
<220> FEATURE:
<223> OTHER INFORMATION: Synthetic Construct

<400> SEQUENCE: 123

Arg Ala Ser Gln Ser Val Ser Ser Asn Leu Ala
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Synthetic Construct

<400> SEQUENCE: 124

Gly Ala Ser Thr Thr Ala Ser
1               5

<210> SEQ ID NO 125
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 125

Gln Gln Tyr Asn Asn Trp Pro Pro Ala Tyr Thr
1               5                   10

<210> SEQ ID NO 126
<211> LENGTH: 115
<212> TYPE: PRT
<213> ORGANISM: Artificial Sequence
<220> FEATURE:
<223> OTHER INFORMATION: Synthetic Construct

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Leu Trp Asn Tyr Trp Gly Gln Gly Thr Leu Val Thr
            100                 105                 110

Val Ser Ser
        115

<210> SEQ ID NO 127
<211> LENGTH: 109
<212> TYPE: PRT
<213> ORGANISM: Artificial Sequence
<220> FEATURE:
<223> OTHER INFORMATION: Synthetic Construct

<400> SEQUENCE: 127

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Ile Ile
            35                  40                  45

Tyr Gly Ala Ser Thr Thr Ala Ser Gly Ile Pro Ala Arg Phe Ser Ala
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ala Tyr Thr Phe Gly Gln Gly Thr Lys Leu Glu Ile Lys
            100                 105

<210> SEQ ID NO 128
<211> LENGTH: 5
<212> TYPE: PRT
```

<213> ORGANISM: Artificial Sequence
<220> FEATURE:
<223> OTHER INFORMATION: Synthetic Construct

<400> SEQUENCE: 128

Asn Tyr Gly Met Asn
1               5

<210> SEQ ID NO 129
<211> LENGTH: 17
<212> TYPE: PRT
<213> ORGANISM: Artificial Sequence
<220> FEATURE:
<223> OTHER INFORMATION: Synthetic Construct

<400> SEQUENCE: 129

Trp Ile Asn Thr Tyr Thr Gly Glu Pro Thr Tyr Gly Glu Asp Phe Lys
1               5                   10                  15

Gly

<210> SEQ ID NO 130
<211> LENGTH: 7
<212> TYPE: PRT
<213> ORGANISM: Artificial Sequence
<220> FEATURE:
<223> OTHER INFORMATION: Synthetic Construct

<400> SEQUENCE: 130

Phe Gly Asn Tyr Val Asp Tyr
1               5

<210> SEQ ID NO 131
<211> LENGTH: 16
<212> TYPE: PRT
<213> ORGANISM: Artificial Sequence
<220> FEATURE:
<223> OTHER INFORMATION: Synthetic Construct

<400> SEQUENCE: 131

Arg Ser Ser Lys Asn Leu Leu His Ser Asn Gly Ile Thr Tyr Leu Tyr
1               5                   10                  15

<210> SEQ ID NO 132
<211> LENGTH: 7
<212> TYPE: PRT
<213> ORGANISM: Artificial Sequence
<220> FEATURE:
<223> OTHER INFORMATION: Synthetic Construct

<400> SEQUENCE: 132

Gln Met Ser Asn Leu Ala Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic Construct

<400> SEQUENCE: 133

Ala Gln Asn Leu Glu Ile Pro Arg Thr
1               5

<210> SEQ ID NO 134
<211> LENGTH: 116

<212> TYPE: PRT
<213> ORGANISM: Artificial Sequence
<220> FEATURE:
<223> OTHER INFORMATION: Synthetic Construct

<400> SEQUENCE: 134

```
Gln Val Gln Leu Val Gln Ser Gly Pro Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Gly Met Asn Trp Val Arg Gln Ala Pro Gly Gln Gly Leu Glu Trp Met
        35                  40                  45
Gly Trp Ile Asn Thr Tyr Thr Gly Glu Pro Thr Tyr Gly Glu Asp Phe
    50                  55                  60
Lys Gly Arg Phe Ala Phe Ser Leu Asp Thr Ser Ala Ser Thr Ala Tyr
65                  70                  75                  80
Met Glu Leu Ser Ser Leu Arg Ser Glu Asp Thr Ala Val Tyr Phe Cys
                85                  90                  95
Ala Arg Phe Gly Asn Tyr Val Asp Tyr Trp Gly Gln Gly Ser Leu Val
            100                 105                 110
Thr Val Ser Ser
        115
```

<210> SEQ ID NO 135
<211> LENGTH: 112
<212> TYPE: PRT
<213> ORGANISM: Artificial Sequence
<220> FEATURE:
<223> OTHER INFORMATION: Synthetic Construct

<400> SEQUENCE: 135

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Lys Asn Leu Leu His Ser
            20                  25                  30
Asn Gly Ile Thr Tyr Leu Tyr Trp Tyr Leu Gln Lys Pro Gly Gln Ser
        35                  40                  45
Pro Gln Leu Leu Ile Tyr Gln Met Ser Asn Leu Ala Ser Gly Val Pro
    50                  55                  60
Asp Arg Phe Ser Ser Ser Gly Ser Gly Thr Asp Phe Thr Leu Lys Ile
65                  70                  75                  80
Ser Arg Val Glu Ala Glu Asp Val Gly Val Tyr Tyr Cys Ala Gln Asn
                85                  90                  95
Leu Glu Ile Pro Arg Thr Phe Gly Gln Gly Thr Lys Val Glu Ile Lys
            100                 105                 110
```

<210> SEQ ID NO 136
<211> LENGTH: 5
<212> TYPE: PRT
<213> ORGANISM: Artificial Sequence
<220> FEATURE:
<223> OTHER INFORMATION: Synthetic Construct

<400> SEQUENCE: 136

```
Lys Tyr Gly Met Asn
1               5
```

<210> SEQ ID NO 137
<211> LENGTH: 17
<212> TYPE: PRT

```
<213> ORGANISM: Artificial Sequence
<220> FEATURE:
<223> OTHER INFORMATION: Synthetic Construct

<400> SEQUENCE: 137

Trp Ile Asn Thr Tyr Thr Glu Glu Pro Thr Tyr Gly Asp Asp Phe Lys
1               5                   10                  15

Gly

<210> SEQ ID NO 138
<211> LENGTH: 7
<212> TYPE: PRT
<213> ORGANISM: Artificial Sequence
<220> FEATURE:
<223> OTHER INFORMATION: Synthetic Construct

<400> SEQUENCE: 138

Phe Gly Ser Ala Val Asp Tyr
1               5

<210> SEQ ID NO 139
<211> LENGTH: 16
<212> TYPE: PRT
<213> ORGANISM: Artificial Sequence
<220> FEATURE:
<223> OTHER INFORMATION: Synthetic Construct

<400> SEQUENCE: 139

Arg Ser Ser Lys Ser Leu Leu His Ser Asn Gly Ile Thr Tyr Leu Tyr
1               5                   10                  15

<210> SEQ ID NO 140
<211> LENGTH: 7
<212> TYPE: PRT
<213> ORGANISM: Artificial Sequence
<220> FEATURE:
<223> OTHER INFORMATION: Synthetic Construct

<400> SEQUENCE: 140

Gln Met Ser Asn Arg Ala Ser
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic Construct

<400> SEQUENCE: 141

Ala Gln Asn Leu Glu Leu Pro Arg Thr
1               5

<210> SEQ ID NO 142
<211> LENGTH: 116
<212> TYPE: PRT
<213> ORGANISM: Artificial Sequence
<220> FEATURE:
<223> OTHER INFORMATION: Synthetic Construct

<400> SEQUENCE: 142

Gln Ile Gln Leu Val Gln Ser Gly Pro Glu Val Lys Lys Pro Gly Glu
1               5                   10                  15

Ser Val Lys Ile Ser Cys Lys Ala Ser Gly Tyr Thr Phe Thr Lys Tyr
                20                  25                  30
```

```
Gly Met Asn Trp Val Lys Gln Ala Pro Gly Gln Gly Leu Lys Trp Met
        35                  40                  45

Gly Trp Ile Asn Thr Tyr Thr Glu Glu Pro Thr Tyr Gly Asp Asp Phe
    50                  55                  60

Lys Gly Arg Phe Thr Phe Thr Leu Asp Thr Ser Thr Ser Thr Ala Tyr
65                  70                  75                  80

Leu Glu Ile Ser Ser Leu Arg Ser Glu Asp Thr Ala Thr Tyr Phe Cys
                85                  90                  95

Ala Arg Phe Gly Ser Ala Val Asp Tyr Trp Gly Gln Gly Thr Leu Val
            100                 105                 110

Thr Val Ser Ser
        115
```

<210> SEQ ID NO 143
<211> LENGTH: 113
<212> TYPE: PRT
<213> ORGANISM: Artificial Sequence
<220> FEATURE:
<223> OTHER INFORMATION: Synthetic Construct

<400> SEQUENCE: 143

```
Asp Ile Val Met Thr Gln Ser Ala Leu Ser Asn Pro Val Thr Leu Gly
1               5                   10                  15

Glu Ser Gly Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Arg Thr Phe Gly Gln Gly Thr Lys Leu Glu Met Lys
            100                 105                 110

Arg
```

<210> SEQ ID NO 144
<211> LENGTH: 5
<212> TYPE: PRT
<213> ORGANISM: Artificial Sequence
<220> FEATURE:
<223> OTHER INFORMATION: Synthetic Construct

<400> SEQUENCE: 144

```
Asp Tyr Ser Met His
1               5
```

<210> SEQ ID NO 145
<211> LENGTH: 17
<212> TYPE: PRT
<213> ORGANISM: Artificial Sequence
<220> FEATURE:
<223> OTHER INFORMATION: Synthetic Construct

<400> SEQUENCE: 145

```
Trp Ile Asn Thr Glu Thr Gly Glu Pro Thr Tyr Ala Asp Asp Phe Lys
1               5                   10                  15

Gly
```

<210> SEQ ID NO 146
<211> LENGTH: 4
<212> TYPE: PRT
<213> ORGANISM: Artificial Sequence
<220> FEATURE:
<223> OTHER INFORMATION: Synthetic Construct

<400> SEQUENCE: 146

Thr Ala Val Tyr
1

<210> SEQ ID NO 147
<211> LENGTH: 11
<212> TYPE: PRT
<213> ORGANISM: Artificial Sequence
<220> FEATURE:
<223> OTHER INFORMATION: Synthetic Construct

<400> SEQUENCE: 147

Arg Ala Ser Gln Glu Ile Ser Val Ser Leu Ser
1               5                   10

<210> SEQ ID NO 148
<211> LENGTH: 7
<212> TYPE: PRT
<213> ORGANISM: Artificial Sequence
<220> FEATURE:
<223> OTHER INFORMATION: Synthetic Construct

<400> SEQUENCE: 148

Ala Thr Ser Thr Leu Asp Ser
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic Construct

<400> SEQUENCE: 149

Leu Gln Tyr Ala Ser Tyr Pro Trp Thr
1               5

<210> SEQ ID NO 150
<211> LENGTH: 113
<212> TYPE: PRT
<213> ORGANISM: Artificial Sequence
<220> FEATURE:
<223> OTHER INFORMATION: Synthetic Construct

<400> SEQUENCE: 150

Gln Val Lys Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

```
Ala Arg Thr Ala Val Tyr Trp Gly Gln Gly Thr Thr Val Thr Val Ser
                100                 105                 110
Ser

<210> SEQ ID NO 151
<211> LENGTH: 108
<212> TYPE: PRT
<213> ORGANISM: Artificial Sequence
<220> FEATURE:
<223> OTHER INFORMATION: Synthetic Construct

<400> SEQUENCE: 151

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Val Ser
            20                  25                  30

Leu Ser Trp Leu Gln Gln Glu Pro Asp Gly Thr Ile Lys Arg Leu Ile
        35                  40                  45

Tyr Ala Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Tyr Pro Trp
                85                  90                  95

Thr Phe Gly Gly Gly Thr Lys Leu Glu Ile Lys Arg
                100                 105

<210> SEQ ID NO 152
<211> LENGTH: 5
<212> TYPE: PRT
<213> ORGANISM: Artificial Sequence
<220> FEATURE:
<223> OTHER INFORMATION: Synthetic Construct

<400> SEQUENCE: 152

Asn Tyr Gly Met Asn
1               5

<210> SEQ ID NO 153
<211> LENGTH: 17
<212> TYPE: PRT
<213> ORGANISM: Artificial Sequence
<220> FEATURE:
<223> OTHER INFORMATION: Synthetic Construct

<400> SEQUENCE: 153

Trp Ile Asn Thr Tyr Ser Gly Glu Pro Arg Tyr Ala Asp Asp Phe Lys
1               5                   10                  15

Gly

<210> SEQ ID NO 154
<211> LENGTH: 9
<212> TYPE: PRT
<213> ORGANISM: Artificial Sequence
<220> FEATURE:
<223> OTHER INFORMATION: Synthetic Construct

<400> SEQUENCE: 154

Asp Tyr Gly Arg Trp Tyr Phe Asp Val
1               5
```

```
<210> SEQ ID NO 155
<211> LENGTH: 10
<212> TYPE: PRT
<213> ORGANISM: Artificial Sequence
<220> FEATURE:
<223> OTHER INFORMATION: Synthetic Construct

<400> SEQUENCE: 155

Arg Ala Ser Ser Val Ser His Met His
1               5                   10

<210> SEQ ID NO 156
<211> LENGTH: 7
<212> TYPE: PRT
<213> ORGANISM: Artificial Sequence
<220> FEATURE:
<223> OTHER INFORMATION: Synthetic Construct

<400> SEQUENCE: 156

Ala Thr Ser Asn Leu Ala Ser
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic Construct

<400> SEQUENCE: 157

Gln Gln Trp Ser Ser Thr Pro Arg Thr
1               5

<210> SEQ ID NO 158
<211> LENGTH: 118
<212> TYPE: PRT
<213> ORGANISM: Artificial Sequence
<220> FEATURE:
<223> OTHER INFORMATION: Synthetic Construct

<400> SEQUENCE: 158

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Asp Leu Lys Trp Met
            35                  40                  45

Gly Trp Ile Asn Thr Tyr Ser Gly Glu Pro Arg Tyr Ala Asp Asp Phe
        50                  55                  60

Lys Gly Arg Phe Val Phe Ser Leu Asp Lys Ser Val Asn Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Arg Trp Tyr Phe Asp Val Trp Gly Gln Gly Thr
                100                 105                 110

Thr Val Thr Val Ser Ser
        115

<210> SEQ ID NO 159
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 159

Gln Ile Val Leu Ser Gln Ser Pro Ala Thr Leu Ser Leu Ser Pro Gly
1               5                   10                  15

Glu Arg Ala Thr Met Ser Cys Arg Ala Ser Ser Val Ser His Met
            20                  25                  30

His Trp Tyr Gln Gln Lys Pro Gly Gln Ala Pro Arg Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Thr Pro Arg Thr
                85                  90                  95

Phe Gly Gly Gly Thr Lys Val Glu Ile Lys Arg
            100                 105

<210> SEQ ID NO 160
<211> LENGTH: 5
<212> TYPE: PRT
<213> ORGANISM: Artificial Sequence
<220> FEATURE:
<223> OTHER INFORMATION: Synthetic Construct

<400> SEQUENCE: 160

Arg Tyr Trp Met Ser
1               5

<210> SEQ ID NO 161
<211> LENGTH: 17
<212> TYPE: PRT
<213> ORGANISM: Artificial Sequence
<220> FEATURE:
<223> OTHER INFORMATION: Synthetic Construct

<400> SEQUENCE: 161

Glu Ile Asn Pro Asp Ser Ser Thr Ile Asn Tyr Ala Pro Ser Leu Lys
1               5                   10                  15

Asp

<210> SEQ ID NO 162
<211> LENGTH: 10
<212> TYPE: PRT
<213> ORGANISM: Artificial Sequence
<220> FEATURE:
<223> OTHER INFORMATION: Synthetic Construct

<400> SEQUENCE: 162

Pro Asp Gly Asn Tyr Trp Tyr Phe Asp Val
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Synthetic Construct

<400> SEQUENCE: 163

Lys Ala Ser Gln Asp Val Gly Ile Ala Val Ala
1               5                   10

```
<210> SEQ ID NO 164
<211> LENGTH: 7
<212> TYPE: PRT
<213> ORGANISM: Artificial Sequence
<220> FEATURE:
<223> OTHER INFORMATION: Synthetic Construct

<400> SEQUENCE: 164

Trp Ala Ser Thr Arg His Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic Construct

<400> SEQUENCE: 165

Gln Gln Tyr Ser Ser Tyr Pro Tyr Thr
1               5

<210> SEQ ID NO 166
<211> LENGTH: 119
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Tyr Phe Asp Val Trp Gly Gln Gly
            100                 105                 110

Thr Leu Val Thr Val Ser Ser
        115

<210> SEQ ID NO 167
<211> LENGTH: 108
<212> TYPE: PRT
<213> ORGANISM: Artificial Sequence
<220> FEATURE:
<223> OTHER INFORMATION: Synthetic Construct

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
```

```
            50                  55                  60
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Ser Ser Tyr Pro Tyr
                 85                  90                  95

Thr Phe Gly Gln Gly Thr Lys Val Glu Ile Lys Arg
            100                 105
```

<210> SEQ ID NO 168
<211> LENGTH: 5
<212> TYPE: PRT
<213> ORGANISM: Artificial Sequence
<220> FEATURE:
<223> OTHER INFORMATION: Synthetic Construct

<400> SEQUENCE: 168

```
Ser Phe Ala Met Ser
 1               5
```

<210> SEQ ID NO 169
<211> LENGTH: 17
<212> TYPE: PRT
<213> ORGANISM: Artificial Sequence
<220> FEATURE:
<223> OTHER INFORMATION: Synthetic Construct

<400> SEQUENCE: 169

```
Ala Ile Ser Gly Ser Gly Gly Thr Tyr Tyr Ala Asp Ser Val Lys
 1               5                  10                  15
Gly
```

<210> SEQ ID NO 170
<211> LENGTH: 13
<212> TYPE: PRT
<213> ORGANISM: Artificial Sequence
<220> FEATURE:
<223> OTHER INFORMATION: Synthetic Construct

<400> SEQUENCE: 170

```
Asp Lys Ile Leu Trp Phe Gly Glu Pro Val Phe Asp Tyr
 1               5                  10
```

<210> SEQ ID NO 171
<211> LENGTH: 11
<212> TYPE: PRT
<213> ORGANISM: Artificial Sequence
<220> FEATURE:
<223> OTHER INFORMATION: Synthetic Construct

<400> SEQUENCE: 171

```
Arg Ala Ser Gln Ser Val Ser Ser Tyr Leu Ala
 1               5                  10
```

<210> SEQ ID NO 172
<211> LENGTH: 7
<212> TYPE: PRT
<213> ORGANISM: Artificial Sequence
<220> FEATURE:
<223> OTHER INFORMATION: Synthetic Construct

<400> SEQUENCE: 172

```
Asp Ala Ser Asn Arg Ala Thr
 1               5
```

<210> SEQ ID NO 173
<211> LENGTH: 9
<212> TYPE: PRT
<213> ORGANISM: Artificial Sequence
<220> FEATURE:
<223> OTHER INFORMATION: Synthetic Construct

<400> SEQUENCE: 173

```
Gln Gln Arg Ser Asn Trp Pro Pro Thr
1               5
```

<210> SEQ ID NO 174
<211> LENGTH: 122
<212> TYPE: PRT
<213> ORGANISM: Artificial Sequence
<220> FEATURE:
<223> OTHER INFORMATION: Synthetic Construct

<400> SEQUENCE: 174

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120
```

<210> SEQ ID NO 175
<211> LENGTH: 108
<212> TYPE: PRT
<213> ORGANISM: Artificial Sequence
<220> FEATURE:
<223> OTHER INFORMATION: Synthetic Construct

<400> SEQUENCE: 175

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg
            100                 105
```

<210> SEQ ID NO 176

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 176

Ser Tyr Arg Met His
1               5

<210> SEQ ID NO 177
<211> LENGTH: 17
<212> TYPE: PRT
<213> ORGANISM: Artificial Sequence
<220> FEATURE:
<223> OTHER INFORMATION: Synthetic Construct

<400> SEQUENCE: 177

Tyr Ile Asn Pro Ser Thr Gly Tyr Thr Glu Tyr Asn Gln Lys Phe Lys
1               5                   10                  15

Asp

<210> SEQ ID NO 178
<211> LENGTH: 7
<212> TYPE: PRT
<213> ORGANISM: Artificial Sequence
<220> FEATURE:
<223> OTHER INFORMATION: Synthetic Construct

<400> SEQUENCE: 178

Gly Gly Gly Val Phe Asp Tyr
1               5

<210> SEQ ID NO 179
<211> LENGTH: 10
<212> TYPE: PRT
<213> ORGANISM: Artificial Sequence
<220> FEATURE:
<223> OTHER INFORMATION: Synthetic Construct

<400> SEQUENCE: 179

Ser Ala Ser Ser Ser Ile Ser Tyr Met His
1               5                   10

<210> SEQ ID NO 180
<211> LENGTH: 7
<212> TYPE: PRT
<213> ORGANISM: Artificial Sequence
<220> FEATURE:
<223> OTHER INFORMATION: Synthetic Construct

<400> SEQUENCE: 180

Thr Thr Ser Asn Leu Ala Ser
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic Construct

<400> SEQUENCE: 181

His Gln Arg Ser Thr Tyr Pro Leu Thr
1               5
```

```
<210> SEQ ID NO 182
<211> LENGTH: 116
<212> TYPE: PRT
<213> ORGANISM: Artificial Sequence
<220> FEATURE:
<223> OTHER INFORMATION: Synthetic Construct

<400> SEQUENCE: 182

Gln Val Gln Leu Val Gln Ser Gly Ala Glu Val Lys Pro Gly Ser
1               5                   10                  15

Ser Val Lys Val Ser Cys Lys Ala Ser Gly Tyr Thr Phe Thr Ser Tyr
                20                  25                  30

Arg Met His Trp Val Arg Gln Ala Pro Gly Gln Gly Leu Glu Trp Ile
            35                  40                  45

Gly Tyr Ile Asn Pro Ser Thr Gly Tyr Thr Glu Tyr Asn Gln Lys Phe
        50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 183
<211> LENGTH: 106
<212> TYPE: PRT
<213> ORGANISM: Artificial Sequence
<220> FEATURE:
<223> OTHER INFORMATION: Synthetic Construct

<400> SEQUENCE: 183

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
                20                  25                  30

His Trp Tyr Gln Gln Lys Pro Gly Lys Ala Pro Lys Leu Leu Ile Tyr
            35                  40                  45

Thr Thr Ser Asn Leu Ala Ser Gly Val Pro Ala Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Gln Gly Thr Lys Val Glu Val Lys
            100                 105

<210> SEQ ID NO 184
<211> LENGTH: 4
<212> TYPE: PRT
<213> ORGANISM: Artificial Sequence
<220> FEATURE:
<223> OTHER INFORMATION: Synthetic Construct

<400> SEQUENCE: 184

Ser Tyr Trp Met
1

<210> SEQ ID NO 185
```

```
<211> LENGTH: 17
<212> TYPE: PRT
<213> ORGANISM: Artificial Sequence
<220> FEATURE:
<223> OTHER INFORMATION: Synthetic Construct

<400> SEQUENCE: 185

Glu Ile Ile Pro Ile Asn Gly His Thr Asn Tyr Asn Glu Lys Phe Lys
1               5                   10                  15

Ser

<210> SEQ ID NO 186
<211> LENGTH: 14
<212> TYPE: PRT
<213> ORGANISM: Artificial Sequence
<220> FEATURE:
<223> OTHER INFORMATION: Synthetic Construct

<400> SEQUENCE: 186

Gly Gly Tyr Tyr Tyr Tyr Gly Ser Arg Asp Tyr Phe Asp Tyr
1               5                   10

<210> SEQ ID NO 187
<211> LENGTH: 15
<212> TYPE: PRT
<213> ORGANISM: Artificial Sequence
<220> FEATURE:
<223> OTHER INFORMATION: Synthetic Construct

<400> SEQUENCE: 187

Lys Ala Ser Gln Ser Val Asp Tyr Asp Gly Asp Ser Tyr Met Asn
1               5                   10                  15

<210> SEQ ID NO 188
<211> LENGTH: 7
<212> TYPE: PRT
<213> ORGANISM: Artificial Sequence
<220> FEATURE:
<223> OTHER INFORMATION: Synthetic Construct

<400> SEQUENCE: 188

Ala Ala Ser Asp Leu Glu Ser
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Construct

<400> SEQUENCE: 189

Gln Gln Ser His Glu Asp Pro Phe Thr
1               5

<210> SEQ ID NO 190
<211> LENGTH: 123
<212> TYPE: PRT
<213> ORGANISM: Artificial Sequence
<220> FEATURE:
<223> OTHER INFORMATION: Synthetic Construct

<400> SEQUENCE: 190

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
```

```
                 20                  25                  30
Trp Met His Trp Val Lys Gln Arg Pro Gly Gln Gly Leu Glu Trp Ile
            35                  40                  45
Gly Glu Ile Ile Pro Ile Asn Gly His Thr Asn Tyr Asn Glu Lys Phe
        50                  55                  60
Lys Ser Lys Ala Thr Leu Thr Leu Asp Lys Ser Ser Ser Thr Ala Tyr
65                  70                  75                  80
Met Gln Leu Ser Ser Leu Ala Ser Glu Asp Ser Ala Val Tyr Tyr Cys
                85                  90                  95
Ala Arg Gly Gly Tyr Tyr Tyr Gly Ser Arg Asp Tyr Phe Asp Tyr
            100                 105                 110
Trp Gly Gln Gly Thr Thr Leu Thr Val Ser Ser
        115                 120
```

<210> SEQ ID NO 191
<211> LENGTH: 111
<212> TYPE: PRT
<213> ORGANISM: Artificial Sequence
<220> FEATURE:
<223> OTHER INFORMATION: Synthetic Construct

<400> SEQUENCE: 191

```
Asp Ile Val Leu Thr Gln Ser Pro Ala Ser Leu Ala Val Ser Leu Gly
1               5                   10                  15
Gln Arg Ala Thr Ile Ser Cys Lys Ala Ser Gln Ser Val Asp Tyr Asp
            20                  25                  30
Gly Asp Ser Tyr Met Asn Trp Tyr Gln Gln Ile Pro Gly Gln Pro Pro
        35                  40                  45
Lys Leu Leu Ile Tyr Ala Ala Ser Asp Leu Glu Ser Gly Ile Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln Gln Ser His
                85                  90                  95
Glu Asp Pro Phe Thr Phe Gly Gly Gly Thr Lys Leu Glu Ile Lys
            100                 105                 110
```

<210> SEQ ID NO 192
<211> LENGTH: 4
<212> TYPE: PRT
<213> ORGANISM: Artificial Sequence
<220> FEATURE:
<223> OTHER INFORMATION: Synthetic Construct

<400> SEQUENCE: 192

```
Ser Tyr Trp Met
1
```

<210> SEQ ID NO 193
<211> LENGTH: 17
<212> TYPE: PRT
<213> ORGANISM: Artificial Sequence
<220> FEATURE:
<223> OTHER INFORMATION: Synthetic Construct

<400> SEQUENCE: 193

```
Glu Ile Ile Pro Ile Phe Gly His Thr Asn Tyr Asn Glu Lys Phe Lys
1               5                   10                  15
Ser
```

<210> SEQ ID NO 194
<211> LENGTH: 14
<212> TYPE: PRT
<213> ORGANISM: Artificial Sequence
<220> FEATURE:
<223> OTHER INFORMATION: Synthetic Construct

<400> SEQUENCE: 194

Gly Gly Tyr Tyr Tyr Tyr Pro Arg Gln Gly Phe Leu Asp Tyr
1               5                   10

<210> SEQ ID NO 195
<211> LENGTH: 16
<212> TYPE: PRT
<213> ORGANISM: Artificial Sequence
<220> FEATURE:
<223> OTHER INFORMATION: Synthetic Construct

<400> SEQUENCE: 195

Lys Ala Ser Gln Ser Val Asp Tyr Asp Ser Gly Asp Ser Tyr Met Asn
1               5                   10                  15

<210> SEQ ID NO 196
<211> LENGTH: 7
<212> TYPE: PRT
<213> ORGANISM: Artificial Sequence
<220> FEATURE:
<223> OTHER INFORMATION: Synthetic Construct

<400> SEQUENCE: 196

Ala Ala Ser Asp Leu Glu Ser
1               5

<210> SEQ ID NO 197
<211> LENGTH: 9
<212> TYPE: PRT
<213> ORGANISM: Artificial Sequence
<220> FEATURE:
<223> OTHER INFORMATION: Synthetic Construct

<400> SEQUENCE: 197

Gln Gln Ser His Glu Asp Pro Phe Thr
1               5

<210> SEQ ID NO 198
<211> LENGTH: 123
<212> TYPE: PRT
<213> ORGANISM: Artificial Sequence
<220> FEATURE:
<223> OTHER INFORMATION: Synthetic Construct

<400> SEQUENCE: 198

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Gly Glu Ile Ile Pro Ile Phe Gly His Thr Asn Tyr Asn Glu Lys Phe
    50                  55                  60

Lys Ser Arg Phe Thr Ile Ser Leu Asp Asn Ser Lys Asn Thr Leu Tyr
65                  70                  75                  80

Leu Gln Met Gly Ser Leu Arg Ala Glu Asp Thr Ala Val Tyr Tyr Cys
                85                  90                  95

Ala Arg Gly Gly Tyr Tyr Tyr Pro Arg Gln Gly Phe Leu Asp Tyr
            100                 105                 110

Trp Gly Gln Gly Thr Thr Val Thr Val Ser Ser
        115                 120

<210> SEQ ID NO 199
<211> LENGTH: 111
<212> TYPE: PRT
<213> ORGANISM: Artificial Sequence
<220> FEATURE:
<223> OTHER INFORMATION: Synthetic Construct

<400> SEQUENCE: 199

Asp Ile Val Met Thr Gln Ser Pro Asp Ser Leu Ala Val Ser Leu Gly
1               5                   10                  15

Glu Arg Ala Thr Ile Ser Cys Lys Ala Ser Gln Ser Val Asp Tyr Ser
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asp Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Tyr Cys Gln Gln Ser His
                85                  90                  95

Glu Asp Pro Phe Thr Phe Gly Gln Gly Thr Lys Leu Glu Ile Lys
            100                 105                 110

<210> SEQ ID NO 200
<211> LENGTH: 4
<212> TYPE: PRT
<213> ORGANISM: Artificial Sequence
<220> FEATURE:
<223> OTHER INFORMATION: Synthetic Construct

<400> SEQUENCE: 200

Tyr Gly Met Asn
1

<210> SEQ ID NO 201
<211> LENGTH: 16
<212> TYPE: PRT
<213> ORGANISM: Artificial Sequence
<220> FEATURE:
<223> OTHER INFORMATION: Synthetic Construct

<400> SEQUENCE: 201

Tyr Ile Ser Ser Ser Ser Ser Thr Ile Tyr Ala Asp Ser Val Lys Gly
1               5                   10                  15

<210> SEQ ID NO 202
<211> LENGTH: 6
<212> TYPE: PRT
<213> ORGANISM: Artificial Sequence
<220> FEATURE:
<223> OTHER INFORMATION: Synthetic Construct

<400> SEQUENCE: 202

Gly Pro Gly Met Asp Val
1               5

<210> SEQ ID NO 203

```
<210> SEQ ID NO 203
<211> LENGTH: 17
<212> TYPE: PRT
<213> ORGANISM: Artificial Sequence
<220> FEATURE:
<223> OTHER INFORMATION: Synthetic Construct

<400> SEQUENCE: 203

Lys Ser Ser Gln Ser Val Leu Tyr Ser Ser Asn Asn Lys Asn Tyr Leu
1               5                   10                  15
Ala

<210> SEQ ID NO 204
<211> LENGTH: 7
<212> TYPE: PRT
<213> ORGANISM: Artificial Sequence
<220> FEATURE:
<223> OTHER INFORMATION: Synthetic Construct

<400> SEQUENCE: 204

Trp Ala Ser Thr Arg Glu Ser
1               5

<210> SEQ ID NO 205
<211> LENGTH: 10
<212> TYPE: PRT
<213> ORGANISM: Artificial Sequence
<220> FEATURE:
<223> OTHER INFORMATION: Synthetic Construct

<400> SEQUENCE: 205

Gln Gln Tyr Tyr Ser Thr Pro Gln Leu Thr
1               5                   10

<210> SEQ ID NO 206
<211> LENGTH: 112
<212> TYPE: PRT
<213> ORGANISM: Artificial Sequence
<220> FEATURE:
<223> OTHER INFORMATION: Synthetic Construct

<400> SEQUENCE: 206

Gln Val Gln Leu Gln Gln Ser Gly Gly Val Val Gln Pro Gly Arg
1               5                   10                  15

Ser Leu Gly Leu Ser Cys Ala Ala Ser Phe Thr Phe Ser Ser Tyr Gly
            20                  25                  30

Met Asn Trp Val Arg Gln Ala Pro Gly Lys Gly Leu Glu Trp Val Ser
        35                  40                  45

Tyr Ile Ser Ser Ser Ser Ser Thr Ile Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Pro Gly Met Asp Val Trp Gly Gln Gly Thr Thr Val Thr Val Ser
            100                 105                 110

<210> SEQ ID NO 207
<211> LENGTH: 114
<212> TYPE: PRT
<213> ORGANISM: Artificial Sequence
<220> FEATURE:
<223> OTHER INFORMATION: Synthetic Construct

<400> SEQUENCE: 207
```

```
Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Pro Ala
65                  70                  75                  80

Ile Ser Ser Leu Gln Ala Glu Asp Val Ala Val Tyr Tyr Cys Gln Gln
                85                  90                  95

Tyr Tyr Ser Thr Pro Gln Leu Thr Phe Gly Gly Gly Thr Lys Val Asp
            100                 105                 110

Ile Lys
```

```
<210> SEQ ID NO 208
<211> LENGTH: 7
<212> TYPE: PRT
<213> ORGANISM: Artificial Sequence
<220> FEATURE:
<223> OTHER INFORMATION: Synthetic Construct

<400> SEQUENCE: 208

Thr Ser Gly Met Gly Val Gly
1               5
```

```
<210> SEQ ID NO 209
<211> LENGTH: 16
<212> TYPE: PRT
<213> ORGANISM: Artificial Sequence
<220> FEATURE:
<223> OTHER INFORMATION: Synthetic Construct

<400> SEQUENCE: 209

His Ile Trp Trp Asp Asp Asp Lys Arg Tyr Asn Pro Ala Leu Lys Ser
1               5                   10                  15
```

```
<210> SEQ ID NO 210
<211> LENGTH: 10
<212> TYPE: PRT
<213> ORGANISM: Artificial Sequence
<220> FEATURE:
<223> OTHER INFORMATION: Synthetic Construct

<400> SEQUENCE: 210

Met Glu Leu Trp Ser Tyr Tyr Phe Asp Tyr
1               5                   10
```

```
<210> SEQ ID NO 211
<211> LENGTH: 10
<212> TYPE: PRT
<213> ORGANISM: Artificial Sequence
<220> FEATURE:
<223> OTHER INFORMATION: Synthetic Construct

<400> SEQUENCE: 211

Ser Ala Ser Ser Ser Val Ser Tyr Met His
1               5                   10
```

```
<210> SEQ ID NO 212
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 212

Asp Thr Ser Lys Leu Ala Ser
1               5

<210> SEQ ID NO 213
<211> LENGTH: 9
<212> TYPE: PRT
<213> ORGANISM: Artificial Sequence
<220> FEATURE:
<223> OTHER INFORMATION: Synthetic Construct

<400> SEQUENCE: 213

Phe Gln Gly Ser Val Tyr Pro Phe Thr
1               5

<210> SEQ ID NO 214
<211> LENGTH: 120
<212> TYPE: PRT
<213> ORGANISM: Artificial Sequence
<220> FEATURE:
<223> OTHER INFORMATION: Synthetic Construct

<400> SEQUENCE: 214

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 215
<211> LENGTH: 107
<212> TYPE: PRT
<213> ORGANISM: Artificial Sequence
<220> FEATURE:
<223> OTHER INFORMATION: Synthetic Construct

<400> SEQUENCE: 215

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60
```

Gly Ser Gly Thr Asp Phe Thr Leu Thr Ile Ser Ser Leu Glu Pro Glu
65                  70                  75                  80

Asp Val Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 216
<211> LENGTH: 5
<212> TYPE: PRT
<213> ORGANISM: Artificial Sequence
<220> FEATURE:
<223> OTHER INFORMATION: Synthetic Construct

<400> SEQUENCE: 216

Asn Tyr Gly Met Asn
1               5

<210> SEQ ID NO 217
<211> LENGTH: 17
<212> TYPE: PRT
<213> ORGANISM: Artificial Sequence
<220> FEATURE:
<223> OTHER INFORMATION: Synthetic Construct

<400> SEQUENCE: 217

Trp Ile Asn Thr Tyr Thr Gly Glu Pro Thr Tyr Ala Asp Ala Phe Lys
1               5                   10                  15

Gly

<210> SEQ ID NO 218
<211> LENGTH: 9
<212> TYPE: PRT
<213> ORGANISM: Artificial Sequence
<220> FEATURE:
<223> OTHER INFORMATION: Synthetic Construct

<400> SEQUENCE: 218

Asp Tyr Gly Asp Tyr Gly Met Asp Tyr
1               5

<210> SEQ ID NO 219
<211> LENGTH: 15
<212> TYPE: PRT
<213> ORGANISM: Artificial Sequence
<220> FEATURE:
<223> OTHER INFORMATION: Synthetic Construct

<400> SEQUENCE: 219

Arg Ala Ser Lys Ser Val Ser Thr Ser Gly Tyr Ser Phe Met His
1               5                   10                  15

<210> SEQ ID NO 220
<211> LENGTH: 7
<212> TYPE: PRT
<213> ORGANISM: Artificial Sequence
<220> FEATURE:
<223> OTHER INFORMATION: Synthetic Construct

<400> SEQUENCE: 220

Leu Ala Ser Asn Leu Glu Ser
1               5

<210> SEQ ID NO 221
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 221

Gln His Ser Arg Glu Val Pro Trp Thr
1               5

<210> SEQ ID NO 222
<211> LENGTH: 118
<212> TYPE: PRT
<213> ORGANISM: Artificial Sequence
<220> FEATURE:
<223> OTHER INFORMATION: Synthetic Construct

<400> SEQUENCE: 222

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 223
<211> LENGTH: 111
<212> TYPE: PRT
<213> ORGANISM: Artificial Sequence
<220> FEATURE:
<223> OTHER INFORMATION: Synthetic Construct

<400> SEQUENCE: 223

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys
            100                 105                 110

<210> SEQ ID NO 224
<211> LENGTH: 6
<212> TYPE: PRT
```

```
<213> ORGANISM: Artificial Sequence
<220> FEATURE:
<223> OTHER INFORMATION: Synthetic Construct

<400> SEQUENCE: 224

Ser Gly Tyr Ser Trp His
1               5

<210> SEQ ID NO 225
<211> LENGTH: 16
<212> TYPE: PRT
<213> ORGANISM: Artificial Sequence
<220> FEATURE:
<223> OTHER INFORMATION: Synthetic Construct

<400> SEQUENCE: 225

Tyr Ile His Ser Ser Gly Ser Thr Asn Tyr Asn Pro Ser Leu Lys Ser
1               5                   10                  15

<210> SEQ ID NO 226
<211> LENGTH: 7
<212> TYPE: PRT
<213> ORGANISM: Artificial Sequence
<220> FEATURE:
<223> OTHER INFORMATION: Synthetic Construct

<400> SEQUENCE: 226

Tyr Asp Asp Tyr Phe Glu Tyr
1               5

<210> SEQ ID NO 227
<211> LENGTH: 11
<212> TYPE: PRT
<213> ORGANISM: Artificial Sequence
<220> FEATURE:
<223> OTHER INFORMATION: Synthetic Construct

<400> SEQUENCE: 227

Lys Ala Ser Gln Asn Val Gly Phe Asn Val Ala
1               5                   10

<210> SEQ ID NO 228
<211> LENGTH: 7
<212> TYPE: PRT
<213> ORGANISM: Artificial Sequence
<220> FEATURE:
<223> OTHER INFORMATION: Synthetic Construct

<400> SEQUENCE: 228

Ser Ala Ser Tyr Arg Tyr Ser
1               5

<210> SEQ ID NO 229
<211> LENGTH: 9
<212> TYPE: PRT
<213> ORGANISM: Artificial Sequence
<220> FEATURE:
<223> OTHER INFORMATION: Synthetic Construct

<400> SEQUENCE: 229

Gln Gln Tyr Asn Trp Tyr Pro Phe Thr
1               5

<210> SEQ ID NO 230
<211> LENGTH: 116
<212> TYPE: PRT
<213> ORGANISM: Artificial Sequence
```

<220> FEATURE:
<223> OTHER INFORMATION: Synthetic Construct

<400> SEQUENCE: 230

Glu Val Gln Leu Gln Glu Ser Gly Pro Gly Leu Val Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Met Gly Tyr Ile His Ser Ser Gly Ser Thr Asn Tyr Asn Pro Ser Leu
    50                  55                  60

Lys Ser Arg Ile Ser Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Gly Tyr Asp Asp Tyr Phe Glu Tyr Trp Gly Gln Gly Thr Thr Val
            100                 105                 110

Thr Val Ser Ser
        115

<210> SEQ ID NO 231
<211> LENGTH: 107
<212> TYPE: PRT
<213> ORGANISM: Artificial Sequence
<220> FEATURE:
<223> OTHER INFORMATION: Synthetic Construct

<400> SEQUENCE: 231

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Phe Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Trp Tyr Pro Phe
                85                  90                  95

Thr Phe Gly Gln Gly Thr Lys Leu Glu Ile Lys
            100                 105

<210> SEQ ID NO 232
<211> LENGTH: 5
<212> TYPE: PRT
<213> ORGANISM: Artificial Sequence
<220> FEATURE:
<223> OTHER INFORMATION: Synthetic Construct

<400> SEQUENCE: 232

Asn Tyr Trp Ile Glu
1               5

<210> SEQ ID NO 233
<211> LENGTH: 17
<212> TYPE: PRT
<213> ORGANISM: Artificial Sequence
<220> FEATURE:

<223> OTHER INFORMATION: Synthetic Construct

<400> SEQUENCE: 233

Glu Ile Leu Pro Gly Thr Gly Arg Thr Ile Tyr Asn Glu Lys Phe Lys
1               5                   10                  15

Gly

<210> SEQ ID NO 234
<211> LENGTH: 13
<212> TYPE: PRT
<213> ORGANISM: Artificial Sequence
<220> FEATURE:
<223> OTHER INFORMATION: Synthetic Construct

<400> SEQUENCE: 234

Arg Asp Tyr Tyr Gly Asn Phe Tyr Tyr Ala Met Asp Tyr
1               5                   10

<210> SEQ ID NO 235
<211> LENGTH: 11
<212> TYPE: PRT
<213> ORGANISM: Artificial Sequence
<220> FEATURE:
<223> OTHER INFORMATION: Synthetic Construct

<400> SEQUENCE: 235

Ser Ala Ser Gln Gly Ile Asn Asn Tyr Leu Asn
1               5                   10

<210> SEQ ID NO 236
<211> LENGTH: 7
<212> TYPE: PRT
<213> ORGANISM: Artificial Sequence
<220> FEATURE:
<223> OTHER INFORMATION: Synthetic Construct

<400> SEQUENCE: 236

Tyr Thr Ser Thr Leu Gln Ser
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic Construct

<400> SEQUENCE: 237

Gln Gln Tyr Ser Lys Leu Pro Arg Thr
1               5

<210> SEQ ID NO 238
<211> LENGTH: 122
<212> TYPE: PRT
<213> ORGANISM: Artificial Sequence
<220> FEATURE:
<223> OTHER INFORMATION: Synthetic Construct

<400> SEQUENCE: 238

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
                20                  25                  30

Trp Ile Glu Trp Val Lys Gln Arg Pro Gly His Gly Leu Glu Trp Ile
            35                  40                  45

-continued

```
Gly Glu Ile Leu Pro Gly Thr Gly Arg Thr Ile Tyr Asn Glu Lys Phe
 50                  55                  60

Lys Gly Lys Ala Thr Phe Thr Ala Asp Ile Ser Asn Thr Val Gln
 65                  70                  75                  80

Met Gln Leu Ser Ser Leu Thr Ser Glu Asp Ser Ala Val Tyr Tyr Cys
                 85                  90                  95

Ala Arg Arg Asp Tyr Tyr Gly Asn Phe Tyr Tyr Ala Met Asp Tyr Trp
             100                 105                 110

Gly Gln Gly Thr Ser Val Thr Val Ser Ser
            115                 120

<210> SEQ ID NO 239
<211> LENGTH: 107
<212> TYPE: PRT
<213> ORGANISM: Artificial Sequence
<220> FEATURE:
<223> OTHER INFORMATION: Synthetic Construct

<400> SEQUENCE: 239

Asp Ile Gln Met Thr Gln Ser Thr Ser Ser Leu Ser Ala Ser Leu Gly
 1               5                  10                  15

Asp Arg Val Thr Ile Ser Cys Ser Ala Ser Gln Gly Ile Asn Asn Tyr
                 20                  25                  30

Leu Asn Trp Tyr Gln Gln Lys Pro Asp Gly Thr Val Glu Leu Leu Ile
             35                  40                  45

Tyr Tyr Thr Ser Thr Leu Gln Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Glu Asp Ile Gly Thr Tyr Tyr Cys Gln Gln Tyr Ser Lys Leu Pro Arg
                 85                  90                  95

Thr Phe Gly Gly Gly Thr Lys Leu Glu Ile Lys
            100                 105

<210> SEQ ID NO 240
<211> LENGTH: 7
<212> TYPE: PRT
<213> ORGANISM: Artificial Sequence
<220> FEATURE:
<223> OTHER INFORMATION: Synthetic Construct

<400> SEQUENCE: 240

Thr Tyr Gly Met Gly Val Gly
 1               5

<210> SEQ ID NO 241
<211> LENGTH: 16
<212> TYPE: PRT
<213> ORGANISM: Artificial Sequence
<220> FEATURE:
<223> OTHER INFORMATION: Synthetic Construct

<400> SEQUENCE: 241

Asn Ile Trp Trp Ser Glu Asp Lys His Tyr Ser Pro Ser Leu Lys Ser
 1               5                  10                  15

<210> SEQ ID NO 242
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 242

Ile Asp Tyr Gly Asn Asp Tyr Ala Phe Thr Tyr
1               5                   10

<210> SEQ ID NO 243
<211> LENGTH: 16
<212> TYPE: PRT
<213> ORGANISM: Artificial Sequence
<220> FEATURE:
<223> OTHER INFORMATION: Synthetic Construct

<400> SEQUENCE: 243

Arg Ser Ser Lys Ser Leu Leu His Ser Asn Gly Ile Thr Tyr Leu Tyr
1               5                   10                  15

<210> SEQ ID NO 244
<211> LENGTH: 7
<212> TYPE: PRT
<213> ORGANISM: Artificial Sequence
<220> FEATURE:
<223> OTHER INFORMATION: Synthetic Construct

<400> SEQUENCE: 244

Gln Met Ser Asn Leu Ala Ser
1               5

<210> SEQ ID NO 245
<211> LENGTH: 9
<212> TYPE: PRT
<213> ORGANISM: Artificial Sequence
<220> FEATURE:
<223> OTHER INFORMATION: Synthetic Construct

<400> SEQUENCE: 245

Ala Gln Asn Leu Glu Leu Pro Tyr Thr
1               5

<210> SEQ ID NO 246
<211> LENGTH: 121
<212> TYPE: PRT
<213> ORGANISM: Artificial Sequence
<220> FEATURE:
<223> OTHER INFORMATION: Synthetic Construct

<400> SEQUENCE: 246

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
                20                  25                  30

Gly Met Gly Val Gly Trp Ile Arg Gln Pro Pro Gly Lys Ala Leu Glu
            35                  40                  45

Trp Leu Ala Asn Ile Trp Trp Ser Glu Asp Lys His Tyr Ser Pro Ser
        50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Val Gln Ile Asp Tyr Gly Asn Asp Tyr Ala Phe Thr Tyr Trp Gly
            100                 105                 110

Gln Gly Thr Leu Val Thr Val Ser Ser
            115                 120

<210> SEQ ID NO 247
<211> LENGTH: 112
<212> TYPE: PRT
<213> ORGANISM: Artificial Sequence
<220> FEATURE:
<223> OTHER INFORMATION: Synthetic Construct

<400> SEQUENCE: 247

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gln Gly Thr Lys Leu Glu Ile Lys
            100                 105                 110

<210> SEQ ID NO 248
<211> LENGTH: 5
<212> TYPE: PRT
<213> ORGANISM: Artificial Sequence
<220> FEATURE:
<223> OTHER INFORMATION: Synthetic Construct

<400> SEQUENCE: 248

Arg Tyr Thr Met His
1               5

<210> SEQ ID NO 249
<211> LENGTH: 17
<212> TYPE: PRT
<213> ORGANISM: Artificial Sequence
<220> FEATURE:
<223> OTHER INFORMATION: Synthetic Construct

<400> SEQUENCE: 249

Val Ile Ser Phe Asp Gly Ser Asn Lys Tyr Tyr Val Asp Ser Val Lys
1               5                   10                  15

Gly

<210> SEQ ID NO 250
<211> LENGTH: 10
<212> TYPE: PRT
<213> ORGANISM: Artificial Sequence
<220> FEATURE:
<223> OTHER INFORMATION: Synthetic Construct

<400> SEQUENCE: 250

Glu Ala Arg Gly Ser Tyr Ala Phe Asp Ile
1               5                   10

<210> SEQ ID NO 251
<211> LENGTH: 11
<212> TYPE: PRT
<213> ORGANISM: Artificial Sequence
<220> FEATURE:

```
<223> OTHER INFORMATION: Synthetic Construct

<400> SEQUENCE: 251

Arg Ala Ser Gln Ser Val Ser Ser Tyr Leu Ala
1               5                   10

<210> SEQ ID NO 252
<211> LENGTH: 7
<212> TYPE: PRT
<213> ORGANISM: Artificial Sequence
<220> FEATURE:
<223> OTHER INFORMATION: Synthetic Construct

<400> SEQUENCE: 252

Asp Ala Ser Asn Arg Ala Thr
1               5

<210> SEQ ID NO 253
<211> LENGTH: 10
<212> TYPE: PRT
<213> ORGANISM: Artificial Sequence
<220> FEATURE:
<223> OTHER INFORMATION: Synthetic Construct

<400> SEQUENCE: 253

Gln Gln Arg Ser Asn Trp Pro Pro Phe Thr
1               5                   10

<210> SEQ ID NO 254
<211> LENGTH: 119
<212> TYPE: PRT
<213> ORGANISM: Artificial Sequence
<220> FEATURE:
<223> OTHER INFORMATION: Synthetic Construct

<400> SEQUENCE: 254

Gln Val Gln Leu Val Glu Ser Gly Gly Gly Val Val Gln Pro Gly Arg
1               5                   10                  15

Ser Arg Arg Leu Ser Cys Ala Ala Ser Gly Phe Thr Phe Ser Arg Tyr
            20                  25                  30

Thr Met His Trp Val Arg Gln Ala Pro Gly Lys Gly Leu Glu Trp Val
        35                  40                  45

Ala Val Ile Ser Phe Asp Gly Ser Asn Lys Tyr Tyr Val Asp Ser Val
    50                  55                  60

Lys Gly Arg Phe Thr Ile Ser Arg Asp Asn Ser Glu Asn Thr Leu Tyr
65                  70                  75                  80

Leu Gln Val Asn Ile Leu Arg Ala Glu Asp Thr Ala Val Tyr Tyr Cys
                85                  90                  95

Ala Arg Glu Ala Arg Gly Ser Tyr Ala Phe Asp Ile Trp Gly Gln Gly
            100                 105                 110

Thr Met Val Thr Val Ser Ser
        115

<210> SEQ ID NO 255
<211> LENGTH: 108
<212> TYPE: PRT
<213> ORGANISM: Artificial Sequence
<220> FEATURE:
<223> OTHER INFORMATION: Synthetic Construct

<400> SEQUENCE: 255

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105

<210> SEQ ID NO 256
<211> LENGTH: 5
<212> TYPE: PRT
<213> ORGANISM: Artificial Sequence
<220> FEATURE:
<223> OTHER INFORMATION: Synthetic Construct

<400> SEQUENCE: 256

Ser Phe Gly Met His
1               5

<210> SEQ ID NO 257
<211> LENGTH: 17
<212> TYPE: PRT
<213> ORGANISM: Artificial Sequence
<220> FEATURE:
<223> OTHER INFORMATION: Synthetic Construct

<400> SEQUENCE: 257

Tyr Ile Ser Ser Gly Ser Phe Thr Ile Tyr Tyr Ala Asp Ser Val Lys
1               5                   10                  15

Gly

<210> SEQ ID NO 258
<211> LENGTH: 9
<212> TYPE: PRT
<213> ORGANISM: Artificial Sequence
<220> FEATURE:
<223> OTHER INFORMATION: Synthetic Construct

<400> SEQUENCE: 258

Met Arg Lys Gly Tyr Ala Met Asp Tyr
1               5

<210> SEQ ID NO 259
<211> LENGTH: 16
<212> TYPE: PRT
<213> ORGANISM: Artificial Sequence
<220> FEATURE:
<223> OTHER INFORMATION: Synthetic Construct

<400> SEQUENCE: 259

Arg Ser Ser Gln Ile Ile Ile His Ser Asp Gly Asn Thr Tyr Leu Glu
1               5                   10                  15

<210> SEQ ID NO 260
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 260

Lys Val Ser Asn Arg Phe Ser
1               5

<210> SEQ ID NO 261
<211> LENGTH: 9
<212> TYPE: PRT
<213> ORGANISM: Artificial Sequence
<220> FEATURE:
<223> OTHER INFORMATION: Synthetic Construct

<400> SEQUENCE: 261

Phe Gln Gly Ser His Val Pro His Thr
1               5

<210> SEQ ID NO 262
<211> LENGTH: 118
<212> TYPE: PRT
<213> ORGANISM: Artificial Sequence
<220> FEATURE:
<223> OTHER INFORMATION: Synthetic Construct

<400> SEQUENCE: 262

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Phe Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Arg Lys Gly Tyr Ala Met Asp Tyr Trp Gly Gln Gly Thr
            100                 105                 110

Leu Val Thr Val Ser Ser
        115

<210> SEQ ID NO 263
<211> LENGTH: 112
<212> TYPE: PRT
<213> ORGANISM: Artificial Sequence
<220> FEATURE:
<223> OTHER INFORMATION: Synthetic Construct

<400> SEQUENCE: 263

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ile Ile His Ser
            20                  25                  30

Asp Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Phe Gln Gly
                85                  90                  95

Ser His Val Pro His Thr Phe Gly Gln Gly Thr Lys Val Glu Ile Lys
            100                 105                 110

<210> SEQ ID NO 264
<211> LENGTH: 5
<212> TYPE: PRT
<213> ORGANISM: Artificial Sequence
<220> FEATURE:
<223> OTHER INFORMATION: Synthetic Construct

<400> SEQUENCE: 264

Asn Tyr Gly Val Asn
1               5

<210> SEQ ID NO 265
<211> LENGTH: 17
<212> TYPE: PRT
<213> ORGANISM: Artificial Sequence
<220> FEATURE:
<223> OTHER INFORMATION: Synthetic Construct

<400> SEQUENCE: 265

Trp Ile Asn Pro Asn Thr Gly Glu Pro Thr Phe Asp Asp Asp Phe Lys
1               5                   10                  15

Gly

<210> SEQ ID NO 266
<211> LENGTH: 11
<212> TYPE: PRT
<213> ORGANISM: Artificial Sequence
<220> FEATURE:
<223> OTHER INFORMATION: Synthetic Construct

<400> SEQUENCE: 266

Ser Arg Gly Lys Asn Glu Ala Trp Phe Ala Tyr
1               5                   10

<210> SEQ ID NO 267
<211> LENGTH: 16
<212> TYPE: PRT
<213> ORGANISM: Artificial Sequence
<220> FEATURE:
<223> OTHER INFORMATION: Synthetic Construct

<400> SEQUENCE: 267

Arg Ser Ser Gln Ser Leu Val His Arg Asn Gly Asn Thr Tyr Leu His
1               5                   10                  15

<210> SEQ ID NO 268
<211> LENGTH: 7
<212> TYPE: PRT
<213> ORGANISM: Artificial Sequence
<220> FEATURE:
<223> OTHER INFORMATION: Synthetic Construct

<400> SEQUENCE: 268

Thr Val Ser Asn Arg Phe Ser
1               5

<210> SEQ ID NO 269
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 269

Ser Gln Ser Ser His Val Pro Pro Thr
1               5

<210> SEQ ID NO 270
<211> LENGTH: 120
<212> TYPE: PRT
<213> ORGANISM: Artificial Sequence
<220> FEATURE:
<223> OTHER INFORMATION: Synthetic Construct

<400> SEQUENCE: 270

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Val Asn Trp Ile Lys Gln Ala Pro Gly Gln Gly Leu Gln Trp Met
            35                  40                  45

Gly Trp Ile Asn Pro Asn Thr Gly Glu Pro Thr Phe Asp Asp Asp Phe
        50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ser Arg Ser Arg Gly Lys Asn Glu Ala Trp Phe Ala Tyr Trp Gly Gln
                100                 105                 110

Gly Thr Leu Val Thr Val Ser Ser
            115                 120

<210> SEQ ID NO 271
<211> LENGTH: 112
<212> TYPE: PRT
<213> ORGANISM: Artificial Sequence
<220> FEATURE:
<223> OTHER INFORMATION: Synthetic Construct

<400> SEQUENCE: 271

Asp Ile Gln Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val His Arg
                20                  25                  30

Asn Gly Asn Thr Tyr Leu His Trp Phe Gln Arg Pro Gly Gln Ser
            35                  40                  45

Pro Arg Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ser His Val Pro Pro Thr Phe Gly Ala Gly Thr Arg Leu Glu Ile Lys
                100                 105                 110

<210> SEQ ID NO 272
<211> LENGTH: 5
<212> TYPE: PRT
<213> ORGANISM: Artificial Sequence
<220> FEATURE:
<223> OTHER INFORMATION: Synthetic Construct

```
<400> SEQUENCE: 272

Thr Tyr Trp Met Ser
1               5

<210> SEQ ID NO 273
<211> LENGTH: 17
<212> TYPE: PRT
<213> ORGANISM: Artificial Sequence
<220> FEATURE:
<223> OTHER INFORMATION: Synthetic Construct

<400> SEQUENCE: 273

Glu Ile His Pro Asp Ser Ser Thr Ile Asn Tyr Ala Pro Ser Leu Lys
1               5                   10                  15

Asp

<210> SEQ ID NO 274
<211> LENGTH: 10
<212> TYPE: PRT
<213> ORGANISM: Artificial Sequence
<220> FEATURE:
<223> OTHER INFORMATION: Synthetic Construct

<400> SEQUENCE: 274

Leu Tyr Phe Gly Phe Pro Trp Phe Ala Tyr
1               5                   10

<210> SEQ ID NO 275
<211> LENGTH: 11
<212> TYPE: PRT
<213> ORGANISM: Artificial Sequence
<220> FEATURE:
<223> OTHER INFORMATION: Synthetic Construct

<400> SEQUENCE: 275

Lys Ala Ser Gln Asp Val Gly Thr Ser Val Ala
1               5                   10

<210> SEQ ID NO 276
<211> LENGTH: 7
<212> TYPE: PRT
<213> ORGANISM: Artificial Sequence
<220> FEATURE:
<223> OTHER INFORMATION: Synthetic Construct

<400> SEQUENCE: 276

Trp Thr Ser Thr Arg His Thr
1               5

<210> SEQ ID NO 277
<211> LENGTH: 8
<212> TYPE: PRT
<213> ORGANISM: Artificial Sequence
<220> FEATURE:
<223> OTHER INFORMATION: Synthetic Construct

<400> SEQUENCE: 277

Gln Gln Tyr Ser Leu Tyr Arg Ser
1               5

<210> SEQ ID NO 278
<211> LENGTH: 119
<212> TYPE: PRT
<213> ORGANISM: Artificial Sequence
<220> FEATURE:
```

<223> OTHER INFORMATION: Synthetic Construct

<400> SEQUENCE: 278

Glu Val Gln Leu Val Glu Ser Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser
        115

<210> SEQ ID NO 279
<211> LENGTH: 106
<212> TYPE: PRT
<213> ORGANISM: Artificial Sequence
<220> FEATURE:
<223> OTHER INFORMATION: Synthetic Construct

<400> SEQUENCE: 279

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys
            100                 105

<210> SEQ ID NO 280
<211> LENGTH: 5
<212> TYPE: PRT
<213> ORGANISM: Artificial Sequence
<220> FEATURE:
<223> OTHER INFORMATION: Synthetic Construct

<400> SEQUENCE: 280

Tyr Tyr Gly Met Asn
1               5

<210> SEQ ID NO 281
<211> LENGTH: 17
<212> TYPE: PRT
<213> ORGANISM: Artificial Sequence
<220> FEATURE:
<223> OTHER INFORMATION: Synthetic Construct

<400> SEQUENCE: 281

Trp Ile Asp Thr Thr Thr Gly Glu Pro Thr Tyr Ala Gln Lys Phe Gln
1               5                   10                  15

Gly

<210> SEQ ID NO 282
<211> LENGTH: 10
<212> TYPE: PRT
<213> ORGANISM: Artificial Sequence
<220> FEATURE:
<223> OTHER INFORMATION: Synthetic Construct

<400> SEQUENCE: 282

Arg Gly Pro Tyr Asn Trp Tyr Phe Asp Val
1               5                   10

<210> SEQ ID NO 283
<211> LENGTH: 16
<212> TYPE: PRT
<213> ORGANISM: Artificial Sequence
<220> FEATURE:
<223> OTHER INFORMATION: Synthetic Construct

<400> SEQUENCE: 283

Arg Ser Ser Lys Ser Leu Leu His Ser Asn Gly Asn Thr Tyr Leu Tyr
1               5                   10                  15

<210> SEQ ID NO 284
<211> LENGTH: 7
<212> TYPE: PRT
<213> ORGANISM: Artificial Sequence
<220> FEATURE:
<223> OTHER INFORMATION: Synthetic Construct

<400> SEQUENCE: 284

Arg Met Ser Asn Leu Val Ser
1               5

<210> SEQ ID NO 285
<211> LENGTH: 9
<212> TYPE: PRT
<213> ORGANISM: Artificial Sequence
<220> FEATURE:
<223> OTHER INFORMATION: Synthetic Construct

<400> SEQUENCE: 285

Leu Gln His Leu Glu Tyr Pro Phe Thr
1               5

<210> SEQ ID NO 286
<211> LENGTH: 119
<212> TYPE: PRT
<213> ORGANISM: Artificial Sequence
<220> FEATURE:
<223> OTHER INFORMATION: Synthetic Construct

<400> SEQUENCE: 286

Gln Val Gln Leu Val Gln Ser Gly Ala Glu Val Lys Lys Pro Gly Glu
1               5                   10                  15

Thr Val Lys Ile Ser Cys Lys Ala Ser Asp Tyr Thr Phe Thr Tyr Tyr
            20                  25                  30

Gly Met Asn Trp Val Lys Gln Ala Pro Gly Gln Gly Leu Lys Trp Met
        35                  40                  45

```
Gly Trp Ile Asp Thr Thr Thr Gly Glu Pro Thr Tyr Ala Gln Lys Phe
    50                  55                  60

Gln Gly Arg Ile Ala Phe Ser Leu Glu Thr Ser Ala Ser Thr Ala Tyr
 65                 70                  75                  80

Leu Gln Ile Lys Ser Leu Lys Ser Glu Asp Thr Ala Thr Tyr Phe Cys
                 85                  90                  95

Ala Arg Arg Gly Pro Tyr Asn Trp Tyr Phe Asp Val Trp Gly Gln Gly
                100                 105                 110

Thr Thr Val Thr Val Ser Ser
            115

<210> SEQ ID NO 287
<211> LENGTH: 112
<212> TYPE: PRT
<213> ORGANISM: Artificial Sequence
<220> FEATURE:
<223> OTHER INFORMATION: Synthetic Construct

<400> SEQUENCE: 287

Asp Ile Val Met Thr Gln Ser Pro Leu Ser Val Pro Val Thr Pro Gly
 1               5                  10                  15

Glu Pro Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
             35                  40                  45

Pro Gln Leu Leu Ile Tyr Arg Met Ser Asn Leu Val Ser Gly Val Pro
     50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Leu Gln His
                 85                  90                  95

Leu Glu Tyr Pro Phe Thr Phe Gly Pro Gly Thr Lys Leu Glu Leu Lys
                100                 105                 110

<210> SEQ ID NO 288
<211> LENGTH: 5
<212> TYPE: PRT
<213> ORGANISM: Artificial Sequence
<220> FEATURE:
<223> OTHER INFORMATION: Synthetic Construct

<400> SEQUENCE: 288

Asn Tyr Gly Met Asn
 1               5

<210> SEQ ID NO 289
<211> LENGTH: 17
<212> TYPE: PRT
<213> ORGANISM: Artificial Sequence
<220> FEATURE:
<223> OTHER INFORMATION: Synthetic Construct

<400> SEQUENCE: 289

Trp Ile Asn Thr Tyr Thr Gly Glu Pro Thr Tyr Ala Asp Asp Phe Lys
 1               5                  10                  15

Gly

<210> SEQ ID NO 290
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 290

Ile Gly Asp Ser Ser Pro Ser Asp Tyr
1               5

<210> SEQ ID NO 291
<211> LENGTH: 11
<212> TYPE: PRT
<213> ORGANISM: Artificial Sequence
<220> FEATURE:
<223> OTHER INFORMATION: Synthetic Construct

<400> SEQUENCE: 291

Lys Ala Ser Gln Ser Val Ser Asn Asp Val Val
1               5                   10

<210> SEQ ID NO 292
<211> LENGTH: 7
<212> TYPE: PRT
<213> ORGANISM: Artificial Sequence
<220> FEATURE:
<223> OTHER INFORMATION: Synthetic Construct

<400> SEQUENCE: 292

Tyr Ala Ser Asn Arg Tyr Thr
1               5

<210> SEQ ID NO 293
<211> LENGTH: 9
<212> TYPE: PRT
<213> ORGANISM: Artificial Sequence
<220> FEATURE:
<223> OTHER INFORMATION: Synthetic Construct

<400> SEQUENCE: 293

Gln Gln Asp Tyr Thr Ser Pro Trp Thr
1               5

<210> SEQ ID NO 294
<211> LENGTH: 118
<212> TYPE: PRT
<213> ORGANISM: Artificial Sequence
<220> FEATURE:
<223> OTHER INFORMATION: Synthetic Construct

<400> SEQUENCE: 294

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ile Gly Asp Ser Ser Pro Ser Asp Tyr Trp Gly Gln Gly Thr
            100                 105                 110

Leu Val Thr Val Ser Ser
```

```
                         115
```

<210> SEQ ID NO 295
<211> LENGTH: 107
<212> TYPE: PRT
<213> ORGANISM: Artificial Sequence
<220> FEATURE:
<223> OTHER INFORMATION: Synthetic Construct

<400> SEQUENCE: 295

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Val Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Thr Ser Pro Trp
                85                  90                  95

Thr Phe Gly Gln Gly Thr Lys Leu Glu Ile Lys
            100                 105

<210> SEQ ID NO 296
<211> LENGTH: 5
<212> TYPE: PRT
<213> ORGANISM: Artificial Sequence
<220> FEATURE:
<223> OTHER INFORMATION: Synthetic Construct

<400> SEQUENCE: 296

Ser Tyr Trp Ile Glu
1               5

<210> SEQ ID NO 297
<211> LENGTH: 17
<212> TYPE: PRT
<213> ORGANISM: Artificial Sequence
<220> FEATURE:
<223> OTHER INFORMATION: Synthetic Construct

<400> SEQUENCE: 297

Glu Ile Leu Pro Gly Ser Gly Asn Thr Tyr Tyr Asn Glu Arg Phe Lys
1               5                   10                  15

Asp

<210> SEQ ID NO 298
<211> LENGTH: 14
<212> TYPE: PRT
<213> ORGANISM: Artificial Sequence
<220> FEATURE:
<223> OTHER INFORMATION: Synthetic Construct

<400> SEQUENCE: 298

Arg Ala Ala Ala Tyr Tyr Ser Asn Pro Glu Trp Phe Ala Tyr
1               5                   10

<210> SEQ ID NO 299
<211> LENGTH: 12
<212> TYPE: PRT
<213> ORGANISM: Artificial Sequence
<220> FEATURE:
<223> OTHER INFORMATION: Synthetic Construct

<400> SEQUENCE: 299

Thr Ala Ser Ser Val Asn Ser Phe Tyr Leu His
1               5                   10

<210> SEQ ID NO 300
<211> LENGTH: 7
<212> TYPE: PRT
<213> ORGANISM: Artificial Sequence
<220> FEATURE:
<223> OTHER INFORMATION: Synthetic Construct

<400> SEQUENCE: 300

Ser Thr Ser Asn Leu Ala Ser
1               5

<210> SEQ ID NO 301
<211> LENGTH: 9
<212> TYPE: PRT
<213> ORGANISM: Artificial Sequence
<220> FEATURE:
<223> OTHER INFORMATION: Synthetic Construct

<400> SEQUENCE: 301

His Gln Tyr His Arg Ser Pro Tyr Thr
1               5

<210> SEQ ID NO 302
<211> LENGTH: 123
<212> TYPE: PRT
<213> ORGANISM: Artificial Sequence
<220> FEATURE:
<223> OTHER INFORMATION: Synthetic Construct

<400> SEQUENCE: 302

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Trp Ile Glu Trp Val Arg Gln Ala Pro Gly Gln Gly Leu Glu Trp Met
            35                  40                  45

Gly Glu Ile Leu Pro Gly Ser Gly Asn Thr Tyr Tyr Asn Glu Arg Phe
        50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Ala Ala Tyr Tyr Ser Asn Pro Glu Trp Phe Ala Tyr
                100                 105                 110

Trp Gly Gln Gly Thr Leu Val Thr Val Ser Ser
            115                 120

<210> SEQ ID NO 303
<211> LENGTH: 108
<212> TYPE: PRT
<213> ORGANISM: Artificial Sequence
<220> FEATURE:
<223> OTHER INFORMATION: Synthetic Construct

<400> SEQUENCE: 303

Glu Ile Val Leu Thr Gln Ser Pro Ala Thr Leu Ser Leu Ser Pro Gly

```
                1               5                   10                  15
            Glu Arg Ala Thr Leu Ser Cys Thr Ala Ser Ser Ser Val Asn Ser Phe
                            20                  25                  30

Tyr Leu His Trp Tyr Gln Gln Lys Pro Gly Leu Ala Pro Arg Leu Leu
                        35                  40                  45

Ile Tyr Ser Thr Ser Asn Leu Ala Ser Gly Ile Pro Asp Arg Phe Ser
                    50                  55                  60

Gly Ser Gly Ser Gly Thr Asp Phe Thr Leu Thr Ile Ser Arg Leu Glu
             65                 70                  75                  80

Pro Glu Asp Phe Ala Val Tyr Tyr Cys His Gln Tyr His Arg Ser Pro
                            85                  90                  95

Tyr Thr Phe Gly Gln Gly Thr Lys Leu Glu Ile Lys
                        100                 105

<210> SEQ ID NO 304
<211> LENGTH: 5
<212> TYPE: PRT
<213> ORGANISM: Artificial Sequence
<220> FEATURE:
<223> OTHER INFORMATION: Synthetic Construct

<400> SEQUENCE: 304

Ser Tyr Trp Met Gln
1               5

<210> SEQ ID NO 305
<211> LENGTH: 17
<212> TYPE: PRT
<213> ORGANISM: Artificial Sequence
<220> FEATURE:
<223> OTHER INFORMATION: Synthetic Construct

<400> SEQUENCE: 305

Thr Ile Tyr Pro Gly Asp Gly Asp Thr Thr Tyr Thr Gln Lys Phe Gln
1               5                   10                  15

Gly

<210> SEQ ID NO 306
<211> LENGTH: 10
<212> TYPE: PRT
<213> ORGANISM: Artificial Sequence
<220> FEATURE:
<223> OTHER INFORMATION: Synthetic Construct

<400> SEQUENCE: 306

Tyr Asp Ala Pro Gly Tyr Ala Met Asp Tyr
1               5                   10

<210> SEQ ID NO 307
<211> LENGTH: 11
<212> TYPE: PRT
<213> ORGANISM: Artificial Sequence
<220> FEATURE:
<223> OTHER INFORMATION: Synthetic Construct

<400> SEQUENCE: 307

Arg Ala Ser Gln Asp Ile Asn Asn Tyr Leu Ala
1               5                   10

<210> SEQ ID NO 308
<211> LENGTH: 7
<212> TYPE: PRT
<213> ORGANISM: Artificial Sequence
```

<220> FEATURE:
<223> OTHER INFORMATION: Synthetic Construct

<400> SEQUENCE: 308

Tyr Thr Ser Thr Leu His Pro
1               5

<210> SEQ ID NO 309
<211> LENGTH: 9
<212> TYPE: PRT
<213> ORGANISM: Artificial Sequence
<220> FEATURE:
<223> OTHER INFORMATION: Synthetic Construct

<400> SEQUENCE: 309

Leu Gln Tyr Asp Asn Leu Leu Tyr Thr
1               5

<210> SEQ ID NO 310
<211> LENGTH: 119
<212> TYPE: PRT
<213> ORGANISM: Artificial Sequence
<220> FEATURE:
<223> OTHER INFORMATION: Synthetic Construct

<400> SEQUENCE: 310

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Tyr Thr Gln Lys Phe
    50                  55                  60

Gln Gly Lys Ala Thr Leu Thr Ala Asp Lys Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser
        115

<210> SEQ ID NO 311
<211> LENGTH: 107
<212> TYPE: PRT
<213> ORGANISM: Artificial Sequence
<220> FEATURE:
<223> OTHER INFORMATION: Synthetic Construct

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

```
Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105

<210> SEQ ID NO 312
<211> LENGTH: 6
<212> TYPE: PRT
<213> ORGANISM: Artificial Sequence
<220> FEATURE:
<223> OTHER INFORMATION: Synthetic Construct

<400> SEQUENCE: 312

Arg Asp Phe Ala Trp Asn
1               5

<210> SEQ ID NO 313
<211> LENGTH: 16
<212> TYPE: PRT
<213> ORGANISM: Artificial Sequence
<220> FEATURE:
<223> OTHER INFORMATION: Synthetic Construct

<400> SEQUENCE: 313

Tyr Ile Ser Tyr Asn Gly Asn Thr Arg Tyr Gln Pro Ser Leu Lys Ser
1               5                   10                  15

<210> SEQ ID NO 314
<211> LENGTH: 7
<212> TYPE: PRT
<213> ORGANISM: Artificial Sequence
<220> FEATURE:
<223> OTHER INFORMATION: Synthetic Construct

<400> SEQUENCE: 314

Ala Ser Arg Gly Phe Pro Tyr
1               5

<210> SEQ ID NO 315
<211> LENGTH: 11
<212> TYPE: PRT
<213> ORGANISM: Artificial Sequence
<220> FEATURE:
<223> OTHER INFORMATION: Synthetic Construct

<400> SEQUENCE: 315

His Ser Ser Gln Asp Ile Asn Ser Asn Ile Gly
1               5                   10

<210> SEQ ID NO 316
<211> LENGTH: 7
<212> TYPE: PRT
<213> ORGANISM: Artificial Sequence
<220> FEATURE:
<223> OTHER INFORMATION: Synthetic Construct

<400> SEQUENCE: 316

His Gly Thr Asn Leu Asp Asp
1               5

<210> SEQ ID NO 317
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 317

Val Gln Tyr Ala Gln Phe Pro Trp Thr
1               5

<210> SEQ ID NO 318
<211> LENGTH: 116
<212> TYPE: PRT
<213> ORGANISM: Artificial Sequence
<220> FEATURE:
<223> OTHER INFORMATION: Synthetic Construct

<400> SEQUENCE: 318

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Arg Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Asn Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Tyr Trp Gly Gln Gly Thr Leu Val
            100                 105                 110

Thr Val Ser Ser
        115

<210> SEQ ID NO 319
<211> LENGTH: 107
<212> TYPE: PRT
<213> ORGANISM: Artificial Sequence
<220> FEATURE:
<223> OTHER INFORMATION: Synthetic Construct

<400> SEQUENCE: 319

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 320
<211> LENGTH: 6
<212> TYPE: PRT
<213> ORGANISM: Artificial Sequence
<220> FEATURE:
<223> OTHER INFORMATION: Synthetic Construct

<400> SEQUENCE: 320

Arg Asp Phe Ala Trp Asn
1               5

<210> SEQ ID NO 321
<211> LENGTH: 16
<212> TYPE: PRT
<213> ORGANISM: Artificial Sequence
<220> FEATURE:
<223> OTHER INFORMATION: Synthetic Construct

<400> SEQUENCE: 321

Tyr Ile Ser Tyr Asn Gly Asn Thr Arg Tyr Gln Pro Ser Leu Lys Ser
1               5                   10                  15

<210> SEQ ID NO 322
<211> LENGTH: 7
<212> TYPE: PRT
<213> ORGANISM: Artificial Sequence
<220> FEATURE:
<223> OTHER INFORMATION: Synthetic Construct

<400> SEQUENCE: 322

Ala Ser Arg Gly Phe Pro Tyr
1               5

<210> SEQ ID NO 323
<211> LENGTH: 11
<212> TYPE: PRT
<213> ORGANISM: Artificial Sequence
<220> FEATURE:
<223> OTHER INFORMATION: Synthetic Construct

<400> SEQUENCE: 323

His Ser Ser Gln Asp Ile Asn Ser Asn Ile Gly
1               5                   10

<210> SEQ ID NO 324
<211> LENGTH: 7
<212> TYPE: PRT
<213> ORGANISM: Artificial Sequence
<220> FEATURE:
<223> OTHER INFORMATION: Synthetic Construct

<400> SEQUENCE: 324

His Gly Thr Asn Leu Asp Asp
1               5

<210> SEQ ID NO 325
<211> LENGTH: 9
<212> TYPE: PRT
<213> ORGANISM: Artificial Sequence
<220> FEATURE:
<223> OTHER INFORMATION: Synthetic Construct

<400> SEQUENCE: 325

Val Gln Tyr Ala Gln Phe Pro Trp Thr
1               5

<210> SEQ ID NO 326
<211> LENGTH: 116
<212> TYPE: PRT
<213> ORGANISM: Artificial Sequence
<220> FEATURE:
<223> OTHER INFORMATION: Synthetic Construct

<400> SEQUENCE: 326

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Arg Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Asn Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Ser Arg Gly Phe Pro Tyr Trp Gly Gln Gly Thr Leu Val
            100                 105                 110

Thr Val Ser Ser
            115

<210> SEQ ID NO 327
<211> LENGTH: 107
<212> TYPE: PRT
<213> ORGANISM: Artificial Sequence
<220> FEATURE:
<223> OTHER INFORMATION: Synthetic Construct

<400> SEQUENCE: 327

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 328
<211> LENGTH: 5
<212> TYPE: PRT
<213> ORGANISM: Artificial Sequence
<220> FEATURE:
<223> OTHER INFORMATION: Synthetic Construct

<400> SEQUENCE: 328

Asn Tyr Gly Val His
1               5

<210> SEQ ID NO 329
<211> LENGTH: 16
<212> TYPE: PRT
<213> ORGANISM: Artificial Sequence
<220> FEATURE:
<223> OTHER INFORMATION: Synthetic Construct

<400> SEQUENCE: 329

```
Val Ile Trp Ser Gly Gly Asn Thr Asp Tyr Asn Thr Pro Phe Thr Ser
1               5                   10                  15
```

<210> SEQ ID NO 330
<211> LENGTH: 11
<212> TYPE: PRT
<213> ORGANISM: Artificial Sequence
<220> FEATURE:
<223> OTHER INFORMATION: Synthetic Construct

<400> SEQUENCE: 330

```
Ala Leu Thr Tyr Tyr Asp Tyr Glu Phe Ala Tyr
1               5                   10
```

<210> SEQ ID NO 331
<211> LENGTH: 11
<212> TYPE: PRT
<213> ORGANISM: Artificial Sequence
<220> FEATURE:
<223> OTHER INFORMATION: Synthetic Construct

<400> SEQUENCE: 331

```
Arg Ala Ser Gln Ser Ile Gly Thr Asn Ile His
1               5                   10
```

<210> SEQ ID NO 332
<211> LENGTH: 7
<212> TYPE: PRT
<213> ORGANISM: Artificial Sequence
<220> FEATURE:
<223> OTHER INFORMATION: Synthetic Construct

<400> SEQUENCE: 332

```
Tyr Ala Ser Glu Ser Ile Ser
1               5
```

<210> SEQ ID NO 333
<211> LENGTH: 9
<212> TYPE: PRT
<213> ORGANISM: Artificial Sequence
<220> FEATURE:
<223> OTHER INFORMATION: Synthetic Construct

<400> SEQUENCE: 333

```
Gln Gln Asn Asn Asn Trp Pro Thr Thr
1               5
```

<210> SEQ ID NO 334
<211> LENGTH: 119
<212> TYPE: PRT
<213> ORGANISM: Artificial Sequence
<220> FEATURE:
<223> OTHER INFORMATION: Synthetic Construct

<400> SEQUENCE: 334

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80
```

```
Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 335
<211> LENGTH: 107
<212> TYPE: PRT
<213> ORGANISM: Artificial Sequence
<220> FEATURE:
<223> OTHER INFORMATION: Synthetic Construct

<400> SEQUENCE: 335

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 336
<211> LENGTH: 5
<212> TYPE: PRT
<213> ORGANISM: Artificial Sequence
<220> FEATURE:
<223> OTHER INFORMATION: Synthetic Construct

<400> SEQUENCE: 336

Gly Tyr Phe Met Asn
1               5

<210> SEQ ID NO 337
<211> LENGTH: 17
<212> TYPE: PRT
<213> ORGANISM: Artificial Sequence
<220> FEATURE:
<223> OTHER INFORMATION: Synthetic Construct

<400> SEQUENCE: 337

Arg Ile His Pro Tyr Asp Gly Asp Thr Phe Tyr Asn Gln Lys Phe Gln
1               5                   10                  15

Gly

<210> SEQ ID NO 338
<211> LENGTH: 9
<212> TYPE: PRT
<213> ORGANISM: Artificial Sequence
<220> FEATURE:
<223> OTHER INFORMATION: Synthetic Construct

<400> SEQUENCE: 338
```

```
Tyr Asp Gly Ser Arg Ala Met Asp Tyr
1               5
```

<210> SEQ ID NO 339
<211> LENGTH: 15
<212> TYPE: PRT
<213> ORGANISM: Artificial Sequence
<220> FEATURE:
<223> OTHER INFORMATION: Synthetic Construct

<400> SEQUENCE: 339

```
Lys Ala Ser Gln Ser Val Ser Phe Ala Gly Thr Ser Leu Met His
1               5                   10                  15
```

<210> SEQ ID NO 340
<211> LENGTH: 7
<212> TYPE: PRT
<213> ORGANISM: Artificial Sequence
<220> FEATURE:
<223> OTHER INFORMATION: Synthetic Construct

<400> SEQUENCE: 340

```
Arg Ala Ser Asn Leu Glu Ala
1               5
```

<210> SEQ ID NO 341
<211> LENGTH: 9
<212> TYPE: PRT
<213> ORGANISM: Artificial Sequence
<220> FEATURE:
<223> OTHER INFORMATION: Synthetic Construct

<400> SEQUENCE: 341

```
Gln Gln Ser Arg Glu Tyr Pro Tyr Thr
1               5
```

<210> SEQ ID NO 342
<211> LENGTH: 118
<212> TYPE: PRT
<213> ORGANISM: Artificial Sequence
<220> FEATURE:
<223> OTHER INFORMATION: Synthetic Construct

<400> SEQUENCE: 342

```
Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115
```

<210> SEQ ID NO 343
<211> LENGTH: 111

```
<212> TYPE: PRT
<213> ORGANISM: Artificial Sequence
<220> FEATURE:
<223> OTHER INFORMATION: Synthetic Construct

<400> SEQUENCE: 343

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys
            100                 105                 110

<210> SEQ ID NO 344
<211> LENGTH: 5
<212> TYPE: PRT
<213> ORGANISM: Artificial Sequence
<220> FEATURE:
<223> OTHER INFORMATION: Synthetic Construct

<400> SEQUENCE: 344

Gly Tyr Gly Leu Ser
1               5

<210> SEQ ID NO 345
<211> LENGTH: 17
<212> TYPE: PRT
<213> ORGANISM: Artificial Sequence
<220> FEATURE:
<223> OTHER INFORMATION: Synthetic Construct

<400> SEQUENCE: 345

Met Ile Ser Ser Gly Gly Ser Tyr Thr Tyr Tyr Ala Asp Ser Val Lys
1               5                   10                  15

Gly

<210> SEQ ID NO 346
<211> LENGTH: 10
<212> TYPE: PRT
<213> ORGANISM: Artificial Sequence
<220> FEATURE:
<223> OTHER INFORMATION: Synthetic Construct

<400> SEQUENCE: 346

His Gly Asp Asp Pro Ala Trp Phe Ala Tyr
1               5                   10

<210> SEQ ID NO 347
<211> LENGTH: 12
<212> TYPE: PRT
<213> ORGANISM: Artificial Sequence
<220> FEATURE:
<223> OTHER INFORMATION: Synthetic Construct

<400> SEQUENCE: 347
```

Ser Val Ser Ser Ser Ile Ser Ser Asn Asn Leu His
1               5                   10

<210> SEQ ID NO 348
<211> LENGTH: 7
<212> TYPE: PRT
<213> ORGANISM: Artificial Sequence
<220> FEATURE:
<223> OTHER INFORMATION: Synthetic Construct

<400> SEQUENCE: 348

Gly Thr Ser Asn Leu Ala Ser
1               5

<210> SEQ ID NO 349
<211> LENGTH: 11
<212> TYPE: PRT
<213> ORGANISM: Artificial Sequence
<220> FEATURE:
<223> OTHER INFORMATION: Synthetic Construct

<400> SEQUENCE: 349

Gln Gln Trp Ser Ser Tyr Pro Tyr Met Tyr Thr
1               5                   10

<210> SEQ ID NO 350
<211> LENGTH: 119
<212> TYPE: PRT
<213> ORGANISM: Artificial Sequence
<220> FEATURE:
<223> OTHER INFORMATION: Synthetic Construct

<400> SEQUENCE: 350

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
                20                  25                  30

Gly Leu Ser Trp Val Arg Gln Ala Pro Gly Lys Gly Leu Glu Trp Val
            35                  40                  45

Ala Met Ile Ser Ser Gly Gly Ser Tyr Thr Tyr Tyr Ala Asp Ser Val
        50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 351
<211> LENGTH: 110
<212> TYPE: PRT
<213> ORGANISM: Artificial Sequence
<220> FEATURE:
<223> OTHER INFORMATION: Synthetic Construct

<400> SEQUENCE: 351

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
                20                  25                  30

```
Asn Leu His Trp Tyr Gln Gln Lys Pro Gly Lys Ala Pro Lys Pro Trp
             35                  40                  45

Ile Tyr Gly Thr Ser Asn Leu Ala Ser Gly Val Pro Ser Arg Phe Ser
 50                  55                  60

Gly Ser Gly Ser Gly Thr Asp Tyr Thr Phe Thr Ile Ser Ser Leu Gln
 65                  70                  75                  80

Pro Glu Asp Ile Ala Thr Tyr Tyr Cys Gln Gln Trp Ser Ser Tyr Pro
                 85                  90                  95

Tyr Met Tyr Thr Phe Gly Gln Gly Thr Lys Val Glu Ile Lys
            100                 105                 110
```

<210> SEQ ID NO 352
<211> LENGTH: 5
<212> TYPE: PRT
<213> ORGANISM: Artificial Sequence
<220> FEATURE:
<223> OTHER INFORMATION: Synthetic Construct

<400> SEQUENCE: 352

```
Asn Tyr Trp Met Asn
 1               5
```

<210> SEQ ID NO 353
<211> LENGTH: 19
<212> TYPE: PRT
<213> ORGANISM: Artificial Sequence
<220> FEATURE:
<223> OTHER INFORMATION: Synthetic Construct

<400> SEQUENCE: 353

```
Glu Ile Arg Leu Lys Ser Asn Asn Tyr Thr Thr His Tyr Ala Glu Ser
 1               5                  10                  15

Val Lys Gly
```

<210> SEQ ID NO 354
<211> LENGTH: 6
<212> TYPE: PRT
<213> ORGANISM: Artificial Sequence
<220> FEATURE:
<223> OTHER INFORMATION: Synthetic Construct

<400> SEQUENCE: 354

```
His Tyr Tyr Phe Asp Tyr
 1               5
```

<210> SEQ ID NO 355
<211> LENGTH: 16
<212> TYPE: PRT
<213> ORGANISM: Artificial Sequence
<220> FEATURE:
<223> OTHER INFORMATION: Synthetic Construct

<400> SEQUENCE: 355

```
Arg Ser Ser Lys Ser Leu Leu His Ser Asn Gly Ile Thr Tyr Phe Phe
 1               5                  10                  15
```

<210> SEQ ID NO 356
<211> LENGTH: 7
<212> TYPE: PRT
<213> ORGANISM: Artificial Sequence
<220> FEATURE:
<223> OTHER INFORMATION: Synthetic Construct

<400> SEQUENCE: 356

Gln Met Ser Asn Leu Ala Ser
1               5

<210> SEQ ID NO 357
<211> LENGTH: 9
<212> TYPE: PRT
<213> ORGANISM: Artificial Sequence
<220> FEATURE:
<223> OTHER INFORMATION: Synthetic Construct

<400> SEQUENCE: 357

Ala Gln Asn Leu Glu Leu Pro Pro Thr
1               5

<210> SEQ ID NO 358
<211> LENGTH: 117
<212> TYPE: PRT
<213> ORGANISM: Artificial Sequence
<220> FEATURE:
<223> OTHER INFORMATION: Synthetic Construct

<400> SEQUENCE: 358

Glu Val Gln Leu Val Glu Ser Gly Gly Gly Leu Val Gln Pro Gly Gly
1               5                   10                  15

Ser Met Arg Leu Ser Cys Val Ala Ser Gly Phe Pro Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
        115

<210> SEQ ID NO 359
<211> LENGTH: 112
<212> TYPE: PRT
<213> ORGANISM: Artificial Sequence
<220> FEATURE:
<223> OTHER INFORMATION: Synthetic Construct

<400> SEQUENCE: 359

Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gln Gly Thr Lys Val Glu Ile Lys

<210> SEQ ID NO 360
<211> LENGTH: 5
<212> TYPE: PRT
<213> ORGANISM: Artificial Sequence
<220> FEATURE:
<223> OTHER INFORMATION: Synthetic Construct

<400> SEQUENCE: 360

Ser Tyr Trp Ile Gly
1               5

<210> SEQ ID NO 361
<211> LENGTH: 17
<212> TYPE: PRT
<213> ORGANISM: Artificial Sequence
<220> FEATURE:
<223> OTHER INFORMATION: Synthetic Construct

<400> SEQUENCE: 361

Ile Ile Asp Pro Gly Asp Ser Arg Thr Arg Tyr Ser Pro Ser Phe Gln
1               5                   10                  15

Gly

<210> SEQ ID NO 362
<211> LENGTH: 11
<212> TYPE: PRT
<213> ORGANISM: Artificial Sequence
<220> FEATURE:
<223> OTHER INFORMATION: Synthetic Construct

<400> SEQUENCE: 362

Gly Gln Leu Tyr Gly Gly Thr Tyr Met Asp Gly
1               5                   10

<210> SEQ ID NO 363
<211> LENGTH: 14
<212> TYPE: PRT
<213> ORGANISM: Artificial Sequence
<220> FEATURE:
<223> OTHER INFORMATION: Synthetic Construct

<400> SEQUENCE: 363

Thr Gly Thr Ser Ser Asp Ile Gly Gly Tyr Asn Ser Val Ser
1               5                   10

<210> SEQ ID NO 364
<211> LENGTH: 7
<212> TYPE: PRT
<213> ORGANISM: Artificial Sequence
<220> FEATURE:
<223> OTHER INFORMATION: Synthetic Construct

<400> SEQUENCE: 364

Gly Val Asn Asn Arg Pro Ser
1               5

<210> SEQ ID NO 365
<211> LENGTH: 11
<212> TYPE: PRT
<213> ORGANISM: Artificial Sequence
<220> FEATURE:
<223> OTHER INFORMATION: Synthetic Construct

<400> SEQUENCE: 365

```
Ser Ser Tyr Asp Ile Glu Ser Ala Thr Pro Val
1               5                   10
```

<210> SEQ ID NO 366
<211> LENGTH: 120
<212> TYPE: PRT
<213> ORGANISM: Artificial Sequence
<220> FEATURE:
<223> OTHER INFORMATION: Synthetic Construct

<400> SEQUENCE: 366

```
Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Ala Pro Gly Lys Gly Leu Glu Trp Met
            35                  40                  45

Gly Ile Ile Asp Pro Gly Asp Ser Arg Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gln Leu Tyr Gly Gly Thr Tyr Met Asp Gly Trp Gly Gln
                100                 105                 110

Gly Thr Leu Val Thr Val Ser Ser
            115                 120
```

<210> SEQ ID NO 367
<211> LENGTH: 111
<212> TYPE: PRT
<213> ORGANISM: Artificial Sequence
<220> FEATURE:
<223> OTHER INFORMATION: Synthetic Construct

<400> SEQUENCE: 367

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
                20                  25                  30

Asn Ser Val Ser Trp Tyr Gln Gln His Pro Gly Lys Ala Pro Lys Leu
            35                  40                  45

Met Ile Tyr Gly Val Asn Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Ile Glu
                85                  90                  95

Ser Ala Thr Pro Val Phe Gly Gly Gly Thr Lys Leu Thr Val Leu
                100                 105                 110
```

<210> SEQ ID NO 368
<211> LENGTH: 5
<212> TYPE: PRT
<213> ORGANISM: Artificial Sequence
<220> FEATURE:
<223> OTHER INFORMATION: Synthetic Construct

<400> SEQUENCE: 368

Ala Tyr Asn Ile His

```
<210> SEQ ID NO 369
<211> LENGTH: 17
<212> TYPE: PRT
<213> ORGANISM: Artificial Sequence
<220> FEATURE:
<223> OTHER INFORMATION: Synthetic Construct

<400> SEQUENCE: 369

Ser Phe Asp Pro Tyr Asp Gly Gly Ser Ser Tyr Asn Gln Lys Phe Lys
1               5                   10                  15

Asp

<210> SEQ ID NO 370
<211> LENGTH: 7
<212> TYPE: PRT
<213> ORGANISM: Artificial Sequence
<220> FEATURE:
<223> OTHER INFORMATION: Synthetic Construct

<400> SEQUENCE: 370

Gly Trp Tyr Tyr Phe Asp Tyr
1               5

<210> SEQ ID NO 371
<211> LENGTH: 11
<212> TYPE: PRT
<213> ORGANISM: Artificial Sequence
<220> FEATURE:
<223> OTHER INFORMATION: Synthetic Construct

<400> SEQUENCE: 371

Arg Ala Ser Lys Ser Ile Ser Lys Tyr Leu Ala
1               5                   10

<210> SEQ ID NO 372
<211> LENGTH: 7
<212> TYPE: PRT
<213> ORGANISM: Artificial Sequence
<220> FEATURE:
<223> OTHER INFORMATION: Synthetic Construct

<400> SEQUENCE: 372

Ser Gly Ser Thr Leu Gln Ser
1               5

<210> SEQ ID NO 373
<211> LENGTH: 9
<212> TYPE: PRT
<213> ORGANISM: Artificial Sequence
<220> FEATURE:
<223> OTHER INFORMATION: Synthetic Construct

<400> SEQUENCE: 373

Gln Gln His Asp Glu Ser Pro Tyr Thr
1               5

<210> SEQ ID NO 374
<211> LENGTH: 116
<212> TYPE: PRT
<213> ORGANISM: Artificial Sequence
<220> FEATURE:
<223> OTHER INFORMATION: Synthetic Construct

<400> SEQUENCE: 374
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Ser Ser Tyr Asn Gln Lys Phe
50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
            85                  90                  95

Ala Arg Gly Trp Tyr Tyr Phe Asp Tyr Trp Gly His Gly Thr Leu Val
            100                 105                 110

Thr Val Ser Ser
            115

<210> SEQ ID NO 375
<211> LENGTH: 107
<212> TYPE: PRT
<213> ORGANISM: Artificial Sequence
<220> FEATURE:
<223> OTHER INFORMATION: Synthetic Construct

<400> SEQUENCE: 375

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
            35                  40                  45

Tyr Ser Gly Ser Thr Leu Gln Ser Gly Ile Pro Pro Arg Phe Ser Gly
50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
            85                  90                  95

Thr Phe Gly Glu Gly Thr Lys Val Glu Ile Lys
            100                 105

<210> SEQ ID NO 376
<211> LENGTH: 11
<212> TYPE: PRT
<213> ORGANISM: Artificial Sequence
<220> FEATURE:
<223> OTHER INFORMATION: Synthetic Construct

<400> SEQUENCE: 376

Gly Ser Ile Lys Ser Gly Ser Tyr Tyr Trp Gly
1               5                   10

<210> SEQ ID NO 377
<211> LENGTH: 16
<212> TYPE: PRT
<213> ORGANISM: Artificial Sequence
<220> FEATURE:
<223> OTHER INFORMATION: Synthetic Construct

<400> SEQUENCE: 377

Asn Ile Tyr Tyr Ser Gly Ser Thr Tyr Tyr Asn Pro Ser Leu Arg Ser

<210> SEQ ID NO 378
<211> LENGTH: 12
<212> TYPE: PRT
<213> ORGANISM: Artificial Sequence
<220> FEATURE:
<223> OTHER INFORMATION: Synthetic Construct

<400> SEQUENCE: 378

Ala Arg Glu Gly Ser Tyr Pro Asn Gln Phe Asp Pro
1               5                   10

<210> SEQ ID NO 379
<211> LENGTH: 11
<212> TYPE: PRT
<213> ORGANISM: Artificial Sequence
<220> FEATURE:
<223> OTHER INFORMATION: Synthetic Construct

<400> SEQUENCE: 379

Arg Ala Ser Gln Ser Val Ser Ser Asn Leu Ala
1               5                   10

<210> SEQ ID NO 380
<211> LENGTH: 7
<212> TYPE: PRT
<213> ORGANISM: Artificial Sequence
<220> FEATURE:
<223> OTHER INFORMATION: Synthetic Construct

<400> SEQUENCE: 380

Gly Ala Ser Thr Arg Ala Thr
1               5

<210> SEQ ID NO 381
<211> LENGTH: 9
<212> TYPE: PRT
<213> ORGANISM: Artificial Sequence
<220> FEATURE:
<223> OTHER INFORMATION: Synthetic Construct

<400> SEQUENCE: 381

Gln Gln Tyr His Ser Phe Pro Phe Thr
1               5

<210> SEQ ID NO 382
<211> LENGTH: 120
<212> TYPE: PRT
<213> ORGANISM: Artificial Sequence
<220> FEATURE:
<223> OTHER INFORMATION: Synthetic Construct

<400> SEQUENCE: 382

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
                20                  25                  30

Ser Tyr Tyr Trp Gly Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Pro Ser
        50                  55                  60

Leu Arg Ser Arg Val Thr Ile Ser Val Asp Thr Ser Lys Asn Gln Phe
65                  70                  75                  80

```
Ser Leu Lys Leu Ser Ser Val Thr Ala Ala Asp Thr Ala Val Tyr Tyr
            85                  90                  95

Cys Ala Arg Glu Gly Ser Tyr Pro Asn Gln Phe Asp Pro Trp Gly Gln
            100                 105                 110

Gly Thr Leu Val Thr Val Ser Ser
        115                 120

<210> SEQ ID NO 383
<211> LENGTH: 107
<212> TYPE: PRT
<213> ORGANISM: Artificial Sequence
<220> FEATURE:
<223> OTHER INFORMATION: Synthetic Construct

<400> SEQUENCE: 383

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys
            100                 105

<210> SEQ ID NO 384
<211> LENGTH: 5
<212> TYPE: PRT
<213> ORGANISM: Artificial Sequence
<220> FEATURE:
<223> OTHER INFORMATION: Synthetic Construct

<400> SEQUENCE: 384

Ser Phe Gly Met His
1               5

<210> SEQ ID NO 385
<211> LENGTH: 11
<212> TYPE: PRT
<213> ORGANISM: Artificial Sequence
<220> FEATURE:
<223> OTHER INFORMATION: Synthetic Construct

<400> SEQUENCE: 385

Tyr Ile Ser Ser Asp Ser Ser Ala Ile Tyr Tyr
1               5                   10

<210> SEQ ID NO 386
<211> LENGTH: 12
<212> TYPE: PRT
<213> ORGANISM: Artificial Sequence
<220> FEATURE:
<223> OTHER INFORMATION: Synthetic Construct

<400> SEQUENCE: 386

Gly Arg Glu Asn Ile Tyr Tyr Gly Ser Arg Leu Asp
1               5                   10
```

<210> SEQ ID NO 387
<211> LENGTH: 7
<212> TYPE: PRT
<213> ORGANISM: Artificial Sequence
<220> FEATURE:
<223> OTHER INFORMATION: Synthetic Construct

<400> SEQUENCE: 387

Lys Ala Ser Gln Asn Val Asp
1               5

<210> SEQ ID NO 388
<211> LENGTH: 11
<212> TYPE: PRT
<213> ORGANISM: Artificial Sequence
<220> FEATURE:
<223> OTHER INFORMATION: Synthetic Construct

<400> SEQUENCE: 388

Ser Ala Ser Tyr Arg Tyr Ser Gly Val Pro Asp
1               5                   10

<210> SEQ ID NO 389
<211> LENGTH: 12
<212> TYPE: PRT
<213> ORGANISM: Artificial Sequence
<220> FEATURE:
<223> OTHER INFORMATION: Synthetic Construct

<400> SEQUENCE: 389

Gln Gln Tyr Asn Asn Tyr Pro Phe Thr Phe Gly Ser
1               5                   10

<210> SEQ ID NO 390
<211> LENGTH: 122
<212> TYPE: PRT
<213> ORGANISM: Artificial Sequence
<220> FEATURE:
<223> OTHER INFORMATION: Synthetic Construct

<400> SEQUENCE: 390

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
        115                 120

<210> SEQ ID NO 391
<211> LENGTH: 107
<212> TYPE: PRT
<213> ORGANISM: Artificial Sequence
<220> FEATURE:

<223> OTHER INFORMATION: Synthetic Construct

<400> SEQUENCE: 391

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys
            100                 105

<210> SEQ ID NO 392
<211> LENGTH: 10
<212> TYPE: PRT
<213> ORGANISM: Artificial Sequence
<220> FEATURE:
<223> OTHER INFORMATION: Synthetic Construct

<400> SEQUENCE: 392

Ser Tyr Trp Met Gln Trp Val Arg Gln Ala
1               5                   10

<210> SEQ ID NO 393
<211> LENGTH: 11
<212> TYPE: PRT
<213> ORGANISM: Artificial Sequence
<220> FEATURE:
<223> OTHER INFORMATION: Synthetic Construct

<400> SEQUENCE: 393

Thr Ile Tyr Pro Gly Asp Gly Asp Thr Arg Tyr
1               5                   10

<210> SEQ ID NO 394
<211> LENGTH: 12
<212> TYPE: PRT
<213> ORGANISM: Artificial Sequence
<220> FEATURE:
<223> OTHER INFORMATION: Synthetic Construct

<400> SEQUENCE: 394

Arg Gly Ile Pro Arg Leu Trp Tyr Phe Asp Val Met
1               5                   10

<210> SEQ ID NO 395
<211> LENGTH: 10
<212> TYPE: PRT
<213> ORGANISM: Artificial Sequence
<220> FEATURE:
<223> OTHER INFORMATION: Synthetic Construct

<400> SEQUENCE: 395

Ile Thr Cys Arg Ala Ser Gln Asp Ile Ser
1               5                   10

<210> SEQ ID NO 396

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 396

Tyr Thr Ser Arg Leu His Ser Gly Val Pro Ser
1               5                   10

<210> SEQ ID NO 397
<211> LENGTH: 12
<212> TYPE: PRT
<213> ORGANISM: Artificial Sequence
<220> FEATURE:
<223> OTHER INFORMATION: Synthetic Construct

<400> SEQUENCE: 397

Gln Gln Gly Asn Thr Leu Pro Pro Phe Thr Gly Gly
1               5                   10

<210> SEQ ID NO 398
<211> LENGTH: 122
<212> TYPE: PRT
<213> ORGANISM: Artificial Sequence
<220> FEATURE:
<223> OTHER INFORMATION: Synthetic Construct

<400> SEQUENCE: 398

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Asp Ser Ser Ala Ile Tyr Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
        115                 120

<210> SEQ ID NO 399
<211> LENGTH: 107
<212> TYPE: PRT
<213> ORGANISM: Artificial Sequence
<220> FEATURE:
<223> OTHER INFORMATION: Synthetic Construct

<400> SEQUENCE: 399

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60
```

```
Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys
            100                 105

<210> SEQ ID NO 400
<211> LENGTH: 10
<212> TYPE: PRT
<213> ORGANISM: Artificial Sequence
<220> FEATURE:
<223> OTHER INFORMATION: Synthetic Construct

<400> SEQUENCE: 400

Ser Tyr Gly Met Ser Trp Val Arg Gln Ala
1               5                   10

<210> SEQ ID NO 401
<211> LENGTH: 10
<212> TYPE: PRT
<213> ORGANISM: Artificial Sequence
<220> FEATURE:
<223> OTHER INFORMATION: Synthetic Construct

<400> SEQUENCE: 401

Ile Asn Ser Gly Gly Ser Asn Thr Tyr Tyr
1               5                   10

<210> SEQ ID NO 402
<211> LENGTH: 9
<212> TYPE: PRT
<213> ORGANISM: Artificial Sequence
<220> FEATURE:
<223> OTHER INFORMATION: Synthetic Construct

<400> SEQUENCE: 402

His Asp Gly Gly Ala Met Asp Tyr Trp
1               5

<210> SEQ ID NO 403
<211> LENGTH: 14
<212> TYPE: PRT
<213> ORGANISM: Artificial Sequence
<220> FEATURE:
<223> OTHER INFORMATION: Synthetic Construct

<400> SEQUENCE: 403

Ile Thr Cys Arg Ala Ser Glu Ser Ile Tyr Ser Tyr Leu Ala
1               5                   10

<210> SEQ ID NO 404
<211> LENGTH: 7
<212> TYPE: PRT
<213> ORGANISM: Artificial Sequence
<220> FEATURE:
<223> OTHER INFORMATION: Synthetic Construct

<400> SEQUENCE: 404

Asn Thr Lys Thr Leu Pro Glu
1               5

<210> SEQ ID NO 405
<211> LENGTH: 11
<212> TYPE: PRT
```

<213> ORGANISM: Artificial Sequence
<220> FEATURE:
<223> OTHER INFORMATION: Synthetic Construct

<400> SEQUENCE: 405

```
His His Tyr Gly Thr Pro Pro Trp Thr Phe Gly
1               5                   10
```

<210> SEQ ID NO 406
<211> LENGTH: 117
<212> TYPE: PRT
<213> ORGANISM: Artificial Sequence
<220> FEATURE:
<223> OTHER INFORMATION: Synthetic Construct

<400> SEQUENCE: 406

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Asp Gly Gly Ala Met Asp Tyr Trp Gly Gln Gly Thr Thr
            100                 105                 110

Val Thr Val Ser Ser
        115
```

<210> SEQ ID NO 407
<211> LENGTH: 108
<212> TYPE: PRT
<213> ORGANISM: Artificial Sequence
<220> FEATURE:
<223> OTHER INFORMATION: Synthetic Construct

<400> SEQUENCE: 407

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Thr Lys Thr Leu Pro Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Pro
                85                  90                  95

Trp Thr Phe Gly Gln Gly Thr Arg Leu Glu Ile Lys
            100                 105
```

<210> SEQ ID NO 408
<211> LENGTH: 10
<212> TYPE: PRT
<213> ORGANISM: Artificial Sequence

```
<220> FEATURE:
<223> OTHER INFORMATION: Synthetic Construct

<400> SEQUENCE: 408

Ser Phe Gly Met His Trp Val Arg Gln Ala
1               5                   10

<210> SEQ ID NO 409
<211> LENGTH: 20
<212> TYPE: PRT
<213> ORGANISM: Artificial Sequence
<220> FEATURE:
<223> OTHER INFORMATION: Synthetic Construct

<400> SEQUENCE: 409

Ile Ser Ser Gly Ser Gly Thr Ile Tyr Tyr Ala Asp Thr Val Lys Gly
1               5                   10                  15

Arg Phe Thr Ile
            20

<210> SEQ ID NO 410
<211> LENGTH: 12
<212> TYPE: PRT
<213> ORGANISM: Artificial Sequence
<220> FEATURE:
<223> OTHER INFORMATION: Synthetic Construct

<400> SEQUENCE: 410

His Gly Tyr Arg Tyr Glu Gly Phe Asp Tyr Trp Gly
1               5                   10

<210> SEQ ID NO 411
<211> LENGTH: 14
<212> TYPE: PRT
<213> ORGANISM: Artificial Sequence
<220> FEATURE:
<223> OTHER INFORMATION: Synthetic Construct

<400> SEQUENCE: 411

Ile Thr Cys Lys Ala Ser Gln Asn Val Asp Thr Asn Val Ala
1               5                   10

<210> SEQ ID NO 412
<211> LENGTH: 11
<212> TYPE: PRT
<213> ORGANISM: Artificial Sequence
<220> FEATURE:
<223> OTHER INFORMATION: Synthetic Construct

<400> SEQUENCE: 412

Ser Ala Ser Tyr Arg Tyr Ser Gly Val Pro Ser
1               5                   10

<210> SEQ ID NO 413
<211> LENGTH: 12
<212> TYPE: PRT
<213> ORGANISM: Artificial Sequence
<220> FEATURE:
<223> OTHER INFORMATION: Synthetic Construct

<400> SEQUENCE: 413

Gln Gln Tyr Asn Asn Tyr Pro Phe Thr Phe Gly Gln
1               5                   10

<210> SEQ ID NO 414
<211> LENGTH: 119
```

```
<212> TYPE: PRT
<213> ORGANISM: Artificial Sequence
<220> FEATURE:
<223> OTHER INFORMATION: Synthetic Construct

<400> SEQUENCE: 414

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Gly Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Gly Tyr Arg Tyr Glu Gly Phe Asp Tyr Trp Gly Gln Gly
            100                 105                 110

Thr Thr Val Thr Val Ser Ser
        115

<210> SEQ ID NO 415
<211> LENGTH: 107
<212> TYPE: PRT
<213> ORGANISM: Artificial Sequence
<220> FEATURE:
<223> OTHER INFORMATION: Synthetic Construct

<400> SEQUENCE: 415

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 416
<211> LENGTH: 5
<212> TYPE: PRT
<213> ORGANISM: Artificial Sequence
<220> FEATURE:
<223> OTHER INFORMATION: Synthetic Construct

<400> SEQUENCE: 416

Asn Tyr Val Met His
1               5

<210> SEQ ID NO 417
<211> LENGTH: 17
<212> TYPE: PRT
```

```
<213> ORGANISM: Artificial Sequence
<220> FEATURE:
<223> OTHER INFORMATION: Synthetic Construct

<400> SEQUENCE: 417

Tyr Ile Asn Pro Tyr Asn Asp Asp Val Lys Tyr Asn Glu Lys Phe Lys
1               5                   10                  15
Gly

<210> SEQ ID NO 418
<211> LENGTH: 13
<212> TYPE: PRT
<213> ORGANISM: Artificial Sequence
<220> FEATURE:
<223> OTHER INFORMATION: Synthetic Construct

<400> SEQUENCE: 418

Trp Gly Tyr Tyr Gly Ser Pro Leu Tyr Tyr Phe Asp Tyr
1               5                   10

<210> SEQ ID NO 419
<211> LENGTH: 10
<212> TYPE: PRT
<213> ORGANISM: Artificial Sequence
<220> FEATURE:
<223> OTHER INFORMATION: Synthetic Construct

<400> SEQUENCE: 419

Arg Ala Ser Ser Arg Leu Ile Tyr Met His
1               5                   10

<210> SEQ ID NO 420
<211> LENGTH: 7
<212> TYPE: PRT
<213> ORGANISM: Artificial Sequence
<220> FEATURE:
<223> OTHER INFORMATION: Synthetic Construct

<400> SEQUENCE: 420

Ala Thr Ser Asn Leu Ala Ser
1               5

<210> SEQ ID NO 421
<211> LENGTH: 9
<212> TYPE: PRT
<213> ORGANISM: Artificial Sequence
<220> FEATURE:
<223> OTHER INFORMATION: Synthetic Construct

<400> SEQUENCE: 421

Gln Gln Trp Asn Ser Asn Pro Pro Thr
1               5

<210> SEQ ID NO 422
<211> LENGTH: 122
<212> TYPE: PRT
<213> ORGANISM: Artificial Sequence
<220> FEATURE:
<223> OTHER INFORMATION: Synthetic Construct

<400> SEQUENCE: 422

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
                20                  25                  30
```

Val Met His Trp Val Lys Gln Lys Pro Gly Gln Gly Leu Glu Trp Ile
            35                  40                  45

Gly Tyr Ile Asn Pro Tyr Asn Asp Asp Val Lys Tyr Asn Glu Lys Phe
         50                  55                  60

Lys Gly Lys Ala Thr Gln Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Gly Tyr Tyr Gly Ser Pro Leu Tyr Tyr Phe Asp Tyr Trp
            100                 105                 110

Gly Gln Gly Thr Thr Leu Thr Val Ser Ser
            115                 120

<210> SEQ ID NO 423
<211> LENGTH: 106
<212> TYPE: PRT
<213> ORGANISM: Artificial Sequence
<220> FEATURE:
<223> OTHER INFORMATION: Synthetic Construct

<400> SEQUENCE: 423

Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Arg Leu Ile Tyr Met
            20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Asn Ser Asn Pro Pro Thr
                85                  90                  95

Phe Gly Thr Gly Thr Lys Leu Glu Leu Lys
            100                 105

<210> SEQ ID NO 424
<211> LENGTH: 5
<212> TYPE: PRT
<213> ORGANISM: Artificial Sequence
<220> FEATURE:
<223> OTHER INFORMATION: Synthetic Construct

<400> SEQUENCE: 424

Asn Tyr Val Met His
1               5

<210> SEQ ID NO 425
<211> LENGTH: 17
<212> TYPE: PRT
<213> ORGANISM: Artificial Sequence
<220> FEATURE:
<223> OTHER INFORMATION: Synthetic Construct

<400> SEQUENCE: 425

Tyr Ile Asn Pro Tyr Asn Asp Asp Val Lys Tyr Asn Glu Lys Phe Lys
1               5                   10                  15

Gly

<210> SEQ ID NO 426

```
<211> LENGTH: 13
<212> TYPE: PRT
<213> ORGANISM: Artificial Sequence
<220> FEATURE:
<223> OTHER INFORMATION: Synthetic Construct

<400> SEQUENCE: 426

Trp Gly Tyr Tyr Gly Ser Pro Leu Tyr Tyr Phe Asp Tyr
1               5                   10

<210> SEQ ID NO 427
<211> LENGTH: 10
<212> TYPE: PRT
<213> ORGANISM: Artificial Sequence
<220> FEATURE:
<223> OTHER INFORMATION: Synthetic Construct

<400> SEQUENCE: 427

Arg Ala Ser Ser Arg Leu Ile Tyr Met His
1               5                   10

<210> SEQ ID NO 428
<211> LENGTH: 7
<212> TYPE: PRT
<213> ORGANISM: Artificial Sequence
<220> FEATURE:
<223> OTHER INFORMATION: Synthetic Construct

<400> SEQUENCE: 428

Ala Thr Ser Asn Leu Ala Ser
1               5

<210> SEQ ID NO 429
<211> LENGTH: 9
<212> TYPE: PRT
<213> ORGANISM: Artificial Sequence
<220> FEATURE:
<223> OTHER INFORMATION: Synthetic Construct

<400> SEQUENCE: 429

Gln Gln Trp Asn Ser Asn Pro Pro Thr
1               5

<210> SEQ ID NO 430
<211> LENGTH: 122
<212> TYPE: PRT
<213> ORGANISM: Artificial Sequence
<220> FEATURE:
<223> OTHER INFORMATION: Synthetic Construct

<400> SEQUENCE: 430

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Asp Val Lys Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Tyr Tyr Gly Ser Pro Leu Tyr Tyr Phe Asp Tyr Trp
```

```
                    100                 105                 110
Gly Gln Gly Thr Leu Val Thr Val Ser Ser
            115                 120

<210> SEQ ID NO 431
<211> LENGTH: 106
<212> TYPE: PRT
<213> ORGANISM: Artificial Sequence
<220> FEATURE:
<223> OTHER INFORMATION: Synthetic Construct

<400> SEQUENCE: 431

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Arg Leu Ile Tyr Met
            20                  25                  30

His Trp Tyr Gln Gln Lys Pro Gly Gln Ala Pro Arg Pro Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Asn Ser Asn Pro Pro Thr
                85                  90                  95

Phe Gly Gln Gly Thr Lys Val Glu Ile Lys
            100                 105

<210> SEQ ID NO 432
<211> LENGTH: 10
<212> TYPE: PRT
<213> ORGANISM: Artificial Sequence
<220> FEATURE:
<223> OTHER INFORMATION: Synthetic Construct

<400> SEQUENCE: 432

Gly Tyr Ser Phe Thr Ser Tyr Thr Ile His
1               5                   10

<210> SEQ ID NO 433
<211> LENGTH: 17
<212> TYPE: PRT
<213> ORGANISM: Artificial Sequence
<220> FEATURE:
<223> OTHER INFORMATION: Synthetic Construct

<400> SEQUENCE: 433

Tyr Ile Asn Pro Asn Ser Arg Asn Thr Asp Tyr Ala Gln Lys Phe Gln
1               5                   10                  15

Gly

<210> SEQ ID NO 434
<211> LENGTH: 12
<212> TYPE: PRT
<213> ORGANISM: Artificial Sequence
<220> FEATURE:
<223> OTHER INFORMATION: Synthetic Construct

<400> SEQUENCE: 434

Tyr Ser Gly Ser Thr Pro Tyr Trp Tyr Phe Asp Val
1               5                   10

<210> SEQ ID NO 435
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 435

Arg Ala Ser Ser Ser Val Ser Tyr Met Asn
1               5                   10

<210> SEQ ID NO 436
<211> LENGTH: 7
<212> TYPE: PRT
<213> ORGANISM: Artificial Sequence
<220> FEATURE:
<223> OTHER INFORMATION: Synthetic Construct

<400> SEQUENCE: 436

Ala Thr Ser Asn Leu Ala Ser
1               5

<210> SEQ ID NO 437
<211> LENGTH: 9
<212> TYPE: PRT
<213> ORGANISM: Artificial Sequence
<220> FEATURE:
<223> OTHER INFORMATION: Synthetic Construct

<400> SEQUENCE: 437

Gln Gln Trp Ser Ser Asn Pro Leu Thr
1               5

<210> SEQ ID NO 438
<211> LENGTH: 121
<212> TYPE: PRT
<213> ORGANISM: Artificial Sequence
<220> FEATURE:
<223> OTHER INFORMATION: Synthetic Construct

<400> SEQUENCE: 438

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
                20                  25                  30

Thr Ile His Trp Val Arg Gln Ala Pro Gly Gln Gly Leu Glu Trp Met
            35                  40                  45

Gly Tyr Ile Asn Pro Asn Ser Arg Asn Thr Asp Tyr Ala Gln Lys Phe
        50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Ser Gly Ser Thr Pro Tyr Trp Tyr Phe Asp Val Trp Gly
                100                 105                 110

Gln Gly Thr Thr Val Thr Val Ser Ser
            115                 120

<210> SEQ ID NO 439
<211> LENGTH: 107
<212> TYPE: PRT
<213> ORGANISM: Artificial Sequence
<220> FEATURE:
<223> OTHER INFORMATION: Synthetic Construct
```

-continued

<400> SEQUENCE: 439

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Phe Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Trp Tyr Pro Phe
                85                  90                  95

Thr Phe Gly Gln Gly Thr Lys Leu Glu Ile Lys
            100                 105

<210> SEQ ID NO 440
<211> LENGTH: 10
<212> TYPE: PRT
<213> ORGANISM: Artificial Sequence
<220> FEATURE:
<223> OTHER INFORMATION: Synthetic Construct

<400> SEQUENCE: 440

Gly Tyr Thr Phe Ser Ser Tyr Trp Met His
1               5                   10

<210> SEQ ID NO 441
<211> LENGTH: 17
<212> TYPE: PRT
<213> ORGANISM: Artificial Sequence
<220> FEATURE:
<223> OTHER INFORMATION: Synthetic Construct

<400> SEQUENCE: 441

Leu Ile His Pro Asp Ser Gly Ser Thr Asn Tyr Asn Glu Met Phe Lys
1               5                   10                  15

Asn

<210> SEQ ID NO 442
<211> LENGTH: 7
<212> TYPE: PRT
<213> ORGANISM: Artificial Sequence
<220> FEATURE:
<223> OTHER INFORMATION: Synthetic Construct

<400> SEQUENCE: 442

Gly Gly Arg Leu Tyr Phe Asp
1               5

<210> SEQ ID NO 443
<211> LENGTH: 16
<212> TYPE: PRT
<213> ORGANISM: Artificial Sequence
<220> FEATURE:
<223> OTHER INFORMATION: Synthetic Construct

<400> SEQUENCE: 443

Arg Ser Ser Gln Ser Leu Val His Ser Asn Gly Asp Thr Tyr Leu Arg
1               5                   10                  15

<210> SEQ ID NO 444

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 444

Lys Val Ser Asn Arg Phe Ser
1               5

<210> SEQ ID NO 445
<211> LENGTH: 9
<212> TYPE: PRT
<213> ORGANISM: Artificial Sequence
<220> FEATURE:
<223> OTHER INFORMATION: Synthetic Construct

<400> SEQUENCE: 445

Ser Gln Ser Thr His Val Pro Tyr Thr
1               5

<210> SEQ ID NO 446
<211> LENGTH: 117
<212> TYPE: PRT
<213> ORGANISM: Artificial Sequence
<220> FEATURE:
<223> OTHER INFORMATION: Synthetic Construct

<400> SEQUENCE: 446

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Trp Met His Trp Val Arg Gln Ala Pro Gly Gln Gly Leu Glu Trp Ile
            35                  40                  45

Gly Leu Ile His Pro Asp Ser Gly Ser Thr Asn Tyr Asn Glu Met Phe
        50                  55                  60

Lys Asn Arg Ala Thr Leu Thr Val Asp Arg Ser Thr Ser Thr Ala Tyr
65                  70                  75                  80

Val Glu Leu Ser Ser Leu Arg Ser Glu Asp Thr Ala Val Tyr Phe Cys
                85                  90                  95

Ala Gly Gly Gly Arg Leu Tyr Phe Asp Tyr Trp Gly Gln Gly Thr Thr
            100                 105                 110

Val Thr Val Ser Ser
        115

<210> SEQ ID NO 447
<211> LENGTH: 112
<212> TYPE: PRT
<213> ORGANISM: Artificial Sequence
<220> FEATURE:
<223> OTHER INFORMATION: Synthetic Construct

<400> SEQUENCE: 447

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asp Thr Tyr Leu Arg Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Tyr Thr Phe Gly Gly Gly Thr Lys Val Glu Ile Lys
            100                 105                 110

<210> SEQ ID NO 448
<211> LENGTH: 10
<212> TYPE: PRT
<213> ORGANISM: Artificial Sequence
<220> FEATURE:
<223> OTHER INFORMATION: Synthetic Construct

<400> SEQUENCE: 448

Gly Tyr Thr Phe Ser Ser Tyr Trp Met His
 1               5                   10

<210> SEQ ID NO 449
<211> LENGTH: 17
<212> TYPE: PRT
<213> ORGANISM: Artificial Sequence
<220> FEATURE:
<223> OTHER INFORMATION: Synthetic Construct

<400> SEQUENCE: 449

Leu Ile His Pro Glu Ser Gly Ser Thr Asn Tyr Asn Glu Met Phe Lys
 1               5                   10                  15

Asn

<210> SEQ ID NO 450
<211> LENGTH: 8
<212> TYPE: PRT
<213> ORGANISM: Artificial Sequence
<220> FEATURE:
<223> OTHER INFORMATION: Synthetic Construct

<400> SEQUENCE: 450

Gly Gly Arg Leu Tyr Phe Asp Tyr
 1               5

<210> SEQ ID NO 451
<211> LENGTH: 16
<212> TYPE: PRT
<213> ORGANISM: Artificial Sequence
<220> FEATURE:
<223> OTHER INFORMATION: Synthetic Construct

<400> SEQUENCE: 451

Arg Ser Ser Gln Ser Leu Val His Ser Asn Gln Asp Thr Tyr Leu Arg
 1               5                   10                  15

<210> SEQ ID NO 452
<211> LENGTH: 7
<212> TYPE: PRT
<213> ORGANISM: Artificial Sequence
<220> FEATURE:
<223> OTHER INFORMATION: Synthetic Construct

<400> SEQUENCE: 452

Lys Val Ser Asn Arg Phe Ser
 1               5

<210> SEQ ID NO 453
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 453

Ser Gln Ser Thr His Val Pro Tyr Thr
1               5

<210> SEQ ID NO 454
<211> LENGTH: 117
<212> TYPE: PRT
<213> ORGANISM: Artificial Sequence
<220> FEATURE:
<223> OTHER INFORMATION: Synthetic Construct

<400> SEQUENCE: 454

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Trp Met His Trp Val Arg Gln Ala Pro Gly Gln Gly Leu Glu Trp Ile
            35                  40                  45

Gly Leu Ile His Pro Glu Ser Gly Ser Thr Asn Tyr Asn Glu Met Phe
        50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
                100                 105                 110

Val Thr Val Ser Ser
            115

<210> SEQ ID NO 455
<211> LENGTH: 113
<212> TYPE: PRT
<213> ORGANISM: Artificial Sequence
<220> FEATURE:
<223> OTHER INFORMATION: Synthetic Construct

<400> SEQUENCE: 455

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gln Asp Thr Tyr Leu Arg Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Lys
65                  70                  75                  80

Ile Ser Arg Val Glu Ala Glu Asp Val Gly Val Tyr Tyr Cys Ser Gln
                85                  90                  95

Ser Thr His Val Pro Tyr Thr Phe Gly Gly Gly Thr Lys Val Glu Ile
                100                 105                 110

Lys
```

```
<210> SEQ ID NO 456
<211> LENGTH: 12
<212> TYPE: PRT
<213> ORGANISM: Artificial Sequence
<220> FEATURE:
<223> OTHER INFORMATION: Synthetic Construct

<400> SEQUENCE: 456

Thr Gly Tyr Ser Ile Thr Ser Gly Tyr Ser Trp His
1               5                   10

<210> SEQ ID NO 457
<211> LENGTH: 16
<212> TYPE: PRT
<213> ORGANISM: Artificial Sequence
<220> FEATURE:
<223> OTHER INFORMATION: Synthetic Construct

<400> SEQUENCE: 457

Tyr Ile His Ser Ser Gly Ser Thr Asn Tyr Asn Pro Ser Leu Lys Ser
1               5                   10                  15

<210> SEQ ID NO 458
<211> LENGTH: 7
<212> TYPE: PRT
<213> ORGANISM: Artificial Sequence
<220> FEATURE:
<223> OTHER INFORMATION: Synthetic Construct

<400> SEQUENCE: 458

Tyr Asp Asp Tyr Phe Glu Tyr
1               5

<210> SEQ ID NO 459
<211> LENGTH: 12
<212> TYPE: PRT
<213> ORGANISM: Artificial Sequence
<220> FEATURE:
<223> OTHER INFORMATION: Synthetic Construct

<400> SEQUENCE: 459

Lys Ala Ser Gln Asn Val Gly Phe Asn Val Ala Trp
1               5                   10

<210> SEQ ID NO 460
<211> LENGTH: 7
<212> TYPE: PRT
<213> ORGANISM: Artificial Sequence
<220> FEATURE:
<223> OTHER INFORMATION: Synthetic Construct

<400> SEQUENCE: 460

Ser Ala Ser Tyr Arg Tyr Ser
1               5

<210> SEQ ID NO 461
<211> LENGTH: 9
<212> TYPE: PRT
<213> ORGANISM: Artificial Sequence
<220> FEATURE:
<223> OTHER INFORMATION: Synthetic Construct

<400> SEQUENCE: 461

Gln Gln Tyr Asn Trp Tyr Pro Phe Thr
1               5

<210> SEQ ID NO 462
```

```
<211> LENGTH: 116
<212> TYPE: PRT
<213> ORGANISM: Artificial Sequence
<220> FEATURE:
<223> OTHER INFORMATION: Synthetic Construct

<400> SEQUENCE: 462

Glu Val Gln Leu Gln Glu Ser Gly Pro Gly Leu Val Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Met Gly Tyr Ile His Ser Ser Gly Ser Thr Asn Tyr Asn Pro Ser Leu
    50                  55                  60

Lys Ser Arg Ile Ser Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Gly Tyr Asp Asp Tyr Phe Glu Tyr Trp Gly Gln Gly Thr Thr Val
            100                 105                 110

Thr Val Ser Ser
        115

<210> SEQ ID NO 463
<211> LENGTH: 108
<212> TYPE: PRT
<213> ORGANISM: Artificial Sequence
<220> FEATURE:
<223> OTHER INFORMATION: Synthetic Construct

<400> SEQUENCE: 463

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Gly Phe
            20                  25                  30

Asn Val Ala Trp Tyr Gln Gln Lys Pro Gly Lys Ser Pro Lys Ala Leu
        35                  40                  45

Ile Tyr Ser Ala Ser Tyr Arg Tyr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Glu Tyr Phe Cys Gln Gln Tyr Asn Trp Tyr Pro
                85                  90                  95

Phe Thr Phe Gly Gln Gly Thr Lys Leu Glu Ile Lys
            100                 105

<210> SEQ ID NO 464
<211> LENGTH: 5
<212> TYPE: PRT
<213> ORGANISM: Artificial Sequence
<220> FEATURE:
<223> OTHER INFORMATION: Synthetic Construct

<400> SEQUENCE: 464

Asn Tyr Asp Ile Asn
1               5

<210> SEQ ID NO 465
<211> LENGTH: 20
```

```
<212> TYPE: PRT
<213> ORGANISM: Artificial Sequence
<220> FEATURE:
<223> OTHER INFORMATION: Synthetic Construct

<400> SEQUENCE: 465

Trp Ile Gly Trp Ile Phe Pro Gly Asp Asp Ser Thr Gln Tyr Asn Glu
1               5                   10                  15

Lys Phe Lys Gly
            20

<210> SEQ ID NO 466
<211> LENGTH: 9
<212> TYPE: PRT
<213> ORGANISM: Artificial Sequence
<220> FEATURE:
<223> OTHER INFORMATION: Synthetic Construct

<400> SEQUENCE: 466

Gln Thr Thr Gly Thr Trp Phe Ala Tyr
1               5

<210> SEQ ID NO 467
<211> LENGTH: 11
<212> TYPE: PRT
<213> ORGANISM: Artificial Sequence
<220> FEATURE:
<223> OTHER INFORMATION: Synthetic Construct

<400> SEQUENCE: 467

Arg Ala Ser Gln Ser Ile Ser Asp Tyr Leu Tyr
1               5                   10

<210> SEQ ID NO 468
<211> LENGTH: 7
<212> TYPE: PRT
<213> ORGANISM: Artificial Sequence
<220> FEATURE:
<223> OTHER INFORMATION: Synthetic Construct

<400> SEQUENCE: 468

Tyr Ala Ser Gln Ser Ile Ser
1               5

<210> SEQ ID NO 469
<211> LENGTH: 9
<212> TYPE: PRT
<213> ORGANISM: Artificial Sequence
<220> FEATURE:
<223> OTHER INFORMATION: Synthetic Construct

<400> SEQUENCE: 469

Cys Gln Asn Gly His Ser Phe Pro Leu
1               5

<210> SEQ ID NO 470
<211> LENGTH: 118
<212> TYPE: PRT
<213> ORGANISM: Artificial Sequence
<220> FEATURE:
<223> OTHER INFORMATION: Synthetic Construct

<400> SEQUENCE: 470

Gln Val Gln Leu Val Gln Ser Gly Ala Glu Val Val Lys Pro Gly Ala
1               5                   10                  15

Ser Val Lys Leu Ser Cys Lys Thr Ser Gly Tyr Thr Phe Thr Asn Tyr
```

```
                20                  25                  30
Asp Ile Asn Trp Val Arg Gln Arg Pro Gly Gln Gly Leu Glu Trp Ile
            35                  40                  45
Gly Trp Ile Phe Pro Gly Asp Asp Ser Thr Gln Tyr Asn Glu Lys Phe
        50                  55                  60
Lys Gly Lys Ala Thr Leu Thr Thr Asp Thr Ser Thr Ser Thr Ala Tyr
 65                  70                  75                  80
Met Glu Leu Ser Ser Leu Arg Ser Glu Asp Thr Ala Val Tyr Phe Cys
                85                  90                  95
Ala Arg Gln Thr Thr Gly Thr Trp Phe Ala Tyr Trp Gly Gln Gly Thr
                100                 105                 110
Leu Val Thr Val Ser Ser
            115

<210> SEQ ID NO 471
<211> LENGTH: 107
<212> TYPE: PRT
<213> ORGANISM: Artificial Sequence
<220> FEATURE:
<223> OTHER INFORMATION: Synthetic Construct

<400> SEQUENCE: 471

Glu Ile Val Met Thr Gln Ser Pro Ala Thr Leu Ser Val Ser Pro Gly
 1               5                  10                  15
Glu Arg Val Thr Leu Ser Cys Arg Ala Ser Gln Ser Ile Ser Asp Tyr
                20                  25                  30
Leu Tyr Trp Tyr Gln Gln Lys Ser His Glu Ser Pro Arg Leu Leu Ile
            35                  40                  45
Lys Tyr Ala Ser Gln Ser Ile Ser Gly Ile Pro Ala Arg Phe Ser Gly
        50                  55                  60
Ser Gly Ser Gly Ser Glu Phe Thr Leu Thr Ile Asn Ser Val Glu Pro
 65                  70                  75                  80
Glu Asp Val Gly Val Tyr Tyr Cys Gln Asn Gly His Ser Phe Pro Leu
                85                  90                  95
Thr Phe Gly Gln Gly Thr Lys Leu Glu Leu Lys
                100                 105

<210> SEQ ID NO 472
<211> LENGTH: 119
<212> TYPE: PRT
<213> ORGANISM: Artificial Sequence
<220> FEATURE:
<223> OTHER INFORMATION: Synthetic Construct

<400> SEQUENCE: 472

Gln Val Gln Leu Gln Gln Ser Gly Ala Glu Val Lys Lys Pro Gly Ser
 1               5                  10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Leu Gly Ile Ala Asn Tyr Ala Gln Lys Phe
        50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
```

Ala Arg Gly Gly Ser Gly Ser Tyr His Met Asp Val Trp Gly Lys Gly
            100                 105                 110

Thr Thr Val Thr Val Ser Ser
        115

<210> SEQ ID NO 473
<211> LENGTH: 109
<212> TYPE: PRT
<213> ORGANISM: Artificial Sequence
<220> FEATURE:
<223> OTHER INFORMATION: Synthetic Construct

<400> SEQUENCE: 473

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Arg Ile Thr Phe Gly Gln Gly Thr Arg Leu Glu Ile Lys
            100                 105

<210> SEQ ID NO 474
<211> LENGTH: 5
<212> TYPE: PRT
<213> ORGANISM: Artificial Sequence
<220> FEATURE:
<223> OTHER INFORMATION: Synthetic Construct

<400> SEQUENCE: 474

Ile Tyr Asn Val His
1               5

<210> SEQ ID NO 475
<211> LENGTH: 17
<212> TYPE: PRT
<213> ORGANISM: Artificial Sequence
<220> FEATURE:
<223> OTHER INFORMATION: Synthetic Construct

<400> SEQUENCE: 475

Thr Ile Phe Pro Gly Asn Gly Asp Thr Ser Tyr Asn Gln Lys Phe Lys
1               5                   10                  15

Asp

<210> SEQ ID NO 476
<211> LENGTH: 10
<212> TYPE: PRT
<213> ORGANISM: Artificial Sequence
<220> FEATURE:
<223> OTHER INFORMATION: Synthetic Construct

<400> SEQUENCE: 476

Trp Asp Asp Gly Asn Val Gly Phe Ala His
1               5                   10

```
<210> SEQ ID NO 477
<211> LENGTH: 11
<212> TYPE: PRT
<213> ORGANISM: Artificial Sequence
<220> FEATURE:
<223> OTHER INFORMATION: Synthetic Construct

<400> SEQUENCE: 477

Arg Ala Ser Glu Asn Ile Asn Asn Tyr Leu Thr
1               5                   10

<210> SEQ ID NO 478
<211> LENGTH: 7
<212> TYPE: PRT
<213> ORGANISM: Artificial Sequence
<220> FEATURE:
<223> OTHER INFORMATION: Synthetic Construct

<400> SEQUENCE: 478

His Ala Lys Thr Leu Ala Glu
1               5

<210> SEQ ID NO 479
<211> LENGTH: 9
<212> TYPE: PRT
<213> ORGANISM: Artificial Sequence
<220> FEATURE:
<223> OTHER INFORMATION: Synthetic Construct

<400> SEQUENCE: 479

Gln His His Tyr Gly Thr Pro Pro Thr
1               5

<210> SEQ ID NO 480
<211> LENGTH: 119
<212> TYPE: PRT
<213> ORGANISM: Artificial Sequence
<220> FEATURE:
<223> OTHER INFORMATION: Synthetic Construct

<400> SEQUENCE: 480

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ile Tyr
            20                  25                  30

Asn Val His Trp Ile Lys Gln Thr Pro Gly Gln Gly Leu Glu Trp Met
        35                  40                  45

Gly Thr Ile Phe Pro Gly Asn Gly Asp Thr Ser Tyr Asn Gln Lys Phe
    50                  55                  60

Lys Asp Lys Ala Thr Leu Thr Thr Asp Lys Ser Ser Lys Thr Ala Tyr
65                  70                  75                  80

Met Gln Leu Asn Ser Leu Thr Ser Glu Asp Ser Ala Val Tyr Tyr Cys
                85                  90                  95

Ala Arg Trp Asp Asp Gly Asn Val Gly Phe Ala His Trp Gly Gln Gly
                100                 105                 110

Thr Leu Val Thr Val Ser Ala
        115

<210> SEQ ID NO 481
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 481

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Asn Asn Tyr
            20                  25                  30

Leu Thr Trp Phe Gln Gln Lys Gln Gly Lys Ser Pro Gln Leu Leu Val
        35                  40                  45

Tyr His Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Pro
                85                  90                  95

Thr Phe Gly Gly Gly Thr Lys Leu Glu Ile Lys
            100                 105

<210> SEQ ID NO 482
<211> LENGTH: 119
<212> TYPE: PRT
<213> ORGANISM: Artificial Sequence
<220> FEATURE:
<223> OTHER INFORMATION: Synthetic Construct

<400> SEQUENCE: 482

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Asn Val His Trp Val Arg Gln Ala Pro Gly Gln Gly Leu Glu Trp Met
        35                  40                  45

Gly Thr Ile Phe Pro Gly Asn Gly Asp Thr Ser Tyr Asn Gln Lys Phe
    50                  55                  60

Lys Asp Lys Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Asp Gly Asn Val Gly Phe Ala His Trp Gly Gln Gly
            100                 105                 110

Thr Leu Val Thr Val Ser Ser
        115

<210> SEQ ID NO 483
<211> LENGTH: 107
<212> TYPE: PRT
<213> ORGANISM: Artificial Sequence
<220> FEATURE:
<223> OTHER INFORMATION: Synthetic Construct

<400> SEQUENCE: 483

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Asn Asn Tyr
            20                  25                  30

Leu Thr Trp Phe Gln Gln Lys Gln Gly Lys Ser Pro Gln Leu Leu Ile
        35                  40                  45

Tyr His Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Gly Thr Pro Pro
                85                  90                  95

Thr Phe Gly Gly Gly Thr Lys Val Glu Ile Lys
            100                 105

<210> SEQ ID NO 484
<211> LENGTH: 119
<212> TYPE: PRT
<213> ORGANISM: Artificial Sequence
<220> FEATURE:
<223> OTHER INFORMATION: Synthetic Construct

<400> SEQUENCE: 484

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
                20                  25                  30

Asn Val His Trp Ile Arg Gln Ala Pro Gly Gln Gly Leu Glu Trp Met
            35                  40                  45

Gly Thr Ile Phe Pro Gly Asn Gly Asp Thr Ser Tyr Asn Gln Lys Phe
        50                  55                  60

Lys Asp Arg Ala Thr Leu Thr Thr Asp Lys Ser Thr Lys Thr Ala Tyr
65                  70                  75                  80

Met Glu Leu Arg Ser Leu Arg Ser Asp Thr Ala Val Tyr Tyr Cys
                85                  90                  95

Ala Arg Trp Asp Asp Gly Asn Val Gly Phe Ala His Trp Gly Gln Gly
                100                 105                 110

Thr Leu Val Thr Val Ser Ser
        115

<210> SEQ ID NO 485
<211> LENGTH: 107
<212> TYPE: PRT
<213> ORGANISM: Artificial Sequence
<220> FEATURE:
<223> OTHER INFORMATION: Synthetic Construct

<400> SEQUENCE: 485

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Asn Asn Tyr
                20                  25                  30

Leu Thr Trp Phe Gln Gln Lys Pro Gly Lys Ala Pro Lys Leu Leu Val
            35                  40                  45

Tyr His Ala Lys Thr Leu Ala Glu Gly Val Pro Ser Arg Phe Ser Gly
        50                  55                  60

Ser Gly Ser Gly Thr Gln Phe Thr Leu Thr Ile Ser Ser Leu Gln Pro
65                  70                  75                  80

Glu Asp Phe Ala Thr Tyr Tyr Cys Gln His His Tyr Gly Thr Pro Pro
                85                  90                  95

Thr Phe Gly Gln Gly Thr Lys Leu Glu Ile Lys
            100                 105

<210> SEQ ID NO 486
<211> LENGTH: 447
<212> TYPE: PRT

<213> ORGANISM: Artificial Sequence
<220> FEATURE:
<223> OTHER INFORMATION: Synthetic Construct

<400> SEQUENCE: 486

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 487
<211> LENGTH: 220
<212> TYPE: PRT
<213> ORGANISM: Artificial Sequence
<220> FEATURE:
<223> OTHER INFORMATION: Synthetic Construct

<400> SEQUENCE: 487

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
                20                  25                  30

Ser Ser Asn Arg Asn Tyr Leu Ala Trp Tyr Gln Gln Asn Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 488
<211> LENGTH: 445
<212> TYPE: PRT
<213> ORGANISM: Artificial Sequence
<220> FEATURE:
<223> OTHER INFORMATION: Synthetic Construct

<400> SEQUENCE: 488

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
                20                  25                  30
```

-continued

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 489
<211> LENGTH: 217
<212> TYPE: PRT
<213> ORGANISM: Artificial Sequence
<220> FEATURE:
<223> OTHER INFORMATION: Synthetic Construct

<400> SEQUENCE: 489

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Ser Ile Phe Val Ile Phe Gly Gly Gly Thr Lys Val Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Val Ser Asp Phe
    130                 135                 140

Tyr Pro Gly Ala Val Thr Val Ala Trp Lys Ala Asp Gly Ser Pro Val
145                 150                 155                 160

Lys Val Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Arg Val Thr His Glu Gly Ser Thr Val Glu
        195                 200                 205

Lys Thr Val Ala Pro Ala Glu Cys Ser
    210                 215
```

<210> SEQ ID NO 490
<211> LENGTH: 447
<212> TYPE: PRT
<213> ORGANISM: Artificial Sequence
<220> FEATURE:
<223> OTHER INFORMATION: Synthetic Construct

<400> SEQUENCE: 490

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Gln Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Trp Gly Asp Glu Gly Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 491
<211> LENGTH: 214
<212> TYPE: PRT
<213> ORGANISM: Artificial Sequence
<220> FEATURE:
<223> OTHER INFORMATION: Synthetic Construct

<400> SEQUENCE: 491

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Phe Pro Thr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 492
<211> LENGTH: 449
<212> TYPE: PRT
<213> ORGANISM: Artificial Sequence
<220> FEATURE:
<223> OTHER INFORMATION: Synthetic Construct

<400> SEQUENCE: 492

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Ser
            20                  25                  30

Tyr Ile Ser Trp Val Arg Gln Ala Pro Gly Gln Gly Leu Glu Trp Met
        35                  40                  45

Gly Trp Ile Tyr Ala Gly Thr Gly Ser Pro Ser Tyr Asn Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg His Arg Asp Tyr Tyr Ser Asn Ser Leu Thr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 493
<211> LENGTH: 220
<212> TYPE: PRT
<213> ORGANISM: Artificial Sequence
<220> FEATURE:
<223> OTHER INFORMATION: Synthetic Construct

<400> SEQUENCE: 493

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr

```
              65                  70                  75                  80
Ile Ser Ser Leu Gln Ala Glu Asp Val Ala Val Tyr Tyr Cys Gln Ser
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 494
<211> LENGTH: 7
<212> TYPE: PRT
<213> ORGANISM: Artificial Sequence
<220> FEATURE:
<223> OTHER INFORMATION: Synthetic Construct

<400> SEQUENCE: 494

```
Thr Ser Asn Met Gly Val Gly
1               5
```

<210> SEQ ID NO 495
<211> LENGTH: 16
<212> TYPE: PRT
<213> ORGANISM: Artificial Sequence
<220> FEATURE:
<223> OTHER INFORMATION: Synthetic Construct

<400> SEQUENCE: 495

```
His Ile Trp Trp Asp Asp Asp Lys Tyr Tyr Ser Pro Ser Leu Lys Ser
1               5                  10                  15
```

<210> SEQ ID NO 496
<211> LENGTH: 10
<212> TYPE: PRT
<213> ORGANISM: Artificial Sequence
<220> FEATURE:
<223> OTHER INFORMATION: Synthetic Construct

<400> SEQUENCE: 496

```
Ser Asn Tyr Gly Tyr Ala Trp Phe Ala Tyr
1               5                  10
```

<210> SEQ ID NO 497
<211> LENGTH: 11
<212> TYPE: PRT
<213> ORGANISM: Artificial Sequence
<220> FEATURE:
<223> OTHER INFORMATION: Synthetic Construct

<400> SEQUENCE: 497

```
Lys Ala Ser Gln Asp Ile Tyr Pro Tyr Leu Asn
```

<210> SEQ ID NO 498
<211> LENGTH: 7
<212> TYPE: PRT
<213> ORGANISM: Artificial Sequence
<220> FEATURE:
<223> OTHER INFORMATION: Synthetic Construct

<400> SEQUENCE: 498

```
Arg Thr Asn Arg Leu Leu Asp
1               5
```

<210> SEQ ID NO 499
<211> LENGTH: 9
<212> TYPE: PRT
<213> ORGANISM: Artificial Sequence
<220> FEATURE:
<223> OTHER INFORMATION: Synthetic Construct

<400> SEQUENCE: 499

```
Leu Gln Tyr Asp Glu Phe Pro Leu Thr
1               5
```

<210> SEQ ID NO 500
<211> LENGTH: 120
<212> TYPE: PRT
<213> ORGANISM: Artificial Sequence
<220> FEATURE:
<223> OTHER INFORMATION: Synthetic Construct

<400> SEQUENCE: 500

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Asn Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Val Arg Ser Asn Tyr Gly Tyr Ala Trp Phe Ala Tyr Trp Gly Gln
            100                 105                 110

Gly Thr Leu Val Thr Val Ser Ser
        115                 120
```

<210> SEQ ID NO 501
<211> LENGTH: 107
<212> TYPE: PRT
<213> ORGANISM: Artificial Sequence
<220> FEATURE:
<223> OTHER INFORMATION: Synthetic Construct

<400> SEQUENCE: 501

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Pro Tyr
            20                  25                  30

Leu Asn Trp Phe Gln Gln Lys Pro Gly Lys Ala Pro Lys Thr Leu Ile
```

```
                35                  40                  45
Tyr Arg Thr Asn Arg Leu Leu Asp Gly Val Pro Ser Arg Phe Ser Gly
         50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Leu Gln Tyr Asp Glu Phe Pro Leu
                 85                  90                  95
Thr Phe Gly Ala Gly Thr Lys Leu Glu Ile Lys
            100                 105
```

<210> SEQ ID NO 502
<211> LENGTH: 5
<212> TYPE: PRT
<213> ORGANISM: Artificial Sequence
<220> FEATURE:
<223> OTHER INFORMATION: Synthetic Construct

<400> SEQUENCE: 502

```
Asp Tyr Ala Val His
1               5
```

<210> SEQ ID NO 503
<211> LENGTH: 17
<212> TYPE: PRT
<213> ORGANISM: Artificial Sequence
<220> FEATURE:
<223> OTHER INFORMATION: Synthetic Construct

<400> SEQUENCE: 503

```
Val Ile Ser Thr Tyr Asn Asp Tyr Thr Tyr Asn Asn Gln Asp Phe Lys
1               5                   10                  15
Gly
```

<210> SEQ ID NO 504
<211> LENGTH: 10
<212> TYPE: PRT
<213> ORGANISM: Artificial Sequence
<220> FEATURE:
<223> OTHER INFORMATION: Synthetic Construct

<400> SEQUENCE: 504

```
Gly Asn Ser Tyr Phe Tyr Ala Leu Asp Tyr
1               5                   10
```

<210> SEQ ID NO 505
<211> LENGTH: 15
<212> TYPE: PRT
<213> ORGANISM: Artificial Sequence
<220> FEATURE:
<223> OTHER INFORMATION: Synthetic Construct

<400> SEQUENCE: 505

```
Arg Ala Ser Glu Ser Val Asp Ser Tyr Gly Lys Ser Phe Met His
1               5                   10                  15
```

<210> SEQ ID NO 506
<211> LENGTH: 7
<212> TYPE: PRT
<213> ORGANISM: Artificial Sequence
<220> FEATURE:
<223> OTHER INFORMATION: Synthetic Construct

<400> SEQUENCE: 506

```
Arg Ala Ser Asn Leu Glu Ser
```

-continued

```
<210> SEQ ID NO 507
<211> LENGTH: 9
<212> TYPE: PRT
<213> ORGANISM: Artificial Sequence
<220> FEATURE:
<223> OTHER INFORMATION: Synthetic Construct

<400> SEQUENCE: 507

Gln Gln Ser Asn Glu Asp Pro Trp Thr
1               5

<210> SEQ ID NO 508
<211> LENGTH: 119
<212> TYPE: PRT
<213> ORGANISM: Artificial Sequence
<220> FEATURE:
<223> OTHER INFORMATION: Synthetic Construct

<400> SEQUENCE: 508

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Val His Trp Val Arg Gln Ala Pro Gly Lys Arg Leu Glu Trp Ile
        35                  40                  45

Gly Val Ile Ser Thr Tyr Asn Asp Tyr Thr Tyr Asn Asn Gln Asp Phe
    50                  55                  60

Lys Gly Arg Val Thr Met Thr Arg Asp Thr Ser Ala Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Asn Ser Tyr Phe Tyr Ala Leu Asp Tyr Trp Gly Gln Gly
            100                 105                 110

Thr Ser Val Thr Val Ser Ser
        115

<210> SEQ ID NO 509
<211> LENGTH: 111
<212> TYPE: PRT
<213> ORGANISM: Artificial Sequence
<220> FEATURE:
<223> OTHER INFORMATION: Synthetic Construct

<400> SEQUENCE: 509

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Ser Tyr
            20                  25                  30

Gly Lys Ser Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Glu Asp Pro Trp Thr Phe Gly Gly Gly Thr Lys Leu Glu Ile Lys
            100                 105                 110
```

```
<210> SEQ ID NO 510
<211> LENGTH: 5
<212> TYPE: PRT
<213> ORGANISM: Artificial Sequence
<220> FEATURE:
<223> OTHER INFORMATION: Synthetic Construct

<400> SEQUENCE: 510

Arg Tyr Trp Met Ser
1               5

<210> SEQ ID NO 511
<211> LENGTH: 17
<212> TYPE: PRT
<213> ORGANISM: Artificial Sequence
<220> FEATURE:
<223> OTHER INFORMATION: Synthetic Construct

<400> SEQUENCE: 511

Asp Leu Asn Pro Asp Ser Ser Ala Ile Asn Tyr Val Asp Ser Val Lys
1               5                   10                  15

Gly

<210> SEQ ID NO 512
<211> LENGTH: 11
<212> TYPE: PRT
<213> ORGANISM: Artificial Sequence
<220> FEATURE:
<223> OTHER INFORMATION: Synthetic Construct

<400> SEQUENCE: 512

Ile Thr Thr Leu Val Pro Tyr Thr Met Asp Phe
1               5                   10

<210> SEQ ID NO 513
<211> LENGTH: 11
<212> TYPE: PRT
<213> ORGANISM: Artificial Sequence
<220> FEATURE:
<223> OTHER INFORMATION: Synthetic Construct

<400> SEQUENCE: 513

Ile Thr Asn Thr Asp Ile Asp Asp Met Asn
1               5                   10

<210> SEQ ID NO 514
<211> LENGTH: 7
<212> TYPE: PRT
<213> ORGANISM: Artificial Sequence
<220> FEATURE:
<223> OTHER INFORMATION: Synthetic Construct

<400> SEQUENCE: 514

Glu Gly Asn Gly Leu Arg Pro
1               5

<210> SEQ ID NO 515
<211> LENGTH: 9
<212> TYPE: PRT
<213> ORGANISM: Artificial Sequence
<220> FEATURE:
<223> OTHER INFORMATION: Synthetic Construct

<400> SEQUENCE: 515

Leu Gln Ser Asp Asn Leu Pro Leu Thr
```

-continued

<210> SEQ ID NO 516
<211> LENGTH: 120
<212> TYPE: PRT
<213> ORGANISM: Artificial Sequence
<220> FEATURE:
<223> OTHER INFORMATION: Synthetic Construct

<400> SEQUENCE: 516

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Asp Leu Asn Pro Asp Ser Ser Ala Ile Asn Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Leu Ile Thr Thr Leu Val Pro Tyr Thr Met Asp Phe Trp Gly Gln
            100                 105                 110

Gly Thr Ser Val Thr Val Ser Ser
        115                 120

<210> SEQ ID NO 517
<211> LENGTH: 107
<212> TYPE: PRT
<213> ORGANISM: Artificial Sequence
<220> FEATURE:
<223> OTHER INFORMATION: Synthetic Construct

<400> SEQUENCE: 517

Glu Thr Thr Leu Thr Gln Ser Pro Ala Phe Met Ser Ala Thr Pro Gly
1               5                   10                  15

Asp Lys Val Asn Ile Ser Cys Ile Thr Asn Thr Asp Ile Asp Asp Asp
            20                  25                  30

Met Asn Trp Tyr Gln Gln Lys Pro Gly Glu Ala Ala Ile Leu Leu Ile
        35                  40                  45

Ser Glu Gly Asn Gly Leu Arg Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Ser Gly Thr Lys Leu Glu Ile Lys
            100                 105

<210> SEQ ID NO 518
<211> LENGTH: 5
<212> TYPE: PRT
<213> ORGANISM: Artificial Sequence
<220> FEATURE:
<223> OTHER INFORMATION: Synthetic Construct

<400> SEQUENCE: 518

Asp Tyr Tyr Met His
1               5

<210> SEQ ID NO 519
<211> LENGTH: 17
<212> TYPE: PRT
<213> ORGANISM: Artificial Sequence
<220> FEATURE:
<223> OTHER INFORMATION: Synthetic Construct

<400> SEQUENCE: 519

Trp Ile Asp Pro Glu Asn Gly Asp Thr Glu Tyr Gly Pro Lys Phe Gln
1               5                   10                  15
Gly

<210> SEQ ID NO 520
<211> LENGTH: 11
<212> TYPE: PRT
<213> ORGANISM: Artificial Sequence
<220> FEATURE:
<223> OTHER INFORMATION: Synthetic Construct

<400> SEQUENCE: 520

His Asn Ala His Tyr Gly Thr Trp Phe Ala Tyr
1               5                   10

<210> SEQ ID NO 521
<211> LENGTH: 16
<212> TYPE: PRT
<213> ORGANISM: Artificial Sequence
<220> FEATURE:
<223> OTHER INFORMATION: Synthetic Construct

<400> SEQUENCE: 521

Arg Ser Ser Gln Ser Leu Leu His Ser Ser Gly Asn Thr Tyr Leu Glu
1               5                   10                  15

<210> SEQ ID NO 522
<211> LENGTH: 7
<212> TYPE: PRT
<213> ORGANISM: Artificial Sequence
<220> FEATURE:
<223> OTHER INFORMATION: Synthetic Construct

<400> SEQUENCE: 522

Lys Ile Ser Thr Arg Phe Ser
1               5

<210> SEQ ID NO 523
<211> LENGTH: 9
<212> TYPE: PRT
<213> ORGANISM: Artificial Sequence
<220> FEATURE:
<223> OTHER INFORMATION: Synthetic Construct

<400> SEQUENCE: 523

Phe Gln Gly Ser His Val Pro Tyr Thr
1               5

<210> SEQ ID NO 524
<211> LENGTH: 120
<212> TYPE: PRT
<213> ORGANISM: Artificial Sequence
<220> FEATURE:
<223> OTHER INFORMATION: Synthetic Construct

<400> SEQUENCE: 524

Gln Val Gln Leu Val Gln Ser Gly Ala Glu Val Lys Lys Pro Gly Ala

```
                1               5                  10                 15
        Ser Val Lys Val Ser Cys Lys Ala Ser Gly Leu Thr Ile Glu Asp Tyr
                        20                  25                 30

Tyr Met His Trp Val Arg Gln Ala Pro Gly Gln Gly Leu Glu Trp Met
                    35                  40                 45

Gly Trp Ile Asp Pro Glu Asn Gly Asp Thr Glu Tyr Gly Pro Lys Phe
                50                  55                 60

Gln Gly Arg Val Thr Met Thr Arg Asp Thr Ser Ile Asn Thr Ala Tyr
        65                  70                  75                 80

Met Glu Leu Ser Arg Leu Arg Ser Asp Asp Thr Ala Val Tyr Tyr Cys
                        85                  90                 95

Ala Val His Asn Ala His Tyr Gly Thr Trp Phe Ala Tyr Trp Gly Gln
                        100                 105                110

Gly Thr Leu Val Thr Val Ser Ser
                    115                 120
```

<210> SEQ ID NO 525
<211> LENGTH: 112
<212> TYPE: PRT
<213> ORGANISM: Artificial Sequence
<220> FEATURE:
<223> OTHER INFORMATION: Synthetic Construct

<400> SEQUENCE: 525

```
        Asp Val Val Met Thr Gln Ser Pro Leu Ser Leu Pro Val Thr Leu Gly
        1               5                  10                 15

Gln Pro Ala Ser Ile Ser Cys Arg Ser Ser Gln Ser Leu Leu His Ser
                        20                  25                 30

Ser Gly Asn Thr Tyr Leu Glu Trp Tyr Gln Gln Arg Pro Gly Gln Ser
                    35                  40                 45

Pro Arg Pro Leu Ile Tyr Lys Ile Ser Thr Arg Phe Ser Gly Val Pro
                50                  55                 60

Asp Arg Phe Ser Gly Ser Gly Ser Gly Thr Asp Phe Thr Leu Lys Ile
        65                  70                  75                 80

Ser Arg Val Glu Ala Glu Asp Val Gly Val Tyr Tyr Cys Phe Gln Gly
                        85                  90                 95

Ser His Val Pro Tyr Thr Phe Gly Gly Gly Thr Lys Val Glu Ile Lys
                        100                 105                110
```

<210> SEQ ID NO 526
<211> LENGTH: 5
<212> TYPE: PRT
<213> ORGANISM: Artificial Sequence
<220> FEATURE:
<223> OTHER INFORMATION: Synthetic Construct

<400> SEQUENCE: 526

```
        Asp Tyr Asn Val Asn
        1               5
```

<210> SEQ ID NO 527
<211> LENGTH: 17
<212> TYPE: PRT
<213> ORGANISM: Artificial Sequence
<220> FEATURE:
<223> OTHER INFORMATION: Synthetic Construct

<400> SEQUENCE: 527

```
        Val Ile Asn Pro Lys Tyr Gly Thr Thr Arg Tyr Asn Gln Lys Phe Lys
        1               5                  10                 15
```

Gly

<210> SEQ ID NO 528
<211> LENGTH: 7
<212> TYPE: PRT
<213> ORGANISM: Artificial Sequence
<220> FEATURE:
<223> OTHER INFORMATION: Synthetic Construct

<400> SEQUENCE: 528

Gly Leu Asn Ala Trp Asp Tyr
1               5

<210> SEQ ID NO 529
<211> LENGTH: 11
<212> TYPE: PRT
<213> ORGANISM: Artificial Sequence
<220> FEATURE:
<223> OTHER INFORMATION: Synthetic Construct

<400> SEQUENCE: 529

Gly Ala Ser Glu Asn Ile Tyr Gly Ala Leu Asn
1               5                   10

<210> SEQ ID NO 530
<211> LENGTH: 7
<212> TYPE: PRT
<213> ORGANISM: Artificial Sequence
<220> FEATURE:
<223> OTHER INFORMATION: Synthetic Construct

<400> SEQUENCE: 530

Gly Ala Thr Asn Leu Glu Asp
1               5

<210> SEQ ID NO 531
<211> LENGTH: 9
<212> TYPE: PRT
<213> ORGANISM: Artificial Sequence
<220> FEATURE:
<223> OTHER INFORMATION: Synthetic Construct

<400> SEQUENCE: 531

Gln Asn Val Leu Thr Thr Pro Tyr Thr
1               5

<210> SEQ ID NO 532
<211> LENGTH: 116
<212> TYPE: PRT
<213> ORGANISM: Artificial Sequence
<220> FEATURE:
<223> OTHER INFORMATION: Synthetic Construct

<400> SEQUENCE: 532

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Asn Val Asn Trp Val Arg Gln Ala Pro Gly Gln Gly Leu Glu Trp Ile
            35                  40                  45

Gly Val Ile Asn Pro Lys Tyr Gly Thr Thr Arg Tyr Asn Gln Lys Phe
        50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser
        115

<210> SEQ ID NO 533
<211> LENGTH: 107
<212> TYPE: PRT
<213> ORGANISM: Artificial Sequence
<220> FEATURE:
<223> OTHER INFORMATION: Synthetic Construct

<400> SEQUENCE: 533

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Glu Asp Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 534
<211> LENGTH: 5
<212> TYPE: PRT
<213> ORGANISM: Artificial Sequence
<220> FEATURE:
<223> OTHER INFORMATION: Synthetic Construct

<400> SEQUENCE: 534

Gly Tyr Phe Met Asn
1               5

<210> SEQ ID NO 535
<211> LENGTH: 17
<212> TYPE: PRT
<213> ORGANISM: Artificial Sequence
<220> FEATURE:
<223> OTHER INFORMATION: Synthetic Construct

<400> SEQUENCE: 535

Leu Ile Asn Pro Tyr Asn Gly Asp Ser Phe Tyr Asn Gln Lys Phe Lys
1               5                   10                  15

Gly

<210> SEQ ID NO 536
<211> LENGTH: 8
<212> TYPE: PRT
<213> ORGANISM: Artificial Sequence
<220> FEATURE:
<223> OTHER INFORMATION: Synthetic Construct

<400> SEQUENCE: 536

```
Gly Leu Arg Arg Asp Phe Asp Tyr
1               5
```

<210> SEQ ID NO 537
<211> LENGTH: 16
<212> TYPE: PRT
<213> ORGANISM: Artificial Sequence
<220> FEATURE:
<223> OTHER INFORMATION: Synthetic Construct

<400> SEQUENCE: 537

```
Lys Ser Ser Gln Ser Leu Leu Asp Ser Asp Gly Lys Thr Tyr Leu Asn
1               5                   10                  15
```

<210> SEQ ID NO 538
<211> LENGTH: 7
<212> TYPE: PRT
<213> ORGANISM: Artificial Sequence
<220> FEATURE:
<223> OTHER INFORMATION: Synthetic Construct

<400> SEQUENCE: 538

```
Leu Val Ser Glu Leu Asp Ser
1               5
```

<210> SEQ ID NO 539
<211> LENGTH: 9
<212> TYPE: PRT
<213> ORGANISM: Artificial Sequence
<220> FEATURE:
<223> OTHER INFORMATION: Synthetic Construct

<400> SEQUENCE: 539

```
Trp Gln Gly Thr His Phe Pro Arg Thr
1               5
```

<210> SEQ ID NO 540
<211> LENGTH: 117
<212> TYPE: PRT
<213> ORGANISM: Artificial Sequence
<220> FEATURE:
<223> OTHER INFORMATION: Synthetic Construct

<400> SEQUENCE: 540

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
                20                  25                  30

Phe Met Asn Trp Val Arg Gln Ala Pro Gly Gln Gly Leu Glu Trp Met
            35                  40                  45

Gly Leu Ile Asn Pro Tyr Asn Gly Asp Ser Phe Tyr Asn Gln Lys Phe
        50                  55                  60

Lys Gly Arg Val Thr Met Thr Arg Gln Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Gly Leu Arg Arg Asp Phe Asp Tyr Trp Gly Gln Gly Thr Leu
            100                 105                 110

Val Thr Val Ser Ser
            115
```

<210> SEQ ID NO 541
<211> LENGTH: 112

<212> TYPE: PRT
<213> ORGANISM: Artificial Sequence
<220> FEATURE:
<223> OTHER INFORMATION: Synthetic Construct

<400> SEQUENCE: 541

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Phe Gln Arg Pro Gly Gln Ser
        35                  40                  45

Pro Arg Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Thr Lys Leu Glu Ile Lys
            100                 105                 110
```

<210> SEQ ID NO 542
<211> LENGTH: 5
<212> TYPE: PRT
<213> ORGANISM: Artificial Sequence
<220> FEATURE:
<223> OTHER INFORMATION: Synthetic Construct

<400> SEQUENCE: 542

```
Asp Phe Gly Met Asn
1               5
```

<210> SEQ ID NO 543
<211> LENGTH: 17
<212> TYPE: PRT
<213> ORGANISM: Artificial Sequence
<220> FEATURE:
<223> OTHER INFORMATION: Synthetic Construct

<400> SEQUENCE: 543

```
Trp Ile Asn Thr Phe Thr Gly Glu Pro Ser Tyr Gly Asn Val Phe Lys
1               5                   10                  15

Gly
```

<210> SEQ ID NO 544
<211> LENGTH: 10
<212> TYPE: PRT
<213> ORGANISM: Artificial Sequence
<220> FEATURE:
<223> OTHER INFORMATION: Synthetic Construct

<400> SEQUENCE: 544

```
Arg His Gly Asn Gly Asn Val Phe Asp Ser
1               5                   10
```

<210> SEQ ID NO 545
<211> LENGTH: 11
<212> TYPE: PRT
<213> ORGANISM: Artificial Sequence
<220> FEATURE:
<223> OTHER INFORMATION: Synthetic Construct

<400> SEQUENCE: 545

Arg Ala Ser Gln Ser Ile Gly Ser Asn Ile His
1               5                   10

<210> SEQ ID NO 546
<211> LENGTH: 7
<212> TYPE: PRT
<213> ORGANISM: Artificial Sequence
<220> FEATURE:
<223> OTHER INFORMATION: Synthetic Construct

<400> SEQUENCE: 546

Tyr Thr Ser Glu Ser Ile Ser
1               5

<210> SEQ ID NO 547
<211> LENGTH: 9
<212> TYPE: PRT
<213> ORGANISM: Artificial Sequence
<220> FEATURE:
<223> OTHER INFORMATION: Synthetic Construct

<400> SEQUENCE: 547

Gln Gln Ser Asn Ser Trp Pro Leu Thr
1               5

<210> SEQ ID NO 548
<211> LENGTH: 119
<212> TYPE: PRT
<213> ORGANISM: Artificial Sequence
<220> FEATURE:
<223> OTHER INFORMATION: Synthetic Construct

<400> SEQUENCE: 548

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Phe
                20                  25                  30

Gly Met Asn Trp Val Arg Gln Ala Pro Gly Gln Gly Leu Glu Trp Met
            35                  40                  45

Gly Trp Ile Asn Thr Phe Thr Gly Glu Pro Ser Tyr Gly Asn Val Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Arg His Gly Asn Gly Asn Val Phe Asp Ser Trp Gly Gln Gly
            100                 105                 110

Thr Leu Val Thr Val Ser Ser
        115

<210> SEQ ID NO 549
<211> LENGTH: 108
<212> TYPE: PRT
<213> ORGANISM: Artificial Sequence
<220> FEATURE:
<223> OTHER INFORMATION: Synthetic Construct

<400> SEQUENCE: 549

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Asn
                20                  25                  30

```
Ile His Trp Tyr Gln Gln Lys Pro Asp Gln Ser Pro Lys Leu Leu Ile
            35                  40                  45
Lys Tyr Thr Ser Glu Ser Ile Ser Gly Val Pro Ser Arg Phe Ser Gly
 50                  55                  60
Ser Gly Ser Gly Thr Asp Phe Thr Leu Thr Ile Asn Ser Leu Glu Ala
 65                  70                  75                  80
Glu Asp Ala Ala Thr Tyr Tyr Cys Gln Gln Ser Asn Ser Trp Pro Leu
                 85                  90                  95
Thr Phe Gly Gly Gly Thr Lys Val Glu Ile Lys Arg
            100                 105
```

<210> SEQ ID NO 550
<211> LENGTH: 5
<212> TYPE: PRT
<213> ORGANISM: Artificial Sequence
<220> FEATURE:
<223> OTHER INFORMATION: Synthetic Construct

<400> SEQUENCE: 550

```
Thr Ala Ala Ile Ser
1               5
```

<210> SEQ ID NO 551
<211> LENGTH: 17
<212> TYPE: PRT
<213> ORGANISM: Artificial Sequence
<220> FEATURE:
<223> OTHER INFORMATION: Synthetic Construct

<400> SEQUENCE: 551

```
Gly Ile Ile Pro Ile Phe Gly Lys Ala His Tyr Ala Gln Lys Phe Gln
1               5                   10                  15
Gly
```

<210> SEQ ID NO 552
<211> LENGTH: 14
<212> TYPE: PRT
<213> ORGANISM: Artificial Sequence
<220> FEATURE:
<223> OTHER INFORMATION: Synthetic Construct

<400> SEQUENCE: 552

```
Lys Phe His Phe Val Ser Gly Ser Pro Phe Gly Met Asp Val
1               5                   10
```

<210> SEQ ID NO 553
<211> LENGTH: 11
<212> TYPE: PRT
<213> ORGANISM: Artificial Sequence
<220> FEATURE:
<223> OTHER INFORMATION: Synthetic Construct

<400> SEQUENCE: 553

```
Arg Ala Ser Gln Ser Val Ser Ser Tyr Leu Ala
1               5                   10
```

<210> SEQ ID NO 554
<211> LENGTH: 7
<212> TYPE: PRT
<213> ORGANISM: Artificial Sequence
<220> FEATURE:
<223> OTHER INFORMATION: Synthetic Construct

<400> SEQUENCE: 554

```
Asp Ala Ser Asn Arg Ala Thr
1               5
```

<210> SEQ ID NO 555
<211> LENGTH: 8
<212> TYPE: PRT
<213> ORGANISM: Artificial Sequence
<220> FEATURE:
<223> OTHER INFORMATION: Synthetic Construct

<400> SEQUENCE: 555

```
Gln Gln Arg Ser Asn Trp Pro Thr
1               5
```

<210> SEQ ID NO 556
<211> LENGTH: 123
<212> TYPE: PRT
<213> ORGANISM: Artificial Sequence
<220> FEATURE:
<223> OTHER INFORMATION: Synthetic Construct

<400> SEQUENCE: 556

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Ala
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Lys Ala His Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120
```

<210> SEQ ID NO 557
<211> LENGTH: 106
<212> TYPE: PRT
<213> ORGANISM: Artificial Sequence
<220> FEATURE:
<223> OTHER INFORMATION: Synthetic Construct

<400> SEQUENCE: 557

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
```

-continued

<210> SEQ ID NO 558
<211> LENGTH: 5
<212> TYPE: PRT
<213> ORGANISM: Artificial Sequence
<220> FEATURE:
<223> OTHER INFORMATION: Synthetic Construct

<400> SEQUENCE: 558

Ser Tyr Ala Ile Ser
1               5

<210> SEQ ID NO 559
<211> LENGTH: 17
<212> TYPE: PRT
<213> ORGANISM: Artificial Sequence
<220> FEATURE:
<223> OTHER INFORMATION: Synthetic Construct

<400> SEQUENCE: 559

Gly Ile Ile Pro Ile Phe Gly Thr Ala Asn Tyr Ala Gln Lys Phe Gln
1               5                   10                  15

Gly

<210> SEQ ID NO 560
<211> LENGTH: 21
<212> TYPE: PRT
<213> ORGANISM: Artificial Sequence
<220> FEATURE:
<223> OTHER INFORMATION: Synthetic Construct

<400> SEQUENCE: 560

Ala Pro Leu Arg Phe Leu Glu Trp Ser Thr Gln Asp His Tyr Tyr Tyr
1               5                   10                  15

Tyr Tyr Met Asp Val
            20

<210> SEQ ID NO 561
<211> LENGTH: 11
<212> TYPE: PRT
<213> ORGANISM: Artificial Sequence
<220> FEATURE:
<223> OTHER INFORMATION: Synthetic Construct

<400> SEQUENCE: 561

Gln Gly Asp Ser Leu Arg Ser Tyr Tyr Ala Thr
1               5                   10

<210> SEQ ID NO 562
<211> LENGTH: 7
<212> TYPE: PRT
<213> ORGANISM: Artificial Sequence
<220> FEATURE:
<223> OTHER INFORMATION: Synthetic Construct

<400> SEQUENCE: 562

Gly Glu Asn Lys Arg Pro Ser
1               5

<210> SEQ ID NO 563
<211> LENGTH: 11
<212> TYPE: PRT
<213> ORGANISM: Artificial Sequence
<220> FEATURE:
<223> OTHER INFORMATION: Synthetic Construct

<400> SEQUENCE: 563

Lys Ser Arg Asp Gly Ser Gly Gln His Leu Val
1               5                   10

<210> SEQ ID NO 564
<211> LENGTH: 130
<212> TYPE: PRT
<213> ORGANISM: Artificial Sequence
<220> FEATURE:
<223> OTHER INFORMATION: Synthetic Construct

<400> SEQUENCE: 564

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser
    130

<210> SEQ ID NO 565
<211> LENGTH: 108
<212> TYPE: PRT
<213> ORGANISM: Artificial Sequence
<220> FEATURE:
<223> OTHER INFORMATION: Synthetic Construct

<400> SEQUENCE: 565

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu
            100                 105

<210> SEQ ID NO 566
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 566

Ser Tyr Trp Ile Asn
1               5

<210> SEQ ID NO 567
<211> LENGTH: 17
<212> TYPE: PRT
<213> ORGANISM: Artificial Sequence
<220> FEATURE:
<223> OTHER INFORMATION: Synthetic Construct

<400> SEQUENCE: 567

Asn Ile Tyr Pro Ser Asp Ser Tyr Thr Asn Tyr Asn Gln Lys Phe Lys
1               5                   10                  15

Asp

<210> SEQ ID NO 568
<211> LENGTH: 9
<212> TYPE: PRT
<213> ORGANISM: Artificial Sequence
<220> FEATURE:
<223> OTHER INFORMATION: Synthetic Construct

<400> SEQUENCE: 568

Ser Trp Arg Gly Asn Ser Phe Asp Tyr
1               5

<210> SEQ ID NO 569
<211> LENGTH: 17
<212> TYPE: PRT
<213> ORGANISM: Artificial Sequence
<220> FEATURE:
<223> OTHER INFORMATION: Synthetic Construct

<400> SEQUENCE: 569

Lys Ser Ser Gln Ser Leu Leu Asn Ser Gly Asn Gln Lys Asn Tyr Leu
1               5                   10                  15

Thr

<210> SEQ ID NO 570
<211> LENGTH: 7
<212> TYPE: PRT
<213> ORGANISM: Artificial Sequence
<220> FEATURE:
<223> OTHER INFORMATION: Synthetic Construct

<400> SEQUENCE: 570

Trp Ala Ser Thr Arg Glu Ser
1               5

<210> SEQ ID NO 571
<211> LENGTH: 9
<212> TYPE: PRT
<213> ORGANISM: Artificial Sequence
<220> FEATURE:
<223> OTHER INFORMATION: Synthetic Construct

<400> SEQUENCE: 571

Gln Asn Asp Tyr Ser Tyr Pro Phe Thr
1               5

<210> SEQ ID NO 572
```

```
<211> LENGTH: 118
<212> TYPE: PRT
<213> ORGANISM: Artificial Sequence
<220> FEATURE:
<223> OTHER INFORMATION: Synthetic Construct

<400> SEQUENCE: 572

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
                100                 105                 110

Thr Leu Thr Val Ser Ser
            115

<210> SEQ ID NO 573
<211> LENGTH: 113
<212> TYPE: PRT
<213> ORGANISM: Artificial Sequence
<220> FEATURE:
<223> OTHER INFORMATION: Synthetic Construct

<400> SEQUENCE: 573

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
                100                 105                 110

Lys

<210> SEQ ID NO 574
<211> LENGTH: 5
<212> TYPE: PRT
<213> ORGANISM: Artificial Sequence
<220> FEATURE:
<223> OTHER INFORMATION: Synthetic Construct

<400> SEQUENCE: 574

Asn Tyr Gly Met Asn
1               5
```

```
<210> SEQ ID NO 575
<211> LENGTH: 17
<212> TYPE: PRT
<213> ORGANISM: Artificial Sequence
<220> FEATURE:
<223> OTHER INFORMATION: Synthetic Construct

<400> SEQUENCE: 575

Trp Ile Asn Thr Asn Thr Gly Glu Pro Thr Tyr Ala Glu Glu Phe Lys
1               5                   10                  15

Gly

<210> SEQ ID NO 576
<211> LENGTH: 9
<212> TYPE: PRT
<213> ORGANISM: Artificial Sequence
<220> FEATURE:
<223> OTHER INFORMATION: Synthetic Construct

<400> SEQUENCE: 576

Leu Gly Phe Gly Asn Ala Met Asp Tyr
1               5

<210> SEQ ID NO 577
<211> LENGTH: 17
<212> TYPE: PRT
<213> ORGANISM: Artificial Sequence
<220> FEATURE:
<223> OTHER INFORMATION: Synthetic Construct

<400> SEQUENCE: 577

Lys Ser Ser Gln Ser Leu Leu Asn Ser Gly Asn Gln Lys Asn Tyr Leu
1               5                   10                  15

Thr

<210> SEQ ID NO 578
<211> LENGTH: 7
<212> TYPE: PRT
<213> ORGANISM: Artificial Sequence
<220> FEATURE:
<223> OTHER INFORMATION: Synthetic Construct

<400> SEQUENCE: 578

Trp Ala Ser Thr Arg Glu Ser
1               5

<210> SEQ ID NO 579
<211> LENGTH: 9
<212> TYPE: PRT
<213> ORGANISM: Artificial Sequence
<220> FEATURE:
<223> OTHER INFORMATION: Synthetic Construct

<400> SEQUENCE: 579

Gln Asn Asp Tyr Ser Tyr Pro Leu Thr
1               5

<210> SEQ ID NO 580
<211> LENGTH: 118
<212> TYPE: PRT
<213> ORGANISM: Artificial Sequence
<220> FEATURE:
<223> OTHER INFORMATION: Synthetic Construct

<400> SEQUENCE: 580

Gln Ile Gln Leu Val Gln Ser Gly Pro Glu Leu Lys Lys Pro Gly Glu
```

```
  1               5                  10                 15
Thr Val Lys Ile Ser Cys Lys Ala Ser Gly Tyr Thr Phe Thr Asn Tyr
                20                 25                 30
Gly Met Asn Trp Val Lys Gln Ala Pro Gly Lys Gly Leu Lys Trp Met
            35                 40                 45
Gly Trp Ile Asn Thr Asn Thr Gly Glu Pro Thr Tyr Ala Glu Glu Phe
        50                 55                 60
Lys Gly Arg Phe Ala Phe Ser Leu Glu Thr Ser Ala Ser Thr Ala Tyr
 65                 70                 75                 80
Leu Gln Ile Asn Asn Leu Lys Asn Glu Asp Thr Ala Thr Tyr Phe Cys
                85                 90                 95
Ala Arg Leu Gly Phe Gly Asn Ala Met Asp Tyr Trp Gly Gln Gly Thr
            100                105                110
Ser Val Thr Val Ser Ser
            115
```

<210> SEQ ID NO 581
<211> LENGTH: 113
<212> TYPE: PRT
<213> ORGANISM: Artificial Sequence
<220> FEATURE:
<223> OTHER INFORMATION: Synthetic Construct

<400> SEQUENCE: 581

```
Asp Ile Val Met Thr Gln Ser Pro Ser Ser Leu Thr Val Thr Ala Gly
 1               5                  10                 15
Glu Lys Val Thr Met Ser Cys Lys Ser Ser Gln Ser Leu Leu Asn Ser
                20                 25                 30
Gly Asn Gln Lys Asn Tyr Leu Thr Trp Tyr Gln Gln Lys Pro Gly Gln
            35                 40                 45
Pro Pro Lys Leu Leu Ile Tyr Trp Ala Ser Thr Arg Glu Ser Gly Val
        50                 55                 60
Pro Asp Arg Phe Thr Gly Ser Gly Ser Gly Thr Asp Phe Thr Leu Thr
 65                 70                 75                 80
Ile Ser Ser Val Gln Ala Glu Asp Leu Ala Val Tyr Tyr Cys Gln Asn
                85                 90                 95
Asp Tyr Ser Tyr Pro Leu Thr Phe Gly Ala Gly Thr Lys Leu Glu Leu
            100                105                110
Lys
```

<210> SEQ ID NO 582
<211> LENGTH: 5
<212> TYPE: PRT
<213> ORGANISM: Artificial Sequence
<220> FEATURE:
<223> OTHER INFORMATION: Synthetic Construct

<400> SEQUENCE: 582

```
Ser Tyr Asn Met Asn
 1               5
```

<210> SEQ ID NO 583
<211> LENGTH: 17
<212> TYPE: PRT
<213> ORGANISM: Artificial Sequence
<220> FEATURE:
<223> OTHER INFORMATION: Synthetic Construct

<400> SEQUENCE: 583

Tyr Ile Ser Ser Ser Ser Thr Ile Tyr Tyr Ala Asp Ser Val Lys
1               5                   10                  15

Gly

<210> SEQ ID NO 584
<211> LENGTH: 8
<212> TYPE: PRT
<213> ORGANISM: Artificial Sequence
<220> FEATURE:
<223> OTHER INFORMATION: Synthetic Construct

<400> SEQUENCE: 584

Ala Tyr Tyr Tyr Gly Met Asp Val
1               5

<210> SEQ ID NO 585
<211> LENGTH: 11
<212> TYPE: PRT
<213> ORGANISM: Artificial Sequence
<220> FEATURE:
<223> OTHER INFORMATION: Synthetic Construct

<400> SEQUENCE: 585

Arg Ala Ser Gln Gly Ile Ser Gly Trp Leu Ala
1               5                   10

<210> SEQ ID NO 586
<211> LENGTH: 7
<212> TYPE: PRT
<213> ORGANISM: Artificial Sequence
<220> FEATURE:
<223> OTHER INFORMATION: Synthetic Construct

<400> SEQUENCE: 586

Ala Ala Ser Thr Leu Gln Ser
1               5

<210> SEQ ID NO 587
<211> LENGTH: 9
<212> TYPE: PRT
<213> ORGANISM: Artificial Sequence
<220> FEATURE:
<223> OTHER INFORMATION: Synthetic Construct

<400> SEQUENCE: 587

Gln Gln Ala Asn Ser Phe Pro Pro Thr
1               5

<210> SEQ ID NO 588
<211> LENGTH: 117
<212> TYPE: PRT
<213> ORGANISM: Artificial Sequence
<220> FEATURE:
<223> OTHER INFORMATION: Synthetic Construct

<400> SEQUENCE: 588

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

```
Lys Gly Arg Phe Thr Ile Ser Arg Asp Asn Ala Lys Asn Ser Leu Ser
 65                  70                  75                  80

Leu Gln Met Asn Ser Leu Arg Asp Glu Asp Thr Ala Val Tyr Tyr Cys
                 85                  90                  95

Ala Arg Ala Tyr Tyr Tyr Gly Met Asp Val Trp Gly Gln Gly Thr Thr
            100                 105                 110

Val Thr Val Ser Ser
        115

<210> SEQ ID NO 589
<211> LENGTH: 107
<212> TYPE: PRT
<213> ORGANISM: Artificial Sequence
<220> FEATURE:
<223> OTHER INFORMATION: Synthetic Construct

<400> SEQUENCE: 589

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Gly Trp
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Pro
                 85                  90                  95

Thr Phe Gly Gly Gly Thr Lys Val Glu Ile Lys
            100                 105

<210> SEQ ID NO 590
<211> LENGTH: 5
<212> TYPE: PRT
<213> ORGANISM: Artificial Sequence
<220> FEATURE:
<223> OTHER INFORMATION: Synthetic Construct

<400> SEQUENCE: 590

Ser Tyr Gly Met His
 1               5

<210> SEQ ID NO 591
<211> LENGTH: 17
<212> TYPE: PRT
<213> ORGANISM: Artificial Sequence
<220> FEATURE:
<223> OTHER INFORMATION: Synthetic Construct

<400> SEQUENCE: 591

Val Ile Trp Tyr Asp Gly Ser Asn Gln Tyr Tyr Ala Asp Ser Val Lys
 1               5                  10                  15

Gly

<210> SEQ ID NO 592
<211> LENGTH: 11
<212> TYPE: PRT
<213> ORGANISM: Artificial Sequence
<220> FEATURE:
<223> OTHER INFORMATION: Synthetic Construct
```

```
<400> SEQUENCE: 592

Gly Leu Thr Ser Gly Arg Tyr Gly Met Asp Val
1               5                   10

<210> SEQ ID NO 593
<211> LENGTH: 16
<212> TYPE: PRT
<213> ORGANISM: Artificial Sequence
<220> FEATURE:
<223> OTHER INFORMATION: Synthetic Construct

<400> SEQUENCE: 593

Arg Ser Ser Gln Ser Leu Leu Ser His Gly Phe Asn Tyr Leu Asp
1               5                   10                  15

<210> SEQ ID NO 594
<211> LENGTH: 7
<212> TYPE: PRT
<213> ORGANISM: Artificial Sequence
<220> FEATURE:
<223> OTHER INFORMATION: Synthetic Construct

<400> SEQUENCE: 594

Leu Gly Ser Ser Arg Ala Ser
1               5

<210> SEQ ID NO 595
<211> LENGTH: 9
<212> TYPE: PRT
<213> ORGANISM: Artificial Sequence
<220> FEATURE:
<223> OTHER INFORMATION: Synthetic Construct

<400> SEQUENCE: 595

Met Gln Pro Leu Gln Ile Pro Trp Thr
1               5

<210> SEQ ID NO 596
<211> LENGTH: 120
<212> TYPE: PRT
<213> ORGANISM: Artificial Sequence
<220> FEATURE:
<223> OTHER INFORMATION: Synthetic Construct

<400> SEQUENCE: 596

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met His Ser Leu Arg Ala Glu Asp Thr Ala Val Tyr Tyr Cys
                85                  90                  95

Ala Arg Gly Leu Thr Ser Gly Arg Tyr Gly Met Asp Val Trp Gly Gln
            100                 105                 110

Gly Thr Thr Val Thr Val Ser Ser
        115                 120
```

```
<210> SEQ ID NO 597
<211> LENGTH: 112
<212> TYPE: PRT
<213> ORGANISM: Artificial Sequence
<220> FEATURE:
<223> OTHER INFORMATION: Synthetic Construct

<400> SEQUENCE: 597
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Leu Ser
            20                  25                  30

His Gly Phe Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Pro
                85                  90                  95

Leu Gln Ile Pro Trp Thr Phe Gly Gln Gly Thr Lys Val Glu Ile Lys
            100                 105                 110

```
<210> SEQ ID NO 598
<211> LENGTH: 5
<212> TYPE: PRT
<213> ORGANISM: Artificial Sequence
<220> FEATURE:
<223> OTHER INFORMATION: Synthetic Construct

<400> SEQUENCE: 598
```

Ser Gly Tyr Trp Asn
1               5

```
<210> SEQ ID NO 599
<211> LENGTH: 16
<212> TYPE: PRT
<213> ORGANISM: Artificial Sequence
<220> FEATURE:
<223> OTHER INFORMATION: Synthetic Construct

<400> SEQUENCE: 599
```

Tyr Ile Ser Asp Ser Gly Ile Thr Tyr Tyr Asn Pro Ser Leu Lys Ser
1               5                   10                  15

```
<210> SEQ ID NO 600
<211> LENGTH: 11
<212> TYPE: PRT
<213> ORGANISM: Artificial Sequence
<220> FEATURE:
<223> OTHER INFORMATION: Synthetic Construct

<400> SEQUENCE: 600
```

Arg Thr Leu Ala Thr Tyr Tyr Ala Met Asp Tyr
1               5                   10

```
<210> SEQ ID NO 601
<211> LENGTH: 16
<212> TYPE: PRT
<213> ORGANISM: Artificial Sequence
<220> FEATURE:
<223> OTHER INFORMATION: Synthetic Construct

<400> SEQUENCE: 601
```

```
Arg Ala Ser Gln Ser Leu Val His Ser Asp Gly Asn Thr Tyr Leu His
1               5                   10                  15
```

<210> SEQ ID NO 602
<211> LENGTH: 7
<212> TYPE: PRT
<213> ORGANISM: Artificial Sequence
<220> FEATURE:
<223> OTHER INFORMATION: Synthetic Construct

<400> SEQUENCE: 602

```
Arg Val Ser Asn Arg Phe Ser
1               5
```

<210> SEQ ID NO 603
<211> LENGTH: 9
<212> TYPE: PRT
<213> ORGANISM: Artificial Sequence
<220> FEATURE:
<223> OTHER INFORMATION: Synthetic Construct

<400> SEQUENCE: 603

```
Ser Gln Ser Thr His Val Pro Pro Thr
1               5
```

<210> SEQ ID NO 604
<211> LENGTH: 119
<212> TYPE: PRT
<213> ORGANISM: Artificial Sequence
<220> FEATURE:
<223> OTHER INFORMATION: Synthetic Construct

<400> SEQUENCE: 604

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Tyr Trp Asn Trp Ile Arg Gln Pro Pro Gly Lys Gly Leu Glu Tyr Ile
        35                  40                  45

Gly Tyr Ile Ser Asp Ser Gly Ile Thr Tyr Tyr Asn Pro Ser Leu Lys
    50                  55                  60

Ser Arg Val Thr Ile Ser Arg Asp Thr Ser Lys Asn Gln Tyr Ser Leu
65                  70                  75                  80

Lys Leu Ser Ser Val Thr Ala Ala Asp Thr Ala Val Tyr Tyr Cys Ala
                85                  90                  95

Arg Arg Thr Leu Ala Thr Tyr Tyr Ala Met Asp Tyr Trp Gly Gln Gly
            100                 105                 110

Thr Leu Val Thr Val Ser Ser
        115
```

<210> SEQ ID NO 605
<211> LENGTH: 113
<212> TYPE: PRT
<213> ORGANISM: Artificial Sequence
<220> FEATURE:
<223> OTHER INFORMATION: Synthetic Construct

<400> SEQUENCE: 605

```
Asp Phe Val Met Thr Gln Ser Pro Leu Ser Leu Pro Val Thr Leu Gly
1               5                   10                  15

Gln Pro Ala Ser Ile Ser Cys Arg Ala Ser Gln Ser Leu Val His Ser
            20                  25                  30
```

-continued

Asp Gly Asn Thr Tyr Leu His Trp Tyr Gln Gln Arg Pro Gly Gln Ser
            35                  40                  45

Pro Arg Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Pro Thr Phe Gly Gln Gly Thr Lys Leu Glu Ile Lys
            100                 105                 110

Arg

<210> SEQ ID NO 606
<211> LENGTH: 5
<212> TYPE: PRT
<213> ORGANISM: Artificial Sequence
<220> FEATURE:
<223> OTHER INFORMATION: Synthetic Construct

<400> SEQUENCE: 606

Asn Tyr Ala Met Ser
1               5

<210> SEQ ID NO 607
<211> LENGTH: 17
<212> TYPE: PRT
<213> ORGANISM: Artificial Sequence
<220> FEATURE:
<223> OTHER INFORMATION: Synthetic Construct

<400> SEQUENCE: 607

Ser Ile Ser Gly Ser Gly Asp Tyr Thr Tyr Tyr Thr Asp Ser Val Lys
1               5                  10                  15

Gly

<210> SEQ ID NO 608
<211> LENGTH: 9
<212> TYPE: PRT
<213> ORGANISM: Artificial Sequence
<220> FEATURE:
<223> OTHER INFORMATION: Synthetic Construct

<400> SEQUENCE: 608

Ser Pro Trp Gly Tyr Tyr Leu Asp Ser
1               5

<210> SEQ ID NO 609
<211> LENGTH: 11
<212> TYPE: PRT
<213> ORGANISM: Artificial Sequence
<220> FEATURE:
<223> OTHER INFORMATION: Synthetic Construct

<400> SEQUENCE: 609

Arg Ala Ser Gln Gly Ile Ser Ser Arg Leu Ala
1               5                  10

<210> SEQ ID NO 610
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 610

Ala Ala Ser Ser Leu Gln Ser
1               5

<210> SEQ ID NO 611
<211> LENGTH: 9
<212> TYPE: PRT
<213> ORGANISM: Artificial Sequence
<220> FEATURE:
<223> OTHER INFORMATION: Synthetic Construct

<400> SEQUENCE: 611

Gln Gln Tyr Asn Ser Tyr Pro Tyr Thr
1               5

<210> SEQ ID NO 612
<211> LENGTH: 118
<212> TYPE: PRT
<213> ORGANISM: Artificial Sequence
<220> FEATURE:
<223> OTHER INFORMATION: Synthetic Construct

<400> SEQUENCE: 612

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
        115

<210> SEQ ID NO 613
<211> LENGTH: 107
<212> TYPE: PRT
<213> ORGANISM: Artificial Sequence
<220> FEATURE:
<223> OTHER INFORMATION: Synthetic Construct

<400> SEQUENCE: 613

Asp Ile Gln Met Thr Gln Ser Pro Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95
```

Thr Phe Gly Gln Gly Thr Lys Leu Glu Ile Lys
            100                 105

<210> SEQ ID NO 614
<211> LENGTH: 5
<212> TYPE: PRT
<213> ORGANISM: Artificial Sequence
<220> FEATURE:
<223> OTHER INFORMATION: Synthetic Construct

<400> SEQUENCE: 614

Asp His Ala Ile His
1               5

<210> SEQ ID NO 615
<211> LENGTH: 17
<212> TYPE: PRT
<213> ORGANISM: Artificial Sequence
<220> FEATURE:
<223> OTHER INFORMATION: Synthetic Construct

<400> SEQUENCE: 615

Tyr Phe Ser Pro Gly Asn Asp Asp Ile Lys Tyr Asn Glu Lys Phe Arg
1               5                   10                  15

Gly

<210> SEQ ID NO 616
<211> LENGTH: 6
<212> TYPE: PRT
<213> ORGANISM: Artificial Sequence
<220> FEATURE:
<223> OTHER INFORMATION: Synthetic Construct

<400> SEQUENCE: 616

Ser Leu Ser Thr Pro Tyr
1               5

<210> SEQ ID NO 617
<211> LENGTH: 17
<212> TYPE: PRT
<213> ORGANISM: Artificial Sequence
<220> FEATURE:
<223> OTHER INFORMATION: Synthetic Construct

<400> SEQUENCE: 617

Lys Ser Ser Gln Ser Leu Leu Asn Arg Gly Asn His Lys Asn Tyr Leu
1               5                   10                  15

Thr

<210> SEQ ID NO 618
<211> LENGTH: 7
<212> TYPE: PRT
<213> ORGANISM: Artificial Sequence
<220> FEATURE:
<223> OTHER INFORMATION: Synthetic Construct

<400> SEQUENCE: 618

Trp Ala Ser Thr Arg Glu Ser
1               5

<210> SEQ ID NO 619
<211> LENGTH: 9
<212> TYPE: PRT
<213> ORGANISM: Artificial Sequence
<220> FEATURE:

<223> OTHER INFORMATION: Synthetic Construct

<400> SEQUENCE: 619

Gln Asn Asp Tyr Thr Tyr Pro Tyr Thr
1               5

<210> SEQ ID NO 620
<211> LENGTH: 115
<212> TYPE: PRT
<213> ORGANISM: Artificial Sequence
<220> FEATURE:
<223> OTHER INFORMATION: Synthetic Construct

<400> SEQUENCE: 620

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser
        115

<210> SEQ ID NO 621
<211> LENGTH: 113
<212> TYPE: PRT
<213> ORGANISM: Artificial Sequence
<220> FEATURE:
<223> OTHER INFORMATION: Synthetic Construct

<400> SEQUENCE: 621

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Tyr Thr Phe Gly Gln Gly Thr Lys Val Glu Ile
            100                 105                 110

Lys

<210> SEQ ID NO 622
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 622

Ser Tyr Asn Met His
1               5

<210> SEQ ID NO 623
<211> LENGTH: 17
<212> TYPE: PRT
<213> ORGANISM: Artificial Sequence
<220> FEATURE:
<223> OTHER INFORMATION: Synthetic Construct

<400> SEQUENCE: 623

Ala Ile Tyr Pro Gly Asn Gly Asp Thr Ser Tyr Asn Gln Lys Phe Lys
1               5                   10                  15
Gly

<210> SEQ ID NO 624
<211> LENGTH: 12
<212> TYPE: PRT
<213> ORGANISM: Artificial Sequence
<220> FEATURE:
<223> OTHER INFORMATION: Synthetic Construct

<400> SEQUENCE: 624

Ser Thr Tyr Tyr Gly Gly Asp Trp Tyr Phe Asn Val
1               5                   10

<210> SEQ ID NO 625
<211> LENGTH: 10
<212> TYPE: PRT
<213> ORGANISM: Artificial Sequence
<220> FEATURE:
<223> OTHER INFORMATION: Synthetic Construct

<400> SEQUENCE: 625

Arg Ala Ser Ser Ser Val Ser Tyr Ile His
1               5                   10

<210> SEQ ID NO 626
<211> LENGTH: 7
<212> TYPE: PRT
<213> ORGANISM: Artificial Sequence
<220> FEATURE:
<223> OTHER INFORMATION: Synthetic Construct

<400> SEQUENCE: 626

Ala Thr Ser Asn Leu Ala Ser
1               5

<210> SEQ ID NO 627
<211> LENGTH: 9
<212> TYPE: PRT
<213> ORGANISM: Artificial Sequence
<220> FEATURE:
<223> OTHER INFORMATION: Synthetic Construct

<400> SEQUENCE: 627

Gln Gln Trp Thr Ser Asn Pro Pro Thr
1               5

<210> SEQ ID NO 628
<211> LENGTH: 121
<212> TYPE: PRT
```

<213> ORGANISM: Artificial Sequence
<220> FEATURE:
<223> OTHER INFORMATION: Synthetic Construct

<400> SEQUENCE: 628

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 629
<211> LENGTH: 106
<212> TYPE: PRT
<213> ORGANISM: Artificial Sequence
<220> FEATURE:
<223> OTHER INFORMATION: Synthetic Construct

<400> SEQUENCE: 629

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 630
<211> LENGTH: 5
<212> TYPE: PRT
<213> ORGANISM: Artificial Sequence
<220> FEATURE:
<223> OTHER INFORMATION: Synthetic Construct

<400> SEQUENCE: 630

Asp Thr Tyr Ile His
1               5

<210> SEQ ID NO 631
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 631

Arg Ile Tyr Pro Thr Asn Gly Tyr Thr Arg Tyr Ala Asp Ser Val Lys
1               5                   10                  15
Gly

<210> SEQ ID NO 632
<211> LENGTH: 11
<212> TYPE: PRT
<213> ORGANISM: Artificial Sequence
<220> FEATURE:
<223> OTHER INFORMATION: Synthetic Construct

<400> SEQUENCE: 632

Trp Gly Gly Asp Gly Phe Tyr Ala Met Asp Tyr
1               5                   10

<210> SEQ ID NO 633
<211> LENGTH: 11
<212> TYPE: PRT
<213> ORGANISM: Artificial Sequence
<220> FEATURE:
<223> OTHER INFORMATION: Synthetic Construct

<400> SEQUENCE: 633

Arg Ala Ser Gln Asp Val Asn Thr Ala Val Ala
1               5                   10

<210> SEQ ID NO 634
<211> LENGTH: 7
<212> TYPE: PRT
<213> ORGANISM: Artificial Sequence
<220> FEATURE:
<223> OTHER INFORMATION: Synthetic Construct

<400> SEQUENCE: 634

Ser Ala Ser Phe Leu Tyr Ser
1               5

<210> SEQ ID NO 635
<211> LENGTH: 9
<212> TYPE: PRT
<213> ORGANISM: Artificial Sequence
<220> FEATURE:
<223> OTHER INFORMATION: Synthetic Construct

<400> SEQUENCE: 635

Gln Gln His Tyr Thr Thr Pro Pro Thr
1               5

<210> SEQ ID NO 636
<211> LENGTH: 120
<212> TYPE: PRT
<213> ORGANISM: Artificial Sequence
<220> FEATURE:
<223> OTHER INFORMATION: Synthetic Construct

<400> SEQUENCE: 636

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
```

```
                35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser
            115                 120
```

<210> SEQ ID NO 637
<211> LENGTH: 107
<212> TYPE: PRT
<213> ORGANISM: Artificial Sequence
<220> FEATURE:
<223> OTHER INFORMATION: Synthetic Construct

<400> SEQUENCE: 637

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Val Asn Thr Ala
             20                  25                  30
Val Ala Trp Tyr Gln Gln Lys Pro Gly Lys Ala Pro Lys Leu Leu Ile
         35                  40                  45
Tyr Ser Ala Ser Phe Leu Tyr Ser Gly Val Pro Ser Arg Phe Ser Gly
 50                  55                  60
Ser Arg Ser Gly Thr Asp Phe Thr Leu Thr Ile Ser Ser Leu Gln Pro
 65                  70                  75                  80
Glu Asp Phe Ala Thr Tyr Tyr Cys Gln Gln His Tyr Thr Thr Pro Pro
                 85                  90                  95
Thr Phe Gly Gln Gly Thr Lys Val Glu Ile Lys
            100                 105
```

<210> SEQ ID NO 638
<211> LENGTH: 5
<212> TYPE: PRT
<213> ORGANISM: Artificial Sequence
<220> FEATURE:
<223> OTHER INFORMATION: Synthetic Construct

<400> SEQUENCE: 638

```
Ser Tyr Trp Ile Glu
 1               5
```

<210> SEQ ID NO 639
<211> LENGTH: 17
<212> TYPE: PRT
<213> ORGANISM: Artificial Sequence
<220> FEATURE:
<223> OTHER INFORMATION: Synthetic Construct

<400> SEQUENCE: 639

```
Glu Ile Leu Pro Gly Gly Gly Asp Thr Asn Tyr Asn Glu Ile Phe Lys
 1               5                  10                  15
Gly
```

<210> SEQ ID NO 640
<211> LENGTH: 8

```
<212> TYPE: PRT
<213> ORGANISM: Artificial Sequence
<220> FEATURE:
<223> OTHER INFORMATION: Synthetic Construct

<400> SEQUENCE: 640

Arg Val Pro Ile Arg Leu Asp Tyr
1               5

<210> SEQ ID NO 641
<211> LENGTH: 15
<212> TYPE: PRT
<213> ORGANISM: Artificial Sequence
<220> FEATURE:
<223> OTHER INFORMATION: Synthetic Construct

<400> SEQUENCE: 641

Lys Ala Ser Gln Ser Val Asp Tyr Glu Gly Asp Ser Phe Leu Asn
1               5                   10                  15

<210> SEQ ID NO 642
<211> LENGTH: 7
<212> TYPE: PRT
<213> ORGANISM: Artificial Sequence
<220> FEATURE:
<223> OTHER INFORMATION: Synthetic Construct

<400> SEQUENCE: 642

Ala Ala Ser Asn Leu Glu Ser
1               5

<210> SEQ ID NO 643
<211> LENGTH: 9
<212> TYPE: PRT
<213> ORGANISM: Artificial Sequence
<220> FEATURE:
<223> OTHER INFORMATION: Synthetic Construct

<400> SEQUENCE: 643

Gln Gln Ser Asn Glu Asp Pro Leu Thr
1               5

<210> SEQ ID NO 644
<211> LENGTH: 117
<212> TYPE: PRT
<213> ORGANISM: Artificial Sequence
<220> FEATURE:
<223> OTHER INFORMATION: Synthetic Construct

<400> SEQUENCE: 644

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110
```

Val Thr Val Ser Ser
        115

<210> SEQ ID NO 645
<211> LENGTH: 111
<212> TYPE: PRT
<213> ORGANISM: Artificial Sequence
<220> FEATURE:
<223> OTHER INFORMATION: Synthetic Construct

<400> SEQUENCE: 645

Asp Ile Gln Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys
            100                 105                 110

<210> SEQ ID NO 646
<211> LENGTH: 5
<212> TYPE: PRT
<213> ORGANISM: Artificial Sequence
<220> FEATURE:
<223> OTHER INFORMATION: Synthetic Construct

<400> SEQUENCE: 646

Asp Phe Ala Met Ser
1               5

<210> SEQ ID NO 647
<211> LENGTH: 17
<212> TYPE: PRT
<213> ORGANISM: Artificial Sequence
<220> FEATURE:
<223> OTHER INFORMATION: Synthetic Construct

<400> SEQUENCE: 647

Thr Ile Gly Arg Val Ala Phe His Thr Tyr Tyr Pro Asp Ser Met Lys
1               5                   10                  15

Gly

<210> SEQ ID NO 648
<211> LENGTH: 11
<212> TYPE: PRT
<213> ORGANISM: Artificial Sequence
<220> FEATURE:
<223> OTHER INFORMATION: Synthetic Construct

<400> SEQUENCE: 648

His Arg Gly Phe Asp Val Gly His Phe Asp Phe
1               5                   10

<210> SEQ ID NO 649
<211> LENGTH: 16

```
<212> TYPE: PRT
<213> ORGANISM: Artificial Sequence
<220> FEATURE:
<223> OTHER INFORMATION: Synthetic Construct

<400> SEQUENCE: 649

Arg Ser Ser Glu Thr Leu Val His Ser Ser Gly Asn Thr Tyr Leu Glu
1               5                   10                  15

<210> SEQ ID NO 650
<211> LENGTH: 7
<212> TYPE: PRT
<213> ORGANISM: Artificial Sequence
<220> FEATURE:
<223> OTHER INFORMATION: Synthetic Construct

<400> SEQUENCE: 650

Arg Val Ser Asn Arg Phe Ser
1               5

<210> SEQ ID NO 651
<211> LENGTH: 9
<212> TYPE: PRT
<213> ORGANISM: Artificial Sequence
<220> FEATURE:
<223> OTHER INFORMATION: Synthetic Construct

<400> SEQUENCE: 651

Phe Gln Gly Ser Phe Asn Pro Leu Thr
1               5

<210> SEQ ID NO 652
<211> LENGTH: 120
<212> TYPE: PRT
<213> ORGANISM: Artificial Sequence
<220> FEATURE:
<223> OTHER INFORMATION: Synthetic Construct

<400> SEQUENCE: 652

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110

Gly Thr Leu Val Thr Val Ser Ser
        115                 120

<210> SEQ ID NO 653
<211> LENGTH: 112
<212> TYPE: PRT
<213> ORGANISM: Artificial Sequence
<220> FEATURE:
<223> OTHER INFORMATION: Synthetic Construct

<400> SEQUENCE: 653
```

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110
```

<210> SEQ ID NO 654
<211> LENGTH: 6
<212> TYPE: PRT
<213> ORGANISM: Artificial Sequence
<220> FEATURE:
<223> OTHER INFORMATION: Synthetic Construct

<400> SEQUENCE: 654

```
Asn Asp Tyr Ala Trp Asn
1               5
```

<210> SEQ ID NO 655
<211> LENGTH: 16
<212> TYPE: PRT
<213> ORGANISM: Artificial Sequence
<220> FEATURE:
<223> OTHER INFORMATION: Synthetic Construct

<400> SEQUENCE: 655

```
Tyr Ile Ser Tyr Ser Gly Tyr Thr Thr Tyr Asn Pro Ser Leu Lys Ser
1               5                   10                  15
```

<210> SEQ ID NO 656
<211> LENGTH: 7
<212> TYPE: PRT
<213> ORGANISM: Artificial Sequence
<220> FEATURE:
<223> OTHER INFORMATION: Synthetic Construct

<400> SEQUENCE: 656

```
Trp Thr Ser Gly Leu Asp Tyr
1               5
```

<210> SEQ ID NO 657
<211> LENGTH: 11
<212> TYPE: PRT
<213> ORGANISM: Artificial Sequence
<220> FEATURE:
<223> OTHER INFORMATION: Synthetic Construct

<400> SEQUENCE: 657

```
Lys Ala Ser Asp Leu Ile His Asn Trp Leu Ala
1               5                   10
```

<210> SEQ ID NO 658
<211> LENGTH: 7
<212> TYPE: PRT
<213> ORGANISM: Artificial Sequence

```
<220> FEATURE:
<223> OTHER INFORMATION: Synthetic Construct

<400> SEQUENCE: 658

Gly Ala Thr Ser Leu Glu Thr
1               5

<210> SEQ ID NO 659
<211> LENGTH: 9
<212> TYPE: PRT
<213> ORGANISM: Artificial Sequence
<220> FEATURE:
<223> OTHER INFORMATION: Synthetic Construct

<400> SEQUENCE: 659

Gln Gln Tyr Trp Thr Thr Pro Phe Thr
1               5

<210> SEQ ID NO 660
<211> LENGTH: 116
<212> TYPE: PRT
<213> ORGANISM: Artificial Sequence
<220> FEATURE:
<223> OTHER INFORMATION: Synthetic Construct

<400> SEQUENCE: 660

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Thr Ser Gly Leu Asp Tyr Trp Gly Gln Gly Thr Leu Val
            100                 105                 110

Thr Val Ser Ser
        115

<210> SEQ ID NO 661
<211> LENGTH: 107
<212> TYPE: PRT
<213> ORGANISM: Artificial Sequence
<220> FEATURE:
<223> OTHER INFORMATION: Synthetic Construct

<400> SEQUENCE: 661

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Trp Thr Thr Pro Phe
            85                  90                  95

Thr Phe Gly Gln Gly Thr Lys Val Glu Ile Lys
            100                 105

<210> SEQ ID NO 662
<211> LENGTH: 6
<212> TYPE: PRT
<213> ORGANISM: Artificial Sequence
<220> FEATURE:
<223> OTHER INFORMATION: Synthetic Construct

<400> SEQUENCE: 662

Ser Asp Tyr Ala Trp Asn
1               5

<210> SEQ ID NO 663
<211> LENGTH: 16
<212> TYPE: PRT
<213> ORGANISM: Artificial Sequence
<220> FEATURE:
<223> OTHER INFORMATION: Synthetic Construct

<400> SEQUENCE: 663

Tyr Ile Ser Asn Ser Gly Ser Thr Ser Tyr Asn Pro Ser Leu Lys Ser
1               5                   10                  15

<210> SEQ ID NO 664
<211> LENGTH: 15
<212> TYPE: PRT
<213> ORGANISM: Artificial Sequence
<220> FEATURE:
<223> OTHER INFORMATION: Synthetic Construct

<400> SEQUENCE: 664

Glu Arg Asn Tyr Asp Tyr Asp Asp Tyr Tyr Tyr Ala Met Asp Tyr
1               5                   10                  15

<210> SEQ ID NO 665
<211> LENGTH: 17
<212> TYPE: PRT
<213> ORGANISM: Artificial Sequence
<220> FEATURE:
<223> OTHER INFORMATION: Synthetic Construct

<400> SEQUENCE: 665

Lys Ser Ser Gln Ser Leu Leu Tyr Arg Ser Asn Gln Lys Asn Tyr Leu
1               5                   10                  15

Ala

<210> SEQ ID NO 666
<211> LENGTH: 7
<212> TYPE: PRT
<213> ORGANISM: Artificial Sequence
<220> FEATURE:
<223> OTHER INFORMATION: Synthetic Construct

<400> SEQUENCE: 666

Trp Ala Ser Thr Arg Glu Ser
1               5

<210> SEQ ID NO 667
<211> LENGTH: 9
<212> TYPE: PRT
<213> ORGANISM: Artificial Sequence
<220> FEATURE:
<223> OTHER INFORMATION: Synthetic Construct

<400> SEQUENCE: 667

Gln Gln Tyr Tyr Asn Tyr Pro Arg Thr
1               5

<210> SEQ ID NO 668
<211> LENGTH: 124
<212> TYPE: PRT
<213> ORGANISM: Artificial Sequence
<220> FEATURE:
<223> OTHER INFORMATION: Synthetic Construct

<400> SEQUENCE: 668

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Ser Tyr Asn Pro Ser Leu
50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Asp Asp Tyr Tyr Ala Met Asp
            100                 105                 110

Tyr Trp Gly Gln Gly Thr Leu Val Thr Val Ser Ser
        115                 120

<210> SEQ ID NO 669
<211> LENGTH: 113
<212> TYPE: PRT
<213> ORGANISM: Artificial Sequence
<220> FEATURE:
<223> OTHER INFORMATION: Synthetic Construct

<400> SEQUENCE: 669

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys

<210> SEQ ID NO 670
<211> LENGTH: 5
<212> TYPE: PRT

```
<213> ORGANISM: Artificial Sequence
<220> FEATURE:
<223> OTHER INFORMATION: Synthetic Construct

<400> SEQUENCE: 670

Asn Tyr Trp Met His
1               5

<210> SEQ ID NO 671
<211> LENGTH: 17
<212> TYPE: PRT
<213> ORGANISM: Artificial Sequence
<220> FEATURE:
<223> OTHER INFORMATION: Synthetic Construct

<400> SEQUENCE: 671

Ala Thr Tyr Arg Gly His Ser Asp Thr Tyr Tyr Asn Gln Lys Phe Lys
1               5                   10                  15

Gly

<210> SEQ ID NO 672
<211> LENGTH: 12
<212> TYPE: PRT
<213> ORGANISM: Artificial Sequence
<220> FEATURE:
<223> OTHER INFORMATION: Synthetic Construct

<400> SEQUENCE: 672

Gly Ala Ile Tyr Asp Gly Tyr Asp Val Leu Asp Asn
1               5                   10

<210> SEQ ID NO 673
<211> LENGTH: 11
<212> TYPE: PRT
<213> ORGANISM: Artificial Sequence
<220> FEATURE:
<223> OTHER INFORMATION: Synthetic Construct

<400> SEQUENCE: 673

Ser Ala Ser Gln Asp Ile Ser Asn Tyr Leu Asn
1               5                   10

<210> SEQ ID NO 674
<211> LENGTH: 7
<212> TYPE: PRT
<213> ORGANISM: Artificial Sequence
<220> FEATURE:
<223> OTHER INFORMATION: Synthetic Construct

<400> SEQUENCE: 674

Tyr Thr Ser Asn Leu His Ser
1               5

<210> SEQ ID NO 675
<211> LENGTH: 9
<212> TYPE: PRT
<213> ORGANISM: Artificial Sequence
<220> FEATURE:
<223> OTHER INFORMATION: Synthetic Construct

<400> SEQUENCE: 675

Gln Gln Tyr Arg Lys Leu Pro Trp Thr
1               5

<210> SEQ ID NO 676
<211> LENGTH: 121
```

```
<212> TYPE: PRT
<213> ORGANISM: Artificial Sequence
<220> FEATURE:
<223> OTHER INFORMATION: Synthetic Construct

<400> SEQUENCE: 676
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Met His Trp Val Arg Gln Ala Pro Gly Gln Gly Leu Glu Trp Met
        35                  40                  45

Gly Ala Thr Tyr Arg Gly His Ser Asp Thr Tyr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Tyr Asp Gly Tyr Asp Val Leu Asp Asn Trp Gly
            100                 105                 110

Gln Gly Thr Leu Val Thr Val Ser Ser
        115                 120

```
<210> SEQ ID NO 677
<211> LENGTH: 107
<212> TYPE: PRT
<213> ORGANISM: Artificial Sequence
<220> FEATURE:
<223> OTHER INFORMATION: Synthetic Construct

<400> SEQUENCE: 677
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Lys Leu Pro Trp
                85                  90                  95

Thr Phe Gly Gln Gly Thr Lys Leu Glu Ile Lys
            100                 105

```
<210> SEQ ID NO 678
<211> LENGTH: 5
<212> TYPE: PRT
<213> ORGANISM: Artificial Sequence
<220> FEATURE:
<223> OTHER INFORMATION: Synthetic Construct

<400> SEQUENCE: 678
```

Ala Tyr Thr Met His
1               5

```
<210> SEQ ID NO 679
<211> LENGTH: 17
<212> TYPE: PRT
```

```
<213> ORGANISM: Artificial Sequence
<220> FEATURE:
<223> OTHER INFORMATION: Synthetic Construct

<400> SEQUENCE: 679

Trp Ile Lys Pro Asn Asn Gly Leu Ala Asn Tyr Ala Gln Lys Phe Gln
1               5                   10                  15

Gly

<210> SEQ ID NO 680
<211> LENGTH: 9
<212> TYPE: PRT
<213> ORGANISM: Artificial Sequence
<220> FEATURE:
<223> OTHER INFORMATION: Synthetic Construct

<400> SEQUENCE: 680

Ser Glu Ile Thr Thr Glu Phe Asp Tyr
1               5

<210> SEQ ID NO 681
<211> LENGTH: 15
<212> TYPE: PRT
<213> ORGANISM: Artificial Sequence
<220> FEATURE:
<223> OTHER INFORMATION: Synthetic Construct

<400> SEQUENCE: 681

Lys Ser Ser Glu Ser Val Asp Ser Tyr Ala Asn Ser Phe Leu His
1               5                   10                  15

<210> SEQ ID NO 682
<211> LENGTH: 7
<212> TYPE: PRT
<213> ORGANISM: Artificial Sequence
<220> FEATURE:
<223> OTHER INFORMATION: Synthetic Construct

<400> SEQUENCE: 682

Arg Ala Ser Thr Arg Glu Ser
1               5

<210> SEQ ID NO 683
<211> LENGTH: 9
<212> TYPE: PRT
<213> ORGANISM: Artificial Sequence
<220> FEATURE:
<223> OTHER INFORMATION: Synthetic Construct

<400> SEQUENCE: 683

Gln Gln Ser Lys Glu Asp Pro Leu Thr
1               5

<210> SEQ ID NO 684
<211> LENGTH: 118
<212> TYPE: PRT
<213> ORGANISM: Artificial Sequence
<220> FEATURE:
<223> OTHER INFORMATION: Synthetic Construct

<400> SEQUENCE: 684

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30
```

```
Thr Met His Trp Val Arg Gln Ala Pro Gly Gln Gly Leu Glu Trp Met
            35                  40                  45

Gly Trp Ile Lys Pro Asn Asn Gly Leu Ala Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Ala Arg Ser Glu Ile Thr Thr Glu Phe Asp Tyr Trp Gly Gln Gly Thr
            100                 105                 110

Leu Val Thr Val Ser Ser
            115
```

```
<210> SEQ ID NO 685
<211> LENGTH: 111
<212> TYPE: PRT
<213> ORGANISM: Artificial Sequence
<220> FEATURE:
<223> OTHER INFORMATION: Synthetic Construct

<400> SEQUENCE: 685
```

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
            35                  40                  45

Lys Leu Leu Ile Tyr Arg Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Asp Pro Leu Thr Phe Gly Gly Gly Thr Lys Val Glu Ile Lys
            100                 105                 110
```

```
<210> SEQ ID NO 686
<211> LENGTH: 6
<212> TYPE: PRT
<213> ORGANISM: Artificial Sequence
<220> FEATURE:
<223> OTHER INFORMATION: Synthetic Construct

<400> SEQUENCE: 686
```

```
Ser Asp Phe Ala Trp Asn
 1               5
```

```
<210> SEQ ID NO 687
<211> LENGTH: 16
<212> TYPE: PRT
<213> ORGANISM: Artificial Sequence
<220> FEATURE:
<223> OTHER INFORMATION: Synthetic Construct

<400> SEQUENCE: 687
```

```
Tyr Ile Ser Tyr Ser Gly Asn Thr Arg Tyr Gln Pro Ser Leu Lys Ser
 1               5                  10                  15
```

```
<210> SEQ ID NO 688
<211> LENGTH: 7
<212> TYPE: PRT
```

<213> ORGANISM: Artificial Sequence
<220> FEATURE:
<223> OTHER INFORMATION: Synthetic Construct

<400> SEQUENCE: 688

Ala Gly Arg Gly Phe Pro Tyr
1               5

<210> SEQ ID NO 689
<211> LENGTH: 11
<212> TYPE: PRT
<213> ORGANISM: Artificial Sequence
<220> FEATURE:
<223> OTHER INFORMATION: Synthetic Construct

<400> SEQUENCE: 689

His Ser Ser Gln Asp Ile Asn Ser Asn Ile Gly
1               5                   10

<210> SEQ ID NO 690
<211> LENGTH: 7
<212> TYPE: PRT
<213> ORGANISM: Artificial Sequence
<220> FEATURE:
<223> OTHER INFORMATION: Synthetic Construct

<400> SEQUENCE: 690

His Gly Thr Asn Leu Asp Asp
1               5

<210> SEQ ID NO 691
<211> LENGTH: 9
<212> TYPE: PRT
<213> ORGANISM: Artificial Sequence
<220> FEATURE:
<223> OTHER INFORMATION: Synthetic Construct

<400> SEQUENCE: 691

Val Gln Tyr Ala Gln Phe Pro Trp Thr
1               5

<210> SEQ ID NO 692
<211> LENGTH: 116
<212> TYPE: PRT
<213> ORGANISM: Artificial Sequence
<220> FEATURE:
<223> OTHER INFORMATION: Synthetic Construct

<400> SEQUENCE: 692

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg Gln Pro Pro Gly Lys Gly Leu Glu Trp
        35                  40                  45

Met Gly Tyr Ile Ser Tyr Ser Gly Asn Thr Arg Tyr Gln Pro Ser Leu
    50                  55                  60

Lys Ser Arg Ile Thr Ile Ser Arg Asp Thr Ser Lys Asn Gln Phe Phe
65                  70                  75                  80

Leu Lys Leu Asn Ser Val Thr Ala Ala Asp Thr Ala Thr Tyr Tyr Cys
                85                  90                  95

Val Thr Ala Gly Arg Gly Phe Pro Tyr Trp Gly Gln Gly Thr Leu Val
            100                 105                 110

Thr Val Ser Ser
        115

<210> SEQ ID NO 693
<211> LENGTH: 107
<212> TYPE: PRT
<213> ORGANISM: Artificial Sequence
<220> FEATURE:
<223> OTHER INFORMATION: Synthetic Construct

<400> SEQUENCE: 693

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys Ser Phe Lys Gly Leu Ile
        35                  40                  45

Tyr His Gly Thr Asn Leu Asp Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Val Gln Tyr Ala Gln Phe Pro Trp
                85                  90                  95

Thr Phe Gly Gly Gly Thr Lys Leu Glu Ile Lys
            100                 105

<210> SEQ ID NO 694
<211> LENGTH: 5
<212> TYPE: PRT
<213> ORGANISM: Artificial Sequence
<220> FEATURE:
<223> OTHER INFORMATION: Synthetic Construct

<400> SEQUENCE: 694

Asp Tyr Tyr Met Ala
1               5

<210> SEQ ID NO 695
<211> LENGTH: 17
<212> TYPE: PRT
<213> ORGANISM: Artificial Sequence
<220> FEATURE:
<223> OTHER INFORMATION: Synthetic Construct

<400> SEQUENCE: 695

Ser Ile Asn Tyr Asp Gly Ser Ser Thr Tyr Tyr Val Asp Ser Val Lys
1               5                   10                  15

Gly

<210> SEQ ID NO 696
<211> LENGTH: 8
<212> TYPE: PRT
<213> ORGANISM: Artificial Sequence
<220> FEATURE:
<223> OTHER INFORMATION: Synthetic Construct

<400> SEQUENCE: 696

Asp Arg Gly Tyr Tyr Phe Asp Tyr
1               5

<210> SEQ ID NO 697
<211> LENGTH: 16
<212> TYPE: PRT

<213> ORGANISM: Artificial Sequence
<220> FEATURE:
<223> OTHER INFORMATION: Synthetic Construct

<400> SEQUENCE: 697

Arg Ser Ser Gln Ser Leu Val His Ser Asn Gly Asn Thr Tyr Leu His
1               5                   10                  15

<210> SEQ ID NO 698
<211> LENGTH: 7
<212> TYPE: PRT
<213> ORGANISM: Artificial Sequence
<220> FEATURE:
<223> OTHER INFORMATION: Synthetic Construct

<400> SEQUENCE: 698

Lys Val Ser Asn Arg Phe Ser
1               5

<210> SEQ ID NO 699
<211> LENGTH: 10
<212> TYPE: PRT
<213> ORGANISM: Artificial Sequence
<220> FEATURE:
<223> OTHER INFORMATION: Synthetic Construct

<400> SEQUENCE: 699

Ser Gln Ser Thr His Val Pro Pro Phe Thr
1               5                   10

<210> SEQ ID NO 700
<211> LENGTH: 117
<212> TYPE: PRT
<213> ORGANISM: Artificial Sequence
<220> FEATURE:
<223> OTHER INFORMATION: Synthetic Construct

<400> SEQUENCE: 700

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Ser Ser Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Tyr Tyr Phe Asp Tyr Trp Gly Gln Gly Thr Thr
            100                 105                 110

Val Thr Val Ser Ser
        115

<210> SEQ ID NO 701
<211> LENGTH: 113
<212> TYPE: PRT
<213> ORGANISM: Artificial Sequence
<220> FEATURE:
<223> OTHER INFORMATION: Synthetic Construct

<400> SEQUENCE: 701

-continued

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Pro Phe Thr Phe Gly Gly Gly Thr Lys Val Glu Ile
                100                 105                 110

Lys
```

<210> SEQ ID NO 702
<211> LENGTH: 5
<212> TYPE: PRT
<213> ORGANISM: Artificial Sequence
<220> FEATURE:
<223> OTHER INFORMATION: Synthetic Construct

<400> SEQUENCE: 702

```
Ser Tyr Gly Met His
1               5
```

<210> SEQ ID NO 703
<211> LENGTH: 17
<212> TYPE: PRT
<213> ORGANISM: Artificial Sequence
<220> FEATURE:
<223> OTHER INFORMATION: Synthetic Construct

<400> SEQUENCE: 703

```
Val Ile Trp Tyr Asp Gly Ser Asn Gln Tyr Tyr Ala Asp Ser Val Lys
1               5                   10                  15

Gly
```

<210> SEQ ID NO 704
<211> LENGTH: 11
<212> TYPE: PRT
<213> ORGANISM: Artificial Sequence
<220> FEATURE:
<223> OTHER INFORMATION: Synthetic Construct

<400> SEQUENCE: 704

```
Gly Leu Thr Ser Gly Arg Tyr Gly Met Asp Val
1               5                   10
```

<210> SEQ ID NO 705
<211> LENGTH: 16
<212> TYPE: PRT
<213> ORGANISM: Artificial Sequence
<220> FEATURE:
<223> OTHER INFORMATION: Synthetic Construct

<400> SEQUENCE: 705

```
Arg Ser Ser Gln Ser Leu Leu Leu Ser His Gly Phe Asn Tyr Leu Asp
1               5                   10                  15
```

<210> SEQ ID NO 706

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 706

Leu Gly Ser Ser Arg Ala Ser
1               5

<210> SEQ ID NO 707
<211> LENGTH: 9
<212> TYPE: PRT
<213> ORGANISM: Artificial Sequence
<220> FEATURE:
<223> OTHER INFORMATION: Synthetic Construct

<400> SEQUENCE: 707

Met Gln Pro Leu Gln Ile Pro Trp Thr
1               5

<210> SEQ ID NO 708
<211> LENGTH: 120
<212> TYPE: PRT
<213> ORGANISM: Artificial Sequence
<220> FEATURE:
<223> OTHER INFORMATION: Synthetic Construct

<400> SEQUENCE: 708

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met His Ser Leu Arg Ala Glu Asp Thr Ala Val Tyr Tyr Cys
                85                  90                  95

Ala Arg Gly Leu Thr Ser Gly Arg Tyr Gly Met Asp Val Trp Gly Gln
            100                 105                 110

Gly Thr Thr Val Thr Val Ser Ser
        115                 120

<210> SEQ ID NO 709
<211> LENGTH: 112
<212> TYPE: PRT
<213> ORGANISM: Artificial Sequence
<220> FEATURE:
<223> OTHER INFORMATION: Synthetic Construct

<400> SEQUENCE: 709

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Leu Ser
            20                  25                  30

His Gly Phe Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Pro
                85                  90                  95

Leu Gln Ile Pro Trp Thr Phe Gly Gln Gly Thr Lys Val Glu Ile Lys
            100                 105                 110

<210> SEQ ID NO 710
<211> LENGTH: 5
<212> TYPE: PRT
<213> ORGANISM: Artificial Sequence
<220> FEATURE:
<223> OTHER INFORMATION: Synthetic Construct

<400> SEQUENCE: 710

Asn Ala Trp Met Ser
1               5

<210> SEQ ID NO 711
<211> LENGTH: 17
<212> TYPE: PRT
<213> ORGANISM: Artificial Sequence
<220> FEATURE:
<223> OTHER INFORMATION: Synthetic Construct

<400> SEQUENCE: 711

Tyr Ile Ser Ser Ser Gly Ser Thr Ile Tyr Tyr Ala Asp Ser Val Lys
1               5                   10                  15

Gly

<210> SEQ ID NO 712
<211> LENGTH: 8
<212> TYPE: PRT
<213> ORGANISM: Artificial Sequence
<220> FEATURE:
<223> OTHER INFORMATION: Synthetic Construct

<400> SEQUENCE: 712

Glu Gly Leu Trp Ala Phe Asp Tyr
1               5

<210> SEQ ID NO 713
<211> LENGTH: 14
<212> TYPE: PRT
<213> ORGANISM: Artificial Sequence
<220> FEATURE:
<223> OTHER INFORMATION: Synthetic Construct

<400> SEQUENCE: 713

Thr Gly Ser Ser Ser Asn Ile Gly Ala Gly Tyr Val Val His
1               5                   10

<210> SEQ ID NO 714
<211> LENGTH: 7
<212> TYPE: PRT
<213> ORGANISM: Artificial Sequence
<220> FEATURE:
<223> OTHER INFORMATION: Synthetic Construct

<400> SEQUENCE: 714

Asp Asn Asn Lys Arg Pro Ser
1               5

<210> SEQ ID NO 715

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 715

Ala Ala Trp Asp Asp Arg Leu Asn Gly Pro Val
1               5                   10

<210> SEQ ID NO 716
<211> LENGTH: 117
<212> TYPE: PRT
<213> ORGANISM: Artificial Sequence
<220> FEATURE:
<223> OTHER INFORMATION: Synthetic Construct

<400> SEQUENCE: 716

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Trp Ala Phe Asp Tyr Trp Gly Gln Gly Thr Leu
            100                 105                 110

Val Thr Val Ser Ser
        115

<210> SEQ ID NO 717
<211> LENGTH: 111
<212> TYPE: PRT
<213> ORGANISM: Artificial Sequence
<220> FEATURE:
<223> OTHER INFORMATION: Synthetic Construct

<400> SEQUENCE: 717

Glu Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Asp Asn Asn Lys Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Arg
                85                  90                  95

Leu Asn Gly Pro Val Phe Gly Gly Gly Thr Lys Leu Thr Val Leu
            100                 105                 110

<210> SEQ ID NO 718
<211> LENGTH: 5
```

```
<212> TYPE: PRT
<213> ORGANISM: Artificial Sequence
<220> FEATURE:
<223> OTHER INFORMATION: Synthetic Construct

<400> SEQUENCE: 718

Gly Tyr Tyr Trp Ser
1               5

<210> SEQ ID NO 719
<211> LENGTH: 16
<212> TYPE: PRT
<213> ORGANISM: Artificial Sequence
<220> FEATURE:
<223> OTHER INFORMATION: Synthetic Construct

<400> SEQUENCE: 719

Glu Ile Asn His Arg Gly Asn Thr Asn Asp Asn Pro Ser Leu Lys Ser
1               5                   10                  15

<210> SEQ ID NO 720
<211> LENGTH: 11
<212> TYPE: PRT
<213> ORGANISM: Artificial Sequence
<220> FEATURE:
<223> OTHER INFORMATION: Synthetic Construct

<400> SEQUENCE: 720

Glu Arg Gly Tyr Thr Tyr Gly Asn Phe Asp His
1               5                   10

<210> SEQ ID NO 721
<211> LENGTH: 11
<212> TYPE: PRT
<213> ORGANISM: Artificial Sequence
<220> FEATURE:
<223> OTHER INFORMATION: Synthetic Construct

<400> SEQUENCE: 721

Arg Ala Ser Gln Ser Val Ser Arg Asn Leu Ala
1               5                   10

<210> SEQ ID NO 722
<211> LENGTH: 7
<212> TYPE: PRT
<213> ORGANISM: Artificial Sequence
<220> FEATURE:
<223> OTHER INFORMATION: Synthetic Construct

<400> SEQUENCE: 722

Gly Ala Ser Thr Arg Ala Thr
1               5

<210> SEQ ID NO 723
<211> LENGTH: 9
<212> TYPE: PRT
<213> ORGANISM: Artificial Sequence
<220> FEATURE:
<223> OTHER INFORMATION: Synthetic Construct

<400> SEQUENCE: 723

Gln Gln Tyr Lys Thr Trp Pro Arg Thr
1               5

<210> SEQ ID NO 724
<211> LENGTH: 119
<212> TYPE: PRT
```

<213> ORGANISM: Artificial Sequence
<220> FEATURE:
<223> OTHER INFORMATION: Synthetic Construct

<400> SEQUENCE: 724

Gln Val Gln Leu Gln Gln Trp Gly Ala Gly Leu Leu Lys Pro Ser Glu
1               5                   10                  15

Thr Leu Ser Leu Thr Cys Ala Val Phe Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Asp Asn Pro Ser Leu Lys
    50                  55                  60

Ser Arg Val Thr Ile Ser Val Asp Thr Ser Lys Asn Gln Phe Ala Leu
65                  70                  75                  80

Lys Leu Ser Ser Val Thr Ala Ala Asp Thr Ala Val Tyr Tyr Cys Ala
                85                  90                  95

Arg Glu Arg Gly Tyr Thr Tyr Gly Asn Phe Asp His Trp Gly Gln Gly
            100                 105                 110

Thr Leu Val Thr Val Ser Ser
        115

<210> SEQ ID NO 725
<211> LENGTH: 107
<212> TYPE: PRT
<213> ORGANISM: Artificial Sequence
<220> FEATURE:
<223> OTHER INFORMATION: Synthetic Construct

<400> SEQUENCE: 725

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys
            100                 105

<210> SEQ ID NO 726
<211> LENGTH: 5
<212> TYPE: PRT
<213> ORGANISM: Artificial Sequence
<220> FEATURE:
<223> OTHER INFORMATION: Synthetic Construct

<400> SEQUENCE: 726

Ser Tyr Ala Met Asn
1               5

<210> SEQ ID NO 727
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 727

Thr Thr Ser Gly Ser Gly Ala Ser Thr Tyr Tyr Ala Asp Ser Val Lys
1               5                   10                  15

Gly

<210> SEQ ID NO 728
<211> LENGTH: 7
<212> TYPE: PRT
<213> ORGANISM: Artificial Sequence
<220> FEATURE:
<223> OTHER INFORMATION: Synthetic Construct

<400> SEQUENCE: 728

Ile Trp Ile Ala Phe Asp Ile
1               5

<210> SEQ ID NO 729
<211> LENGTH: 12
<212> TYPE: PRT
<213> ORGANISM: Artificial Sequence
<220> FEATURE:
<223> OTHER INFORMATION: Synthetic Construct

<400> SEQUENCE: 729

Arg Ala Ser Gln Ser Val Ser Ser Ser Tyr Leu Ala
1               5                   10

<210> SEQ ID NO 730
<211> LENGTH: 7
<212> TYPE: PRT
<213> ORGANISM: Artificial Sequence
<220> FEATURE:
<223> OTHER INFORMATION: Synthetic Construct

<400> SEQUENCE: 730

Gly Ala Ser Ser Arg Ala Thr
1               5

<210> SEQ ID NO 731
<211> LENGTH: 9
<212> TYPE: PRT
<213> ORGANISM: Artificial Sequence
<220> FEATURE:
<223> OTHER INFORMATION: Synthetic Construct

<400> SEQUENCE: 731

Gln Gln Tyr Gly Ser Ser Pro Tyr Thr
1               5

<210> SEQ ID NO 732
<211> LENGTH: 116
<212> TYPE: PRT
<213> ORGANISM: Artificial Sequence
<220> FEATURE:
<223> OTHER INFORMATION: Synthetic Construct

<400> SEQUENCE: 732

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
```

```
                    35                  40                  45
Ser Thr Thr Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Trp Ile Ala Phe Asp Ile Trp Gly Gln Gly Thr Met Val
            100                 105                 110

Thr Val Ser Ser
        115

<210> SEQ ID NO 733
<211> LENGTH: 108
<212> TYPE: PRT
<213> ORGANISM: Artificial Sequence
<220> FEATURE:
<223> OTHER INFORMATION: Synthetic Construct

<400> SEQUENCE: 733

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 734
<211> LENGTH: 7
<212> TYPE: PRT
<213> ORGANISM: Artificial Sequence
<220> FEATURE:
<223> OTHER INFORMATION: Synthetic Construct

<400> SEQUENCE: 734

Ser Phe Asn Tyr Tyr Trp Ser
1               5

<210> SEQ ID NO 735
<211> LENGTH: 16
<212> TYPE: PRT
<213> ORGANISM: Artificial Sequence
<220> FEATURE:
<223> OTHER INFORMATION: Synthetic Construct

<400> SEQUENCE: 735

Tyr Ile Tyr Tyr Ser Gly Ser Thr Tyr Ser Asn Pro Ser Leu Lys Ser
1               5                   10                  15

<210> SEQ ID NO 736
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 736

Gly Tyr Asn Trp Asn Tyr Phe Asp Tyr
1               5

<210> SEQ ID NO 737
<211> LENGTH: 11
<212> TYPE: PRT
<213> ORGANISM: Artificial Sequence
<220> FEATURE:
<223> OTHER INFORMATION: Synthetic Construct

<400> SEQUENCE: 737

Arg Ala Ser Gln Ser Val Asp Asn Asn Leu Val
1               5                   10

<210> SEQ ID NO 738
<211> LENGTH: 7
<212> TYPE: PRT
<213> ORGANISM: Artificial Sequence
<220> FEATURE:
<223> OTHER INFORMATION: Synthetic Construct

<400> SEQUENCE: 738

Gly Ala Ser Thr Arg Ala Thr
1               5

<210> SEQ ID NO 739
<211> LENGTH: 10
<212> TYPE: PRT
<213> ORGANISM: Artificial Sequence
<220> FEATURE:
<223> OTHER INFORMATION: Synthetic Construct

<400> SEQUENCE: 739

Gln Gln Tyr Asn Asn Trp Pro Pro Trp Thr
1               5                   10

<210> SEQ ID NO 740
<211> LENGTH: 119
<212> TYPE: PRT
<213> ORGANISM: Artificial Sequence
<220> FEATURE:
<223> OTHER INFORMATION: Synthetic Construct

<400> SEQUENCE: 740

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Asn Tyr Tyr Trp Ser Trp Ile Arg His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Gly Tyr Asn Trp Asn Tyr Phe Asp Tyr Trp Gly Gln Gly
            100                 105                 110

Thr Leu Val Thr Val Ser Ser
```

```
<210> SEQ ID NO 741
<211> LENGTH: 108
<212> TYPE: PRT
<213> ORGANISM: Artificial Sequence
<220> FEATURE:
<223> OTHER INFORMATION: Synthetic Construct

<400> SEQUENCE: 741

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Val Asp Asn Asn
            20                  25                  30
Leu Val Trp Tyr Gln Gln Lys Pro Gly Gln Ala Pro Arg Leu Leu Ile
        35                  40                  45
Tyr Gly Ala Ser Thr Arg Ala Thr Gly Ile Pro Ala Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Asn Asn Trp Pro Pro
                85                  90                  95
Trp Thr Phe Gly Gln Gly Thr Lys Val Glu Ile Lys
            100                 105

<210> SEQ ID NO 742
<211> LENGTH: 5
<212> TYPE: PRT
<213> ORGANISM: Artificial Sequence
<220> FEATURE:
<223> OTHER INFORMATION: Synthetic Construct

<400> SEQUENCE: 742

Thr Tyr Trp Met His
1               5

<210> SEQ ID NO 743
<211> LENGTH: 17
<212> TYPE: PRT
<213> ORGANISM: Artificial Sequence
<220> FEATURE:
<223> OTHER INFORMATION: Synthetic Construct

<400> SEQUENCE: 743

Glu Ile Asp Pro Ser Asp Ser Tyr Ser Asn Tyr Asn Gln Lys Phe Lys
1               5                   10                  15
Asp

<210> SEQ ID NO 744
<211> LENGTH: 11
<212> TYPE: PRT
<213> ORGANISM: Artificial Sequence
<220> FEATURE:
<223> OTHER INFORMATION: Synthetic Construct

<400> SEQUENCE: 744

Asn Gly Gly Leu Gly Pro Ala Trp Phe Ser Tyr
1               5                   10

<210> SEQ ID NO 745
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 745

Lys Ala Ser Gln Tyr Val Gly Thr Ala Val Ala
1               5                   10

<210> SEQ ID NO 746
<211> LENGTH: 7
<212> TYPE: PRT
<213> ORGANISM: Artificial Sequence
<220> FEATURE:
<223> OTHER INFORMATION: Synthetic Construct

<400> SEQUENCE: 746

Ser Ala Ser Asn Arg Tyr Thr
1               5

<210> SEQ ID NO 747
<211> LENGTH: 9
<212> TYPE: PRT
<213> ORGANISM: Artificial Sequence
<220> FEATURE:
<223> OTHER INFORMATION: Synthetic Construct

<400> SEQUENCE: 747

Gln Gln Tyr Ser Ser Tyr Pro Trp Thr
1               5

<210> SEQ ID NO 748
<211> LENGTH: 120
<212> TYPE: PRT
<213> ORGANISM: Artificial Sequence
<220> FEATURE:
<223> OTHER INFORMATION: Synthetic Construct

<400> SEQUENCE: 748

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Ser Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Gly Gly Leu Gly Pro Ala Trp Phe Ser Tyr Trp Gly Gln
            100                 105                 110

Gly Thr Leu Val Thr Val Ser Ser
        115                 120

<210> SEQ ID NO 749
<211> LENGTH: 107
<212> TYPE: PRT
<213> ORGANISM: Artificial Sequence
<220> FEATURE:
<223> OTHER INFORMATION: Synthetic Construct

<400> SEQUENCE: 749

Asp Ile Gln Met Thr Gln Ser Pro Ser Ser Val Ser Ala Ser Val Gly
```

```
                1               5                  10                 15
            Asp Arg Val Thr Ile Thr Cys Lys Ala Ser Gln Tyr Val Gly Thr Ala
                               20                  25                 30
            Val Ala Trp Tyr Gln Gln Lys Pro Gly Lys Ser Pro Lys Leu Leu Ile
                          35                  40                 45
            Tyr Ser Ala Ser Asn Arg Tyr Thr Gly Val Pro Ser Arg Phe Ser Asp
                     50                  55                  60
            Ser Gly Ser Gly Thr Asp Phe Thr Leu Thr Ile Ser Ser Leu Gln Pro
             65                  70                  75                  80
            Glu Asp Phe Ala Thr Tyr Phe Cys Gln Gln Tyr Ser Ser Tyr Pro Trp
                             85                  90                  95
            Thr Phe Gly Gly Gly Thr Lys Val Glu Ile Lys
                        100                 105
```

```
<210> SEQ ID NO 750
<211> LENGTH: 5
<212> TYPE: PRT
<213> ORGANISM: Artificial Sequence
<220> FEATURE:
<223> OTHER INFORMATION: Synthetic Construct

<400> SEQUENCE: 750

Ser Tyr Ala Met Ser
1               5

<210> SEQ ID NO 751
<211> LENGTH: 17
<212> TYPE: PRT
<213> ORGANISM: Artificial Sequence
<220> FEATURE:
<223> OTHER INFORMATION: Synthetic Construct

<400> SEQUENCE: 751

Ala Ile Ser Gly Ser Gly Thr Ser Thr Tyr Tyr Ala Asp Ser Val Lys
1               5                   10                  15

Gly

<210> SEQ ID NO 752
<211> LENGTH: 13
<212> TYPE: PRT
<213> ORGANISM: Artificial Sequence
<220> FEATURE:
<223> OTHER INFORMATION: Synthetic Construct

<400> SEQUENCE: 752

Val Arg Tyr Asn Trp Asn His Gly Asp Trp Phe Asp Pro
1               5                   10

<210> SEQ ID NO 753
<211> LENGTH: 13
<212> TYPE: PRT
<213> ORGANISM: Artificial Sequence
<220> FEATURE:
<223> OTHER INFORMATION: Synthetic Construct

<400> SEQUENCE: 753

Ser Gly Ser Ser Ser Asn Ile Gly Asn Asn Tyr Val Ser
1               5                   10

<210> SEQ ID NO 754
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 754

Glu Asn Tyr Asn Arg Pro Ala
1               5

<210> SEQ ID NO 755
<211> LENGTH: 11
<212> TYPE: PRT
<213> ORGANISM: Artificial Sequence
<220> FEATURE:
<223> OTHER INFORMATION: Synthetic Construct

<400> SEQUENCE: 755

Ser Ser Trp Asp Asp Ser Leu Asn Tyr Trp Val
1               5                   10

<210> SEQ ID NO 756
<211> LENGTH: 122
<212> TYPE: PRT
<213> ORGANISM: Artificial Sequence
<220> FEATURE:
<223> OTHER INFORMATION: Synthetic Construct

<400> SEQUENCE: 756

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Tyr Asn Trp Asn His Gly Asp Trp Phe Asp Pro Trp
            100                 105                 110

Gly Gln Gly Thr Leu Val Thr Val Ser Ser
        115                 120

<210> SEQ ID NO 757
<211> LENGTH: 110
<212> TYPE: PRT
<213> ORGANISM: Artificial Sequence
<220> FEATURE:
<223> OTHER INFORMATION: Synthetic Construct

<400> SEQUENCE: 757

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Glu Asn Tyr Asn Arg Pro Ala Gly Val Pro Asp Arg Phe Ser
    50                  55                  60

Gly Ser Lys Ser Gly Thr Ser Ala Ser Leu Ala Ile Ser Gly Leu Arg
65                  70                  75                  80
```

```
Ser Glu Asp Glu Ala Asp Tyr Tyr Cys Ser Ser Trp Asp Asp Ser Leu
                85                  90                  95

Asn Tyr Trp Val Phe Gly Gly Gly Thr Lys Leu Thr Val Leu
            100                 105                 110

<210> SEQ ID NO 758
<211> LENGTH: 5
<212> TYPE: PRT
<213> ORGANISM: Artificial Sequence
<220> FEATURE:
<223> OTHER INFORMATION: Synthetic Construct

<400> SEQUENCE: 758

Ser Tyr Gly Met Ser
1               5

<210> SEQ ID NO 759
<211> LENGTH: 17
<212> TYPE: PRT
<213> ORGANISM: Artificial Sequence
<220> FEATURE:
<223> OTHER INFORMATION: Synthetic Construct

<400> SEQUENCE: 759

Thr Ile Ser Ser Gly Gly Ser Tyr Lys Tyr Tyr Val Asp Ser Val Lys
1               5                   10                  15

Gly

<210> SEQ ID NO 760
<211> LENGTH: 11
<212> TYPE: PRT
<213> ORGANISM: Artificial Sequence
<220> FEATURE:
<223> OTHER INFORMATION: Synthetic Construct

<400> SEQUENCE: 760

His Pro Asp Tyr Asp Gly Val Trp Phe Ala Tyr
1               5                   10

<210> SEQ ID NO 761
<211> LENGTH: 10
<212> TYPE: PRT
<213> ORGANISM: Artificial Sequence
<220> FEATURE:
<223> OTHER INFORMATION: Synthetic Construct

<400> SEQUENCE: 761

Ser Val Ser Ser Ser Val Phe Tyr Val His
1               5                   10

<210> SEQ ID NO 762
<211> LENGTH: 7
<212> TYPE: PRT
<213> ORGANISM: Artificial Sequence
<220> FEATURE:
<223> OTHER INFORMATION: Synthetic Construct

<400> SEQUENCE: 762

Asp Thr Ser Lys Leu Ala Ser
1               5

<210> SEQ ID NO 763
<211> LENGTH: 9
<212> TYPE: PRT
<213> ORGANISM: Artificial Sequence
```

<220> FEATURE:
<223> OTHER INFORMATION: Synthetic Construct

<400> SEQUENCE: 763

Gln Gln Trp Asn Ser Asn Pro Pro Thr
1               5

<210> SEQ ID NO 764
<211> LENGTH: 120
<212> TYPE: PRT
<213> ORGANISM: Artificial Sequence
<220> FEATURE:
<223> OTHER INFORMATION: Synthetic Construct

<400> SEQUENCE: 764

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ser Tyr Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Pro Asp Tyr Asp Val Trp Phe Ala Tyr Trp Gly Gln
            100                 105                 110

Gly Thr Leu Val Thr Val Ser Ser
        115                 120

<210> SEQ ID NO 765
<211> LENGTH: 107
<212> TYPE: PRT
<213> ORGANISM: Artificial Sequence
<220> FEATURE:
<223> OTHER INFORMATION: Synthetic Construct

<400> SEQUENCE: 765

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Val Phe Tyr Val
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Trp Asn Ser Asn Pro Pro
                85                  90                  95

Thr Phe Gly Gly Gly Thr Lys Val Glu Ile Lys
            100                 105

<210> SEQ ID NO 766
<211> LENGTH: 5
<212> TYPE: PRT
<213> ORGANISM: Artificial Sequence
<220> FEATURE:

```
<223> OTHER INFORMATION: Synthetic Construct

<400> SEQUENCE: 766

Ser Tyr Gly Met Ser
1               5

<210> SEQ ID NO 767
<211> LENGTH: 17
<212> TYPE: PRT
<213> ORGANISM: Artificial Sequence
<220> FEATURE:
<223> OTHER INFORMATION: Synthetic Construct

<400> SEQUENCE: 767

Thr Ile Ser Ser Gly Gly Ser Tyr Thr Tyr Tyr Pro Asp Ser Val Lys
1               5                   10                  15

Gly

<210> SEQ ID NO 768
<211> LENGTH: 11
<212> TYPE: PRT
<213> ORGANISM: Artificial Sequence
<220> FEATURE:
<223> OTHER INFORMATION: Synthetic Construct

<400> SEQUENCE: 768

His Pro Asp Tyr Asp Gly Val Trp Phe Ala Tyr
1               5                   10

<210> SEQ ID NO 769
<211> LENGTH: 10
<212> TYPE: PRT
<213> ORGANISM: Artificial Sequence
<220> FEATURE:
<223> OTHER INFORMATION: Synthetic Construct

<400> SEQUENCE: 769

Ser Val Ser Ser Ser Val Phe Tyr Val His
1               5                   10

<210> SEQ ID NO 770
<211> LENGTH: 7
<212> TYPE: PRT
<213> ORGANISM: Artificial Sequence
<220> FEATURE:
<223> OTHER INFORMATION: Synthetic Construct

<400> SEQUENCE: 770

Asp Thr Ser Lys Leu Ala Ser
1               5

<210> SEQ ID NO 771
<211> LENGTH: 9
<212> TYPE: PRT
<213> ORGANISM: Artificial Sequence
<220> FEATURE:
<223> OTHER INFORMATION: Synthetic Construct

<400> SEQUENCE: 771

Gln Gln Trp Asn Ser Asn Pro Pro Thr
1               5

<210> SEQ ID NO 772
<211> LENGTH: 120
<212> TYPE: PRT
<213> ORGANISM: Artificial Sequence
```

```
<220> FEATURE:
<223> OTHER INFORMATION: Synthetic Construct

<400> SEQUENCE: 772

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Asn Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Pro Asp Tyr Asp Gly Val Trp Phe Ala Tyr Trp Gly Gln
            100                 105                 110

Gly Thr Leu Val Thr Val Ser Ala
        115                 120

<210> SEQ ID NO 773
<211> LENGTH: 105
<212> TYPE: PRT
<213> ORGANISM: Artificial Sequence
<220> FEATURE:
<223> OTHER INFORMATION: Synthetic Construct

<400> SEQUENCE: 773

Gln Ile Val Leu Thr Gln Ser Pro Ala Ile Met Ala Ser Pro Gly Glu
1               5                   10                  15

Lys Val Thr Met Thr Cys Ser Val Ser Ser Val Phe Tyr Val His
            20                  25                  30

Trp Tyr Gln Gln Lys Ser Gly Thr Ser Pro Lys Arg Trp Ile Tyr Asp
            35                  40                  45

Thr Ser Lys Leu Ala Ser Gly Val Pro Ala Arg Phe Ser Gly Ser Gly
        50                  55                  60

Ser Gly Thr Ser Tyr Ser Leu Thr Ile Ser Ser Met Glu Ala Glu Asp
65                  70                  75                  80

Ala Ala Thr Tyr Tyr Cys Gln Gln Trp Asn Ser Asn Pro Pro Thr Phe
                85                  90                  95

Gly Gly Gly Thr Lys Leu Glu Ile Lys
            100                 105

<210> SEQ ID NO 774
<211> LENGTH: 5
<212> TYPE: PRT
<213> ORGANISM: Artificial Sequence
<220> FEATURE:
<223> OTHER INFORMATION: Synthetic Construct

<400> SEQUENCE: 774

Ser Tyr Tyr Met His
1               5

<210> SEQ ID NO 775
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 775

Ile Ile Asn Pro Ser Gly Gly Ser Thr Ser Tyr Ala Gln Lys Phe Gln
1               5                   10                  15

Gly

<210> SEQ ID NO 776
<211> LENGTH: 16
<212> TYPE: PRT
<213> ORGANISM: Artificial Sequence
<220> FEATURE:
<223> OTHER INFORMATION: Synthetic Construct

<400> SEQUENCE: 776

Asp Gly Val Leu Arg Tyr Phe Asp Trp Leu Leu Asp Tyr Tyr Tyr Tyr
1               5                   10                  15

<210> SEQ ID NO 777
<211> LENGTH: 11
<212> TYPE: PRT
<213> ORGANISM: Artificial Sequence
<220> FEATURE:
<223> OTHER INFORMATION: Synthetic Construct

<400> SEQUENCE: 777

Arg Ala Ser Gln Ser Val Gly Ser Tyr Leu Ala
1               5                   10

<210> SEQ ID NO 778
<211> LENGTH: 7
<212> TYPE: PRT
<213> ORGANISM: Artificial Sequence
<220> FEATURE:
<223> OTHER INFORMATION: Synthetic Construct

<400> SEQUENCE: 778

Asp Ala Ser Asn Arg Ala Thr
1               5

<210> SEQ ID NO 779
<211> LENGTH: 8
<212> TYPE: PRT
<213> ORGANISM: Artificial Sequence
<220> FEATURE:
<223> OTHER INFORMATION: Synthetic Construct

<400> SEQUENCE: 779

Gln Gln Arg Ala Asn Val Phe Thr
1               5

<210> SEQ ID NO 780
<211> LENGTH: 128
<212> TYPE: PRT
<213> ORGANISM: Artificial Sequence
<220> FEATURE:
<223> OTHER INFORMATION: Synthetic Construct

<400> SEQUENCE: 780

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Val Leu Arg Tyr Phe Asp Trp Leu Leu Asp Tyr Tyr
            100                 105                 110

Tyr Tyr Met Asp Val Trp Gly Lys Gly Thr Thr Val Thr Val Ser Ser
            115                 120                 125

<210> SEQ ID NO 781
<211> LENGTH: 106
<212> TYPE: PRT
<213> ORGANISM: Artificial Sequence
<220> FEATURE:
<223> OTHER INFORMATION: Synthetic Construct

<400> SEQUENCE: 781

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
                20                  25                  30

Leu Ala Trp Tyr Gln Gln Arg Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ala Asn Val Phe Thr
                85                  90                  95

Phe Gly Gln Gly Thr Lys Val Glu Ile Lys
            100                 105

<210> SEQ ID NO 782
<211> LENGTH: 5
<212> TYPE: PRT
<213> ORGANISM: Artificial Sequence
<220> FEATURE:
<223> OTHER INFORMATION: Synthetic Construct

<400> SEQUENCE: 782

Ser Tyr Tyr Met His
1               5

<210> SEQ ID NO 783
<211> LENGTH: 17
<212> TYPE: PRT
<213> ORGANISM: Artificial Sequence
<220> FEATURE:
<223> OTHER INFORMATION: Synthetic Construct

<400> SEQUENCE: 783

Ile Ile Asn Pro Ser Gly Gly Ser Thr Ser Tyr Ala Gln Lys Phe Gln
1               5                   10                  15

Gly

<210> SEQ ID NO 784
<211> LENGTH: 19
<212> TYPE: PRT

```
<213> ORGANISM: Artificial Sequence
<220> FEATURE:
<223> OTHER INFORMATION: Synthetic Construct

<400> SEQUENCE: 784

Asp Ala Glu Leu Arg His Phe Asp His Leu Leu Asp Tyr His Tyr Tyr
1               5                   10                  15

Met Asp Val

<210> SEQ ID NO 785
<211> LENGTH: 11
<212> TYPE: PRT
<213> ORGANISM: Artificial Sequence
<220> FEATURE:
<223> OTHER INFORMATION: Synthetic Construct

<400> SEQUENCE: 785

Arg Ala Ser Gln Ser Val Gly Ser Tyr Leu Ala
1               5                   10

<210> SEQ ID NO 786
<211> LENGTH: 7
<212> TYPE: PRT
<213> ORGANISM: Artificial Sequence
<220> FEATURE:
<223> OTHER INFORMATION: Synthetic Construct

<400> SEQUENCE: 786

Asp Ala Ser Asn Arg Ala Thr
1               5

<210> SEQ ID NO 787
<211> LENGTH: 8
<212> TYPE: PRT
<213> ORGANISM: Artificial Sequence
<220> FEATURE:
<223> OTHER INFORMATION: Synthetic Construct

<400> SEQUENCE: 787

Gln Gln Arg Ala Gln Glu Phe Thr
1               5

<210> SEQ ID NO 788
<211> LENGTH: 128
<212> TYPE: PRT
<213> ORGANISM: Artificial Sequence
<220> FEATURE:
<223> OTHER INFORMATION: Synthetic Construct

<400> SEQUENCE: 788

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Glu Leu Arg His Phe Asp His Leu Leu Asp Tyr His
```

100                 105                 110
Tyr Tyr Met Asp Val Trp Gly Gln Gly Thr Thr Val Thr Val Ser Ser
            115                 120                 125

<210> SEQ ID NO 789
<211> LENGTH: 106
<212> TYPE: PRT
<213> ORGANISM: Artificial Sequence
<220> FEATURE:
<223> OTHER INFORMATION: Synthetic Construct

<400> SEQUENCE: 789

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Arg Ala Gln Glu Phe Thr
                85                  90                  95

Phe Gly Gln Gly Thr Lys Val Glu Ile Lys
            100                 105

<210> SEQ ID NO 790
<211> LENGTH: 120
<212> TYPE: PRT
<213> ORGANISM: Artificial Sequence
<220> FEATURE:
<223> OTHER INFORMATION: Synthetic Construct

<400> SEQUENCE: 790

Gln Val Gln Leu Val Gln Ser Gly Ser Glu Leu Lys Lys Pro Gly Ala
1               5                   10                  15

Pro Val Lys Val Ser Cys Lys Ala Ser Gly Tyr Thr Phe Ser Thr Phe
            20                  25                  30

Gly Met Ser Trp Val Arg Gln Ala Pro Gly Gln Gly Leu Lys Trp Met
        35                  40                  45

Gly Trp Ile His Thr Tyr Ala Gly Val Pro Ile Tyr Gly Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Arg Ser Asp Asn Tyr Arg Tyr Phe Phe Asp Tyr Trp Gly Gln
            100                 105                 110

Gly Thr Thr Val Thr Val Ser Ser
        115                 120

<210> SEQ ID NO 791
<211> LENGTH: 107
<212> TYPE: PRT
<213> ORGANISM: Artificial Sequence
<220> FEATURE:
<223> OTHER INFORMATION: Synthetic Construct

<400> SEQUENCE: 791

-continued

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                      60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Leu Glu Ile Lys
            100                 105

<210> SEQ ID NO 792
<211> LENGTH: 120
<212> TYPE: PRT
<213> ORGANISM: Artificial Sequence
<220> FEATURE:
<223> OTHER INFORMATION: Synthetic Construct

<400> SEQUENCE: 792

Gln Ile Gln Leu Val Gln Ser Gly Pro Glu Leu Lys Lys Pro Gly Ala
1               5                   10                  15

Pro Val Lys Ile Ser Cys Lys Ala Ser Gly Tyr Thr Phe Thr Thr Phe
            20                  25                  30

Gly Met Ser Trp Val Lys Gln Ala Pro Gly Gln Gly Leu Lys Trp Met
        35                  40                  45

Gly Trp Ile His Thr Tyr Ala Gly Val Pro Ile Tyr Gly Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Val Lys Ala Glu Asp Thr Ala Thr Tyr Phe Cys
                85                  90                  95

Ala Arg Arg Ser Asp Asn Tyr Arg Tyr Phe Phe Asp Tyr Trp Gly Gln
            100                 105                 110

Gly Thr Thr Leu Thr Val Ser Ser
        115                 120

<210> SEQ ID NO 793
<211> LENGTH: 107
<212> TYPE: PRT
<213> ORGANISM: Artificial Sequence
<220> FEATURE:
<223> OTHER INFORMATION: Synthetic Construct

<400> SEQUENCE: 793

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro

```
                65                  70                  75                  80
        Glu Asp Phe Ala Thr Tyr Phe Cys Gln Gln Gly His Thr Leu Pro Pro
                        85                  90                  95
        Thr Phe Gly Gln Gly Thr Lys Leu Glu Ile Lys
                        100                 105
```

<210> SEQ ID NO 794
<211> LENGTH: 5
<212> TYPE: PRT
<213> ORGANISM: Artificial Sequence
<220> FEATURE:
<223> OTHER INFORMATION: Synthetic Construct

<400> SEQUENCE: 794

```
Asn Tyr Tyr Met Ala
1               5
```

<210> SEQ ID NO 795
<211> LENGTH: 17
<212> TYPE: PRT
<213> ORGANISM: Artificial Sequence
<220> FEATURE:
<223> OTHER INFORMATION: Synthetic Construct

<400> SEQUENCE: 795

```
Ser Ile Thr Lys Gly Gly Gly Asn Thr Tyr Tyr Arg Asp Ser Val Lys
1               5                   10                  15
Gly
```

<210> SEQ ID NO 796
<211> LENGTH: 14
<212> TYPE: PRT
<213> ORGANISM: Artificial Sequence
<220> FEATURE:
<223> OTHER INFORMATION: Synthetic Construct

<400> SEQUENCE: 796

```
Gln Val Thr Ile Ala Ala Val Ser Thr Ser Tyr Phe Asp Ser
1               5                   10
```

<210> SEQ ID NO 797
<211> LENGTH: 15
<212> TYPE: PRT
<213> ORGANISM: Artificial Sequence
<220> FEATURE:
<223> OTHER INFORMATION: Synthetic Construct

<400> SEQUENCE: 797

```
Lys Thr Asn Gln Lys Val Asp Tyr Tyr Gly Asn Ser Tyr Val Tyr
1               5                   10                  15
```

<210> SEQ ID NO 798
<211> LENGTH: 7
<212> TYPE: PRT
<213> ORGANISM: Artificial Sequence
<220> FEATURE:
<223> OTHER INFORMATION: Synthetic Construct

<400> SEQUENCE: 798

```
Leu Ala Ser Asn Leu Ala Ser
1               5
```

<210> SEQ ID NO 799
<211> LENGTH: 9
<212> TYPE: PRT

<213> ORGANISM: Artificial Sequence
<220> FEATURE:
<223> OTHER INFORMATION: Synthetic Construct

<400> SEQUENCE: 799

Gln Gln Ser Arg Asn Leu Pro Tyr Thr
1               5

<210> SEQ ID NO 800
<211> LENGTH: 123
<212> TYPE: PRT
<213> ORGANISM: Artificial Sequence
<220> FEATURE:
<223> OTHER INFORMATION: Synthetic Construct

<400> SEQUENCE: 800

Glu Val Gln Leu Val Glu Ser Gly Gly Gly Leu Val Gln Ser Gly Arg
1               5                   10                  15

Ser Ile Arg Leu Ser Cys Ala Ala Ser Gly Phe Ser Phe Ser Asn Tyr
            20                  25                  30

Tyr Met Ala Trp Val Arg Gln Ala Pro Ser Lys Gly Leu Glu Trp Val
        35                  40                  45

Ala Ser Ile Thr Lys Gly Gly Asn Thr Tyr Tyr Arg Asp Ser Val
    50                  55                  60

Lys Gly Arg Phe Thr Phe Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Gln Val Thr Ile Ala Ala Val Ser Thr Ser Tyr Phe Asp Ser
            100                 105                 110

Trp Gly Gln Gly Val Met Val Thr Val Ser Ser
        115                 120

<210> SEQ ID NO 801
<211> LENGTH: 110
<212> TYPE: PRT
<213> ORGANISM: Artificial Sequence
<220> FEATURE:
<223> OTHER INFORMATION: Synthetic Construct

<400> SEQUENCE: 801

Asp Ile Val Leu Thr Gln Ser Pro Ala Leu Ala Val Ser Leu Gly Gln
1               5                   10                  15

Arg Ala Thr Ile Ser Cys Lys Thr Asn Gln Lys Val Asp Tyr Tyr Gly
            20                  25                  30

Asn Ser Tyr Val Tyr Trp Tyr Gln Gln Lys Pro Gly Gln Gln Pro Lys
        35                  40                  45

Leu Leu Ile Tyr Leu Ala Ser Asn Leu Ala Ser Gly Ile Pro Ala Arg
    50                  55                  60

Phe Ser Gly Arg Gly Ser Gly Thr Asp Phe Thr Leu Thr Ile Asp Pro
65                  70                  75                  80

Val Glu Ala Asp Asp Thr Ala Thr Tyr Tyr Cys Gln Gln Ser Arg Asn
                85                  90                  95

Leu Pro Tyr Thr Phe Gly Ala Gly Thr Lys Leu Glu Leu Lys
            100                 105                 110

<210> SEQ ID NO 802
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 802

Asp Tyr Tyr Met Lys
1               5

<210> SEQ ID NO 803
<211> LENGTH: 17
<212> TYPE: PRT
<213> ORGANISM: Artificial Sequence
<220> FEATURE:
<223> OTHER INFORMATION: Synthetic Construct

<400> SEQUENCE: 803

Asp Ile Ile Pro Ser Asn Gly Ala Thr Phe Tyr Asn Gln Lys Phe Lys
1               5                   10                  15

Gly

<210> SEQ ID NO 804
<211> LENGTH: 11
<212> TYPE: PRT
<213> ORGANISM: Artificial Sequence
<220> FEATURE:
<223> OTHER INFORMATION: Synthetic Construct

<400> SEQUENCE: 804

Ser His Leu Leu Arg Ala Ser Trp Phe Ala Tyr
1               5                   10

<210> SEQ ID NO 805
<211> LENGTH: 17
<212> TYPE: PRT
<213> ORGANISM: Artificial Sequence
<220> FEATURE:
<223> OTHER INFORMATION: Synthetic Construct

<400> SEQUENCE: 805

Lys Ser Ser Gln Ser Leu Leu Asn Ser Gly Asn Gln Lys Asn Tyr Leu
1               5                   10                  15

Thr

<210> SEQ ID NO 806
<211> LENGTH: 7
<212> TYPE: PRT
<213> ORGANISM: Artificial Sequence
<220> FEATURE:
<223> OTHER INFORMATION: Synthetic Construct

<400> SEQUENCE: 806

Trp Ala Ser Thr Arg Glu Ser
1               5

<210> SEQ ID NO 807
<211> LENGTH: 9
<212> TYPE: PRT
<213> ORGANISM: Artificial Sequence
<220> FEATURE:
<223> OTHER INFORMATION: Synthetic Construct

<400> SEQUENCE: 807

Gln Asn Asp Tyr Ser Tyr Pro Tyr Thr
1               5

<210> SEQ ID NO 808
```

```
<211> LENGTH: 120
<212> TYPE: PRT
<213> ORGANISM: Artificial Sequence
<220> FEATURE:
<223> OTHER INFORMATION: Synthetic Construct

<400> SEQUENCE: 808

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
                20                  25                  30

Tyr Met Lys Trp Val Lys Gln Ala Pro Gly Gln Gly Leu Glu Trp Ile
            35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120

<210> SEQ ID NO 809
<211> LENGTH: 113
<212> TYPE: PRT
<213> ORGANISM: Artificial Sequence
<220> FEATURE:
<223> OTHER INFORMATION: Synthetic Construct

<400> SEQUENCE: 809

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Thr Trp Tyr Leu Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys

<210> SEQ ID NO 810
<211> LENGTH: 5
<212> TYPE: PRT
<213> ORGANISM: Artificial Sequence
<220> FEATURE:
<223> OTHER INFORMATION: Synthetic Construct

<400> SEQUENCE: 810

Asp Tyr Glu Met His
1               5
```

-continued

```
<210> SEQ ID NO 811
<211> LENGTH: 20
<212> TYPE: PRT
<213> ORGANISM: Artificial Sequence
<220> FEATURE:
<223> OTHER INFORMATION: Synthetic Construct

<400> SEQUENCE: 811

Trp Ile Gly Gly Ile Asp Pro Glu Thr Gly Gly Thr Ala Tyr Asn Gln
1               5                   10                  15

Lys Phe Lys Gly
            20

<210> SEQ ID NO 812
<211> LENGTH: 6
<212> TYPE: PRT
<213> ORGANISM: Artificial Sequence
<220> FEATURE:
<223> OTHER INFORMATION: Synthetic Construct

<400> SEQUENCE: 812

Tyr Tyr Ser Phe Ala Tyr
1               5

<210> SEQ ID NO 813
<211> LENGTH: 16
<212> TYPE: PRT
<213> ORGANISM: Artificial Sequence
<220> FEATURE:
<223> OTHER INFORMATION: Synthetic Construct

<400> SEQUENCE: 813

Arg Ser Ser Gln Ser Ile Val His Ser Asn Gly Asn Thr Tyr Leu Gln
1               5                   10                  15

<210> SEQ ID NO 814
<211> LENGTH: 7
<212> TYPE: PRT
<213> ORGANISM: Artificial Sequence
<220> FEATURE:
<223> OTHER INFORMATION: Synthetic Construct

<400> SEQUENCE: 814

Lys Val Ser Asn Arg Phe Ser
1               5

<210> SEQ ID NO 815
<211> LENGTH: 9
<212> TYPE: PRT
<213> ORGANISM: Artificial Sequence
<220> FEATURE:
<223> OTHER INFORMATION: Synthetic Construct

<400> SEQUENCE: 815

Phe Gln Val Ser His Val Pro Tyr Thr
1               5

<210> SEQ ID NO 816
<211> LENGTH: 115
<212> TYPE: PRT
<213> ORGANISM: Artificial Sequence
<220> FEATURE:
<223> OTHER INFORMATION: Synthetic Construct

<400> SEQUENCE: 816

Glu Val Gln Leu Val Gln Ser Gly Ala Glu Val Lys Lys Pro Gly Ala
1               5                   10                  15
```

Thr Val Lys Ile Ser Cys Lys Val Ser Gly Tyr Thr Phe Thr Asp Tyr
            20                  25                  30

Glu Met His Trp Val Gln Gln Ala Pro Gly Lys Gly Leu Glu Trp Met
        35                  40                  45

Gly Gly Ile Asp Pro Glu Thr Gly Gly Thr Ala Tyr Asn Gln Lys Phe
50                      55                  60

Lys Gly Arg Val Thr Leu Thr Ala Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Gly Arg Tyr Tyr Ser Phe Ala Tyr Trp Gly Gln Gly Thr Leu Val Thr
            100                 105                 110

Val Ser Ser
        115

<210> SEQ ID NO 817
<211> LENGTH: 112
<212> TYPE: PRT
<213> ORGANISM: Artificial Sequence
<220> FEATURE:
<223> OTHER INFORMATION: Synthetic Construct

<400> SEQUENCE: 817

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Ala Asn Thr Tyr Leu Gln Trp Phe Gln Gln Arg Pro Gly Gln Ser
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Val
                85                  90                  95

Ser His Val Pro Tyr Thr Phe Gly Gln Gly Thr Lys Leu Glu Ile Lys
            100                 105                 110

<210> SEQ ID NO 818
<211> LENGTH: 5
<212> TYPE: PRT
<213> ORGANISM: Artificial Sequence
<220> FEATURE:
<223> OTHER INFORMATION: Synthetic Construct

<400> SEQUENCE: 818

Asp Tyr Asn Val Asn
1               5

<210> SEQ ID NO 819
<211> LENGTH: 17
<212> TYPE: PRT
<213> ORGANISM: Artificial Sequence
<220> FEATURE:
<223> OTHER INFORMATION: Synthetic Construct

<400> SEQUENCE: 819

Val Ile Asn Pro Lys Tyr Gly Thr Thr Arg Tyr Asn Gln Lys Phe Lys
1               5                   10                  15

-continued

Gly

<210> SEQ ID NO 820
<211> LENGTH: 7
<212> TYPE: PRT
<213> ORGANISM: Artificial Sequence
<220> FEATURE:
<223> OTHER INFORMATION: Synthetic Construct

<400> SEQUENCE: 820

Gly Leu Asn Ala Trp Asp Tyr
1               5

<210> SEQ ID NO 821
<211> LENGTH: 11
<212> TYPE: PRT
<213> ORGANISM: Artificial Sequence
<220> FEATURE:
<223> OTHER INFORMATION: Synthetic Construct

<400> SEQUENCE: 821

Gly Ala Ser Glu Asn Ile Tyr Gly Ala Leu Asn
1               5                   10

<210> SEQ ID NO 822
<211> LENGTH: 7
<212> TYPE: PRT
<213> ORGANISM: Artificial Sequence
<220> FEATURE:
<223> OTHER INFORMATION: Synthetic Construct

<400> SEQUENCE: 822

Gly Ala Thr Asn Leu Glu Asp
1               5

<210> SEQ ID NO 823
<211> LENGTH: 9
<212> TYPE: PRT
<213> ORGANISM: Artificial Sequence
<220> FEATURE:
<223> OTHER INFORMATION: Synthetic Construct

<400> SEQUENCE: 823

Gln Asn Val Leu Thr Thr Pro Tyr Thr
1               5

<210> SEQ ID NO 824
<211> LENGTH: 116
<212> TYPE: PRT
<213> ORGANISM: Artificial Sequence
<220> FEATURE:
<223> OTHER INFORMATION: Synthetic Construct

<400> SEQUENCE: 824

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Asn Val Asn Trp Val Arg Gln Ala Pro Gly Gln Gly Leu Glu Trp Ile
            35                  40                  45

Gly Val Ile Asn Pro Lys Tyr Gly Thr Thr Arg Tyr Asn Gln Lys Phe
        50                  55                  60

Lys Gly Arg Ala Thr Leu Thr Val Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser
        115

<210> SEQ ID NO 825
<211> LENGTH: 107
<212> TYPE: PRT
<213> ORGANISM: Artificial Sequence
<220> FEATURE:
<223> OTHER INFORMATION: Synthetic Construct

<400> SEQUENCE: 825

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Glu Asp Gly Val Pro Ser Arg Phe Ser Gly
50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 826
<211> LENGTH: 5
<212> TYPE: PRT
<213> ORGANISM: Artificial Sequence
<220> FEATURE:
<223> OTHER INFORMATION: Synthetic Construct

<400> SEQUENCE: 826

Gly Tyr Phe Met Asn
1               5

<210> SEQ ID NO 827
<211> LENGTH: 17
<212> TYPE: PRT
<213> ORGANISM: Artificial Sequence
<220> FEATURE:
<223> OTHER INFORMATION: Synthetic Construct

<400> SEQUENCE: 827

Leu Ile Asn Pro Tyr Asn Gly Asp Ser Phe Tyr Asn Gln Lys Phe Lys
1               5                   10                  15

Gly

<210> SEQ ID NO 828
<211> LENGTH: 8
<212> TYPE: PRT
<213> ORGANISM: Artificial Sequence
<220> FEATURE:
<223> OTHER INFORMATION: Synthetic Construct

<400> SEQUENCE: 828

Gly Leu Arg Arg Asp Phe Asp Tyr
```

-continued

<210> SEQ ID NO 829
<211> LENGTH: 16
<212> TYPE: PRT
<213> ORGANISM: Artificial Sequence
<220> FEATURE:
<223> OTHER INFORMATION: Synthetic Construct

<400> SEQUENCE: 829

Lys Ser Ser Gln Ser Leu Leu Asp Ser Asp Gly Lys Thr Tyr Leu Asn
1               5                   10                  15

<210> SEQ ID NO 830
<211> LENGTH: 7
<212> TYPE: PRT
<213> ORGANISM: Artificial Sequence
<220> FEATURE:
<223> OTHER INFORMATION: Synthetic Construct

<400> SEQUENCE: 830

Leu Val Ser Glu Leu Asp Ser
1               5

<210> SEQ ID NO 831
<211> LENGTH: 9
<212> TYPE: PRT
<213> ORGANISM: Artificial Sequence
<220> FEATURE:
<223> OTHER INFORMATION: Synthetic Construct

<400> SEQUENCE: 831

Trp Gln Gly Thr His Phe Pro Arg Thr
1               5

<210> SEQ ID NO 832
<211> LENGTH: 117
<212> TYPE: PRT
<213> ORGANISM: Artificial Sequence
<220> FEATURE:
<223> OTHER INFORMATION: Synthetic Construct

<400> SEQUENCE: 832

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
    50                  55                  60

Lys Gly Arg Val Thr Met Thr Arg Gln Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Gly Leu Arg Arg Asp Phe Asp Tyr Trp Gly Gln Gly Thr Leu
            100                 105                 110

Val Thr Val Ser Ser
        115

<210> SEQ ID NO 833
<211> LENGTH: 112
<212> TYPE: PRT

<213> ORGANISM: Artificial Sequence
<220> FEATURE:
<223> OTHER INFORMATION: Synthetic Construct

<400> SEQUENCE: 833

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Phe Gln Arg Pro Gly Gln Ser
        35                  40                  45

Pro Arg Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 834
<211> LENGTH: 5
<212> TYPE: PRT
<213> ORGANISM: Artificial Sequence
<220> FEATURE:
<223> OTHER INFORMATION: Synthetic Construct

<400> SEQUENCE: 834

Thr Ala Ala Ile Ser
1               5

<210> SEQ ID NO 835
<211> LENGTH: 17
<212> TYPE: PRT
<213> ORGANISM: Artificial Sequence
<220> FEATURE:
<223> OTHER INFORMATION: Synthetic Construct

<400> SEQUENCE: 835

Gly Ile Ile Pro Ile Phe Gly Lys Ala His Tyr Ala Gln Lys Phe Gln
1               5                   10                  15

Gly

<210> SEQ ID NO 836
<211> LENGTH: 14
<212> TYPE: PRT
<213> ORGANISM: Artificial Sequence
<220> FEATURE:
<223> OTHER INFORMATION: Synthetic Construct

<400> SEQUENCE: 836

Lys Phe His Phe Val Ser Gly Ser Pro Phe Gly Met Asp Val
1               5                   10

<210> SEQ ID NO 837
<211> LENGTH: 11
<212> TYPE: PRT
<213> ORGANISM: Artificial Sequence
<220> FEATURE:
<223> OTHER INFORMATION: Synthetic Construct

<400> SEQUENCE: 837

Arg Ala Ser Gln Ser Val Ser Ser Tyr Leu Ala

-continued

```
1               5                   10
```

<210> SEQ ID NO 838
<211> LENGTH: 7
<212> TYPE: PRT
<213> ORGANISM: Artificial Sequence
<220> FEATURE:
<223> OTHER INFORMATION: Synthetic Construct

<400> SEQUENCE: 838

```
Asp Ala Ser Asn Arg Ala Thr
1               5
```

<210> SEQ ID NO 839
<211> LENGTH: 8
<212> TYPE: PRT
<213> ORGANISM: Artificial Sequence
<220> FEATURE:
<223> OTHER INFORMATION: Synthetic Construct

<400> SEQUENCE: 839

```
Gln Gln Arg Ser Asn Trp Pro Thr
1               5
```

<210> SEQ ID NO 840
<211> LENGTH: 123
<212> TYPE: PRT
<213> ORGANISM: Artificial Sequence
<220> FEATURE:
<223> OTHER INFORMATION: Synthetic Construct

<400> SEQUENCE: 840

```
Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Ala
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120
```

<210> SEQ ID NO 841
<211> LENGTH: 106
<212> TYPE: PRT
<213> ORGANISM: Artificial Sequence
<220> FEATURE:
<223> OTHER INFORMATION: Synthetic Construct

<400> SEQUENCE: 841

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

-continued

```
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 842
<211> LENGTH: 9
<212> TYPE: PRT
<213> ORGANISM: Artificial Sequence
<220> FEATURE:
<223> OTHER INFORMATION: Synthetic Construct

<400> SEQUENCE: 842

Gly Thr Phe Ser Ser Tyr Ala Ile Ser
1               5

<210> SEQ ID NO 843
<211> LENGTH: 17
<212> TYPE: PRT
<213> ORGANISM: Artificial Sequence
<220> FEATURE:
<223> OTHER INFORMATION: Synthetic Construct

<400> SEQUENCE: 843

Ser Ile Ile Pro Ile Phe Gly Thr Ala Asn Tyr Ala Gln Lys Phe Gln
1               5                   10                  15

Gly

<210> SEQ ID NO 844
<211> LENGTH: 18
<212> TYPE: PRT
<213> ORGANISM: Artificial Sequence
<220> FEATURE:
<223> OTHER INFORMATION: Synthetic Construct

<400> SEQUENCE: 844

Ala Arg Gly Pro Ser Glu Val Gly Ala Ile Leu Gly Tyr Val Trp Phe
1               5                   10                  15

Asp Pro

<210> SEQ ID NO 845
<211> LENGTH: 16
<212> TYPE: PRT
<213> ORGANISM: Artificial Sequence
<220> FEATURE:
<223> OTHER INFORMATION: Synthetic Construct

<400> SEQUENCE: 845

Arg Ser Ser Gln Ser Leu Leu His Ser Asn Gly Tyr Asn Tyr Leu Asp
1               5                   10                  15

<210> SEQ ID NO 846
<211> LENGTH: 7
<212> TYPE: PRT
<213> ORGANISM: Artificial Sequence
<220> FEATURE:
<223> OTHER INFORMATION: Synthetic Construct

<400> SEQUENCE: 846
```

```
Leu Gly Ser Asn Arg Ala Ser
1               5

<210> SEQ ID NO 847
<211> LENGTH: 9
<212> TYPE: PRT
<213> ORGANISM: Artificial Sequence
<220> FEATURE:
<223> OTHER INFORMATION: Synthetic Construct

<400> SEQUENCE: 847

Met Gln Ala Arg Arg Ile Pro Ile Thr
1               5

<210> SEQ ID NO 848
<211> LENGTH: 125
<212> TYPE: PRT
<213> ORGANISM: Artificial Sequence
<220> FEATURE:
<223> OTHER INFORMATION: Synthetic Construct

<400> SEQUENCE: 848

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Ser Glu Val Gly Ala Ile Leu Gly Tyr Val Trp Phe
            100                 105                 110

Asp Pro Trp Gly Gln Gly Thr Leu Val Thr Val Ser Ser
        115                 120                 125

<210> SEQ ID NO 849
<211> LENGTH: 112
<212> TYPE: PRT
<213> ORGANISM: Artificial Sequence
<220> FEATURE:
<223> OTHER INFORMATION: Synthetic Construct

<400> SEQUENCE: 849

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

```
Arg Arg Ile Pro Ile Thr Phe Gly Gly Gly Thr Lys Val Glu Ile Lys
            100                 105                 110
```

<210> SEQ ID NO 850
<211> LENGTH: 12
<212> TYPE: PRT
<213> ORGANISM: Artificial Sequence
<220> FEATURE:
<223> OTHER INFORMATION: Synthetic Construct

<400> SEQUENCE: 850

```
Gly Tyr Thr Phe Thr Asp His Ala Ile His Trp Val
1               5                   10
```

<210> SEQ ID NO 851
<211> LENGTH: 10
<212> TYPE: PRT
<213> ORGANISM: Artificial Sequence
<220> FEATURE:
<223> OTHER INFORMATION: Synthetic Construct

<400> SEQUENCE: 851

```
Phe Ser Pro Gly Asn Asp Asp Ile Lys Tyr
1               5                   10
```

<210> SEQ ID NO 852
<211> LENGTH: 8
<212> TYPE: PRT
<213> ORGANISM: Artificial Sequence
<220> FEATURE:
<223> OTHER INFORMATION: Synthetic Construct

<400> SEQUENCE: 852

```
Lys Arg Ser Leu Ser Thr Pro Tyr
1               5
```

<210> SEQ ID NO 853
<211> LENGTH: 12
<212> TYPE: PRT
<213> ORGANISM: Artificial Sequence
<220> FEATURE:
<223> OTHER INFORMATION: Synthetic Construct

<400> SEQUENCE: 853

```
Gln Ser Leu Leu Asn Arg Gly Asn His Lys Asn Tyr
1               5                   10
```

<210> SEQ ID NO 854
<211> LENGTH: 7
<212> TYPE: PRT
<213> ORGANISM: Artificial Sequence
<220> FEATURE:
<223> OTHER INFORMATION: Synthetic Construct

<400> SEQUENCE: 854

```
Trp Ala Ser Thr Arg Glu Ser
1               5
```

<210> SEQ ID NO 855
<211> LENGTH: 9
<212> TYPE: PRT
<213> ORGANISM: Artificial Sequence
<220> FEATURE:
<223> OTHER INFORMATION: Synthetic Construct

<400> SEQUENCE: 855

```
Gln Asn Asp Tyr Thr Tyr Pro Tyr Thr
```

<210> SEQ ID NO 856
<211> LENGTH: 115
<212> TYPE: PRT
<213> ORGANISM: Artificial Sequence
<220> FEATURE:
<223> OTHER INFORMATION: Synthetic Construct

<400> SEQUENCE: 856

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Gly Leu Glu Trp Met
        35                  40                  45

Gly Tyr Phe Ser Pro Gly Asn Asp Asp Ile Lys Tyr Asn Glu Lys Phe
    50                  55                  60

Arg Gly Arg Val Thr Met Thr Ala Asp Lys Ser Ser Thr Ala Tyr
65                  70                  75                  80

Met Glu Leu Arg Ser Leu Arg Ser Asp Asp Thr Ala Val Tyr Phe Cys
                85                  90                  95

Lys Arg Ser Leu Ser Thr Pro Tyr Trp Gly Gln Gly Thr Leu Val Thr
            100                 105                 110

Val Ser Ser
        115

<210> SEQ ID NO 857
<211> LENGTH: 113
<212> TYPE: PRT
<213> ORGANISM: Artificial Sequence
<220> FEATURE:
<223> OTHER INFORMATION: Synthetic Construct

<400> SEQUENCE: 857

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Arg
            20                  25                  30

Gly Asn His Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Thr Tyr Pro Tyr Thr Phe Gly Gln Gly Thr Lys Val Glu Ile
            100                 105                 110

Lys

<210> SEQ ID NO 858
<211> LENGTH: 5
<212> TYPE: PRT
<213> ORGANISM: Artificial Sequence
<220> FEATURE:
<223> OTHER INFORMATION: Synthetic Construct

<400> SEQUENCE: 858

Asn Tyr Asp Ile Asn
1               5

<210> SEQ ID NO 859
<211> LENGTH: 17
<212> TYPE: PRT
<213> ORGANISM: Artificial Sequence
<220> FEATURE:
<223> OTHER INFORMATION: Synthetic Construct

<400> SEQUENCE: 859

Trp Ile Tyr Pro Gly Asp Gly Ser Thr Lys Tyr Asn Glu Lys Phe Lys
1               5                   10                  15

Ala

<210> SEQ ID NO 860
<211> LENGTH: 8
<212> TYPE: PRT
<213> ORGANISM: Artificial Sequence
<220> FEATURE:
<223> OTHER INFORMATION: Synthetic Construct

<400> SEQUENCE: 860

Gly Tyr Glu Asp Ala Met Asp Tyr
1               5

<210> SEQ ID NO 861
<211> LENGTH: 11
<212> TYPE: PRT
<213> ORGANISM: Artificial Sequence
<220> FEATURE:
<223> OTHER INFORMATION: Synthetic Construct

<400> SEQUENCE: 861

Lys Ala Ser Gln Asp Ile Asn Ser Tyr Leu Ser
1               5                   10

<210> SEQ ID NO 862
<211> LENGTH: 7
<212> TYPE: PRT
<213> ORGANISM: Artificial Sequence
<220> FEATURE:
<223> OTHER INFORMATION: Synthetic Construct

<400> SEQUENCE: 862

Arg Ala Asn Arg Leu Val Asp
1               5

<210> SEQ ID NO 863
<211> LENGTH: 9
<212> TYPE: PRT
<213> ORGANISM: Artificial Sequence
<220> FEATURE:
<223> OTHER INFORMATION: Synthetic Construct

<400> SEQUENCE: 863

Leu Gln Tyr Asp Glu Phe Pro Leu Thr
1               5

<210> SEQ ID NO 864
<211> LENGTH: 117
<212> TYPE: PRT
<213> ORGANISM: Artificial Sequence
<220> FEATURE:
<223> OTHER INFORMATION: Synthetic Construct

<400> SEQUENCE: 864

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asn Tyr
            20                  25                  30

Asp Ile Asn Trp Val Arg Gln Ala Pro Gly Gln Gly Leu Glu Trp Ile
        35                  40                  45

Gly Trp Ile Tyr Pro Gly Asp Gly Ser Thr Lys Tyr Asn Glu Lys Phe
50                  55                  60

Lys Ala Lys Ala Thr Leu Thr Ala Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Ser Gly Tyr Glu Asp Ala Met Asp Tyr Trp Gly Gln Gly Thr Thr
            100                 105                 110

Val Thr Val Ser Ser
        115
```

```
<210> SEQ ID NO 865
<211> LENGTH: 105
<212> TYPE: PRT
<213> ORGANISM: Artificial Sequence
<220> FEATURE:
<223> OTHER INFORMATION: Synthetic Construct

<400> SEQUENCE: 865

Asp Ile Gln Met Thr Gln Ser Pro Ser Ser Leu Ser Ala Ser Val Gly
1               5                   10                  15

Asp Arg Val Thr Ile Asn Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Leu
                85                  90                  95

Thr Phe Gly Gly Gly Thr Lys Val Glu
            100                 105
```

```
<210> SEQ ID NO 866
<211> LENGTH: 5
<212> TYPE: PRT
<213> ORGANISM: Artificial Sequence
<220> FEATURE:
<223> OTHER INFORMATION: Synthetic Construct

<400> SEQUENCE: 866

Asn Tyr Gly Met Asn
1               5
```

```
<210> SEQ ID NO 867
<211> LENGTH: 17
<212> TYPE: PRT
<213> ORGANISM: Artificial Sequence
<220> FEATURE:
<223> OTHER INFORMATION: Synthetic Construct

<400> SEQUENCE: 867
```

```
Trp Ile Asn Thr Tyr Ser Gly Glu Pro Arg Tyr Ala Asp Asp Phe Lys
1               5                   10                  15

Gly

<210> SEQ ID NO 868
<211> LENGTH: 9
<212> TYPE: PRT
<213> ORGANISM: Artificial Sequence
<220> FEATURE:
<223> OTHER INFORMATION: Synthetic Construct

<400> SEQUENCE: 868

Asp Tyr Gly Arg Trp Tyr Phe Asp Val
1               5

<210> SEQ ID NO 869
<211> LENGTH: 10
<212> TYPE: PRT
<213> ORGANISM: Artificial Sequence
<220> FEATURE:
<223> OTHER INFORMATION: Synthetic Construct

<400> SEQUENCE: 869

Arg Ala Ser Ser Ser Val Ser His Met His
1               5                   10

<210> SEQ ID NO 870
<211> LENGTH: 7
<212> TYPE: PRT
<213> ORGANISM: Artificial Sequence
<220> FEATURE:
<223> OTHER INFORMATION: Synthetic Construct

<400> SEQUENCE: 870

Ala Thr Ser Asn Leu Ala Ser
1               5

<210> SEQ ID NO 871
<211> LENGTH: 9
<212> TYPE: PRT
<213> ORGANISM: Artificial Sequence
<220> FEATURE:
<223> OTHER INFORMATION: Synthetic Construct

<400> SEQUENCE: 871

Gln Gln Trp Ser Ser Thr Pro Arg Thr
1               5

<210> SEQ ID NO 872
<211> LENGTH: 118
<212> TYPE: PRT
<213> ORGANISM: Artificial Sequence
<220> FEATURE:
<223> OTHER INFORMATION: Synthetic Construct

<400> SEQUENCE: 872

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Asp Leu Lys Trp Met
            35                  40                  45

Gly Trp Ile Asn Thr Tyr Ser Gly Glu Pro Arg Tyr Ala Asp Asp Phe
        50                  55                  60
```

```
Lys Gly Arg Phe Val Phe Ser Leu Asp Lys Ser Val Asn Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Tyr Gly Arg Trp Tyr Phe Asp Val Trp Gly Gln Gly Thr
            100                 105                 110

Thr Val Thr Val Ser Ser
        115
```

<210> SEQ ID NO 873
<211> LENGTH: 106
<212> TYPE: PRT
<213> ORGANISM: Artificial Sequence
<220> FEATURE:
<223> OTHER INFORMATION: Synthetic Construct

<400> SEQUENCE: 873

```
Gln Ile Val Leu Ser Gln Ser Pro Ala Thr Leu Ser Leu Ser Pro Gly
 1               5                  10                  15

Glu Arg Ala Thr Met Ser Cys Arg Ala Ser Ser Ser Val Ser His Met
                20                  25                  30

His Trp Tyr Gln Gln Lys Pro Gly Gln Ala Pro Arg Pro Trp Ile Tyr
             35                  40                  45

Ala Thr Ser Asn Leu Ala Ser Gly Val Pro Ala Arg Phe Ser Gly Ser
         50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Gln Trp Ser Ser Thr Pro Arg Thr
                 85                  90                  95

Phe Gly Gly Gly Thr Lys Val Glu Ile Lys
            100                 105
```

<210> SEQ ID NO 874
<211> LENGTH: 5
<212> TYPE: PRT
<213> ORGANISM: Artificial Sequence
<220> FEATURE:
<223> OTHER INFORMATION: Synthetic Construct

<400> SEQUENCE: 874

```
Asp Tyr Tyr Ile His
 1               5
```

<210> SEQ ID NO 875
<211> LENGTH: 17
<212> TYPE: PRT
<213> ORGANISM: Artificial Sequence
<220> FEATURE:
<223> OTHER INFORMATION: Synthetic Construct

<400> SEQUENCE: 875

```
Tyr Ile Asn Pro Asn Ser Gly Tyr Thr Asn Tyr Ala Gln Lys Phe Gln
 1               5                  10                  15

Gly
```

<210> SEQ ID NO 876
<211> LENGTH: 12
<212> TYPE: PRT
<213> ORGANISM: Artificial Sequence
<220> FEATURE:
<223> OTHER INFORMATION: Synthetic Construct

```
<400> SEQUENCE: 876

Tyr Met Trp Glu Arg Val Thr Gly Phe Phe Asp Phe
1               5                   10

<210> SEQ ID NO 877
<211> LENGTH: 11
<212> TYPE: PRT
<213> ORGANISM: Artificial Sequence
<220> FEATURE:
<223> OTHER INFORMATION: Synthetic Construct

<400> SEQUENCE: 877

Leu Ala Ser Glu Asp Ile Ser Asp Asp Leu Ala
1               5                   10

<210> SEQ ID NO 878
<211> LENGTH: 7
<212> TYPE: PRT
<213> ORGANISM: Artificial Sequence
<220> FEATURE:
<223> OTHER INFORMATION: Synthetic Construct

<400> SEQUENCE: 878

Thr Thr Ser Ser Leu Gln Ser
1               5

<210> SEQ ID NO 879
<211> LENGTH: 9
<212> TYPE: PRT
<213> ORGANISM: Artificial Sequence
<220> FEATURE:
<223> OTHER INFORMATION: Synthetic Construct

<400> SEQUENCE: 879

Gln Gln Thr Tyr Lys Phe Pro Pro Thr
1               5

<210> SEQ ID NO 880
<211> LENGTH: 121
<212> TYPE: PRT
<213> ORGANISM: Artificial Sequence
<220> FEATURE:
<223> OTHER INFORMATION: Synthetic Construct

<400> SEQUENCE: 880

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Ile
            35                  40                  45

Gly Tyr Ile Asn Pro Asn Ser Gly Tyr Thr Asn Tyr Ala Gln Lys Phe
        50                  55                  60

Gln Gly Arg Ala Thr Met Thr Ala Asp Lys Ser Ile Asn Thr Ala Tyr
65                  70                  75                  80

Val Glu Leu Ser Arg Leu Arg Ser Asp Asp Thr Ala Val Tyr Phe Cys
                85                  90                  95

Thr Arg Tyr Met Trp Glu Arg Val Thr Gly Phe Phe Asp Phe Trp Gly
            100                 105                 110

Gln Gly Thr Met Val Thr Val Ser Ser
        115                 120
```

<210> SEQ ID NO 881
<211> LENGTH: 107
<212> TYPE: PRT
<213> ORGANISM: Artificial Sequence
<220> FEATURE:
<223> OTHER INFORMATION: Synthetic Construct

<400> SEQUENCE: 881

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Ser Asp Asp
            20                  25                  30

Leu Ala Trp Tyr Gln Gln Lys Pro Gly Lys Ala Pro Lys Val Leu Val
        35                  40                  45

Tyr Thr Thr Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Thr Tyr Lys Phe Pro Pro
                85                  90                  95

Thr Phe Gly Gly Gly Thr Lys Val Glu Ile Lys
            100                 105

<210> SEQ ID NO 882
<211> LENGTH: 8
<212> TYPE: PRT
<213> ORGANISM: Artificial Sequence
<220> FEATURE:
<223> OTHER INFORMATION: Synthetic Construct

<400> SEQUENCE: 882

Gly Phe Thr Phe Ser Asn Tyr Ala
1               5

<210> SEQ ID NO 883
<211> LENGTH: 8
<212> TYPE: PRT
<213> ORGANISM: Artificial Sequence
<220> FEATURE:
<223> OTHER INFORMATION: Synthetic Construct

<400> SEQUENCE: 883

Ile Ser Gly Ser Gly Asp Tyr Thr
1               5

<210> SEQ ID NO 884
<211> LENGTH: 11
<212> TYPE: PRT
<213> ORGANISM: Artificial Sequence
<220> FEATURE:
<223> OTHER INFORMATION: Synthetic Construct

<400> SEQUENCE: 884

Ala Arg Ser Pro Trp Gly Tyr Tyr Leu Asp Ser
1               5                   10

<210> SEQ ID NO 885
<211> LENGTH: 6
<212> TYPE: PRT
<213> ORGANISM: Artificial Sequence
<220> FEATURE:
<223> OTHER INFORMATION: Synthetic Construct

<400> SEQUENCE: 885

Gln Gly Ile Ser Ser Arg
1               5

<210> SEQ ID NO 886
<211> LENGTH: 3
<212> TYPE: PRT
<213> ORGANISM: Artificial Sequence
<220> FEATURE:
<223> OTHER INFORMATION: Synthetic Construct

<400> SEQUENCE: 886

Ala Ala Ser
1

<210> SEQ ID NO 887
<211> LENGTH: 9
<212> TYPE: PRT
<213> ORGANISM: Artificial Sequence
<220> FEATURE:
<223> OTHER INFORMATION: Synthetic Construct

<400> SEQUENCE: 887

Gln Gln Tyr Asn Ser Tyr Pro Tyr Thr
1               5

<210> SEQ ID NO 888
<211> LENGTH: 118
<212> TYPE: PRT
<213> ORGANISM: Artificial Sequence
<220> FEATURE:
<223> OTHER INFORMATION: Synthetic Construct

<400> SEQUENCE: 888

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
        115

<210> SEQ ID NO 889
<211> LENGTH: 107
<212> TYPE: PRT
<213> ORGANISM: Artificial Sequence
<220> FEATURE:
<223> OTHER INFORMATION: Synthetic Construct

<400> SEQUENCE: 889

Asp Ile Gln Met Thr Gln Ser Pro Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

```
Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
                100                 105

<210> SEQ ID NO 890
<211> LENGTH: 449
<212> TYPE: PRT
<213> ORGANISM: Artificial Sequence
<220> FEATURE:
<223> OTHER INFORMATION: Synthetic Construct

<400> SEQUENCE: 890

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Phe
             20                  25                  30

Asn Tyr Tyr Trp Ser Trp Ile Arg His Pro Gly Lys Gly Leu Glu
             35                  40                  45

Trp Ile Gly Tyr Ile Tyr Tyr Ser Gly Ser Thr Tyr Ser Asn Pro Ser
 50                  55                  60

Leu Lys Ser Arg Val Thr Ile Ser Val Asp Thr Ser Lys Asn Gln Phe
 65                  70                  75                  80

Ser Leu Thr Leu Ser Ser Val Thr Ala Ala Asp Thr Ala Val Tyr Tyr
                 85                  90                  95

Cys Ala Arg Gly Tyr Asn Trp Asn Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 891
<211> LENGTH: 215
<212> TYPE: PRT
<213> ORGANISM: Artificial Sequence
<220> FEATURE:
<223> OTHER INFORMATION: Synthetic Construct

<400> SEQUENCE: 891

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Asn Asn
                20                  25                  30

Leu Val Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys

Ser Phe Asn Arg Gly Glu Cys
    210                 215

<210> SEQ ID NO 892
<211> LENGTH: 120
<212> TYPE: PRT
<213> ORGANISM: Artificial Sequence
<220> FEATURE:
<223> OTHER INFORMATION: Synthetic Construct

<400> SEQUENCE: 892

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Asn Tyr Tyr Trp Ser Trp Ile Arg His His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

Cys Ala Arg Gly Tyr Asn Trp Asn Tyr Phe Asp Tyr Trp Gly Gln Gly
            100                 105                 110

Thr Leu Val Thr Val Ser Ser Ala
        115                 120

<210> SEQ ID NO 893
<211> LENGTH: 109
<212> TYPE: PRT
<213> ORGANISM: Artificial Sequence
<220> FEATURE:
<223> OTHER INFORMATION: Synthetic Construct

<400> SEQUENCE: 893

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Asn Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg
            100                 105

<210> SEQ ID NO 894
<211> LENGTH: 7
<212> TYPE: PRT
<213> ORGANISM: Artificial Sequence
<220> FEATURE:
<223> OTHER INFORMATION: Synthetic Construct

<400> SEQUENCE: 894

Ser Phe Asn Tyr Tyr Trp Ser
1               5

<210> SEQ ID NO 895
<211> LENGTH: 16
<212> TYPE: PRT
<213> ORGANISM: Artificial Sequence
<220> FEATURE:
<223> OTHER INFORMATION: Synthetic Construct

<400> SEQUENCE: 895

Tyr Ile Tyr Tyr Ser Gly Ser Thr Tyr Ser Asn Pro Ser Leu Lys Ser
1               5                   10                  15

<210> SEQ ID NO 896
<211> LENGTH: 9
<212> TYPE: PRT
<213> ORGANISM: Artificial Sequence
<220> FEATURE:
<223> OTHER INFORMATION: Synthetic Construct

<400> SEQUENCE: 896

Gly Tyr Asn Trp Asn Tyr Phe Asp Tyr
1               5

<210> SEQ ID NO 897
<211> LENGTH: 11
<212> TYPE: PRT
<213> ORGANISM: Artificial Sequence
<220> FEATURE:
<223> OTHER INFORMATION: Synthetic Construct

<400> SEQUENCE: 897

Arg Ala Ser Gln Ser Val Asp Asn Asn Leu Val
1               5                   10

<210> SEQ ID NO 898
<211> LENGTH: 7
<212> TYPE: PRT
<213> ORGANISM: Artificial Sequence
<220> FEATURE:
<223> OTHER INFORMATION: Synthetic Construct

<400> SEQUENCE: 898

Gly Ala Ser Thr Arg Ala Thr
1               5

<210> SEQ ID NO 899
<211> LENGTH: 10
<212> TYPE: PRT
<213> ORGANISM: Artificial Sequence
<220> FEATURE:
<223> OTHER INFORMATION: Synthetic Construct

<400> SEQUENCE: 899

Gln Gln Tyr Asn Asn Trp Pro Pro Trp Thr
1               5                   10

<210> SEQ ID NO 900
<211> LENGTH: 5
<212> TYPE: PRT
<213> ORGANISM: Artificial Sequence
<220> FEATURE:
<223> OTHER INFORMATION: Synthetic Construct

<400> SEQUENCE: 900

Ser Gly Tyr Trp Asn
1               5

<210> SEQ ID NO 901
<211> LENGTH: 16
<212> TYPE: PRT
<213> ORGANISM: Artificial Sequence
<220> FEATURE:
<223> OTHER INFORMATION: Synthetic Construct

<400> SEQUENCE: 901

Tyr Ile Ser Asp Ser Gly Ile Thr Tyr Tyr Asn Pro Ser Leu Lys Ser
1               5                   10                  15

<210> SEQ ID NO 902
<211> LENGTH: 11
<212> TYPE: PRT
<213> ORGANISM: Artificial Sequence
<220> FEATURE:
<223> OTHER INFORMATION: Synthetic Construct

<400> SEQUENCE: 902

Arg Thr Leu Ala Thr Tyr Tyr Ala Met Asp Tyr
1               5                   10

<210> SEQ ID NO 903
<211> LENGTH: 16
<212> TYPE: PRT
<213> ORGANISM: Artificial Sequence
<220> FEATURE:
<223> OTHER INFORMATION: Synthetic Construct

<400> SEQUENCE: 903

Arg Ala Ser Gln Ser Leu Val His Ser Asp Gly Asn Thr Tyr Leu His
1               5                   10                  15

<210> SEQ ID NO 904
<211> LENGTH: 7
<212> TYPE: PRT
<213> ORGANISM: Artificial Sequence
<220> FEATURE:
<223> OTHER INFORMATION: Synthetic Construct

<400> SEQUENCE: 904

Arg Val Ser Asn Arg Phe Ser
1               5

<210> SEQ ID NO 905
<211> LENGTH: 9
<212> TYPE: PRT
<213> ORGANISM: Artificial Sequence
<220> FEATURE:
<223> OTHER INFORMATION: Synthetic Construct

<400> SEQUENCE: 905

Ser Gln Ser Thr His Val Pro Pro Thr
1               5

<210> SEQ ID NO 906
<211> LENGTH: 119
<212> TYPE: PRT
<213> ORGANISM: Artificial Sequence
<220> FEATURE:
<223> OTHER INFORMATION: Synthetic Construct

<400> SEQUENCE: 906

Gln Val Gln Leu Gln Glu Ser Gly Pro Gly Leu Val Lys Pro Ser Glu

-continued

```
                1               5                   10                  15
            Thr Leu Ser Leu Thr Cys Thr Val Ser Gly Asp Ser Ile Thr Ser Gly
                            20                  25                  30

Tyr Trp Asn Trp Ile Arg Gln Pro Gly Lys Gly Leu Glu Tyr Ile
                        35                  40                  45

Gly Tyr Ile Ser Asp Ser Gly Ile Thr Tyr Tyr Asn Pro Ser Leu Lys
                    50                  55                  60

Ser Arg Val Thr Ile Ser Arg Asp Thr Ser Lys Asn Gln Tyr Ser Leu
             65                 70                  75                  80

Lys Leu Ser Ser Val Thr Ala Ala Asp Thr Ala Val Tyr Tyr Cys Ala
                            85                  90                  95

Arg Arg Thr Leu Ala Thr Tyr Tyr Ala Met Asp Tyr Trp Gly Gln Gly
                        100                 105                 110

Thr Leu Val Thr Val Ser Ser
                        115
```

<210> SEQ ID NO 907
<211> LENGTH: 112
<212> TYPE: PRT
<213> ORGANISM: Artificial Sequence
<220> FEATURE:
<223> OTHER INFORMATION: Synthetic Construct

<400> SEQUENCE: 907

```
            Asp Phe Val Met Thr Gln Ser Pro Leu Ser Leu Pro Val Thr Leu Gly
             1               5                   10                  15

Gln Pro Ala Ser Ile Ser Cys Arg Ala Ser Gln Ser Leu Val His Ser
                            20                  25                  30

Asp Gly Asn Thr Tyr Leu His Trp Tyr Gln Gln Arg Pro Gly Gln Ser
                        35                  40                  45

Pro Arg Leu Leu Ile Tyr Arg Val Ser Asn Arg Phe Ser Gly Val Pro
                    50                  55                  60

Asp Arg Phe Ser Gly Ser Gly Ser Gly Thr Asp Phe Thr Leu Lys Ile
             65                 70                  75                  80

Ser Arg Val Glu Ala Glu Asp Val Gly Val Tyr Tyr Cys Ser Gln Ser
                            85                  90                  95

Thr His Val Pro Pro Thr Phe Gly Gln Gly Thr Lys Leu Glu Ile Lys
                        100                 105                 110
```

<210> SEQ ID NO 908
<211> LENGTH: 329
<212> TYPE: PRT
<213> ORGANISM: Artificial Sequence
<220> FEATURE:
<223> OTHER INFORMATION: Synthetic Construct

<400> SEQUENCE: 908

```
            Ala Ser Thr Lys Gly Pro Ser Val Phe Pro Leu Ala Pro Ser Ser Lys
             1               5                   10                  15

Ser Thr Ser Gly Gly Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                    50                  55                  60

Leu Ser Ser Val Val Thr Val Pro Ser Ser Ser Leu Gly Thr Gln Thr
             65                 70                  75                  80
```

-continued

```
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 909
<211> LENGTH: 106
<212> TYPE: PRT
<213> ORGANISM: Artificial Sequence
<220> FEATURE:
<223> OTHER INFORMATION: Synthetic Construct

<400> SEQUENCE: 909

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105
```

<210> SEQ ID NO 910
<211> LENGTH: 446
<212> TYPE: PRT
<213> ORGANISM: Artificial Sequence
<220> FEATURE:
<223> OTHER INFORMATION: Synthetic Construct

<400> SEQUENCE: 910

```
Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Val Asn Trp Val Arg Gln Ala Pro Gly Gln Gly Leu Glu Trp Ile
        35                  40                  45

Gly Val Ile Asn Pro Lys Tyr Gly Thr Thr Arg Tyr Asn Gln Lys Phe
50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 911
<211> LENGTH: 214
<212> TYPE: PRT
<213> ORGANISM: Artificial Sequence
<220> FEATURE:
<223> OTHER INFORMATION: Synthetic Construct

<400> SEQUENCE: 911

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Glu Asp Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 912
<211> LENGTH: 116
<212> TYPE: PRT
<213> ORGANISM: Artificial Sequence
<220> FEATURE:
<223> OTHER INFORMATION: Synthetic Construct

<400> SEQUENCE: 912

Gln Phe Gln Leu Val Gln Ser Gly Ala Glu Val Lys Lys Pro Gly Ala
1               5                   10                  15
```

Ser Val Lys Val Ser Cys Lys Ala Ser Gly Tyr Ser Phe Thr Asp Tyr
            20                  25                  30

Asn Val Asn Trp Val Arg Gln Ala Pro Gly Gln Gly Leu Glu Trp Ile
            35                  40                  45

Gly Val Ile Asn Pro Lys Tyr Gly Thr Thr Arg Tyr Asn Gln Lys Phe
 50                  55                  60

Lys Gly Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser
        115

<210> SEQ ID NO 913
<211> LENGTH: 107
<212> TYPE: PRT
<213> ORGANISM: Artificial Sequence
<220> FEATURE:
<223> OTHER INFORMATION: Synthetic Construct

<400> SEQUENCE: 913

Asp Ile Gln Met Thr Gln Ser Pro Ser Ser Leu Ser Ala Ser Val Gly
1               5                  10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Asn Leu Glu Asp Gly Val Pro Ser Arg Phe Ser Gly
 50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 914
<211> LENGTH: 5
<212> TYPE: PRT
<213> ORGANISM: Artificial Sequence
<220> FEATURE:
<223> OTHER INFORMATION: Synthetic Construct

<400> SEQUENCE: 914

Asp Tyr Asn Val Asn
1               5

<210> SEQ ID NO 915
<211> LENGTH: 17
<212> TYPE: PRT
<213> ORGANISM: Artificial Sequence
<220> FEATURE:
<223> OTHER INFORMATION: Synthetic Construct

<400> SEQUENCE: 915

Val Ile Asn Pro Lys Tyr Gly Thr Thr Arg Tyr Asn Gln Lys Phe Lys
1               5                  10                  15

Gly

<210> SEQ ID NO 916
<211> LENGTH: 7
<212> TYPE: PRT
<213> ORGANISM: Artificial Sequence
<220> FEATURE:
<223> OTHER INFORMATION: Synthetic Construct

<400> SEQUENCE: 916

Gly Leu Asn Ala Trp Asp Tyr
1               5

<210> SEQ ID NO 917
<211> LENGTH: 11
<212> TYPE: PRT
<213> ORGANISM: Artificial Sequence
<220> FEATURE:
<223> OTHER INFORMATION: Synthetic Construct

<400> SEQUENCE: 917

Gly Ala Ser Glu Asn Ile Tyr Gly Ala Leu Asn
1               5                   10

<210> SEQ ID NO 918
<211> LENGTH: 7
<212> TYPE: PRT
<213> ORGANISM: Artificial Sequence
<220> FEATURE:
<223> OTHER INFORMATION: Synthetic Construct

<400> SEQUENCE: 918

Gly Ala Thr Asn Leu Glu Asp
1               5

<210> SEQ ID NO 919
<211> LENGTH: 9
<212> TYPE: PRT
<213> ORGANISM: Artificial Sequence
<220> FEATURE:
<223> OTHER INFORMATION: Synthetic Construct

<400> SEQUENCE: 919

Gln Asn Val Leu Thr Thr Pro Tyr Thr
1               5

<210> SEQ ID NO 920
<211> LENGTH: 5
<212> TYPE: PRT
<213> ORGANISM: Artificial Sequence
<220> FEATURE:
<223> OTHER INFORMATION: Synthetic Construct

<400> SEQUENCE: 920

Asp Tyr Tyr Ile Thr
1               5

<210> SEQ ID NO 921
<211> LENGTH: 17
<212> TYPE: PRT
<213> ORGANISM: Artificial Sequence
<220> FEATURE:
<223> OTHER INFORMATION: Synthetic Construct

<400> SEQUENCE: 921

Trp Ile Tyr Pro Gly Ser Gly Asn Thr Lys Tyr Asn Glu Lys Phe Lys
1               5                   10                  15

Gly

<210> SEQ ID NO 922
<211> LENGTH: 8
<212> TYPE: PRT
<213> ORGANISM: Artificial Sequence
<220> FEATURE:
<223> OTHER INFORMATION: Synthetic Construct

<400> SEQUENCE: 922

Tyr Gly Asn Tyr Trp Phe Ala Tyr
1               5

<210> SEQ ID NO 923
<211> LENGTH: 15
<212> TYPE: PRT
<213> ORGANISM: Artificial Sequence
<220> FEATURE:
<223> OTHER INFORMATION: Synthetic Construct

<400> SEQUENCE: 923

Lys Ala Ser Gln Ser Val Asp Phe Asp Gly Asp Ser Tyr Met Asn
1               5                   10                  15

<210> SEQ ID NO 924
<211> LENGTH: 7
<212> TYPE: PRT
<213> ORGANISM: Artificial Sequence
<220> FEATURE:
<223> OTHER INFORMATION: Synthetic Construct

<400> SEQUENCE: 924

Ala Ala Ser Asn Leu Glu Ser
1               5

<210> SEQ ID NO 925
<211> LENGTH: 9
<212> TYPE: PRT
<213> ORGANISM: Artificial Sequence
<220> FEATURE:
<223> OTHER INFORMATION: Synthetic Construct

<400> SEQUENCE: 925

Gln Gln Ser Asn Glu Asp Pro Trp Thr
1               5

<210> SEQ ID NO 926
<211> LENGTH: 117
<212> TYPE: PRT
<213> ORGANISM: Artificial Sequence
<220> FEATURE:
<223> OTHER INFORMATION: Synthetic Construct

<400> SEQUENCE: 926

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115

<210> SEQ ID NO 927
<211> LENGTH: 111
<212> TYPE: PRT
<213> ORGANISM: Artificial Sequence
<220> FEATURE:
<223> OTHER INFORMATION: Synthetic Construct

<400> SEQUENCE: 927

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 928
<211> LENGTH: 447
<212> TYPE: PRT
<213> ORGANISM: Artificial Sequence
<220> FEATURE:
<223> OTHER INFORMATION: Synthetic Construct

<400> SEQUENCE: 928

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser

```
                145                 150                 155                 160
Gly Ala Leu Thr Ser Gly Val His Thr Phe Pro Ala Val Leu Gln Ser
                    165                 170                 175
Ser Gly Leu Tyr Ser Leu Ser Ser Val Val Thr Val Pro Ser Ser Ser
                    180                 185                 190
Leu Gly Thr Gln Thr Tyr Ile Cys Asn Val Asn His Lys Pro Ser Asn
                    195                 200                 205
Thr Lys Val Asp Lys Lys Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                    245                 250                 255
Pro Glu Val Thr Cys Val Val Val Asp Val Ser His Glu Asp Pro Glu
                    260                 265                 270
Val Lys Phe Asn Trp Tyr Val Asp Gly Val Glu Val His Asn Ala Lys
                    275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                    325                 330                 335
Ser Lys Ala Lys Gly Gln Pro Arg Glu Pro Gln Val Tyr Thr Leu Pro
                    340                 345                 350
Pro Ser Arg Asp Glu Leu Thr Lys Asn Gln Val Ser Leu Thr Cys Leu
                    355                 360                 365
Val Lys Gly Phe Tyr Pro Ser Asp Ile Ala Val Glu Trp Glu Ser Asn
                    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                    405                 410                 415
Trp Gln Gln Gly Asn Val Phe Ser Cys Ser Val Met His Glu Ala Leu
                    420                 425                 430
His Asn His Tyr Thr Gln Lys Ser Leu Ser Leu Ser Pro Gly Lys
                    435                 440                 445

<210> SEQ ID NO 929
<211> LENGTH: 446
<212> TYPE: PRT
<213> ORGANISM: Artificial Sequence
<220> FEATURE:
<223> OTHER INFORMATION: Synthetic Construct

<400> SEQUENCE: 929

Gln Ile Gln Leu Gln Gln Ser Gly Pro Glu Val Val Lys Pro Gly Ala
1               5                   10                  15
Ser Val Lys Ile Ser Cys Lys Ala Ser Gly Tyr Thr Phe Thr Asp Tyr
                20                  25                  30
Tyr Ile Thr Trp Val Lys Gln Pro Gly Gln Gly Leu Glu Trp Ile
                35                  40                  45
Gly Trp Ile Tyr Pro Gly Ser Gly Asn Thr Lys Tyr Asn Glu Lys Phe
            50                  55                  60
Lys Gly Lys Ala Thr Leu Thr Val Asp Thr Ser Ser Ser Thr Ala Phe
```

```
            65                  70                  75                  80
Met Gln Leu Ser Ser Leu Thr Ser Glu Asp Thr Ala Val Tyr Phe Cys
                    85                  90                  95

Ala Asn Tyr Gly Asn Tyr Trp Phe Ala Tyr Trp Gly Gln Gly Thr Gln
            100                 105                 110

Val Thr Val Ser Ala Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 930
<211> LENGTH: 218
<212> TYPE: PRT
<213> ORGANISM: Artificial Sequence
<220> FEATURE:
<223> OTHER INFORMATION: Synthetic Construct
```

-continued

<400> SEQUENCE: 930

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 931
<211> LENGTH: 755
<212> TYPE: PRT
<213> ORGANISM: Artificial Sequence
<220> FEATURE:
<223> OTHER INFORMATION: Synthetic Construct

<400> SEQUENCE: 931

Met Ala Arg Lys Leu Ser Val Ile Leu Ile Leu Thr Phe Ala Leu Ser
1               5                   10                  15

Val Thr Asn Pro Leu His Glu Leu Lys Ala Ala Ala Phe Pro Gln Thr
            20                  25                  30

Thr Glu Lys Ile Ser Pro Asn Trp Glu Ser Gly Ile Asn Val Asp Leu
        35                  40                  45

Ala Ile Ser Thr Arg Gln Tyr His Leu Gln Gln Leu Phe Tyr Arg Tyr
    50                  55                  60

Gly Glu Asn Asn Ser Leu Ser Val Glu Gly Phe Arg Lys Leu Leu Gln
65                  70                  75                  80

Asn Ile Gly Ile Asp Lys Ile Lys Arg Ile His Ile His His Asp His
                85                  90                  95

Asp His His Ser Asp His Glu His Ser Asp His Glu Arg His Ser
            100                 105                 110

Asp His Glu His His Ser Glu His Glu His Ser Asp His Asp His
        115                 120                 125

His Ser His His Asn His Ala Ala Ser Gly Lys Asn Lys Arg Lys Ala

```
                130                 135                 140
Leu Cys Pro Asp His Asp Ser Asp Ser Ser Gly Lys Asp Pro Arg Asn
145                 150                 155                 160

Ser Gln Gly Lys Gly Ala His Arg Pro Glu His Ala Ser Gly Arg Arg
                165                 170                 175

Asn Val Lys Asp Ser Val Ser Ala Ser Glu Val Thr Ser Thr Val Tyr
                180                 185                 190

Asn Thr Val Ser Glu Gly Thr His Phe Leu Glu Thr Ile Glu Thr Pro
                195                 200                 205

Arg Pro Gly Lys Leu Phe Pro Lys Asp Val Ser Ser Thr Pro Pro
210                 215                 220

Ser Val Thr Ser Lys Ser Arg Val Ser Arg Leu Ala Gly Arg Lys Thr
225                 230                 235                 240

Asn Glu Ser Val Ser Glu Pro Arg Lys Gly Phe Met Tyr Ser Arg Asn
                245                 250                 255

Thr Asn Glu Asn Pro Gln Glu Cys Phe Asn Ala Ser Lys Leu Leu Thr
                260                 265                 270

Ser His Gly Met Gly Ile Gln Val Pro Leu Asn Ala Thr Glu Phe Asn
                275                 280                 285

Tyr Leu Cys Pro Ala Ile Ile Asn Gln Ile Asp Ala Arg Ser Cys Leu
                290                 295                 300

Ile His Thr Ser Glu Lys Lys Ala Glu Ile Pro Pro Lys Thr Tyr Ser
305                 310                 315                 320

Leu Gln Ile Ala Trp Val Gly Phe Ile Ala Ile Ser Ile Ile Ser
                325                 330                 335

Phe Leu Ser Leu Leu Gly Val Ile Leu Val Pro Leu Met Asn Arg Val
                340                 345                 350

Phe Phe Lys Phe Leu Leu Ser Phe Leu Val Ala Leu Ala Val Gly Thr
                355                 360                 365

Leu Ser Gly Asp Ala Phe Leu His Leu Leu Pro His Ser His Ala Ser
370                 375                 380

His His His Ser His Ser His Glu Glu Pro Ala Met Glu Met Lys Arg
385                 390                 395                 400

Gly Pro Leu Phe Ser His Leu Ser Ser Gln Asn Ile Glu Glu Ser Ala
                405                 410                 415

Tyr Phe Asp Ser Thr Trp Lys Gly Leu Thr Ala Leu Gly Gly Leu Tyr
                420                 425                 430

Phe Met Phe Leu Val Glu His Val Leu Thr Leu Ile Lys Gln Phe Lys
                435                 440                 445

Asp Lys Lys Lys Lys Asn Gln Lys Lys Pro Glu Asn Asp Asp Asp Val
450                 455                 460

Glu Ile Lys Lys Gln Leu Ser Lys Tyr Glu Ser Gln Leu Ser Thr Asn
465                 470                 475                 480

Glu Glu Lys Val Asp Thr Asp Asp Arg Thr Glu Gly Tyr Leu Arg Ala
                485                 490                 495

Asp Ser Gln Glu Pro Ser His Phe Asp Ser Gln Gln Pro Ala Val Leu
                500                 505                 510

Glu Glu Glu Glu Val Met Ile Ala His Ala His Pro Gln Glu Val Tyr
                515                 520                 525

Asn Glu Tyr Val Pro Arg Gly Cys Lys Asn Lys Cys His Ser His Phe
                530                 535                 540

His Asp Thr Leu Gly Gln Ser Asp Asp Leu Ile His His His His Asp
545                 550                 555                 560
```

-continued

```
Tyr His His Ile Leu His His His His Gln Asn His His Pro His
                565                 570                 575

Ser His Ser Gln Arg Tyr Ser Arg Glu Leu Lys Asp Ala Gly Val
            580                 585                 590

Ala Thr Leu Ala Trp Met Val Ile Met Gly Asp Gly Leu His Asn Phe
        595                 600                 605

Ser Asp Gly Leu Ala Ile Gly Ala Ala Phe Thr Glu Gly Leu Ser Ser
    610                 615                 620

Gly Leu Ser Thr Ser Val Ala Val Phe Cys His Glu Leu Pro His Glu
625                 630                 635                 640

Leu Gly Asp Phe Ala Val Leu Leu Lys Ala Gly Met Thr Val Lys Gln
                645                 650                 655

Ala Val Leu Tyr Asn Ala Leu Ser Ala Met Leu Ala Tyr Leu Gly Met
                660                 665                 670

Ala Thr Gly Ile Phe Ile Gly His Tyr Ala Glu Asn Val Ser Met Trp
            675                 680                 685

Ile Phe Ala Leu Thr Ala Gly Leu Phe Met Tyr Val Ala Leu Val Asp
690                 695                 700

Met Val Pro Glu Met Leu His Asn Asp Ala Ser Asp His Gly Cys Ser
705                 710                 715                 720

Arg Trp Gly Tyr Phe Phe Leu Gln Asn Ala Gly Met Leu Leu Gly Phe
                725                 730                 735

Gly Ile Met Leu Leu Ile Ser Ile Phe Glu His Lys Ile Val Phe Arg
                740                 745                 750

Ile Asn Phe
        755

<210> SEQ ID NO 932
<211> LENGTH: 449
<212> TYPE: PRT
<213> ORGANISM: Artificial Sequence
<220> FEATURE:
<223> OTHER INFORMATION: Synthetic Construct

<400> SEQUENCE: 932

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 933
<211> LENGTH: 219
<212> TYPE: PRT
<213> ORGANISM: Artificial Sequence
<220> FEATURE:
<223> OTHER INFORMATION: Synthetic Construct

<400> SEQUENCE: 933

Asp Val Val Met Thr Gln Ser Pro Leu Ser Leu Pro Val Thr Leu Gly
1               5                   10                  15
Gln Pro Ala Ser Ile Ser Cys Arg Ser Ser Gln Ser Leu Leu His Ser
            20                  25                  30
Ser Gly Asn Thr Tyr Leu Glu Trp Tyr Gln Gln Arg Pro Gly Gln Ser
        35                  40                  45
Pro Arg Pro Leu Ile Tyr Lys Ile Ser Thr Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 934
<211> LENGTH: 120
<212> TYPE: PRT
<213> ORGANISM: Artificial Sequence
<220> FEATURE:
<223> OTHER INFORMATION: Synthetic Construct

<400> SEQUENCE: 934

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
                20                  25                  30

Tyr Met His Trp Val Arg Gln Ala Pro Gly Gln Gly Leu Glu Trp Met
            35                  40                  45

Gly Trp Ile Asp Pro Glu Asn Gly Asp Thr Glu Tyr Gly Pro Lys Phe
        50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser
        115                 120

<210> SEQ ID NO 935
<211> LENGTH: 112
<212> TYPE: PRT
<213> ORGANISM: Artificial Sequence
<220> FEATURE:
<223> OTHER INFORMATION: Synthetic Construct

<400> SEQUENCE: 935

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
                20                  25                  30

```
Ser Gly Asn Thr Tyr Leu Glu Trp Tyr Gln Gln Arg Pro Gly Gln Ser
         35                  40                  45

Pro Arg Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 936
<211> LENGTH: 5
<212> TYPE: PRT
<213> ORGANISM: Artificial Sequence
<220> FEATURE:
<223> OTHER INFORMATION: Synthetic Construct

<400> SEQUENCE: 936

Asp Tyr Tyr Met His
1               5

<210> SEQ ID NO 937
<211> LENGTH: 17
<212> TYPE: PRT
<213> ORGANISM: Artificial Sequence
<220> FEATURE:
<223> OTHER INFORMATION: Synthetic Construct

<400> SEQUENCE: 937

Trp Ile Asp Pro Glu Asn Gly Asp Thr Glu Tyr Gly Pro Lys Phe Gln
1               5                   10                  15

Gly

<210> SEQ ID NO 938
<211> LENGTH: 11
<212> TYPE: PRT
<213> ORGANISM: Artificial Sequence
<220> FEATURE:
<223> OTHER INFORMATION: Synthetic Construct

<400> SEQUENCE: 938

His Asn Ala His Tyr Gly Thr Trp Phe Ala Tyr
1               5                   10

<210> SEQ ID NO 939
<211> LENGTH: 16
<212> TYPE: PRT
<213> ORGANISM: Artificial Sequence
<220> FEATURE:
<223> OTHER INFORMATION: Synthetic Construct

<400> SEQUENCE: 939

Arg Ser Ser Gln Ser Leu Leu His Ser Ser Gly Asn Thr Tyr Leu Glu
1               5                   10                  15

<210> SEQ ID NO 940
<211> LENGTH: 7
<212> TYPE: PRT
<213> ORGANISM: Artificial Sequence
<220> FEATURE:
<223> OTHER INFORMATION: Synthetic Construct

<400> SEQUENCE: 940
```

```
Lys Ile Ser Thr Arg Phe Ser
1               5
```

<210> SEQ ID NO 941
<211> LENGTH: 9
<212> TYPE: PRT
<213> ORGANISM: Artificial Sequence
<220> FEATURE:
<223> OTHER INFORMATION: Synthetic Construct

<400> SEQUENCE: 941

```
Phe Gln Gly Ser His Val Pro Tyr Thr
1               5
```

<210> SEQ ID NO 942
<211> LENGTH: 8
<212> TYPE: PRT
<213> ORGANISM: Artificial Sequence
<220> FEATURE:
<223> OTHER INFORMATION: Synthetic Construct

<400> SEQUENCE: 942

```
Lys Gly Ala His Arg Pro Glu His
1               5
```

<210> SEQ ID NO 943
<211> LENGTH: 120
<212> TYPE: PRT
<213> ORGANISM: Artificial Sequence
<220> FEATURE:
<223> OTHER INFORMATION: Synthetic Construct

<400> SEQUENCE: 943

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120
```

<210> SEQ ID NO 944
<211> LENGTH: 7
<212> TYPE: PRT
<213> ORGANISM: Artificial Sequence
<220> FEATURE:
<223> OTHER INFORMATION: Synthetic Construct

<400> SEQUENCE: 944

```
Thr Ser Gly Met Gly Val Gly
1               5
```

<210> SEQ ID NO 945

```
<211> LENGTH: 16
<212> TYPE: PRT
<213> ORGANISM: Artificial Sequence
<220> FEATURE:
<223> OTHER INFORMATION: Synthetic Construct

<400> SEQUENCE: 945

His Ile Trp Trp Asp Asp Asp Lys Arg Tyr Asn Pro Ala Leu Lys Ser
1               5                   10                  15

<210> SEQ ID NO 946
<211> LENGTH: 10
<212> TYPE: PRT
<213> ORGANISM: Artificial Sequence
<220> FEATURE:
<223> OTHER INFORMATION: Synthetic Construct

<400> SEQUENCE: 946

Met Glu Leu Trp Ser Tyr Tyr Phe Asp Tyr
1               5                   10

<210> SEQ ID NO 947
<211> LENGTH: 107
<212> TYPE: PRT
<213> ORGANISM: Artificial Sequence
<220> FEATURE:
<223> OTHER INFORMATION: Synthetic Construct

<400> SEQUENCE: 947

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Val Ala Val Tyr Tyr Cys Phe Gln Gly Ser Val Tyr Pro Phe Thr
                85                  90                  95

Phe Gly Gln Gly Thr Lys Leu Glu Ile Lys Arg
            100                 105

<210> SEQ ID NO 948
<211> LENGTH: 10
<212> TYPE: PRT
<213> ORGANISM: Artificial Sequence
<220> FEATURE:
<223> OTHER INFORMATION: Synthetic Construct

<400> SEQUENCE: 948

Ser Ala Ser Ser Ser Val Ser Tyr Met His
1               5                   10

<210> SEQ ID NO 949
<211> LENGTH: 7
<212> TYPE: PRT
<213> ORGANISM: Artificial Sequence
<220> FEATURE:
<223> OTHER INFORMATION: Synthetic Construct

<400> SEQUENCE: 949

Asp Thr Ser Lys Leu Ala Ser
```

<210> SEQ ID NO 950
<211> LENGTH: 9
<212> TYPE: PRT
<213> ORGANISM: Artificial Sequence
<220> FEATURE:
<223> OTHER INFORMATION: Synthetic Construct

<400> SEQUENCE: 950

Phe Gln Gly Ser Val Tyr Pro Phe Thr
1               5

<210> SEQ ID NO 951
<211> LENGTH: 450
<212> TYPE: PRT
<213> ORGANISM: Artificial Sequence
<220> FEATURE:
<223> OTHER INFORMATION: Synthetic Construct

<400> SEQUENCE: 951

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

-continued

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 952
<211> LENGTH: 213
<212> TYPE: PRT
<213> ORGANISM: Artificial Sequence
<220> FEATURE:
<223> OTHER INFORMATION: Synthetic Construct

<400> SEQUENCE: 952

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Val Ala Val Tyr Tyr Cys Phe Gln Gly Ser Val Tyr Pro Phe Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

-continued

```
Cys Glu Val Thr His Gln Gly Leu Ser Ser Pro Val Thr Lys Ser Phe
        195                 200                 205
Asn Arg Gly Glu Cys
    210

<210> SEQ ID NO 953
<211> LENGTH: 4
<212> TYPE: PRT
<213> ORGANISM: Artificial Sequence
<220> FEATURE:
<223> OTHER INFORMATION: Synthetic Construct

<400> SEQUENCE: 953

Gly Lys Gly Gly
```

SELECTIVE DRUG RELEASE FROM INTERNALIZED CONJUGATES OF BIOLOGICALLY ACTIVE COMPOUNDS

CROSS-REFERENCE TO RELATED APPLICATIONS

This application claims the benefit of priority to U.S. Provisional 63/163,017, filed Mar. 18, 2021, U.S. Provisional 63/163,012, filed Mar. 18, 2021, U.S. Provisional 63/162,653, filed Mar. 18, 2021, U.S. Provisional 63/162,660, filed Mar. 18, 2021, U.S. Provisional 63/162,773, filed Mar. 18, 2021, U.S. Provisional 63/162,776, filed Mar. 18, 2021, U.S. Provisional 63/162,781, filed Mar. 18, 2021, U.S. Provisional 63/162,786, filed Mar. 18, 2021, and U.S. Provisional 63/221,295, filed Jul. 13, 2021, all of which are incorporated by reference herein in their entireties and for all purposes

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 761682005940SEQLIST.TXT, date recorded: Mar. 16, 2022, size: 464 KB).

BACKGROUND OF THE INVENTION

The invention relates to Ligand Drug Conjugate (LDC) compounds and compositions thereof, including Antibody Drug Conjugates (ADCs), that have improved selectivity for targeted cells in comparison to non-targeted cells. The invention also relates to Drugs and Drug-Linkers and compositions thereof, which are useful as part of the Ligand Drug Conjugate compounds. The invention also relates to novel anti-GPNMB, anti-CD228, anti anti-αvβ6, anti-CD30, anti-LIV1, and anti-CD19 antibody-drug conjugates and methods of using such anti-GPNMB, anti-CD228, anti-αvβ6, anti-CD30, anti-LIV1, and anti-CD19 antibody-drug conjugates to treat cancer.

Traditional Ligand Drug Conjugates exhibit biological activity towards targeted cells, which display the targeted moiety that is recognized by the Ligand Unit of the Conjugate, by binding to the targeted moiety and then entering into the cell by internalization of the bound Conjugate. Selectivity for the targeted cells over non-targeted cells is primarily achieved by a traditional Ligand Drug Conjugate as a result of the targeted moiety being present in greater abundance on the targeted cells in comparison to non-targeted normal cells, which are cells not intended to be acted upon by the Conjugate. When conditional release of a conjugated compound, which is cytotoxic in free form, is to be affected by an intracellular protease, internalization of bound Conjugate is followed by enzymatic processing of a peptide-based Linker Unit of the Conjugate.

Reduction in premature release of the cytotoxic compound, which otherwise would cause undesired side effects, from traditional dipeptide-based Ligand Drug Conjugates is accomplished by optimizing for selectivity for a specific lysosomal protease that is believed to be upregulated in cancer cells. As the protease responsible for intracellular processing of the traditional Ligand Drug Conjugates is common to all cells, selectivity for the targeted cells is primarily due to the greater abundance of the targeted moiety on the cells intended to be acted upon by the Conjugate, notwithstanding the differing intracellular activity levels of the processing protease within targeted cancer cells and non-targeted normal cells. However, that approach does not take into consideration possible exposure differences of the released cytotoxic compound between tumor and normal tissue, which are presently exploited by the Ligand Drug Conjugates of the present invention.

Thus, the dipeptide sequences of traditional Ligand Drug Conjugates, which were designed to be selectively acted upon by an intracellular protease upregulated in cancer cells of the tumor tissue, are still capable of being acted upon by proteases confined within normal tissue. Such action can occur either within the microenvironment of the normal tissue or within cells of the normal tissue after immunologically specific or non-specific uptake into these cells, resulting in on-target or off-target toxicity, respectively. Those toxicities are a more acute problem to be solved for targeted delivery of highly cytotoxic compounds. It is therefore believed a Ligand Drug Conjugate with an improved peptide sequence that provides lower exposure to normal tissue in comparison to a traditional dipeptide-based Ligand Drug Conjugates, and hence reduces exposure to a cytotoxic compound released therefrom, while maintaining the efficacy provided by these traditional conjugates, would improve tolerability to therapy.

It is further believed that a Ligand Drug Conjugate having an improved peptide sequence that is more prone to proteolysis by tumor tissue over proteolysis by normal tissue in comparison to proteolysis of a traditional dipeptide-based Ligand Drug Conjugate by these tissues would also decrease exposure to the released cytotoxic compound, which would contribute to improving tolerability to therapy. Determining those proteolytic differences using tissue homogenates should capture those differences driven by the microenvironment of these tissues and/or subsequent to cellular internalization.

To provide the solution to that problem in the art, disclosed herein are Ligand Drug Conjugates having peptide-based Linker Units whose sequences result in more selective exposure of targeted cells of the tumor tissue to the cytotoxic compound released from the Conjugate in comparison to exposure of cells of normal tissue to the free cytotoxin such that tolerability to the Conjugate is improved while retaining the efficacy of the traditional dipeptide-based Conjugates in treating cancer in a mammalian subject. That difference in exposure may result from greater selectivity for proteolysis of Ligand Drug Conjugates having the selectivity conferring peptide sequences within tumor tissue over proteolysis within normal tissue in comparison to proteolysis of the traditional dipeptide-based Conjugate. Because altering the peptide sequence may also affect the physiochemical properties of the Conjugate compound, greater exposure from improved biodistribution into tumor tissue and not normal tissue and/or improved disposition once distributed into these tissues, which preferentially retains the Conjugate compound in tumor tissue and/or preferentially eliminates the Conjugate compound from normal tissue, respectively, can occur. Those biodistribution effects may even become the dominant factors over preferential proteolysis, which could be difficult to observe in vivo.

Thus, Conjugate compounds having peptide sequences providing enhanced exposure of released free cytotoxic compound to tumor tissue in comparison to normal tissue should exhibit reduced undesired toxicities due to the peptide sequences being overall less susceptible to proteolysis within normal tissue or cells thereof in comparison to those of the tumor and/or from improved pharmacokinetic properties for Conjugate compounds incorporating those peptide sequences that favor tumor tissue over normal tissue.

The Ligand Drug Conjugates of the present invention therefore have two levels of selectivity for targeted cells over non-targeted normal cells: (1) selective entry into targeted cells and (2) decreased exposure of normal tissue in comparison to tumor tissue to the Conjugate compound. From that second level of selectivity, reduction in normal tissue toxicities is expected to provide reduced adverse events associated with conventional targeted therapies.

GPNMB, which is also known as glycoprotein non-metastatic melanoma protein B, is a transmembrane protein found on the cell surface of certain tumor cells. GPNMB is upregulated in multiple cancers, including melanoma, soft tissue tumors, hepatocellular carcinoma, breast cancer, stomach cancer, non-small cell lung cancer (NSCLC), head-and-neck cancer, ovarian, and pancreatic cancer.

CD228, which is also known as melanotransferrin, MELTF, p97 and MF12, is a glycosylphosphatidylinositol-anchored glycoprotein and was first identified as a 97-kDa cell-surface marker for malignant melanoma cells. CD228 is overexpressed on a majority of clinical melanoma isolates and is also observed on many human carcinomas. CD228 has been shown to be expressed in a variety of cancers.

αvβ6, which is also known as alpha-v beta-6, is a cell adhesion receptor that binds extracellular matrix proteins such as fibronectin. αvβ6 is composed of an alpha v subunit and a beta 6 subunit, and is upregulated in multiple cancers, including non-small cell lung cancer (NSCLC). NSCLC is the most common type of lung cancer. In the past year, over 200,000 people were diagnosed with lung cancer, which is the leading cause of cancer death.

CD30 is a membrane glycoprotein and member of the TNF-receptor superfamily that is upregulated in various cancers, autoimmune, and other infectious diseases. CD30 is a proven marker of malignant cells in Hodgkin's disease and anaplastic large cell lymphoma, a subset of non-Hodgkin's lymphomas.

LIV1 is a member of the LZT (LIV-1-ZIP Zinc Transporters) subfamily of zinc transporter proteins. Taylor et al., *Biochim. Biophys. Acta* 1611:16-30 (2003). Computer analysis of the LIV1 protein reveals a potential metalloprotease motif, fitting the consensus sequence for the catalytic zinc-binding site motif of the zinc metalloprotease. LIV1 mRNA is primarily expressed in breast, prostate, pituitary gland and brain tissue. The LIV1 protein has also been implicated in certain cancerous conditions, e.g., breast cancer and prostate cancer. The detection of LIV1 is associated with estrogen receptor-positive breast cancer, McClelland et al., *Br. J. Cancer* 77:1653-1656 (1998), and the metastatic spread of these cancers to the regional lymph nodes. Manning et al., *Eur. J Cancer* 30A:675-678 (1994).

CD19 is a pan-B cell membrane glycoprotein that is expressed from early stages of pre-B cell development through terminal differentiation, regulating B lymphocyte development and function. Expression of CD19 was identified on most cancers of lymphoid origin, on the vast majority of Non-Hodgkin lymphoma (NHL) and on leukemias, including Chronic Lymphocytic Leukemia (CLL), Acute Lymphoblastic Leukemia (ALL) and Waldenstrom's Macroglobulinemia (WM).

There is a need for improved treatments for each of these aforementioned diseases.

All references cited herein, including patent applications, patent publications, and scientific literature, are herein incorporated by reference in their entirety, as if each individual reference were specifically and individually indicated to be incorporated by reference.

SUMMARY OF THE INVENTION

One principle embodiment of the invention provides a Ligand Drug Conjugate composition represented by Formula 1:

L-[LU-D']$_p$     (1)

or a salt thereof, in particular a pharmaceutically acceptable salt, wherein
L is a Ligand Unit;
LU is a Linker Unit; and
D' represents from 1 to Drug Units (D) in each drug linker moiety of formula -LU-D'; and
subscript p is a number from 1 to 12, from 1 to 10 or from 1 to 8 or is about 4 or about 8,
wherein the Ligand Unit is of an antibody, or an antigen-binding fragment of an antibody, that is capable of selective binding to an antigen of tumor tissue for subsequent release of the Drug Unit as free cytotoxic compound,
wherein the drug linker moiety of formula -LU-D' in each of the Ligand Drug Conjugate compounds of the composition has the structure of Formula 1A:

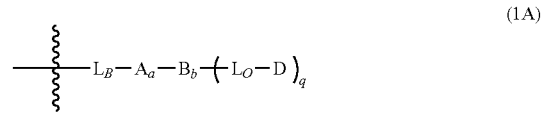

(1A)

or a salt thereof, in particular a pharmaceutically acceptable salt,
wherein the wavy line indicates covalent attachment to L;
D is the Drug Unit of the cytotoxic compound;
L$_B$ is a ligand covalent binding moiety;
A is a first optional Stretcher Unit;
subscript a is 0 or 1 indicating the absence or presence of A, respectively;
B is an optional Branching Unit;
subscript b is 0 or 1, indicating the absence or presence of B, respectively;
L$_O$ Is a secondary linker moiety, wherein the secondary linker has the formula of;

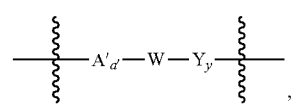

wherein the wavy line adjacent to Y indicates the site of covalent attachment of L$_O$ to the Drug Unit and the wavy line adjacent to A' indicates the site of covalent attachment to the remainder of the drug linker moiety;
A' is a second optional Stretcher Unit, which in the absence of B becomes a subunit of A,
subscript a' is 0 or 1, indicating the absence or presence of A', respectively,
W is a Peptide Cleavable Unit, wherein the Peptide Cleavable Unit is a contiguous sequence of up to 12 (e.g., 3-12 or 3-10) amino acids, wherein the sequence is comprised of a selectivity conferring tripeptide that provides improved selectivity for exposure of tumor tissue over normal tissue to free cytotoxic compound released from the Ligand Drug Conjugate compounds of the composition in comparison to the cytotoxic compound released from Ligand Drug Conjugate compounds of a comparator Ligand-Drug Conjugate composition in which the peptide sequence of its Peptide Cleavable Unit is the dipeptide -valine-citrulline- or -valine-alanine-;

wherein the tumor and normal tissues are of rodent species and wherein the Formula 1 composition provides said improved exposure selectivity demonstrated by:

retaining efficacy in a tumor xenograft model of the comparator Ligand-Drug Conjugate conjugate composition when administered at the same effective amount and dose schedule previously determined for the comparator Ligand-Drug Conjugate conjugate composition, and showing a reduction in plasma concentration of the free cytotoxic compound released from the Ligand Drug Conjugate compounds of the composition, and/or preservation of normal cells in tissue when administered at the same effective amount and dose schedule as in the tumor xenograft model to a non-tumor bearing rodent in comparison to the equivalent (e.g., same) administration of the comparator Ligand-Drug Conjugate composition in which the Ligand Units of both conjugate compositions are replaced by a non-binding antibody, wherein cytotoxicity to cells in human tissue of the same type as the normal cells in the tissue of the non-tumor bearing rodent is responsible at least in part to an adverse event in a human subject to whom is administered a therapeutically effective amount of the comparator conjugate composition;

Y is a self-immolative Spacer Unit; and subscript y is 0, 1 or 2 indicating the absence or presence of 1 or 2 of Y, respectively; subscript q is an integer ranging from 1 to 4 or 1 to 3, provided that subscript q is 1 when subscript b is 0 and subscript q is 2, 3 or 4 when subscript b is 1; and wherein the Ligand Drug Conjugate compounds of the composition have the structure of Formula 1 in which subscript p is replaced by subscript p', wherein subscript p' is an integer from 1 to 12, 1 to 10 or 1 to 8 or is 4 or 8.

A related principle embodiment provides for a Drug Linker compound of Formula I:

LU'-(D') (I)

or a salt thereof, in particular a pharmaceutically acceptable salt thereof, wherein LU' is capable of providing a covalent bond between L and LU of Formula 1, and therefore is sometimes referred to as a Linker Unit precursor; and D' represents from 1 to 4 Drug Units, wherein the Drug Linker compound is further defined by the structure of Formula IA:

(IA)

wherein $L_B'$ is capable of transformation to $L_B$ of Formula 1A thereby forming a covalent bond to L of Formula 1, and therefore is sometimes referred to a ligand covalent binding precursor moiety, and the remaining variable groups of Formula IA are as defined for Formula 1A.

In some embodiments, provided herein is a Ligand Drug Conjugate composition represented by Formula 1:

L-[LU-D']$_p$ (1)

or a pharmaceutically acceptable salt thereof, wherein
L is a Ligand Unit;
LU is a Linker Unit;
D' represents from 1 to 4 Drug Units (D) in each drug linker moiety of formula -LU-D'; and
subscript p is a number from 1 to 12, from 1 to 10 or from 1 to 8 or is about 4 or about 8,
wherein the Ligand Unit is from an antibody or an antigen-binding fragment of an antibody that is capable of selective binding to an antigen of tumor tissue for subsequent release of the Drug Unit(s) as free drug,
wherein the drug linker moiety of formula -LU-D' in each of the Ligand Drug Conjugate compounds of the composition has the structure of Formula 1A:

(1A)

or a salt thereof, in particular a pharmaceutically acceptable salt,
wherein the wavy line indicates covalent attachment to L;
D is the Drug Unit;
$L_B$ is a ligand covalent binding moiety;
A is a first optional Stretcher Unit;
subscript a is 0 or 1, indicating the absence or presence of A, respectively;
B is an optional Branching Unit;
subscript b is 0 or 1, indicating the absence or presence of B, respectively;
$L_O$ is a secondary linker moiety, wherein the secondary linker has the formula of;

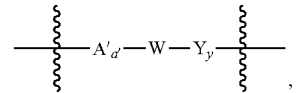

wherein the wavy line adjacent to Y indicates the site of covalent attachment of $L_O$ to the Drug Unit and the wavy line adjacent to A' indicates the site of covalent attachment to the remainder of the drug linker moiety;
A' is a second optional Stretcher Unit, which in the absence of B becomes a subunit of A,
subscript a' is 0 or 1, indicating the absence or presence of A', respectively,
W is a Peptide Cleavable Unit, wherein the Peptide Cleavable Unit comprises a tripeptide having the sequence -P3-P2-P1-, wherein P1, P2, and P3 are each an amino acid, wherein:
a first one of the amino acids P1, P2, or P3 is negatively charged or is serine;
a second one of the amino acids P1, P2, or P3 has an aliphatic side chain with hydrophobicity no greater than that of leucine, or is glycine or serine or proline; and
a third one of the amino acids P1, P2, or P3 has hydrophobicity lower than that of leucine, or is proline, wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3, provided that -P3-P2-P1- is not -Glu-Val-Cit- or -Asp-Val-Cit-;

Y is a self-immolative Spacer Unit;

subscript y is 0, 1 or 2 indicating the absence or presence of 1 or 2 of Y, respectively; and subscript q is an integer ranging from 1 to 4, provided that subscript q is 1 when subscript b is 0 and subscript q is 2, 3 or 4 when subscript b is 1; and wherein the Ligand Drug Conjugate compounds of the composition have the structure of Formula 1 in which subscript p is replaced by subscript p', wherein subscript p' is independently an integer from 1 to 12, 1 to 10 or 1 to 8 or is 4 or 8.

In some embodiments, a first one of the amino acids P1, P2, or P3 is negatively charged; a second one of the amino acids P1, P2, or P3 has an aliphatic side chain with hydrophobicity no greater than that of leucine; and a third one of the amino acids P1, P2, or P3 has hydrophobicity lower than that of leucine.

In some embodiments, provided herein is the Ligand Drug Conjugate composition of Formula 1, wherein the Ligand Drug Conjugate compounds in the Ligand Drug Conjugate composition predominately have drug linker moieties of Formula 1H:

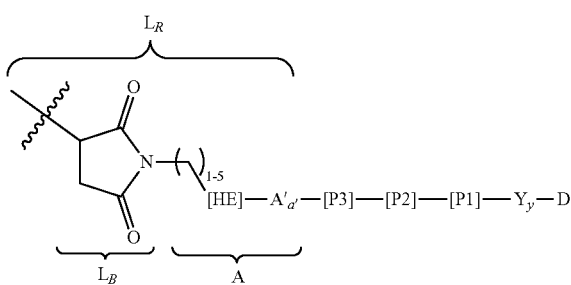

(Formula 1H)

or pharmaceutically acceptable salts thereof, and optionally having a minority of Ligand Drug Conjugate compounds in which one or more of the drug linker moieties in each of such compounds has its succinimide ring in hydrolyzed form and wherein HE is a Hydrolysis Enhancing Unit;

A' is a subunit, when present, of the indicated first Stretcher Unit (A); subscript a' is 0 or 1, indicating the absence or presence of A'; and the wavy line indicates the site of covalent binding to a sulfur atom of the Ligand Unit.

In some embodiments, which may be combined with any of the preceding embodiments, provided herein is the Ligand Drug Conjugate composition wherein HE is —(C=O).

In some embodiments, which may be combined with any of the preceding embodiments, provided herein is the Ligand Drug Conjugate composition wherein —$Y_y$-D has the structure of:

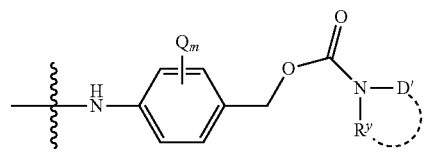

wherein —N($R^y$)D' represents D, wherein D' is the remainder of D;

the wavy line indicates the site of covalent attachment to P1;

the dotted line indicates optional cyclization of R to D';

$R^y$ is optionally substituted $C_1$-$C_6$ alkyl in absence of cyclization to D' or optionally substituted $C_1$-$C_6$ alkylene when cyclized to D';

each Q is independently selected from the group consisting of —$C_1$-$C_8$ alkyl, —O—($C_1$-$C_8$ alkyl), halogen, nitro and cyano; and subscript m is 0, 1 or 2.

In some embodiments, which may be combined with any of the preceding embodiments, provided herein is the Ligand Drug Conjugate composition wherein D is a cytotoxic drug wherein the cytotoxic drug is a secondary amine-containing auristatin compound wherein the nitrogen atom of the secondary amine is the site of covalent attachment to the drug linker moiety and the secondary amine-containing auristatin compound has the structure of Formula $D_{F/E-3}$:

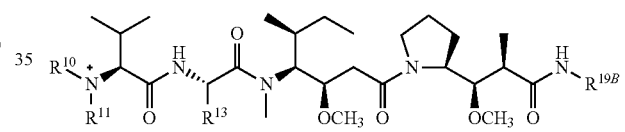

$D_{F/E-3}$ wherein the dagger indicates the site of covalent attachment of the nitrogen atom that provides the carbamate functional group;

one of $R^{10}$ and $R^{11}$ is hydrogen and the other is methyl;

$R^{13}$ is isopropyl or —$CH_2$—$CH(CH_3)_2$; and $R^{19B}$ is —$CH(CH_3)$—$CH(OH)$-Ph, —$CH(CO_2H)$—$CH(OH)$—$CH_3$, —$CH(CO_2H)$—$CH_2Ph$, —$CH(CH_2Ph)$-2-thiazolyl, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, —$CH(CH_2CH_2SCH_3)C(=O)NH$-quinol-3-yl, —$CH(CH_2Ph)C(=O)NH$-p-Cl-Ph, or $R^{19B}$ has the structure of

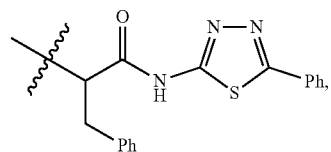

wherein the wavy line indicates covalent attachment to the remainder of the auristatin compound.

In some embodiments, which may be combined with any of the preceding embodiments, provided herein is the Ligand Drug Conjugate composition wherein the secondary amine-containing auristatin compound is monomethylauristatin E (MMAE) or monomethylauristatin F (MMAF).

In some embodiments, which may be combined with any of the preceding embodiments, provided herein is the Ligand Drug Conjugate composition wherein subscript q is 1 and the Ligand Drug Conjugate compounds in the Ligand Drug Conjugate composition predominately have drug linker moieties of Formula 1H-MMAE:

acids has an aliphatic side chain with hydrophobicity lower than that of leucine; and the other of the P2 and P1 amino acids is negatively charged. In some embodiments, the P3 amino acid is D-Leu or D-Ala. In some embodiments, one of the P2 or P1 amino acid has an aliphatic side chain with hydrophobicity no greater than that of valine, and the other (Formula 1H-MMAE)

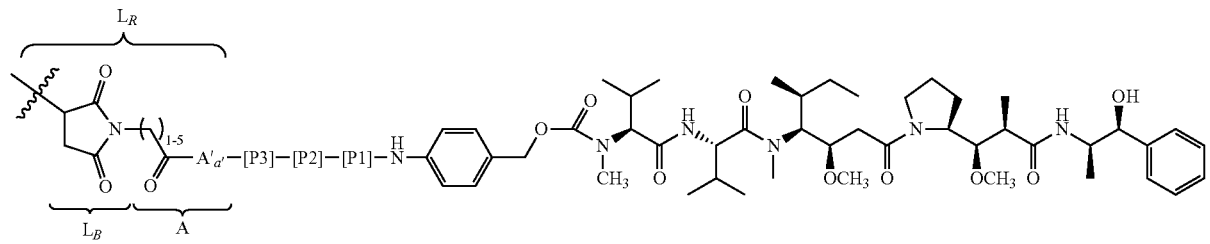

or a pharmaceutical acceptable salt thereof, and optionally having a minority of Ligand Drug Conjugate compounds in which one or more of the drug linker moieties in each of such compounds has its the succinimide ring in hydrolyzed form and wherein:
subscript a' is 0, and A' is absent; and
the wavy line indicates the site of covalent binding to a sulfur atom of the Ligand Unit.

In some embodiments, which may be combined with any of the preceding embodiments, provided herein is the Ligand Drug Conjugate composition wherein the Peptide Cleavable Unit is a tripeptide having the sequence -P3-P2-P1-, wherein P1, P2, and P3 are each an amino acid, wherein: the P3 amino acid of the tripeptide is in the D-amino acid configuration; one of the P2 and P1 amino of the P2 or P1 amino acid is negatively charged at plasma physiological pH. In some embodiments, P2 amino acid has an aliphatic side chain with hydrophobicity no greater than that of valine, and the P1 amino acid is negatively charged at plasma physiological pH. In some embodiments, -P2-P1- is -Ala-Glu- or -Ala-Asp-. In some embodiments, -P3-P2-P1- is -D-Leu-Ala-Asp-, -D-Leu-Ala-Glu-, -D-Ala-Ala-Asp-, or -D-Ala-Ala-Glu-. In some embodiments, the P3 amino acid is D-Leu or D-Ala, the P2 amino acid is Ala, Glu, or Asp, and the P1 amino acid is Ala, Glu, or Asp.

In some embodiments, provided herein is the Ligand Drug Conjugate composition wherein the compound has the structure of:

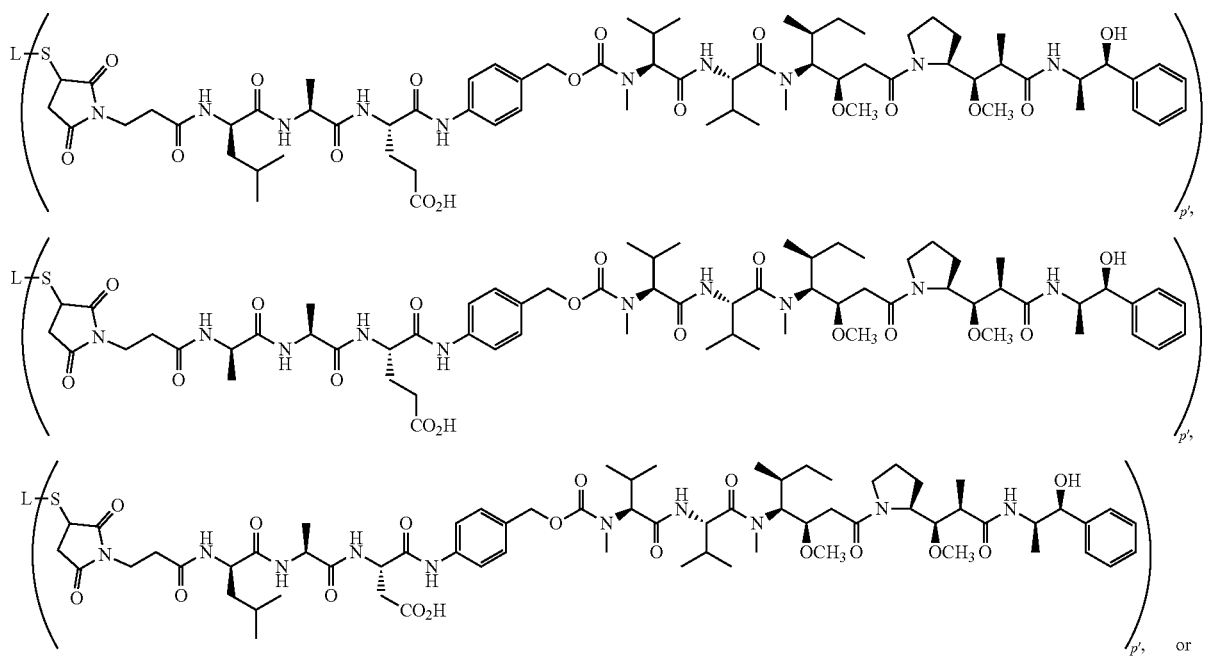

-continued

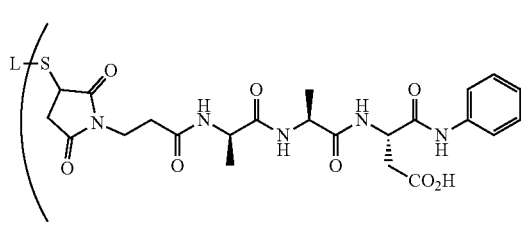 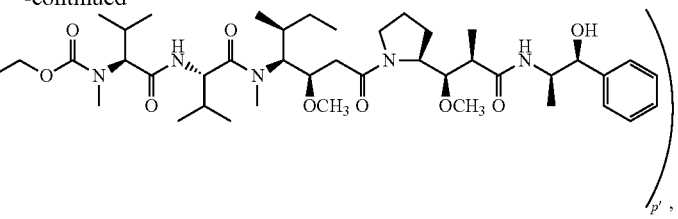

or a pharmaceutically acceptable salt thereof,
wherein L is a Ligand Unit, and subscript p' is an integer from 1 to 24.

In some embodiments, which may be combined with any of the preceding embodiments, provided herein is the Ligand Drug Conjugate composition wherein L is an antibody Ligand Unit of an intact antibody or an antigen-binding fragment thereof. In some embodiments, the intact antibody or fragment thereof is capable of selectively binding to a cancer cell antigen. In some embodiments, the intact antibody is a chimeric, humanized or human antibody, wherein the antibody is capable of selectively binding to a cancer cell antigen or the antibody is a non-binding control antibody thereby defining a non-binding control Conjugate composition.

In some embodiments, which may be combined with any of the preceding embodiments, provided herein is the Ligand Drug Conjugate composition wherein subscript p ranges from about 2 to about 12, or from about 2 to about 10, or from about 2 to about 8, in particular subscript p is about 2, about 4 or about 8.

In some embodiments, which may be combined with any of the preceding embodiments, provided herein are pharmaceutically acceptable formulations, wherein the formulation comprises an effective amount of a Ligand Drug Conjugate composition or an equivalent amount of a non-binding control Conjugate described herein and at least one pharmaceutically acceptable excipient. In some embodiments, the least one pharmaceutically acceptable excipient is a liquid carrier that provides a liquid formulation, wherein the liquid formulation is suitable for lyophilization or administration to a subject in need thereof. In some embodiments, the formulation is a solid from lyophilization or a liquid formulation described herein, wherein the at least one excipient of the solid formulation is a lyoprotectant.

In some embodiments, provided herein is a Drug Linker compound of Formula IA:

 (IA)

or a salt thereof, wherein
D is a Drug Unit;
$L_B'$ is a ligand covalent binding precursor moiety;
A is a first optional Stretcher Unit;
subscript a is 0 or 1, indicating the absence or presence of A, respectively;
B is an optional Branching Unit;
subscript b is 0 or 1, indicating the absence or presence of B, respectively;
$L_O$ is a secondary linker moiety, wherein the secondary linker has the formula of,

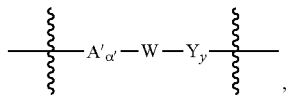

wherein the wavy line adjacent to Y indicates the site of covalent attachment of $L_O$ to the Drug Unit and the wavy line adjacent to A' indicates the site of covalent attachment to the remainder of the Drug Linker compound;

A' is a second optional Stretcher Unit, which in the absence of B becomes a subunit of A;
subscript a' is 0 or 1, indicating the absence or presence of A', respectively,
W is a Peptide Cleavable Unit, wherein the Peptide Cleavable Unit comprises a tripeptide having the sequence -P3-P2-P1-, wherein P1, P2, and P3 are each an amino acid, wherein:
a first one of the amino acids P1, P2, or P3 is negatively charged or is serine;
a second one of the amino acids P1, P2, or P3 has an aliphatic side chain with hydrophobicity no greater than that of leucine, or is glycine or serine or proline; and
a third one of the amino acids P1, P2, or P3 has hydrophobicity lower than that of leucine, or is proline,
wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
provided that -P3-P2-P1- is not -Glu-Val-Cit- or -Asp-Val-Cit-;
Y is a self-immolative Spacer Unit;
subscript y is 0, 1 or 2 indicating the absence or presence of 1 or 2 of Y, respectively; and
subscript q is an integer ranging from 1 to 4,
provided that subscript q is 1 when subscript b is 0 and subscript q is 2, 3 or 4 when subscript b is 1.

In some embodiments, a first one of the amino acids P1, P2, or P3 is negatively charged; a second one of the amino acids P1, P2, or P3 has an aliphatic side chain with hydrophobicity no greater than that of leucine; and a third one of the amino acids P1, P2, or P3 has hydrophobicity lower than that of leucine.

In some embodiments, provided herein is the Drug Linker compound of Formula IA, wherein the Drug Linker compound has the structure of Formula IH:

(Formula IH)

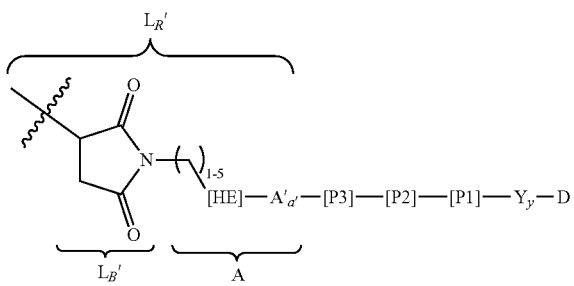

or salt thereof, wherein:
HE is a Hydrolysis Enhancing Unit; and
A' is a subunit, when present, of the indicated first Stretcher Unit (A); subscript a' is 0 or 1, indicating the absence or presence of A'.

In some embodiments, which may be combined with any of the preceding embodiments, provided herein is the Drug Linker compound wherein HE is —(C=O).

In some embodiments, which may be combined with any of the preceding embodiments, provided herein is the Drug Linker compound wherein —$Y_y$-D has the structure of:

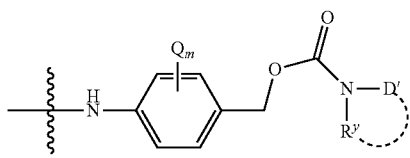

wherein —$N(R^y)D'$ represents D, wherein D' is the remainder of D;
the wavy line indicates the site of covalent attachment to P1;
the dotted line indicates optional cyclization of R to D';
$R^y$ is optionally substituted $C_1$-$C_6$ alkyl in absence of cyclization to D' or optionally substituted $C_1$-$C_6$ alkylene when cyclized to D';

each Q is independently selected from the group consisting of —$C_1$-$C_8$ alkyl, —O—($C_1$-$C_8$ alkyl), halogen, nitro and cyano; and
subscript m is 0, 1 or 2.

In some embodiments, which may be combined with any of the preceding embodiments, provided herein is the Drug Linker compound wherein D is a cytotoxic drug wherein the cytotoxic drug is a secondary amine-containing auristatin compound wherein the nitrogen atom of the secondary amine is the site of covalent attachment to the drug linker moiety and the secondary amine-containing auristatin compound has the structure of Formula $D_{F/E-3}$:

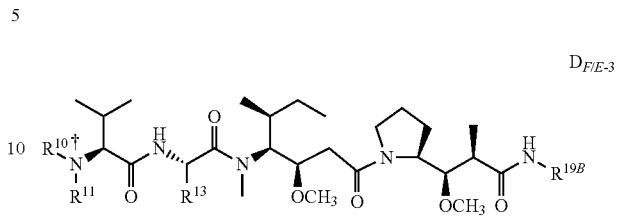

$D_{F/E-3}$ wherein the dagger indicates the site of covalent attachment of the nitrogen atom that provides the carbamate functional group;
one of $R^{10}$ and $R^{11}$ is hydrogen and the other is methyl;
$R^{13}$ is isopropyl or —$CH_2$—$CH(CH_3)_2$; and
$R^{19B}$ is —$CH(CH_3)$—$CH(OH)$-Ph, —$CH(CO_2H)$—$CH(OH)$—$CH_3$, —$CH(CO_2H)$—$CH_2Ph$, —$CH(CH_2Ph)$-2-thiazolyl, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, —$CH(CH_2CH_2SCH_3)C(=O)NH$-quinol-3-yl, —$CH(CH_2Ph)C(=O)NH$-p-Cl-Ph, or $R^{19B}$ has the structure of

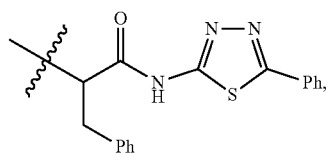 [SMILES: *C(Cc1ccccc1)C(=O)Nc1nnc(-c2ccccc2)s1]

wherein the wavy line indicates covalent attachment to the remainder of the auristatin compound.

In some embodiments, which may be combined with any of the preceding embodiments, provided herein is the Drug Linker compound wherein the secondary amine-containing auristatin compound is monomethylauristatin E (MMAE) or monomethylauristatin F (MMAF).

In some embodiments, which may be combined with any of the preceding embodiments, provided herein is the Drug Linker compound wherein the Drug Linker compound has the structure of Formula IH-MMAE:

(Formula IH-MMAE)

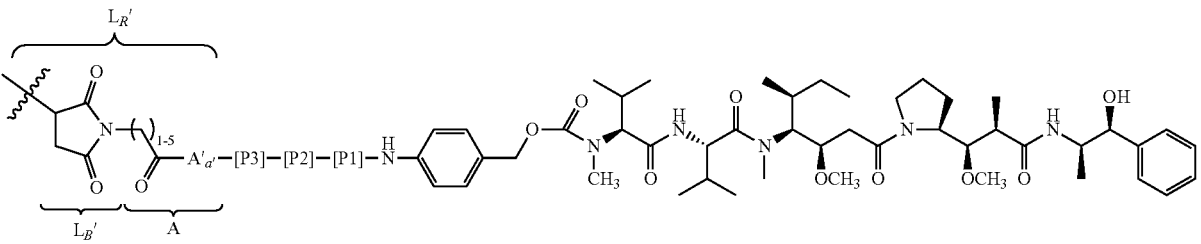

or a salt thereof, wherein
subscript a' is 0, and A' is absent.

In some embodiments, which may be combined with any of the preceding embodiments, provided herein is the Drug Linker compound wherein the Peptide Cleavable Unit is a tripeptide having the sequence -P3-P2-P1-, wherein P1, P2, and P3 are each an amino acid, wherein: the P3 amino acid of the tripeptide is in the D-amino acid configuration; one of the P2 and P1 amino acids has an aliphatic side chain with hydrophobicity lower than that of leucine; and the other of the P2 and P1 amino acids is negatively charged. In some embodiments, the P3 amino acid is D-Leu or D-Ala. In some embodiments, one of the P2 or P1 amino acid has an aliphatic side chain with hydrophobicity no greater than that of valine, and the other of the P2 or P1 amino acid is negatively charged at plasma physiological pH. In some embodiments, P2 amino acid has an aliphatic side chain with hydrophobicity no greater than that of valine, and the P1 amino acid is negatively charged at plasma physiological pH. In some embodiments, -P2-P1- is -Ala-Glu- or -Ala-Asp-. In some embodiments, -P3-P2-P1- is -D-Leu-Ala-Asp-, -D-Leu-Ala-Glu-, -D-Ala-Ala-Asp-, or -D-Ala-Ala-Glu-. In some embodiments, the P3 amino acid is D-Leu or D-Ala, the P2 amino acid is Ala, Glu, or Asp, and the P1 amino acid is Ala, Glu, or Asp.

In some embodiments, provided herein is the Drug Linker compound wherein the Drug Linker compound has the structure of:

subscript a is 0 or 1, indicating the absence or presence of A, respectively;

B is an optional Branching Unit;

subscript b is 0 or 1, indicating the absence or presence of B, respectively;

$L_O$ is a secondary linker moiety, wherein the secondary linker has the formula of,

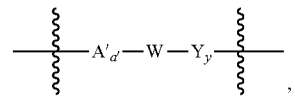

wherein the wavy line adjacent to Y indicates the site of covalent attachment of $L_O$ to the Drug Unit and the wavy line adjacent to A' indicates the site of covalent attachment to the remainder of the Drug Linker compound;

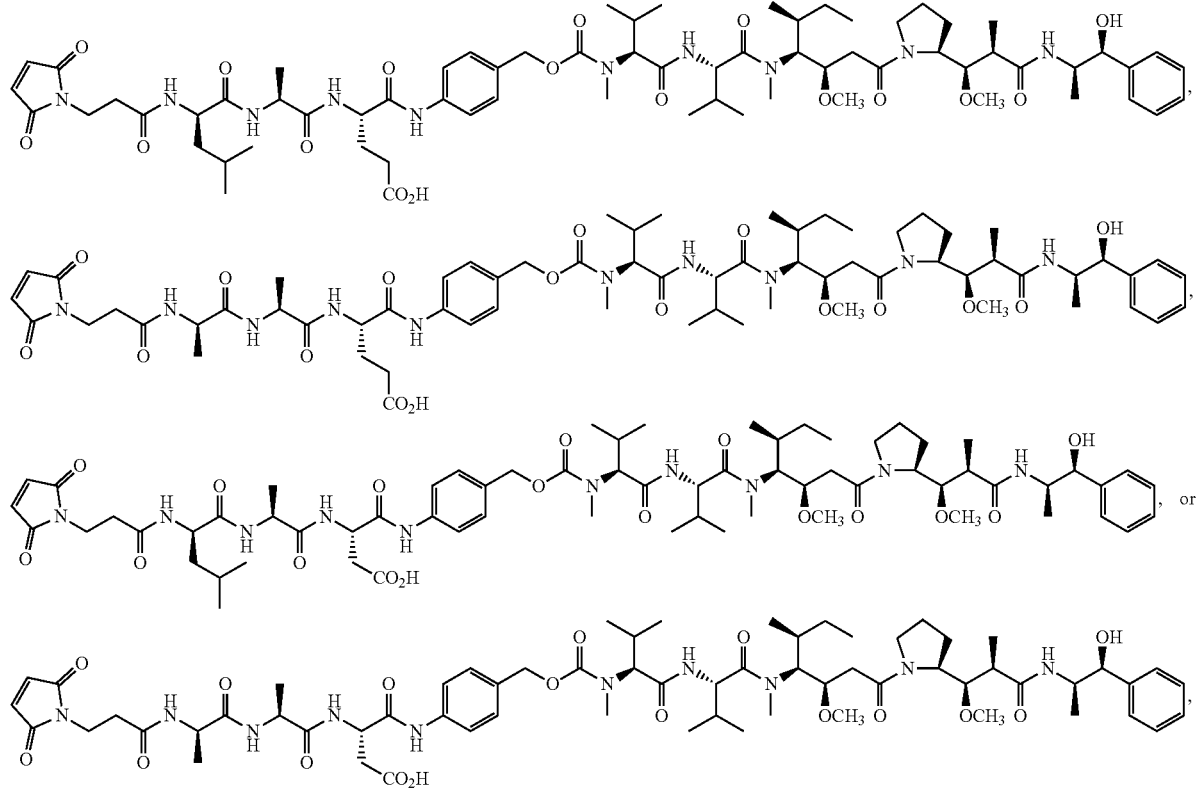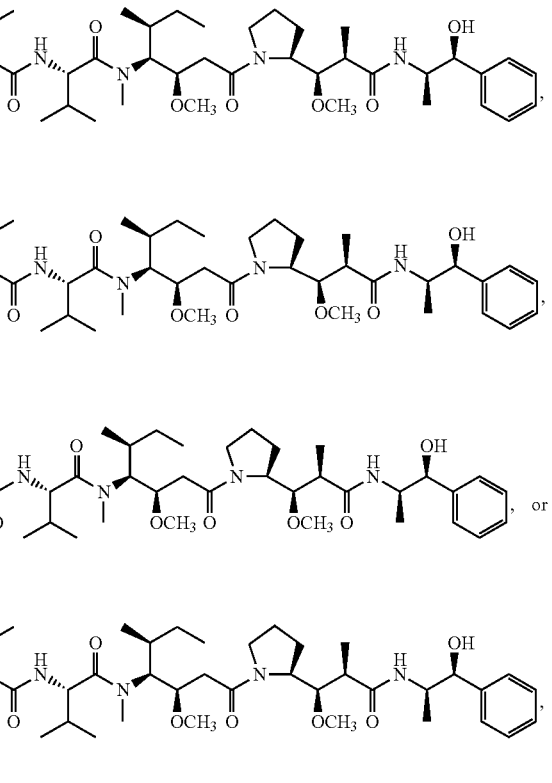

or a salt thereof.

In some embodiments, provided herein is a Linker compound of Formula IA-L:

(IA-L)

or a salt thereof, wherein

RG is a reactive group;

$L_B'$ is a ligand covalent binding precursor moiety;

A is a first optional Stretcher Unit;

A' is a second optional Stretcher Unit, which in the absence of B becomes a subunit of A;

subscript a' is 0 or 1, indicating the absence or presence of A', respectively,

W is a Peptide Cleavable Unit, wherein the Peptide Cleavable Unit comprises a tripeptide having the sequence -P3-P2-P1-, wherein P1, P2, and P3 are each an amino acid, wherein:

a first one of the amino acids P1, P2, or P3 is negatively charged or is serine;

a second one of the amino acids P1, P2, or P3 has an aliphatic side chain with hydrophobicity no greater than that of leucine, or is glycine or serine or proline; and a third one of the amino acids P1, P2, or P3 has hydrophobicity lower than that of leucine, or is proline,
wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
provided that -P3-P2-P1- is not -Glu-Val-Cit- or -Asp-Val-Cit-;
Y is a self-immolative Spacer Unit;
subscript y is 0, 1 or 2 indicating the absence or presence of 1 or 2 of Y, respectively; and
subscript q is an integer ranging from 1 to 4,
provided that subscript q is 1 when subscript b is 0 and subscript q is 2, 3 or 4 when subscript b is 1.

In some embodiments, a first one of the amino acids P1, P2, or P3 is negatively charged; a second one of the amino acids P1, P2, or P3 has an aliphatic side chain with hydrophobicity no greater than that of leucine; and a third one of the amino acids P1, P2, or P3 has hydrophobicity lower than that of leucine.

In some embodiments, provided herein is the Linker compound, wherein the Peptide Cleavable Unit is a tripeptide having the sequence -P3-P2-P1-, wherein P1, P2, and P3 are each an amino acid, wherein: the P3 amino acid of the tripeptide is in the D-amino acid configuration; one of the P2 and P1 amino acids has an aliphatic side chain with hydrophobicity lower than that of leucine; and the other of the P2 and P1 amino acids is negatively charged.

In some embodiments, provide herein is the Linker compound wherein the Linker compound has the structure of Formula IA-L-3:

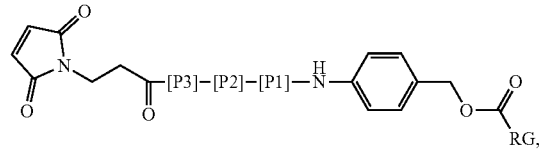

(IA-L-3)

or a salt thereof.

In some embodiments, provided herein is a Linker compound wherein the Linker compound has the structure of:

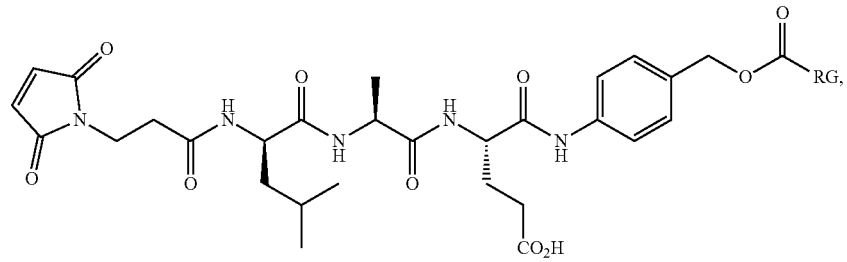

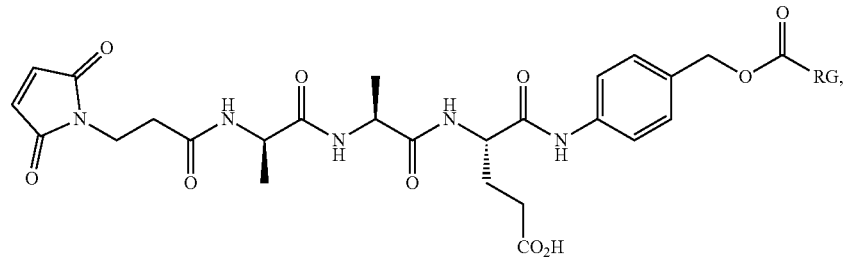

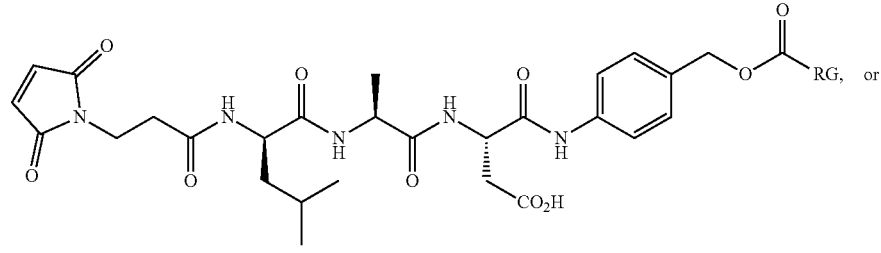

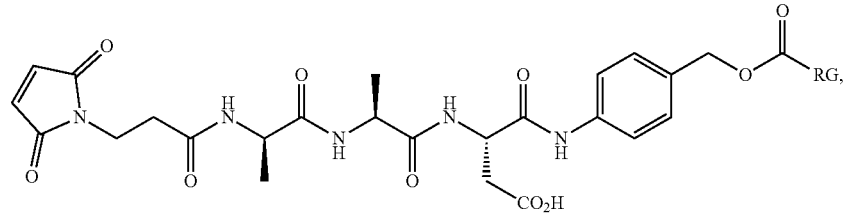

or a salt thereof.

In another aspect, provided herein is a Ligand Drug Conjugate composition represented by Formula 1:

$$L\text{-}[LU\text{-}D']_p \qquad (1)$$

or a pharmaceutically acceptable salt thereof, wherein L is a Ligand Unit; LU is a Linker Unit; D' represents from 1 to 4 Drug Units (D) in each drug linker moiety of formula -LU-D'; and subscript p is a number from 1 to 12, from 1 to 10 or from 1 to 8 or is about 4 or about 8, wherein the Ligand Unit is from an antibody or an antigen-binding fragment of an antibody, wherein the antibody or the antigen-binding fragment is capable of selective binding to an antigen of tumor tissue for subsequent release of the Drug Unit(s) as a free drug, wherein the drug linker moiety of formula -LU-D' in each of the Ligand Drug Conjugate compounds of the composition has the structure of Formula 1A:

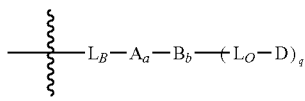
(1A)

or a salt thereof, wherein the wavy line indicates covalent attachment to L; D is the Drug Unit; $L_B$ is a ligand covalent binding moiety; A is a first optional Stretcher Unit; subscript a is 0 or 1, indicating the absence or presence of A, respectively; B is an optional Branching Unit; subscript b is 0 or 1, indicating the absence or presence of B, respectively; $L_O$ is a secondary linker moiety, wherein the secondary linker has the formula of,

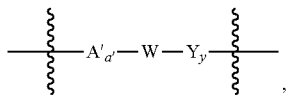

wherein the wavy line adjacent to Y indicates the site of covalent attachment of $L_O$ to the Drug Unit and the wavy line adjacent to A' indicates the site of covalent attachment of $L_O$ to the remainder of the drug linker moiety; A' is a second optional Stretcher Unit, which when present and in the absence of B becomes a subunit of A, subscript a' is 0 or 1, indicating the absence or presence of A', respectively, W is a Peptide Cleavable Unit, wherein the Peptide Cleavable Unit comprises a tripeptide having the sequence -P3-P2-P1-, wherein P1, P2, and P3 are each an amino acid, wherein: a first one of the amino acids P1, P2, or P3 is negatively charged or is serine; a second one of the amino acids P1, P2, or P3 has an aliphatic side chain with hydrophobicity no greater than that of leucine, or is glycine or serine or proline; and a third one of the amino acids P1, P2, or P3 has hydrophobicity lower than that of leucine, or is proline, wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acid P1, P2, or P3, provided that -P3-P2-P1- is not -Glu-Val-Cit- or -Asp-Val-Cit-; each Y when present is a self-immolative Spacer Unit; subscript y is 0, 1 or 2 indicating the absence or presence of 1 or 2 of Y, respectively; and subscript q is an integer ranging from 1 to 3 or 1 to 4, and provided that subscript q is 1 when subscript b is 0 and subscript q is 2, 3, or 4 when subscript b is 1; and wherein the Ligand Drug Conjugate compounds of the composition have the structure of Formula 1 in which subscript p is replaced by subscript p', wherein subscript p' is an integer from 1 to 12, 1 to 10 or 1 to 8 or is 4 or 8. In some embodiments, a first one of the amino acids P1, P2, or P3 is negatively charged; a second one of the amino acids P1, P2, or P3 has an aliphatic side chain with hydrophobicity no greater than that of leucine; and a third one of the amino acids P1, P2, or P3 has hydrophobicity lower than that of leucine. In some embodiments, W is a Peptide Cleavable Unit, wherein the Peptide Cleavable Unit comprises a tripeptide having the sequence -P3-P2-P1-, wherein wherein one of the amino acids is negatively charged, another of the amino acids has a aliphatic side chain with hydrophobicity no greater than that of leucine and the remaining amino acid has hydrophobicity lower than that of leucine. In some embodiments protease action upon the Peptide Cleavable Unit is capable of releasing D as the free drug. In some embodiments, the Ligand Drug Conjugate compounds in the Ligand Drug Conjugate composition are in salt form.

In some embodiments, the Ligand Drug Conjugate compounds in the Ligand Drug Conjugate composition predominately have drug linker moieties of Formula 1H:

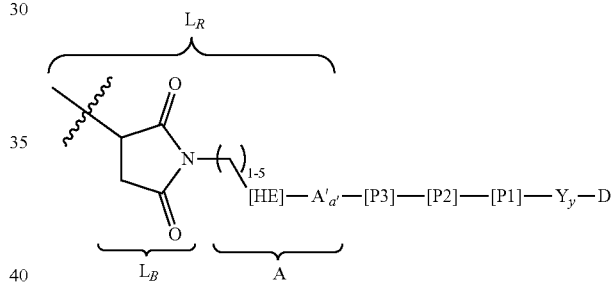
(Formula 1H)

or pharmaceutically acceptable salts thereof, and optionally having a minority of Ligand Drug Conjugate compounds in which one or more of the drug linker moieties in each of such compounds has its succinimide ring in hydrolyzed form and wherein HE is a Hydrolysis Enhancing Unit; A' is a subunit, when present, of the indicated first Stretcher Unit (A); subscript a' is 0 or 1, indicating the absence or presence of A', respectively; and the wavy line indicates the site of covalent attachment to a sulfur atom of the Ligand Unit. In some embodiments, HE is —C(═O). In some embodiments, —$Y_y$-D has the structure of:

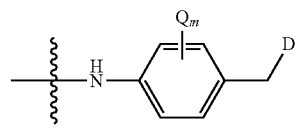

wherein each Q, when present, is independently selected from the group consisting of —$C_1$-$C_8$ alkyl, —O—($C_1$-$C_8$ alkyl), halogen, nitro and cyano; and subscript m is 0, 1 or 2. In some embodiments, —$Y_y$-D has the structure of

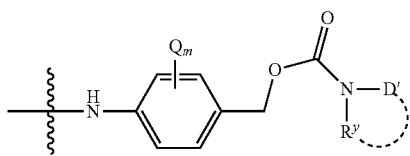

wherein —N(R^y)D' represents D, wherein D' is the remainder of D; the wavy line indicates the site of covalent attachment to P1; the dotted line indicates optional cyclization of R^y to D'; R^y is optionally substituted $C_1$-$C_6$ alkyl in absence of cyclization to D' or optionally substituted $C_1$-$C_6$ alkylene when cyclized to D'; each Q, when present, is independently selected from the group consisting of —$C_1$-$C_8$ alkyl, —O—($C_1$-$C_8$ alkyl), halogen, nitro and cyano; and subscript m is 0, 1 or 2.

In some embodiments, D incorporates the structure of a tubulin disrupting agent, a DNA minor groove binder, a DNA damaging agent, or a DNA replication inhibitor. In some embodiments, D incorporates the structure of a tubulysin. In some embodiments, D incorporates the structure of a camptothecin. In some embodiments, D incorporates the structure of an auristatin. In some embodiments, D incorporates the structure of an anthracycline. In some embodiments, D incorporates the structure of a camptothecin selected from the group consisting of.

CPT1

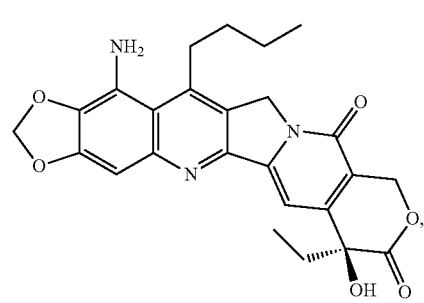

CPT2

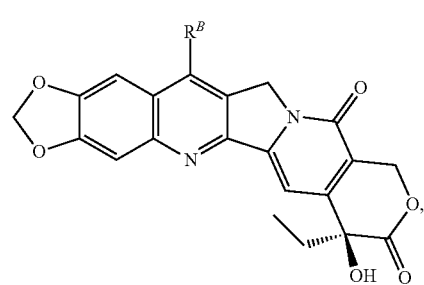

CPT3

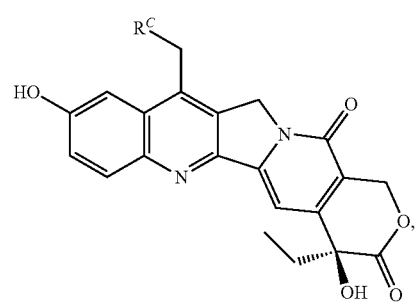

CPT4

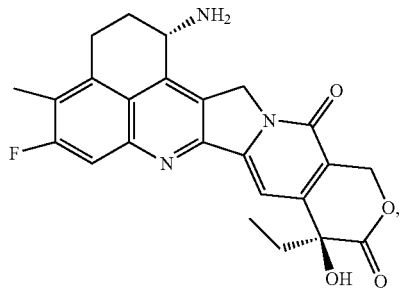

CPT5

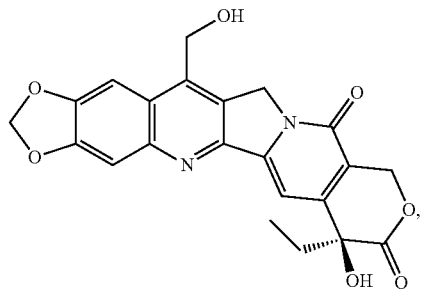

CPT6

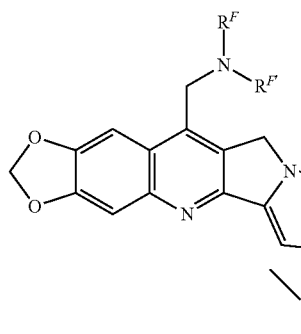

and

CPT7 wherein $R^B$ is selected from the group consisting of H, $C_1$-$C_8$ alkyl, $C_1$-$C_8$ haloalkyl, $C_3$-$C_8$ cycloalkyl, ($C_3$-$C_8$ cycloalkyl)-$C_1$-$C_4$ alkyl, phenyl, and phenyl-$C_1$-$C_4$ alkyl; $R^C$ is selected from the group consisting of $C_1$-$C_6$ alkyl and $C_3$-$C_6$ cycloalkyl; and each $R^F$ and $R^{F'}$ is independently selected from the group consisting of —H, $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$—$C_8$ aminoalkyl, $C_1$-$C_8$ alkyl-C(O)—, $C_1$-$C_8$ hydoxyalkyl-C(O)—, $C_1$-$C_8$ aminoalkyl-C(O)—, $C_3$-$C_{10}$ cycloalkyl, ($C_3$-$C_{10}$ cycloalkyl)-C$_1$-C$_4$ alkyl-, C$_3$-C$_{10}$ heterocycloalkyl, (C$_3$-C$_{10}$ heterocycloalkyl)-C$_1$-C$_4$ alkyl-, phenyl, phenyl-C$_1$-C$_4$ alkyl-, diphenyl-C$_1$-C$_4$ alkyl-, heteroaryl, and heteroaryl-C$_1$-C$_4$ alkyl-, or R$^F$ and R$^{F'}$ are combined with the nitrogen atom to which each is attached to form a 5-, 6- or 7-membered ring having 0 to 3 substituents selected from the group consisting of halogen, C$_1$-C$_4$ alkyl, —OH, —OC$_1$-C$_4$ alkyl, —NH$_2$, —NH—C$_1$-C$_4$ alkyl, —N(C$_1$-C$_4$ alkyl)$_2$; and wherein the cycloalkyl, heterocycloalkyl, phenyl and heteroaryl portions of R$^B$, R$^C$, R$^F$ and R$^{F'}$ are substituted with from 0 to 3 substituents selected from the group consisting of halogen, C$_1$-C$_4$ alkyl, —OH, —OC$_1$-C$_4$ alkyl, —NH$_2$, —NHC$_1$-C$_4$ alkyl, and —N(C$_1$-C$_4$ alkyl)$_2$.

In some embodiments, D has a formula selected from the group consisting of

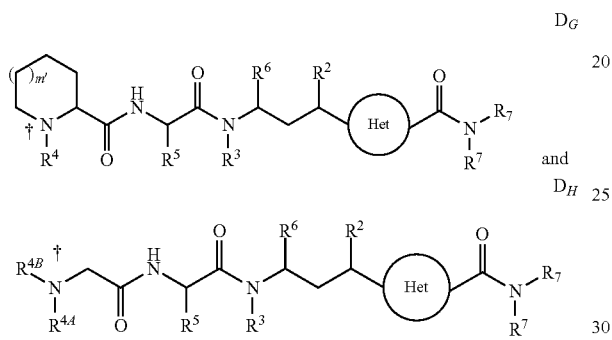

D$_G$

D$_H$ wherein the dagger represents the point of attachment of D to the secondary linker of the drug linker moiety and the circle represents an 5-membered or 6-membered nitrogen heteroarylene wherein the indicated required substituents to that heteroarylene are in a 1,3- or meta-relationship to each other with optional substitution at the remaining positions; R$^2$ is X$^A$—R$^{2A}$, wherein X$^A$ is —O—, —S—, —N(R$^{2B}$)—, —CH$_2$—, —(C=O)N(R$^{2B}$)— or —O(C=O)N(R$^{2B}$)— wherein R$^{2B}$ is hydrogen or optionally substituted alkyl, R$^{2A}$ is hydrogen, optionally substituted alkyl, optionally substituted aryl, or —C(=O)R$^C$, wherein R$^C$ is hydrogen, optionally substituted alkyl, or optionally substituted aryl or R$^2$ is an O-linked substituent; R$^3$ is hydrogen or optionally substituted alkyl; R$^4$, R$^{4A}$, R$^{4B}$, R$^5$ and R$^6$ are optionally substituted alkyl, independently selected, one R$^7$ is hydrogen or optionally substituted alkyl and the other R$^7$ is optionally substituted arylalkyl or optionally substituted heteroarylalkyl, and subscript m' is 0 or 1. In some embodiments, R$^4$ is methyl or R$^{4A}$ and R$^{4B}$ are methyl. In some embodiments, the 5-membered heteroarylene is represented by the structure

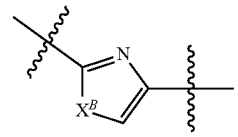

wherein X$^B$ is O, S, or N—R$^B$ wherein R$^B$ is hydrogen or lower alkyl. In some embodiments, the 5-membered heteroarylene is a divalent thiazole moiety. In some embodiments, subscript m' is 1.

In some embodiments, D has a formula selected from the group consisting of

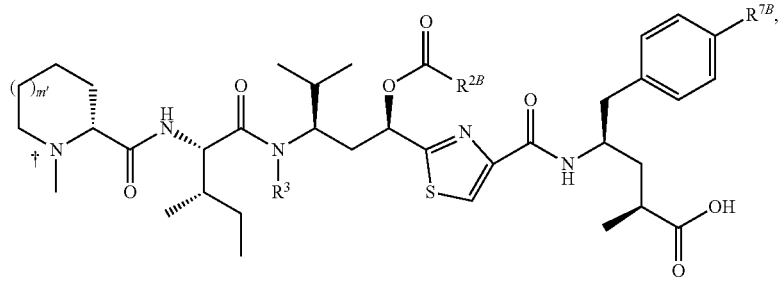

D$_{G-3}$

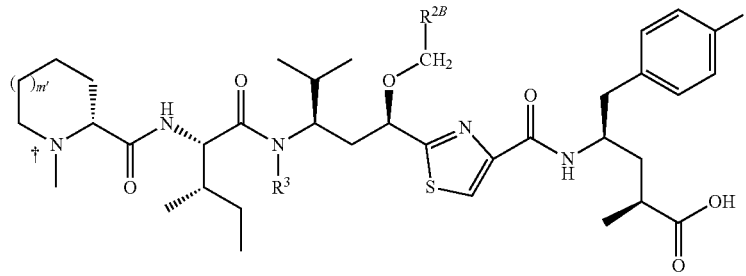

D$_{G-4}$ and

-continued

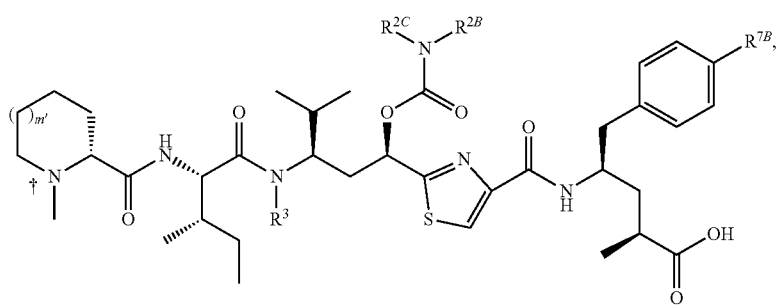

D$_{G-5}$ wherein R$^{7B}$ is hydrogen or —OH, R$^3$ is lower alkyl, and R$^{2B}$ and R$^{2C}$ are independently hydrogen or lower alkyl. In some embodiments, subscript q is 1 and the Ligand Drug Conjugate compounds in the Ligand Drug Conjugate composition predominately have drug linker moieties of:

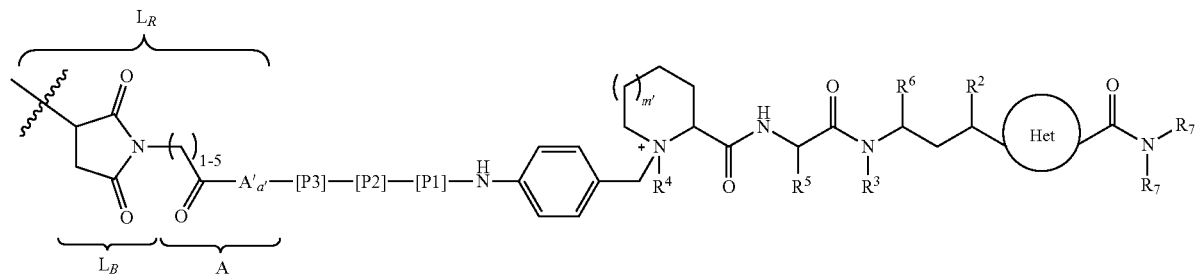

or a pharmaceutical acceptable salt thereof, and optionally having a minority of Ligand Drug Conjugate compounds in which one or more of the drug linker moieties in each of such compounds has the succinimide ring in hydrolyzed form, and wherein: subscript a' is 0, and A' is absent; and the wavy line indicates the site of covalent attachment to a sulfur atom of the Ligand Unit. In some embodiments, subscript q is 1 and the Ligand Drug Conjugate compounds in the Ligand Drug Conjugate composition predominately have drug linker moieties of:

or a pharmaceutical acceptable salt thereof, and optionally having a minority of Ligand Drug Conjugate compounds in which one or more of the drug linker moieties in each of such compounds has the succinimide ring in hydrolyzed form, and wherein: subscript a' is 0, and A' is absent; and the wavy line indicates the site of covalent attachment to a sulfur atom of the Ligand Unit.

In some embodiments, D is a cytotoxic drug wherein the cytotoxic drug is a secondary amine-containing auristatin compound wherein the nitrogen atom of the secondary amine is the site of covalent attachment to the drug linker moiety and the secondary amine-containing auristatin compound has the structure of Formula D$_{F/E-3}$:

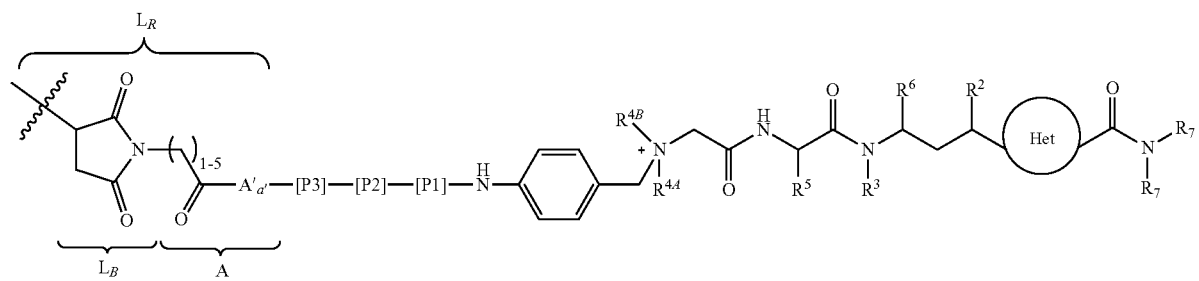

$D_{F/E-3}$

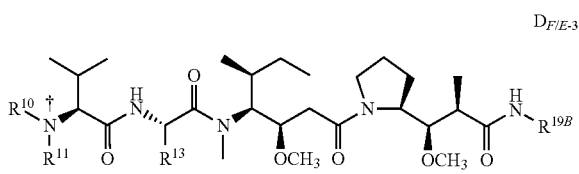

wherein the dagger indicates the site of covalent attachment of the nitrogen atom that provides the carbamate functional group; one of $R^{10}$ and $R^{11}$ is hydrogen and the other is methyl; $R^{13}$ is isopropyl or —$CH_2$—$CH(CH_3)_2$; and $R^{19B}$ is —$CH(CH_3)$—$CH(OH)$-Ph, —$CH(CO_2H)$—$CH(OH)$—$CH_3$, —$CH(CO_2H)$—$CH_2Ph$, —$CH(CH_2Ph)$-2-thiazolyl, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, —$CH(CH_2CH_2SCH_3)C(=O)NH$-quinol-3-yl, —$CH(CH_2Ph)C(=O)NH$-p-Cl-Ph, or $R^{19B}$ has the structure of

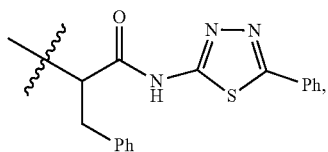 [SMILES: *C(Cc1ccccc1)C(=O)Nc1nnc(-c2ccccc2)s1]

wherein the wavy line indicates covalent attachment to the remainder of the auristatin compound. In some embodiments, the secondary amine-containing auristatin compound is monomethylauristatin E (MMAE) or monomethylauristatin F (MMAF).

In some embodiments, the Peptide Cleavable Unit is a tripeptide having the sequence -P3-P2-P1-, wherein P1, P2, and P3 are each an amino acid, wherein: the P3 amino acid of the tripeptide is in the D-amino acid configuration; one of the P2 and P1 amino acids has an aliphatic side chain with hydrophobicity lower than that of leucine; and the other of the P2 and P1 amino acids is negatively charged. In some embodiments, the P3 amino acid is D-Leu or D-Ala. In some embodiments, one of the P2 or P1 amino acid has an aliphatic side chain with hydrophobicity no greater than that of valine, and the other of the P2 or P1 amino acid is negatively charged at plasma physiological pH. In some embodiments, the P2 amino acid has an aliphatic side chain with hydrophobicity no greater than that of valine, and the P1 amino acid is negatively charged at plasma physiological pH. In some embodiments, -P2-P1- is -Ala-Glu- or -Ala-Asp-. In some embodiments, -P3-P2-P1- is -D-Leu-Ala-Asp-, -D-Leu-Ala-Glu-, -D-Ala-Ala-Asp-, or -D-Ala-Ala-Glu-. In some embodiments, the P3 amino acid is D-Leu or D-Ala, the P2 amino acid is Ala, Glu, or Asp, and the P1 amino acid is Ala, Glu, or Asp.

In some embodiments, the composition comprises Ligand Drug Conjugate compounds having the structure of:

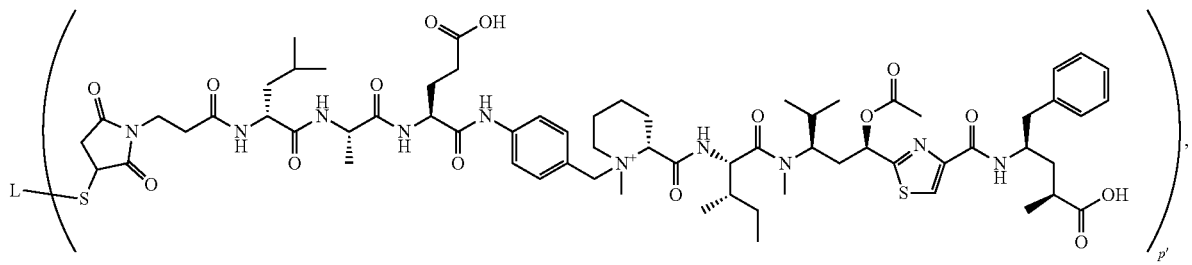

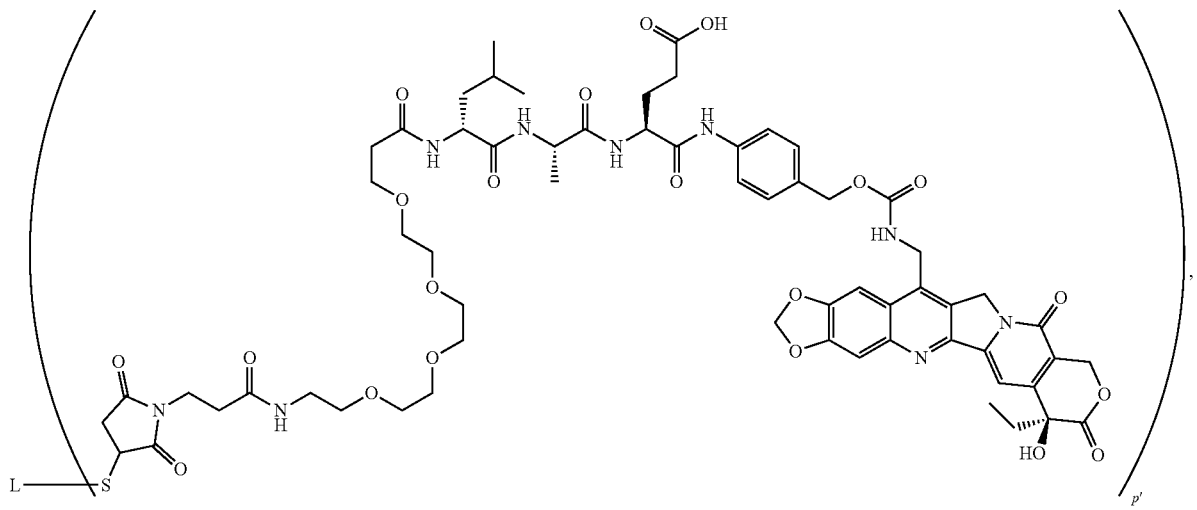

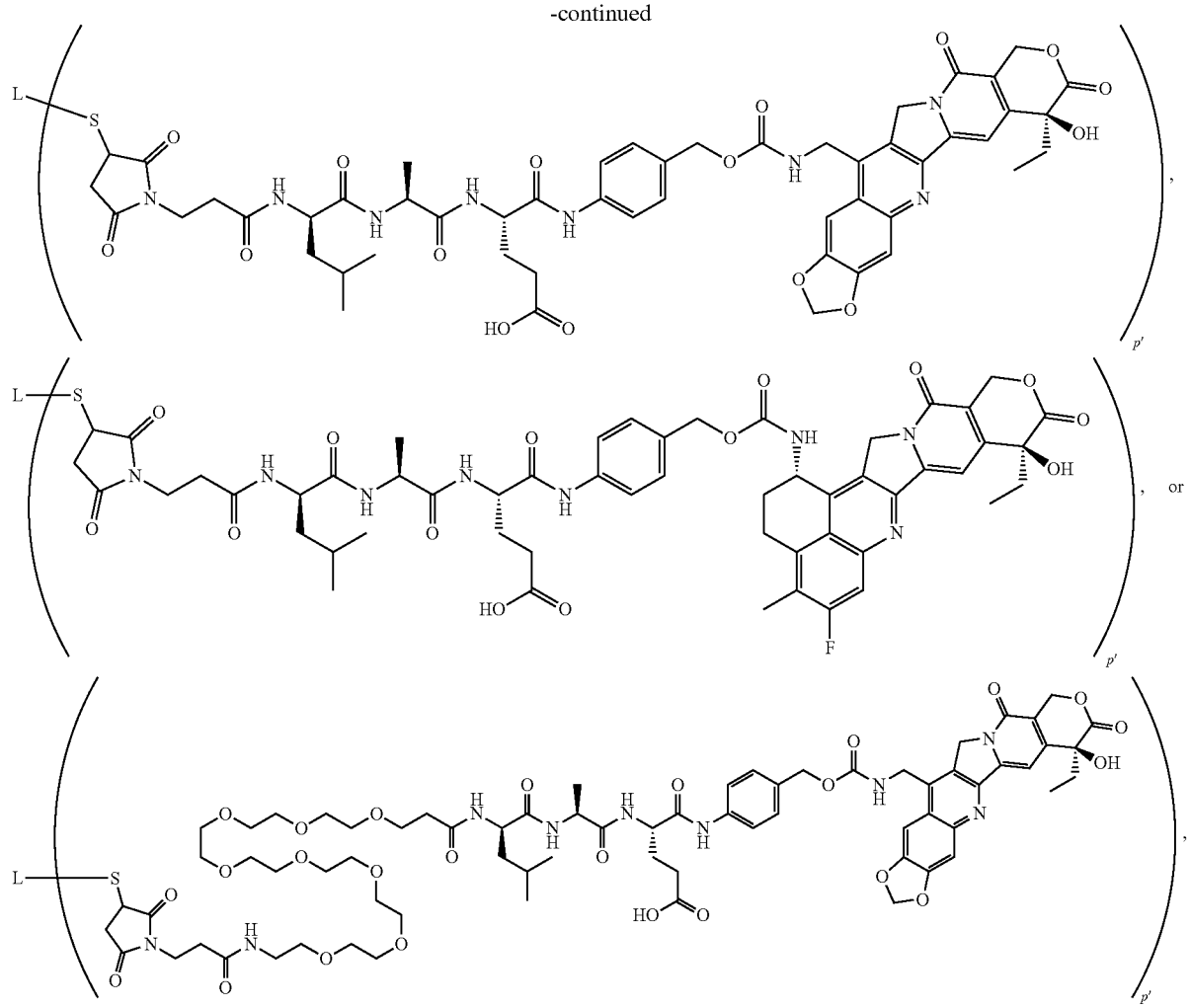

or a pharmaceutically acceptable salt thereof, wherein L is the Ligand Unit, and subscript p' is an integer from 1 to 12. In some embodiments, L is an antibody Ligand Unit of an intact antibody or an antigen-binding fragment thereof. In some embodiments, the intact antibody is a an intact chimeric, humanized or human antibody. In some embodiments, the intact antibody or fragment thereof is capable of selectively binding to a cancer cell antigen. In some embodiments, the intact antibody or fragment thereof is capable of selectively binding to an immune cell antigen. In some embodiments, the intact antibody or fragment thereof is capable of selectively binding CD30. In some embodiments, the intact antibody or fragment thereof comprises CDR-H1, CDR-H2, CDR-H3, CDR-L1, CDR-L2, and CDR-L3 comprising the amino acid sequences of SEQ ID NOs: 1, 2, 3, 4, 5, and 6, respectively. In some embodiments, the intact antibody or fragment thereof comprises a heavy chain variable region comprising the amino acid sequence of SEQ ID NO: 7 and a light chain variable region comprising the amino acid sequence of SEQ ID NO: 8. In some embodiments, the intact antibody is cAC10. In some embodiments, the intact antibody or fragment thereof is capable of selectively binding LIV1. In some embodiments, intact antibody or fragment thereof comprises CDR-H1, CDR-H2, CDR-H3, CDR-L1, CDR-L2, and CDR-L3 comprising the amino acid sequences of SEQ ID NOs: 518, 519, 520, 521, 522, and 523, respectively. In some embodiments, the intact antibody or fragment thereof comprises a heavy chain variable region comprising the amino acid sequence of SEQ ID NO: 524 and a light chain variable region comprising the amino acid sequence of SEQ ID NO: 525. In some embodiments, the intact antibody is ladiratuzumab. In some embodiments, the intact antibody or fragment thereof is capable of selectively binding TROP2. In some embodiments, the intact antibody is sacituzumab or datopotamab. In some embodiments, the intact antibody or fragment thereof is capable of selectively binding ALPP. In some embodiments, the intact antibody or fragment thereof is capable of selectively binding IL1RAP. In some embodiments, the intact antibody or fragment thereof comprises CDR-H1, CDR-H2, CDR-H3, CDR-L1, CDR-L2, and CDR-L3 comprising the amino acid sequences of SEQ ID NOs: 96, 97, 98, 99, 100, and 101, respectively. In some embodiments, the intact antibody or fragment thereof comprises a heavy chain variable region comprising the amino acid sequence of SEQ ID NO: 102 and a light chain variable region comprising the amino acid sequence of SEQ ID NO: 103. In some embodiments, the intact antibody is nidanilimab. In some embodiments, the intact antibody or fragment thereof is capable of selectively binding ASCT2. In some embodiments, the intact antibody or fragment thereof comprises CDR-H1, CDR-H2, CDR-H3, CDR-L1, CDR-L2, and CDR-L3 comprising the amino acid sequences of SEQ ID NOs: 794, 795, 796, 797, 798, and 799, respectively. In some embodiments, the intact antibody or fragment thereof comprises a heavy chain variable region comprising the amino acid sequence of SEQ ID NO: 801 and a light chain variable region comprising the amino acid sequence of SEQ ID NO: 802. In some embodiments, the intact antibody or fragment thereof comprises a heavy chain variable region comprising the amino acid sequence of SEQ ID NO: 790 and a light chain variable region comprising the amino acid sequence of SEQ ID NO: 791. In some embodiments, the intact antibody or fragment thereof comprises a heavy chain variable region comprising the amino acid sequence of SEQ ID NO: 792 and a light chain variable region comprising the amino acid sequence of SEQ ID NO: 793.

In some embodiments, subscript q is 1 and the Ligand Drug Conjugate compounds in the Ligand Drug Conjugate composition predominately have drug linker moieties of Formula 1H-MMAE:

(Formula 1H-MMAE)

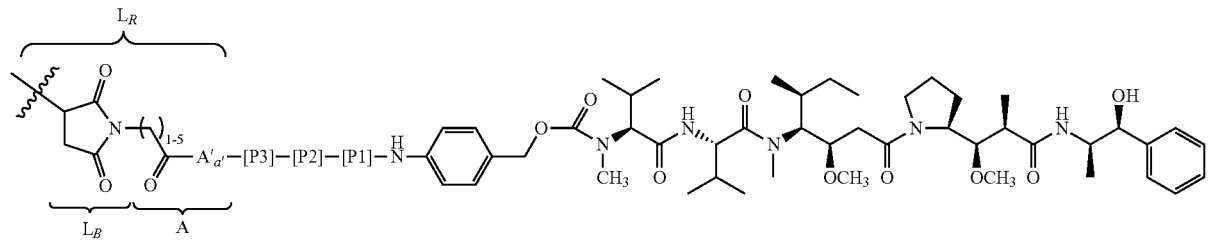

or a pharmaceutical acceptable salt thereof, and optionally having a minority of Ligand Drug Conjugate compounds in which one or more of the drug linker moieties in each of such compounds has its the succinimide ring in hydrolyzed form and wherein: subscript a' is 0, and A' is absent; and the wavy line indicates the site of covalent binding to a sulfur atom of the Ligand Unit. In some embodiments, the composition comprises Ligand Drug Conjugate compounds having the structure of

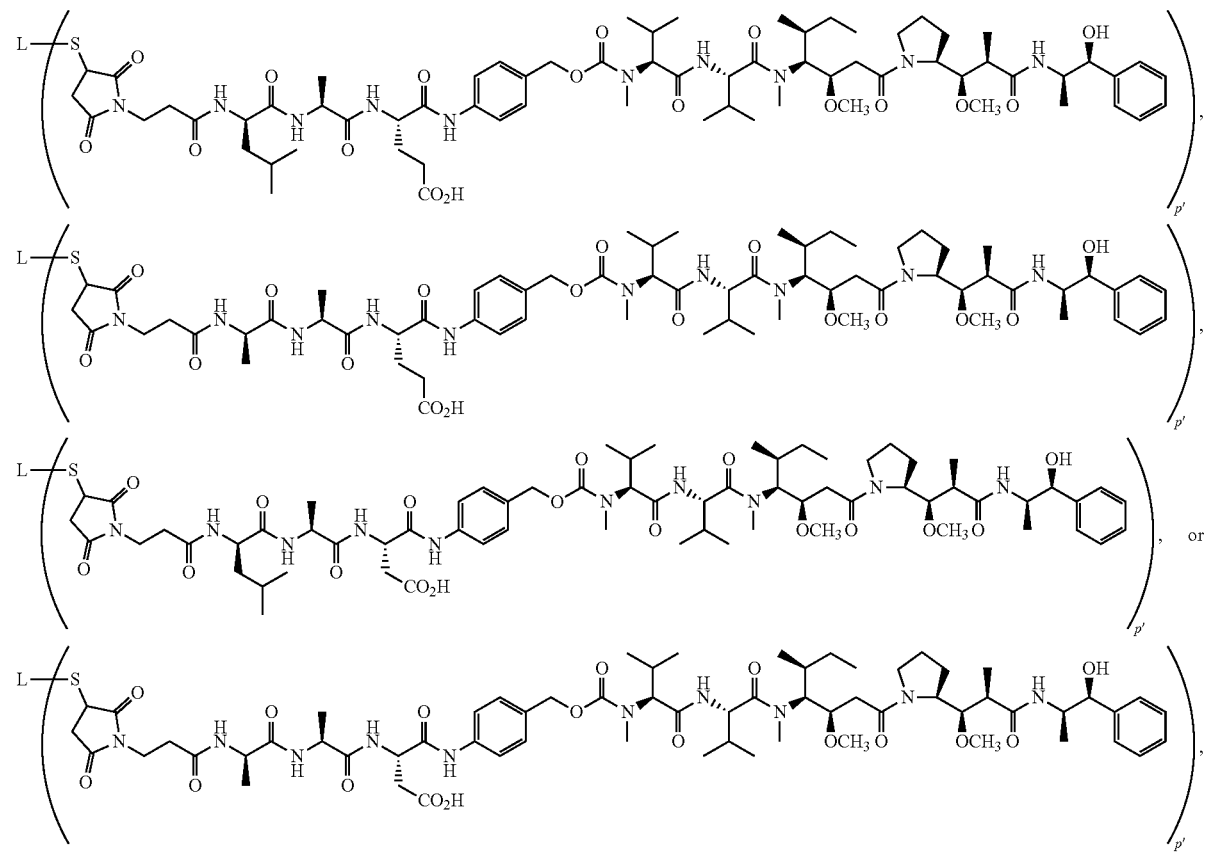

or a pharmaceutically acceptable salt thereof, wherein L is the Ligand Unit, and subscript p is an integer from 1 to 12.

In some embodiments, p ranges from about 2 to about 12, or from about 2 to about 10, or from about 2 to about 8, or subscript p is about 2, about 4 or about 8.

In another aspect, provided herein is a pharmaceutically acceptable formulation, wherein the formulation comprises an effective amount of a Ligand Drug Conjugate composition described herein and at least one pharmaceutically acceptable excipient. In some embodiments, the least one pharmaceutically acceptable excipient is a liquid carrier that provides a liquid formulation, wherein the liquid formulation is suitable for lyophilization or administration to a subject in need thereof. In some embodiments, the formulation is a lyophilized solid or a liquid formulation, wherein the at least one excipient of the solid formulation is a lyoprotectant.

In another aspect, provided is a method of treating cancer comprising administering to a subject in need thereof a therapeutically effective amount of a Ligand Drug Conjugate composition described herein or a pharmaceutically acceptable formulation of any Ligand Drug Conjugate composition described herein.

In another aspect, provided herein is a Drug Linker compound of Formula IA:

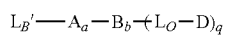
(IA)

or a salt thereof, wherein D is a Drug Unit; $L_B'$ is a ligand covalent binding precursor moiety; A is a first optional Stretcher Unit; subscript a is 0 or 1, indicating the absence or presence of A, respectively; B is an optional Branching Unit; subscript b is 0 or 1, indicating the absence or presence of B, respectively; $L_O$ is a secondary linker moiety, wherein the secondary linker has the formula of;

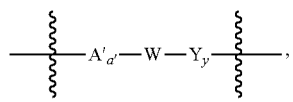

wherein the wavy line adjacent to Y indicates the site of covalent attachment of $L_O$ to the Drug Unit and the wavy line adjacent to A' indicates the site of covalent attachment of $L_O$ to the remainder of the Drug Linker compound; A' is a second optional Stretcher Unit, which when present and in the absence of B becomes a subunit of A; subscript a' is 0 or 1, indicating the absence or presence of A', respectively, W is a Peptide Cleavable Unit, wherein the Peptide Cleavable Unit comprises a tripeptide having the sequence -P3-P2-P1-, wherein P1, P2, and P3 are each an amino acid, wherein: a first one of the amino acids P1, P2, or P3 is negatively charged or is serine; a second one of the amino acids P1, P2, or P3 has an aliphatic side chain with hydrophobicity no greater than that of leucine, or is glycine or serine or proline; and a third one of the amino acids P1, P2, or P3 has hydrophobicity lower than that of leucine, or is proline, wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acid P1, P2, or P3, provided that -P3-P2-P1- is not -Glu-Val-Cit- or -Asp-Val-Cit-; each Y when present is a self-immolative Spacer Unit; subscript y is 0, 1 or 2 indicating the absence or presence of 1 or 2 of Y, respectively; and subscript q is an integer ranging from 1 to 3, and provided that subscript q is 1 when subscript b is 0 and subscript q is 2 or 3 when subscript b is 1. In some embodiments, a first one of the amino acids P1, P2, or P3 is negatively charged; a second one of the amino acids P1, P2, or P3 has an aliphatic side chain with hydrophobicity no greater than that of leucine; and a third one of the amino acids P1, P2, or P3 has hydrophobicity lower than that of leucine. In some embodiments, the Drug Linker compound is in a salt form.

In some embodiments, the Drug Linker compound has the structure of Formula IH:

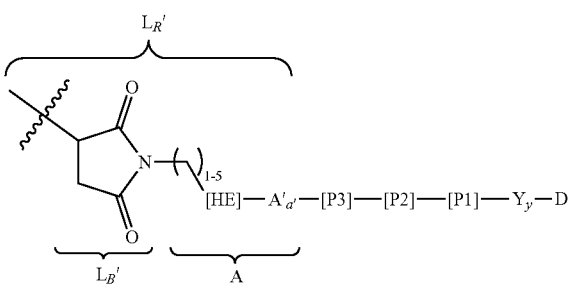
(Formula IH)

or salt thereof, wherein: HE is a Hydrolysis Enhancing Unit; and A' is a subunit, when present, of the indicated first Stretcher Unit (A); subscript a' is 0 or 1, indicating the absence or presence of A', respectively. In some embodiments, HE is —C(=O). In some embodiments, —$Y_y$-D has the structure of:

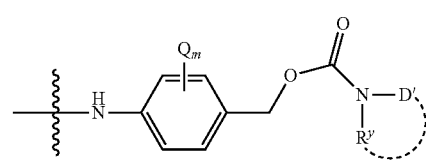

wherein —N(R$^y$)D' represents D, wherein D' is the remainder of D; the wavy line indicates the site of covalent attachment to P1; the dotted line indicates optional cyclization of R to D'; R$^y$ is optionally substituted $C_1$-$C_6$ alkyl in absence of cyclization to D' or optionally substituted $C_1$-$C_6$ alkylene when cyclized to D'; each Q is independently selected from the group consisting of —$C_1$-$C_8$ alkyl, —O—($C_1$-$C_8$ alkyl), halogen, nitro and cyano; and subscript m is 0, 1 or 2.

In some embodiments, D incorporates the structure of a tubulin disrupting agent, a DNA minor groove binder, a DNA damaging agent, or a DNA replication inhibitor. In some embodiments, D incorporates the structure of a tubulysin. In some embodiments, D incorporates the structure of a camptothecin. In some embodiments, D incorporates the structure of an auristatin. In some embodiments, D incorporates the structure of an anthracycline. In some embodiments, D incorporates the structure of a camptothecin having the structure selected from the group consisting of

CPT1

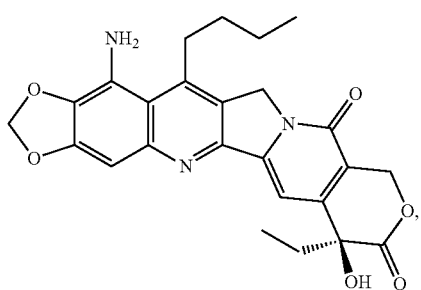

CPT2

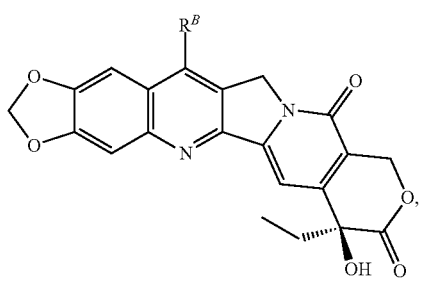

CPT3

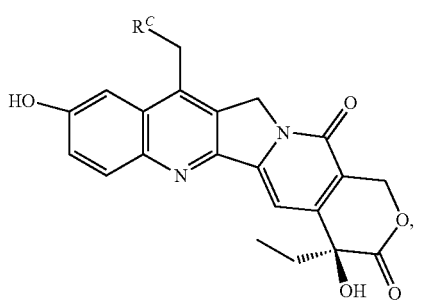

CPT4

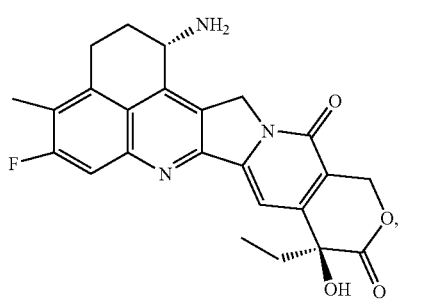

CPT5

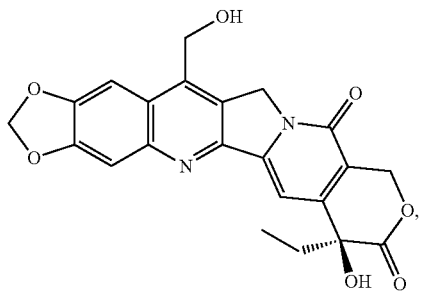

CPT6

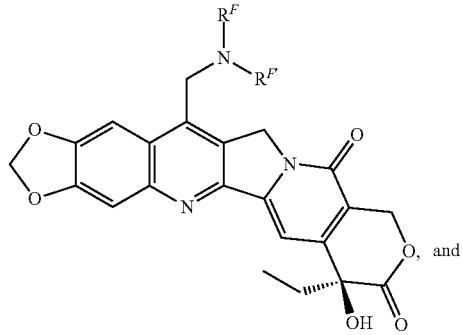

CPT7

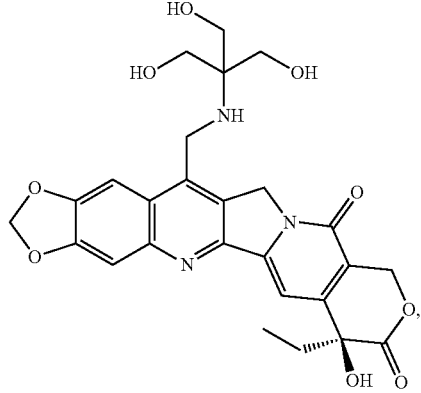

wherein $R^B$ is selected from the group consisting of H, $C_1$-$C_8$ alkyl, $C_1$-$C_8$ haloalkyl, $C_3$-$C_8$ cycloalkyl, ($C_3$-$C_8$ cycloalkyl)-$C_1$-$C_4$ alkyl, phenyl, and phenyl-$C_1$-$C_4$ alkyl; $R^C$ is selected from the group consisting of $C_1$-$C_6$ alkyl and $C_3$-$C_6$ cycloalkyl; and each $R^F$ and $R^{F'}$ is independently selected from the group consisting of —H, $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$—$C_8$ aminoalkyl, $C_1$-$C_8$ alkyl-C(O)—, $C_1$-$C_8$ hydoxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl, and heteroaryl-$C_1$-$C_4$ alkyl-, or $R^F$ and $R^{F'}$ are combined with the nitrogen atom to which each is attached to form a 5-, 6- or 7-membered ring having 0 to 3 substituents selected from the group consisting of halogen, $C_1$-$C_4$ alkyl, —OH, —O$C_1$-$C_4$ alkyl, —$NH_2$, —NH—$C_1$-$C_4$ alkyl, —N($C_1$-$C_4$ alkyl)$_2$; and wherein the cycloalkyl, heterocycloalkyl, phenyl and heteroaryl portions of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —$NH_2$, —NH$C_1$-$C_4$ alkyl, and —N($C_1$-$C_4$ alkyl)$_2$. In some embodiments, D has a formula selected from the group consisting of $D_G$

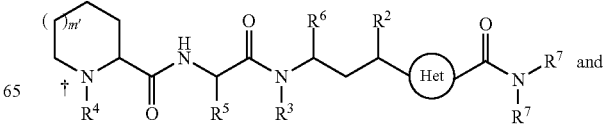

and

-continued

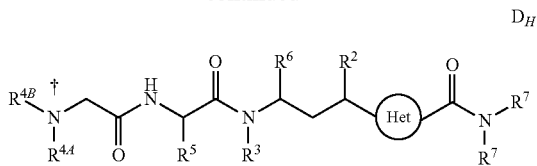
$D_H$ wherein the dagger represents the point of attachment of D to the remainder of the Drug Linker compound and the circle represents an 5-membered or 6-membered nitrogen heteroarylene wherein the indicated required substituents to that heteroarylene are in a 1,3- or meta-relationship to each other with optional substitution at the remaining positions; $R^2$ is $X^A$—$R^{2A}$, wherein $X^A$ is —O—, —S—, —N($R^{2B}$)—, —CH$_2$—, —(C=O)N($R^{2B}$)— or —O(C=O)N($R^{2B}$)— wherein $R^{2B}$ is hydrogen or optionally substituted alkyl, $R^{2A}$ is hydrogen, optionally substituted alkyl, optionally substituted aryl, or —C(=O)$R^C$, wherein $R^C$ is hydrogen, optionally substituted alkyl, or optionally substituted aryl or $R^2$ is an O-linked substituent; $R^3$ is hydrogen or optionally substituted alkyl; $R^4$, $R^{4A}$, $R^{4B}$, $R^5$ and $R^6$ are optionally substituted alkyl, independently selected, one $R^7$ is hydrogen or optionally substituted alkyl and the other $R^7$ is optionally substituted arylalkyl or optionally substituted heteroarylalkyl, and subscript m' is 0 or 1. In some embodiments, $R^4$ is methyl or $R^{4A}$ and $R^{4B}$ are methyl. In some embodiments, the 5-membered heteroarylene is represented by the structure

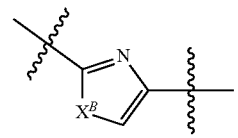

wherein $X^B$ is O, S, or N—$R^B$ wherein $R^B$ is hydrogen or lower alkyl. In some embodiments, the 5-membered heteroarylene is a divalent thiazole moiety. In some embodiments, subscript m' is 1.

In some embodiments, D has a formula selected from the group consisting of

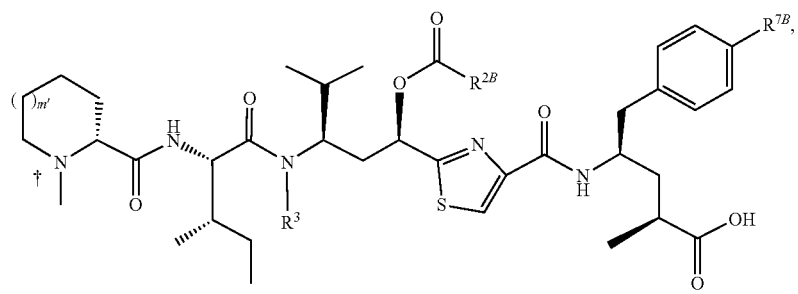
$D_{G-3}$

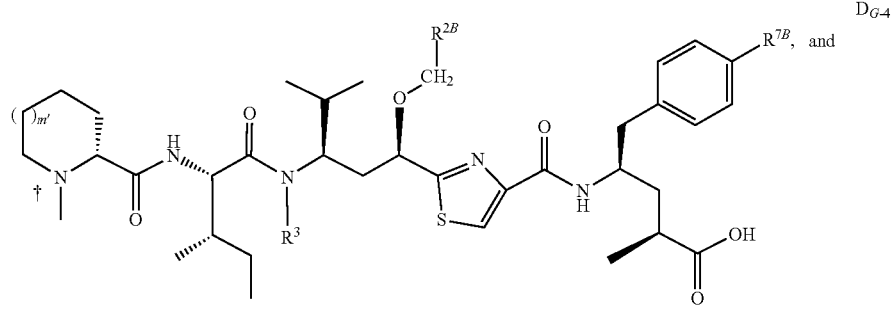
$D_{G-4}$, and

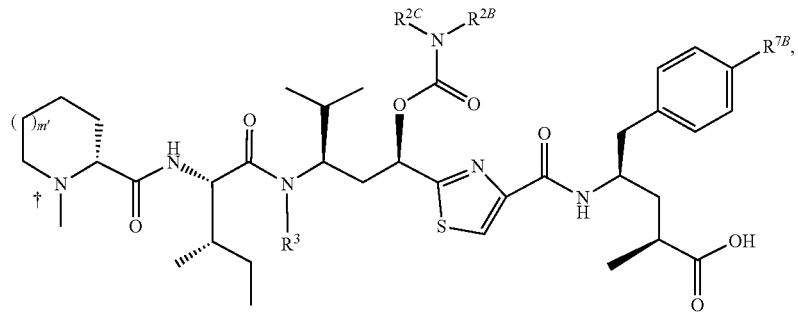
$D_{G-5}$ wherein R$^{7B}$ is hydrogen or —OH, R$^3$ is lower alkyl, and R$^{2B}$ and R$^{2C}$ are independently hydrogen or lower alkyl. In some embodiments, the Drug Linker compound has the structure:

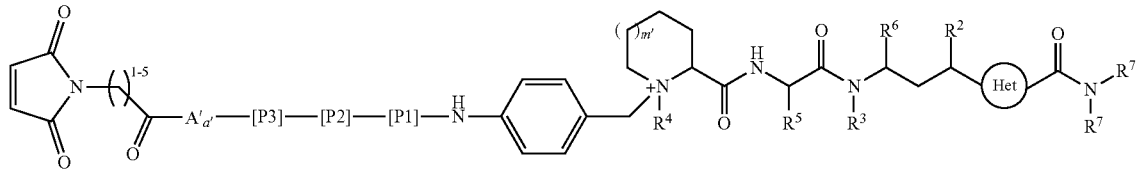

or a salt thereof, wherein subscript a' is 0, and A' is absent. In some embodiments, the Drug Linker compound has the structure:

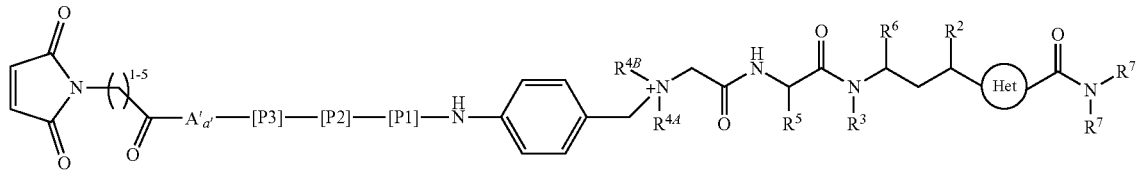

or a salt thereof, wherein subscript a' is 0, and A' is absent.

In some embodiments, D is a cytotoxic drug wherein the cytotoxic drug is a secondary amine-containing auristatin compound wherein the nitrogen atom of the secondary amine is the site of covalent attachment to the drug linker moiety and the secondary amine-containing auristatin compound has the structure of Formula D$_{F/E-3}$:

D$_{F/E-3}$

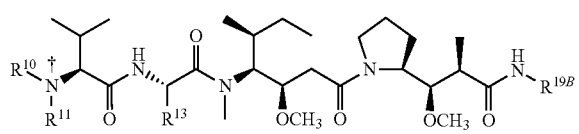

wherein the dagger indicates the site of covalent attachment of the nitrogen atom that provides the carbamate functional group; one of R$^{10}$ and R$^{11}$ is hydrogen and the other is methyl; R$^{13}$ is isopropyl or —CH$_2$—CH(CH$_3$)$_2$; and R$^{19B}$ is —CH(CH$_3$)—CH(OH)-Ph, —CH(CO$_2$H)—CH(OH)—CH$_3$, —CH(CO$_2$H)—CH$_2$Ph, —CH(CH$_2$Ph)-2-thiazolyl, —CH(CH$_2$Ph)-2-pyridyl, —CH(CH$_2$-p-Cl-Ph), —CH(CO$_2$Me)-CH$_2$Ph, —CH(CO$_2$Me)-CH$_2$CH$_2$SCH$_3$, —CH(CH$_2$CH$_2$SCH$_3$)C(=O)NH-quinol-3-yl, —CH(CH$_2$Ph)C(=O)NH-p-Cl-Ph, or R$^{19B}$ has the structure of

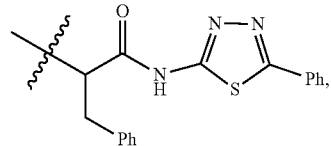 [SMILES: *C(Cc1ccccc1)C(=O)Nc1nnc(-c2ccccc2)s1]

wherein the wavy line indicates covalent attachment to the remainder of the auristatin compound. In some embodiments, the secondary amine-containing auristatin compound is monomethylauristatin E (MMAE) or monomethylauristatin F (MMAF).

In some embodiments, the Peptide Cleavable Unit is a tripeptide having the sequence -P3-P2-P1-, wherein P1, P2, and P3 are each an amino acid, wherein: the P3 amino acid of the tripeptide is in the D-amino acid configuration; one of the P2 and P1 amino acids has an aliphatic side chain with hydrophobicity lower than that of leucine; and the other of the P2 and P1 amino acids is negatively charged. In some embodiments, the P3 amino acid is D-Leu or D-Ala. In some embodiments, one of the P2 or P1 amino acid has an aliphatic side chain with hydrophobicity no greater than that of valine, and the other of the P2 or P1 amino acid is negatively charged at plasma physiological pH. In some embodiments, the P2 amino acid has an aliphatic side chain with hydrophobicity no greater than that of valine, and the P1 amino acid is negatively charged at plasma physiological pH. In some embodiments, -P2-P1- is -Ala-Glu- or -Ala-Asp-. In some embodiments, -P3-P2-P1- is -D-Leu-Ala-Asp-, -D-Leu-Ala-Glu-, -D-Ala-Ala-Asp-, or -D-Ala-Ala-Glu-. In some embodiments, the P3 amino acid is D-Leu or D-Ala, the P2 amino acid is Ala, Glu, or Asp, and the P1 amino acid is Ala, Glu, or Asp. In some embodiments, the Drug Linker compound has the structure of 41 42
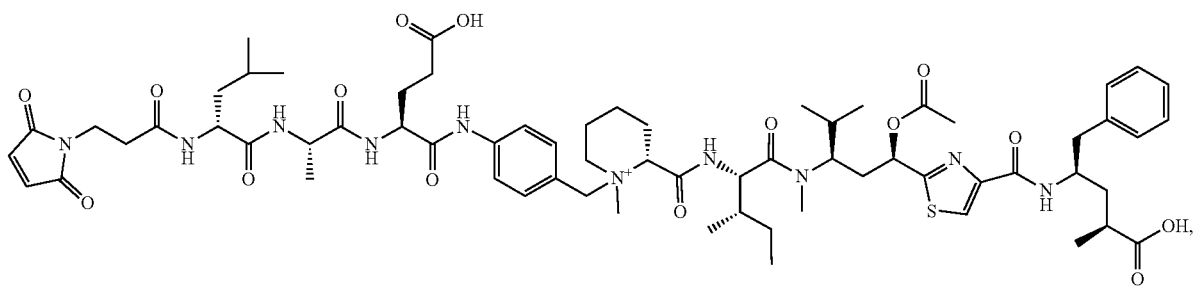
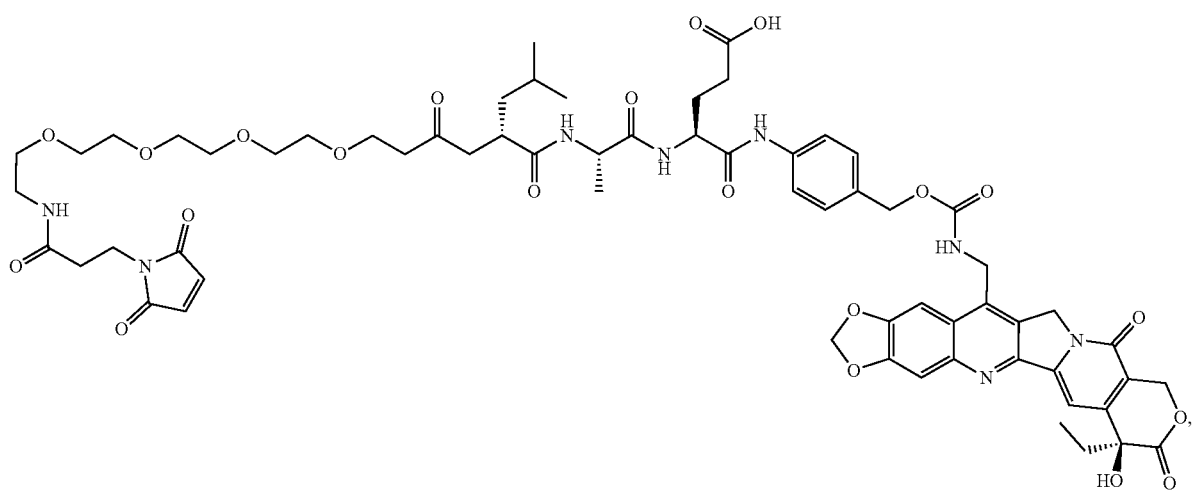
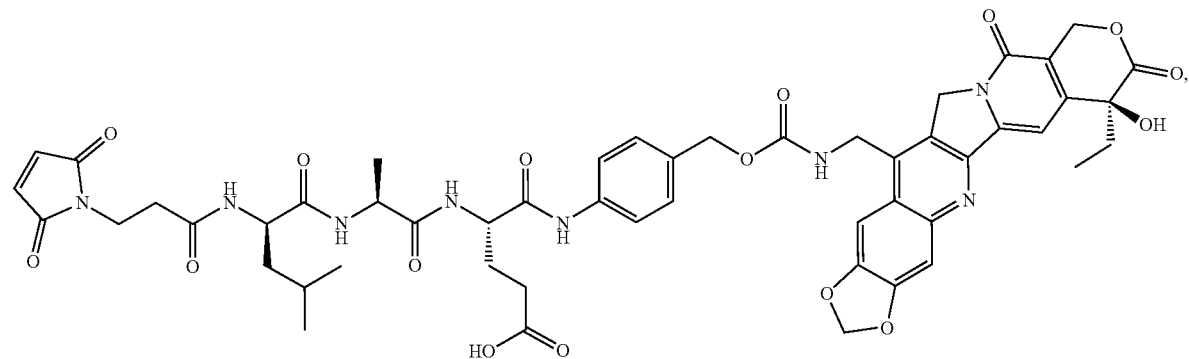
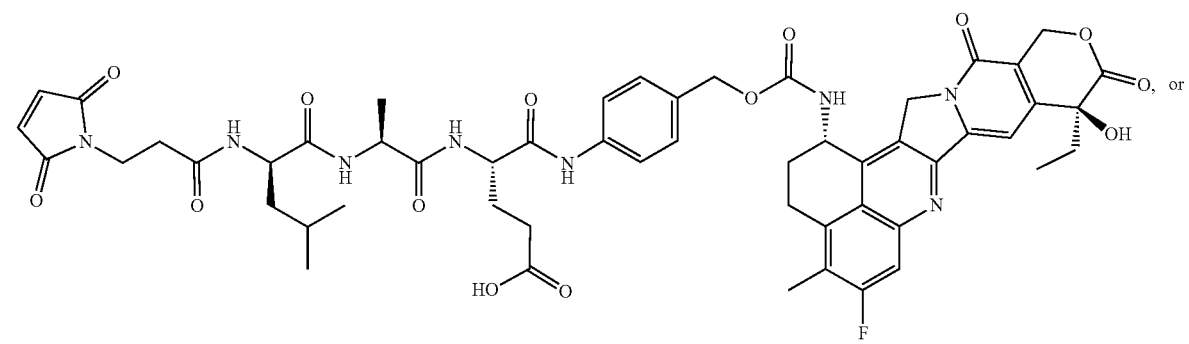

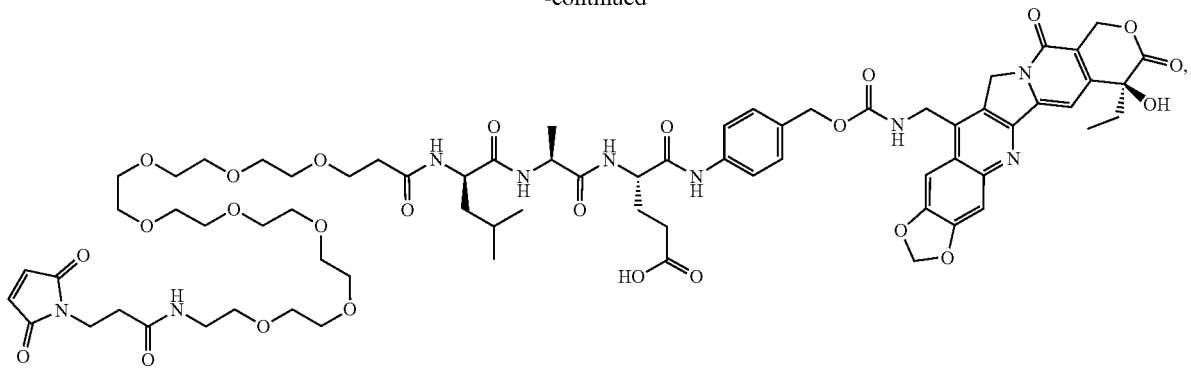
or a salt thereof.
In another aspect, provided herein is a method of preparing a compound having the structure of
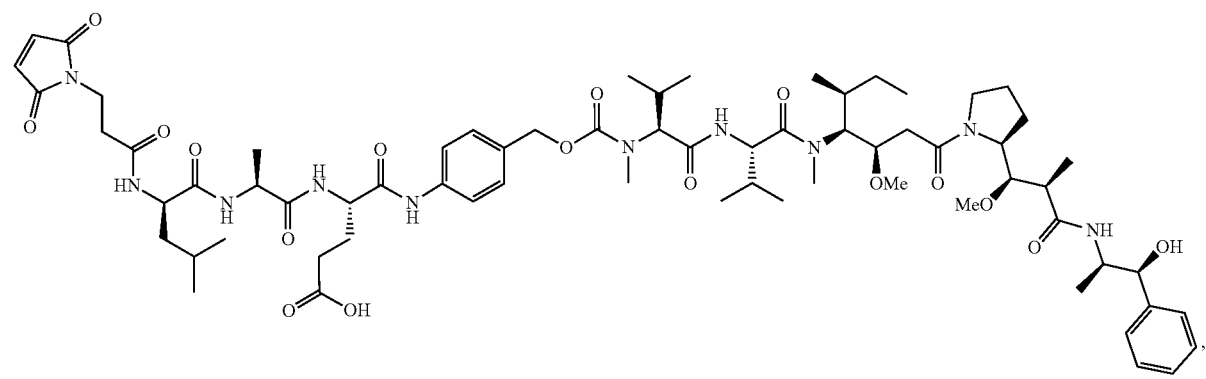 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCC(=O)O)NC(=O)[C@H](C)NC(=O)[C@@H](CC(C)C)NC(=O)CCN2C(=O)C=CC2=O)cc1)C(C)C]
or a salt thereof, comprising a) reacting
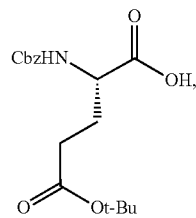 [SMILES: CC(C)(C)OC(=O)CC[C@H](NC(=O)OCc1ccccc1)C(=O)O]
or a salt thereof, with 4-aminobenzyl alcohol followed by reduction to form
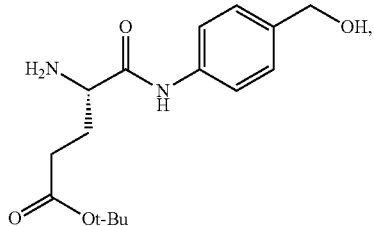 [SMILES: CC(C)(C)OC(=O)CC[C@H](N)C(=O)Nc1ccc(CO)cc1]
or a salt thereof, b) reacting the
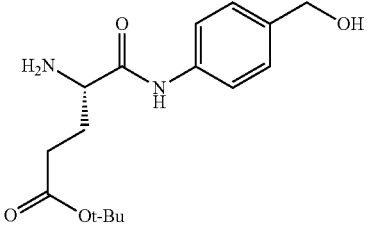 [SMILES: CC(C)(C)OC(=O)CC[C@H](N)C(=O)Nc1ccc(CO)cc1]
or salt thereof with
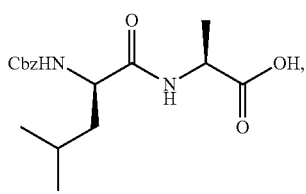 [SMILES: CC(C)C[C@@H](NC(=O)OCc1ccccc1)C(=O)N[C@@H](C)C(=O)O]

or a salt thereof, followed by reduction to form

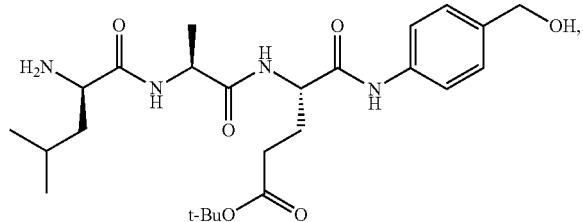 [SMILES: CC(C)C[C@@H](N)C(=O)N[C@@H](C)C(=O)N[C@@H](CCC(=O)OC(C)(C)C)C(=O)Nc1ccc(CO)cc1]

or a salt thereof; c) reacting the

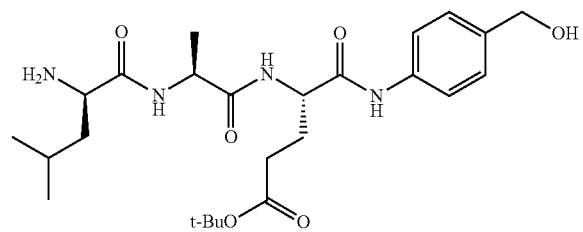 [SMILES: CC(C)C[C@@H](N)C(=O)N[C@@H](C)C(=O)N[C@@H](CCC(=O)OC(C)(C)C)C(=O)Nc1ccc(CO)cc1]

or salt thereof with 3-maleimidopropionic acid to form

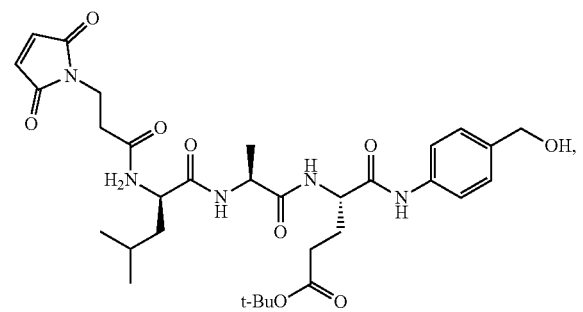 [SMILES: CC(C)C[C@@H](NC(=O)CCN1C(=O)C=CC1=O)C(=O)N[C@@H](C)C(=O)N[C@@H](CCC(=O)OC(C)(C)C)C(=O)Nc1ccc(CO)cc1]

or a salt thereof, and d) converting the

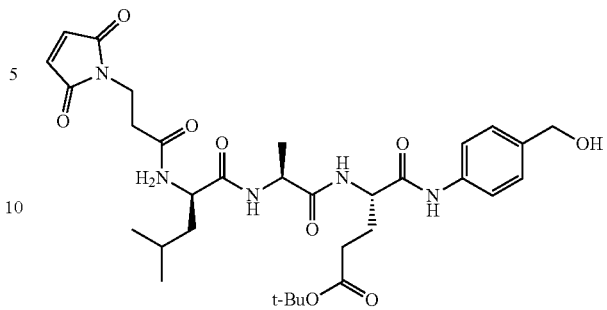

or salt thereof to the compound

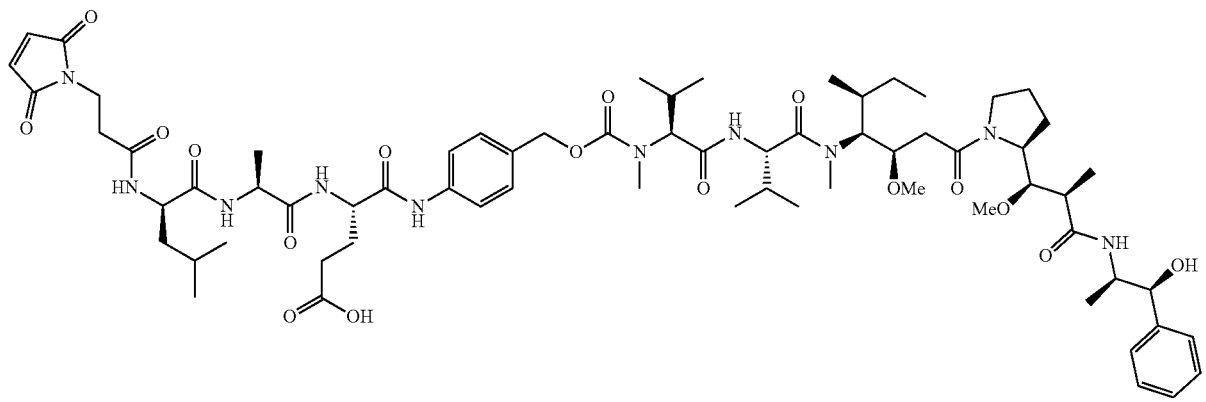 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCC(=O)O)NC(=O)[C@H](C)NC(=O)[C@@H](CC(C)C)NC(=O)CCN2C(=O)C=CC2=O)cc1)C(C)C]

or salt thereof.

In another aspect, antigen binding proteins (ABPs), including antigen binding fragments thereof, (e.g., antibodies and antigen binding fragments thereof) that bind GPNMB, CD228, αvβ6, CD30, LIV1, or CD19 are provided herein. The antigen binding proteins and fragments contain an antigen binding domain that specifically binds to GPNMB, CD228, αvβ6, CD30, LIV1, or CD19, including to human GPNMB, CD228, αvβ6, CD30, LIV1 (e.g., SEQ ID NO: 931), or CD19. In some embodiments, anti-GPNMB, anti-CD228, anti-αvβ6, anti-CD30, anti-LIV1, or anti-CD19 antibody-drug conjugates (ADCs) comprise an anti-GPNMB, anti-CD228, anti-αvβ6, anti-CD30, anti-LIV1, or anti-CD19 ABP as described above conjugated to a dLAE-MMAE (sometimes referred to herein as mp-dLAE-PABC-MMAE or mp-dLAE-MMAE) drug-linker. In some embodiments, these anti-GPNMB ADCs can be used to treat GPNMB-expressing cancers such as melanoma, lung, breast, head and neck, ovarian, sarcoma, mesothelioma, and cervical cancers. In some embodiments, these anti-CD228 ADCs can be used to treat CD228-expressing cancers such as melanoma, pancreatic cancer, mesothelioma, colorectal cancer, lung cancer, thyroid cancer, breast cancer, choliangiocarcinoma, esophageal cancer and head and neck cancer. In some embodiments, these anti-αvβ6 ADCs can be used to treat αvβ6-expressing cancers such as non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer. In some embodiments, these anti-CD30 ADCs can be used to treat CD30-expressing diseases such as cancer, autoimmune diseases, and other infectious diseases. In further embodiments, these anti-CD30 ADCs can be used to treat solid and liquid tumors, and autoimmune diseases such as HIV and AIDS. In some embodiments, these anti- LIV1 ADCs can be used to treat LIV1-expressing cancers such as breast cancer, prostate cancer, ovarian cancer, endometrial cancer, cervical, liver, gastric, kidney, and squamous cell carcinomas (e.g., bladder, head and neck, esophageal, and lung, e.g., non-small cell lung cancer); skin cancers, e.g., melanoma; small lung cell carcinoma or lung carcinoid or non-squamous non-small cell lung cancer. Breast cancers include, e.g., HER2 positive breast cancers, including HER-low breast cancers, hormone responsive breast cancers, such as estrogen receptor positive breast cancers, and triple negative breast cancers. Other cancers treated with an mp-dLAE-PABC-MMAE LIV1-ADC include gastric and gastroesophageal adenocarcinoma, castration resistant prostate cancer. In some embodiments, these anti-CD19 ADCs can be used to treat CD19-expressing cancers such as chronic leukemia, lymphoma, multiple myeloma, B type acute lymphoblastic leukemia, chronic myelocytic leukemia, chronic lymphocytic leukemia, non-Hodgkin lymphoma and Hodgkin lymphoma, B cell lymphoma, or diffuse large B-cell lymphoma.

Those and other embodiments of the invention are described in more detail in the following "Detailed Description of the Invention" and "Claims".

BRIEF DESCRIPTION OF THE DRAWINGS

FIG. 18. Histology of bone on days 5 and 8 after dose by non-targeted tripeptide ADCs after administration in rats at 20 mg/kg.

FIGS. 44A and 44B, respectively, show neurite cultures treated with a non-targeting antibody conjugated with vcMMAE (h00-1006) and conjugated with dLAE-MMAE (h00-7092). FIGS. 44C and 44D, respectively, shows a comparison of the data for the non-targeting antibody conjugated with vcMMAE (h00-1006) and conjugated with dLAE-MMAE (h00-7092) with and without addition of 50% serum.

DETAILED DESCRIPTION OF THE INVENTION

General

Figure 1A:
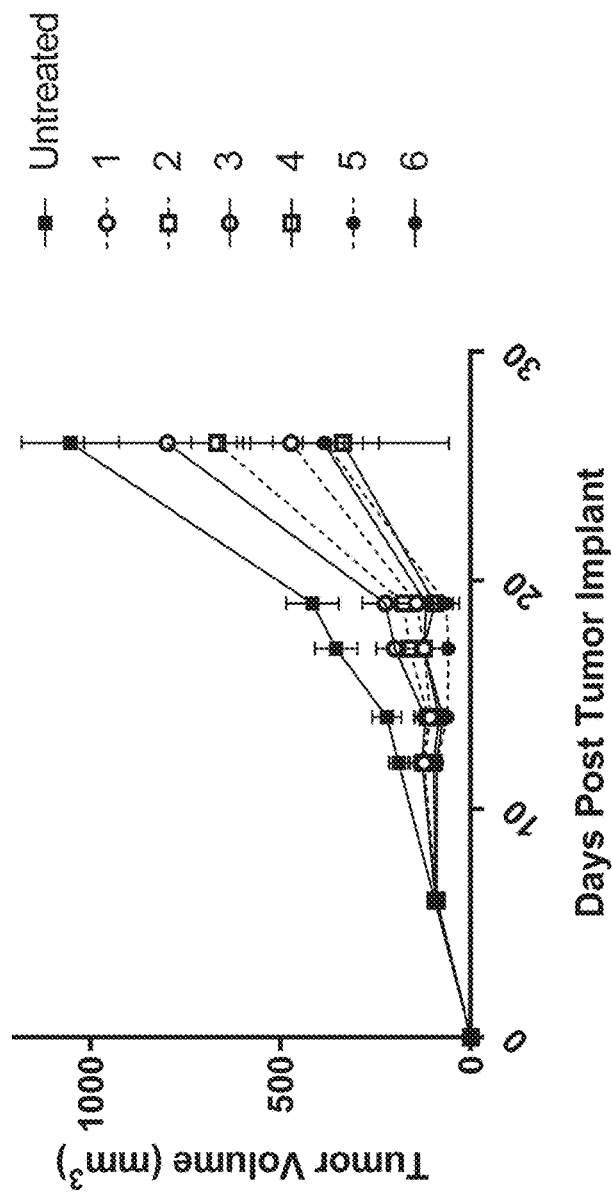
FIGS. 1A, 1B, 1C, and 1D. Tumor volume vs days post implant in a xenograft model treated with a series of 4-loaded ADCs having varying tripeptide sequences as the Peptide Cleavable Unit with drug-linker moieties represented by the formula of mp-$P_3$-$P_2$-$P_1$-PABC-MMAE at sub-curative doses compared to a subcurative dose of a 4-loaded ADC targeting the same cancer cell antigen and having drug-linker moieties represented by the formula of mc-val-cit-PABC-MMAE. Compounds in FIG. 1A were tested at at 4 mg/kg. Compounds in FIG. 1B and FIG. 1D were tested at 3 mg/kg. Compounds in FIG. 1C were tested at 6 mg/kg.

The present invention is based, in part, on the unexpected finding that protease activities in tumor tissue are sufficiently different from that of non-targeted normal tissue for providing additional selectivity towards cancer cells that are targeted by a Ligand Drug Conjugate having a protease activatable peptide sequence for conditional release of its conjugated cytotoxic compound. That difference is exploited by the protease cleavable peptide sequences disclosed herein, when those sequences are incorporated into a peptide cleavable Linker Unit of a Ligand Drug Conjugate compound. It is believed that sequences having that property in some instances provide Conjugate compounds whose biodistribution and/or sensitivity to proteolysis to release free cytotoxic compound favor tumor tissue in comparison to normal tissue.

The section headings used herein are for organizational purposes only and are not to be construed as limiting the subject matter described.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 4th edition (2012) Cold Spring Harbor Laboratory Press, Cold Spring Harbor N.Y.; Current Protocols In Molecular Biology (F. M. Ausubel, et al. eds., (2003)); the series METHODS IN ENZYMOLOGY (Academic Press, Inc.); PCR 2: A Practical Approach (M. J. MacPherson, B. D. Hames and G. R. Taylor eds. (1995)); Greenfield, ed. (2013) Antibodies, A Laboratory Manual, $2^{nd}$ edition, Cold Spring Harbor Laboratory Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); Cancer: Principles and Practice of Oncology (V. T. DeVita et al., eds., J.B. Lippincott Company, 1993); and updated versions thereof. Each of the foregoing references in this paragraph is incorporated herein by reference in its entirety.

1. Definitions

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, $5^{th}$ ed., 2013, Academic Press; and the Oxford Dictionary Of Biochemistry And Molecular Biology, $2^{nd}$ ed., 2006, Oxford University Press, provide one of skill with a general dictionary of many of the terms used in this disclosure.

Unless otherwise required by context or expressly indicated, singular terms shall include pluralities and plural terms shall include the singular.

It is understood that aspect and embodiments of the invention described herein include "comprising," "consisting," and/or "consisting essentially of" aspects and embodiments.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless otherwise stated or implied by context, terms that are used herein have the meanings defined below. Unless otherwise contraindicated or implied, e.g., by including mutually exclusive elements or options, in those definitions and throughout this specification, the terms "a" and "an" mean one or more and the term "or" means and/or where permitted by context. Thus, as presented in the specification and the appended claims, the singular forms "a," "an," and "the" include plural referents unless the context clearly dictates otherwise. At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are, or that consist of, or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open-ended, and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed, and they would not include or read on those compositions or methods having appreciable amounts of an additional component(s) or an additional step(s). Furthermore, the term "consisting essentially of" admits for the inclusion of unrecited elements that have no material effect on the functionality of the disclosed compositions, devices, articles of manufacture or methods for its intended purpose as further defined herein. The section headings used herein are for organizational purposes only and are not to be construed as limiting the subject matter described. Unless otherwise indicated, conventional methods of mass spectroscopy, NMR, HPLC, protein chemistry, biochemistry, recombinant DNA techniques, and pharmacology are employed.

The term "about" refers to a value or composition that is within an acceptable error range for the particular value or composition as determined by one of ordinary skill in the art, which will depend in part on how the value or composition is measured or determined, i.e., the limitations of the measurement system. As is understood by one skilled in the art, reference to "about" a value or parameter herein includes (and describes) embodiments that are directed to that value or parameter per se. For example, description referring to "about X" includes description of "X". "About", as the term is used herein, unless otherwise stated or implied by context, in connection with a numeric value or range of values to describe a particular property of a compound or composition, indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values can vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, or 0.01% of the recited value or range of values, typically by 10% to 0.5%, more typically by 5% to 1%, while still describing the particular property.

With respect to subscript p, which denotes the average number of drug linker moieties in a Ligand Drug Conjugate composition as further defined herein, the term "about" reflects the accepted uncertainty in the art for determining that value from a distribution of Ligand Drug Conjugate compounds within that composition as determined by standard methods of size exclusion, HIC chromatography or HPLC-MS.

"Essentially retains", "essentially retaining" and like terms, as used herein, unless otherwise stated or implied by context, refers to a property, characteristic, function or activity of a compound or composition or moiety thereof that has not detectably changed or is within experimental error of determination of that same activity, characteristic or property of a compound or composition or moiety of related structure.

"Substantially retains", "substantially retaining" and like terms, as used herein, unless otherwise stated or implied by context, refers to a measured value of a physical property or characteristic of a compound or composition or moiety thereof that may be statistically different from the determination of that same physical property of another compound or composition or moiety of related structure, but which such difference does not translate to a statistically significant or meaningful difference in biological activity or pharmacological property in a suitable biological test system for evaluating that activity or property (i.e., biological activity or property is retained or is essentially retained). Thus, the phrase "substantially retains" is made in reference to the effect that a physical property or characteristic of a compound or composition has on a physiochemical or pharmacological property or biological activity that is explicitly associated with that physical property or characteristic.

"Negligibly", "negligible" and like terms, as used herein, unless otherwise stated or implied by context, is an amount of an impurity below the level of quantification by HPLC analysis. Depending on context, those terms may alternatively mean that no statistically significant difference is observed between measured values or outcomes or are within experimental error of the instrumentation used to obtain those values. Negligible differences in values of a parameter determined experimentally do not imply that an impurity characterized by that parameter is present in negligible amount.

"Predominately containing", "predominately having" and like terms, as used herein, unless otherwise stated or implied by context, refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

"Electron-withdrawing group", as the term is used herein, unless otherwise stated or implied by context, refers to a functional group or electronegative atom that draws electron density away from an atom to which it is bonded either inductively and/or through resonance, whichever is more dominant (i.e., a functional group or atom may be electron-donating through resonance but may overall be electron withdrawing inductively), and tends to stabilize anions or electron-rich moieties. The electron-withdrawing effect is typically transmitted inductively, albeit in attenuated form, to other atoms attached to the bonded atom that has been made electron-deficient by the electron-withdrawing group (EWG), thus reducing the electron density of a more remote reactive center.

An electron-withdrawing group (EWG) is typically selected from the group consisting of —C(=O)R', —CN, —NO$_2$, —CX$_3$, —X, —C(=O)OR', —C(=O)NH$_2$, —C(=O)N(R')R$^{op}$, —C(=O)R', —C(=O)X, —S(=O)$_2$R$^{op}$, —S(=O)$_2$OR', —SO$_3$H$_2$, —S(=O)$_2$NH$_2$, —S(=O)$_2$N(R')R$^{op}$, -PO$_3$H$_2$, —P(=O)(OR')(OR$^{op}$)$_2$, —NO, —NH$_2$, —N(R')(R$^{op}$), —N(R$^{op}$)$_3$$^+$, and salts thereof, wherein X is —F, —Br, —Cl, or —I, R$^{op}$ is, at each occurrence, independently selected from a grouping previously described for optional substituents and R' is —H or R$^{op}$, wherein R$^{op}$ is a previously defined. In some aspects, each R$^{op}$ is independently C$_1$-C$_{12}$ alkyl, C$_1$-C$_8$ alkyl, C$_1$-C$_6$ alkyl or C$_1$-C$_4$ alkyl, or is independently selected from the group consisting of C$_1$-C$_6$ alkyl and optionally substituted phenyl, and R' is hydrogen. An EWG can also be an aryl (e.g., phenyl) or heteroaryl depending on its substitution and certain electron deficient heteroaryl groups (e.g., pyridyl). Thus, in some aspects, an "electron-withdrawing group" further encompasses electron-deficient C$_5$-C$_{24}$ heteroaryls and C$_6$-C$_{24}$ aryls that are substituted with electron-withdrawing substituents. More typically, an electron-withdrawing group is independently selected from the group consisting of —C(=O)R', —CN, —NO$_2$, —CX$_3$, and —X, wherein X is halogen, typically from the group consisting of —F and —Cl and R' is H, C$_1$-C$_6$ alkyl or C$_1$-C$_4$ alkyl. Depending on its substituents, an optionally substituted alkyl moiety may also be an electron withdrawing group and thus in such cases these aspects would be encompassed by the term for an electron-withdrawing group.

"Electron-donating group", as the term is used herein, unless otherwise stated or implied by context, refers to a functional group or electropositive atom that increases electron density of an atom to which it is bonded either inductively and/or through resonance, whichever is more dominant (i.e., a functional group or atom may be electron-withdrawing inductively but may overall be electron-donating through resonance), and tends to stabilize cations or electron poor systems. The electron-donating effect is typically transmitted through resonance to other atoms attached to the bonded atom that has been made electron rich by the electron-donating group (EDG) thus increasing the electron density of a more remote reactive center. Typically, an electron donating group is selected from the group consisting of —OH, —OR', —NH$_2$, —NHR', and N(R')$_2$, wherein each R' is an independently selected from C$_1$-C$_{12}$ alkyl, typically C$_1$-C$_6$ alkyl. Depending on its substituents, a C$_6$-C$_{24}$ aryl, C$_5$-C$_{24}$ heteroaryl, or unsaturated C$_1$-C$_{12}$ alkyl moiety may also be an electron-donating group, and in some aspects, such moieties are encompassed by the term for an electron-donating group.

"Compound" as the term is used herein, unless otherwise stated or implied by context, refers to and encompasses the chemical compound itself, either named or represented by structure, and salt form(s) thereof, whether explicitly stated or not, unless context makes clear that such salt forms are to be excluded. Compound salts include zwitterionic salt forms and acid addition and base addition salt forms having organic counterions or inorganic counterions and salt forms involving two or more counterions, which may be the same or different. In some aspects, the salt form is a pharmaceutically acceptable salt form of the compound. The term "compound" further encompasses solvate forms of the compound, in which solvent is noncovalently associated with the compound or is reversibly associated covalently with the compound, as when a carbonyl group of the compound is hydrated to form a gem-diol. Solvate forms include those of the compound itself and its salt form(s) and are inclusive of hemisolvates, monosolvates, disolvates, including hydrates; and when a compound can be associated with two or more solvent molecules, the two or more solvent molecules may be the same or different. In some instances, a compound of the invention will include an explicit reference to one or more of the above forms, e.g., salts and solvates, which does not imply any solid state form of the compound; however, this reference is for emphasis only, and is not to be construed as excluding any other of the forms as identified above. Furthermore, when explicit reference to a salt and/or solvate form of a compound or a Ligand Drug Conjugate composition is not made, that omission is not to be construed as excluding the salt and/or solvate form(s) of the compound or Conjugate unless context make clear that such salt and/or solvate forms are to be excluded.

"Optical isomer", as the term is used herein, unless otherwise stated or implied by context, refers to a related compound in comparison to a reference compound both having identical atom connectivities but differing structurally by one or more chiral centers in opposite stereochemical configuration(s).

"Moiety", as the term is used herein, unless otherwise stated or implied by context, means a specified segment, fragment, or functional group of a molecule or compound. Chemical moieties are sometimes indicated as chemical entities that are embedded in or appended to (i.e., a substituent or variable group) a molecule, compound or chemical formula.

Unless indicated otherwise or implied by context, for any substituent group or moiety described herein by a given range of carbon atoms, the designated range means that any individual number of carbon atoms is described. Thus, reference to, e.g., "optionally substituted $C_1$-$C_4$ alkyl" or "optionally substituted $C_2$-$C_6$ alkenyl" specifically means that a 1, 2, 3, or 4 carbon alkyl moiety, optionally substituted, as defined herein, is present, or a 2, 3, 4, 5, or 6 carbon alkenyl moiety, optionally substituted, as defined herein, is present, respectively. All such numerical designations are expressly intended to disclose all of the individual carbon atom groups; and thus "optionally substituted $C_1$-$C_4$ alkyl" includes, methyl, ethyl, 3-carbon alkyls, and 4-carbon alkyls, including all of their positional isomers, whether substituted or unsubstituted. Thus, when an alkyl moiety is substituted, the numerical designations refer to an unsubstituted base moiety and are not intended to include carbon atoms not directly attached to the base moiety that may be present in the substituents of that base moiety. For esters, carbonates, carbamates, and ureas as defined herein that are identified by a given range of carbon atoms, the designated range includes the carbonyl carbon of the respective functional group. Thus, a $C_1$ ester refers to a formate ester and a $C_2$ ester refers to an acetate ester.

The organic substituents, moieties, and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as the term is used herein, by itself or as part of another term, unless otherwise stated or implied by context, refers to methyl or a collection of contiguous carbon atoms, one of which is monovalent, wherein one or more of the carbon atoms are saturated (i.e., is comprised of one or more $sp^3$ carbons) and are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are, in some aspects, referred to as carbocyclyls as further defined herein.

When referring to an alkyl moiety or group as an alkyl substituent, that alkyl substituent to a Markush structure or another organic moiety with which it is associated is methyl or that chain of contiguous carbon atoms covalently attached to the structure or moiety through a $sp^3$ carbon of the alkyl substituent. An alkyl substituent, as used herein, therefore contains at least one saturated moiety and may also be substituted with cycloalkyl or aromatic or heteroaromatic moieties or groups or by an alkenyl or alkynyl moiety resulting in an unsaturated alkyl. Thus, an optionally substituted alkyl substituent may additionally contain one, two, three or more independently selected double bonds and/or triple bonds or may be substituted by alkenyl or alkynyl moieties or some combination thereof to define an unsaturated alkyl substituent and may be substituted by other moieties that include appropriate optional substituents as described herein. The number of carbon atoms in a saturated alkyl can vary and typically is 1-50, 1-30 or 1-20, and more typically is 1-8 or 1-6, and in an unsaturated alkyl moiety or group typically varies between 3-50, 3-30 or 3-20, and more typically varies between 3-8.

A saturated alkyl moiety contains saturated, acyclic carbon atoms (i.e., acyclic $sp^3$ carbons) and no $sp^2$ or sp carbon atoms, but may be substituted with an optional substituent as described herein, provided that such substitution is not through an $sp^3$, $sp^2$ or sp carbon atom of the optional substituent as that would affect the identity of the base alkyl moiety so substituted in carbon atom number except when the optional substituent is a Basic Unit as defined herein. Unless otherwise indicated or implied by context, the term "alkyl" will indicate a saturated, non-cyclic hydrocarbon radical, wherein the hydrocarbon radical has the indicated number of covalently linked saturated carbon atoms so that terms such as "$C_1$-$C_6$ alkyl" or "$C_1$-$C_6$ alkyl" means an alkyl moiety or group containing 1 saturated carbon atom (i.e., is methyl) or 2, 3, 4, 5 or 6 contiguous, non-cyclic saturated carbon atoms and "$C_1$-$C_8$ alkyl" refers to an alkyl moiety or group having 1 saturated carbon atom or 2, 3, 4, 5, 6, 7 or 8 contiguous saturated, non-cyclic carbon atoms. Typically a saturated alkyl is a $C_1$-$C_6$ or $C_1$-$C_4$ alkyl moiety containing no $sp^2$ or sp carbon atoms in its contiguous carbon chain, with the latter sometimes referred to as lower alkyl and in some aspects will refer to a saturated $C_1$-$C_8$ alkyl moiety having from 1 to 8 contiguous acyclic $sp^3$ carbon atoms containing no $sp^2$ or sp carbon atoms in its contiguous carbon chain when the number of carbon atoms is not indicated. In other aspects when a range of contiguous carbon atoms defines the term "alkyl" but without specifying it as saturated or unsaturated, then that term encompasses saturated alkyl with the specified range and unsaturated alkyl in which the lower limit of the range is increased by two carbon atoms. For example, the term "$C_1$-$C_8$ alkyl without limitation to a saturated alkyl includes saturated $C_1$-$C_8$ alkyl and $C_3$-$C_8$ unsaturated alkyl.

When a saturated alkyl substituent, moiety or group is specified, species include those derived from removing a hydrogen atom from a parent alkane (i.e., an alkyl moiety is monovalent) and may include methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear and branch chain alkyl moieties.

"Alkylene," as the term is used herein, by itself of as part of another term, unless otherwise stated or implied by context, refers to a saturated, branched or straight chain hydrocarbon diradical, substituted or unsubstituted, wherein one or more of the carbon atoms is saturated (i.e., is comprised of one or more $sp^3$ carbons), of the stated number of carbon atoms ranging from 1 to 50 or 1 to 30, typically 1 to 20 or 1 to 12 carbon atoms, more typically 1 to 8, 1 or 6, or 1 to 4 carbon atoms and having two radical centers (i.e., is divalent) derived by the removal of two hydrogen atoms from the same or two different saturated (i.e., $sp^3$) carbon atoms of a parent alkane. An alkylene moiety, in some aspects, is an alkyl radical as described herein in which a hydrogen atom has been removed from another of its saturated carbons or from the radical carbon of an alkyl radical to form a diradical. In other aspects, an alkylene moiety is or is further encompassed by a divalent moiety derived from removing a hydrogen atom from a saturated carbon atom of a parent alkyl moiety and are exemplified without limitation by methylene (—CH$_2$—), 1,2-ethylene (—CH₂CH₂—), 1,3-propylene (—CH₂CH₂CH₂—), 1,4-butylene (—CH₂CH₂CH₂CH₂—), and like diradicals. Typically, an alkylene is a branched or straight chain hydrocarbon containing only sp³ carbons (i.e., is fully saturated notwithstanding the radical carbon atoms) and, in some aspects, is unsubstituted. In other aspects, an alkylene contains an internal site of unsaturation(s) in the form of one or more double and/or triple bond functional groups, typically 1 or 2 such functional groups, more typically 1, so that the terminal carbons of the unsaturated alkylene moiety are monovalent sp³ carbon atoms. In still other aspects, the alkylene is substituted with 1 to 4, typically 1 to 3, or 1 or 2 substituents, as defined herein for optional substituents, at saturated carbon atom(s) of a saturated alkylene moiety or saturated and/or unsaturated carbon atom(s) of an unsaturated alkylene moiety, excluding alkyl, arylalkyl, alkenyl, alkynyl and any other moiety when the resulting substituted alkylene would differ by the number of contiguous non-aromatic carbon atoms relative to the unsubstituted alkylene, except when the optional substituent is a Basic Unit as defined herein.

"Carbocyclyl" as the term is used herein, by itself of as part of another term, unless otherwise stated or implied by context, refers to a radical of a monocyclic, bicyclic or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more sp³ carbons). Thus, a carbocyclyl is a cyclic arrangement of saturated carbons but may also contain unsaturated carbon atom(s) and therefore its carbocyclic ring may be saturated or partially unsaturated or may be fused with an aromatic moiety, wherein the points of fusion to the cycloalkyl and aromatic rings are to adjacent unsaturated carbons of the carbocyclyl moiety and adjacent aromatic carbon atoms of the aromatic moiety.

Unless otherwise specified, a carbocyclyl can be substituted (i.e. optionally substituted) with moieties described for alkyl, alkenyl, alkynyl, aryl, arylalkyl, alkylaryl and the like or can be substituted with another cycloalkyl moiety. Cycloalkyl moieties, groups or substituents include cyclopropyl, cyclopentyl, cyclohexyl, adamantly or other cyclic moieties that have only carbon atoms in their cyclic ring systems.

When carbocyclyl is used as a Markush group (i.e., a substituent) the carbocyclyl is attached to a Markush formula or another organic moiety with which it is associated through a carbon atom that is involved in the carbocyclic ring system of the carbocyclyl moiety provided that carbon is not an aromatic carbon. When an unsaturated carbon atom of an alkene moiety comprising the carbocyclyl substituent is attached to a Markush formula with which it is associated that carbocyclyl is sometimes referred to as a cycloalkenyl substituent. The number of carbon atoms in a carbocyclyl substituent is defined by the total number of skeletal atoms of its carbocyclic ring system. That number can vary and typically ranges from 3 to 50, 1-30 or 1-20, and more typically 3-8 or 3-6 unless otherwise specified, e.g., $C_3$-$C_8$ carbocyclyl means an carbocyclyl substituent, moiety or group containing 3, 4, 5, 6, 7 or 8 carbocyclic carbon atoms and $C_3$-$C_6$ carbocyclyl means an carbocyclyl substituent, moiety or group containing 3, 4, 5 or 6 carbocyclic carbon atoms. A carbocyclyl may be derived by the removal of one hydrogen atom from a ring atom of a parent cycloalkane or cycloalkene. Representative $C_3$-$C_8$ carbocyclyls include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Therefore, carbocyclyl substituents, moieties or groups typically have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share two carbon atoms and a tricyclic ring system may share a total of 3 or 4 carbon atoms. In some aspects, a carbocyclyl is a $C_3$-$C_8$ or $C_3$-$C_6$ carbocyclyl that may be substituted (i.e. optionally substituted) with one or more, 1 to 4, typically 1 to 3, or 1 or 2 moieties described herein for alkyl, alkenyl, alkynyl, aryl, arylalkyl, and alkylaryl and/or with other moieties, including substituent(s) as defined herein for optional substituents, and in some aspects is unsubstituted. In other aspects, a cycloalkyl moiety, group or substituent is a $C_3$-$C_6$ cycloalkyl selected from the group consisting of cyclopropyl, cyclopentyl and cyclohexyl, or is a $C_3$-$C_8$ cycloalkyl that encompasses that group and is further encompasses other cyclic moieties that have no more than 8 carbon atoms in their cyclic ring systems. When the number of carbon atoms is not indicated, a carbocyclyl moiety, group or substituent has from 3 to 8 carbon atoms in its carbocylic ring system.

"Carbocyclo", as the term is used herein by itself or as part of another term, unless otherwise stated or implied by context, refers to an optionally substituted carbocyclyl as defined above wherein another hydrogen atom of its cycloalkyl ring system has been removed (i.e., it is divalent) and is a $C_3$-$C_{50}$ or $C_3$-$C_{30}$ carbocyclo, typically a $C_3$-$C_{20}$ or $C_3$-$C_{12}$ carbocyclo, more typically a $C_3$-$C_8$ or $C_3$-$C_6$ carbocyclo and in some aspects is unsubstituted or an optionally substituted $C_3$, $C_5$ or $C_6$ carbocyclo. When the number of carbon atoms is not indicated, a carbocyclo moiety, group or substituent has from 3 to 8 carbon atoms in its carbocylic ring system.

In some aspects, that other hydrogen atom is removed from the monovalent carbon atom of the cycloalkyl to provide a divalent carbon atom, which in some instances is a spiro carbon atom that interrupts an alkyl moiety with that carbocyclic carbon atom. In such instances, the spiro carbon atom is attributed to the carbon atom count of the interrupted alkyl moiety and the carbocyclo ring system with the carbocyclo indicated as being incorporated into the alkyl moiety. In those aspects, a carbocyclo moiety, group or substituent is a $C_3$-$C_6$ carbocyclo in the form of a spiro ring system and is selected from the group consisting of cycloprop-1,1-diyl, cyclobutyl-1,1-diyl, cyclopent-1,1-diyl and cyclohex-1,1-diyl, or is a $C_3$-$C_8$ carbocyclo, which encompasses that group and is further encompassed by other divalent cyclic moieties that have no more than 8 carbon atoms in their cyclic ring systems. A carbocyclo may be a saturated or an unsaturated carbocyclo, and/or may be unsubstituted or unsubstituted in the same manner as described for a carbocyclyl moiety. If unsaturated, one or both monovalent carbon atoms of the carbocyclo moiety may be sp² carbon atoms from the same or a different double bond functional group or both monovalent carbon atoms may be adjacent or non-adjacent sp³ carbon atoms.

"Alkenyl" as the term is used herein, by itself or as part of another term, unless otherwise stated or implied by context, refers to an organic moiety, substituent or group that comprises one or more double bond functional groups (e.g., a —CH═CH— moiety) or 1, 2, 3, 4, 5 or 6 or more, typically 1, 2 or 3 of such functional groups, more typically one such functional group, and in some aspects may be substituted (i.e., is optionally substituted) with an aryl moiety or group such as phenyl, or may contain non-aromatic linked normal, secondary, tertiary or cyclic carbon atoms, i.e., linear, branched, cyclic or any combination thereof as part of the base moiety unless the alkenyl substituent, moiety or group is a vinyl moiety (e.g., a —CH═CH$_2$ moiety). An alkenyl moiety, group or substituent having multiple double bonds may have the double bonds arranged contiguously (i.e., a 1,3-butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

An alkenyl moiety, group or substituent contains at least one sp$^2$ carbon atom in which that carbon atom is divalent and is doubly bonded to another organic moiety or Markush structure to which it is associated, or contains at least two sp$^2$ carbon atoms in conjugation to each other in which one of the sp$^2$ carbon atoms is monovalent and is singly bonded to another organic moiety or Markush structure to which it is associated. Typically, when alkenyl is used as a Markush group (i.e., is a substituent) the alkenyl is singly bonded to a Markush formula or another organic moiety with which it is associated through a sp$^2$ carbon of an alkene functional group of the alkenyl moiety. In some aspects, when an alkenyl moiety is specified, species encompasses those corresponding to any of the optionally substituted alkyl or carbocyclyl, groups moieties or substituents described herein that has one or more endo double bonds in which a sp$^2$ carbon atom thereof is monovalent and monovalent moieties derived from removal of a hydrogen atom from a sp$^2$ carbon of a parent alkene compound. Such monovalent moieties are exemplified without limitation by vinyl (—CH═CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, and cyclohexenyl. In some aspects, the term alkenyl encompasses those and/or other linear, cyclic and branched chained, all carbon-containing moieties containing at least one double bond functional group in which one of the sp$^2$ carbon atoms is monovalent.

The number of carbon atoms in an alkenyl moiety is defined by the number of sp$^2$ carbon atoms of the alkene functional group(s) that defines it as an alkenyl substituent and the total number of contiguous non-aromatic carbon atoms appended to each of these sp$^2$ carbons not including any carbon atom of the other moiety or Markush structure for which the alkenyl moiety is a variable group and carbon atoms from any optional substituent to the alkenyl moiety. That number ranges from 1 to 50 or 1 to 30, typically 1 to 20 or 1 to 12, more typically, 1 to 8, 1 to 6 or 1 to 4 carbon atoms when the double bond functional group is doubly bonded to a Markush structure (e.g. ═CH$_2$), or ranges from 2 to 50, typically 2 to 30, 2 to 20 or 2 to 12, more typically 2 to 8, 2 to 6 or 2 to 4 carbon atoms, when the double bond functional group is singly bonded to the Markush structure (e.g., —CH═CH$_2$). For example, $C_2$-$C_8$ alkenyl or $C_2$-$C_8$ alkenyl means an alkenyl moiety containing 2, 3, 4, 5, 6, 7 or 8 carbon atoms in which at least two are sp$^2$ carbon atoms in conjugation with each other with one of these carbon atoms being monovalent, and $C_2$-$C_6$ alkenyl or $C_2$-$C_6$ alkenyl means an alkenyl moiety containing 2, 3, 4, 5 or 6 carbon atoms in which at least two are sp$^2$ carbons that are in conjugation with each other with one of these carbon atoms being monovalent. In some aspects, an alkenyl substituent or group is a $C_2$-$C_6$ or $C_2$-$C_4$ alkenyl moiety having only two sp$^2$ carbons that are in conjugation with each other with one of these carbon atoms being monovalent, and in other aspects that alkenyl moiety is unsubstituted or is substituted with 1 to 4 or more, typically 1 to 3, more typically 1 or 2, independently selected moieties as disclosed herein, including substituents as defined herein for optional substituents, excluding alkyl, arylalkyl, heteroarylalkyl, alkenyl, alkynyl and any other moiety when the substituted alkenyl would differ by the number of contiguous non-aromatic carbon atoms relative to the unsubstituted alkenyl, wherein the substitution(s) may be at any of the alkenyl moiety's contiguous sp$^2$ carbon and sp$^3$ carbon atoms, if any. Typically, an alkenyl substituent is a $C_2$-$C_6$ or $C_2$-$C_4$ alkenyl moiety having only two sp$^2$ carbons that are in conjugation with each other. When the number of carbon atoms is not indicated, an alkenyl moiety has from 2 to 8 carbon atoms.

"Alkenylene" as the term is used herein, by itself of as part of another term, unless otherwise stated or implied by context, refers to an organic moiety, substituent or group that comprises one or more double bond moieties, as previously described for alkenyl, of the stated number of carbon atoms and has two radical centers derived by the removal of two hydrogen atoms from the same or two different sp$^2$ carbon atoms of an alkene functional group or removal of two hydrogen atoms from two separate alkene functional groups in a parent alkene. In some aspects, an alkenylene moiety is that of an alkenyl radical as described herein in which a hydrogen atom has been removed from the same or different sp$^2$ carbon atom of a double bond functional group of the alkenyl radical, or from a sp$^2$ carbon from a different double bonded moiety to provide a diradical. Typically, alkenylene moieties encompass diradicals containing the structure of —C═C— or —C═C—X$^1$—C═C— wherein X$^1$ is absent or is an optionally substituted saturated alkylene as defined herein, which is typically a $C_1$-$C_6$ alkylene, which is more typically unsubstituted. The number of carbon atoms in an alkenylene moiety is defined by the number of sp$^2$ carbon atoms of its alkene functional group(s) that defines it as an alkenylene moiety and the total number of contiguous non-aromatic carbon atoms appended to each of its sp$^2$ carbons not including any carbon atoms of the other moiety or Markush structure in which the alkenyl moiety is a present as a variable group. That number, unless otherwise specified, ranges from 2 to 50 or 2 to 30, typically from 2 to 20 or 2 to 12, more typically from 2 to 8, 2 to 6 or 2 to 4 carbon atoms. For example, $C_2$-$C_8$ alkenylene or C2-C8 alkenylene means an alkenylene moiety containing 2, 3, 4, 5, 6, 7 or 8 carbon atoms, in which at least two are sp$^2$ carbons in which one is divalent or both are monovalent, that are in conjugation with each other and $C_2$-$C_6$ alkenylene or C2-C6 alkenylene means an alkenyl moiety containing 2, 3, 4, 5 or 6 carbon atoms in which at least two are sp$^2$ carbons, in which at least two are sp$^2$ carbons in which one is divalent or both are monovalent, that are in conjugation with each other. In some aspects, an alkenylene moiety is a $C_2$-$C_6$ or $C_2$-$C_4$ alkenylene having two sp$^2$ carbons that are in conjugation with each other in which both sp$^2$ carbon atoms are monovalent, and in some aspects is unsubstituted. When the number of carbon atoms is not indicated, an alkenylene moiety has from 2 to 8 carbon atoms and is unsubstituted or substituted in the same manner described for an alkenyl moiety.

"Alkynyl" as the term is used herein, by itself or as part of another term, unless otherwise stated or implied by context, refers to an organic moiety, substituent or group that comprises one or more triple bond functional groups (e.g., a —C≡C— moiety) or 1, 2, 3, 4, 5, or 6 or more, typically 1, 2, or 3 of such functional groups, more typically one such functional group, and in some aspects may be substituted (i.e., is optionally substituted) with an aryl moiety such as phenyl, or by an alkenyl moiety or linked normal, secondary, tertiary or cyclic carbon atoms, i.e., linear, branched, cyclic or any combination thereof unless the alkynyl substituent, moiety or group is —C≡CH). An alkynyl moiety, group or substituent having multiple triple bonds may have the triple bonds arranged contiguously or non-contiguously with one or more intervening saturated or unsaturated carbon atoms or a combination thereof, provided that a cyclic, contiguous arrangement of triple bonds do not form a cyclic conjugated system of 4n+2 electrons (i.e., is not aromatic).

An alkynyl moiety, group or substituent contains at least two sp carbon atom in which the carbon atoms are conjugation to each other and in which one of the sp carbon atoms is singly bonded, to another organic moiety or Markush structure to which it is associated. When alkynyl is used as a Markush group (i.e., is a substituent) the alkynyl is singly bonded to a Markush formula or another organic moiety with which it is associated through a triple-bonded carbon (i.e., a sp carbon) of a terminal alkyne functional group. In some aspects when an alkynyl moiety, group or substituent is specified, species encompasses are any of the optionally substituted alkyl or carbocyclyl, groups moieties or substituents described herein that has one or more endo triple bonds and monovalent moieties derived from removal of a hydrogen atom from a sp carbon of a parent alkyne compound. Such monovalent moieties are exemplified without limitation by —C≡CH, and —C≡C—CH$_3$, and —C≡C-Ph.

The number of carbon atoms in an alkynyl substituent is defined by the number of sp carbon atoms of the alkene functional group that defines it as an alkynyl substituent and the total number of contiguous non-aromatic carbon atoms appended to each of these sp carbons not including any carbon atom of the other moiety or Markush structure for which the alkenyl moiety is a variable group. That number can vary ranging from 2 to 50, typically 2 to 30, 2 to 20, or 2 to 12, more typically 2 to 8, 2 to 6, or 2 to 4 carbon atoms, when the triple bond functional group is singly bonded to the Markush structure (e.g., —CH≡CH). For example, $C_2$-$C_8$ alkynyl or C2-C8 alkynyl means an alkynyl moiety containing 2, 3, 4, 5, 6, 7, or 8 carbon atoms in which at least two are sp carbon atoms in conjugation with each other with one of these carbon atoms being monovalent, and $C_2$-$C_6$ alkynyl or C2-C6 alkynyl means an alkynyl moiety containing 2, 3, 4, 5, or 6 carbon atoms in which at least two are sp carbons that are in conjugation with each other with one of these carbon atoms being monovalent. In some aspects, an alkynyl substituent or group is a $C_2$-$C_6$ or $C_2$-$C_4$ alkynyl moiety having two sp carbons that are in conjugation with each other with one of these carbon atoms being monovalent, and in other aspects that alkynyl moiety is unsubstituted. When the number of carbon atoms is not indicated, an alkynyl moiety, group or substituent has from 2 to 8 carbon atoms. An alkynyl moiety may be substituted or unsubstituted in the same manner as described for an alkenyl moiety, except that substitution at the monovalent sp carbon is not permitted.

"Aryl" as the term is used herein, by itself or as part of another term, unless otherwise stated or implied by context, refers to an organic moiety, substituent or group having an aromatic or fused aromatic ring system with no ring heteroatoms comprising or consisting of 1, 2, 3 or 4 to 6 aromatic rings each of which are independently optionally substituted, typically consisting of 1 to 3 aromatic rings, more typically 1 or 2 aromatic rings each of which are independently optionally substituted, wherein the rings are composed of only carbon atoms that participate in a cyclically conjugated system of 4n+2 electrons (Hückel rule), typically 6, 10 or 14 electrons, some of which may additionally participate in exocyclic conjugation with a heteroatom (cross-conjugated, e.g., quinone). Aryl substituents, moieties or groups are typically formed by six, eight, ten or more contiguous aromatic carbon atoms up to 24 to include $C_6$-$C_{24}$ aryl and in some aspects is a $C_6$-$C_{20}$ or $C_6$-$C_{12}$ aryl. Aryl substituents, moieties or groups are optionally substituted and in some aspects are unsubstituted or substituted with 1, 2, 3 or more, typically 1 or 2, independently selected substituents as defined herein for alkyl, alkenyl, alkynyl or other moiety described herein including another aryl or a heteroaryl to form a biaryl and other optional substituents as defined herein. In other aspects, aryls are $C_6$-$C_{10}$ aryls such as phenyl and naphthalenyl and phenanthryl. As aromaticity in a neutral aryl moiety requires an even number or electrons, it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group.

"Heterocyclyl" as the term is used herein, by itself or as part of another term, unless otherwise stated or implied by context, refers to a carbocyclyl in which one or more, but not all of the skeletal carbon atoms with their attached hydrogen atoms within the carbocyclic ring system are replaced by independently selected heteroatoms or heteroatom moieties, optionally substituted where permitted, including without limitation N/NH, O, S, Se, B, Si and P, wherein two or more heteroatoms or heteroatom moieties, typically 2, may be adjacent to each other or separated by one or more carbon atoms within the same ring system, typically by 1 to 3 carbon atoms. Those heteroatoms or heteroatom moieties typically are N/NH, O and S. A heterocyclyl typically contains a monovalent skeletal carbon atom or a monovalent heteroatom or heteroatom moiety and has a total of one to ten heteroatoms and/or heteroatom moieties, typically a total of 1 to 5, or more typically a total of 1 to 3, or 1 or 2, provided that not all of the skeletal atoms in any one of the heterocyclic ring(s) in the heterocyclyl are heteroatoms and/or heteroatom moieties (i.e. at least one carbon atom is not replaced in each ring with at least one having been replaced in one of the rings), wherein each heteroatom or heteroatom moiety in the ring(s), optionally substituted where permitted, is independently selected from the group consisting of N/NH, O and S, with the proviso that any one ring does not contain two adjacent O or S atoms. Exemplary heterocyclyls and heteroaryls are collectively referred to as heterocycles, are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocyclyl is used as a Markush group (i.e., a substituent) a saturated or partially unsaturated heterocyclic ring of the heterocyclyl is attached to a Markush structure or other moiety with which it is associated through a carbon atom or a heteroatom of that heterocyclic ring, where such attachment does not result in an unstable or disallowed formal oxidation state of that carbon atom or heteroatom. A heterocyclyl in that context is a monovalent moiety in which a heterocyclic ring of the heterocyclic ring system defining it as a heterocyclyl is non-aromatic, but may be fused with a carbocyclic, aryl or heteroaryl ring and includes phenyl- (i.e., benzo) fused heterocyclic moieties.

A heterocyclyl is a $C_3$-$C_{50}$ or $C_3$-$C_{30}$ carbocyclyl, typically a $C_3$-$C_{20}$ or $C_3$-$C_{12}$ carbocyclyl, more typically a $C_3$-$C_8$ or $C_3$-$C_6$ carbocyclyl wherein 1, 2 or 3 or more, but not all of its carbons of its cycloalkyl ring system are replaced along with its attached hydrogens, typically 1, 2, 3 or 4, more typically 1 or 2, are replaced with a heteroatom or heteroatom moiety independently selected from the group consisting of N/NH, O and S, optionally substituted where permitted, and thus is a $C_3$-$C_{50}$ or $C_3$-$C_{30}$ heterocyclyl, typically a $C_3$-$C_{20}$ or $C_3$-$C_{12}$ heterocyclyl, more typically a $C_3$-$C_6$, or $C_5$-$C_6$ heterocyclyl, in which the subscript indicates the total number of skeletal atoms (inclusive of its carbon atoms and heteroatoms) of the heterocyclic ring system(s) of the heterocyclyl. In some aspects, a heterocyclyl contains 0 to 2 N, 0 to 2 O or 0 to 1 S skeletal heteroatoms, optionally substituted or some combination thereof provided at least one of said heteroatoms is present in a heterocyclic ring system of the heterocyclyl. A heterocyclyl may be saturated or partially unsaturated and/or unsubstituted or substituted at a skeletal carbon atom with an oxo (=O) moiety, as in pyrrolidin-2-one, and/or at a skeletal heteroatom with one or two oxo moieties so as to contain an oxidized heteroatom as exemplified, but not limited to, —N(=O), —S(=O)— or —S(=O)$_2$—. A fully saturated or partially unsaturated heterocyclyl may be substituted or further substituted with an alkyl, (hetero)aryl, (hetero)aryl-alkyl, alkenyl, alkynyl or other moiety as described herein, including optional substituents as defined herein or a combination of 2, 3 or more, typically 1 or 2, such substituents. In certain aspects, heterocyclyl is selected from the group consisting of pyrrolidinyl, piperidinyl, morpholinyl and piperazinyl.

"Heterocyclo", as the term is used herein, by itself or as part of another term, unless otherwise stated or implied by context, refers to a heterocyclyl moiety, group or substituent as defined above wherein a hydrogen atom from its monovalent carbon atom, a hydrogen atom from a different skeletal atom (carbon or nitrogen atom if the latter is present), or an electron from a skeletal nitrogen atom, where permitted, is removed or an electron from a nitrogen ring atom that is not already monovalent is removed and is replaced with a bond (i.e., it is divalent). In some aspects, the replaced second hydrogen is that of the monovalent carbon atom of the parent heterocyclyl thus forming a spiro carbon atom, which in some instances may interrupt an alkyl moiety with that carbocyclic carbon atom. In such instances, the spiro carbon atom is attributed to the carbon atom count of the interrupted alkyl moiety with the heterocyclo indicated as being incorporated into the alkyl moiety.

"Heteroaryl" as the term is used herein, by itself or as part of another term, unless otherwise stated or implied by context, refers to an aryl moiety, group or substituent as defined herein in which one or more but not all of the aromatic carbons of an aromatic ring system of an aryl is replaced by a heteroatom. A heteroaryl typically contains a total one to four skeletal heteroatoms in the ring(s) of the heteroaryl ring system, provided that not all of the skeletal atoms of any one ring system in the heteroaryl are heteroatoms, which are optionally substituted where permitted, and have 0 to 3 N, 1 to 3 N or 0 to 3 N skeletal heteroatoms, typically 0 to 1 O, and/or 0 to 1 S skeletal heteroatoms, provided that at least one skeletal heteroatom is present. A heteroaryl may be monocyclic, bicyclic or polycyclic. A polycyclic heteroaryl is typically a $C_5$-$C_{50}$ or $C_5$-$C_{30}$ heteroaryl, more typically a $C_5$-$C_{20}$ or $C_5$-$C_{12}$ heteroaryl, a bicyclic heteroaryl is typically a $C_5$-$C_{10}$ heteroaryl, and a monocyclic heteroaryl is a typically is $C_5$-$C_6$ heteroaryl, in which the subscript indicates the total number of skeletal atoms (inclusive of its carbon atoms and heteroatoms) of the aromatic ring system(s) of the heteroaryl. In some aspects, a heteroaryl is a bicyclic aryl moiety wherein one 1, 2, 3, 4 or more, typically 1, 2 or 3, of the carbon atoms of the aromatic ring(s) and their attached hydrogen atoms of a parent bicyclic aryl moiety are replaced by an independently selected heteroatom or heteroatom moiety, or is a monocyclic aryl moiety wherein one 1, 2, 3 or more, typically 1 or 2, of the carbon atoms of the aromatic ring(s) and their attached hydrogen atoms of a parent monocyclic aryl moiety are replaced by an independently selected heteroatom or heteroatom moiety, wherein the heteroatom or heteroatom moiety is optionally substituted where permitted, including N/NH, O and S, provided that not all of the skeletal atoms of any one aromatic ring system in the parent aryl moiety are replaced by heteroatoms and more typically are replaced by oxygen (—O—), sulfur (—S—) nitrogen (=N—) or —NR—, so that the nitrogen heteroatom is optionally substituted, wherein R is —H, a nitrogen protecting group or optionally substituted $C_1$-$C_{20}$ alkyl or is an optionally substituted $C_6$-$C_{24}$ aryl or $C_5$-$C_{24}$ heteroaryl to form a heterobiaryl. In other aspects, 1, 2 or 3 of the carbon atoms of the aromatic ring(s) and their attached hydrogen atoms of a parent aryl moiety are replaced by nitrogen substituted with another organic moiety in a manner which retains the cyclic conjugated system. In still other aspects, the aromatic carbon radical of a parent aryl moiety is replaced with an aromatic nitrogen radical. In either of those aspects, the nitrogen, sulfur or oxygen heteroatom participates in the conjugated system either through pi-bonding with an adjacent atom in the ring system or through a lone pair of electrons on the heteroatom. In still other aspects, a heteroaryl has the structure of a heterocyclyl as defined herein in which its ring system has been aromatized.

Typically, a heteroaryl is monocyclic, which, in some aspects, has a 5-membered or 6-membered heteroaromatic ring system. A 5-membered heteroaryl is a monocyclic $C_5$-heteroaryl containing 1 to 4 aromatic carbon atoms and the requisite number of aromatic heteroatoms within its heteroaromatic ring system. A 6-membered heteroaryl is a monocyclic $C_6$ heteroaryl containing 1 to 5 aromatic carbon atoms and the requisite number of aromatic heteroatoms within its heteroaromatic ring system. Heteroaryls that are 5-membered have four, three, two or one aromatic heteroatom(s), and heteroaryls that are 6-membered include heteroaryls having five, four, three, two or one aromatic heteroatom(s).

$C_5$-heteroaryls, also referred to as 5-membered heteroaryl, are monovalent moieties derived from removing a hydrogen atom from a skeletal aromatic carbon or an electron from a skeletal aromatic heteroatom, where permitted, from a parent aromatic heterocycle compound, which is some aspects is selected from the group consisting of pyrrole, furan, thiophene, oxazole, isoxazole, thiazole, isothiazole, imidazole, pyrazole, triazole and tetrazole. In other aspects, the parent heterocycle is selected from the group consisting of thiazole, imidazole, oxazole, and triazole and is typically thiazole or oxazole, more typically thiazole.

$C_6$ heteroaryls, which are 6-membered, are monovalent moieties derived from removing a hydrogen atom from an aromatic carbon or an electron from an aromatic heteroatom, where permitted, from a parent aromatic heterocycle compound, which is certain aspects is selected from the group consisting of pyridine, pyridazine, pyrimidine, and triazine. A heteroaryl may be substituted or further substituted with an alkyl, (hetero)arylalkyl, alkenyl or alkynyl, or with an aryl or another heteroaryl to form a biaryl, or with other moieties as described herein, including optional substituents as defined herein, or a combination of 2, 3 or more, typically 1 or 2, such substituents.

"Arylalkyl" or "heteroarylalkyl" as the terms are used herein, by itself or as part of another term, refers to an aryl or heteroaryl moiety bonded to an alkyl moiety, i.e., (aryl)-alkyl-, where alkyl and aryl groups are as described above. Typically, an arylalkyl is a ($C_6$-$C_{24}$ aryl)-$C_1$-$C_{12}$ alkyl- moiety, group or substituent, and heteroarylalkyl is a ($C_5$-$C_{24}$ heteroaryl)-$C_1$-$C_{12}$ alkyl- moiety, group or substituent. When (hetero)arylalkyl is used as a Markush group (i.e., a substituent) the alkyl moiety of the (hetero)arylalkyl is attached to a Markush formula with which it is associated through a sp$^3$ carbon of its alkyl moiety. In some aspects, an arylalkyl is a ($C_6$-$C_{24}$ aryl)-$C_1$-$C_{12}$ alkyl- or a ($C_6$-$C_{20}$ aryl)-$C_1$-$C_{20}$ alkyl-, typically a ($C_6$-$C_{12}$ aryl)-$C_1$-$C_{12}$ alkyl- or ($C_6$-$C_{10}$ aryl)-$C_1$-$C_{12}$ alkyl-, more typically a ($C_6$-$C_{10}$ aryl)-$C_1$-$C_6$ alkyl-exemplified without limitation, by $C_6H_5$—$CH_2$—, $C_6H_5$—$CH(CH_3)CH_2$— and $C_6H_5$—$CH_2$—$CH(CH_2CH_3)$—. An (hetero)arylalkyl may be unsubstituted or substituted in the same manner as described for (hetero)aryl and/or alkyl moieties.

"Arylene," or "heteroarylene" as the terms are used herein, by itself or as part of another term, unless otherwise stated or implied by context, is an aromatic or heteroaromatic diradical moiety that forms two covalent bonds (i.e., it is divalent) within another organic moiety, for which the bonds are in the ortho, meta, or para configuration. Arylene and some heteroarylenes include divalent species by removal of a hydrogen atom from a parent aryl or heteroaryl moiety, group or substituent as defined herein. Other heteroarylenes are divalent species in which hydrogen atoms have been removed from two different aromatic carbon atoms of a parent aromatic heterocycle to form a diradical species, or from removal of a hydrogen atom from an aromatic carbon atom or heteroatom and of another hydrogen atom or electron from a different aromatic heteroatom from a parent aromatic heterocycle to form a diradical species in which one aromatic carbon atom and one aromatic heteroatom is monovalent or two different aromatic heteroatoms are each monovalent. Heteroarylene further include those in which heteroatom(s) and/or heteroatom moiety(ies) replace one or more but not all of the aromatic carbon atoms of a parent arylene.

Non-limiting exemplary arylenes, which are optionally substituted at the remaining positions, are phenyl-1,2-ene, phenyl-1,3-ene, and phenyl-1,4-ene, as shown in the following structures:

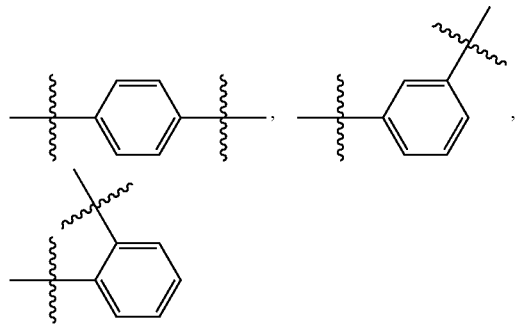

"Heteroalkyl," as the term is used herein by itself or in combination with another term, unless otherwise stated or implied by context, refers to an optionally substituted straight or branched chain hydrocarbon, fully saturated or containing from 1 to 3 degrees of unsaturation and having 1 to 12 carbon atom and 1 to 6 heteroatoms, typically 1 to 5 heteroatoms, more typically one or two heteroatoms or heteroatom moieties, selected from the group consisting of O, N/NH, Si and S, optionally substituted where permitted, and includes each nitrogen and sulfur atom independently optionally oxidized to an N-oxide, a sulfoxide or sulfone, or wherein one or more of the nitrogen atoms is optionally substituted or quaternized. The heteroatom(s) or heteroatom moiety(ies) O, N/NH, S, and/or Si may be placed at any interior position of the heteroalkyl group or at a terminal position of the optionally substituted alkyl group of the heteroalkyl. In some aspects, the heteroalkyl is fully saturated or contains 1 degree of unsaturation and contain 1 to 6 carbon atoms and 1 to 2 heteroatoms, and in other aspects that heteroalkyl is unsubstituted. Non-limiting examples are —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, as exemplified by —$CH_2$—NH—$OCH_3$ and —$CH_2$—O—Si($CH_3$)$_3$.

A heteroalkyl is typically denoted by the number of its contiguous heteroatom(s) and non-aromatic carbon atoms, which includes those contiguous carbon atom(s) attached to the heteroatom(s), unless indicated otherwise (e.g., as described for aminoalkyl) or by context. Thus, —$CH_2$—$CH_2$—O—$CH_3$ and —$CH_2$—$CH_2$—S(O)—$CH_3$ are both $C_4$-heteroalkyls and —$CH_2$—CH=N—O—$CH_3$, and —CH=CH—N($CH_3$)$_2$ are both $C_5$ heteroalkyls. A heteroalkyl may be unsubstituted or substituted (i.e., optionally substituted) at its heteroatom or heteroatom component with any one of the moieties described herein, including an optional substituent as defined herein, and/or at its alkyl component with 1 to 4 or more, typically 1 to 3 or 1 or 2 independently selected moieties as described herein, including optional substituent(s) as defined herein, excluding alkyl, (hetero)arylalkyl, alkenyl, alkynyl, another heteroalkyl or any other moiety when the substituted alkenyl would differ by the number of contiguous non-aromatic carbon atoms relative to the unsubstituted aminoalkyl.

"Hydroxyalkyl" as the term is used herein by itself or in combination with another term, unless otherwise stated or implied by context, refers to an alkyl moiety, group, or substituent having a hydroxyl radical in place of one or more hydrogen atoms. In some aspects, one or two hydrogen atoms are replaced with a hydroxyl substituent in a hydroxyalkyl group. A hydroxyalkyl is typically denoted by the number of contiguous carbon atoms of its alkyl or alkylene moiety. Thus, a $C_1$ hydroxyalkyl is exemplified without limitation by —$CH_2OH$, and a $C_2$ hydroxyalkyl is exemplified without limitation by —$CH_2CH_2OH$ or —$CH_2(OH)CH_3$.

An aminoalkyl as defined herein is an exemplary heteroalkyl in which a terminal carbon atom of an alkyl moiety other than its monovalent carbon atom is replaced by an amino group. When indicated as a substituent to a Markush structure or other organic moiety to which it is associated, the monovalent carbon atom of the alkyl moiety is attached to another organic moiety with which it is to be associated, which typically is a different carbon atom to that attached to the amino group. An aminoalkyl differs from other heteroalkyls by denotation in numbering by only indicating the number of contiguous carbon atoms of its alkylene moiety.

"Heteroalkylene" as the term is used herein by itself or in combination with another term, unless otherwise stated or implied by context, means a divalent group derived from a heteroalkyl (as discussed above), by removal of a hydrogen atom or a heteroatom electron form a parent heteroalkyl to provide a divalent moiety exemplified by, but not limited to, —$CH_2$—$CH_2$—S—$CH_2$—$CH_2$— and —$CH_2$—S—$CH_2$—$CH_2$—NH—$CH_2$—. For a heteroalkylene, heteroatom(s) thereof may be interior to or may occupy either or both termini of its optionally substituted alkylene chain so that one or both of these heteroatoms are monovalent. When a heteroalkylene is a component of a Linker Unit both orientations of that component within the Linker Unit is permitted unless indicated or implied by context. A heteroalkylene is typically denoted by the number of its contiguous heteroatom(s) and non-aromatic carbon atoms, which includes those contiguous carbon atom(s) attached to the heteroatom(s), unless indicated otherwise or by context. A alkylene diamine is a heteroalkylene in which the two monovalent carbon atoms of an alkylene are replaced by amino groups so that each of their nitrogen atoms is monovalent and differs from other heteroalkylenes by denotation in numbering by only indicating the number of contiguous carbon atoms of its alkylene moiety.

"Aminoalkyl" as the term is used herein by itself or in combination with another term, unless otherwise stated or implied by context, refers to a moiety, group or substituent having a basic nitrogen bonded to one radical terminus of an alkylene moiety as defined above to provide a primary amine in which the basic nitrogen is not further substituted, or to provide a secondary or tertiary amine in which the basic amine is further substituted by one or two independent selected optional substituted $C_1$-$C_{12}$ alkyl moieties, respectively, as described above. In some aspects, the optionally substituted alkyl is a $C_1$-$C_8$ alkyl or $C_1$-$C_6$ alkyl and in other aspects that alkyl is unsubstituted. In still other aspects, the basic nitrogen together with its substituents defines an optionally substituted $C_3$-$C_8$ heterocyclyl containing the basic nitrogen as a skeletal atom, typically in the form of a nitrogen-containing $C_3$-$C_6$ or $C_5$-$C_6$ heterocyclyl, optionally substituted. When aminoalkyl is used as a variable group to a Markush structure, the alkylene moiety of the aminoalkyl is attached to a Markush formula with which it is associated through a $sp^3$ carbon of that moiety, which, in some aspects, is the other radical terminus of the aforementioned alkylene. An aminoalkyl is typically denoted by the number of contiguous carbon atoms of its alkylene moiety. Thus, a $C_1$ aminoalkyl is exemplified without limitation by —$CH_2NH_2$, —$CH_2NHCH_3$ and —$CH_2N(CH_3)_2$ and a $C_2$ amino alkyl is exemplified without limitation by —$CH_2CH_2NH_2$, —$CH_2CH_2NHCH_3$ and —$CH_2CH_2N(CH_3)_2$.

"Optionally substituted alkyl", "optionally substituted alkenyl", "optionally substituted alkynyl", "optionally substituted arylalkyl", "optionally substituted heterocycle", "optionally substituted aryl", "optionally substituted heteroaryl", "optionally substituted heteroarylalkyl" and like terms as used herein, unless otherwise stated or implied by context, refer to an alkyl, alkenyl, alkynyl, arylalkyl, heterocycle, aryl, heteroaryl, heteroarylalkyl, or other substituent, moiety or group as defined or disclosed herein wherein hydrogen atom(s) of that substituent, moiety or group has been optionally replaced with different moiety(ies) or group(s), or wherein an alicyclic carbon chain that comprise one of those substituents, moiety or group is interrupted by replacing carbon atom(s) of that chain with different moiety(ies) or group(s). In some aspects, an alkene functional group replaces two contiguous $sp^3$ carbon atoms of an alkyl substituent, provided that the radical carbon of the alkyl moiety is not replaced, so that the optionally substituted alkyl becomes an unsaturated alkyl substituent.

Optional substituents replacing hydrogen(s) in any one of the foregoing substituents, moieties, or groups is independently selected from the group consisting of $C_6$-$C_{24}$ aryl, $C_5$-$C_{24}$ heteroaryl, hydroxyl, $C_1$-$C_{20}$ alkoxy, $C_6$-$C_{24}$ aryloxy, cyano, halogen, nitro, $C_1$-$C_{20}$ fluoroalkoxy, and amino, which encompasses —$NH_2$ and mono-, di-, and tri-substituted amino groups, and the protected derivatives thereof, or is selected from the group consisting of —X, —OR', —SR', —$NH_2$, —N(R')($R^{op}$), —N($R^{op}$)$_3$, =NR', —$CX_3$, —CN, —$NO_2$, —NR'C(=O)H, —NR'C(=O)$R^{op}$, —NR'C(=O)$R^{op}$, —C(=O)R', —C(=O)$NH_2$, —C(=O)N(R')$R^{op}$, —S(=O)$_2R^{op}$, —S(=O)$_2NH_2$, —S(=O)$_2$N(R')$R^{op}$, —S(=O)$_2NH_2$, —S(=O)$_2$N(R')$R^{op}$, —S(=O)$_2$OR', —S(=O)$R^{op}$, —OP(=O)(OR')(O$R^{op}$), —OP(OH)$_3$, -P(=O)(OR')(O$R^{op}$), -PO$_3H_2$, —C(=O)R', —C(=S)$R^{op}$, —CO$_2$R', —C(=S)O$R^{op}$, —C(=O)SR', —C(=S)SR', —C(=S)$NH_2$, —C(=S)N(R')($R^{op}$)$_2$, —C(=NR')$NH_2$, —C(=NR')N(R')$R^{op}$, and salts thereof, wherein each X is independently selected from the group consisting of halogens: —F, —Cl, —Br, and —I; and wherein each $R^{op}$ is independently selected from the group consisting of $C_1$-$C_{20}$ alkyl, $C_2$-$C_{20}$ alkenyl, $C_2$-$C_{20}$ alkynyl, $C_6$-$C_{24}$ aryl, $C_3$-$C_{24}$ heterocyclyl, $C_5$-$C_{24}$ heteroaryl, a protecting group, and a prodrug moiety or two of $R^{op}$ together with the heteroatom to which they are attached defines a $C_3$-$C_{24}$ heterocyclyl; and R' is hydrogen or $R^{op}$, wherein $R^{op}$ is selected from the group consisting of $C_1$-$C_{20}$ alkyl, $C_6$-$C_{24}$ aryl, $C_3$-$C_{24}$ heterocyclyl, $C_5$-$C_{24}$ heteroaryl, and a protecting group.

Typically, optional substituents that are present are selected from the group consisting of —X, —OH, —O$R^{op}$, —SH, —S$R^{op}$, —$NH_2$, —NH($R^{op}$), —NR'($R^{op}$)$_2$, —N($R^{op}$)$_3$, =NH, =N$R^{op}$, —$CX_3$, —CN, —$NO_2$, —NR'C(=O)H, NR'C(=O)$R^{op}$, —CO$_2$H, —C(=O)H, —C(=O)$R^{op}$, —C(=O)$NH_2$, —C(=O)NR'$R^{op}$, —S(=O)$_2R^{op}$, —S(=O)$_2NH_2$, —S(=O)$_2$N(R')$R^{op}$, —S(=O)$_2NH_2$, —S(=O)$_2$N(R')($R^{op}$), —S(=O)$_{20}$R', —S(=O)$R^{op}$, —C(=S)$R^{op}$, —C(=S)$NH_2$, —C(=S)N(R')$R^{op}$, —C(=NR')N($R^{op}$)$_2$, and salts thereof, wherein each X is independently selected from the group consisting of —F and —$C_1$, wherein $R^{op}$ is typically selected from the group consisting of $C_1$-$C_6$ alkyl, $C_6$-$C_{10}$ aryl, $C_3$-$C_{10}$ heterocyclyl, $C_5$-$C_{10}$ heteroaryl, and a protecting group; and R' is independently selected from the group typically consisting of hydrogen, $C_1$-$C_6$ alkyl, $C_6$-$C_{10}$ aryl, $C_3$-$C_{10}$ heterocyclyl, $C_5$-$C_{10}$ heteroaryl, and a protecting group, independently selected from $R^{op}$.

More typically, optional substituents that are present are selected from the group consisting of —X, —$R^{op}$, —OH, —O$R^{op}$, —$NH_2$, —NH($R^{op}$), —N($R^{op}$)$_2$, —N($R^{op}$)$_3$, —$CX_3$, —$NO_2$, —NHC(=O)H, —NHC(=O)$R^{op}$, —C(=O)$NH_2$, —C(=O)NH$R^{op}$, —C(=O)N($R^{op}$)$_2$, —CO$_2$H, —CO$_2R^{op}$, —C(=O)H, —C(=O)$R^{op}$, —C(=O)$NH_2$, —C(=O)NH($R^{op}$), —C(=O)N($R^{op}$)$_2$, —C(=NR')$NH_2$, —C(=NR')NH($R^{op}$), —C(=NR')N($R^{op}$)$_2$, a protecting group and salts thereof, wherein each X is —F, wherein $R^{op}$ is independently selected from the group consisting of $C_1$-$C_6$ alkyl, $C_6$-$C_{10}$ aryl, $C_5$-$C_{10}$ heteroaryl and a protecting group; and R' is selected from the group consisting of hydrogen, $C_1$-$C_6$ alkyl and a protecting group, independently selected from $R^{op}$.

In some aspects, an optional alkyl substituent that is present is selected from the group consisting of —NH$_2$, —NH(R$^{op}$), —N(R$^{op}$)$_2$, —N(R$^{op}$)$_3$, —C(=NR')NH$_2$, —C(=NR')NH(R$^{op}$), and —C(=NR')N(R$^{op}$)$_2$, wherein R' and R$^{op}$ is as defined for any one of the R' or R$^{op}$ groups above. In some of those aspects, the R' and/or R$^{op}$ substituents together with the nitrogen atom to which they are attached provide for the basic functional group of a Basic Unit (BU), as when R$^{op}$ is independently selected from the group consisting of hydrogen and C$_1$-C$_6$ alkyl. Alkylene, carbocyclyl, carbocyclo, aryl, arylene, heteroalkyl, heteroalkylene, heterocyclyl, heterocyclo, heteroaryl, and heteroarylene groups as described above are similarly substituted or are unsubstituted, with exceptions, if any, described in the definitions of these moieties.

Other optional substituents replace a carbon atom in the acyclic carbon chain of an alkyl or alkylene moiety, group or substituent to provide for a C$_3$-C$_{12}$ heteroalkyl or C$_3$-C$_{12}$ heteroalkylene and for that purpose is typically selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$—, —OC(=O)NH—, and —NHC(=O)O, optionally substituted in which —NH— is an optionally substituted heteroatom moiety by replacement of its hydrogen atom by an independently selected substituent from a group previously described for an —NH— optional substituent.

"Optionally substituted heteroatom", as the term is used herein by itself or in combination with another term, unless otherwise stated or implied by context, refers to a heteroatom or heteroatom moiety within a functional group or other organic moiety in which the heteroatom is not further substituted or is substituted by any one of the aforementioned moieties having a monovalent carbon atom including, but not limited to alkyl, cycloalkyl, alkenyl, aryl, heterocyclyl, heteroaryl, heteroalkyl and (hetero)arylalkyl- or is oxidized by substitution with one or two =O substituents. In some aspects, "optionally substituted heteroatom" refers an aromatic or non-aromatic —NH— moiety that is unsubstituted or in which the hydrogen atom is replaced by any one of the aforementioned substituents. In other aspects, "optionally substituted heteroatom" refers to an aromatic skeletal nitrogen atom of a heteroaryl in which an electron of that heteroatom is replaced by any one of the aforementioned substituents. For encompassing both of those aspects, the nitrogen heteroatom is sometime referred to as an optionally substituted N/NH.

Therefore, in some aspects, an optional substituent of a nitrogen atom that is present is selected from the group consisting of C$_1$-C$_{20}$ alkyl, C$_2$-C$_{20}$ alkenyl, C$_2$-C$_{20}$ alkynyl, C$_6$-C$_{24}$ aryl, C$_5$-C$_{24}$ heteroaryl, (C$_6$-C$_{24}$ aryl)-C$_1$-C$_{20}$ alkyl-, and (C$_5$-C$_{24}$ heteroaryl)-C$_1$-C$_{20}$ alkyl-, optionally substituted, as those terms are defined herein. In other aspects, optional substituents of a nitrogen atom that are present are independently selected from the group consisting of C$_1$-C$_{12}$ alkyl, C$_2$-C$_{12}$ alkenyl, C$_2$-C$_{12}$ alkynyl, C$_6$-C$_{24}$ aryl, C$_5$-C$_{24}$ heteroaryl, (C$_6$-C$_{24}$ aryl)-C$_1$-C$_{12}$ alkyl-, and (C$_5$-C$_{24}$ heteroaryl)-C$_1$-C$_{12}$ alkyl-, optionally substituted, from the group consisting of C$_1$-C$_8$ alkyl, C$_2$-C$_8$ alkenyl, C$_2$-C$_8$ alkynyl, C$_6$-C$_{10}$ aryl, C$_5$-C$_{10}$ heteroaryl, (C$_6$-C$_{10}$ aryl)-C$_1$-C$_8$ alkyl-, and (C$_5$-C$_{10}$ heteroaryl)-C$_1$-C$_8$ alkyl, or from the group consisting of C$_1$-C$_6$ alkyl, C$_2$-C$_6$ alkenyl, C$_2$-C$_6$ alkynyl, C$_6$-C$_{10}$ aryl, C$_5$-C$_{10}$ heteroaryl, (C$_6$-C$_{10}$ aryl)-C$_1$-C$_6$ alkyl-, and (C$_5$-C$_{10}$ heteroaryl)-C$_1$-C$_6$ alkyl-.

When the optionally substituted nitrogen atom is the point of covalent attachment of a Peptide Cleavable Unit to a PAB or PAB-type moiety of a self-immolative Spacer Unit, sometimes designated as J, an optional substituent of that nitrogen atom when present is limited to one having a monovalent sp$^3$ carbon atom attached thereto that does not adversely impact the electron donating ability of the nitrogen atom, as compared to the unsubstituted nitrogen atom, once its electron donating ability is restored on cleavage of the Cleavable Unit, so as to allow for self-immolation to occur for release of the Drug Unit as free drug.

"O-linked moiety", as the term is used herein by itself or in combination with another term, unless otherwise stated or implied by context, refers to a moiety, group or substituent that is attached to a Markush structure or another organic moiety with which it is associated directly through an oxygen atom of the O-linked moiety. A monovalent O-linked moiety has that attachment through a monovalent oxygen and is typically —OH, —OC(=O)R$^b$ (acyloxy), wherein R$^b$ is —H, optionally substituted saturated C$_1$-C$_{20}$ alkyl, optionally substituted unsaturated C$_1$-C$_{20}$ alkyl, optionally substituted C$_3$-C$_{20}$ cycloalkyl, wherein the cycloalkyl moiety is saturated or partially unsaturated, optionally substituted C$_3$-C$_{20}$ alkenyl, optionally substituted C$_2$-C$_{20}$ alkynyl, optionally substituted C$_6$-C$_{24}$ aryl, optionally substituted C$_5$-C$_{24}$ heteroaryl or optionally substituted C$_3$-C$_{24}$ heterocyclyl, or R$^b$ is optionally substituted C$_1$-C$_{12}$ alkyl, optionally substituted C$_3$-C$_{12}$ cycloalkyl, optionally substituted C$_3$-C$_{12}$ alkenyl or optionally substituted C$_2$-C$_{12}$ alkynyl, and wherein an monovalent O-linked moiety further encompasses ether groups which are C$_1$-C$_{12}$ alkyloxy (i.e., C$_1$-C$_{12}$ aliphatic ether) moieties, optionally substituted, wherein the alkyl moiety is saturated or unsaturated.

In other aspects, a monovalent O-linked moiety is a monovalent moiety selected from the group consisting of optionally substituted phenoxy, optionally substituted C$_1$-C$_8$ alkyloxy (i.e., C$_1$-C$_8$ aliphatic ether) and —OC(=O)R$^b$, wherein R$^b$ is optionally substituted C$_1$-C$_8$ alkyl, which is typically saturated or is an unsaturated C$_3$-C$_8$ alkyl, optionally substituted.

In still other aspects, an O-linked moiety is a monovalent moiety selected from the group consisting of —OH, and saturated C$_1$-C$_6$ alkyl ether, unsaturated C$_3$-C$_6$ alkyl ether, optionally substituted, and —OC(=O)R$^b$, wherein R$^b$ is typically C$_1$-C$_6$ saturated alkyl, C$_3$-C$_6$ unsaturated alkyl, C$_3$-C$_6$ cycloalkyl, C$_2$-C$_6$ alkenyl, or phenyl, optionally substituted, or is selected from that group excluding —OH and/or phenyl, or R$^b$ is a monovalent moiety selected from the group consisting of C$_1$-C$_6$ saturated alkyl, C$_3$-C$_6$ unsaturated alkyl and C$_2$-C$_6$ alkenyl, optionally substituted, or a monovalent O-linked moiety is an unsubstituted O-linked substituent selected from the group consisting of saturated C$_1$-C$_6$ alkyl ether, unsaturated C$_3$-C$_6$ alkyl ether, and —OC(=O)R$^b$, wherein R$^b$ is an unsubstituted, saturated C$_1$-C$_6$ alkyl or unsubstituted, unsaturated C$_3$-C$_6$ alkyl.

Other exemplary O-linked substituents are provided by definitions for carbamate, ether and carbonate as disclosed herein in which the monovalent oxygen atom of the carbamate, ether or carbonate functional group is bonded to the Markush structure or other organic moiety with which it is associated.

In other aspects, an O-linked moiety to carbon is divalent and encompasses =O and —X—(CH$_2$)$_n$—Y—, wherein X and Y independently are S and O and subscript n is 2 or 3, to form a spiro ring system with the carbon to which X and Y are both attached.

"Halogen" as the term is used herein by itself or in combination with another term, unless otherwise stated or implied by context, refers to fluorine, chlorine, bromine or iodine and is typically —F or —Cl.

"Protecting group" as the term is used herein by itself or in combination with another term, unless otherwise stated or implied by context, refers to a moiety that prevents or substantially reduces the ability of the atom or functional group to which it is linked from participating in unwanted reactions. Typical protecting groups for atoms or functional groups are given in Greene (1999), "Protective groups in organic synthesis, $3^{rd}$ ed.", Wiley Interscience. Protecting groups for heteroatoms such as oxygen, sulfur and nitrogen are sometime used to minimize or avoid their unwanted reactions with electrophilic compounds. Other times the protecting group is used to reduce or eliminate the nucleophilicity and/or basicity of the unprotected heteroatom. Non-limiting examples of protected oxygen are given by —$OR^{PR}$, wherein $R^{PR}$ is a protecting group for hydroxyl, wherein hydroxyl is typically protected as an ester (e.g., acetate, propionate or benzoate). Other protecting groups for hydroxyl avoid its interference with the nucleophilicity of organometallic reagents or other highly basic reagents, for which purpose hydroxyl is typically protected as an ether, including without limitation alkyl or heterocyclyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —$NHR^{PR}$ or —$N(R^{PR})_2$, wherein least one of $R^{PR}$ is a nitrogen atom protecting group or both $R^{PR}$ together define a nitrogen atom protecting group.

A protecting group is a suitable for protecting when it is capable of preventing or substantially avoiding unwanted side-reactions and/or premature loss of the protecting group under reaction conditions required to effect desired chemical transformation(s) elsewhere in the molecule and during purification of the newly formed molecule when desired, and can be removed under conditions that do not adversely affect the structure or stereochemical integrity of that newly formed molecule. In some aspects, suitable protecting groups are those previously described for protecting functional groups. In other aspects, a suitable protecting group is a protecting group used in peptide coupling reactions. For example, a suitable protecting group for the basic nitrogen atom of an acyclic or cyclic Basic Unit is an acid-labile carbamate protecting group such as t-butyloxycarbonyl (BOC).

"Ester" as the term is used herein by itself or in combination with another term, unless otherwise stated or implied by context, refers to a substituent, moiety or group having the structure of —C(=O)—O— to define an ester functional group in which the carbonyl carbon atom of that structure is not directly connected to another heteroatom but is directly connected to hydrogen or another carbon atom of an organic moiety with which it is associated, and wherein the monovalent oxygen atom is either attached to the same organic moiety at a different carbon atom to provide a lactone or to a Markush structure or to some other organic moiety. Typically, esters in addition to the ester functional group comprise or consist of an organic moiety containing 1 to 50 carbon atoms, typically 1 to 20 carbon atoms or more typically 1 to 8, 1 to 6 or 1 to 4 carbon atoms and 0 to 10 independently selected heteroatoms (e.g., O, S, N, P, Si, but usually O, S and N), typically 0 to 2 heteroatoms, wherein the organic moiety is bonded to the —C(=O)—O— structure (i.e., through the ester functional group) so as to provide structure having the formula of organic moiety —C(=O)—O— or —C(=O)—O— organic moiety.

When an ester is a substituent or variable group of a Markush structure or other organic moiety with which it is associated, that substituent is bonded to the structure or other organic moiety through the monovalent oxygen atom of the ester functional group so that it is a monovalent O-linked substituent, which sometimes referred to as an acyloxy. In such instances, the organic moiety attached to the carbonyl carbon of the ester functional group typically is a $C_1$-$C_{20}$ alkyl, $C_2$-$C_{20}$ alkenyl, $C_2$-$C_{20}$ alkynyl, $C_6$-$C_{24}$ aryl, $C_5$-$C_{24}$ heteroaryl, $C_3$-$C_{24}$ heterocyclyl or is a substituted derivative of any one of these, e.g., having 1, 2, 3 or 4 substituents, more typically is $C_1$-$C_{12}$ alkyl, $C_2$-$C_{12}$ alkenyl, $C_2$-$C_{12}$ alkynyl, $C_6$-$C_{10}$ aryl, $C_5$—$C_{10}$ heteroaryl, $C_3$-$C_{10}$ heterocyclyl or a substituted derivative of one any of these, e.g., having 1, 2, or 3 substituents or is $C_1$-$C_8$ alkyl, $C_2$-$C_8$ alkenyl, $C_2$-$C_8$ alkynyl, or phenyl or a substituted derivative of any one of these, e.g., having 1 or 2 substituents, wherein each independently selected substituent is as defined herein for optional alkyl substituents, or is unsubstituted $C_1$-$C_6$ alkyl or unsubstituted $C_2$-$C_6$ alkenyl.

Exemplary esters by way of example and not limitation, are acetate, propionate, isopropionate, isobutyrate, butyrate, valerate, isovalerate, caproate, isocaproate, hexanoate, heptanoate, octanoate, phenylacetate esters and benzoate esters or have the structure of —OC(=O)$R^b$ in which $R^b$ is as defined for acyloxy O-linked substituents and is typically selected from the group consisting of methyl, ethyl, propyl, iso-propyl, 2-methyl-prop-1-yl, 2,2-dimethyl-prop-1-yl, prop-2-ene-1-yl, and vinyl.

"Ether" as the term is used herein by itself or in combination with another term, unless otherwise stated or implied by context, refers to an organic moiety, group or substituent that comprises 1, 2, 3, 4 or more —O— (i.e., oxy) moieties that are not bonded to carbonyl moiety(ies), typically 1 or 2, wherein no two —O— moieties are immediately adjacent (i.e., directly attached) to each other. Typically, an ether contains the formula of —O-organic moiety wherein organic moiety is as described for an organic moiety bonded to an ester functional group or is as described herein for an optionally substituted alkyl group. When ether is recited as a substituent or variable group of a Markush structure or other organic moiety with which it is associated, the oxygen of the ether functional group is attached to a Markush formula with which it is associated and is sometimes designated as an "alkoxy" group, which is an exemplary O-linked substituent. In some aspects, an ether O-linked substituent is a $C_1$-$C_{20}$ alkoxy or a $C_1$-$C_{12}$ alkoxy, optionally substituted with 1, 2, 3 or 4 substituents, typically 1, 2 or 3, and in other aspects is a $C_1$-$C_8$ alkoxy or $C_1$-$C_6$ alkoxy, optionally substituted with 1 or 2 substituents, wherein each independently selected substituent is as defined herein for optional alkyl substituents, and in still other aspects an ether O-linked substituent is an unsubstituted, saturated or unsaturated $C_1$-$C_4$ alkoxy such as, by way of example and not limitation, methoxy, ethoxy, propoxy, iso-propoxy, butoxy and allyloxy (i.e., —OCH$_2$CH=CH$_2$).

"Amide" as the term is used herein by itself or in combination with another term, unless otherwise stated or implied by context, refers to a moiety having an optionally substituted functional group having the structure of R—C(=O)N($R^c$)— or —C(=O)N($R^c$)$_2$ to which no other heteroatom is directly attached to the carbonyl carbon and wherein each $R^c$ is independently hydrogen, a protecting group or an independently selected organic moiety, and R is hydrogen or an organic moiety, wherein organic moiety, independently selected from $R^e$, is as described herein for an organic moiety bonded to an ester functional group or is as described herein for an optionally substituted alkyl group. When an amide is recited as a substituent or variable group of a Markush structure or other organic moiety with which it is associated, the amide nitrogen atom or carbonyl carbon atom of the amide functional group is bonded to that structure or other organic moiety. Amides are typically prepared by condensing an acid halide, such an acid chloride, with a molecule containing a primary or secondary amine. Alternatively, amide coupling reactions well-known in the art of peptide synthesis, which in some aspects proceeds through an activated ester of a carboxylic acid-containing molecule, are used. Exemplary preparations of amide bonds through peptide coupling methods are provided in Benoiton (2006) "Chemistry of peptide synthesis", CRC Press; Bodansky (1988) "Peptide synthesis: A practical textbook" Springer-Verlag; Frinkin, M. et al. "Peptide Synthesis" *Ann. Rev. Biochem.* (1974) 43: 419-443. Reagents used in the preparation of activated carboxylic acids is provided in Han, et al. "Recent development of peptide coupling agents in organic synthesis" *Tet.* (2004) 60: 2447-2476.

Thus, in some aspects, amides are be prepared by reacting a carboxylic acid with an amine in the presence of a coupling agent. As used herein, "in the presence of a coupling agent" includes contacting the carboxylic acid with the coupling agent thereby converting the acid to its activated derivative, such as an activated ester or a mixed anhydride, with or without isolation of the resulting activated derivative of the acid, followed by or simultaneously contacting the resulting activated derivative with the amine. In some instances, the activated derivative is prepared in situ. In other instances, the activated derivative may be isolated to remove any undesired impurities.

"Carbonate" as the term is used herein by itself or in combination with another term, unless otherwise stated or implied by context, means a substituent, moiety or group that contains a functional group having the structure —O—C(=O)—O— which defines a carbonate functional group. Typically, carbonate groups as used herein are comprised of an organic moiety bonded to the —O—C(=O)—O— structure, wherein the organic moiety is as described herein for an organic moiety bonded to an ester functional group, e.g., organic moiety-O—C(=O)—O—. When carbonate is recited as a substituent or variable group of a Markush structure or other organic moiety with which it is associated, one of the monovalent oxygen atoms of the carbonate functional group is attached to that structure or organic moiety and the other is bonded to a carbon atom of another organic moiety as previously described for an organic moiety bonded to an ester functional group or is as described herein for an optionally substituted alkyl group. In such instances, carbonate is an exemplary O-linked substituent.

"Carbamate" as the term is used herein by itself or in combination with another term, unless otherwise stated or implied by context, means a substituent, moiety or group that contains an optionally substituted carbamate functional group structure represented by —O—C(=O)N($R^e$)— or —O—C(=O)N($R^e$)$_2$, or —O—C(=O)NH(optionally substituted alkyl)- or —O—C(=O)N(optionally substituted alkyl)$_2$ in which the independently selected optionally substituted alkyl(s) are exemplary carbamate functional group substituents, and typically are $C_1$-$C_{12}$ alkyl or $C_1$-$C_8$ alkyl, optionally substituted, more typically $C_1$-$C_6$ alkyl or $C_1$-$C_4$ alkyl, optionally substituted, wherein each $R^e$ is independently selected, wherein independently selected $R^e$ is hydrogen, a protecting group or an organic moiety, wherein the organic moiety is as described herein for an organic moiety bonded to an ester functional group or is as described herein for an optionally substituted alkyl group. Typically, carbamate groups are additionally comprised of an organic moiety, independently selected from $R^e$, wherein the organic moiety is as described herein for an organic moiety bonded to an ester functional group, bonded through the —O—C(=O)—N($R^e$)— structure, wherein the resulting structure has the formula of organic moiety-O—C(=O)—N($R^e$)— or —O—C(=O)—N($R^e$)-organic moiety. When carbamate is recited as a substituent or variable group of a Markush structure or other organic moiety with which it is associated, the monovalent oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked substituents.

"Ligand Drug Conjugate", as the term is used herein, unless otherwise stated or implied by context, refers to a construct comprised of a Ligand Unit (L) incorporating or corresponding in structure to a targeting agent and a Drug Unit (D) incorporating or corresponding in structure to free drug, wherein L and D are bonded to each other through a Linker Unit (LU), wherein the Ligand Drug Conjugate is capable of selective binding to a targeted moiety of a targeted cell. The term Ligand Drug Conjugate (LDC) in one aspect refers to a plurality (i.e., composition) of individual Conjugate compounds having the same or differing to some extent by the number of auristatin Drug Units conjugated to each Ligand Unit and/or the location on the Ligand Unit to which the Drug Units are conjugated. In some aspects the term refers to a collection (i.e., population or plurality) of Conjugate compounds having essentially the same Ligand Unit, and the same Drug Unit and Linker Unit, which in some aspects have variable loading and/or distribution of auristatin drug linker moieties attached to each antibody residue (as, for example, when the number of Drug Units of any two Ligand Drug Conjugate compounds in a plurality of such compounds is the same but the locations of their sites of attachment to the Ligand Unit are different). In those instances, a Ligand Drug Conjugate is described by the averaged drug loading of the Conjugate compounds.

The average number Drug Units per Ligand Unit in a Ligand Drug Conjugate composition is an averaged number for a population of Ligand Drug Conjugate compounds, sometimes designated by subscript p, which in some aspects reflects a distribution of these compounds differing primarily by the number of conjugated Drug Units to the Ligand Unit and/or by their location on the Ligand Unit to which they are conjugated.

A Ligand Drug Conjugate compound, by itself or within a Ligand Drug Conjugate composition, of the present invention is typically represented by the structure of Formula 1:

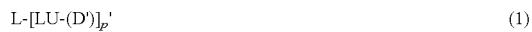

or a salt thereof, which in some aspects is a pharmaceutically acceptable salt, wherein L is a Ligand Unit; LU is a Linker Unit; subscript p' is an integer ranging from 1 to 24; and D' represents from 1 to 4 Drug Units. In some aspects a Ligand Unit incorporates or corresponds in structure to an antibody or an antigen-binding fragment thereof thereby defining an antibody Ligand Unit. In those aspects, an antibody Ligand Unit is capable of selective binding to an antigen of a targeted cell for subsequent release of free drug, wherein the targeted antigen in one aspect is a cancer cell antigen selectively recognized by an antibody Ligand Unit and is capable of internalization into said cancer cell along with the bound ADC compound upon said binding for initiating intracellular release of free drug subsequent to said internalization. In any of those aspects each drug linker moiety in a Ligand Drug Conjugate compound has the structure of Formula 1A:

(1A)

or a salt thereof, which is some aspects is a pharmaceutically acceptable salt, wherein D in each drug linker moiety is the Drug Unit; the wavy line indicates covalent binding to L; $L_B$ is an ligand covalent binding moiety; A is a first optional Stretcher Unit; subscript a is 0 or 1 indicating the absence or presence of A, respectively; B is an optional Branching Unit; subscript b is 0 or 1, indicating the absence or presence of B, respectively; $L_O$ is an secondary linker moiety; D is the Drug Unit, wherein the Drug Unit corresponds in structure to free drug; and subscript q is an integer ranging from 1 to 4,
wherein a Ligand Drug Conjugate composition comprised of a distribution or collection of Ligand Drug Conjugate compounds is represented by structure of Formula 1 in which subscript p' is replaced by subscript p, wherein subscript p is a number ranging from about 2 to about 24.

"Ligand Unit" as the term is used herein, unless otherwise stated or implied by context, refers to a targeting moiety of a Ligand Drug Conjugate composition or compound that is capable of binding selectively to its cognate targeted moiety and incorporates or corresponds to the structure of a targeting agent. A Ligand Unit (L) includes without limitation those from receptor ligands, antibodies to cell-surface antigens, and transporter substrates. In some aspects, the receptor, antigen or transporter to be bound by a Conjugate compound of a Ligand Drug Conjugate composition is present in greater abundance on abnormal cells in contrast to normal cells so as to effect a desired improvement in tolerability or reduce the potential occurrence or severity of one or more adverse events that are associated with administration of a drug in unconjugated form. In other aspects, the receptor, antigen or transporter to be bound to the Ligand Unit of a Ligand Drug Conjugate compound is present in greater abundance on normal cells in the vicinity of abnormal cells in contrast to normal cells that are distant from the site of the abnormal cells, so as to selectively expose the nearby abnormal cells to free drug. Various aspects of Ligand Units, including antibody Ligand Units, are further described by embodiments of the invention.

"Targeting agent" as used herein, unless otherwise stated or implied by context, refers to an agent that is capable of selective binding to a targeted moiety and which substantially retains that capability when it is incorporated into a Ligand Drug Conjugate as a Ligand Unit. The Ligand Unit of a Ligand Drug Conjugate therefore corresponds in structure to the targeting agent so that the Ligand Unit is the targeting moiety of the Conjugate. In some aspects, the targeting agent is an antibody or fragment thereof that selectively binds to an accessible antigen that is characteristic of an abnormal cell or is present in higher copy number in comparison to normal cells or is an accessible antigen that is particular to the surrounding environment in which these cells are found to an extent that achieves an improved tolerability in comparison to administration of free drug. In other aspects, the targeting agent is a receptor ligand that selectively binds to an accessible receptor characteristic of, or in greater abundance on, abnormal cells, or to an accessible receptor on nominally normal cells that are peculiar to environment surrounding the abnormal cells. Typically, a targeting agent is an antibody as defined herein that binds selectively to a targeted moiety of an abnormal mammalian cell, more typically a targeted moiety of an abnormal human cell.

"Targeted moiety" as defined herein is a moiety to be selectively recognized by a targeting agent or the targeting moiety of a Ligand Drug Conjugate, which is its Ligand Unit that incorporates or corresponds in structure to the targeting agent. In some aspects, a targeted moiety is present on, within, or in the vicinity of abnormal cells and is typically present in greater abundance or copy number on these cells in comparison to normal cells or to the environment of normal cells distant from the site of the abnormal cells so as to provide for improved tolerability relative to administration of free drug or reduces the potential for one or more adverse events from that administration. In some aspects, the targeted moiety is an antigen accessible to selective binding by an antibody, which is an exemplary targeting agent that that been incorporated into or corresponds in structure to an antibody Ligand Unit in an Antibody Drug Conjugate composition or compound thereof. In other aspects, the targeting moiety is that of a ligand for an extracellularly accessible cell membrane receptor, which in some aspects is internalized upon binding of the cognate targeting moiety by the Ligand Unit of a Ligand Drug Conjugate compound, wherein the Ligand Unit incorporates or corresponds in structure to the receptor ligand, and in other aspects the receptor is capable of passive or facilitative transport of the Ligand Drug Conjugate compound subsequent to its binding to the cell-surface receptor. In some aspects, the targeted moiety is present on abnormal mammalian cells or on mammalian cells characteristic of the environment of such abnormal cells. In some of those aspects, the targeted moiety is an antigen of an abnormal mammalian cell, more typically a targeted moiety of an abnormal human cell.

"Targeted cells", as the term is used herein, unless otherwise stated or implied by context, are the intended cells to which Ligand Drug Conjugate is designed to interact in order to inhibit the proliferation or other unwanted activity of abnormal cells. In some aspects, the targeted cells are hyper-proliferating cells or hyper-activated immune cells, which are exemplary abnormal cells. Typically, those abnormal cells are mammalian cells and more typically are human cells. In other aspects, the targeted cells are within the vicinity of the abnormal cells so that action of the Ligand Drug Conjugate on the nearby cells has an intended effect on the abnormal cells. For example, the nearby cells may be epithelial cells that are characteristic of the abnormal vasculature of a tumor. Targeting of those vascular cells by a Ligand Drug Conjugate compound will either have a cytotoxic or a cytostatic effect on these cells, which is believed to result in inhibition of nutrient delivery to the nearby abnormal cells of the tumor. Such inhibition indirectly has a cytotoxic or cytostatic effect on the abnormal cells and may also have a direct cytotoxic or cytostatic effect on the nearby abnormal cells by releasing its drug payload in the vicinity of these cells.

An "antibody-drug-conjugate" or simply "ADC" refers to an antibody conjugated to a cytotoxic agent or cytostatic agent. An antibody-drug-conjugate typically binds to the target antigen (e.g., GPNMB, CD228, αvβ6, CD30, LIV1, or CD19) on a cell surface followed by internalization of the antibody-drug-conjugate into the cell where the drug is released. "Antibody Drug Conjugate", as the term is used herein, unless otherwise stated or implied by context, is a subset of Ligand Drug Conjugates of Formula 1 and therefore refers to a construct comprised of an antibody Ligand Unit (L) incorporating or corresponding to an antibody or antigen-binding fragment thereof, and a Drug Unit (D) incorporating or corresponding in structure to a biologically active compound, often referred to as free drug, wherein L and D are bonded to each other through a Linker Unit (LU), wherein the Antibody Drug Conjugate is capable of selective binding to a targeted antigen of a targeted cell, which in some aspects is an antigen of an abnormal cell such as a cancer cell, through its targeting antibody Ligand Unit.

The term Antibody Drug Conjugate (ADC) in one aspect refers to a plurality (i.e., composition) of individual Conjugate compounds having the same or differing to some extent by the number of Drug Units conjugated to each antibody Ligand Unit and/or the locations on the antibody Ligand Unit to which the Drug Units are conjugated. In some aspects the term refers to a distribution or collection (i.e., population or plurality) of Conjugate compounds having the same drug-linker moieties and antibody Ligand Units, allowing for mutational amino acid variations and varying glycosylation patterns as described herein occurring during production of antibodies from cell culture, which in some aspects have variable loading and/or distribution of the drug linker moieties attached to each antibody residue (as, for example, when the number of Drug Units of any two Antibody Drug Conjugate compounds in a plurality of such compounds is the same but the locations of their sites of attachment of the drug linker moieties to the targeting antibody Ligand Unit differ). In those instances, an Antibody Drug Conjugate is described by the averaged drug loading of the Conjugate compounds.

The average number Drug Units per antibody Ligand Unit, or antigen-binding fragment thereof, in an Antibody Drug Conjugate composition having intact drug linker moieties in which the Linker Units are unbranched is an averaged number for a population of Antibody Drug Conjugate compounds and in some aspects reflects a distribution of these compounds differing primarily by the number of conjugated Drug Units to the antibody Ligand Unit and/or by their location. When the Linker Units are branched then the average number reflects the distribution of drug linker moieties for a population of Antibody Drug Conjugate compounds. In either context p is a number ranging from about 2 to about 24 or about 2 to about 20 and is typically about 2, about 4, or about 10 or about 8. In other contexts, p represents the number of Drug Units that are covalently bonded to a single antibody Ligand Unit of an Antibody Drug Conjugate within a population of Antibody Drug Conjugate compounds in which the compounds of that population in some aspects primarily differ by the number and/or locations of the Drug Units or drug linker moieties. In that context p is designated as p' and is an integer ranging from 1 to 24 or from 1 to 20, typically from 1 to 12 or 1 to 10, and more typically from 1 to 8. In other aspects, essentially all of the available reactive functional groups of an antibody targeting agent form covalent bonds to drug linker moieties to provide an antibody Ligand Unit attached to the maximum number of drug linker moieties, so that the p value of the Antibody Drug Conjugate composition is the same or nearly the same as each of the p' values for each of the Antibody Drug Conjugate compounds of the composition, so that only minor amounts of Antibody Drug Conjugate compounds with lower p' values are present, if at all, as detected using an appropriate chromatographic method, such as electrophoresis, HIC, reverse phase HPLC or size-exclusion chromatography.

The average number of Drug Units or drug linker moieties per antibody Ligand Unit in a preparation from a conjugation reaction in some aspects is characterized by conventional chromatographic means as described above in conjunction with mass spectroscopy detection. In other aspects, the quantitative distribution of conjugate compounds in terms of p' values are determined. In those instances, separation, purification, and characterization of homogeneous Antibody Drug Conjugate compounds in which p' is a certain value from an Antibody Drug Conjugate composition from those with other Drug Unit or drug linker moiety loadings is achievable by means such as an aforementioned chromatographic method.

"Drug Linker compound" as the term is used herein, unless otherwise stated or implied by context, refers to a compound having an Drug Unit covalently attached to a Linker Unit precursor (LU'), wherein LU' is comprised of $L_B'$ sometimes referred to as a ligand covalent binding precursor ($L_B'$) moiety because that moiety contains a reactive or activatable functional group, wherein that reactive functional group or activatable functional group subsequent to activation is capable of reacting with a targeting agent to form a covalent bond between a ligand covalent binding moiety ($L_B$) and a Ligand Unit, thus providing a drug linker moiety of Formula 1A for an Ligand Drug Conjugate compound of Formula 1, in particular a covalent bond to an antibody Ligand Unit, which incorporates or corresponds in structure to an antibody, A Drug Linker compound of the present invention typically has the general formula of Formula I:

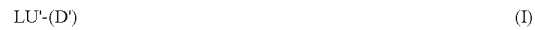

$$LU'\text{-}(D') \qquad (I)$$

or a salt thereof, which in some aspects is a pharmaceutically acceptable salt, wherein LU' is a LU precursor; and D' represents from 1 to 4 Drug Units, wherein the Drug Linker compound is further defined by the structure of Formula IA:

$$L_B'\text{—}A_a\text{—}B_b\text{—}(L_O\text{—}D)_q \qquad (1A)$$

wherein $L_B'$ is comprised of the reactive or activatable functional group and the remaining variable groups are as defined for Formula 1A.

A "cytotoxic agent" refers to an agent that has a cytotoxic effect on a cell. "Cytotoxic agent" as the term is used herein, unless otherwise stated or implied by context, is a compound capable of inducing cell death or inhibiting the proliferation or continued survival of cells, which typically are abnormal mammalian cells, in vitro or in vivo. Cytostatic agents, which primarily exert a therapeutic effect by inhibiting proliferation of abnormal cells and not by direct cell killing, are encompassed by the definition of cytotoxic agent. In some aspects, a cytotoxic agent is the free drug resulting from release of a Drug Unit from an Antibody Drug Conjugate.

A "cytotoxic effect" refers to the depletion, elimination and/or killing of a target cell.

A "cytostatic effect" refers to the inhibition of cell proliferation.

A "cytostatic agent" refers to an agent that has a cytostatic effect on a cell, thereby inhibiting the growth of and/or expansion of a specific subset of cells. Cytostatic agents can be conjugated to an antibody or administered in combination with an antibody.

"Drug Unit" as the phrase is used herein, unless otherwise stated or implied by context, refers to a residue of a drug covalently attached to a Linker Unit (LU) in a drug linker moiety of a Ligand Drug Conjugate (LDC) or is covalently attached to the Linker Unit precursor (LU') of a Drug Linker compound and is releasable from the drug linker moiety or Drug linker compound as free drug. The free drug may be directly incorporated into a Drug Unit, or a component of the free drug may be covalently attached to LU or LU' or an intermediate thereof followed by further elaboration to complete the structure of the Drug Unit. The term "Drug," as used herein alone or in connection with another term (such as "Drug Unit"), is not intended to imply that a compound is approved, approvable, or intended to be approved by a government agency for a medical or veterinary treatment.

In some aspects the free drug incorporated into a Drug Unit is a cytotoxic compound, typically one that has a secondary aliphatic amine as the conjugation handle, and includes auristatin compounds as defined herein.

"Auristatin drug", "auristatin compound" and like terms as used herein, unless otherwise stated or implied by context, refer to a peptide-based tubulin disrupting agent having cytotoxic, cytostatic or anti-inflammatory activity that is comprised of a dolaproline and a dolaisoleucine residue or amino acid residues related thereto.

Some exemplary auristatins have the structure of $D_E$ or $D_F$:

further described in the embodiments of the invention. The synthesis and structure of auristatins are described in U.S. Patent Application Publication Nos. 2003-0083263, 2005-0238649 2005-0009751, 2009-0111756, and 2011-0020343; International Patent Publication No. WO 04/010957, International Patent Publication No. WO 02/088172, and U.S. Pat. Nos. 7,659,241 and 8,343,928. Their structures and methods of their syntheses disclosed therein are specifically incorporated by reference herein.

"Salt thereof" as the phrase is used herein, unless otherwise stated or implied by context, refers to a salt form of a compound (e.g., a Drug, a Drug Linker compound or a LDC compound). A salt form of a compound is of one or more internal salt forms and/or involves the inclusion of another molecule such as an acetate ion, a succinate ion or other counterion. The counterion in a salt form of a compound is typically an organic or inorganic moiety that stabilizes the charge on the parent compound. A salt form of a compound has one or more than one charged atom in its structure. In instances where multiple charged atoms are part of the salt form, multiple counter ions and/or multiple charged counter ions are present. Hence, a salt form of a compound typically has one or more charged atoms corresponding to those of the non-salt form of the compound and one or more counterions. In some aspects, the non-salt form of a compound contains at least one amino group or other basic moiety, and accordingly in the presence of an acid, an acid addition salt with the basic moiety is obtained. In other aspects, the non-salt form of a compound contains at least one carboxylic acid group or other acidic moiety, and accordingly in the presence of a base, a carboxylate or other anionic moiety is obtained.

Exemplary counteranion and countercations in compound salt forms include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pan-

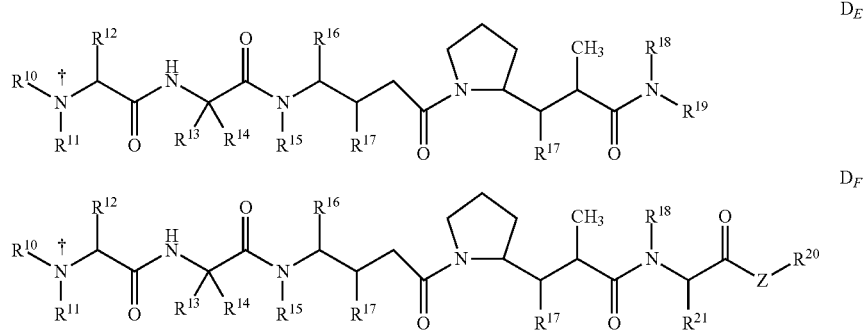

wherein Z is —O—, —S—, or —N($R^{19}$)—, and wherein $R^{10}$—$R^{21}$ are as defined in embodiments for auristatin Drug Units and the indicated nitrogen atom (†) is that of a secondary amine (e.g., one of $R^{10}$, $R^{11}$ is hydrogen and the other is —$CH_3$). In those aspects the auristatin is incorporated into a Drug Unit through a carbamate functional group comprised of that nitrogen atom. That carbamate functional group is an exemplary second Spacer Unit (Y') and is capable of undergoing self-immolation, which is turn is attached to a PAB or PAB-type Spacer Unit (Y) so that subscript y in any one of the drug linker moieties described herein is 2.

Other exemplary auristatins include, but are not limited to, AE, AFP, AEB, AEVB, MMAF, and MMAE and those tothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2-hydroxy-3-naphthoate)) salts.

Selection of a salt form of a compound is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

A "pharmaceutically acceptable salt" is a salt form of a compound that is suitable for administration to a subject as described herein and in some aspects includes counteractions or counteranions as described by P. H. Stahl and C. G. Wermuth, editors, *Handbook of Pharmaceutical Salts: Properties, Selection and Use*, Weinheim/Zürich:Wiley-VCH/VHCA, 2002.

"Antibody" as the term is used herein is used in the broadest sense, unless otherwise stated or implied by context, and specifically encompasses intact monoclonal antibodies, polyclonal antibodies, monospecific antibodies, multispecific antibodies (e.g., bispecific antibodies), and antibody fragments that exhibit the desired biological activity which requires the antibody fragment to have the requisite number of sites for attachment to the desired number of drug-linker moieties and be capable of specific and selective binding to the targeted cancer cell antigen. The native form of an antibody is a tetramer and typically consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs". In some aspects, the constant regions are recognized by and interact with the immune system (see, e.g., Janeway et al., 2001, *Immunol. Biology*, 5th Ed., Garland Publishing, New York) so as to exert an effector function. An antibody includes any isotype (e.g., IgG, IgE, IgM, IgD, and IgA) or subclass thereof (e.g., IgG1, IgG2, IgG3, IgG4, IgA1 and IgA2). The antibody is derivable from any suitable species. In some aspects, the antibody is of human or murine origin. Such antibodies include human, humanized or chimeric antibodies.

The term "antibody" also specifically covers, for example, monoclonal antibodies (including full length or intact monoclonal antibodies), antibodies with polyepitopic or monoepitopic specificity, polyclonal or monovalent antibodies, multivalent antibodies, multispecific antibodies (e.g., bispecific antibodies so long as they exhibit the desired biological activity), single chain antibodies, and fragments of the foregoing, as described below. An antibody can be human, humanized, chimeric and/or affinity matured, as well as an antibody from other species, for example, mouse and rabbit, etc. The term "antibody" thus includes, for instance, a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). The term "antibody" also includes, but is not limited to, synthetic antibodies, recombinantly produced antibodies, camelized antibodies, intrabodies, anti-idiotypic (anti-Id) antibodies, and functional fragments (e.g., antigen-binding fragments) of any of the above, which refers to a portion of an antibody heavy and/or light chain polypeptide that retains some or all of the binding activity of the antibody from which the fragment was derived. Non-limiting examples of functional fragments (e.g., antigen-binding fragments) include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabodies, tetrabodies, and minibodies. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990).

In some aspects, the antibody is in reduced form in which the antibody has undergone reduction of its hinge disulfide bonds. The antibody is then incorporated into an Antibody Drug Conjugate as an antibody Ligand Unit by reaction of one or more of the cysteine thiols obtained by that reduction with an appropriate electrophile of a Drug Linker compound resulting in covalent binding of a drug linker moiety to the antibody Ligand Unit or of a Linker intermediate that is further elaborated to its final form as the drug linker moiety.

"Monoclonal antibody" as used herein refers to an antibody obtained from a population of substantially homogeneous antibodies, i.e., the individual antibodies comprising the population are identical except for possible naturally occurring mutations that may be present in minor amounts and/or differences in glycosylation patterns. Monoclonal antibodies are highly specific, being directed against a single antigenic site. In contrast to polyclonal antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method.

"Selective binding" and "selectively binds" as the terms are used herein, unless otherwise stated or implied by context, refers to an antibody, a fragment thereof, or an antibody Ligand Unit of an Antibody Drug Conjugate that is capable of binding in an immunologically selective and specific manner with its cognate cancer cell antigen and not with a multitude of other antigens. Typically, the antibody or antigen-binding fragment thereof binds its targeted cancer cell antigen with an affinity of at least about $1 \times 10^{-7}$ M, and preferably about $1 \times 10^{-8}$ M to $1 \times 10^{-9}$ M, $1 \times 10^{-10}$ M, or $1 \times 10^{-11}$ M and binds to that predetermined antigen with an affinity that is at least two-fold greater than its affinity for binding to a non-specific antigen (e.g., BSA, casein) other than for a closely-related antigen, wherein said affinities are substantially retained when the antibody or antigen-binding fragment thereof corresponds to or is incorporated into an Antibody Drug Conjugate as an antibody Ligand Unit.

"Antigen" as the term is used herein, unless otherwise stated or implied by context, is a moiety that is capable of specific binding by an unconjugated antibody or an antigen-binding fragment thereof or to an Antibody Drug Conjugate compound, which is comprised of an antibody Ligand Unit that incorporates or corresponds in structure to the unconjugated antibody. In some aspects, the antigen is an extracellularly accessible cell-surface protein, glycoprotein, or carbohydrate preferentially displayed by abnormal cells in comparison to normal cells distant from the site of the abnormal cells, in particular, a protein or glycoprotein. In those aspects, the cell-surface antigen is capable of internalization upon selective binding by a Conjugate compound of an Antibody Drug Conjugate composition. Subsequent to internalization, intracellular processing of a Linker Unit of an Antibody Drug Conjugate compound of the composition releases its Drug Unit as free drug. Antigens associated with hyper-proliferating cells that are cell-surface accessible to an Antibody Drug Conjugate compound include by way of example and not limitation to a cancer specific antigen as described herein.

Typically, the antigen is associated with a cancer. In some of those aspects the antigen is preferentially displayed by cancer cells in comparison to normal cells that are not localized to the abnormal cells, in particular, the cancer cells displaying the antigen are mammalian cancer cells. In other aspects, the cancer cell antigen is an extracellularly accessible antigen preferentially displayed by nearby normal cells that are peculiar to the environment of the cancer cells in comparison to normal cells distant from the site of the cancer cells. For example, the nearby cells may be epithelial cells that are characteristic of the abnormal vasculature of a tumor. Targeting of those vascular cells by an Antibody Drug Conjugate will have a cytotoxic or a cytostatic effect on these cells, which is believed to result in inhibition of nutrient delivery to the nearby cancer cells of the tumor. Such inhibition will indirectly have a cytotoxic or cytostatic effect on the cancer cells and may also have a direct cytotoxic or cytostatic effect on nearby cancer cells subsequent to release of its Drug Unit as free drug subsequent to immunological selective binding by an Antibody Drug Conjugate (ADC) compound. In either of those aspects, the cell-surface antigen is capable of internalization to allow for intracellular delivery of free drug on its release from the Conjugate into the targeted cell.

Preferred internalizable antigens are those expressed on the surface of cancer cells with a copy number of 10,000 per cell or more, 20,000 per cell or more or 40,000 per cell or more. Antigens associated with cancer cells that are cell-surface accessible to an ADC and are internalizable include an antigen expressed on Hodgkin's Lymphoma cells, particularly those of Reed-Sternberg cells, as exemplified by Karpas 299 cells and certain cancer cells of high grade lymphomas sometimes referred to a Ki-1 lymphomas. Other antigens include cancer cells of renal cell adenocarcinoma, as exemplified by 789-O cells, cancer cells of B-cell lymphomas or leukemias, including non-Hodgkin's lymphoma, chronic lymphocytic leukemia (CLL) and acute lympholytic leukemia (ALL), as exemplified by CHO cells, cancer cells of acute myeloid leukemia (AML), as exemplified by HL-60, and certain transporter receptors that are ubiquitously expressed on these and other cancer cells.

"Linker Unit" as the term is used herein, unless otherwise stated or implied by context, refers to an organic moiety in a Ligand Drug Conjugate intervening between and covalently attached to a Drug Unit and a Ligand Unit (L), as these terms are defined herein, or is an organic moiety in a Drug Linker compound that is covalently attached to a Drug Unit and has a reactive functional group or moiety for interaction with a targeting agent to form a covalent bond between L, which incorporates or corresponds in structure to the targeting agent, and the Linker Unit (LU). As the Linker Unit in a Drug Linker is capable of forming such a bond, it is considered a precursor to a Linker Unit in a Ligand Drug Conjugate and is sometimes so indicated as LU'. A Linker Unit is comprised of a primary linker ($L_R$) and a secondary linker ($L_O$) that intervenes between $L_R$ and D within a drug linker moiety of a Ligand Drug Conjugate compound or between $L_R$ and D of a Drug Linker compound, which in the latter instance may be represented as $L_R'$ to explicitly indicate that is a precursor to $L_R$ in a Ligand Drug Conjugate.

"Primary linker" as the term is used herein, unless otherwise stated or implied by context, refers to a required component of a Linker Unit (LU) in Ligand Drug Conjugate that is covalently attached to the Ligand Unit and the remainder of LU. One component of the primary linker ($L_R$) is a ligand covalent binding ($L_B$) moiety, which in some aspects of Ligand Drug Conjugates (LDCs) and Drug Linker compounds described herein provides for a self-stabilizing ($L_{SS}$) linker, thereby defining a $L_{SS}$ primary linker, and in other aspects of LDCs provides for a self-stabilized ($L_S$) linker derivable from $L_{SS}$, thereby defining a $L_S$ primary linker, as these terms are further described herein. The primary linker optionally contains a Branching Unit (B) and a first optional Stretcher Unit (A), dependent on the values of subscripts a and b in Formula 1A, provided that A is present when $L_R$ is a $L_{SS}$ or a $L_S$ primary linker.

A $L_{SS}$ primary linker in a LDC or Drug Linker compound is characterized by a succinimide ($M^2$) or maleimide ($M^1$) moiety, respectively, in proximity to a Basic Unit, while a $L_S$ primary linker in a LDC composition or compound thereof is characterized by a succinic acid amide ($M^3$) moiety in proximity to a Basic Unit. An $L_{SS}$ or $L_S$ primary linker of the present invention is also characterized by a first optional Stretcher Unit (A) that is present and comprised of an optionally substituted $C_1$-$C_{12}$ alkylene moiety bonded to the imide nitrogen of the maleimide or succinimide ring system of $M^1$ or $M^2$ or the amide nitrogen of $M^3$, wherein the alkylene moiety in some aspects is substituted by an acyclic Basic Unit and may be further substituted by optional substituents, or in other aspects is optionally substituted and incorporates a cyclic Basic Unit that is optionally substituted.

A maleimide ($M^1$) moiety of a ligand covalent binding precursor of a $L_{SS}$ primary linker in a Drug Linker Compound, sometimes shown as $L_{SS}'$ to explicitly indicate that it is a precursor to $L_{SS}$ in a Ligand Drug Conjugate, is capable of reacting with a sulfur atom of a reactive thiol functional group of a targeting agent resulting in a thio-substituted succinimide moiety ($M^2$) in a ligand covalent binding moiety of a $L_{SS}$ primary linker of an Ligand Drug Conjugate, wherein the thio-substituent is a Ligand Unit incorporating or corresponding in structure to the targeting agent. In aspects in which the targeting agent is an antibody or antigen-binding fragment thereof, the antibody becomes bonded to $M^2$ through a sulfur atom of a cysteine residue derived from disulfide bond reduction or introduced through genetic engineering. As a result, the antibody or antigen-binding fragment thereof is covalently bonded to the $L_{SS}$ primary linker as an antibody Ligand Unit. Subsequent hydrolysis of $M^2$ in a $L_{SS}$ primary linker results in a $L_S$ primary linker in which $M^2$ is converted to a succinic acid amide moiety ($M^3$). That linker moiety may exist as a mixture of two regioisomers ($M^{3A}$ and $M^{3B}$), depending on the relative reactivity of the two carbonyl groups of the succinimide ring system to hydrolysis.

"Ligand covalent binding moiety" as the term is used herein, unless otherwise stated or implied by context, refers to a moiety of a Linker Unit (LU) in Ligand Drug Conjugate that interconnects its Ligand Unit (L) and the remainder of the Linker Unit and is derived from reaction between the corresponding ligand covalent binding precursor ($L_B'$) moiety of a Linker Unit precursor (LU') in a Drug Linker compound and a targeting agent, such as an antibody or antigen-binding fragment thereof. For example, when $L_B'$ is comprised of a maleimide moiety ($M^1$), reaction of that moiety with a reactive thiol functional group of a targeting agent converts $L_B'$ to a ligand covalent binding ($L_B$) moiety so that a thio-substituted succinimide moiety is obtained. When the targeting agent is an antibody or antigen-binding fragment thereof, the thio-substituent is comprised of a sulfur atom of an antibody Ligand Unit, which in some aspects is provided by a cysteine residue obtained by interchain disulfide bond reduction or genetic engineering.

In another example, when $L_B'$ is comprised of an activated carboxylic acid functional group, reaction of that functional group with a reactive amino group of a targeting agent, such as an epsilon amino group of a lysine residue in an antibody or antigen-binding fragment thereof, converts the functional group to an amide, wherein that amide functional group resulting from that reaction is shared between $L_B$ and the attached Ligand Unit, which in the case of an antibody or antigen-binding fragment is an antibody Ligand Unit. Other $L_B$ moieties and their conversion from $L_B'$-containing moieties are described in the embodiments of the invention. In yet another example, a targeting agent having a reactive amino group is derivatized with a bi-functional molecule to provide an intermediate, which in some instances results in a reactive thiol functional group, that is condensed with a $L_B'$ moiety. As a result of that condensation the $L_B$ moiety so formed has atoms attributable to the bi-functional molecule and $L_B'$.

"Ligand covalent binding precursor moiety" is a moiety of a Linker Unit of a Drug Linker compound or Intermediate thereof that comprised of a reactive or activatable functional group, wherein the reactive functional group or activatable functional group subsequent to activation is capable of covalent binding to a targeting agent, such as an antibody or antigen-binding fragment thereof, during the preparation of a Ligand Drug Conjugate (LDC), including an Antibody Drug Conjugate (ADC), whereupon the ligand binding moiety precursor ($L_B'$) moiety is converted to a ligand covalent binding ($L_B$) moiety. In some aspects, a $L_B'$ moiety has a functional group capable of reacting with a nucleophile or electrophile native to an antibody or antigen-binding fragment thereof, or is introduced into the antibody or antigen binding fragment by chemical transformation or genetic engineering (vide supra) for its conversion to an antibody Ligand Unit. In some of those aspects, the nucleophile is an N-terminal amino group of a light or heavy chain of an antibody or antigen-binding fragment thereof, or the epsilon amino group of a lysine residue of that light or heavy chain.

In other aspects, the nucleophile is the sulfhydryl group of a cysteine residue introduced by genetic engineering into a light or heavy chain of an antibody or antigen-binding fragment thereof or from chemical reduction of an interchain disulfide of the antibody or antigen-binding fragment. In still some aspects, the electrophile is an aldehyde introduced by selective oxidation of a carbohydrate moiety in a glycan component of an antibody or antigen-binding fragment thereof, or is a ketone from an unnatural amino acid introduced into a light or heavy chain of an antibody or antigen-binding fragment thereof using a genetically engineered tRNA/tRNA synthetase pair. Those and other methods for introducing a reactive functional group to provide for a conjugation site in an antibody are reviewed by Behrens and Liu "Methods for site-specific drug conjugation to antibodies" *mAB* (2014) 6(1): 46-53.

"Secondary linker", "secondary linker moiety" and like terms as used herein, unless otherwise stated or implied by context, refer to an organic moiety in a Linker Unit (LU), wherein the secondary linker ($L_O$) is a component of LU that interconnects a Drug Unit to a primary linker ($L_R$) and contains a ligand covalent binding ($L_B$) moiety, a first optional Stretcher Unit and/or an optional Branching Unit (B) and in some aspects provides for a self-stabilizing ($L_{SS}$) primary linker of a Ligand Drug Conjugate (LDC), such as an Antibody Drug Conjugate (ADC), or of a Drug Linker compound useful for the preparation of the Conjugate, or provides for a self-stabilized ($L_S$) primary linker of a LDC/ADC compound upon hydrolysis of $L_{SS}$. In instances when $L_R$ is $L_{SS}$ or $L_S$, the first optional Stretcher Unit is present. In those aspects, $L_R$ is attached to $L_O$ through a heteroatom or functional group from the first optional Stretcher Unit (A) that is present.

A secondary linker of a Ligand Drug Conjugate compound or a Drug Linker compound typically has the structure of:

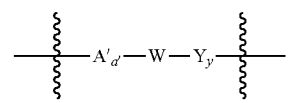

when subscript b is 0 wherein the wavy line adjacent to A' indicates the site of covalent attachment of $L_O$ to the primary linker; the wavy line adjacent to Y indicates the site of covalent attachment of $L_O$ to the Drug Unit; A' is a second optional Spacer Unit, or in some aspects is a subunit of a first optional Stretcher Unit that is present, subscript a' is 0 or 1, indicating the absence or presence of A', respectively; Y is a Spacer Unit, and subscript y is 0, 1 or 2, indicating the absence or presence of one or two Spacer Units, respectively; and W is a Peptide Cleavable Unit, wherein the Peptide Cleavable Unit provides for a recognition site that has overall greater selectivity for proteases of tumor tissue homogenate in comparison to proteases in normal tissue homogenate, wherein the tumor tissue is comprised of targeted cancer cells and the normal tissue is comprised of non-targeted normal cells for which off-target cytotoxicity by the Ligand Drug Conjugate is responsible at least in part for an adverse event often associated with administration of a therapeutically effective amount to a mammalian subject in need thereof. When subscript b is 0, A', when present, becomes a subunit of A in which case the secondary linker has the structure of —W—$Y_y$—. In either of those aspects W, Y and D are arranged in a linear configuration with respect to the remainder of LU/LU', as represented by —W—$Y_y$-D, in which W is the Peptide Cleavable Unit and subscript y is 0, 1 or 2. When subscript y is 1 or 2, protease cleavage is followed by self-immolation of a self-immolative Spacer Unit attached to W so as to release D or Y'-D, if a second Spacer Unit (Y') is present, which decomposes to complete release of D as free drug.

A secondary linker ($L_O$) bonded to D in a Linker Unit as exemplified when only one Drug Unit is attached to LU in which W is a Peptide Cleavable Unit is typically represented by the structure of

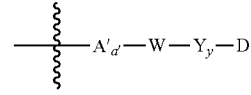

when subscript b is 1 or

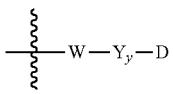

due to A'$_{a'}$ being treated as a subunit of a first optional Stretcher unit when subscript b is 0 and subscript a' is 1;
wherein D is a Drug Unit and the remaining variable groups are as defined herein for $L_O$; and a drug linker moiety or a Drug Linker compound comprised of that secondary linker typically has the structure of Formula 1B and Formula IB, respectively:

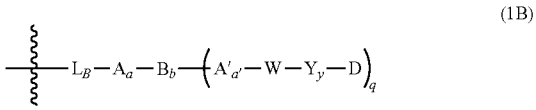 (1B)

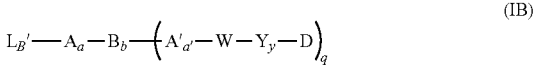 (IB)

wherein $L_B$ is a ligand covalent binding moiety as defined herein, which is a component of a primary linker ($L_R$) of a Linker Unit (LU) of a drug linker moiety of a Ligand Drug Conjugate compound; and $L_B$' is a ligand covalent binding moiety as defined herein, which is a component of a primary linker ($L_R$') of a Linker Unit (LU') in a Drug Linker compound, and are sometimes referred to as a ligand covalent binding moiety precursor, a primary linker precursor and a Linker Unit precursor for $L_R$, $L_B$ and LU, respectively, of a Ligand Drug Conjugate when the Drug Linker Compound is used in the preparation of the Ligand Drug Conjugate; A is a first optional Stretcher Unit; subscript a is 0 or 1, indicating the absence or presence of A, respectively; B is an optional Branching Unit, subscript b is 0 or 1, indicating the absence or presence of B, respectively, wherein A' is a subunit of A when subscript b is 0, subscript a is 1 and subscript a' is 1; subscript q ranges from 1 to 4, wherein $L_B/L_B$' and A and B, when present, are components of $L_R/L_R$' and provided that subscript q ranges from 2 to 4 when subscript b is 1, and subscript q is 1 when subscript b is 0; and the remaining variable groups are as defined herein for $L_O$.

"Maleimide moiety" as used herein, unless otherwise stated or implied by context, refers to a component of a primary linker of a Drug Linker compound, which in some aspects is a component of a self-stabilizing linker, wherein that primary linker is sometimes represented as $L_R$' or $L_{SS}$' to explicitly indicated that it is a precursor to $L_R/L_{SS}$ in a Ligand Drug Conjugate. A maleimide moiety ($M^1$) is capable of participating in Michael addition (i.e., 1,4-conjugate addition) by a sulfur atom of a reactive thiol functional group of targeting agent, such as an antibody or antigen-binding fragment thereof, to provide a thio-substituted succinimide ($M^2$) moiety, wherein the thio substituent is a Ligand Unit that incorporates or corresponds to the structure of the targeting agent as exemplified herein for an antibody Ligand Unit of an Antibody Drug Conjugate composition or compound thereof. That $M^1$ moiety of a Drug Linker compound is attached to the remainder of the primary linker, typically to a first optional Stretcher Unit (A) that is present as the $M^1$ moiety is a component of $L_{SS}$' or to a secondary linker ($L_O$) if both A and B are absent, through its imide nitrogen atom.

Other than the imide nitrogen atom, an $M^1$ moiety is typically unsubstituted, but may be asymmetrically substituted at the cyclic double bond of its maleimide ring system. Such substitution can result in regiochemically preferred conjugate addition of a sulfur atom of a reactive thiol functional group of a targeting agent to the less hindered or more electronically deficient double bonded carbon atom (dependent on the more dominant contribution) of the maleimide ring system. That conjugate addition results in a succinimide ($M^2$) moiety, which is thio-substituted by the Ligand Unit though a sulfur atom from a thiol functional group provided by the targeting agent.

"Succinimide moiety" as used herein, unless otherwise stated or implied by context, refers one type of ligand covalent binding ($L_B$) moiety in of primary linker, which in turn is a component of a Linker Unit of a Ligand Drug Conjugate, such as an Antibody Drug Conjugate, and results from Michael addition of a sulfur tom of a reactive thiol functional group of an antibody or antigen-binding fragment thereof to the maleimide ring system of a maleimide moiety ($M^1$), which is one type of ligand covalent binding precursor ($L_B$') moiety in a Drug Linker compound or a $M^1$-containing intermediate thereof. A succinimide ($M^2$) moiety is therefore comprised of a thio-substituted succinimide ring system that has its imide nitrogen atom substituted with the remainder of the primary linker, which typically would be a first optional Stretcher Unit (A) that is present. In some aspects, that nitrogen atom is attached to the first optional Stretcher Unit (A) that is present through an optionally substituted $C_1$-$C_{12}$ alkylene moiety comprising that Unit. When the primary linker is a self-stabilizing linker, that alkylene moiety incorporates a cyclic Basic Unit into a first optional Stretcher Unit that is present or is substituted by an acyclic Basic Unit as described elsewhere, and is otherwise optionally substituted, and has its $M^2$ moiety optionally substituted with substituent(s) at its succinimide ring system, which may have been present on the $M^1$ precursor.

Thus, the optionally substituted $C_1$-$C_{12}$ alkylene moiety of A, in optional combination with [HE], which is an optional hydrolysis-enhancing unit, is either covalently attached directly to the optional secondary linker ($L_O$) that is present, when subscript b is 0 or indirectly to $L_O$ through -[HE]-B— when subscript b is 1 in a drug linker moiety of Formula 1B or the Drug Linker compound of Formula IB. In those instances in which subscript b is 0, subscript a is 1 and subscript a' is 1, A is represented by the formula -A$_1$[HE]-A2-, wherein A$_1$ is a first subunit of A and is comprised of the optionally substituted $C_1$-$C_{12}$ alkylene moiety in optional combination with HE, and A', previously indicated as a component of $L_O$, becomes A2, which is now the second subunit of A. In those instances when subscript b is 1 and subscript a is 1 and subscript a' is 1, A' is a component of the secondary linker and A is a single unit in optional combination with [HE] or is optionally comprised of two subunits, which is represented by -A[HE]-A$_O$-, wherein A$_O$ is an optional subunit of A. When A$_O$ is present, A is also represented by the formula -A$_1$[HE]-A$_2$-.

When present in a self-stabilizing linker ($L_{SS}$) in a Ligand Drug Conjugate compound, hydrolysis of the succinimide ring system of the thio-substituted succinimide ($M^2$) moiety, which is pH controllable due to the nearby presence of the basic functional group of the acyclic or cyclic Basic Unit, provides in some instances regiochemical isomers of succinic acid-amide ($M^3$) moieties in a self-stabilized linker ($L_S$) due to its asymmetric substitution by the thio substituent. The relative amounts of those isomers will be due at least in part to differences in reactivity of the two carbonyl carbons of $M^2$, which can be attributed at least in part to any substituent(s) that were present in the $M^1$ precursor. Hydrolysis is also expected to occur to some extent when $L_R$ having a $M^2$ moiety that does not contain a Basic Unit but is highly variable in comparison to the controlled hydrolysis provided by the Basic Unit.

In some aspects, those optional substituents on the succinimide ring system of $M^2$ are not present and the first optional Stretcher Unit is present and is comprised of an optionally substituted $C_1$-$C_{12}$ alkylene moiety optionally attached to [HE], which is an optional hydrolysis-enhancing unit, at a position distal to its attachment site to the imide nitrogen atom. In that aspect, A is a single unit or is further comprised of A', which is an optional subunit of A that is present when subscript b is 0 and subscript a' is 1, and is attached to [HE] that is also present so that A has the formula of -A[HE]-A'- or when subscript b is 1 and subscript a' is 1, A' is a component that is present of the secondary linker so that A is represented by the formula of -A[HE]-$A_O$-.

"Succinic acid-amide moiety" as used herein, unless otherwise stated or implied by context, refers to component of a self-stabilized linker ($L_S$) of a Linker Unit within a Ligand Drug Conjugate, such as an Antibody Drug Conjugate, and has the structure of a succinic amide hemi-acid residue with substitution of its amide nitrogen by another component of $L_S$, wherein that component is typically a first optional Stretcher Unit (A) or subunit thereof that is present and is comprised of an $C_1$-$C_{12}$ alkylene moiety optionally attached to [HE]. The possible structures for A when subscript b is 0 and subscript a is 0 or 1 are indicated by the formulae of -A[HE]-A'$_a$-, in which A' previously associated with the secondary linker is either absent so that subscript a' is 0 or when subscript a' is 1 A' is present as a subunit of A. When that subunit is present, A is represented by the formula of $A_1$[HE]-$A_2$-, wherein $A_1$ is the first subunit of A, which is comprised of the optionally substituted $C_1$-$C_{12}$ alkylene moiety optionally attached to [HE], and A2 is the second subunit of A, previously indicated as A'. The possible structures for A when subscript b is 1 and subscript a is 1 are indicated by the formula of -A[HE]-$A_O$-, in which $A_O$ is an optional subunit of A when present. When that subunit is absent A is a single discrete unit and when $A_O$ is present A is represented by the formula of $A_1$[HE]-A2-, wherein $A_1$ is the first subunit of A, which is comprised of the optionally substituted $C_1$-$C_{12}$ alkylene moiety optionally attached to [HE], and A2, previously indicated as $A_O$, is the second subunit of A.

In some aspects, the alkylene moiety incorporates a cyclic Basic Unit and in other aspects is substituted by an acyclic Basic Unit and in either aspect is otherwise optionally substituted, wherein the succinic acid amide ($M^3$) moiety has further substitution by L-S—, wherein L is a Ligand Unit such as an antibody Ligand Unit incorporating or corresponding in structure to a targeting agent such as an antibody or antigen-binding fragment thereof and S is a sulfur atom from that targeting agent, antibody or antigen-binding fragment. A $M^3$ moiety results from the thio-substituted succinimide ring system of a succinimide ($M^2$) moiety in self-stabilizing primary linker having undergone breakage of one of its carbonyl-nitrogen bonds by hydrolysis, which is assisted by the Basic Unit.

Thus, a $M^3$ moiety has a free carboxylic acid functional group and an amide functional group whose nitrogen heteroatom is attached to the remainder of the primary linker and is substituted by L-S— at the carbon that is alpha to that carboxylic acid or amide functional group, depending on the site of hydrolysis of its $M^2$ precursor. Without being bound by theory, it is believed the aforementioned hydrolysis resulting in a $M^3$ moiety provides a Linker Unit (LU) in an Ligand Drug Conjugate that is less likely to suffer premature loss from the Conjugate of its targeting Ligand Unit (L) through elimination of the thio substituent.

"Self-stabilizing linker" as used herein, unless otherwise stated or implied by context, refers to a primary linker of a Linker Unit (LU) in a Ligand Drug Conjugate, such as an Antibody Drug Conjugate, having a $M^2$-containing component or a primary linker of a Linker Unit precursor (LU') in a Drug Linker compound having a $M^1$-containing component, wherein that component may be designated as $L_{SS}$' to indicate that it is a precursor to the $M^2$- containing component of $L_{SS}$ in an LDC. The self-stabilizing linker subsequently undergoes conversion under controlled hydrolysis conditions to the corresponding self-stabilized linker ($L_S$). That hydrolysis is facilitated by the Basic Unit component of $L_{SS}$, such that an LDC/ADC comprised of $L_{SS}$ becomes more resistant to premature loss of its Ligand Unit by virtue of its Linker Unit (LU) now being comprised of $L_S$. The $L_{SS}$ primary linker, in addition to its $M^1$ or $M^2$ moiety, is further comprised of a first optional Stretcher Unit (A) that is required to be present, wherein A is comprised of an $C_1$-$C_{12}$ alkylene moiety optionally in combination with [HE], wherein that combination is sometimes designated as $A_1$ when A is further comprised of an optional subunit ($A_O$) that is present when subscript b is 1 or A is further comprised of A' when subscript b is 0 and subscript a' is 1, wherein with either value of subscript b that additionally present subunit is designated a A2. When A may exist as a single discrete unit or in the form of two discrete units, both possibilities are represented by the formula of -A[HE]-$A_O$-, when subscript b is 1 or A[HE]-A'$_a$, when subscript b is 0, which for either value of subscript b becomes -A[HE]- or -$A_1$[HE]-$A_2$-, depending on the absence or presence, respectively, of a second subunit. In either variation of A within $L_{SS}$, its alkylene moiety incorporates a cyclic Basic Unit or is substituted by an acyclic Basic Unit and is otherwise optionally substituted.

Thus, when the primary linker of a Drug Linker compound is $L_{SS}$, sometimes shown as $L_{SS}$' to indicate that it is a precursor of $L_{SS}$ in a Ligand Drug Conjugate, that primary linker contains a first optional Stretcher Unit (A) that is required to be present and a maleimide ($M^1$) moiety through which a targeting agent is to be attached, which in the case of an antibody or antigen-binding fragment thereof provides an antibody Ligand Unit. In those aspects, the $C_1$-$C_{12}$ alkylene moiety of A of $L_{SS}$ is attached to the imide nitrogen of the maleimide ring system of $M^1$ and to the remainder of the Linker Unit, the latter of which optionally occurs through [HE]-$A_O$-B— when subscript b is 1 or [HE]-A'$_a$- when subscript b is 0, depending on the absence or presence of $A_O$/A' and [HE]. In some of those aspects, [HE], which is a hydrolysis-enhancing moiety, consists or is comprised of an optionally substituted electron withdrawing heteroatom or functional group, which in some aspects in addition to BU may enhance the hydrolysis rate of the $M^2$ moiety in the corresponding $L_{SS}$ moiety of a LDC/ADC compound. After incorporation of the Drug Linker compound into an LDC/ADC compound, $L_{SS}$ now contains a succinimide ($M^2$) moiety that is thio-substituted by the Ligand Unit (i.e., attachment of the Ligand Unit to its drug linker moiety has occurred through Michael addition of a sulfur atom of a reactive thiol functional group of a targeting agent to the maleimide ring system of $M^1$).

In some aspects, a cyclized Basic unit (cBU) corresponds in structure to an acyclic Basic Unit through formal cyclisation to the basic nitrogen of that Unit so that the cyclic Basic Unit structure is incorporated into the first optional Stretcher Unit that is present as an optionally substituted spiro $C_4$-$C_{12}$ heterocyclo. In such constructs, the spiro carbon is attached to the maleimide imide nitrogen of $M^1$, and hence to that nitrogen in $M^2$, and is further attached to the remainder of the $L_{SS}$ primary linker, which is comprised of the afore-described first optional Stretcher Unit (A) that is present optionally through -[HE]-$A_O$- or [HE]-$A_{a'}$-, in a drug linker moiety of Formula 1B or a Drug Linker compound of Formula IB.

In those aspects, a cyclic BU assists in the hydrolysis of the succinimide moiety of $M^2$ to its corresponding ring-opened form(s) represented by $M^3$ in qualitatively similar manner to that of an acyclic Basic Unit, which may also be enhanced by [HE].

In some aspects, $L_B'$-A-$B_b$— of a $L_{SS}$ primary linker, which is sometimes shown as $L_{SS}'$ to explicitly indicate that it is a precursor to a self-stabilizing ($L_{SS}$) primary linker in a Drug Linker compound of Formula IB, is represented by the general formula of $M^1$-A(BU)-[HE]-$A_O$-B— when subscript b is 1 or $M^1$-A(BU)-[HE]-$A'_{a'}$- when subscript b is 0, wherein $M^1$ is a maleimide moiety and A is a $C_1$-$C_{12}$ alkylene that incorporates or is substituted by BU and is otherwise optionally substituted and is in optional combination with [HE], which is an optional hydrolysis-enhancing moiety, wherein that formula for becomes $M^1$-A(BU)-[HE]-B- or $M^1$-A(BU)[HE]- when A is a single discreet unit or $M^1$-$A_1$(BU)-[HE]-$A_2$-B— or $M^1$-$A_1$(BU)-[HE]-$A_2$- when A is of two subunits, wherein $A_1$ and $A_2$ are the subunits of A.

In other aspects, a $L_{SS}$ primary linker in a drug linker moiety of Formula 1B of an ADC of Formula 1A, is represented by the general formula of -$M^2$-A(BU)-[HE]-$A_O$-B—, when subscript b is 1 or -$M^2$-A(BU)-[HE]-$A_{a'}$- when subscript b is 0, wherein $M^2$ is a succinimide moiety, A is a first optional Stretcher Unit that is present and is comprised of an $C_1$-$C_{12}$ alkylene that incorporates or is substituted by BU and is otherwise optionally substituted and is in optional combination with [HE], which is an optional hydrolysis-enhancing moiety, and $A_O$/A' is an optional subunit of A. When A is a single discreet unit, $L_{SS}$ is represented by the formula of -$M^2$-A(BU)-[HE]-B— or -$M^2$-A(BU)-[HE]- and when A is of two subunits, $L_{SS}$ is represented by the formula of -$M^2$-$A_1$(BU)-[HE]-$A_2$- or -$M^2$-$A_1$(BU)-[HE]-$A_2$-B— when subscript b is 0 or 1, respectively.

In still other aspects, a $L_S$ primary linker in a drug linker moiety of Formula 1B of a LDC/ADC of Formula 1A is represented by the general formula of -$M^3$-A(BU)-[HE]-$A_O$-B—, when subscript b is 1 or -$M^3$-A(BU)-[HE]-$A_{a'}$- when subscript b is 0, wherein $M^3$ is a succinimide acid amide moiety and A is a $C_1$-$C_{12}$ alkylene that incorporates or is substituted by BU, and is otherwise optionally substituted, and is in optional combination with [HE], which is an optional hydrolysis-enhancing moiety, and $A_O$/A' is an optional subunit of A, wherein -A(BU)-[HE]-$A_O$- or -A(BU)-[HE]-$A_{a'}$- becomes -A(BU)-[HE]- when A is a single discreet unit or -$A_1$(BU)-[HE]-$A_2$- when A is or is comprised of two subunits.

Exemplary, but non-limiting -$L_B$-A- structures comprising a $L_{SS}$ primary linker within a drug linker moiety of Formula 1B for some Ligand Drug Conjugates of Formula 1 are represented by:

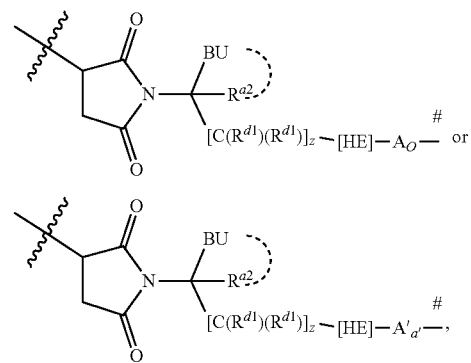

wherein the wavy line indicates the site of covalent attachment to a Ligand Unit, the pound sign (#) in the upper structure for which subscript b is 1 indicates the site of covalent attachment in Formula 1B to a Branching Unit (B) or in the lower structure in which subscript b is 0 to W of an optional secondary linker ($L_O$) that is present and wherein the dotted curved line indicates optional cyclization which is present when BU is a cyclic Basic Unit or is absent when BU is an acyclic Basic Unit, wherein [HE] is an optional hydrolysis-enhancing moiety, $A_O$/A' is an optional subunit of A, subscript z is 0 or an integer ranging from 1 to 6; each $R^{d1}$ is independently selected from the group consisting of hydrogen and optionally substituted $C_1$-$C_6$ alkyl, or two of $R^{d1}$, the carbon atom(s) to which they are attached and any intervening carbon atoms define an optionally substituted $C_3$-$C_8$ carbocyclo, and the remaining $R^{d1}$, if any, are independently hydrogen or optionally substituted $C_1$-$C_6$; and $R_{a2}$ is —H or an optionally substituted $C_1$-$C_8$ alkyl when BU is an acyclic Basic Unit, and when BU a cyclic Basic Unit, $R_{a2}$ is required to be other than —H and along with the carbon atom to which BU and $R_{a2}$ are attached define an optionally substituted spiro $C_4$-$C_{12}$ heterocyclo having a skeletal secondary or tertiary basic nitrogen atom, such that the acyclic or cyclic BU is capable of increasing the rate of hydrolysis of the shown succinimide ($M^2$) moiety to provide a succinic acid amide ($M^3$) moiety at a suitable pH in comparison to the corresponding Conjugate in which $R^{a2}$ is hydrogen and BU is replaced by hydrogen, and for a cyclic Basic Unit substantially retains the increase in the rate of hydrolysis of the drug linker moiety corresponding to that of the LDC/ADC in which in $R^{a2}$ is hydrogen and BU is an acyclic BU over the aforementioned Conjugate in which $R^{a2}$ is hydrogen and BU is replaced by hydrogen.

Exemplary, but non-limiting, $L_B'$-A- structures comprising $L_{SS}'$, which are sometimes present in Drug Linker compounds of Formula I used as intermediates in the preparation of Ligand Drug Conjugate compositions, are represented by:

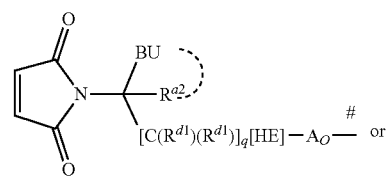

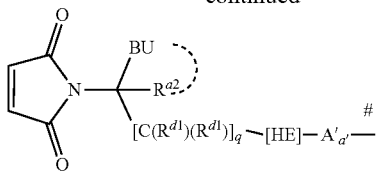

wherein BU and the other variable groups are as defined above for $L_B$-A- structures of LDCs/ADCs having $L_{SS}$ primary linkers. When a Drug Linker compound having a self-stabilizing linker precursor ($L_{SS}'$), which is comprised of a maleimide moiety, is used in the preparation of an LDC/ADC, that $L_{SS}'$ moiety is converted into an $L_{SS}$ primary linker comprised of a succinimide moiety. Prior to condensation with a reactive thiol functional group from a targeting agent such as an antibody or antigen-binding fragment thereof, the basic nitrogen atom of BU is typically protonated or protected by an acid-labile protecting group.

"Self-stabilized linker" is an organic moiety derived from a $M^2$-containing moiety of a self-stabilizing linker ($L_{SS}$) in a Ligand Drug Conjugate, such as an Antibody Drug Conjugate, that has undergone hydrolysis under controlled conditions so as to provide a corresponding $M^3$-moiety of a self-stabilized linker ($L_S$), wherein that LU component is less likely to reverse the condensation reaction of a targeting moiety with a $M^1$-containing moiety that provided the original $M^2$-containing $L_{SS}$ moiety. In addition to the $M^3$ moiety, a self-stabilized linker ($L_S$) is comprised of a first optional Stretcher Unit (A) that is present and incorporates a cyclic Basic Unit or is substituted by an acyclic Basic Unit, wherein A is covalently attached to $M^3$ and the remainder of the $L_S$ primary linker (i.e., B) or to a secondary linker ($L_O$) when B is absent. The $M^3$ moiety is obtained from conversion of a succinimide moiety ($M^2$) of $L_{SS}$ in an Ligand Drug Conjugate, wherein the $M^2$ moiety has a thio-substituted succinimide ring system resulting from Michael addition of a sulfur atom of a reactive thiol functional group of a targeting agent to the maleimide ring system of $M^1$ of a $L_{SS}'$ moiety in a Drug Linker compound, wherein that $M^2$-derived moiety has reduced reactivity for elimination of its thio-substituent in comparison to the corresponding substituent in $M^2$. In those aspects, the $M^2$-derived moiety has the structure of a succinic acid-amide ($M^3$) moiety corresponding to $M^2$ wherein $M^2$ has undergone hydrolysis of one of its carbonyl-nitrogen bonds of its succinimide ring system, which is assisted by the basic functional group of BU due to its appropriate proximity as a result of that attachment. The product of that hydrolysis therefore has a carboxylic acid functional group and an amide functional group substituted at its amide nitrogen atom, which corresponds to the imide nitrogen atom in the $M^2$-containing $L_{SS}$ precursor to $L_S$, with the remainder of the primary linker, which is will include at minimum the optional Stretcher Unit that is present. In some aspects, the basic functional group is a primary, secondary or tertiary amine of an acyclic Basic Unit or secondary or tertiary amine of a cyclic Basic Unit. In other aspects, the basic nitrogen of BU is a heteroatom of an optionally substituted basic functional group as in a guanidino moiety. In either aspect, the reactivity of the basic functional group of BU for base-catalyzed hydrolysis is controlled by pH by reducing the protonation state of the basic nitrogen atom.

Thus, a self-stabilized linker ($L_S$) typically has the structure of an $M^3$ moiety covalently bond to a first optional Stretcher Unit that is present and incorporating a cyclic Basic Unit or substituted by an acyclic Basic Unit. In some aspects, A is a discrete single unit and in other aspects is of two or more subunits, typically represented by $A_1$-$A_2$ if two subunits are present with $A/A_1$ optionally in combination with [HE]. Stretcher Unit A in turn is covalently bonded to B of the $L_S$ primary linker or to W of $L_O$ with its $M^3$, A, $A'_a$/B and BU components arranged in the manner represented by the general formula of -$M^3$-A(BU)-[HE]-$A'_{a'}$- or $M^3$-A(BU)-[HE]-$A_O$-B—, in which subscript b is 0 or 1, respectively. When A is a single discreet unit, $L_S$ is represented by -$M^3$-A(BU)-[HE]-B— when subscript b is 1 or -$M^3$-A(BU)-[HE]- and when A is of two subunits represent $L_S$ is represented by -$M^3$-$A_1$(BU)-$A_2$- or -$M^3$-$A_1$(BU)-$A_2$-B— in which subscript b is 0 or 1, respectively, wherein BU represents either type of Basic Unit (cyclic or acyclic).

Exemplary non-limiting structures of -$L_B$-A- in $L_{SS}$ and $L_S$ primary linkers for LDCs/ADCs in which $L_B$ is $M^2$ or $M^3$; and A(BU)/$A_1$(BU), and [HE] within these structures are arranged in the manner indicated above in which BU is an acyclic Basic Unit is shown by way of example but not limitation by the structures of.

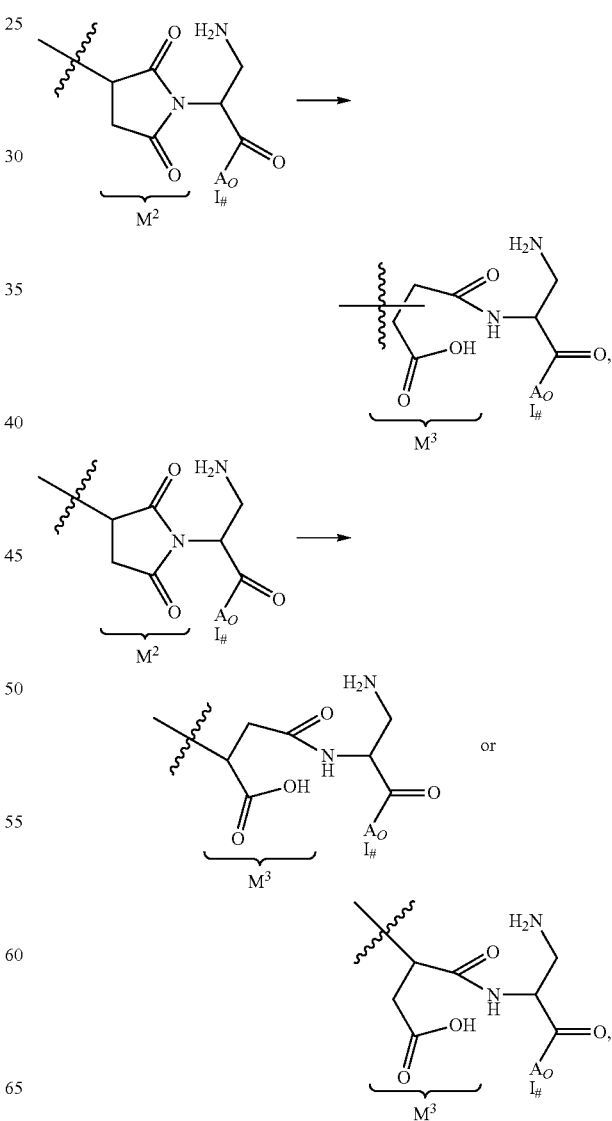

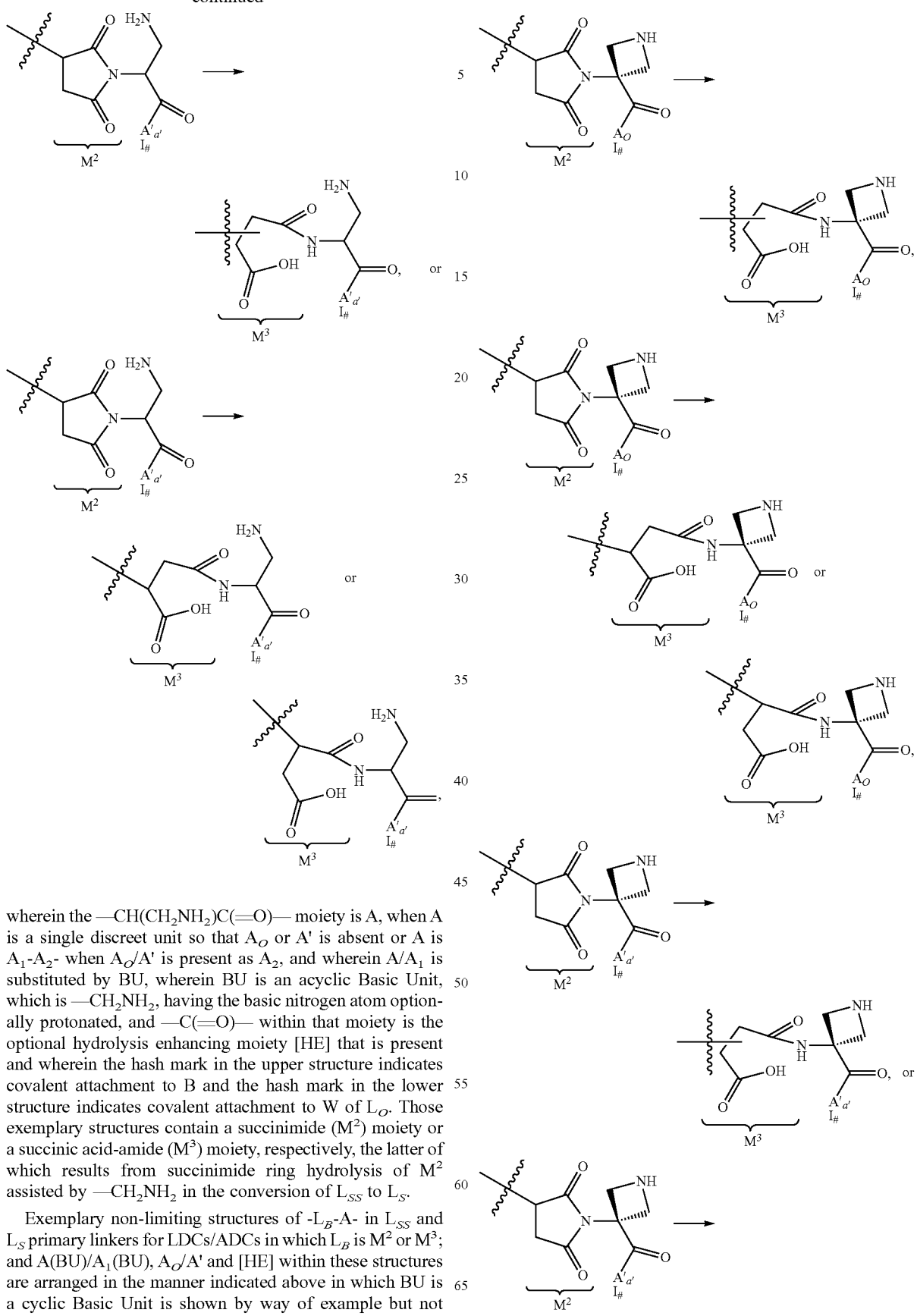

wherein the —CH(CH$_2$NH$_2$)C(=O)— moiety is A, when A is a single discreet unit so that A$_O$ or A' is absent or A is A$_1$-A$_2$- when A$_O$/A' is present as A$_2$, and wherein A/A$_1$ is substituted by BU, wherein BU is an acyclic Basic Unit, which is —CH$_2$NH$_2$, having the basic nitrogen atom optionally protonated, and —C(=O)— within that moiety is the optional hydrolysis enhancing moiety [HE] that is present and wherein the hash mark in the upper structure indicates covalent attachment to B and the hash mark in the lower structure indicates covalent attachment to W of L$_O$. Those exemplary structures contain a succinimide (M$^2$) moiety or a succinic acid-amide (M$^3$) moiety, respectively, the latter of which results from succinimide ring hydrolysis of M$^2$ assisted by —CH$_2$NH$_2$ in the conversion of L$_{SS}$ to L$_S$.

Exemplary non-limiting structures of -L$_B$-A- in L$_{SS}$ and L$_S$ primary linkers for LDCs/ADCs in which L$_B$ is M$^2$ or M$^3$; and A(BU)/A$_1$(BU), A$_O$/A' and [HE] within these structures are arranged in the manner indicated above in which BU is a cyclic Basic Unit is shown by way of example but not limitation by the structures of:

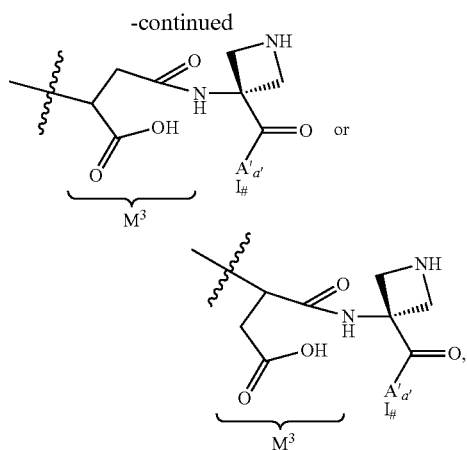

wherein these -M²-A(BU)-[HE]-A_O/A'_a'- and -M³-A(BU)-[HE]-A_O/A'_a'- structures become -M²-A(BU)-[HE]- and -M³-A(BU)-[HE]-, when A_O is absent or subscript a' is 0 so that A is present as a single discreet unit or become -M²-A₁(BU)-[HE]-A₂- and -M³-A'(BU)-[HE]-A₂-when A_O/A' is present as a subunit of A indicated as A₂ and wherein in either structure BU is a cyclic Basic Unit in the form of an optionally protonated azetidin-3,3-diyl, the structure of which is an exemplary heterocyclo Basic Unit incorporated into A/A₁. That heterocyclo corresponds to the aminoalkyl of an acyclic Basic Unit in an -A₁(BU)— or -A(BU)- moiety in which the basic nitrogen of the acyclic Basic Unit has been formally cyclized at least in part back through R^{a2} to the carbon atom that is alpha to the succinimide nitrogen of M² to which the acyclic Basic Unit is attached.

The wavy line in each of the above -L_B-A- structures indicates the site of covalent attachment of a sulfur atom of a Ligand Unit derived from a reactive thiol functional group of a targeting agent upon Michael addition of that sulfur atom to the maleimide ring system of an M¹ moiety in a structurally corresponding Drug Linker compound or M¹-containing intermediate thereof. The hash mark (#) in the upper structure indicates the site of covalent attachment to B, which is the remainder of the L_{SS} or L_S primary linker and in the lower structure indicates the site of covalent attachment to W of L_O. Since the succinimide ring system of M² is asymmetrically substituted due to its thio substituent, regiochemical isomers of succinic acid-amide (M³) moieties as defined herein differing in position relative to the liberated carboxylic acid group may result on M² hydrolysis. In the above structures, the carbonyl functional group shown adjacent to A_O exemplifies a hydrolysis enhancer [HE] as defined herein.

The above -M³-A(BU)-[HE]-A_O/A'_a'-, -M³-A(BU)- and -M³-A₁(BU)-[HE]-A₂-moieties wherein BU is acyclic or cyclic Basic Unit represent exemplary -L_B-A- structures that comprise self-stabilized linker (L_S) primary linkers, so named because these structures are less likely to eliminate the thio substituent of the Ligand Unit, and thus cause loss of that targeting moiety, in comparison to the corresponding L_{SS} moieties comprised of formula -M²-A(BU)-[HE]-A_O/A'_a'-, -M²-A(BU)- or -M²-A₁(BU)-[HE]-A₂- from which they are derived. Without being bound by theory, it is believed the increased stability results from the greater conformational flexibility in M³ in comparison to M², which no longer constrains the thio substituent in a conformation favorable for E2 elimination.

"Basic Unit" as used herein, unless otherwise stated or implied by context, refers to an organic moiety within a self-stabilizing linker (L_{SS}) primary linker, as described herein, which is carried forward into a corresponding L_S moiety by BU participating in base catalyzed hydrolysis of the succinimide ring system within a M² moiety comprising L_{SS} (i.e., catalyzes addition of a water molecule to one of the succinimide carbonyl-nitrogen bonds). In some aspects, the base-catalyzed hydrolysis is initiated under controlled conditions tolerable by the targeting Ligand Unit attached to L_{SS}. In other aspects, the base-catalyzed hydrolysis is initiated on contact of the Drug Linker compound comprised of L_{SS}' with a targeting agent in which Michael addition of a sulfur atom of a reactive thiol functional group of the targeting agent competes with hydrolysis of the M¹ moiety of L_{SS}' of the Drug Linker compound. Without being bound by theory, the following aspects describe various considerations for design of a suitable Basic Unit. In one such aspect, the basic functional group of an acyclic Basic Unit and its relative position in L_{SS} with respect to its M² component are selected for the ability of BU to hydrogen bond to a carbonyl group of M², which effectively increases its electrophilicity and hence its susceptibility to water attack. In another such aspect, those selections are made so that a water molecule, whose nucleophilicity is increased by hydrogen bonding to the basic functional group of BU, is directed to an M² carbonyl group. In a third such aspect, those selections are made so the basic nitrogen on protonation does not increase the electrophilicity of the succinimide carbonyls by inductive electron withdrawal to an extent that would promote premature hydrolysis requiring compensation from an undesired excess of Drug Linker compound. In a further such aspect, some combination of those mechanistic effects contributes to catalysis for controlled hydrolysis of L_{SS} to L_S.

Typically, an acyclic Basic Unit, which may act through any of the above mechanistic aspects, is comprised of 1 carbon atom or 2 to 6 contiguous carbon atoms, more typically of 1 carbon atom or 2 or 3 contiguous carbon atoms, wherein the carbon atom(s) connect the basic amino functional group of the acyclic Basic Unit to the remainder of the L_{SS} primary linker to which it is attached. In order for that basic amine nitrogen atom to be in the required proximity to assist in the hydrolysis of a succinimide (M²) moiety to its corresponding ring-opened succinic acid amide (M³) moiety, the amine-bearing carbon chain of an acyclic Basic Unit is typically attached to A of the -L_B-A- moiety of L_{SS} at the alpha carbon of the C₁-C₁₂ alkylene of that moiety relative to the site of attachment of A to the succinimide nitrogen of M² (and hence to the maleimide nitrogen of its corresponding M¹-A- structure). Typically, that alpha carbon in an acyclic Basic Unit has the (S) stereochemical configuration or the configuration corresponding to that of the alpha carbon of L-amino acids.

As previously described, BU in acyclic form or BU in cyclized form is typically connected to M¹ or M² of L_{SS} or M³ of L_S through an otherwise optionally substituted C₁-C₁₂ alkylene moiety in which that moiety incorporates the cyclized Basic Unit or is substituted by the acyclic Basic Unit and is bonded to the maleimide or succinimide nitrogen of M¹ or M², respectively, or the amide nitrogen atom of M³. In some aspects, the otherwise optionally substituted C₁-C₁₂ alkylene moiety incorporating the cyclic Basic Unit is covalently bonded to [HE] and typically occurs through intermediacy of an ether, ester, carbonate, urea, disulfide, amide carbamate or other functional group, more typically through an ether, amide or carbamate functional group. Likewise, BU in acyclic form is typically connected to M¹ or $M^2$ of $L_{SS}$ or $M^3$ of $L_S$ through the otherwise optionally substituted $C_1$-$C_{12}$ alkylene moiety of A in $L_B$'-A-, in which $L_B$' is $M^1$, or -$L_B$-A-, in which $L_B$ is $M^2$ or $M^3$, that is substitution by the acyclic Basic unit at the same carbon of the $C_1$-$C_{12}$ alkylene moiety that is attached to the imino nitrogen atom of the maleimide or succinimide ring system of $M^1$ or $M^2$ or the amide nitrogen of $M^3$, which results from hydrolysis of the succinimide ring system of $M^2$.

In some aspects, a cyclic Basic Unit incorporates the structure of an acyclic BU by formally cyclizing an acyclic Basic Unit to an otherwise optionally substituted $C_1$-$C_{12}$ alkyl ($R^{a2}$), independently selected from that of A/$A_1$, that is bonded to the same alpha carbon as the acyclic Basic Unit, thus forming a spirocyclic ring system so that a cyclic Basic Unit is incorporated into the structure of A/$A_1$ rather than being a substituent of A/$A_1$ as when BU is acyclic. In those aspects, the formal cyclization is to the basic amine nitrogen of an acyclic Basic Unit thus providing a cyclic Basic Unit as an optionally substituted symmetrical or asymmetrical spiro $C_4$-$C_{12}$ heterocyclo, depending on the relative carbon chain lengths in the two alpha carbon substituents, in which the basic nitrogen is now a basic skeletal heteroatom. In order for that cyclization to substantially retain the basic properties of the acyclic Basic Unit in a cyclic Basic Unit, the basic nitrogen atom of the acyclic Basic Unit nitrogen should be that of a primary or secondary amine and not a tertiary amine since that would result in a quaternized skeletal nitrogen in the heterocyclo of the cyclic Basic Unit. In that aspect of formal cyclization of an acyclic Basic Unit to a cyclic Basic Unit, in order to substantially retain the ability of the basic nitrogen to assist in hydrolysis of $M^2$ to $M^3$ in conversion of $L_{SS}$ to $L_S$, the resulting structure of the cyclic Basic Unit in these primary linkers will typically have its basic nitrogen located so that no more than three, and typically one or two, intervening carbon atoms between the basic nitrogen atom and the spiro carbon of the spiro $C_4$-$C_{12}$ heterocyclo component. Cyclic Basic Units incorporated into A/$A_1$ and the $L_{SS}$ and $L_S$ primary linkers having these as components are further described by the embodiments of the invention.

"Hydrolysis-enhancing moiety" as used herein, unless otherwise stated or implied by context, refers to an electron withdrawing group or moiety that is optionally present within a first optional Stretcher Unit (A) in $L_B$'-A- or -$L_B$-A- of an $L_{SS}$ primary linker and its hydrolysis product $L_S$. A hydrolysis-enhancing [HE] moiety, when present as component of A/$A_1$ of $L_{SS}$ in a drug linker moiety of an LDC/ADC in which A/$A_1$ is bonded to the imide nitrogen of an $M^2$ moiety in some aspects increases or has minimal effects on the electrophilicity of the succinimide carbonyl groups in that moiety, depending on its proximity to that $M^2$ moiety due to the electron withdrawing effect of [HE], to facilitate its conversion to a $M^3$ moiety of a $L_S$ primary linker With A/$A_1$ incorporating or substituted by a cyclic Basic Unit or an acyclic Basic Unit, respectively, the potential effect of [HE] on the carbonyl groups of $M^2$ for increasing the hydrolysis rate to $M^3$ by induction and the aforementioned effect(s) of either type of BU, are adjusted so that premature hydrolysis of $M^1$ does not occur to an appreciable extent during preparation of a Ligand Drug Conjugate from a Drug Linker compound comprised of the $L_B$'-A- structure of formula $M^1$-A(BU)-[HE]-$A_O$/$A'_{a}$-, with the two variations represented by the formulae of $M^1$-A(BU)- and $M^1$-$A_1$(BU)-[HE]-$A_2$-, in which A/$A_1$ is in combination with [HE]. Instead, the combined effects of BU and [HE] to promote hydrolysis, which covert the -$L_B$-A- structure of general formula -$M^2$-A(BU)-[HE]-$A_O$/$A'_{a}$-, or more specifically of formula -$M^2$-A(BU)- or -$M^2$-$A_1$(BU)-$A_2$-, of a Ligand Drug Conjugate compound to its corresponding -$M^3$-A(BU)-[HE]-$A_O$/$A'_{a}$-, -$M^3$-A(BU)- or $M^3$-$A_1$(BU)-[HE]-$A_2$- formula, under controlled conditions (as when pH is purposely increased so as to decrease the protonation state of the Basic Unit) are such that an undue molar excess of Drug Linker compound to compensate for hydrolysis of its $M^1$ moiety is not required. Therefore, Michael addition of the sulfur atom of a reactive thiol functional group of the targeting agent to the maleimide ring system of $M^1$, which provides a targeting Ligand Unit attached to a succinimide ring system of $M^2$, typically occurs at a rate that effectively competes with $M^1$ hydrolysis. Without being bound by theory, it is believed that at low pH, as for example when the basic amine of BU is in the form of a TFA salt, premature hydrolysis of $M^1$ in a Drug Linker product is much slower than when the pH is raised to that suitable for base catalysis using an appropriate buffering agent and that an acceptable molar excess of Drug Linker compound can adequately compensate for any loss due to premature $M^1$ hydrolysis that does occur during the time course for completion or near completion of the Michael addition of a sulfur atom of a targeting agent's reactive thiol functional group to a Drug Linker compound's $M^1$ moiety.

As previously discussed, enhancement of carbonyl hydrolysis by either type of Basic Unit is dependent on the basicity of its functional group and the distance of that basic functional group in relation to the $M^1$/$M^2$ carbonyl groups. Typically, [HE] is a carbonyl moiety or other carbonyl-containing functional group located distal to the end of the $C_1$-$C_{12}$ alkylene of A/$A_1$ that is bonded to $M^2$, or $M^3$ derived therefrom and also provides for covalent attachment to $A_2$ or to the optional secondary linker this is present, when B is absent and A is a single discreet unit. Carbonyl-containing functional groups other than ketone include esters, carbamates, carbonates and ureas. When [HE] is a carbonyl-containing functional group other than ketone in a drug linker moiety of an ADC having a $L_{SS}$ primary linker, the carbonyl moiety of that functional group, which is shared with A/$A_1$, is typically bonded to the otherwise optionally substituted $C_1$-$C_{12}$ alkylene of A/$A_1$ distal to its attachment site to the imide nitrogen atom of $M^2$ as when [HE] is —C(=O)—X—, wherein X is —O— or optionally substituted —NH—. In some aspects, the [HE] moiety may be sufficiently distant from the imide nitrogen to which of A/$A_1$ is covalently bonded so that no discernable or minor effect on hydrolytic sensitivity of the succinimide carbonyl-nitrogen bonds of an $M^2$-containing moiety is observable, but instead is driven primarily by BU.

"Stretcher Unit" as used herein, unless otherwise stated or implied by context, refers to an optional organic moiety in a primary or secondary linker of a Linker Unit in a Drug Linker compound or drug linker moiety of Ligand Drug Conjugate, such as an Antibody Drug Conjugate, that physically separates the targeting Ligand Unit (L) from an optional secondary linker when that linker is present is present. When the Linker Unit is comprised of an $L_{SS}$ or $L_S$ primary linker a first optional Stretcher is present since it provides the Basic Unit for these types of primary linkers. The presence of a first optional Stretcher Unit (A) in $L_R$ may also be required in any type of primary linker when there is insufficient steric relief from the Ligand Unit absent that optional Stretcher Unit to allow for efficient processing of the secondary linker for release of the Drug Unit as a free drug. Alternatively, or in addition to steric relief, those optional components may be included for synthetic ease in preparing a Drug Linker compound. In some aspects when subscript b is 1 a first or second optional Stretcher Unit (A or A', respectively) is a single unit or can contain multiple subunits (as for example when A has two subunits represented by -$A_1$-[HE]-$A_2$-). In other aspects when subscript b is 0 typically, A is one distinct unit or has two distinct subunits when subscript b is 0 and subscript a' is 1. In still other aspects B/A' has 2 to 4 independently selected distinct subunits.

In some aspects, when $L_R$ is $L_{SS}/L_S$, in addition to covalent attachment to $M^1$ of a Drug Linker compound or $M^2/M^3$ of a drug linker moiety in a LDC/ADC compound, A is bonded to a Branching Unit (B), or W of an optional secondary linker ($L_O$) that is present optionally through $A_O/A'_a$, as in A[HE] ($A_O/A'$ is absent) or $A_1$-[HE]-$A_2$ ($A_O/A'$ present), represented in general as A-[HE]-$A_O/A_a$-, in which A/$A_1$ and $A_O/A_a$, when present as $A_2$ is also a component of $L_{SS}/L_S$.

In some aspects, A or A' or a subunit of either of these Stretcher Units has the formula of -$L^P$(PEG)- in which $L^P$ is a Parallel Connecter Unit and PEG is a PEG Unit as defined elsewhere. Thus, in some of those aspects a Linker Unit in drug linker moiety of a Ligand Drug Conjugate or Drug Linker compound in which subscript b is 0 and subscript a' is 1 contains the formula of -$A_1$-[HE]-$L^P$(PEG)- in which A' is -$L^P$(PEG)- and is present as $A_2$. In other of those aspects in which subscript b is 1 and $A_O$ is present as $A_2$, a Linker Unit in drug linker moiety of a Ligand Drug Conjugate or Drug Linker compound contains the formula of -$A_1$-[HE]-$L^P$(PEG)-B—. In still other aspects subscript b is 1 and subscript a' is 1, a Ligand Drug Conjugate or Drug Linker compound contains the formula of -A-[HE]-$A_O$-B-$L^P$(PEG) in which A' is $L^P$(PEG)

In some aspects when subscript a is 1 so that a first optional Stretcher Unit (A) is present, that Unit typically has at least one carbon atom, wherein that atom connects $L_B/L_B'$ to [HE]. In some of those aspects in which $L_B'$ is that of a $L_{SS}'$ primary linker of a Drug Linker compound, that Stretcher Unit is comprised of $C_1$-$C_{12}$ alkylene moiety substituted by or incorporating a Basic Unit and is otherwise optionally substituted and has one of its radical carbon atoms attached to the maleimide nitrogen atom and the other to [HE], wherein [HE] is an optional hydrolysis enhancing moiety that is present. In other aspects, when $L_R'$ is other than $L_{SS}'$, but nonetheless is comprised of a maleimide moiety or some other $L_B'$ moiety, $L_B'$ is attached to an optional first Stretcher Unit (A), which in some aspects is an optionally substituted $C_1$-$C_{12}$ alkylene, which is optionally in combination with [HE]. Thus, in some aspects in which $L_R'$ is $L_{SS}'$ the first optional Stretcher Unit is present and is comprised of a $C_1$-$C_{12}$ alkylene moiety, [HE] and an optional subunit ($A_O$ when subscript b is 1 or $A'_a$, when subscript b is 0), all of which are components of $L_R'$ when $L_R'$ is $L_{SS}$, wherein A is attached to B, which is a component of $L_R'$ or W, which is a component of $L_O$, distal to the attachment site of the $C_1$-$C_{12}$ alkylene moiety to the imide nitrogen atom. In other aspects, when subscript a is 1 and A is present as a single discreet unit or of two subunits, A has the general formula of -A-[HE]-$A_O/A_a$- wherein $A_O/A'_a$ is an optional subunit of A, or more specifically has the formula of -$A_1$-[HE]-$A_2$- when $A_O$ is present as a second subunit of A and subscript b is 1 or when subscript a' is 1 and subscript b is 0 so that A' is present as a second subunit of A. In such aspects, $A_O/A_2$ or A'/$A_2$ is an α-amino acid, a β-amino acid or other amine-containing acid residue.

"Branching Unit" as used herein, unless otherwise stated or implied by context, refers to a tri-functional or multi-functional organic moiety that is an optional component of a Linker Unit (LU). A Branching Unit (B) is present in a primary linker of drug linker moiety of Formula 1A of LDC/ADC of Formula 1A, when multiple -$L_O$-D moieties are present is a single drug linker moiety. In an LDC/ADC having the afore-described generalized formula, the absence or presence of a Branching Unit is indicated by subscript b of $B_b$, in which subscript b is 0 or 1, respectively. A Branching Unit is at least trifunctional in order to be incorporated into a primary linker. Drug Linker or LDC/ADC compounds having a Branching Unit, which is due to multiple -$L_O$-D moieties per drug linker moiety of formula -LU-D, typically have each secondary linker ($L_O$) containing the formula -$A'_a$-W—$Y_y$—, wherein A' is a second optional Stretcher Unit; subscripts a' is 0 or 1, indicating the absence or presence of A', respectively; W is a Peptide Cleavable Unit; Y is a Spacer Unit; and subscript y is 0, 1 or 2, indicating the absence or presence of one or two Spacer Units, respectively.

In some aspects, a natural or un-natural amino acid residue or residue of another amine-containing acid compound having a functionalized side chain serves as a tri-functional Branching Unit for attachment of two -$L_O$-D moieties. In some of those aspects B is a lysine, glutamic acid or aspartic acid residue in the L- or D-configuration in which the epsilon-amino, gamma-carboxylic acid or beta-carboxylic acid functional group, respectively, along with their amino and carboxylic acid termini, interconnects B within the remainder of LU. A Branching Unit of greater functionality for attachment of 3 or 4 -$L_O$-D moieties is typically comprised of the requisite number of tri-functional subunits.

"Natural amino acid" as used herein, unless otherwise stated or implied by context, refers to a naturally occurring amino acid, namely, arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine or a residue thereof, in the L or D-configuration, unless otherwise specified or implied by context.

"Un-natural amino acid" as used herein, unless otherwise stated or implied by context, refers to an alpha-amino-containing acid or residue thereof, which has the backbone structure of a natural amino acid, but has a side chain group attached to the alpha carbon that is not present in natural amino acids.

"Non-classical amino acid" as used herein, unless otherwise stated or implied by context, refers to an amine-containing acid compound that does not have its amine substituent bonded to the carbon alpha to the carboxylic acid and therefore is not an alpha-amino acid. Non-classical amino acids include β-amino acids in which a methylene is inserted between the carboxylic acid and amino functional groups in a natural amino acid or an un-natural amino acid.

"Peptide" as used herein, unless otherwise stated or implied by context, refers to a polymer of two or more amino acids wherein carboxylic acid group of one amino acid forms an amide bond with the alpha-amino group of the next amino acid in the peptide sequence. Methods for preparing amide bonds in polypeptides are additionally provided in the definition of amide. Peptides may be comprised of naturally occurring amino acids in the L- or D-configuration and/or unnatural and/or non-classical amino acids.

"Protease" as defined herein refers to a protein capable of enzymatic cleavage of a carbonyl-nitrogen bond such as an amide bond typically found in a peptide. Proteases are classified into major six classes: serine proteases, threonine proteases, cysteine proteases, glutamic acid proteases, aspartic acid proteases and metalloproteases so named for the catalytic residue in the active site that is primarily responsible for cleaving the carbonyl-nitrogen bond of its substrate. Proteases are characterized by various specificities, which are dependent of identities of the residues at the N-terminal and/or C-terminal side of the carbonyl-nitrogen bond and their various distributions (intracellular and extracellular).

Regulatory proteases are typically intracellular proteases that are required for the regulation of cellular activities that sometimes becomes aberrant or dysregulated in abnormal or other unwanted cells. In some instances, when a Peptide Cleavable Unit is directed to a protease having preferential distribution intracellularly, that protease is a regulatory protease, which is involved in cellular maintenance or proliferation. Those proteases include cathepsins. Cathepsins include the serine proteases, Cathepsin A, Cathepsin G, aspartic acid proteases Cathepsin D, Cathepsin E and the cysteine proteases, Cathepsin B, Cathepsin C, Cathepsin F, Cathepsin H, Cathepsin K, Cathepsin L1, Cathepsin L2, Cathepsin O, Cathepsin S, Cathepsin W and Cathepsin Z.

"Peptide Cleavable Unit" as used herein, unless otherwise stated or implied by context, refers to an organic moiety within a secondary linker of a Ligand Drug Conjugate compound's drug linker moiety or a Drug Linker compound that provides for a recognition site for a protease and is capable of enzymatically releasing its conjugated Drug Unit (D) as free drug upon enzymatic action of that protease.

A recognition site for cleavage by a protease is sometimes limited to those recognized by proteases found in abnormal cells, such as cancer cells, or within nominally normal cells targeted by the Ligand Drug Conjugate that are particular to the environment of the nearby abnormal cells, but which may also be found within normal cells. For that purpose, the peptide is typically resistant to circulating proteases in order to minimize premature release of free drug or precursor thereof that otherwise could cause off-target adverse events from systemic exposure to that drug. In some aspects, the peptide will have one or more D-amino acids or an unnatural or non-classical amino acids in order to have that resistance. In some of those aspects the sequence will comprise a dipeptide or tripeptide in which the P2' site contains a D-amino acid and the P1' site contains one of the 20 naturally occurring L-amino acids other than L-proline.

In those aspects, the reactive site is more likely operated upon enzymatically subsequent to immunologically selective binding to the targeted antigen. In some of those aspects, the targeted antigen is on abnormal cells so that the recognition site is more likely operated upon enzymatically subsequent to cellular internalization of a Ligand Drug Conjugate compound into targeted abnormal cells. Consequently, those abnormal cells should display the targeted antigen in higher copy number in comparison to normal cells to mitigate on-target adverse events. In other of those aspects, the targeted antigen is on normal cells that are within and are peculiar to the environment of abnormal cells so that the recognition site is more likely operated upon enzymatically subsequent to cellular internalization of a Ligand Drug Conjugate compound into these targeted normal cells. Consequently, those normal cells should display the targeted antigen in higher copy number in comparison to normal cells distant from the site of the cancer cells to mitigate on-target adverse events.

In any one of the above aspects, protease reactivity towards the recognition site is greater within tumor tissue homogenate in comparison to normal tissue homogenate. That greater reactivity in some aspects is due to a greater amount of intracellular protease activity within the targeted cells of the tumor tissue as compared to intracellular protease activity in normal cells of the normal tissue and/or reduced protease activity in the interstitial space of normal tissue in comparison to that activity of Peptide Cleavable Units of traditional Ligand Drug Conjugates. In those aspects, the intracellular protease is a regulatory protease and the peptide bond of the Peptide Cleavable Unit is capable of being selectively cleaved by an intracellular regulatory protease in comparison to serum proteases in addition to being selectively cleaved by proteases of tumor tissue homogenate in comparison to proteases in normal tissue homogenate.

A secondary linker containing a Peptide Cleavable Unit typically has the formula of -A'$_{a'}$—W—Y$_y$—, wherein A' is a second optional Spacer Unit when subscript b is 1; subscript a' is 0 or 1, W is a Peptide Cleavable Unit; Y is an optional Spacer Unit; and subscript y is 0, 1 or 2. When subscript b is 0 and subscript a' is 1, A' becomes a subunit of A so that the secondary linker has the formula of —W—Y$_y$—. For either formula of the secondary linker which protease action on the peptide sequence comprising the Peptide Cleavable Unit results in direct release of D when subscript y is 0 or when subscript y is 1 results in a drug-linker fragment of formula Y-D as the precursor to free drug, in which Y typically undergoes self-immolation to provide free drug, or when subscript y is 2 results in a first drug-linker fragment of formula Y—Y'-D, in which Y is a first Spacer Unit that undergoes self-immolation to provide a second drug linker fragment of formula Y'-D, in which Y' is a second Spacer Unit that decomposes to complete release of D as free drug.

In some aspects, Drug Linker compounds in which the secondary linker contains a Peptide Cleavable Unit are represented by the structures of Formula IC:

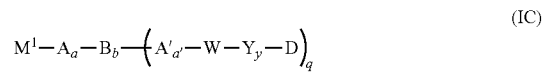
(IC)

and corresponding drug linker moieties of Ligand Drug Conjugates are represented by the structures of Formula 1D or Formula 1E:

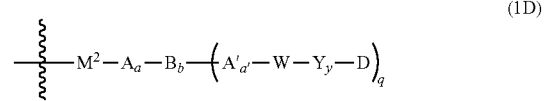
(1D)

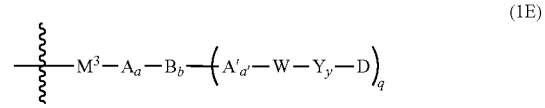
(1E)

wherein W is the Peptide Cleavable Unit and M$^1$-A$_a$-B$_b$— of Formula IC, -M$^2$-A$_a$-B$_b$— of Formula 1D and -M$^3$-A$_a$-B$_b$— of Formula 1E are primary linkers, wherein M$^1$ is a maleimide moiety; M$^2$ is a succinimide moiety; M$^3$ is a succinic acid amide moiety; Y is an optional Spacer Unit so that subscript y is 0 or 1 or Y$_y$ is —Y—Y' so that subscript y is 2 and Y and Y' are a first and second Spacer Unit, respectively, and the remaining variable groups are as defined for Drug Linker compounds of Formula IA and for drug linker moieties of Formula 1A. L$_{SS}$' primary linkers of Drug Linker compounds, which contain an M$^1$ moiety, and $L_{SS}$ primary linkers of drug linker moieties in some LDCs/ADCs, which contain $M^2$ moieties, of the present invention are those formulae in which A or a subunit thereof is substituted by or incorporates a Basic Unit. Other primary linkers are $L_S$ primary linkers that are derived from the above $M^2$-containing $L_{SS}$ primary linker of Formula 1C by hydrolysis of their succinimide moieties to provide $M^3$-containing moieties of Formula 1D.

In any one of the above aspects, the amide bond that is specifically cleaved by a protease produced by or within a targeted cell is to the amino group of the Spacer Unit (Y) or Drug Unit, if Y is absent. Thus, protease action on the peptide sequence in W results in release of D as free drug or its precursor $Y_y$-D, which spontaneously fragments to provide free drug.

"Spacer Unit" as used herein, unless otherwise stated or implied by context, refers to a moiety in a secondary linker ($L_O$) of formula -A'$_{a'}$-W—Y$_y$— in which subscript y is 1 or 2, indicating the presence of 1 or 2 Spacer Units, within a Drug Linker compound or the Linker Unit of a drug linker moiety of a Ligand Drug Conjugate, wherein A' is a second optional Spacer Unit, which is some aspects as described herein becomes part of a primary linker to which the secondary linker is covalently attached as a subunit of a first optional Spacer Unit that is present, subscript a' is 0 or 1 indicating the absence or presence of A'; Y is a Spacer Unit and W is a Peptide Cleavable Unit of formula -P$_n$ . . . [P3]-[P2]-[P1]- or -P$_n$ . . . [P3]-[P2]-[P1]-[P-1]-, wherein subscript n ranges from 0 to 12 (e.g., 0-10, 3-12 or 3-10) and P1, P2 and P3 are amino acid residues that confer selectivity for protease cleavage by tumor tissue homogenate over normal tissue homogenate as described herein. When subscript y is 1, a Spacer Unit is covalently bonded to W and to a Drug Unit (D), or when subscript y is 2 to another such moiety (Y') covalently bonded to D. Protease action upon W initiates release D as free drug as further described by the embodiments of the invention.

"Self-immolating moiety" as used herein refers to a bifunctional moiety within a self-immolative Spacer Unit (Y) wherein the self-immolative moiety is covalently attached to a heteroatom of D, or to a shared functional group between Y and D, optionally substituted where permitted, and is also covalently attached to a Peptide Cleavable Unit through another optionally substituted heteroatom (J), wherein J is —NH— or an appropriately substituted nitrogen atom within an amide functional group, so that the self-immolative moiety incorporates these drug linker components into a normally stable tripartite molecule unless activated.

On cleavage of the peptide bond between P1/P-1 and Y, D or a first drug linker fragment, which is Y'-D, spontaneously separates from the tripartite molecule by self-destruction of the self-immolative moiety of its self-immolative Spacer Unit. In some aspects, a component of a self-immolative moiety Spacer Unit intervening between Y'-D or D and the optionally substituted heteroatom J of Y bonded to W has the formula of —C$_6$-C$_{24}$ arylene-C(R$^8$)(R$^9$)—, —C$_5$-C$_{24}$ heteroarylene- C(R$^8$)(R$^9$)—, —C$_6$-C$_{24}$ arylene-C(R$^8$)=C(R$^9$)— or —C$_5$-C$_{24}$ heteroarylene- C(R$^8$)=C(R$^9$)—, optionally substituted, wherein R$^8$ and R$^9$ are as described by the embodiments of the invention, and typically is C$_6$-C$_{10}$ arylene-CH$_2$— or C$_5$-C$_{10}$ heteroarylene-CH$_2$—, in which the (hetero)arylene is optionally substituted, wherein the component of the self-immolative moiety Spacer Unit is capable of undergoing fragmentation to form a imino-quinone methide or related structure by 1,4 or 1,6-elimination with concomitant release of D or Y'-D on cleavage of the protease cleavable bond between J and W. In some aspects, a self-immolative Spacer Unit having the aforementioned component bonded to J is exemplified by an optionally substituted p-aminobenzyl alcohol (PAB) moiety, ortho or para-aminobenzylacetals, or other aromatic compounds that are electronically similar to the PAB group (i.e., PAB-type) such as 2-aminoimidazol-5-methanol derivatives (see, e.g., Hay et al., 1999, *Bioorg. Med. Chem. Lett.* 9:2237) or those in which the phenyl group of the p-aminobenzyl alcohol (PAB) moiety is replaced by a heteroarylene.

Without being bound by theory an aromatic carbon of an arylene or heteroarylene group of a PAB or PAB-type moiety of a self-immolative Spacer Unit that is incorporated into a Linker Unit is substituted by J wherein the electron-donating heteroatom of J is attached to the cleavage site of W so that the electron-donating capacity of that heteroatom is attenuated (i.e., its EDG ability is masked by incorporation of a self-immolative moiety of a Self-immolative Spacer Unit into a Linker Unit). The other substituent of the hetero (arylene) is a benzylic carbon that is attached to an optionally substituted heteroatom of D an optionally substituted functional group shared between Y and D or a second Spacer Unit (Y') bonded to the Drug Unit (D), wherein the benzylic carbon is attached to another aromatic carbon atom of the central arylene or heteroarylene, wherein the aromatic carbon bearing the attenuated electron-donating heteroatom is adjacent to (i.e., 1,2-relationship), or two additional positions removed (i.e., 1,4-relationship) from that benzylic carbon atom. The functionalized EDG heteroatom is chosen so that upon processing of the cleavage site of W the electron-donating capacity of the masked heteroatom is restored thus triggering a 1,4- or 1,6-elimination to expel -D as free drug from the benzylic substituent, or when Y'-D is released subsequent self-immolation of Y' provides free drug, to elicit a therapeutic effect. Exemplary self-immolative moieties and self-immolative Spacer Unit having those self-immolative moieties are exemplified by the embodiments of the invention.

Other examples of self-immolative groups include, but are not limited to, aromatic compounds that are electronically similar to the PAB group such as 2-aminoimidazol-5-methanol derivatives (see, e.g., Hay et al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et al., 1995, Chemistry Biology 2:223), appropriately substituted bicyclo[2.2.1] and bicyclo[2.2.2] ring systems (see, e.g., Storm et al., 1972, J. Amer. Chem. Soc. 94:5815) and 2-aminophenylpropionic acid amides (see, e.g., Amsberry et al., 1990, J. Org. Chem. 55:5867). Elimination of amine-containing drugs that are substituted at the a-position of glycine (see, e.g., Kingsbury et al., 1984, J. Med. Chem. 27:1447) are also examples of self-immolative groups. In one embodiment, the Spacer unit is a branched bis(hydroxymethyl)styrene (BHMS) unit, as described in WO 2007/011968, which can be used to incorporate and release multiple drugs. Additional self-immolative spacers are described in WO 2005/082023.

"Methylene Carbamate Unit" as used herein, unless otherwise stated or implied by context, refers to an organic moiety capable of self-immolation and intervenes between a first self-immolative Spacer Unit and a Drug Unit within a Linker Unit of a Ligand Drug Conjugate or Drug linker compound and as such is an exemplary second Spacer Unit.

A Methylene Carbamate (MAC) Unit bonded to a Drug Unit is represented by formula III:

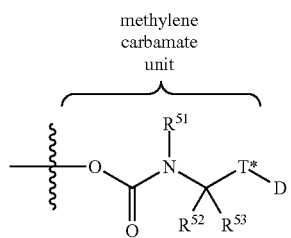

(III)

methylene carbamate unit or a pharmaceutically acceptable salt thereof, wherein the wavy line indicates covalent attachment of the methylene carbamate unit to a first self-immolative Spacer Unit (Y); D is a Drug Unit having a functional group (e.g., hydroxyl, thiol, amide or amine functional group) that is incorporated into the methylene carbamate unit; T* is a heteroatom from said functional group, which includes oxygen, sulfur, or nitrogen as optionally substituted —NH—. Upon cleavage of a Linker Unit comprised of a MAC Unit, a first self-immolative Spacer Unit (Y) bonded to that MAC Unit as the second self-immolative Spacer Unit (Y') undergoes fragmentation to release —Y'-D of formula III. The MAC Unit then spontaneous decomposes to complete release D as free drug, the presumed mechanism for which is indicated by the embodiments of the invention.

"PEG Unit" as used herein refers to a group comprising a polyethylene glycol moiety (PEG) having a repetition of ethylene-oxy subunits (PEGs or PEG subunits), also referred to as ethylene glycol subunits having the formula of

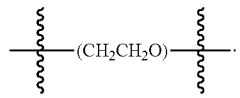

PEGs include polydisperse PEGs, monodisperse PEGs and discrete PEGs. Polydisperse PEGs are a heterogeneous mixture of sizes and molecular weights whereas monodisperse PEGs are typically purified from heterogeneous mixtures and are therefore provide a single chain length and molecular weight. Preferred PEG Units comprises discrete PEGs, compounds that are synthesized in step-wise fashion and not via a polymerization process. Discrete PEGs are compounds that are synthesized in step-wise fashion and not via a polymerization process. Discrete PEGs provide a single molecule with defined and specified chain length.

A PEG Unit comprises at least 2 subunits, at least 3 subunits, at least 4 subunits, at least 5 subunits, least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. Some PEG Units comprise up to 72 subunits.

The PEG Unit provided herein comprises one or multiple polyethylene glycol chains, each comprised of one or more ethyleneoxy subunits, covalently attached to each other. The polyethylene glycol chains can be linked together, for example, in a linear, branched or star shaped configuration. Typically, at least one of the polyethylene glycol chains prior to incorporation into a camptothecin conjugate is derivatized at one end with an alkyl moiety substituted with an electrophilic group for covalent attachment to the carbamate nitrogen of a methylene carbamate unit (i.e., represents an instance of R). Typically, the terminal ethyleneoxy subunit in each polyethylene glycol chains not involved in covalent attachment to the remainder of the Linker Unit is modified with a PEG Capping Unit, typically an optionally substituted alkyl such as —$CH_3$, $CH_2CH_3$ or $CH_2CH_2CO_2H$. A preferred PEG Unit has a single polyethylene glycol chain with 2 to 24 —$CH_2CH_2O$— subunits covalently attached in series and terminated at one end with a PEG Capping Unit.

"PEG Capping Unit" as used herein is a nominally unreactive organic moiety or functional group that terminates the free and untethered end of a PEG Unit and in some aspects is other than hydrogen. In those aspects a PEG Capping Unit is methoxy, ethoxy, or other $C_1$-$C_6$ ether, or is —$CH_2$—$CO_2H$, or other suitable moiety. The ether, —$CH_2$—$CO_2H$, —$CH_2CH_2CO_2H$, or other suitable organic moiety thus acts as a "cap" for the terminal PEG subunit of the PEG Unit.

"Parallel Connector Unit" as used herein, unless otherwise stated or implied by context, refers to an organic moiety of a Drug Linker compound or a Ligand Drug Conjugate compound's drug linker moiety, which is typically present in its Linker Unit as a subunit of a first or second Stretcher Unit, wherein the Parallel Connector Unit ($L^P$) is capable of orienting the PEG Unit attached thereto in parallel orientation to a Drug Unit that is hydrophobic, referred herein as a hydrophobic Drug Unit, so as to reduce at least in part the hydrophobicity of that Drug Unit. Structures of $L^P$ and associated PEG Units and PEG Capping Units are described by WO 2015/5057699, which are specifically incorporated by reference herein, and in some aspects, $L^P$ is a tri-functional α-amino acid, β-amino acid or other tri-functional amine-containing acid residue.

"Intracellularly cleaved", "intracellular cleavage" and like terms used herein refer to a metabolic process or reaction within a targeted cell occurring upon a Ligand Drug Conjugate or the like, whereby covalent attachment through its Linker Unit between the Drug Unit and the Ligand Unit of the Conjugate is broken, resulting in release of D as free drug within the targeted cell. As described herein, in some embodiments D is initially released as an adduct of the Drug Unit with one or more self-immolative spacers, which self-immolative spacers subsequently spontaneously separate from the Drug Unit to release D as the free drug.

"Hematological malignancy" as used herein, unless otherwise stated or implied by context, refers to a blood cell tumor that originates from cells of lymphoid or myeloid origin and is synonymous with the term "liquid tumor". Hematological malignancies may be categorized as indolent, moderately aggressive or highly aggressive.

"Lymphoma" as used herein, unless otherwise stated or implied by context, refers to is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sezary's disease, peripheral T-cell lymphomas not otherwise specified, nodular sclerosis of Hodgkin lymphoma, and mixed-cellularity subtype of Hodgkin lymphoma.

"Leukemia" as used herein, unless otherwise stated or implied by context, refers to a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocyctic leukemia (AMoL). Other leukemias include hairy cell leukemia (HCL), T-cell lymphatic leukemia (T-PLL), large granular lymphocytic leukemia and adult T-cell leukemia.

"Hyper-proliferating cells" as used herein, unless otherwise stated or implied by context, refer to abnormal cells that are characterized by unwanted cellular proliferation or an abnormally high rate or persistent state of cell division or other cellular activity that is unrelated or uncoordinated with that of the surrounding normal tissues. In some aspects, hyper-proliferating cells are hyper-proliferating mammalian cells. In other aspects, hyper-proliferating cells are hyper-stimulated immune cells as defined herein whose persistent state of cell division or activation occurs after the cessation of the stimulus that may have initially evoked the change in their cell division. In other aspects, the hyper-proliferating cells are transformed normal cells or cancer cells and their uncontrolled and progressive state of cell proliferation may result in a tumor that is benign, potentially malignant (premalignant) or frankly malignant. Hyperproliferation conditions resulting from transformed normal cells or cancer cells include, but are not limited to, those characterized as a precancer, hyperplasia, dysplasia, adenoma, sarcoma, blastoma, carcinoma, lymphoma, leukemia or papilloma. Precancers are usually defined as lesions that exhibit histological changes and are associated with an increased risk of cancer development and sometimes have some, but not all, of the molecular and phenotypic properties that characterize the cancer. Hormone associated or hormone sensitive precancers include without limitation, prostatic intraepithelial neoplasia (PIN), particularly high-grade PIN (HGPIN), atypical small acinar proliferation (ASAP), cervical dysplasia and ductal carcinoma in situ. Hyperplasias generally refers to the proliferation of cells within an organ or tissue beyond that which is ordinarily seen that may result in the gross enlargement of an organ or in the formation of a benign tumor or growth. Hyperplasias include, but are not limited to, endometrial hyperplasia (endometriosis), benign prostatic hyperplasia and ductal hyperplasia.

"Normal cells" as used herein, unless otherwise stated or implied by context, refer to cells undergoing coordinated cell division related to maintenance of cellular integrity of normal tissue or replenishment of circulating lymphatic or blood cells that is required by regulated cellular turnover, or tissue repair necessitated by injury, or to a regulated immune or inflammatory response resulting from pathogen exposure or other cellular insult, where the provoked cell division or immune response terminates on completion of the necessary maintenance, replenishment or pathogen clearance. Normal cells include normally proliferating cells, normal quiescent cells and normally activated immune cells. Normal cells include normal quiescent cells, which are noncancerous cells in their resting $G_o$ state and have not been stimulated by stress or a mitogen or are immune cells that are normally inactive or have not been activated by pro-inflammatory cytokine exposure.

"Abnormal cells" as the term is used herein, unless otherwise stated or implied by context, refers to normal cells that have become dysfunctional either in disproportionate response to external stimuli or from failure to appropriately regulate their spontaneous intracellular activity, which in some instances has a mutational origin. Abnormal cells include hyper-proliferating cells and hyper-stimulated immune cells, as these terms are defined elsewhere. Those cells when present in an organism typically interfere with the functioning of otherwise normal cells causing harm to the organism and over time will increase in destructive capacity. Abnormal cells include cancer cells, hyperactivate immune cells and other unwanted cells of the organism. Abnormal cells may also refer to nominally normal cells that are in the environment of outwardly abnormal cells, but which nonetheless support the proliferation and/or survival of these other abnormal cells, such as tumor cells, so that targeting the nominally normal cells indirectly inhibits the proliferation and/or survival of the tumor cells.

"Hyper-stimulated immune cells" as used herein, unless otherwise stated or implied by context, refer to cells involved in innate or adaptive immunity characterized by an abnormally persistent proliferation or inappropriate state of stimulation that occurs after the cessation of the stimulus that may have initially evoked the change in proliferation or stimulation or that occurs in the absence of any external insult. Oftentimes, the persistent proliferation or inappropriate state of stimulation results in a chronic state of inflammation characteristic of a disease state or condition. In some instances, the stimulus that may have initially evoked the change in proliferation or stimulation is not attributable to an external insult but is internally derived, as in an autoimmune disease. In some aspects, a hyper-stimulated immune cell is a pro-inflammatory immune cell that has been hyper-activated through chronic pro-inflammatory cytokine exposure.

In some aspects of the invention, a Ligand Drug Conjugate compound of a Ligand Drug Conjugate composition binds to an antigen preferentially displayed by pro-inflammatory immune cells that are abnormally proliferating or are inappropriately or persistently activated. Those immune cells include classically activated macrophages or Type 1 T helper (Th1) cells, which produce interferon-gamma (INF-γ), interleukin-2 (IL-2), interleukin-10 (IL-10), and tumor necrosis factor-beta (TNF-β), which are cytokines that are involved in macrophage and $CD8^+$ T cell activation.

"Bioavailability" unless otherwise stated or implied by context, refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The terms "individual", "subject", or patient are used interchangeably herein to refer to an animal, for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some instances, the "individual" or "subject" is a human. In some examples, an "individual" or "subject" refers to an individual or subject (e.g., a human) in need of treatment for a disease or disorder. In some embodiments, "subject" unless otherwise stated or implied by context, refers to a human, non-human primate or mammal having a hyper-proliferation, inflammatory or immune disorder or other disorder attributable to abnormal cells or is prone to such a disorder who would benefit from administering an effective amount of a Ligand Drug Conjugate. Non-limiting examples of a subject include human, rat, mouse, guinea pig, monkey, pig, goat, cow, horse, dog, cat, bird and fowl. Typically, the subject is a human, non-human primate, rat, mouse or dog.

"Carrier" unless otherwise stated or implied by context refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a subject, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

"Salt form" as used herein, unless otherwise indicated by context, refers to a charged compound in ionic association with a countercation(s) and/or counteranions so as to form an overall neutral species. In some aspects, a salt form of a compound occurs through interaction of the parent compound's basic or acid functional group with an external acid or base, respectively. In other aspects the charged atom of the compound that is associated with a counteranion is permanent in the sense that spontaneous disassociation to a neural species cannot occur without altering the structural integrity of the parent compound as when a nitrogen atom is quaternized. Accordingly, a salt form of a compound may involve a quaternized nitrogen atom within that compound and/or a protonated form of a basic functional group and/or ionized carboxylic acid of that compound each of which is in ionic association with a counteranion.

In some aspects a salt form may result from interaction of a basic functional group and an ionized acid functional group within the same compound or involve inclusion of a negatively charged molecule such as an acetate ion, a succinate ion or other counteranion. Thus, a compound in salt form may have more than one charged atom in its structure. In instances where multiple charged atoms of the parent compound are part of the salt form, that salt from can have multiple counter ions so that a salt form of a compound may have one or more charged atoms and/or one or more counterions. The counterion may be any charged organic or inorganic moiety that stabilizes an opposite charge on the parent compound.

A protonated salt form of a compound is typically obtained when a basic functional group of a compound, such as a primary, secondary or tertiary amine or other basic amine functional group interacts with an organic or inorganic acid of suitable pKa for protonation of the basic functional group, or when an acid functional group of a compound with a suitable $pK_a$, such as a carboxylic acid, interacts with a hydroxide salt, such as NaOH or KOH, or an organic base of suitable strength, such as triethylamine, for deprotonation of the acid functional group. In some aspects, a compound in salt form contains at least one basic amine functional group, and accordingly acid addition salts can be formed with this amine group, which includes the basic amine functional group of a cyclic or acyclic Basic Unit. A suitable salt form in the context of a Drug Linker compound is one that does not unduly interfere with the condensation reaction between a targeting agent and the Drug Linker compound that provides a Ligand drug Conjugate.

"Pharmaceutically acceptable salt" as used herein, unless otherwise indicated by context, refers to a salt form of a compound in which its counterion is acceptable for administration of the salt form to an intended subject and include inorganic and organic countercations and counteranions. Exemplary pharmaceutically acceptable counteranions for basic amine functional groups, such as those in cyclic or acyclic Basic Units, include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, mesylate, besylate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

Typically, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability as when in a lyophilized formulation under accelerated conditions (i.e., for determining degradation or solid-state changes when stored at 40° C. and 75% relative humidity).

In some embodiments, the phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 4,4'-methylene-bis -(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Inhibit", "inhibition of" and like terms, unless otherwise stated or implied by context, means to reduce by a measurable amount, or to prevent entirely an undesired activity or outcome. In some aspects, the undesired outcome or activity is related to abnormal cells and includes hyper-proliferation, or hyper-stimulation or other dysregulated cellular activity underlying a disease state. Inhibition of such a dysregulated cellular activity by a Ligand Drug Conjugate is typically determined relative to untreated cells (sham treated with vehicle) in a suitable test system as in cell culture (in vitro) or in a xenograft model (in vivo). Typically, a Ligand Drug Conjugate that targets an antigen that is not present or has low copy number on the abnormal cells of interest or is genetically engineered to not recognize any known antigen is used as a negative control.

"Treat", "treatment," and like terms, unless otherwise indicated by context, refer to a therapeutic treatment, including prophylactic measures to prevent relapse, wherein the object is to inhibit or slow down (lessen) an undesired physiological change or disorder, such as the development or spread of cancer or tissue damage from chronic inflammation. Typically, beneficial or desired clinical benefits of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival or quality of life as compared to expected survival or quality of life if not receiving treatment. Those in need of treatment include those already having the condition or disorder as well as those prone to have the condition or disorder.

In some embodiments, as used herein, "treatment" is an approach for obtaining beneficial or desired clinical results. "Treatment" as used herein, covers any administration or application of a therapeutic for disease in a mammal, including a human. Beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease.

In the context of cancer, the term "treating" includes any or all of: inhibiting growth of cancer cells, inhibiting replication of cancer cells, reducing the number of cancer cells, reducing the rate of cancer cell infiltration into peripheral organs, reducing the rate or extent of tumor metastasis, lessening of overall tumor burden, and ameliorating one or more symptoms associated with the cancer.

In the context of cancer, the term "treating" includes any or all of inhibiting growth of tumor cells, cancer cells, or of a tumor; inhibiting replication of tumor cells or cancer cells, inhibiting dissemination of tumor cells or cancer cell, lessening of overall tumor burden or decreasing the number of cancerous cells, or ameliorating one or more symptoms associated with cancer. "Therapeutically effective amount" as the term is used herein, unless otherwise stated or implied by context, refers to an amount of free drug or Ligand Drug Conjugate having a Drug Unit, which is released as a free drug, effective to treat a disease or disorder in a mammal. In the case of cancer, the therapeutically effective amount of the free drug or Ligand Drug Conjugate may reduce the number of cancer cells; reduce the tumor size, inhibit (i.e., slow to some extent and preferably stop) cancer cell infiltration into peripheral organs, inhibit (i.e., slow to some extent and preferably stop) tumor metastasis, inhibit, to some extent, tumor growth, and/or relieve to some extent one or more of the symptoms associated with the cancer. To the extent the free drug or Ligand Drug Conjugate may inhibit growth and/or kill existing cancer cells, it may be cytostatic or cytotoxic. For cancer therapy, efficacy can, for example, be measured by assessing the time to disease progression (TTP) determining the response rate (RR) and/or overall survival (OS).

In the case of immune disorders resulting from hyper-stimulated immune cells, a therapeutically effective amount of the drug may reduce the number of hyper-stimulated immune cells, the extent of their stimulation and/or infiltration into otherwise normal tissue and/or relieve to some extent one or more of the symptoms associated with a dysregulated immune system due to hyper-stimulated immune cells. For immune disorders due to hyper-stimulated immune cells, efficacy can, for example, be measured by assessing one or more inflammatory surrogates, including one or more cytokines levels such as those for IL-1$\beta$, TNF$\alpha$, INF$\gamma$ and MCP-1, or numbers of classically activated macrophages.

In some aspects of the invention, a Ligand Drug Conjugate compound associates with an antigen on the surface of a targeted cell (i.e., an abnormal cell such as a hyper-proliferating cell or a hyper-stimulated immune cell), and the Conjugate compound is then taken up inside the targeted cell through receptor-mediated endocytosis. Once inside the cell, one or more Cleavage Units within a Linker Unit of the Conjugate are cleaved, resulting in release of Drug Unit (D) as free drug. The free drug so released is then able to migrate within the cytosol and induce cytotoxic or cytostatic activities, or in the case of hyper-stimulated immune cells may alternatively inhibit pro-inflammatory signal transduction. In another aspect of the invention, the Drug Unit (D) is released from a Ligand Drug Conjugate compound outside the targeted cell but within the vicinity of the targeted cell so that the resulting free drug from that release is localized to the desired site of action and is able to subsequently penetrate the cell rather than being prematurely released at distal sites.

As described herein, any concentration range, percentage range, ratio range, or integer range is to be understood to include the value of any integer within the recited range and, when appropriate, fractions thereof (such as one tenth and one hundredth of an integer), unless otherwise indicated.

When a trade name is used herein, reference to the trade name also refers to the product formulation, the generic drug, and the active pharmaceutical ingredient(s) of the trade name product, unless otherwise indicated by context.

The terms GPNMB, glycoprotein non-metastatic melanoma protein B, glycoprotein NMB, and PLCA3 are used interchangeably herein, and, unless otherwise specified, include any naturally occurring variants (e.g., splice variants, allelic variants), isoforms, and vertebrate species homologs of human GPNMB. The term encompasses "full length," unprocessed GPNMB as well as any form of GPNMB that results from processing within a cell. The amino acid sequence of an exemplary human GPNMB is provided in Uniprot #Q14956.

The terms CD228, melanotransferrin, MELTF, p97 and MF12 are used interchangeably herein, and, unless otherwise specified, include any naturally occurring variants (e.g., splice variants, allelic variants), isoforms, and vertebrate species homologs of human CD228. The term encompasses "full length," unprocessed CD228 as well as any form of CD228 that results from processing within a cell. The amino acid sequence of an exemplary human CD228 is provided in Uniprot #P08582.

The terms "αvβ6," "avb6," "alpha-v beta-6," or "β6" are used interchangeably herein, and, unless otherwise specified, include any naturally occurring variants (e.g., splice variants, allelic variants), isoforms, and vertebrate species homologs of human αvβ6. The term encompasses "full length," unprocessed αvβ6 as well as any form of αvβ6 that results from processing within a cell. An exemplary β6 human sequence is assigned GenBank accession number AAA36122. An exemplary αv human sequence is assigned NCBI NP_002201.1.

The terms CD30, TNF receptor superfamily member 8, TNFRSF8, and D1S166E are used interchangeably herein, and, unless otherwise specified, include any naturally occurring variants (e.g., splice variants, allelic variants), isoforms, and vertebrate species homologs of human CD30. The term encompasses "full length," unprocessed CD30 as well as any form of CD30 that results from processing within a cell. The amino acid sequence of an exemplary human CD30 is provided in Uniprot #P28908 (TNR8_HUMAN). The amino acid sequence of one specific example of a mature human CD30 protein is set forth in NP_001234.3.

The terms LIV1, LIV-1, LIV 1, BCR4, BCR 4, BCR-4, ZIP6, ZIP-6, ZIP 6 or SLC39A6 are used interchangeably herein, and, unless otherwise specified, include any naturally occurring variants (e.g., splice variants, allelic variants), isoforms, and vertebrate species homologs of human LIV1. The term encompasses "full length," unprocessed LIV1 as well as any form of LIV1 that results from processing within a cell. The amino acid sequence of an exemplary human LIV1 is provided in Uniprot #Q13433. The amino acid sequence of one specific example of a mature human LIV1 protein is set forth in SEQ ID NO: 931. The terms CD19, B-lymphocyte surface antigen B4, and CVID3 are used interchangeably herein, and, unless otherwise specified, include any naturally occurring variants (e.g., splice variants, allelic variants), isoforms, and vertebrate species homologs of human CD19. The term encompasses "full length," unprocessed CD19 as well as any form of CD19 that results from processing within a cell. The amino acid sequence of an exemplary human CD19 is provided in Uniprot #Q71UW0.

An "antigen binding protein" ("ABP") as used herein means any protein that binds a specified target antigen other than the naturally occurring cognate ligand(s) or fragments of such ligand(s) that bind the specified antigen. In some embodiments of the instant application, the specified target antigen is GPNMB or a fragment of GPNMB. In some embodiments of the instant application, the specified target antigen is CD228 or a fragment of CD228. In some embodiments of the instant application, the specified target antigen is αvβ6 or a fragment of αvβ6. In some embodiments of the instant application, the specified target antigen is CD30 or a fragment of CD30. In some embodiments of the instant application, the specified target antigen is LIV1 or a fragment of LIV1. In some embodiments of the instant application, the specified target antigen is CD19 or a fragment of CD19. αvβ6αvβ6An "antigen binding protein" includes, proteins that include at least one antigen binding region or domain (e.g., at least one hypervariable region (HVR) or complementarity determining region (CDR) as defined herein). In some embodiments, an antigen binding protein comprises a scaffold, such as a polypeptide or polypeptides, into which one or more (e.g., 1, 2, 3, 4, 5 or 6) HVR(s) or CDR(s), as described herein, are embedded and/or joined. In some antigen binding proteins, the HVRs or CDRs are embedded into a "framework" region, which orients the HVR(s) or CDR(s) such that the proper antigen binding properties of the CDR(s) are achieved. For some antigen binding proteins, the scaffold is the immunoglobulin heavy and/or light chain(s) from an antibody or a fragment thereof. Additional examples of scaffolds include, but are not limited to, human fibronectin (e.g., the $10^{th}$ extracellular domain of human fibronectin III), neocarzinostatin CBM4-2, anticalines derived from lipocalins, designed ankyrin repeat domains (DARPins), protein-A domain (protein Z), Kunitz domains, Im9, TPR proteins, zinc finger domains, pVIII, GC4, transferrin, B-domain of SPA, Sac7d, A-domain, SH3 domain of Fyn kinase, and C-type lectin-like domains (see, e.g., Gebauer and Skerra (2009) Curr. Opin. Chem. Biol., 13:245-255; Binz et al. (2005) Nat. Biotech. 23:1257-1268; and Yu et al. (2017) Annu Rev Anal Chem 10:293-320, each of which is incorporated herein by reference in its entirety). Accordingly, antigen binding proteins include, but are not limited to, monoclonal antibodies, bispecific antibodies, minibodies, domain antibodies such as Nanobodies®, synthetic antibodies (sometimes referred to herein as "antibody mimetics"), chimeric antibodies, humanized antibodies, human antibodies, antibody fusions, and portions or fragments of each, respectively. In some instances, the antigen binding protein is a functional fragment of a complete antibody (e.g., a Fab, a Fab', a F(ab')$_2$, a scFv, a domain antibody or a minibody). Peptibodies are another example of antigen binding proteins. In some embodiments, the term "antigen binding protein" includes derivatives, for example an antigen binding protein that has been chemically-modified, for example an antigen binding protein that is joined to another agent such as a label or a cytotoxic or cytostatic agent (e.g., an antigen binding protein conjugate such as an antibody drug conjugate).

An "antigen-binding fragment" (or simply "fragment") or "antigen-binding domain", of an antigen binding protein (e.g., an antibody) as used herein refers to one or more fragments of an antigen binding protein (e.g., an antibody), regardless of how obtained or synthesized, that retain the ability to specifically bind to the antigen bound by the whole antigen binding protein. Examples of antibody fragments include, but are not limited to, Fv; Fab; Fab'; Fab'-SH; F(ab')$_2$; diabodies; linear antibodies; single-chain antibody molecules (e.g. scFv); and multispecific antibodies formed from antibody fragments. A "Fv" fragment includes a non-covalently-linked dimer of one heavy chain variable domain and one light chain variable domain. A "Fab" fragment includes, the constant domain of the light chain and the first constant domain (CHI) of the heavy chain, in addition to the heavy and light chain variable domains of the Fv fragment. A "F(ab')$_2$" fragment includes two Fab fragments joined, near the hinge region, by disulfide bonds.

The terms "polypeptide" and "protein" are used interchangeably to refer to a polymer of amino acid residues and are not limited to a minimum length. Such polymers of amino acid residues can contain natural or non-natural amino acid residues, and include, but are not limited to, dimers, trimers, peptides, oligopeptides, and multimers of amino acid residues. Both full-length proteins and fragments thereof are encompassed by the definition. The terms also include post-expression modifications of the polypeptide, for example, glycosylation, sialylation, acetylation, phosphorylation, and the like. The term "polypeptide" also refers to a protein which includes modifications, such as deletions, additions, and substitutions (generally conservative in nature), to the native sequence, so long as the protein maintains the desired activity. The terms "polypeptide" and "protein" encompass GPNMB, CD228, αvβ6, CD30, LIV1, and CD19 antigen binding proteins, including antibodies, antibody fragments, or sequences that have deletions from, additions to, and/or substitutions of one or more amino acids of the antigen binding protein.

A "native sequence" or a "naturally-occurring" polypeptide comprises a polypeptide having the same amino acid sequence as a polypeptide found in nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

A polypeptide "variant" means a biologically active polypeptide (e.g., an antigen binding protein or antibody) having at least about 70%, 80%, or 90% amino acid sequence identity with the native or a reference sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "Percent (%) amino acid sequence identity" and "homology" with respect to a peptide, polypeptide or antigen binding protein (e.g., antibody) sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared. For example, the % sequence identity of a given amino acid sequence A to, with, or against a given amino acid sequence B (which can alternatively be phrased as a given amino acid sequence A that has or comprises a certain % sequence identity to, with, or against a given amino acid sequence B) is calculated as follows:

100 times the fraction X/Y where X is the number of amino acid residues scored as identical matches by the sequence in that program's alignment of A and B, and where Y is the total number of amino acid residues in B. Unless specifically stated otherwise, all % amino acid sequence identity values used herein are calculated according to this formula using the ALIGN-2 computer program. It will be appreciated that where the length of amino acid sequence A is not equal to the length of amino acid sequence B, the % sequence identity of A to B will not equal the % sequence identity of B to A.

The term "leader sequence" refers to a sequence of amino acid residues located at the N-terminus of a polypeptide that facilitates secretion of a polypeptide from a mammalian cell. A leader sequence may be cleaved upon export of the polypeptide from the mammalian cell, forming a mature protein. Leader sequences can be natural or synthetic, and they can be heterologous or homologous to the protein to which they are attached.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See, for instance, Fundamental Immunology (Paul, W., ed., 7$^{th}$ ed. Raven Press, N.Y. (2013)). Briefly, each heavy chain typically is comprised of a heavy chain variable region (abbreviated herein as $V_H$ or VH) and a heavy chain constant region (CH or CH). The heavy chain constant region typically is comprised of three domains, $C_H1$, $C_H^2$, and $C_H^3$. The heavy chains are generally inter-connected via disulfide bonds in the so-called "hinge region." Each light chain typically is comprised of a light chain variable region (abbreviated herein as $V_L$ or VL) and a light chain constant region ($C_L$ or CL). The light chain constant region typically is comprised of one domain, $C_L$. The CL can be of κ (kappa) or λ (lambda) isotype. The terms "constant domain" and "constant region" are used interchangeably herein. An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes.

The term "hypervariable region" or "HVR," as used herein, refers to each of the regions of an antibody variable domain which are hypervariable in sequence. HVRs can form structurally defined loops ("hypervariable loops"). Generally, native four-chain antibodies comprise six HVRs; three in the VH (H1, H2, H3), and three in the VL (L1, L2, L3). In native antibodies, $H_3$ and L3 display the most diversity of the six HVRs, and $H_3$ in particular is believed to play a unique role in conferring fine specificity to antibodies. See, e.g., Xu et al., Immunity 13:37-45 (2000); Johnson and Wu, in Methods in Molecular Biology 248:1-25 ($L_O$, ed., Human Press, Totowa, NJ, 2003). Indeed, naturally-occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

HVRs generally comprise amino acid residues from the hypervariable loops and/or from the "complementary determining regions" (CDRs), CDRs being of highest sequence variability and/or involved in antigen recognition. A variety of schemes for defining the boundaries of a given CDR are known in the art. For example, the Kabat Complementarity Determining Regions (CDRs) are based on sequence variability and are the most commonly used (Kabat et at., Sequences of Proteins of Immunological Interest, 5th Ed. Public Health Service, National Institutes of Health, Bethesda, MD. (1991)). Chothia refers instead to the location of the structural loops (Chothia and Lesk, J. Mol. Biol. 196:901-917 (1987)). The AbM CDRs represent a compromise between the Kabat CDRs and Chothia structural loops and are used by Oxford Molecular's AbM antibody modeling software. The "contact" CDRs are based on an analysis of the available complex crystal structures. Additional details on the foregoing schemes as well as other numbering conventions are provided in the following references: Al-Lazikani et al., (1997) J. Mol. Biol. 273: 927-948 ("Chothia" numbering scheme); MacCallum et al., (1996) J. Mol. Biol. 262:732-745 (1996), (Contact" numbering scheme); Lefranc M-P., et al., (2003) Dev. Comp. Immunol. 27:55-77 ("IMGT" numbering scheme); and Honegger A. & Plueckthun A. (2001) J. Mol/Biol. 309:657-70, (AHo numbering scheme).

In some embodiments, the HVR regions and associated sequences are the same as the CDR regions and associated sequences based upon one of the foregoing numbering conventions. As such, residues for exemplary HVRs and/or CDRs are summarized in Table A below.

TABLE A

Summary of Different CDR Numbering Schemes

| Loop | IMGT | Kabat | AbM | Chothia | Contact |
| --- | --- | --- | --- | --- | --- |
| CDR-H1 | 27-38 | 31-35 | 26-35 | 26-32 | 30-35 |
| CDR-H2 | 56-65 | 50-65 | 50-58 | 52-56 | 47-58 |
| CDR-H3 | 105-117 | 95-102 | 95-102 | 95-102 | 93-101 |
| CDR-L1 | 27-38 | 24-34 | 24-34 | 24-34 | 30-36 |
| CDR-L2 | 56-65 | 50-56 | 50-56 | 50-56 | 46-55 |
| CDR-L3 | 105-117 | 89-97 | 89-97 | 89-97 | 89-96 |

In some embodiments, HVRs can comprise extended HVRs as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et at., supra, for each of these definitions.

Unless otherwise specified, the terms "CDR" and "complementary determining region" of a given antibody or region thereof, such as a variable region, as well as individual CDRs (e.g., "CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the IMGT, Kabat, AbM, Chothia, or Contact method. In other instances, the particular amino acid sequence of a CDR is given.

Thus, in some embodiments, the antigen binding protein comprises CDRs and/or HVRs as defined by the IMGT system. In other embodiments, the antigen binding protein comprises CDRs or HVRs as defined by the Kabat system. In still other embodiments, the antigen binding protein comprises CDRs or HVRs as defined by the AbM system. In further embodiments, the antigen binding protein comprises CDRs or HVRs as defined by the Chothia system. In yet other embodiments, the antigen binding protein comprises CDRs or HVRs as defined by the IMGT system.

The term "variable region" or "variable domain" refers to the domain of an antigen binding protein (e.g., an antibody) heavy or light chain that is involved in binding the antigen binding protein (e.g., antibody) to antigen. The variable regions or domains of the heavy chain and light chain (VH and VL, respectively) of an antigen binding protein such as an antibody can be further subdivided into regions of hypervariability (or hypervariable regions, which may be hypervariable in sequence and/or form of structurally defined loops), such as hypervariable regions (HVRs) or complementarity-determining regions (CDRs), interspersed with regions that are more conserved, termed framework regions (FRs). In general, there are three HVRs (HVR-H1, HVR-H2, HVR-H3) or CDRs (CDR-H1, CDR-H2, CDR-H3) in each heavy chain variable region, and three HVRs (HVR-L1, HVR-L2, HVR-L3) or CDRs in (CDR-L1, CDR-L2, CDR-L3) in each light chain variable region. "Framework regions" and "FR" are known in the art to refer to the non-HVR or non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). Within each VH and VL, three HVRs or CDRs and four FRs are typically arranged from amino-terminus to carboxy-terminus in the following order: FR1, HVR1, FR2, HVR2, FR3, HVR3, FR4 in the case of HVRs, or FR1, CDR1, FR2, CDR2, FR3, CDR3, FR4 in the case of CDRs (See also Chothia and Lesk J. Mot. Biol., 195, 901-917 (1987)). A single VH or VL domain can be sufficient to confer antigen-binding specificity. In addition, antibodies that bind a particular antigen can be isolated using a VH or VL domain from an antibody that binds the antigen to screen a library of complementary VL or VH domains, respectively. See, e.g., Portolano et al. J. Immunol. 150:880-887 (1993); Clarkson et al., Nature 352:624-628 (1991).

The term "heavy chain variable region" (VH) as used herein refers to a region comprising heavy chain HVR-H1, FR-H2, HVR-H2, FR-H3, and HVR-H3. For example, a heavy chain variable region may comprise heavy chain CDR-H1, FR-H2, CDR-H2, FR-H3, and CDR-H3. In some embodiments, a heavy chain variable region also comprises at least a portion of an FR-H1 and/or at least a portion of an FR-H4.

The term "heavy chain constant region" as used herein refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a 73 constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" (HC) as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" (VL) as used herein refers to a region comprising light chain HVR-L1, FR-L2, HVR-L2, FR-L3, and HVR-L3. In some embodiments, the light chain variable region comprises light chain CDR-L1, FR-L2, CDR-L2, FR-L3, and CDR-L3. In some embodiments, a light chain variable region also comprises an FR-L1 and/or an FR-L4.

The term "light chain constant region" as used herein refers to a region comprising a light chain constant domain, $C_L$. Nonlimiting exemplary light chain constant regions include λ and κ.

The term "light chain" (LC) as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

The "EU numbering system" or "EU index" is generally used when referring to a residue in an immunoglobulin heavy chain constant region (e.g., the EU index reported in Kabat et al., Sequences of Proteins of Immunological Interest, 5th Ed. Public Health Service, National Institutes of Health, Bethesda, Md., 1991). The "EU index as in Kabat" refers to the residue numbering of the human IgG1 EU antibody. Unless stated otherwise herein, references to residue numbers in the constant domain of antibodies means residue numbering by the EU numbering system.

A "bispecific" antibody as used herein refers to an antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al., Nature 305:537-39 (1983). Alternatively, bispecific antibodies can be prepared using chemical linkage. See, e.g., Brennan, et al., Science 229:81 (1985). Bispecific antibodies include bispecific antibody fragments. See, e.g., Hollinger, et al., Proc. Natl. Acad. Sci. U.S.A. 90:6444-48 (1993), Gruber, et al., J. Immunol. 152:5368 (1994).

A "dual variable domain immunoglobulin" or "DVD-Ig" refers to multivalent and multispecific binding proteins as described, e.g., in DiGiammarino et al., Methods Mol. Biol. 899:145-156, 2012; Jakob et al., MABs 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

A "dual-affinity re-targeting protein" or a "DART" is a form of a bispecific antibody in which the heavy variable domain from one antibody is linked with the light variable domain of another, and the two chains associate, and are described in, e.g., Garber, Nature Reviews Drug Discovery 13:799-801, 2014.

A "Bispecific T-cell Engager" or BiTE®", is the genetic fusion of two scFv fragments resulting in tandem scFv molecules, and are described, e.g., in Baeuerle et al., Cancer Res. 69: 4941-4944, 2009.

A "chimeric antibody" as used herein refers to an antibody in which a portion of the heavy and/or light chain is derived from a particular source or species, while the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequence. A "human antibody" is one having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework derived from a human immunoglobulin framework or a human consensus framework can comprise the same amino acid sequence thereof, or it can contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

An "affinity matured" antibody refers to an antibody with one or more alterations in one or more hypervariable regions (HVRs) compared to a parent antibody which does not possess such alterations, such alterations resulting in an improvement in the affinity of the antibody for antigen. In some examples, an affinity matured antibody refers to an antibody with one or more alterations in one or more complementarity determining regions (CDRs) compared to a parent antibody which does not possess such alterations, such alterations resulting in an improvement in the affinity of the antibody for antigen.

The term "derivative" refers to a molecule (e.g., an antigen binding protein such as an antibody or fragment thereof) that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a derivative of a particular antigen binding protein can have a greater circulating half-life than an antigen binding protein that is not chemically modified. In certain embodiments, a derivative can have improved targeting capacity for desired cells, tissues, and/or organs. In some embodiments, a derivative of an antigen binding protein is covalently modified to include one or more polymers, including, but not limited to, monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. See, e.g., U.S. Pat. Nos. 4,640,835, 4,496,689, 4,301,144, 4,670,417, 4,791,192 and 4,179,337.

As used herein, the term "epitope" refers to a site on an antigen (e.g., GPNMB, CD228, αvβ6, CD30, LIV1, or CD19), to which an antigen-binding protein (e.g., an antibody or fragments thereof) that targets that antigen binds. Epitopes often consist of a chemically active surface grouping of molecules such as amino acids, polypeptides, sugar side chains, phosphoryl or sulfonyl groups, and have specific three-dimensional structural characteristics as well as specific charge characteristics. Epitopes can be formed both from contiguous or noncontiguous amino acids of the antigen that are juxtaposed by tertiary folding. Epitopes formed from contiguous residues typically are retained on exposure to denaturing solvents, whereas epitopes formed by tertiary folding typically are lost on treatment with denaturing solvents. In certain embodiments, an epitope can include, but is not limited to, at least 3, at least 4, at least 5, at least 6, at least 7, amino acids in a unique spatial arrangement. In some embodiments, the epitope refers to 3-5, 4-6, or 8-10 amino acids in a unique spatial conformation. In further embodiments, an epitope is less than 20 amino acids in length, less than 15 amino acids or less than 12 amino acids, less than 10 amino acids, or less than 8 amino acids in length. The epitope can comprise amino acids residues directly involved in the binding (also called immunodominant component of the epitope) and other amino acid residues that are not directly involved in the binding, including amino acid residues that are effectively blocked or covered by the antigen binding molecule (i.e., the amino acids are within the footprint of the antigen binding molecule). Methods of determining spatial conformation of epitopes include, for example, x-ray crystallography, two-dimensional nuclear magnetic resonance, and HDX-MS (see, e.g., Epitope Mapping Protocols in *Methods in Molecular Biology*, Vol. 66, G. E. Morris, Ed. (1996)). Once a desired epitope of an antigen is determined, antigen binding proteins (e.g., antibodies or fragments thereof) to that epitope can be generated using established techniques. It is then possible to screen the resulting antigen binding proteins in competition assays to identify antigen binding proteins that bind the same or overlapping epitopes. Methods for binning antibodies based upon cross-competition studies are described in WO 03/48731. The epitope for the hLIV22 antibody is KGAH-RPEH (SEQ ID NO: 942).

A "nonlinear epitope" or "conformational epitope" comprises noncontiguous polypeptides, amino acids, and/or sugars within the antigenic protein to which an antibody specific to the epitope binds.

A "linear epitope" comprises contiguous polypeptides, amino acids, and/or sugars within the antigenic protein to which an antigen binding protein (e.g., an antibody or fragment thereof) specific to the epitope binds.

A "paratope" or "antigen binding site" is the site on the antigen binding protein (e.g., antibody or fragment thereof) that binds the epitope and typically includes the amino acids that are in close proximity to the epitope once the antibody is bound (see, e.g., Sela-Culang et al., 2013, *Front Immunol.* 4:302).

The term "compete" when used in the context of antigen binding proteins (e.g., antibodies or fragments thereof) that compete for the same epitope means competition between antigen binding proteins as determined by an assay in which the antigen binding protein (e.g., an antibody or fragment thereof) being tested (e.g., a test antibody) prevents or inhibits (partially or completely) specific binding of a reference antigen binding protein (e.g., a reference antibody) to a common antigen (e.g., GPNMB, CD228, αvβ6, CD30, LIV1, or CD19 or a fragment thereof). Numerous types of competitive binding assays can be used to determine if one antigen binding protein competes with another, including various label-free biosensor approaches such as surface plasmon resonance (SPR) analysis (see, e.g., Abdiche, et al., 2009, *Anal. Biochem.* 386:172-180; Abdiche, et al., 2012, *J Immunol Methods* 382:101-116; and Abdiche, et al., 2014 *PLoS One* 9:e92451. Other assays that can be used include: solid phase direct or indirect radioimmunoassay (RIA), solid phase direct or indirect enzyme immunoassay (EIA), sandwich competition assay (see, e.g., Stahli et al., 1983, *Methods in Enzymology* 9:242-253); solid phase direct biotin-avidin EIA (see, e.g., Kirkland et al., 1986, *J. Immunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using I-125 label (see, e.g., Morel et al., 1988, *Mol. Immunol.* 25:7-15); solid phase direct biotin-avidin EIA (see, e.g., Cheung, et al., 1990, *Virology* 176:546-552); direct labeled RIA (Moldenhauer et al., 1990, *Scand. J Immunol.* 32:77-82). Typically, the test antigen binding protein is present in excess (e.g., at least 2×, 5×, 10×, 20× or 100×). Usually, when a competing antigen binding protein is present in excess, it will inhibit specific binding of a reference antigen binding protein to a common antigen by at least 40%, 50%, 60%, 70%, 80%, 90%, 95% or 100%. In instances in in which each antigen binding protein (e.g., an antibody or fragment thereof) detectably inhibits the binding of the other antigen binding protein with its cognate epitope, whether to the same, greater, or lesser extent, the antigen binding proteins are said to "cross-compete" with each other for binding of their respective epitope(s) or to "cross-block" one another. Typically, such cross-competition studies are done using the conditions and methods described above for competition studies and the extent of blocking is at least 30%, at least 40%, or at least 50% each way.

"Affinity" refers to the strength of the sum total of noncovalent interactions between a single binding site of a molecule (e.g., an antibody) and its binding partner (e.g., an antigen). The affinity of a molecule X for its partner Y can generally be represented by the dissociation constant ($K_d$). Affinity can be measured by common methods known in the art, including those described herein.

An "affinity matured" antibody refers to an antibody with one or more alterations in one or more hypervariable regions (HVRs) compared to a parent antibody which does not possess such alterations, such alterations resulting in an improvement in the affinity of the antibody for antigen. In some examples, an affinity matured antibody refers to an antibody with one or more alterations in one or more complementarity determining regions (CDRs) compared to a parent antibody which does not possess such alterations, such alterations resulting in an improvement in the affinity of the antibody for antigen.

As used herein, the term "specifically binds", "binding" or simply "binds" or other related terms in the context of the binding of an antigen binding protein to its target antigen means that the antigen binding protein exhibits essentially background binding to non-target molecules. An antigen binding protein that specifically binds the target antigen (e.g., GPNMB, CD228, αvβ6, CD30, LIV1, or CD19) may, however, cross-react with GPNMB, CD228, αvβ6, CD30, LIV1, or CD19 proteins from different species.

The term "$K_D$" (M), as used herein, refers to the dissociation equilibrium constant of a particular antigen binding protein-antigen interaction (e.g., antibody-antigen interaction). Affinity, as used herein, and $K_D$ are inversely related, such that higher affinity is intended to refer to lower $K_D$, and lower affinity is intended to refer to higher $K_D$.

The abbreviation LAE refers to the tripeptide linker leucine-alanine-glutamic acid. The abbreviation dLAE refers to the tripeptide linker D-leucine-alanine-glutamic acid, where the leucine in the tripeptide linker is in the D-configuration.

The abbreviation VKG refers to the tripeptide linker valine-lysine-glycine.

The abbreviation "PABC" refers to the self-immolative spacer:

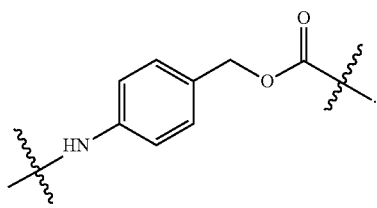

The abbreviation "mc" refers to the stretcher maleimido-caproyl:

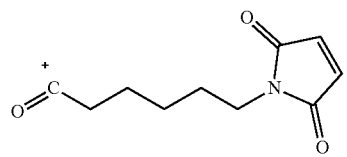 [SMILES: O=[C+]CCCCCN1C(=O)C=CC1=O]

The abbreviation "mp" refers to the stretcher maleimido-propionyl:

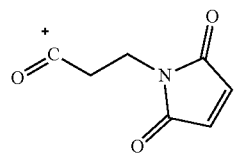 [SMILES: O=[C+]CCN1C(=O)C=CC1=O]

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

A "functional Fc region" possesses an "effector function" of a native sequence Fc region. Exemplary "effector functions" include Fc receptor binding; C1q binding; complement dependent cytotoxicity (CDC); antibody-dependent cell-mediated cytotoxicity (ADCC); antibody-dependent cellular phagocytosis (ADCP); down regulation of cell surface receptors (e.g. B cell receptor; BCR), etc. Such effector functions generally require the Fc region to be combined with a binding domain (e.g., an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term "Fe receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8): 6213-6216 (2004); WO 2004/92219 (Hinton et al.).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP); down regulation of cell surface receptors (e.g. B cell receptor); and B cell activation. Such functions can be affected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the CD33 targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by CD16$^+$ effector cells through the secretion of membrane pore-forming proteins and proteases, while phagocytosis is mediated by CD32$^+$ and CD64$^+$ effector cells (see, e.g., *Fundamental Immunology,* 4$^{th}$ ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207.

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a mechanism of cytotoxicity in which the Fc region of antibodies bound to antigen on the cell surface of target cells interact with Fc receptors (FcRs) present on certain cytotoxic effector cells (e.g. NK cells, neutrophils, and macrophages). This interaction enables these cytotoxic effector cells to subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821, 337 or U.S. Pat. No. 6,737,056 (Presta), can be performed. Useful effector cells for such assays include PBMC and NK cells. ADCC activity of the molecule of interest can also be assessed in vivo, e.g., in an animal model such as that disclosed in Clynes et al. *Proc. Natl. Acad. Sci. (USA)* 95:652-656 (1998). Additional polypeptide variants with altered Fc region amino acid sequences (polypeptides with a variant Fc region) and increased or decreased ADCC activity are described, e.g., in U.S. Pat. Nos. 7,923,538, and 7,994,290.

"Complement dependent cytotoxicity" or "CDC" refers to the lysis of a target cell in the presence of complement. Activation of the classical complement pathway is initiated by the binding of the first component of the complement system (C1q) to the Fc region of antibodies (of the appropriate subclass), which are bound to their cognate antigen on a target cell. This binding activates a series of enzymatic reactions culminating in the formation of holes in the target cell membrane and subsequent cell death. Activation of complement may also result in deposition of complement components on the target cell surface that facilitate ADCC by binding complement receptors (e.g., CR3) on leukocytes. To assess complement activation, a CDC assay, e.g., as described in Gazzano-Santoro et al., *J. Immunol. Methods* 202:163 (1996), can be performed. Polypeptide variants with altered Fc region amino acid sequences (polypeptides such as an antibody with a variant Fc region) and increased or decreased C1q binding capability are described, e.g., in U.S. Pat. No. 6,194,551 B1, U.S. Pat. Nos. 7,923,538, 7,994,290 and WO 1999/51642. See also, e.g., Idusogie et al., *J. Immunol.* 164: 4178-4184 (2000).

The term "antibody-dependent cellular phagocytosis", or simply "ADCP", refers to the process by which antibody-coated cells are internalized, either in whole or in part, by phagocytic immune cells (e.g., macrophages, neutrophils and dendritic cells) that bind to an Fc region of Ig.

A polypeptide variant with "altered" FcR binding affinity or ADCC activity (e.g., an antibody) is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The polypeptide variant which "displays decreased binding" to an FcR, binds at least one FcR with lower affinity than a parent polypeptide. In some embodiments, such variants which display decreased binding to an FcR may possess little or no appreciable binding to an FcR, e.g., 0-20% binding to the FcR compared to a native sequence IgG Fc region.

The terms "nucleic acid molecule", "nucleic acid" and "polynucleotide" are used interchangeably herein and refer to a polymer of nucleotides of any length. Such polymers of nucleotides can contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The term "vector" means any molecule or entity (e.g., nucleic acid, plasmid, bacteriophage or virus) used to transfer a nucleic acid molecule into a host cell. A vector typically includes a nucleic acid molecule engineered to contain a cloned polynucleotide or polynucleotides encoding a polypeptide or polypeptides of interest that can be propagated in a host cell. Examples of vectors include, but are not limited to, plasmids, viral vectors, and expression vectors, for example, recombinant expression vectors. A vector may include one or more of the following elements: an origin of replication, one or more regulatory sequences (such as, for example, promoters and/or enhancers) that regulate the expression of the polypeptide of interest, and/or one or more selectable marker genes. The term includes vectors which are self-replicating nucleic acid molecules as well as vectors incorporated into the genome of a host cell into which it has been introduced.

The term "expression vector" refers to a vector that is suitable for transformation of a host cell and that can be used to express a polypeptide of interest in a host cell.

The terms "host cell" or "host cell line" are used interchangeably herein and refer to a cell or population of cells that may be or has been a recipient of a vector or isolated polynucleotide. Host cells can be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively. Such terms refer not only to the original cell, but also to the progeny of such a cell. Certain modifications may occur in succeeding generations due to, for example, mutation or environmental influences. Such progeny are also encompassed by the terms so long as the cells have the same function or biological activity as the original cells.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. Control sequences for eukaryotes can include, for example, promoters comprising one or a plurality of recognition sites for transcription factors, transcription enhancer sequences, and transcription termination sequence. "Control sequences" can include leader sequences and/or fusion partner sequences.

As used herein, "operably linked" means that the components to which the term is applied are in a relationship that allows them to carry out their inherent functions under suitable conditions. For example, a control sequence in a vector that is "operably linked" to a protein coding sequence is ligated thereto such that expression of the protein coding sequence is achieved under conditions compatible with the transcriptional activity of the control sequences. In the case in which two encoding sequences are operably linked, the phrase means that the two DNA fragments or encoding sequences are joined such that the amino acid sequences encoded by the two fragments remain in-frame.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated".

A "disease" or "disorder" as used herein refers to a condition where treatment is needed.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. A solid tumor is an abnormal growth or mass of tissue that usually does not contain cysts or liquid areas. Examples of cancer include but are not limited to, carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

The terms "metastatic cancer" and "metastatic disease" mean cancers that have spread from the site of origin to another part of the body, e.g., to regional lymph nodes or to distant sites.

The terms "advanced cancer", "locally advanced cancer", "advanced disease" and "locally advanced disease" mean cancers that have extended through the relevant tissue capsule. Surgery is typically not recommended for patients with locally advanced disease, and these patients have substantially less favorable outcomes compared to patients having clinically localized (organ-confined) cancer.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

A "reference" as used herein, refers to any sample, standard, or level that is used for comparison purposes. A reference can be obtained from a healthy and/or non-diseased sample. In some examples, a reference can be obtained from an untreated sample. In some examples, a reference is obtained from a non-diseased on non-treated sample of a subject individual. In some examples, a reference is obtained from one or more healthy individuals who are not the subject or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

An "effective amount" or "therapeutically effective amount" or "therapeutically effective dosage" of a drug or therapeutic agent is any amount of the drug or agent that, when used alone or in combination with another therapeutic agent provides a treatment effect, such as protecting a subject against the onset of a disease or promoting disease regression as evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

A therapeutically effective amount of a drug includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

"Administering" or "administration" refer to the physical introduction of a therapeutic agent to a subject, using any of the various methods and delivery systems known to those skilled in the art. Exemplary routes of administration include intravenous, intramuscular, subcutaneous, intraperitoneal, spinal or other parenteral routes of administration, for example by injection or infusion (e.g., intravenous infusion). Administration can also be performed, for example, once, a plurality of times, and/or over one or more extended periods.

The term "monotherapy" as used herein means that the anti-GPNMB antibody or ADC, anti-CD228 antibody or ADC, anti-$\alpha v\beta 6$ antibody or ADC, CD30 antibody or ADC, anti-LIV1 antibody or ADC, or anti-CD19 antibody or ADC of the invention is the only anti-cancer agent administered to the subject during the treatment cycle. Other therapeutic agents, however, can be administered to the subject. For example, anti-inflammatory agents or other agents administered to a subject with cancer to treat symptoms associated with cancer, but not the underlying cancer itself, including, for example inflammation, pain, weight loss, and general malaise, can be administered during the period of monotherapy.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered simultaneously or with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

The term "chemotherapeutic agent" refers to all chemical compounds that are effective in inhibiting tumor growth. Non-limiting examples of chemotherapeutic agents include alkylating agents (e.g., nitrogen mustards, ethyleneimine compounds and alkyl sulphonates); antimetabolites (e.g., folic acid, purine or pyrimidine antagonists); mitotic inhibitors (e.g., anti-tubulin agents such as *vinca* alkaloids, auristatins and derivatives of podophyllotoxin); cytotoxic antibiotics; compounds that damage or interfere with DNA expression or replication (e.g., DNA minor groove binders); and growth factor receptor antagonists, and cytotoxic or cytostatic agents.

The phrase "pharmaceutically acceptable" indicates that the substance or composition is compatible chemically and/or toxicologically with the other ingredients comprising a formulation, and/or the subject being treated therewith.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

Various aspects of the disclosure are described in further detail in the following sections.

2. Embodiments

Various embodiments of the invention are described below followed by a more detailed discussion of the components, e.g., groups, reagents, and steps that are useful in the processes of the present invention. Any of the selected embodiments for the components of the processes can apply to each and every aspect of the invention as described herein or they may relate to a single aspect. In some aspects, the selected embodiments may be combined in any combination appropriate for describing an auristatin Ligand Drug Conjugate, Drug Linker compound or Intermediate thereof having a hydrophobic auristatin F Drug Unit.

2.1 Ligand Drug Conjugates

A Ligand Drug Conjugate (LDC) compound of the present invention is compound having a Drug Unit connected to a Ligand Unit through an intervening Linker Unit (LU) in which LU is comprised of a Peptide Cleavable Unit that is more susceptible to proteolytic cleavage by tumor tissue homogenate compared to normal tissue homogenate to effect release D as free drug, and typically has the structure of Formula 1:

$$L\text{-}[LU\text{-}(D')]_{p'} \quad (1)$$

or a salt thereof, in particular a pharmaceutically acceptable salt thereof, wherein L is the Ligand Unit; LU is the Linker Unit; D' represents from 1 to 4 Drug Units, incorporating or corresponding in structure to the same free drug for each drug linker moiety of formula -LU-(D)'; and subscript p' is an integer ranging from 1 to 24, wherein the Ligand Unit is capable of selective binding to an antigen of targeted abnormal cells, wherein the targeted antigen is capable of internalization along with bound Conjugate compound for subsequent intracellular release of free drug, wherein each drug linker moiety in the Ligand Drug Conjugate compound has the structure of Formula 1A:

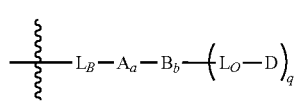

(1A)

or a salt thereof, in particular, a pharmaceutically acceptable salt, wherein the -$L_B$-$A_a$-$B_b$-moiety of a drug linker moiety of Formula 1A in general represents the primary linker ($L_R$) of the Linker Unit (LU) of Formula 1
wherein the wavy line indicates covalent attachment to L; $L_B$ is a Ligand covalent binding moiety; A is a first optional Stretcher Unit; subscript a is 0 or 1 indicating the absence or presence of A, respectively; B is an optional Branching Unit; subscript b is 0 or 1, indicating the absence or presence of B, respectively; D is the Drug Unit; and subscript q is an integer ranging from 1 to 4; and $L_O$ is a secondary linker moiety having the structure of:

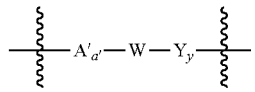

wherein the wavy line adjacent to A' indicates the site of covalent attachment of $L_O$ to the primary linker; the wavy line adjacent to Y indicates the site of covalent attachment of $L_O$ to the Drug Unit; A' is a second optional Spacer Unit, subscript a' is 0 or 1, indicating the absence or presence of A', respectively, W is a Peptide Cleavable Unit, Y is a Spacer Unit, and y is 0, 1 or 2, indicating the absence or presence of 1 or 2 Spacer Units, respectively.

A Ligand Drug Conjugate composition is comprised of a distribution or collection of Ligand Drug Conjugate compounds and is represented by the structure of Formula 1 in which subscript p' is replaced by subscript p, wherein subscript p is an number ranging from about 2 to about 24.

A traditional Ligand Drug Conjugate is also represented by Formula 1, but having a Peptide Cleavable Unit (W) comprised of a dipeptide covalently attached either directly to D or indirectly through Y, in which the dipeptide is designed to be selective for a specific intracellular protease whose activity is upregulated in abnormal cells relative to that of normal cells. In contrast, Conjugates of the present invention are based upon the unexpected finding that the overall protease activity within tissue comprised of the abnormal cells may be differentiated from that activity within normal tissue comprised of the normal cells by an appropriately designed Cleavable Unit while remaining resistant to cleavage by freely circulating proteases. For the Conjugates of the present invention that differentiation is achieved by a Peptide Cleavable Unit incorporating certain tripeptides, wherein these peptides have been identified by a screening method described herein in which protease activity from a tissue homogenate comprised of abnormal cells is compared to that of a normal tissue homogenate, wherein the normal tissue is known to be the source of on-target and/or off-target adverse event(s) experienced by a mammalian subject when administered a therapeutically effective amount of a traditional Ligand Drug Conjugate.

Thus, in a principle embodiment of the invention, W is a Peptide Cleavable Unit comprised of a tripeptide that provides for a recognition site that is selectively acted upon by one or more intracellular proteases of targeted abnormal cells in comparison to freely circulating proteases and is also selectively acted upon by proteases within a tumor tissue homogenate in comparison to proteases within a normal tissue homogenate. For the treatment of a cancer a tripeptide sequence for the Peptide Cleavable Unit is selected so that proteases of normal tissue known to be the source of on-target and/or off-target adverse events from administration of a therapeutically effective amount of a traditional Ligand Drug Conjugate are less likely to act upon the Conjugate having that tripeptide-based Cleavable Unit than proteases of tumor tissue so as to provide greater selectivity for targeting cancer cells. That selection is based upon the lower overall protease activity in the homogenate of the normal tissue compared to homogenate of the tumor tissue of the cancer. In contrast to the improved Conjugates of the present invention, traditional Ligand Drug Conjugate containing a dipeptide Cleavable Unit have been designed to be selectively acted upon by cathepsin B, which is an intracellular protease whose activity is upregulated in cancer cells, and primarily rely upon immunological specificity for selectivity targeting cancer cells over normal cells. Improved Conjugates of the present invention have an additional level of selectivity by being less prone to protease action within normal tissue as compared to the tumor tissue in which the targeted cancer cells reside.

In some embodiments, a drug linker moiety of Formula 1A will have the structure represented by Formula 1B:

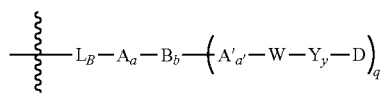
(1B)

wherein $L_B$ is a ligand covalent binding moiety as defined herein for a primary linker ($L_R$) in the Linker Unit (LU) of a drug linker moiety or Drug Linker compound; A and B are a first optional Stretcher Unit and an optional Branching Unit, respectively, of $L_R$; subscript q ranges from 1 to 4; and the remaining variable groups are as defined herein for $L_O$.

In some of those embodiments W contains a tripeptide that is is directly attached to the Drug Unit so that subscript y is 0. When subscript y is 1, the tripeptide is attached to a self-immolative Spacer Unit so that cleavage by the protease provides a drug linker fragment of formula Y-D in which Y undergoes self-immolation so as to complete release of the free drug. When subscript y is 2, the tripeptide is attached to a first self-immolative Spacer Unit (Y) so that cleavage by the protease provides a first drug linker fragment of formula Y-Y'-D in which Y' and is a second Spacer Unit and is followed by self-immolation of the first Spacer Unit so as to provide a second drug linker fragment of formula Y'-D that decomposes to complete the release of the free drug.

Exemplary Ligand Drug Conjugate compounds having drug linker moieties of Formula 1B in which the tripeptide of the Peptide Cleavable Unit (W) is directly attached to the Drug Unit or to an intervening Spacer Unit have the structure of Scheme 1a, wherein P1, P2, and P3 are amino acid residues of the tripeptide sequence and D is attached to a p-amino benzyl alcohol residue through a carbamate or carbonate functional group that together represent $Y_y$ in which subscript y is 2. In those exemplary Ligand Drug Conjugate compounds the carbonyl functional group of the amide bond adjacent to P1 is from the C-terminus of the tripeptide sequence wherein that amide bond is the site of protease cleavage (indicated by the arrow) and the amino group of the amide bond adjacent to P3 is from the N-terminus of the tripeptide sequence. Cleavage of the amide functional group to P1 results in a first drug linker fragment having the structure shown in Scheme 1a, which undergoes self-immolation to provide a second drug linker fragment that spontaneously decomposes with release of $CO_2$ to complete release of D as free drug of formula H-T*-D* having a hydroxy or amine group, the oxygen atom or nitrogen moiety —NH— of which is presented by T*, wherein D* represents the remainder of the free drug.

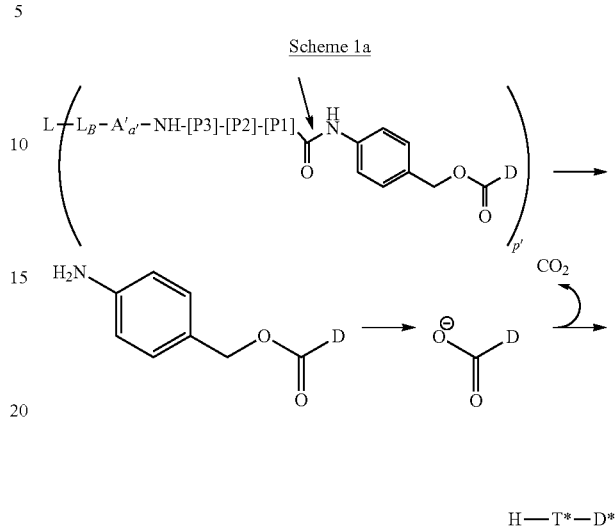

Scheme 1a

In those embodiments, one or more amino acids designated as P4, P5, etc. may be present between the primary linker of formula -$L_B$-A'$_{a'}$- and P3 as part of the peptide sequence comprising the tripeptide that confers selectivity for intracellular proteolysis over proteolysis by freely circulating proteases and proteolysis by tumor tissue homogenate over proteolysis by normal tissue homogenate. The mechanism of free drug release from Ligand Drug Conjugates having such extended peptide sequences is analogous to that of Scheme 1a.

In other embodiments an amino acid residue designated as P-1 intervenes between the specificity-conferring tripeptide of W and D or —$Y_y$-D so that D or the drug linker fragment initially released from protease action at the specificity-conferring tripeptide comprises that amino acid, and thus requires further processing by an intracellular endopeptidase to allow for self-immolation of the Spacer Unit(s) to occur. For those embodiments, exemplary Ligand Drug Conjugate compounds having drug linker moieties of Formula 1B in which the specificity-conferring tripeptide of the Peptide Cleavable Unit is not directly attached to the Drug Unit or to an intervening Spacer Unit have the structure shown in Scheme 1b. Protease cleavage of the susceptible amide bond between P1 and P-1 (indicated by the arrow) provides a drug linker fragment in which a first self-immolative Spacer Unit (Y) is present as an amino acid residue that provides for a substrate of an endopeptidase with attachment to the self-immolative moiety of Y, which is the para-amino benzyl alcohol residue having attachment to D through a carbamate or carbonate function group. Together the amino acid-para-amino benzyl alcohol residue and the carbamate or carbonate functional group represent $Y_y$ in which subscript y is 2. After endopeptidase removal of P-1, self-immolation occurs as in Scheme 1a for release of D as free drug of formula H-T*-D*.

Scheme 1b

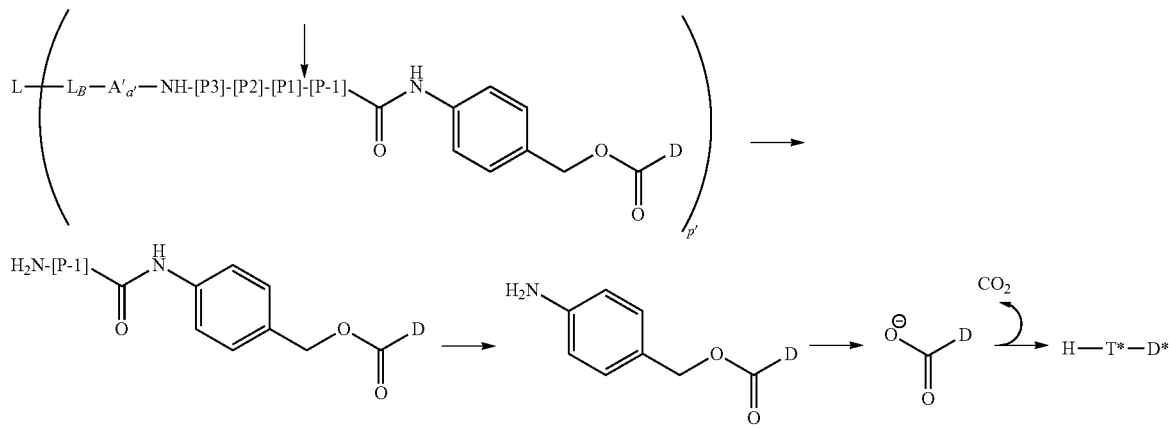

As before one or more amino acids designated as P4, P5, etc. may be present between the primary linker of formula -$L_B$-$A'_{a'}$- and P3 as part of the peptide sequence comprising the tripeptide that confers selectivity for intracellular proteolysis over proteolysis by freely circulating proteases and proteolysis by tumor tissue homogenate over proteolysis by normal tissue homogenate. Although P-1 in Scheme 1b is formally part of a first self-immolative Spacer Unit (Y), for convenience it will be associated with the tripeptide sequence so that W is a tetrapeptide in SEQ IDs describing such Peptide Cleavable Units. Those Units and other components of Ligand Drug Conjugates of the present invention, are further discussed as follows.

2.2.1 Ligand Unit

A Ligand Unit (L) of a Ligand Drug Conjugate is the targeting moiety of the Conjugate that selectively binds to a targeted moiety. In some embodiments the Ligand Unit selectively binds to a cell component (a Cell Binding Agent), which serves as the targeted moiety, or to other target molecules of interest. The Ligand Unit acts to target and present the Drug Unit of the Ligand Drug Conjugate to the particular target cell population with which the Ligand Unit interacts in order to selectively release D as a free drug. Targeting agents that provide for Ligand Units include, but are not limited to, proteins, polypeptides and peptides. Exemplary Ligand Units include, but are not limited to, those provided by proteins, polypeptides and peptides such as antibodies, e.g., full-length antibodies and antigen binding fragments thereof, interferons, lymphokines, hormones, growth factors and colony-stimulating factors. Other suitable Ligand Units are those from vitamins, nutrient-transport molecules, or any other cell binding molecule or substance. In some embodiments a Ligand Unit is from non-antibody protein targeting agent. In other embodiments, a Ligand Unit is from a protein targeting agent such as an antibody. Preferred targeting agents are larger molecular weight proteins, e.g., Cell Binding Agents having a molecular weight of at least about 80 Kd.

A targeting agent reacts with a ligand covalent binding precursor ($L_B'$) moiety of a primary linker precursor ($L_R'$) of a Drug Linker compound to form a Ligand Unit covalently attached to a ligand covalent binding ($L_B$) moiety of a primary linker ($L_R$) of a drug-linker moiety of Formula 1A. The targeting agent has or is modified to have the appropriate number of attachment sites to accommodate the requisite number of drug-linker moieties, defined by subscript p, whether they be naturally occurring or non-naturally occurring (e.g., engineered). For example, for the value of subscript p to be from 6 to 14, a targeting agent must be capable of forming a bond to 6 to 14 drug-linker moieties. The attachment sites can be naturally occurring or engineered into the targeting agent. A targeting agent can form a bond to the $L_{SS}$ moiety of the Linker Unit of a Drug Linker compound via a reactive or activatable heteroatom or a heteroatom-containing functional group of the targeting agent. Reactive or activatable heteroatoms or a heteroatom-containing functional groups that may be present on a targeting agent include sulfur (in one embodiment, from a thiol functional group of a targeting agent), C=O (in one embodiment, from a carbonyl, carboxyl or hydroxyl group of a targeting agent) and nitrogen (in one embodiment, from a primary or secondary amino group of a targeting agent). Those heteroatoms can be present on the targeting agent in the targeting agent's natural state, for example a naturally occurring antibody, or can be introduced into the targeting agent via chemical modification or genetic engineering.

In one embodiment, a targeting agent has a thiol functional group (e.g., of a cysteine residue) and the Ligand Unit therefrom is attached to a drug linker moiety of a Ligand Drug Conjugate compound via the thiol functional group's sulfur atom.

In another embodiment, the targeting agent has lysine residues that can react with an activated ester, including but are not limited to, N-hydroxysuccinimide, pentafluorophenyl, and p-nitrophenyl esters, of $L_R$ of the Linker Unit of a Drug Linker compound and thus results in an amide bond between the nitrogen atom from the Ligand Unit and the C=O functional group from the Linker Unit of the Drug Linker compound.

In yet another embodiment, the targeting agent has one or more lysine residues that can be chemically modified to introduce one or more thiol functional groups. The Ligand Unit from that targeting agent is attached to the Linker Unit via the introduced thiol functional group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the targeting agent can have one or more carbohydrate groups that can be chemically modified to have one or more thiol functional groups. The Ligand Unit from that targeting agent is attached to the Linker Unit via the introduced thiol functional group's sulfur atom, or the targeting agent can have one or more carbohydrate groups that can be oxidized to provide an aldehyde (—CHO) group (see, e.g., Laguzza, et al., 1989, *J. Med. Chem.* 32(3):548-55). The corresponding aldehyde can then react with an $L_{SS}$ moiety of a Drug Linker compound having nucleophilic nitrogen. Other reactive sites on $L_R$ that can react with a carbonyl group on a targeting agent include, but are not limited to, hydrazine and hydroxylamine. Other protocols for the modification of proteins for the attachment of drug linker moieties are described in Coligan et al., *Current Protocols in Protein Science*, vol. 2, John Wiley & Sons (2002) (incorporated herein by reference).

In preferred embodiments, the reactive group of $L_R$ of a Drug Linker compound is a maleimide ($M^1$) moiety and covalent attachment of L to $L_R$ is accomplished through a thiol functional group of a targeting agent so that a thio-substituted succinimide ($M^2$) moiety is formed through Michael addition. The thiol functional group can be present on the targeting agent in the targeting agent's natural state, for example a naturally occurring residue, or can be introduced into the targeting agent via chemical modification and/or genetic engineering.

It has been observed for bioconjugates that the site of drug conjugation can affect numerous parameters including ease of conjugation, drug-linker stability, effects on biophysical properties of the resulting bioconjugates, and in-vitro cytotoxicity. With respect to drug-linker stability, the site of conjugation of a drug-linker to a ligand can affect the ability of the conjugated drug-linker moiety to undergo an elimination reaction and for the drug linker moiety to be transferred from the Ligand Unit of a bioconjugate to an alternative reactive thiol present in the milieu of the bioconjugate, such as, for example, a reactive thiol in albumin, free cysteine, or glutathione when in plasma. Such sites include, for example, the interchain disulfides as well as select cysteine engineered sites. The Ligand-Drug Conjugates described herein can be conjugated to thiol residues at sites that are less susceptible to the elimination reaction (e.g., positions 239 according to the EU index as set forth in Kabat) in addition to other sites.

In preferred embodiments, the Ligand Unit (L) is of an antibody or antigen-binding fragment thereof, thereby defining an antibody Ligand Unit of an Antibody Drug Conjugate (ADC), wherein the antibody Ligand Unit is capable of selective binding to a targeted antigen of a cancer cell for subsequent release of D as free drug, wherein the targeted antigen is capable of internalization into said cancer cell upon said binding in order to initiate intracellular release of free drug.

Useful antibodies include polyclonal antibodies, which are heterogeneous populations of antibody molecules derived from the sera of immunized animals. Other useful antibodies are monoclonal antibodies, which are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to targeted cells (e.g., cancer cell antigens, viral antigens, or microbial antigens) or other antibodies bound to tumor cells or matrix. In this regard, "functionally active" means that the fragment, derivative or analog is able to immunospecifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety). Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety). Such chimeric and humanized monoclonal antibodies can be produced by recombinant DNA techniques known in the art, for example using methods, each of which is specifically incorporated herein by reference, as described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., *Science* (1988) 240:1041-1043; Liu et al., *Proc. Natl. Acad. Sci.* (*USA*) (1987) 84: 3439-3443; Liu et al., *J. Immunol.* (1987) 139: 3521-3526; Sun et al. *Proc. Natl. Acad. Sci.* (*USA*) (1987) 84: 214-218; Nishimura et al. *Cancer. Res.* (1987) 47: 999-1005; Wood et al., *Nature* (1985) 314:446-449; Shaw et al., *J. Natl. Cancer Inst.* (1988) 80: 1553-1559; Morrison, *Science* (1985) 229:1202-1207; Oi et al. *BioTechniques* (1986) 4: 214; U.S. Pat. No. 5,225,539; Jones et al., *Nature* (1986) 321: 552-525; Verhoeyan et al., *Science* (1988) 239: 1534; and Beidler et al., *J Immunol.* (1988) 141: 4053-4060.

Completely human antibodies are particularly preferred and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule if such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivitization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

In specific embodiments, known antibodies for the treatment of cancer are used. In some embodiments, the antibody will selectively bind to a cancer antigen of a hematological malignancy.

An ADC can be conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

2.2.2 Primary Linkers

In one group of embodiments, a Ligand Drug Conjugate is comprised of one or more drug linker moieties of formula -$L_R$-$L_O$-D, wherein $L_O$ is -A'$_{a'}$-W—Y$_y$— as described herein, wherein $L_R$ is a primary linker, A' is a second optional Stretcher Unit, a' is 0 or 1, indicating the absence or presence of A', respectively, Y is a Spacer Unit, subscript y is 0, 1 or 2, indicating the absence or presence of 1 or 2 Spacer Units, respectively, D is a Drug Unit, and W is a Peptide Cleavable Unit, wherein the Peptide Cleavable Unit is a sequence of up to 12 (e.g., 3-12 or 3-10) contiguous amino acids, wherein the sequence comprises a tripeptide that is more susceptible to proteolytic cleavage by a homogenate of tumor tissue as compared to a homogenate of normal tissue for initiating release of D as free drug, wherein cytotoxicity towards cells of the normal tissue due to unintended release of the free drug within and/or in the vicinity of these cells is associated with an adverse event from administration of an effective amount of a comparator Ligand Drug Conjugate to a subject in need thereof in which the sequence of amino acids of its Peptide Cleavable Unit is the dipeptide -valine-citrulline- and/or wherein the tripeptide increases the bioavailability of the Ligand Drug Conjugate to the detriment of its bioavailability to the normal tissue in comparison to the comparator Conjugate. In some of those embodiments -$L_R$- is -$L_B$-$A_a$-$B_b$— in which $L_B$ is a ligand covalent binding moiety, A is a first optional Stretcher Unit, subscript a is 0 or 1, indicating the absence or presence of A, respectively, B is an optional Branching Unit, and subscript b is 0 or 1, indicating the absence or presence of B, respectively.

In some embodiments, a drug linker moiety has the structure of

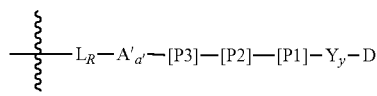

or a salt thereof, in particular a pharmaceutically acceptable salt, wherein $L_R$, A', a', Y, y and D retain their previous meanings and P1, P2 and P3 are amino acid residues that together provide selectivity for proteolysis by tumor tissue homogenate over proteolysis by normal tissue homogenate and/or provide increased bioavailability to tumor tissue to the detriment of normal tissue in comparison to a comparator Ligand Drug Conjugate in which the amino acid sequence of the Peptide Cleavable Unit is the dipeptide -valine-citrulline-, wherein proteolytic cleavage occurs at the covalent bond between P1 and Y if subscript y is 1 or 2 or at the covalent bond between P1 and D if subscript y is 0 and wherein the tumor and normal tissue are of the same species.

As described elsewhere, other embodiments contain an additional amino acid residue between P1 and Y or D, depending on the value of subscript y, which is designated as P-1, so that selective endopeptidase action by a proteolytic enzyme(s) of tumor tissue homogenate occurs at the amide bond between P1 and P-1 to release a drug linker fragment of formula —[P-1]-Y$_y$-D. Release of free drug from that fragment would occur from exopeptidase action of a proteolytic enzyme to remove the P-1 amino acid residue to directly provide free drug if subscript y is 0 (i.e., Y is absent).

In some embodiments in which an additional amino acid residue between P1 and Y or D, is present, a drug linker moiety has the structure of:

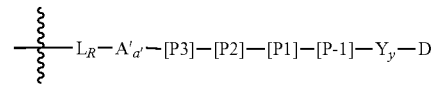

or a salt thereof, in particular a pharmaceutically acceptable salt, wherein $L_R$, A', a', Y, y and D retain their previous meanings and P1, P2 and P3 are amino acid residues, optionally with P-1, that together provide selectivity for proteolysis by tumor tissue homogenate over proteolysis by normal tissue homogenate, wherein proteolytic cleavage occurs at the covalent bond between P1 and P-1 to release a linker fragment having the structure of [P-1]-Y$_y$-D.

In some of those embodiments when subscript y is 0, the [P-1]-D residue resulting from endo-peptidase cleavage of the amide bond between the P1 and P-1 amino acids also exerts cytotoxic activity. In other embodiments, subscript y is 1 or 2 so that exopeptidase action to remove the P-1 amino acid residue provides another drug linker fragment of formula —Y$_y$-D, which spontaneously fragments to provide free drug.

In other embodiments one or more amino acid residues, designated P4, P5 . . . P$_n$, wherein subscript n ranges up to 12 (e.g., 3-12 or 3-10), are between P3 and $L_R$ or A', depending on the value of subscript a', which is some embodiments is in addition to the Peptide Cleavable Unit containing a P-1 amino acid residue. In either instance, the additional P4, P5 . . . P$_n$ amino acid residues are selected so as to not alter the cleavage site that provides the —Y$_y$-D or —[P-1]-Y$_y$-D fragment, but instead are selected to confer a desired physiochemical and/or pharmokinetic property to the Ligand Drug Conjugate, such as improved solubility for decreasing aggregation.

In some embodiments in which there is additional amino acid residue(s)N-terminus to P3 or additionally have a P-1 between P1 and Y or D, a drug linker moiety has the structure of:

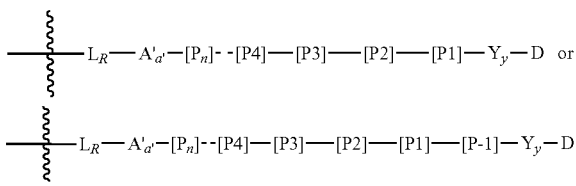

or a salt thereof, in particular a pharmaceutically acceptable salt, wherein $L_R$, A', a', Y, y and D retain their previous meanings and P-1 and P1, P2, P3 . . . $P_n$ are amino acid residues, wherein subscript n ranges up to 12 (e.g., 3-12 or 3-10) and P1, P2 and P3, optionally with P-1, together provide selectivity for proteolysis by tumor tissue homogenate over proteolysis by normal tissue homogenate, wherein proteolytic cleavage occurs at the covalent bond between P1 and $Y_y$-D or between and P1 and P-1 to release a linker fragment having the structure of $Y_y$-D or [P-1]-$Y_y$-D, respectively, in which the later subsequently undergoes exopeptidase cleavage to release the linker fragment having the structure of $Y_y$-D. In both instances the $Y_y$-D linker fragment undergoes spontaneous decomposition to complete release of D as free drug.

In any one of those embodiments when subscript b is 0, $L_R$ of a drug linker moiety has the formula of -$L_B$-$A_a$-, wherein $L_B$ is a ligand covalent binding moiety and A is a first optional Stretcher Unit. In such embodiments if a is 1 and subscript a' is 1, then A' is present as subunit of A and therefore is considered a component of the primary linker.

In some preferred embodiments in which subscript b is 0 and subscript a is 1, $L_R$ of formula -$L_B$-A- is a self-stabilizing linker ($L_{SS}$) moiety or a self-stabilized linker ($L_S$) moiety obtained from controlled hydrolysis of the succinimide ($M^2$) moiety of $L_{SS}$. Exemplary $L_{SS}$ and $L_S$ primary linkers of a drug linker moiety of a Ligand Drug Conjugate composition, or Conjugate compound thereof, having either type of primary linker is represented by the structures of

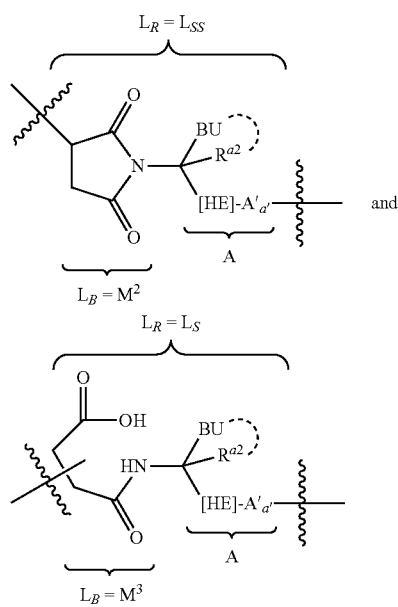

respectively, or a salt thereof, in particular a pharmaceutically acceptable salt, wherein the wavy line indicates the site of covalent attachments to A' or W, depending on the value of subscript a'; A' is an optional subunit of A; [HE] is an optional Hydrolysis Enhancing Unit, which is a component provided by A; BU is a Basic Unit; $R^{a2}$ is an optionally substituted $C_1$-$C_{12}$ alkyl group; and the dotted curved line indicates optional cyclization so that in the absence of said cyclization, BU is an acyclic Basic Unit having a primary, secondary or tertiary amine functional group as the basic function group of the acyclic Basic Unit, or in the presence of said cyclization, BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom or is optionally protonated.

In other preferred embodiments in which subscript b is 0 and subscript a is 1 the primary linker of formula -$L_B$-A- does not contain a Basic Unit, which are exemplified by the structure of:

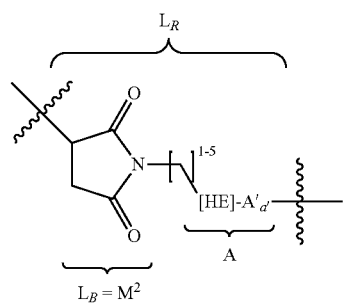

or a salt thereof, in particular, a pharmaceutically acceptable salt, wherein the variable groups are as previously described for $L_{SS}$ or $L_S$ primary linkers.

Representative L-$L_R$- structures, in which $L_R$ is covalently attached to a Ligand Unit (L) of a LDC, are the following:

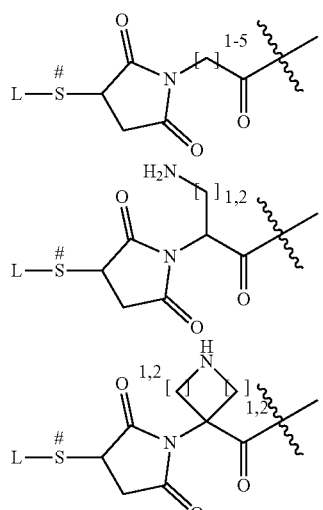

and salts thereof, in particular, pharmaceutically acceptable salts, and structures in which the succinimide ring system is hydrolyzed to a ring opened form, wherein the indicated (#) sulfur atom is from the Ligand Unit; and wherein the wavy line indicates the site of covalent attachment to the remainder of the Conjugate structure.

Other representative L-L$_R$- structures are the following:

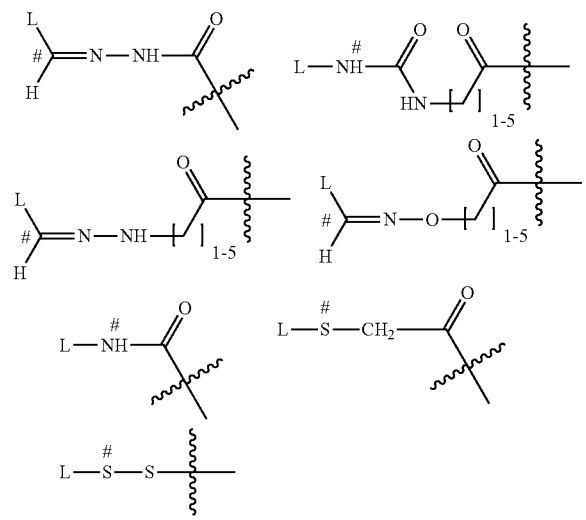

wherein the indicated (#) nitrogen, carbon or sulfur atom is from the Ligand Unit; and wherein the wavy line indicates the site of covalent attachment to the remainder of the Conjugate structure.

In another group of embodiments, a Drug Linker Compound, which is useful in preparing a Ligand Drug Conjugate as described in the previous group of embodiments, has the formula of L$_R$'-A'$_{a'}$-W—Y$_y$-D as described herein, wherein L$_R$' is a primary linker of the Drug Linker Compound, which is converted to the primary linker L$_R$ of a drug linker moiety of a Ligand Drug Conjugate when the Drug Linker compound is used in the preparation of that Conjugate, A' is a second optional Stretcher Unit, a' is 0 or 1, indicating the absence or presence of A', respectively, wherein when L$_R$' does not contain a Branching Unit and subscript a' is 1, A' is considered part of L$_R$' as a subunit of A which is present as a component of L$_R$', Y is a Spacer Unit, subscript y is 0, 1 or 2, indicating the absence or presence of 1 or 2 Spacer Units, respectively, D is a Drug Unit, and W is a Peptide Cleavable Unit comprising a tripeptide that is more susceptible to proteolytic cleavage by a homogenate of tumor tissue as compared to a homogenate of normal tissue, wherein cytotoxicity towards cells of the normal tissue due to unintended release of D as free drug within and/or in the vicinity of these cells is associated with an adverse event from administration of the Ligand Drug Conjugate intended for targeting the cancer cells of the tumor tissue. In some of those embodiments L$_R$'- is L$_B$'-A$_a$-B$_b$— wherein L$_B$' is a ligand covalent binding moiety of the primary linker of the Drug Linker compound, sometimes referred to as ligand covalent binding precursor moiety since it is a precursor to a ligand covalent binding moiety (L$_B$) of a primary linker (L$_R$) of a drug linker moiety of a Ligand Drug Conjugate when the Drug Linker compound is used in the preparation of that Conjugate, A is a first optional Stretcher Unit, subscript a is 0 or 1, indicating the absence or presence of A, respectively, B is an optional Branching Unit, and subscript b is 0 or 1, indicating the absence or presence of B, respectively.

In some embodiments, a Drug Linker compound has the structure of

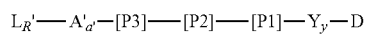

or a salt thereof, in particular a pharmaceutically acceptable salt, wherein L$_R$', A', a', Y, y and D retain their previous meanings and P1, P2 and P3 are amino acid residues that together provide selectivity for proteolysis by tumor tissue homogenate over proteolysis by normal tissue homogenate, wherein proteolytic cleavage occurs at the covalent bond between P1 and Y if subscript y is 1 or 2 or at the covalent bond between P1 and D if subscript y is 0.

As described elsewhere, other embodiments contain an additional amino acid residue between P1 and Y or D, depending on the value of subscript y, which is designated as P-1, so that selective endopeptidase action by a proteolytic enzyme(s) of tumor tissue homogenate occurs at the amide bond between P1 and P-1 to release a drug linker fragment of formula —[P-1]-Y$_y$-D. Release of free drug from that fragment would occur from exopeptidase action of a proteolytic enzyme to remove the P-1 amino acid residue to directly provide free drug if subscript y is 0 (i.e., Y is absent).

In some embodiments in which an additional amino acid residue between P1 and Y or D, is present, a Drug Linker Compound has the structure of:

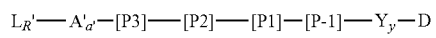

or a salt thereof, in particular a pharmaceutically acceptable salt, wherein L$_R$', A', a', Y, y and D retain their previous meanings and P1, P2 and P3 are amino acid residues, optionally with P-1, that together provide selectivity for proteolysis by tumor tissue homogenate over proteolysis by normal tissue homogenate, wherein proteolytic cleavage occurs at the covalent bond between P1 and P-1 to release a linker fragment having the structure of [P-1]-Y$_y$-D.

In some of those embodiments when subscript y is 0, the [P-1]-D residue resulting from endo-peptidase cleavage of the amide bond between the P1 and P-1 amino acids also exerts cytotoxic activity. In other embodiments, subscript y is 1 or 2 so that exopeptidase action to remove the P-1 amino acid residue provides another drug linker fragment of formula —Y$_y$-D, which spontaneously fragments to provide free drug.

In other embodiments one or more amino acid residues, designated P4, P5 . . . P$_n$, wherein subscript n ranges up to 12 (e.g., 3-12 or 3-10), are between P3 and L$_R$ or A', depending on the value of subscript a', which is some embodiments is in addition to the Peptide Cleavable Unit containing a P-1 amino acid residue. In either instance, the additional P4, P5 . . . P$_n$ amino acid residues are selected so as to not alter the cleavage site that provides the —Y$_y$-D or —[P-1]-Y$_y$-D fragment, but instead are selected to confer a desired physiochemical and/or pharmokinetic property to the Ligand Drug Conjugate, such as improved solubility for decreasing aggregation.

In some embodiments in which there is additional amino acid residue(s)N-terminus to P3 or additionally have a P-1 between P1 and Y or D, a Drug Linker compound has the structure of:

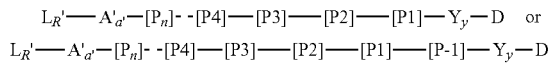

or a salt thereof, in particular a pharmaceutically acceptable salt, wherein $L_R'$, A', a', Y, y and D retain their previous meanings and P-1 and P1, P2, P3 . . . $P_n$ are amino acid residues, wherein subscript n ranges up to 12 (e.g., 3-12 or 3-10) and P1, P2 and P3, optionally with P-1, together provide selectivity for proteolysis by tumor tissue homogenate over proteolysis by normal tissue homogenate, wherein proteolytic cleavage occurs at the covalent bond between P1 and $Y_y$-D or between and P1 and P-1 to release a linker fragment having the structure of $Y_y$-D or [P-1]-$Y_y$-D, respectively, in which the later subsequently undergoes exopeptidase cleavage to release the linker fragment having the structure of $Y_y$-D. In both instances the $Y_y$-D linker fragment undergoes spontaneous decomposition (also referred to as self-immolation) to complete release of D as free drug.

In any one of those embodiments when subscript b is 0, $L_R'$ of a Drug Linker compound has the formula of $L_B'$-$A_a$-, wherein $L_B'$ is a ligand covalent binding precursor moiety and A is a first optional Stretcher Unit. In such embodiments if subscript a is 1 and subscript a' is 1, then A' is present as subunit of A and therefore is considered a component of the primary linker.

In some preferred embodiments in which subscript b is 0 and subscript a is 1, $L_R'$ of formula $L_B'$-A- of a Drug Linker compound is a self-stabilizing linker precursor ($L_{SS}'$) moiety so named since it converts to self-stabilizing linker ($L_{SS}$) moiety of a Ligand Drug Conjugate when the Drug Linker compound is used in the preparation of the Conjugate. Exemplary $L_{SS}'$ primary linkers of a Drug Linker compound are represented by the structures of:

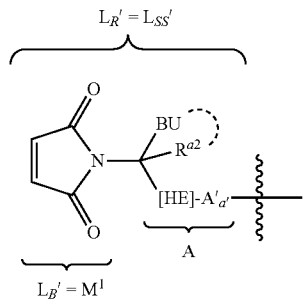

or a salt thereof, in particular a pharmaceutically acceptable salt, wherein the wavy line indicates the site of covalent attachments to A' or W, depending on the value of subscript a'; A' is an optional subunit of A; [HE] is an optional Hydrolysis Enhancing Unit, which is a component provided by A; BU is a Basic Unit; $R^{a2}$ is an optionally substituted $C_1$-$C_{12}$ alkyl group; and the dotted curved line indicates optional cyclization so that in the absence of said cyclization, BU is an acyclic Basic Unit having a primary, secondary or tertiary amine functional group as the basic function group of the acyclic Basic Unit, or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom or is optionally protonated.

In other preferred embodiments in which subscript b is 0 and subscript a is 1 the primary linker of formula $L_B$-A- does not contain a Basic Unit, which are exemplified by the structure of:

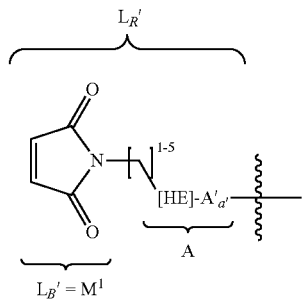

or a salt thereof, in particular, a pharmaceutically acceptable salt, wherein the variable groups are as previously described for $L_{SS}$ or $L_S$ primary linkers.

Representative $L_R'$- structures of a Drug Linker compound are the following:

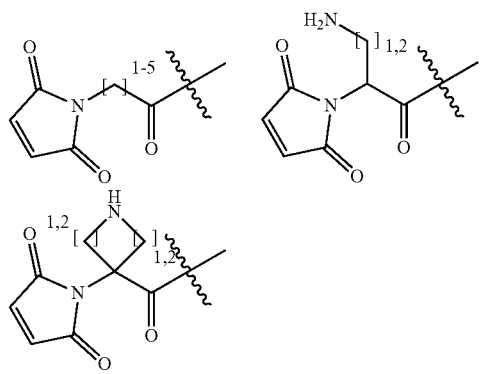

and salts thereof, in particular pharmaceutically acceptable salts, wherein the wavy line indicates the site of covalent attachment to the remainder of LU' of the Drug Linker compound structure and wherein the basic nitrogen atom in the second or third structure is optionally protonated as an acid addition salt or is optionally protected. When protected, the protecting group is preferably an acid-labile protecting group such as BOC.

2.2.3 Peptide Cleavable Units

In some embodiments a Peptide Cleavable Unit (W) of a Ligand Drug Conjugate is a peptide sequence containing a tripeptide directly attached to D or indirectly through one or two self-immolative Spacer Units, wherein the tripeptide is recognized by at least one intracellular protease, preferably by more than one, wherein the at least one protease is upregulated in tumor cells in comparison to normal cells, and is more susceptible to proteolysis by a homogenate of tumor tissue comprised of the tumor cells to be targeted by the Ligand Drug Conjugate in comparison to a homogenate of normal tissue wherein cytotoxicity to the normal tissue is associated with an adverse event from administration of a comparator Ligand Drug Conjugate. In other embodiments, the tripeptide improves the biodistribution of the Conjugate to the tumor tissue to the detriment of biodistribution to the normal tissue, which in some of these embodiments is in addition to the selectivity for proteolysis by tumor tissue homogenate in comparison to proteolysis by normal tissue homogenate. In either one of those embodiments, the normal tissue is sometimes bone marrow and the adverse event to be ameliorated is neutropenia. In another embodiment, the normal tissue is bone marrow, liver, kidney, esophageal, breast, or corneal tissue and the adverse event to be ameliorated is neutropenia. In some embodiments, the tripeptide is directly attached to D or indirectly attached to D through one or two self-immolative Spacer Units. In other embodiments, the Peptide Cleavable Unit (W) comprising a tripeptide as described herein is directly attached to D or indirectly attached to D through one or two self-immolative Spacer Units via an amino acid that is not part of the tripeptide.

The Peptide Cleavable Unit (W) of the comparator Conjugate is typically a dipeptide that confers selectivity for a specific intracellular protease that is upregulated in cancer cells over freely circulating proteases, wherein the specific protease is capable of cleaving the amide bond between the C-terminal amino acid of the dipeptide and the amino group of a self-immolative Spacer Unit (Y) to initiate release of the Drug Unit as free drug.

In some embodiments, the Ligand Drug Conjugate comprising the tripeptide as disclosed herein shows improved tolerability in comparison to a comparator Ligand Drug Conjugate in which the Peptide Cleavable Unit is a dipeptide that confers selectivity for a specific intracellular protease that is upregulated in cancer cells over freely circulating proteases, wherein the specific protease is capable of cleaving the amide bond between the C-terminal amino acid of the dipeptide and the amino group of a self-immolative Spacer Unit (Y) to initiate release of the Drug Unit as free drug. In some embodiments, the dipeptide is known to be selectively cleavable by Cathepsin B. In some embodiments, the dipeptide in the comparator Ligand-Drug Conjugate is -valine-citrulline- or -valine-alanine-. In some embodiments, the dipeptide in the comparator Ligand-Drug Conjugate is -valine-citrulline-. In some embodiments, the dipeptide in the comparator Ligand-Drug Conjugate is -valine-alanine-. In some embodiments, tolerability refers to the degree to which adverse events associated with the Ligand-Drug Conjugate's administration affect the ability or desire of the patient to adhere to the dose or intensity of therapy. As such, improved tolerability may be achieved by reducing the occurrence or severity of the adverse events.

Without being bound by theory, aggregated Ligand Drug Conjugate compounds are more likely to be distributed in a normal tissue (e.g., bone marrow), wherein the normal tissue is known to be the source of on-target and/or off-target adverse event(s) experienced by a mammalian subject when administered a therapeutically effective amount of a Ligand Drug Conjugate. In some embodiments, the improved tolerability is demonstrated by the decreased aggregation rate of the Ligand Drug Conjugate comprising the tripeptide in comparison to the comparator Ligand Drug Conjugate. In some embodiments, the aggregation rates of the Ligand Drug Conjugate comprising the tripeptide and the comparator Ligand Drug Conjugate are determined by measuring the concentrations of high molecular weight aggregates after incubating the conjugates in rat plasma, cynomolgus monkey plasma, or human plasma at a same concentration for 12, 24, 36, 48, 60, 72, 84, or 96 hours.

In some embodiments, the improved tolerability of the Ligand Drug Conjugate comprising the tripeptide is demonstrated by an improved selectivity for exposure of a tumor tissue over a normal tissue to free cytotoxic compound released from the Ligand Drug Conjugate comprising the tripeptide in comparison to the cytotoxic compound released from the comparator Ligand Drug Conjugate. In some embodiments, the tumor tissue and the normal tissue are from a rodent species (e.g., rat or mouse) or a primate species (e.g., cynomolgus monkey or human). In some embodiments, when the tumor tissue and the normal tissue are from a species different from human, the normal tissue is of the same tissue type in human and wherein cytotoxicity to cells of that tissue is responsible at least in part to an adverse event in a human subject to whom is administered a therapeutically effective amount of the comparator Ligand Drug Conjugate. In some embodiments, the normal tissue is bone marrow, liver, kidney, esophageal, breast, or corneal tissue. In some embodiments, the normal tissue is bone marrow.

In some embodiments, the improved exposure selectivity is demonstrated by a reduction in plasma concentration of the free cytotoxic compound released from the Ligand Drug Conjugate comprising the tripeptide in comparison to the comparator Ligand Drug Conjugate when the conjugates are administered at a same dose. In some embodiments, the Ligand Drug Conjugate comprising the tripeptide retains efficacy (e.g., achieves substantially same reduction in tumor volume in comparison with the comparator Ligand Drug Conjugate) in a tumor xenograft model when administered at the same effective amount and dose schedule previously determined for the comparator Ligand-Drug Conjugate.

In some embodiments, the improved exposure selectivity is demonstrated by decreased non-target mediated cytotoxicity or preservation of normal cells in the normal tissue in comparison to the comparator Ligand-Drug Conjugate when the conjugates are administered at a same dose. In some embodiments, the normal tissue is bone marrow, liver, kidney, esophageal, breast, or corneal tissue. In some embodiments, the normal tissue is bone marrow. In some embodiments, the decreased non-target mediated cytotoxicity or preservation of normal cells in the normal tissue is demonstrated by bone marrow histology (e.g., reduced loss of nuclei staining of mononuclear cells). In some embodiments, the decreased non-target mediated cytotoxicity or preservation of normal cells is demonstrated by reduction in neutrophil and/or reticulocyte loss and/or more rapid rebound from that loss. In some embodiments, the decreased non-target mediated cytotoxicity or preservation of normal cells is demonstrated by a reduction in neutrophil loss. In some embodiments, the decreased non-target mediated cytotoxicity or preservation of normal cells is demonstrated by a reduction in reticulocyte loss. In some embodiments, the Ligand Drug Conjugate comprising the tripeptide retains efficacy in a tumor xenograft model when administered at the same effective amount and dose schedule previously determined for the comparator Ligand-Drug Conjugate. In some embodiments, when comparing the exposure selectivity between the Ligand Drug Conjugate comprising the tripeptide and the comparator Ligand Drug Conjugate, the Ligand Units of both conjugates are replaced by a non-binding antibody.

In some embodiments, provided are Ligand-Drug Conjugates (e.g., ADCs) that are less active than the comparator Ligand Drug Conjugate (e.g., dipeptide ADC containing -val-cit-), either in vivo or in vitro, but are also significantly less toxic. Without being bound by theory, the Ligand-Drug Conjugate is not required to be as active because the therapeutic window will still be increased if it is less active and less toxic.

In preferred embodiments, the amide bond between the carboxylic acid of the C-terminal amino acid of the tripeptide and the amino group of a self-immolative Spacer Unit (Y) is cleavable by at least one, preferably by more than one, intracellular protease to initiate release of a Drug Unit as free drug. When the Drug Unit is that of MMAE, the drug linker moieties of the comparator Conjugate have the formula of mc-val-cit-PABC-MMAE or mp-val-cit-PABC-MMAE, which have the structures of:

sequence is cleavable by the at least one intracellular protease to initiate release of free drug by first releasing an amino acid-containing linker fragment that subsequently undergoes exopeptidase removal of its amino acid component to provide a second linker fragment. Thus, the P1-[P-1] bond in the tetrapeptide -P3-P2-P1-[P-1]- is cleaved to release the drug linker fragment of —[P-1]-$Y_y$-D. The second linker fragment then undergoes self-immolation of its Spacer Unit(s) that had intervened between D and the tetrapeptide of W to complete release of D as free drug.

In any one of the above embodiments the at least one protease, which is preferably upregulated within targeted cancer cells, includes certain cathepsins such as Cathepsin B. In other embodiments the P1-D, P1-Y- or P1-[P-1] bond is cleavable by anon-excreted intracellular protease or collection of such intracellular proteases of targeted cancer cells and one or more extracellular proteases that are associated with or are upregulated within the tissue microenvironment of tumor cells and which are absent or are present at reduced levels in the tissue microenvironment of normal

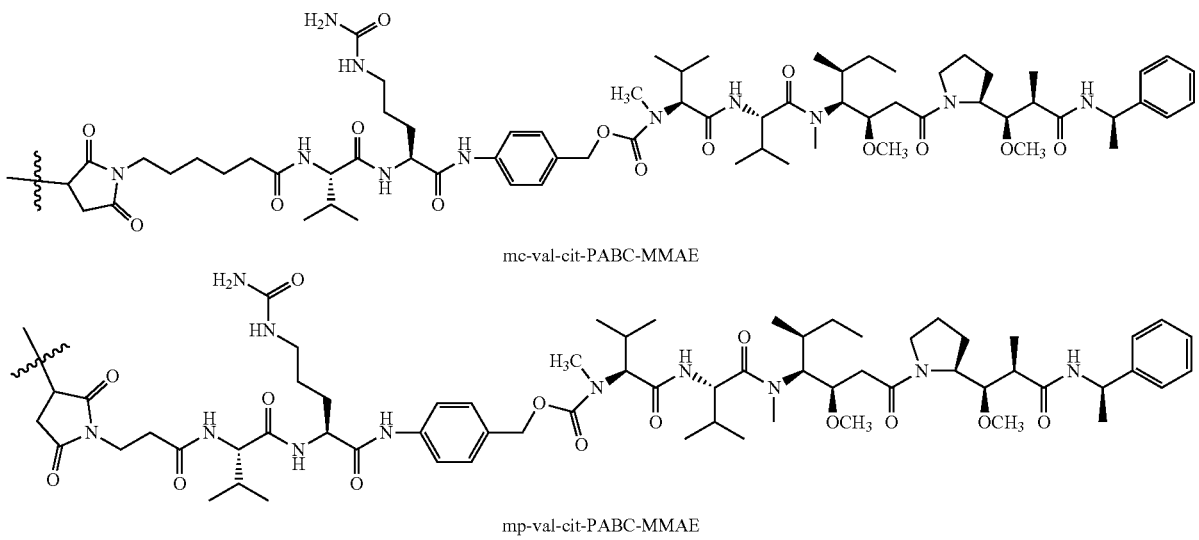

mc-val-cit-PABC-MMAE mp-val-cit-PABC-MMAE

In other embodiments a Peptide Cleavable Unit (W) of a Ligand Drug Conjugate is a peptide sequence comprised of a tetrapeptide residue directly attached to D or indirectly through at least one self-immolative Spacer Unit, wherein the tetrapeptide sequence -P3-P2-P1-[P-1]- is recognized by at least one intracellular protease, preferably by more than one, wherein the at least one intracellular protease is upregulated within tumor cells in comparison to normal cells, and is more selective for proteolysis by a homogenate of tumor tissue that are comprised of the tumor cells to be targeted by the Ligand Drug Conjugate in comparison to a homogenate of normal tissue wherein cytotoxicity to the normal tissue is associated with an adverse event from administration of a comparator Ligand Drug Conjugate. The Peptide Cleavable Unit of the comparator Conjugate is a dipeptide that confers selectivity for a specific intracellular protease over freely circulating proteases. In those tetrapeptide embodiments said selectivity is primarily attributed to the N-terminal tripeptide sequence of the tetrapeptide.

In preferred embodiments in which the peptide sequence is comprised of the tetrapeptide residue, the amide bond between the carboxylic acid of the C-terminal amino acid and the remaining amino acid residue of that tetrapeptide cells, wherein cytotoxicity towards these normal cells is typically associated with an adverse event from administration of an effective amount of a comparator Conjugate in which the Peptide Cleavable Unit is a dipeptide that confers selectivity for an intracellular protease over freely circulating proteases. In other embodiments the P1-D, P1-Y- or P1-[P-1] bond is cleavable by anon-excreted intracellular protease or collection of such intracellular proteases of targeted cancer cells and is less susceptible to proteolysis by extracellular protease(s) that are associated with normal tissue in comparison to a comparator Conjugate in which the Peptide Cleavable Unit is the aforementioned dipeptide. In some of those embodiments, the secreted protease within normal tissue is a neutrophil protease such as those selected from the group consisting of Neu Elastase, cathepsin G and proteinase 3.

In other preferred embodiments a tripeptide in a Ligand Drug Conjugate of the present invention confers global selectivity for proteolysis by a homogenate of tumor tissue that is comprised of the tumor cells to be targeted by the Ligand Drug Conjugate in comparison to a homogenate of normal tissue wherein cytotoxicity to the normal tissue is associated with an adverse event from administration of a comparator Ligand Drug Conjugate. The Peptide Cleavable Unit (W) in drug linker moieties of the comparator Conjugate is the aforementioned dipeptide that confers selectivity for a specific intracellular protease upregulated in cancer cells of the tumor tissue over freely circulating proteases. Other preferred tripeptides increase the biodistribution of the Conjugate into tumor tissue to the detriment of biodistribution into normal tissue wherein cytotoxicity to the normal tissue is associated with an adverse event from administration of a comparator Ligand Drug Conjugate in which W is a dipeptide that confers selectivity for a specific intracellular protease over freely circulating proteases. When the Drug Unit is that of MMAE the drug linker moieties of the comparator Conjugate have the formula of mc-val-cit-PABC-MMAE or mp-val-cit-PABC-MMAE.

It was determined that Ligand Drug Conjugates having linkers containing certain 3-residue amino acid sequences have advantageous properties, such as reduced toxicity in one or more normal tissues (which may be due to differential proteolysis) and improved biophysical properties (e.g., reduced aggregation, longer residence time prior to clearance). These advantageous properties may be obtained in Ligand Drug Conjugates having linkers containing a 3-amino acid sequence in which the N-terminal amino acid of the 3-residue sequence is a D-amino acid, and the central and C-terminal residues of the 3-residue sequence are, in either order, an amino acid that is negatively charged (e.g., at plasma physiological pH) and an amino acid that is polar or that has an aliphatic side chain with hydrophobicity no greater than that of leucine. In some embodiments, the tripeptide contains an amino acid in the D-amino acid configuration. In some embodiments, the tripeptide contains D-Leu or D-Ala. In some embodiments, the tripeptide contains D-Leu. In some embodiments, the tripeptide contains D-Ala. In some embodiments, the tripeptide contains an amino acid having an aliphatic side chain with hydrophobicity no greater than that of leucine. In some embodiments, the tripeptide contains an amino acid having an aliphatic side chain with hydrophobicity no greater than that of valine. In some embodiments, the tripeptide contains alanine. In some embodiments, the tripeptide contains a polar amino acid. In some embodiments, the tripeptide contains serine. In some embodiments, the tripeptide contains an amino acid that is negatively charged (e.g., at plasma physiological pH). In some embodiments, the tripeptide contains an amino acid selected from the group consisting of aspartic acid and glutamic acid. In some embodiments, the P3 amino acid of the tripeptide is in the D-amino acid configuration. In some embodiments, the P3 amino acid is D-Leu or D-Ala. In some embodiments, the P3 amino acid is D-Leu. In some embodiments, the P3 amino acid is D-Ala. In some embodiments, the P2 amino acid of the tripeptide has an aliphatic side chain with hydrophobicity no greater than that of leucine. In some embodiments, the P2 amino acid has an aliphatic side chain with hydrophobicity no greater than that of valine. In some embodiments, P2 amino acid is alanine. In some embodiments, the P2 amino acid of the tripeptide is a polar amino acid. In some embodiments, P2 amino acid is serine. In some embodiments, the P2 amino acid of the tripeptide is negatively charged (e.g., at plasma physiological pH). In some embodiments, the P2 amino acid is selected from the group consisting of aspartic acid and glutamic acid. In some embodiments, the P1 amino acid of the tripeptide has an aliphatic side chain with hydrophobicity no greater than that of leucine. In some embodiments, the P1 amino acid has an aliphatic side chain with hydrophobicity no greater than that of valine. In some embodiments, P1 amino acid is alanine. In some embodiments, the P1 amino acid of the tripeptide is a polar amino acid. In some embodiments, P1 amino acid is serine. In some embodiments, the P1 amino acid of the tripeptide is negatively charged (e.g., at plasma physiological pH). In some embodiments, the P1 amino acid is selected from the group consisting of aspartic acid and glutamic acid. In some embodiments, one of the P2 or P1 amino acid of the tripeptide has an aliphatic side chain with hydrophobicity no greater than that of leucine (e.g., no greater than that of valine), and the other of the P2 or P1 amino acid is a polar amino acid or is negatively charged (e.g., at plasma physiological pH). In some embodiments, the P2 amino acid has an aliphatic side chain with hydrophobicity no greater than that of leucine (e.g., no greater than that of valine), and the P1 amino acid is a polar amino acid or is negatively charged (e.g., at plasma physiological pH). In some embodiments, the P1 amino acid has an aliphatic side chain with hydrophobicity no greater than that of leucine (e.g., no greater than that of valine), and the P2 amino acid is a polar amino acid or is negatively charged (e.g., at plasma physiological pH). In some embodiments, -P2-P1- is -Ala-Glu-. In some embodiments, -P2-P1- is -Ala-Asp-. In some embodiments, the P3 amino acid of the tripeptide is in the D-amino acid configuration, one of the P2 or P1 amino acid has an aliphatic side chain with hydrophobicity no greater than that of leucine (e.g., no greater than that of valine), and the other of the P2 or P1 amino acid is negatively charged (e.g., at plasma physiological pH). In some embodiments, the P3 amino acid is in the D-amino acid configuration, the P2 amino acid has an aliphatic side chain with hydrophobicity no greater than that of leucine (e.g., no greater than that of valine), and the P1 amino acid is negatively charged (e.g., at plasma physiological pH). In some embodiments, the P3 amino acid is in the D-amino acid configuration, the P1 amino acid has an aliphatic side chain with hydrophobicity no greater than that of leucine (e.g., no greater than that of valine), and the P2 amino acid is negatively charged (e.g., at plasma physiological pH). In some embodiments, -P3-P2-P1- is selected from the group consisting of -D-Leu-Ala-Asp-, -D-Leu-Ala-Glu-, -D-Ala-Ala-Asp-, and -D-Ala-Ala-Glu-.

In some embodiments, the tripeptide contains an amino acid selected from the group consisting of alanine, citrulline, proline, isoleucine, leucine and valine. In some embodiments, the tripeptide contains an amino acid in the D-amino acid configuration. In some embodiments, the tripeptide contains D-Leu. In some embodiments, the tripeptide contains D-Ala. In some embodiments, the tripeptide contains an amino acid in the D-amino acid configuration. In another embodiment, the tripeptide contains an amino acid selected from the group consisting of D-leucine and D-alanine. In another embodiment, tripeptide contains D-leucine. In another embodiment, tripeptide contains D-alanine. In some embodiments, the tripeptide contains an amino acid having a side chain with at least one charged (e.g., negatively charged at plasma physiological pH) substituent or at least one uncharged substituent with a permanent electric dipole moment and one or two additional amino acids having hydrophobicity no greater than that of leucine. In some embodiments, the tripeptide contains an amino acid having a side chain with at least one charged (e.g., negatively charged at plasma physiological pH) substituent or at least one uncharged substituent with a permanent electric dipole moment and one or two additional amino acids having aliphatic side chains with hydrophobicity no greater than that of leucine. In some embodiments, the tripeptide contains an amino acid having a side chain with at least one uncharged substituent with a permanent electric dipole moment and one or two additional amino acids having hydrophobicity no greater than that of leucine. In some embodiments, the tripeptide contains an amino acid having a side chain with at least one uncharged substituent with a permanent electric dipole moment and one or two additional amino acids having aliphatic side chains with hydrophobicity no greater than that of leucine. In some embodiments, the side chains of the tripeptide all have neutral charge (e.g., at plasma physiological pH). In some embodiments, the tripeptide does not contain any ionizable side chains. In some embodiments, the tripeptide contains an amino acid having an aliphatic side chain with hydrophobicity no greater than that of leucine, such as alanine or valine. In some embodiments, the tripeptide contains an amino acid having an aliphatic side chain with hydrophobicity no greater than that of valine, such as alanine. In some embodiments, the tripeptide is contains a polar amino acid, such as aspartic acid, glutamic acid, asparagine, glutamine, serine, threonine, tyrosine, citrulline, methionine sulfoxide, or γ-carboxy-glutamic acid. In some embodiments, the tripeptide contains an amino acid that is negatively charged (e.g., at plasma physiological pH), such as glutamic acid, aspartic acid, or γ-carboxy-glutamic acid. In some embodiments, the tripeptide contains an amino acid having a side chain with at least one charged substituent or at least one uncharged substituent with a permanent electric dipole moment, preferably greater than that of —C(O)NH$_2$. In some embodiments, the tripeptide contains an amino acid having a side chain with at least one charged substituent or at least one uncharged substituent with a permanent electric dipole moment, preferably greater than that of —NH—C(O)NH$_2$. In some embodiments, the tripeptide contains an amino acid selected from the group consisting of alanine, α-aninobuyric acid, α-aminoisobutyric acid, aspartic acid, citrulline, γ-carboxy-glutamic acid, glutamic acid, glutamine, glycine, leucine, norvaline proline, isoleucine, leucine, lysine, methionine sulfoxide, naphthylalanine, O-allyl tyrosine, phenylalanine, propargylglycine, 2-aminobut-3-ynoic acid, proline, selenomethionine, serine, threonine, and valine. In some embodiments, the tripeptide contains and amino acid selected the group consisting of alanine, aspartic acid, citrulline, γ-carboxyglutamic acid, glutamic acid, glutamine, glycine, leucine, proline, isoleucine, leucine, lysine, methionine sulfoxide, naphthylalanine, O-allyl tyrosine, phenylalanine, proline, selenomethionine, serine, threonine, and valine. It is understood that the amino acid in any of the embodiments herein can be a natural or un-natural amino acid. For example, alanine can be D-alanine or L-alanine and leucine can be D-leucine or L-leucine.

In some embodiments, P3 is selected from the group consisting of alanine, arginine, asparagine, aspartic acid, cysteine, gamma-carboxyglutamate, glutamine, glycine, histidine, homoserine, hydroxylysine, hydroxyproline, isoleucine, leucine, lysine, methionine, ornithine, phenylalanine, proline, sarcosine, serine, threonine, tryptophan, tyrosine, valine, p-fluorophenylalanine, p-fluorophenylalanine, and o-fluorophenylalanine; P2 is selected from the group consisting of aminobutyric acid (Abu), 2-aminoisobutyric acid (Aib), norvaline (Nva), aminohippuric acid (Pra), alanine, arginine, asparagine, aspartic acid, cysteine, glutamine, glutamic acid, glycine, histidine, homoserine, hydroxylysine, hydroxyproline, isoleucine, leucine, methionine, ornithine, phenylalanine, proline, sarcosine, serine, threonine, tryptophan, tyrosine, and valine; and P1 is selected from the group consisting of glutamic acid, methionine sulfoxide, aspartic acid, proline, glycine, serine, valine, tyrosine, phenylalanine, tryptophan, histidine, glutamine, isoleucine, methionine, and gamma-carboxyglutamate. In some embodiments, P3 is selected from the group consisting of alanine, arginine, asparagine, aspartic acid, cysteine, gamma-carboxyglutamate, glutamine, glutamic acid, glycine, histidine, homoserine, hydroxylysine, hydroxyproline, isoleucine, leucine, lysine, methionine, ornithine, phenylalanine, proline, sarcosine, serine, threonine, tryptophan, tyrosine, valine, p-fluorophenylalanine, p-fluorophenylalanine, and o-fluorophenylalanine; P2 is selected from the group consisting of aminobutyric acid (Abu), 2-aminoisobutyric acid (Aib), norvaline (Nva), aminohippuric acid (Pra), alanine, arginine, asparagine, aspartic acid, cysteine, glutamine, glutamic acid, glycine, histidine, homoserine, hydroxylysine, hydroxyproline, isoleucine, leucine, methionine, ornithine, phenylalanine, proline, sarcosine, serine, threonine, tryptophan, tyrosine, and valine; and P1 is selected from the group consisting of alanine, asparagine, aspartic acid, glutamic acid, methionine sulfoxide, aspartic acid, proline, glycine, serine, valine, tyrosine, phenylalanine, tryptophan, histidine, glutamine, isoleucine, methionine, and gamma-carboxyglutamate. In some embodiments P3 is a D-amino acid. In some embodiments, P3 is selected from the group consisting of D-alanine, D-arginine, D-asparagine, D-aspartic acid, D-cysteine, D-gamma-carboxyglutamate, D-glutamine, D-glycine, D-histidine, D-homoserine, D-hydroxylysine, D-hydroxyproline, D-isoleucine, D-leucine, D-lysine, D-methionine, D-ornithine, D-phenylalanine, D-proline, D-sarcosine, D-serine, D-threonine, D-tryptophan, D-tyrosine, D-valine, D-p-fluorophenylalanine, D-p-fluorophenylalanine, and D-o-fluorophenylalanine. In some embodiments, P3 is selected from the group consisting of L-alanine, L-arginine, L-asparagine, L-aspartic acid, L-cysteine, L-gamma-carboxyglutamate, L-glutamine, L-glycine, L-histidine, L-homoserine, L-hydroxylysine, L-hydroxyproline, L-isoleucine, L-leucine, L-lysine, L-methionine, L-ornithine, L-phenylalanine, L-proline, L-sarcosine, L-serine, L-threonine, L-tryptophan, L-tyrosine, L-valine, L-p-fluorophenylalanine, L-p-fluorophenylalanine, and L-o-fluorophenylalanine. In some embodiments, P3 is L-phenylalanine or D-phenylalanine.

Structures for selected amino acids can be found below:

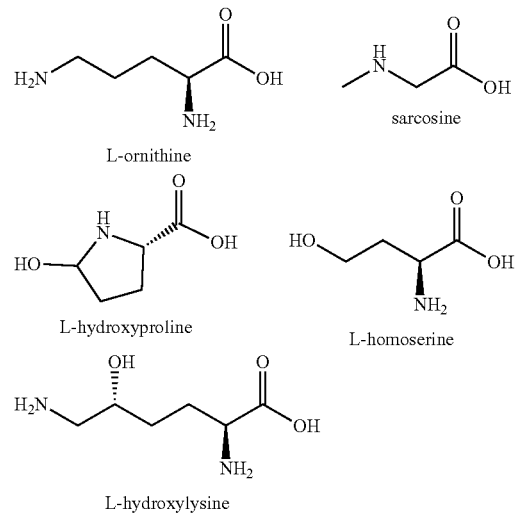

In more preferred tripeptides, the P3 amino acid is selected from the group consisting of alanine, citrulline, proline, isoleucine, leucine and valine preferably in the D-amino acid configuration with D-Leu particularly preferred. In another embodiment, the P3 amino acid is in the D-amino acid configuration. In another embodiment, the P3 amino acid in the tripeptide is selected from the group consisting of alanine, leucine, glutamic acid, lysine, O-allyl tyrosine, phenylalanine, proline, and threonine. In another embodiment, the P3 amino acid in the tripeptide is selected from the group consisting of D-alanine, D-leucine, glutamic acid, lysine, O-allyl tyrosine, phenylalanine, proline, and threonine. In another embodiment, the P3 amino acid in the tripeptide is D-leucine or D-alanine. In another embodiment, the P3 amino acid in the tripeptide is D-leucine. In another embodiment, the P3 amino acid in the tripeptide is D-alanine.

In other more preferred tripeptides, the P2 amino acid is a natural or un-natural amino acid having an aliphatic side chain with hydrophobicity no greater than that of leucine, with lower hydrophobicity more preferred with greater hydrophobicity of the P3 side chain. In another embodiment, the P2 amino acid is a natural or un-natural amino acid having an aliphatic side chain with hydrophobicity no greater than that of valine. In some embodiments, the P2 amino acid in the tripeptide is selected from the group consisting of alanine, valine, leucine and methionine. In some embodiments, the P2 amino acid in a tripeptide is selected from the group consisting of alanine, valine, and methionine. In some embodiments, the P2 amino acid in the tripeptide is alanine. In some embodiments, P2 is selected from the group consisting of Asn, Asp, Gln, Glu, Gly, and Ser. In some of those preferred tripeptides P2 is selected from the group consisting of Abu, Aib, Ala, Gly, Leu, Nva, Pra, Egl and Val in which the un-natural amino acids have the structures of.

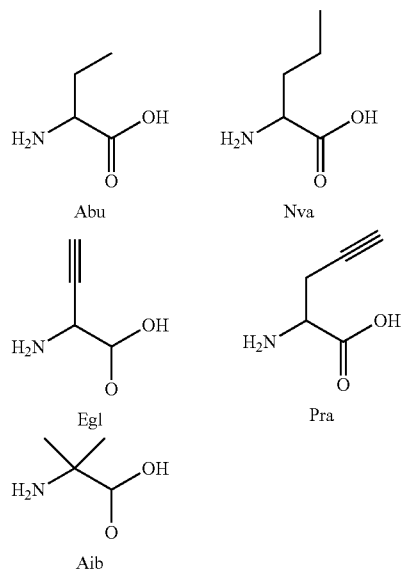

Abu
Nva
Egl
Pra
Aib

For Abu, Ala, Leu, Nva and Pra as the P2 amino acid residue the side chain is preferably in an L-configuration. In another embodiment, the P2 amino acid in the tripeptide is a polar amino acid. In some embodiments, the P2 amino acid in the tripeptide is selected from the group consisting of aspartic acid, glutamic acid, asparagine, glutamine, serine, threonine, tyrosine, citrulline, methionine sulfoxide, and γ-carboxy-glutamic acid. In another embodiment, the P2 amino acid in the tripeptide is negatively charged (e.g., at plasma physiological pH). In some embodiments, the P2 amino acid in the tripeptide is selected from the group consisting of aspartic acid, glutamic acid, and γ-carboxy-glutamic acid. In some embodiments, the P2 amino acid in the tripeptide is selected from the group consisting of aspartic acid and glutamic acid. In some embodiments, the P2 amino acid in the tripeptide is alanine. In some embodiments, the P2 amino acid in the tripeptide is serine. In some embodiments, the P2 amino acid in the tripeptide is selected from the group consisting of alanine, valine, leucine, methionine, aspartic acid, glutamic acid, asparagine, glutamine, serine, threonine, tyrosine, citrulline, methionine sulfoxide, and γ-carboxy-glutamic acid.

In still other more preferred tripeptides, the P1 amino acid is a natural or un-natural amino acid having a side chain with at least one charged substituent or at least one uncharged substituent with a permanent electric dipole moment, preferably greater than that of —C(O)NH$_2$. In another embodiment, the P1 amino acid is a natural or un-natural amino acid having a side chain with at least one charged substituent or at least one uncharged substituent with a permanent electric dipole moment, preferably greater than that of —NH—C(O)NH$_2$. In some of those preferred tripeptides P1 is selected from the group consisting of Glu, Asp, γ-carboxy-glutamic acid, lysine, methionine sulfoxide, sometimes indicated as Met(O) and phospho-threonine in which the side chain is preferably in the L- stereochemical configuration, with Glu, Asp, γ-carboxy-glutamic acid and Met(O), more preferred and Glu particularly preferred. In some of those preferred tripeptides P1 is selected from the group consisting of Glu, Asp, γ-carboxy-glutamic acid, lysine, proline, methionine sulfoxide, sometimes indicated as Met(O) and phospho-threonine in which the side chain is preferably in the L- stereochemical configuration, with Glu, Asp, γ-carboxy-glutamic acid and Met(O), more preferred and Glu particularly preferred. In some embodiments, the P1 amino acid in the tripeptide is selected from the group consisting of alanine, aspartic acid, citrulline, γ-carboxy-glutamic acid, glutamic acid, glutamine, leucine, lysine, methionine sulfoxide, and selenomethionine. In some embodiments, the P1 amino acid in the tripeptide is glutamic acid. In some embodiments, the P1 amino acid is a natural or un-natural amino acid having an aliphatic side chain with hydrophobicity no greater than that of leucine, with lower hydrophobicity more preferred with greater hydrophobicity of the P3 side chain. In another embodiment, the P1 amino acid is a natural or un-natural amino acid having an aliphatic side chain with hydrophobicity no greater than that of valine. In some embodiments, the P1 amino acid in the tripeptide is selected from the group consisting of alanine, valine, leucine, and methionine. In some embodiments, the P1 amino acid in the tripeptide is selected from the group consisting of alanine, valine, and methionine. In some embodiments, the P1 amino acid in a tripeptide is alanine. In another embodiment, the P1 amino acid in the tripeptide is a polar amino acid. In some embodiments, the P1 amino acid in the tripeptide is selected from the group consisting of aspartic acid, glutamic acid, asparagine, glutamine, serine, threonine, tyrosine, citrulline, methionine sulfoxide, and γ-carboxy-glutamic acid. In another embodiment, the P1 amino acid in the tripeptide is negatively charged (e.g., at plasma physiological pH). In some embodiments, the P1 amino acid in the tripeptide is selected from the group consisting of aspartic acid, glutamic acid, and γ-carboxy-glutamic acid. In some embodiments, the P1 amino acid in the tripeptide is selected from the group consisting of aspartic acid and glutamic acid. In some embodiments, the P1 amino acid in the tripeptide is alanine. In some embodiments, the P1 amino acid in the tripeptide is serine.

In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is selected from the group consisting of alanine, valine, leucine, methionine, aspartic acid, glutamic acid, asparagine, glutamine, serine, threonine, tyrosine, citrulline, methionine sulfoxide, and γ-carboxy-glutamic acid, and the P1 amino acid in the tripeptide is selected from the group consisting of alanine, aspartic acid, citrulline, γ-carboxy-glutamic acid, glutamic acid, glutamine, leucine, lysine, methionine sulfoxide, and selenomethionine. In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is selected from the group consisting of alanine, valine, leucine, methionine, aspartic acid, glutamic acid, asparagine, glutamine, serine, threonine, tyrosine, citrulline, methionine sulfoxide, and γ-carboxy-glutamic acid, and the P1 amino acid in the tripeptide is selected from the group consisting of aspartic acid and glutamic acid. In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is selected from the group consisting of alanine, valine, leucine, methionine, aspartic acid, glutamic acid, asparagine, glutamine, serine, threonine, tyrosine, citrulline, methionine sulfoxide, and γ-carboxy-glutamic acid, and the P1 amino acid in the tripeptide is alanine.

In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is selected from the group consisting of aspartic acid and glutamic acid, and the P1 amino acid in the tripeptide is selected from the group consisting of alanine, aspartic acid, citrulline, γ-carboxy-glutamic acid, glutamic acid, glutamine, leucine, lysine, methionine sulfoxide, and selenomethionine. In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is selected from the group consisting of aspartic acid and glutamic acid, and the P1 amino acid in the tripeptide is selected from the group consisting of aspartic acid and glutamic acid. In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is selected from the group consisting of aspartic acid and glutamic acid, and the P1 amino acid in the tripeptide is alanine.

In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is alanine, and the P1 amino acid in the tripeptide is selected from the group consisting of alanine, aspartic acid, citrulline, γ-carboxy-glutamic acid, glutamic acid, glutamine, leucine, lysine, methionine sulfoxide, and selenomethionine. In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is alanine, and the P1 amino acid in the tripeptide is selected from the group consisting of aspartic acid and glutamic acid. In another embodiment, the P3 amino acid in the tripeptide is selected from the group consisting of alanine, leucine, glutamic acid, lysine, O-allyl tyrosine, phenylalanine, proline, and threonine, the P2 amino acid in the tripeptide is alanine, and the P1 amino acid in the tripeptide is alanine.

In another embodiment, the P3 amino acid in the tripeptide is D-leucine or D-alanine, the P2 amino acid in the tripeptide is selected from the group consisting alanine, valine, leucine, methionine, aspartic acid, glutamic acid, asparagine, glutamine, serine, threonine, tyrosine, citrulline, methionine sulfoxide, and γ-carboxy-glutamic acid, and the P1 amino acid in the tripeptide is selected from the group consisting of alanine, aspartic acid, citrulline, γ-carboxy-glutamic acid, glutamic acid, glutamine, leucine, lysine, methionine sulfoxide, and selenomethionine. In another embodiment, the P3 amino acid in the tripeptide is D-leucine or D-alanine, the P2 amino acid in the tripeptide is selected from the group consisting alanine, valine, leucine, methionine, aspartic acid, glutamic acid, asparagine, glutamine, serine, threonine, tyrosine, citrulline, methionine sulfoxide, and γ-carboxy-glutamic acid, and the P1 amino acid in the tripeptide is selected from the group consisting of aspartic acid and glutamic acid. In another embodiment, the P3 amino acid in the tripeptide is D-leucine or D-alanine, the P2 amino acid in the tripeptide is selected from the group consisting alanine, valine, leucine, methionine, aspartic acid, glutamic acid, asparagine, glutamine, serine, threonine, tyrosine, citrulline, methionine sulfoxide, and γ-carboxy-glutamic acid, and the P1 amino acid in the tripeptide is alanine.

In another embodiment, the P3 amino acid in the tripeptide is D-leucine or D-alanine, the P2 amino acid in the tripeptide is selected from the group consisting of aspartic acid and glutamic acid, and the P1 amino acid in the tripeptide is selected from the group consisting of alanine, aspartic acid, citrulline, γ-carboxy-glutamic acid, glutamic acid, glutamine, leucine, lysine, methionine sulfoxide, and selenomethionine. In another embodiment, the P3 amino acid in the tripeptide is D-leucine or D-alanine, the P2 amino acid in the tripeptide is selected from the group consisting of aspartic acid and glutamic acid, and the P1 amino acid in the tripeptide is selected from the group consisting of aspartic acid and glutamic acid. In another embodiment, the P3 amino acid in the tripeptide is D-leucine or D-alanine, the P2 amino acid in the tripeptide is selected from the group consisting of aspartic acid and glutamic acid, and the P1 amino acid in the tripeptide is alanine.

In another embodiment, the P3 amino acid in the tripeptide is D-leucine or D-alanine, the P2 amino acid in the tripeptide is alanine, and the P1 amino acid in the tripeptide is selected from the group consisting of alanine, aspartic acid, citrulline, γ-carboxy-glutamic acid, glutamic acid, glutamine, leucine, lysine, methionine sulfoxide, and selenomethionine.

In another embodiment, the P3 amino acid in the tripeptide is D-leucine or D-alanine, the P2 amino acid in the tripeptide is alanine, and the P1 amino acid in the tripeptide is selected from the group consisting of aspartic acid and glutamic acid.

In some embodiments, the P3 amino acid in the tripeptide is selected from the group consisting of alanine, D-alanine, D-leucine, glutamic acid, L-leucine, O-allyl tyrosine, phenylalanine, proline, threonine, and valine.

In some embodiments, the P2 amino acid in the tripeptide is selected from the group consisting of α-aminoisobutyric acid, alanine, D-leucine, glutamic acid, glutamine, glycine, leucine, proline, serine, and valine.

In some embodiments, the P1 amino acid in the tripeptide is selected from the group consisting of alanine, aspartic acid, citrulline, gamma-carboxy-glutamic acid, glutamic acid, glutamine, leucine, and lysine.

In some embodiments, the P3 amino acid in the tripeptide is selected from the group consisting of alanine, D-alanine, D-leucine, glutamic acid, L-leucine, O-allyl tyrosine, phenylalanine, proline, threonine, and valine, the P2 amino acid in the tripeptide is selected from the group consisting of α-aminoisobutyric acid, alanine, D-leucine, glutamic acid, glutamine, glycine, leucine, proline, serine, and valine, and the P1 amino acid in the tripeptide is selected from the group consisting of alanine, aspartic acid, citrulline, gamma-carboxy-glutamic acid, glutamic acid, glutamine, leucine, and lysine, wherein -P3-P2-P1- is not -Glu-Val-Cit- or -Asp-Val-Cit-. In some embodiments of any of the variations provided herein, -P3-P2-P1- is not -Glu-Val-Cit- or -Asp-Val-Cit-.

In some embodiments of tripeptides, the P3 amino acid is in the D-amino acid configuration, one of the P2 or P1 amino acid has an aliphatic side chain with hydrophobicity no greater than that of leucine (e.g., no greater than that of valine), and the other of the P2 or P1 amino acid is a polar amino acid or is negatively charged (e.g., at plasma physiological pH). In some embodiments, the P3 amino acid is in the D-amino acid configuration, the P2 amino acid has an aliphatic side chain with hydrophobicity no greater than that of leucine (e.g., no greater than that of valine), and the P1 amino acid is a polar amino acid or is negatively charged (e.g., at plasma physiological pH). In some embodiments, the P3 amino acid is in the D-amino acid configuration, the P1 amino acid has an aliphatic side chain with hydrophobicity no greater than that of leucine (e.g., no greater than that of valine), and the P2 amino acid is a polar amino acid or is negatively charged (e.g., at plasma physiological pH). In some embodiments, -P3-P2-P1- is selected from the group consisting of -D-Leu-Ala-Asp-, -D-Leu-Ala-Glu-, -D-Ala-Ala-Asp-, and -D-Ala-Ala-Glu-. In some embodiments, -P3-P2-P1- is selected from the group consisting of -D-Leu-Asp-Ala-, -D-Leu-Glu-Ala-, -D-Ala-Asp-Ala-, and -D-Ala-Glu-Ala-.

In other particularly preferred embodiments -P2-P1- is selected from the group consisting of -Ala-Glu-, -Leu-Glu-, -Ala-Met(O)— and -Leu-Met(O)— with the side chains of both amino acids in the L-stereochemical configuration. In some embodiment, -P2-P1- is selected from the group consisting of -Ala-Ala-, -Ala-Asp-, -Ala-Cit-, -Ala-(γ-carboxsy-glutamic acid)-, -Ala-Glu-, -Ala-Gln-, -Ala-Leu-, -Ala-Lys-, -Ala-Met(O)—, -Ala-selenomethionine-, -D-Leu-Glu-, -Leu-Glu-, -Glu-Ala-, -Glu-Cit-, -Glu-Leu-, -Gly-Glu-, -Leu-Cit-, -Leu-Glu-, -Leu-Lys-, -Leu-Met(O)—, -(naphthylalanine)-Lys-, -Pro-Cit-, -Ser-Asp-, -Ser-Glu-, -Val-Cit-, and -Val-Gln-. In some embodiments, -P2-P1- is -Ala-Glu-. In some embodiments, -P2-P1- is -Ala-Asp-. In some embodiments, -P2-P1- is selected from the group consisting of -Asn-Asn-, -Asn-Glu-, -Asp-Pro-, -Asp-Ser-, -Gln-Asp-, -Gln-Glu-, -Glu-Pro-, -Gly-Asp-, -Gly-Pro-, -Nal-Lys-, -Ser-Ala-, -Ser-Pro-, and -Ser-Ser-.

In some embodiments, -P3-P2- is selected from the group consisting of -Ala-Ser-, -Ala-Ala-, -Leu-Ala-, -Leu-Glu-, -Leu-Gly-, -Leu-Leu-, Leu-Ser-, Leu-Val-, -Glu-Ala-, -Glu-Leu-, -Glu-Pro-, -Glu-Val-, -Lys-Leu-, —(O-allyl tyrosine)-Leu-, —(O-allyl tyrosine)-Pro-, -Phe-Ser-, -Pro-Leu-, -Pro-(naphthylalanine)-, and -Thr-Glu-. In some embodiments, -P3-P2- is selected from the group consisting of -Ala-Ser-, -D-Ala-Ala-, -D-Leu-Ala-, -D-Leu-Glu-, -D-Leu-Gly-, -D-Leu-Leu-, D-Leu-Ser-, -D-Leu-Val-, -Glu-Ala-, -Glu-Leu-, -Glu-Pro-, -Glu-Val-, L-Leu-Ala-, -Lys-Leu-, —(O-allyl tyrosine)-D-Leu-, —(O-allyl tyrosine)-Pro-, -Phe-Ser-, -Pro-Leu-, -Pro-(naphthylalanine)-, and -Thr-Glu-. In some embodiments, -P3-P2- is -D-Leu-Ala- or -L-Leu-Ala-. In some embodiments, -P3-P2- is -D-Leu-Ala-. In some embodiments, -P3-P2- is -D-Ala-Ala-. In some embodiments, -P3-P2- is selected from the group consisting of -Ala-Asp-, -Ala-Gln-, -D-Ala-Gln-, -Ala-Glu-, -D-Ala-Ser-, -Asp-Gly-, -Gln-Ser-, -Glu-Ser-, -D-Glu-Ser-, -Phe-Gln-, -Pro-Asp-, -Pro-Gln-, -Pro-Gly-, -Pro-Ser-, -Ser-Asn-, -Ser-Ser-, -D-Ser-Ser-, and -Val-Asn-.

In some embodiments, -P3-P2-P1- is selected from the group consisting of -Ala-Ser-Asp-, -Ala-Ser-Glu-, -Ala-Ala-Cit-, -Ala-Ala-Glu-, -Leu-Ala-Ala-, -Leu-Ala-Asp-, -Leu-Ala-Cit-, -Leu-Ala-(γ-carboxy-glutamic acid)-, -Leu-Ala-Glu-, -Leu-Ala-Gln-, -Leu-Ala-Leu-, -Leu-Ala-Lys-, -Leu-Ala-Met(O)—, -Leu-Ala-(selenomethionine)-, -Leu-Glu-Ala-, -Leu-Glu-Cit-, -Leu-Gly-Glu-, -Leu-Leu-Cit-, -Leu-Leu-Glu-, -Leu-Leu-Lys-, -Leu-Leu-Met(O)—, Leu-Ser-Glu-, -Leu-Val-Gln-, -Glu-Ala-Leu-, -Glu-Leu-Cit-, -Glu-Pro-Cit-, -Lys-Leu-Cit-, —(O-allyl tyrosine)-Leu-Glu-, —(O-allyl tyrosine)-Pro-Cit-, -Phe-Ser-Glu-, -Pro-Leu-Glu-, -Pro-(naphthylalanine)-Lys-, and -Thr-Glu-Leu-. In some embodiments, -P3-P2-P1- is selected from the group consisting of -Ala-Ser-Asp-, -Ala-Ser-Glu-, -D-Ala-Ala-Cit-, -D-Ala-Ala-Glu-, -D-Leu-Ala-Ala-, -D-Leu-Ala-Asp-, -D-Leu-Ala-Cit-, -D-Leu-Ala-(γ-carboxy-glutamic acid)-, -D-Leu-Ala-Glu-, -D-Leu-Ala-Gln-, -D-Leu-Ala-Leu-, -D-Leu-Ala-Lys-, -D-Leu-Ala-Met(O)—, -D-Leu-Ala-(selenomethionine)-, -D-Leu-Glu-Ala-, -D-Leu-Glu-Cit-, -D-Leu-Gly-Glu-, -D-Leu-Leu-Cit-, -D-Leu-Leu-Glu-, -D-Leu-Leu-Lys-, -D-Leu-Leu-Met(O)—, -D-Leu-Ser-Glu-, -D-Leu-Val-Gln-, -Glu-Ala-Leu-, -Glu-Leu-Cit-, -Glu-Pro-Cit-, -L-Leu-Ala-Glu-, -Lys-Leu-Cit-, —(O-allyl tyrosine)-D-Leu-Glu-, —(O-allyl tyrosine)-Pro-Cit-, -Phe-Ser-Glu-, -Pro-Leu-Glu-, -Pro-(naphthylalanine)-Lys-, and -Thr-Glu-Leu-. In some embodiments, -P3-P2-P1- is selected from the group consisting of Ala-Cit-Cit-, —Cit-Cit-Cit-, —Cit-Glu-Cit-, —Cit-Glu-Glu-, -D-Leu-Ala-Glu-, -D-Leu-Ala-Lys-, -D-Leu-Cit-Glu-, -D-Leu-Glu-Lys-, -D-Leu-Leu-Cit-, -D-Leu-Leu-Glu-, -D-Leu-Leu-Lys-, -D-Leu-Leu-Met(O)—, -D-Leu-Phe-Glu-, -Glu-Ala-Glu-, -Glu-Ala-Met(O)—, -Glu-Glu-Cit-, -Leu-(naphthylalanine)-Lys-, -Lys-Glu-Met(O)—, -Pro-Ala-Cit-, -Pro-Ala-Glu-, -Pro-Cit-Cit-, -Pro-Cit-Glu-, -Pro-Glu-Ala-, -Pro-Glu-Cit-, -Pro-Glu-Glu-, -Pro-Glu-Lys-, -Pro-Lys-Glu-, -Pro-(naphthylalanine)-Lys-, -Thr-Cit-Cit-, -Pro-Ser-Asp-, -Phe-Ser-Asp-, -Ala-Asp-Pro-, -Ala-Ser-Pro-, -D-Ala-Ser-Asp-, -Pro-Gly-Glu-, -Pro-Asp-Ser-, -D-Ala-Asp-Ser-, and -D-Ser-Ser-Asp-. In some embodiments, -P3-P2-P1- is selected from the group consisting of -Ala-Glu-Pro-, D-Ala-Ser-Glu-, -Asp-Gly-Pro-, -Phe-Gln-Glu-, -Val-Asn-Glu-, -D-Ala-Gln-Glu-, D-Glu-Ser-Glu-, -Ser-Ser-Pro-, -Pro-Ser-Ser-, -Ser-Ser-Glu-, -Pro-Gly-Asp-, -Pro-Gln-Asp-, -Pro-Gln-Glu-, -D-Ser-Ser-Glu-, -Gln-Ser-Ala-, -Glu-Ser-Ala-, and -Ser-Asn-Asn-.

It is understood that the Peptide Cleavable Unit (W) of a Ligand Drug Conjugate is a peptide sequence that can contain more than three amino acids. In peptide sequences containing four or more amino acids, the tripeptide described herein is any three contiguous amino acids within the sequence (i.e., the tripeptide can occupy any three adjacent positions of the sequence). Therefore, the embodiments described herein for P1, P2, and P3 can be applied to amino acids of any positions corresponding to three contiguous amino acids of the Peptide Cleavable Unit (W). For example, if the tripeptide that is recognized by the intracellular protease is located at positions -P6-P5-P4-, embodiments for P3 described herein apply to P6, embodiments for P2 described herein apply to P5, and embodiments for P1 described herein apply to P4. In another example, if the tripeptide that is recognized by the intracellular protease is located at positions -P4-P3-P2-, embodiments for P3 described herein apply to P4, embodiments for P2 described herein apply to P3, and embodiments for P1 described herein apply to P2. It is further understood that for a Peptide Cleavable Unit (W) in which the tripeptide is located at positions other than -P3-P2-P1-, the P1 amino acid of the Peptide Cleavable Unit (W) is an amino acid that is amenable to cleavage, for example by endopeptidase action. In some embodiments P1 amino acid is not in D-configuration. In some embodiments, the C-terminal amino acid is γ-carboxy-glutamic acid. In some embodiments, wherein the Peptide Cleavable Unit contains four or more amino acids, the amino acid(s) extrinsic to the tripeptide do not increase the overall hydrophobicity of the peptide sequence. In some embodiments, when the Peptide Cleavable Unit contains amino acid(s) in addition to the tripeptide, the additional amino acid(s) do not contain hydrophobic residues (e.g., residues more hydrophobic than leucine or residues more hydrophobic than valine).

The hydrophobicity of a given compound, including relative hydrophobicities of different compounds, can be assessed experimentally or computationally by methods known in the art. Hydrophobicity can be assessed, for example, by determination of a partition coefficient P, which may be determined experimentally and expressed as log P, or which can be determined computationally and expressed as c log P. Values of c log P can be computed using various types of commercially available software, such as ChemDraw or DataWarrior. Such methods may be used to assess the hydrophobicity of an amino acid or to assess the relative hydrophobicities of different amino acids. Such methods may also be used to assess the hydrophobicity of a Drug-Linker Compound as described herein or to assess the relative hydrophobicities of different Drug-Linker Compounds.

In some embodiments, provided are Ligand-Drug Conjugates (e.g., ADCs) that are less active than the comparator Ligand Drug Conjugate (e.g., dipeptide ADC containing -val-cit-), either in vivo or in vitro, but are also significantly less toxic. Without being bound by theory, the Ligand-Drug Conjugate is not required to be as active because the therapeutic window will still be increased if it is less active and less toxic. Exemplary compound exhibiting this effect may include Compounds 38 and 39 herein with AIB in position P2.

In still other particularly preferred embodiments the tripeptide has the structure of:

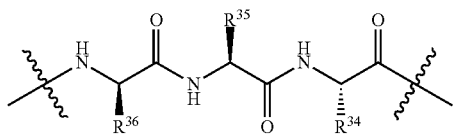

or a salt thereof, in particular a pharmaceutical acceptable salt, wherein the wavy line at the nitrogen atom of the tripeptide N-terminal amino acid, which is indicated as P3 in the afore-described Drug Linker compounds and drug linker moieties of Ligand Drug Conjugates derived therefrom, indicates the site of covalent attachment as an amide bond to the P4 amino acid residue when W is comprised of a tetrapeptide in which the selectivity conferring tripeptide is the C-terminal component of the tetrapeptide, or to A' or $L_R/L_R'$ when W consists of the tripeptide and subscript a' is 1 or 0, respectively, and the wavy line at the tripeptide's C-terminal amino acid residue, which is indicated as P1 in the afore-described Drug Linker compounds and drug linker moieties of Ligand Drug Conjugates derived therefrom, is the site of covalent attachment to the P-1 residue, when W is comprised of a tetrapeptide in which the selectivity conferring tripeptide is the N-terminal component of the tetrapeptide or to $—Y_y-D$ when W consists of the tripeptide; and wherein $R^{36}$, in the R stereochemical configuration, is $—CH(CH_3)_2$, $R^{35}$ is $—CH(CH_3)_2$, or $—CH_3$, and $R^{34}$ is $—CH_2SH$, $—CH_2CH_2CH_2CH_2NH_2$, $—CH(OH)CH_3$ or $—CH_2CH_2CO_2H$.

In more particular preferred drug linker moieties and Drug Linker compounds, $R^{36}$ is $—CH(CH_3)_2$, $—CH_2CH(CH_3)_2$, or $—CH_2CH_2CH_3$ in the R stereochemical configuration and $R^{34}$ is $—CH_2CH_2CO_2H$. In especially preferred embodiments $R^{36}$ is $—CH(CH_3)_2$ in the R stereochemical configuration; and $R^{35}$ is $—CH_3$ and $R^{34}$ is $—CH_2CH_2CO_2H$, both of which are in the S stereochemical configuration as shown.

In some embodiments, the normal tissue homogenate is from bone marrow and the tumor tissue homogenate is from the tumor of a xenograft model of the same species, wherein greater selectivity for proteolysis by tumor tissue homogenate over the normal tissue homogenate is in comparison to a comparator Conjugate having a val-cit dipeptide Cleavable Unit. In some embodiments greater selectivity for tumor tissue over normal tissue by an Antibody Drug Conjugate in which the Peptide Cleavable Unit is comprised of the selectivity conferring tripeptide is shown in a xenograft model by substantial retention of the tumor growth profile obtained from administering an Antibody Drug Conjugate in which the Peptide Cleavable Unit is val-cit and with administration of the corresponding tripeptide-based non-binding control Conjugate showing reduced non-target mediated cytoxicity to normal bone marrow when compared to the corresponding dipeptide-based non-binding control, wherein that cytoxicity to normal cells is responsible for an adverse event associated with administering the dipeptide-based ADC at its maximum tolerated dose. In some embodiments, the normal tissue is bone marrow, liver, kidney, esophageal, breast, or corneal.

In some of those embodiments reduced non-target mediated cytoxicity is observed from histology of normal tissue (e.g., bone marrow, liver, kidney, esophageal, breast, or corneal tissue) from the same or different rodent species as used in the xenograft model on administering a non-binding control conjugate corresponding to the targeting tripeptide-based Antibody Drug Conjugate by showing reduced loss of nuclei staining of mononuclear cells in comparison to that from administration of the dipeptide-based non-binding control, so as to provide an improved therapeutic window for the tripeptide-based ADC. In some embodiments, the normal tissue is bone marrow. In a preferred embodiment mouse is used in the xenograft study and bone marrow is from rat, because rat is more sensitive to MMAE toxicity than mouse. In other embodiments the improvement in tolerability is shown by reduction in neutrophil and/or reticulocyte loss and/or from more rapid rebound from that loss.

2.2.4 Stretcher Units

In the above and following embodiments, a primary linker within a drug linker moiety of a Ligand Drug Conjugate may exemplify the general formula of -$M^2$-A(BU)-[HE]-$A_O$-B—, -$M^2$-A(BU)-[HE]-$A'_a$-, -$M^2$-A-[HE]-$A_O$-B—, -$M^2$-A-[HE]-$A'_a$-, -$M^3$-A(BU)-[HE]-$A_O$-B— or -$M^3$-A(BU)-[HE]-$A'_a$-, and a primary linker of a Drug Linker compound, which can be used to prepare a Ligand Drug Conjugate, may exemplify the general formula of $M^1$-A(BU)-[HE]-$A_O$-B—, $M^1$-A(BU)-[HE]-$A'_a$-, $M^1$-A-[HE]-$A_O$-B— or $M^1$-A-[HE]-$A'_a$-, wherein BU is an acyclic or cyclic Basic Unit; [HE] when present is -preferably —C(=O)—, which is provided by a first optional Stretcher Unit (A) that is present; $M^2$ is succinimide moiety; $M^3$ is succinic acid amide moiety and $M^1$ is a maleimide moiety, wherein A represents either a single discreet unit or a first subunit of A, which is sometimes indicated as $A_1$ when $A_O$ is present as a second subunit of A, which is sometimes indicated as $A_2$, wherein $A/A_2$ is covalently attached to A' in those primary linkers with no Branching Unit (B) and in which subscript a' is 1 so that A' becomes a subunit of A, or is covalently attached to W when subscript a' is 0, or is covalently attached to B in those primary linkers containing a Branching Unit.

When either $A_O$ or A' is present in any one those embodiments, that subunit of a first Stretcher Unit (A) is indicated as $A_2$ to signify it as a subunit of A, wherein preferably $A_O$/A' correspond independently in structure to an optionally substituted amine-containing acid (e.g., an amino acid) residue, wherein the residue of the carboxylic acid terminus of the amine-containing acid is covalently attached to B in those primary linkers in which that component is present, or to A', if present as $A_2$, or to W in those primary linkers in which B and A' are absent, wherein said covalent attachment is through an amide functional group and the residue of the amine terminus is covalently attached to the remainder of A. If B is present and $A_O$ is absent, A is a single discreet unit that is bonded to B, and if B is absent and A is a single discreet unit then A is bonded to W through [HE], which is provided by A, wherein [HE] is —C(=O)—.

In some of those embodiments, $A_O$/A' has or is comprised of the formula of -$L^P$(PEG)-, wherein $L^P$ is a Parallel Connector Unit and PEG is a PEG Unit. In those embodiments, the PEG Unit contains a total of 2 to 36 ethyleneoxy monomer units and $L^P$ is an amine-containing acid residue, preferably an amino acid residue, covalently attached within LU of a drug linker moiety of a Ligand Drug Conjugate compound or LU' of a Drug Linker compound through amide functional groups. In preferred embodiments, the PEG Unit contains a total of 4 to 24 contiguous ethyleneoxy monomer units.

In other of those embodiments, $A_O$/A' is an amine-containing acid residue having the structure of formula 3a, formula 4a or formula 5a:

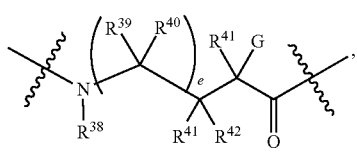

(3a)

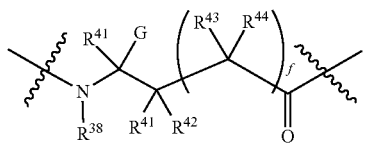

(4a)

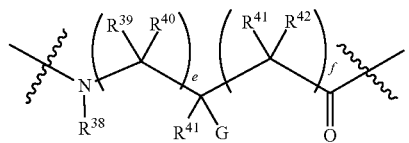

(5a)

wherein the wavy line adjacent to the nitrogen atom indicates the site of covalent attachment to the remainder of A, and the wavy line adjacent to the carbonyl carbon atom indicates the site of covalent attachment to B if B is present or to A'/W when B is absent; subscripts e and f are independently 0 or 1; and G is hydrogen, —OH, —$OR^{PR}$, —$CO_2H$, —$CO_2R^{PR}$ or an optionally substituted $C_1$-$C_6$ alkyl, wherein the optional substituent when present is selected from the group consisting of —OH, —$OR^{PR}$, —$CO_2H$, and —$CO_2R^{PR}$; and wherein $R^{PR}$ is a suitable protecting group, or G is $N(R^{PR})(R^{PR})$ or an optionally substituted $C_1$-$C_6$ alkyl, wherein the optional substituent when present is $N(R^{PR})(R^{PR})$, wherein $R^{PR}$ are independently a protecting group or $R^{PR}$ together form a suitable protecting group, or G is —$N(R^{45})(R^{46})$, or an optionally substituted $C_1$-$C_6$ alkyl, wherein the optional substituent when present is —$N(R^{45})(R^{46})$, wherein one of $R^{45}$ and $R^{46}$ is hydrogen or $R^{PR}$, wherein $R^{PR}$ is a suitable protecting group, and the other is hydrogen or optionally substituted $C_1$-$C_6$ alkyl;

$R^{38}$ is hydrogen or optionally substituted $C_1$-$C_6$ alkyl; and $R^{39}$-$R^{44}$ are independently selected from the group consisting of hydrogen, optionally substituted $C_1$-$C_6$ alkyl, optionally substituted $C_6$-$C_{20}$ aryl, and optionally substituted $C_5$-$C_{20}$ heteroaryl, or $R^{39}$, $R^{40}$ together with the carbon atom to which both are attached define a $C_3$-$C_6$ carbocyclo, and $R^{41}$-$R^{44}$ are as defined herein, or $R^{43}$, $R^{44}$ together with the carbon atom to which both are attached define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, or $A_O$/A' is an α-amino or β-amino acid residue, wherein the nitrogen atom of the α-amino residue is covalently attached to the remainder of A, and the carbonyl carbon atom of its carboxylic acid residue is covalently attached to B if B is present or to W when B is absent, wherein both attachments are preferably through amide functional groups.

2.2.5 Spacer Units

A Spacer Unit is a component of a secondary linker ($L_O$) of Drug Linker Compound or a Linker Unit in a drug linker moiety of a Ligand Drug Conjugate compound represented by the structure of:

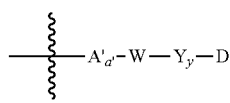

in which subscript y is 1 or 2, indicating the presence of one or two Spacer Unit, so that $Y_y$ is Y or —Y—Y'—, wherein subscript a is 0 or 1, A' is an optional first Stretcher Unit, which becomes a component of the primary linker ($L_R/L_R'$) as a subunit of a first optional Stretcher Unit (A) that is present when subscript a' is 1 are there is no Branching Unit (B) in $L_R/L_R'$; W is a Peptide Cleavable Unit of formula —[$P_n$] . . . [P3]-[P2]-[P1]- or [$P_n$] . . . [P3]-[P2]-[P1]-[P-1]-, wherein subscript n ranges from 0 to 12 (e.g., 0-10, 3-12 or 3-10) and $P_n$ . . . P3, P2, P1, P-1 are amino acid residues wherein the P1, P2 and P3 are the tripeptide amino acid residues conferring selectivity for protease cleavage by tumor tissue homogenate over normal tissue homogenate as described herein and/or which alters the biodistribution of a Ligand Drug Conjugate so that the Conjugate whose Peptide Cleavable Unit is comprised of the P3-P2-P1 tripeptide favors the tumor tissue in comparison to the normal tissue when compared to the biodistribution of a comparator peptide in which the Peptide Cleavable Unit is the dipeptide val-cit.

When W does not contain a P-1 residue, proteolytic action on $L_O$ releases a drug linker fragment of formula —Y-D, when subscript y is 1, or —Y—Y'-D, when subscript y is 2, wherein Y is a first Spacer Unit and Y' is a second Spacer Unit, whereupon the Spacer Units in those fragments undergo self-immolation to complete release of D as free drug. When W does contain a P-1 residue, proteolytic action on $L_O$ releases a first drug linker fragment of formula [P-1]-Y-D or [P-1]-Y—Y'-D. However, for convenience the P-1 residue will be associated with the sequence in SEQ IDs describing such Peptide Cleavable Units. Completing release of free drug then requires exopeptidase action to remove the [P-1] amino acid residue to provide either Y-D or —Y—Y'-D as a second drug linker fragment similarly to when W does not contain a P-1 residue. The —Y—Y'-D linker fragment then proceeds to a third drug linker fragment of formula Y'-D. In either variant, Y-D or Y'-D spontaneously decomposes to complete release of D as free drug.

A self-immolative Spacer Unit (Y) covalently bonded to P1 or P-1 of a peptide Cleavage Unit (W) is comprised or consists of a self-immolating moiety as defined herein so that enzymatic processing of W activates the self-immolative moiety of Y for its self-destruction thus initiating release of the Drug Unit as free Drug. In those aspects in which subscript y is 1, the self-immolative moiety of Y is directly attached to an optionally substituted heteroatom of the Drug Unit. As previously discussed when subscript y is 2, then $Y_y$ is —Y—Y'— wherein Y is a first self-immolative Spacer covalently attached to the Peptide Cleavable Unit (W) and Y' is second self-immolative Spacer Unit, which in some aspects is a carbamate functional group shared between Y and D. In other aspects Y' is a methylene carbamate unit. In either aspect $Y_y$ is bonded to the Drug Unit (D) such that spontaneous self-destruction of the first self-immolative Spacer Unit Y initiated by endopeptidase action on the amide bond covalently attaching W to Y or exopeptidase action on the amide bond of [P-1]-D releases Y'-D, which then spontaneously decomposes to complete release of D as free drug.

In some embodiments Y contains a PAB or PAB-related self-immolative moiety bonded to -D or —Y'-D, in which subscript y is 1 or 2, respectively, which have a central arylene or heteroarylene substituted by a masked electron donating group (EDG) and a benzylic carbon bonded to D through a shared heteroatom or functional group, or bonded to D indirectly through an intervening second Spacer Unit (Y'), wherein the masked EDG and benzylic carbon substituents are ortho or para to each other (i.e., 1,2 or 1,4 substitution pattern). In those embodiments the second Spacer Unit (Y') is capable of self-immolation or spontaneous decomposition or is absent.

Exemplary structures of self-immolative Spacer Units having a PAB or PAB-related self-immolative moiety in which the central (hetero)arylene has the requisite 1,2 or 1,4 substitution pattern that allows for 1,4- or 1,6-fragmentation for release D or [P-1]-D, when subscript y is 1, or —Y'-D, or —[P-1]-Y'-D in which subscript y is 2, wherein Y' is capable of self-immolation or spontaneous decomposition, are represented by:

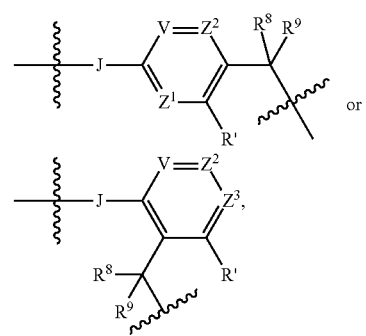

wherein the wavy line adjacent to J indicates the site of covalent attachment to P1 if the selectivity conferring tripeptide is directly attached —Y'-D or to P-1 if the selectivity conferring tripeptide is indirectly attached —Y'-D through that amino acid residue, and the other wavy line indicates the site of covalent attachment to —Y'-D, wherein J is a heteroatom, optionally substituted where permitted (i.e., optionally substituted —NH—), Y' is an optional second Spacer Unit, D is a Drug Unit, wherein when Y' is absent Y' is replaced by a heteroatom from D so that D becomes D', which is the remainder of the Drug Unit; and wherein V, $Z^1$, $Z^2$, $Z^3$ are independently =N or =C($R^{24}$)—, wherein each $R^{24}$ is independently selected from the group consisting of hydrogen and optionally substituted $C_1$-$C_{12}$ alkyl, optionally substituted $C_2$-$C_{12}$ alkenyl, optionally substituted $C_2$-$C_{12}$ alkynyl, optionally substituted $C_6$-$C_{20}$ aryl, optionally substituted ($C_6$-$C_{20}$ aryl)-$C_1$-$C_6$ alkyl-, optionally substituted $C_5$-$C_{20}$ heteroaryl and optionally substituted ($C_5$-$C_{20}$ heteroaryl)-$C_1$-$C_6$ alkyl-, and halogen and an electron withdrawing group; R' is hydrogen or optionally substituted $C_1$-$C_{12}$ alkyl, optionally substituted $C_2$-$C_{12}$ alkenyl, optionally substituted $C_2$-$C_{12}$ alkynyl, optionally substituted $C_6$-$C_{20}$ aryl, optionally substituted ($C_6$-$C_{20}$ aryl)-$C_1$-$C_6$ alkyl-, optionally substituted $C_5$-$C_{20}$ heteroaryl, or optionally substituted $C_5$-$C_{20}$ heteroaryl)-$C_1$-$C_6$ alkyl-, or an electron donating group; and $R^8$ and $R^9$ are independently selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_6$-$C_{20}$ aryl and optionally substituted $C_5$-$C_{20}$ heteroaryl, or both $R^8$ and $R^9$ together with the carbon atom to which they are attached define a $C_3$-$C_8$ carbocyclo. In preferred embodiments, one or more of V, $Z^1$, $Z^2$ or one or more of V, $Z^2$, $Z^3$ is =CH—. In other preferred embodiments R' is hydrogen or an electron donating group, including $C_1$-$C_6$ ethers such as —$OCH_3$ and —$OCH_2CH_3$, or one of $R^8$, $R^9$ is hydrogen and the other is hydrogen or $C_1$-$C_4$ alkyl. In more preferred embodiments two or more of V, $Z^1$ and $Z^2$ are =CH— or two or more of V, $Z^2$ and $Z^3$ are =CH—. In other more preferred embodiments $R^8$, $R^9$ and R' are each hydrogen.

Intracellular cleavage of the bond to J or the amide bond between P1 and P-1 results in release of Y'-D or —[P-1]-Y'-D, respectively, wherein —[P-1]-Y'-D is convertible to —Y'-D by exopeptidase activity of an intracellular protease of a targeted cell.

In some preferred embodiments, —$Y_y$-D in which subscript y is 2 has the structure of —Y—Y'-D is as follows:

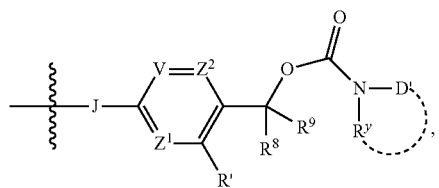

wherein —N($R^y$)D' represents D, wherein D' is the remainder of D, and wherein the dotted line indicates optional cyclization of R to D, wherein $R^y$ is optionally substituted $C_1$-$C_6$ alkyl in absence of cyclization to D' or optionally substituted $C_1$-$C_6$ alkylene when cyclized to D'; -J- is an optionally substituted heteroatom where permitted, including O, S and optionally substituted —NH—, wherein J, a functional group comprised of J, or P-1 is bonded to P1, as indicated by the adjacent wavy line, of the tripeptide that confers selectivity for intracellular proteolysis over proteolysis by freely circulating proteases and selectivity for proteolysis by tumor tissue homogenate over proteolysis by normal tissue homogenate and/or selective biodistribution to tumor tissue over biodistribution to normal tissue, wherein cleavage of that bond initiates release of D as a secondary amine-containing biologically active compound from a compound of a Ligand Drug Conjugate composition and wherein the remaining variable groups are as defined above. Those variables are selected so that reactivity of J when released from processing of Peptide Cleavable Unit W within the targeted cells is balanced with the pKa of Y'-D or D eliminated from the PAB or PAB-type self-immolative moiety and the stability of the quinone-methide type intermediate resulting from that elimination.

In those embodiments, the intervening moiety between D and the benzylic carbon of the PAB or PAB-related self-immolative moiety of Spacer Unit Y represents Y' in —C($R^8$)($R^9$)—Y'-D so that a carbamate functional group is shared between Y and D. In such embodiments fragmentation of the Spacer Unit Y with expulsion of Y'-D is followed by loss of $CO_2$ for release of D as biologically active compound having a primary or secondary amine whose nitrogen atom was bonded to the secondary linker comprised of the PAB or PAB-related self-immolative moiety.

In other preferred embodiments, —$Y_y$-D having a PAB or PAB-type moiety bound to —Y'-D or -D has the structure of.

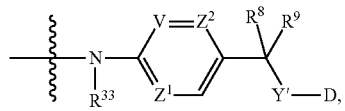

wherein the wavy line adjacent to the nitrogen atom indicates the point of covalent attachment to P-1 or the tripeptide of W that confers selectivity for intracellular proteolysis over proteolysis by freely circulating proteases and proteolysis by tumor tissue homogenate over proteolysis by normal tissue homogenate, wherein that bond is susceptible to the intracellular proteolysis, Y' is an optional Spacer Unit that when absent is replaced with a phenolic oxygen atom or a sulfur atom from D, and when present is a carbamate functional group the nitrogen atom of which is from D; $R^{33}$ is hydrogen or optionally substituted $C_1$-$C_6$ alkyl, in particular hydrogen or $C_1$-$C_4$ alkyl, preferably hydrogen, —$CH_3$ or —$CH_2CH_3$, more preferably hydrogen. In more preferred embodiments, V, $Z^1$ and $Z^2$ are each =CH— and $R^{33}$ is hydrogen.

In some embodiments, —$Y_y$-D having a PAB or PAB-type moiety bound to —Y'-D or -D has the structure of:

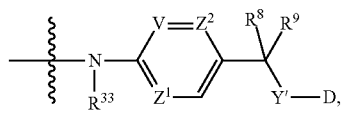

wherein the wavy line adjacent to the nitrogen atom indicates the point of covalent attachment to P-1 or the tripeptide of W that confers selectivity for intracellular proteolysis over proteolysis by freely circulating proteases and proteolysis by tumor tissue homogenate over proteolysis by normal tissue homogenate, wherein that bond is susceptible to the intracellular proteolysis, Y' is an optional Spacer Unit that when absent is replaced with a phenolic oxygen atom, a quaternized tertiary amine, or a sulfur atom from D. Y', when present, is a carbamate functional group the nitrogen atom of which is from D, a methylene-alkoxy-carbamate functional group wherein the oxygen atom of the alkoxy moiety is shared with D, or a carbonate functional wherein one oxygen atom is shared with D; $R^{33}$ is hydrogen or optionally substituted $C_1$-$C_6$ alkyl, in particular hydrogen or $C_1$-$C_4$ alkyl, preferably hydrogen, —$CH_3$ or —$CH_2CH_3$, more preferably hydrogen. In more preferred embodiments, V, $Z^1$ and $Z^2$ are each =CH— and $R^{33}$ is hydrogen.

In particularly preferred embodiments-$Y_y$-D has the structure of:

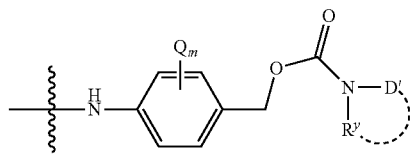

wherein —N($R^y$)D' has its previous meaning and the wavy line indicates covalent attachment to P1; Q is —$C_1$-$C_8$ alkyl, —O—($C_1$-$C_8$ alkyl), or other electron donating group, -halogen, -nitro or -cyano or other electron withdrawing group (preferably, Q is —$C_1$-$C_8$ alkyl, —O—($C_1$-$C_8$ alkyl), halogen, nitro or cyano); and subscript m is an integer ranging from 0-4 (i.e., the central arylene has no other substituents or 1-4 other substituents). In preferred embodiments subscript m is 0, 1 or 2 and each Q is an independently selected electron donating group.

In especially preferred embodiments, —$Y_y$— has the structure of:

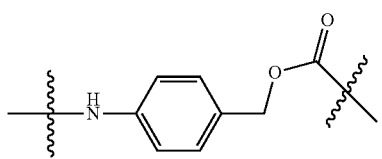

respectively, wherein the wavy line adjacent to the carbonyl carbon atom indicates the site of covalent attachment to an oxygen or sulfur atom of D to form a carbonate or thiocarbamate functional group that is shared between D and Y wherein that shared functional group is Y', or to a secondary nitrogen atom to form a carbamate that is shared between D and Y, wherein that shared functional group is Y', and the wavy line adjacent to the nitrogen atom indicates the site of covalent attachment as an amide bond to the carboxylic acid residue of P1.

In some embodiments, —$Y_{y'}$— has the structure of:

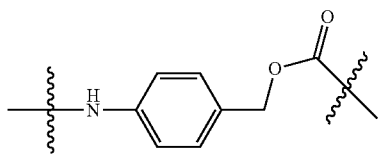 [SMILES: *Nc1ccc(COC(*)=O)cc1]

respectively, wherein the wavy line adjacent to the carbonyl carbon atom indicates the site of covalent attachment to an oxygen, nitrogen, or sulfur atom of D to form a carbonate, carbamate, or thiocarbamate functional group that is shared between D and Y wherein that shared functional group is Y', or to a secondary nitrogen atom to form a carbamate that is shared between D and Y, wherein that shared functional group is Y', and the wavy line adjacent to the nitrogen atom indicates the site of covalent attachment as an amide bond to the carboxylic acid residue of P1.

In some embodiments, —$Y_{y'}$— has the structure of:

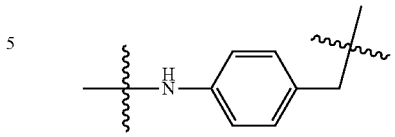

wherein the wavy line adjacent to the methylene carbon atom indicates the site of covalent attachment to a quaternized, tertiary amine containing Drug Unit, such that —$Y_{y'}$— is attached to the Drug Unit by way of a quaternized nitrogen atom that is part of the Drug Unit, and the wavy line adjacent to the nitrogen atom indicates the site of covalent attachment as an amide bond to the carboxylic acid residue of P1.

In some embodiments, —$Y_{y'}$— has the structure of:

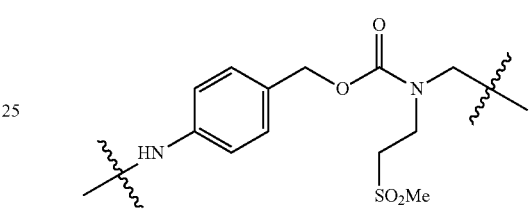

wherein the wavy line adjacent to the carbon atom of the methylene carbamate moiety indicates the site of covalent attachment to an oxygen atom on D to form a methylene alkoxy carbamate moiety that is shared between D and Y wherein that shared functional group is Y' and the wavy line adjacent to the nitrogen atom indicates the site of covalent attachment as an amide bond to the carboxylic acid residue of P1.

Other structures of general formula —Y—Y'— in which Y is a self-immolative Spacer Unit are other than a PAB or PAB-type self-immolative Spacer Unit are illustrated in the following drug linker moieties.

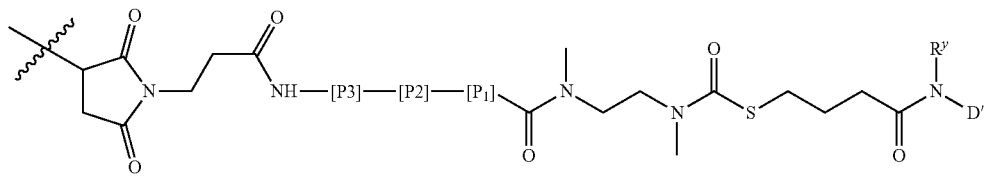

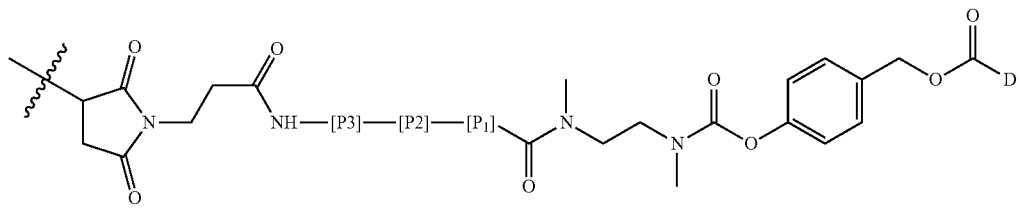

Without being bound by theory, the sequential self-immolation of Y in which Y is a PAB self-immolative Spacer Unit and Y' is a carbamate functional group is illustrated for the secondary linker of Ligand Drug Conjugates and Drug Linker compounds having a tripeptide Peptide Cleavable Unit are as follows:

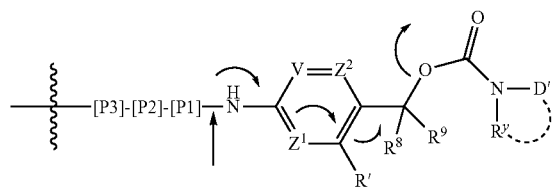
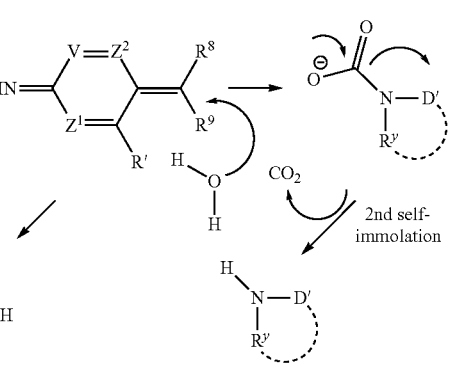

2.2.6 Drug Linkers

In general, a drug linker moiety of Formula 1A has the structure of:

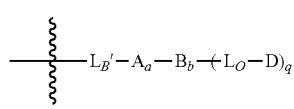

(IA)

wherein the wavy line indicates covalent attachment of $L_B$ to a Ligand Unit, A is a first optional Stretcher Unit; subscript a is 0 or 1 indicating the absence or presence of A, B is an optional Branching Unit; subscript b is 0 or 1 indicating the absence or presence of B, respectively, provided that subscript b is 1 when subscript q ranges from 2 to 4 and $L_O$ is a secondary linker having the formula of:

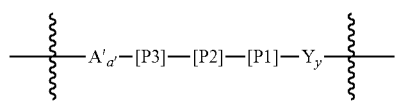

or a salt thereof, in particular a pharmaceutically acceptable salt, wherein A' is a second optional Stretcher Unit, subscript a' is 0 or 1 indicating the absence or presence of A', respectively, Y is an optional Spacer Unit, subscript y is 0, 1 or 2 indicating the absence or presence of 1 or 2 Spacer Units, respectively, and P1, P2 and P3 are amino acid residues that together provide selectivity for proteolysis by a homogenate of tumor tissue over proteolysis by a homogenate of normal tissue, and/or together provide for preferred biodistribution of a Formula 1 Conjugate into tumor tissue in comparison to normal tissue, wherein cytotoxicity of the free drug released from the Conjugate towards the normal tissue is responsible at least in part for an adverse event typically associated with administration of a therapeutically effective amount of a comparator dipeptide-based Conjugate, wherein proteolytic cleavage occurs at the covalent bond between P1 and Y if subscript y is 1 or 2, or at the covalent bond between P1 and D if subscript y is 0 or $L_O$ is a secondary linker having the formula of:

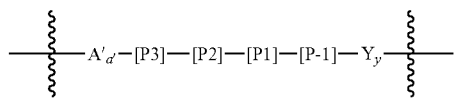

or a salt thereof, in particular a pharmaceutically acceptable salt, wherein A', a', Y, and y retain their previous meanings and P1, P2 and P3 are amino acid residues, optionally with the P-1 amino acid, that together provide selectivity for proteolysis by tumor tissue homogenate over proteolysis by normal tissue homogenate, and/or together provide for preferred biodistribution of the Formula 1 Conjugate into tumor tissue in comparison to normal tissue, wherein cytotoxicity of the free drug released from the Conjugate towards the normal tissue is responsible at least in part for an adverse event typically associated with administration of a therapeutically effective amount of a comparator dipeptide-based Conjugate, wherein proteolytic cleavage occurs at the covalent bond between P1 and P-1 to release a linker fragment having the structure of [P-1]-$Y_y$-D, or $L_O$ is a secondary linker having the formula of.

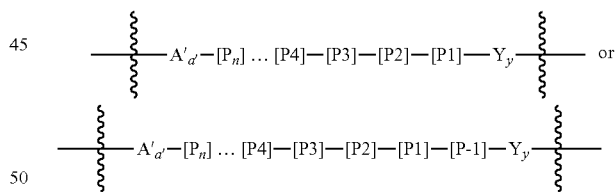

or a salt thereof, in particular a pharmaceutically acceptable salt, wherein A', a', Y, and y retain their previous meanings and P-1 and P1, P2, P3 . . . $P_n$ are amino acid residues, wherein subscript n ranges from 0 to 12 (e.g., 0-10, 3-12 or 3-10) and P1, P2 and P3, optionally with P-1, together provide selectivity for proteolysis by tumor tissue homogenate over proteolysis by normal tissue homogenate and/or together provide for preferred biodistribution of the Formula 1 Conjugate prepared from the Drug Linker compound into tumor tissue in comparison to normal tissue, wherein cytotoxicity of the free drug released from the Conjugate towards the normal tissue is responsible at least in part for an adverse event typically associated with administration of a therapeutically effective amount of a comparator dipeptide-base Conjugate, wherein proteolytic cleavage occurs at the covalent bond between P1 and $Y_y$-D or between and P1 and P-1 to release a linker fragment having the structure of $Y_y$-D or [P-1]-$Y_y$-D, respectively, in which the later subsequently undergoes exopeptidase cleavage to release the linker fragment having the structure of $Y_y$-D. In both instances the $Y_y$-D linker fragment undergoes spontaneous decomposition to complete release of D as free drug.

The additional P4, P5 . . . $P_n$ amino acid residues are selected so as to not alter the cleavage site that provides the —$Y_y$-D or —[P-1]-$Y_y$-D fragment, but instead are selected to retain a desired physiochemical and/or pharmokinetic property to the Ligand Drug Conjugate provided primarily by the P1, P2 and P3 amino acid residues, such as increased biodistribution of the Conjugate into tumor tissue, which is at the detriment for normal tissue distribution or to enhance that physiochemical and/or pharmokinetic property in comparison to a comparator dipeptide-based Conjugate.

In either one of those embodiments of $L_O$ if subscript q is 1, then subscript b is 0 so that B is absent and A' becomes an optional subunit of A and if subscript q is 2, 3 or 4, then subscript b is 1 so that B is present, A' remains a component of $L_O$ as shown and an optional subunit of A is indicated as $A_O$.

In some embodiments, in addition to improving global selectivity and/or improving biodistribution favoring tumor-associated proteases in comparison to that of normal tissue, the P1, P2 and P3 amino acid residues also reduce aggregation of a Conjugate that incorporates an amino acid sequence comprised of these amino acids in comparison to a dipeptide comparator conjugate. In some of those embodiments in which the Drug Unit is that of MMAE the drug linker moieties of the comparator Conjugate have the formula of mc-vc-PABC-MMAE.

In preferred embodiments of -$L_{SS}$ and -$L_S$-containing drug linker moieties of a Formula 1A Ligand Drug Conjugate compound, the $L_{SS}$ and $L_S$ moieties contain a heterocyclo cyclic Basic Unit. Exemplary drug linker moieties in which subscript q is 1 and having those primary linkers in which the Peptide Cleavable Unit is a tripeptide are represented by the structures of Formula 1B, Formula 1C and Formula 1D:

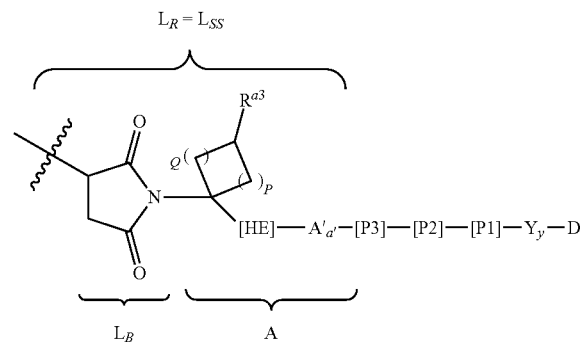

(Formula 1B)

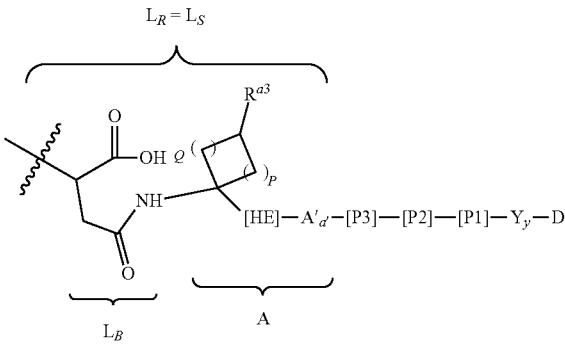

(Formula 1C)

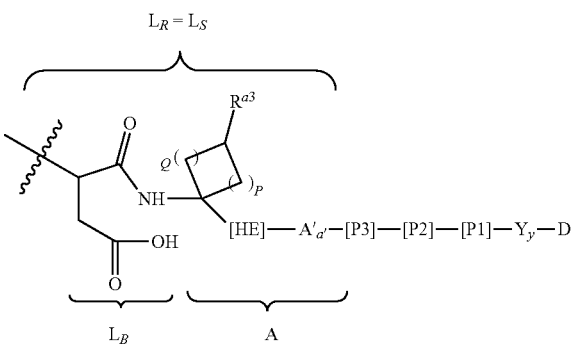

(Formula 1D)

or a salt thereof, in particular a pharmaceutical acceptable salt, wherein HE is an optional Hydrolysis Enhancing Unit; A' is an subunit, when present, of a first Stretcher Unit (A); subscript a' is 0 or 1, indicating the absence or presence of A', respectively; subscript P is 1 or 2; subscript Q ranges from 1 to 6, preferably subscript Q is 1 or 2, more preferably subscript Q has the same value as subscript P; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated in a salt form, preferably in a pharmaceutically acceptable salt form, or $R^{a3}$ is a nitrogen protecting group such as a suitable acid-labile protecting group; the wavy line indicated covalent binding to a sulfur atom of a Ligand Unit; P1, P2 and P3 are as previously defined for any one of the embodiments of Peptide Cleavable Units; and the remaining variable groups are as described for any one of the embodiments of a drug linker moiety of Formula 1A.

In other preferred embodiments of -$L_{SS}$ and -$L_S$-containing drug linker moieties of Formula 1A of a Ligand Drug Conjugate compound, the $L_{SS}$ and $L_S$ moieties contain a acyclic cyclic Basic Unit. Exemplary drug linker moieties having those primary linkers in which the Peptide Cleavable Unit is a dipeptide are represented by the structures of Formula 1E, Formula 1F and Formula 1G:

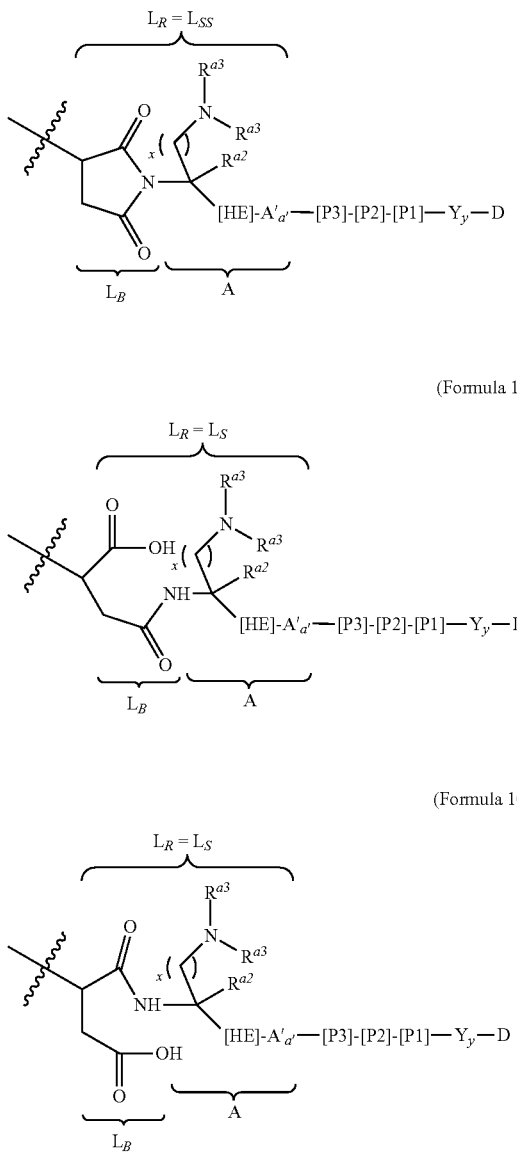

(Formula 1E)
(Formula 1F)
(Formula 1G)

or a salt thereof, in particular a pharmaceutical acceptable salt, wherein HE is an optional Hydrolysis Enhancing Unit; A' is an subunit, when present, of a first Stretcher Unit (A); subscript a' is 0 or 1, indicating the absence or presence of A', respectively; subscript x is 1 or 2; $R^{a2}$ is —H, optionally substituted $C_1$-$C_6$ alkyl, —$CH_3$ or —$CH_2CH_3$; $R^{a3}$, at each instance, is independently a nitrogen protecting group, —H or optionally substituted $C_1$-$C_6$ alkyl, preferably —H, an acid-labile protecting group, —$CH_3$ or —$CH_2CH_3$, or both $R^{a3}$ together with the nitrogen to which they are attached define a nitrogen protecting group or an azetidinyl, pyrrolidinyl or piperidinyl heterocyclyl, in which a basic primary, secondary or tertiary amine so defined is optionally protonated in a salt form, preferably a pharmaceutically acceptable salt form; the wavy line indicated covalent binding to a sulfur atom of a Ligand Unit; P1, P2 and P3 are as previously defined for any one of the embodiments of Peptide Cleavable Units and the remaining variable groups are as described for any one of the embodiments of a drug linker moiety of Formula 1A.

In other preferred embodiments, a primary linker does not have a Basic Unit. Exemplary drug linker moieties having that primary linker in which the Peptide Cleavable Unit is a tripeptide are represented by the structures of Formula 1H, Formula 1J and Formula 1K:

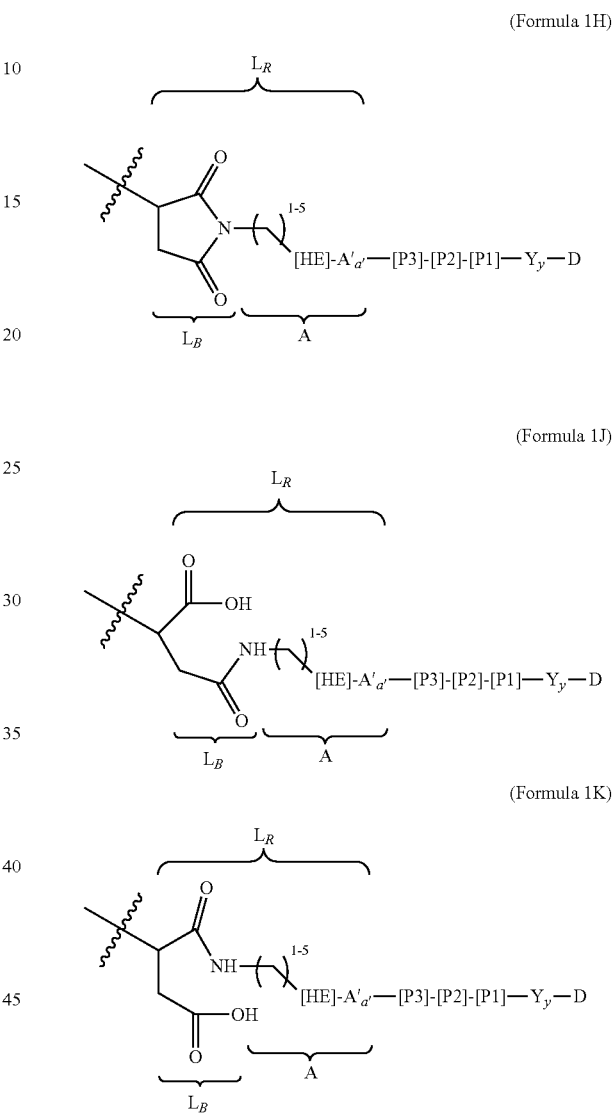

(Formula 1H)
(Formula 1J)
(Formula 1K)

or a salt thereof, in particular a pharmaceutical acceptable salt, wherein HE is an optional Hydrolysis Enhancing Unit; A' is a subunit ($A_2$), when present, of a first Stretcher Unit (A); subscript a' is 0 or 1, indicating the absence or presence of A'; the wavy line indicates covalent binding to a sulfur atom of a Ligand Unit; P1, P2 and P3 are as previously defined for any one of the embodiments of Peptide Cleavable Units and the remaining variable groups are as described for any one of the embodiments of a drug linker moiety of Formula 1A.

In more preferred embodiments in which there is a heterocyclo cyclic Basic Unit in the Linker Unit, a majority of Ligand Drug Conjugate compounds in a Ligand Drug Conjugate composition have drug linker moieties represented by the structures of:

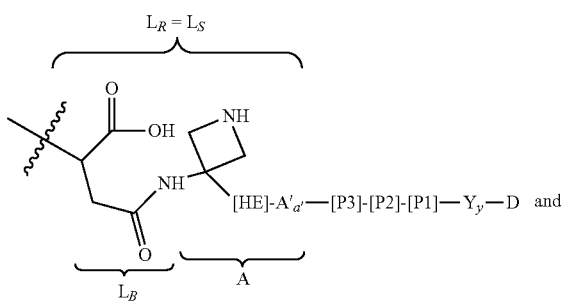

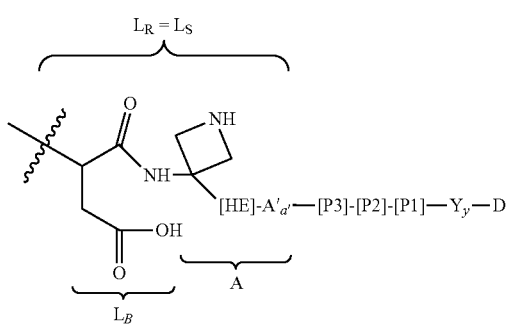

optionally in a salt form, in particular in pharmaceutical acceptable salt form, and in more preferred embodiments in which there is an acyclic Basic Unit in the Linker Unit, a majority of Ligand Drug Conjugate compounds in a Ligand Drug Conjugate composition have drug linker moieties represented by the structures of:

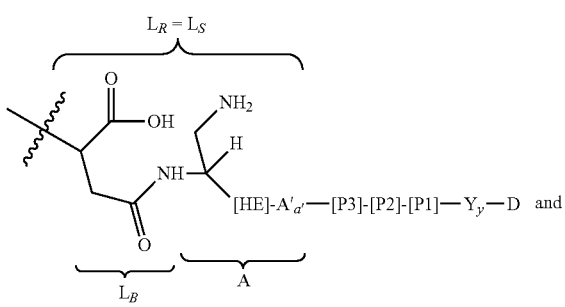

optionally in salt form, in particular in pharmaceutical acceptable salt form, wherein the variable groups of the $L_{SS}$ and $L_S$-containing drug linker moieties are as previously described for drug linker moieties having a acyclic or heterocyclo cyclic Basic Unit, and in other more preferred embodiments in which there is no Basic Unit in the Linker Unit, the predominate Ligand Drug Conjugate compound in a Ligand Drug Conjugate composition has drug linker moieties represented by the structure of Formula 1H, wherein the variable groups are as previously described for drug linker moieties of that formula.

In any one of the preceding drug linker moieties, HE is preferably present as —C(=O) and/or subscript y is 1 or 2, indicating the presence of one or two self-immolative Spacer Units, respectively.

In particularly preferred embodiments the —[P3]-[P2]-[P1] tripeptide in in any one of the above drug linker moieties is, D-Leu-Leu-Met(O) or D-Leu-Ala-Glu, wherein Met(O) is methionine in which its sulfur atom is oxidized to a sulfoxide.

In especially preferred embodiments in which there is a heterocyclo cyclic Basic Unit in the Linker Unit, a majority of Ligand Drug Conjugate compounds in a Ligand Drug Conjugate composition have drug linker moieties represented by the structure of:

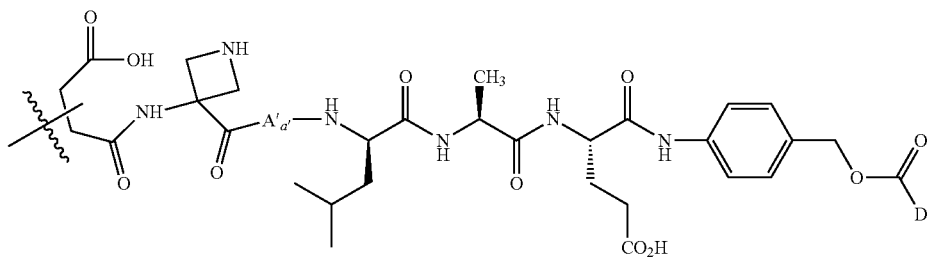

and salts thereof, in particular pharmaceutically acceptable salts, wherein the wavy line indicates covalent attachment to a sulfur atom from a Ligand Unit; subscript a' is 0 or 1, indicating the absence or presence of A, respectively, wherein A' is an amine-containing acid residue of formula 3a, 4a or 5a as described herein for a second optional Stretcher Unit or a subunit of a first optional Stretcher Unit, or A' is an α-amino acid or β-amino acid residue; and D is a cytotoxic drug having a secondary amino group as the site of attachment to the Linker Unit of the drug linker moiety.

In other especially preferred embodiments in which there is a acyclic Basic Unit in the Linker Unit, a majority of Ligand Drug Conjugate compounds in a Ligand Drug Conjugate composition have drug linker moieties represented by the structure of:

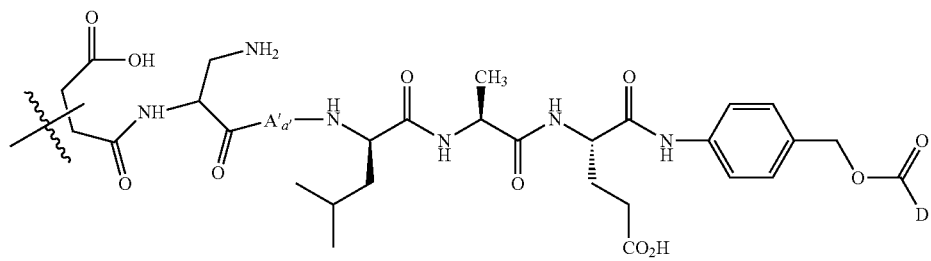

and salts thereof, in particular pharmaceutically acceptable salts, wherein the variable groups are as previously described for drug linker moieties having a cyclic Basic Unit.

In other especially preferred embodiments in which there is no Basic Unit, the predominate Ligand Drug Conjugate compound in a Ligand Drug Conjugate composition has drug linker moieties represented by the structure of

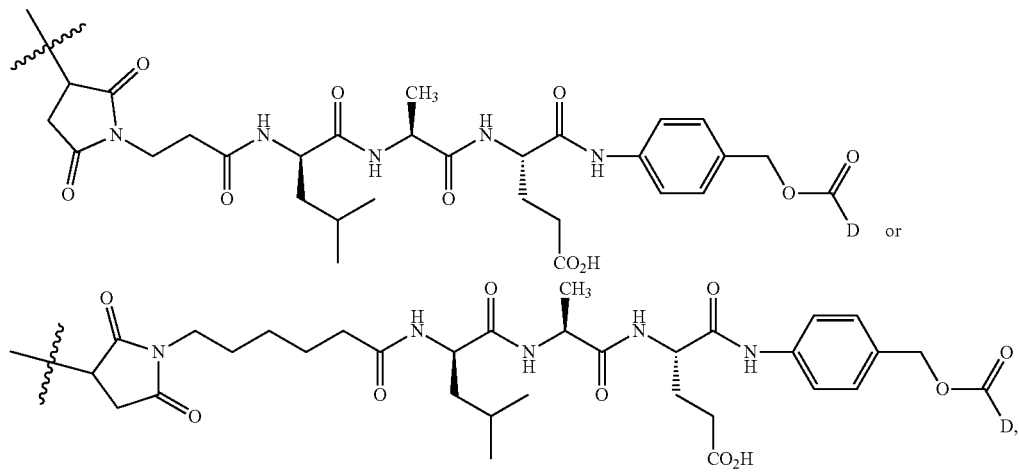

or a salt thereof, in particular a pharmaceutically acceptable salt, wherein the variable groups are as previously described for drug linker moieties having a cyclic Basic Unit. In those embodiments in which no BU is present, a Ligand Drug Conjugate composition comprised of either predominate Ligand Drug Conjugate compound is optionally further comprised of Ligand Drug Conjugate compounds in which the succinimide ring is in hydrolyzed form.

2.2.7 Drugs and Drug Units

In some embodiments, D is a free drug or a pharmaceutically acceptable salt thereof and may be useful for pharmaceutical treatment of hyperproliferative diseases and disorders. In some embodiments, D is a Drug Unit that is conjugated to a Drug Linker compound or to a Ligand Drug Conjugate compound. In some embodiments, D is a cytotoxic, cytostatic, immunosuppressive, immunostimulatory, or immunomodulatory drug. In some embodiments, D is a tubulin disrupting agent, DNA minor groove binder, DNA damaging agent or DNA replication inhibitor.

Useful classes of cytotoxic, cytostatic, immunosuppressive, immunostimulatory, or immunomodulatory agents include, for example, antitubulin agents (which may also be referred to as tubulin disrupting agents), DNA minor groove binders, DNA replication inhibitors, DNA damaging agents, alkylating agents, antibiotics, antifolates, antimetabolites, chemotherapy sensitizers, Toll-like receptor (TLR) agonists, STimulator of Interferon Genes (STING) agonists, Retinoic acid-inducible gene I (RIG-I) agonists, topoisomerase inhibitors (including topoisomerase I and II inhibitors), vinca alkaloids, auristatins, camptothecins, enediynes, lexitropsins, anthracyclins, taxanes, and the like. Particularly examples of useful classes of cytotoxic agents include, for example, DNA minor groove binders (enediynes and lexitropsins), DNA alkylating agents, and tubulin inhibitors. Exemplary agents include, for example, anthracyclines, auristatins (e.g., auristatin T, auristatin E, AFP, monomethyl auristatin F (MMAF), lipophilic monomethyl aurstatin F, monomethyl auristatin E (MMAE)), camptothecins, CC-1065 analogues, calicheamicin, analogues of dolastatin 10, duocarmycins, etoposides, maytansines and maytansinoids, melphalan, methotrexate, mitomycin C, taxanes (e.g., paclitaxel and docetaxel), nicotinamide phosphoribosyltranferase inhibitor (NAMPTi), tubulysin M, benzodiazepines and benzodiazepine containing drugs (e.g., pyrrolo[1,4]-benzodiazepines (PBDs), indolinobenzodiazepines, rhizoxin, paltoxin, and oxazolidinobenzodiazepines) and vinca alkaloids. Select benzodiazepine containing drugs are described in WO 2010/091150, WO 2012/112708, WO 2007/085930, and WO 2011/023883.

Particularly useful classes of cytotoxic agents include, for example, DNA minor groove binders, DNA alkylating agents, tubulin disrupting agents, anthracyclines and topoisomerase II inhibitors. Other particularly useful cytotoxic agents include, for example, auristatins (e.g., auristatin T, auristatin E, AFP, monomethyl auristatin F (MMAF), lipophilic analogs of monomethyl auristatin F, monomethyl auristatin E (MMAE)) and camptothecins (e.g., camptothecin, irinotecan and topotecan).

The cytotoxic agent can be a chemotherapeutic agent such as, for example, doxorubicin, paclitaxel, melphalan, *vinca* alkaloids, methotrexate, mitomycin C or etoposide. The agent can also be a CC-1065 analogue, calicheamicin, maytansine, an analog of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatins include auristatin T, AFP, MMAF, and MMAE. The synthesis and structure of various auristatins are described in, for example, US 2005-0238649 and US2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin).

The cytotoxic or cytostatic agent can be an anti-tubulin agent. Examples of anti-tubulin agents include taxanes (e.g., Taxol® (paclitaxel), Taxotere® (docetaxel)), T67 (Tularik), *vinca* alkyloids (e.g., vincristine, vinblastine, vindesine, and vinorelbine), and auristatins (e.g., auristatin E, AFP, MMAF, MMAE, AEB, AEVB). Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermoide and eleuthrobin.

The cytotoxic agent can be mytansine or a maytansinoid, another group of anti-tubulin agents (e.g., DM1, DM2, DM3, DM4). For example, the maytansinoid can be maytansine or a maytansine containing drug linker such as DM-1 or DM-4 (ImmunoGen, Inc.; see also Chari et al., 1992, Cancer Res.).

In some embodiments, D is a tubulin disrupting agent. In some embodiments, D is an auristatin or a tubulysin. In some embodiments, D is an auristatin. In some embodiments, D is a tubulysin.

In some embodiments, D is a TLR agonist. Exemplary TLR agonists include, but are not limited to, a TLR1 agonist, a TLR2 agonist, a TLR3 agonist, a TLR4 agonist, a TLR5 agonist, a TLR6 agonist, a TLR7 agonist, a TLR8 agonist, a TLR7/8 agonist, a TLR9 agonist, or a TLR10 agonist.

In some embodiments, D is a STING agonist. Exemplary STING agonists include, but are not limited to, cyclic di-nucleotides (CDNs), and non-nucleotide STING agonists.

An auristatin Drug Unit of a Ligand Drug Conjugate compound or Drug Linker compound incorporates an auristatin drug through covalent attachment of a Linker Unit of the Conjugate or Drug Linker compound to the secondary amine of an auristatin free drug having structure of $D_E$ or $D_F$ as follows:

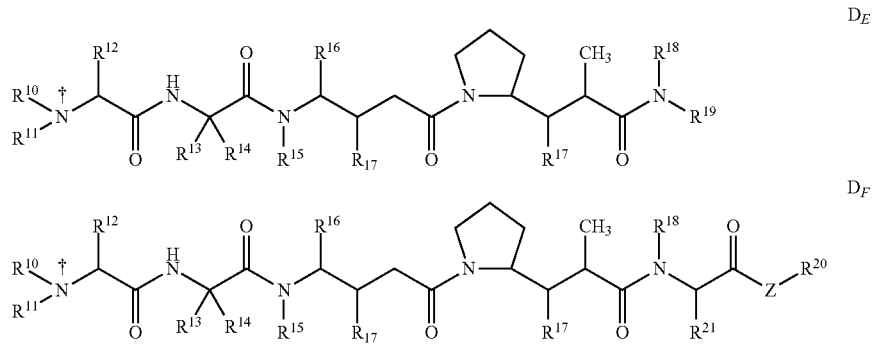

wherein the dagger indicates the site of covalent attachment of the nitrogen atom that provides a carbamate functional group, wherein —OC(=O)— of that functional group is Y' on incorporation of the auristatin drug compound as -D into any one of the drug linker moieties of a Ligand Drug Conjugate compound or into any one of the Drug Linker compounds as described herein, so that for either type of compound subscript y is 2; and one $R^{10}$ and $R^{11}$ is hydrogen and the other is $C_1$-$C_8$ alkyl; $R^{12}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl or —$X^1$—($C_3$-$C_8$ heterocyclyl); $R^{13}$ is hydrogen, $C_1$-$C_8$ alkyl, $C_3$-$C_8$ carbocyclyl, $C_6$-$C_{24}$ aryl, —$X^1$— $C_6$-$C_{24}$ aryl, —$X^1$—($C_3$-$C_8$ carbocyclyl), $C_3$-$C_8$ heterocyclyl and —$X^1$—($C_3$-$C_8$ heterocyclyl); $R^{14}$ is hydrogen or methyl, or $R^{13}$ and $R^{14}$ taken together with the carbon to which they are attached comprise a spiro $C_3$-$C_8$ carbocyclo; $R^{15}$ is hydrogen or $C_1$-$C_8$ alkyl; $R^{16}$ is hydrogen, $C_1$-$C_8$ alkyl, $C_3$-$C_8$ carbocyclyl, $C_6$-$C_{24}$ aryl, —$C_6$-$C_{24}$—$X^1$-aryl, —$X^1$—($C_3$-$C_8$ carbocyclyl), $C_3$-$C_8$ heterocyclyl and —$X^1$—($C_3$-$C_8$ heterocyclyl); $R^{17}$ independently are hydrogen, —OH, $C_1$-$C_8$ alkyl, $C_3$-$C_8$ carbocyclyl and O—($C_1$-$C_8$ alkyl); $R^{18}$ is hydrogen or optionally substituted $C_1$-$C_8$ alkyl; $R^{19}$ is —C($R^{19A}$)$_2$—C($R^{19A}$)$_2$—$C_6$-$C_{24}$ aryl, —C($R^{19A}$)$_2$—C($R^{19A}$)$_2$—($C_3$-$C_8$ heterocyclyl) or —C($R^{19A}$)$_2$—C($R^{19A}$)$_2$—($C_3$-$C_8$ carbocyclyl), wherein $C_6$-$C_{24}$ aryl and $C_3$-$C_8$ heterocyclyl are optionally substituted; $R^{19A}$ independently are hydrogen, optionally substituted $C_1$-$C_8$ alkyl, —OH or optionally substituted —O—$C_1$-$C_8$ alkyl; $R^{20}$ is hydrogen or optionally substituted $C_1$-$C_{20}$ alkyl, optionally substituted $C_6$-$C_{24}$ aryl or optionally substituted $C_3$-$C_8$ heterocyclyl, or —($R^{47}$O)$_m$—$R^{48}$, or —($R^{47}$O)$_m$—CH($R^{49}$)$_2$; $R^{21}$ is optionally substituted —$C_1$-$C_8$ alkylene-($C_6$-$C_{24}$ aryl) or optionally substituted —$C_1$-$C_8$ alkylene-($C_5$-$C_{24}$ heteroaryl), or $C_1$-$C_8$ hydroxylalkyl, or optionally substituted $C_3$-$C_8$ heterocyclyl; Z is O, S, NH, or $NR^{46}$; $R^{46}$ is optionally substituted $C_1$-$C_8$ alkyl; subscript m is an integer ranging from 1-1000; $R^{47}$ is $C_2$-$C_8$ alkyl; $R^{48}$ is hydrogen or $C_1$-$C_8$ alkyl; $R^{49}$ inde pendently are —COOH, —(CH$_2$)$_n$—N(R$^{50}$)$_2$, —(CH$_2$)$_n$—SO$_3$H, or —(CH$_2$)$_n$—SO$_3$—C$_1$-C$_8$ alkyl; R$^{50}$ independently are C$_1$-C$_8$ alkyl, or —(CH$_2$)$_n$—COOH; subscript n is an integer ranging from 0 to 6; and X$^1$ is C$_1$-C$_{10}$ alkylene.

In some embodiments the auristatin drug compound has the structure of Formula D$_{E-1}$, Formula D$_{E-2}$ or Formula D$_{F-1}$:

wherein one of R$^{10}$ and R$^{11}$ is hydrogen and the other is methyl; R$^{13}$ is isopropyl or —CH$_2$—CH(CH$_3$)$_2$; and R$^{19B}$ is —CH(CH$_3$)—CH(OH)-Ph, —CH(CO$_2$H)—CH(OH)—CH$_3$, —CH(CO$_2$H)—CH$_2$Ph, —CH(CH$_2$Ph)-2-thiazolyl, —CH(CH$_2$Ph)-2-pyridyl, —CH(CH$_2$-p-Cl-Ph), —CH(CO$_2$Me)-CH$_2$Ph, —CH(CO$_2$Me)-CH$_2$CH$_2$SCH$_3$, —CH(CH$_2$CH$_2$SCH$_3$)C(=O)NH-quinol-3-yl, —CH(CH$_2$Ph)C(=O)NH-p-Cl-Ph, or R$^{19B}$ has the structure of

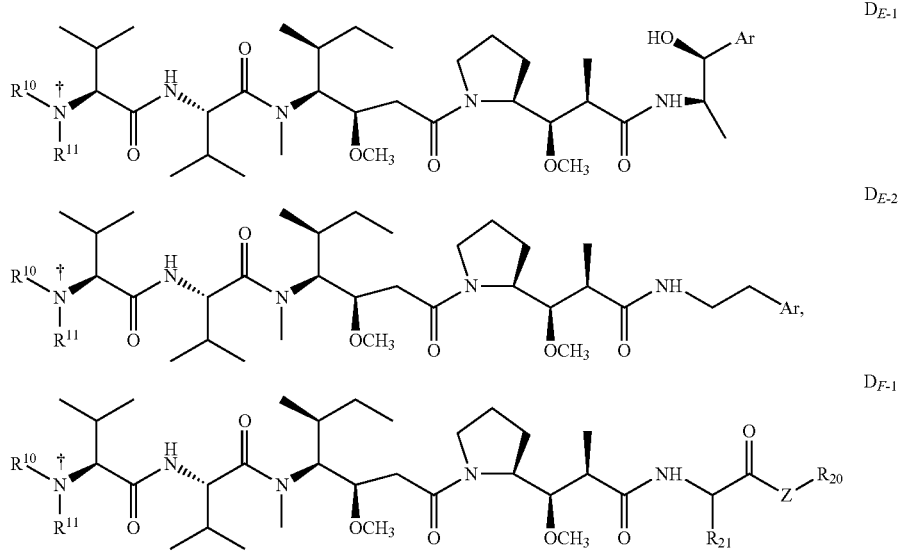

wherein Ar in Formula D$_{E-1}$ or Formula D$_{E-2}$ IS C$_6$-C$_{10}$ aryl or C$_5$-C$_{10}$ heteroaryl, and in Formula D$_{F-1}$, Z is —O—, or —NH—; R$^{20}$ is hydrogen or optionally substituted C$_1$-C$_6$ alkyl, optionally substituted C$_6$-C$_{10}$ aryl or optionally substituted C$_5$-C$_{10}$ heteroaryl; and R$^{21}$ is optionally substituted C$_1$-C$_6$ alkyl, optionally substituted —C$_1$-C$_6$ alkylene-(C$_6$-C$_{10}$ aryl) or optionally substituted —C$_1$-C$_6$ alkylene-(C$_5$-C$_{10}$ heteroaryl).

In some embodiments of Formula D$_E$, D$_F$, D$_{E-1}$, D$_{E-2}$ or D$_{F-1}$, one of R$^{10}$ and R$^{11}$ is hydrogen and the other is methyl.

In some embodiments of Formula D$_{E-1}$ or D$_{E-2}$, Ar is phenyl or 2-pyridyl.

In some embodiments of Formula D$_{F-1}$, R$^{21}$ is X$^1$—S—R$^{21a}$ or X$^1$—Ar, wherein X$^1$ is C$_1$-C$_6$ alkylene, R$^{21a}$ is C$_1$-C$_4$ alkyl and Ar is phenyl or C$_5$-C$_6$ heteroaryl and/or —Z— is —O— and R$^{20}$ is C$_1$-C$_4$ alkyl or Z is —NH— and R$^{20}$ is phenyl or C$_5$-C$_6$ heteroaryl.

In some embodiments the auristatin drug compound has the structure of Formula D$_{F/E-3}$:

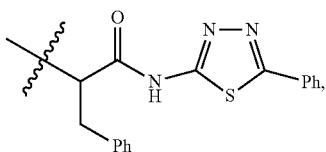

wherein the wavy line indicates covalent attachment to the remainder of the auristatin compound.

In some embodiments the auristatin drug compound incorporated into -D is monomethylauristatin E (MMAE) or monomethylauristatin F (MMAF).

In some embodiments, D is a tertiary amine-containing tubulysin compound wherein the nitrogen atom of the tertiary amine is the site of covalent attachment to the drug linker moiety. The attachment of D to the drug linker moiety may result in a quaternary amine. In some embodiments, D$^+$ may be used to refer to such a quaternary amine-containing drug within a drug linker moiety or Linker Drug compound. In some embodiments, the free drug that is conjugated within a Ligand Drug Conjugate or Drug Liker compound is an amine-containing tubulysin compound wherein the nitrogen atom of the amine is the site of covalent attachment to the Linker Unit of the Ligand Drug Conjugate or Drug Liker compound and the amine-containing tubulysin compound has the structure of Formula D$_G$ or D$_H$:

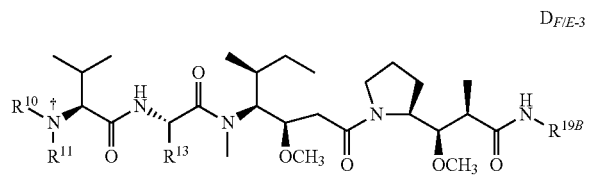

$D_G$

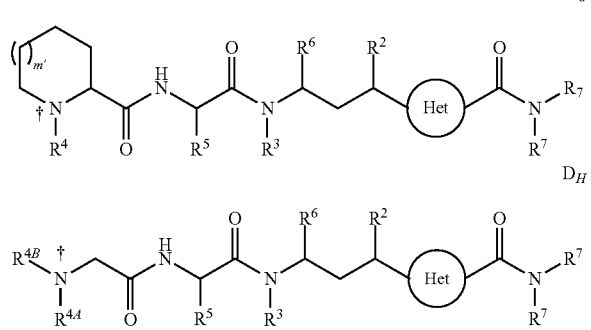

$D_H$

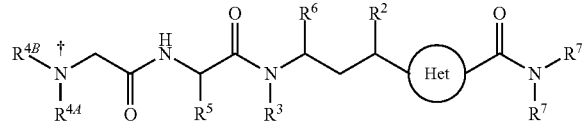

wherein the dagger represents the point of covalent attachment of the Drug Unit to the Linker Unit, in which the nitrogen atom so indicated becomes quaternized, in a Drug Linker compound or Ligand Drug Conjugate compound and the circle represents an 5-membered or 6-membered nitrogen heteroaryl wherein the indicated required substituents to that heteroaryl are in a 1,3- or meta-relationship to each other with optional substitution at the remaining positions; $R^2$ is $X^A$—$R^{2A}$, wherein $X^A$ is —O—, —S—, —N($R^{2B}$)—, —CH$_2$—, —(C=O)N($R^{2B}$)— or —O(C=O)N($R^{2B}$)— wherein $R^{2B}$ is hydrogen or optionally substituted alkyl, $R^{2A}$ is hydrogen, optionally substituted alkyl, optionally substituted aryl, or —C(=O)$R^C$, wherein $R^C$ is hydrogen, optionally substituted alkyl, or optionally substituted aryl or $R^2$ is an O-linked substituent; $R^3$ is hydrogen or optionally substituted alkyl; $R^4$, $R^{4A}$, $R^{4B}$, $R^5$ and PP are optionally substituted alkyl, independently selected, one P7 is hydrogen or optionally substituted alkyl and the other P7 is optionally substituted arylalkyl or optionally substituted heteroarylalkyl, and m is 0 or 1. In other embodiments the quaternized drug is a tubulysin represented by structure DG wherein one P7 is hydrogen or optionally substituted alkyl, the other P7 is an independently selected optionally substituted alkyl, and subscript m' is 0 or 1, wherein the other variable groups are as previously defined. In some embodiments, one P7 is hydrogen or optionally substituted lower alkyl, the other P7 is an independently selected optionally substituted $C_1$-$C_6$ alkyl, and subscript m' is 1, wherein the other variable groups are as previously defined.

In some embodiments, $R^2$ is $X^A$—$R^{2A}$, wherein $X^A$ is —O—, —S—, —N($R^{2B}$)—, —CH$_2$—, or —O(C=O)N ($R^{2B}$)— wherein $R^{2B}$ is hydrogen or optionally substituted alkyl, $R^{2A}$ is hydrogen, optionally substituted alkyl, optionally substituted aryl, or —C(=O)$R^C$, wherein $R^C$ is hydrogen, optionally substituted alkyl, or optionally substituted aryl or $R^2$ is an O-linked substituent.

In some embodiments, $R^2$ is $X^A$—$R^{2A}$, wherein $X^A$ is —O—, —S—, —N($R^{2B}$)— or —(C=O)N($R^{2B}$)— wherein $R^{2A}$ and $R^{2B}$ are independently hydrogen or optionally substituted alkyl, or $R^2$ is an O-linked substituent.

In some embodiments —N($R^7$)($R^7$) in DG or $D_H$ is replaced by —N($R^7$)—CH($R^{10}$)(CH$_2$$R^{11}$) to define tubulysin compounds of formula $D_H'$ and $D_G'$:

$D_G$

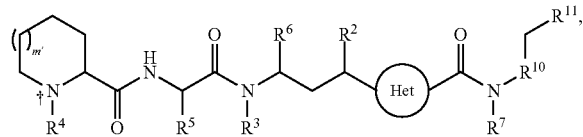

$D_H$

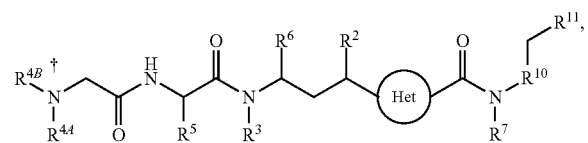

wherein the dagger represents the point of covalent attachment to the Linker Unit, in which the nitrogen atom so indicated becomes quaternized, in a Drug Linker compound or Ligand Drug Conjugate compound; $R^{10}$ is $C_1$-$C_6$ alkyl substituted with —CO$_2$H, or ester thereof, and $R^7$ is hydrogen or a $C_1$-$C_6$ alkyl independently selected from $R^{10}$, or $R^7$ and $R^{10}$ together with the atoms to which they are attached define a 5 or 6-membered heterocycle; and $R^{11}$ is aryl or 5- or 6-membered heteroaryl, optionally substituted with one or more, substituent(s) independently selected from the group consisting of halogen, lower alkyl, —OH and —O—$C_1$-$C_6$ alkyl; and the remaining variable groups are as defined for $D_G$ and $D_H$. In some embodiments, $R^{11}$ is substituted with one or two substituents selected from the group consisting of halogen, lower alkyl, —OH and —O—$C_1$-$C_6$ alkyl. In some embodiments, $R^{11}$ is substituted with one substitutent selected from the group consisting of halogen, lower alkyl, —OH and —O—$C_1$-$C_6$ alkyl. In some embodiments, the halogen is F. In some embodiments, the —O—$C_1$-$C_6$ alkyl is —OCH$_3$. In some embodiments, the lower alkyl is —CH$_3$.

In still other embodiments one $R^7$ in —N($R^7$)($R^7$) in $D_G$ or $D_H$ is hydrogen or $C_1$-$C_6$ alkyl, and the other $R^7$ is an independently selected $C_1$-$C_6$ alkyl optionally substituted by —CO$_2$H or an ester thereof, or by an optionally substituted phenyl.

In some embodiments of structure $D_G$ and $D_H$, one $R^7$ is hydrogen and the other $R^7$ is an optionally substituted arylalkyl having the structure of:

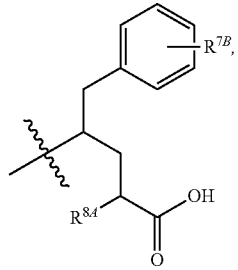

wherein $R^{7B}$ is hydrogen or an O-linked substituent, and $R^{8A}$ is hydrogen or lower alkyl; and wherein the wavy line indicates the point of attachment to the remainder of $D_G$ or $D_H$. In some embodiments, $R^{7B}$ is hydrogen or —OH in the para position. In some embodiments, $R^{8A}$ is methyl.

In some embodiments of structure $D_G$ or $D_H$, one $R^7$ is hydrogen, and the other $R^7$ is an optionally substituted arylalkyl having the structure of

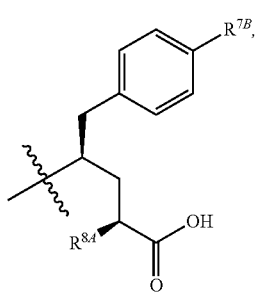

wherein $R^{7B}$ is —H or —OH; and wherein the wavy line indicates the point of attachment to the remainder of $D_G$ or $D_H$.

In some embodiments of structure $D_G$ and $D_H$, one $R^7$ is hydrogen or lower alkyl, and the other $R^7$ is optionally substituted arylalkyl having the structure of one of

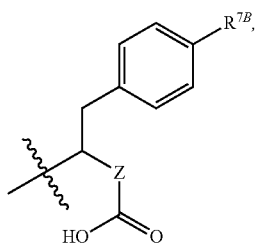

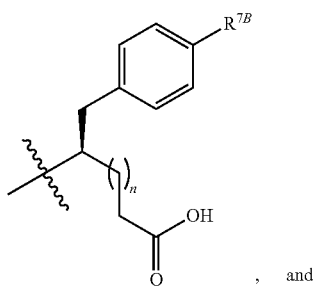

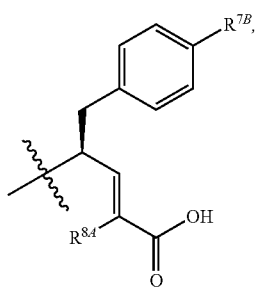, and wherein Z is an optionally substituted alkylene or an optionally substituted alkenylene, $R^{7B}$ is hydrogen or an O-linked substituent, $R^{8A}$ is hydrogen or lower alkyl, and the subscript n is 0, 1 or 2; and wherein the wavy line indicates the point of attachment to the remainder of $D_G$ or $D_H$. In some embodiments, subscript n is 0 or 1. In still other embodiments of structure $D_G$ and $D_H$-N($R^7$)($R^7$) is —NH($C_1$-$C_6$ alkyl) wherein the $C_1$-$C_6$ alkyl is optionally substituted by —$CO_2H$ or an ester thereof, or by an optionally substituted phenyl. In some embodiments —N($R^7$)($R^7$) is selected from the group consisting of —NH($CH_3$), —$CH_2CH_2Ph$, —$CH_2$—$CO_2H$, —$CH_2CH_2CO_2H$ and —$CH_2CH_2CH_2CO_2H$. In some embodiments, one $R^7$ is hydrogen or methyl and the other $R^7$ is an optionally substituted arylalkyl having the structure of:

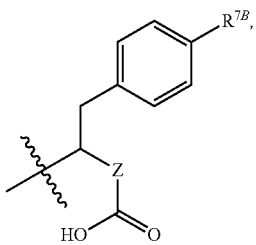

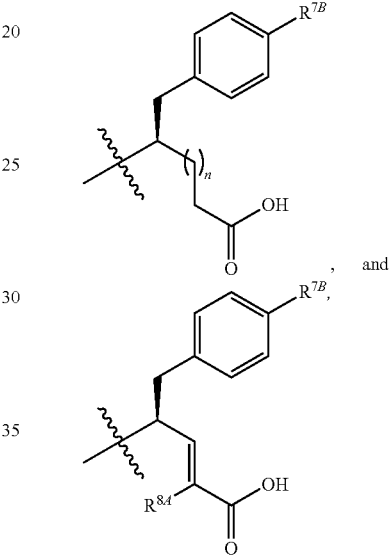

wherein Z is an optionally substituted alkylene or an optionally substituted alkenylene, $R^{7B}$ is hydrogen or —OH in the para position, $R^{8A}$ is hydrogen or methyl, and the subscript n is 0, 1 or 2

In some embodiments of structure $D_G'$ and $D_H'$, $R^7$ and $R^{10}$ together with the atoms to which they are attached define an optionally substituted 5 or 6-membered heterocycle wherein —N($R^7$)—CH($R^{10}$)($CH_2R^1$) has the structure of:

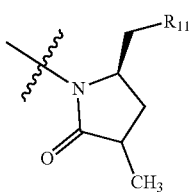

wherein the wavy line indicates the point of attachment to the remainder of $D_G'$ or $D_H'$.

In some embodiments, the tubulysin compound is represented by the following formula wherein the indicated nitrogen (†) is the site of quaternization when such compounds are incorporated into an LDC as a quaternized drug unit ($D^+$):

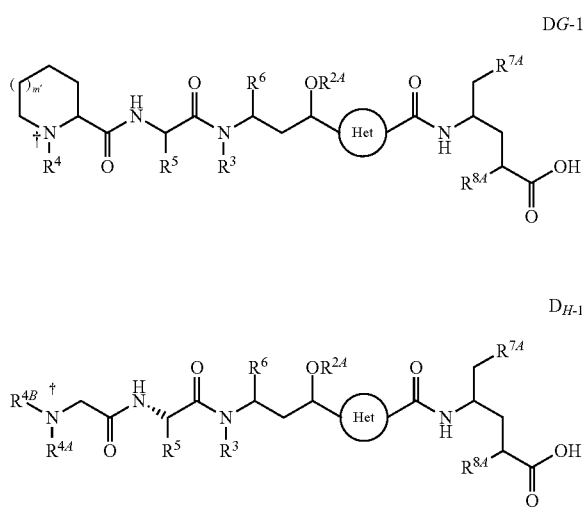

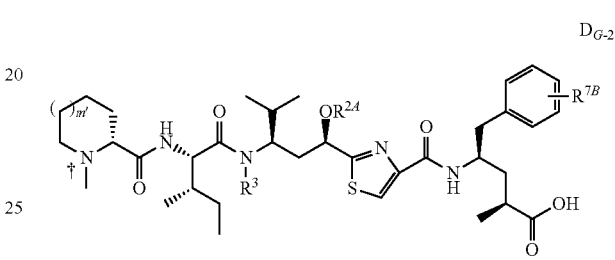

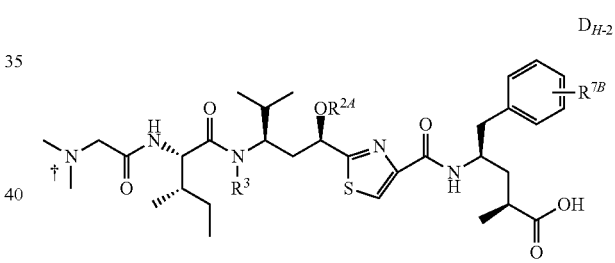

wherein the dagger represents the point of attachment of the Drug Unit to the Linker Unit in a Drug Linker compound or Ligand Drug Conjugate compound in which the nitrogen atom so indicated becomes quaternized, and the circle represents an 5-membered or 6-membered nitrogen-heteroaryl wherein the indicated required substituents to that heteroaryl are in a 1,3- or meta-relationship to each other with optional substitution at the remaining positions; $R^{2A}$ is hydrogen or optionally substituted alkyl or $R^{2A}$ along with the oxygen atom to which it is attached defines an O-linked substituent; $R^3$ is hydrogen or optionally substituted alkyl; $R^4$, $R^{4A}$, $R^{4B}$, $R^5$ and $R^6$ are optionally substituted alkyl, independently selected; $R^{7A}$ is optionally substituted aryl or optionally substituted heteroaryl, $R^{8A}$ is hydrogen or optionally substituted alkyl and subscript m' is 0 or 1.

In some embodiments of structure DG, $D_{G-1}$, $D_H$, or $D_{H-1}$, $R^4$ is methyl or $R^{4A}$ and $R^{4B}$ are methyl. In other embodiments of structure DG' or $D_H$' $R^4$ is methyl or $R^{4A}$ and $R^{4B}$ are methyl. In other embodiments, $R^{7A}$ is optionally substituted phenyl. In some embodiments $R^{8A}$ is methyl in the (S)-configuration. In other embodiments, $R^{2A}$ along with the oxygen atom to which it is attached defines an O-linked substituent other than —OH. In some embodiments, $R^{2A}$ along with the oxygen atom to which it is attached defines an ester, ether, or an O-linked carbamate. In some embodiments the circle represents a 5-membered nitrogen-heteroarylene. Some embodiments, the circle represents a divalent oxazole or thiazole moiety. In some embodiments $R^4$ is methyl or $R^{4A}$ and $R^{4B}$ are methyl. In some embodiments $R^7$ is optionally substituted arylalkyl, wherein aryl is phenyl and $R^{7A}$ is optionally substituted phenyl.

In other embodiments of $D_G$, $D_G$', $D_{G-1}$, $D_H$, $D_H$' or $D_{H-1}$ the circle represents a 5-membered nitrogen heteroarylene. In some embodiments, the 5-membered heteroarylene is represented by the structure

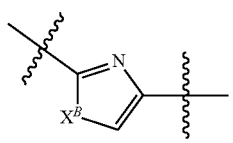

wherein $X^B$ is O, S, or N—$R^B$ wherein $R^B$ is hydrogen or lower alkyl. In some embodiments, the quaternized drug is a tubulysin represented by structure $D_G$, $D_G$' or $D_{G-1}$, wherein m is 1. In some embodiments, the tubulysins are represented by structure $D_G$, wherein m is 1 and the circle represents an optionally substituted divalent thiazole moiety.

In some embodiments, the tubulysin compound is represented by the following formula wherein the indicated nitrogen atom (†) is the site of quaternization when such compounds are incorporated into an LDC as a quaternized drug unit (D$^+$):

wherein $R^{2A}$ along with the oxygen atom to which it is attached defines an O-linked substituent, $R^3$ is lower alkyl or —CH$_2$OC(=O)R$^{3A}$ wherein $R^{3A}$ is optionally substituted lower alkyl, and $R^{7B}$ is hydrogen or an O-linked substituent. In some embodiments, $R^{2A}$ along with the oxygen atom to which it is attached defines an ester, ether or O-linked carbamate. In some embodiments, $R^{7B}$ is an O-linked substituent in the para position. In some embodiments, $R^3$ is methyl or $R^{3A}$ is methyl, ethyl, propyl, iso-propyl, iso-butyl or —CH$_2$C=(CH$_3$)$_2$. In some embodiments $R^{2A}$ is methyl, ethyl, propyl (i.e., —OR$^{2A}$ is an ether) or is —C(=O)R$^{2B}$ (i.e., —OR$^{2A}$ is an ester) wherein $R^{2B}$ is lower alkyl. In some embodiments, $R^{2B}$ is methyl (i.e., —OR$^{2A}$ is acetate).

In some embodiments, the tubulysin compound that is incorporated into a Ligand Drug Conjugate or Drug Linker compound has the structure of one of the following formulae:

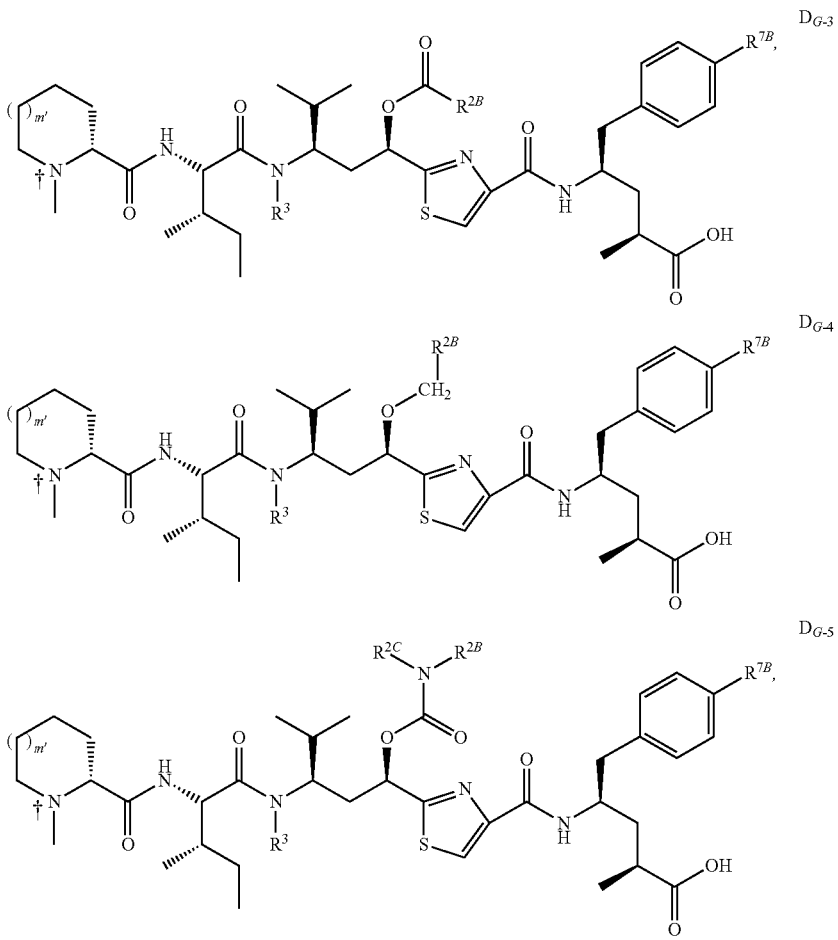

wherein $R^{7B}$ is hydrogen or —OH, $R^3$ is lower alkyl, and $R^{2B}$ and $R^{2C}$ are independently hydrogen or lower alkyl. In some embodiments, $R^3$ is methyl or ethyl. In some embodiments of any one of structures DG, $D_{G-1}$, $D_{G-2}$, $D_{G-3}$, $D_{G-4}$, $D_{G-5}$, $D_H$, $D_{H-1}$ and $D_{H-2}$, $R^3$ is methyl or is —CH$_2$OC(=O)$R^{3A}$, wherein $R^{3A}$ is optionally substituted alkyl. In some embodiments of any one of structures DG' and $D_H'$, $R^3$ is methyl or is —CH$_2$OC(=O)$R^{3A}$, wherein $R^{3A}$ is optionally substituted alkyl. In some embodiments of any one of those structures $R^3$ is —C($R^{3A}$)($R^{3A}$)C(=O)—$X^C$, wherein $X^C$ is —$OR^{3B}$ or —N($R^{3C}$)($R^{3C}$), wherein each $R^{3A}$, $R^{3B}$ and $R^{3C}$ independently is hydrogen, optionally substituted alkyl or optionally substituted cycloalkyl. In some embodiments, $R^3$ is —C($R^{3A}$)($R^{3A}$)C(=O)—N($R^{3C}$)($R^{3C}$), with each $R^{3A}$ hydrogen, one $R^{3C}$ hydrogen and the other $R^{3C}$ n-butyl or isopropyl.

In some embodiments of any one of structures DG, $D_{G'}$, $D_{G-1}$, $D_{G-2}$, $D_{G-3}$, $D_{G-4}$, $D_{G-5}$, $D_H$, $D_{H'}$, $D_{H-1}$ and $D_{H-2}$, $R^3$ is ethyl or propyl.

In some embodiments of any one of structures $D_{G-1}$, $D_{G-2}$, $D_{G-3}$, $D_{G-4}$, $D_{G-5}$, $D_{G-6}$, $D_{H-1}$ and $D_{H-2}$, the thiazole core heterocycle

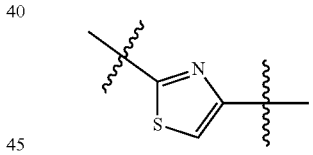

is replaced with

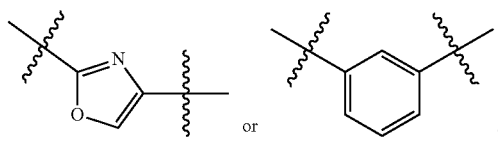

In some embodiments of any one of structures DG, $D_{G-1}$, $D_{G-2}$, $D_{G-3}$, $D_{G-4}$, $D_{G-5}$, $D_H$, $D_{H-1}$, $D_{H-2}$, $D_{H-3}$ and $D_{H-4}$, $R^3$ is methyl or is —CH$_2$OC(=O)$R^{3A}$, wherein $R^{3A}$ is optionally substituted alkyl. In some embodiments of any one of those structures $R^3$ is —C($R^{3A}$)($R^{3A}$)C(=O)—$X^C$, wherein $X^C$ is —$OR^{3B}$ or —N($R^{3C}$)($R^{3C}$), wherein each $R^{3A}$, $R^{3B}$ and $R^{3C}$ independently is hydrogen, optionally substituted alkyl or optionally substituted cycloalkyl. In some embodiments, $R^3$ is —C($R^{3A}$)($R^{3A}$)C(=O)—N($R^{3C}$)($R^{3C}$), with each $R^{3A}$ hydrogen, one $R^{3C}$ hydrogen and the other $R^{3C}$ is optionally substituted alkyl or optionally substituted cycloalkyl. In some embodiments, $R^3$ is —C($R^{3A}$)($R^{3A}$)C(=O)—N($R^{3C}$)($R^{3C}$), with each $R^{3A}$ hydrogen, one $R^{3C}$ hydrogen and the other $R^{3C}$ is n-butyl or isopropyl.

In some embodiments of any one of structures $D_{G-3}$, $D_{G-4}$, $D_{G-5}$, $D_{H-3}$ and $D_{H-4}$, the thiazole core heterocycle

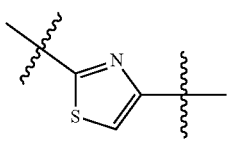 [SMILES: *c1csc(*)n1]

is replaced with

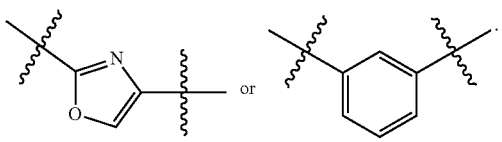 [SMILES: *c1coc(*)n1 ; *c1cccc(*)c1]

In some embodiments, the tubulysin has structure $D_{G-3}$ or $D_{G-4}$ wherein m is 1, $R^3$ is optionally substituted methyl, ethyl or propyl. In some embodiments, $R^3$ is unsubstituted methyl, ethyl or propyl.

In some embodiments, the tubulysin compound has structure $D_{G-3}$, wherein subscript m' is 1, $R^3$ is methyl, ethyl or propyl, —OC(O)$R^{2B}$ is —O—C(O)H, O—C(O)—$C_1$-$C_6$ alkyl, or —O$C_2$-$C_6$ alkenyl, optionally substituted. In some embodiments, —OC(O)$R^{2B}$ is —OC(O)CH$_3$, —OC(O)CH$_2$CH$_3$, —OC(O)CH(CH$_3$)$_2$, —OC(O)C(CH$_3$)$_3$, or —OC(O)CH=CH$_2$.

In some embodiments, the tubulysin compound has structure $D_{G-4}$, wherein subscript m' is 1, $R^3$ is methyl, ethyl or propyl and —OCH$_2R^{2B}$ is —OCH$_3$, —OCH$_2$CH$_3$, —OCH$_2$CH$_2$CH$_3$ or —OCH$_2$OCH$_3$.

In some embodiments, the tubulysin has the structure of

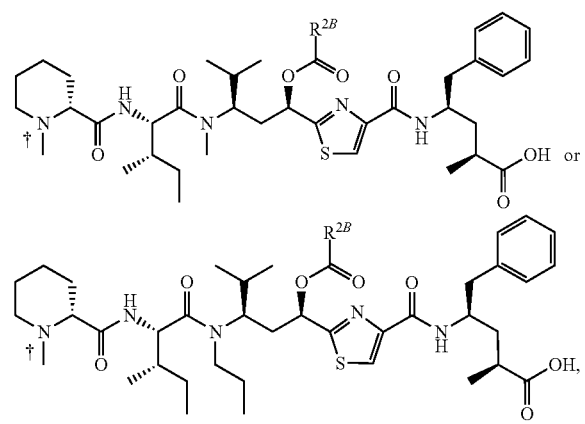

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, —CH$_2$C(CH$_3$)$_3$ and the indicated nitrogen atom (†) is the site of quaternization when such compounds are incorporated into an LDC or Drug Linker compound as a quaternized drug unit (D$^+$).

In some embodiments, the tubulysin has the structure of

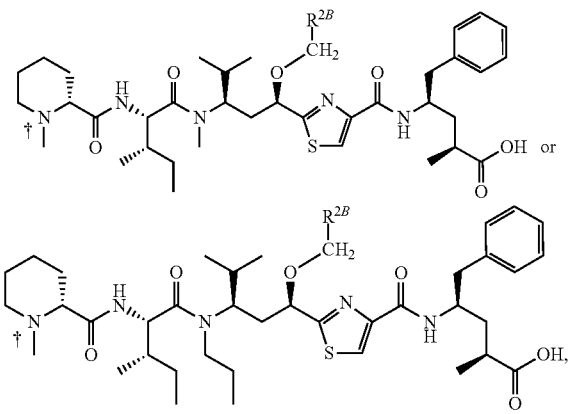

wherein $R^{2B}$ is hydrogen, methyl or —OCH$_3$ (i.e., —OCH$_2R^{2B}$ is a methyl ethyl, methoxymethyl ether substituent).

In some embodiments, the tubulysin incorporated as D$^+$ in an LDC is a naturally occurring tubulysin including Tubulysin A, Tubulysin B, Tubulysin C, Tubulysin D, Tubulysin E, Tubulysin F, Tubulysin G, Tubulysin H, Tubulysin I, Tubulysin U, Tubulysin V, Tubulysin W, Tubulysin X or Tubulysin Z, whose structures are given by the following structure and variable group definitions wherein the indicated nitrogen atom (†) is the site of quaternization when such compounds are incorporated into an LDC or Drug Linker compound as a quaternized drug unit (D$^+$):

$D_{G-6}$

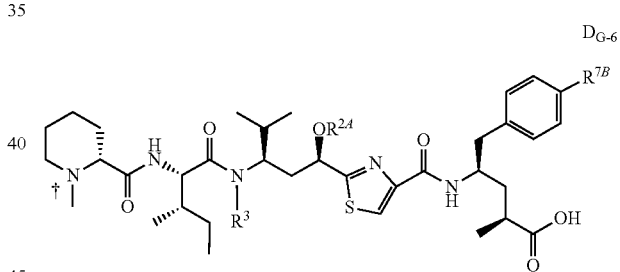

TABLE 1

| Some Naturally Occurring Tubulysins | | | |
|---|---|---|---|
| Tubulysin | $R^{7B}$ | $R^{2A}$ | $R^3$ |
| A | OH | C(=O)CH$_3$ | CH$_2$OC(=O)i-Bu |
| B | OH | C(=O)CH$_3$ | CH$_2$OC(=O)n-Pr |
| C | OH | C(=O)CH$_3$ | CH$_2$OC(=O)Et |
| D | H | C(=O)CH$_3$ | CH$_2$OC(=O)i-Bu |
| E | H | C(=O)CH$_3$ | CH$_2$OC(=O)n-Pr |
| F | H | C(=O)CH$_3$ | CH$_2$OC(=O)Et |
| G | OH | C(=O)CH$_3$ | CH$_2$OC(=O)CH=CH$_2$ |
| H | H | C(=O)CH$_3$ | CH$_2$OC(=O)Me |
| I | OH | C(=O)CH$_3$ | CH$_2$OC(=O)Me |
| U | H | C(=O)CH$_3$ | H |
| V | H | OH | H |
| Z | OH | OH | H |

In some embodiments of structure $D_{G-6}$ the tubulysin compound incorporated into an LDC or Drug Linker compound as a quaternized Drug Unit is Tubulysin M, wherein $R^3$ is —CH$_3$, $R^2$ is C(=O)CH$_3$ and $R^{7B}$ is hydrogen.

In some embodiments, D incorporates the structure of a a DNA damaging agent. In some embodiments, D incorporates the structure of a a DNA replication inhibitor. In some embodiments, D incorporates the structure of a a camptothecin. In some embodiments, that camptothecin compound has a formula selected from the group consisting of CPT1
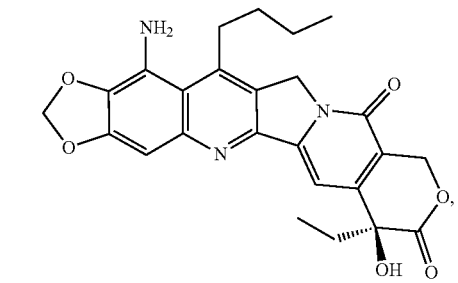

CPT2
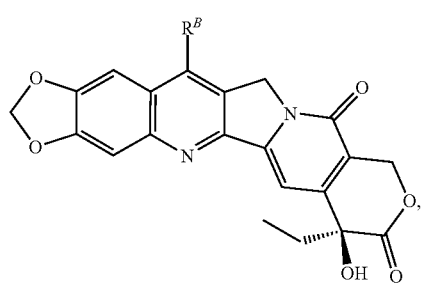

CPT3
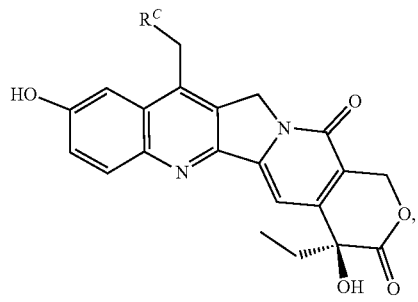

CPT4
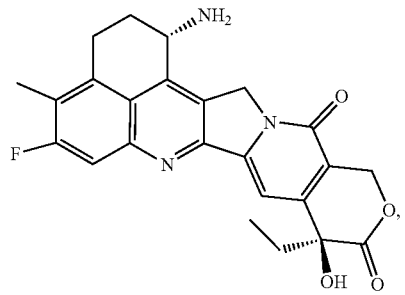

CPT5
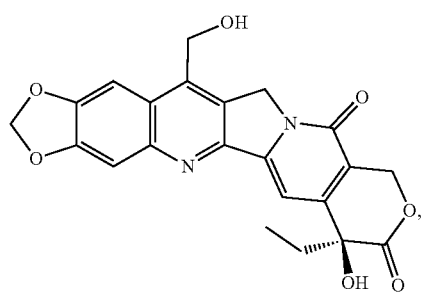

CPT6
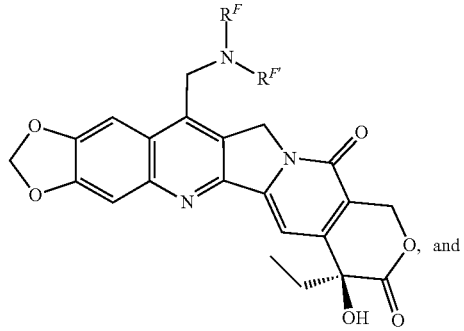

CPT7
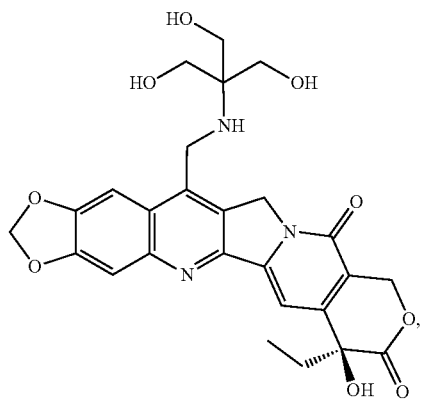

wherein $R^B$ is selected from the group consisting of H, $C_1$-$C_8$ alkyl, $C_1$-$C_8$ haloalkyl, $C_3$-$C_8$ cycloalkyl, ($C_3$-$C_8$ cycloalkyl)-$C_1$-$C_4$ alkyl, phenyl, and phenyl-$C_1$-$C_4$ alkyl;

$R^C$ is selected from the group consisting of $C_1$-$C_6$ alkyl and $C_3$-$C_6$ cycloalkyl; and each $R^F$ and $R^{F'}$ is independently selected from the group consisting of —H, $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydoxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl, and heteroaryl-$C_1$-$C_4$ alkyl-, or $R^F$ and $R^{F'}$ are combined with the nitrogen atom to which each is attached to form a 5-, 6- or 7-membered ring having 0 to 3 substituents selected from the group consisting of halogen, $C_1$-$C_4$ alkyl, —OH, —O$C_1$-$C_4$ alkyl, —NH$_2$, —NH—$C_1$-$C_4$ alkyl, —N($C_1$-$C_4$ alkyl)$_2$; and wherein the cycloalkyl, heterocycloalkyl, phenyl and heteroaryl portions of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —NH$_2$, —NH$C_1$-$C_4$ alkyl, and —N($C_1$-$C_4$ alkyl)$_2$.

In some embodiments, the camptothecin compound, whose structure is incorporated as a Drug Unit in a LDC or Drug Linker compound, has the formula CPT1, the structure of which is:

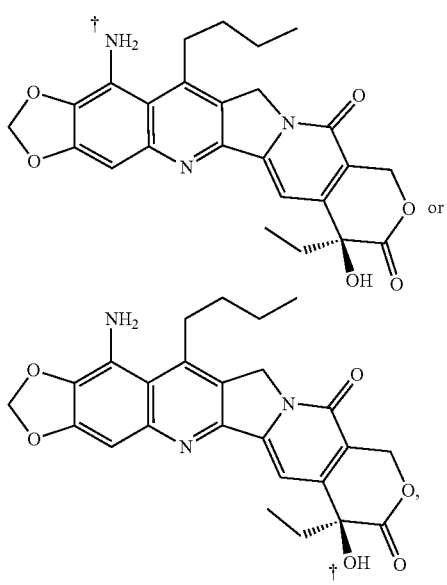

wherein the dagger represents the point of attachment of the Drug Unit to the Linker Unit in a Drug Linker compound or Ligand Drug Conjugate compound.

In some embodiments, the camptothecin compound, whose structure is incorporated as a Drug Unit in a LDC or Drug Linker compound, has the formula CPT2, the structure of which is:

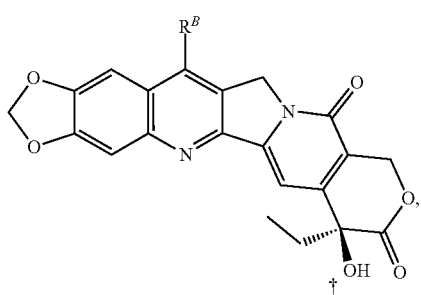

wherein the dagger represents the point of attachment of the Drug Unit to the Linker Unit in a Drug Linker compound or Ligand Drug Conjugate compound.

In some embodiments, the camptothecin compound, whose structure is incorporated as a Drug Unit in a LDC or Drug Linker compound, has the formula CPT3, the structure of which is:

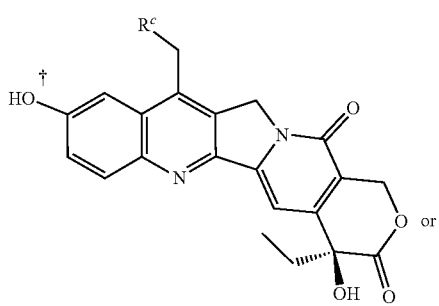

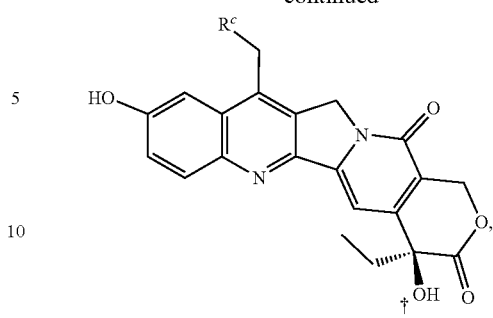

wherein the dagger represents the point of attachment of the Drug Unit to the Linker Unit in a Drug Linker compound or Ligand Drug Conjugate compound.

In some embodiments, the camptothecin compound, whose structure is incorporated as a Drug Unit in a LDC or Drug Linker compound, has the formula CPT4, the structure of which is:

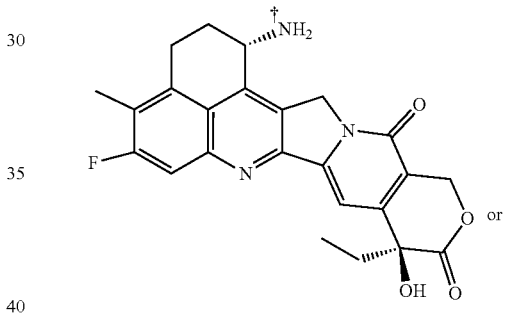

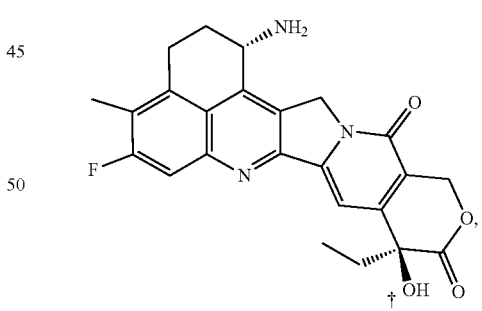

wherein the dagger represents the point of covalent attachment of the Drug Unit to the Linker Unit when the formula CPT4 compound is in the form of a Drug Unit in a Drug Linker compound or Ligand Drug Conjugate compound. In some embodiments, D incorporates the structure of exatecan.

In some embodiments, the camptothecin compound, whose structure is incorporated as a Drug Unit in a LDC or Drug Linker compound, has the formula CPT5, the structure of which is:

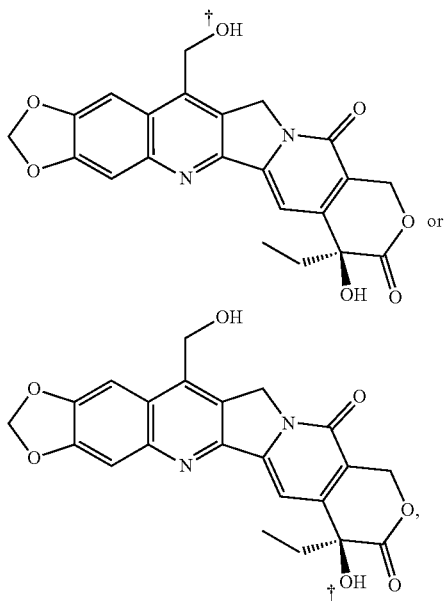

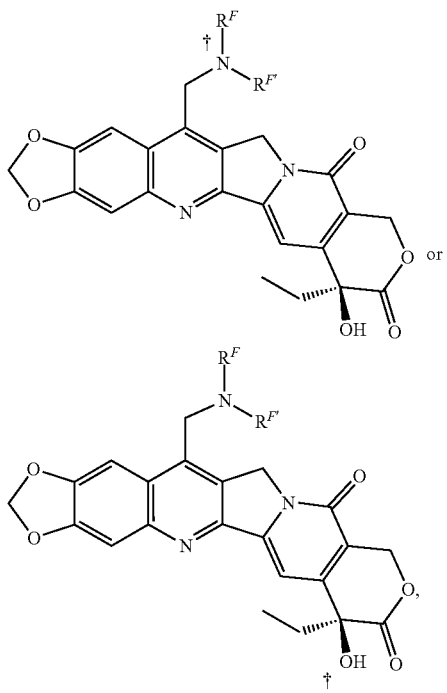

wherein the dagger represents the point of attachment to the Linker Unit when the formula CPT5 compound is in the form of a Drug Unit in a Drug Linker compound or Ligand Drug Conjugate compound.

In some embodiments, the camptothecin compound, whose structure is incorporated as a Drug Unit in a LDC or Drug Linker compound, has the formula CPT6, the structure of which is:

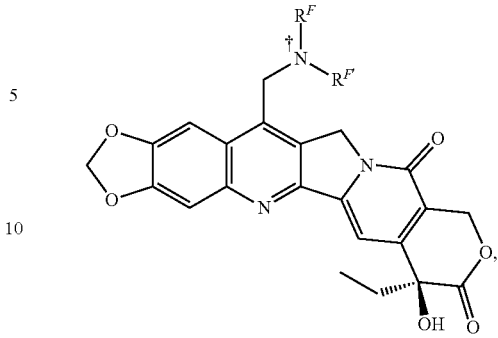

wherein the dagger represents the point of attachment to the Linker Unit when the formula CPT6 compound is in the form of a Drug Unit in a Drug Linker compound or Ligand Drug Conjugate compound. In some embodiments, CPT6 has the structure of:

wherein the dagger represents the point of attachment to the Linker Unit when the formula CPT6 compound is in the form of a Drug Unit in a Drug Linker compound or Ligand Drug Conjugate compound. In some embodiments, the camptothecin compound whose structure is incorporated as a Drug Unit in a LDC or a Drug Linker Compound is selected from Table X.

In some embodiments, the camptothecin compound, whose structure is incorporated as a Drug Unit in a LDC or Drug Linker compound, has the formula CPT7 the structure of which is:

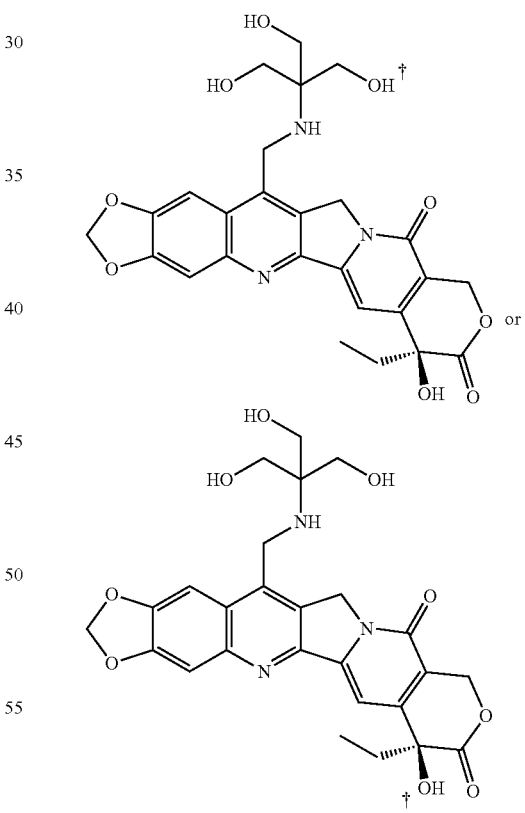

wherein the dagger represents the point of attachment to the Linker Unit in a Drug Linker compound or Ligand Drug Conjugate compound when the formula CPT7 compound is in the form of a Drug Unit.

In some embodiments, the camptothecin compound, whose structure is incorporated as a Drug Unit in a LDC or Drug Linker compound, has the formula

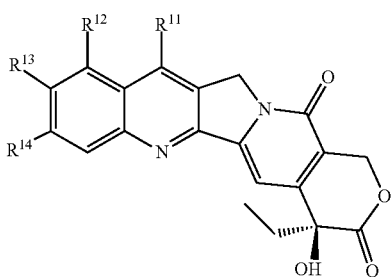

wherein one of $R^{11}$ is n-butyl and one of $R^{12}$—$R^{14}$ is —$NH_2$ and the other are hydrogen, or $R^{12}$ is —$NH_2$ and $R^{13}$ and $R^{14}$ together are —OCHO—.

In some embodiments, $R^B$ is selected from the group consisting of $C_3$-$C_8$ cycloalkyl, ($C_3$-$C_8$ cycloalkyl)-$C_1$-$C_4$ alkyl, phenyl, and phenyl-$C_1$-$C_4$ alkyl, and wherein the cycloalkyl and phenyl portions of $R^B$ are substituted with from 0 to 3 substituents selected from halogen, $C_1$-$C_4$ alkyl, OH, —O—$C_1$-$C_4$ alkyl, $NH_2$, —NH—$C_1$-$C_4$ alkyl and —N($C_1$-$C_4$ alkyl)$_2$. In some embodiments, $R^B$ is selected from the group consisting of H, $C_1$-$C_8$ alkyl, and $C_1$-$C_8$ haloalkyl. In some embodiments, $R^B$ is H, methyl, ethyl, propyl, isopropyl, butyl, isobutyl, sec-butyl, tert-butyl, pentyl, isopentyl, 1-ethylpropyl, or hexyl. In some embodiments, $R^B$ is chloromethyl or bromomethyl. In some embodiments, $R^B$ is phenyl or halo-substituted phenyl. In some embodiments, $R^B$ is phenyl or fluorophenyl.

In some embodiments, $R^C$ is $C_1$-$C_6$ alkyl. In some embodiments, $R^C$ is methyl. In some embodiments, $R^C$ is $C_3$-$C_6$ cycloalkyl.

In some embodiments, $R^F$ and $R^{F'}$ are both H. In some embodiments, at least one of $R^F$ and $R^{F'}$ is selected from the group consisting of $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$—$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydoxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-. In some embodiments, one of $R^F$ and $R^{F'}$ is H and the other is selected from the group consisting of $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydroxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-. In some embodiments, one of $R^F$ and $R^{F'}$ is selected from the group consisting of $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydroxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-, and the other is selected from the group consisting of H, $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydoxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-. In some embodiments, $R^F$ and $R^{F'}$ are both independently selected from the group consisting of $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydoxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-.

In some embodiments, the cycloalkyl, heterocycloalkyl, phenyl and heteroaryl moieties of $R^F$ or $R^{F'}$ are substituted with from 0 to 3 substituents independently selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$.

In some embodiments, $R^F$ and $R^{F'}$ are combined with the nitrogen atom to which each is attached to form a 5-, 6- or 7-membered ring having 0 to 3 substituents selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$.

In some embodiments, D incorporates the structure of AMDCPT:

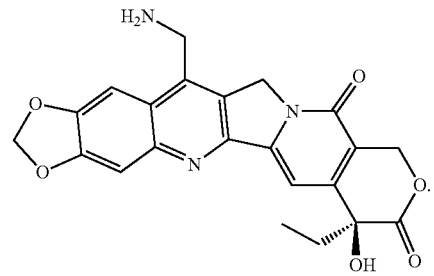 [SMILES: CC[C@@]1(O)C(=O)OCc2c1cc1n(c2=O)Cc2c-1nc1cc3c(cc1c2CN)OCO3]

In some embodiments, D incorporates the structure of exatecan:

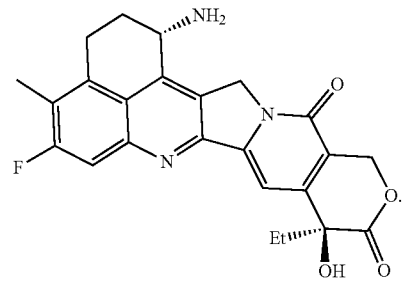 [SMILES: CC[C@@]1(O)C(=O)OCc2c1cc1n(c2=O)Cc2c-1nc1cc(F)c(C)c3c1c2[C@@H](N)CC3]

In some embodiments, D incorporates the structure of irinotecan:

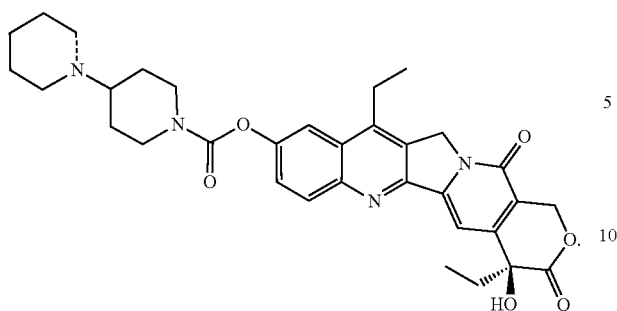

In some embodiments, D incorporates the structure of a DNA minor groove binder. In some embodiments, D incorporates the structure of a pyrrolobenzodiazepine (PBD) compound with the following structure:

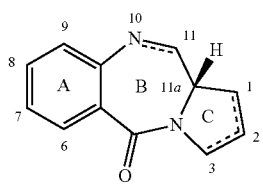

In some embodiments, D is a PBD Drug Unit that incorporates a Drug PBD dimer that is a DNA minor groove binder and has the general structure of Formula X:

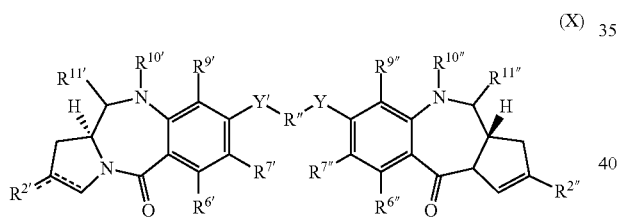

(X)

or a salt thereof, wherein: the dotted lines represent a tautomeric double bond; $R^{2''}$ is of formula XI:

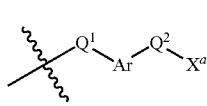

(XI)

wherein the wavy line indicates the site of covalent attachment to the remainder of the Formula X structure; Ar is an optionally substituted $C_{5-7}$ arylene; $X^a$ is from a reactive or activatable group for conjugation to a Linker Unit, wherein $X^a$ is selected from the group comprising: —O—, —S—, —C(O)O—, —C(O)—, —NHC(O)—, and —N($R^N$)—, wherein $R^N$ is H or $C_1$-$C_4$ alkyl, and $(C_2H_4O)_mCH_3$, where subscript m is 1, 2 or 3; and either:
(i) $Q^1$ is a single bond; and $Q^2$ is a single bond or —Z—$(CH_2)_n$—, wherein Z is selected from the group consisting of a single bond, O, S, and NH; and subscript n is 1, 2 or 3, or (ii) $Q^1$ is —CH=CH—, and $Q^2$ is a single bond; and $R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent, wherein the dotted lines indicate a single bond to $R^{2'}$, or $R^{2'}$ an optionally substituted $C_1$-$C_4$ alkenylene, wherein the dotted lines indicate a double bond to $R^{2'}$; $R^{6'''}$ and $R^{9'''}$ are independently selected from the group consisting of H, R, OH, OR, SH, SR, $NH_2$, NHR, NRR', nitro, $Me_3Sn$ and halo; $R^{7'''}$ is selected from the group consisting of H, R, OH, OR, SH, SR, $NH_2$, NHR, NRR', nitro, $Me_3Sn$ and halo; and R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl; either:
(a) $R^{10'''}$ is H, and $R^{11'''}$ is OH or $OR^A$, wherein $R^A$ is $C_1$-$C_4$ alkyl, (b) $R^{10'''}$ and $R^{11'''}$ form a nitrogen-carbon double bond between the nitrogen and carbon atoms to which they are bound, or (c) $R^{10'''}$ is H and $R^{11'''}$ is $SO_zM$, wherein subscript z is 2 or 3 and M is a monovalent pharmaceutically acceptable cation, or (d) $R^{10'}$, $R^{11'}$ and $R^{10'''}$ are each H and $R^{11'''}$ is $SO_2M$, or $R^{10'}$ and $R^{11'}$ are each H and $R^{10'''}$ and $R^{11'''}$ form a nitrogen-carbon double bond between the nitrogen and carbon atoms to which they are bound, or $R^{10'''}$, $R^{11'''}$ and $R^{10'}$ are each H and $R^{11'}$ is $SO_zM$, or $R^{10'''}$ and $R^{11'''}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and
R" is a $C_{3-12}$ alkylene group, the carbon chain of which is optionally interrupted by one or more heteroatoms, in particular by one of O, S or $NR^{N2}$ (where $R^{N2}$ is H or $C_1$-$C_4$ alkyl), and/or by aromatic rings, in particular by one of benzene or pyridine; Y and Y' are selected from the group consisting of O, S, and NH; $R^{6'}$, $R^{7'}$, $R^{9'}$ are selected from the same groups as $R^{6'''}$, $R^{7'''}$ and $R^{9'''}$, respectively, and $R^{10'}$ and $R^{11'}$ are the same as $R^{10'''}$ and $R^{11'''}$, respectively, wherein if $R^{11'''}$ and $R^{11'}$ are $SO_2M$, each M is either a monovalent pharmaceutically acceptable cation or together represent a divalent pharmaceutically acceptable cation.

In some embodiments, a PBD Drug Unit that incorporates a PBD dimer that is a DNA minor groove binder has the general structure of Formula XI or XII:

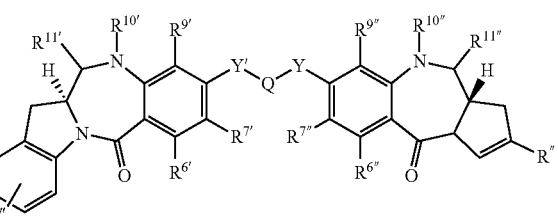

or a salt thereof, wherein: the dotted lines indicate a tautomeric double bond; Q is of formula XIV:

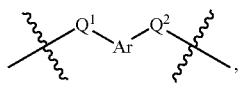

wherein the wavy lines indicate the sites of covalent attachment to Y' and Y in either orientation; Ar is a $C_{5-7}$ arylene group substituted by $X^a$ and is otherwise optionally substituted, wherein $X^a$ is from an activatable group for conjugation to a Linker Unit, wherein $X^a$ is selected from the group comprising: —O—, —S—, —C(O)O—, —C(O)—, —NHC(O)—, and —N($R^N$)—, wherein $R^N$ is H or $C_1$-$C_4$ alkyl, and $(C_2H_4O)_mCH_3$, where subscript m is 1, 2 or 3; and either:
(i) $Q^1$ is a single bond; and $Q^2$ is a single bond or —$(CH_2)_n$—, wherein subscript n is 1, 2 or 3, or (ii) $Q^1$ is —CH=CH—, and $Q^2$ is a single bond or —CH=CH—; and $R^{2'}$ is a optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent, wherein the dotted lines indicate a single bond to $R^{2'}$, or $R^{2'}$ an optionally substituted $C_1$-$C_4$ alkenylene wherein the dotted lines indicate a double bond to $R^{2'}$; and $R^{2''}$ is an optionally substituted $C_1$-$C_4$ alkyl or a $C_{5-10}$ aryl group, optionally substituted by one or more substituents selected from the group consisting of halo, nitro, cyano, $C_1$-$C_6$ ether, $C_1$-$C_7$ alkyl, $C_3$-$C_7$ heterocyclyl and bis-oxy-$C_1$-$C_3$ alkylene, in particular by one such substituent; $R^{6''}$ and $R^{9''}$ are independently selected from the group consisting of H, R, OH, OR, SH, SR, $NH_2$, NHR, NRR', nitro, $Me_3Sn$ and halo; $R^{7''}$ is selected from the group consisting of H, R, OH, OR, SH, SR, $NH_2$, NHR, NRR', nitro, $Me_3Sn$ and halo; and R and R' are independently selected from the group consisting of optionally substituted $C_1$-$C_{12}$ alkyl, optionally substituted $C_3$-$C_{20}$ heterocyclyl and optionally substituted $C_5$-$C_{20}$ aryl; and either:
(a) $R^{10''}$ is H, and $R^{11''}$ is OH or $OR^A$, wherein $R^A$ is $C_1$-$C_4$ alkyl, or (b) $R^{10''}$ and $R^{11''}$ form a nitrogen-carbon double bond between the nitrogen and carbon atoms to which they are bound, or (c) $R^{10''}$ is H and $R^{11''}$ is $SO_2M$, wherein subscript z is 2 or 3 and M is a monovalent pharmaceutically acceptable cation, or (d) $R^{10'}$, $R^{11'}$ and $R^{10''}$ are each H and $R^{11''}$ is $SO_2M$, or $R^{10'}$ and $R^{11'}$ are each H and $R^{10''}$ and $R^{11''}$ form a nitrogen-carbon double bond between the nitrogen and carbon atoms to which they are bound, or $R^{10''}$, $R^{11''}$ and $R^{10'}$ are each H and $R^{11'}$ is $SO_2M$, or $R^{10'}$ and $R^{11'}$ are each H and $R^{10'}$ and $R^{11'}$ form a nitrogen-carbon double bond between the nitrogen and carbon atoms to which they are bound; wherein subscript z is 2 or 3 and M is a monovalent pharmaceutically acceptable cation; and Y and Y' are selected from the group consisting of O, S, and NH; R'' represents one or more optional substituents; and $R^{6'}$, $R^{7'}$, $R^{9'}$ are selected from the same groups as $R^{6''}$, $R^{7''}$ and $R^{9''}$, respectively, and $R^{10'}$ and $R^{11'}$ are the same as $R^{10''}$ and $R^{11''}$, respectively, wherein if $R^{11''}$ and $R^{11'}$ are $SO_zM$, each M is either a monovalent pharmaceutically acceptable cation or together represent a divalent pharmaceutically acceptable cation.

In some embodiments, the PBD dimer has the general structure of Formula X, Formula XII or Formula XIII in which one, $R^{7''}$ is selected from the group consisting of H, OH and OR, wherein R is a previously defined for each of the formula, or is a $C_{1-4}$ alkyloxy group, in particular $R^{7''}$ is —$OCH_3$. In some embodiments, Y and Y' are O, $R^{9''}$ is H, or $R^{6''}$ is selected from the group consisting of H and halo.

In some embodiments, the PBD dimer has the general structure of Formula X in which Ar is phenylene; $X^a$ is selected from the group consisting of —O—, —S— and —NH—; and $Q^1$ is a single bond, and in some embodiments of Formula XII Ar is phenylene, X is selected from the group consisting of —O—, —S—, and —NH—, $Q^1$ -$CH_2$— and $Q_2$ is —$CH_2$—.

In some embodiments, the PBD dimer has the general structure of Formula X in which $X^a$ is NH. In some embodiments, the PBD Drug Units are of Formula X in which $Q^1$ is a single bond and $Q^2$ is a single bond.

In some embodiments, the PBD dimer has the general structure of Formula X, Formula XII or Formula XIII in which $R^{2'}$ is an optionally substituted $C_{5-7}$ aryl group so that the dotted lines indicate a single bond to $R^{2'}$ and the substituents when present are independently selected from the group consisting of halo, nitro, cyano, $C_{1-7}$ alkoxy, $C_{5-20}$ aryloxy, $C_{3-20}$ heterocyclyoxy, $C_{1-7}$ alkyl, $C_{3-7}$ heterocyclyl and bis-oxy-$C_{1-3}$ alkylene wherein the $C_{1-7}$ alkoxy group is optionally substituted by an amino group, and if the $C_{3-7}$ heterocyclyl group is a $C_6$ nitrogen containing heterocyclyl group, it is optionally substituted by a $C_{1-4}$ alkyl group.

In some embodiments, the PBD dimer has the general structure of Formula X, Formula XI or Formula XII in which Ar is an optionally substituted phenyl that has one to three such substituents when substituted.

In some embodiments, the PBD dimer has the general structure of Formula X, Formula XI or Formula XII in which $R^{10''}$ and $R^{11''}$ form a nitrogen-carbon double bond and/or $R^{6''}$, $R^{7''}$, $R^{9''}$, and Y' are the same as $R^{6''}$, $R^{7''}$, $R^{9''}$, and Y respectively.

In some embodiments, the PBD Drug Unit has the structure of:

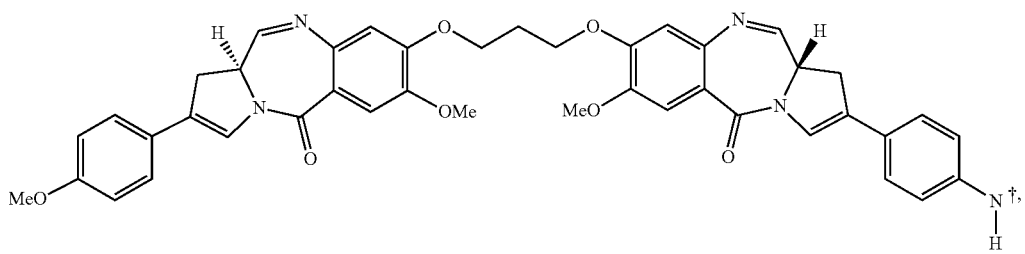

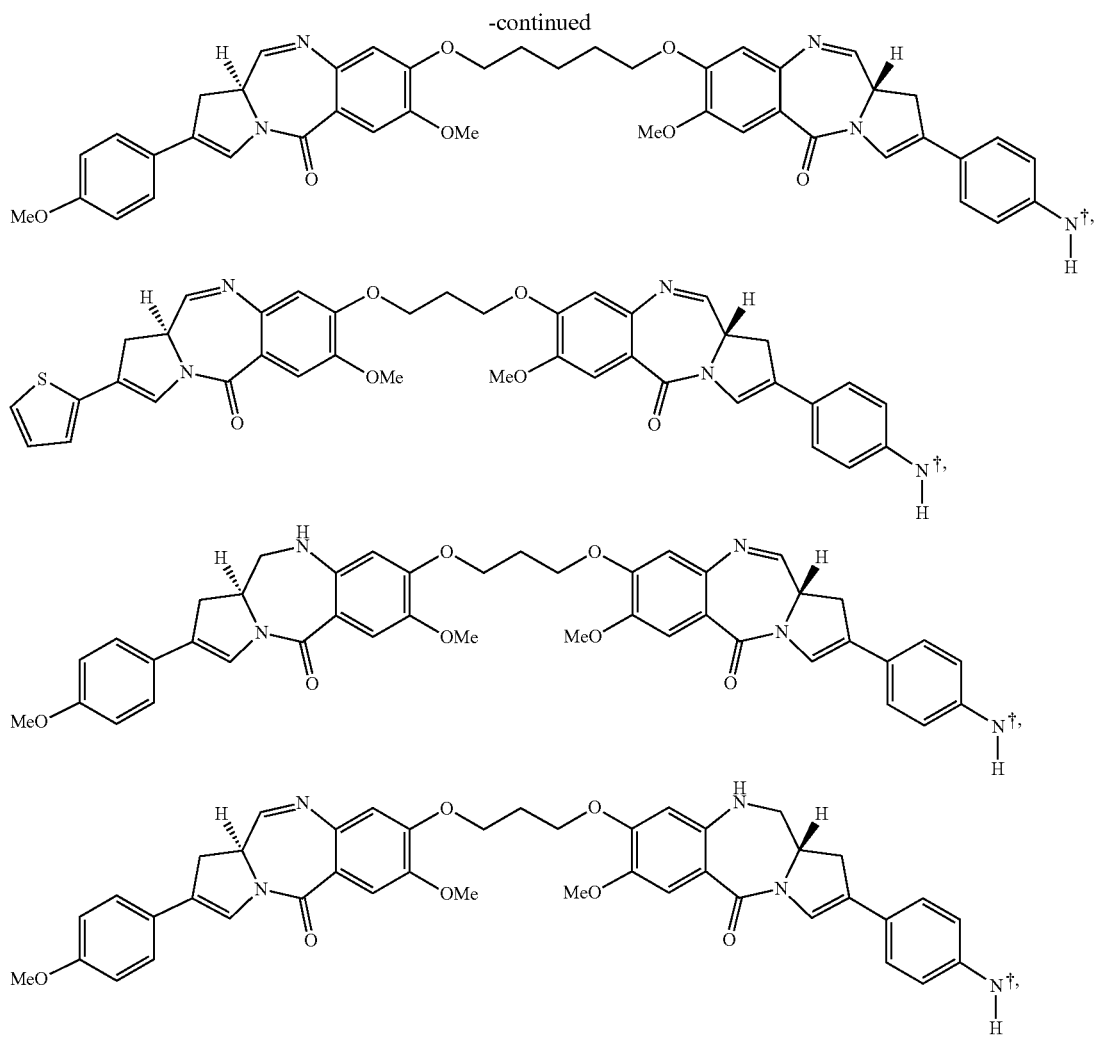

or a salt thereof, wherein the dagger represents the point of attachment of the Drug Unit to the Linker Unit in a Drug Linker compound or Ligand Drug Conjugate compound.

In some embodiments, the PBD Drug Unit has the structure of:

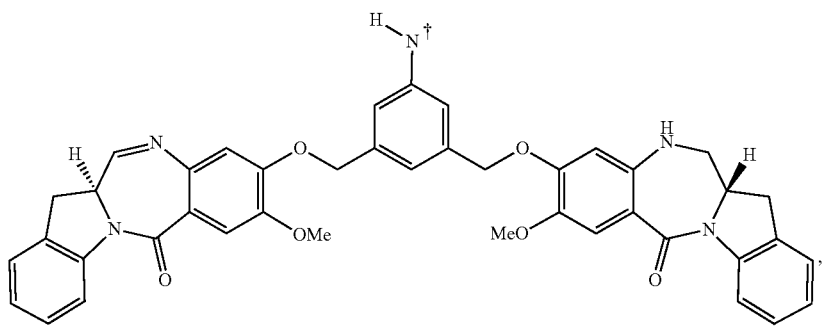

or a salt thereof, wherein the dagger represents the point of attachment of the Drug Unit to the Linker Unit in a Drug Linker compound or Ligand Drug Conjugate compound.

In some embodiments, the Drug Unit incorporates the structure of an anthracyclin compound. Without being bound by theory, the cytotoxicity of those compounds to some extent may also be due to topoisomerase inhibition. In some of those embodiments the anthracyclin compound has a structure disclosed in Minotti, G., et al., "Anthracyclins: molecular advances and pharmacologic developments in antitumor activity and cardiotoxicity" *Pharmacol Rev.* (2004) 56(2): 185-229. In some embodiments, the anthracyclin compound is doxorubicin, idarubicin, daunorubicin, doxorubicin propyloxazoline (DPO), morpholino-doxorubicin, or cyanomorpholino-doxorubicin.

In more preferred embodiments the auristatin drug compound incorporated into -D is monomethylauristatin E (MMAE) or monomethylauristatin F (MMAF).

In some embodiments, the Ligand-Drug Conjugate composition is represented by the structure of:

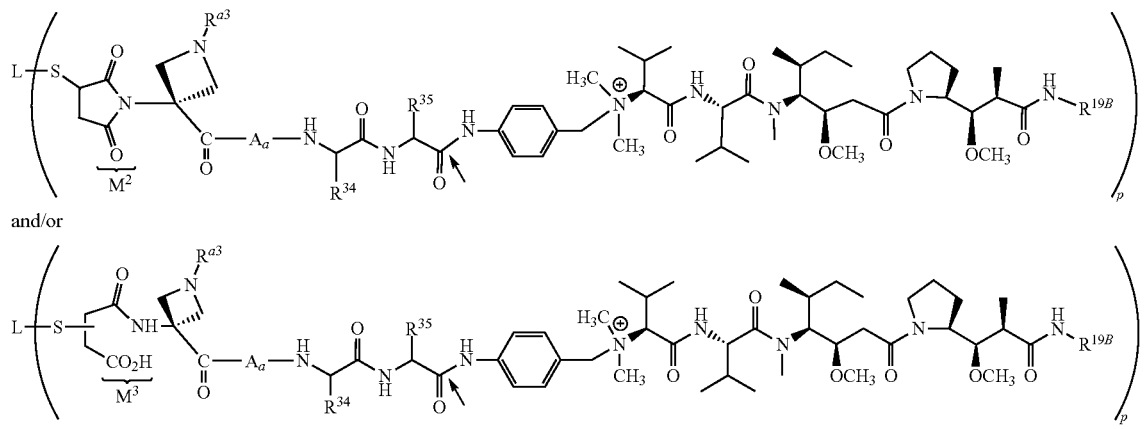

and/or wherein subscript a is 1, so that A is present, wherein A is an α-amino acid or β-amino acid residue; $R^{a3}$ is —H, optionally substituted $C_1$-$C_6$ alkyl, optionally substituted —$C_1$-$C_4$ alkylene-($C_6$-$C_{10}$ aryl), —$R^{PEG1}$—O—($CH_2CH_2O)_{n'}$—$R^{PEG2}$, wherein $R^{PEG1}$ is $C_1$-$C_4$ alkylene, $R^{PEG2}$ is —H or $C_1$-$C_4$ alkyl, and subscript n' ranges from 1 to 36, wherein the basic nitrogen bonded to $R^{a3}$ is optionally protonated; $R^{19B}$ is —CH($CH_3$)—CH(OH)-Ph, —CH($CO_2$H)—CH(OH)—$CH_3$, or —CH($CO_2$H)—$CH_2$Ph; $R^{34}$ is isopropyl and $R^{35}$ is methyl or —($CH_2)_3$NH(C=O)$NH_2$.

In some embodiments, the Ligand-Drug Conjugate composition is represented by the structure of:

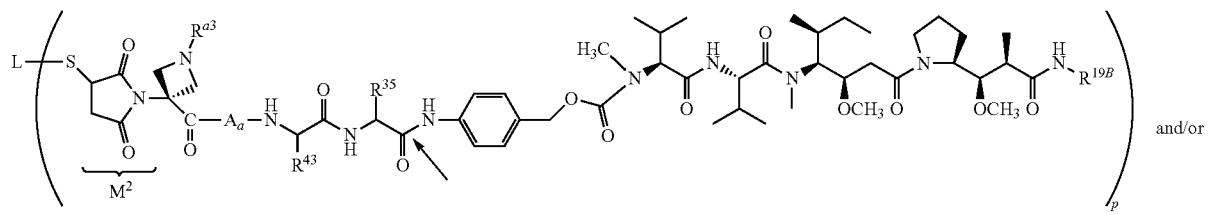

and/or

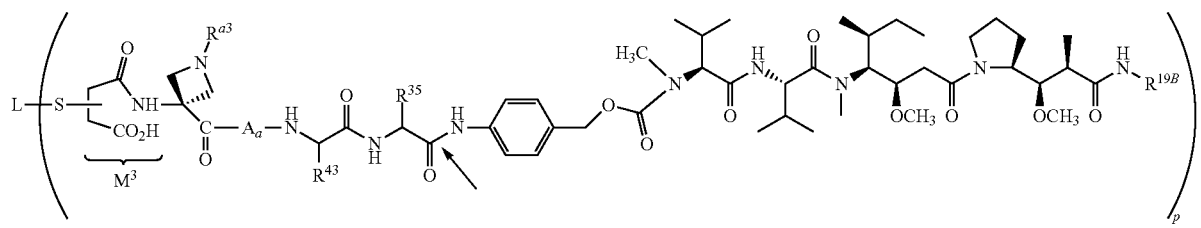

wherein subscript a is 1 so that A is present, wherein A is an α-amino acid or β-amino acid residue; $R^{a3}$ is —H, optionally substituted $C_1$-$C_6$ alkyl, optionally substituted —$C_1$-$C_4$ alkylene-($C_6$-$C_{10}$ aryl), —$R^{PEG1}$—O—($CH_2CH_2O)_{n'}$—$R^{PEG2}$; $R^{PEG1}$ is $C_1$-$C_4$ alkylene; $R^{PEG2}$ is —H or $C_1$-$C_4$ alkyl; subscript n' ranges from 1 to 36; and wherein the basic nitrogen atom bonded to $R^{a3}$ is optionally protonated; $R^{19B}$ is —CH($CH_3$)—CH(OH)-Ph, —CH($CO_2$H)—CH(OH)—$CH_3$, or —CH($CO_2$H)—$CH_2$Ph; $R^{34}$ is isopropyl; and $R^{35}$ is methyl or —($CH_2)_3$NH(C=O)$NH_2$.

In some embodiments, the Ligand Drug Conjugate compound is represented by:

213 214
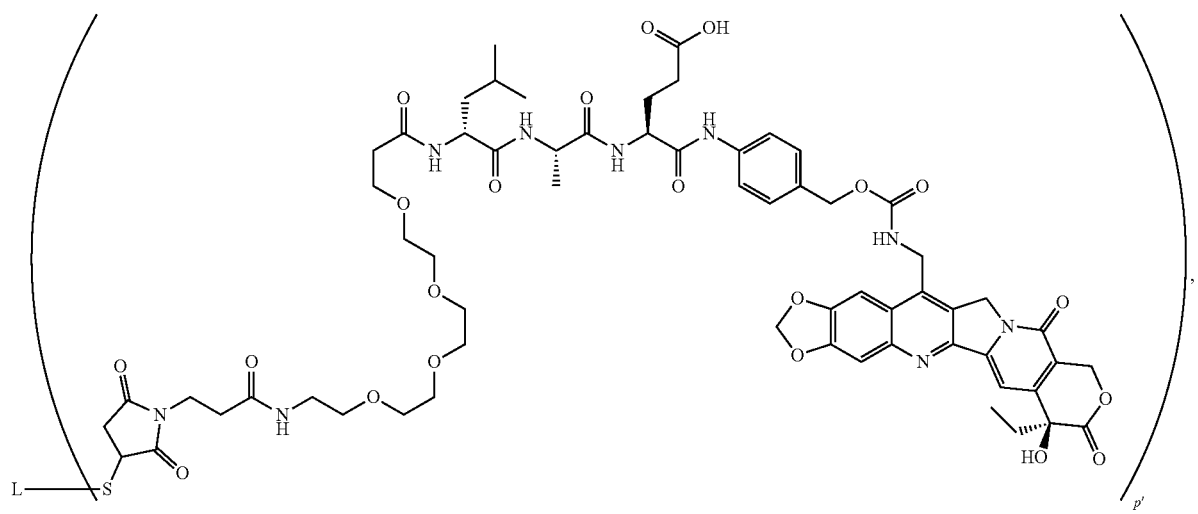
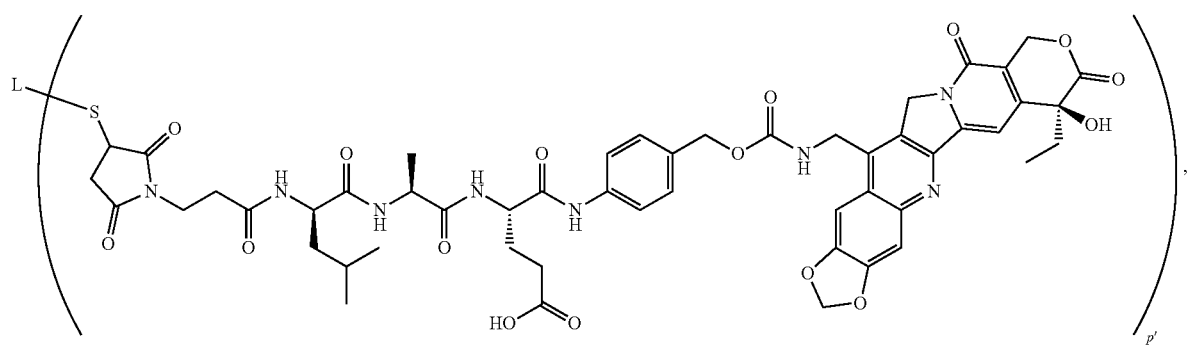
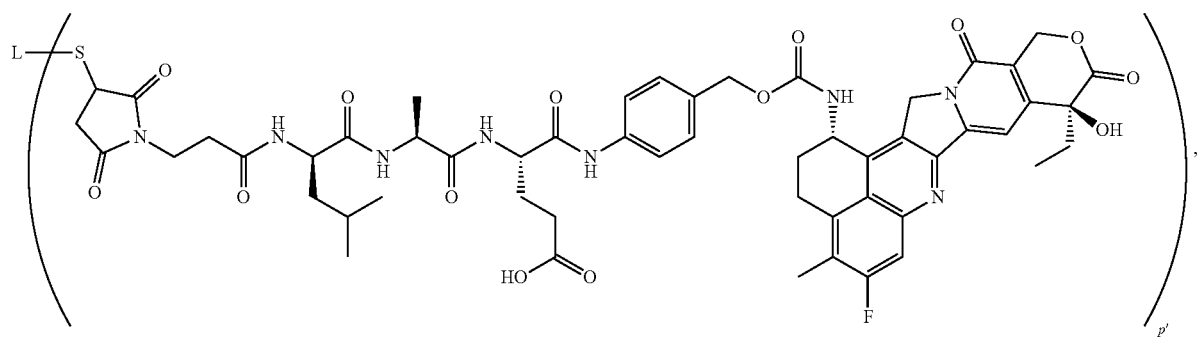
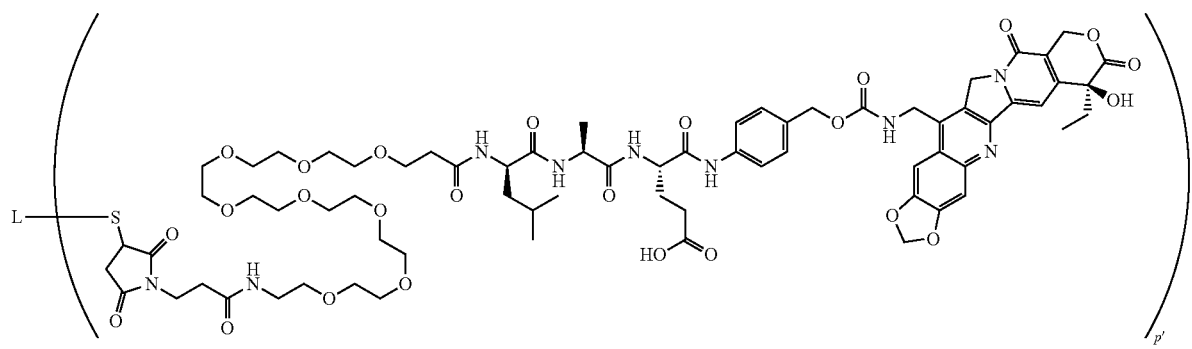

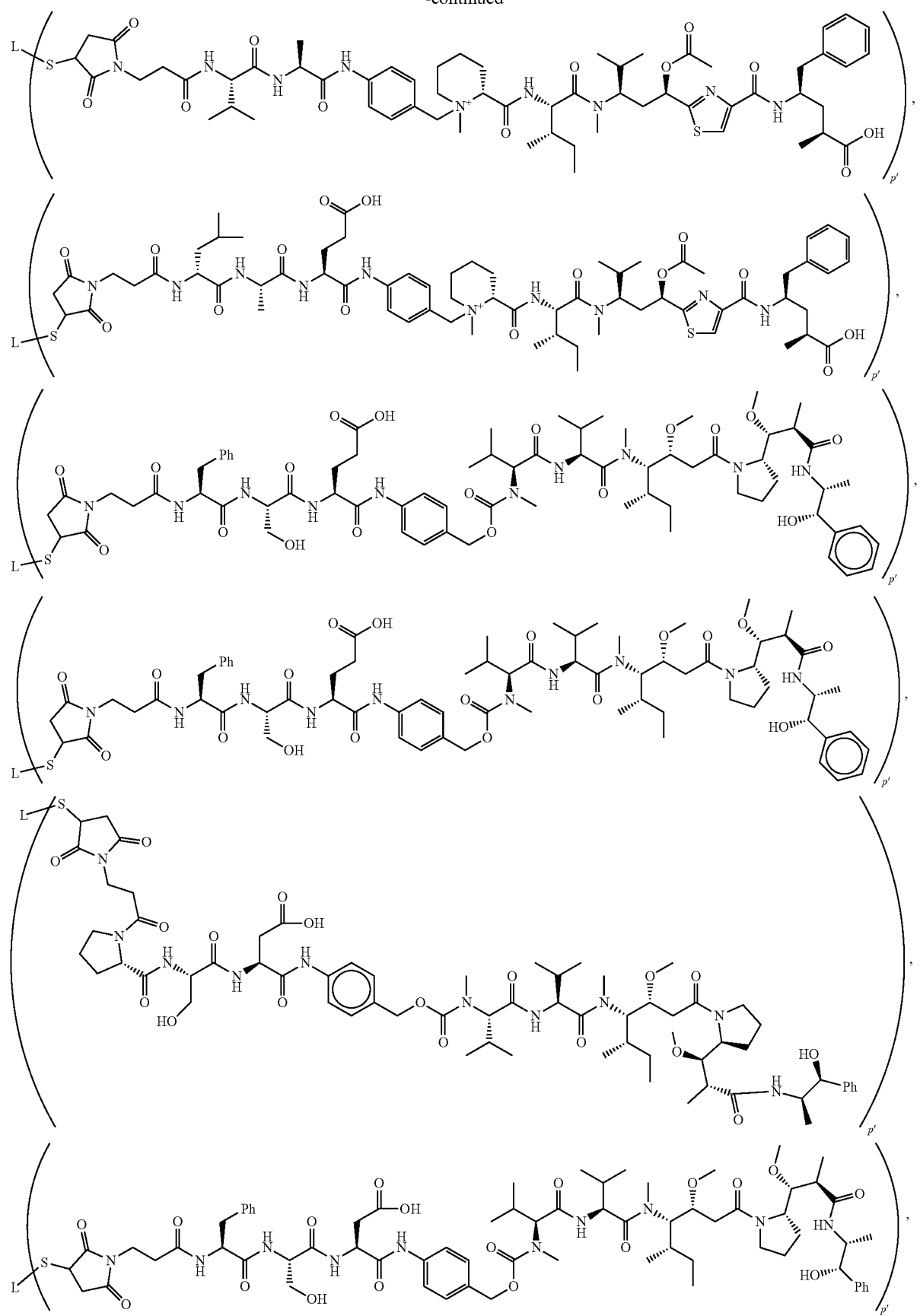

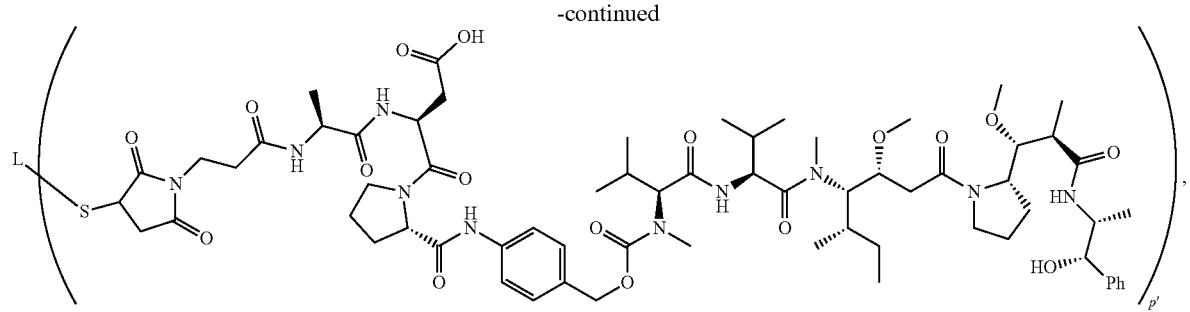
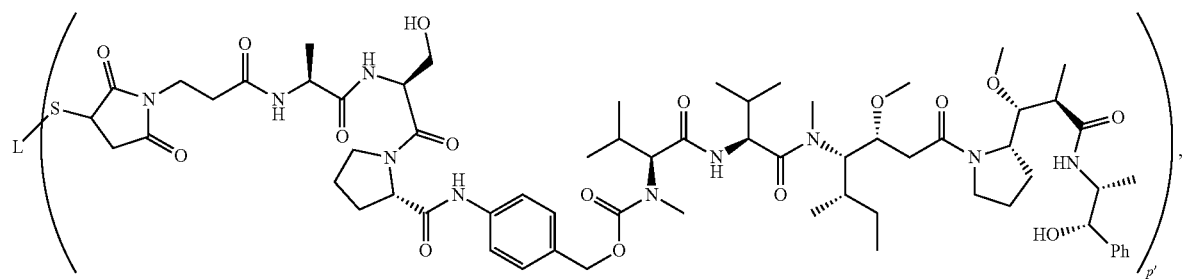
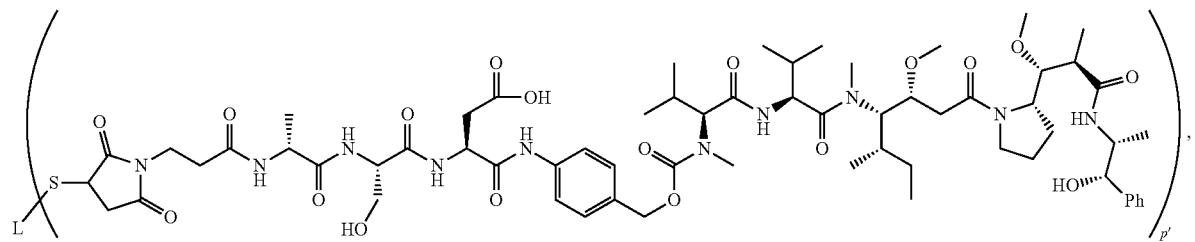
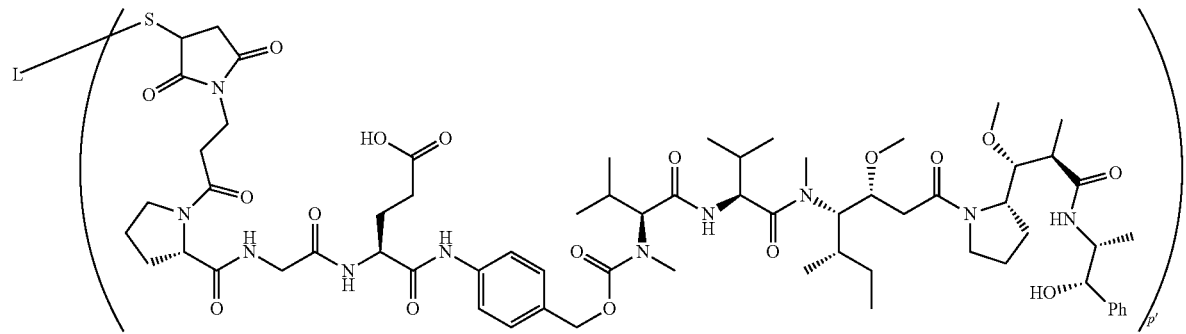
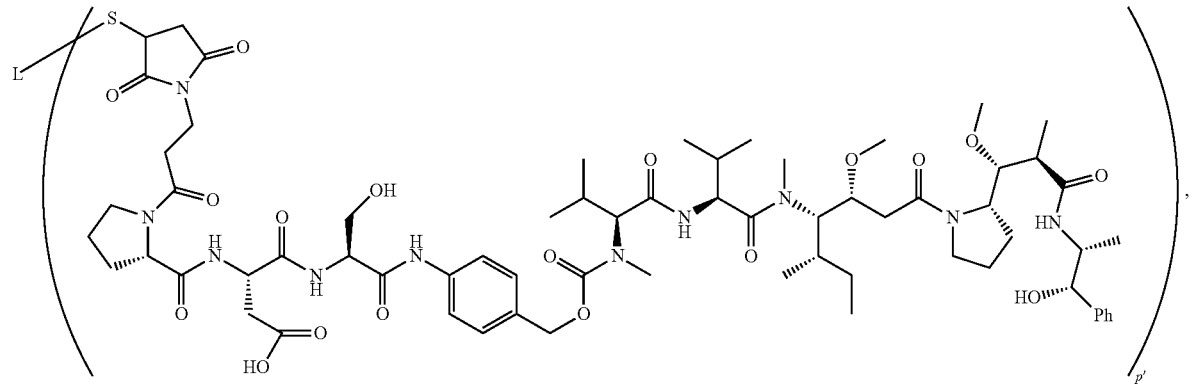

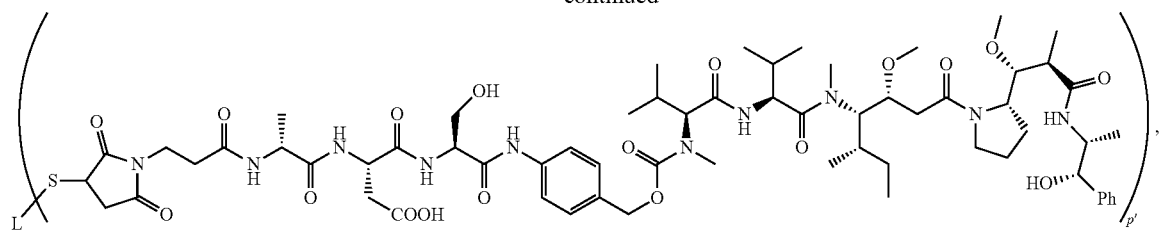
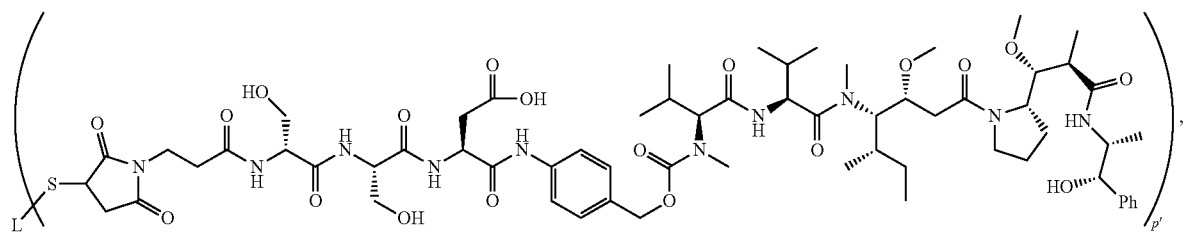
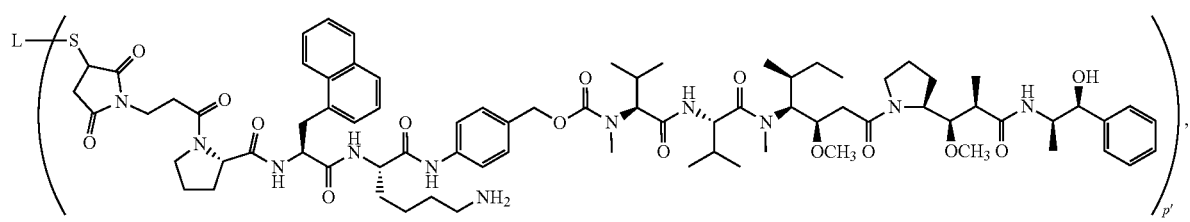
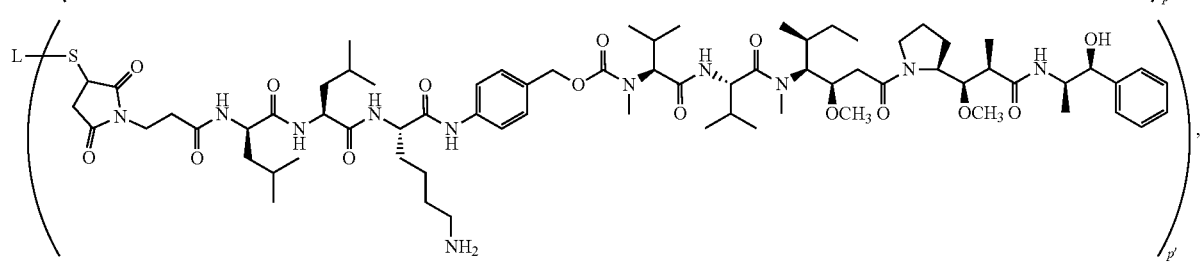
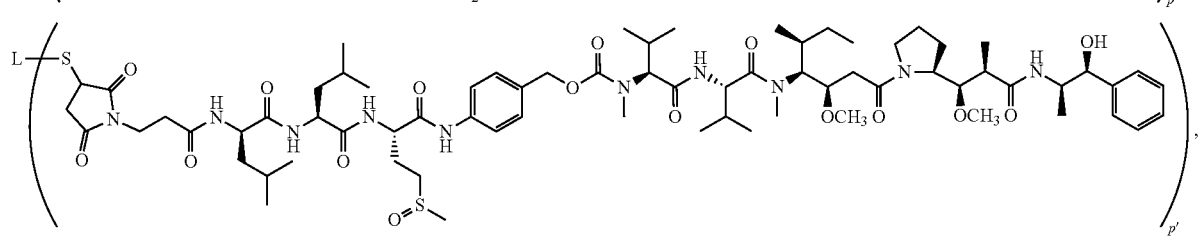
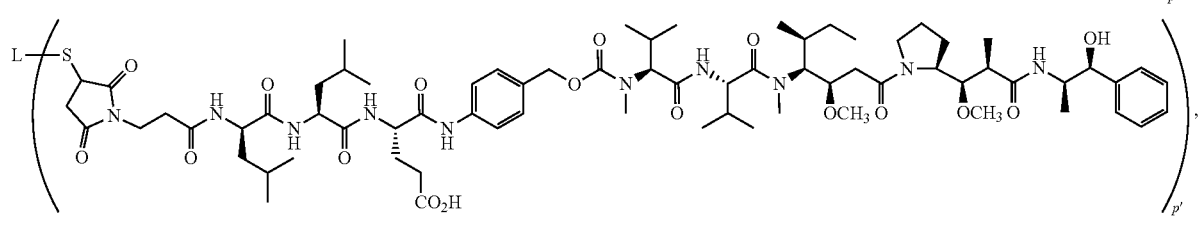
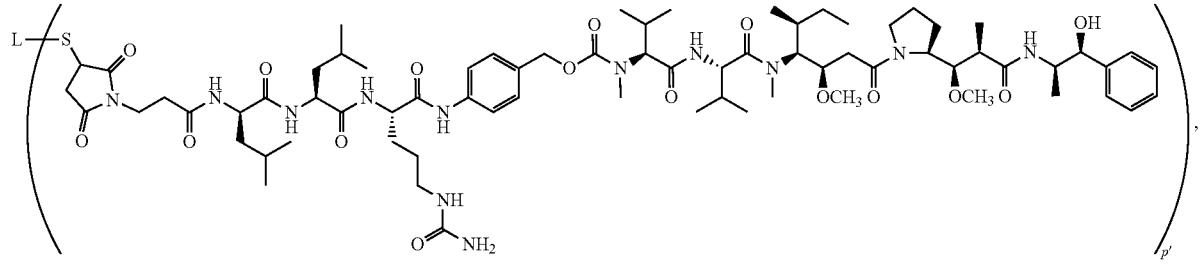

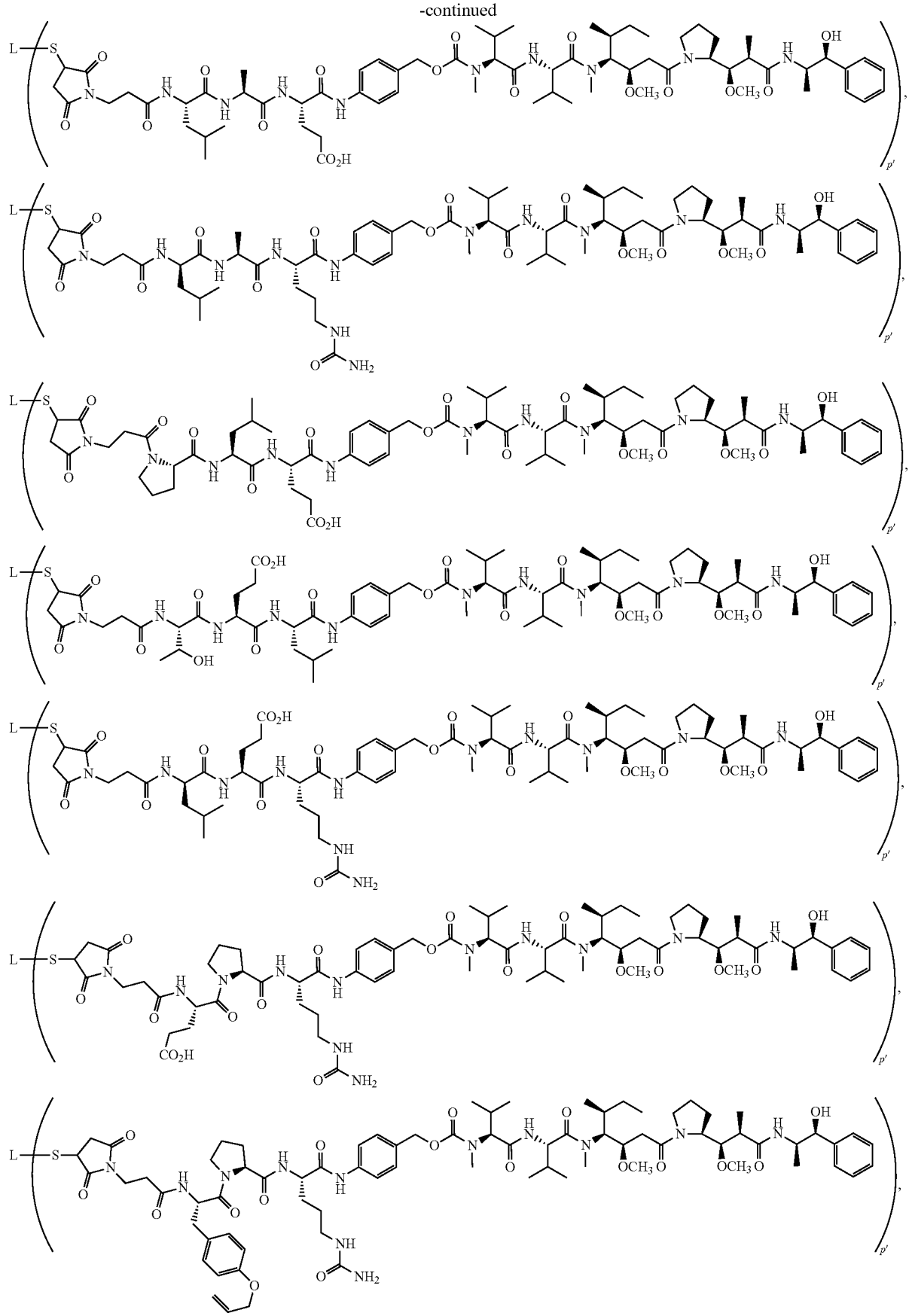

-continued
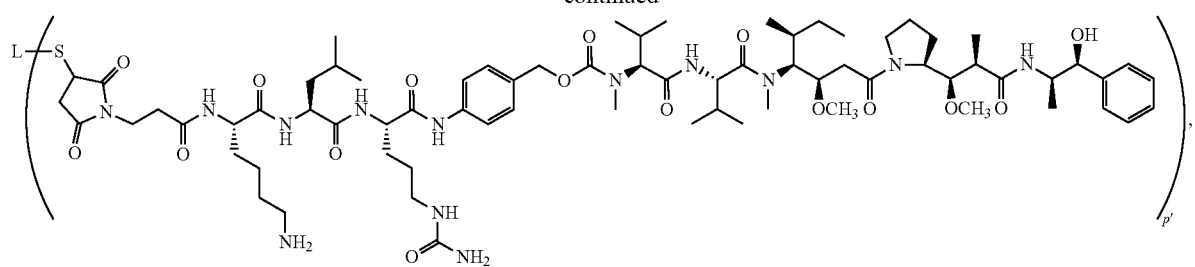
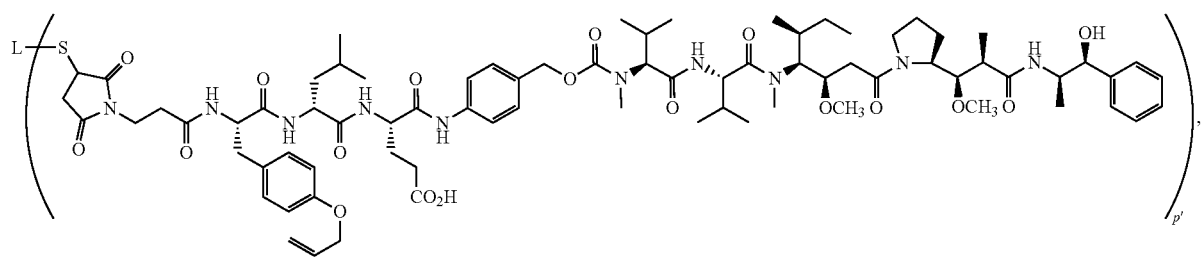
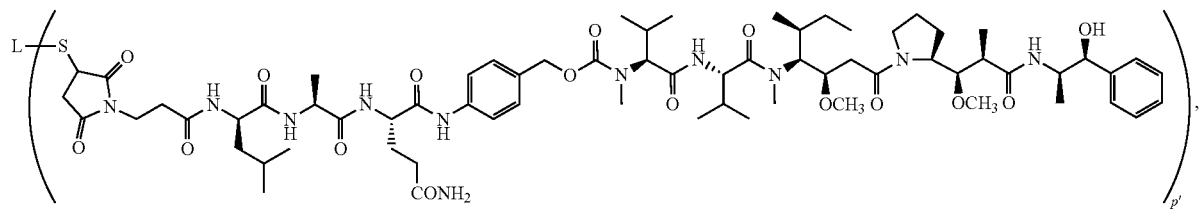
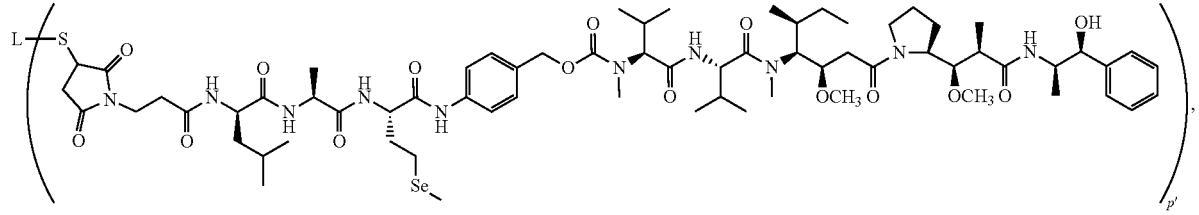
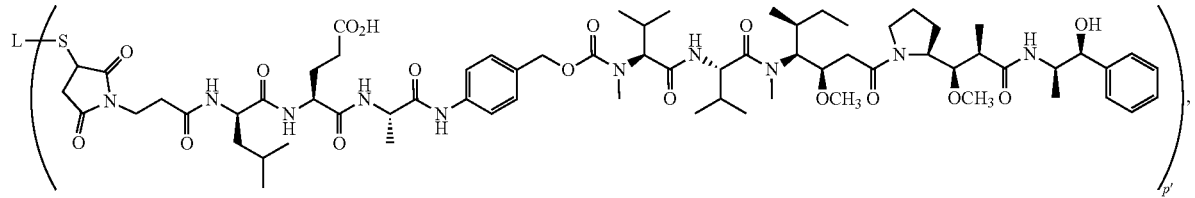
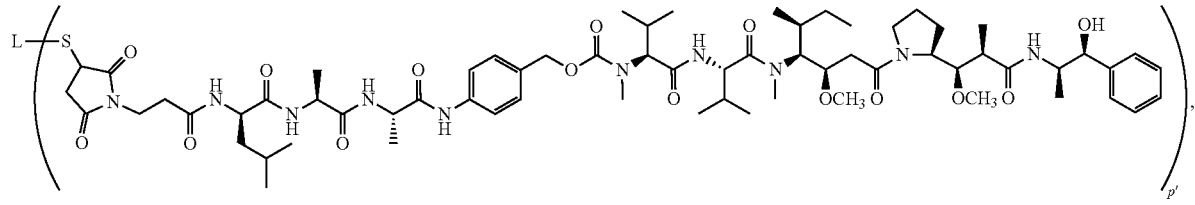
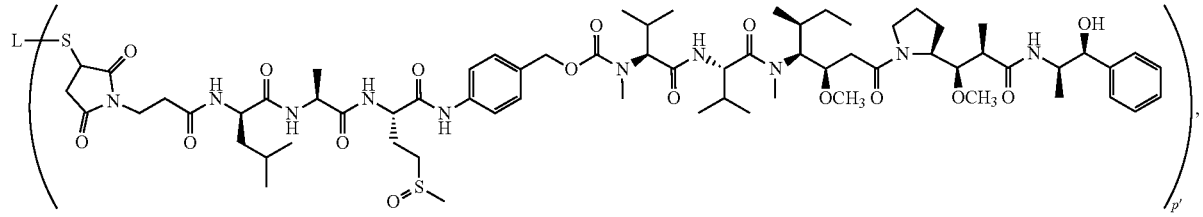

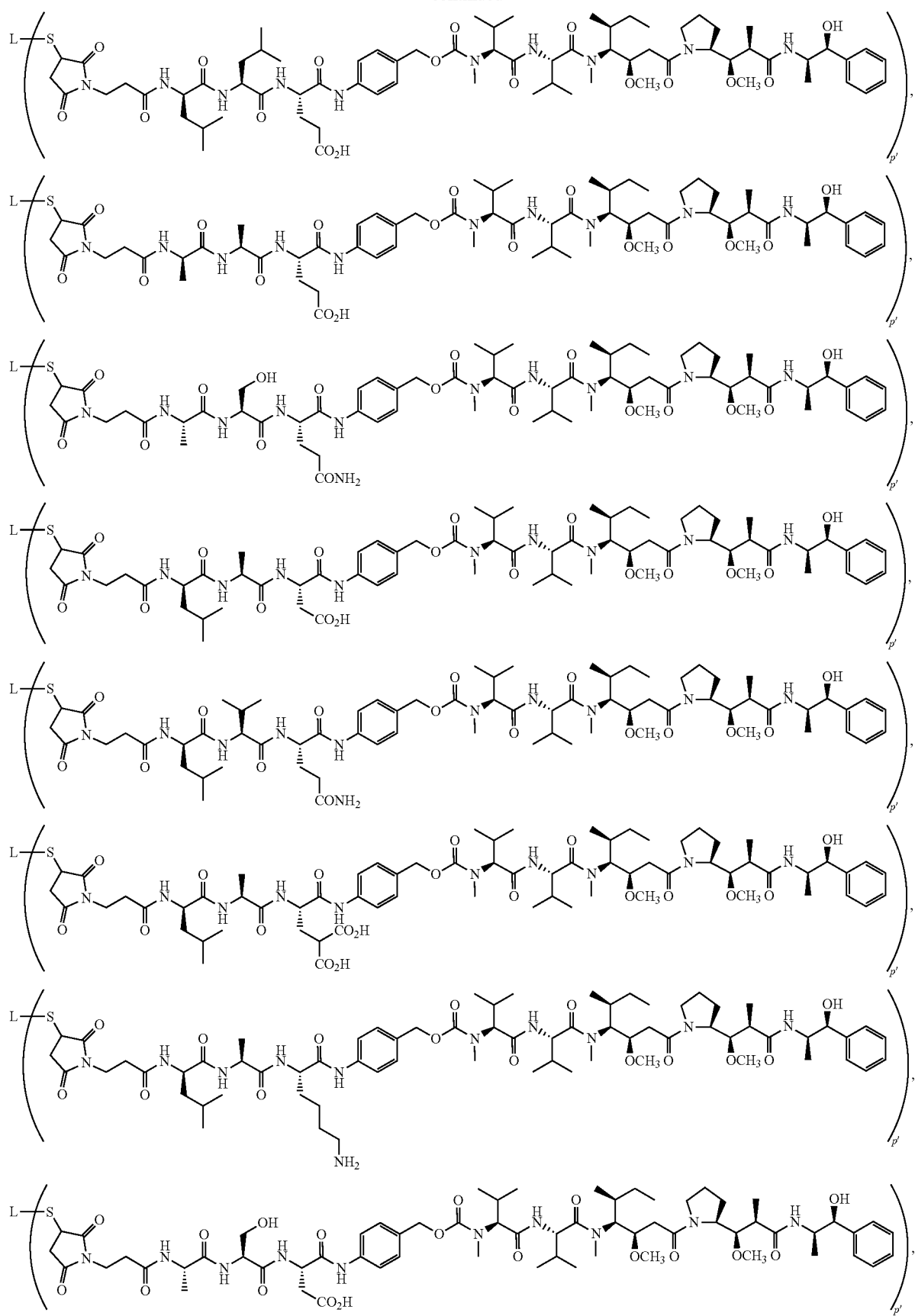

-continued
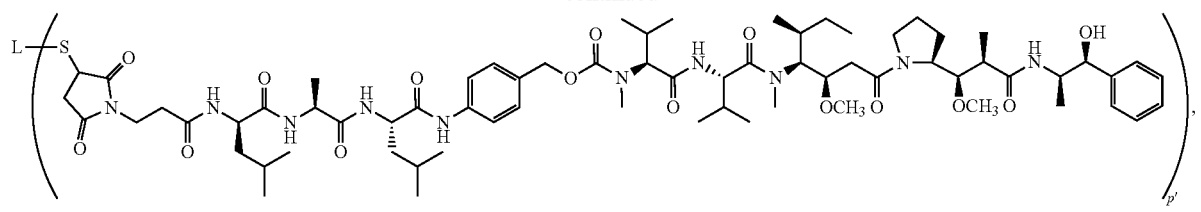
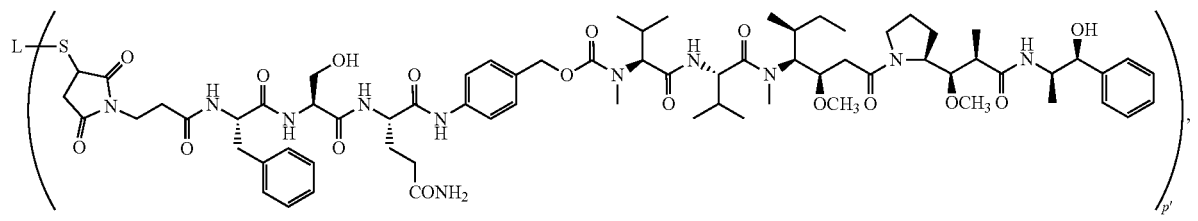
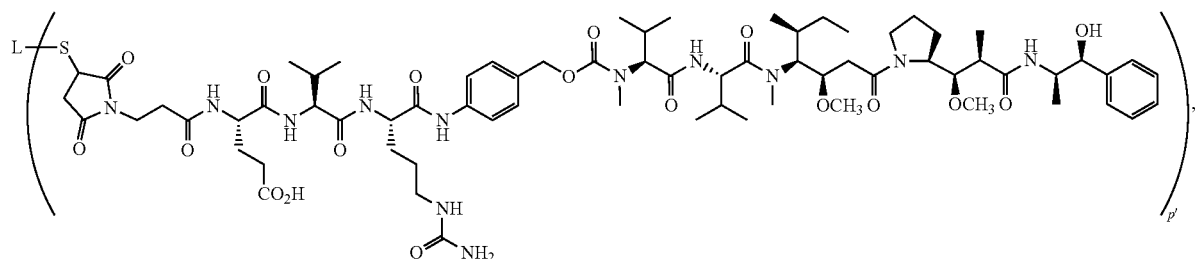
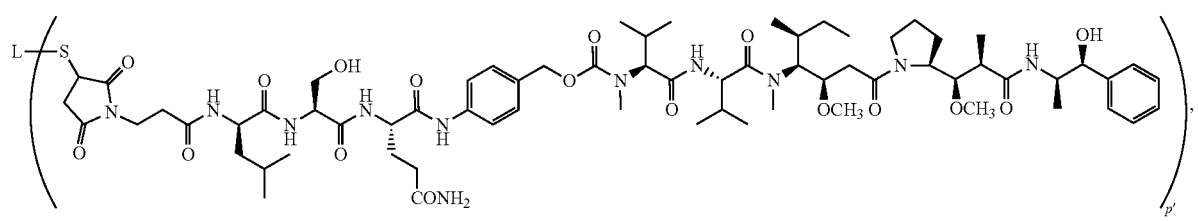
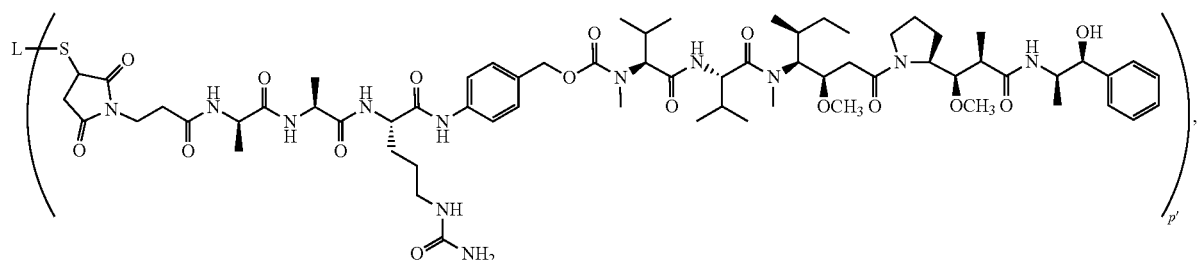
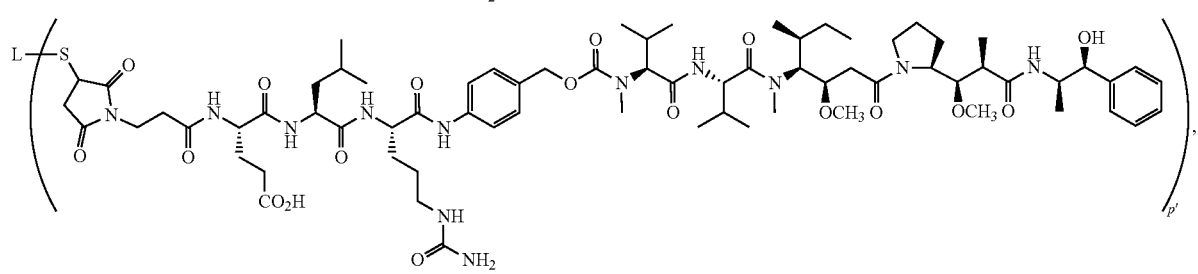
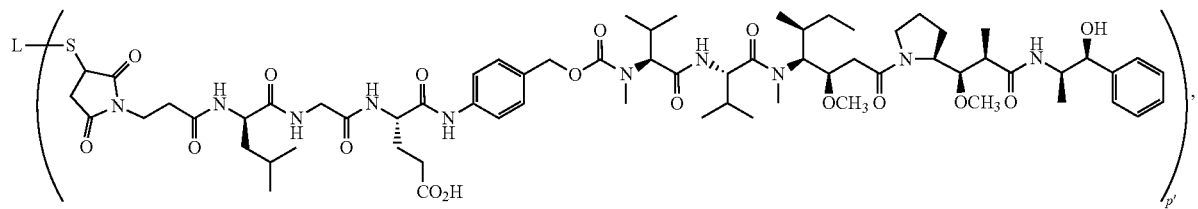

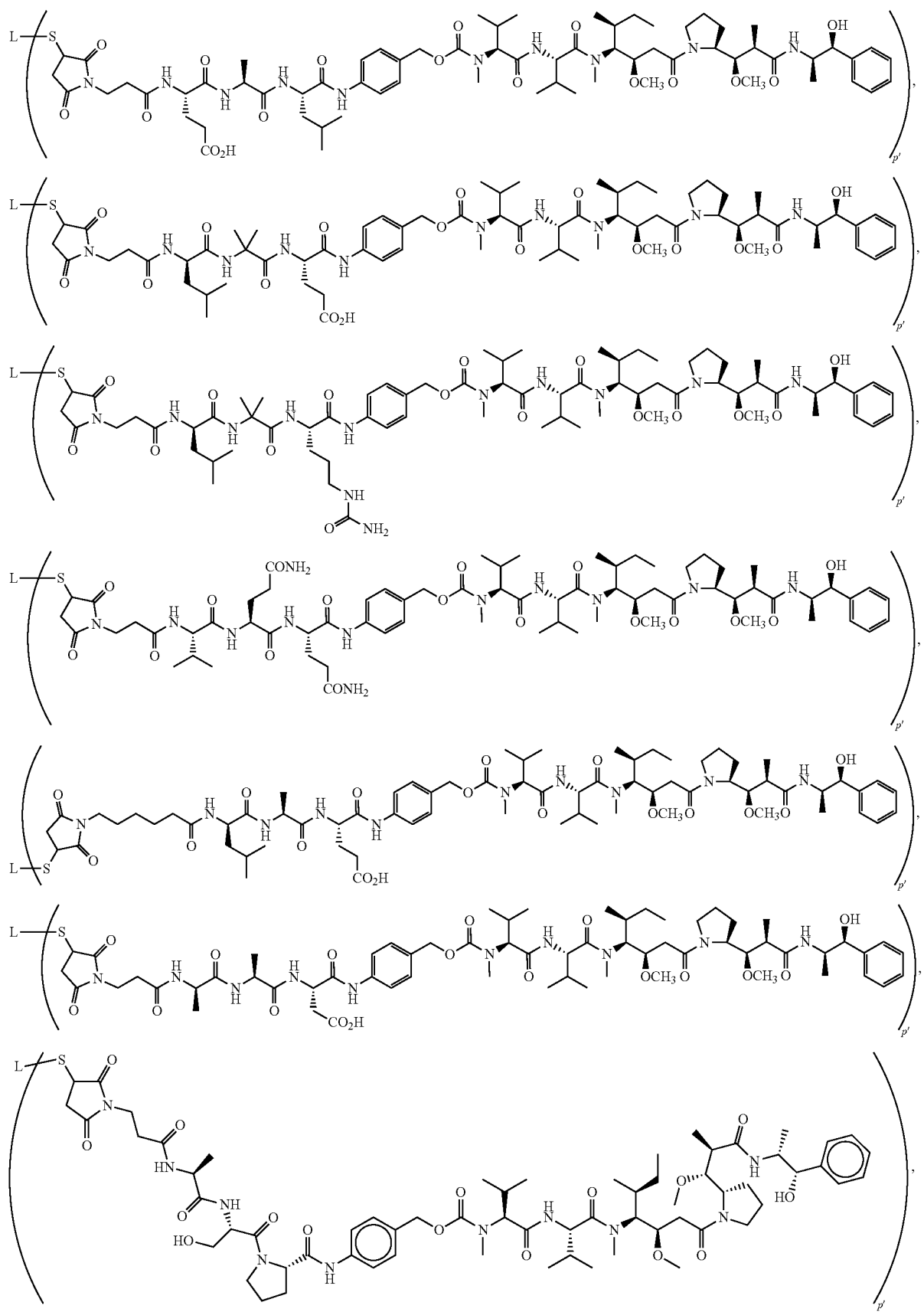

231
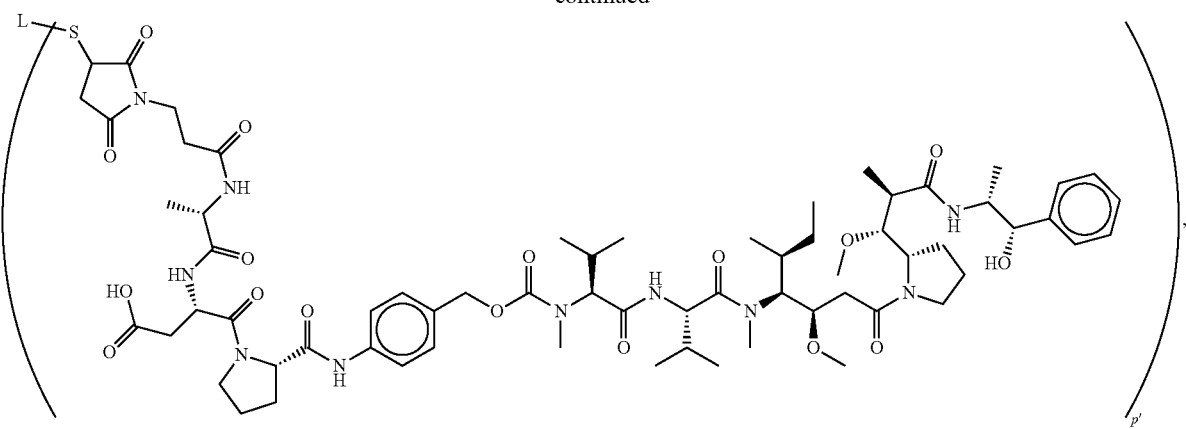
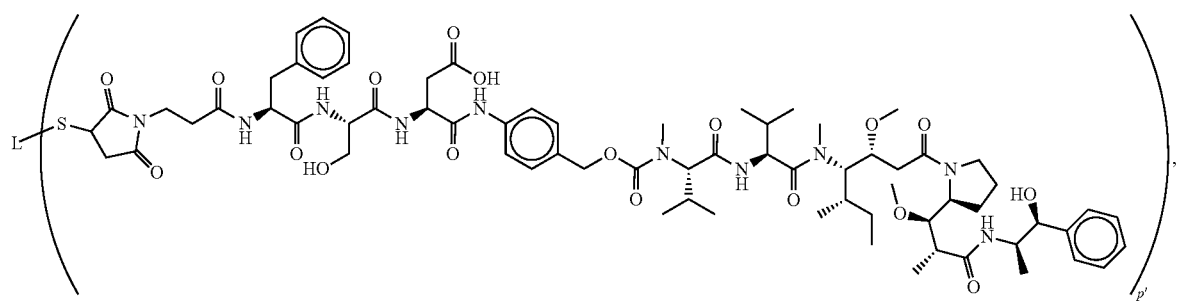
232
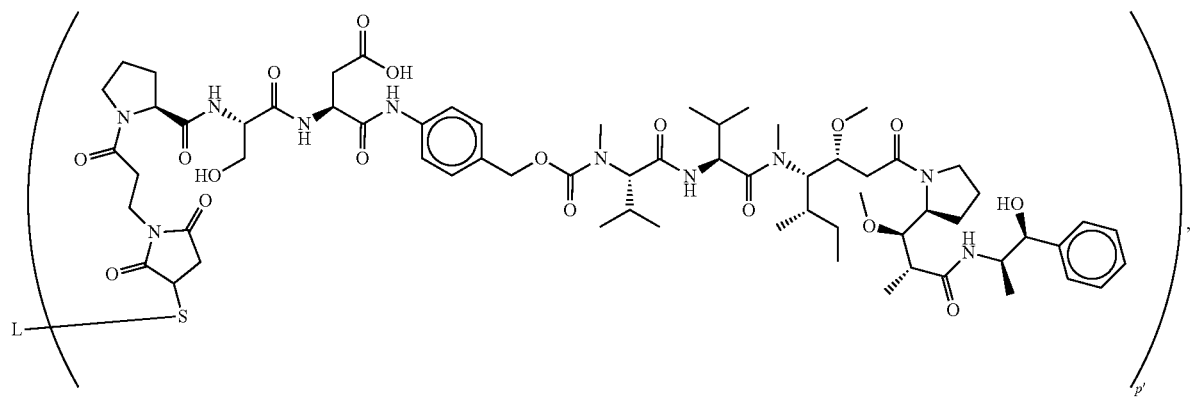
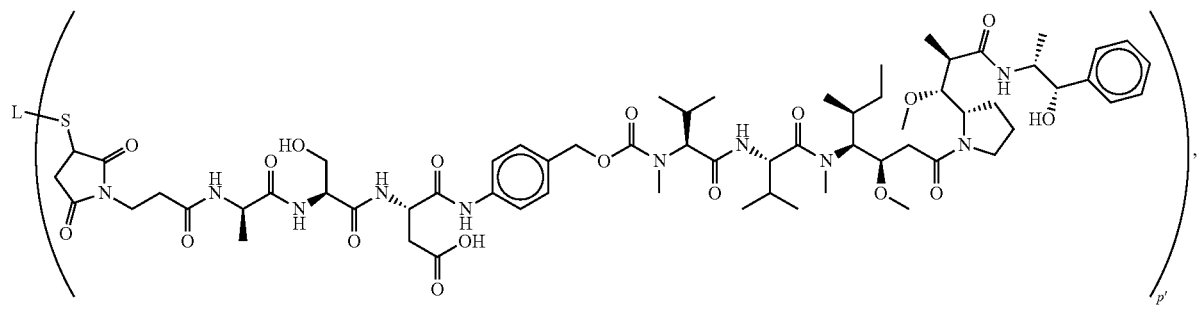

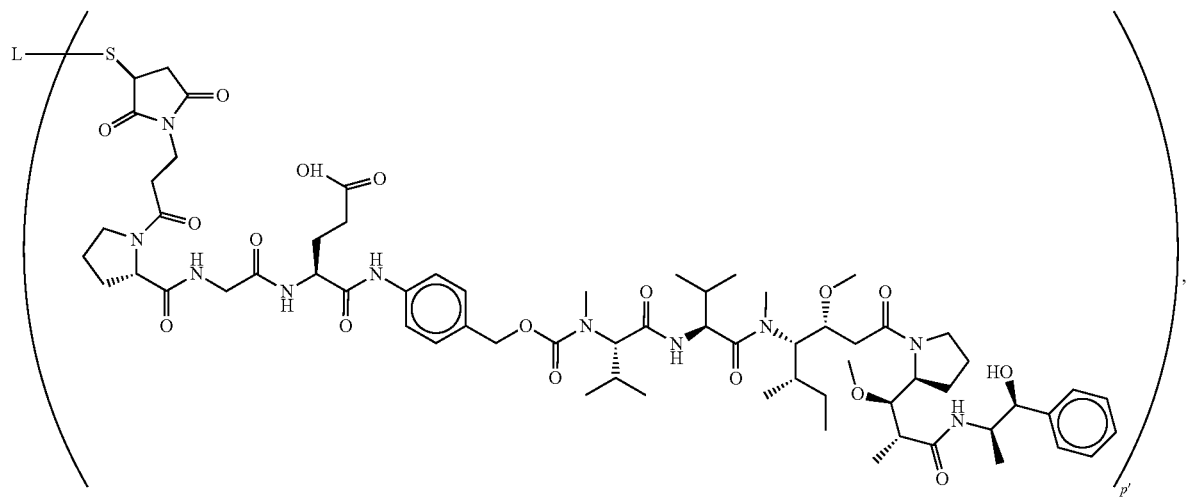
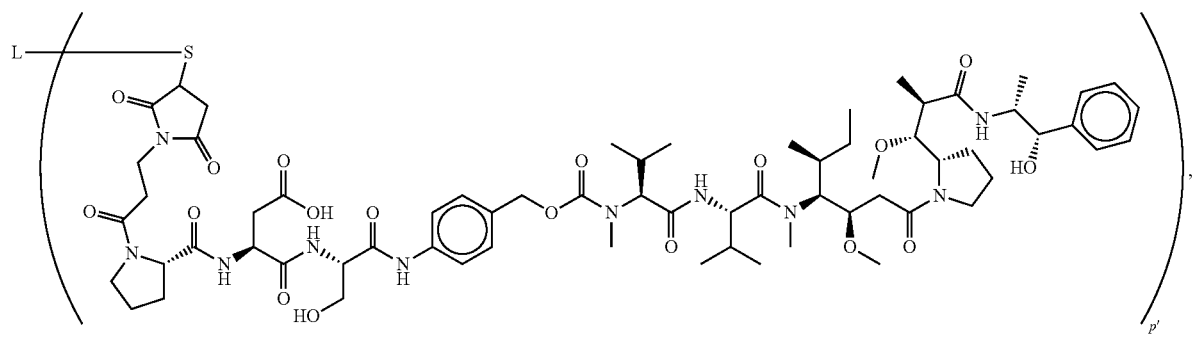
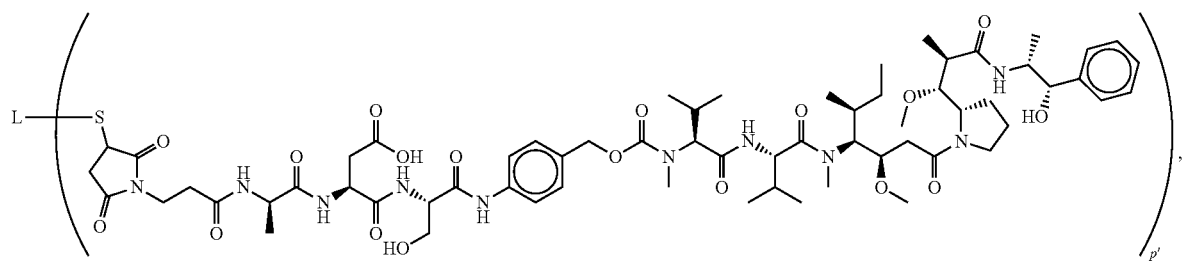
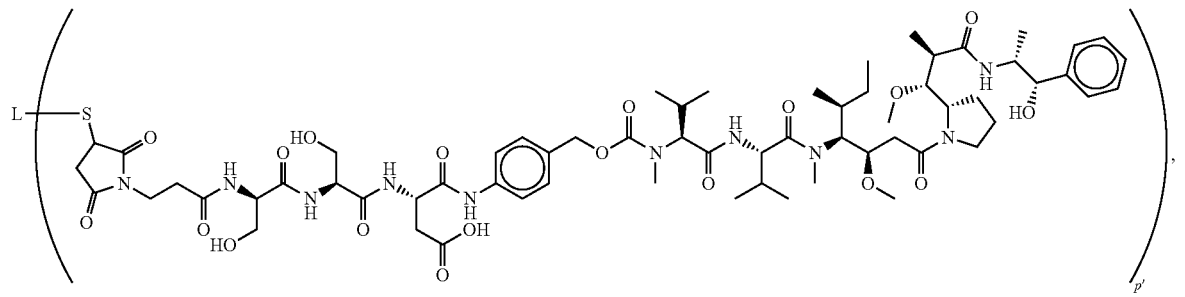

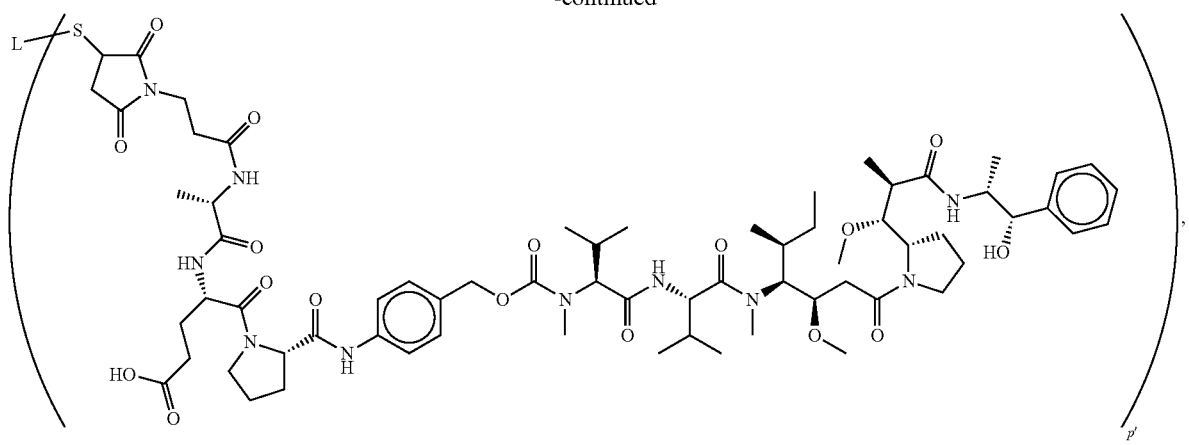
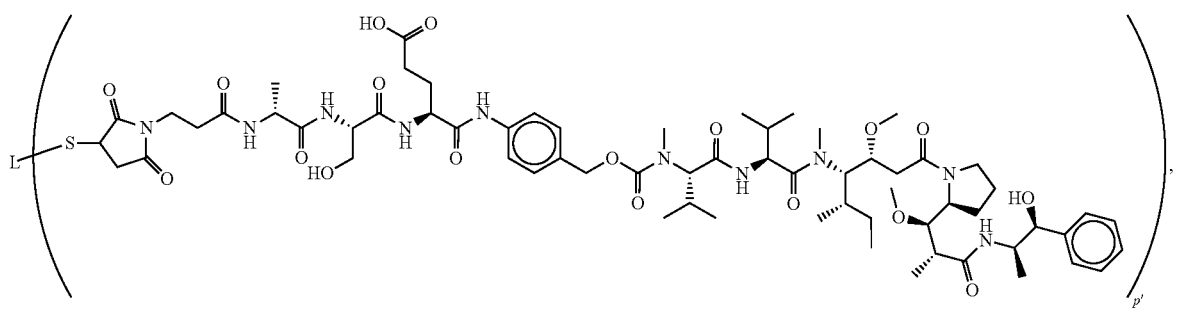
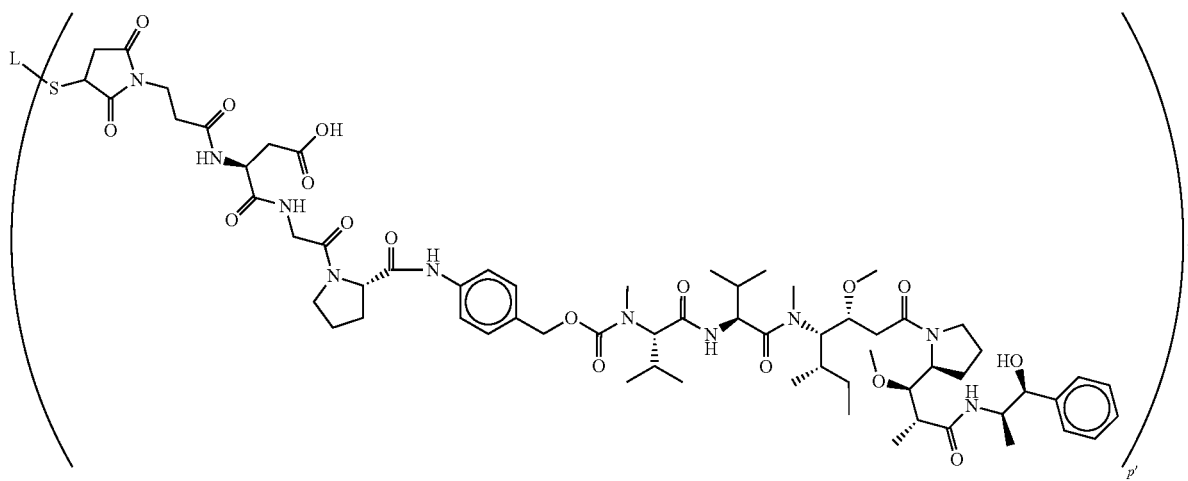
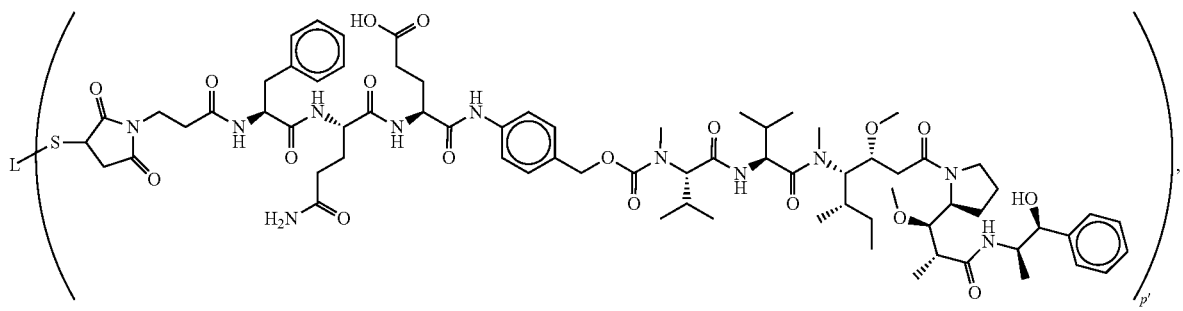

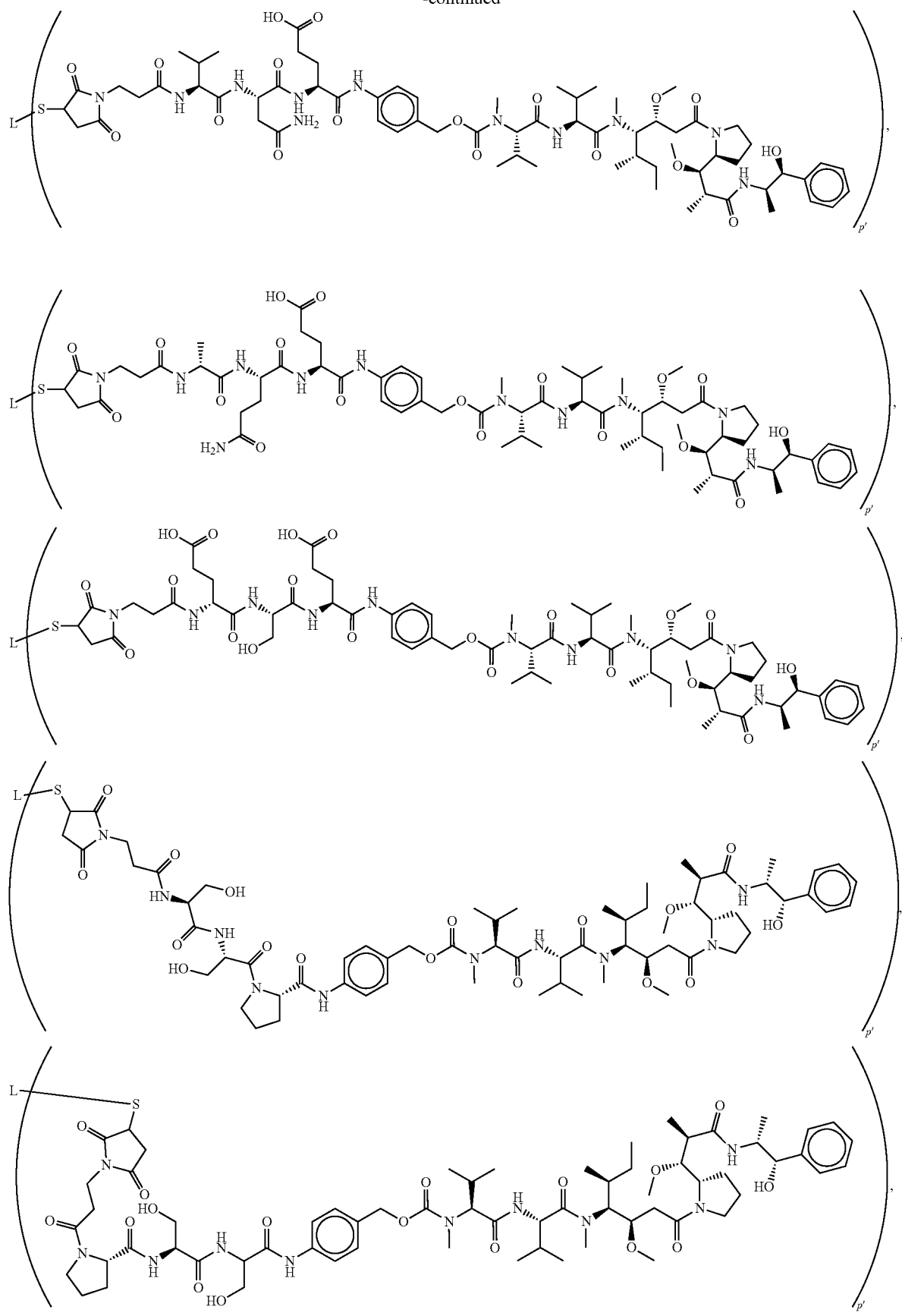

-continued
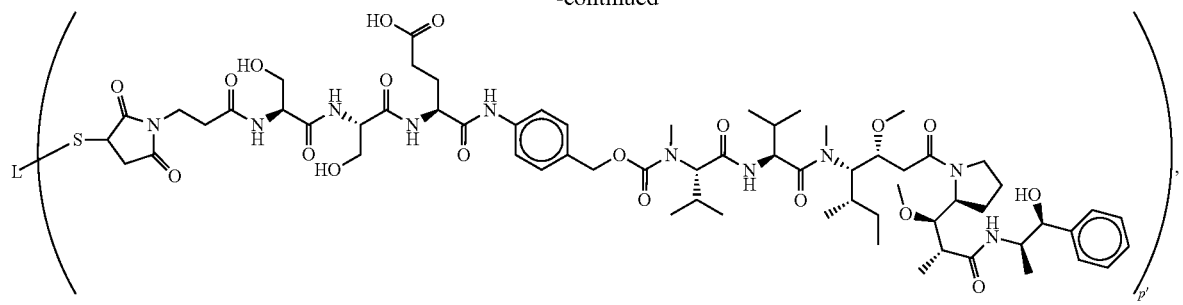
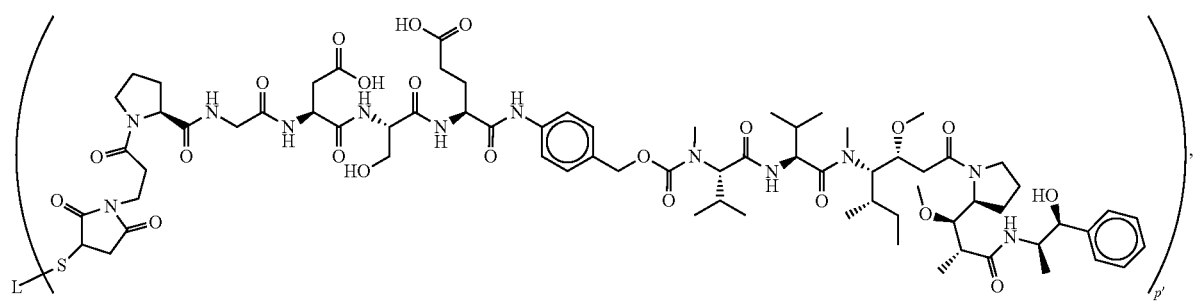
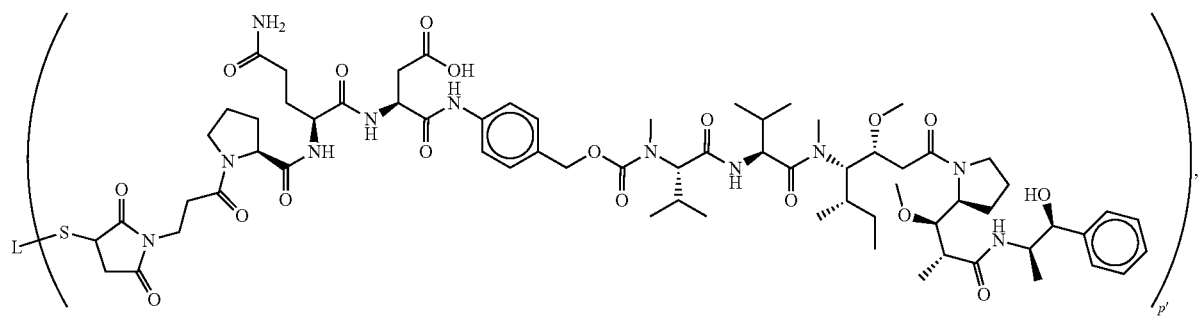
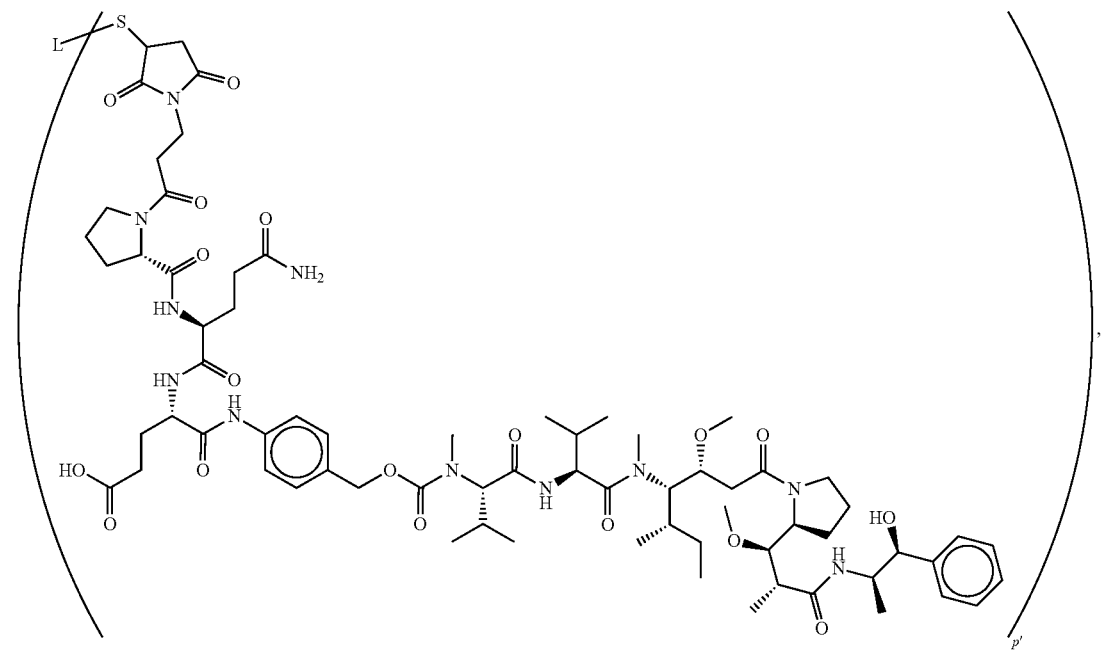

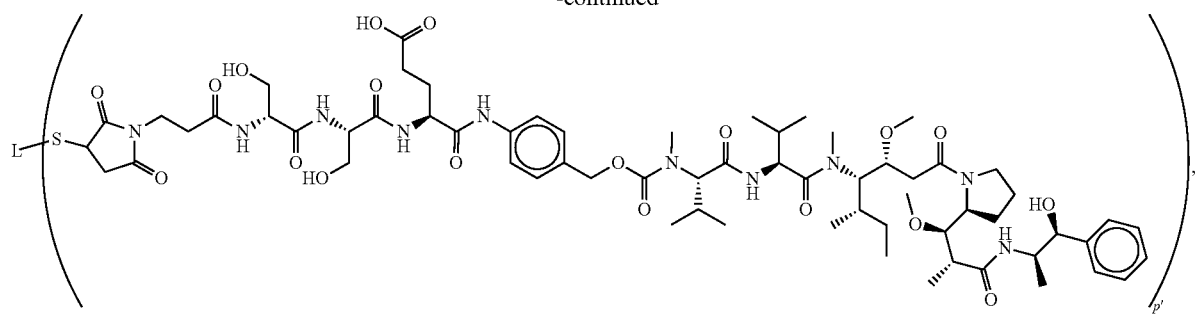
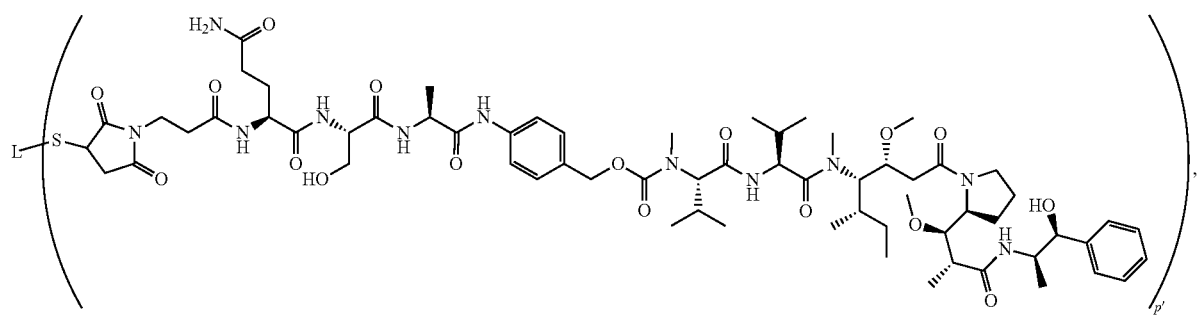
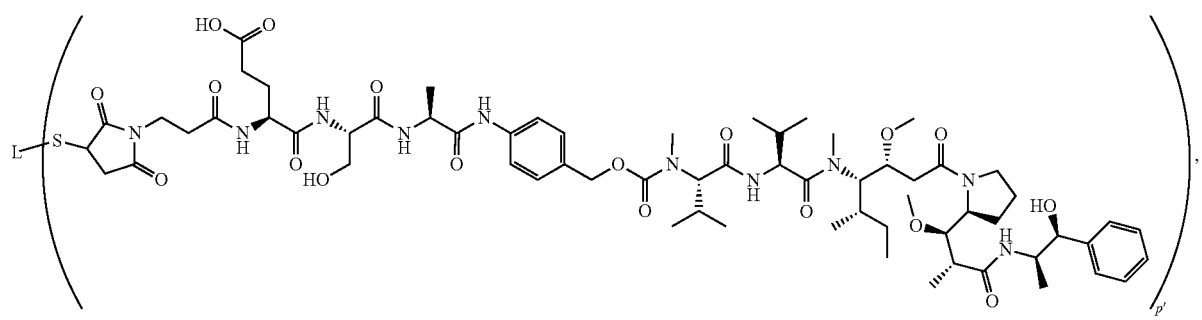
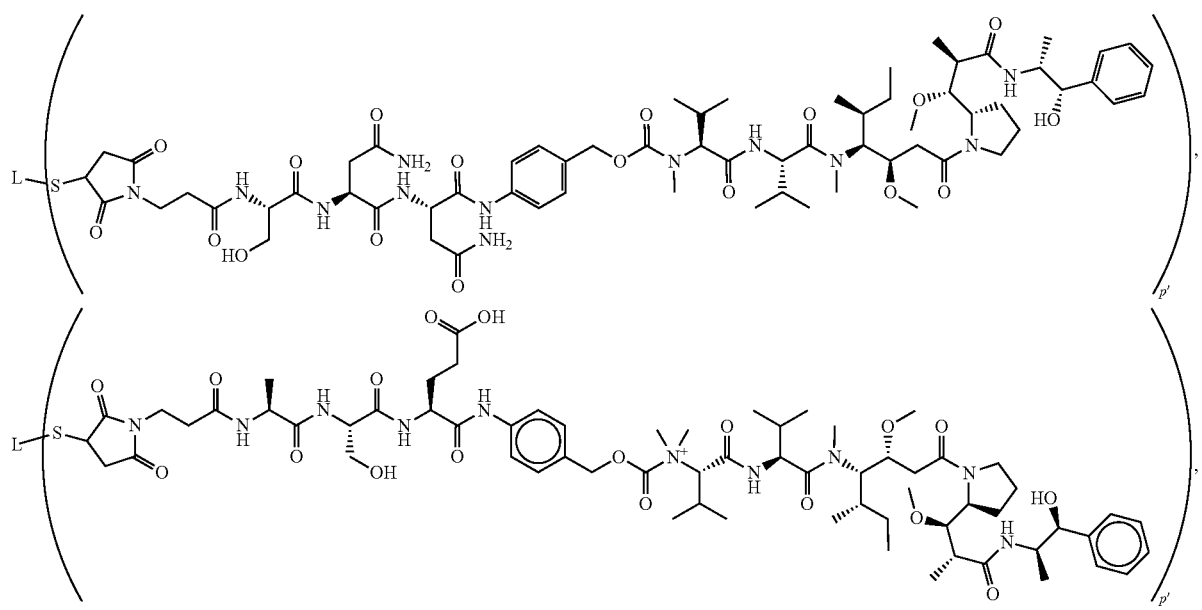

-continued

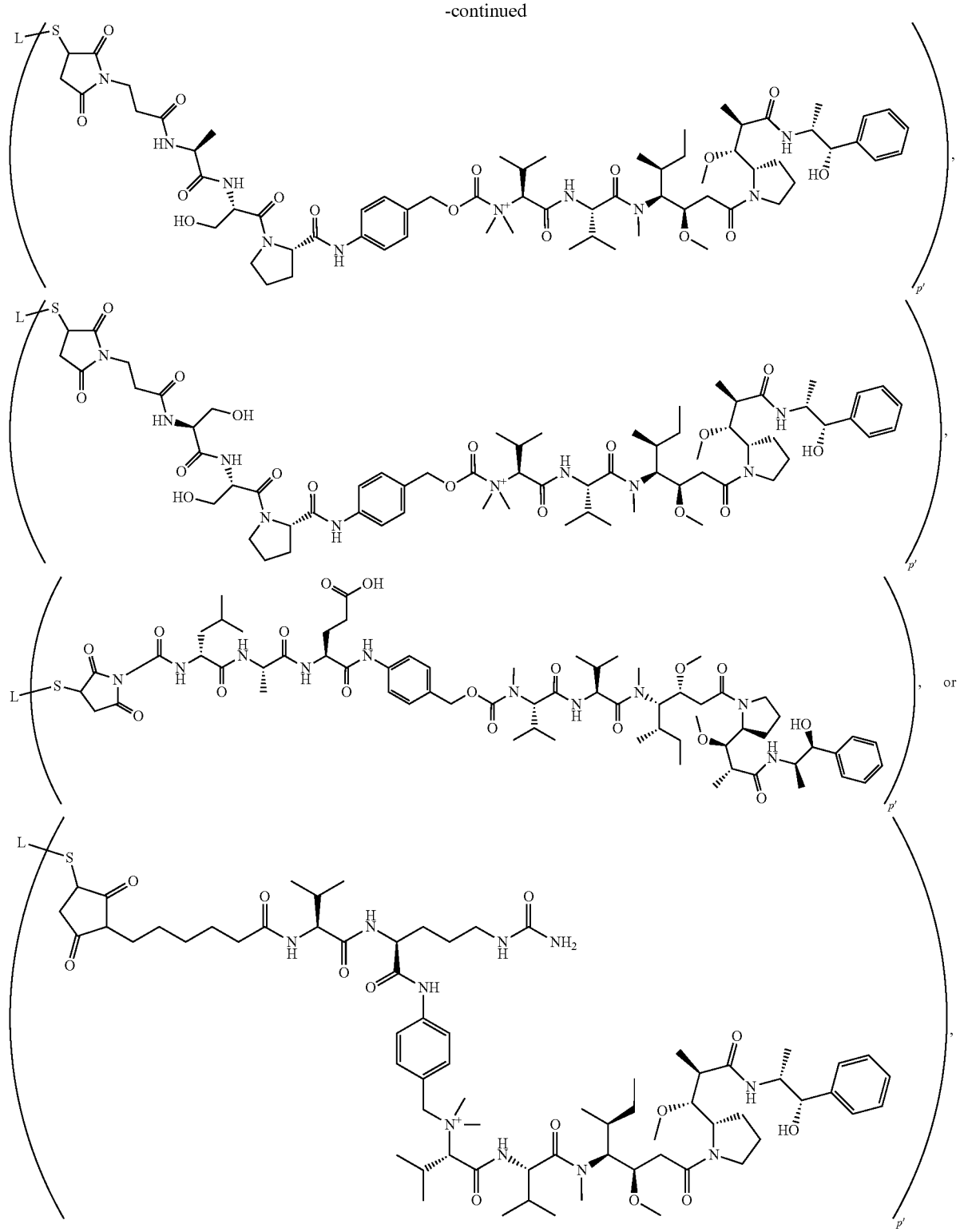

or a salt thereof (e.g., a pharmaceutically acceptable salt thereof), wherein L is a Ligand Unit, and subscript p' is an integer from 1 to 24. It is understood that where L is an antibody, a sulfur atom S bonded to L in the aforementioned chemical structures represents a sulfur of the side chain of a cysteine residue of the antibody. In some embodiments, the subscript p' is an integer from 1 to 12, 1 to 10 or 1 to 8 or is 4 or 8. In some embodiments, the subscript p' is 1, 2, 3, 4, 5, 6, 7, 8, 9, 10, 11, 12, 13, 14, 15, 16, 17, 18, 19, 20, 21, 22, 23, or 24. In some embodiments, the subscript p' is 2, 4, 6, or 8. In some embodiments, the subscript p' is 2. In some embodiments, the subscript p' is 4. In some embodiments, the subscript p' is 6. In some embodiments, the subscript p' is 8. Also included are Ligand Drug Conjugate compositions containing any of the Ligand Drug Conjugate compounds listed above wherein p' is replaced with p as described herein.

2.3 Drug Linker Compounds

A Drug Linker compound is represented by the structure of Formula I:

LU'-(D')    (I)

or a salt thereof, wherein LU' is LU precursor; and D' represents from 1 to 4 Drug Units, which are preferably identical to each other, wherein the Drug Linker compound is further defined by the structure of Formula IA:

$(L_B'\text{—}A_a\text{—}B_b\text{—}L_O\text{—}D)_q$    (IA)

wherein $L_B'$ is an ligand covalent binding moiety precursor; A is a first optional Stretcher Unit; subscript a is 0 or 1 indicating the absence or presence of A, respectively, B is an optional Branching Unit; subscript b is 0 or 1 indicating the absence or presence of B, respectively, provided that subscript b is 1 when subscript q is selected from 2 to 4 and $L_O$ is a secondary linker having the formula of:

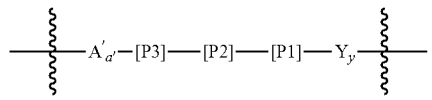

or a salt thereof, in particular a pharmaceutically acceptable salt, wherein A' is a second optional Stretcher Unit, subscript a' is 0 or 1 indicating the absence or presence of A', respectively, Y is an optional Spacer Unit, subscript y is 0, 1 or 2 indicating the absence or presence of 1 or 2 Spacer Units, respectively, and P1, P2 and P3 are amino acid residues that together provide selectivity for proteolysis by a homogenate of tumor tissue over proteolysis by a homogenate of normal tissue, and/or together provide for preferred biodistribution of a Conjugate prepared from the Formula IA Drug Linker compound into tumor tissue in comparison to normal tissue, wherein cytotoxicity of the free drug released from the Conjugate towards the normal tissue is responsible at least in part for an adverse event typically associated with administration of a therapeutically effective amount of a comparator dipeptide-base Conjugate, wherein proteolytic cleavage occurs at the covalent bond between P1 and Y if subscript y is 1 or 2, or at the covalent bond between P1 and D if subscript y is 0 or $L_O$ is a secondary linker having the formula of:

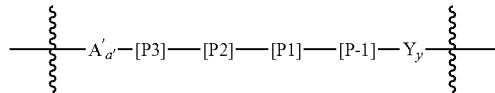

or a salt thereof, in particular a pharmaceutically acceptable salt, wherein A', a', Y, and y retain their previous meanings and P1, P2 and P3 are amino acid residues, optionally with the P-1 amino acid, that together provide selectivity for proteolysis by tumor tissue homogenate over proteolysis by normal tissue homogenate, and/or together provide for preferred biodistribution of a Conjugate prepared from the Formula IA Drug Linker compound into tumor tissue in comparison to normal tissue, wherein cytotoxicity of the free drug released from the Conjugate towards the normal tissue is responsible at least in part for an adverse event typically associated with administration of a therapeutically effective amount of a comparator dipeptide-base Conjugate, wherein proteolytic cleavage occurs at the covalent bond between P1 and P-1 to release a linker fragment having the structure of [P-1]—$Y_y$-D, or $L_O$ is a secondary linker having the formula of:

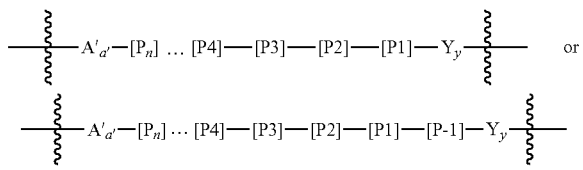

or a salt thereof, in particular a pharmaceutically acceptable salt, wherein A', a', Y, and y retain their previous meanings and P-1 and P1, P2, P3 . . . $P_n$ are contiguous amino acid residues, wherein subscript n is an integer value providing for up to 12 (e.g., 3-12 or 3-10) of these amino acids and P1, P2 and P3, optionally with P-1, together provide selectivity for proteolysis by tumor tissue homogenate over proteolysis by normal tissue homogenate and/or together provide for preferred biodistribution of a Conjugate prepared from the Drug Linker compound into tumor tissue in comparison to normal tissue, wherein cytotoxicity of the free drug released from the Conjugate towards the normal tissue is responsible at least in part for an adverse event typically associated with administration of a therapeutically effective amount of a comparator dipeptide-base Conjugate, wherein proteolytic cleavage occurs at the covalent bond between P1 and $Y_y$-D or between and P1 and P-1 to release a linker fragment having the structure of $Y_y$-D or [P-1]-$Y_y$-D, respectively, in which the later subsequently undergoes exopeptidase cleavage to release the linker fragment having the structure of $Y_y$-D. In both instances the $Y_y$-D linker fragment undergoes spontaneous decomposition to complete release of D as free drug.

The additional P4, P5 . . . $P_n$ amino acid residues are selected so as to not alter the cleavage site that provides the —$Y_y$-D or —[P-1]-$Y_y$-D fragment, but instead are selected to retain a desired physiochemical and/or pharmokinetic property for the Ligand Drug Conjugate that is prepared from the Formula IA Drug Linker compound, wherein the desired physiochemical and/or pharmokinetic property is provided primarily by the P1, P2 and P3 amino acid residues, such as increased biodistribution of the Conjugate into tumor tissue, which is to the detriment of normal tissue distribution, or to enhance that physiochemical and/or pharmokinetic property in comparison to a comparator dipeptide-base Conjugate.

In either one of those embodiments of $L_O$ if subscript q is 1, then subscript b is 0 so that B is absent and A' becomes an optional subunit of A and if subscript q is 2, 3 or 4, then subscript b is 1 so that B is present, A' remains a component of $L_O$ as shown and an optional subunit of A is then indicated as $A_O$.

A Drug Linker compound is particularly useful in preparing a Ligand Drug Conjugate of Formula 1 so that LU' is a LU precursor for a drug linker moiety of a Ligand Drug Conjugate compound.

In some embodiments $L_B$'-A- of a Drug Linker compound has or is comprised of one of the structures of:

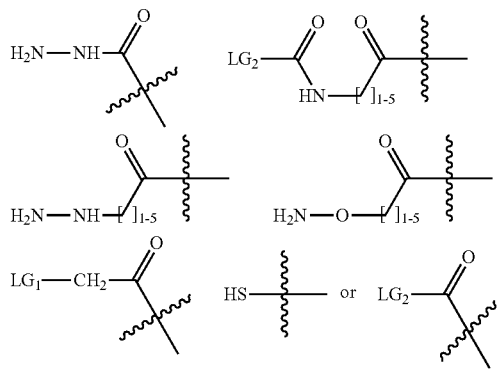

or a salt thereof, wherein $LG_1$ is a leaving group suitable for nucleophilic displacement by a targeting agent nucleophile; $LG_2$ is a leaving group suitable for amide bond formation to a targeting agent, or —OH to provide an activatable carboxylic acid suitable for amide bond formation to a targeting agent; and the wavy line indicates the site of covalent attachment to the remainder of the Drug Linker compound structure.

In other embodiments of a Formula IA Drug Linker compound in which subscript q is 1, $L_B$'-A- of has or is comprised of one of the structures of:

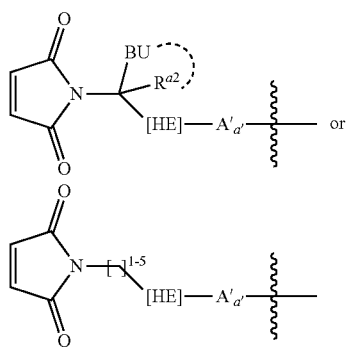

or a salt thereof, wherein A' is an optional second subunit of A, sometimes indicated as $A_2$ if that subunit is present; subscript a' is 0 or 1, indicating the absence or presence of A', respectively; the wavy line adjacent to A' indicates the site of covalent attachment to another subunit of A or to the Peptide Cleavable Unit; [HE] is an optional Hydrolysis Enhancing Unit, which is a component provided by A or a first subunit thereof; BU is a Basic Unit; $R^{a2}$ is an optionally substituted $C_1$-$C_{12}$ alkyl group; and the dotted curved line indicates optional cyclization so that in the absence of said cyclization, BU is an acyclic Basic Unit having a primary, secondary or tertiary amine functional group as the basic function group of the acyclic Basic Unit, or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom, or is optionally protonated In other embodiments in which subscript q is 2, 3 or 4, $L_B$'-A- is comprised of one of the structures of:

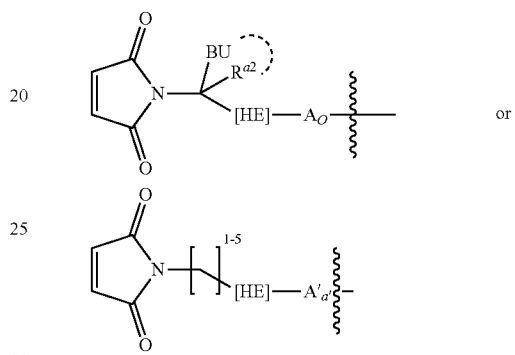

or a salt thereof, wherein the wavy line adjacent to $A_O$ indicates the site of covalent attachment to B, $A_O$ is an optional subunit of A, sometimes indicated as $A_2$ if that subunit is present and the remaining variable groups are as defined for Formula IA drug linker compounds in which subscript q is 1.

In some preferred embodiments in which subscript q is 1, $L_B$'-A- of a Drug Linker compound has or is comprised of one of the structures of:

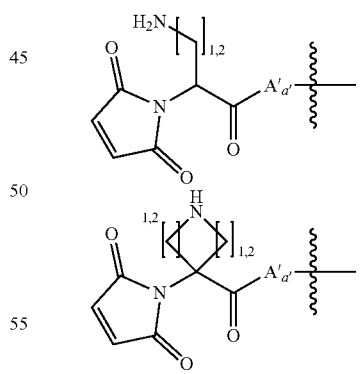

or a salt thereof, in particular as an acid addition salt, wherein A' and subscript a' are as previously described. Those $L_B$'-A- structures are exemplary self-stabilizing precursor moieties, sometimes indicated as $L_{SS}$', since each is capable of being converted to a $L_{SS}$ moiety of a Ligand Drug Conjugate compound.

In other preferred embodiments $L_B$'-A- of a Drug Linker compound has or is comprised of one of the structures of:

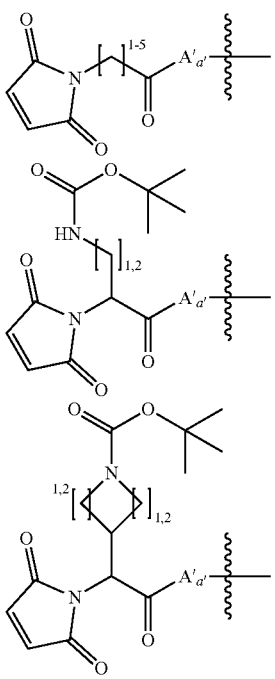

wherein A' and subscript a' are as previously described for Formula IA drug linker compounds in which subscript q is 1.

In preferred embodiments of $L_{SS}$'-containing Drug Linker compounds, the $L_{SS}$' moiety contains a heterocyclo cyclic Basic Unit. Exemplary Drug Linker compounds having those primary linkers in which the Peptide Cleavable Unit is a tripeptide is represented by the structure of Formula IB:

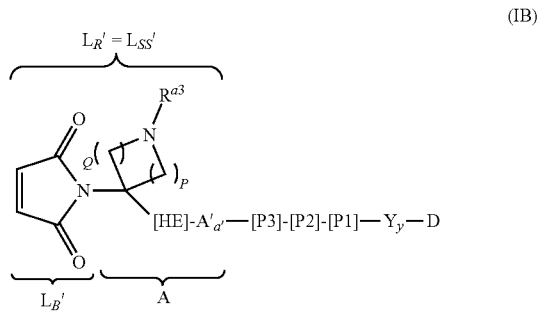

(IB)

or a salt thereof, wherein HE is an optional Hydrolysis Enhancing Unit; A' is an subunit, when present, of a first Stretcher Unit (A); subscript a' is 0 or 1, indicating the absence or presence of A', respectively; subscript P is 1 or 2; subscript Q ranges from 1 to 6, preferably subscript Q is 1 or 2, more preferably subscript Q has the same value as subscript P; and wherein $R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—$(CH_2CH_2O)_{1-36}$—$R^{PEG2}$, wherein $R^{PEG1}$ is $C_1$-$C_4$ alkylene, $R^{PEG2}$ is —H or $C_1$-$C_4$ alkylene, wherein the basic nitrogen bonded to $R^{a3}$ is optionally protonated in a salt form, preferably in a pharmaceutically acceptable salt form, or $R^{a3}$ is a nitrogen protecting group such as a suitable acid-labile protecting group; P1, P2 and P3 are as previously defined for any one of the embodiments of Peptide Cleavable Units for a drug linker moiety of a Ligand Drug Conjugate compound; and the remaining variable groups are as described for a Drug Linker compound of Formula IA.

In other preferred embodiments of $L_{SS}$'-containing Drug Linker compounds of Formula IA the $L_{SS}$' moiety contains an acyclic cyclic Basic Unit. Exemplary Drug Linker compounds having that primary linker in which the Peptide Cleavable Unit is a dipeptide are represented by the structures of Formula IE:

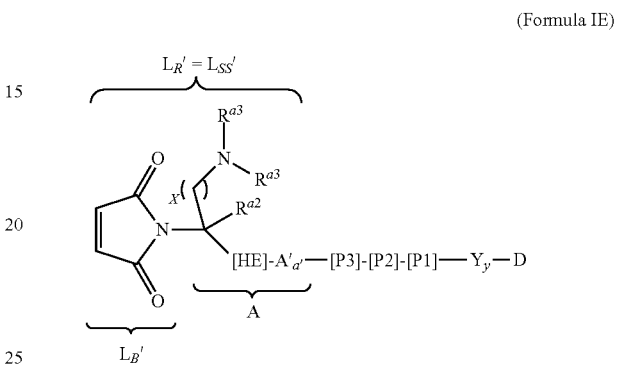

(Formula IE)

or a salt thereof, wherein HE is an optional Hydrolysis Enhancing Unit; A' is an subunit, when present, of a first Stretcher Unit (A); subscript a' is 0 or 1, indicating the absence or presence of A', respectively; subscript x is 1 or 2; $R^{a2}$ is hydrogen or —$CH_3$ or —$CH_2CH_3$; $R^{a3}$, at each instance, is independently hydrogen, —$CH_3$ or —$CH_2CH_3$, or both $R^{a3}$ together with the nitrogen to which they are attached define an azetidinyl, pyrrolidinyl or piperidinyl heterocyclyl, in which a basic primary, secondary or tertiary amine so defined is optionally protonated in a salt form, preferably a pharmaceutically acceptable salt form; P1, P2 and P3 are as previously defined for any one of the embodiments of Peptide Cleavable Units and the remaining variable groups are as described for a Drug Linker compound of Formula IA.

In other preferred embodiments, a primary linker does not have a Basic Unit. Exemplary Drug Linker compounds having that primary linker in which the Peptide Cleavable Unit is a tripeptide are represented by the structure of Formula IH:

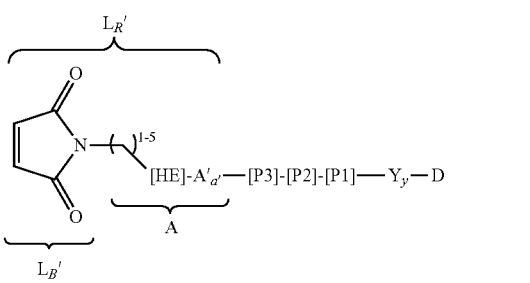

(Formula IH)

or a salt thereof, wherein HE is an optional Hydrolysis Enhancing Unit; A' is an subunit, when present, of a first Stretcher Unit (A); subscript a' is 0 or 1, indicating the absence or presence of A'; P1, P2 and P3 are as previously defined for any one of the embodiments of Peptide Cleavable Units of a drug linker moiety of a Ligand Drug Conjugate compound and the remaining variable groups are as described for any one of the embodiments of a Drug Linker compound of Formula IA.

In more preferred embodiments in which there is a heterocyclo cyclic Basic Unit in the Linker Unit, a Drug Linker compound is represented by the structure of:

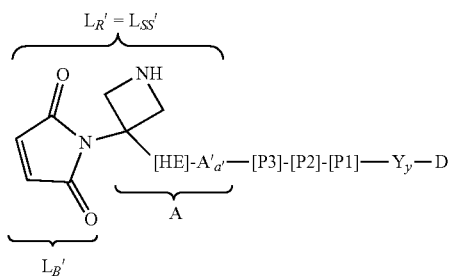

optionally in a salt form, in particular in pharmaceutical acceptable salt form, and in more preferred embodiments in which there is an acyclic Basic Unit in the Linker Unit, a Drug Linker compound is represented by the structure of:

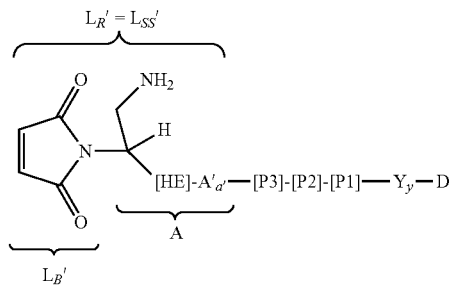

optionally in salt form, wherein the variable groups of the $L_{SS}'$-containing Drug Linker compound is as previously described for a Drug Linker compound having a acyclic or heterocyclo cyclic Basic Unit.

In any one of the preceding drug linker moieties, HE is preferably present as —C(=O) and/or subscript y is 1 or 2, indicating the presence of one or two self-immolative Spacer Units, respectively.

In particularly preferred embodiments the —[P3]-[P2]-[P1]- tripeptide in any one of the above Drug Linker compounds is D-Leu-Leu-Cit, D-Leu-Leu-Lys, D-Leu-Leu-Met(O), D-Leu-Ala-Glu or Pro-Ala(Nap)-Lys, wherein Met (O) is methionine in which its sulfur atom is oxidized to a sulfoxide, Cit is citrulline, and Ala(Nap) is alanine in which its methyl side chain is substituted by naphth-1-yl.

In especially preferred embodiments in which there is a heterocyclo cyclic Basic Unit in the Linker Unit, the Drug Linker compound is represented by the structure of:

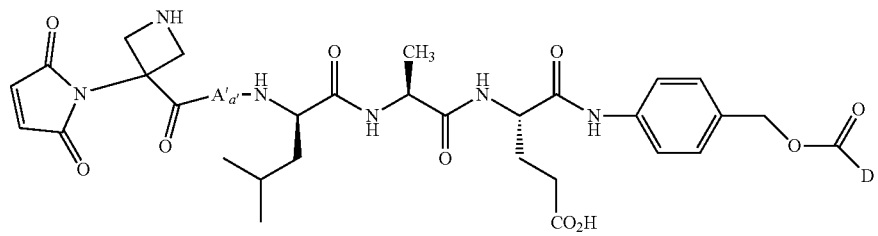

or salt thereof, wherein subscript a' is 0 or 1, indicating the absence or presence of A', respectively, wherein A' is an amine-containing acid residue of formula 3a, 4a or 5a as described herein for a second optional Stretcher Unit or a subunit of a first optional Stretcher Unit, or A' is an α-amino acid or β-amino acid residue; and D is a cytotoxic drug having a secondary amino group as the site of attachment to the Linker Unit of the drug linker moiety.

In other especially preferred embodiments in which there is an acyclic Basic Unit in the Linker Unit, the Drug linker compound is represented by the structure of

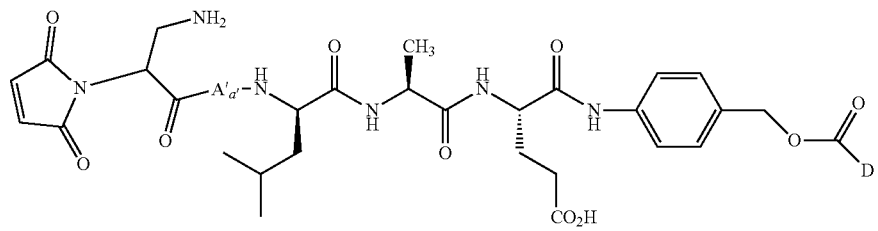

or salt thereof, wherein the variable groups are as previously described for Drug Linker compounds having a cyclic Basic Unit.

In other especially preferred embodiments in which there is no Basic Unit, the Drug Linker compound is represented by the structure of

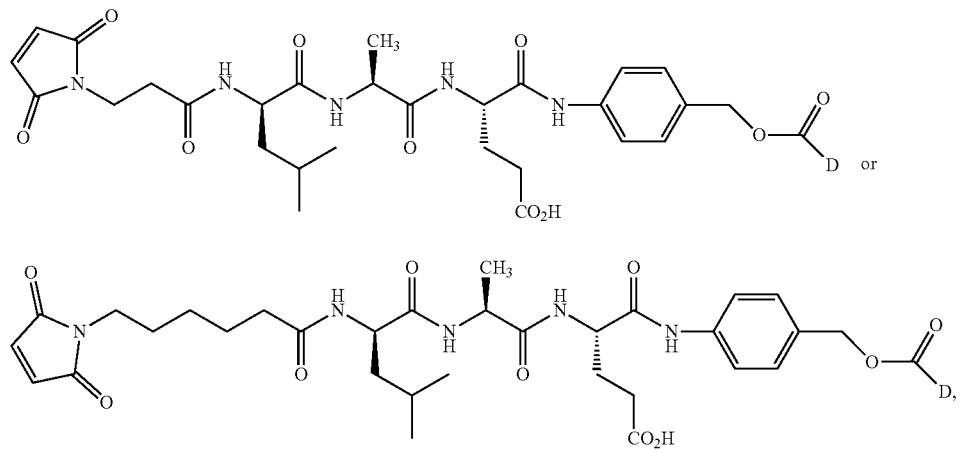

or salt thereof, wherein the variable groups are as previously described for Drug Linker compounds having a cyclic Basic Unit.

In some embodiments, the Drug Linker compound is represented by:

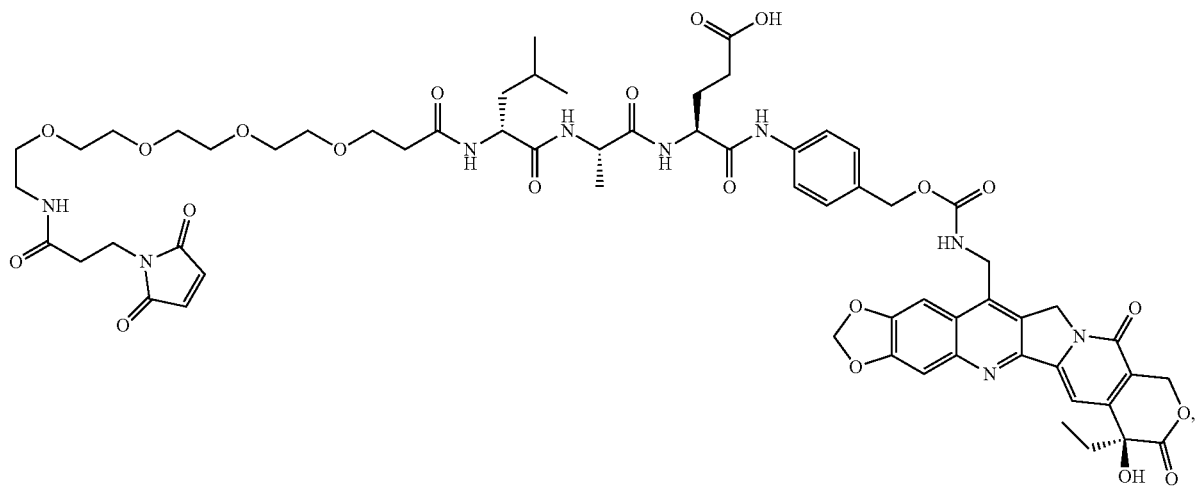

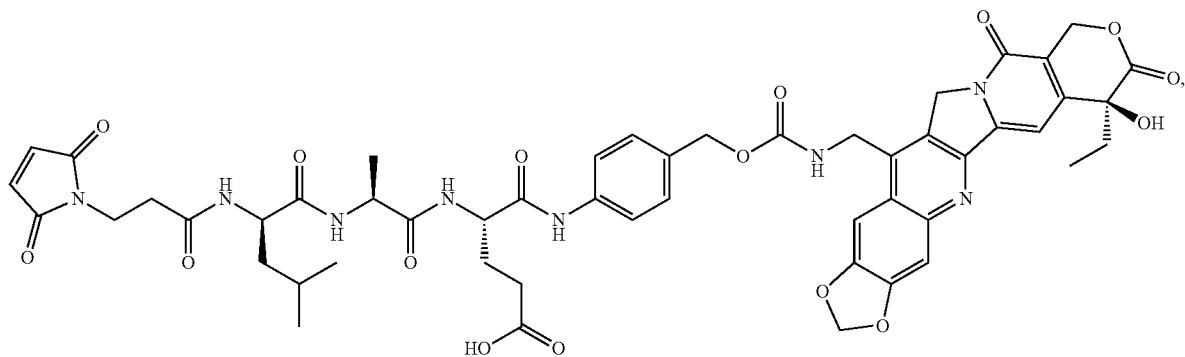

255 256
-continued
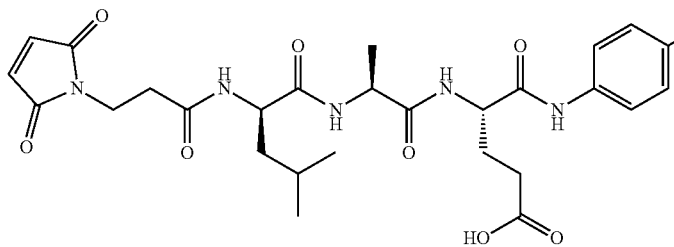 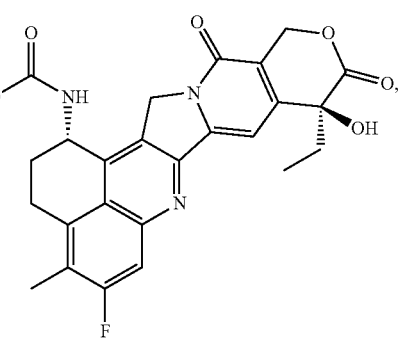
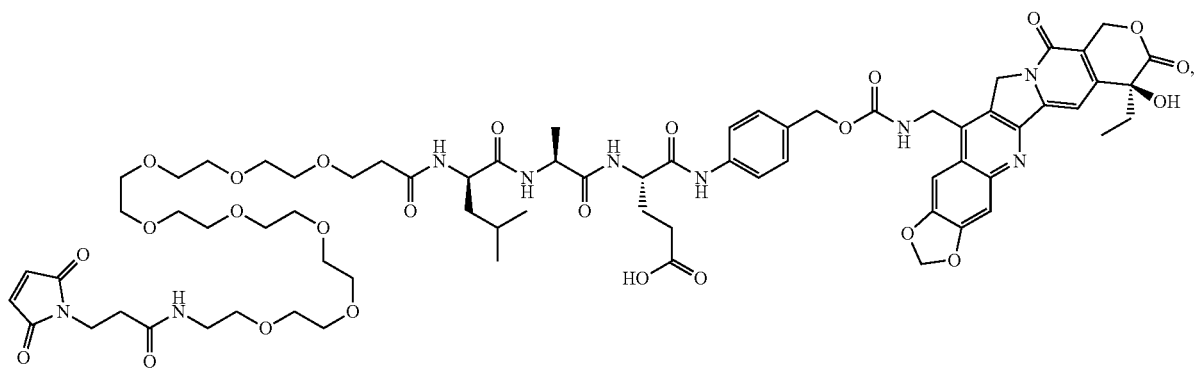
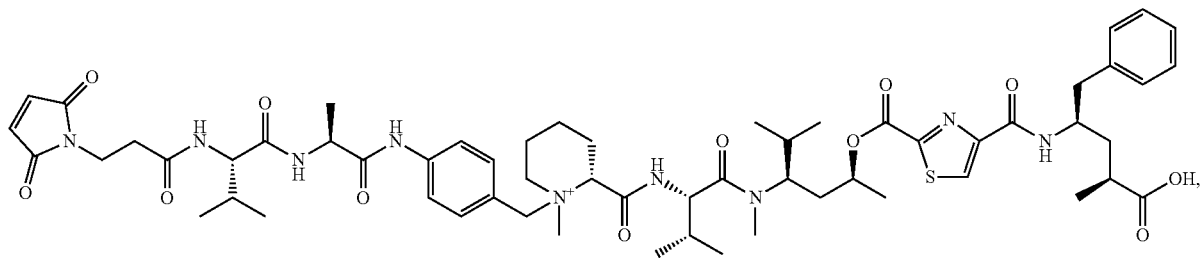
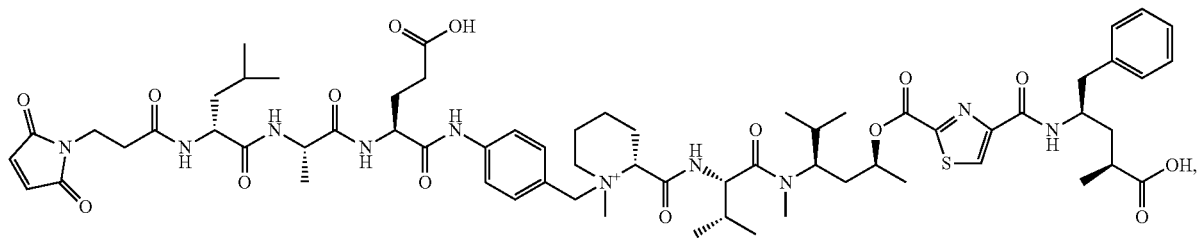
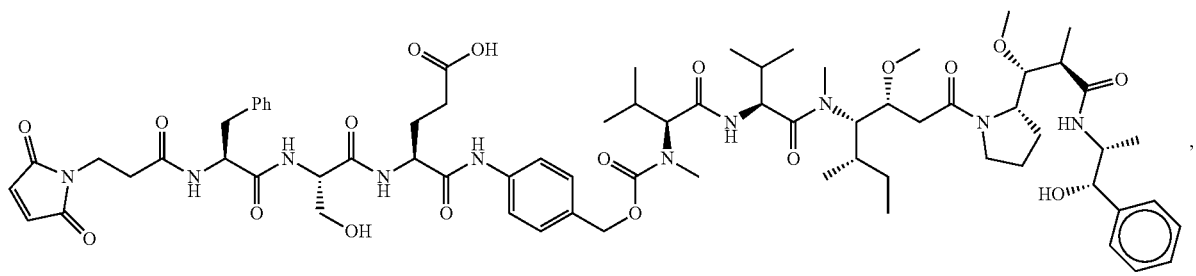

-continued
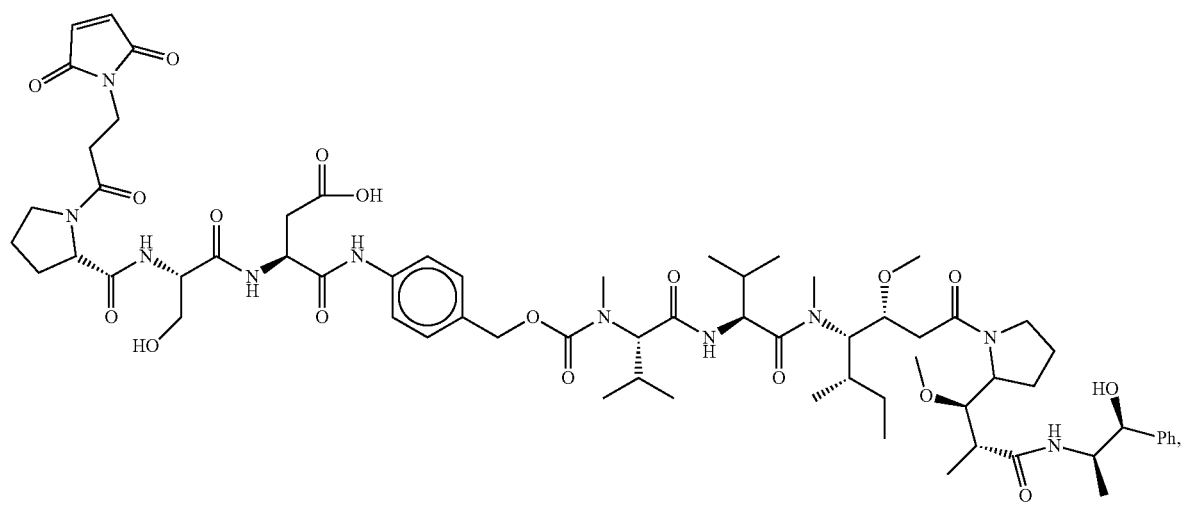
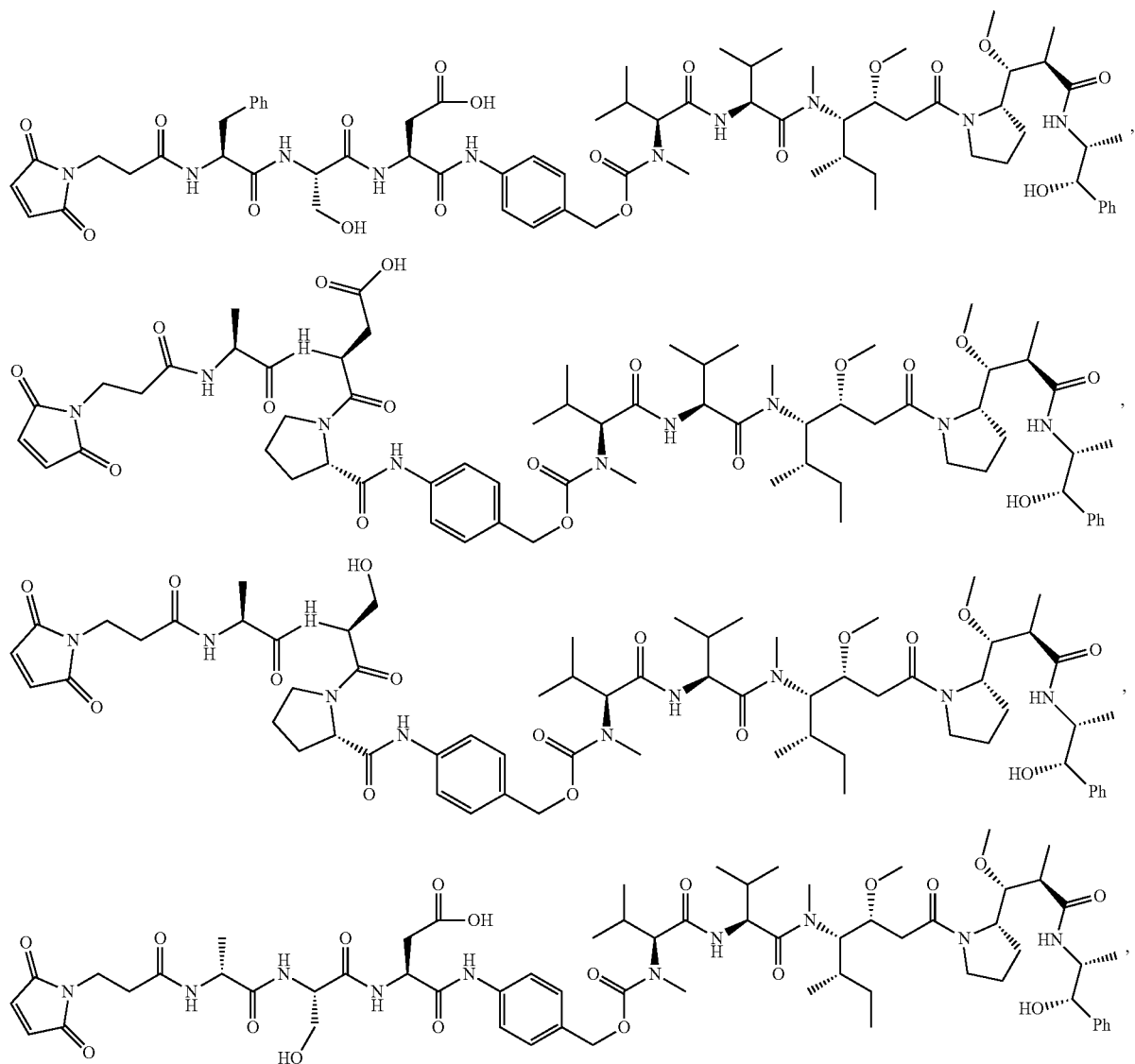

-continued
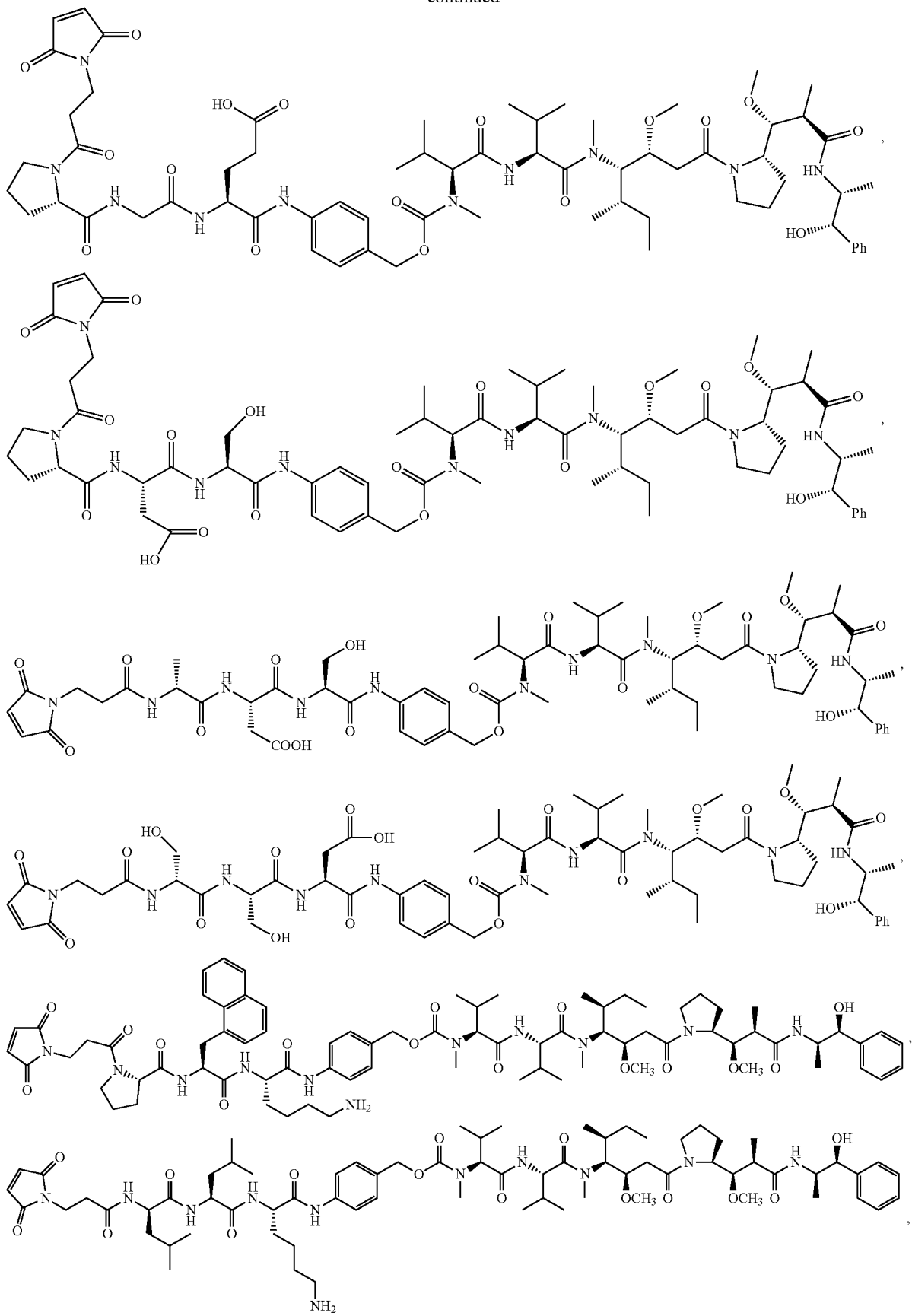

-continued
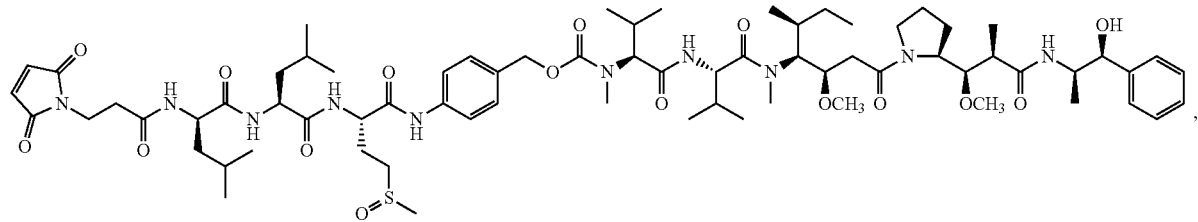
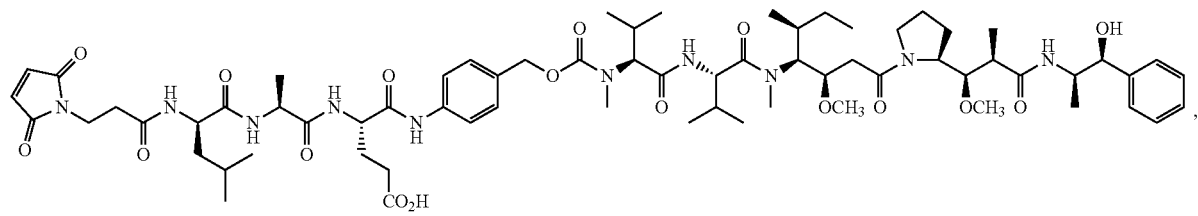
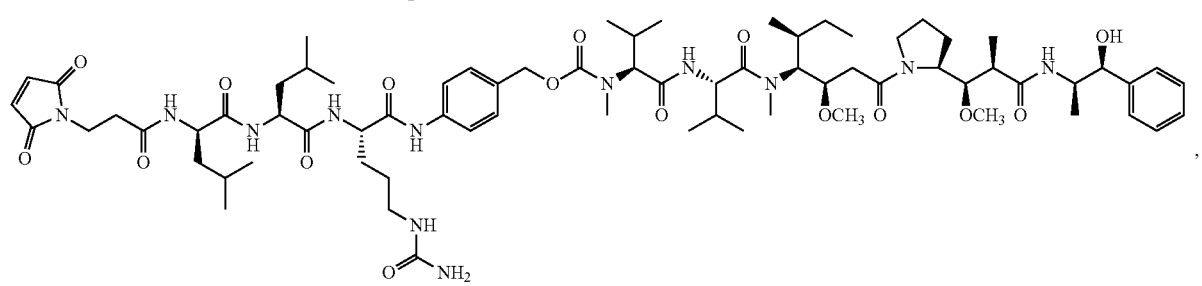
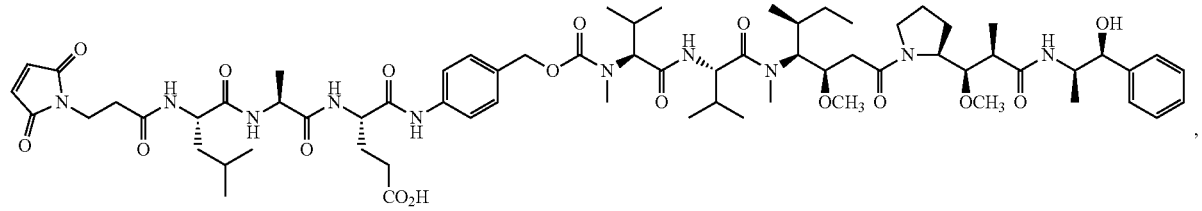
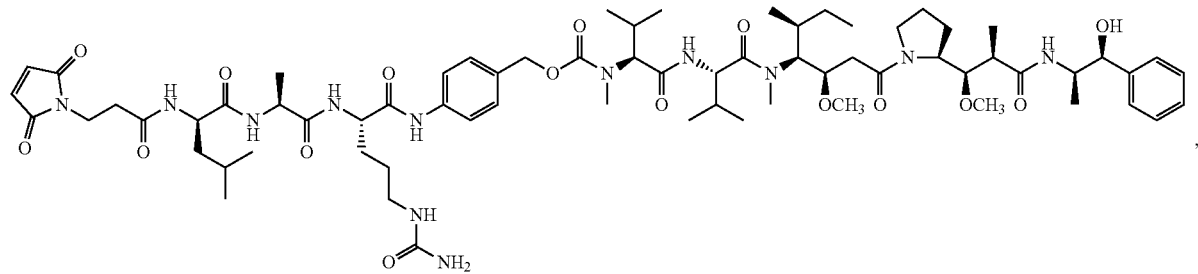
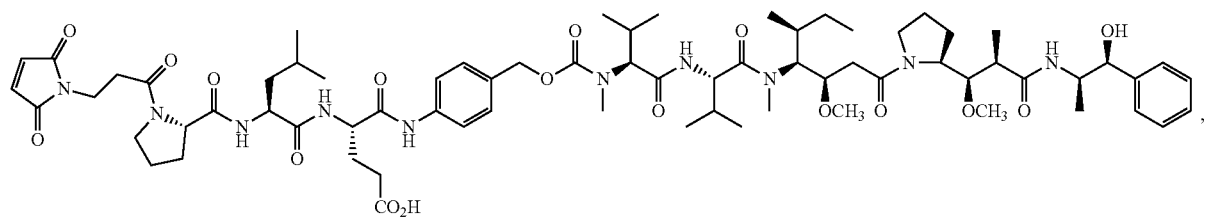
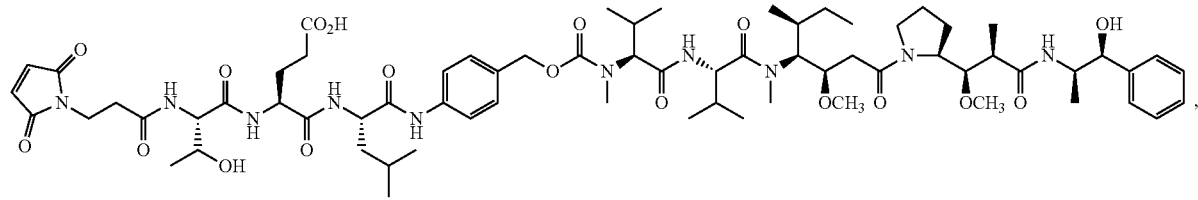

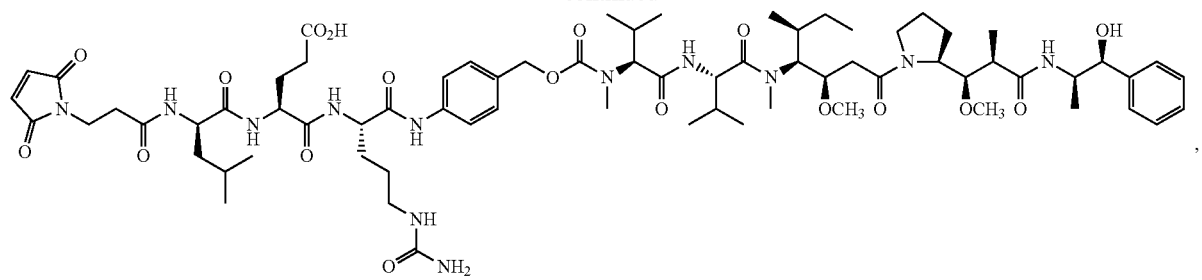,
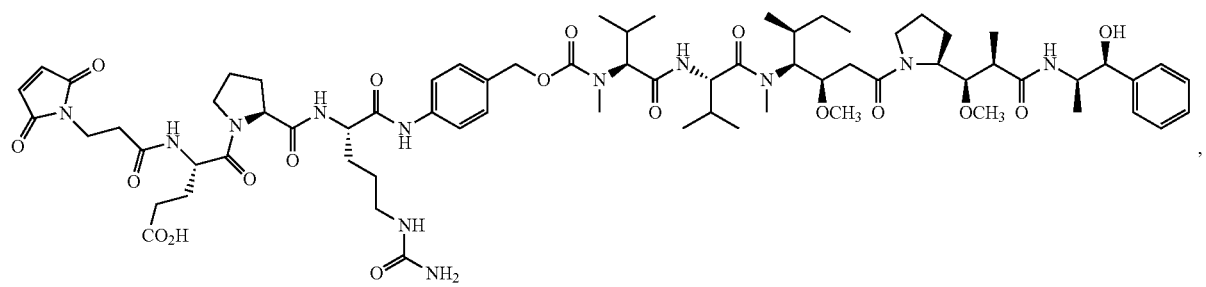,
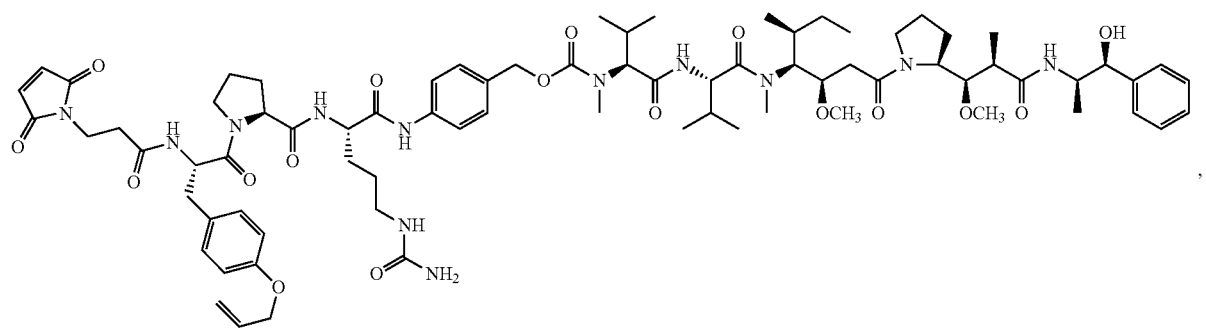,
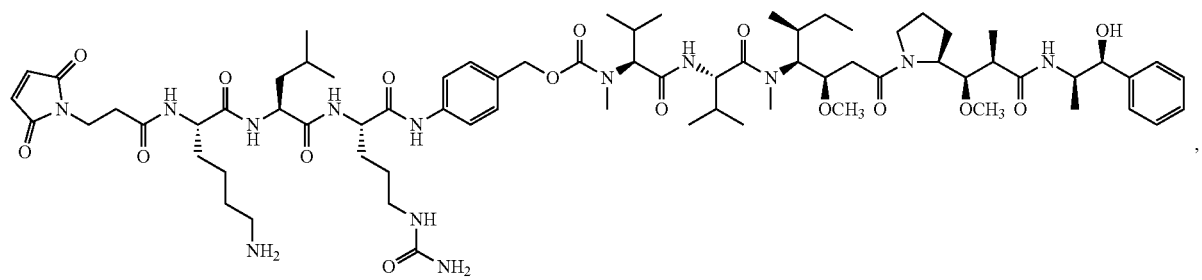,
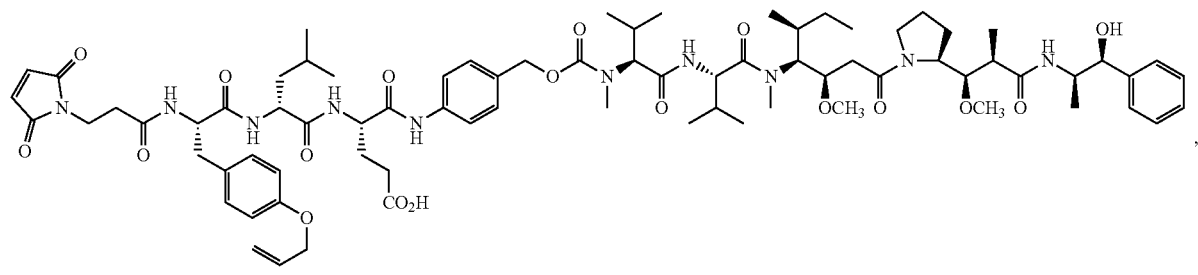,
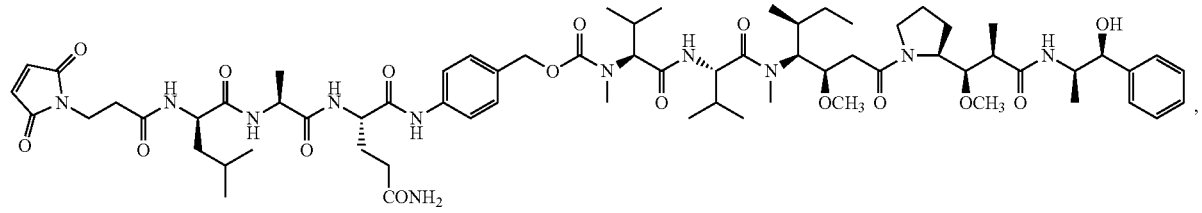,

-continued
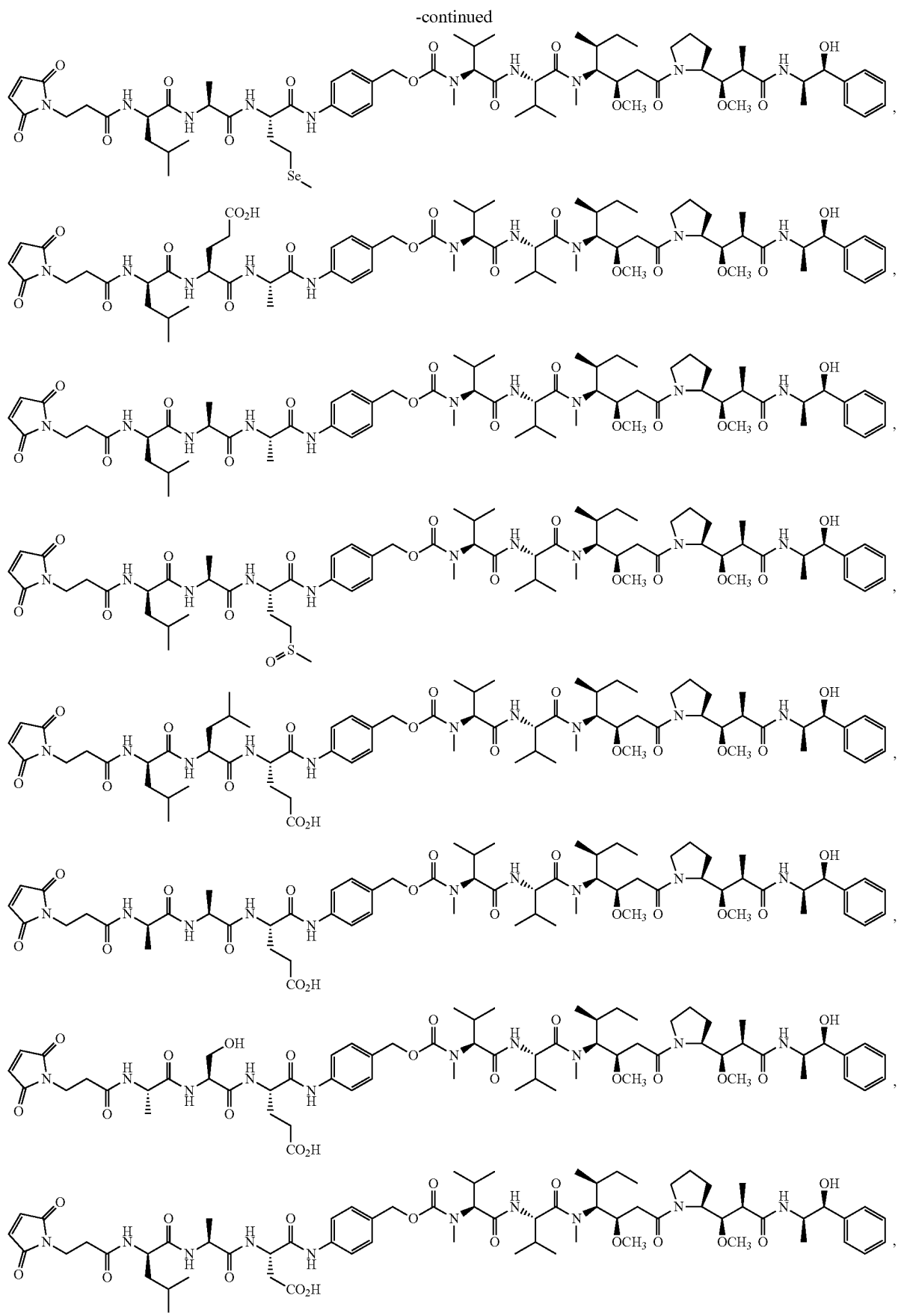

-continued
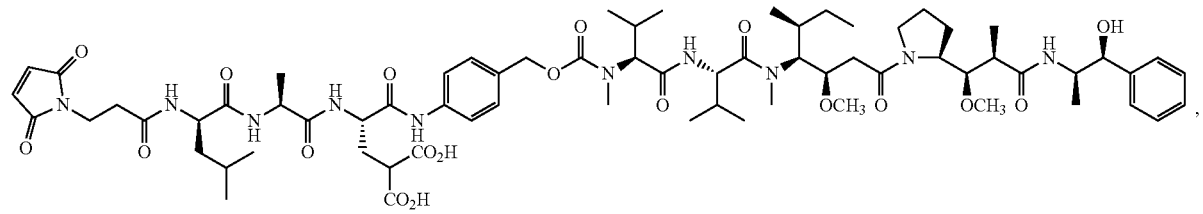
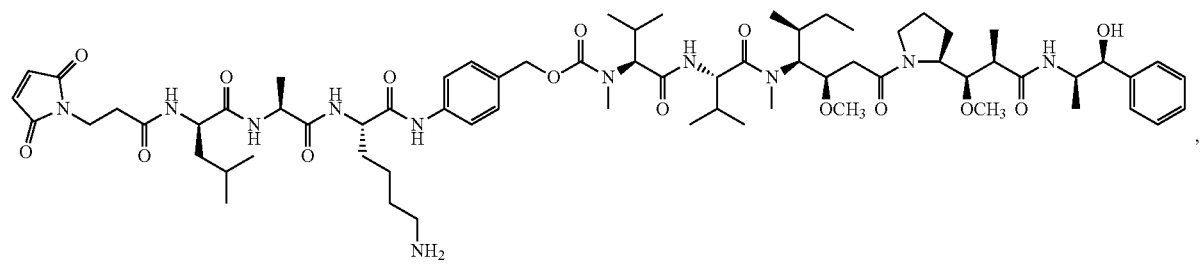
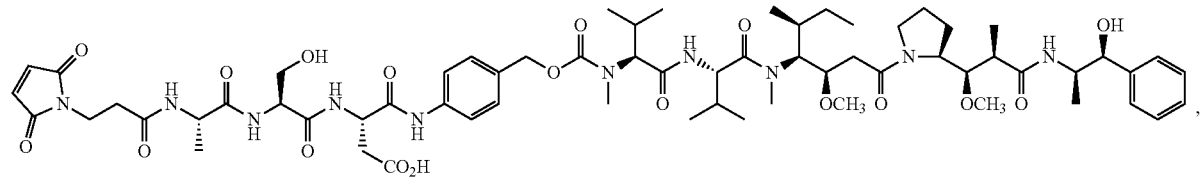
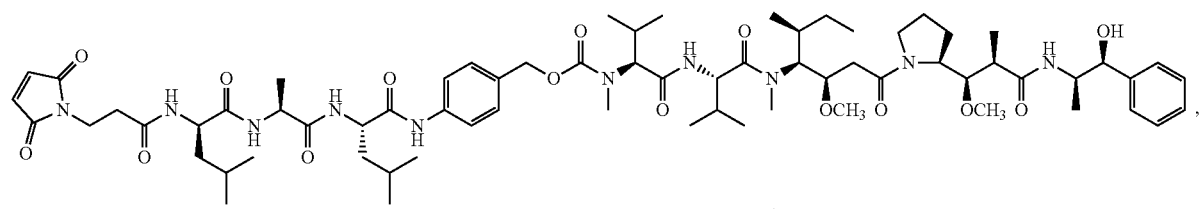
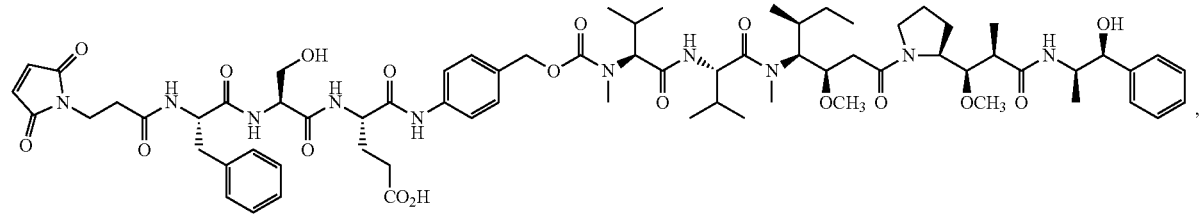
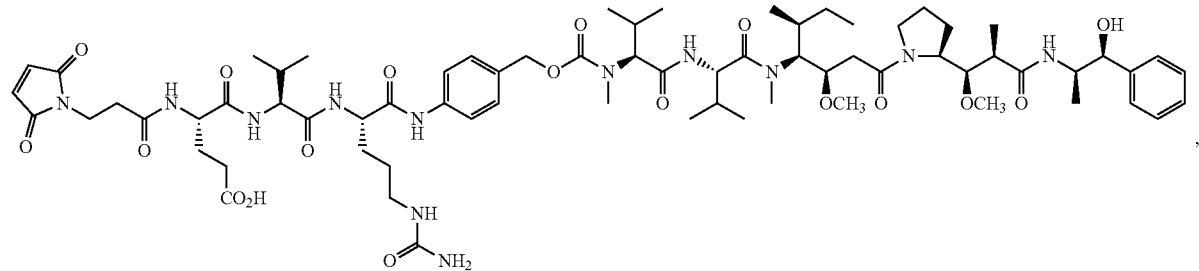

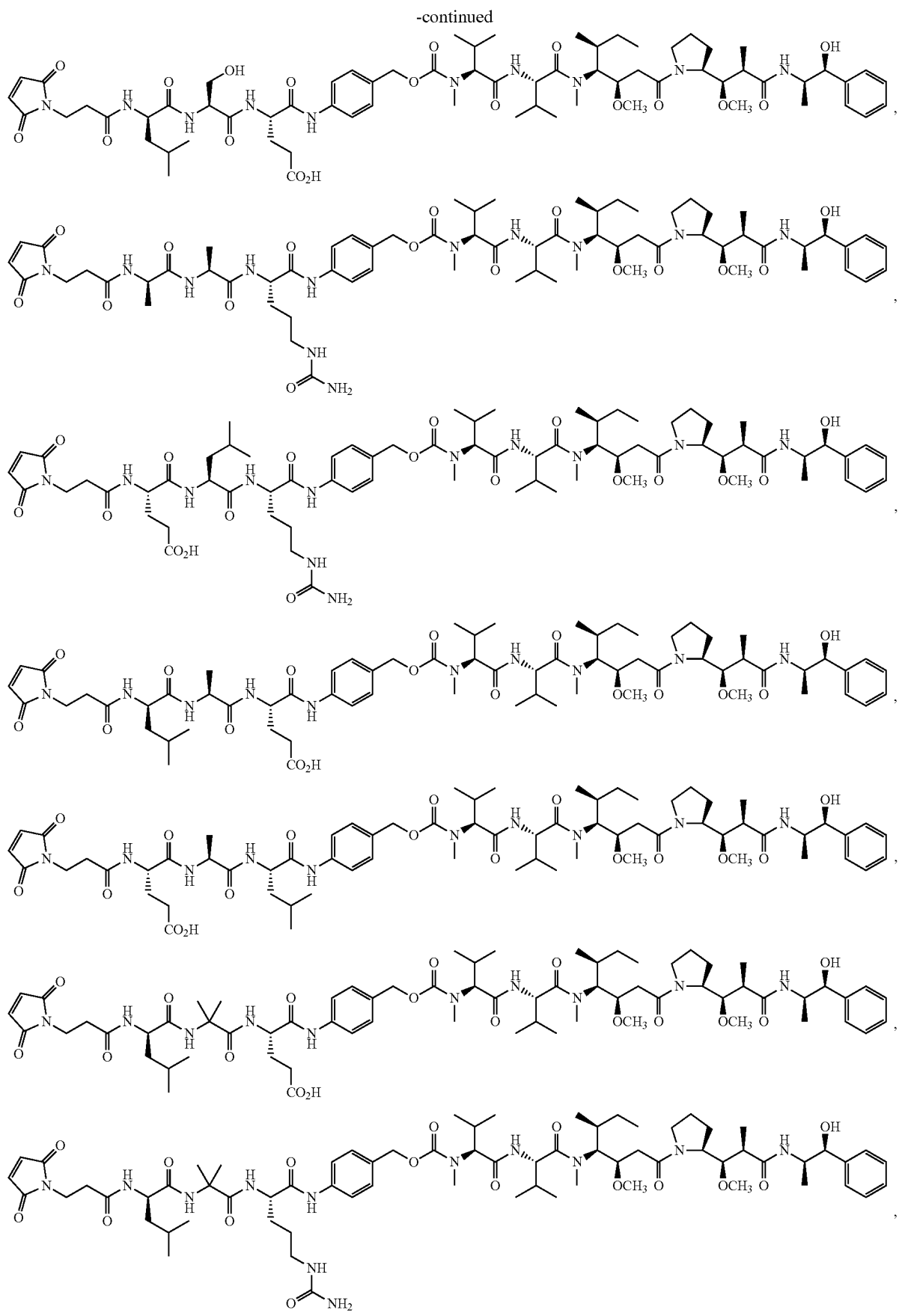

-continued
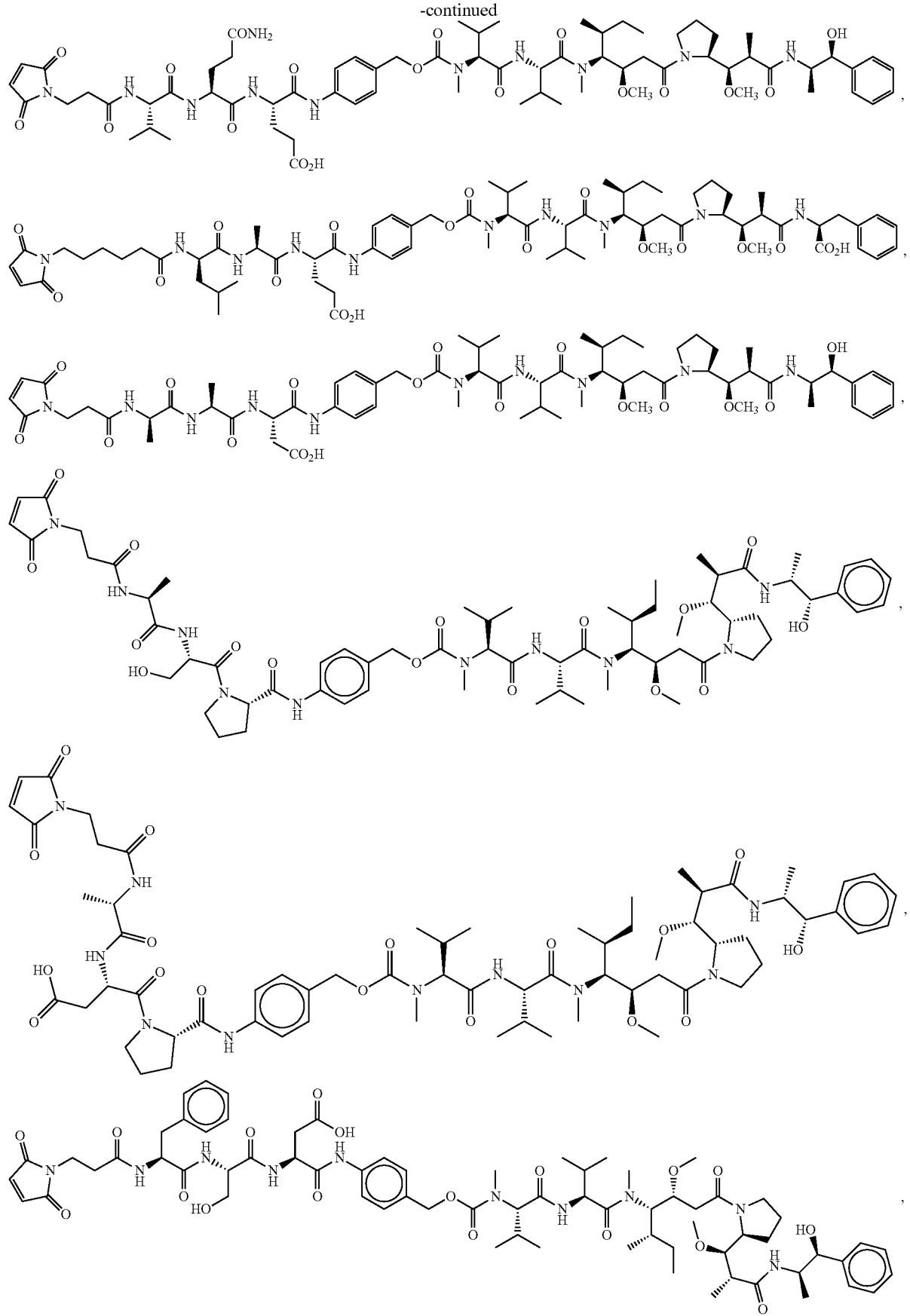

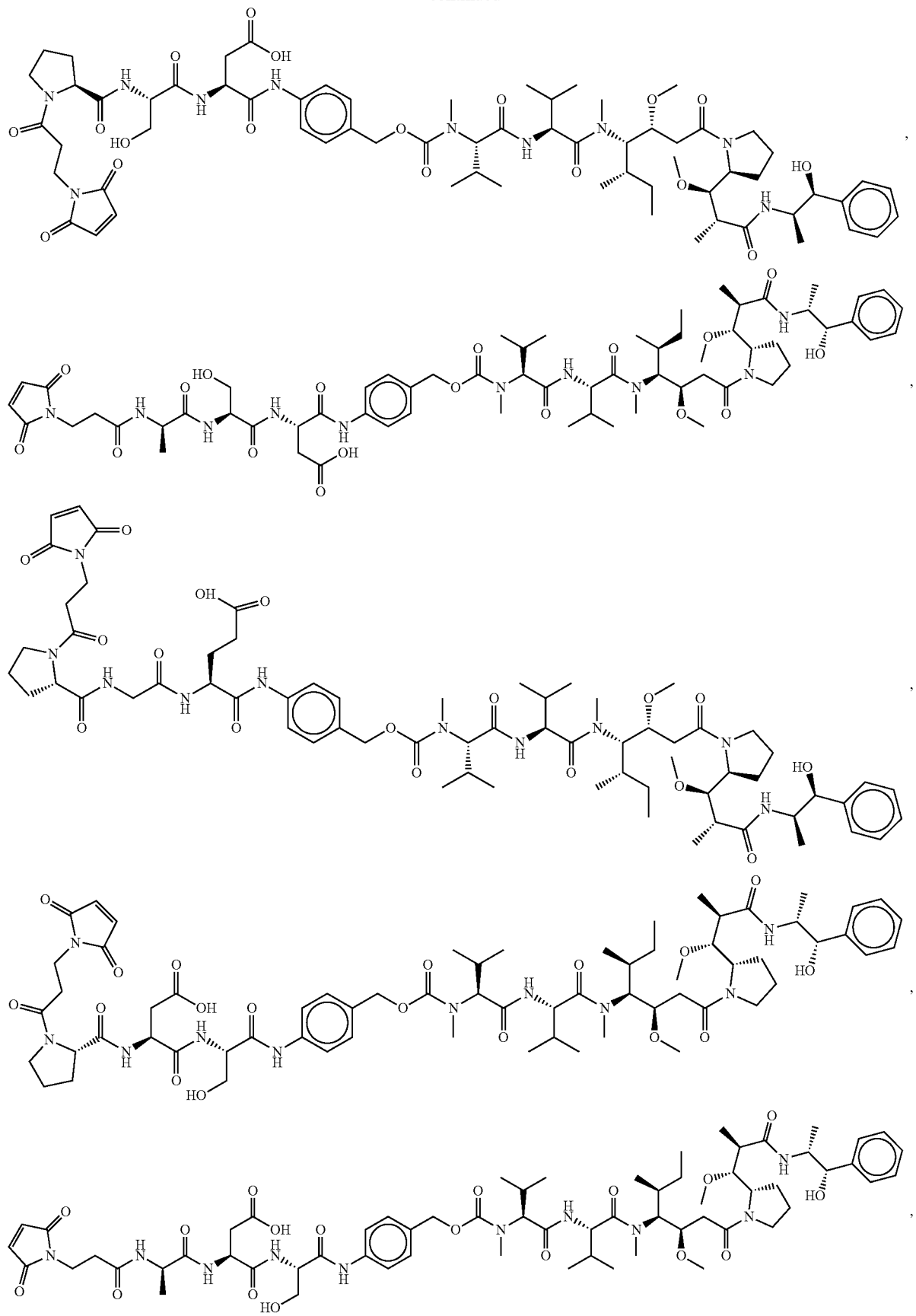

-continued
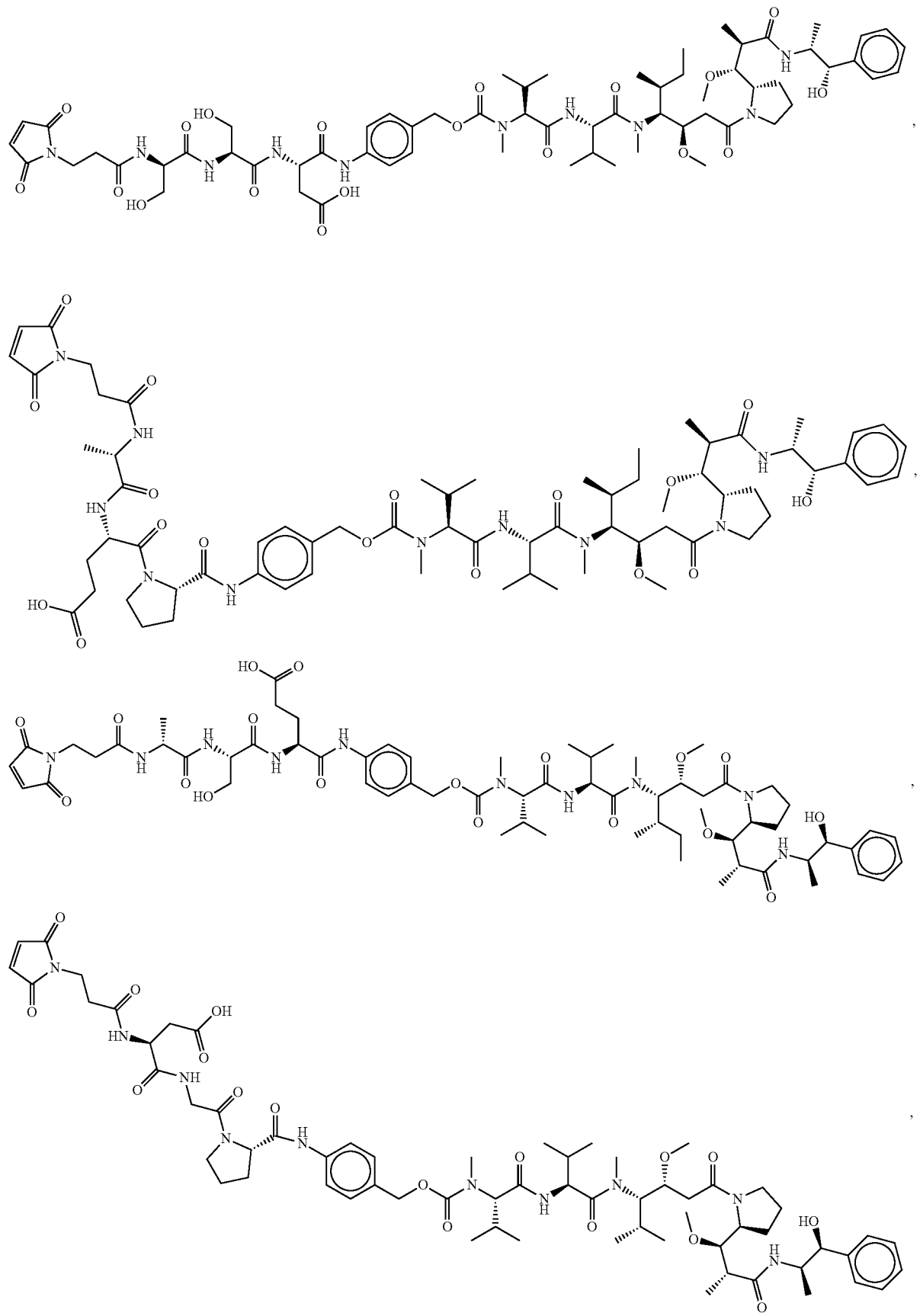

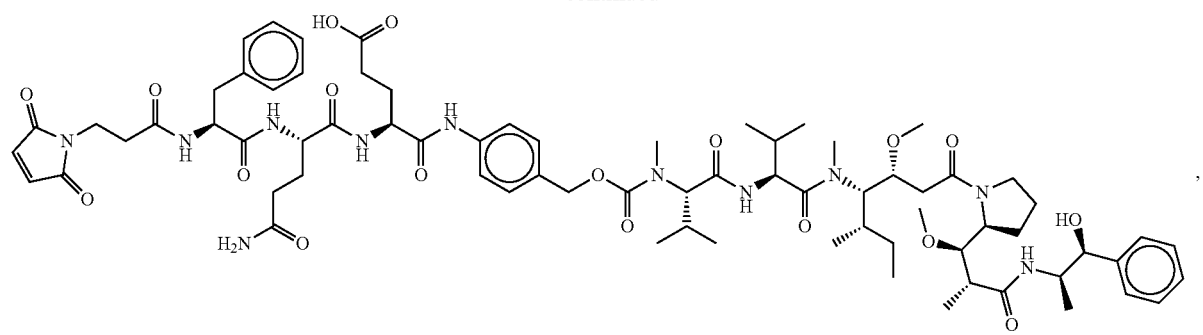
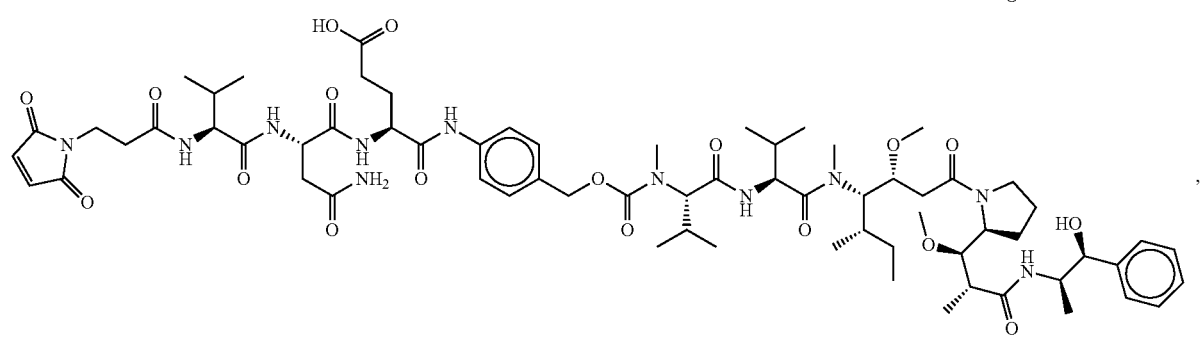
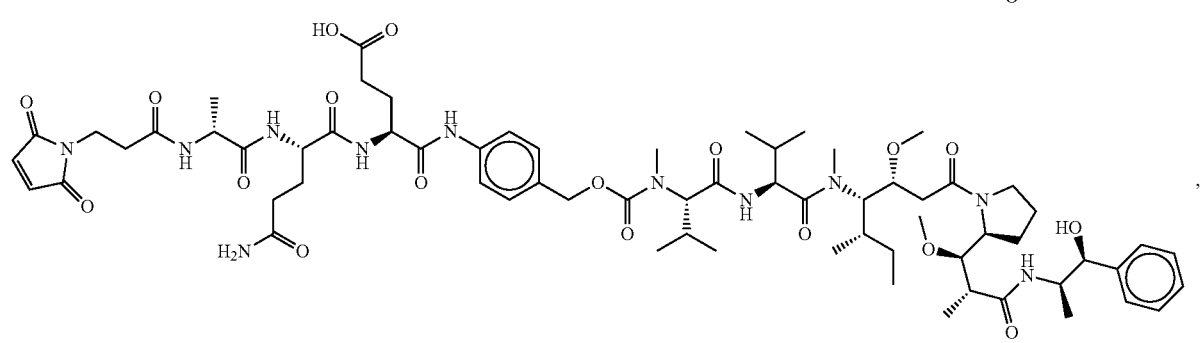
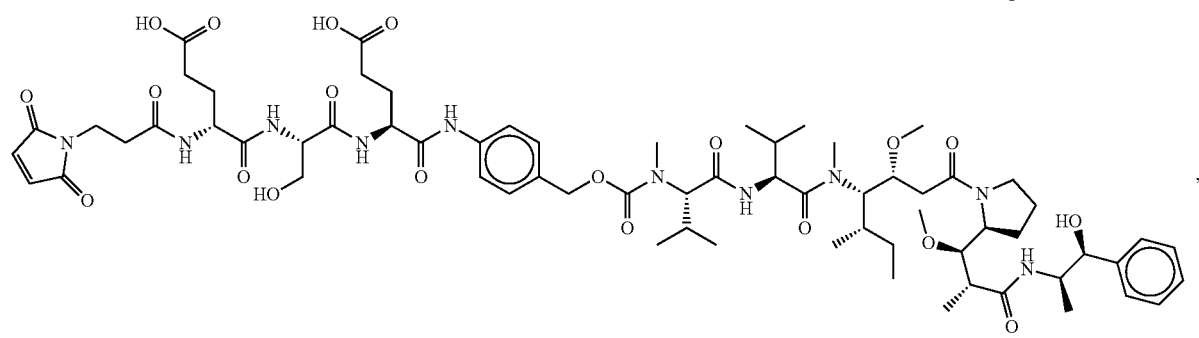
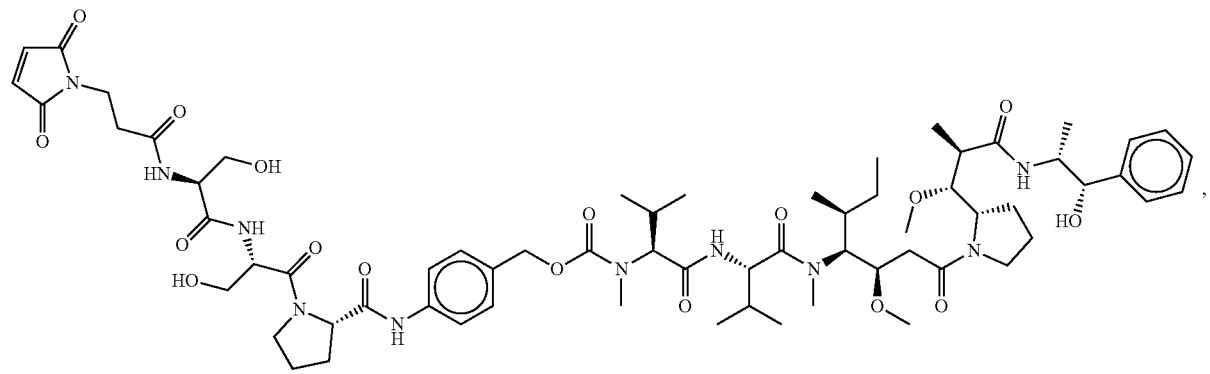

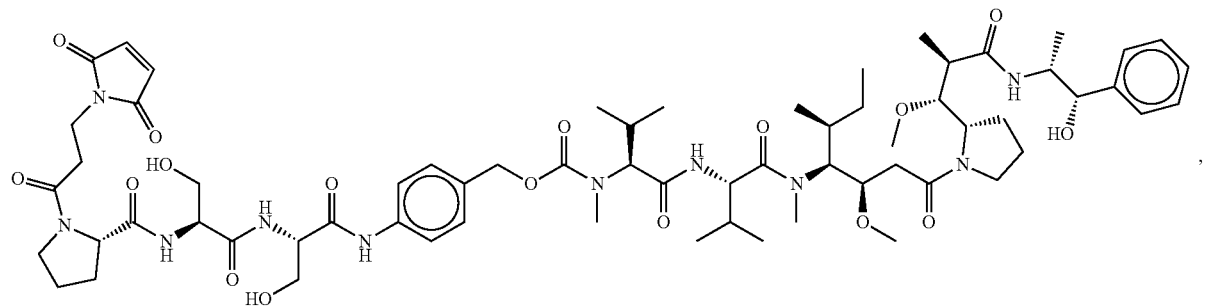
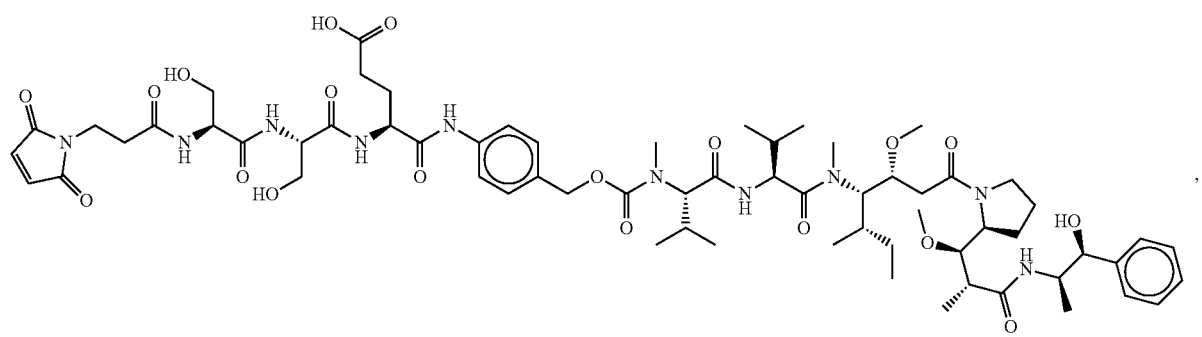
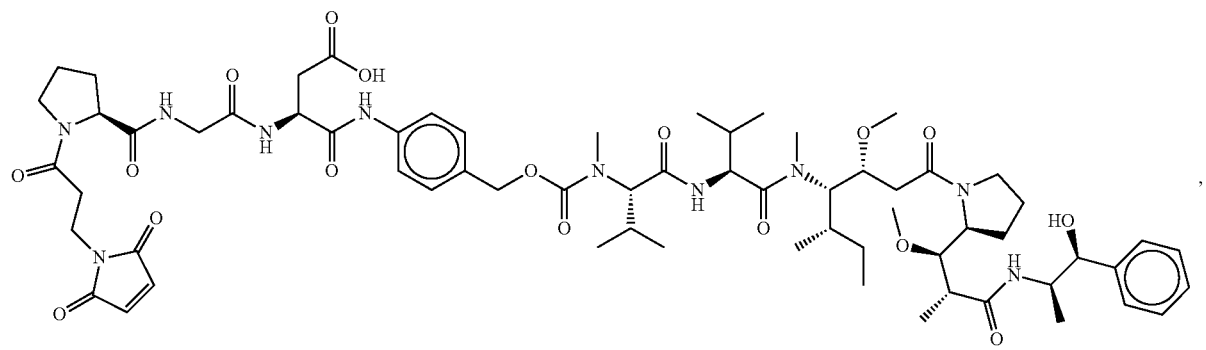
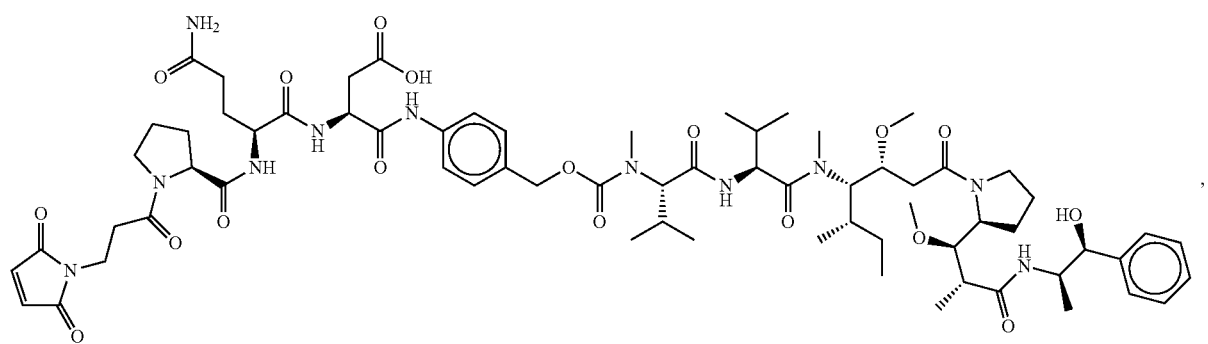

-continued
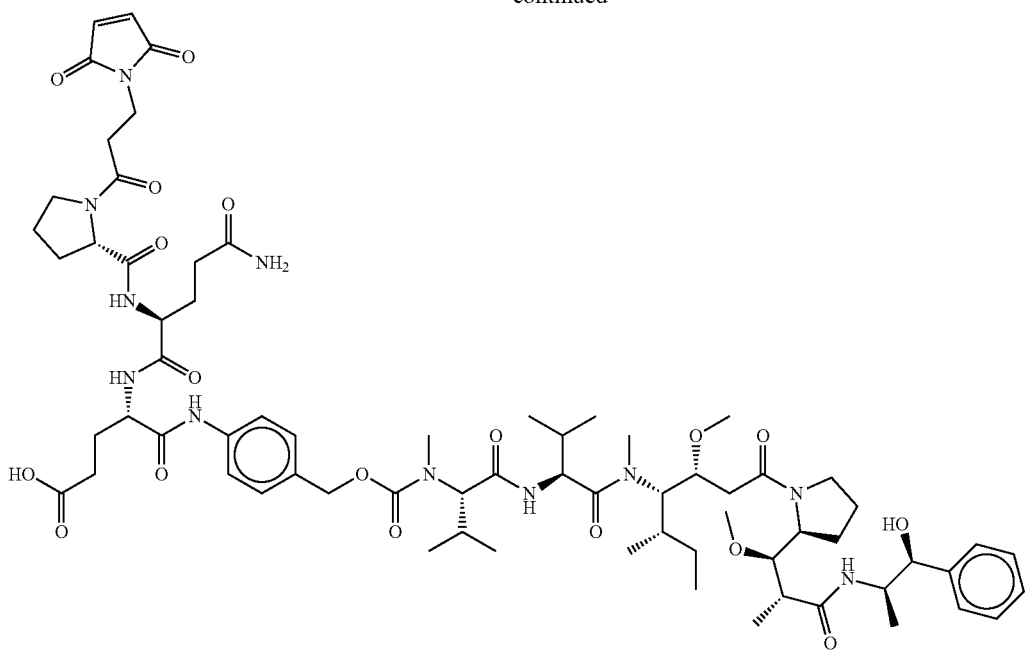
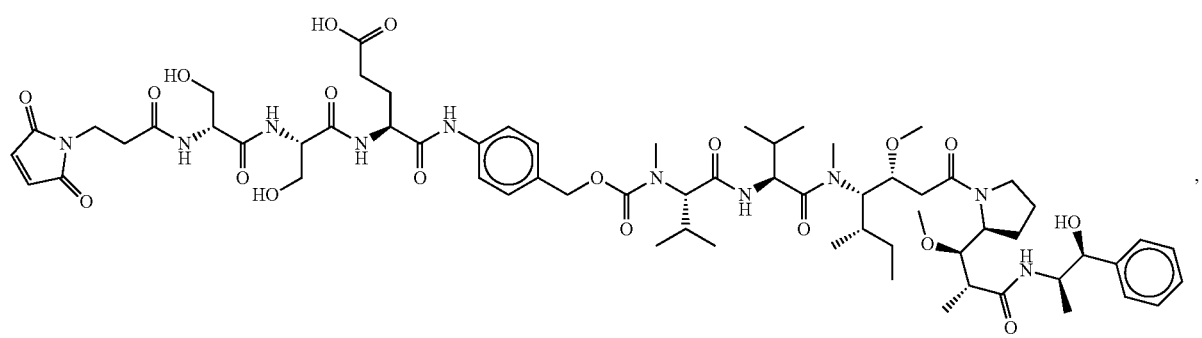
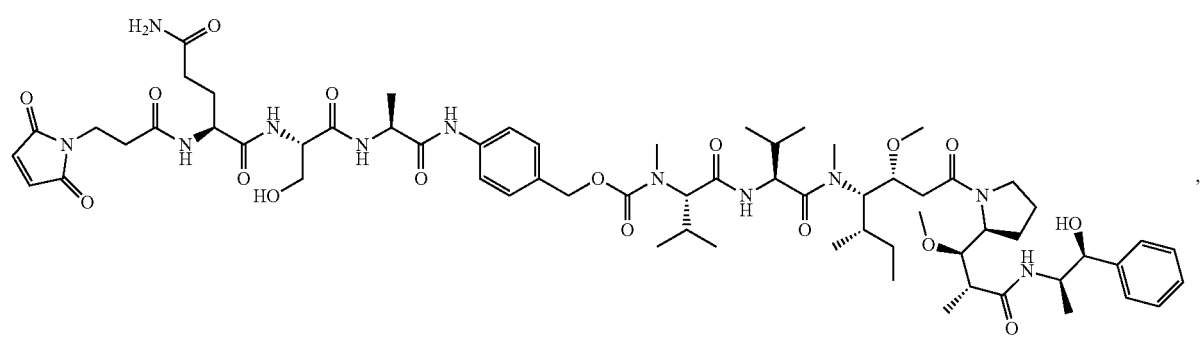
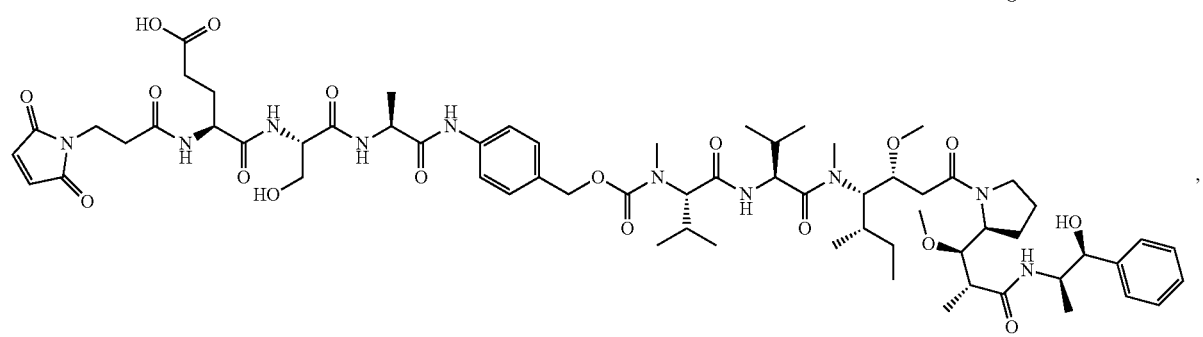

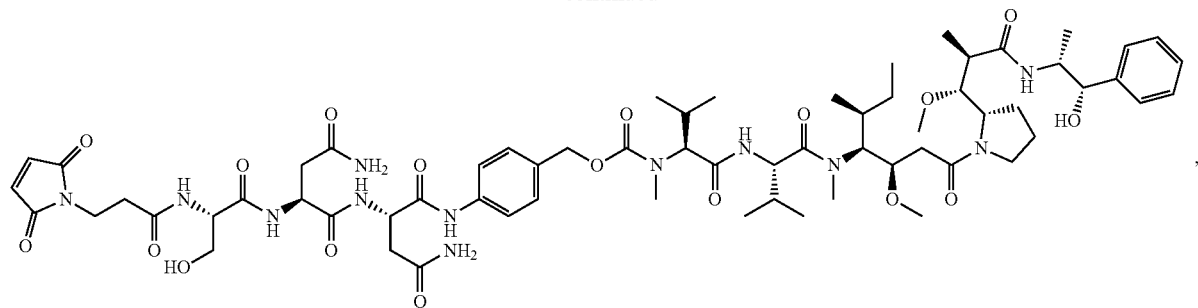
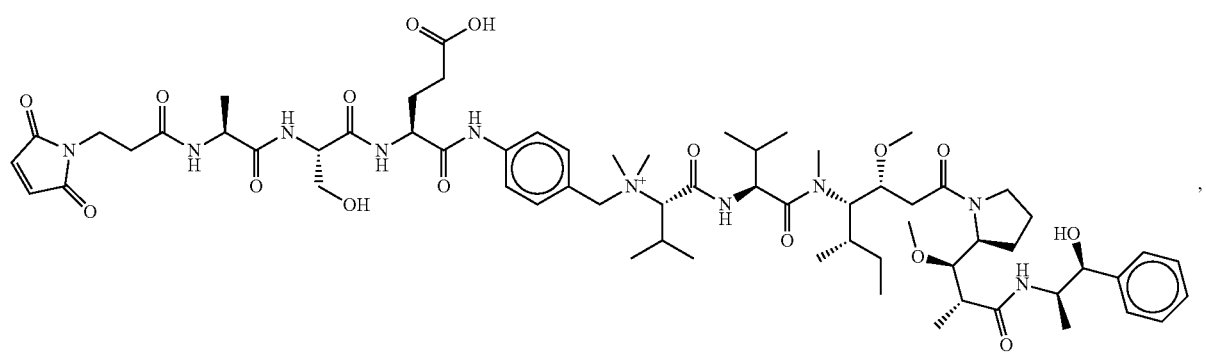
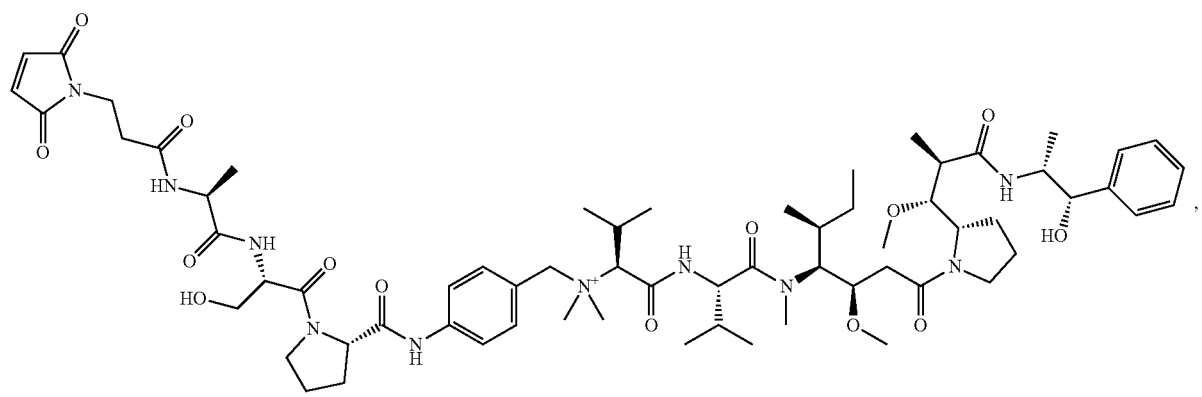
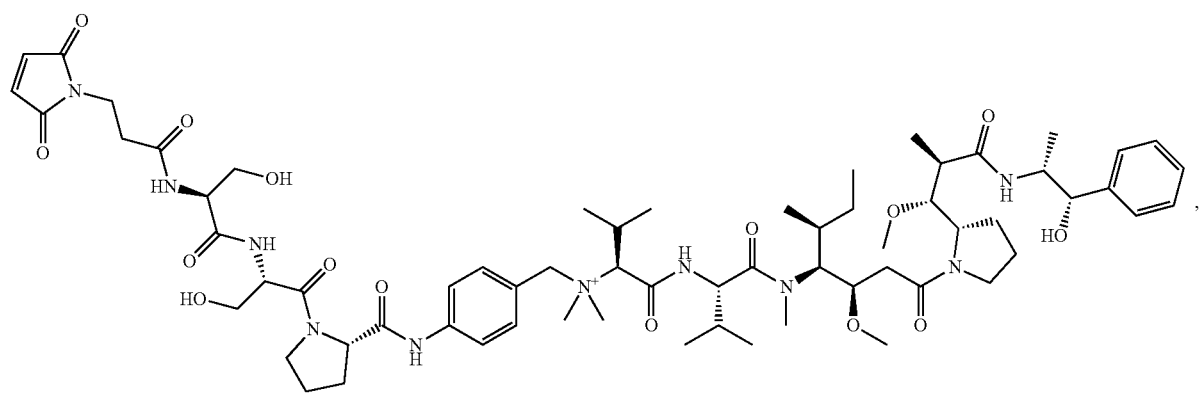

-continued

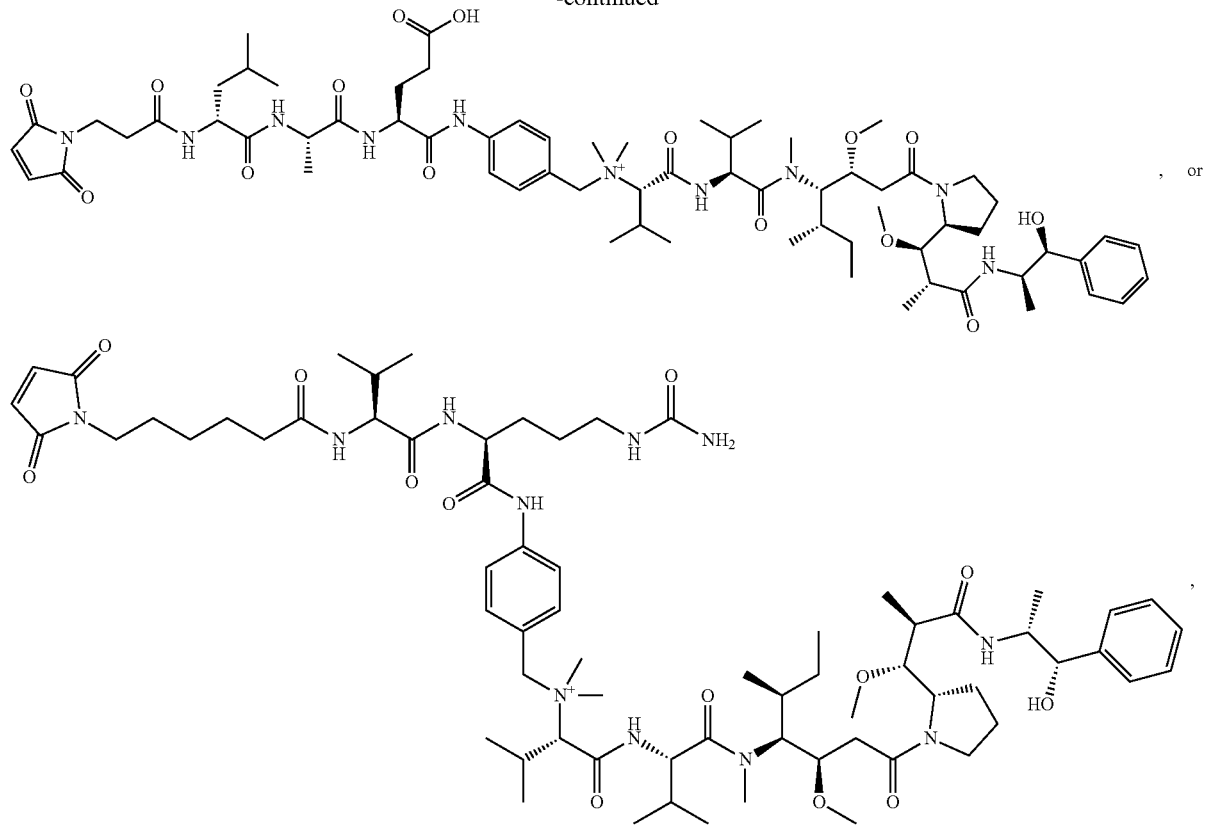

, or or a salt thereof.

In some embodiments, provided is a Drug Linker Precursor compound represented by the structure:

PG-W—Y$_y$-D or a salt thereof, wherein W, Y, subscript y, and D retain their previous meanings, and PG is an amine protecting group or hydrogen. In some embodiments, the amine protecting group is Fmoc.

In some embodiments, Drug Linker Precursor compound represented by the structure:

PG-[P3]-[P2]-[P1]-Y$_y$-D

PG-[P3]-[P2]-[P1]-[P-1]-Y$_y$-D

PG-[P$_n$] . . . [P4]-[P3]-[P2]-[P1]-Y$_y$-D

PG-[P$_n$] . . . [P4]-[P3]-[P2]-[P1]-[P-1]-Y$_y$-D or a salt thereof, wherein P-1, P1, P2, P3 . . . P$_n$, Y, subscript y, and D retain their previous meanings, and PG is an amine protecting group or hydrogen.

In some embodiments, Drug Linker Precursor compound represented by the structure:

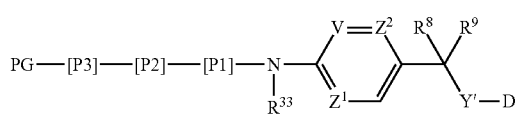

or a salt thereof, wherein P1, P2, P3, $R^8$, $R^9$, $R^{33}$, V, Y', $Z^1$, $Z^2$, and D retain their previous meanings, and PG is an amine protecting group or hydrogen.

In any of the Drug Linker compounds described herein, the $L_B'$-$A_a$-$B_b$-$A'_a$- portion can be replaced by PG to form a Drug Linker Precursor compound represented by the structure:

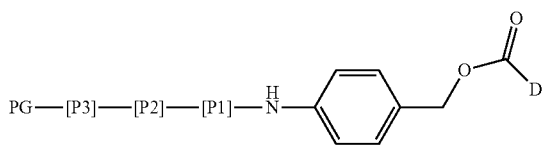

or a salt thereof, wherein P1, P2, P3, and D retain their previous meanings, and PG is an amine protecting group or hydrogen.

It is understood that a Drug Linker Precursor can be further modified with a stretcher unit for attachment to a ligand such as an antibody. In some embodiments, the Drug Linker Precursor may be further reacted with a stretcher unit suitable for attachment to a cysteine residue of an antibody. Suitable stretcher units for attachment to a cysteine residue of an antibody are described herein, including stretcher units comprising an maleimide moiety. In some embodiments, the Drug Linker Precursor may be further reacted with a stretcher unit suitable for attachment to a lysine residue of an antibody. Suitable stretcher units for attachment to a lysine residue of an antibody are described herein, including stretcher units comprising an NHS ester moiety. In some embodiments, the Drug Linker Precursor is an intermediate in the synthesis of Drug Linker compounds.

In any of the embodiments described herein for W, P-1, P1, P2, P3 . . . $P_n$, Y, subscript y, $R^8$, $R^9$, $R^{33}$, V, Y', $Z^1$, $Z^2$, and D with respect to, for example, Ligand Drug Conjugate (LDC) compounds, Drug Linker compounds, drug linker moieties, Peptide Cleavable Units, Spacer Units, and Drug Units, the embodiments are also applicable for Drug Linker Precursor compounds described herein.

In some embodiments, the Drug Linker Precursor compound is represented by:

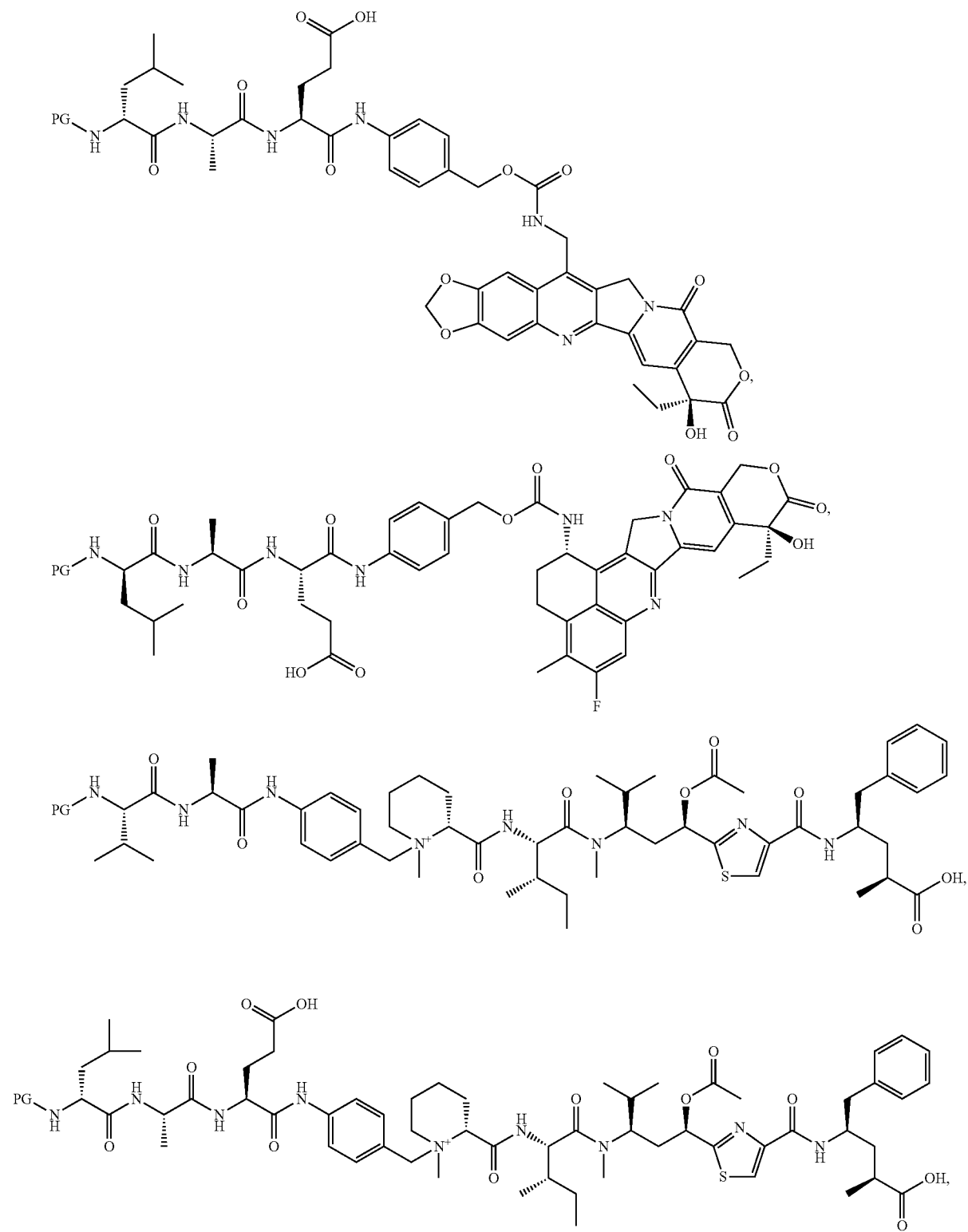

-continued
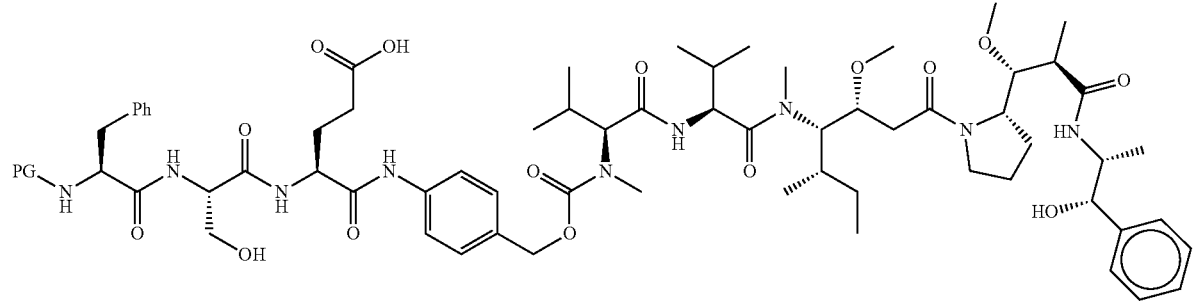
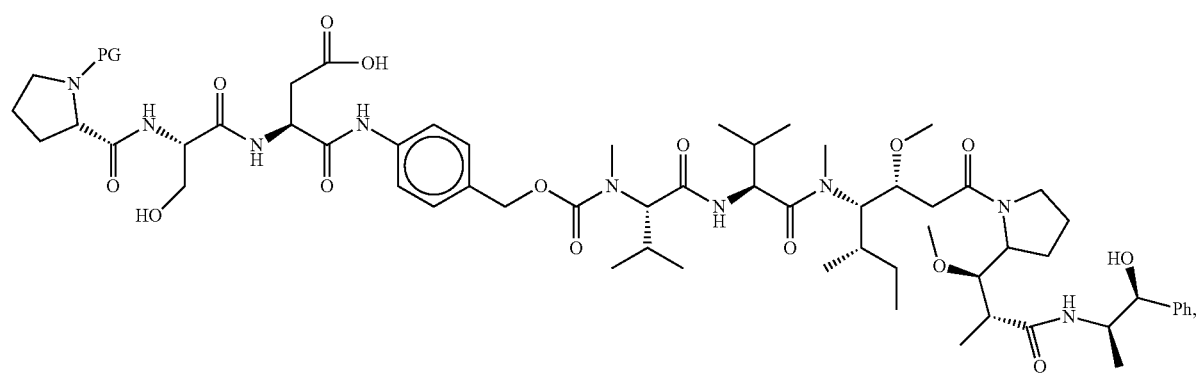
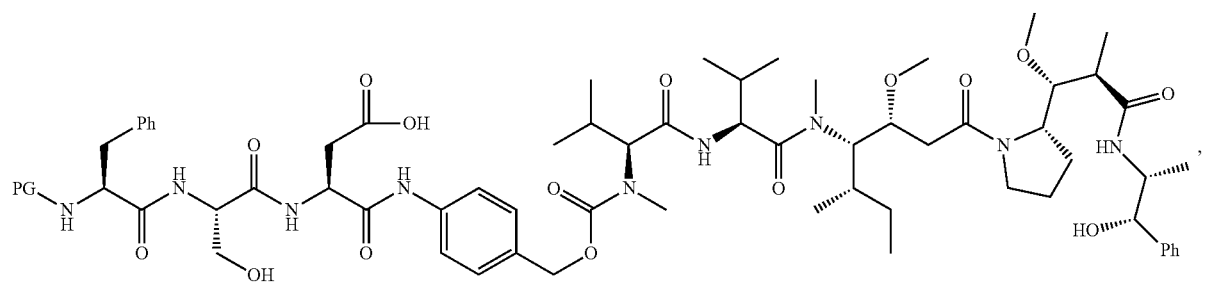
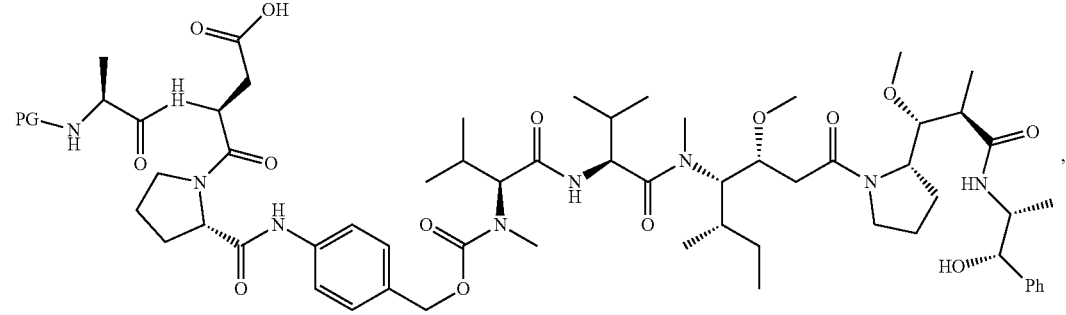
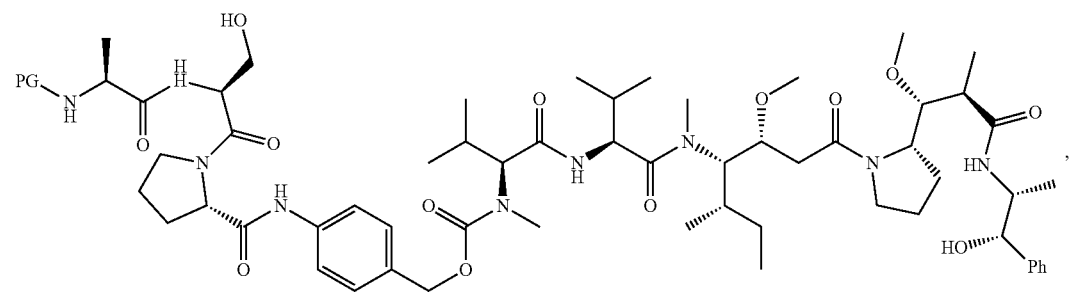

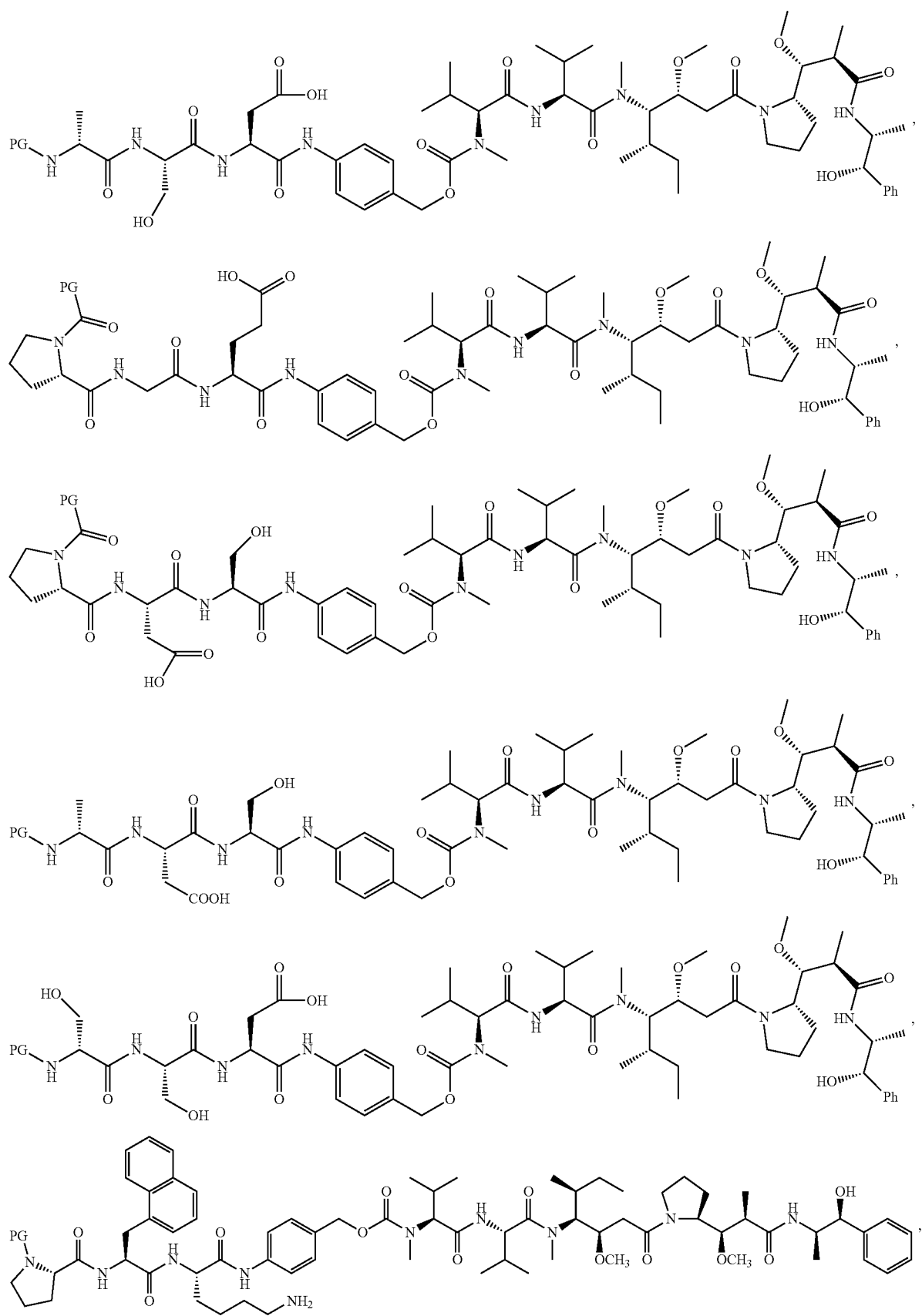

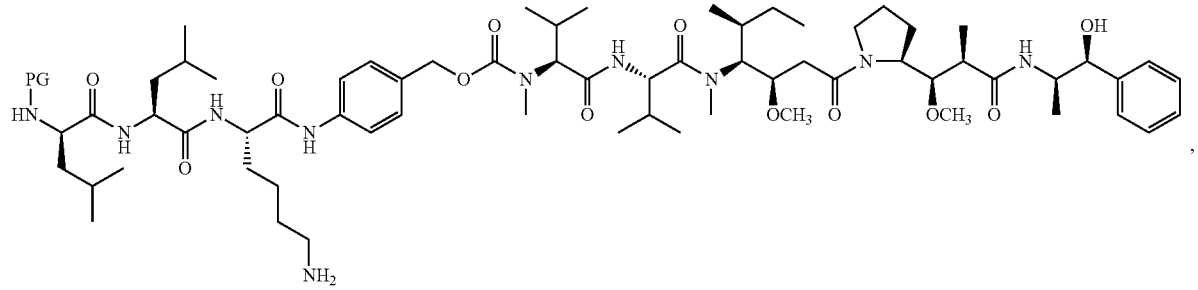
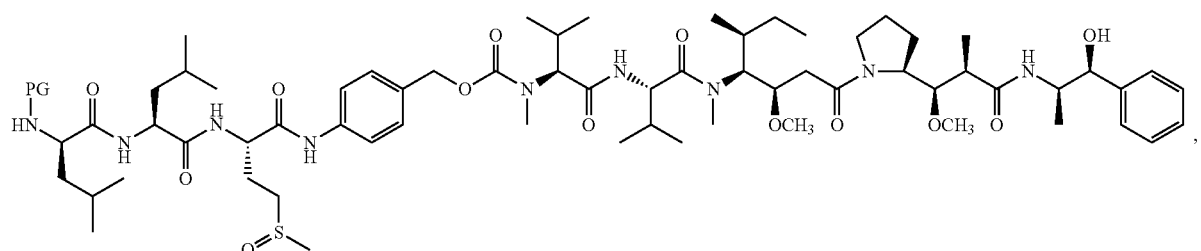
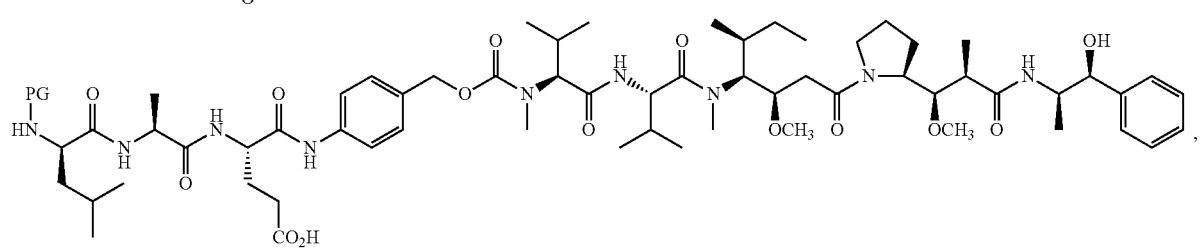
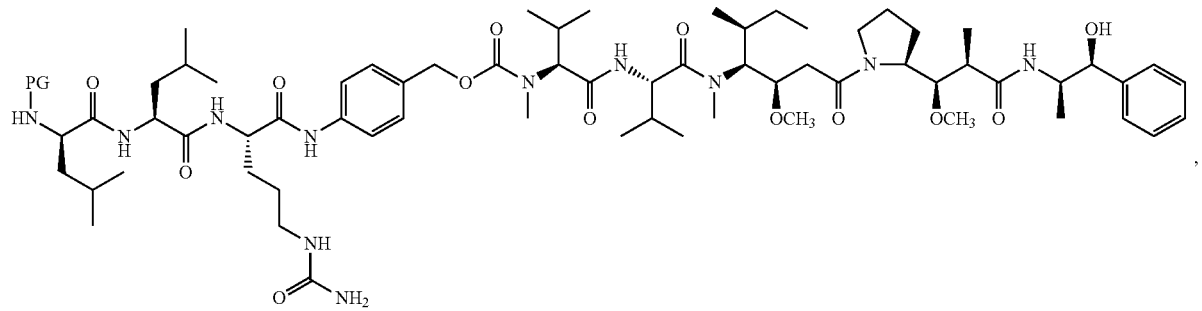
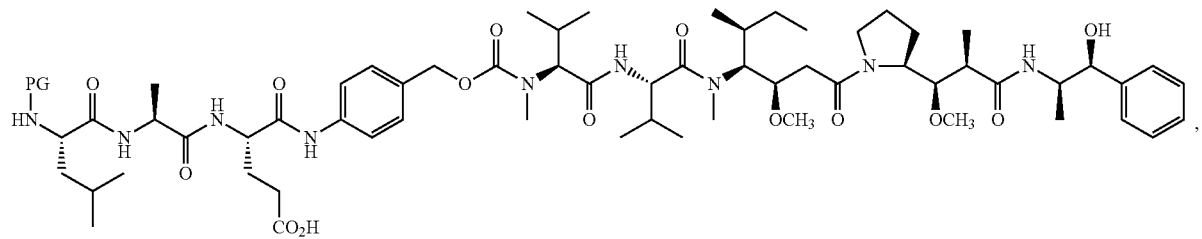
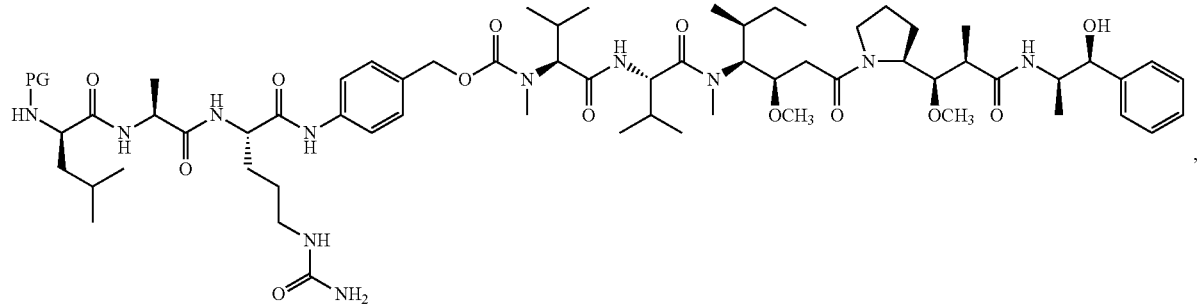

295
-continued
296
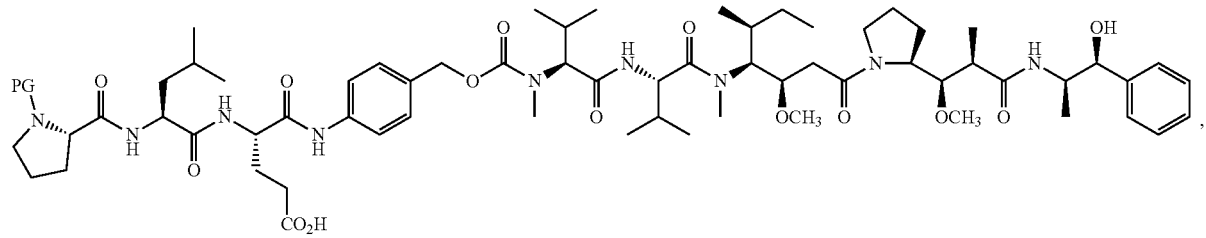
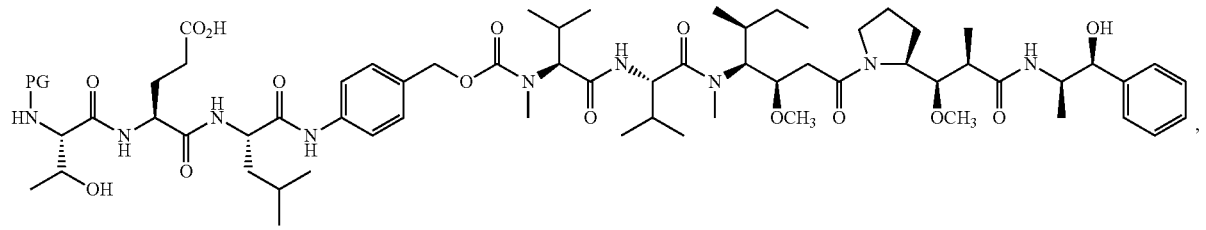
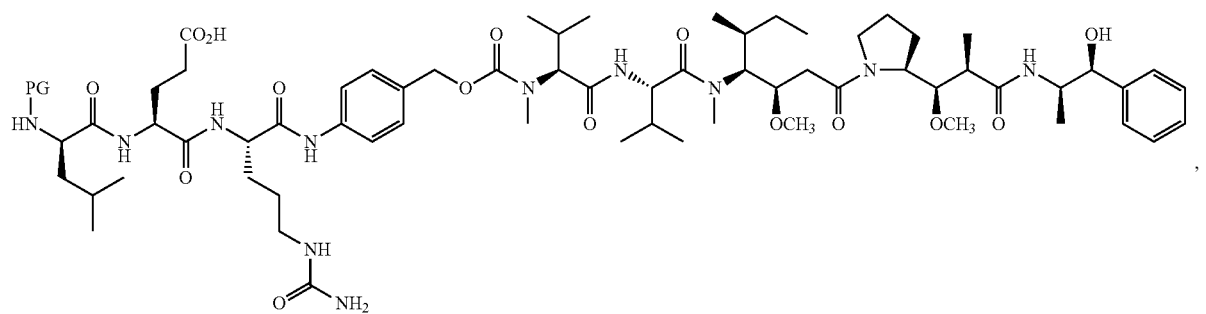
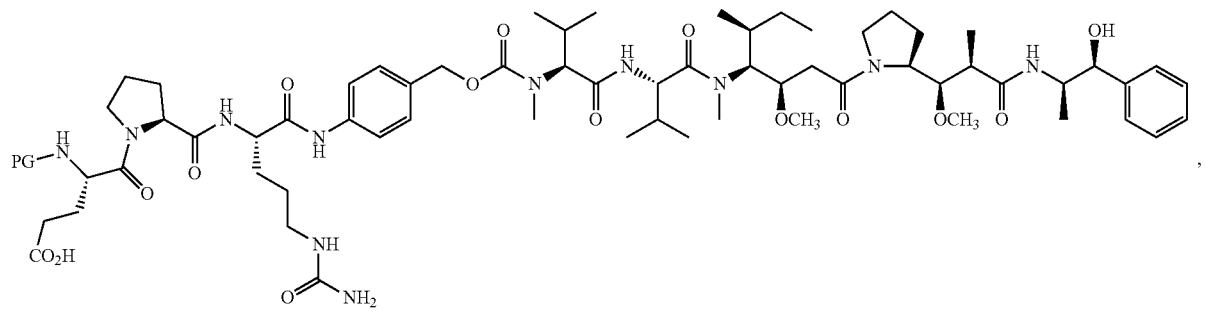
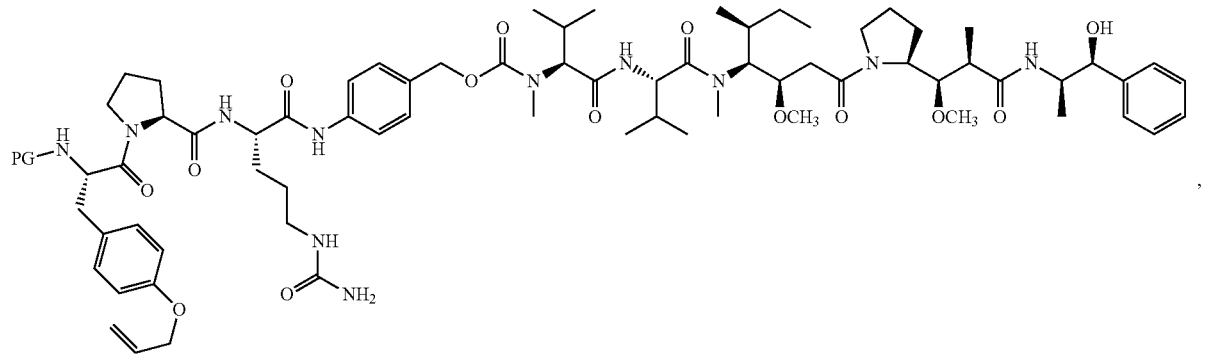

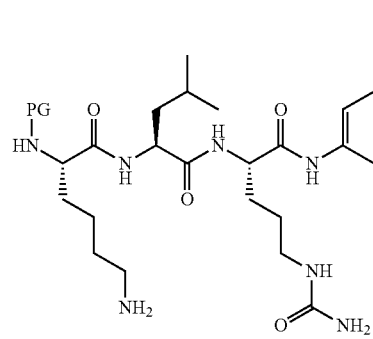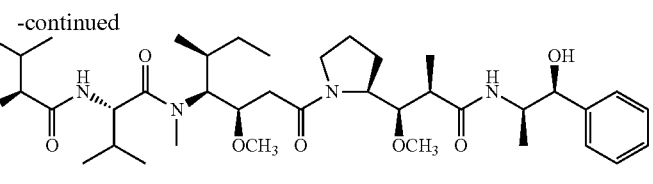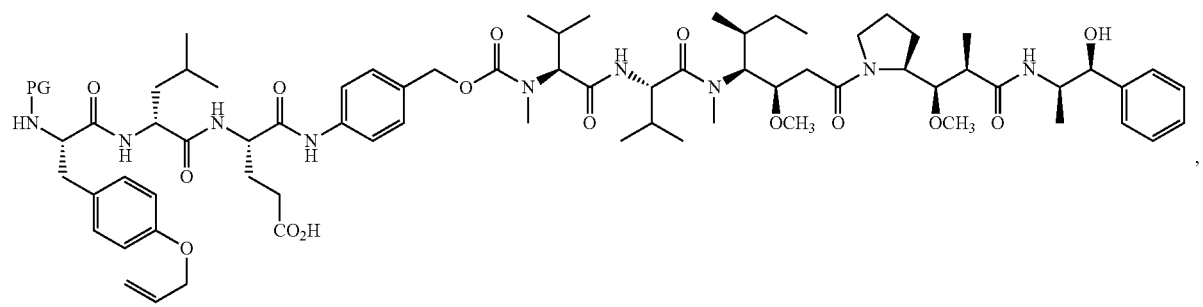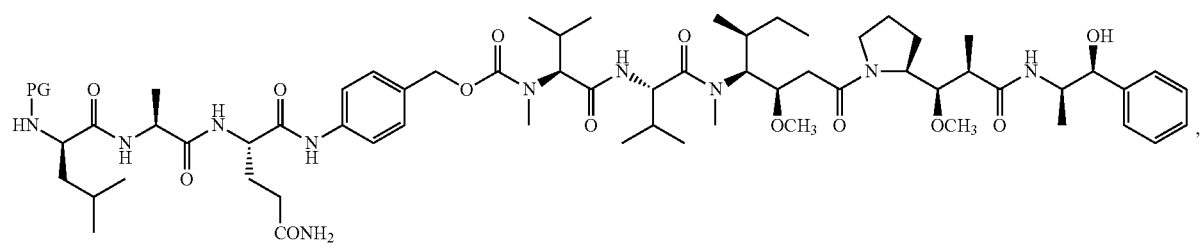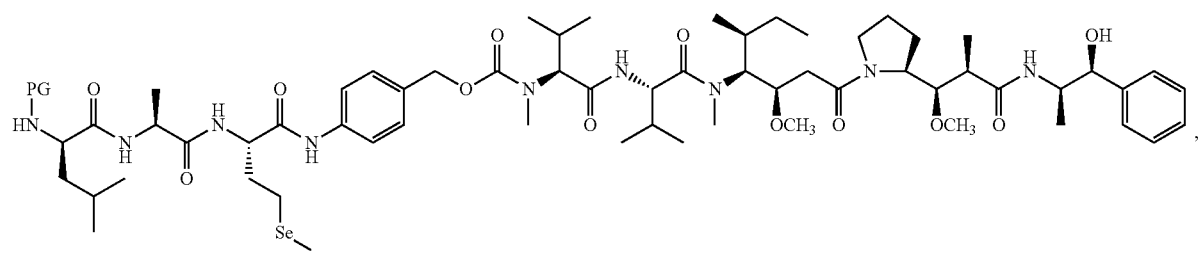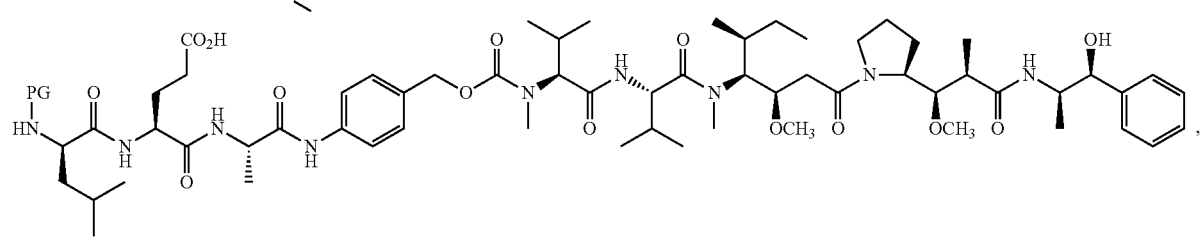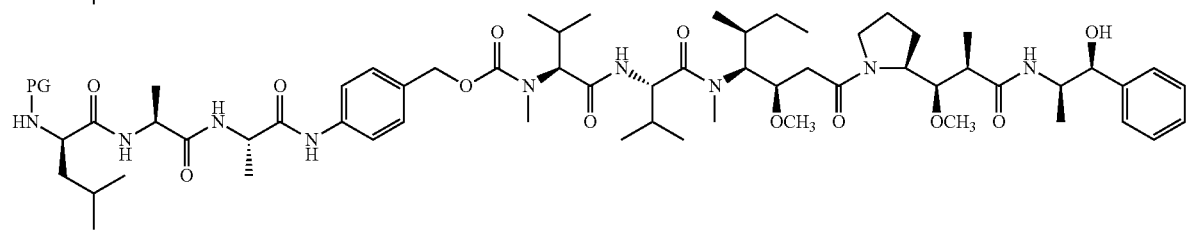

-continued
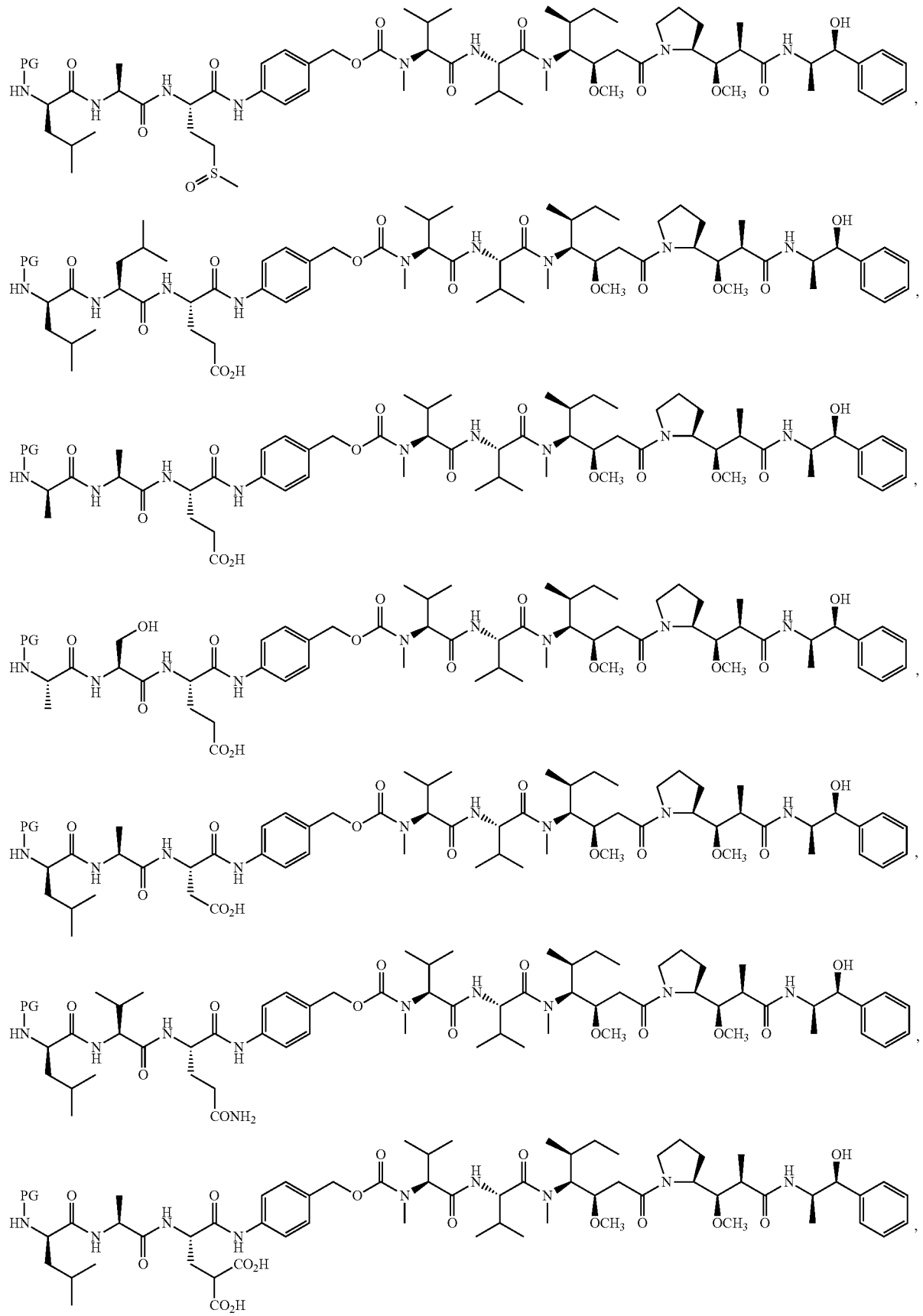

-continued
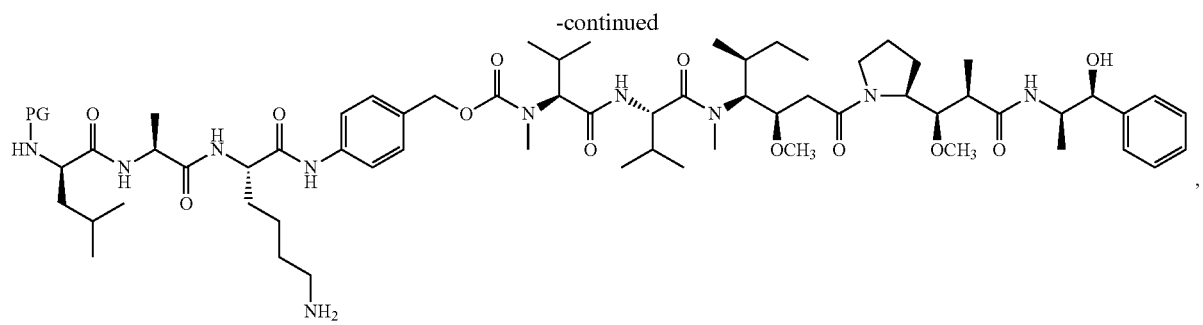
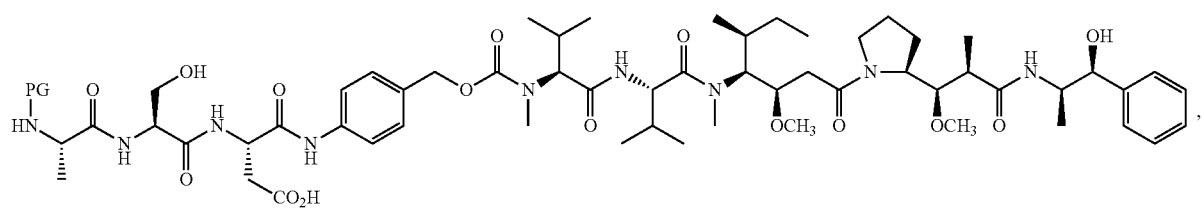
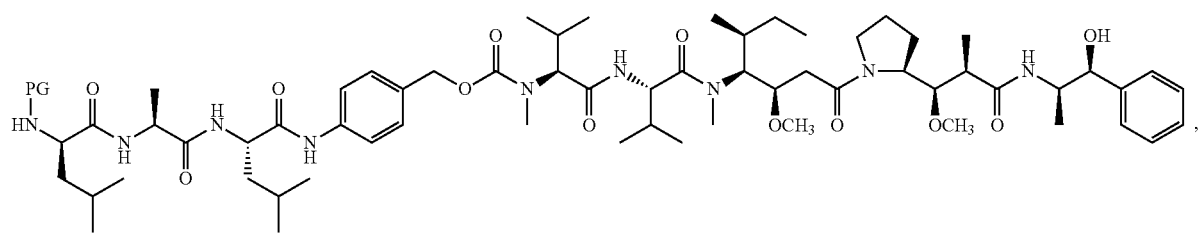
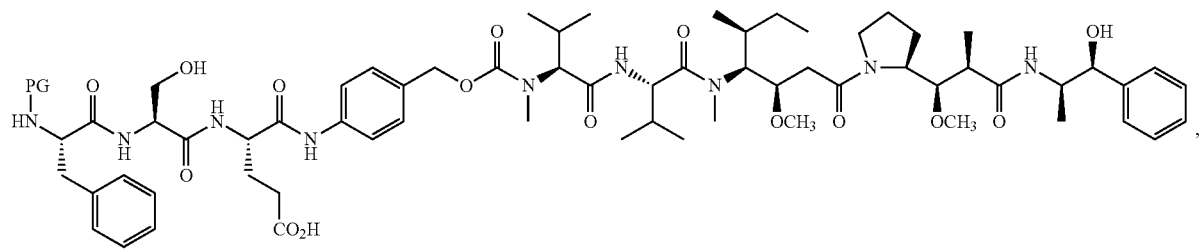
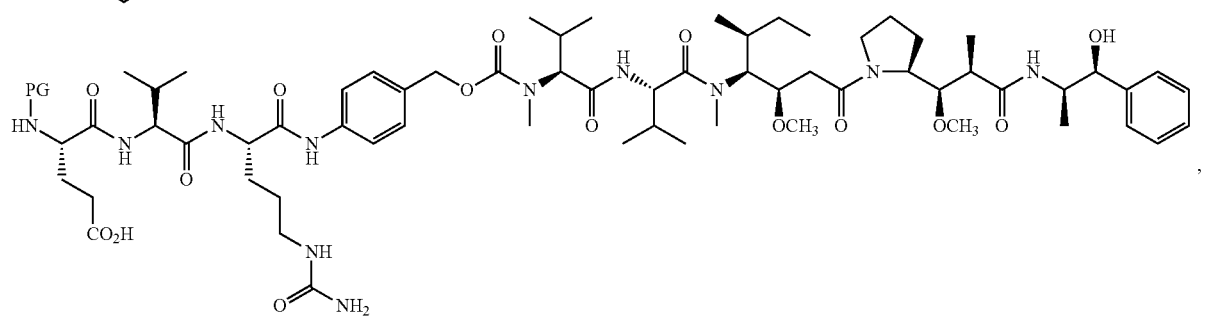
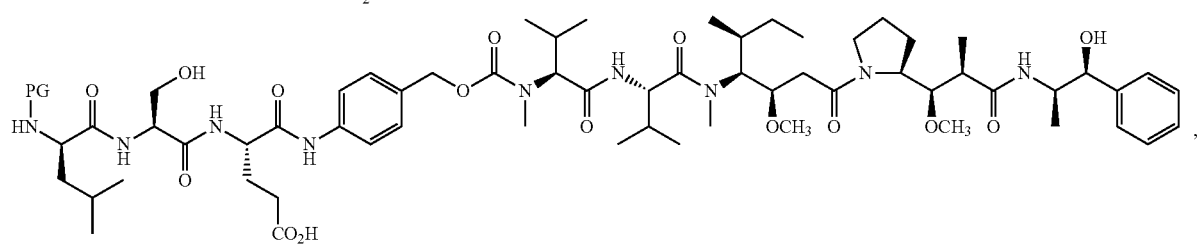

-continued
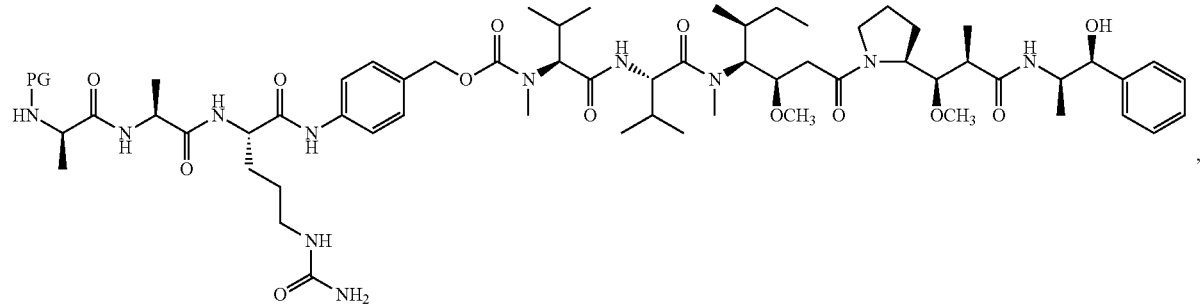
,
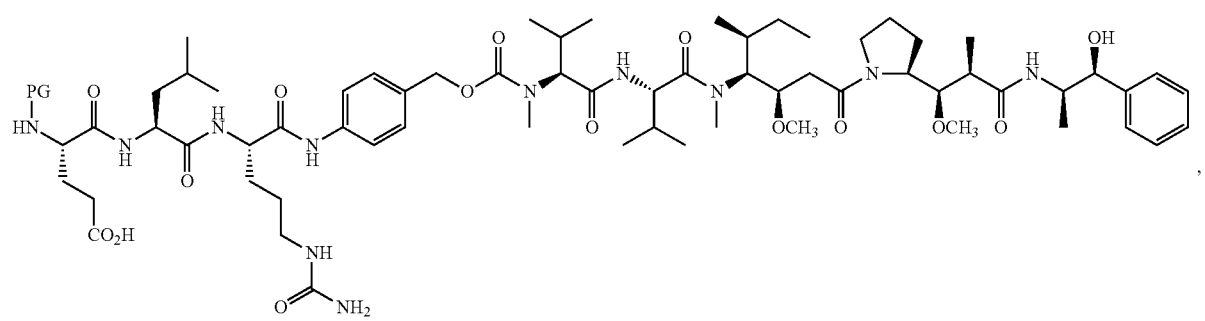
,
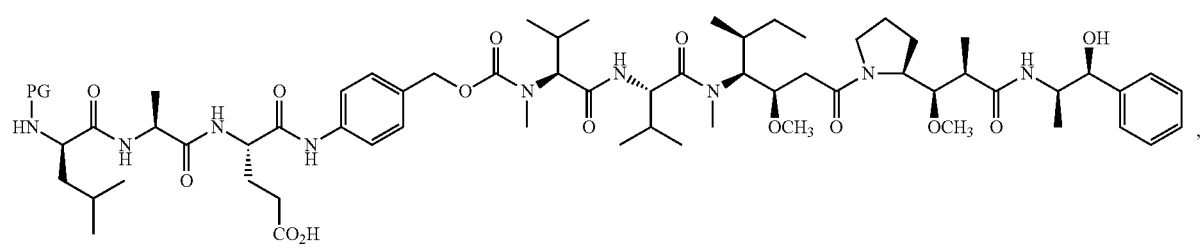
,
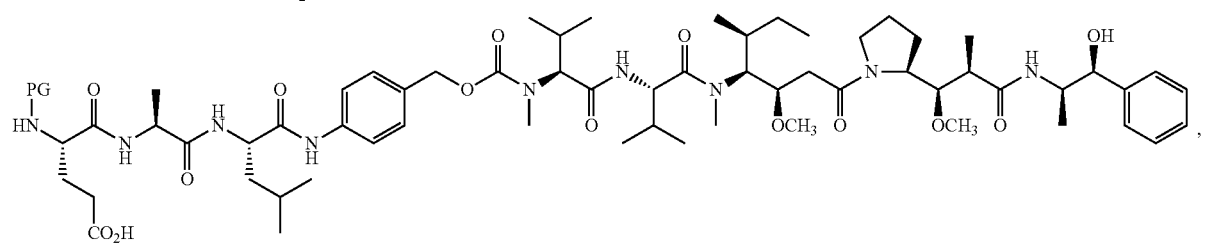
,
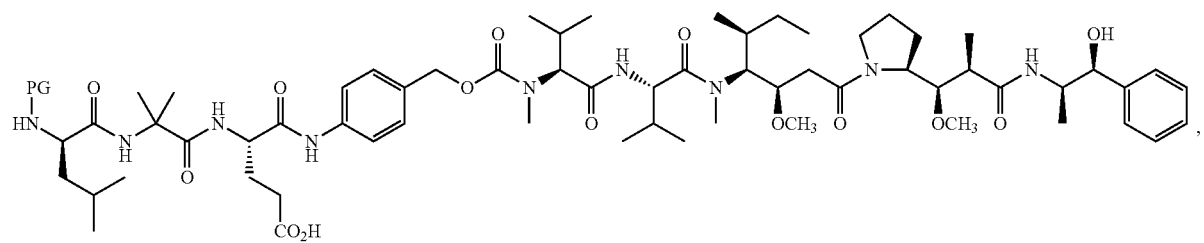
,
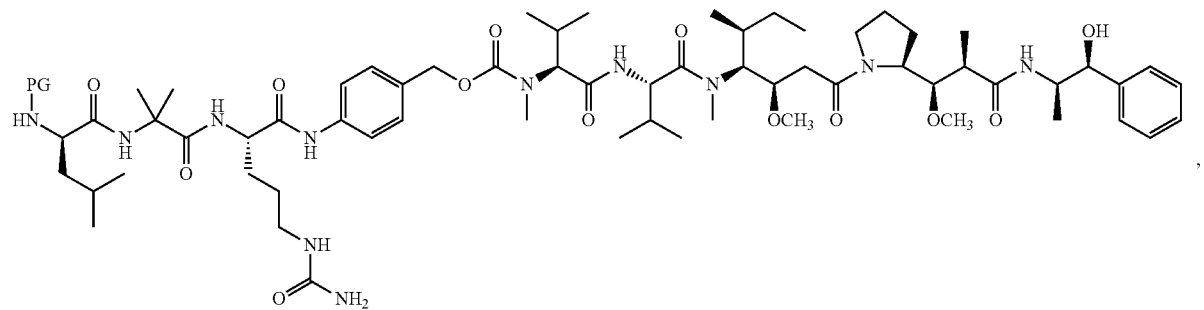
,

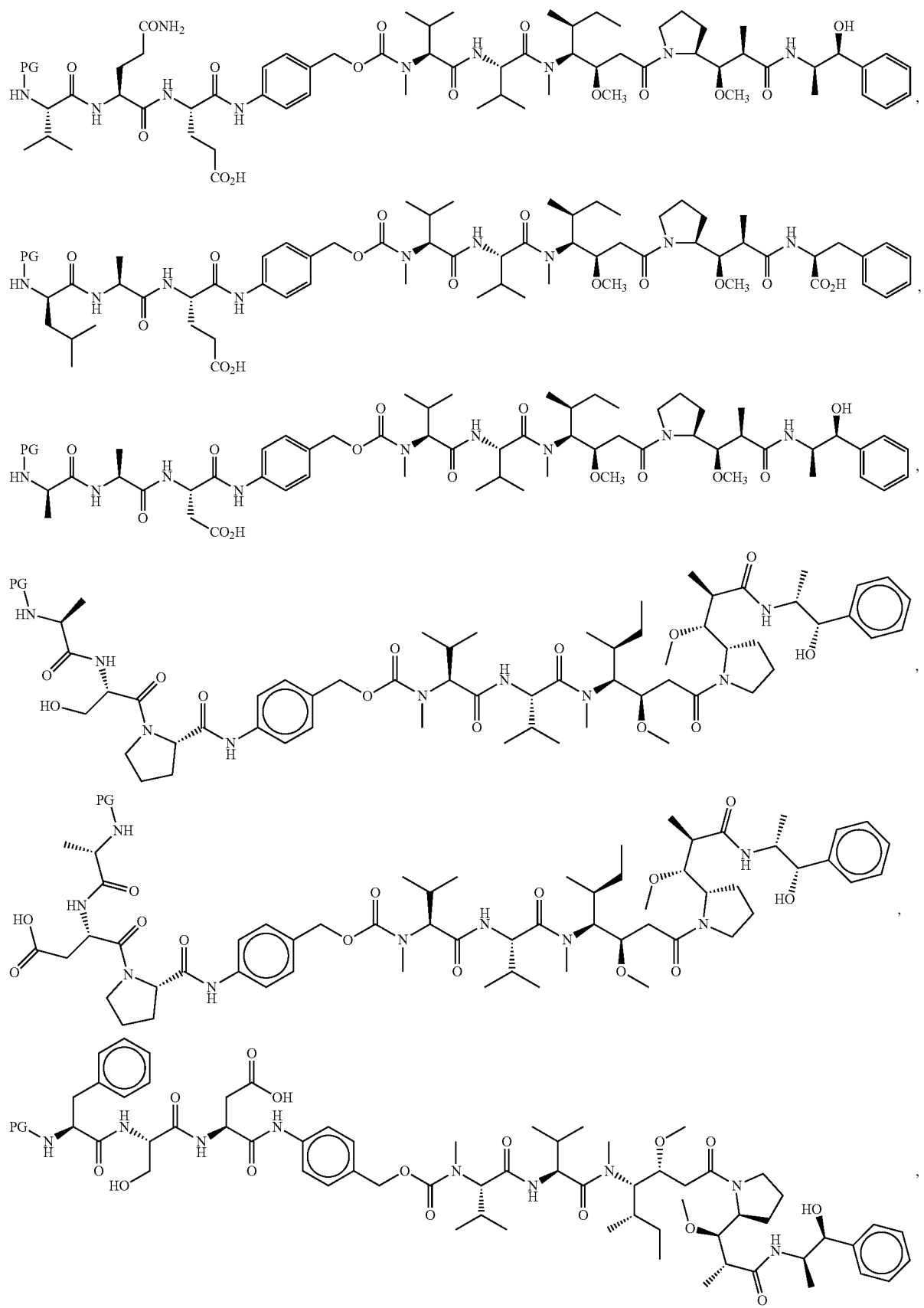

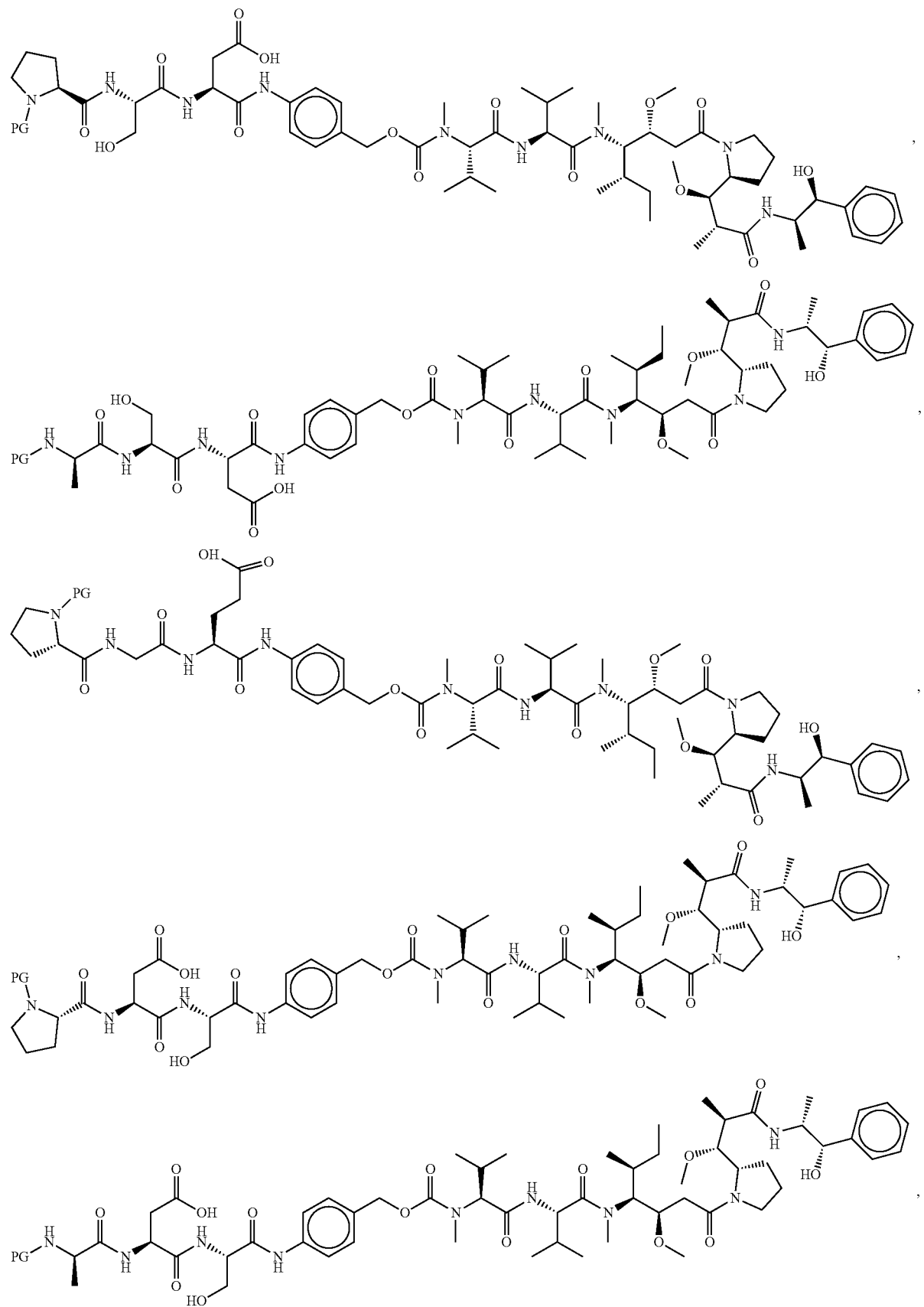

-continued
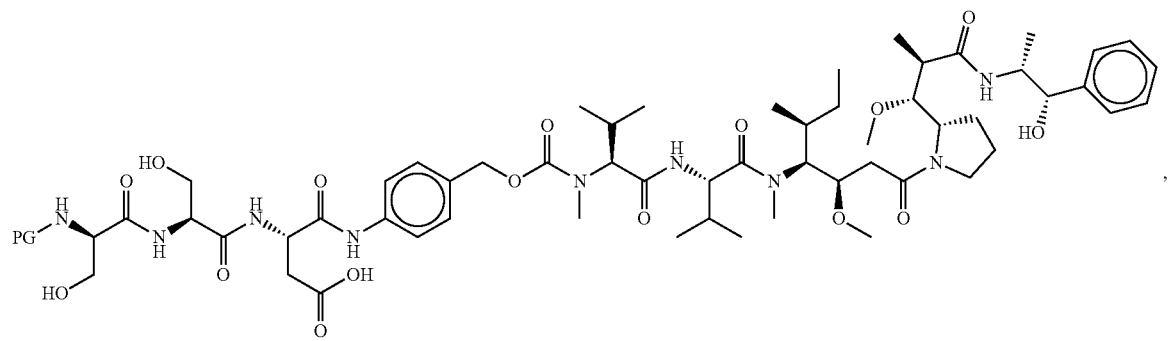
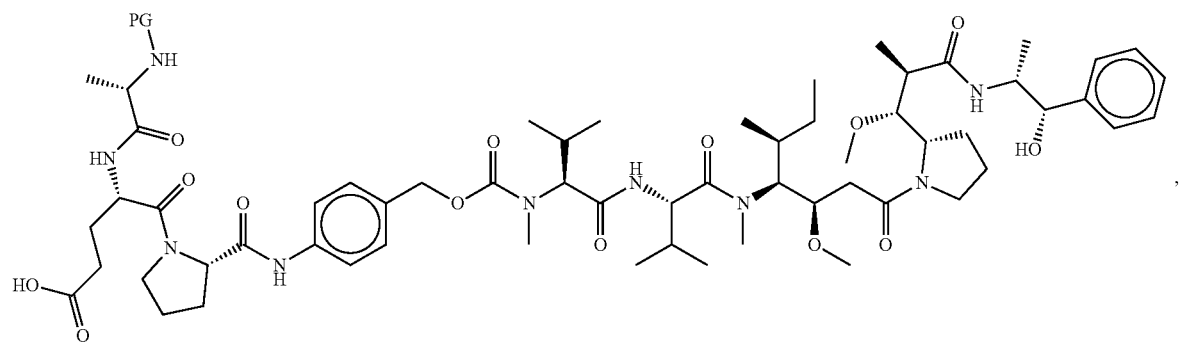
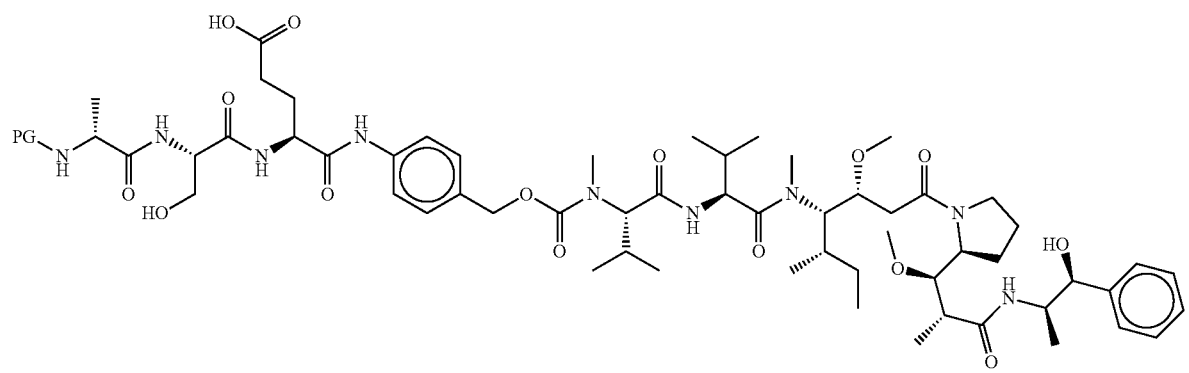
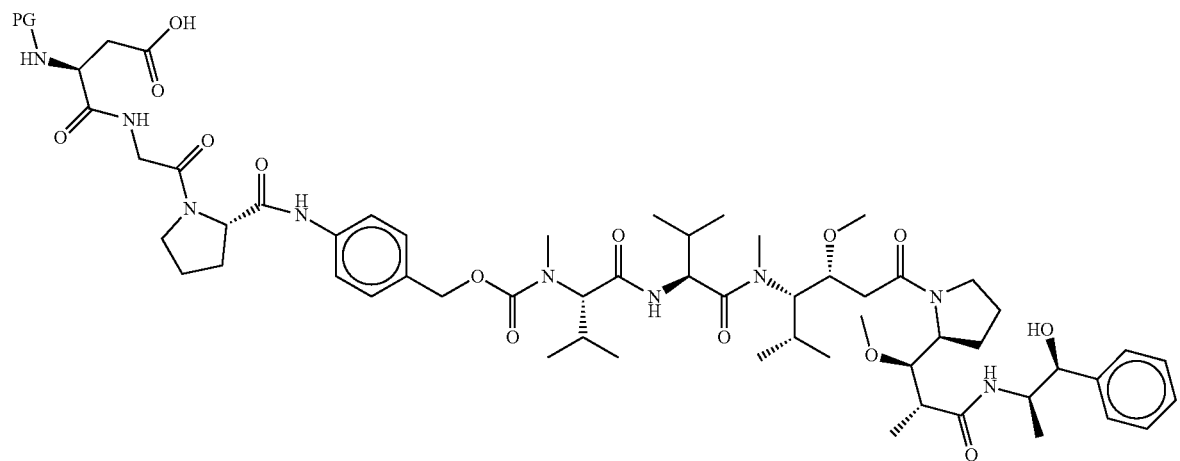

-continued
311
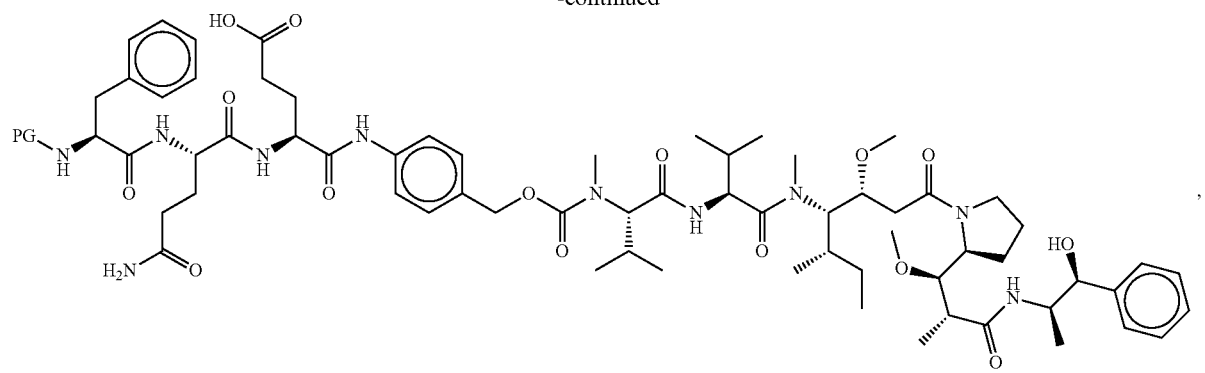
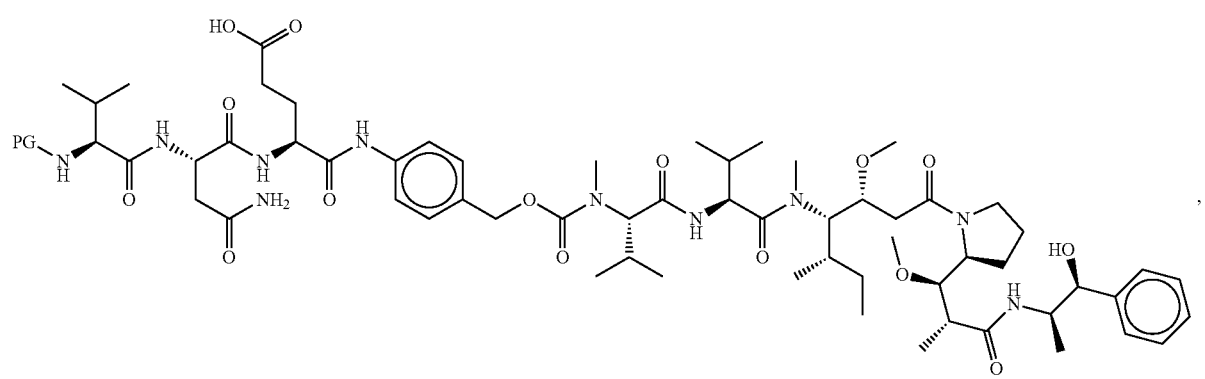
312
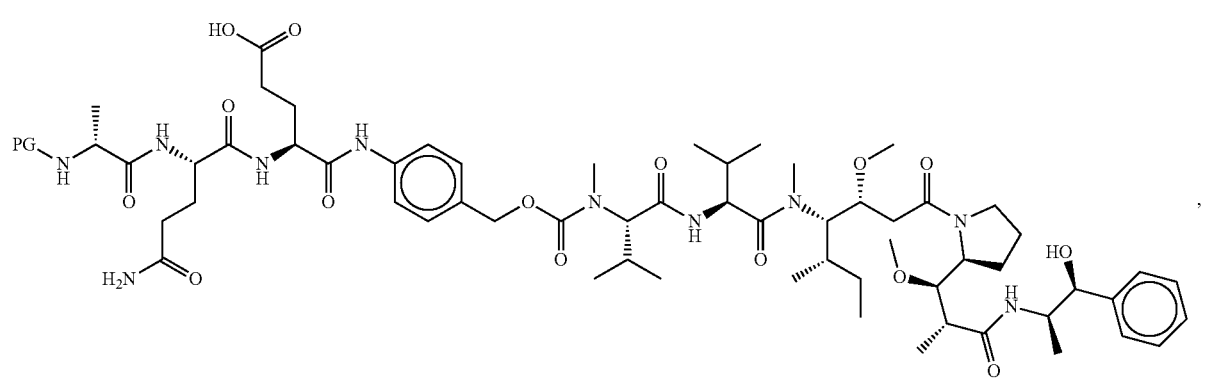
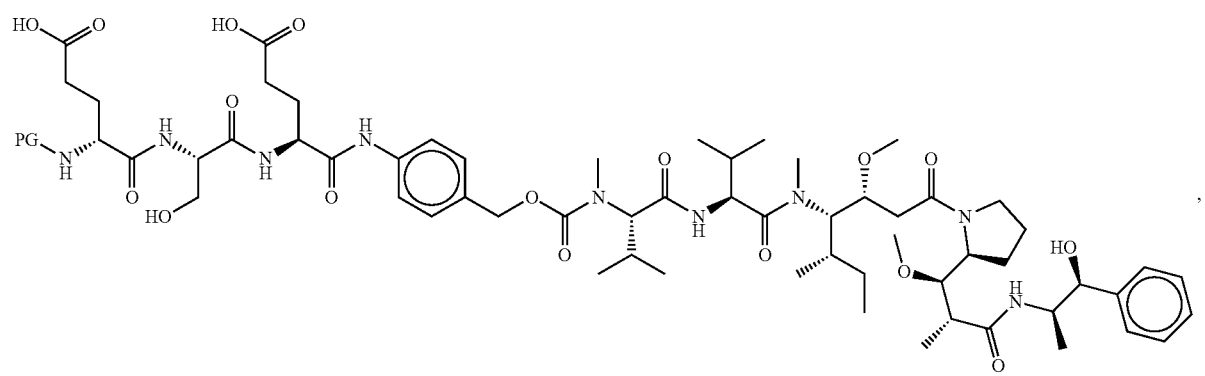

-continued
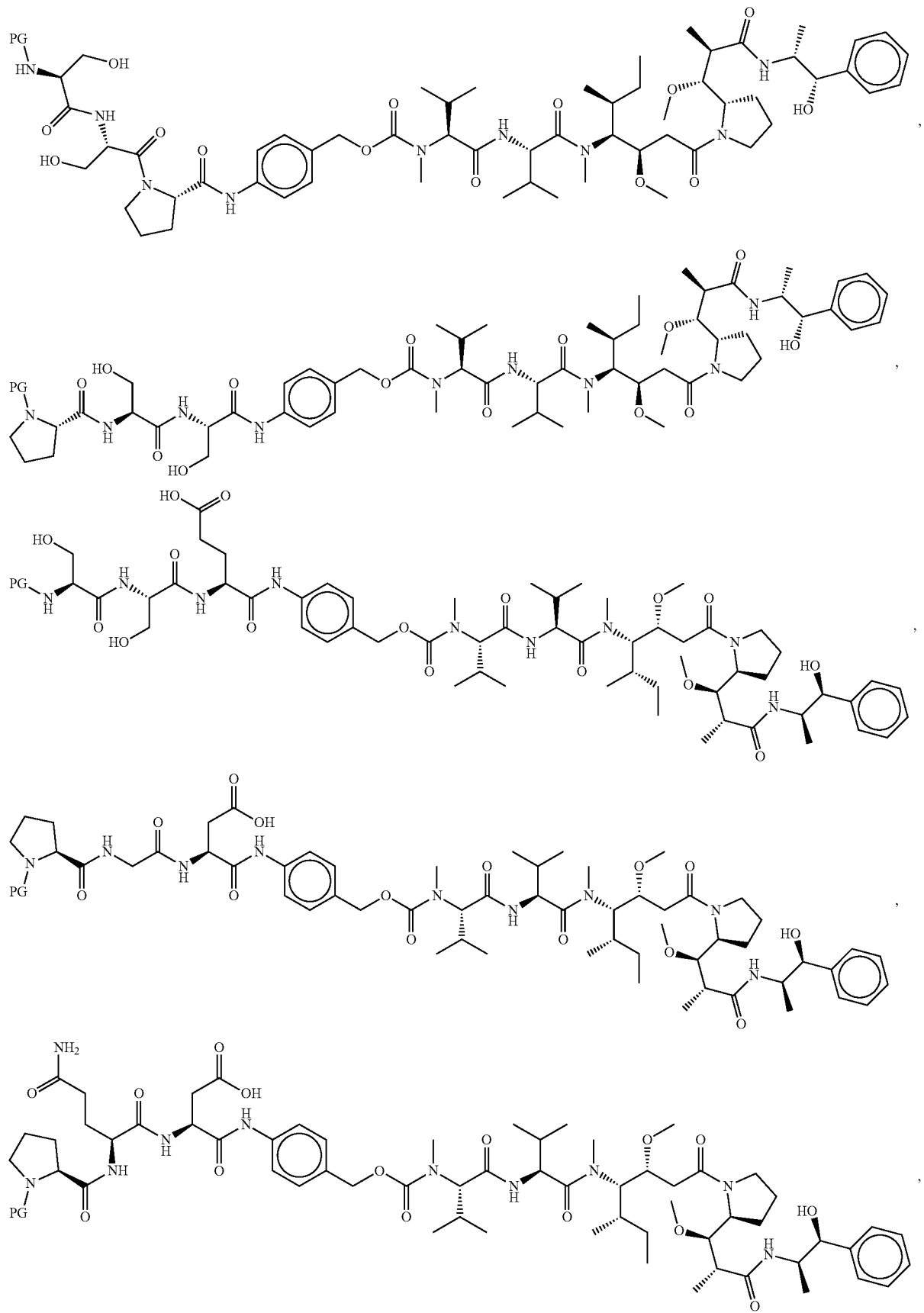

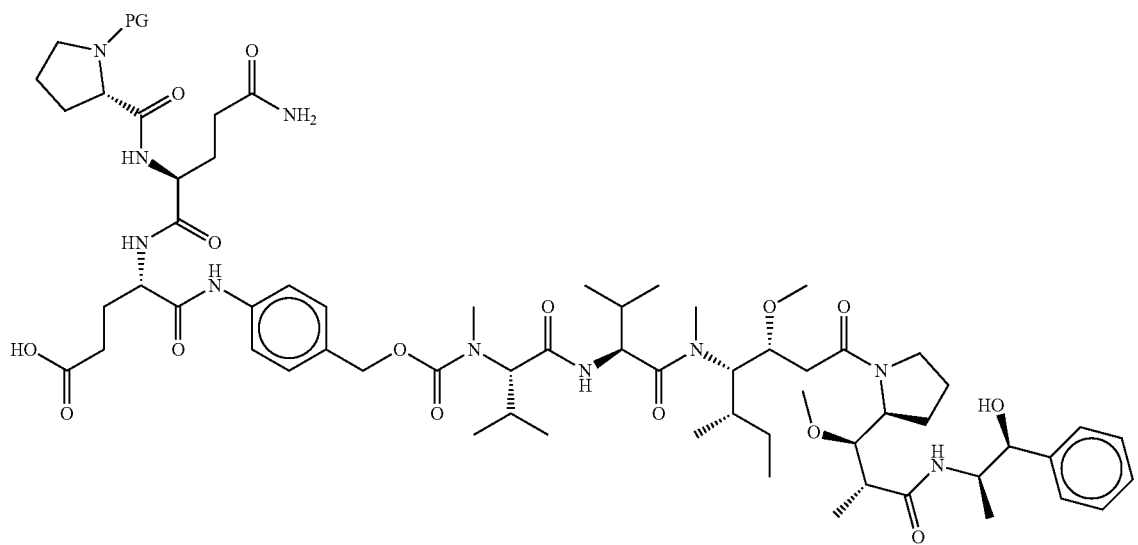
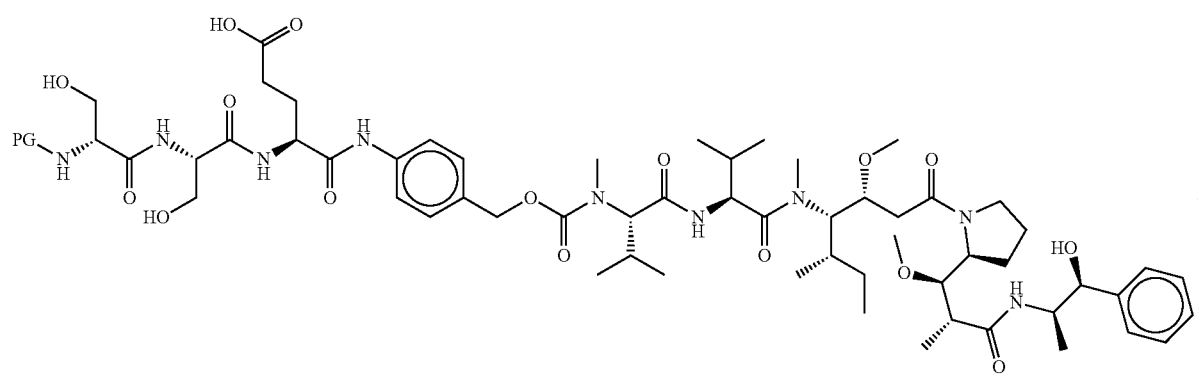
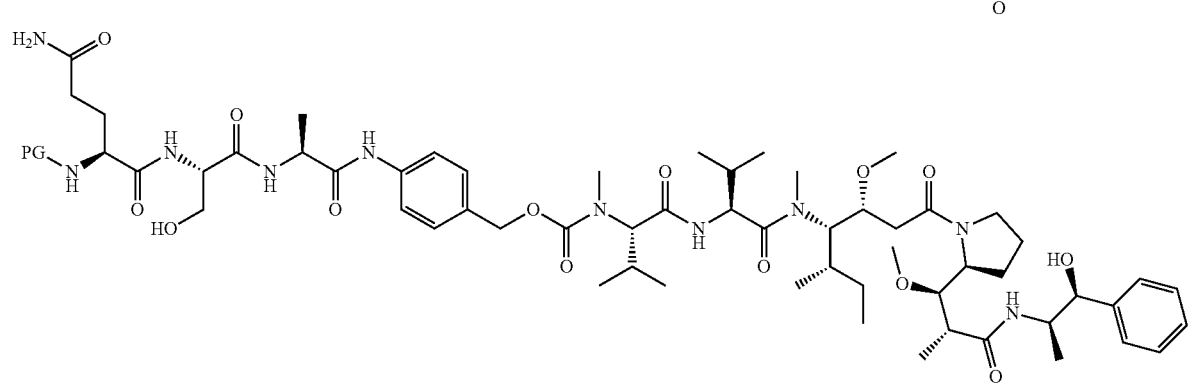
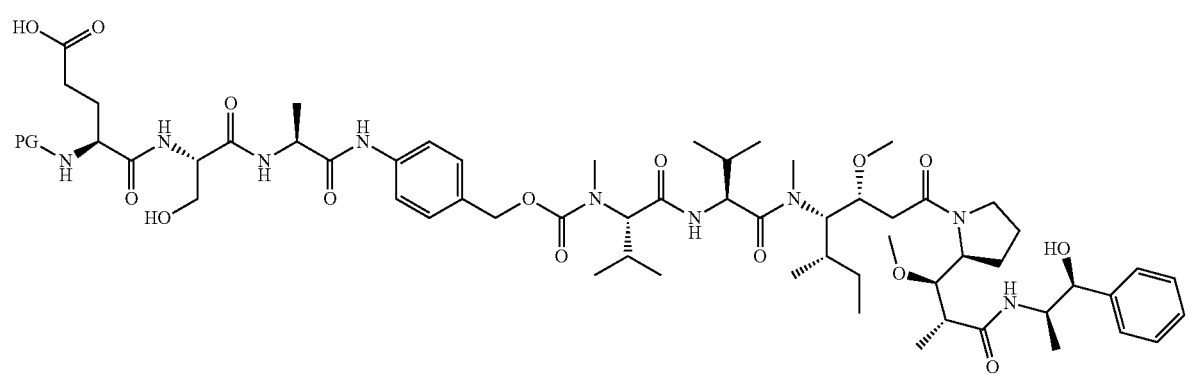

-continued
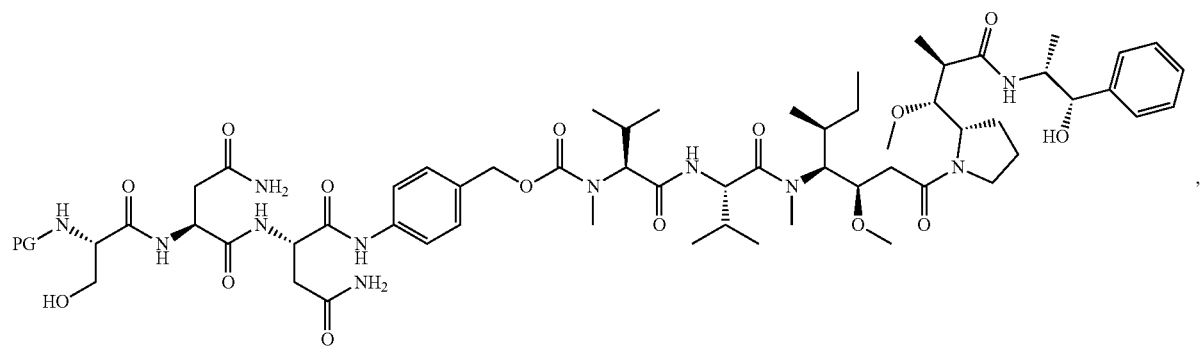
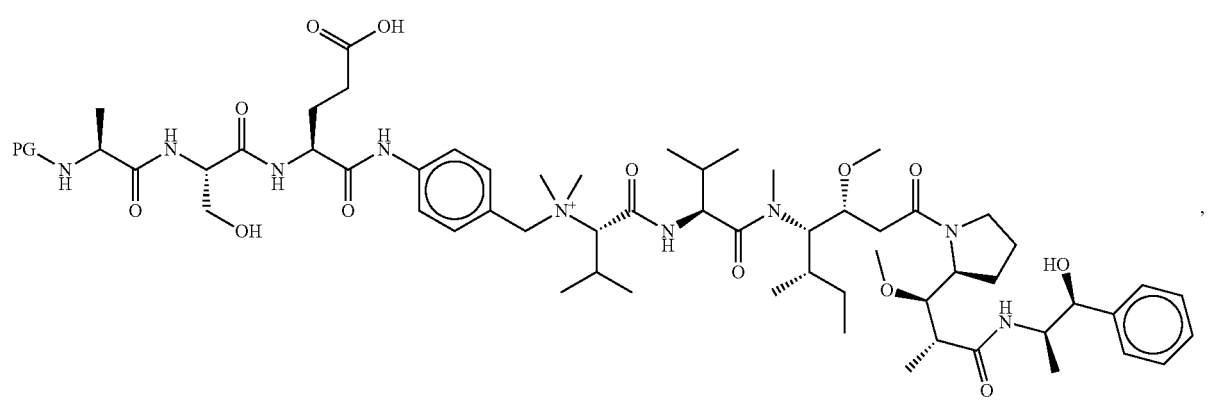
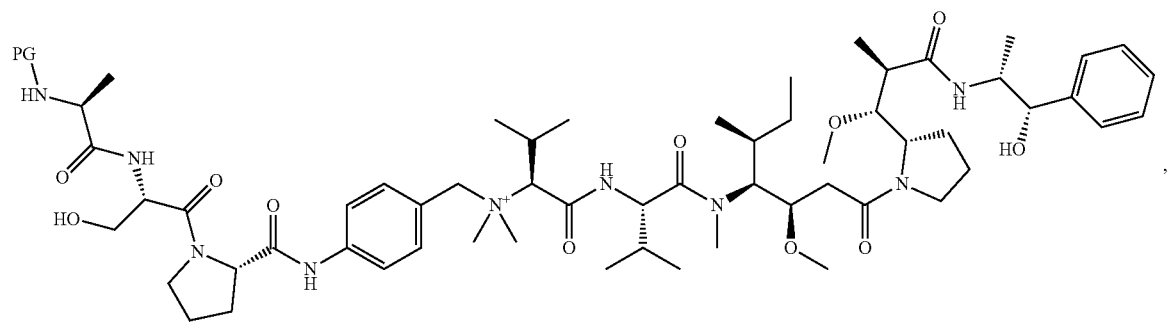
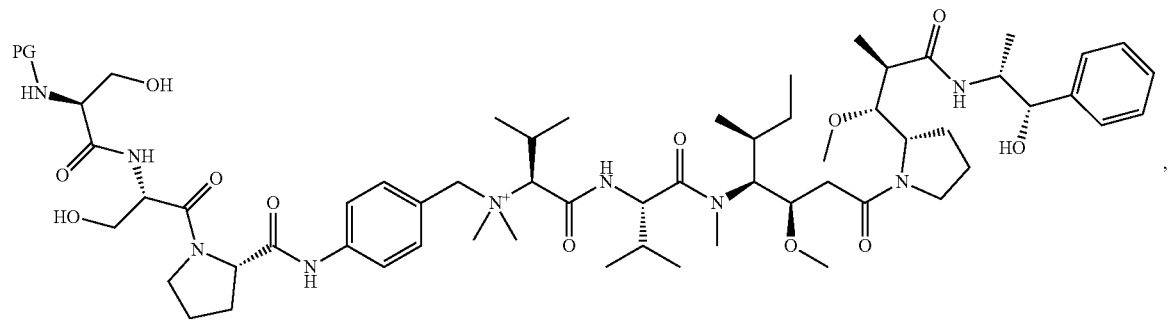

-continued

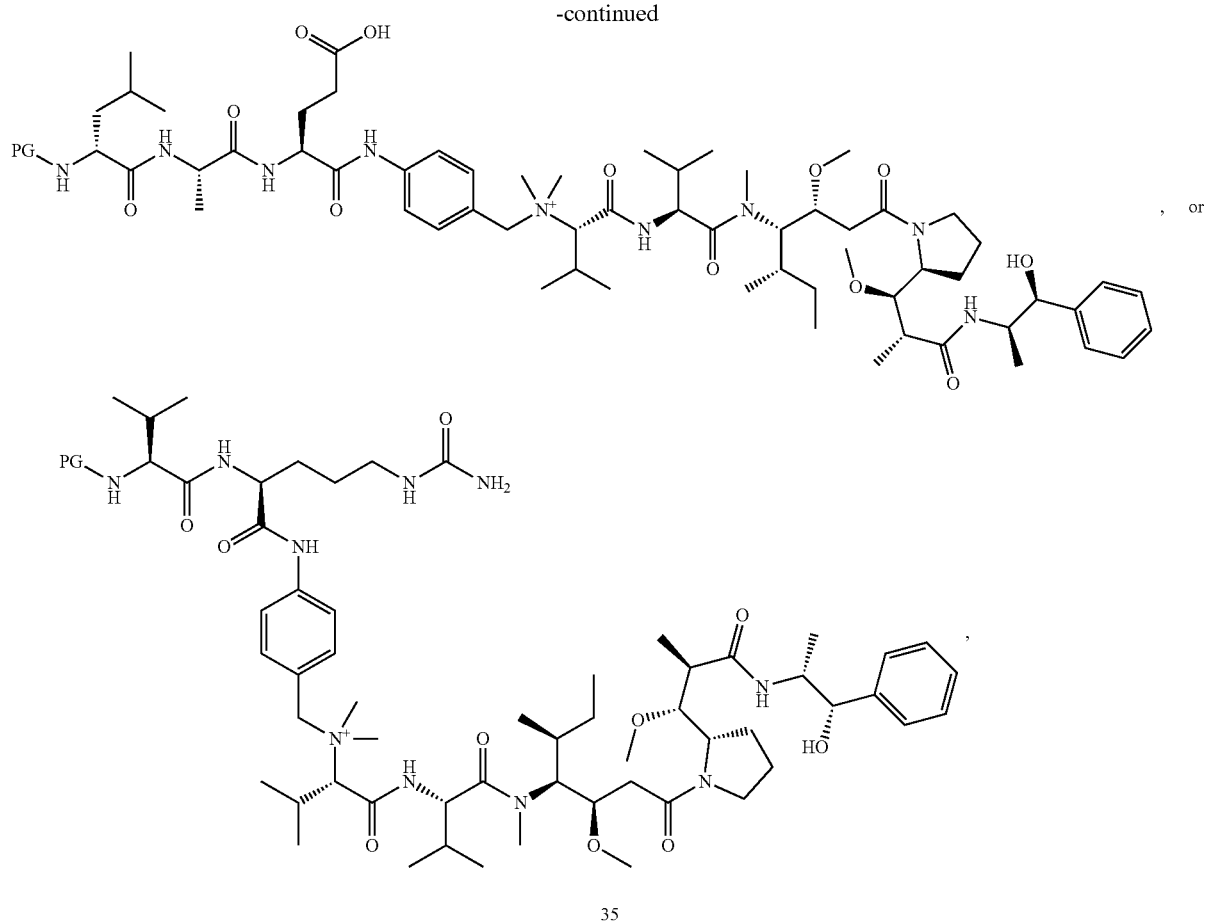

, or or a salt thereof, wherein PG is an amine protecting group (e.g., Fmoc) or hydrogen.

2.4 Linker Compounds

A Linker compound is represented by the structure of Formula IA-L:

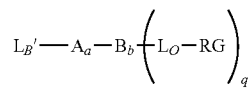

(IA-L)

or a salt thereof, wherein $L_B'$, A, subscript a, B, subscript b, $L_O$, and subscript q retain their previous meanings, and RG is a reactive group. In some embodiments, the reactive group is 4-nitrophenoxy or perfluorophenoxy. In some embodiments, the reactive group is 4-nitrophenoxy.

In some some embodiments, the Linker compound is represented by the structure of Formula IA-L-1:

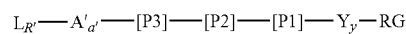

(I-A-L-1)

or a salt thereof, wherein $L_R'$, A', subscript a', P1, P2, P3, Y, and subscript y retain their previous meanings, and RG is a reactive group.

In some some embodiments, the Linker compound is represented by the structure of Formula IA-L-2:

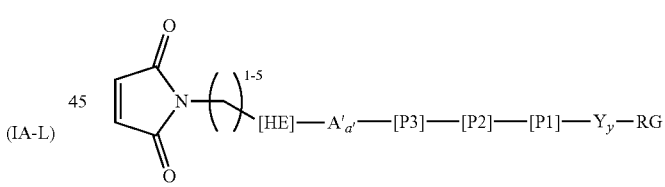

(IA-L-2)

or a salt thereof, wherein HE, A', subscript a', P1, P2, P3, Y, and subscript y retain their previous meanings, and RG is a reactive group.

In some some embodiments, the Linker compound is represented by the structures of Formula IA-L-3 or Formula IA-L-4:

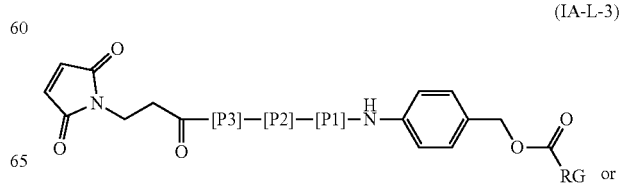

(IA-L-3)

RG or

321

-continued (IA-L-4)

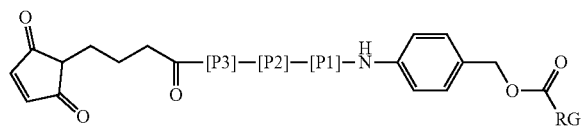

or a salt thereof, wherein P1, P2, and P3 retain their previous meanings, and RG is a reactive group. In some embodiments, RG is perfluorophenoxy. In some embodiments, RG is 4-nitrophenoxy.

In any of the embodiments described herein for $L_B'$, A, subscript a, B, subscript b, $L_O$, subscript q, $L_R'$, A', subscript a', P1, P2, P3, Y, subscript y, and HE with respect to Ligand Drug Conjugate (LDC) compounds, primary linkers, secondary linkers, Drug Linker compounds, drug linker moieties, Peptide Cleavable Units, Stretcher Units, and Spacer Units, the embodiments are also applicable for Linker compounds described herein, such as compounds of Formula IA-L, Formula IA-L-1, Formula IA-L-2, Formula IA-L-3, or Formula IA-L-4.

In any of the Drug Linker compounds described herein, the Drug Unit (D) can be replaced by a suitable reactive group (i.e., a group suitable for attachment to the Drug Unit (D)) to form a Linker compound, for example a structure represented by Formula IA-L, Formula IA-L-1, Formula IA-L-2, Formula IA-L-3, or Formula IA-L-4. The reactive group is a group suitable for reacting the linker compound with an auristatin drug compound as described herein (such as MMAE or MMAF) to form a Drug Linker compound.

In some embodiments, the Linker compound is represented by:

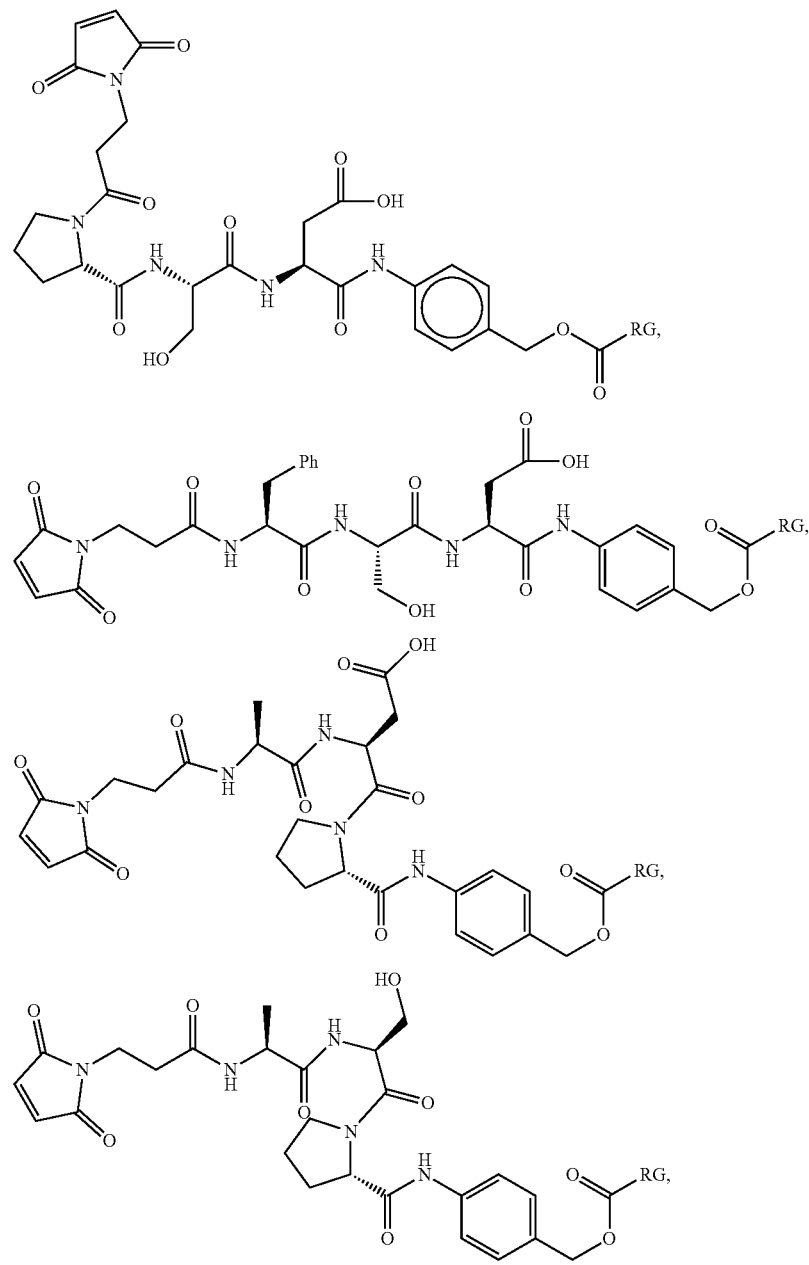

-continued
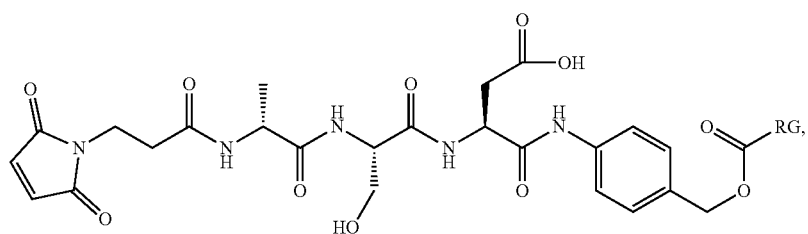
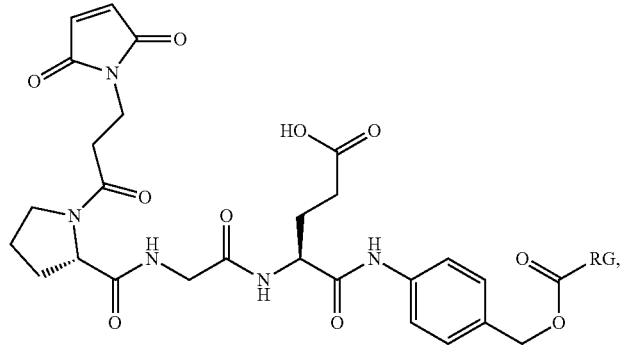
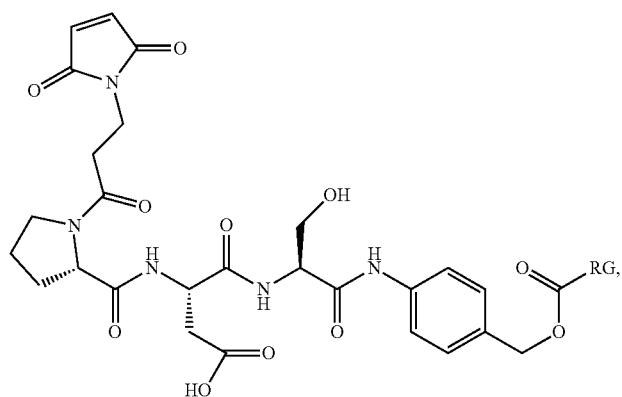
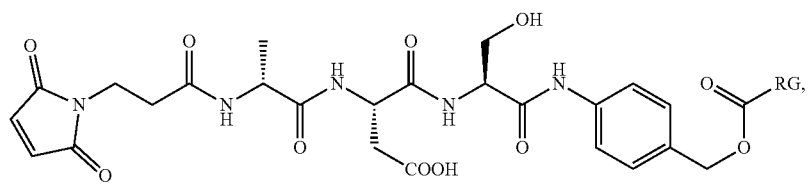
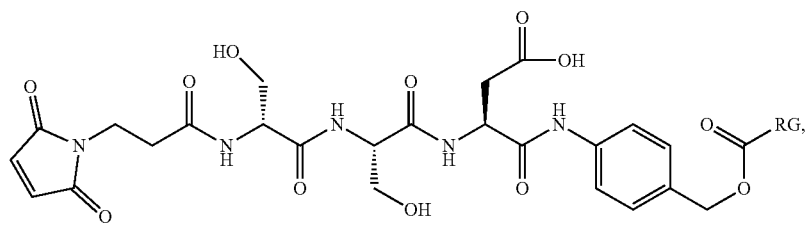
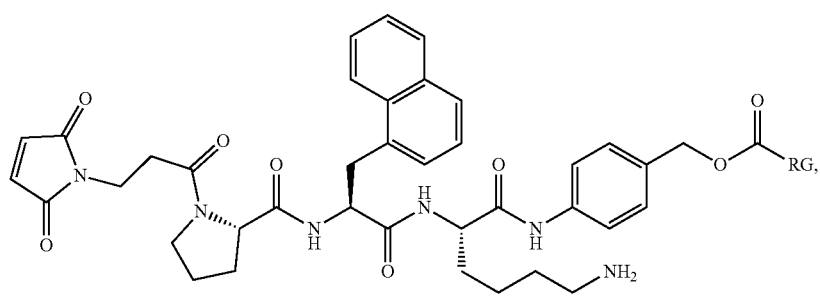

-continued
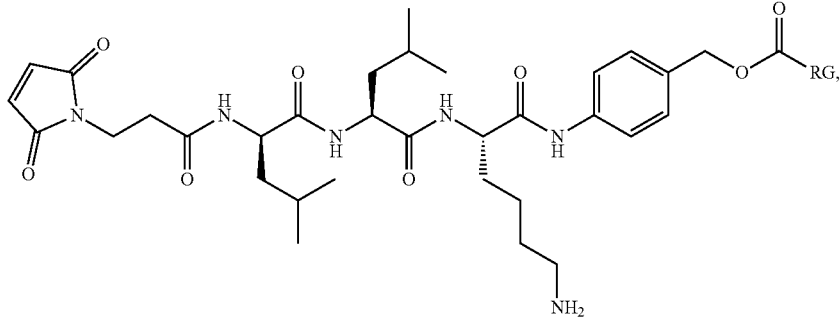
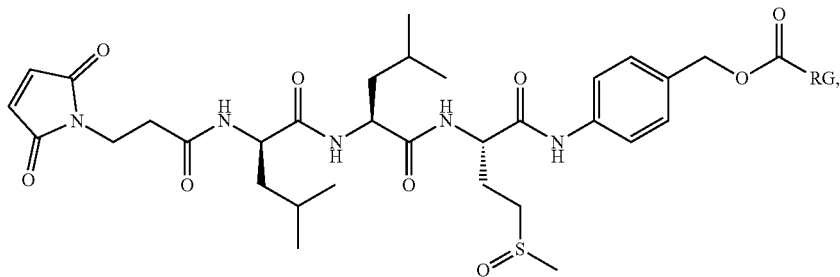
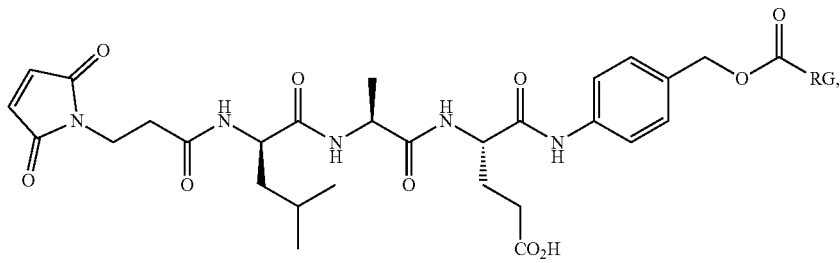
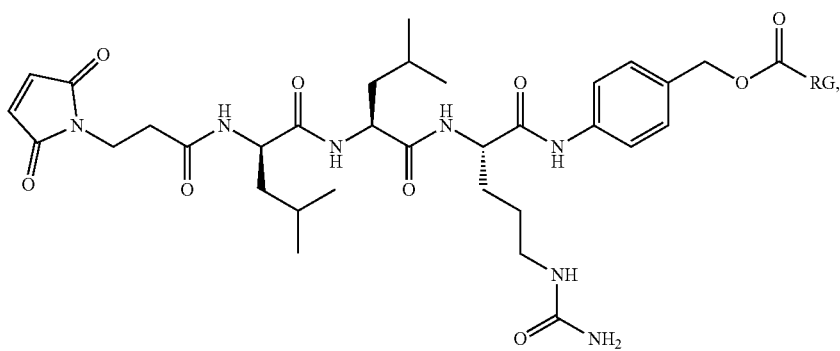
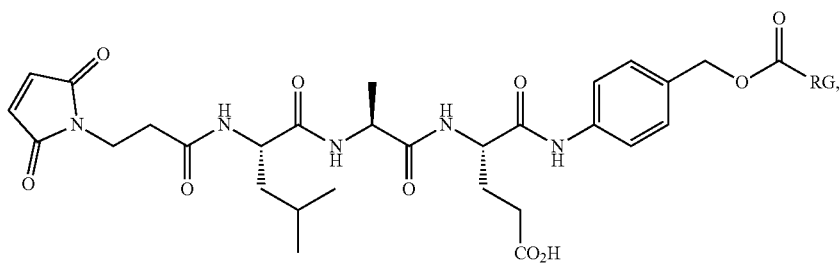

-continued
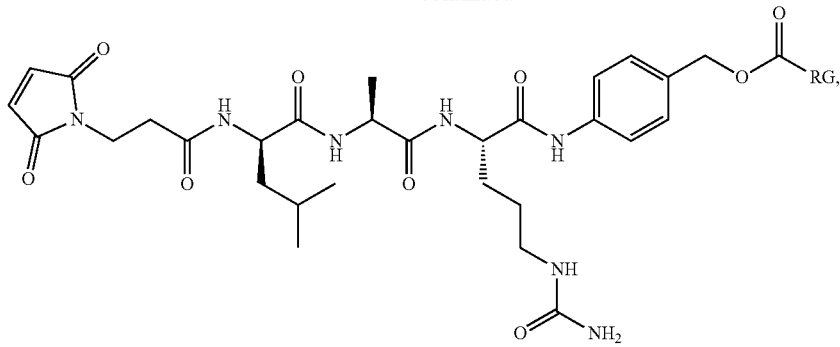
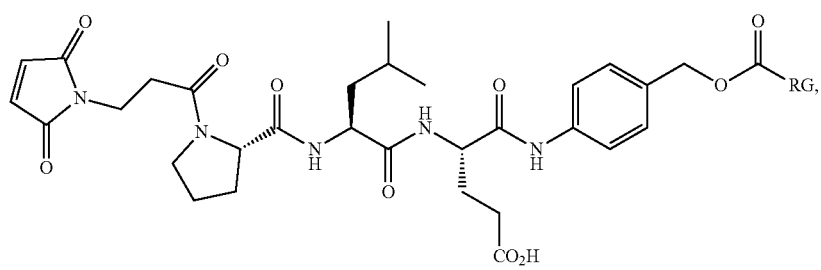
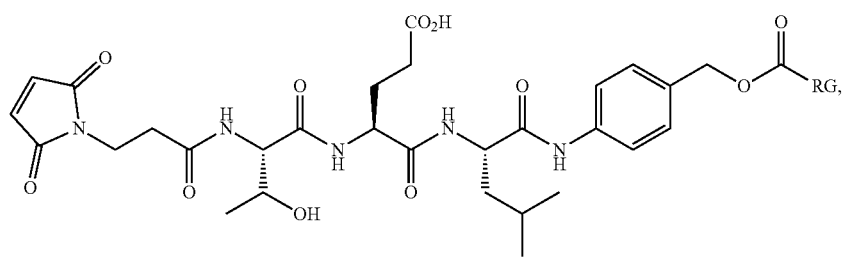
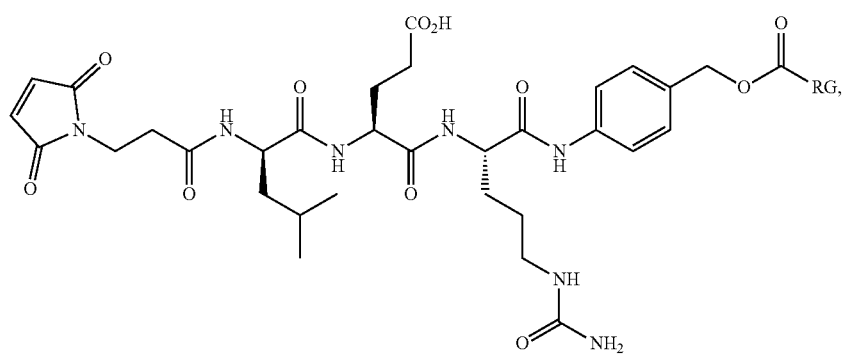
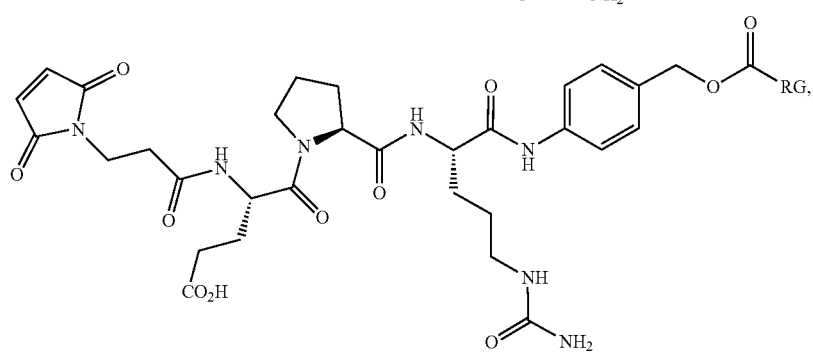

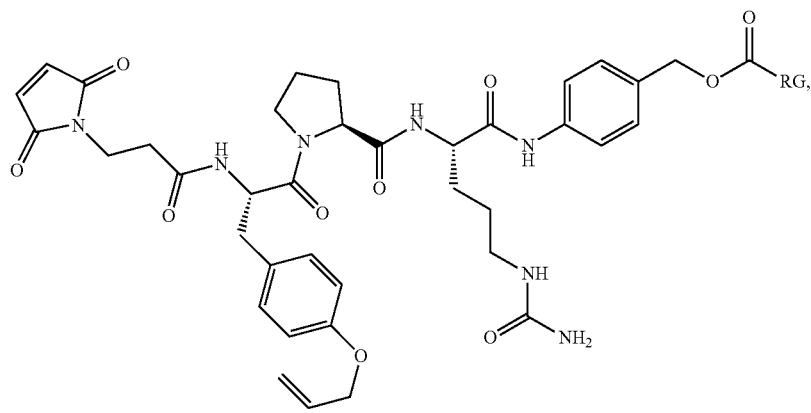
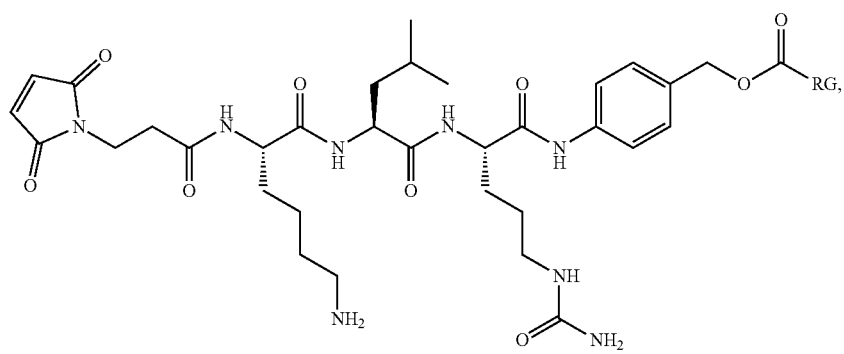
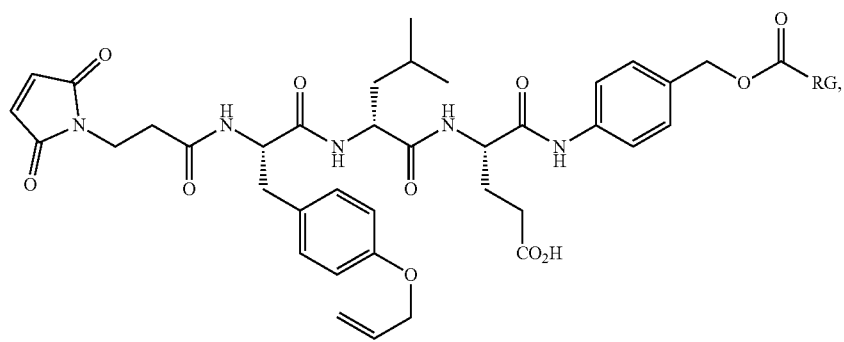
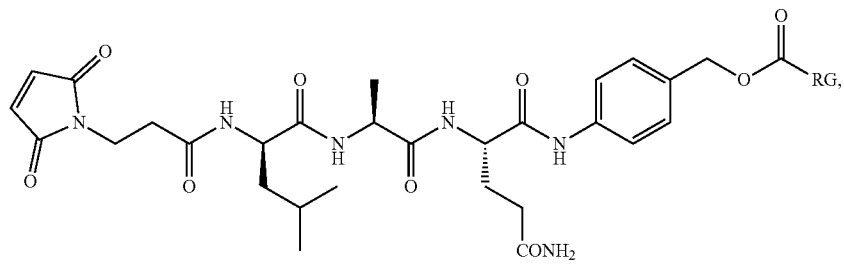
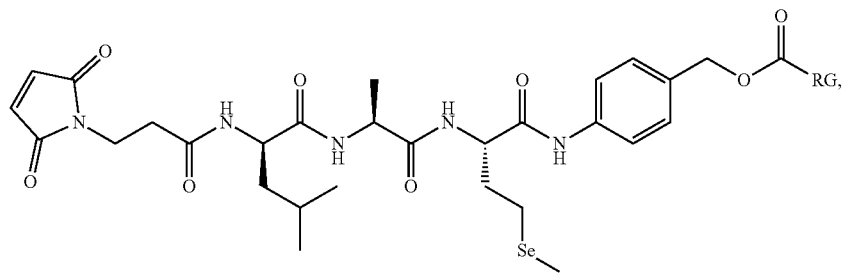

-continued
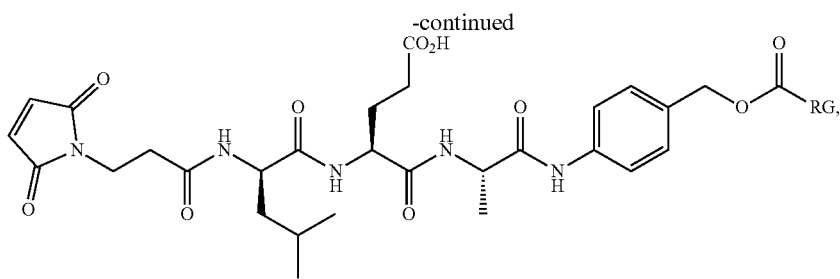
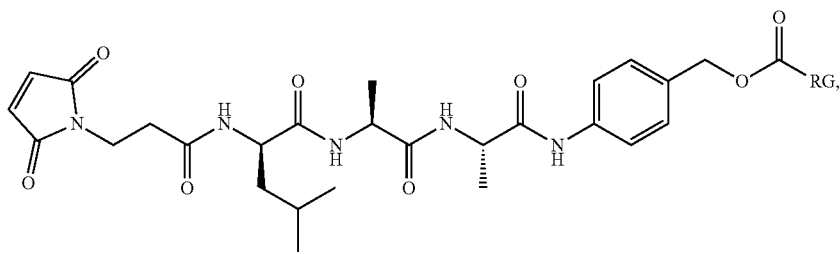
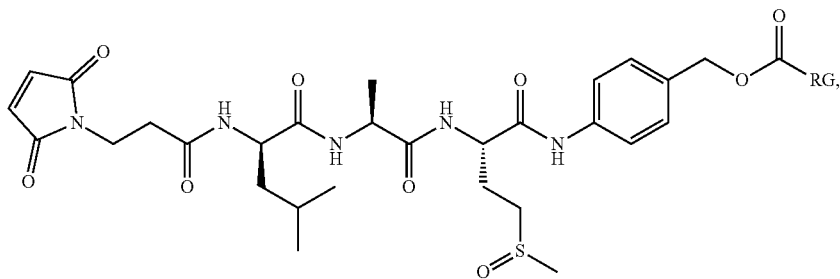
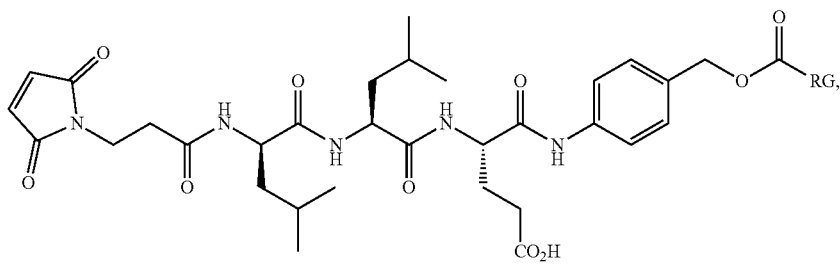
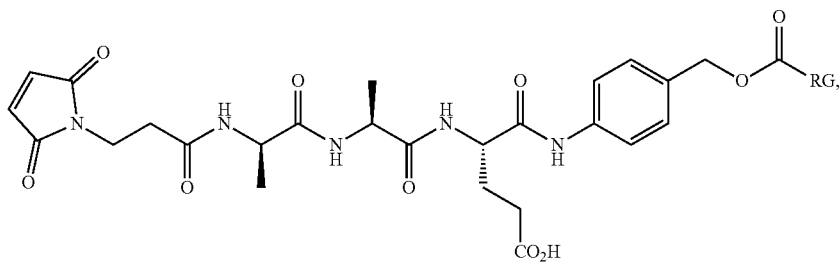
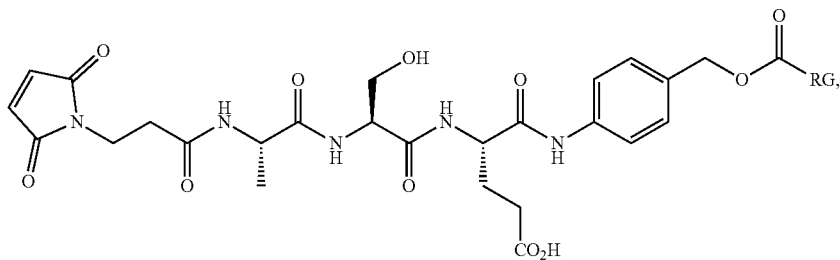

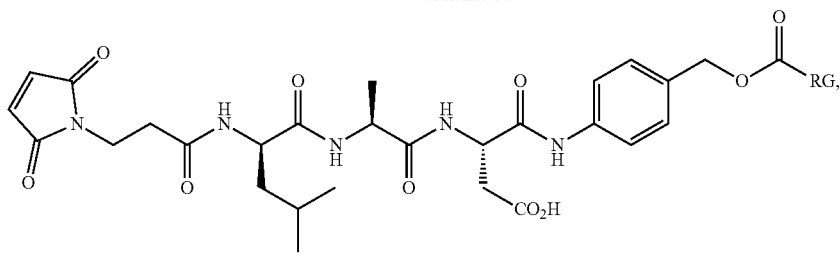
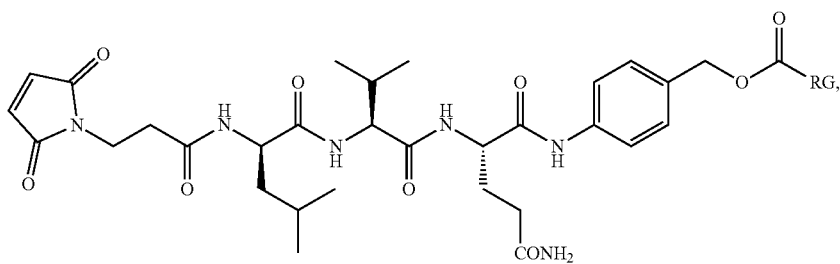
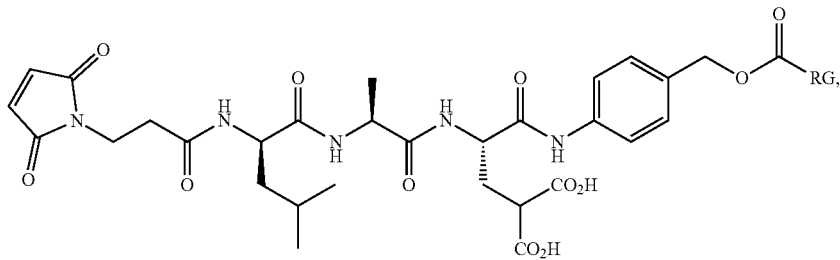
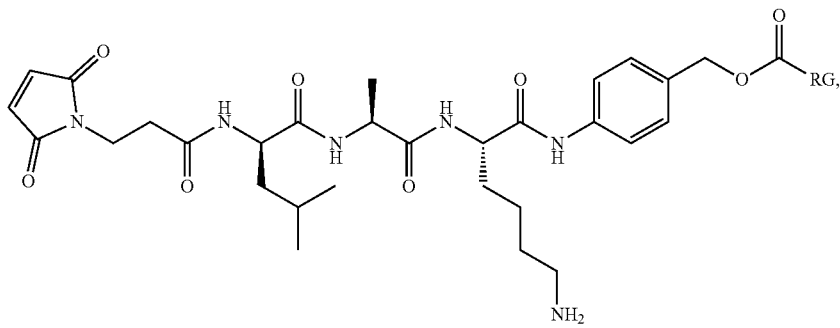
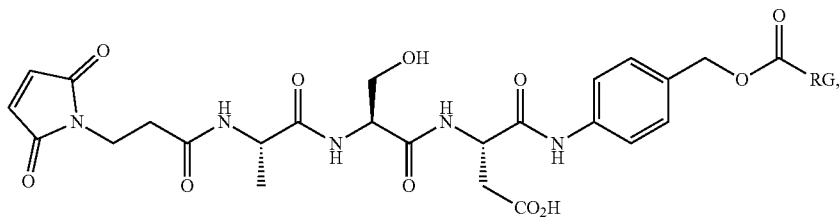
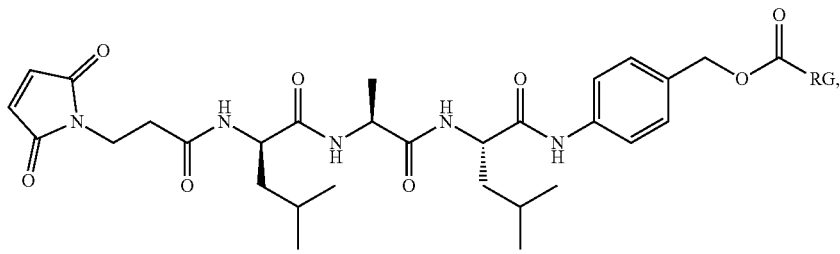

-continued
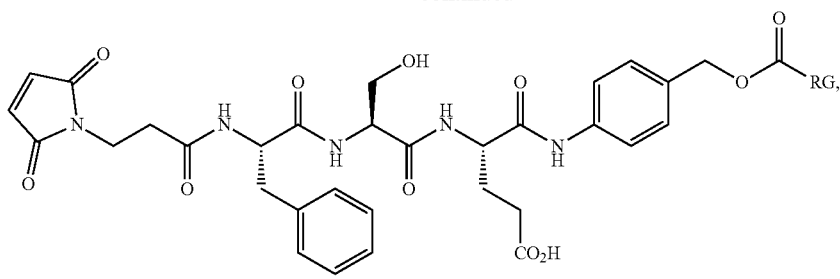
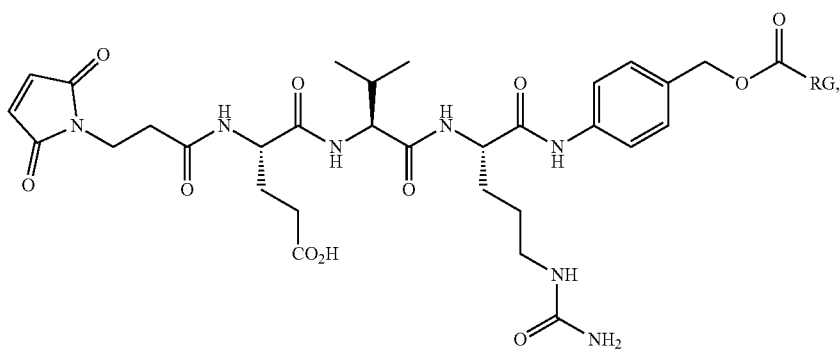
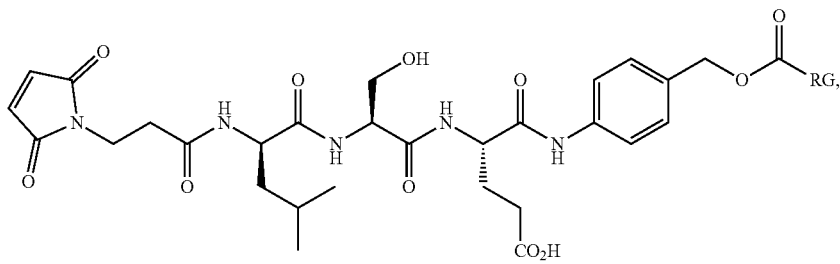
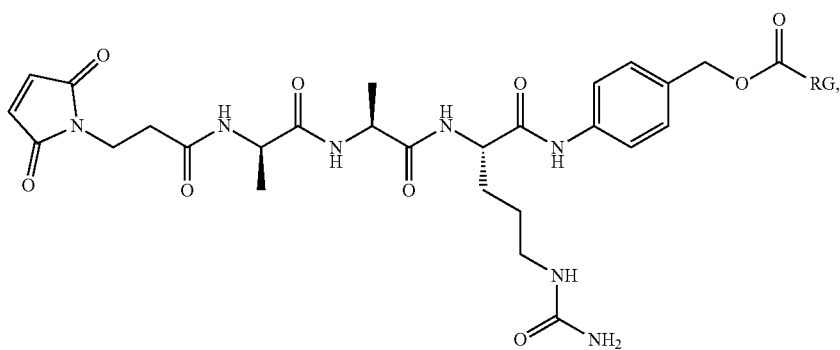
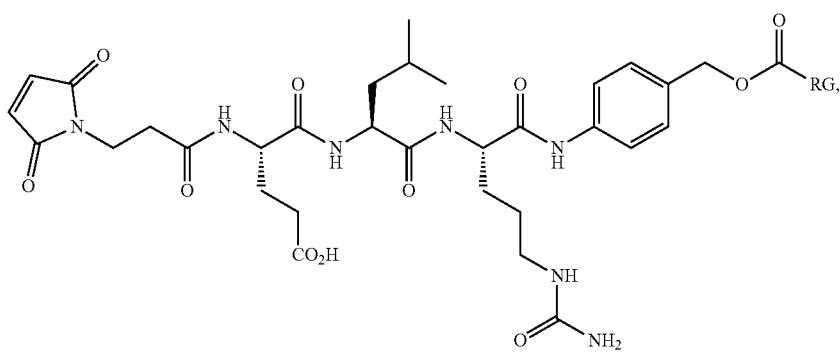

-continued
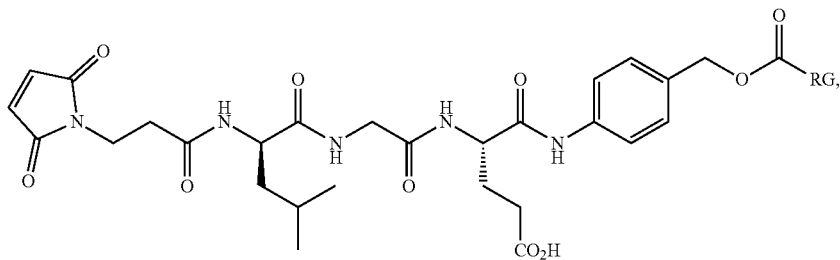
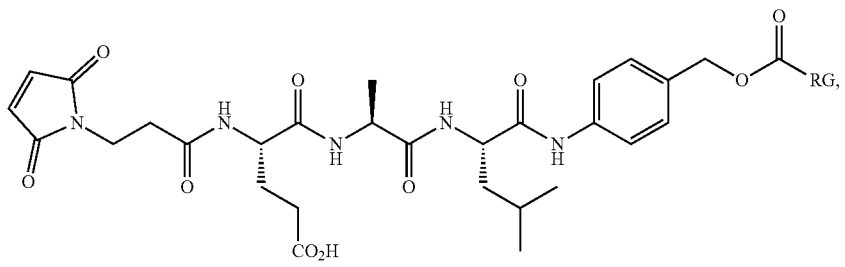
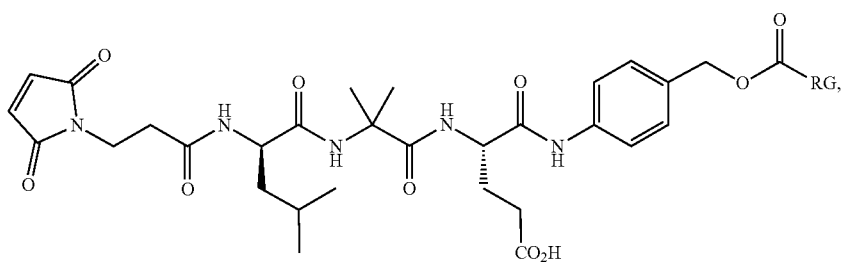
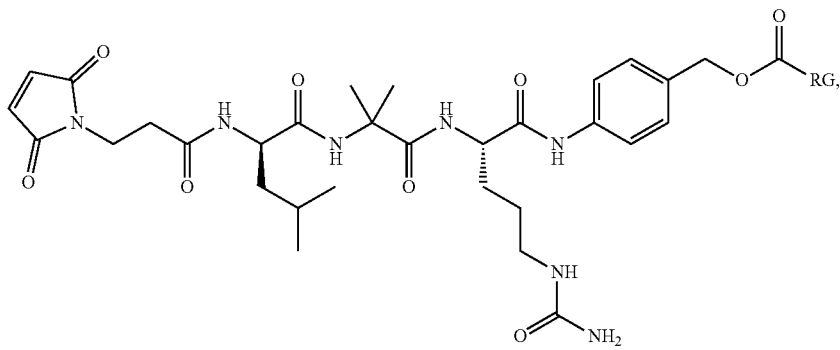
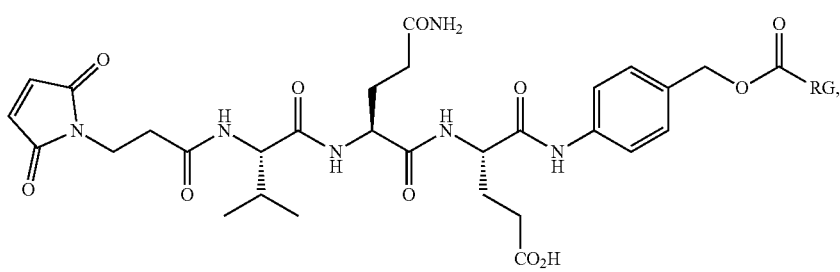
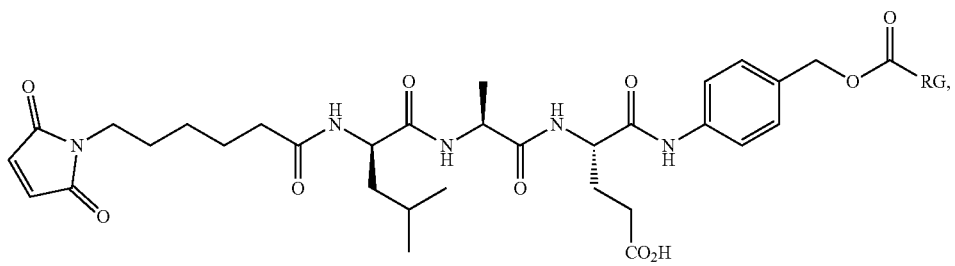

-continued
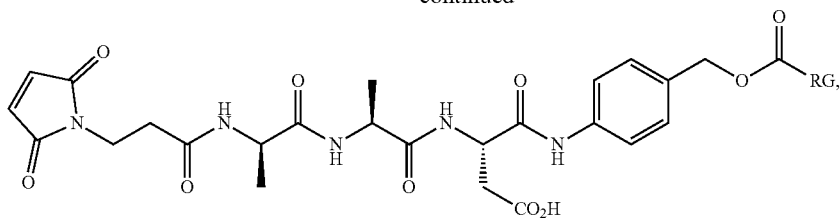
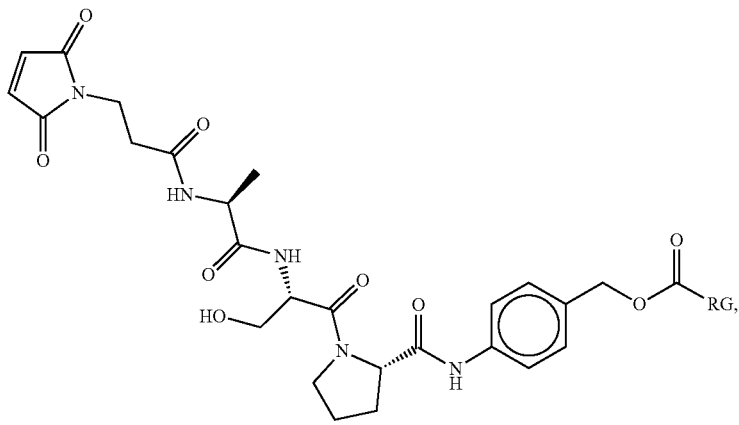
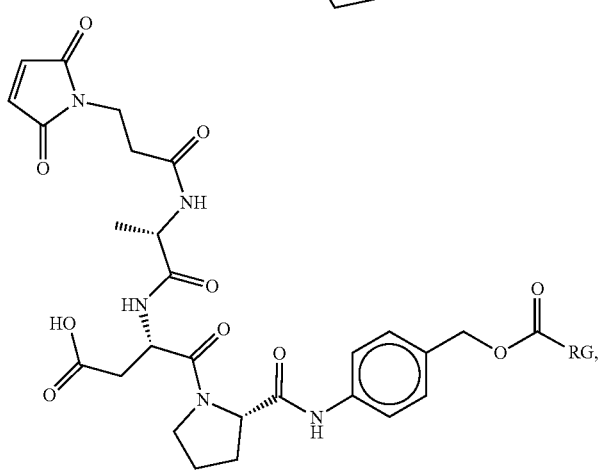
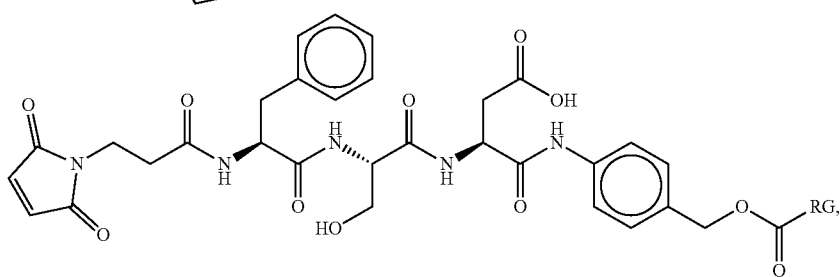
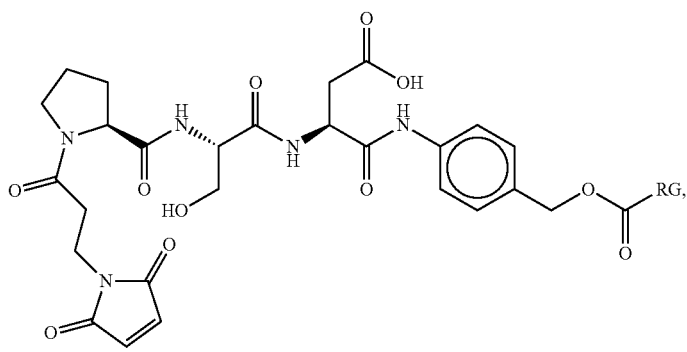

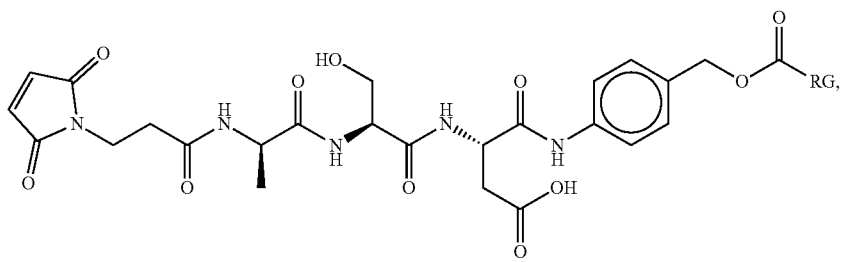
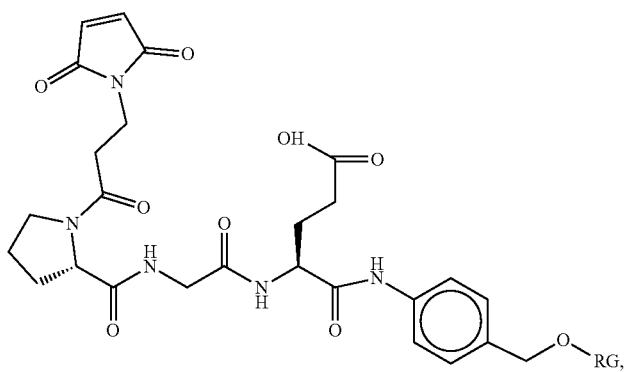
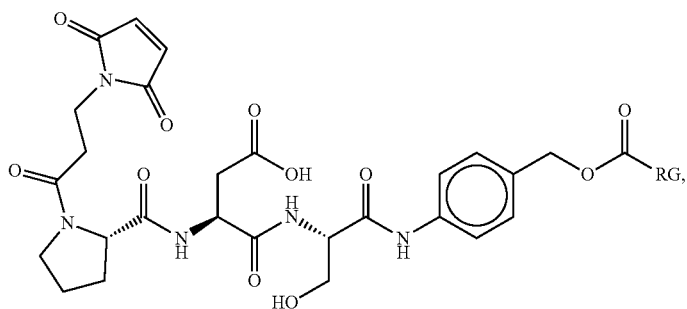
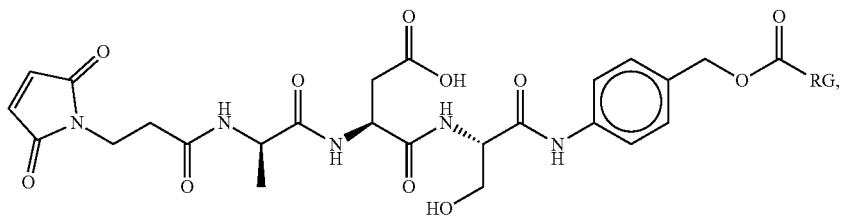
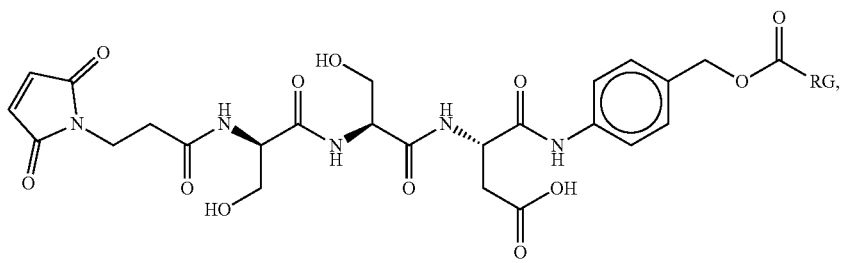

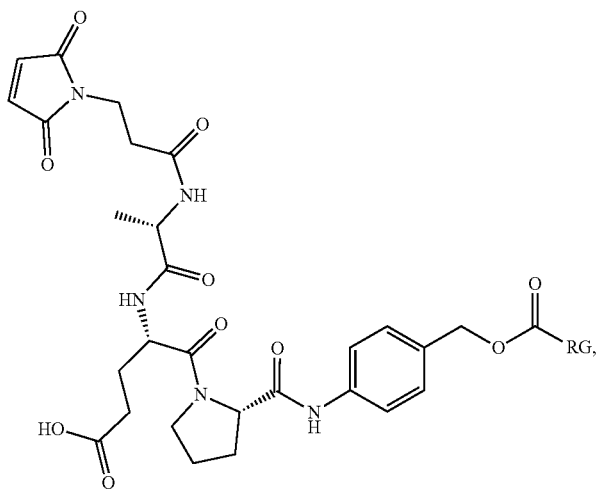
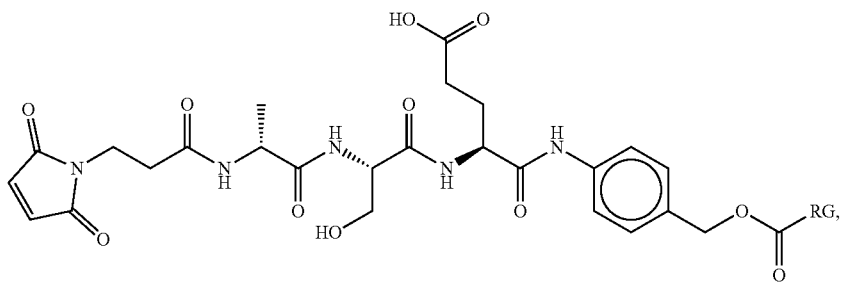
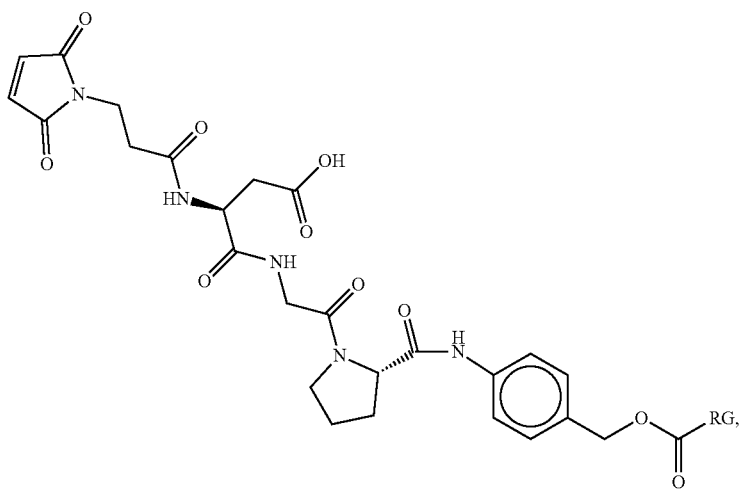
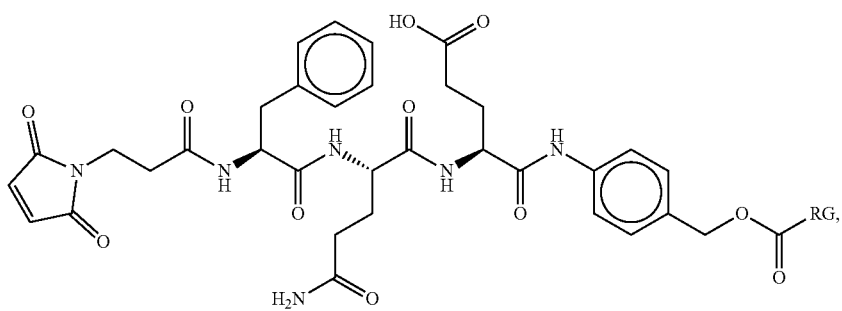

-continued
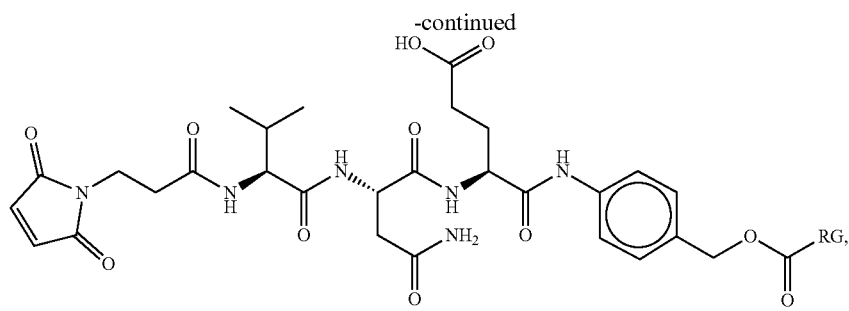
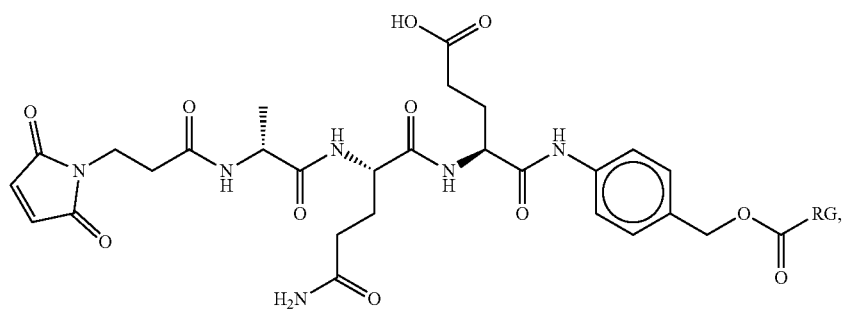
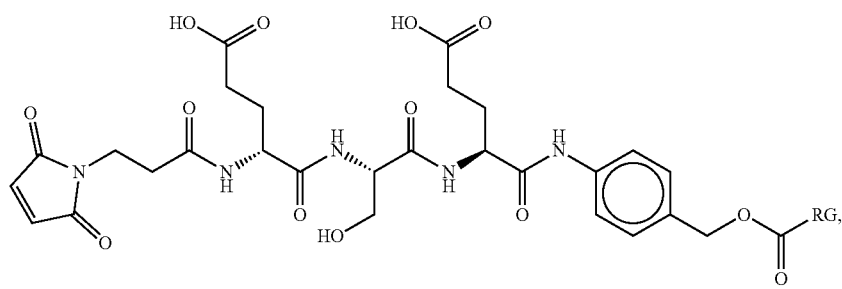
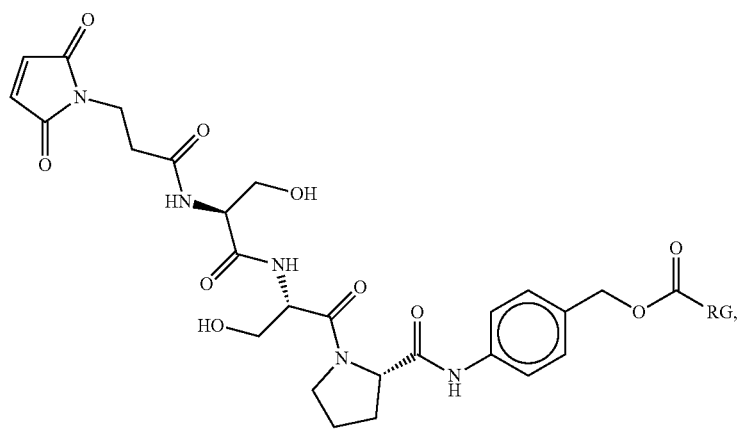
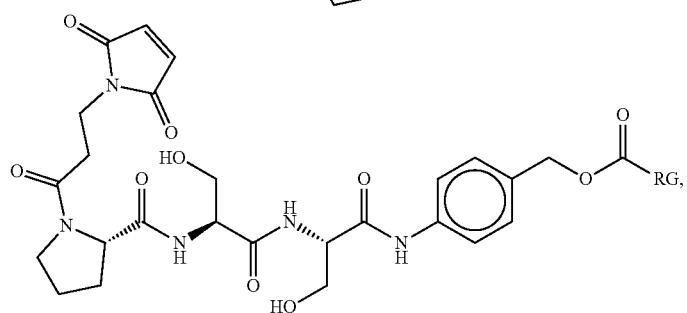

-continued
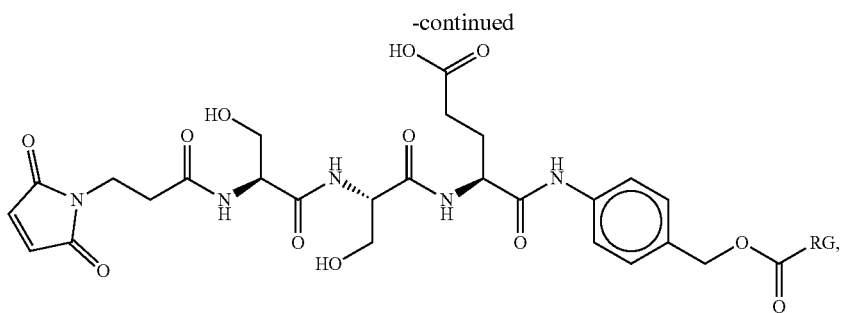
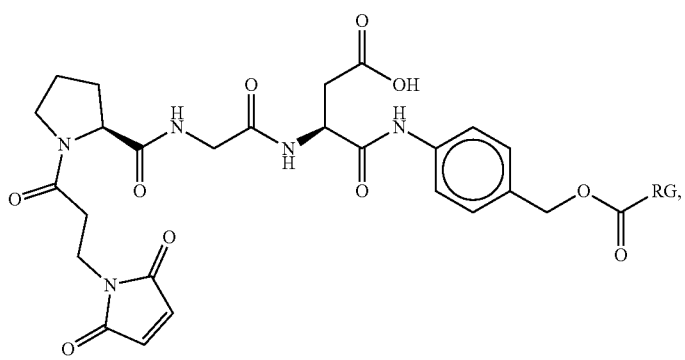
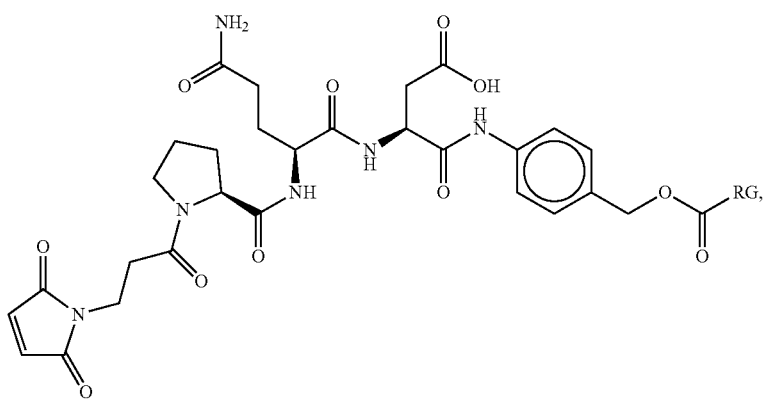
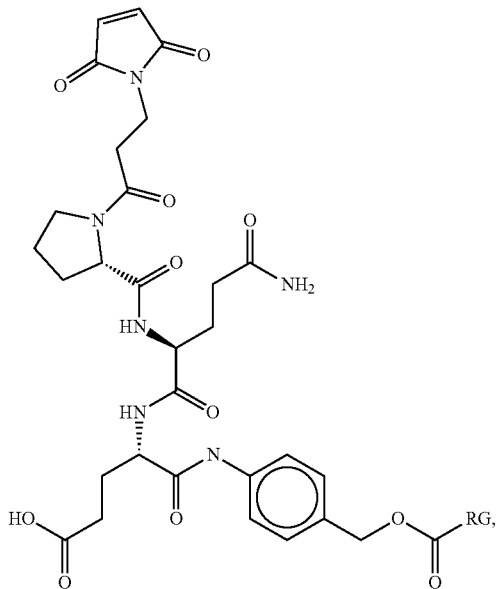

-continued
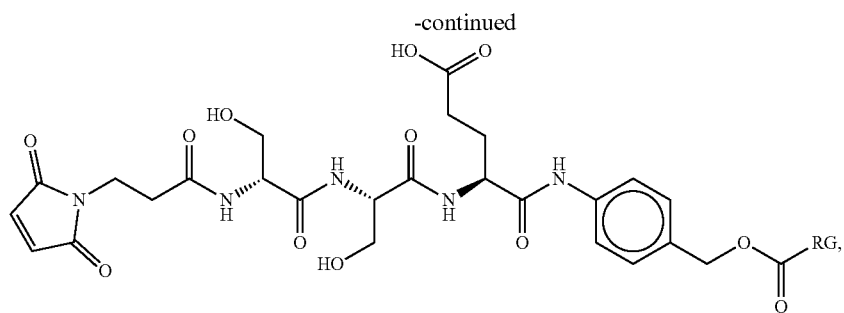
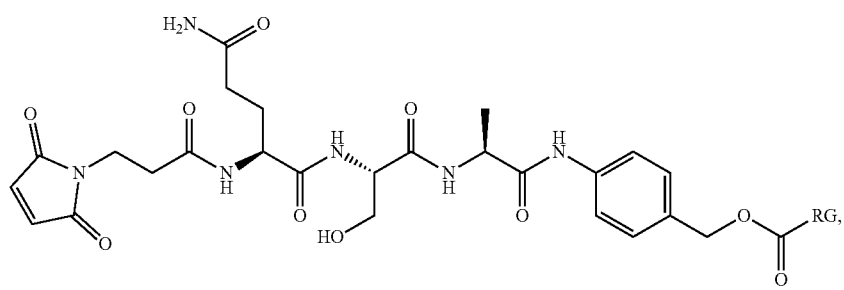
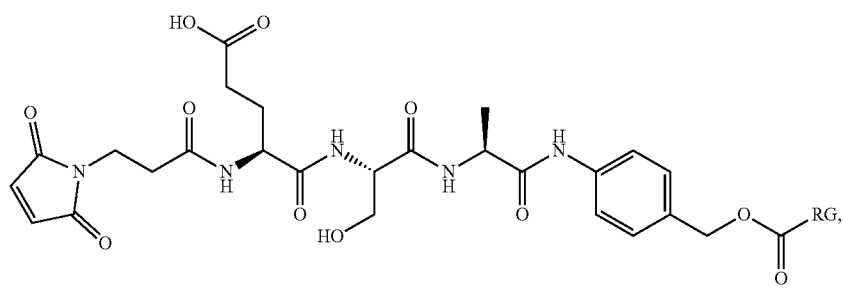
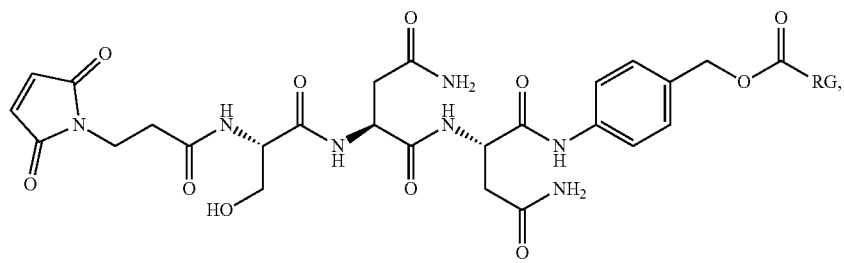
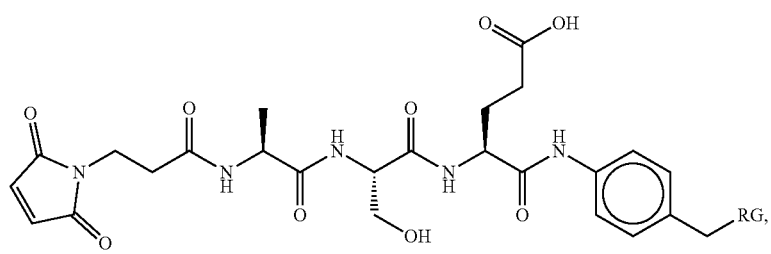

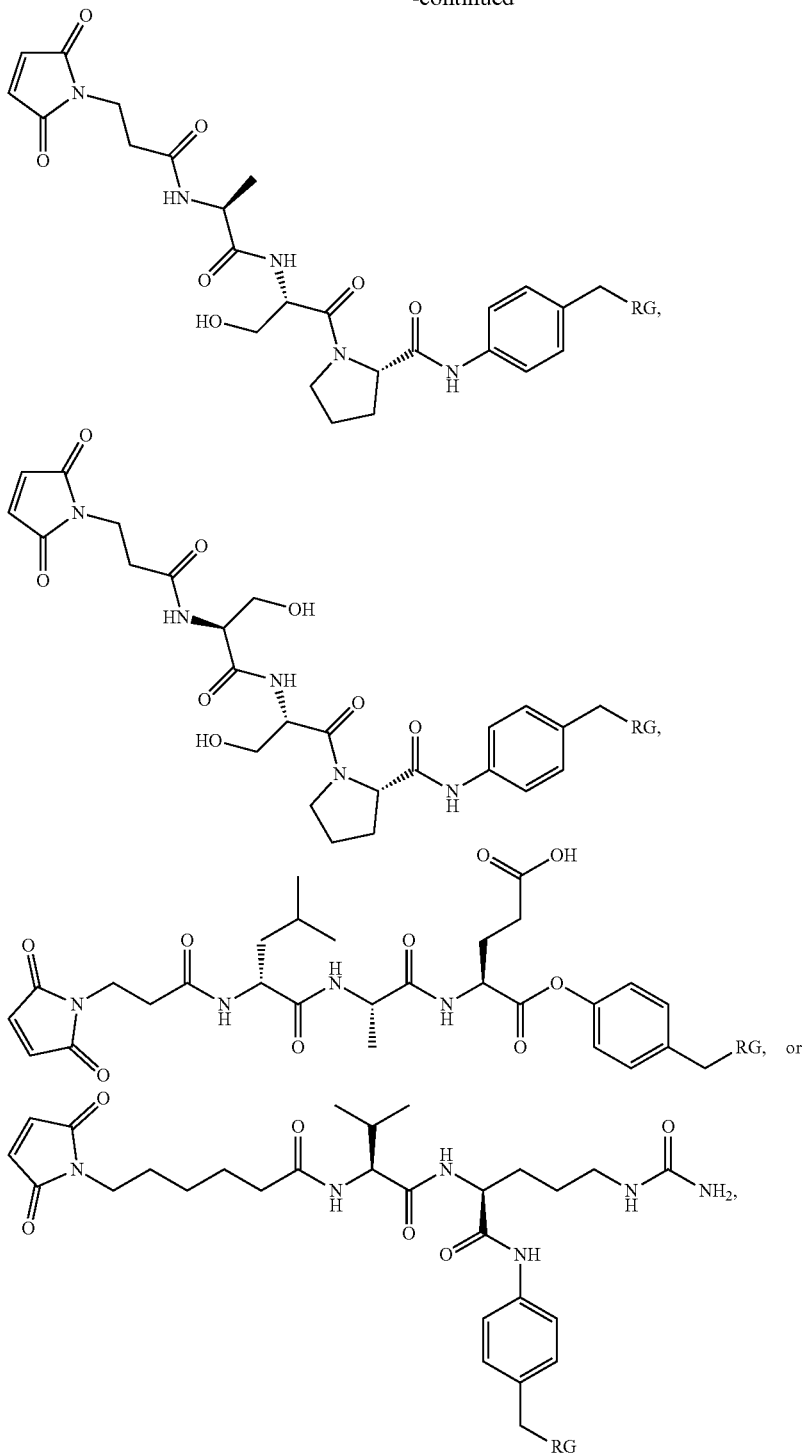

or a salt thereof, wherein RG is a reactive group.

3. Ligands

Exemplary antigens are provided below. Exemplary antibodies that bind the indicated antigen are shown in parentheses.

In some embodiments, the antigen is a tumor-associated antigen. In some embodiments, the tumor-associated antigen is a transmembrane protein. For example, the following antigens are transmembrane proteins: ANTXR1, BAFF-R, CA9 (exemplary antibodies include girentuximab), CD147 (exemplary antibodies include gavilimomab and metuzumab), CD19, CD20 (exemplary antibodies include divozilimab and ibritumomab tiuxetan), CD274 also known as PD-L1 (exemplary antibodies include adebrelimab, atezolizumab, garivulimab, durvalumab, and avelumab), CD30 (exemplary antibodies include iratumumab and brentuximab), CD33 (exemplary antibodies include lintuzumab), CD352, CD45 (exemplary antibodies include apamistamab), CD47 (exemplary antibodies include letaplimab and magrolimab), CLPTM1L, DPP4, EGFR, ERVMER34-1, FASL, FSHR, FZD5, FZD8, GUCY2C (exemplary antibodies include indusatumab), IFNAR1 (exemplary antibodies include faralimomab), IFNAR2, LMP2, MLANA, SIT1, TLR2/4/1 (exemplary antibodies include tomaralimab), TM4SF5, TMEM132A, TMEM40, UPK1B, VEGF, and VEFGR2 (exemplary antibodies include gentuximab).

In some embodiments, the tumor-associated antigen is a transmembrane transport protein. For example, the following antigens are transmembrane transport proteins: ASCT2 (exemplary antibodies include idactamab), MFSD13A, Mincle, NOX1, SLC10A2, SLC12A2, SLC17A2, SLC38A1, SLC39A5, SLC39A6 also known as LIV1 (exemplary antibodies include ladiratuzumab), SLC44A4, SLC6A15, SLC6A6, SLC7A11, and SLC7A5.

In some embodiments, the tumor-associated antigen is a transmembrane or membrane-associated glycoprotein. For example, the following antigens are transmembrane or membrane-associated glycoproteins: CA-125, CA19-9, CAMPATH-1 (exemplary antibodies include alemtuzumab), carcinoembryonic antigen (exemplary antibodies include arcitumomab, cergutuzumab, amunaleukin, and labetuzumab), CD112, CD155, CD24, CD247, CD37 (exemplary antibodies include lilotomab), CD38 (exemplary antibodies include felzartamab), CD3D, CD3E (exemplary antibodies include foralumab and teplizumab), CD3G, CD96, CDCP1, CDH17, CDH3, CDH6, CEACAM1, CEACAM6, CLDN1, CLDN16, CLDN18.1 (exemplary antibodies include zolbetuximab), CLDN18.2 (exemplary antibodies include zolbetuximab), CLDN19, CLDN2, CLEC12A (exemplary antibodies include tepoditamab), DPEP1, DPEP3, DSG2, endosialin (exemplary antibodies include ontuxizumab), ENPP1, EPCAM (exemplary antibodies include adecatumumab), FN, FN1, Gp100, GPA33, gpNMB (exemplary antibodies include glembatumumab), ICAM1, L1CAM, LAMP1, MELTF also known as CD228, NCAM1, Nectin-4 (exemplary antibodies include enfortumab), PDPN, PMSA, PROM1, PSCA, PSMA, Siglecs 1-16, SIRPa, SIRPg, TACSTD2, TAG-72, Tenascin, Tissue Factor also known as TF (exemplary antibodies include tisotumab), and ULBP1/2/3/4/5/6.

In some embodiments, the tumor-associated antigen is a transmembrane or membrane-associated receptor kinase. For example, the following antigens are transmembrane or membrane-associated receptor kinases: ALK, Axl (exemplary antibodies include tilvestamab), BMPR2, DCLK1, DDR1, EPHA receptors, EPHA2, ERBB2 also known as HER2 (exemplary antibodies include trastuzumab, bevacizumab, pertuzumab, and margetuximab), ERBB3, FLT3, PDGFR-B (exemplary antibodies include rinucumab), PTK7 (exemplary antibodies include cofetuzumab), RET, ROR1 (exemplary antibodies include cirmtuzumab), ROR2, ROS1, and Tie3.

In some embodiments, the tumor-associated antigen is a membrane-associated or membrane-localized protein. For example, the following antigens are membrane-associated or membrane-localized proteins: ALPP, ALPPL2, ANXA1, FOLR1 (exemplary antibodies include farletuzumab), IL13Ra2, IL1RAP (exemplary antibodies include nidanilimab), NT5E, OX40, Ras mutant, RGS5, RhoC, SLAMF7 (exemplary antibodies include elotuzumab), and VSIR.

In some embodiments, the tumor-associated antigen is a transmembrane G-protein coupled receptor (GPCR). For example, the following antigens are GPCRs: CALCR, CD97, GPR87, and KISS1R.

In some embodiments, the tumor-associated antigen is cell-surface-associated or a cell-surface receptor. For example, the following antigens are cell-surface-associated and/or cell-surface receptors: B7-DC, BCMA, CD137, CD 244, CD3 (exemplary antibodies include otelixizumab and visilizumab), CD48, CD5 (exemplary antibodies include zolimomab aritox), CD70 (exemplary antibodies include cusatuzumab and vorsetuzumab), CD74 (exemplary antibodies include milatuzumab), CD79A, CD-262 (exemplary antibodies include tigatuzumab), DR4 (exemplary antibodies include mapatumumab), FAS, FGFR1, FGFR2 (exemplary antibodies include aprutumab), FGFR3 (exemplary antibodies include vofatamab), FGFR4, GITR (exemplary antibodies include ragifilimab), Gpc3 (exemplary antibodies include ragifilimab), HAVCR2, HLA-E, HLA-F, HLA-G, LAG-3 (exemplary antibodies include encelimab), LY6G6D, LY9, MICA, MICB, MSLN, MUC1, MUC5AC, NY-ESO-1, OY-TES1, PVRIG, Sialyl-Thomsen-Nouveau Antigen, Sperm protein 17, TNFRSF12, and uPAR.

In some embodiments, the tumor-associated antigen is a chemokine receptor or cytokine receptor. For example, the following antigens are chemokine receptors or cytokine receptors: CD115 (exemplary antibodies include axatilimab, cabiralizumab, and emactuzumab), CD123, CXCR 4 (exemplary antibodies include ulocuplumab), IL-21R, and IL-5R (exemplary antibodies include benralizumab).

In some embodiments, the tumor-associated antigen is a co-stimulatory, surface-expressed protein. For example, the following antigens are co-stimulatory, surface-expressed proteins: B7-H3 (exemplary antibodies include enoblituzumab and omburtamab), B7-H4, B7-H6, and B7-H7.

In some embodiments, the tumor-associated antigen is a transcription factor or a DNA-binding protein. For example, the following antigens are transcription factors: ETV6-AML, MYCN, PAX3, PAX5, and WT1. The following protein is a DNA-binding protein: BORIS.

In some embodiments, the tumor-associated antigen is an integral membrane protein. For example, the following antigens are integral membrane proteins: SLITRK6 (exemplary antibodies include sirtratumab), UPK2, and UPK3B.

In some embodiments, the tumor-associated antigen is an integrin. For example, the following antigens are integrin antigens: alpha v beta 6, ITGAV (exemplary antibodies include abituzumab), ITGB6, and ITGB8.

In some embodiments, the tumor-associated antigen is a glycolipid. For example, the following are glycolipid antigens: FucGM1, GD2 (exemplary antibodies include dinutuximab), GD3 (exemplary antibodies include mitumomab), GloboH, GM2, and GM3 (exemplary antibodies include racotumomab).

In some embodiments, the tumor-associated antigen is a cell-surface hormone receptor. For example, the following antigens are cell-surface hormone receptors: AMHR2 and androgen receptor.

In some embodiments, the tumor-associated antigen is a transmembrane or membrane-associated protease. For example, the following antigens are transmembrane or membrane-associated proteases: ADAM12, ADAM9, TMPRSS11D, and metalloproteinase.

In some embodiments, the tumor-associated antigen is aberrantly expressed in individuals with cancer. For example, the following antigens may be aberrantly expressed in individuals with cancer: AFP, AGR2, AKAP-4, ARTN, BCR-ABL, C5 complement, CCNB1, CSPG4, CYP1B1, De2-7 EGFR, EGF, Fas-related antigen 1, FBP, G250, GAGE, HAS3, HPV E6 E7, hTERT, IDO1, LCK, Legumain, LYPD1, MAD-CT-1, MAD-CT-2, MAGEA3, MAGEA4, MAGEC2, MerTk, ML-IAP, NA17, NY-BR-1, p53, p53 mutant, PAP, PLAV1, polysialic acid, PR1, PSA, Sarcoma translocation breakpoints, SART3, sLe, SSX2, Survivin, Tn, TRAIL, TRAIL1, TRP-2, and XAGE1.

In some embodiments, the antigen is an immune-cell-associated antigen. In some embodiments, the immune-cell-associated antigen is a transmembrane protein. For example, the following antigens are transmembrane proteins: BAFF-R, CD163, CD19, CD20 (exemplary antibodies include rituximab, ocrelizumab, divozilimab; ibritumomab tiuxetan), CD25 (exemplary antibodies include basiliximab), CD274 also known as PD-L1 (exemplary antibodies include adebrelimab, atezolizumab, garivulimab, durvalumab, and avelumab), CD30 (exemplary antibodies include iratumumab and brentuximab), CD33 (exemplary antibodies include lintuzumab), CD352, CD45 (exemplary antibodies include apamistamab), CD47 (exemplary antibodies include letaplimab and magrolimab), CTLA4 (exemplary antibodies include ipilimumab), FASL, IFNAR1 (exemplary antibodies include faralimomab), IFNAR2, LAYN, LILRB2, LILRB4, PD-1 (exemplary antibodies include ipilimumab, nivolumab, pembrolizumab, balstilimab, budigalimab, geptanolimab, toripalimab, and pidilizumabsf), SIT1, and TLR2/4/1 (exemplary antibodies include tomaralimab).

In some embodiments, the immune-cell-associated antigen is a transmembrane transport protein. For example, Mincle is a transmembrane transport protein.

In some embodiments, the immune-cell-associated antigen is a transmembrane or membrane-associated glycoprotein. For example, the following antigens are transmembrane or membrane-associated glycoproteins: CD112, CD155, CD24, CD247, CD28, CD30L, CD37 (exemplary antibodies include lilotomab), CD38 (exemplary antibodies include felzartamab), CD3D, CD3E (exemplary antibodies include foralumab and teplizumab), CD3G, CD44, CLEC12A (exemplary antibodies include tepoditamab), DCIR, DCSIGN, Dectin 1, Dectin 2, ICAM1, LAMP1, Siglecs 1-16, SIRPa, SIRPg, and ULBP1/2/3/4/5/6.

In some embodiments, the immune-cell-associated antigen is a transmembrane or membrane-associated receptor kinase. For example, the following antigens are transmembrane or membrane-associated receptor kinases: Axl (exemplary antibodies include tilvestamab) and FLT3.

In some embodiments, the immune-cell-associated antigen is a membrane-associated or membrane-localized protein. For example, the following antigens are membrane-associated or membrane-localized proteins: CD83, IL1RAP (exemplary antibodies include nidanilimab), OX40, SLAMF7 (exemplary antibodies include elotuzumab), and VSIR.

In some embodiments, the immune-cell-associated antigen is a transmembrane G-protein coupled receptor (GPCR). For example, the following antigens are GPCRs: CCR4 (exemplary antibodies include mogamulizumab-kpkc), CCR8, and CD97.

In some embodiments, the immune-cell-associated antigen is cell-surface-associated or a cell-surface receptor. For example, the following antigens are cell-surface-associated and/or cell-surface receptors: B7-DC, BCMA, CD137, CD2 (exemplary antibodies include siplizumab), CD 244, CD27 (exemplary antibodies include varlilumab), CD278 (exemplary antibodies include feladilimab and vopratelimab), CD3 (exemplary antibodies include otelixizumab and visilizumab), CD40 (exemplary antibodies include dacetuzumab and lucatumumab), CD48, CD5 (exemplary antibodies include zolimomab aritox), CD70 (exemplary antibodies include cusatuzumab and vorsetuzumab), CD74 (exemplary antibodies include milatuzumab), CD79A, CD-262 (exemplary antibodies include tigatuzumab), DR4 (exemplary antibodies include mapatumumab), GITR (exemplary antibodies include ragifilimab), HAVCR2, HLA-DR, HLA-E, HLA-F, HLA-G, LAG-3 (exemplary antibodies include encelimab), MICA, MICB, MRC1, PVRIG, Sialyl-Thomsen-Nouveau Antigen, TIGIT (exemplary antibodies include etigilimab), Trem2, and uPAR.

In some embodiments, the immune-cell-associated antigen is a chemokine receptor or cytokine receptor. For example, the following antigens are chemokine receptors or cytokine receptors: CD115 (exemplary antibodies include axatilimab, cabiralizumab, and emactuzumab), CD123, CXCR4 (exemplary antibodies include ulocuplumab), IL-21R, and IL-5R (exemplary antibodies include benralizumab).

In some embodiments, the immune-cell-associated antigen is a co-stimulatory, surface-expressed protein. For example, the following antigens are co-stimulatory, surface-expressed proteins: B7-H 3 (exemplary antibodies include enoblituzumab and omburtamab), B7-H4, B7-H6, and B7-H7.

In some embodiments, the immune-cell-associated antigen is a peripheral membrane protein. For example, the following antigens are peripheral membrane proteins: B7-1 (exemplary antibodies include galiximab) and B7-2.

In some embodiments, the immune-cell-associated antigen is aberrantly expressed in individuals with cancer. For example, the following antigens may be aberrantly expressed in individuals with cancer: C5 complement, IDO1, LCK, MerTk, and Tyrol.

In some embodiments, the antigen is a stromal-cell-associated antigen. In some embodiments, the stromal-cell-associated antigens is a transmembrane or membrane-associated protein. For example, the following antigens are transmembrane or membrane-associated proteins: FAP (exemplary antibodies include sibrotuzumab), IFNAR1 (exemplary antibodies include faralimomab), and IFNAR2.

In some embodiments, the antigen is CD30. In some embodiments, the antibody is an antibody or antigen-binding fragment that binds to CD30, such as described in International Patent Publication No. WO 02/43661. In some embodiments, the anti-CD30 antibody is cAC10, which is described in International Patent Publication No. WO 02/43661. cAC10 is also known as brentuximab. In some embodiments, the anti-CD30 antibody comprises the CDRs of cAC10. In some embodiments, the CDRs are as defined by the Kabat numbering scheme. In some embodiments, the CDRs are as defined by the Chothia numbering scheme. In some embodiments, the CDRs are as defined by the IMGT numbering scheme. In some embodiments, the CDRs are as defined by the AbM numbering scheme. In some embodiments, the anti-CD30 antibody comprises CDR-H1, CDR-H2, CDR-H3, CDR-L1, CDR-L2, and CDR-L3 comprising the amino acid sequences of SEQ ID NOs: 1, 2, 3, 4, 5, and 6, respectively. In some embodiments, the anti-CD30 antibody comprises a heavy chain variable region comprising an amino acid sequence that is at least 95%, at least 96%, at least 97%, at last 98%, at least 99%, or 100% identical to the amino acid sequence of SEQ ID NO: 7 and a light chain variable region comprising an amino acid sequence that is at least 95% at least 96%, at least 97%, at last 98%, at least 99%, or 100% identical to the amino acid sequence of SEQ ID NO: 8. In some embodiments, the anti-CD30 antibody comprises a heavy chain comprising the amino acid sequence of SEQ ID NO: 9 or SEQ ID NO: 10 and a light chain comprising the amino acid sequence of SEQ ID NO: 11.

In some embodiments, the antigen is CD70. In some embodiments, the antibody is an antibody or antigen-binding fragment that binds to CD70, such as described in International Patent Publication No. WO 2006/113909. In some embodiments, the antibody is a h1F6 anti-CD70 antibody, which is described in International Patent Publication No. WO 2006/113909. h1F6 is also known as vorsetuzumab. In some embodiments, the anti-CD70 antibody comprises a heavy chain variable region comprising the three CDRs of SEQ ID NO:12 and a light chain variable region comprising the three CDRs of SEQ ID NO:13. In some embodiments, the CDRs are as defined by the Kabat numbering scheme. In some embodiments, the CDRs are as defined by the Chothia numbering scheme. In some embodiments, the CDRs are as defined by the IMGT numbering scheme. In some embodiments, the CDRs are as defined by the AbM numbering scheme. In some embodiments, the anti-CD70 antibody comprises a heavy chain variable region comprising an amino acid sequence that is at least 95%, at least 96%, at least 97%, at last 98%, at least 99%, or 100% identical to the amino acid sequence of SEQ ID NO: 12 and a light chain variable region comprising an amino acid sequence that is at least 95% at least 96%, at least 97%, at last 98%, at least 99%, or 100% identical to the amino acid sequence of SEQ ID NO: 13. In some embodiments, the anti-CD30 antibody comprises a heavy chain comprising the amino acid sequence of SEQ ID NO: 14 and a light chain comprising the amino acid sequence of SEQ ID NO: 15.

In some embodiments, the antigen is interleukin-1 receptor accessory protein (IL1RAP). IL1RAP is a co-receptor of the IL1 receptor (IL1R1) and is required for interleukin-1 (IL1) signaling. IL1 has been implicated in the resistance to certain chemotherapy regimens. IL1RAP is overexpressed in various solid tumors, both on cancer cells and in the tumor microenvironment, but has low expression on normal cells. IL1RAP is also overexpressed in hematopoietic stem and progenitor cells, making it a candidate to target for chronic myeloid leukemia (CML). IL1RAP has also been shown to be overexpressed in acute myeloid leukemia (AML). Antibody binding to IL1RAP could block signal transduction from IL-1 and IL-33 into cells and allow NK-cells to recognize tumor cells and subsequent killing by antibody dependent cellular cytotoxicity (ADCC).

In some embodiments, the antigen is ASCT2. ASCT2 is also known as SLC1A5. ASCT2 is a ubiquitously expressed, broad-specificity, sodium-dependent neutral amino acid exchanger. ASCT2 is involved in glutamine transport. ASCT2 is overexpressed in different cancers and is closely related to poor prognosis. Downregulating ASCT2 has been shown to suppress intracellular glutamine levels and downstream glutamine metabolism, including glutathione production. Due to its high expression in many cancers, ASCT2 is a potential therapeutic target. These effects attenuated growth and proliferation, increased apoptosis and autophagy, and increased oxidative stress and mTORC1 pathway suppression in head and neck squamous cell carcinoma (HNSCC). Additionally, silencing ASCT2 improved the response to cetuximab in HNSCC.

In some embodiments, an antibody-drug conjugate provided herein binds to TROP2. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 16, 17, 18, 19, 20, and 21, respectively. In some embodiments, the antibody of the antibody drug conjugate comprises a heavy chain variable region comprising the amino acid sequence of SEQ ID NO: 22 and a light chain variable region comprising the amino acid sequence of SEQ ID NO: 23. In some embodiments, the antibody of the antibody drug conjugate is sacituzumab. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 24, 25, 26, 27, 28, and 29, respectively. In some embodiments, the antibody of the antibody drug conjugate comprises a heavy chain variable region comprising the amino acid sequence of SEQ ID NO: 30 and a light chain variable region comprising the amino acid sequence of SEQ ID NO: 31. In some embodiments, the antibody of the antibody drug conjugate is datopotamab.

In some embodiments, an antibody-drug conjugate provided herein binds to MICA. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 32, 33, 34, 35, 36, and 37, respectively. In some embodiments, the antibody of the antibody drug conjugate comprises a heavy chain variable region comprising the amino acid sequence of SEQ ID NO: 38 and a light chain variable region comprising the amino acid sequence of SEQ ID NO: 39. In some embodiments, the antibody of the antibody drug conjugate is h1D5v11 hIgG1K. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 40, 41, 42, 43, 44, and 45, respectively. In some embodiments, the antibody of the antibody drug conjugate comprises a heavy chain variable region comprising the amino acid sequence of SEQ ID NO: 46 and a light chain variable region comprising the amino acid sequence of SEQ ID NO: 47. In some embodiments, the antibody of the antibody drug conjugate is MICA.36 hIgG1K G236A. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 48, 49, 50, 51, 52, and 53, respectively. In some embodiments, the antibody of the antibody drug conjugate comprises a heavy chain variable region comprising the amino acid sequence of SEQ ID NO: 54 and a light chain variable region comprising the amino acid sequence of SEQ ID NO: 55. In some embodiments, the antibody of the antibody drug conjugate is h3F9 H1L3 hIgG1K. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 56, 57, 58, 59, 60, and 61, respectively. In some embodiments, the antibody of the antibody drug conjugate comprises a heavy chain variable region comprising the amino acid sequence of SEQ ID NO: 62 and a light chain variable region comprising the amino acid sequence of SEQ ID NO: 63. In some embodiments, the antibody of the antibody drug conjugate is CM33322 Ab28 hIgG1K.

In some embodiments, an antibody-drug conjugate provided herein binds to CD24. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 64, 65, 66, 67, 68, and 69, respectively. In some embodiments, the antibody of the antibody drug conjugate comprises a heavy chain variable region comprising the amino acid sequence of SEQ ID NO: 70 and a light chain variable region comprising the amino acid sequence of SEQ ID NO: 71. In some embodiments, the antibody of the antibody drug conjugate is SWA11.

In some embodiments, an antibody-drug conjugate provided herein binds to ITGav. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 72, 73, 74, 75, 76, and 77, respectively. In some embodiments, the antibody of the antibody drug conjugate comprises a heavy chain variable region comprising the amino acid sequence of SEQ ID NO: 78 and a light chain variable region comprising the amino acid sequence of SEQ ID NO: 79. In some embodiments, the antibody of the antibody drug conjugate is intetumumab. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 80, 81, 82, 83, 84, and 85, respectively. In some embodiments, the antibody of the antibody drug conjugate comprises a heavy chain variable region comprising the amino acid sequence of SEQ ID NO: 86 and a light chain variable region comprising the amino acid sequence of SEQ ID NO: 87. In some embodiments, the antibody of the antibody drug conjugate is abituzumab.

In some embodiments, an antibody-drug conjugate provided herein binds to gpA33. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 88, 89, 90, 91, 92, and 93, respectively. In some embodiments, the antibody of the antibody drug conjugate comprises a heavy chain variable region comprising the amino acid sequence of SEQ ID NO: 94 and a light chain variable region comprising the amino acid sequence of SEQ ID NO: 95.

In some embodiments, an antibody-drug conjugate provided herein binds to IL1Rap. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 96, 97, 98, 99, 100, and 101, respectively. In some embodiments, the antibody of the antibody drug conjugate comprises a heavy chain variable region comprising the amino acid sequence of SEQ ID NO: 102 and a light chain variable region comprising the amino acid sequence of SEQ ID NO: 103. In some embodiments, the antibody of the antibody drug conjugate is nidanilimab.

In some embodiments, an antibody-drug conjugate provided herein binds to EpCAM. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 104, 105, 106, 017, 108, and 109, respectively. In some embodiments, the antibody of the antibody drug conjugate comprises a heavy chain variable region comprising the amino acid sequence of SEQ ID NO: 110 and a light chain variable region comprising the amino acid sequence of SEQ ID NO: 111. In some embodiments, the antibody of the antibody drug conjugate is adecatumumab. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 112, 113, 114, 115, 116, and 117, respectively. In some embodiments, the antibody of the antibody drug conjugate comprises a heavy chain variable region comprising the amino acid sequence of SEQ ID NO: 118 and a light chain variable region comprising the amino acid sequence of SEQ ID NO: 119. In some embodiments, the antibody of the antibody drug conjugate is Ep157305. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 120, 121, 122, 123, 124, and 125, respectively. In some embodiments, the antibody of the antibody drug conjugate comprises a heavy chain variable region comprising the amino acid sequence of SEQ ID NO: 126 and a light chain variable region comprising the amino acid sequence of SEQ ID NO: 127. In some embodiments, the antibody of the antibody drug conjugate is Ep3-171. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 128, 129, 130, 131, 132, and 133, respectively. In some embodiments, the antibody of the antibody drug conjugate comprises a heavy chain variable region comprising the amino acid sequence of SEQ ID NO: 134 and a light chain variable region comprising the amino acid sequence of SEQ ID NO: 135. In some embodiments, the antibody of the antibody drug conjugate is Ep3622w94. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 136, 137, 138, 139, 140, and 141, respectively. In some embodiments, the antibody of the antibody drug conjugate comprises a heavy chain variable region comprising the amino acid sequence of SEQ ID NO: 142 and a light chain variable region comprising the amino acid sequence of SEQ ID NO: 143. In some embodiments, the antibody of the antibody drug conjugate is EpING1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 144, 145, 146, 147, 148, and 149, respectively. In some embodiments, the antibody of the antibody drug conjugate comprises a heavy chain variable region comprising the amino acid sequence of SEQ ID NO: 150 and a light chain variable region comprising the amino acid sequence of SEQ ID NO: 151. In some embodiments, the antibody of the antibody drug conjugate is EpAb2-6.

In some embodiments, an antibody-drug conjugate provided herein binds to CD352. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 152, 153, 154, 155, 156, and 157, respectively. In some embodiments, the antibody of the antibody drug conjugate comprises a heavy chain variable region comprising the amino acid sequence of SEQ ID NO: 158 and a light chain variable region comprising the amino acid sequence of SEQ ID NO: 159. In some embodiments, the antibody of the antibody drug conjugate is h20F3.

In some embodiments, an antibody-drug conjugate provided herein binds to CS1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 160, 161, 162, 163, 164, and 165, respectively. In some embodiments, the antibody of the antibody drug conjugate comprises a heavy chain variable region comprising the amino acid sequence of SEQ ID NO: 166 and a light chain variable region comprising the amino acid sequence of SEQ ID NO: 167. In some embodiments, the antibody of the antibody drug conjugate is elotuzumab.

In some embodiments, an antibody-drug conjugate provided herein binds to CD38. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 168, 169, 170, 171, 172, and 173, respectively. In some embodiments, the antibody of the antibody drug conjugate comprises a heavy chain variable region comprising the amino acid sequence of SEQ ID NO: 174 and a light chain variable region comprising the amino acid sequence of SEQ ID NO: 175. In some embodiments, the antibody of the antibody drug conjugate is daratumumab.

In some embodiments, an antibody-drug conjugate provided herein binds to CD25. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 176, 177, 178, 179, 180, and 181, respectively. In some embodiments, the antibody of the antibody drug conjugate comprises a heavy chain variable region comprising the amino acid sequence of SEQ ID NO: 182 and a light chain variable region comprising the amino acid sequence of SEQ ID NO: 183. In some embodiments, the antibody of the antibody drug conjugate is daclizumab.

In some embodiments, an antibody-drug conjugate provided herein binds to ADAM9. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 184, 185, 186, 187, 188, and 189, respectively. In some embodiments, the antibody of the antibody drug conjugate comprises a heavy chain variable region comprising the amino acid sequence of SEQ ID NO: 190 and a light chain variable region comprising the amino acid sequence of SEQ ID NO: 191. In some embodiments, the antibody of the antibody drug conjugate is chMAbA9-A. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 192, 193, 194, 195, 196, and 197, respectively. In some embodiments, the antibody of the antibody drug conjugate comprises a heavy chain variable region comprising the amino acid sequence of SEQ ID NO: 198 and a light chain variable region comprising the amino acid sequence of SEQ ID NO: 199. In some embodiments, the antibody of the antibody drug conjugate is hMAbA9-A.

In some embodiments, an antibody-drug conjugate provided herein binds to CD59. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 200, 201, 202, 203, 204, and 205, respectively. In some embodiments, the antibody of the antibody drug conjugate comprises a heavy chain variable region comprising the amino acid sequence of SEQ ID NO: 206 and a light chain variable region comprising the amino acid sequence of SEQ ID NO: 207.

In some embodiments, an antibody-drug conjugate provided herein binds to CD25. In some embodiments, the antibody of the antibody drug conjugate is Clone123.

In some embodiments, an antibody-drug conjugate provided herein binds to CD229. In some embodiments, the antibody of the antibody drug conjugate is h8A10.

In some embodiments, an antibody-drug conjugate provided herein binds to CD19. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 208, 209, 210, 211, 212, and 213, respectively. In some embodiments, the antibody of the antibody drug conjugate comprises a heavy chain variable region comprising the amino acid sequence of SEQ ID NO: 214 and a light chain variable region comprising the amino acid sequence of SEQ ID NO: 215. In some embodiments, the antibody of the antibody drug conjugate is denintuzumab, which is also known as hBU12. See WO2009052431.

In some embodiments, an antibody-drug conjugate provided herein binds to CD70. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 216, 217, 218, 219, 220, and 221, respectively. In some embodiments, the antibody of the antibody drug conjugate comprises a heavy chain variable region comprising the amino acid sequence of SEQ ID NO: 222 and a light chain variable region comprising the amino acid sequence of SEQ ID NO: 223. In some embodiments, the antibody of the antibody drug conjugate is vorsetuzumab.

In some embodiments, an antibody-drug conjugate provided herein binds to B7H4. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 224, 225, 226, 227, 228, and 229, respectively. In some embodiments, the antibody of the antibody drug conjugate comprises a heavy chain variable region comprising the amino acid sequence of SEQ ID NO: 230 and a light chain variable region comprising the amino acid sequence of SEQ ID NO: 231. In some embodiments, the antibody of the antibody drug conjugate is mirzotamab.

In some embodiments, an antibody-drug conjugate provided herein binds to CD138. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 232, 233, 234, 235, 236, and 237, respectively. In some embodiments, the antibody of the antibody drug conjugate comprises a heavy chain variable region comprising the amino acid sequence of SEQ ID NO: 238 and a light chain variable region comprising the amino acid sequence of SEQ ID NO: 239. In some embodiments, the antibody of the antibody drug conjugate is indatuximab.

In some embodiments, an antibody-drug conjugate provided herein binds to CD166. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 240, 241, 242, 243, 244, and 245, respectively. In some embodiments, the antibody of the antibody drug conjugate comprises a heavy chain variable region comprising the amino acid sequence of SEQ ID NO: 246 and a light chain variable region comprising the amino acid sequence of SEQ ID NO: 247. In some embodiments, the antibody of the antibody drug conjugate is praluzatamab.

In some embodiments, an antibody-drug conjugate provided herein binds to CD51. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 248, 249, 250, 251, 252, and 253, respectively. In some embodiments, the antibody of the antibody drug conjugate comprises a heavy chain variable region comprising the amino acid sequence of SEQ ID NO: 254 and a light chain variable region comprising the amino acid sequence of SEQ ID NO: 255. In some embodiments, the antibody of the antibody drug conjugate is intetumumab.

In some embodiments, an antibody-drug conjugate provided herein binds to CD56. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 256, 257, 258, 259, 260, and 261, respectively. In some embodiments, the antibody of the antibody drug conjugate comprises a heavy chain variable region comprising the amino acid sequence of SEQ ID NO: 262 and a light chain variable region comprising the amino acid sequence of SEQ ID NO: 263. In some embodiments, the antibody of the antibody drug conjugate is lorvotuzumab.

In some embodiments, an antibody-drug conjugate provided herein binds to CD74. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 264, 265, 266, 267, 268, and 269, respectively. In some embodiments, the antibody of the antibody drug conjugate comprises a heavy chain variable region comprising the amino acid sequence of SEQ ID NO: 270 and a light chain variable region comprising the amino acid sequence of SEQ ID NO: 271. In some embodiments, the antibody of the antibody drug conjugate is milatuzumab.

In some embodiments, an antibody-drug conjugate provided herein binds to CEACAM5. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 272, 273 274, 275, 276, and 277, respectively. In some embodiments, the antibody of the antibody drug conjugate comprises a heavy chain variable region comprising the amino acid sequence of SEQ ID NO: 278 and a light chain variable region comprising the amino acid sequence of SEQ ID NO: 279. In some embodiments, the antibody of the antibody drug conjugate is labetuzumab.

In some embodiments, an antibody-drug conjugate provided herein binds to CanAg. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 280, 281, 282, 283, 284, and 285, respectively. In some embodiments, the antibody of the antibody drug conjugate comprises a heavy chain variable region comprising the amino acid sequence of SEQ ID NO: 286 and a light chain variable region comprising the amino acid sequence of SEQ ID NO: 287. In some embodiments, the antibody of the antibody drug conjugate is cantuzumab.

In some embodiments, an antibody-drug conjugate provided herein binds to DLL-3. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 288, 289, 290, 291, 292, and 293, respectively. In some embodiments, the antibody of the antibody drug conjugate comprises a heavy chain variable region comprising the amino acid sequence of SEQ ID NO: 294 and a light chain variable region comprising the amino acid sequence of SEQ ID NO: 295. In some embodiments, the antibody of the antibody drug conjugate is rovalpituzumab.

In some embodiments, an antibody-drug conjugate provided herein binds to DPEP-3. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 296, 297, 298, 299, 300, and 301, respectively. In some embodiments, the antibody of the antibody drug conjugate comprises a heavy chain variable region comprising the amino acid sequence of SEQ ID NO: 302 and a light chain variable region comprising the amino acid sequence of SEQ ID NO: 303. In some embodiments, the antibody of the antibody drug conjugate is tamrintamab.

In some embodiments, an antibody-drug conjugate provided herein binds to EGFR. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 304, 305, 306, 307, 308, and 309, respectively. In some embodiments, the antibody of the antibody drug conjugate comprises a heavy chain variable region comprising the amino acid sequence of SEQ ID NO: 310 and a light chain variable region comprising the amino acid sequence of SEQ ID NO: 311. In some embodiments, the antibody of the antibody drug conjugate is laprituximab. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 312, 313, 314, 315, 316, and 317, respectively. In some embodiments, the antibody of the antibody drug conjugate comprises a heavy chain variable region comprising the amino acid sequence of SEQ ID NO: 318 and a light chain variable region comprising the amino acid sequence of SEQ ID NO: 319. In some embodiments, the antibody of the antibody drug conjugate is losatuxizumab. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 320, 321, 322, 323, 324, and 325, respectively. In some embodiments, the antibody of the antibody drug conjugate comprises a heavy chain variable region comprising the amino acid sequence of SEQ ID NO: 326 and a light chain variable region comprising the amino acid sequence of SEQ ID NO: 327. In some embodiments, the antibody of the antibody drug conjugate is serclutamab. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 328, 329, 330, 331, 332, and 333, respectively. In some embodiments, the antibody of the antibody drug conjugate comprises a heavy chain variable region comprising the amino acid sequence of SEQ ID NO: 334 and a light chain variable region comprising the amino acid sequence of SEQ ID NO: 335. In some embodiments, the antibody of the antibody drug conjugate is cetuximab.

In some embodiments, an antibody-drug conjugate provided herein binds to FRa. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 336, 337, 338, 339, 340, and 341, respectively. In some embodiments, the antibody of the antibody drug conjugate comprises a heavy chain variable region comprising the amino acid sequence of SEQ ID NO: 342 and a light chain variable region comprising the amino acid sequence of SEQ ID NO: 343. In some embodiments, the antibody of the antibody drug conjugate is mirvetuximab. In some embodiments, the antibody of the antibody drug conjugate comprises CDR- H1, CDR-H2, CDR-H3, CDR-L1, CDR-L2, and CDR-L3 comprising the amino acid sequences of SEQ ID NOs: 344, 345, 346, 347, 348, and 349, respectively. In some embodiments, the antibody of the antibody drug conjugate comprises a heavy chain variable region comprising the amino acid sequence of SEQ ID NO: 350 and a light chain variable region comprising the amino acid sequence of SEQ ID NO: 351. In some embodiments, the antibody of the antibody drug conjugate is farletuzumab.

In some embodiments, an antibody-drug conjugate provided herein binds to MUC-1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 352, 353, 354, 355, 356, and 357, respectively. In some embodiments, the antibody of the antibody drug conjugate comprises a heavy chain variable region comprising the amino acid sequence of SEQ ID NO: 358 and a light chain variable region comprising the amino acid sequence of SEQ ID NO: 359. In some embodiments, the antibody of the antibody drug conjugate is gatipotuzumab.

In some embodiments, an antibody-drug conjugate provided herein binds to mesothelin. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 360, 361, 362, 363, 364, and 365, respectively. In some embodiments, the antibody of the antibody drug conjugate comprises a heavy chain variable region comprising the amino acid sequence of SEQ ID NO: 366 and a light chain variable region comprising the amino acid sequence of SEQ ID NO: 367. In some embodiments, the antibody of the antibody drug conjugate is anetumab.

In some embodiments, an antibody-drug conjugate provided herein binds to ROR-1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 368, 369, 370, 371, 372, and 373, respectively. In some embodiments, the antibody of the antibody drug conjugate comprises a heavy chain variable region comprising the amino acid sequence of SEQ ID NO: 374 and a light chain variable region comprising the amino acid sequence of SEQ ID NO: 375. In some embodiments, the antibody of the antibody drug conjugate is zilovertamab.

In some embodiments, an antibody-drug conjugate provided herein binds to ASCT2. In some embodiments, an antibody-drug conjugate provided herein binds to B7H4. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 376, 377, 378, 379, 380, and 381, respectively. In some embodiments, the antibody of the antibody drug conjugate comprises a heavy chain variable region comprising the amino acid sequence of SEQ ID NO: 382 and a light chain variable region comprising the amino acid sequence of SEQ ID NO: 383. In some embodiments, the antibody of the antibody drug conjugate is 20502. See WO2019040780.

In some embodiments, an antibody-drug conjugate provided herein binds to B7-H3. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 384, 385, 386, 387, 388, and 389, respectively. In some embodiments, the antibody of the antibody drug conjugate comprises a heavy chain variable region comprising the amino acid sequence of SEQ ID NO: 390 and a light chain variable region comprising the amino acid sequence of SEQ ID NO: 391. In some embodiments, the antibody of the antibody drug conjugate is chAb-A (BRCA84D). In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 392, 393, 394, 395, 396, and 397, respectively. In some embodiments, the antibody of the antibody drug conjugate comprises a heavy chain variable region comprising the amino acid sequence of SEQ ID NO: 398 and a light chain variable region comprising the amino acid sequence of SEQ ID NO: 399. In some embodiments, the antibody of the antibody drug conjugate is hAb-B. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 400, 401, 402, 403, 404, and 405, respectively. In some embodiments, the antibody of the antibody drug conjugate comprises a heavy chain variable region comprising the amino acid sequence of SEQ ID NO: 406 and a light chain variable region comprising the amino acid sequence of SEQ ID NO: 407. In some embodiments, the antibody of the antibody drug conjugate is hAb-C. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 408, 409, 410, 411, 412, and 413, respectively. In some embodiments, the antibody of the antibody drug conjugate comprises a heavy chain variable region comprising the amino acid sequence of SEQ ID NO: 414 and a light chain variable region comprising the amino acid sequence of SEQ ID NO: 415. In some embodiments, the antibody of the antibody drug conjugate is hAb-D. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 416, 417, 418, 419, 420, and 421, respectively. In some embodiments, the antibody of the antibody drug conjugate comprises a heavy chain variable region comprising the amino acid sequence of SEQ ID NO: 422 and a light chain variable region comprising the amino acid sequence of SEQ ID NO: 423. In some embodiments, the antibody of the antibody drug conjugate is chM30. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 424, 425, 426, 427, 428, and 429, respectively. In some embodiments, the antibody of the antibody drug conjugate comprises a heavy chain variable region comprising the amino acid sequence of SEQ ID NO: 430 and a light chain variable region comprising the amino acid sequence of SEQ ID NO: 431. In some embodiments, the antibody of the antibody drug conjugate is hM30-H1-L4. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 432, 433, 434, 435, 436, and 437, respectively. In some embodiments, the antibody of the antibody drug conjugate comprises a heavy chain variable region comprising the amino acid sequence of SEQ ID NO: 438 and a light chain variable region comprising the amino acid sequence of SEQ ID NO: 439. In some embodiments, the antibody of the antibody drug conjugate is AbV_huAb18-v4. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 440, 441, 442, 443, 444, and 445, respectively. In some embodiments, the antibody of the antibody drug conjugate comprises a heavy chain variable region comprising the amino acid sequence of SEQ ID NO: 446 and a light chain variable region comprising the amino acid sequence of SEQ ID NO: 447. In some embodiments, the antibody of the antibody drug conjugate is AbV_huAb3-v6. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 448, 449, 450, 451, 452, and 453, respectively. In some embodiments, the antibody of the antibody drug conjugate comprises a heavy chain variable region comprising the amino acid sequence of SEQ ID NO: 454 and a light chain variable region comprising the amino acid sequence of SEQ ID NO: 455. In some embodiments, the antibody of the antibody drug conjugate is AbV_huAb3-v2.6. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 456, 457, 458, 459, 460, and 461, respectively. In some embodiments, the antibody of the antibody drug conjugate comprises a heavy chain variable region comprising the amino acid sequence of SEQ ID NO: 462 and a light chain variable region comprising the amino acid sequence of SEQ ID NO: 463. In some embodiments, the antibody of the antibody drug conjugate is AbV_huAb13-v1-CR. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 464, 465, 466, 467, 468, and 469, respectively. In some embodiments, the antibody of the antibody drug conjugate comprises a heavy chain variable region comprising the amino acid sequence of SEQ ID NO: 470 and a light chain variable region comprising the amino acid sequence of SEQ ID NO: 471. In some embodiments, the antibody of the antibody drug conjugate is 8H9-6m. In some embodiments, the antibody of the antibody drug conjugate comprises a heavy chain variable region comprising the amino acid sequence of SEQ ID NO: 472 and a light chain variable region comprising the amino acid sequence of SEQ ID NO: 473. In some embodiments, the antibody of the antibody drug conjugate is m8517. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 474, 475, 476, 477, 478, and 479, respectively. In some embodiments, the antibody of the antibody drug conjugate comprises a heavy chain variable region comprising the amino acid sequence of SEQ ID NO: 480 and a light chain variable region comprising the amino acid sequence of SEQ ID NO: 481. In some embodiments, the antibody of the antibody drug conjugate is TPP-5706. In some embodiments, the antibody of the antibody drug conjugate comprises a heavy chain variable region comprising the amino acid sequence of SEQ ID NO: 482 and a light chain variable region comprising the amino acid sequence of SEQ ID NO: 483. In some embodiments, the antibody of the antibody drug conjugate is TPP-6642. In some embodiments, the antibody of the antibody drug conjugate comprises a heavy chain variable region comprising the amino acid sequence of SEQ ID NO: 484 and a light chain variable region comprising the amino acid sequence of SEQ ID NO: 485. In some embodiments, the antibody of the antibody drug conjugate is TPP-6850.

In some embodiments, an antibody-drug conjugate provided herein binds to CDCP1. In some embodiments, the antibody of the antibody drug conjugate is 10D7.

In some embodiments, an antibody-drug conjugate provided herein binds to HER3. In some embodiments, the antibody of the antibody drug conjugate comprises a heavy chain comprising the amino acid sequence of SEQ ID NO: 486 and a light chain comprising the amino acid sequence of SEQ ID NO: 487. In some embodiments, the antibody of the antibody drug conjugate is patritumab. In some embodiments, the antibody of the antibody drug conjugate comprises a heavy chain comprising the amino acid sequence of SEQ ID NO: 488 and a light chain comprising the amino acid sequence of SEQ ID NO: 489. In some embodiments, the antibody of the antibody drug conjugate is seribantumab. In some embodiments, the antibody of the antibody drug conjugate comprises a heavy chain comprising the amino acid sequence of SEQ ID NO: 490 and a light chain comprising the amino acid sequence of SEQ ID NO: 491. In some embodiments, the antibody of the antibody drug conjugate is elgemtumab. In some embodiments, the antibody of the antibody drug conjugate comprises a heavy chain the amino acid sequence of SEQ ID NO: 492 and a light chain comprising the amino acid sequence of SEQ ID NO: 493. In some embodiments, the antibody of the antibody drug conjugate is lumretuzumab.

In some embodiments, an antibody-drug conjugate provided herein binds to RON. In some embodiments, the antibody of the antibody drug conjugate is Zt/g4.

In some embodiments, an antibody-drug conjugate provided herein binds to claudin-2.

In some embodiments, an antibody-drug conjugate provided herein binds to HLA-G.

In some embodiments, an antibody-drug conjugate provided herein binds to PTK7. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 494, 495, 496, 497, 498, and 499, respectively. In some embodiments, the antibody of the antibody drug conjugate comprises a heavy chain variable region comprising the amino acid sequence of SEQ ID NO: 500 and a light chain variable region comprising the amino acid sequence of SEQ ID NO: 501. In some embodiments, the antibody of the antibody drug conjugate is PTK7 mab 1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 502, 503, 504, 505, 506, and 507, respectively. In some embodiments, the antibody of the antibody drug conjugate comprises a heavy chain variable region comprising the amino acid sequence of SEQ ID NO: 508 and a light chain variable region comprising the amino acid sequence of SEQ ID NO: 509. In some embodiments, the antibody of the antibody drug conjugate is PTK7 mab 2. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 510, 511, 512, 513, 514, and 515, respectively. In some embodiments, the antibody of the antibody drug conjugate comprises a heavy chain variable region comprising the amino acid sequence of SEQ ID NO: 516 and a light chain variable region comprising the amino acid sequence of SEQ ID NO: 517. In some embodiments, the antibody of the antibody drug conjugate is PTK7 mab 3.

In some embodiments, an antibody-drug conjugate provided herein binds to LIV1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 518, 519, 520, 521, 522, and 523, respectively. In some embodiments, the antibody of the antibody drug conjugate comprises a heavy chain variable region comprising the amino acid sequence of SEQ ID NO: 524 and a light chain variable region comprising the amino acid sequence of SEQ ID NO: 525. In some embodiments, the antibody of the antibody drug conjugate is ladiratuzumab, which is also known as hLIV22 and hglg. See WO2012078668.

In some embodiments, an antibody-drug conjugate provided herein binds to avb6. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 526, 527, 528, 529, 530, and 531, respectively. In some embodiments, the antibody of the antibody drug conjugate comprises a heavy chain variable region comprising the amino acid sequence of SEQ ID NO: 532 and a light chain variable region comprising the amino acid sequence of SEQ ID NO: 533. In some embodiments, the antibody of the antibody drug conjugate is h2A2. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 534, 535, 536, 537, 538, and 539, respectively. In some embodiments, the antibody of the antibody drug conjugate comprises a heavy chain variable region comprising the amino acid sequence of SEQ ID NO: 540 and a light chain variable region comprising the amino acid sequence of SEQ ID NO: 541. In some embodiments, the antibody of the antibody drug conjugate is h15H3.

In some embodiments, an antibody-drug conjugate provided herein binds to CD48. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 542, 543, 544, 545, 546, and 547, respectively. In some embodiments, the antibody of the antibody drug conjugate comprises a heavy chain variable region comprising the amino acid sequence of SEQ ID NO: 548 and a light chain variable region comprising the amino acid sequence of SEQ ID NO: 549. In some embodiments, the antibody of the antibody drug conjugate is hMEM102. See WO2016149535.

In some embodiments, an antibody-drug conjugate provided herein binds to PD-L1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 550, 551, 552, 553, 554, and 555, respectively. In some embodiments, the antibody of the antibody drug conjugate comprises a heavy chain variable region comprising the amino acid sequence of SEQ ID NO: 556 and a light chain variable region comprising the amino acid sequence of SEQ ID NO: 557. In some embodiments, the antibody of the antibody drug conjugate is SG-559-01 LALA mAb.

In some embodiments, an antibody-drug conjugate provided herein binds to IGF-1R. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 558, 559, 560, 561, 562, and 563, respectively. In some embodiments, the antibody of the antibody drug conjugate comprises a heavy chain variable region comprising the amino acid sequence of SEQ ID NO: 564 and a light chain variable region comprising the amino acid sequence of SEQ ID NO: 565. In some embodiments, the antibody of the antibody drug conjugate is cixutumumab.

In some embodiments, an antibody-drug conjugate provided herein binds to claudin-18.2. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 566, 567, 568, 569, 570, and 571, respectively. In some embodiments, the antibody of the antibody drug conjugate comprises a heavy chain variable region comprising the amino acid sequence of SEQ ID NO: 572 and a light chain variable region comprising the amino acid sequence of SEQ ID NO: 573. In some embodiments, the antibody of the antibody drug conjugate is zolbetuximab (175D10). In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 574, 575, 576, 577, 578, and 579, respectively. In some embodiments, the antibody of the antibody drug conjugate comprises a heavy chain variable region comprising the amino acid sequence of SEQ ID NO: 580 and a light chain variable region comprising the amino acid sequence of SEQ ID NO: 581. In some embodiments, the antibody of the antibody drug conjugate is 163E12.

In some embodiments, an antibody-drug conjugate provided herein binds to Nectin-4. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 582, 583, 584, 585, 586, and 587, respectively. In some embodiments, the antibody of the antibody drug conjugate comprises a heavy chain variable region comprising the amino acid sequence of SEQ ID NO: 588 and a light chain variable region comprising the amino acid sequence of SEQ ID NO: 589. In some embodiments, the antibody of the antibody drug conjugate is enfortumab. See WO 2012047724.

In some embodiments, an antibody-drug conjugate provided herein binds to SLTRK6. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 590, 591, 592, 593, 594, and 595, respectively. In some embodiments, the antibody of the antibody drug conjugate comprises a heavy chain variable region comprising the amino acid sequence of SEQ ID NO: 596 and a light chain variable region comprising the amino acid sequence of SEQ ID NO: 597. In some embodiments, the antibody of the antibody drug conjugate is sirtratumab.

In some embodiments, an antibody-drug conjugate provided herein binds to CD228. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 598, 599, 600, 601, 602, and 603, respectively. In some embodiments, the antibody of the antibody drug conjugate comprises a heavy chain variable region comprising the amino acid sequence of SEQ ID NO: 604 and a light chain variable region comprising the amino acid sequence of SEQ ID NO: 605. In some embodiments, the antibody of the antibody drug conjugate is hL49. See WO 2020/163225.

In some embodiments, an antibody-drug conjugate provided herein binds to CD142 (tissue factor; TF). In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 606, 607, 608, 609, 610, and 611, respectively. In some embodiments, the antibody of the antibody drug conjugate comprises a heavy chain variable region comprising the amino acid sequence of SEQ ID NO: 612 and a light chain variable region comprising the amino acid sequence of SEQ ID NO: 613. In some embodiments, the antibody of the antibody drug conjugate is tisotumab. See WO 2010/066803.

In some embodiments, an antibody-drug conjugate provided herein binds to STn. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 614, 615, 616, 617, 618, and 619, respectively. In some embodiments, the antibody of the antibody drug conjugate comprises a heavy chain variable region comprising the amino acid sequence of SEQ ID NO: 620 and a light chain variable region comprising the amino acid sequence of SEQ ID NO: 621. In some embodiments, the antibody of the antibody drug conjugate is h2G12.

In some embodiments, an antibody-drug conjugate provided herein binds to CD20. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 622, 623, 624, 625, 626, and 627, respectively. In some embodiments, the antibody of the antibody drug conjugate comprises a heavy chain variable region comprising the amino acid sequence of SEQ ID NO: 628 and a light chain variable region comprising the amino acid sequence of SEQ ID NO: 629. In some embodiments, the antibody of the antibody drug conjugate is rituximab.

In some embodiments, an antibody-drug conjugate provided herein binds to HER2. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 630, 631, 632, 633, 634, and 635, respectively. In some embodiments, the antibody of the antibody drug conjugate comprises a heavy chain variable region comprising the amino acid sequence of SEQ ID NO: 636 and a light chain variable region comprising the amino acid sequence of SEQ ID NO: 637. In some embodiments, the antibody of the antibody drug conjugate is trastuzumab.

In some embodiments, an antibody-drug conjugate provided herein binds to FLT3.

In some embodiments, an antibody-drug conjugate provided herein binds to CD46.

In some embodiments, an antibody-drug conjugate provided herein binds to GloboH.

In some embodiments, an antibody-drug conjugate provided herein binds to AG7.

In some embodiments, an antibody-drug conjugate provided herein binds to mesothelin.

In some embodiments, an antibody-drug conjugate provided herein binds to FCRH5.

In some embodiments, an antibody-drug conjugate provided herein binds to ETBR.

In some embodiments, an antibody-drug conjugate provided herein binds to Tim-1.

In some embodiments, an antibody-drug conjugate provided herein binds to SLC44A4.

In some embodiments, an antibody-drug conjugate provided herein binds to ENPP3.

In some embodiments, an antibody-drug conjugate provided herein binds to CD37.

In some embodiments, an antibody-drug conjugate provided herein binds to CA9.

In some embodiments, an antibody-drug conjugate provided herein binds to Notch3.

In some embodiments, an antibody-drug conjugate provided herein binds to EphA2.

In some embodiments, an antibody-drug conjugate provided herein binds to TRFC.

In some embodiments, an antibody-drug conjugate provided herein binds to PSMA.

In some embodiments, an antibody-drug conjugate provided herein binds to LRRC15.

In some embodiments, an antibody-drug conjugate provided herein binds to 5T4.

In some embodiments, an antibody-drug conjugate provided herein binds to CD79b. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 638, 639, 640, 641, 642, and 643, respectively. In some embodiments, the antibody of the antibody drug conjugate comprises a heavy chain variable region comprising the amino acid sequence of SEQ ID NO: 644 and a light chain variable region comprising the amino acid sequence of SEQ ID NO: 645. In some embodiments, the antibody of the antibody drug conjugate is polatuzumab.

In some embodiments, an antibody-drug conjugate provided herein binds to NaPi2B. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 646, 647, 648, 649, 650, and 651, respectively. In some embodiments, the antibody of the antibody drug conjugate comprises a heavy chain variable region comprising the amino acid sequence of SEQ ID NO: 652 and a light chain variable region comprising the amino acid sequence of SEQ ID NO: 653. In some embodiments, the antibody of the antibody drug conjugate is lifastuzumab.

In some embodiments, an antibody-drug conjugate provided herein binds to Muc16. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 654, 655, 656, 657, 658, and 659, respectively. In some embodiments, the antibody of the antibody drug conjugate comprises a heavy chain variable region comprising the amino acid sequence of SEQ ID NO: 660 and a light chain variable region comprising the amino acid sequence of SEQ ID NO: 661. In some embodiments, the antibody of the antibody drug conjugate is sofituzumab.

In some embodiments, an antibody-drug conjugate provided herein binds to STEAPI. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 662, 663, 664, 665, 666, and 667, respectively. In some embodiments, the antibody of the antibody drug conjugate comprises a heavy chain variable region comprising the amino acid sequence of SEQ ID NO: 668 and a light chain variable region comprising the amino acid sequence of SEQ ID NO: 669. In some embodiments, the antibody of the antibody drug conjugate is vandortuzumab.

In some embodiments, an antibody-drug conjugate provided herein binds to BCMA. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 670, 671, 672, 673, 674, and 675, respectively. In some embodiments, the antibody of the antibody drug conjugate comprises a heavy chain variable region comprising the amino acid sequence of SEQ ID NO: 676 and a light chain variable region comprising the amino acid sequence of SEQ ID NO: 677. In some embodiments, the antibody of the antibody drug conjugate is belantamab.

In some embodiments, an antibody-drug conjugate provided herein binds to c-Met. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 678, 679, 680, 681, 682, and 683, respectively. In some embodiments, the antibody of the antibody drug conjugate comprises a heavy chain variable region comprising the amino acid sequence of SEQ ID NO: 684 and a light chain variable region comprising the amino acid sequence of SEQ ID NO: 685. In some embodiments, the antibody of the antibody drug conjugate is telisotuzumab.

In some embodiments, an antibody-drug conjugate provided herein binds to EGFR. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 686, 687, 688, 689, 690, and 691, respectively. In some embodiments, the antibody of the antibody drug conjugate comprises a heavy chain variable region comprising the amino acid sequence of SEQ ID NO: 692 and a light chain variable region comprising the amino acid sequence of SEQ ID NO: 693. In some embodiments, the antibody of the antibody drug conjugate is depatuxizumab.

In some embodiments, an antibody-drug conjugate provided herein binds to SLAMF7. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 694, 695, 696, 697, 698, and 699, respectively. In some embodiments, the antibody of the antibody drug conjugate comprises a heavy chain variable region comprising the amino acid sequence of SEQ ID NO: 700 and a light chain variable region comprising the amino acid sequence of SEQ ID NO: 701. In some embodiments, the antibody of the antibody drug conjugate is azintuxizumab.

In some embodiments, an antibody-drug conjugate provided herein binds to SLITRK6. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 702, 703, 704, 705, 706, and 707, respectively. In some embodiments, the antibody of the antibody drug conjugate comprises a heavy chain variable region comprising the amino acid sequence of SEQ ID NO: 708 and a light chain variable region comprising the amino acid sequence of SEQ ID NO: 709. In some embodiments, the antibody of the antibody drug conjugate is sirtratumab.

In some embodiments, an antibody-drug conjugate provided herein binds to C4.4a. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 710, 711, 712, 713, 714, and 715, respectively. In some embodiments, the antibody of the antibody drug conjugate comprises a heavy chain variable region comprising the amino acid sequence of SEQ ID NO: 716 and a light chain variable region comprising the amino acid sequence of SEQ ID NO: 717. In some embodiments, the antibody of the antibody drug conjugate is lupartumab.

In some embodiments, an antibody-drug conjugate provided herein binds to GCC. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 718, 719, 720, 721, 722, and 723, respectively. In some embodiments, the antibody of the antibody drug conjugate comprises a heavy chain variable region comprising the amino acid sequence of SEQ ID NO: 724 and a light chain variable region comprising the amino acid sequence of SEQ ID NO: 725. In some embodiments, the antibody of the antibody drug conjugate is indusatumab.

In some embodiments, an antibody-drug conjugate provided herein binds to Axl. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 726, 727, 728, 729, 730, and 731, respectively. In some embodiments, the antibody of the antibody drug conjugate comprises a heavy chain variable region comprising the amino acid sequence of SEQ ID NO: 732 and a light chain variable region comprising the amino acid sequence of SEQ ID NO: 733. In some embodiments, the antibody of the antibody drug conjugate is enapotamab.

In some embodiments, an antibody-drug conjugate provided herein binds to gpNMB. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 734, 735, 736, 737, 738, and 739, respectively. In some embodiments, the antibody of the antibody drug conjugate comprises a heavy chain variable region comprising the amino acid sequence of SEQ ID NO: 740 and a light chain variable region comprising the amino acid sequence of SEQ ID NO: 741. In some embodiments, the antibody of the antibody drug conjugate is glembatumumab.

In some embodiments, an antibody-drug conjugate provided herein binds to Prolactin receptor. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 742, 743, 744, 745, 746, and 747, respectively. In some embodiments, the antibody of the antibody drug conjugate comprises a heavy chain variable region comprising the amino acid sequence of SEQ ID NO: 748 and a light chain variable region comprising the amino acid sequence of SEQ ID NO: 749. In some embodiments, the antibody of the antibody drug conjugate is rolinsatamab.

In some embodiments, an antibody-drug conjugate provided herein binds to FGFR2. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 750, 751, 752, 753, 754, and 755, respectively. In some embodiments, the antibody of the antibody drug conjugate comprises a heavy chain variable region comprising the amino acid sequence of SEQ ID NO: 756 and a light chain variable region comprising the amino acid sequence of SEQ ID NO: 757. In some embodiments, the antibody of the antibody drug conjugate is aprutumab.

In some embodiments, an antibody-drug conjugate provided herein binds to CDCP1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 758, 759, 760, 761, 762, and 763, respectively. In some embodiments, the antibody of the antibody drug conjugate comprises a heavy chain variable region comprising the amino acid sequence of SEQ ID NO: 764 and a light chain variable region comprising the amino acid sequence of SEQ ID NO: 765. In some embodiments, the antibody of the antibody drug conjugate is Humanized CUB4 #135 HC4-H. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 766, 767, 768, 769, 770, and 771, respectively. In some embodiments, the antibody of the antibody drug conjugate comprises a heavy chain variable region comprising the amino acid sequence of SEQ ID NO: 772 and a light chain variable region comprising the amino acid sequence of SEQ ID NO: 773. In some embodiments, the antibody of the antibody drug conjugate is CUB4. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 774, 775, 776, 777, 778, 779, respectively. In some embodiments, the antibody of the antibody drug conjugate comprises a heavy chain variable region comprising the amino acid sequence of SEQ ID NO: 780 and a light chain variable region comprising the amino acid sequence of SEQ ID NO: 781. In some embodiments, the antibody of the antibody drug conjugate is CP13E10-WT. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 782, 783, 784, 785, 786, and 787, respectively. In some embodiments, the antibody of the antibody drug conjugate comprises a heavy chain variable region comprising the amino acid sequence of SEQ ID NO: 788 and a light chain variable region comprising the amino acid sequence of SEQ ID NO: 789. In some embodiments, the antibody of the antibody drug conjugate is CP13E10-54HCv13-89LCv1.

In some embodiments, an antibody-drug conjugate provided herein binds to ASCT2. In some embodiments, the antibody of the antibody drug conjugate comprises a heavy chain variable region comprising the amino acid sequence of SEQ ID NO: 790 and a light chain variable region comprising the amino acid sequence of SEQ ID NO: 791. In some embodiments, the antibody of the antibody drug conjugate is KM8094a. In some embodiments, the antibody of the antibody drug conjugate comprises a heavy chain variable region comprising the amino acid sequence of SEQ ID NO: 792 and a light chain variable region comprising the amino acid sequence of SEQ ID NO: 793. In some embodiments, the antibody of the antibody drug conjugate is KM8094b. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 794, 795, 796, 797, 798, and 799, respectively. In some embodiments, the antibody of the antibody drug conjugate comprises a heavy chain variable region comprising the amino acid sequence of SEQ ID NO: 800 and a light chain variable region comprising the amino acid sequence of SEQ ID NO: 801. In some embodiments, the antibody of the antibody drug conjugate is KM4018.

In some embodiments, an antibody-drug conjugate provided herein binds to CD123. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 802, 803, 804, 805, 806, and 807, respectively. In some embodiments, the antibody of the antibody drug conjugate comprises a heavy chain variable region comprising the amino acid sequence of SEQ ID NO: 808 and a light chain variable region comprising the amino acid sequence of SEQ ID NO: 809. In some embodiments, the antibody of the antibody drug conjugate is h7G3. See WO 2016201065.

In some embodiments, an antibody-drug conjugate provided herein binds to GPC3. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 810, 811, 812, 813, 814, and 815, respectively. In some embodiments, the antibody of the antibody drug conjugate comprises a heavy chain variable region comprising the amino acid sequence of SEQ ID NO: 816 and a light chain variable region comprising the amino acid sequence of SEQ ID NO: 817. In some embodiments, the antibody of the antibody drug conjugate is hGPC3-1. See WO 2019161174.

In some embodiments, an antibody-drug conjugate provided herein binds to B6A. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 818, 819, 820, 821, 822, and 823, respectively. In some embodiments, the antibody of the antibody drug conjugate comprises a heavy chain variable region comprising the amino acid sequence of SEQ ID NO: 824 and a light chain variable region comprising the amino acid sequence of SEQ ID NO: 825. In some embodiments, the antibody of the antibody drug conjugate is h2A2. See PCT/US20/63390. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 826, 827, 828, 829, 830, and 831, respectively. In some embodiments, the antibody of the antibody drug conjugate comprises a heavy chain variable region comprising the amino acid sequence of SEQ ID NO: 832 and a light chain variable region comprising the amino acid sequence of SEQ ID NO: 833. In some embodiments, the antibody of the antibody drug conjugate is h15H3. See WO 2013/123152.

In some embodiments, an antibody-drug conjugate provided herein binds to PD-L1. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 834, 835, 836, 837, 838, and 839, respectively. In some embodiments, the antibody of the antibody drug conjugate comprises a heavy chain variable region comprising the amino acid sequence of SEQ ID NO: 840 and a light chain variable region comprising the amino acid sequence of SEQ ID NO: 841. In some embodiments, the antibody of the antibody drug conjugate is SG-559-01. See PCT/US2020/054037.

In some embodiments, an antibody-drug conjugate provided herein binds to TIGIT. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 842, 843, 844, 845, 846, and 847, respectively. In some embodiments, the antibody of the antibody drug conjugate comprises a heavy chain variable region comprising the amino acid sequence of SEQ ID NO: 848 and a light chain variable region comprising the amino acid sequence of SEQ ID NO: 849. In some embodiments, the antibody of the antibody drug conjugate is Clone 13 (also known as ADI-23674 or mAb13). See WO 2020041541.

In some embodiments, an antibody-drug conjugate provided herein binds to STN. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 850, 851, 852, 853, 854, and 855, respectively. In some embodiments, the antibody of the antibody drug conjugate comprises a heavy chain variable region comprising the amino acid sequence of SEQ ID NO: 856 and a light chain variable region comprising the amino acid sequence of SEQ ID NO: 857. In some embodiments, the antibody of the antibody drug conjugate is 2G12-2B2. See WO 2017083582.

In some embodiments, an antibody-drug conjugate provided herein binds to CD33. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 858, 859, 860, 861, 862, and 863, respectively. In some embodiments, the antibody of the antibody drug conjugate comprises a heavy chain variable region comprising the amino acid sequence of SEQ ID NO: 864 and a light chain variable region comprising the amino acid sequence of SEQ ID NO: 865. In some embodiments, the antibody of the antibody drug conjugate is h2H12. See WO2013173496.

In some embodiments, an antibody-drug conjugate provided herein binds to NTBA (also known as CD352). In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 866, 867, 868, 869, 870, and 871, respectively. In some embodiments, the antibody of the antibody drug conjugate comprises a heavy chain variable region comprising the amino acid sequence of SEQ ID NO: 872 and a light chain variable region comprising the amino acid sequence of SEQ ID NO: 873. In some embodiments, the antibody of the antibody drug conjugate is h20F3 HDLD. See WO 2017004330.

In some embodiments, an antibody-drug conjugate provided herein binds to BCMA. In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 874, 875, 876, 877, 878, and 879, respectively. In some embodiments, the antibody of the antibody drug conjugate comprises a heavy chain variable region comprising the amino acid sequence of SEQ ID NO: 880 and a light chain variable region comprising the amino acid sequence of SEQ ID NO: 881. In some embodiments, the antibody of the antibody drug conjugate is SEA-BCMA (also known as hSG16.17). See WO 2017/143069. In some embodiments, an antibody-drug conjugate provided herein binds to Tissue Factor (also known as TF). In some embodiments, the antibody of the antibody drug conjugate comprises CDR-H1, CDR-H2, CDR-H3, CDR-L1, CDR-L2, and CDR-L3 comprising the amino acid sequences of SEQ ID NOs: 882, 883, 884, 885, 886, and 887, respectively. In some embodiments, the antibody of the antibody drug conjugate comprises a heavy chain variable region comprising the amino acid sequence of SEQ ID NO: 888 and a light chain variable region comprising the amino acid sequence of SEQ ID NO: 889. In some embodiments, the antibody of the antibody drug conjugate is tisotumab. See WO 2010/066803 and U.S. Pat. No. 9,150,658.

4. Pharmaceutical Composition

The present invention provides pharmaceutical compositions comprising an LDC composition, which is a collection of Ligand Drug Conjugate compounds described herein, and at least one pharmaceutically acceptable excipient such as a pharmaceutically acceptable carrier. The pharmaceutical compositions are in any form that allows for an LDC composition to be administered to a patient for treatment of a disorder associated with expression of the targeted moiety to which the Ligand Unit of the LDC binds. For example, the pharmaceutical compositions can be in the form of a liquid or a lyophilized solid. The preferred route of administration is parenteral. Parenteral administration includes subcutaneous injections, intravenous, intramuscular, and intrasternal injection or infusion techniques. In preferred embodiments, a pharmaceutical composition comprising an LDC composition is administered intravenously in the form of a liquid solution.

Pharmaceutical compositions are formulated so as to allow a Ligand Drug Conjugate compound to be bioavailable upon administration of the Ligand Drug Conjugate composition to a patient in need thereof. Such pharmaceutical compositions can take the form of one or more dosage units, where for example, a lyophilized solid may provide a single dosage unit when reconstituted as a solution or suspension on addition of a suitable liquid carrier.

Materials used in preparing the pharmaceutical compositions are preferably non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the pharmaceutical composition, the manner of administration, and the LDC composition employed.

The pharmaceutical composition in some embodiments is in the form of a liquid. The liquid is useful for delivery by injection. In a pharmaceutical composition for administration by injection, one or more of a surfactant, preservative, wetting agent, dispersing agent, suspending agent, buffer, stabilizer and isotonic agent is included.

The liquid compositions, whether they are solutions, suspensions or other like form, include one or more pharmaceutically acceptable excipient selected from the group consisting of: sterile diluents such as water for injection, saline solution, preferably physiological saline, Ringer's solution, isotonic sodium chloride, fixed oils such as a synthetic mono or diglyceride, which in some embodiments also serves as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. In preferred embodiments a parenteral composition is enclosed in ampoule, a disposable syringe or a multiple-dose vial made of glass, plastic or other material. Physiological saline is an exemplary adjuvant. An injectable pharmaceutical composition is preferably sterile.

The amount of the Conjugate that is effective in the treatment of a particular disorder or condition will depend on the nature of the disorder or condition, and can be determined by standard clinical techniques. In addition, in vitro or in vivo assays are optionally are employed to help identify optimal dosage ranges. The precise dose to be employed in the compositions will also depend on the route of administration, and the seriousness of the disease or disorder, and should be decided according to the judgment of the practitioner and each patient's circumstances.

The pharmaceutical composition comprises an effective amount of an LDC composition such that a suitable dosage will be obtained for administration to a subject in need thereof. Typically, that amount is at least about 0.01% by weight of the pharmaceutical composition.

For intravenous administration, the pharmaceutical composition comprises from about 0.01 to about 100 mg of an LDC composition per kg of the animal's body weight. In a preferred embodiment, the pharmaceutical composition includes from about 1 to about 100 mg of a LDC composition per kg of the animal's body weight. In more preferred embodiments, the amount administered will be in the range from about 0.1 to about 25 mg/kg of body weight of an LDC composition.

Generally, the dosage of an LDC composition administered to a patient is typically about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, preferably 0.1 to 3.2 mg/kg, or more preferably 0.1 to 2.7 mg/kg of the subject's body weight over a treatment cycle.

An LDC is administered by any convenient route, for example by infusion or bolus injection, by absorption through epithelial or mucocutaneous linings (e.g., oral mucosa, rectal and intestinal mucosa). Administration is systemic or local. Various delivery systems are known, e.g., encapsulation in liposomes, microparticles, microcapsules, capsules, and can be used to administer a compound. In certain embodiments, more than one pharmaceutical composition is administered to a patient.

In one embodiment, a Ligand Drug Conjugate composition is formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions also include a solubilizing agent. Pharmaceutical compositions for intravenous administration optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where a pharmaceutical composition of a Ligand Drug Conjugate composition is to be administered by infusion, it is preferably dispensed with an infusion bottle containing sterile pharmaceutical grade water or saline. Where the pharmaceutical composition of a Ligand Drug Conjugate composition is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Pharmaceutical compositions of the present invention comprise LDC compositions of the present invention and at least one pharmaceutically acceptable excipient such as pharmaceutically acceptable carrier. In some preferred embodiments, all, or substantially all, or more than 50% of the LDC compounds of the LDC composition in the pharmaceutical composition comprises a hydrolyzed thio-substituted succinimide. In some preferred embodiments, more than 55%, 60%, 65%, 70%, 75%, 80%, 85%, 90%, 91%, 92%, 93%, 94%, 95%, 96%, 97%, 98%, or 99% of the Ligand Drug Conjugates present in the pharmaceutical composition comprises a hydrolyzed thio-substituted succinimide.

5. Treatment of Hyper-Proliferating Conditions

The Ligand-Drug Conjugates are useful for inhibiting the multiplication of a tumor cell or cancer cell or causing apoptosis in a tumor or cancer cell. The Ligand-Drug Conjugates are also useful in a variety of settings for the treatment of cancer. Accordingly, The Ligand-Drug Conjugates are used to deliver a drug to a tumor cell or cancer cell. Without being bound by theory, in one embodiment, the Ligand Unit of a Ligand-Drug Conjugate compound binds to or associates with a cell-surface cancer cell- or a tumor cell-associated antigen or receptor, and upon binding, the Ligand-Drug Conjugate compound is taken up (internalized) inside the tumor cell or cancer cell through antigen- or receptor-mediated endocytosis or other internalization mechanism. In another embodiment the antigen is an extracellular matrix protein associated with the tumor cell or cancer cell. Once inside the cell, via an enzymatic proteolysis mechanism, free drug is released within the cell. In an alternative embodiment, the Drug Unit is cleaved from the Ligand-Drug Conjugate compound within the vicinity of the tumor cell or cancer cell, and free drug released as a result subsequently penetrates the cell.

The Ligand-Drug Conjugate compounds provide improved conjugation-specific tumor or cancer drug targeting, thus reducing general toxicity of the drug. That improvement is due to greater selectivity for cleavage of the tripeptide-based Linker Unit of the Ligand Drug Conjugate compound within a tumor to effect intracellular or extracellular delivery of free drug to the cancer cells of the tumor compared to cleavage within normal tissue typically associated with an adverse event with administering a comparator Conjugate having a dipeptide-based Linker Units and/or by increasing bioavailability of the Ligand Drug Conjugate compound for the tumor tissue, which decreases the bioavailability to the normal tissue.

In some embodiments, the peptide-based Linker Units also stabilizes the Ligand-Drug Conjugate compounds to enzymatic action by extracellular proteases in blood yet are capable of liberating drug once inside the cell.

In one embodiment, the Ligand Unit binds to the tumor cell or cancer cell.

In another embodiment, the Ligand Unit binds to a tumor cell or cancer cell antigen that is on the surface of the tumor cell or cancer cell.

In another embodiment, the Ligand Unit binds to a tumor cell or cancer cell antigen which is an extracellular matrix protein associated with the tumor cell or cancer cell.

The specificity of the Ligand Unit for a particular tumor cell or cancer cell is an important consideration for determining those tumors or cancers that are most effectively treated. For example, a Ligand Drug Conjugate having a BR96 Ligand Unit can be useful for treating antigen positive carcinomas including those of the lung, breast, colon, ovaries, and pancreas. Ligand-Drug Conjugates having an anti-CD30 or an anti-CD70 binding Ligand unit can be useful for treating hematologic malignancies.

Other particular types of cancers that can be treated with a Ligand Drug Conjugate include, but are not limited to the following solid tumors, blood-borne cancers, acute and chronic leukemias, and lymphomas.

Solid tumors include but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Blood-borne cancers include but are not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, and multiple myeloma.

Acute and chronic leukemias include but are not limited to lymphoblastic, myelogenous, lymphocytic, and myelocytic leukemias.

Lymphomas include but are not limited to Hodgkin's disease, non-Hodgkin's Lymphoma, Multiple myeloma, Waldenstrom's macroglobulinemia, Heavy chain disease, and Polycythemia vera.

Cancers, including, but not limited to, a tumor, metastasis, or other diseases or disorders characterized by hyper-proliferating cells, are treatable or its progression inhibited in some embodiments by administration of an LDC composition.

In other embodiments, methods for treating cancer are provided, including administering to a patient in need thereof an effective amount of an LDC composition and a chemotherapeutic agent. In one embodiment the cancer to be treated with a chemotherapeutic in combination with an LDC has not been found to be refractory to the chemotherapeutic agent. In another embodiment, the cancer to be treated with a chemotherapeutic in combination with an ADC is refractory to the chemotherapeutic agent. The LDC compositions can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior or subsequent to administration of a ligand drug conjugate.

A chemotherapeutic agent is often administered over a series of sessions. Any one or a combination of the chemotherapeutic agents, such a standard of care chemotherapeutic agent(s), is capable of being administered along with a Ligand Drug Conjugate, but it is preferable that the chemotherapeutic agent(s) effect cell killing by a different mechanism than that of free drug released from the Ligand Drug Conjugate compound.

Additionally, methods of treatment of cancer with a Ligand-Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Also provided is the use of a compound or a composition as detailed herein for the manufacture of a medicament for the treatment of any disease or condition described herein, such as cancer.

Also provided is a compound or a composition as detailed herein for use in medical therapy. Further provided is a compound or a composition as detailed herein for use in treatment of any disease or condition described herein, such as cancer.

Also provided is the use of a compound or a composition as detailed herein for medical therapy. Further provided is the use of a compound or a composition as detailed herein for treatment of any disease or condition described herein, such as cancer.

Further provided is a kit comprising a compound or a composition as detailed herein. In some embodiments, the kit comprises instructions for use according to any of the methods provided herein.

In another aspect, provided is a method of making a compound or a composition as detailed herein.

6. Antigen Binding Protein Expression and Production

A. Nucleic Acid Molecules Encoding Antigen Binding Proteins

Nucleic acid molecules that encode for the antigen binding proteins described herein, or portions thereof, are also provided. Such nucleic acids include, for example: 1) those encoding an antigen binding protein (e.g., an antibody or a fragment thereof), or a derivative, or variant thereof; 2) polynucleotides encoding a heavy and/or light chain, VH and/or VL domains, or 1 or more of the HVRs or CDRs located within a variable domain (e.g., 1, 2 or all 3 of the VH HVRs or CDRs or 1, 2 or all 3 of the VL HVRs or CDRs); 3) polynucleotides sufficient for use as hybridization probes, PCR primers or sequencing primers for identifying, analyzing, mutating or amplifying such encoding polynucleotides; 4) anti-sense nucleic acids for inhibiting expression of such encoding polynucleotides, and 5) complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, or 1,000 or more nucleotides in length, and/or can comprise one or more additional sequences, for example, regulatory sequences, and/or be part of a larger nucleic acid, for example, a vector. The nucleic acids can be single-stranded or double-stranded.

The nucleic acid molecules can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and may or may not contain intronic sequences. In certain embodiments, the nucleic acid is a cDNA molecule.

Thus, nucleic acid molecules comprising polynucleotides that encode one or more chains of an ABP, such as anti-GPNMB, anti-CD228, anti-αvβ6, anti-CD30, LIV1, or anti-CD19 antibodies, are provided. In some embodiments, a nucleic acid molecule comprises a polynucleotide that encodes a heavy chain or a light chain of an ABP (e.g., an anti-GPNMB, anti-CD228, anti-αvβ6, anti-CD30, anti-LIV1, or anti-CD19 antibody). In some embodiments, a nucleic acid molecule comprises both a polynucleotide sequence that encodes a heavy chain and a polynucleotide sequence that encodes a light chain, of an ABP (e.g., an anti-GPNMB, anti-CD228, anti-αvβ6, anti-CD30, anti-LIV1, or anti-CD19 antibody). In some embodiments, a first nucleic acid molecule comprises a first polynucleotide sequence that encodes a heavy chain and a second nucleic acid molecule comprises a second polynucleotide sequence that encodes a light chain.

In one embodiment, the nucleic acid molecule comprises a polynucleotide encoding the VH of one of the antibodies provided herein. In another embodiment, the nucleic acid comprises a polynucleotide encoding the VL of one of the antibodies provided herein. In still another embodiment, the nucleic acid encodes both the VH and the VL of one of the antibodies provided herein.

In a particular embodiment, the nucleic acid encodes a variant of one or more of the above amino acid sequences (e.g., the heavy chain and/or light chain amino acid sequences, or the VH and/or VL amino acid sequences disclosed herein), wherein the variants has at most 25 amino acid modifications, such as at most 20, such as at most 15, 14, 13, 12 or 11 amino acid modifications, such as 10, 9, 8, 7, 6, 5, 4, 3, 2 or 1 amino-acid modifications, such as deletions or insertions, preferably substitutions, such as conservative substitutions.

Once nucleic acids encoding VH and VL segments are obtained, these nucleic acids can be further manipulated by standard recombinant DNA techniques, for example to convert the variable region genes to full-length antibody chain genes, to Fab fragment genes or to a scFv gene. In these manipulations, a VL- or VH-encoding nucleic acid is operatively linked to another nucleic acid encoding another polypeptide, such as an antibody constant region or a flexible linker.

The isolated nucleic acid encoding the VH region can be converted to a full-length heavy chain gene by operatively linking the VH-encoding nucleic acid to another nucleic acid molecule encoding heavy chain constant regions (hinge, CHI, $CH_2$ and/or $CH_3$). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and nucleic acid fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding nucleic can be operatively linked to another nucleic acid molecule encoding only the heavy chain CHI constant region.

The isolated nucleic acid molecule encoding the VL region can be converted to a full-length light chain gene (as well as a Fab light chain gene) by operatively linking the VL-encoding nucleic acid molecule to another nucleic acid molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and nucleic acid fragments encompassing these regions can be obtained by standard PCR amplification. The light chain constant region can be a kappa or lambda constant region.

To create a scFv gene, the VH- and VL-encoding nucleic acid fragments are operatively linked to another fragment encoding a flexible linker, e.g., encoding the amino acid sequence $(Gly_4-Ser)_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

In another aspect, nucleic acid molecules that are suitable for use as primers or hybridization probes for the detection of nucleic acid sequences are also provided. A nucleic acid molecule can comprise only a portion of a nucleic acid sequence encoding a full-length polypeptide, for example, a fragment that can be used as a probe or primer or a fragment encoding an active portion (e.g., GPNMB binding portion, CD228 binding portion, αv06 binding portion, CD30 binding portion, LIV1 binding portion, or CD19 binding portion) of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Vectors, including expression vectors, comprising one or more nucleic acids encoding one or more components of the ABPs (e.g. VH and/or VL; and light chains, and/or heavy chains) are also provided. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

In certain embodiments, nucleic acids encoding the different components of the ABP can be inserted into the same expression vector. For instance, the nucleic acid encoding an anti-GPNMB antibody light chain or variable region can be cloned into the same vector as the nucleic acid encoding an anti-GPNMB antibody heavy chain or variable region. The nucleic acid encoding an anti-CD228 antibody light chain or variable region can be cloned into the same vector as the nucleic acid encoding an anti-CD228 antibody heavy chain or variable region. The nucleic acid encoding an anti-αvβ6 light chain or variable region can be cloned into the same vector as the nucleic acid encoding an anti-αvβ6 antibody heavy chain or variable region. The nucleic acid encoding an anti-CD30 antibody light chain or variable region can be cloned into the same vector as the nucleic acid encoding an anti-CD30 antibody heavy chain or variable region. The nucleic acid encoding an anti-LIV1 antibody light chain or variable region can be cloned into the same vector as the nucleic acid encoding an anti-LIV1 antibody heavy chain or variable region. The nucleic acid encoding an anti-CD19 binding portion antibody light chain or variable region can be cloned into the same vector as the nucleic acid encoding an anti-CD19 antibody heavy chain or variable region. In such embodiments, the two nucleic acids may be separated by an internal ribosome entry site (IRES) and under the control of a single promoter such that the light chain and heavy chain are expressed from the same mRNA transcript. Alternatively, the two nucleic acids can be under the control of two separate promoters such that the light chain and heavy chain are expressed from two separate mRNA transcripts. In some embodiments, the nucleic acid encoding the anti-GPNMB antibody light chain or variable region is cloned into one expression vector and the nucleic acid encoding the anti-GPNMB antibody heavy chain or variable region is cloned into a second expression vector. In some embodiments, the nucleic acid encoding the anti-CD228 antibody light chain or variable region is cloned into one expression vector and the nucleic acid encoding the anti-CD228 antibody heavy chain or variable region is cloned into a second expression vector. In some embodiments, the nucleic acid encoding the anti-αvβ6 antibody light chain or variable region is cloned into one expression vector and the nucleic acid encoding the anti-αvβ6 antibody heavy chain or variable region is cloned into a second expression vector. In some embodiments, the nucleic acid encoding the anti-CD30 antibody light chain or variable region is cloned into one expression vector and the nucleic acid encoding the anti-CD30 antibody heavy chain or variable region is cloned into a second expression vector. In some embodiments, the nucleic acid encoding the anti-LIV1 antibody light chain or variable region is cloned into one expression vector and the nucleic acid encoding the anti-LIV1 antibody heavy chain or variable region is cloned into a second expression vector. In some embodiments, the nucleic acid encoding the anti-CD19 antibody light chain or variable region is cloned into one expression vector and the nucleic acid encoding the anti-CD19 antibody heavy chain or variable region is cloned into a second expression vector. In such embodiments, a host cell may be co-transfected with both expression vectors to produce complete antibodies or antigen-binding fragments of the invention.

B. Host Cells

After the vector has been constructed and the one or more nucleic acid molecules encoding the components of the ABPs described herein has been inserted into the proper site(s) of the vector or vectors, the completed vector(s) may be inserted into a suitable host cell for amplification and/or polypeptide expression.

Thus, in another aspect, host cells comprising nucleic acid molecules or vectors such as described herein are also provided. In various embodiments, ABP heavy chains and/or light chains can be expressed in prokaryotic cells, such as bacterial cells, or in eukaryotic cells, such as fungal cells (such as yeast), plant cells, insect cells, and mammalian cells. The selection of an appropriate host cell depends upon various factors, such as desired expression levels, polypeptide modifications that are desirable or necessary for activity (such as glycosylation or phosphorylation) and ease of folding into a biologically active molecule.

Introduction of one or more nucleic acids into a desired host cell can be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

A variety of mammalian cell lines can be used as hosts and include, but are not limited to, immortalized cell lines available from the American Type Culture Collection (ATCC), including but not limited to Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77: 4216, 1980); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TM cells (Mather et al., Annals N.Y Acad. Sci. 383: 44-68, 1982); MRC 5 cells or FS4 cells; mammalian myeloma cells, and a number of other cell lines.

Once a suitable host cell has been prepared, it can be used to express the desired ABP. Thus, in a further aspect, methods for producing an ABP as described herein are also provided. In general, such methods comprise culturing a host cell comprising one or more expression vectors as described herein in a culture medium under conditions permitting expression of the ABP as encoded by the one or more expression vectors; and recovering the ABP from the culture medium.

In some embodiments, the ABP is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

7. Antigen Binding Protein Conjugates

The ABP that are provided herein can be conjugated to cytotoxic or cytostatic moieties (including pharmaceutically compatible salts thereof) to form a conjugate, such as an antibody drug conjugate (ADC). Particularly suitable moieties for conjugation to ABPs (e.g., antibodies) are cytotoxic agents (e.g., chemotherapeutic agents), prodrug converting enzymes, radioactive isotopes or compounds, or toxins (these moieties being collectively referred to as a therapeutic agent). For example, an ABP (e.g., an anti-GPNMB, anti-CD228, anti-αvβ6, anti-CD30, anti-LIV1, or anti-CD19 antibody) can be conjugated to a cytotoxic agent such as a chemotherapeutic agent, or a toxin (e.g., a cytostatic or cytocidal agent such as, for example, abrin, ricin A, *pseudomonas* exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, calicheamicins, duocarmycins, etoposides, maytansinoids (e.g., DM1, DM2, DM3, DM4), taxanes, benzodiazepines (e.g., pyrrolo[1,4] benzodiazepines, indolinobenzodiazepines, and oxazolidinobenzodiazepines) and *vinca* alkaloids.

In one embodiment, an ABP (e.g., an anti-GPNMB, anti-CD228, anti-αvβ6, anti-CD30, anti-LIV1, or anti-CD19 antibody) is conjugated to a pro-drug converting enzyme. The pro-drug converting enzyme can be recombinantly fused to the antibody or chemically conjugated thereto using known methods. Exemplary pro-drug converting enzymes are carboxypeptidase G2, betaglucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Alley et al., Current Opinion in Chemical Biology 2010 14:1-9; Senter, Cancer J., 2008, 14(3):154-169.) The therapeutic agent can be conjugated in a manner that reduces its activity unless it is cleaved off the antibody (e.g., by hydrolysis, by proteolytic degradation, or by a cleaving agent). In some aspects, the therapeutic agent is attached to the antibody with a cleavable linker that is sensitive to cleavage in the intracellular environment of the GPNMB-expressing, CD228-expressing, αvβ6-expressing, CD30-expressing, LIV1-expressing, or CD19-expressing cancer cell but is not substantially sensitive to the extracellular environment, such that the conjugate is cleaved from the antibody when it is internalized by the GPNMB-expressing, CD228-expressing, αvβ6-expressing, CD30-expressing, LIV1-expressing, or CD19-expressing cancer cell (e.g., in the endosomal or, for example by virtue of pH sensitivity or protease sensitivity, in the lysosomal environment or in the caveolear environment). In some aspects, the therapeutic agent can also be attached to the antibody with a non-cleavable linker.

Typically, the ADC comprises a linker region between the therapeutic agent and the anti-ABP (e.g., anti-GPNMB, anti-CD228, anti-αvβ6, anti-CD30, anti-LIV1, or anti-CD19 antibody). The linker generally is cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Cleaving agents can include cathepsins B and D and plasmin (see, e.g., Dubowchik and Walker, Pharm. Therapeutics 83:67-123, 1999). Most typical are peptidyl linkers that are cleavable by enzymes that are present in GPNMB-expressing, CD228-expressing, αv06-expressing, CD30-expressing, LIV1-expressing, or CD19-expressing cells. For example, a peptidyl linker that is cleavable by the thiol-dependent protease cathepsin-B, which is highly expressed in cancerous tissue, can be used (e.g., a linker comprising a Phe-Leu or a Val-Cit peptide).

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, Pharm. Therapeutics 83:67-123, 1999; Neville et al., Biol. Chem. 264:14653-14661, 1989.) Such linkers are relatively stable under neutral pH conditions, such as those in the blood, but are unstable at below pH 5.5 or 5.0, the approximate pH of the lysosome.

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., Cancer Res. 47:5924-5931, 1987; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

The linker can also be a malonate linker (Johnson et al., Anticancer Res. 15:1387-93, 1995), a maleimidobenzoyl linker (Lau et al., Bioorg-Med-Chem. 3:1299-1304, 1995), or a 3'-N-amide analog (Lau et al., Bioorg-Med-Chem. 3:1305-12, 1995).

In other embodiments, the linker is a non-cleavable linker, such as an maleimido-alkylene- or maleimide-aryl linker that is directly attached to the therapeutic agent and released by proteolytic degradation of the antibody.

Typically, the linker is not substantially sensitive to the extracellular environment, meaning that no more than about 20%, typically no more than about 15%, more typically no more than about 10%, and even more typically no more than about 5%, no more than about 3%, or no more than about 1% of the linkers in a sample of the ADC is cleaved when the ADC is present in an extracellular environment (e.g., in plasma). Whether a linker is not substantially sensitive to the extracellular environment can be determined, for example, by incubating independently with plasma both (a) the ADC (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

The linker can also promote cellular internalization. The linker can promote cellular internalization when conjugated to the therapeutic agent (i.e., in the milieu of the linker-therapeutic agent moiety of the ADC or ADC derivate as described herein). Alternatively, the linker can promote cellular internalization when conjugated to both the therapeutic agent and the antigen binding protein (e.g., anti-GPNMB, anti-CD228, anti-αvβ6, anti-CD30, anti-LIV1, or anti-CD19 antibody) (i.e., in the milieu of the ADC as described herein).

Exemplary antibody-drug conjugates include auristatin based antibody-drug conjugates meaning that the drug component is an auristatin drug. Auristatins bind tubulin, have been shown to interfere with microtubule dynamics and nuclear and cellular division, and have anticancer activity. Typically the auristatin based antibody-drug conjugate comprises a linker between the auristatin drug and the ABP (e.g., anti-GPNMB, anti-CD228, anti-αvβ6, anti-CD30, anti-LIV1, or anti-CD19 antibody). The linker can be, for example, a cleavable linker (e.g., a peptidyl linker) or a non-cleavable linker (e.g., linker released by degradation of the antibody). The auristatin can be auristatin E or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include MMAF, and MMAE. The synthesis and structure of exemplary auristatins are described in U.S. Pat. Nos. 7,659,241, 7,498,298, 2009-0111756, 2009-0018086, and 7,968,687 each of which is incorporated herein by reference in its entirety and for all purposes.

Exemplary auristatin based antibody drug conjugates include mc-vc-PABC-MMAE (also referred to herein as vcMMAE or 1006 or compound 1), mc-vc-PABC-MMAF, mc-MMAF, and mp-dLAE-PABC-MMAE (also referred to herein as dLAE-MMAE, or mp-dLAE-MMAE or 7092 or compound 5), antibody drug conjugates as shown below wherein Ab is an ABP (e.g., an anti-GPNMB, anti-CD228, anti-αvβ6, anti-CD30, anti-LIV1, or anti-CD19 antibody as described herein) and val-cit (vc) represents the valine-citrulline dipeptide, and dLAE represents the D-leucine-alanine-glutamic acid tripeptide:

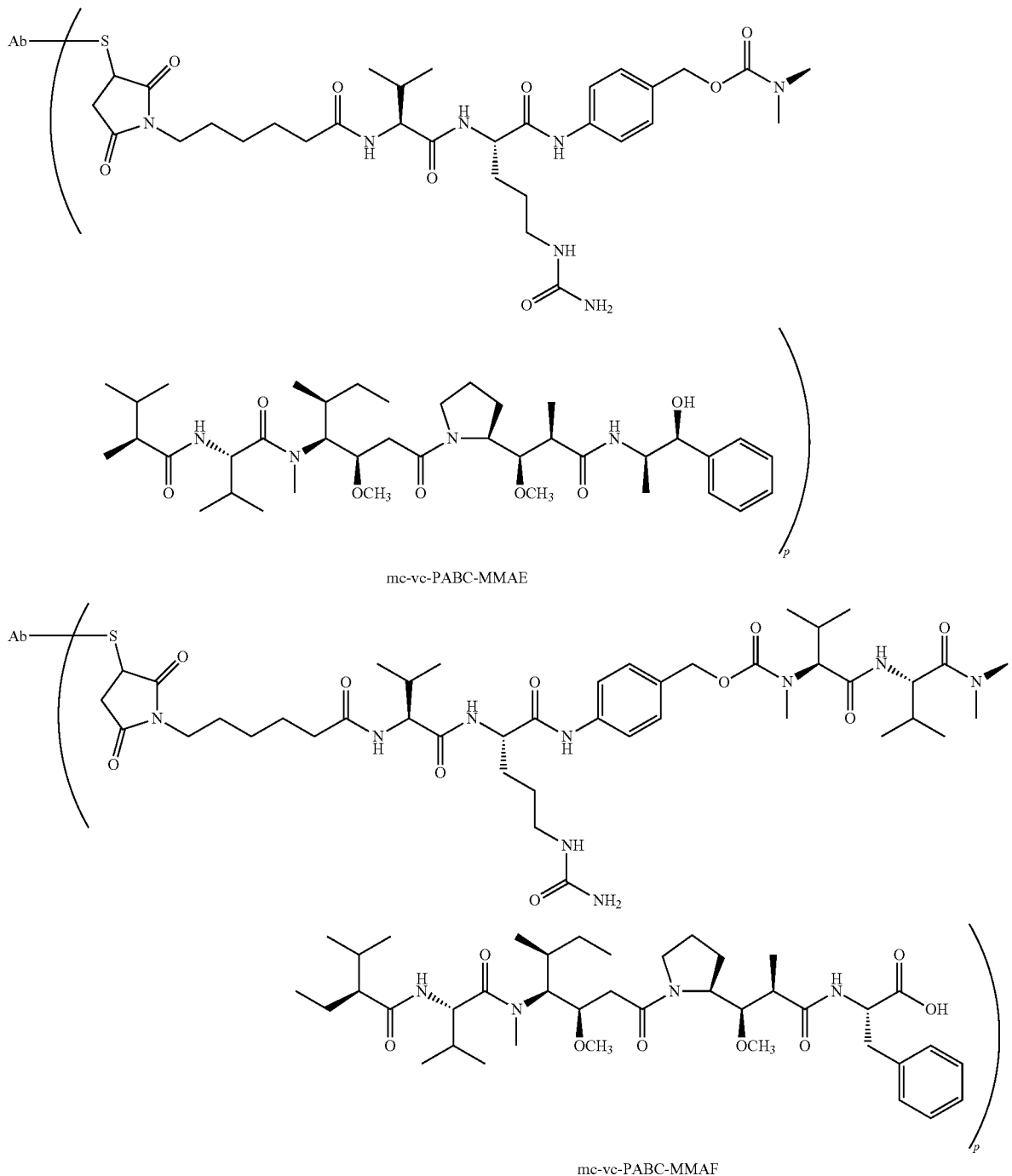

mc-vc-PABC-MMAE mc-vc-PABC-MMAF

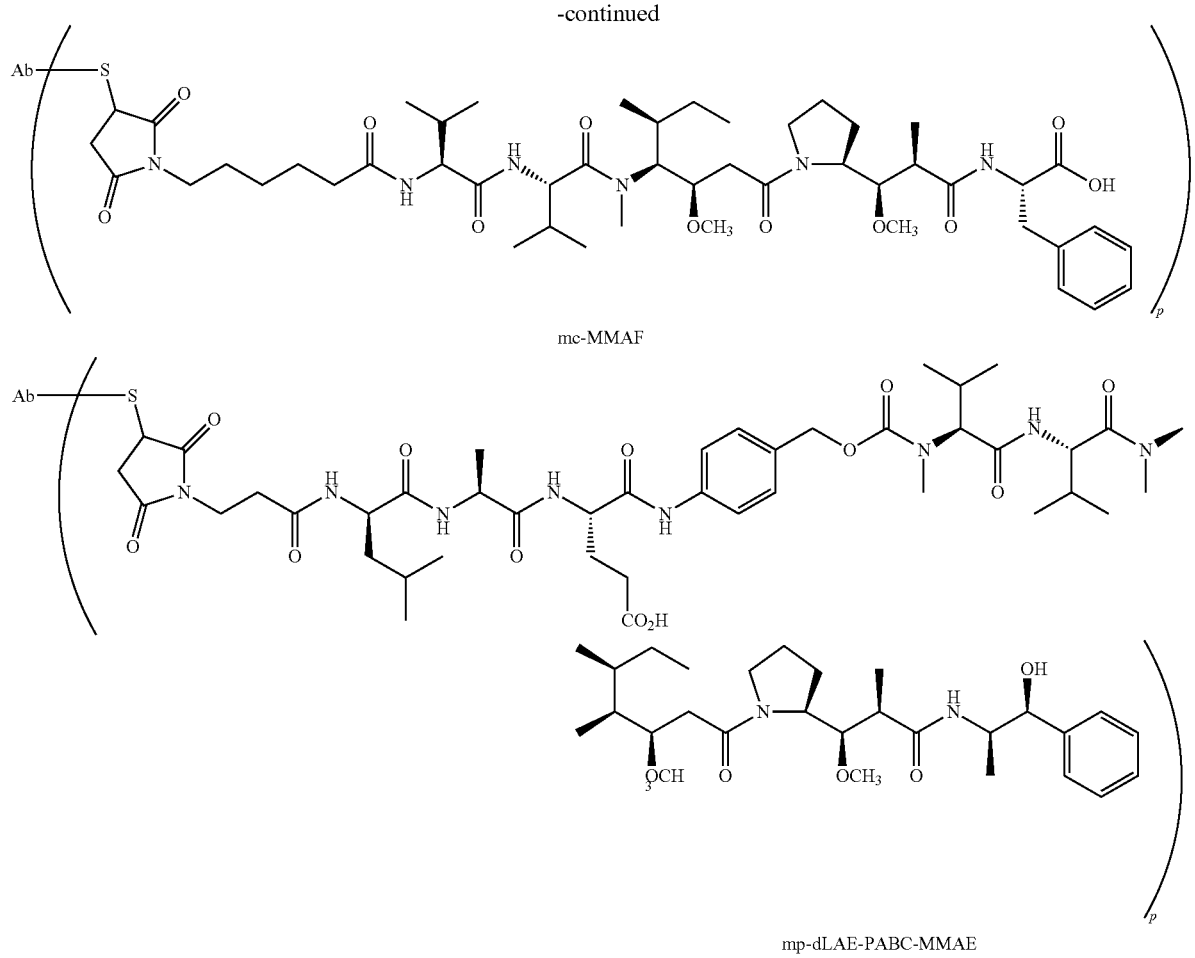

mc-MMAF mp-dLAE-PABC-MMAE or a pharmaceutically acceptable salt thereof. The drug loading is represented by p, the number of drug-linker molecules per antibody. Depending on the context, p can represent the average number of drug-linker molecules per antibody in a composition of antibodies, also referred to the average drug loading. P ranges from 1 to 20 and is preferably from 1 to 8. In some preferred embodiments, when p represents the average drug loading, p ranges from about 2 to about 5. In some embodiments, p is about 2, about 3, about 4, or about 5. The average number of drugs per antibody in a preparation may be characterized by conventional means such as mass spectroscopy, HIC, ELISA assay, and HPLC. In some aspects, the ABP (e.g., anti-GPNMB, anti-CD228, anti-αvβ6, anti-CD30, anti-LIV1, or anti-CD19 antibody) is attached to the drug-linker through a cysteine residue of the antibody. In some embodiments, the cysteine residue is one that is engineered into the antibody. In other aspects, the cysteine residue is an interchain disulfide cysteine residue.

8. Therapeutic Applications

A. Methods of Treating Diseases

In another aspect, methods of treating disorders associated with cells that express GPNMBc, e.g., cancers, are provided. The cells may or may not express elevated levels of GPNMB, CD228, αvβ6, CD30, LIV1, or CD19 relative to cells that are not associated with a disorder of interest.

Thus, certain embodiments involve the use of the ABPs described herein (e.g., anti-GPNMB, anti-CD228, anti-αvβ6, anti-CD30, anti-LIV1, or anti-CD19 antibodies), either as a naked antibody or as a conjugate (e.g., an antibody drug conjugate) to treat a subject, for example a subject with a cancer. In some of these embodiments, the method comprises administering an effective amount of an ABP (e.g., an anti-GPNMB, anti-CD228, anti-αvβ6, anti-CD30, anti-LIV1, or anti-CD19 antibody), or an ADC (e.g., an anti-GPNMB, anti-CD228, anti-αvβ6, anti-CD30, anti-LIV1, or anti-CD19 ADC), or a composition comprising such an ABP or conjugate to a subject in need thereof. In certain exemplary embodiments, the method comprises treating cancer in a cell, tissue, organ, animal or patient. Most typically, the treatment method comprises treating a cancer in a human. In some embodiments the treatment involves monotherapy. In other methods, the antigen binding protein is administered as part of a combination therapy with one or more other therapeutic agents, surgery and/or radiation.

Positive therapeutic effects in cancer can be measured in a number of ways (See, e.g., W. A. Weber, J. Null. Med. 50:15-10S (2009); and Eisenhauer et al., *Eur. J Cancer* 45:228-247 (2009)). In some embodiments, response to treatment with an ABP or conjugate is assessed using RECIST 1.1 criteria. In some embodiments, the treatment achieved by a therapeutically effective amount is any of inhibition of further tumor growth, inducement of tumor regression, a partial response (PR), a complete response (CR), progression free survival (PFS), disease free survival (DFS), objective response (OR) or overall survival (OS). In some embodiments, treatment delays or prevents the onset of metastasis. Progress in treatment can be monitored using various methods. For instance, inhibition can result in reduced tumor size and/or a decrease in metabolic activity within the tumor. Both of these parameters can be measured by MRI or PET scans, for example. Inhibition can also be monitored by biopsy to ascertain the level of necrosis, tumor cell death and the level of vascularity within the tumor. The dosage regimen of a therapy described herein that is effective to treat a cancer patient may vary according to factors such as the disease state, age, and weight of the patient, and the ability of the therapy to elicit an anti-cancer response in the subject. While an embodiment of the treatment method, medicaments and uses of the present invention may not be effective in achieving a positive therapeutic effect in every subject, it should do so in a statistically significant number of subjects as determined by any statistical test known in the art such as the Student's t-test, the chi2-test, the U-test according to Mann and Whitney, the Kruskal-Wallis test (H-test), Jonckheere-Terpstra-test and the Wilcoxon-test.

"RECIST 1.1 Response Criteria" as used herein means the definitions set forth in Eisenhauer et al., Eur. J Cancer 45:228-247 (2009) for target lesions or non-target lesions, as appropriate, based on the context in which response is being measured.

The effective amount of the ABP (e.g., anti-GPNMB, anti-CD228, anti-αvβ6, anti-CD30, anti-LIV1, or anti-CD19 antibody) or ADC (e.g., anti-GPNMB, anti-CD228, anti-αvβ6, anti-CD30, anti-LIV1, or anti-CD19 ADC) can be administered in one or more administrations, applications or dosages and is not intended to be limited to a particular formulation or administration route. Generally, a therapeutically effective amount of active component is in the range of 0.1 mg/kg to 100 mg/kg, e.g., 1 mg/kg to 100 mg/kg, 1 mg/kg to 10 mg/kg.

Exemplary dosages for the ABP (e.g., anti-GPNMB, anti-CD228, anti-αvβ6, anti-CD30, anti-LIV1, or anti-CD19 antibody) are, for example, 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg.

Exemplary dosages for the ADC (e.g., anti-GPNMB, anti-CD228, anti-αvβ6, anti-CD30, anti-LIV1, or anti-CD19 ADC) are, for example, 0.01 mg/kg to 10 mg/kg, 0.1 mg/kg to 10 mg/kg, 0.3 mg/kg to 3 mg/kg, 0.5 mg/kg to 3 mg/kg, 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. In some methods, the patient is administered a dose of at least 1.5 mg/kg, at least 2 mg/kg or at least 3 mg/kg, administered once every three weeks or greater.

The dosage administered can vary depending upon known factors, such as the pharmacodynamic characteristics of the particular agent, and its mode and route of administration; the age, health, and weight of the recipient; the type and extent of disease or indication to be treated, the nature and extent of symptoms, kind of concurrent treatment, frequency of treatment, and the effect desired. The initial dosage can be increased beyond the upper level in order to rapidly achieve the desired blood-level or tissue-level. Alternatively, the initial dosage can be smaller than the optimum, and the daily dosage may be progressively increased during the course of treatment.

The frequency of administration depends on the half-life of the ABP or ADC in the circulation, the condition of the patient and the route of administration among other factors. The frequency can be, for example, daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are weekly, every other week, three out of every four weeks, or every three weeks, over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. In some aspects, for acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Exemplary cancers suitable for treatment with the antigen binding proteins and ADCs provided herein are those that possess GPNMB, CD228, αvβ6, CD30, LIV1, or CD19 expression in a cancerous cell or tissue (i.e., "GPNMB-expressing, CD228-expressing, αvβ6-expressing, CD30-expressing, LIV1-expressing, or CD19-expressing cancers"). Examples of cancers that can be treated with an ABP or conjugate thereof include, but are not limited to, hematopoietic tumors, hematopoietic tumors that give rise to solid tumors, solid tumors, soft tissue tumors, and metastatic lesions. Exemplary cancer for treatment with a LIV1-MC-dLeu-Ala-Glu-PAB-MMAE(4) conjugate include breast cancer, prostate cancer, ovarian cancer, endometrial cancer, cervical, liver, gastric, kidney, and squamous cell carcinomas (e.g., bladder, head, neck and lung), skin cancers, e.g., melanoma, small lung cell carcinoma or lung carcinoid. Breast cancers include, e.g., HER2 positive breast cancers, hormone responsive breast cancers, such as estrogen receptor positive breast cancers, and triple negative breast cancers.

In some of the embodiments herein, a LIV1-MC-dLeu-Ala-Glu-PAB-MMAE(4) conjugate is used to treat a solid tumor that expresses LIV1. The solid tumor is, e.g., selected from lung cancer, head and neck cancer, esophageal cancer, gastric cancer, and gastroesophageal junction cancer.

In some of the embodiments herein, a LIV1-MC-dLeu-Ala-Glu-PAB-MMAE(4) conjugate is used to treat lung cancer. In some of the embodiments herein, the lung cancer is small cell lung cancer. In some of the embodiments herein, the lung cancer is non-small cell lung cancer. In some of the embodiments herein, the non-small cell lung cancer is nonsquamous cell carcinoma. In some of the embodiments herein, the non-small cell lung cancer is squamous cell carcinoma.

In some of the embodiments herein, a LIV1-MC-dLeu-Ala-Glu-PAB-MMAE(4) conjugate is used to treat head and neck cancer. In some of the embodiments herein, the head and neck cancer is squamous cell carcinoma. In some of the embodiments herein, the solid tumor is esophageal carcinoma. In some of the embodiments herein, the esophageal carcinoma is squamous cell carcinoma.

In some of the embodiments herein, a LIV1-MC-dLeu-Ala-Glu-PAB-MMAE(4) conjugate is used to treat gastric cancer. In some of the embodiments herein, the gastric cancer is gastric adenocarcinoma. In some of the embodiments herein, the solid tumor is gastroesophageal junction cancer. In some of the embodiments herein, the gastroesophageal junction cancer is gastroesophageal junction adenocarcinoma.

In some of the embodiments herein, a LIV1-MC-dLeu-Ala-Glu-PAB-MMAE(4) conjugate is used to treat an advanced stage cancer. In some of the embodiments herein, the advanced stage cancer is a stage 3 or stage 4 cancer. In some of the embodiments herein, the advanced stage cancer is metastatic cancer. In some of the embodiments herein, the cancer is recurrent cancer. In some of the embodiments herein, the cancer is unresectable. In some of the embodiments herein, the subject received prior treatment with standard of care therapy for the cancer and failed the prior treatment."

In some embodiments, a LIV1-MC-dLeu-Ala-Glu-PAB-MMAE(4) conjugate is used to treat prostate cancer. In some embodiments, the prostate cancer is castration resistant prostate cancer.

In some embodiments a LIV1-MC-dLeu-Ala-Glu-PAB-MMAE(4) conjugate is used to treat melanoma. In some embodiments, the melanoma is cutaneous malignant melanoma.

Examples of hematopoietic tumors that have the potential to give rise to solid tumors include, but are not limited to, diffuse large B-cell lymphomas (DLBCL), follicular lymphoma, myelodysplastic syndrome (MDS), a lymphoma, Hodgkin's disease, a malignant lymphoma, non-Hodgkin's lymphoma, Burkitt's lymphoma, multiple myeloma, Richter's Syndrome (Richter's Transformation) and the like.

In certain embodiments, the cancer is selected from, but not limited to, leukemia's such as acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, adult T-cell leukemia, and acute monocytic leukemia (AMoL).

In some embodiments, the cancer is another hematological cancer, including, but not limited to, non-Hodgkin lymphoma (e.g., diffuse large B cell lymphoma, mantle cell lymphoma, B lymphoblastic lymphoma, peripheral T cell lymphoma and Burkitt's lymphoma), B-lymphoblastic lymphoma; B-cell chronic lymphocytic leukemia/small lymphocytic lymphoma; lymphoplasmacytic lymphoma; splenic marginal zone B-cell lymphoma (±villous lymphocytes); plasma cell myeloma/plasmacytoma; extranodal marginal zone B-cell lymphoma of the MALT type; nodal marginal zone B-cell lymphoma (monocytoid B cells); follicular lymphoma; diffuse large B-cell lymphomas; Burkitt's lymphoma; precursor T-lymphoblastic lymphoma; T adult T-cell lymphoma (HTLV 1-positive); extranodal NK/T-cell lymphoma, nasal type; enteropathy-type T-cell lymphoma; hepatosplenic γ-δ T-cell lymphoma; subcutaneous panniculitis-like T-cell lymphoma; mycosis fungoides/sezary syndrome; anaplastic large cell lymphoma, T/null cell, primary cutaneous type; anaplastic large cell lymphoma, T-/null-cell, primary systemic type; peripheral T-cell lymphoma, not otherwise characterized; angioimmunoblastic T-cell lymphoma, multiple myeloma, polycythemia vera or myelofibrosis, cutaneous T-cell lymphoma, small lymphocytic lymphoma (SLL), marginal zone lymphoma, CNS lymphoma, immunoblastic large cell lymphoma, precursor B-lymphoblastic lymphoma and the like.

Exemplary solid tumors that can be treated include, but are not limited to, malignancies, e.g., sarcomas (including soft tissue sarcoma and osteosarcoma), adenocarcinomas, and carcinomas, of the various organ systems, such as those affecting head and neck (including pharynx), thyroid, lung (small cell lung carcinoma (SCLC) or non-small cell lung carcinoma (NSCLC)), breast, lymphoid, gastrointestinal tract (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), central nervous system (e.g., neural or glial cells, e.g., neuroblastoma or glioma), skin (e.g., melanoma) and the like. In certain embodiments, the solid tumor is an NMDA receptor positive teratoma. In other embodiments, the cancer is selected from breast cancer, colon cancer, pancreatic cancer (e.g., a pancreatic neuroendocrine tumors (PNET) or a pancreatic ductal adenocarcinoma (PDAC)), stomach cancer, uterine cancer, and ovarian cancer.

In certain embodiments, the cancer is a solid tumor that is associated with ascites. Ascites is a symptom of many types of cancer and can also be caused by a number of conditions, such as advanced liver disease. The types of cancer that are likely to cause ascites include, but are not limited to, cancer of the breast, lung, large bowel (colon), stomach, pancreas, ovary, uterus (endometrium), peritoneum and the like. In some embodiments, the solid tumor associated with ascites is selected from breast cancer, colon cancer, pancreatic cancer, stomach, uterine cancer, and ovarian cancer. In some embodiments, the cancer is associated with pleural effusions, e.g., lung cancer.

In particular embodiments, the cancer is melanoma, lung cancer, breast cancer, head and neck cancer, ovarian cancer, sarcoma, mesothelioma, or cervical cancer.

In particular embodiments, the cancer is pancreatic cancer, mesothelioma, colorectal cancer, lung cancer, thyroid cancer, breast cancer, cholangiocarcinoma, esophageal cancer and head and neck cancer. In some embodiments, the cancer is melanoma. In some embodiments, the melanoma is cutaneous melanoma. In some embodiments, the cutaneous melanoma is selected from the group consisting of superficial spreading melanoma, nodular melanoma, acral lentiginous melanoma, lentigo maligna melanoma, and desmoplastic melanoma. In some embodiments, the cutaneous melanoma is superficial spreading melanoma. In some embodiments, the cutaneous melanoma is nodular melanoma. In some embodiments, the cutaneous melanoma is acral lentiginous melanoma. In some embodiments, the acral lentiginous melanoma is subungual melanoma. In some embodiments, the cutaneous melanoma is lentigo maligna melanoma. In some embodiments, the cutaneous melanoma is desmoplastic melanoma. In some embodiments, the subject received prior therapy with an inhibitor of PD-1 or PD-L1 for the cutaneous melanoma.

In particular embodiments, the cancer is non-small cell lung cancer (NSCLC), head and neck cancer, esophageal cancer, breast cancer, ovarian cancer, bladder cancer, skin cancer (SCC), ovarian cancer, cervical cancer, gastric cancer, or pancreatic cancer. In particular embodiments, the cancer is breast cancer, prostate cancer, ovarian cancer, endometrial cancer, cervical, liver, gastric, kidney, and squamous cell carcinomas (e.g., bladder, head, neck and lung), skin cancers, e.g., melanoma, small lung cell carcinoma or lung carcinoid. In particular embodiments, the cancer is chronic leukemia, lymphoma, multiple myeloma, B type acute lymphoblastic leukemia, chronic myelocytic leukemia, chronic lymphocytic leukemia, non-Hodgkin lymphoma and Hodgkin lymphoma, B cell lymphoma, or diffuse large B-cell lymphoma.

B. Combination Therapies

The methods, the antigen binding proteins and ADCs described herein can be used in combination with other therapeutic agents and/or modalities. In such combination therapeutic methods, two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive (i.e., a synergistic response). The delivery can be such that an effect of the first treatment delivered is still detectable when the second is delivered.

In certain embodiments, the methods provided herein include administering to the subject an ABP (e.g., an anti-GPNMB, anti-CD228, anti-αvβ6, anti-CD30, anti-LIV1, or anti-CD19 antibody) or ADC (e.g., an anti-GPNMB, anti-CD228, anti-αvβ6, anti-CD30, anti-LIV1, or anti-CD19 ADC) as described herein, e.g., a composition or preparation, in combination with one or more additional therapies, e.g., surgery, radiation therapy, or administration of another therapeutic preparation. For example, in some embodiments, the ABP is combined with chemotherapy (e.g., a cytotoxic agent), a targeted therapy (e.g., an antibody against a cancer antigen), an angiogenesis inhibitor, and/or an immunomodulatory agent, such as an inhibitor of an immune checkpoint molecule. In other embodiments, the additional therapy is an anti-inflammatory (e.g., methotrexate), or an anti-fibrotic agent. The ABP (e.g., an anti-GPNMB, anti-CD228, anti-αvβ6, anti-CD30, anti-LIV1, or anti-CD19 antibody) or ADC (e.g., an anti-GPNMB, anti-CD228, anti-αvβ6, anti-CD30, anti-LIV1, or anti-CD19 ADC) and the additional therapy can be administered simultaneously or sequentially.

Exemplary cytotoxic agents that can be used in combination with a LIV1-MC-dLeu-Ala-Glu-PAB-MMAE(4) conjugate in some embodiments include Capecitabine, Atezolizumab, Ipatasertib, Bevacizumab, (Gemcitabine+ Carboplatin or Eribulin), Selicrelumab, Tocilizumab, Nab-Paclitaxel and Sacituzumab Govitecan.

Other agents that can be used in combination with a LIV1-MC-dLeu-Ala-Glu-PAB-MMAE(4) conjugate include checkpoint inhibitors. In some embodiments, the checkpoint inhibitor is an anti-PD-1 antibody, an anti-PD-L1 antibody, an anti-CTLA4 antibody, B7-DC-Fc, LAG3, or TIM3. In some embodiments, the checkpoint inhibitor is selected from the group consisting of MEDI0680, AMP-224, nivolumab, pembrolizumab, pidilizumab, MEDI4736, MPDL3280A, ipilimumab and tremelimumab. In some embodiments, the checkpoint inhibitor is pembrolizumab is used in combination with a LIV1-MC-dLeu-Ala-Glu-PAB-MMAE(4) conjugate to treat a LIV1 expressing cancer.

A LIV1-MC-dLeu-Ala-Glu-PAB-MMAE(4) conjugate can be combined with other agents to treat a HER2 positive cancer, e.g., HER2 positive breast cancer, HER2 positive bladder cancer, HER2 positive cervical cancer, HER2 positive cholangiocarcinomas, HER2 positive colorectal cancers, HER2 positive esophageal or esophagogastric junction cancer, HER2 positive gallbladder cancers, or HER2 positive Gastric adenocarcinomas. Other agents for combination with a LIV1-MC-dLeu-Ala-Glu-PAB-MMAE(4) conjugate can include antibodies or ADCs that target HER2, e.g., trastuzumab or trastuzumab deruxtecan; or kinase inhibitors, e.g., lapatinib, neratinib, or tucatinib. Tucatinib is disclosed at WO2007/059257.

In some embodiments, a LIV1-MC-dLeu-Ala-Glu-PAB-MMAE(4) conjugate is combined with tucatinib to treat a HER2 positive cancer. In a further embodiment, a LIV1-MC-dLeu-Ala-Glu-PAB-MMAE(4) conjugate is combined with tucatinib to treat a HER2 positive cancer, e.g., HER2 positive breast cancer. In a further embodiment, a LIV1-MC-dLeu-Ala-Glu-PAB-MMAE(4) conjugate is combined with tucatinib to treat a HER2 positive cancer, e.g., HER2 positive bladder cancer. In a further embodiment, a LIV1-MC-dLeu-Ala-Glu-PAB-MMAE(4) conjugate is combined with tucatinib to treat a HER2 positive cancer, e.g., HER2 positive cervical cancer. In a further embodiment, a LIV1-MC-dLeu-Ala-Glu-PAB-MMAE(4) conjugate is combined with tucatinib to treat a HER2 positive cancer, e.g., HER2 positive cholangiocarcinomas. In a further embodiment, a LIV1-MC-dLeu-Ala-Glu-PAB-MMAE(4) conjugate is combined with tucatinib to treat a HER2 positive cancer, e.g., HER2 positive colorectal cancers. In a further embodiment, a LIV1-MC-dLeu-Ala-Glu-PAB-MMAE(4) conjugate is combined with tucatinib to treat a HER2 positive cancer, e.g., HER2 positive esophageal or esophagogastric junction cancer. In a further embodiment, a LIV1-MC-dLeu-Ala-Glu-PAB-MMAE(4) conjugate is combined with tucatinib to treat a HER2 positive cancer, e.g., HER2 positive gallbladder cancers. In a further embodiment, a LIV1-MC-dLeu-Ala-Glu-PAB-MMAE(4) conjugate is combined with tucatinib to treat a HER2 positive cancer, e.g., HER2 positive gastric adenocarcinomas. In a further embodiment, a LIV1-MC-dLeu-Ala-Glu-PAB-MMAE(4) conjugate is combined with tucatinib to treat a HER2 positive cancer, e.g., HER2 positive ovarian cancer.

In another embodiment, a LIV1-MC-dLeu-Ala-Glu-PAB-MMAE(4) conjugate is combined with tucatinib to treat HER2 positive breast cancer. In a further embodiment, a LIV1-MC-dLeu-Ala-Glu-PAB-MMAE(4) conjugate is combined with tucatinib and capcitabine to treat HER2 positive breast cancer. In a further embodiment, a LIV1-MC-dLeu-Ala-Glu-PAB-MMAE(4) conjugate is combined with tucatinib, trastuzumanb, and capcitabine to treat HER2 positive breast cancer.

Exemplary cytotoxic agents that can be used in combination with the ABP in some embodiments include anti-microtubule agents, topoisomerase inhibitors, antimetabolites, protein synthesis and degradation inhibitors, mitotic inhibitors, alkylating agents, platinating agents, inhibitors of nucleic acid synthesis, histone deacetylase inhibitors (HDAC inhibitors, e.g., vorinostat (SAHA, MK0683), entinostat (MS-275), panobinostat (LBH589), trichostatin A (TSA), mocetinostat (MGCD0103), belinostat (PXD101), romidepsin (FK228, depsipeptide)), DNA methyltransferase inhibitors, nitrogen mustards, nitrosoureas, ethylenimines, alkyl sulfonates, triazenes, folate analogs, nucleoside analogs, ribonucleotide reductase inhibitors, *vinca* alkaloids, taxanes, epothilones, intercalating agents, agents capable of interfering with a signal transduction pathway, agents that promote apoptosis and radiation, or antibody molecule conjugates that bind surface proteins to deliver a toxic agent. In one embodiment, the cytotoxic agent that can be administered with an ABP described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (e.g., paclitaxel or docetaxel), cytochalasin B, gramicidin D, ethidium bromide, emetine, mitomycin, etoposide, tenoposide, vincristine, vinblastine, vinorelbine, colchicin, anthracyclines (e.g., doxorubicin or epirubicin) daunorubicin, dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, or maytansinoids.

In some embodiments, the antigen binding protein is administered as part of a chemotherapeutic regimen such as CHOP (cyclophosphamide, doxorubicin, vincristine, and prednisone); CVP (cyclophosphamide, vincristine, and prednisone); RCVP (rituximab+CVP); RCHOP (rituximab+CHOP); RCHP (rituximab, cyclophosphamide, doxorubicin, and prednisone); RICE (Rituximab+ifosamide, carboplatin, etoposide); RDHAP, (Rituximab+dexamethasone, cytarabine, cisplatin); RESHAP (rituximab+etoposide, methylprednisolone, cytarabine, cisplatin); R-BENDA (rituximab and Bendamustine), RGDP (rituximab, gemcitabine, dexamethasone, cisplatin). In an embodiment, one of CHOP, CVP, RCVP, RCHOP, RCHP, RICE, RDHAP, RESHAP, R-BENDA, and RGDP is administered in a combination therapy with an antigen binding protein or conjugate as described herein.

Examples of targeted therapies that can be combined with an ABP in certain embodiments include, but are not limited to, use of therapeutic antibodies. Exemplary antibodies include, but are not limited to, those which bind to cell surface proteins such as Her2, CDC20, CDC33, mucin-like glycoprotein, and epidermal growth factor receptor (EGFR) present on tumor cells, and optionally induce a cytostatic and/or cytotoxic effect on tumor cells displaying these proteins. Exemplary antibodies also include HERCEPTIN® (trastuzumab), which may be used to treat breast cancer and other forms of cancer, and RITUXAN® (rituximab), ZEVALIN® (ibritumomab tiuxetan), GLEEVEC® and LYMPHOCIDE® (epratuzumab), which may be used to treat non-Hodgkin's lymphoma and other forms of cancer. Other exemplary antibodies include panitumumab (VECTIBIX®), ERBITUX® (IMC-C225); ertinolib (Iressa); BEXXAR® (iodine 131 tositumomab); KDR (kinase domain receptor) inhibitors; anti VEGF antibodies and antagonists (e.g., Avastin®, motesanib, and VEGAF-TRAP); anti VEGF receptor antibodies and antigen binding regions; anti-Ang-1 and Ang-2 antibodies and antigen binding regions; antibodies to Tie-2 and other Ang-1 and Ang-2 receptors; Tie-2 ligands; antibodies against Tie-2 kinase inhibitors; inhibitors of Hif-1a, and Campath® (Alemtuzumab). In certain embodiments, cancer therapy agents are polypeptides which selectively induce apoptosis in tumor cells, including, but not limited to, the TNF-related polypeptide TRAIL.

In certain embodiments, an antigen binding protein as provided herein is used in combination with one or more anti-angiogenic agents that decrease angiogenesis. Such agents include, but are not limited to, IL-8 antagonists; Campath®, B-FGF; FGF antagonists; Tek antagonists (Cerretti et al., U.S. Publication No. 2003/0162712; Cerretti et al., U.S. Pat. No. 6,413,932, and Cerretti et al., U.S. Pat. No. 6,521,424); anti-TWEAK agents (which include, but are not limited to, antibodies and antigen binding regions); soluble TWEAK receptor antagonists (Wiley, U.S. Pat. No. 6,727,225); an ADAM distintegrin domain to antagonize the binding of integrin to its ligands (Fanslow et al., U.S. Publication No. 2002/0042368); anti-eph receptor and anti-ephrin antibodies, antigen binding regions, or antagonists (U.S. Pat. Nos. 5,981,245; 5,728,813; 5,969,110; 6,596,852; 6,232,447; 6,057,124); anti-VEGF agents (e.g., antibodies or antigen binding regions that specifically bind VEGF, or soluble VEGF receptors or a ligand binding regions thereof) such as Avastin® or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as panitumumab, IRESSA® (gefitinib), TARCEVA® (erlotinib), anti-Ang-1 and anti-Ang-2 agents (e.g., antibodies or antigen binding regions specifically binding thereto or to their receptors, e.g., Tie-2/TEK), and anti-Tie-2 kinase inhibitory agents (e.g., antibodies or antigen binding regions that specifically bind and inhibit the activity of growth factors, such as antagonists of hepatocyte growth factor (HGF, also known as Scatter Factor), and antibodies or antigen binding regions that specifically bind its receptor "c-met"; anti-PDGF-BB antagonists; antibodies and antigen binding regions to PDGF-BB ligands; and PDGFR kinase inhibitors.

Other anti-angiogenic agents that can be used in combination with an antigen binding protein include agents such as MMP-2 (matrix-metalloproteinase 2) inhibitors, MMP-9 (matrix-metalloproteinase 9) inhibitors, and COX-II (cyclooxygenase II) inhibitors. Examples of useful COX-II inhibitors include CELEBREX® (celecoxib), valdecoxib, and rofecoxib.

An "immune checkpoint molecule," as used herein, refers to a molecule in the immune system that either turns up a signal (a stimulatory molecule) and/or turns down a signal (an inhibitory molecule). Many cancers evade the immune system by inhibiting T cell signaling. Exemplary immune checkpoint molecules that can be used with an ABP in certain embodiments include, but are not limited to, programmed cell death protein 1 (PD-1), programmed death-ligand 1 (PD-L1), PD-L2, cytotoxic T lymphocyte-associated protein 4 (CTLA-4), T cell immunoglobulin and mucin domain containing 3 (TIM-3), lymphocyte activation gene 3 (LAG-3), carcinoembryonic antigen related cell adhesion molecule 1 (CEACAM-1), CEACAM-5, V-domain Ig suppressor of T cell activation (VISTA), B and T lymphocyte attenuator (BTLA), T cell immunoreceptor with Ig and ITIM domains (TIGIT), leukocyte-associated immunoglobulin-like receptor 1 (LAIRI), CD160, TGFR, adenosine 2A receptor (A2AR), B7-H3 (also known as CD276), B7-H4 (also called VTCN1), indoleamine 2,3-dioxygenase (IDO), 2B4, killer cell immunoglobulin-like receptor (KIR), OX40, 4-1BB, 4-1BBL, B7-H3, Inducible T-cell Co-stimulator (ICOS/ICOS-L), CD27/CD70, Glucocorticoid-Induced TNF Receptor (GITR), CD47/Signal-Regulatory Protein alpha (SIRPα), and Indoleamine-2,3-Dioxygenase (IDO).

Specific examples of immune checkpoint inhibitors that can be used in combination with the ABP in certain embodiments include, but are not limited to, the following monoclonal antibodies: PD-1 inhibitors such as pembrolizumab (Keytruda®, Merck) and nivolumab (Opdivo®, Bristol-Myers Squibb); PD-L1 inhibitors such as atezolizumab (Tecentriq®, Genentech), avelumab (Bavencio®, Pfizer), durvalumab (Imfinzi®, AstraZeneca); and CTLA-1 inhibitors such as ipilimumab (Yervoy®, Bristol-Myers Squibb) and tremelimumab (AstraZeneca).

9. Diagnostic Applications

In another aspect, the ABP (e.g., an anti-GPNMB, anti-CD228, anti-αvβ6, anti-CD30, anti-LIV1, or anti-CD19 antibody or fragment thereof), polypeptides, and nucleic acids as provided herein can be used in methods for detecting, diagnosing and monitoring of a disease, disorder or condition associated with the GPNMB, CD228, αv06, CD30, LIV1, or CD19.

In some embodiments, the method comprises detecting the expression of GPNMB, CD228, αv06, CD30, LIV1, or CD19 in a sample obtained from a subject suspected of having a disorder associated with GPNMB, CD228, αv06, CD30, LIV1, or CD19. In some embodiments, the method of detection comprises contacting the sample with an antibody, polypeptide, or polynucleotide as described herein and determining whether the level of binding differs from that of a reference or comparison sample. In some embodiments, such methods are useful to determine whether the antibodies or polypeptides described herein are an appropriate treatment for the subject.

For example, in some embodiments, the cells or cell/tissue lysate are contacted with an anti-GPNMB, anti-CD228, anti-αvβ6, anti-CD30, anti-LIV1, or anti-CD19 antibody and the binding between the antibody and the cell or antigen is determined. When the test cells show binding activity as compared to a reference cell of the same tissue type, it may indicate presence of a disease or condition associated with GPNMB, CD228, αv06, CD30, LIV1, or CD19. In some embodiments, the test cells are from human tissues.

Various methods known in the art for detecting specific antibody-antigen binding can be used. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA).

Diagnostic applications provided herein include use of an ABP (e.g., an anti GPNMB, anti-CD228, anti-αvβ6, anti-CD30, anti-LIV1, or anti-CD19 antibody or fragment thereof) to detect expression of GPNMB, CD228, αvβ6, CD30, LIV1, or CD19 and binding of the ligands to GPNMB, CD228, αvβ6, CD30, LIV1, or CD19. For diagnostic applications, the ABP typically is labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the ABP via spacer arms of various lengths to reduce potential steric hindrance. Various methods for labeling proteins are known in the art and may be used. Examples of methods useful in the detection of the presence of GPNMB, CD228, αvβ6, CD30, LIV1, or CD19 include immunoassays such as those described above.

In another aspect, an ABP can be used to identify a cell or cells that express GPNMB, CD228, αvβ6, CD30, LIV1, or CD19. In specific embodiments, the antigen binding protein is labeled with a labeling group and the binding of the labeled antigen binding protein to GPNMB, CD228, αvβ6, CD30, LIV1, or CD19 is detected. In further specific embodiments, the binding of the antigen binding protein to GPNMB, CD228, αvβ6, CD30, LIV1, or CD19 is detected in vivo.

An antigen binding protein (e.g., an anti-GPNMB, anti-CD228, anti-αvβ6, anti-CD30, anti-LIV1, or anti-CD19 antibody or fragment thereof) also can be used as staining reagent in pathology using techniques well known in the art.

10. Pharmaceutical Compositions and Formulations

Pharmaceutical compositions that comprise an ABP (e.g., an anti-GPNMB, anti-CD228, anti-αvβ6, anti-CD30, anti-LIV1, or anti-CD19 antibody or fragment thereof) are also provided and can be utilized in any of the therapeutic applications disclosed herein. In certain embodiments, the pharmaceutical composition comprises a therapeutically effective amount of one or a plurality of the antigen binding protein, together with pharmaceutically acceptable diluent or carrier. In other embodiments, the pharmaceutical composition comprises a therapeutically effective amount of one or a plurality of the antigen binding proteins, a pharmaceutically acceptable diluent, carrier, solubilizer, emulsifier, preservative, and/or adjuvant. Acceptable formulation materials are nontoxic to recipients at the dosages and concentrations employed. The pharmaceutical compositions can be formulated as liquid, frozen or lyophilized compositions.

In certain embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids; antimicrobials; antioxidants; buffers; bulking agents; chelating agents; complexing agents; fillers; carbohydrates such as monosaccharides or disaccharides; proteins; coloring, flavoring and diluting agents; emulsifying agents; hydrophilic polymers; low molecular weight polypeptides; salt-forming counterions (such as sodium); preservatives; solvents (such as glycerin, propylene glycol or polyethylene glycol); sugar alcohols; suspending agents; surfactants or wetting agents; stability enhancing agents; tonicity enhancing agents; delivery vehicles; and/or pharmaceutical adjuvants. Additional details and options for suitable agents that can be incorporated into pharmaceutical compositions are provided in, for example, Remington's Pharmaceutical Sciences, 22$^{nd}$ Edition, (Loyd V. Allen, ed.) Pharmaceutical Press (2013); Ansel et al., Pharmaceutical Dosage Forms and Drug Delivery Systems, 7$^{th}$ ed., Lippencott Williams and Wilkins (2004); and Kibbe et al., Handbook of Pharmaceutical Excipients, 3$^{rd}$ ed., Pharmaceutical Press (2000).

The components of the pharmaceutical composition are selected depending upon, for example, the intended route of administration, delivery format and desired dosage. See, for example, Remington's Pharmaceutical Sciences, 22$^{nd}$ Edition, (Loyd V. Allen, ed.) Pharmaceutical Press (2013). The compositions are selected to influence the physical state, stability, rate of in vivo release and rate of in vivo clearance of the antigen binding proteins disclosed. The primary vehicle or carrier in a pharmaceutical composition can be either aqueous or non-aqueous in nature. For example, a suitable vehicle or carrier can be water for injection or physiological saline solution. In certain embodiments, antigen binding protein compositions can be prepared for storage by mixing the selected composition having the desired degree of purity with optional formulation agents in the form of a lyophilized cake or an aqueous solution. Further, in certain embodiments, the antigen binding protein can be formulated as a lyophilizate using appropriate excipients.

In certain formulations, that antigen binding protein concentration is at least 2 mg/ml, 5 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml or 150 mg/ml. In other embodiments, the antigen binding protein has a concentration of 10-20 mg/ml, 20-40 mg/ml, 40-60 mg/ml, 60-80 mg/ml, or 80-100 mg/ml.

Some compositions include a buffer or a pH adjusting agent. Representative buffers include, but are not limited to: organic acid salts (such as salts of citric acid, acetic acid, ascorbic acid, gluconic acid, carbonic acid, tartaric acid, succinic acid, or phthalic acid); Tris; phosphate buffers; and, in some instances, an amino acid as described below. In certain embodiments, buffers are used to maintain the composition at physiological pH or at a slightly lower pH, typically within a pH range of from about 5 to about 8. Some compositions have a pH from about 5-6, 6-7, or 7-8. In other embodiments, the pH is from 5.5-6.5, 6.5-7.5, or 7.5-8.5.

Free amino acids or proteins are used in some compositions as bulking agents, stabilizers, and/or antioxidants. As an example, lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant. Glutamine and asparagine are included in some embodiments. An amino acid is included in some formulations because of its buffering capacity. Such amino acids include, for instance, alanine, glycine, arginine, betaine, histidine, glutamic acid, aspartic acid, cysteine, lysine, leucine, isoleucine, valine, methionine, phenylalanine, aspartame, and the like. Certain formulations also include a protein excipient such as serum albumin (e.g., human serum albumin (HSA) and recombinant human albumin (rHA)), gelatin, casein, and the like.

Some compositions include a polyol. Polyols include sugars (e.g., mannitol, sucrose, trehalose, and sorbitol) and polyhydric alcohols such as, for instance, glycerol and propylene glycol, and polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Certain compositions include mannitol as a stabilizer. It is generally used with a lyoprotectant, e.g., sucrose. Sorbitol and sucrose are useful for adjusting tonicity and as stabilizers to protect against freeze-thaw stresses during transport or the preparation of bulk product during the manufacturing process. PEG is useful to stabilize proteins and as a cryoprotectant and can be used in the invention in this regard.

Sugars, including monosaccharides, di-, tri-, tetra-, and oligosaccharides; derivatized sugars such as alditols, aldonic acids, esterified sugars and the like; and polysaccharides or sugar polymers can be included in some formulations. For example, suitable carbohydrate excipients include, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like.

Surfactants can be included in certain formulations. Surfactants are typically used to prevent, minimize, or reduce protein adsorption to a surface and subsequent aggregation at air-liquid, solid-liquid, and liquid-liquid interfaces, and to control protein conformational stability. Suitable surfactants include, for example, polysorbate 20, polysorbate 80, other fatty acid esters of sorbitan esters, Triton surfactants, lechithin, tyloxapal, and poloxamer 188.

In some embodiments, one or more antioxidants are included in the pharmaceutical composition. Antioxidant excipients can be used to prevent oxidative degradation of proteins. Reducing agents, oxygen/free-radical scavengers, and chelating agents are useful antioxidants in this regard. Antioxidants typically are water-soluble and maintain their activity throughout the shelf life of a product. EDTA is another useful antioxidant.

Certain formulations include metal ions that are protein co-factors and that are necessary to form protein coordination complexes. Metal ions also can inhibit some processes that degrade proteins. For example, magnesium ions (10-120 mM) can be used to inhibit isomerization of aspartic acid to isoaspartic acid.

A tonicity enhancing agent can also be included in certain formulations. Examples of such agents include alkali metal halides, preferably sodium or potassium chloride, mannitol, and sorbitol.

One or more preservatives can be included in certain formulations. Preservatives are necessary when developing multi-dose parenteral formulations that involve more than one extraction from the same container. Their primary function is to inhibit microbial growth and ensure product sterility throughout the shelf-life or term of use of the drug product. Suitable preservatives include phenol, m-cresol, p-cresol, o-cresol, chlorocresol, benzyl alcohol, phenylmercuric nitrite, phenoxyethanol, phenyl alcohol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate, thimerosal, benzoic acid, salicylic acid, chlorhexidine, or mixtures thereof in an aqueous diluent.

A pharmaceutical composition is formulated to be compatible with its intended route of administration. Examples of routes of administration are intravenous (IV), intradermal, inhalation, transdermal, topical, transmucosal, and rectal administration. A preferred route of administration for an antigen binding protein (e.g., an antibody) is IV infusion. In another preferred embodiment, the preparation is administered by intramuscular or subcutaneous injection.

Formulation components suitable for parenteral administration (e.g., intravenous, subcutaneous, intraocular, intraperitoneal, intramuscular) include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and should be preserved against microorganisms. The carrier can be a solvent or dispersion medium containing, for example, water, ethanol, polyol (for example, glycerol, propylene glycol, and liquid polyethylene glycol), and suitable mixtures thereof.

Further guidance on appropriate formulations depending upon the form of delivery is provided, for example, in Remington's Pharmaceutical Sciences, $22^{nd}$ Edition, (Loyd V. Allen, ed.) Pharmaceutical Press (2013).

Pharmaceutical formulations are preferably sterile. Sterilization can be accomplished by any suitable method, e.g., filtration through sterile filtration membranes. Where the composition is lyophilized, filter sterilization can be conducted prior to or following lyophilization and reconstitution.

11. Kits/Articles of Manufacture

Kits containing an ABP as described herein are also provided. In one embodiment, such kits comprise one or more containers comprising an antigen binding protein (e.g., an anti-GPNMB, anti-CD228, anti-αvβ6, anti-CD30, anti-LIV1, or anti-CD19 antibody), or unit dosage forms and/or articles of manufacture. In some embodiments, a unit dosage is provided wherein the unit dosage contains a predetermined amount of a composition comprising an antigen binding protein, with or without one or more additional agents. In some embodiments, such a unit dosage is supplied in a single-use prefilled syringe for injection. In various embodiments, the composition contained in the unit dosage may comprise: saline; a buffer, other formulation components, and/or be formulated within a stable and effective pH range as described herein. Alternatively, in some embodiments, the composition is provided as a lyophilized powder that can be reconstituted upon addition of an appropriate liquid, for example, sterile water.

Some kits as provided herein further comprise instructions for use in the treatment of a disease associated with GPNMB, CD228, αvβ6, CD30, LIV1, or CD19, in accordance with any of the methods described herein. The kit can further comprise a description of how to select or identify an individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable. In some embodiments, the kit further comprises another therapeutic agent, such as those described above as suitable for use in combination with the antigen binding protein.

In a further aspect, kits for detecting the presence of GPNMB, CD228, αvβ6, CD30, LIV1, or CD19, or a cell expressing GPNMB, CD228, αvβ6, CD30, LIV1, or CD19, in a sample are provided. Such kits typically comprise an antigen binding protein as described herein and instructions for use of the kit.

Certain kits, for example, are for diagnosis of cancer and comprises a container comprising an antigen binding protein (e.g., an anti-GPNMB, anti-CD228, anti-αvβ6, anti-CD30, anti-LIV1, or anti-CD19 antibody), and one or more reagents for detecting binding of the antigen binding protein to GPNMB, CD228, αvβ6, CD30, LIV1, or CD19. Such reagents can include, for example, fluorescent tags, enzymatic tags, or other detectable tags. The reagents can also include secondary or tertiary antibodies or reagents, e.g., for use in enzymatic reactions that produce a product that can be visualized. In one embodiment, a diagnostic kit comprises one or more antigen binding proteins in labeled or unlabeled form in suitable container(s), reagents for the incubations for an indirect assay, and substrates or derivatizing agents for detection in such an assay, depending on the nature of the label.

Kits such as provided herein can be used for in situ detection. Some methods utilizing such kits comprise removing a histological specimen from a patient and then combining the labeled antigen binding protein (e.g., an anti-GPNMB, anti-CD228, anti-αvβ6, anti-CD30, anti-LIV1, or anti-CD19 antibody) with the biological sample. With such methods, it is possible to determine not only the presence of GPNMB, CD228, αvβ6, CD30, LIV1, or CD19 or GPNMB-fragments, CD228-fragments, αvβ6-fragments, CD30-fragments, LIV1-fragments, or CD19-fragments but also the distribution of such peptides in the examined tissue (e.g., in the context of assessing the spread of cancer cells).

In another aspect, an anti-idiotypic antibody (Id) which binds to an antigen binding protein (e.g., an anti-GPNMB, anti-CD228, anti-αvβ6, anti-CD30, anti-LIV1, or anti-CD19 antibody) is provided. An Id antibody can be prepared by immunizing an animal of the same species and genetic type as the source of an anti GPNMB, anti-CD228, anti-αvβ6, anti-CD30, anti-LIV1, or anti-CD19 mAb with the mAb to which an anti-Id is being prepared. The immunized animal typically can recognize and respond to the idiotypic determinants of the immunizing antibody by producing an antibody to these idiotypic determinants (the anti-Id antibody).

Enumerated Embodiments

Embodiment 1. A Ligand Drug Conjugate composition represented by Formula 1:

$$L\text{-}[LU\text{-}D']_p \qquad (1)$$

or a salt thereof, in particular a pharmaceutically acceptable salt, wherein
L is a Ligand Unit;
LU is a Linker Unit;
D' represents from 1 to 4 Drug Units (D) in each drug linker moiety of formula -LU-D'; and
subscript p is a number from 1 to 12, from 1 to 10 or from 1 to 8 or is about 4 or about 8,
wherein the Ligand Unit is from an antibody or an antigen-binding fragment of an antibody that is capable of selective binding to an antigen of tumor tissue for subsequent release of the Drug Unit(s) as free drug,
wherein the drug linker moiety of formula -LU-D' in each of the Ligand Drug Conjugate compounds of the composition has the structure of Formula 1A:

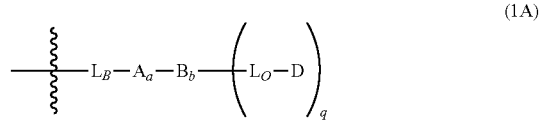

(1A)

or a salt thereof, in particular a pharmaceutically acceptable salt,
wherein the wavy line indicates covalent attachment to L;
D is the Drug Unit;
$L_B$ is a ligand covalent binding moiety;
A is a first optional Stretcher Unit;
subscript a is 0 or 1, indicating the absence or presence of A, respectively;
B is an optional Branching Unit;
subscript b is 0 or 1, indicating the absence or presence of B, respectively;
$L_O$ is a secondary linker moiety, wherein the secondary linker has the formula of;

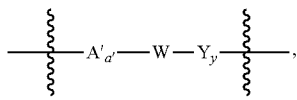

wherein the wavy line adjacent to Y indicates the site of covalent attachment of $L_O$ to the Drug Unit and the wavy line adjacent to A' indicates the site of covalent attachment to the remainder of the drug linker moiety;
A' is a second optional Stretcher Unit, which in the absence of B becomes a subunit of A,
subscript a' is 0 or 1, indicating the absence or presence of A', respectively,
W is a peptide Cleavable Unit, wherein the peptide Cleavable Unit is a contiguous sequence of up to 12 amino acids, wherein the sequence is comprised of a selectivity conferring tripeptide that provides improved selectivity for exposure of tumor tissue over normal tissue to free cytotoxic compound released from the Ligand Drug Conjugate compounds of the composition in comparison to the compounds of a comparator Ligand-Drug Conjugate composition in which the peptide sequence of its peptide Cleavable Unit is the dipeptide -valine-citrulline- or -valine-alanine-;
wherein the tumor and normal tissues are of rodent species and wherein the formula I composition provides said improved exposure selectivity demonstrated by:
retaining efficacy in a tumor xenograft model of the comparator conjugate composition when administered at the same effective amount and dose schedule previously determined for the comparator conjugate composition, and
showing a reduction in plasma concentration of free drug, and/or preservation of normal cells in tissue when administration at the same effective amount and dose schedule as in the tumor xenograft model to a non-tumor bearing rodent in comparison that same administration of the comparator conjugate in which the Ligand Units of both conjugate compositions are replaced by a non-binding antibody,
wherein the normal tissue is of the same tissue type in human and wherein cytotoxicity to cells of that tissue is responsible at least in part to an adverse event in a human subject to whom is administered a therapeutically effective amount of the comparator conjugate composition;
Y is a self-immolative Spacer Unit;
subscript y is 0, 1 or 2 indicating the absence or presence of 1 or 2 of Y, respectively; and
subscript q is an integer ranging from 1 to 4,
provided that subscript q is 1 when subscript b is 0 and subscript q is 2, 3 or 4 when subscript b is 1; and
wherein the Ligand Drug Conjugate compounds of the composition have the structure of Formula 1 in which subscript p is replaced by subscript p', wherein subscript p' is an integer from 1 to 12, 1 to 10 or 1 to 8 or is 4 or 8.

Embodiment 2. The Ligand Drug Conjugate composition of embodiment 1, wherein the xenograft model is SCID or nude mouse implanted with HPAF-II, Ramos SK-MEL-5 or SU-DHL-4 cancer cells, in particular nude mouse implanted with HPAF-II cancer cells.

Embodiment 3. The Ligand Drug Conjugate composition of embodiment 1 or 2, wherein the normal tissue is rat bone marrow.

Embodiment 4. The Ligand Drug Conjugate composition of embodiment 1 or 2, wherein the Formula I composition provides said improved exposure selectivity is further demonstrated by an increased ratio of proteolysis of the Formula 1 composition by homogenized tumor xenograft tissue over proteolysis of the comparator conjugate by homogenized normal tissue when incubated under the same conditions in comparison to that ratio for the comparator conjugate.

Embodiment 5. The Ligand Drug Conjugate composition of embodiment 4, wherein the normal tissue is from bone marrow of rat or of human.

Embodiment 6. The Ligand Drug Conjugate composition of any one of embodiments 1-5, wherein the tumor xenograft tissue is from nude mice implanted with HPAF-II cancer cells.

Embodiment 7. The Ligand Drug Conjugate composition of any one of embodiments 1-6, wherein each drug linker moiety has the formula of.

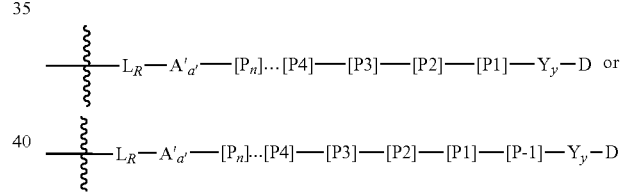

or a salt thereof, in particular a pharmaceutically acceptable salt, wherein
$L_R$ is a primary linker of formula $-L_B-A_a-B_b-$, provided that A' is a subunit of A so that A' is a component of $L_R$ when subscript a and a' are each 1 and subscript b is 0; and
each P is an amino acid residue of the contiguous amino acid sequence of the peptide Cleavable Unit and wherein subscript n has an integer value providing for up to 12 of these residues.

Embodiment 8. The Ligand Drug Conjugate composition of any one of embodiments 1-6, wherein each drug linker moiety has the formula of:

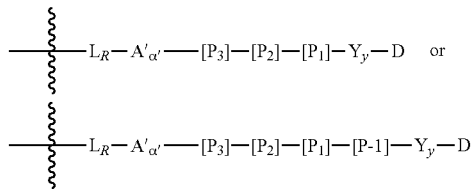

or a salt thereof, in particular a pharmaceutically acceptable salt,
wherein $L_R$ is a primary linker of formula $-L_B-A_a-B_b-$, provided that A' is a subunit of A so that A' is a component of $L_R$ when subscript a and a' are each 1 and subscript b is 0; and
wherein each P is an amino acid residue of the contiguous amino acid sequence of the peptide Cleavable Unit.

Embodiment 9. The Ligand Drug Conjugate composition of any one of embodiments 1-6, wherein each drug linker moiety has the formula of:

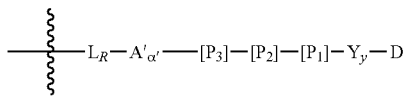

or a salt thereof, in particular a pharmaceutically acceptable salt, wherein
$L_R$ is a primary linker of formula $-L_B-A_a-B_b-$, provided that A' is a subunit of A so that A' is a component of $L_R$ when subscript a and a' are each 1 and subscript b is 0;
each P is an amino acid residue of the contiguous amino acid sequence of the peptide Cleavable Unit and wherein subscript n has an integer value providing for up to 12 of these residues; and
P1 is a L-amino acid residue having at physiological pH a negatively charged side chain or a non-positively charged polar side chain.

Embodiment 10. The Ligand Drug Conjugate composition of any one of embodiments 1-9, wherein P1 is a L-amino acid residue selected from the group consisting of glutamic acid, methionine-sulfoxide, aspartic acid, (S)-3-aminopropane-1,1,3-tricarboxylic acid and phospho-threonine.

Embodiment 11. The Ligand Drug Conjugate composition of any one of embodiments 1-6, wherein each drug linker moiety has the formula of:

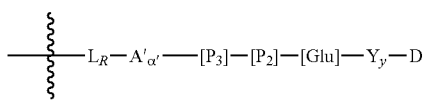

or a salt thereof, in particular a pharmaceutically acceptable salt, wherein
$L_R$ is a primary linker of formula $-L_B-A_a-B_b-$, provided that A' is a subunit of A so that A' is a component of $L_R$ when subscript a and a' are each 1 and subscript b is 0; and
each P is an amino acid residue of the contiguous amino acid sequence of the peptide Cleavable Unit.

Embodiment 12. The Ligand Drug Conjugate composition of any one of embodiments 1-11, wherein P2 is a residue of glycine or an L-amino acid, the side chain of which has no more than three contiguous carbon atoms.

Embodiment 13. The Ligand Drug Conjugate composition of any one of embodiments 1-11, wherein the P2 amino acid is L-alanine, L-valine or glycine or an unnatural amino acid, wherein the unnatural amino acid is Abu, Aib, Ala, Gly, Leu, Nva or Pra, wherein Abu, Aib, Nva, and Pra have the structures of:

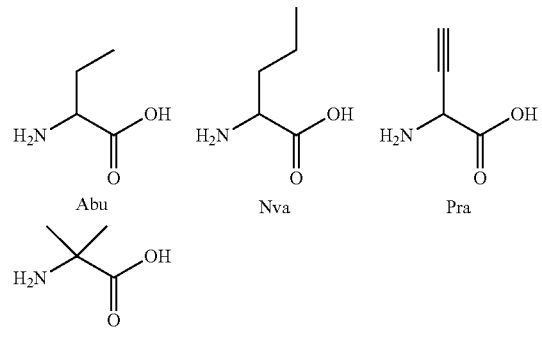

and wherein the side chains of Abu, Nva and Pra are in the same stereochemical configuration of an L-amino acid.

Embodiment 14. The Ligand Drug Conjugate composition of any one of embodiments 1-6, wherein each drug linker moiety has the formula of:

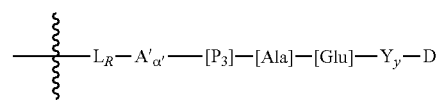

or a salt thereof, in particular a pharmaceutically acceptable salt, wherein
$L_R$ is a primary linker of formula $-L_B-A_a-B_b-$, provided that A' is a subunit of A so that A' is a component of $L_R$ when subscript a and a' are each 1 and subscript b is 0; and
P3 is an amino acid residue of the contiguous amino acid sequence of the peptide Cleavable Unit.

Embodiment 15. The Ligand Drug Conjugate composition of any one of embodiments 1-14, wherein P3 is a D-amino acid, the side chain of which is uncharged at physiological pH.

Embodiment 16. The Ligand Drug Conjugate composition of any one of embodiments 1-14 wherein P3 is a D-Leu, L-Leu, L-Cit or L-Pro, preferably D-Leu.

Embodiment 17. The Ligand Drug Conjugate composition of embodiment 1-9, wherein the selectivity conferring tripeptide, —[P3]-[P2]-[P1]—, is -D-Leu-Ala-Glu-, or a salt thereof, in particular a pharmaceutically acceptable salt.

Embodiment 18. The Ligand Drug Conjugate composition of any one of embodiments 1-17, wherein $-L_R-$ in the drug linker moieties of each Ligand Drug Conjugate compound has or is comprised of one of the structures of:

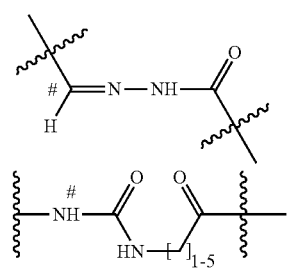

411

-continued

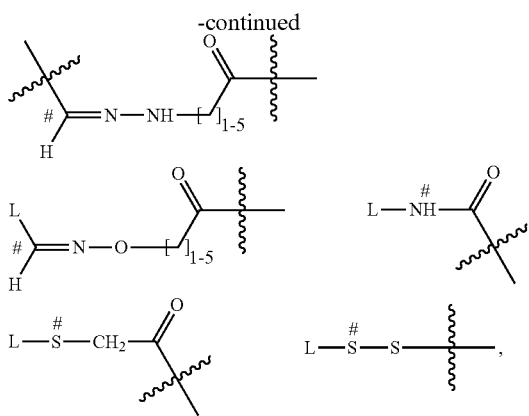

wherein the indicated (#) nitrogen, carbon or sulfur atom is from the Ligand Unit; and wherein the wavy line adjacent thereto indicates the site of covalent attachment to the remainder of the Ligand Unit and the other wavy line indicates the site of covalent attachment to the remainder of one of the drug linker moieties.

Embodiment 19. The Ligand Drug Conjugate composition of any one of embodiments 1-17, wherein subscript q is 1 and $L_R$ is -$L_B$-A-, wherein -$L_B$-A- in the drug linker moieties of each Ligand Drug Conjugate compound predominately has the structure of:

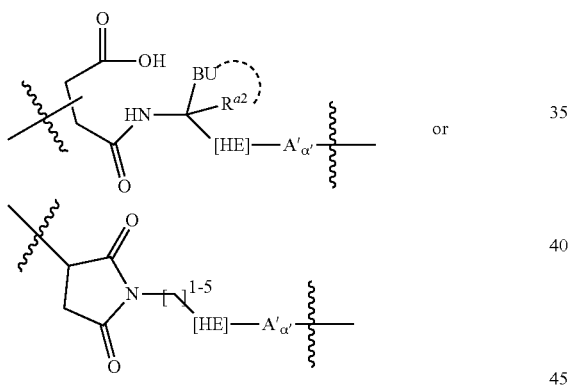

or a salt thereof, in particular a pharmaceutically acceptable salt, wherein
the wavy line adjacent to A'$_{a'}$ indicates the site of covalent attachment to the Peptide Cleavable Unit of one of the drug linker moieties; and the other wavy line indicates the site of covalent attachment to a sulfur atom of the Ligand Unit;
[HE] is a Hydrolysis Enhancing Unit;
BU is a Basic Unit;
$R^{a2}$ is an optionally substituted $C_1$-$C_{12}$ alkyl group; and
the dotted curved line indicates optional cyclization so that in the absence of said cyclization, BU is an acyclic Basic Unit having a primary, secondary or tertiary amine functional group as the basic function group of the acyclic Basic Unit, or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit,

412 wherein the basic nitrogen atom of the acyclic Basic Unit or cyclic Basic Unit is optionally suitably protected by a nitrogen protecting group, dependent on the degree of substitution of the basic nitrogen atom or is optionally protonated.

Embodiment 20. The Ligand Drug Conjugate composition of embodiment 19, wherein -$L_B$-A- in the drug linker moieties of each Ligand Drug Conjugate compound predominately have the structure of:

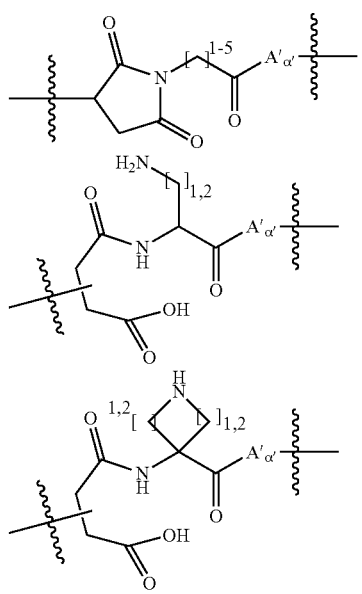

or a salt thereof, in particular a pharmaceutically acceptable salt.

Embodiment 21. The Ligand Drug Conjugate composition of any one of embodiments 1-20, wherein subscript q is 1 and A' is present as a subunit of A, wherein A' is comprised of an amine-containing acid residue having the structure of formula (3) or formula (4):

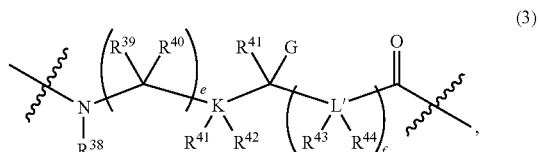
(3)

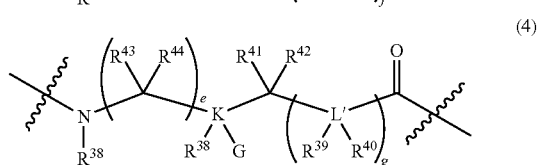
(4)

or a salt thereof, in particular a pharmaceutically acceptable salt, wherein
the wavy line adjacent to the nitrogen atom indicates the site of covalent attachment to [HE], wherein [HE] is —C(═O)— and the wavy line adjacent to the carbonyl carbon atom indicates the site of covalent attachment to the remainder of A' or to the N-terminal amino acid residue of the Peptide Cleavable Unit, wherein both attachments are through amide functional groups;

K and L' independently are C, N, O or S, provided that when K or L' is O or S, $R^{41}$ and $R^{42}$ to K, $R^{38}$ and G to K, $R^{43}$ and $R^{44}$ to L', and $R^{39}$ and $R^{40}$ to L' are absent, and when K or L' are N, one of $R^{41}$ or $R^{42}$ to K and one of $R^{38}$ or G to K, one of $R^{43}$ or $R^{44}$ to L' for each unit of -L'$(R^{43})(R^{44})$, and one of $R^{39}$ or $R^{40}$ to L' for each unit of -L'$(R^{39})(R^{40})$ are absent, and provided that no two adjacent L' are independently selected as N, O, or S;

wherein subscripts e and f are independently selected integers that range from 0 to 12, and subscript g is an integer ranging from 1 to 12:

G is hydrogen, optionally substituted $C_1$-$C_6$ alkyl, —OH or —$CO_2$H;

$R^{38}$ is hydrogen or optionally substituted $C_1$-$C_6$ alkyl;

$R^{39}$-$R^{44}$ are independently selected from the group consisting of hydrogen, optionally substituted $C_1$-$C_6$ alkyl and optionally substituted $C_5$-$C_{10}$ (hetero)aryl, or $R^{39}$ and $R^{40}$ together with the carbon atom to which both are attached, or $R^{41}$ and $R^{42}$ together with K to which both are attached when K is a carbon atom, define a $C_3$-$C_6$ carbocyclo, and the remainder of $R^{39}$-$R^{44}$ are as defined herein, or $R^{43}$ and $R^{44}$ together with L' to which both are attached when L' is a carbon atom define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the optional atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^{44}$ are absent, and when L' is N, one of $R^{43}$, $R^{44}$ is absent, or A' is comprised of an alpha-amino, beta-amino or another amine-containing acid residue, wherein its amino nitrogen atom is covalently attached to the carbonyl carbon atom of HE, and its carboxylic acid carbonyl carbon atom is covalently attached to the remainder of A' or to N-terminal amino acid of the Peptide Cleavable Unit, wherein both covalent attachments are through amide functional groups.

Embodiment 22. The Ligand Drug Conjugate composition of embodiment 21, wherein A' is an amine-containing acid residue having the structure of formula 3a, formula 4a or formula 5a:

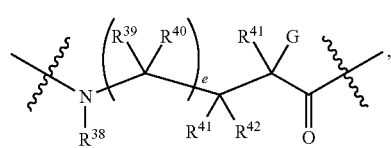

(3a)

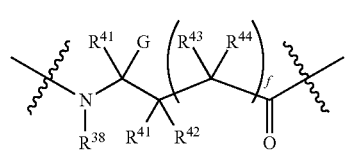

(4a)

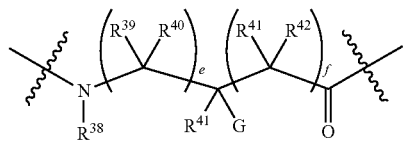

(5a)

or a salt thereof, in particular a pharmaceutically acceptable salt, wherein
subscripts e and f are independently 0 or 1; and
$R^{38}$—$R^{44}$ are each hydrogen;
or A' is an α-amino or β-amino acid residue.

Embodiment 23. The Ligand Drug Conjugate composition of any one of embodiments 1-20, wherein subscript q is 1 and A' is comprised of a β-amino acid residue or -$L^P$(PEG)-, wherein PEG is a PEG Unit and $L^P$ is Parallel Connector Unit having the structure of Formula $L^P$-1 or $L^P$-2:

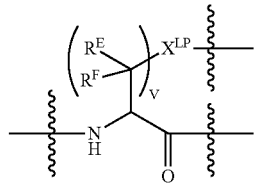

(Formula $L^P$-1)

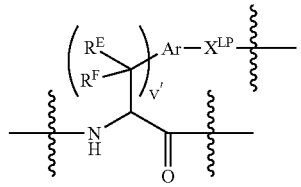

(Formula $L^P$-2)

or wherein -$L^P$(PEG)- or a PEG-containing subunit thereof has the structure of Formula $L^P$-3 or Formula $L^P$-4:

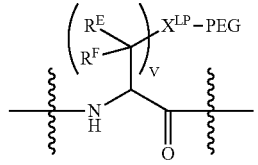

(Formula $L^P$-3)

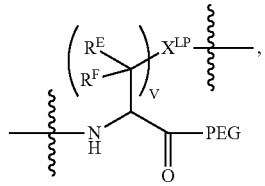

(Formula $L^P$-4)

wherein subscript v is an integer ranging from 1 to 4;
subscript v' is an integer ranging from 0 to 4;
$X^{LP}$ is provided by a natural or un-natural amino acid side chain or is selected from the group consisting of —O—, —$NR^{LP}$—, —S—, —S(=)-, —S(=O)$_2$—, —C(=O)—, —C(=O)N($R^{LP}$)—, —N($R^{LP}$)C(=O)N($R^{LP}$)—, and —N($R^{LP}$)C(=N$R^{LP}$)N($R^{LP}$)—, or $C_3$-$C_8$ heterocyclo;

wherein each $R^{LP}$ is independently selected from the group consisting of hydrogen and optionally substituted $C_1$-$C_6$ alkyl, or two of $R^{LP}$ together along with the carbons atoms to which they are attached, and their intervening atoms define a $C_5$-$C_6$ heterocyclo and any remaining $R^{LP}$ are as previously defined;

Ar is a $C_6$-$C_{10}$ arylene or a $C_5$-$C_{10}$ heteroarylene, each of which is optionally substituted;

each $R^E$ and $R^F$ is independently selected from the group consisting of —H, optionally substituted $C_1$-$C_6$ alkyl, optionally substituted $C_2$-$C_6$ alkylene, optionally substituted $C_6$-$C_{10}$ arylene or optionally substituted $C_5$-$C_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined;

wherein one of the wavy lines indicate the point of covalent attachment of a PEG Unit and the other two wavy lines indicates covalent attachment of Formula $L^P$-1 or Formula $L^P$-2 within the structure representing the Ligand Drug Conjugate composition, or $L^P$ is Parallel Connector Unit having the structure of a tri-functional amine-containing acid residue or; and PEG is a PEG Unit.

Embodiment 24. The Ligand Drug Conjugate composition of any one of embodiment 1-20, wherein A' is comprised of a β-amino acid residue or -$L^P$(PEG)-, wherein PEG is a PEG Unit and $L^P$ is Parallel Connector Unit, wherein the β-amino acid residue has the structure of —NHCH$_2$CH$_2$C(=O)—; and wherein -$L^P$(PEG)- has the structure of:

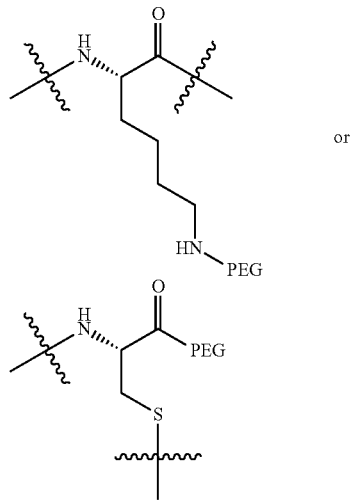

wherein the wavy lines indicate the sites of covalent attachment within the drug linker moiety.

Embodiment 25. The Ligand Drug Conjugate composition of embodiment 23 or 24, wherein the PEG Unit has the structure of:

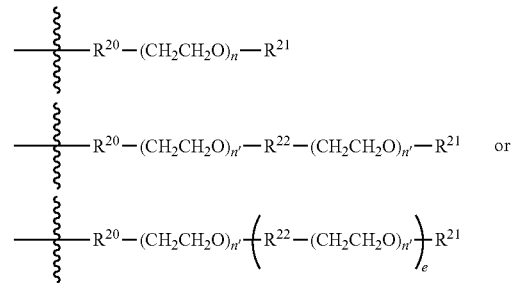

wherein the wavy line indicates the site of covalent attachment to $L^P$;

$R^{20}$ is a PEG Attachment Unit, wherein the PEG Attachment Unit is —C(O)—, —O—, —S—, —S(O)—, —NH—, —C(O)O—, —C(O)$C_1$-$C_{10}$alkyl, —C(O)$C_1$-$C_{10}$alkyl-O—, —C(O)$C_1$-$C_{10}$alkyl-CO$_2$—, —C(O)$C_1$-$C_{10}$alkyl-NH—, —C(O)$C_1$-$C_{10}$ alkyl-S—, —C(O)$C_1$-$C_{10}$ alkyl-C(O)—NH—, —C(O)$C_1$-$C_{10}$alkyl-NH—C(O)—, —$C_1$-$C_{10}$alkyl, —$C_1$-$C_{10}$alkyl-O—, —$C_1$-$C_{10}$alkyl-CO$_2$—, —$C_1$-$C_{10}$alkyl-NH—, —$C_1$-$C_{10}$alkyl-S—, —$C_1$-$C_{10}$alkyl-C(O)—NH—, —$C_1$-$C_{10}$alkyl-NH—C(O)—, —CH$_2$CH$_2$SO$_2$—$C_1$-$C_{10}$alkyl-, —CH$_2$C(O)—$C_{1\text{-}10}$ alkyl-, =N—(O or N)—$C_1$-$C_{10}$alkyl-O—, =N—(O or N)—$C_1$-$C_{10}$alkyl-NH—, =N—(O or N)—$C_1$-$C_{10}$alkyl-CO$_2$—, =N—(O or N)—$C_1$-$C_{10}$alkyl-S—,

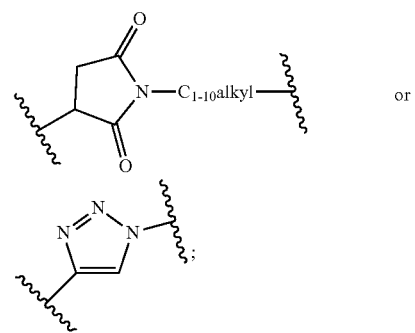

$R^{21}$ is a PEG Capping Unit; wherein the PEG Capping Unit is —$C_1$-$C_{10}$alkyl, —$C_2$-$C_{10}$ alkyl-CO$_2$H, —$C_2$-$C_{10}$ alkyl-OH, —$C_2$-$C_{10}$ alkyl-NH$_2$, $C_2$-$C_{10}$ alkyl-NH($C_1$-$C_3$ alkyl), or $C_2$-$C_{10}$ alkyl-N($C_1$-$C_3$ alkyl)$_2$;

$R^{22}$ is an PEG Coupling Unit for coupling multiple PEG subunit chains together, wherein the PEG Coupling Unit is —$C_{1\text{-}10}$ alkyl-C(O)—NH—, —$C_{1\text{-}10}$ alkyl-NH—C(O)—, —$C_{2\text{-}10}$ alkyl-NH—, —$C_2$-$C_{10}$ alkyl-O—, —$C_1$-$C_{10}$alkyl-S—, or —$C_2$-$C_{10}$ alkyl-NH—;

subscript n is independently selected from 8 to 72, from 10 to 72 or from 12 to 72;

subscript e is selected from 2 to 5; and each n' is independently selected from at least 6 to no more than 72, preferably from at least 8 or at least 10 to no more than 36.

Embodiment 26. The Ligand Drug Conjugate composition of any one of embodiments 1-6, wherein a majority of Ligand Drug Conjugate compounds in the Ligand Drug Conjugate composition have drug linker moieties represented by the structures of Formula 1C and Formula 1D:

(Formula 1C)

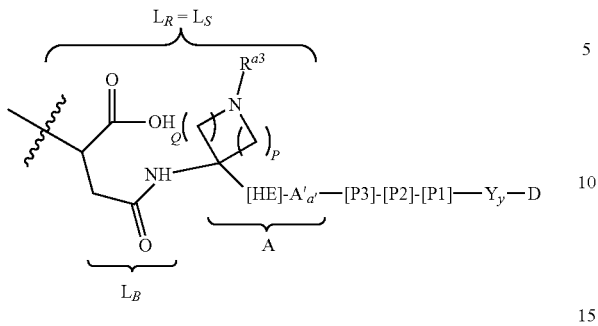

(Formula 1D)

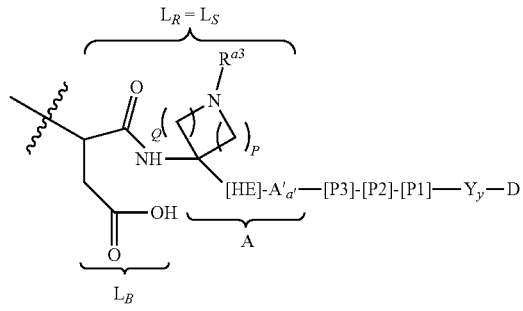

or a salt thereof, in particular a pharmaceutical acceptable salt, wherein

HE is a Hydrolysis Enhancing Unit;

A' is a subunit, when present, of the indicated first Stretcher Unit (A);

subscript a' is 0 or 1, indicating the absence or presence of A', respectively;

subscript P is 1 or 2; and subscript Q ranges from 1 to 6, preferably subscript Q is 1 or 2, more preferably subscript Q has the same value as subscript P;

$R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—($CH_2CH_2O)_{1-36}$—$R^{PEG2}$, wherein $R^{PEG1}$ is $C_1$-$C_4$ alkylene and $R^{PEG2}$ is —H or $C_1$-$C_4$ alkylene, wherein the basic nitrogen bonded to $R^{a3}$ is optionally protonated in a salt form, preferably in a pharmaceutically acceptable salt form, or $R^{a3}$ is a nitrogen protecting group such as a suitable acid-labile protecting group;

each P is an amino acid residue of the contiguous amino acid sequence of the peptide Cleavable Unit; and the wavy line indicates the site of covalent binding to a sulfur atom of the Ligand Unit.

Embodiment 27. The Ligand Drug Conjugate composition of embodiment 1, wherein a majority of Ligand Drug Conjugate compounds in the Ligand Drug Conjugate composition have drug linker moieties represented by the structures of Formula 1F and Formula 1G:

(Formula 1F)

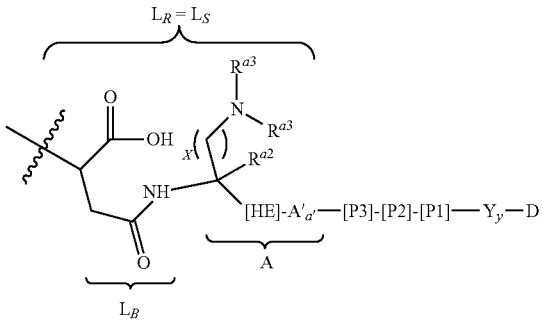

(Formula 1G)

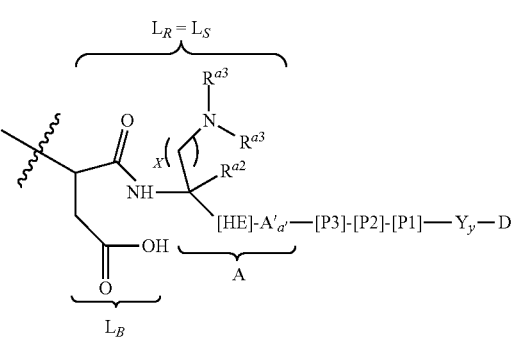

or a salt thereof, in particular a pharmaceutical acceptable salt, wherein

HE is a Hydrolysis Enhancing Unit;

A' is a subunit, when present, of the indicated first Stretcher Unit (A);

subscript a' is 0 or 1, indicating the absence or presence of A', respectively;

subscript x is 1 or 2;

$R^{a2}$ is —H, optionally substituted $C_1$-$C_6$ alkyl, —$CH_3$ or —$CH_2CH_3$;

$R^{a3}$, at each instance, is independently a nitrogen protecting group, —H or optionally substituted $C_1$-$C_6$ alkyl, preferably —H, an acid-labile protecting group, —$CH_3$ or —$CH_2CH_3$, or both $R^{a3}$ together with the nitrogen to which they are attached define a nitrogen protecting group or an azetidinyl, pyrrolidinyl or piperidinyl heterocyclyl, in which a basic primary, secondary or tertiary amine so defined is optionally protonated in a salt form, preferably a pharmaceutically acceptable salt form; and the wavy line indicates the site of covalent binding to a sulfur atom of the Ligand Unit.

Embodiment 28. The Ligand Drug Conjugate composition of embodiment 1, wherein the Ligand Drug Conjugate compounds in the Ligand Drug Conjugate composition predominately have drug linker moieties of Formula 1H:

(Formula 1H)

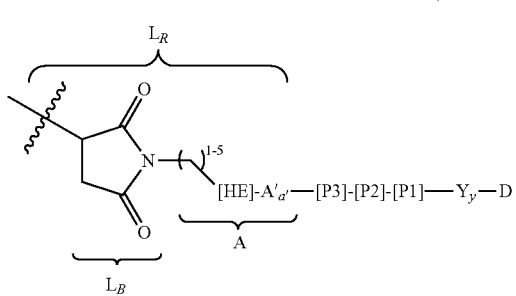

or salts thereof, in particular pharmaceutical acceptable salts, and optionally having a minority of Ligand Drug Conjugate compounds in which one or more of the drug linker moieties in each of such compounds has its the succinimide ring in hydrolyzed form and wherein HE is a Hydrolysis Enhancing Unit;

A' is a subunit, when present, of the indicated first Stretcher Unit (A); subscript a' is 0 or 1, indicating the absence or presence of A'; and the wavy line indicates the site of covalent binding to a sulfur atom of the Ligand Unit.

Embodiment 29. The Ligand Drug Conjugate composition of embodiment 26, wherein a majority of Ligand Drug Conjugate compounds in the Ligand Drug Conjugate composition have drug linker moieties represented by the structures of:

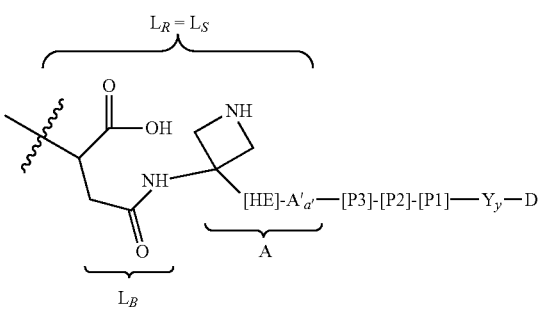

and

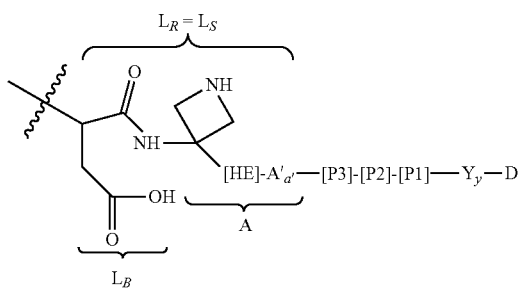

or salts thereof, in particular pharmaceutical acceptable salts.

Embodiment 30. The Ligand Drug Conjugate composition of embodiment 28, wherein a majority of Ligand Drug Conjugate compounds in the Ligand Drug Conjugate composition have drug linker moieties represented by the structures of:

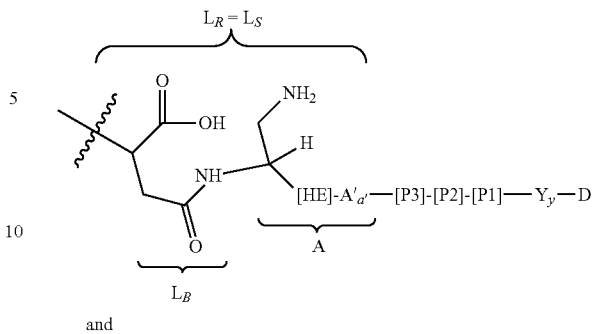

and

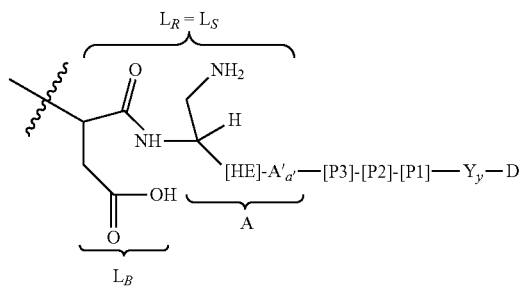

or salts thereof, in particular pharmaceutical acceptable salts.

Embodiment 31. The Ligand Drug Conjugate composition of any one of embodiments 26-30 wherein HE is —C(=O).

Embodiment 32. The Ligand Drug Conjugate composition of any one of embodiments 26-30 wherein HE is —C(=O), subscript a' is 1 and A' has the structure of formula 3a, formula 4a or formula 5a of embodiment 17, or A' is an α-amino acid or β-amino acid residue.

Embodiment 33. The Ligand Drug Conjugate composition of any one of embodiments 26-32, wherein —[P3]-[P2]-[P1]- is D-Leu-Leu-Met(O), D-Leu-Ala-Glu, L-Leu-Ala-Glu or D-Leu-Ala-Cit wherein Met(O) is methionine in which its sulfur atom is oxidized to a sulfoxide and Cit is citrulline.

Embodiment 34. The Ligand Drug Conjugate composition of any one of embodiments 1-33, wherein —$Y_y$-D has the structure of:

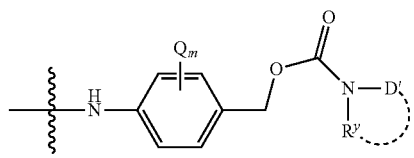

wherein —N($R^y$)D' represents D, wherein D' is the remainder of D;

the wavy line indicates the site of covalent attachment to P1 or P-1;

the dotted line indicates optional cyclization of R to D;

$R^y$ is optionally substituted $C_1$-$C_6$ alkyl in absence of cyclization to D' or optionally substituted $C_1$-$C_6$ alkylene when cyclized to D';

each Q is independently —$C_1$-$C_8$ alkyl, —O—($C_1$-$C_8$ alkyl), or other electron donating group, -halogen, -nitro or -cyano or other electron withdrawing group, in particular each Q is independently selected from the group consisting of —$C_1$-$C_8$ alkyl, —O—($C_1$-$C_8$ alkyl), halogen, nitro and cyano; and subscript m is 0, 1 or 2, in particular subscript m is 0 or 1 and Q when present is an electron donating group, preferably subscript m is 0.

Embodiment 35. The Ligand Drug Conjugate composition of embodiment 1 wherein predominate drug linker moiety in a majority of Ligand Drug Conjugate compounds of the composition are represented by the structure of:

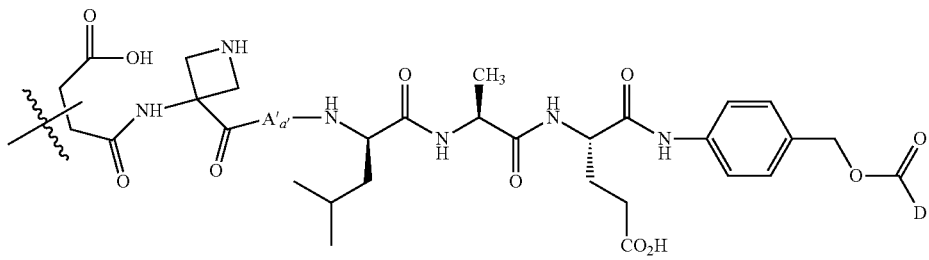

or salts thereof, in particular, pharmaceutically acceptable salts, wherein the wavy line indicates covalent attachment to a sulfur atom from a Ligand Unit;

subscript a' is 1, indicating the presence of A', wherein A' is an amine-containing acid residue of formula 3a, formula 4a or formula 5a of embodiment 22, or an α-amino acid or β-amino acid residue, in particular —NH—CH$_2$CH$_2$—C(=O)—; and D is a cytotoxic drug having a secondary amino group as the site of attachment to the drug linker moiety.

Embodiment 36. The Ligand Drug Conjugate composition of embodiment 1 wherein predominate drug linker moiety in a majority of Ligand Drug Conjugate compounds of the composition are represented by the structure of:

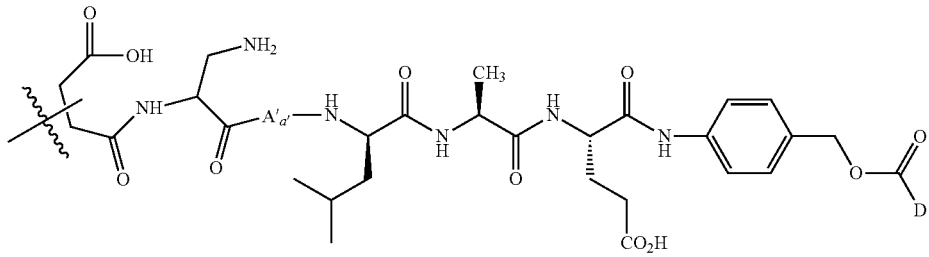

or salts thereof, in particular, pharmaceutically acceptable salts, wherein the wavy line indicates covalent attachment to a sulfur atom from a Ligand Unit;

subscript a' is 1, indicating the presence of A, respectively, wherein A' is an amine-containing acid residue of formula 3a, formula 4a or formula 5a of embodiment 22, or an α-amino acid or β-amino acid residue, in particular —NH—CH$_2$CH$_2$—C(=O)—; and D is a cytotoxic drug having a secondary amino group as the site of attachment to the drug linker moiety.

Embodiment 37. The Ligand Drug Conjugate composition of embodiment 1 wherein predominate drug linker moiety in a majority of Ligand Drug Conjugate compounds of the composition is represented by the structure of:

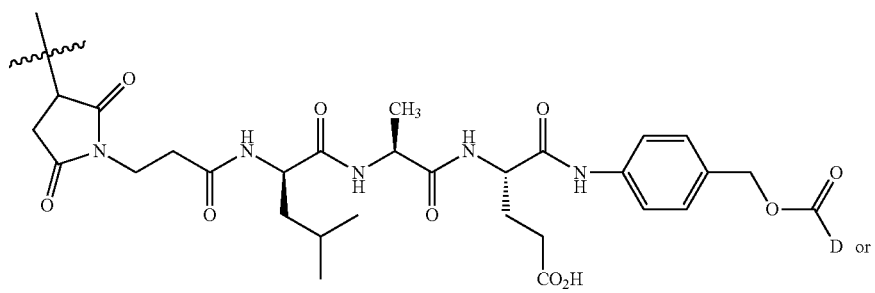

D or

-continued

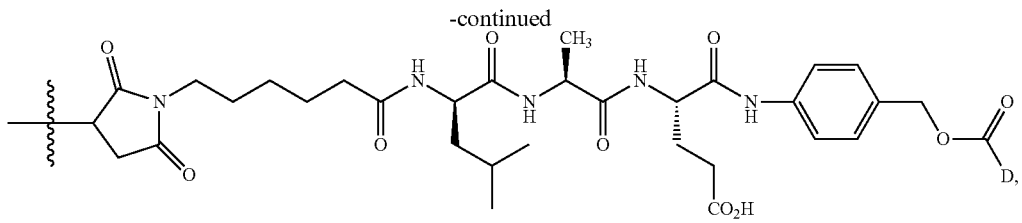

or salts thereof, in particular, pharmaceutically acceptable salts, wherein
the wavy line indicates covalent attachment to a sulfur atom from a Ligand Unit; and
D is a cytotoxic drug having a secondary amino group as the site of attachment to the drug linker moiety.

Embodiment 38. The Ligand Drug Conjugate composition of any one of embodiments 1-37, wherein subscript y' is 2, and $Y_y$ is —Y—Y'—, wherein Y is a first self-immolative Spacer Unit and Y' is a second self-immolative Spacer Unit having the structure of —OC(=O)— and the cytotoxic drug is a secondary amine-containing auristatin compound wherein the nitrogen atom of the secondary amine is the site of covalent attachment to the carbonyl carbon atom of Y' through a carbamate functional group shared between D and Y'.

Embodiment 39. The Ligand Drug Conjugate composition of embodiment 38, wherein the secondary amine-containing auristatin compound has the structure of Formula $D_E$ or $D_F$:

$R^{16}$ is hydrogen, $C_1$-$C_8$ alkyl, $C_3$-$C_8$ carbocyclyl, $C_6$-$C_{24}$ aryl, —$C_6$-$C_{24}$—$X^1$-aryl, —$X^1$—($C_3$-$C_8$ carbocyclyl), $C_3$-$C_8$ heterocyclyl or —$X^1$—($C_3$-$C_8$ heterocyclyl);
each $R^{17}$ independently are hydrogen, —OH, $C_1$-$C_8$ alkyl, $C_3$-$C_8$ carbocyclyl or O—($C_1$-$C_8$ alkyl);
$R^{18}$ is hydrogen or optionally substituted $C_1$-$C_8$ alkyl;
$R^{19}$ is —C($R^{19A}$)$_2$—C($R^{19A}$)$_2$— $C_6$-$C_{24}$ aryl, —C($R^{19A}$)$_2$—C($R^{19A}$)$_2$—($C_3$-$C_8$ heterocyclyl) or —C($R^{19A}$)$_2$—C($R^{19A}$)$_2$—($C_3$-$C_8$ carbocyclyl), wherein $C_6$-$C_{24}$ aryl and $C_3$-$C_8$ heterocyclyl are optionally substituted;
$R^{19A}$ independently are hydrogen, optionally substituted $C_1$-$C_8$ alkyl, —OH or optionally substituted —O—$C_1$-$C_8$ alkyl;
$R^{20}$ is hydrogen or $C_1$-$C_{20}$ alkyl, $C_6$-$C_{24}$ aryl or $C_3$-$C_8$ heterocyclyl, optionally substituted, or —($R^{47}$O)$_m$—$R^{48}$, or —($R^{47}$O)$_m$—CH($R^{49}$)$_2$;
$R^{21}$ is —$C_1$-$C_8$ alkylene-($C_6$-$C_{24}$ aryl) or —$C_1$-$C_8$ alkylene-($C_5$-$C_{24}$ heteroaryl), optionally substituted, or

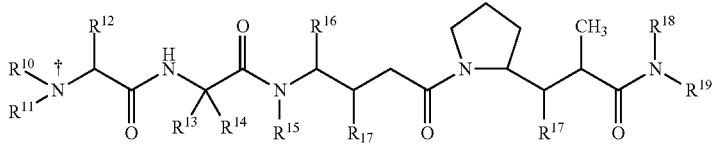

$D_E$

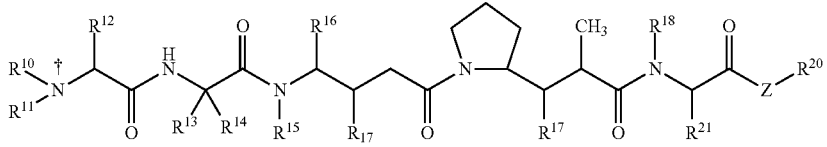

$D_F$ wherein the dagger indicates the site of covalent attachment of the nitrogen atom that provides the carbamate functional group,
one of $R^{10}$ and $R^{11}$ is hydrogen and the other is $C_1$-$C_8$ alkyl, preferably one of $R^{10}$ and $R^{11}$ is hydrogen and the other is methyl;
$R^{12}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl or —$X^1$—($C_3$-$C_8$ heterocyclyl);
$R^{13}$ is hydrogen, $C_1$-$C_8$ alkyl, $C_3$-$C_8$ carbocyclyl, $C_6$-$C_{24}$ aryl, —$X^1$— $C_6$-$C_{24}$ aryl, —$X^1$—($C_3$-$C_8$ carbocyclyl), $C_3$-$C_8$ heterocyclyl or —$X^1$—($C_3$-$C_8$ heterocyclyl);
$R^{14}$ is hydrogen or methyl, or
$R^{13}$ and $R^{14}$ taken together with the carbon to which they are attached comprise a Spiro $C_3$-$C_8$ carbocyclo;
$R^{15}$ is hydrogen or $C_1$-$C_8$ alkyl;

$C_1$-$C_8$ hydroxylalkyl, or optionally substituted $C_3$-$C_8$ heterocyclyl; Z is O, S, NH, or $NR^{46}$.
$R^{46}$ is optionally substituted $C_1$-$C_8$ alkyl; subscript m is an integer ranging from 1-1000;
$R^{47}$ is $C_2$-$C_8$ alkylene; $R^{48}$ is hydrogen or $C_1$-$C_8$ alkyl;
$R^{49}$ independently are —COOH, —(CH$_2$)$_n$—N($R^{50}$)$_2$, —(CH$_2$)$_n$—SO$_3$H, or —(CH$_2$)$_n$—SO$_3$—$C_1$-$C_8$ alkyl; and
each $R^{50}$ independently are $C_1$-$C_8$ alkyl or —(CH$_2$)$_n$—COOH; subscript n is an integer ranging from 0 to 6; and $X^1$ is $C_1$-$C_{10}$ alkylene.

Embodiment 40. The Ligand Drug Conjugate composition of embodiment 39, wherein the secondary amine-containing auristatin compound has the structure of Formula $D_{E-1}$, Formula $D_{E-2}$ or Formula $D_{F-1}$:

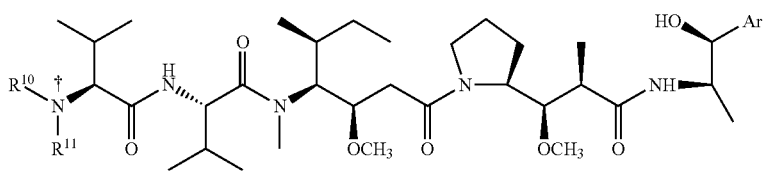

$D_{E-1}$

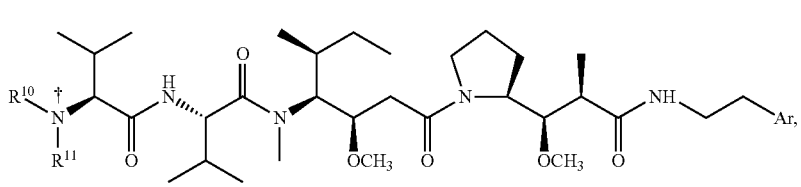

$D_{E-2}$

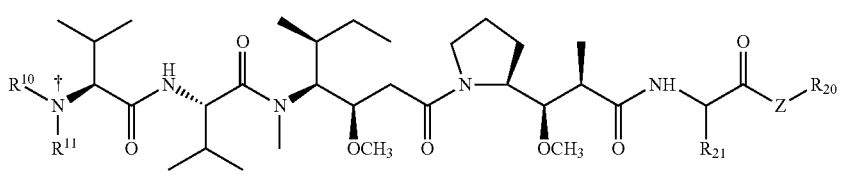

$D_{F-1}$ wherein Ar is $C_6$-$C_{10}$ aryl or $C_5$-$C_{10}$ heteroaryl, preferably Ar is phenyl or 2-pyridyl;

Z is —O— or —NH—; $R^{20}$ is hydrogen, $C_1$-$C_6$ alkyl, $C_6$-$C_{10}$ aryl or $C_5$-$C_{10}$ heteroaryl, wherein $C_1$-$C_6$ alkyl, $C_6$-$C_{10}$ aryl and $C_5$-$C_{10}$ heteroaryl are optionally substituted; and $R^{21}$ is $C_1$-$C_6$ alkyl, —$C_1$-$C_6$ alkylene-($C_6$-$C_{10}$ aryl) or —$C_1$-$C_6$ alkylene-($C_5$-$C_{10}$ heteroaryl), each of which is optionally substituted.

Embodiment 41. The Ligand Drug Conjugate composition of embodiment 40, wherein the secondary amine-containing auristatin compound has the structure of Formula $D_{F-1}$ wherein $R^{21}$ is $X^1$—S—$R^{21a}$ or $X^1$—Ar, wherein $X^1$ is $C_1$-$C_6$ alkylene, $R^{21a}$ is $C_1$-$C_4$ alkyl and Ar is phenyl or $C_5$-$C_6$ heteroaryl; and —Z— is —O— and $R^{20}$ is $C_1$-$C_4$ alkyl, or —Z— is —NH— and $R^{20}$ is phenyl or $C_5$-$C_6$ heteroaryl.

Embodiment 42. The Ligand Drug Conjugate composition of embodiment 40, wherein the secondary amine-containing auristatin compound has the structure of Formula In preferred embodiments the auristatin drug compound has the structure of Formula $D_{F/E-3}$.

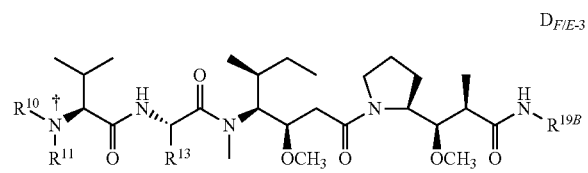

$D_{F/E-3}$ wherein one of $R^{10}$ and $R^{11}$ is hydrogen and the other is methyl;

$R^{13}$ is isopropyl or —$CH_2$—$CH(CH_3)_2$; and $R^{19B}$ is —$CH(CH_3)$—$CH(OH)$-Ph, —$CH(CO_2H)$—$CH(OH)$—$CH_3$, —$CH(CO_2H)$—$CH_2$Ph, —$CH(CH_2Ph)$-2-thiazolyl, —$CH(CH_2Ph)$-2-pyridyl, —$CH(CH_2$-p-Cl-Ph), —$CH(CO_2Me)$-$CH_2$Ph, —$CH(CO_2Me)$-$CH_2CH_2SCH_3$, —$CH(CH_2CH_2SCH_3)C(=O)NH$-quinol-3-yl, —$CH(CH_2Ph)C(=O)NH$-p-Cl-Ph, or $R^{19B}$ has the structure of

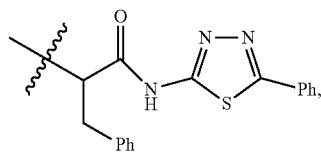 [SMILES: *C(Cc1ccccc1)C(=O)Nc1nnc(-c2ccccc2)s1]

wherein the wavy line indicates covalent attachment to the remainder of the auristatin compound.

Embodiment 43. The Ligand Drug Conjugate composition of embodiment 40 wherein the secondary amine-containing auristatin compound is monomethylauristatin E (MMAE) or monomethylauristatin F (MMAF).

Embodiment 44. The Ligand Drug Conjugate composition of embodiment 1, wherein subscript q is 1 and a majority of Ligand Drug Conjugate compounds in the Ligand Drug Conjugate composition have drug linker moieties represented by the structures of Formula 1C-MMAE and Formula 1D-MMAE:

(Formula 1C-MMAE)

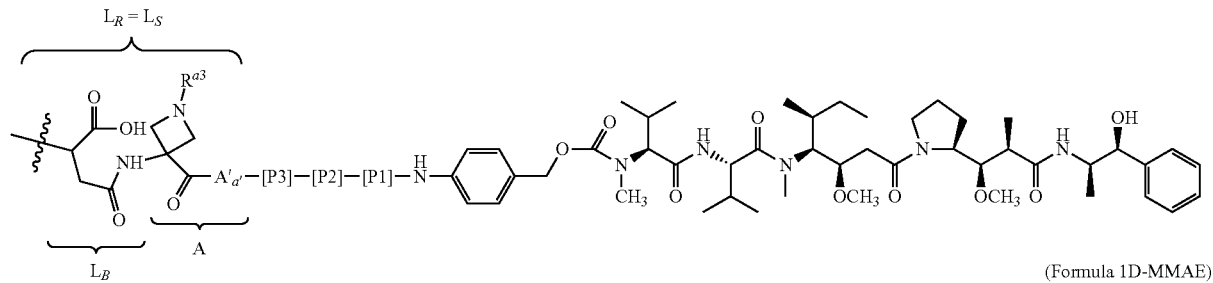

(Formula 1D-MMAE)

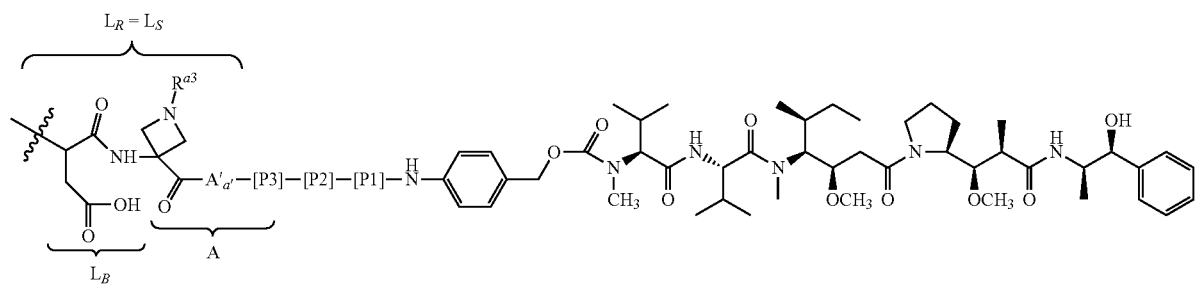

or salts thereof, in particular a pharmaceutical acceptable salts, wherein

A' is a subunit, when present, of the indicated first Stretcher Unit (A) having the structure of formula 3a, formula 4a or formula 5a of embodiment 22, or an α-amino acid or β-amino acid residue, in particular —NH—CH$_2$CH$_2$—C(=O)—;

$R^{a3}$ is —H, optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$, wherein R$^{PEG1}$ is C$_1$-C$_4$ alkylene, R$^{PEG2}$ is —H or C$_1$-C$_4$ alkylene, and wherein the basic nitrogen bonded to $R^{a3}$ is optionally protonated in a salt form, preferably in a pharmaceutically acceptable salt form, or $R^{a3}$ is a nitrogen protecting group such as a suitable acid-labile protecting group; and the wavy line indicates the site of covalent binding to a sulfur atom of the Ligand Unit.

Embodiment 45. The Ligand Drug Conjugate composition of embodiment 1, wherein subscript q is 1 and a majority of Ligand Drug Conjugate compounds in the Ligand Drug Conjugate composition have drug linker moieties represented by the structures of Formula 1F-MMAE and Formula 1G-MMAE:

(Formula 1F-MMAE)

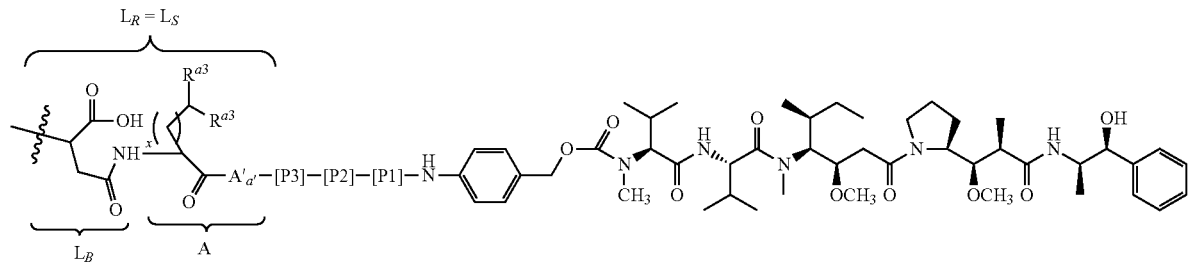

(Formula 1G-MMAE)

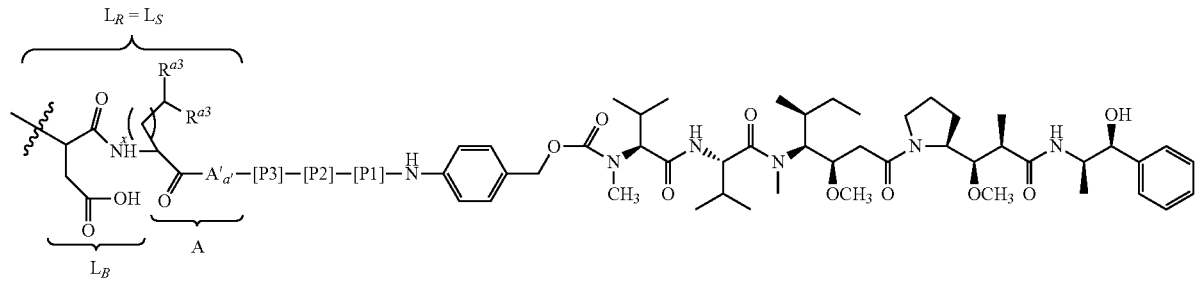

or salt thereof, in particular a pharmaceutical acceptable salts, wherein

A' is a subunit, when present, of the indicated first Stretcher Unit (A) having the structure of formula 3a, formula 4a or formula 5a of embodiment 22, or an α-amino acid or β-amino acid residue, in particular —NH—CH$_2$CH$_2$—C(=O)—;

subscript x is 1 or 2;

$R^{a3}$, at each instance, is independently a nitrogen protecting group, —H or optionally substituted $C_1$-$C_6$ alkyl, preferably —H, an acid-labile protecting group, —CH$_3$ or —CH$_2$CH$_3$, or both $R^{a3}$ together with the nitrogen to which they are attached define a nitrogen protecting group or an azetidinyl, pyrrolidinyl or piperidinyl heterocyclyl, in which a basic primary, secondary or tertiary amine so defined is optionally protonated in a salt form, preferably a pharmaceutically acceptable salt form; and the wavy line indicates the site of covalent binding to a sulfur atom of the Ligand Unit.

Embodiment 46. The Ligand Drug Conjugate composition of embodiment 1, wherein subscript q is 1 and the Ligand Drug Conjugate compounds in the Ligand Drug Conjugate composition predominately have drug linker moieties of Formula 1H-MMAE:

or a salt thereof, in particular a pharmaceutical acceptable salt, and optionally having a minority of Ligand Drug Conjugate compounds in which one or more of the drug linker moieties in each of such compounds has its the succinimide ring in hydrolyzed form and wherein A' is a subunit, when present, of the indicated first Stretcher Unit (A) having the structure of formula 3a, formula 4a or formula 5a of embodiment 22, or an α-amino acid or β-amino acid residue, in particular —NH—CH$_2$CH$_2$—C(=O)—;

subscript a' is 0 or 1, indicating the absence or presence of A'; and the wavy line indicates the site of covalent binding to a sulfur atom of the Ligand Unit.

Embodiment 47. The Ligand Drug Conjugate composition of embodiment 44, 45 or 46, wherein P1 is L-Glu or L-Asp, P2 is L-Val or L-Ala and P3 is L-Leu or D-Leu.

Embodiment 48. The Ligand Drug Conjugate composition of embodiment 1, wherein subscript q is 1 and wherein (Formula 1H-MMAE)

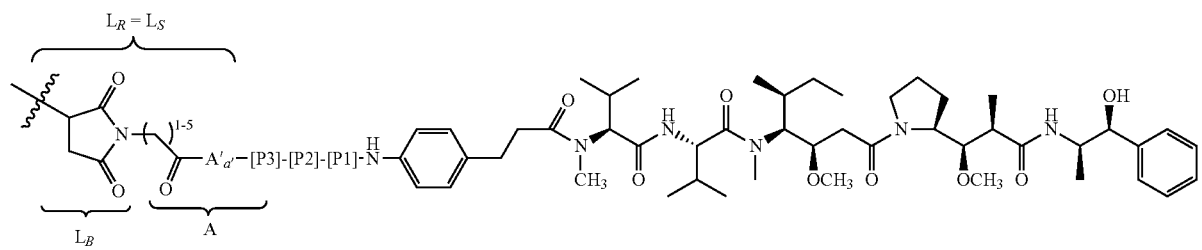

the predominate drug linker moiety in a majority of Ligand Drug Conjugate compounds of the composition is represented by the structure of:

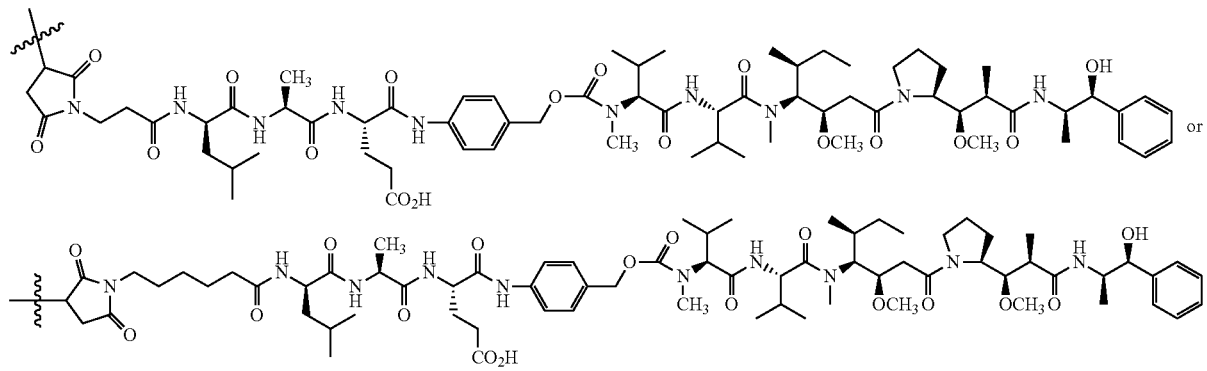

or a salt thereof, in particular a pharmaceutical acceptable salt, and optionally having a minority of Ligand Drug Conjugate compounds in which one or more of the drug linker moieties in each of such compounds has its the succinimide ring in hydrolyzed form Embodiment 49. The Ligand Drug Conjugate composition of any one of embodiments 1-48, wherein L is an antibody Ligand Unit of an intact antibody or an antigen-binding fragment thereof.

Embodiment 50. The Ligand Drug Conjugate composition of embodiment 49, wherein the intact antibody or fragment thereof is capable of selectively binding to a cancer cell antigen.

Embodiment 51. The Ligand Drug Conjugate composition of embodiment 49, wherein the intact antibody is a chimeric, humanized or human antibody, wherein the antibody is capable of selectively binding to a cancer cell antigen or the antibody is a non-binding control antibody thereby defining a non-binding control Conjugate composition.

Embodiment 52. The Ligand Drug Conjugate composition of any one of embodiments 1-51, wherein subscript p ranges from about 2 to about 12, or from about 2 to about 10, or from about 2 to about 8, in particular subscript p is about 2, about 4 or about 8.

Embodiment 53. A pharmaceutically acceptable formulation, wherein the formulation comprises an effective amount of a Ligand Drug Conjugate composition or an equivalent amount of a non-binding control Conjugate of any one of embodiments 1 to 36 and at least one pharmaceutically acceptable excipient.

Embodiment 54. The pharmaceutically acceptable formulation of embodiment 53, wherein the least one pharmaceutically acceptable excipient is a liquid carrier that provides a liquid formulation, wherein the liquid formulation is suitable for lyophilization or administration to a subject in need thereof and.

Embodiment 55. The pharmaceutically acceptable formulation of embodiment 53, wherein the formulation is a solid from lyophilization or a liquid formulation of embodiment 54, wherein the at least one excipient of the solid formulation is a lyoprotectant.

Embodiment 56. A Drug Linker compound of Formula IA:

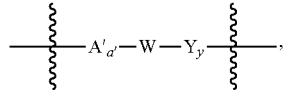

(IA)

or a salt thereof, wherein
D is a Drug Unit;
$L_B'$ is a ligand covalent binding precursor moiety;
A is a first optional Stretcher Unit;
subscript a is 0 or 1, indicating the absence or presence of A, respectively;
B is an optional Branching Unit;
subscript b is 0 or 1, indicating the absence or presence of B, respectively;
$L_O$ is a secondary linker moiety, wherein the secondary linker has the formula of;

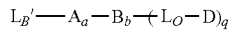

wherein the wavy line adjacent to Y indicates the site of covalent attachment of $L_O$ to the Drug Unit and the wavy line adjacent to A' indicates the site of covalent attachment to the remainder of the Drug Linker compound;

A' is a second optional Stretcher Unit, which in the absence of B becomes a subunit of A;
subscript a' is 0 or 1, indicating the absence or presence of A', respectively,
W is a peptide Cleavable Unit, wherein the peptide Cleavable Unit is a contiguous sequence of up to 12 amino acids, wherein the sequence is comprised of a selectivity conferring tripeptide whose N-terminus provides an amide linkage that is selectively cleavable by a homogenate of tumor tissue to release free drug in comparison to a homogenate of normal tissue, and/or provides improved bioavailability to tumor tissue of a Ligand Drug Conjugate compound of Formula 1 of embodiment 1 in which the Drug Linker compound becomes a drug linker moiety of the Conjugate compound to the detriment of bioavailability to normal tissue in comparison to a comparator Ligand-Drug Conjugate in which the peptide sequence of its peptide Cleavable Unit is the dipeptide -valine-citrulline-;
wherein the tumor and normal tissues are of the same species and wherein an adverse event associated with release of free drug from the comparator Ligand-Drug Conjugate when administered in an effective amount to a subject in need thereof is due to its toxicity towards cells of the normal tissue.
Y is a self-immolative Spacer Unit;
subscript y is 0, 1 or 2 indicating the absence or presence of 1 or 2 of Y, respectively; and
subscript q is an integer ranging from 1 to 4,
provided that subscript q is 1 when subscript b is 0 and subscript q is 2, 3 or 4 when subscript b is 1.

Embodiment 57. The Drug Linker compound of embodiment 56, wherein the Drug Linker compound has the formula of

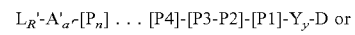

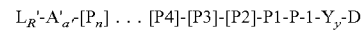

or a salt thereof, wherein
$L_R'$ is a primary linker of formula $L_B'$-$A_a$-$B_b$—, provided that A' is a subunit of A so that A' is a component of $L_R'$ when subscript a and a' are each 1 and subscript b is 0; and
each P is an amino acid residue of the contiguous amino acid sequence of the peptide Cleavable Unit and wherein subscript n has an integer value providing for up to 12 of these residues,
wherein —[P3]-[P2]-[P1]- of the sequence is the selectivity conferring tripeptide.

Embodiment 58. The Drug Linker compound of embodiment 57, wherein the Drug Linker compound has the formula of

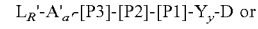

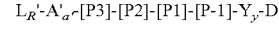

or a salt thereof,
wherein $L_R'$ is a primary linker of formula $L_B'$-$A_a$-$B_b$—, provided that A' is a subunit of A so that A' is a component of $L_R'$ when subscript a and a' are each 1 and subscript b is 0; and
wherein each P is an amino acid residue of the contiguous amino acid sequence of the peptide Cleavable Unit, wherein —[P3]-[P2]-[P1]- of the sequence is the selectivity conferring tripeptide.

Embodiment 59. The Drug Linker compound of embodiment 58, wherein the Drug Linker compound has the formula of

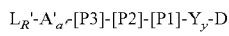

or a salt thereof, wherein P1 is a L-amino acid residue having at physiological pH a negatively charged side chain or a non-positively charged polar side chain.

Embodiment 60. The Drug Linker compound of any one of embodiments 56-59, wherein P1 is a L-amino acid residue selected from the group consisting of glutamic acid, methionine-sulfoxide, aspartic acid, (S)-3-aminopropane-1,1,3-tricarboxylic acid and phospho-threonine.

Embodiment 61. The Drug Linker compound of embodiment 56, wherein the Drug Linker compound has the formula of

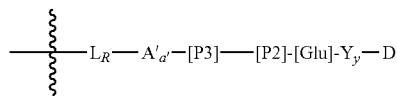

or a salt thereof, in particular a pharmaceutically acceptable salt, wherein each P is an amino acid residue of the contiguous amino acid sequence of the peptide Cleavable Unit.

Embodiment 62. The Drug Linker compound of any one of embodiments 56-61, wherein P2 is a residue of glycine or an L-amino acid, the side chain of which has no more than three contiguous carbon atoms.

Embodiment 63. The Drug Linker compound of embodiment 62, wherein the P2 amino acid is L-alanine, L-valine or glycine or an unnatural amino acid, wherein the unnatural amino acid is Abu, Aib, Ala, Gly, Leu, Nva or Pra which have the structures of:

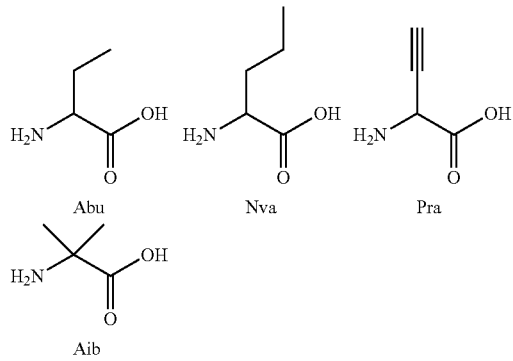

wherein the side chains of Abu, Nva and Pra are in the same stereochemical configuration of an L-amino acid.

Embodiment 64. The Drug Linker compound of embodiment 63, wherein the Drug Linker compound has the formula of:

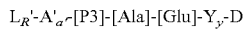

or a salt thereof, wherein P3 is an amino acid residue of the contiguous amino acid sequence of the peptide Cleavable Unit.

Embodiment 65. The Drug Linker compound of any one of embodiments 56-64 wherein P3 is a D-amino acid, the side chain of which is uncharged at physiological pH.

Embodiment 66. The Drug Linker compound of any one of embodiments 56-64 wherein P3 is a D-Leu, L-Leu, L-Cit or L-Pro, preferably D-Leu.

Embodiment 67. The Drug Linker compound of embodiment 66, wherein —[P3]-[P2]-[P1]- is -D-Leu-Ala-Glu-, or a salt thereof, in particular a pharmaceutically acceptable salt.

Embodiment 68. The Drug Linker compound of any one of embodiments 56-67, wherein $L_B'$ is a maleimide moiety capable of reacting with a thiol functional group of a targeting moiety to form a thio-substituted succinimide moiety.

Embodiment 69. The Drug Linker compound of any one of embodiments 56-67, wherein $L_B'$-A- has or is comprised of one of the structures of:

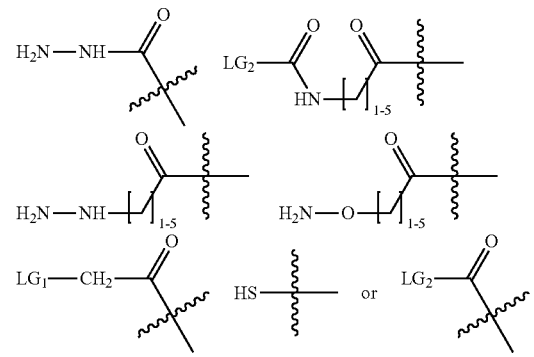

or a salt thereof, wherein $LG_1$ is a leaving group suitable for nucleophilic displacement by a targeting agent nucleophile;

$LG_2$ is a leaving group suitable for amide bond formation to a targeting agent, or —OH to provide an activatable carboxylic acid suitable for amide bond formation to a targeting agent; and the wavy line indicates the site of covalent attachment to the remainder of the Drug Linker compound structure.

Embodiment 70. The Drug Linker compound of embodiment 69, wherein subscript q is 1 and $L_B'$-A- has the structure of:

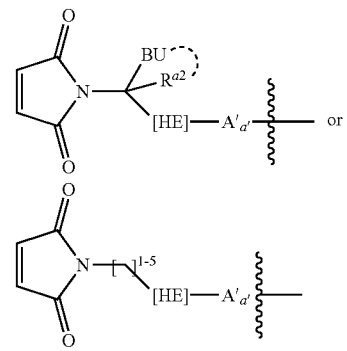

or a salt thereof, wherein the wavy line adjacent to $A'_{a'}$ indicates the site of covalent attachments to the Peptide Cleavable Unit;

[HE] is an optional Hydrolysis Enhancing Unit, which is a component provided by A or a first subunit thereof;

BU is a Basic Unit;

$R^{a2}$ is an optionally substituted $C_1$-$C_{12}$ alkyl group; and the dotted curved line indicates optional cyclization so that in the absence of said cyclization, BU is an acyclic Basic Unit having a primary, secondary or tertiary amine functional group as the basic function group of the acyclic Basic Unit, or in the presence of said cyclization BU is a cyclized Basic Unit in which $R^{a2}$ and BU together with the carbon atom to which both are attached, define an optionally substituted spiro $C_3$-$C_{20}$ heterocyclo containing a skeletal basic nitrogen atom of a secondary or tertiary amine functional group as the basic function group of the cyclic Basic Unit, wherein the basic nitrogen atom of the acyclic Basic Unit or cyclic Basic Unit is optionally suitably protected by a nitrogen protecting group, dependent on the degree of substitution of the basic nitrogen atom or is optionally protonated as an acid addition salt.

Embodiment 71. The Drug Linker compound of embodiment 70, wherein $L_B'$-A- has the structure of:

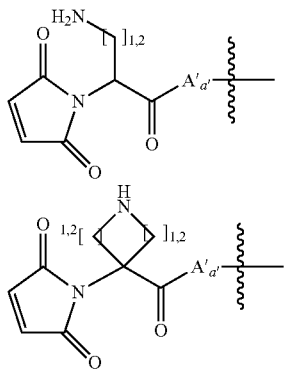

or a salt thereof, in particular as an acid addition salt, or wherein $L_B'$-A- has the structure of:

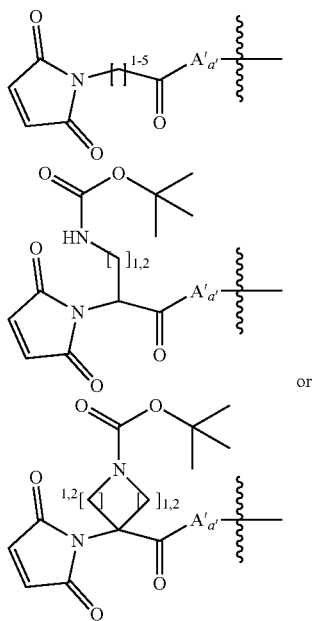

Embodiment 72. The Drug Linker compound of any one of embodiments 56-71, wherein subscript q is 1 and A' is present as a subunit of A, wherein A' is comprised of an amine-containing acid residue having the structure of formula (3) or formula (4):

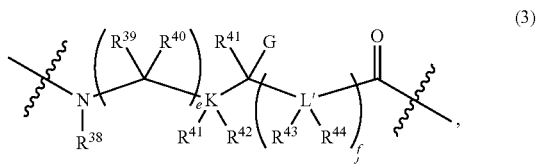

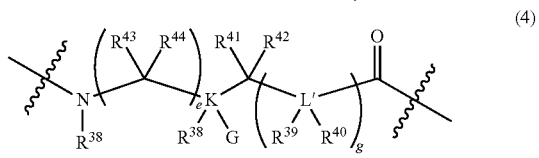

or a salt thereof, wherein the wavy line adjacent to the nitrogen atom indicates the site of covalent attachment to [HE], wherein [HE] is —C(=O)— and the wavy line adjacent to the carbonyl carbon atom indicates the site of covalent attachment to the remainder of A' or to the N-terminal amino acid residue of the Peptide Cleavable Unit, wherein both attachments are through amide functional groups;

K and L' independently are C, N, O or S, provided that when K or L' is O or S, $R^{41}$ and $R^{42}$ to K or $R^{43}$ and $R^{44}$ to L' are absent, and when K or L' are N, one of $R^{41}$, $R^{42}$ to K or one of $R^{42}$, $R^{43}$ to L' are absent, and provided that no two adjacent L' are independently selected as N, O, or S;

wherein subscripts e and f are independently selected integers that range from 0 to 12, and subscript g is an integer ranging from 1 to 12:

G is hydrogen, optionally substituted $C_1$-$C_6$ alkyl, —OH or —$CO_2H$;

$R^{38}$ is hydrogen or optionally substituted $C_1$-$C_6$ alkyl;

$R^{39}$-$R^{44}$ are independently selected from the group consisting of hydrogen, optionally substituted $C_1$-$C_6$ alkyl and optionally substituted $C_5$-$C_{10}$ (hetero)aryl, or $R^{39}$, $R^{40}$ together with the carbon atom to which both are attached, or $R^{41}$, $R^{42}$ together with K to which both are attached when K is a carbon atom, define a $C_3$-$C_6$ carbocyclo, and $R^{41}$-$R^{44}$ are as defined herein, or $R^{43}$, $R^{44}$ together with L' to which both are attached when L' is a carbon atom define a $C_3$-$C_6$ carbocyclo, and $R^{39}$-$R^{42}$ are as defined herein, or $R^{40}$ and $R^{41}$, or $R^{40}$ and $R^{43}$, or $R^{41}$ and $R^{43}$ to together with the carbon atom or heteroatom to which both are attached and the atoms intervening between those carbon atoms and/or heteroatoms define a $C_5$-$C_6$ carbocyclo or a $C_5$-$C_6$ heterocyclo, and $R^{39}$, $R^{44}$ and the remainder of $R^{40}$-$R^{43}$ are as defined herein, provided that when K is O or S, $R^{41}$ and $R^{42}$ are absent, and when K is N, one of $R^{41}$, $R^{42}$ is absent, and when L' is O or S, $R^{43}$ and $R^{44}$ are absent, and when L' is N, one of $R^{43}$, $R^{44}$ is absent, or A' is comprised of an alpha-amino, beta-amino or another amine-containing acid residue, wherein its amino nitrogen atom is covalently attached to the carbonyl carbon atom of HE, and its carboxylic acid carbonyl carbon atom is covalently attached to the remainder of A' or to the N-terminal amino acid of the Peptide Cleavable Unit, wherein both covalent attachments are through amide functional groups.

Embodiment 73. The Drug Linker compound of embodiment 72, wherein A' is an amine-containing acid residue having the structure of formula 3a, formula 4a or formula 5a:

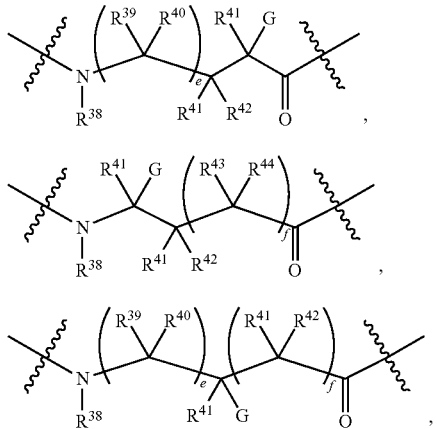

(3a)

(4a)

(5a)

or a salt thereof, wherein subscripts e and f are independently 0 or 1; and $R^{38}$—$R^{44}$ are each hydrogen;

or A' is an α-amino or β-amino acid residue.

Embodiment 74. The Drug Linker compound of any one of embodiments 56-71, wherein subscript q is 1 and A' is comprised of a β-amino acid residue or -$L^P$(PEG)-, wherein $L^P$ is Parallel Connector Unit having the structure of Formula $L^P$-1 or $L^P$-2:

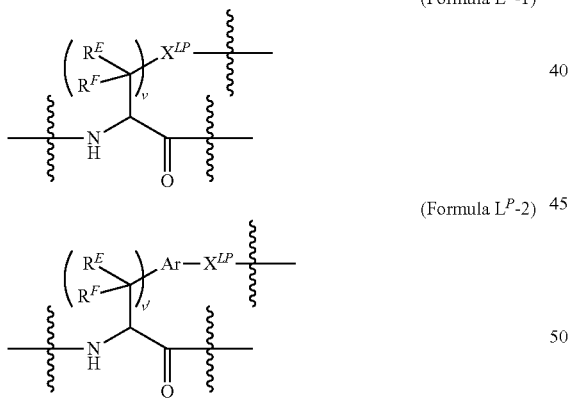

(Formula $L^P$-1)

(Formula $L^P$-2)

or wherein -$L^P$(PEG)- or a PEG-containing subunit thereof has the structure of Formula $L^P$-3 or Formula $L^P$-4:

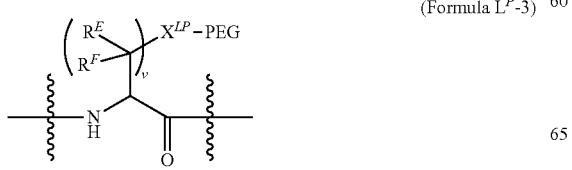

(Formula $L^P$-3)

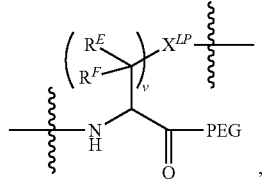

(Formula $L^P$-4)

wherein subscript v is an integer ranging from 1 to 4;

subscript v' is an integer ranging from 0 to 4;

$X^{LP}$ is provided by a natural or un-natural amino acid side chain or is selected from the group consisting of —O—, —$NR^{LP}$—, —S—, —S(=O)—, —$S(=O)_2$—, —C(=O)—, —C(=O)N($R^{LP}$)—, —N($R^{LP}$)C(=O)N ($R^{LP}$)—, and —N($R^{LP}$)C(=N$R^{LP}$)N($R^{LP}$)—, or $C_3$-$C_8$ heterocyclo;

wherein each $R^{LP}$ is independently selected from the group consisting of hydrogen and optionally substituted $C_1$-$C_6$ alkyl, or two of $R^{LP}$ together along with the carbons atoms to which they are attached, and their intervening atoms define a $C_5$-$C_6$ heterocyclo and any remaining $R^{LP}$ are as previously defined;

Ar is a $C_6$-$C_{10}$ arylene or a $C_5$-$C_{10}$ heteroarylene, optionally substituted;

each $R^E$ and $R^F$ is independently selected from the group consisting of —H, optionally substituted $C_1$-$C_6$ alkyl, optionally substituted $C_2$-$C_6$ alkylene, optionally substituted $C_6$-$C_{10}$ arylene or optionally substituted $C_5$-$C_{10}$ heteroarylene, or $R^E$ and $R^F$ together with the carbon atom to which both are attached defines an optionally substituted spiro $C_3$-$C_6$ carbocyclo, or $R^E$ and $R^F$ from adjacent carbon atoms together with these atoms and any intervening carbon atoms defines an optionally substituted $C_5$-$C_6$ carbocyclo with any remaining $R^E$ and $R^F$ as previously defined;

wherein one of the wavy lines indicate the point of covalent attachment of a PEG Unit and the other two wavy lines indicates covalent attachment of Formula $L^P$-1 or Formula $L^P$-2 within the structure representing the Drug Linker Compound, or $L^P$ is Parallel Connector Unit having the structure of a tri-functional amine-containing acid residue or; and PEG is a PEG Unit.

Embodiment 75. The Drug Linker compound of embodiment 74, wherein A' is comprised of a β-amino acid residue or -$L^P$(PEG)-, wherein the β-amino acid residue has the structure of —NHCH$_2$CH$_2$C(=O)—; and wherein -$L^P$(PEG)- has the structure of:

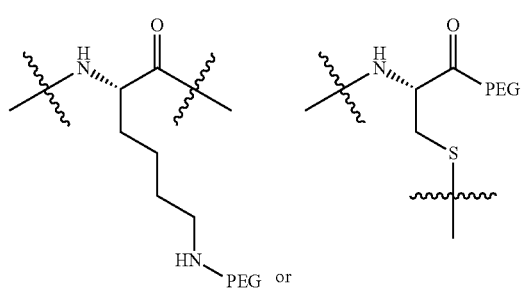

or wherein the wavy lines indicate the sites of covalent attachment within the drug linker moiety.

Embodiment 76. The Drug Linker compound of embodiment 74 or 75, wherein the PEG Unit has the structure of:

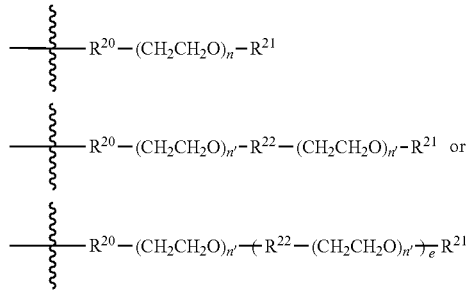

wherein the wavy line indicates the site of covalent attachment to $L^P$;

$R^{20}$ is a PEG Attachment Unit, wherein the PEG Attachment Unit is —C(O)—, —O—, —S—, —S(O)—, —NH—, —C(O)O—, —C(O)$C_1$-$C_{10}$alkyl, —C(O)$C_1$-$C_{10}$alkyl-O—, —C(O)$C_1$-$C_{10}$alkyl-CO$_2$—, —C(O)$C_1$-$C_{10}$alkyl-NH—, —C(O)$C_1$-$C_{10}$ alkyl-S—, —C(O)$C_1$-$C_{10}$ alkyl-C(O)—NH—, —C(O)$C_1$-$C_{10}$alkyl-NH—C(O)—, —$C_1$-$C_{10}$alkyl, —$C_1$-$C_{10}$alkyl-O—, —$C_1$-$C_{10}$alkyl-CO$_2$—, —$C_1$-$C_{10}$alkyl-NH—, —$C_1$-$C_{10}$alkyl-S—, —$C_1$-$C_{10}$alkyl-C(O)—NH—, —$C_1$-$C_{10}$alkyl-NH—C(O)—, —CH$_2$CH$_2$SO$_2$—$C_1$-$C_{10}$alkyl-, —CH$_2$C(O)—$C_{1-10}$ alkyl-, =N—(O or N)—$C_1$-$C_{10}$alkyl-O—, =N—(O or N)—$C_1$-$C_{10}$alkyl-NH—, =N—(O or N)—$C_1$-$C_{10}$alkyl-CO$_2$—, =N—(O or N)—$C_1$-$C_{10}$alkyl-S—,

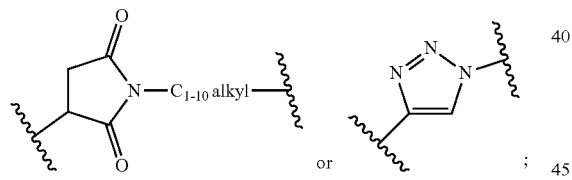

$R^{21}$ is a PEG Capping Unit; wherein the PEG Capping Unit is —$C_1$-$C_{10}$alkyl, —$C_2$-$C_{10}$ alkyl-CO$_2$H, —$C_2$-$C_{10}$ alkyl-OH, —$C_2$-$C_{10}$ alkyl-NH$_2$, $C_2$-$C_{10}$ alkyl-NH($C_1$-$C_3$ alkyl), or $C_2$-$C_{10}$ alkyl-N($C_1$-$C_3$ alkyl)$_2$;

$R^{22}$ is an PEG Coupling Unit for coupling multiple PEG subunit chains together, wherein the PEG Coupling Unit is —$C_{1-10}$ alkyl-C(O)—NH—, —$C_{1-10}$ alkyl-NH—C(O)—, —$C_{2-10}$ alkyl-NH—, —$C_2$-$C_1$O alkyl-O—, —$C_1$-$C_{10}$alkyl-S—, or —$C_2$-$C_1$O alkyl-NH-;

subscript n is independently selected from from 8 to 72, from 10 to 72 or from 12 to 72;

subscript e is selected from 2 to 5; and each n' is independently selected from at least 6 to no more than 72, preferably from at least 8 or at least 10 to no more than 36.

Embodiment 77. The Drug Linker compound of embodiment 56, wherein the Drug Linker compound has the structure of Formula IC:

(Formula IC)

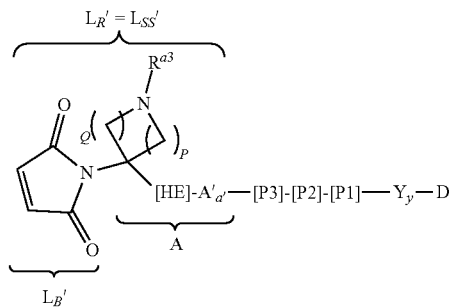

or a salt thereof, wherein

HE is a Hydrolysis Enhancing Unit;

A' is an subunit, when present, of the indicated first Stretcher Unit (A);

subscript a' is 0 or 1, indicating the absence or presence of A', respectively;

subscript P is 1 or 2; and subscript Q ranges from 1 to 6, preferably subscript Q is 1 or 2, more preferably subscript Q has the same value as subscript P;

$R^{a3}$ is —H, optionally substituted $C_1$-$C_6$ alkyl, optionally substituted —$C_1$-$C_4$ alkylene-($C_6$-$C_{10}$ aryl), or —$R^{PEG1}$—O—(CH$_2$CH$_2$O)$_{1-36}$—$R^{PEG2}$ wherein $R^{PEG1}$ is $C_1$-$C_4$ alkylene and $R^{PEG2}$ is —H or $C_1$-$C_4$ alkylene, wherein the basic nitrogen bonded to $R^{a3}$ is protonated in a salt form, or $R^{a3}$ is a suitable nitrogen protecting group, preferably a suitable acid-labile protecting group; and each P is an amino acid residue of the contiguous amino acid sequence of the peptide Cleavable Unit.

Embodiment 78. The Drug Linker compound of embodiment 56, wherein the Drug Linker compound has the structure of Formula IF:

(Formula IF)

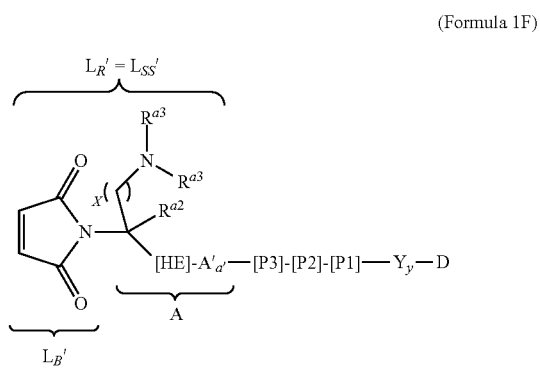

or a salt thereof, wherein

HE is a Hydrolysis Enhancing Unit;

A' is an subunit, when present, of the indicated first Stretcher Unit (A);

subscript a' is 0 or 1, indicating the absence or presence of A', respectively;

subscript x is 1 or 2;

$R^{a2}$ is —H, optionally substituted $C_1$-$C_6$ alkyl, —CH$_3$ or —CH$_2$CH$_3$;

$R^{a3}$, at each instance, is independently a suitable nitrogen protecting group, —H or optionally substituted $C_1$-$C_6$ alkyl, preferably —H, a suitable acid-labile protecting group, —CH₃ or —CH₂CH₃, provided that the nitrogen atom to which both R^{a3} are bound is protonated in salt form when neither R^{a3} is a nitrogen protecting group, or both R^{a3} together with the nitrogen to which they are attached define a nitrogen protecting group or an azetidinyl, pyrrolidinyl or piperidinyl heterocyclyl, in which a basic primary, secondary or tertiary amine so defined is protonated in a salt form.

Embodiment 79. The Drug Linker compound of embodiment 78, wherein the Drug Linker compound has the structure of Formula IH:

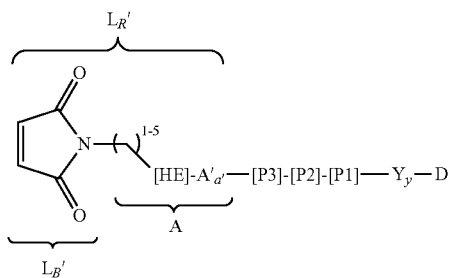

(Formula IH)

or salt thereof,

HE is a Hydrolysis Enhancing Unit; and

A' is a subunit, when present, of the indicated first Stretcher Unit (A); subscript a' is 0 or 1, indicating the absence or presence of A'.

Embodiment 80. The Drug Linker compound of embodiment 77, wherein the Drug Linker compound the structure of:

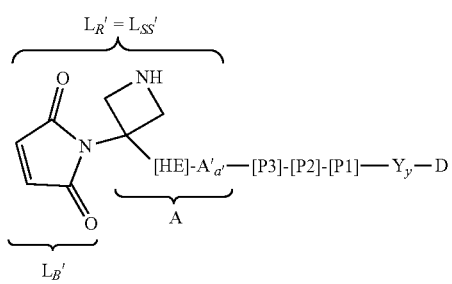

and or a salt thereof, wherein the nitrogen atom of the 4-membered heterocyclo of $L_{SS}'$ is protonated in salt form.

Embodiment 81. The Drug Linker compound of embodiment 56, wherein the Drug Linker compound has the structure of:

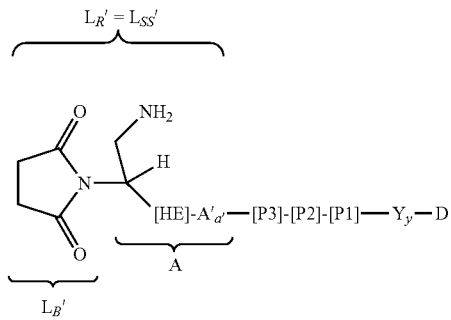

or salt thereof, wherein the primary amine of $L_{SS}'$ is protonated in salt form.

Embodiment 82. The Drug Linker compound of any one of embodiments 77-81 wherein HE is —C(=O).

Embodiment 83. The Drug Linker compound of any one of embodiments 77-81 wherein HE is —C(=O), subscript a' is 1 and A' has the structure of formula 3a, formula 4a or formula 5a of embodiment 73, or A' is an α-amino acid or β-amino acid residue.

Embodiment 84. The Drug Linker compound of any one of embodiments 77-83, wherein —[P3]-[P2]-[P1]- is D-Leu-Leu-Cit, D-Leu-Leu-Lys, D-Leu-Leu-Met(O), Cit-Ala(Nap)-Thr, D-Leu-Ala-Glu or Pro-Ala(Nap)-Lys, wherein Met(O) is methionine in which its sulfur atom is oxidized to a sulfoxide and Ala(Nap) is alanine in which its methyl side chain is substituted by napthth-1-yl.

Embodiment 85. The Drug Linker compound of any one of embodiments 56-84, wherein —Y_y-D has the structure of.

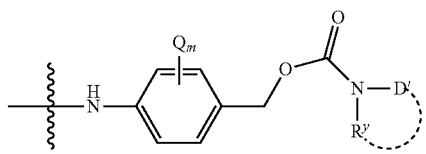

wherein —N(R^y)D' represents D, wherein D' is the remainder of D;

the wavy line indicates the site of covalent attachment to P1 or P-1;

the dotted line indicates optional cyclization of R^y to D';

R^y is optionally substituted $C_1$-$C_6$ alkyl in absence of cyclization to D' or optionally substituted $C_1$-$C_6$ alkylene when cyclized to D';

each Q is independently —$C_1$-$C_8$ alkyl, —O—($C_1$-$C_8$ alkyl), or other electron donating group, -halogen, -nitro or -cyano or other electron withdrawing group, in particular each Q is independently selected from the group consisting of —$C_1$-$C_8$ alkyl, —O—($C_1$-$C_8$ alkyl), halogen, nitro and cyano; and subscript m is 0, 1 or 2, in particular subscript m is 0 or 1 and Q when present is an electron donating group, preferably subscript m is 0.

Embodiment 86. The Drug Linker compound of embodiment 56, wherein the Drug Linker compound has the structure of:

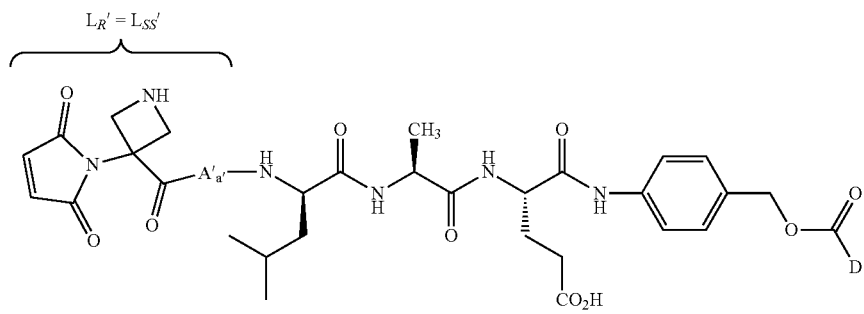

or a salt thereof, wherein
subscript a' is 1, indicating the presence of A', wherein A' is an amine-containing acid residue of formula 3a, formula 4a or formula 5a of embodiment 73, or an α-amino acid or β-amino acid residue, in particular —NH—CH$_2$CH$_2$—C(=O)—; and
D is a cytotoxic drug having a secondary amino group as the site of attachment to the Linker Unit of the Drug Linker compound,
wherein the nitrogen atom of the heterocyclo of $L_{SS}'$ is protonated in salt form.

Embodiment 87. The Drug Linker compound of embodiment 56 wherein the Drug Linker compound has the structure of:

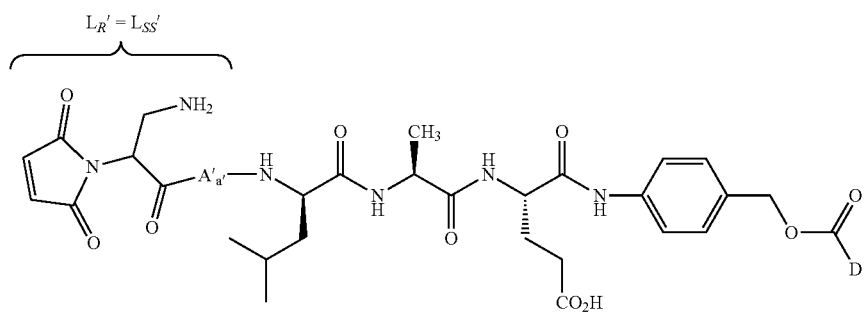

or a salt thereof, wherein
subscript a' is 1, indicating the presence of A', wherein A' is an amine-containing acid residue of formula 3a, formula 4a or formula 5a of embodiment 73, or an α-amino acid or β-amino acid residue, in particular —NH—CH$_2$CH$_2$—C(=O)—; and
D is a cytotoxic drug having a secondary amino group as the site of attachment to the Linker Unit of the Drug Linker compound,
wherein the primary amine of $L_{SS}'$ is protonated in salt form.

Embodiment 88. The Drug Linker compound of embodiment 56 wherein the Drug Linker compound has the structure of:

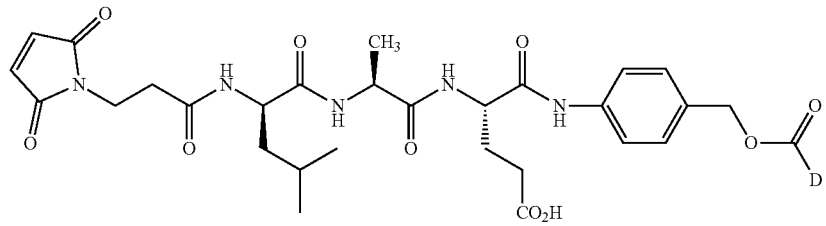

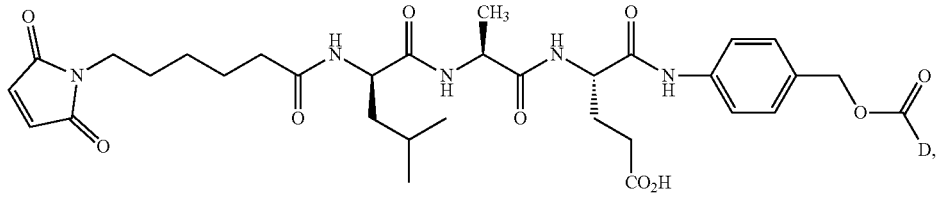

or a salt thereof, wherein

D is a cytotoxic drug having a secondary amino group as the site of attachment to the Linker Unit of the Drug Linker compound.

Embodiment 89. The Drug Linker compound of any one of embodiments 56-88 wherein subscript y' is 2, wherein Y of —Y—Y'— is a first self-immolative Spacer Unit and Y' is a second self-immolative Spacer Unit having the structure of —OC(=O)— and the cytotoxic drug is a secondary amine-containing auristatin compound wherein the nitrogen atom of the secondary amine is the site of covalent attachment to the carbonyl carbon atom of Y' through a carbamate functional group shared between D and Y'.

Embodiment 90. The Drug Linker compound of embodiment 89, wherein the secondary amine-containing auristatin compound has the structure of Formula $D_E$ or $D_F$:

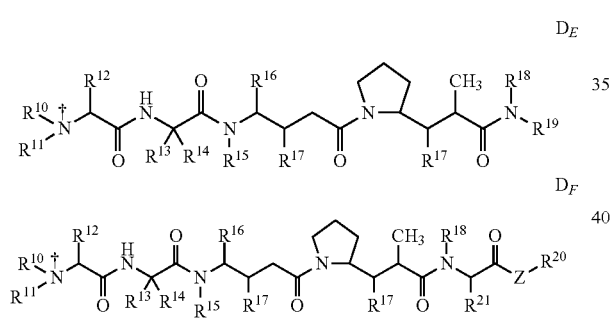

wherein the dagger indicates the site of covalent attachment of the nitrogen atom that provides the carbamate functional group, one of $R^{10}$ and $R^{11}$ is hydrogen and the other is $C_1$-$C_8$ alkyl, preferably one of $R^{10}$ and $R^{11}$ is hydrogen and the other is methyl;

$R^{12}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl or —$X^1$—($C_3$-$C_8$ heterocyclyl);

$R^{13}$ is hydrogen, $C_1$-$C_8$ alkyl, $C_3$-$C_8$ carbocyclyl, $C_6$-$C_{24}$ aryl, —$X^1$—$C_6$-$C_{24}$ aryl, —$X^1$—($C_3$-$C_8$ carbocyclyl), $C_3$-$C_8$ heterocyclyl and —$X^1$—($C_3$-$C_8$ heterocyclyl);

$R^{14}$ is hydrogen or methyl, or $R^{13}$ and $R^{14}$ taken together with the carbon to which they are attached comprise a spiro $C_3$-$C_8$ carbocyclo;

$R^{15}$ is hydrogen or $C_1$-$C_8$ alkyl;

$R^{16}$ is hydrogen, $C_1$-$C_8$ alkyl, $C_3$-$C_8$ carbocyclyl, $C_6$-$C_{24}$ aryl, —$C_6$-$C_{24}$—$X^1$-aryl, —$X^1$—($C_3$-$C_8$ carbocyclyl), $C_3$-$C_8$ heterocyclyl and —$X^1$—($C_3$-$C_8$ heterocyclyl);

$R^{17}$ independently are hydrogen, —OH, $C_1$-$C_8$ alkyl, $C_3$-$C_8$ carbocyclyl and O—($C_1$-$C_8$ alkyl);

$R^{18}$ is hydrogen or optionally substituted $C_1$-$C_8$ alkyl;

$R^{19}$ is —C($R^{19A}$)$_2$—C($R^{19A}$)$_2$—$C_6$-$C_{24}$ aryl, —C($R^{19A}$)$_2$—C($R^{19A}$)$_2$—($C_3$-$C_8$ heterocyclyl) or —C($R^{19A}$)$_2$—C($R^{19A}$)$_2$—($C_3$-$C_8$ carbocyclyl), wherein $C_6$-$C_{24}$ aryl and $C_3$-$C_8$ heterocyclyl are optionally substituted;

$R^{19A}$ independently are hydrogen, optionally substituted $C_1$-$C_8$ alkyl, —OH or optionally substituted —O—$C_1$-$C_8$ alkyl;

$R^{20}$ is hydrogen or $C_1$-$C_{20}$ alkyl, $C_6$-$C_{24}$ aryl or $C_3$-$C_8$ heterocyclyl, optionally substituted, or —($R^{47}$O)$_m$—$R^{48}$, or —($R^{47}$O)$_m$—CH($R^{49}$)$_2$;

$R^{21}$ is —$C_1$-$C_8$ alkylene-($C_6$-$C_{24}$ aryl) or —$C_1$-$C_8$ alkylene-($C_5$-$C_{24}$ heteroaryl), optionally substituted, or $C_1$-$C_8$ hydroxylalkyl, or optionally substituted $C_3$-$C_8$ heterocyclyl;

Z is O, S, NH, or $NR^{46}$.

$R^{46}$ is optionally substituted $C_1$-$C_8$ alkyl; subscript m is an integer ranging from 1-1000;

$R^{47}$ is $C_2$-$C_8$ alkyl; $R^{48}$ is hydrogen or $C_1$-$C_8$ alkyl;

$R^{49}$ independently are —COOH, —$(CH_2)_n$—N$(R^{50})_2$, —$(CH_2)_n$—$SO_3H$, or —$(CH_2)_n$—$SO_3$—$C_1$-$C_8$ alkyl; and $R^{50}$ independently are $C_1$-$C_8$ alkyl, or —$(CH_2)_n$—COOH; subscript n is an integer ranging from 0 to 6; and $X^1$ is $C_1$-$C_{10}$ alkylene.

Embodiment 91. The Drug Linker compound of embodiment 90 wherein the secondary amine-containing auristatin compound has the structure of Formula $D_{E-1}$, Formula $D_{E-2}$ or Formula $D_{F-1}$:

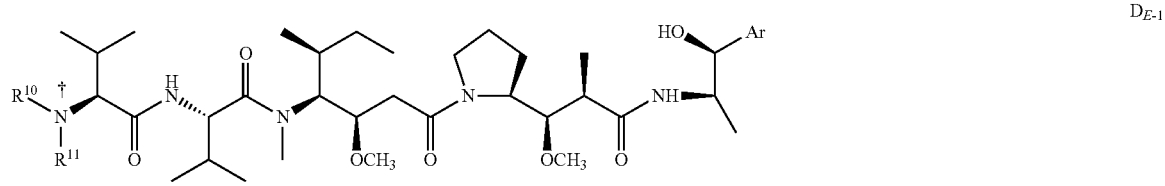

-continued

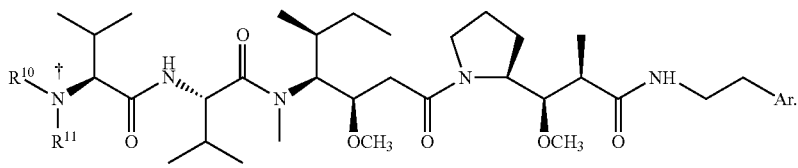

D<sub>E-2</sub>

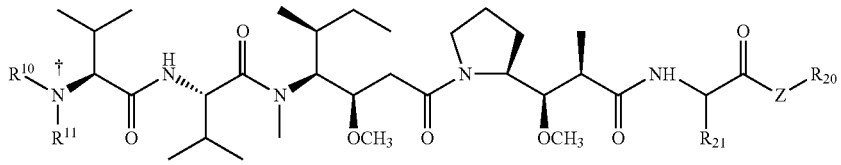

D<sub>F-1</sub> wherein Ar is $C_6$-$C_{10}$ aryl or $C_5$-$C_{10}$ heteroaryl, preferably Ar is phenyl or 2-pyridyl;

Z is —O—, or —NH—; $R^{20}$ is hydrogen or $C_1$-$C_6$ alkyl, $C_6$-$C_{10}$ aryl or $C_5$-$C_{10}$ heteroaryl, optionally substituted; and $R^{21}$ is $C_1$-$C_6$ alkyl, —$C_1$-$C_6$ alkylene-($C_6$-$C_{10}$ aryl) or —$C_1$-$C_6$ alkylene-($C_5$-$C_{10}$ heteroaryl), optionally substituted.

Embodiment 92. The Drug Linker compound of embodiment 91, wherein the secondary amine-containing auristatin compound has the structure of Formula D$_{F-1}$ wherein $R^{21}$ is $X^1$—S—$R^{21a}$ or $X^1$-Ar, wherein $X^1$ is $C_1$-$C_6$ alkylene, $R^{21a}$ is $C_1$-$C_4$ alkyl and Ar is phenyl or $C_5$-$C_6$ heteroaryl; and —Z— is —O— and $R^{20}$ is $C_1$-$C_4$ alkyl, or —Z— is —NH— and $R^{20}$ is phenyl or $C_5$-$C_6$ heteroaryl.

Embodiment 93. The Drug Linker compound of embodiment 91 wherein the secondary amine-containing auristatin compound has the structure of Formula In preferred embodiments the auristatin drug compound has the structure of Formula D$_{F/E-3}$:

D<sub>F/E-3</sub>

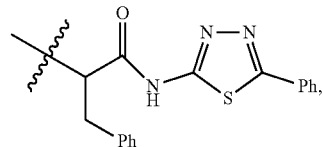 [SMILES: *C(Cc1ccccc1)C(=O)Nc1nnc(-c2ccccc2)s1]

$R^{13}$ is isopropyl or —$CH_2$—$CH(CH_3)_2$; and $R^{19B}$ is —$CH(CH_3)$—$CH(OH)$-Ph, —$CH(CO_2H)$—$CH(OH)$—$CH_3$, —$CH(CO_2H)$—$CH_2$Ph, —$CH(CH_2Ph)$-2-thiazolyl, —$CH(CH_2Ph)$-2-pyridyl, —$CH(CH_2$-p-Cl-Ph), —$CH(CO_2Me)$-$CH_2$Ph, —$CH(CO_2Me)$-$CH_2CH_2SCH_3$, —$CH(CH_2CH_2SCH_3)C(=O)NH$-quinol-3-yl, —$CH(CH_2Ph)C(=O)NH$-p-Cl-Ph, or $R^{19B}$ has the structure of wherein the wavy line indicates covalent attachment to the remainder of the auristatin compound.

Embodiment 94. The Drug Linker compound of embodiment 91 wherein the secondary amine-containing auristatin compound is monomethylauristatin E (MMAE) or monomethylauristatin F (MMAF).

Embodiment 95. The Drug Linker compound of embodiment 56, wherein the Drug Linker compound has the structure of Formula IC-MMAE:

(Formula IC-MMAE)

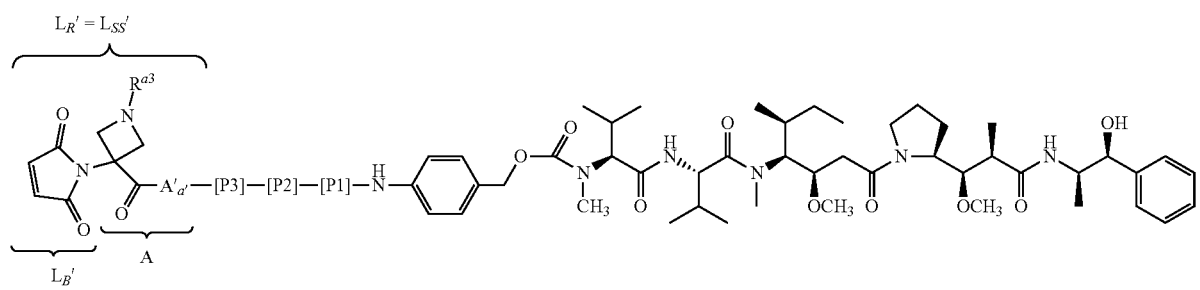

wherein one of $R^{10}$ and $R^{11}$ is hydrogen and the other is methyl;

or salts thereof, in particular a pharmaceutical acceptable salts, wherein

A' is a subunit, when present, of the indicated first Stretcher Unit (A) having the structure of formula 3a, formula 4a or formula 5a of embodiment 73, or an α-amino acid or β-amino acid residue, in particular —NH—CH$_2$CH$_2$—C(=O)—;

R$^{a3}$ is —H, optionally substituted C$_1$-C$_6$ alkyl, optionally substituted —C$_1$-C$_4$ alkylene-(C$_6$-C$_{10}$ aryl), or —R$^{PEG1}$—O—(CH$_2$CH$_2$O)$_{1-36}$—R$^{PEG2}$ wherein R$^{PEG1}$ IS C$_1$-C$_4$ alkylene, R$^{PEG2}$ is —H or C$_1$-C$_4$ alkylene, and wherein the basic nitrogen bonded to R$^{a3}$ is protonated in a salt form, or R$^{a3}$ is a suitable nitrogen protecting group, preferably a suitable acid-labile protecting group.

Embodiment 96. The Drug Linker compound of embodiment 56, wherein the Drug Linker compound has the structure of Formula IF-MMAE:

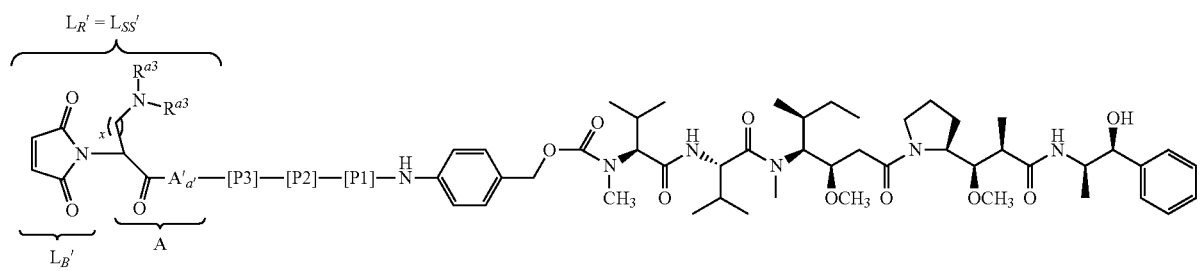

(Formula IF-MMAE)

or a salt thereof, wherein

A' is a subunit, when present, of the indicated first Stretcher Unit (A) having the structure of formula 3a, formula 4a or formula 5a of embodiment 73, or an α-amino acid or β-amino acid residue, in particular —NH—CH$_2$CH$_2$—C(=O)—;

subscript x is 1 or 2;

R$^{a3}$, at each instance, is independently a suitable nitrogen protecting group, —H or optionally substituted C$_1$-C$_6$ alkyl, preferably —H, a suitable acid-labile protecting group, —CH$_3$ or —CH$_2$CH$_3$, provided that the nitrogen atom to which both R$^{a3}$ are bound is protonated in salt form when neither R$^{a3}$ is a nitrogen protecting group, or both R$^{a3}$ together with the nitrogen to which they are attached define a nitrogen protecting group or an azetidinyl, pyrrolidinyl or piperidinyl heterocyclyl, in which a basic primary, secondary or tertiary amine so defined is protonated in a salt form.

Embodiment 97. The Drug Linker compound of embodiment 56, wherein the Drug Linker compound has the structure of Formula IH-MMAE:

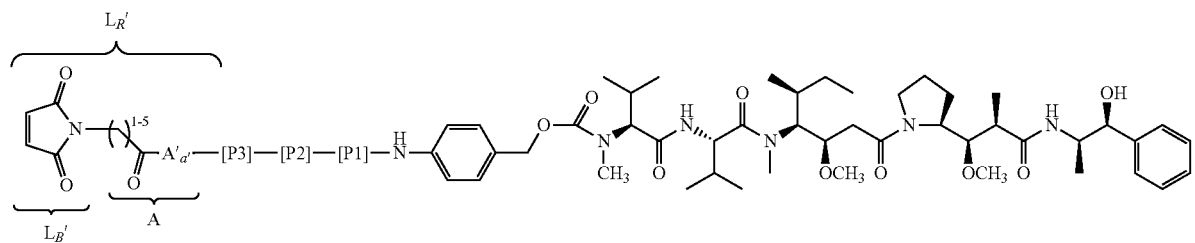

(Formula IH-MMAE)

or a salt thereof, wherein

A' is a subunit, when present, of the indicated first Stretcher Unit (A) having the structure of formula 3a, formula 4a or formula 5a of embodiment 73, or an α-amino acid or β-amino acid residue, in particular —NH—CH$_2$CH$_2$—C(=O)—;

subscript a' is 0 or 1, indicating the absence or presence of A'.

Embodiment 98. The Drug Linker compound of embodiment 95, 96 or 97, wherein P1 is L-Glu or L-Asp, P2 is L-Val or L-Ala and P3 is L-Leu or D-Leu.

Embodiment 99. The Drug Linker compound of embodiment 56, wherein the Drug Linker compound has the structure of:

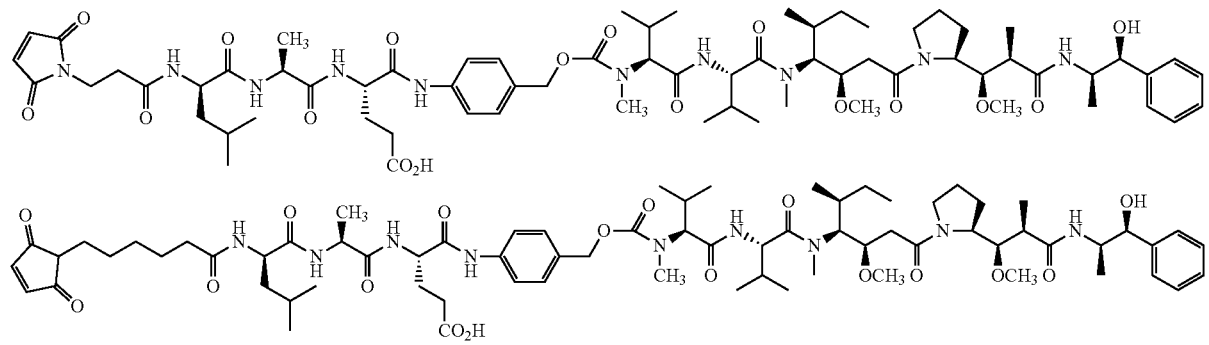

or a salt thereof.

A1. A Ligand Drug Conjugate composition represented by Formula A1:

L-[LU-D']$_p$ (A1)

or a pharmaceutically acceptable salt thereof, wherein

L is a Ligand Unit;

LU is a Linker Unit;

D' represents from 1 to 4 Drug Units (D) in each drug linker moiety of formula -LU-D'; and subscript p is a number from 1 to 12, from 1 to 10 or from 1 to 8 or is about 4 or about 8, wherein the Ligand Unit is from an antibody or an antigen-binding fragment of an antibody, wherein the antibody or the antigen-binding fragment is capable of selective binding to an antigen of tumor tissue for subsequent release of the Drug Unit(s) as a free drug, wherein the drug linker moiety of formula -LU-D' in each of the Ligand Drug Conjugate compounds of the composition has the structure of Formula A1A:

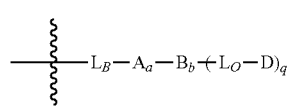

or a salt thereof, wherein the wavy line indicates covalent attachment to L;

D is the Drug Unit;

L$_B$ is a ligand covalent binding moiety;

A is a first optional Stretcher Unit;

subscript a is 0 or 1, indicating the absence or presence of A, respectively;

B is an optional Branching Unit;

subscript b is 0 or 1, indicating the absence or presence of B, respectively;

L$_O$ is a secondary linker moiety, wherein the secondary linker has the formula of:

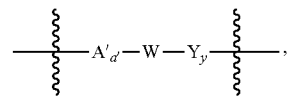

wherein the wavy line adjacent to Y indicates the site of covalent attachment of L$_O$ to the Drug Unit and the wavy line adjacent to A' indicates the site of covalent attachment of L$_O$ to the remainder of the drug linker moiety;

A' is a second optional Stretcher Unit, which when present and in the absence of B becomes a subunit of A, subscript a' is 0 or 1, indicating the absence or presence of A', respectively, W is a Peptide Cleavable Unit, wherein the Peptide Cleavable Unit comprises a tripeptide having the sequence -P3-P2-P1-, wherein P1, P2, and P3 are each an amino acid, wherein:

a first one of the amino acids P1, P2, or P3 is negatively charged;

a second one of the amino acids P1, P2, or P3 has an aliphatic side chain with hydrophobicity no greater than that of leucine; and a third one of the amino acids P1, P2, or P3 has hydrophobicity lower than that of leucine, wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3, provided that -P3-P2-P1- is not -Glu-Val-Cit- or -Asp-Val-Cit-;

each Y when present is a self-immolative Spacer Unit;

subscript y is 0, 1 or 2 indicating the absence or presence of 1 or 2 of Y, respectively; and subscript q is an integer ranging from 1 to 3, and provided that subscript q is 1 when subscript b is 0 and subscript q is 2 or 3 when subscript b is 1; and wherein the Ligand Drug Conjugate compounds of the composition have the structure of Formula A1 in which subscript p is replaced by subscript p', wherein subscript p' is an integer from 1 to 12, 1 to 10 or 1 to 8 or is 4 or 8.

A2. The Ligand Drug Conjugate composition of embodiment A1, wherein the Ligand Drug Conjugate compounds in the Ligand Drug Conjugate composition predominately have drug linker moieties of Formula A1H.

(Formula A1H)

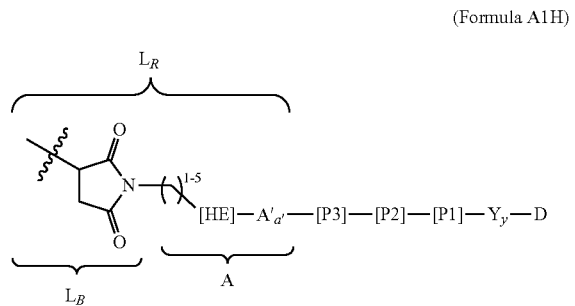

or pharmaceutically acceptable salts thereof, and optionally having a minority of Ligand Drug Conjugate compounds in which one or more of the drug linker moieties in each of such compounds has its succinimide ring in hydrolyzed form and wherein HE is a Hydrolysis Enhancing Unit;

A' is a subunit, when present, of the indicated first Stretcher Unit (A); subscript a' is 0 or 1, indicating the absence or presence of A', respectively; and the wavy line indicates the site of covalent attachment to a sulfur atom of the Ligand Unit.

A3. The Ligand Drug Conjugate composition of embodiment A2, wherein HE is —C(=O).

A4. The Ligand Drug Conjugate composition of any one of embodiments A1-A3, wherein —$Y_{y'}$-D has the structure of:

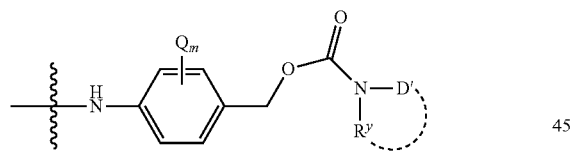

wherein —N($R^y$)D' represents D, wherein D' is the remainder of D;

the wavy line indicates the site of covalent attachment to P1;

the dotted line indicates optional cyclization of $R^y$ to D';

$R^y$ is optionally substituted $C_1$-$C_6$ alkyl in absence of cyclization to D' or optionally substituted $C_1$-$C_6$ alkylene when cyclized to D';

each Q, when present, is independently selected from the group consisting of —$C_1$-$C_8$ alkyl, —O—($C_1$-$C_8$ alkyl), halogen, nitro and cyano; and subscript m is 0, 1 or 2.

A5. The Ligand Drug Conjugate composition of any one of embodiments A1-A4, wherein D incorporates the structure of a tubulin disrupting agent, a DNA minor groove binder, a DNA damaging agent, or a DNA replication inhibitor.

A6. The Ligand Drug Conjugate composition of any one of embodiments A1-A4, wherein D incorporates the structure of a tubulysin.

A7. The Ligand Drug Conjugate composition of any one of embodiments A1-A4, wherein D incorporates the structure of a camptothecin.

A8. The Ligand Drug Conjugate composition of any one of embodiments A1-A4, wherein D incorporates the structure of an auristatin.

A9. The Ligand Drug Conjugate composition of any one of embodiments A1-A4, wherein D incorporates the structure of an anthracycline.

A10. The Ligand Drug Conjugate composition of any one of embodiments A1-A4, wherein D incorporates the structure of a camptothecin selected from the group consisting of

CPT1

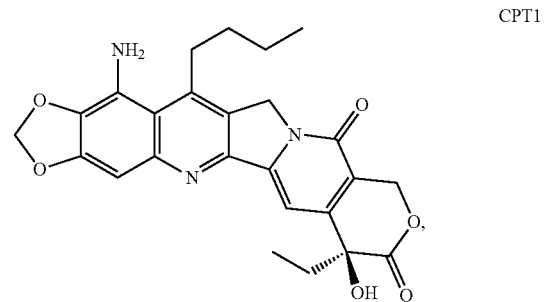

CPT2

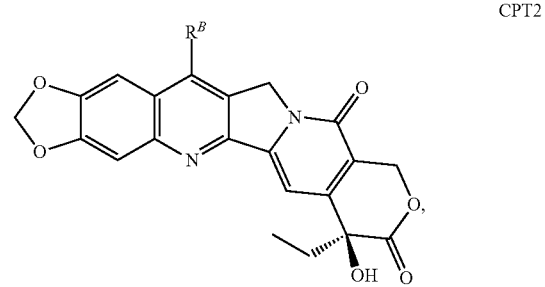

CPT3

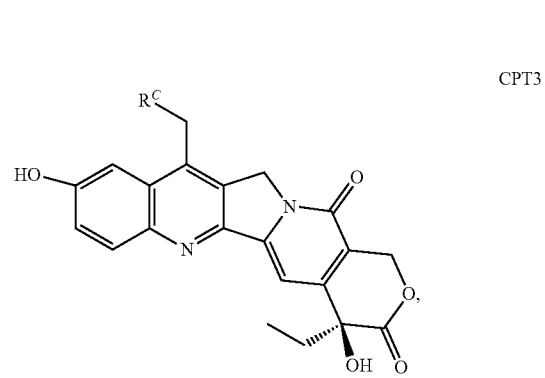

CPT4

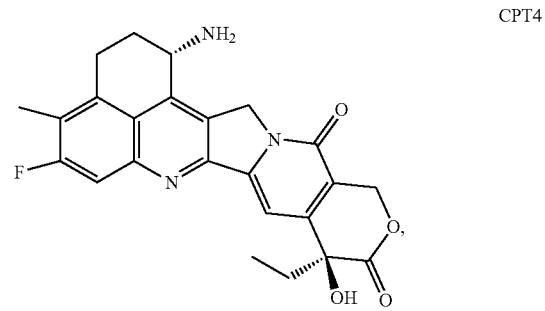

-continued

CPT5

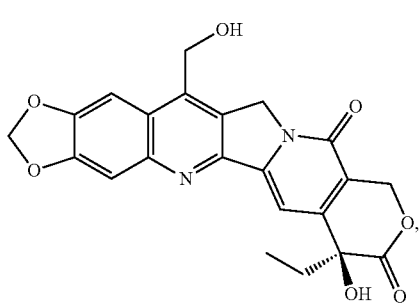

CPT6

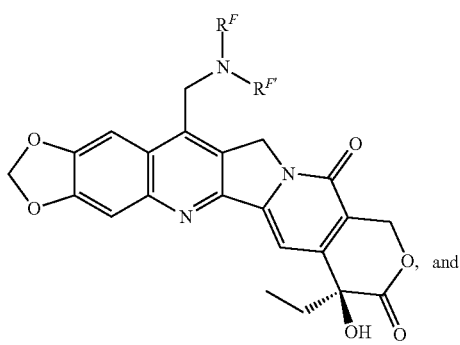
and

CPT7

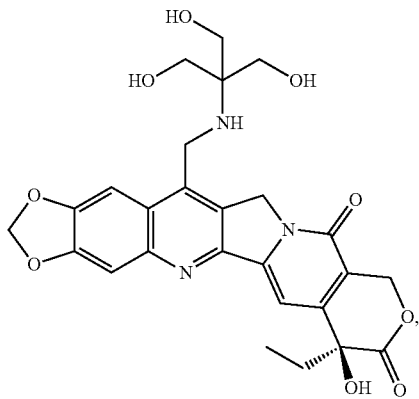

wherein
$R^B$ is selected from the group consisting of H, $C_1$-$C_8$ alkyl, $C_1$-$C_8$ haloalkyl, $C_3$-$C_8$ cycloalkyl, ($C_3$-$C_8$ cycloalkyl)-$C_1$-$C_4$ alkyl, phenyl, and phenyl-$C_1$-$C_4$ alkyl;
$R^C$ is selected from the group consisting of $C_1$-$C_6$ alkyl and $C_3$-$C_6$ cycloalkyl; and
each $R^F$ and $R^{F'}$ is independently selected from the group consisting of —H, $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N-($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydoxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl, and heteroaryl-$C_1$-$C_4$ alkyl-, or
$R^F$ and $R^{F'}$ are combined with the nitrogen atom to which each is attached to form a 5-, 6- or 7-membered ring having 0 to 3 substituents selected from the group consisting of halogen, $C_1$-$C_4$ alkyl, —OH, —O$C_1$-$C_4$ alkyl, —$NH_2$, —NH—$C_1$-$C_4$ alkyl, —N($C_1$-$C_4$ alkyl)$_2$; and wherein the cycloalkyl, heterocycloalkyl, phenyl and heteroaryl portions of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —$NH_2$, —NH$C_1$-$C_4$ alkyl, and —N($C_1$-$C_4$ alkyl)$_2$.

A11. The Ligand Drug Conjugate composition of any one of embodiments A1-A4, wherein D has a formula selected from the group consisting of $D_G$

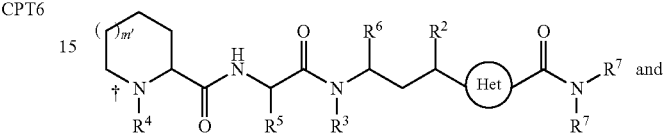
and $D_H$

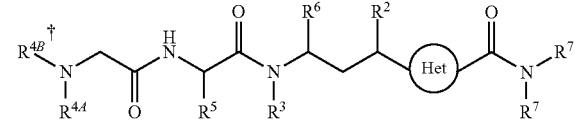

wherein the dagger represents the point of attachment of D to the secondary linker of the drug linker moiety and the circle represents an 5-membered or 6-membered nitrogen heteroarylene wherein the indicated required substituents to that heteroarylene are in a 1,3- or meta-relationship to each other with optional substitution at the remaining positions;

$R^2$ is $X^A$-$R^{2A}$, wherein $X^A$ is —O—, —S—, —N($R^{2B}$)-, —$CH_2$—, —(C=O)N($R^{2B}$)— or —O(C=O)N($R^{2B}$)— wherein $R^{2B}$ is hydrogen or optionally substituted alkyl, $R^{2A}$ is hydrogen, optionally substituted alkyl, optionally substituted aryl, or —C(=O)$R^C$, wherein $R^C$ is hydrogen, optionally substituted alkyl, or optionally substituted aryl or $R^2$ is an O-linked substituent;

$R^3$ is hydrogen or optionally substituted alkyl;

$R^4$, $R^{4A}$, $R^{4B}$, $R^5$ and $R^6$ are optionally substituted alkyl, independently selected, one $R^7$ is hydrogen or optionally substituted alkyl and the other $R^7$ is optionally substituted arylalkyl or optionally substituted heteroarylalkyl, and subscript m' is 0 or 1.

A12. The Ligand Drug Conjugate composition of any one of embodiments A1-A4, wherein D is a cytotoxic drug wherein the cytotoxic drug is a secondary amine-containing auristatin compound wherein the nitrogen atom of the secondary amine is the site of covalent attachment to the drug linker moiety and the secondary amine-containing auristatin compound has the structure of Formula $D_{F/E-3}$:

$D_{F/E-3}$

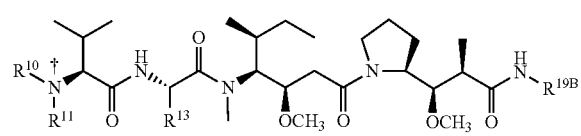

wherein the dagger indicates the site of covalent attachment of the nitrogen atom that provides the carbamate functional group;
one of $R^{10}$ and $R^{11}$ is hydrogen and the other is methyl;
$R^{13}$ is isopropyl or —$CH_2$—$CH(CH_3)_2$; and
$R^{19B}$ is —CH($CH_3$)—CH(OH)-Ph, —CH($CO_2$H)—CH(OH)—$CH_3$, —CH($CO_2$H)—$CH_2$Ph, —CH($CH_2$Ph)-2-thiazolyl, —CH($CH_2$Ph)-2-pyridyl, —CH($CH_2$-p-Cl-Ph), —CH($CO_2$Me)-$CH_2$Ph, —CH($CO_2$Me)-$CH_2CH_2SCH_3$, —CH($CH_2CH_2SCH_3$)C(=O)NH-quinol-3-yl, —CH($CH_2$Ph)C(=O)NH-p-Cl-Ph, or $R^{19B}$ has the structure of

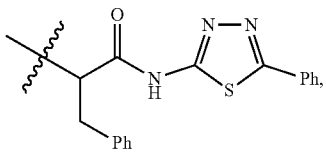 [SMILES: *C(Cc1ccccc1)C(=O)Nc1nnc(-c2ccccc2)s1]

wherein the wavy line indicates covalent attachment to the remainder of the auristatin compound.

A13. The Ligand Drug Conjugate composition of embodiment A12, wherein the secondary amine-containing auristatin compound is monomethylauristatin E (MMAE) or monomethylauristatin F (MMAF).

A14. The Ligand Drug Conjugate composition of any one of embodiments A1-A13, or a pharmaceutically acceptable salt thereof, wherein the Peptide Cleavable Unit is a tripeptide having the sequence -P3-P2-P1-, wherein P1, P2, and P3 are each an amino acid, wherein:

the P3 amino acid of the tripeptide is in the D-amino acid configuration;
one of the P2 and P1 amino acids has an aliphatic side chain with hydrophobicity lower than that of leucine; and
the other of the P2 and P1 amino acids is negatively charged.

A15. The Ligand Drug Conjugate composition of any one of embodiments A1-A14, or a pharmaceutically acceptable salt thereof, wherein the P3 amino acid is D-Leu or D-Ala.

A16. The Ligand Drug Conjugate composition of any one of embodiments A1-A15, or a pharmaceutically acceptable salt thereof, wherein one of the P2 or P1 amino acid has an aliphatic side chain with hydrophobicity no greater than that of valine, and the other of the P2 or P1 amino acid is negatively charged at plasma physiological pH.

A17. The Ligand Drug Conjugate composition of any one of embodiments A1-A16, or a pharmaceutically acceptable salt thereof, wherein the P2 amino acid has an aliphatic side chain with hydrophobicity no greater than that of valine, and the P1 amino acid is negatively charged at plasma physiological pH.

A18. The Ligand Drug Conjugate composition of any one of embodiments A1-A17, or a pharmaceutically acceptable salt thereof, wherein -P2-P1- is -Ala-Glu- or -Ala-Asp-.

A19. The Ligand Drug Conjugate composition of any one of embodiments A1-A18, or a pharmaceutically acceptable salt thereof, wherein -P3-P2-P1- is -D-Leu-Ala-Asp-, -D-Leu-Ala-Glu-, -D-Ala-Ala-Asp-, or -D-Ala-Ala-Glu-.

A20. The Ligand Drug Conjugate composition of any one of embodiments A1-A16, or a salt thereof, wherein the P3 amino acid is D-Leu or D-Ala, the P2 amino acid is Ala, Glu, or Asp, and the P1 amino acid is Ala, Glu, or Asp.

A21. The Ligand Drug Conjugate compound composition of embodiment A1, wherein the composition comprises Ligand Drug Conjugate compounds having the structure of

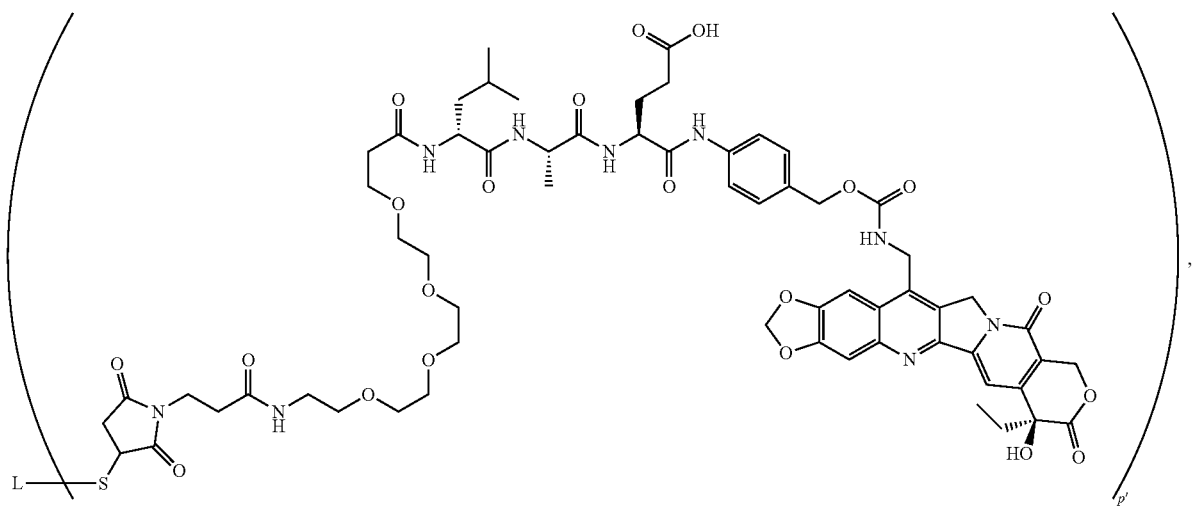

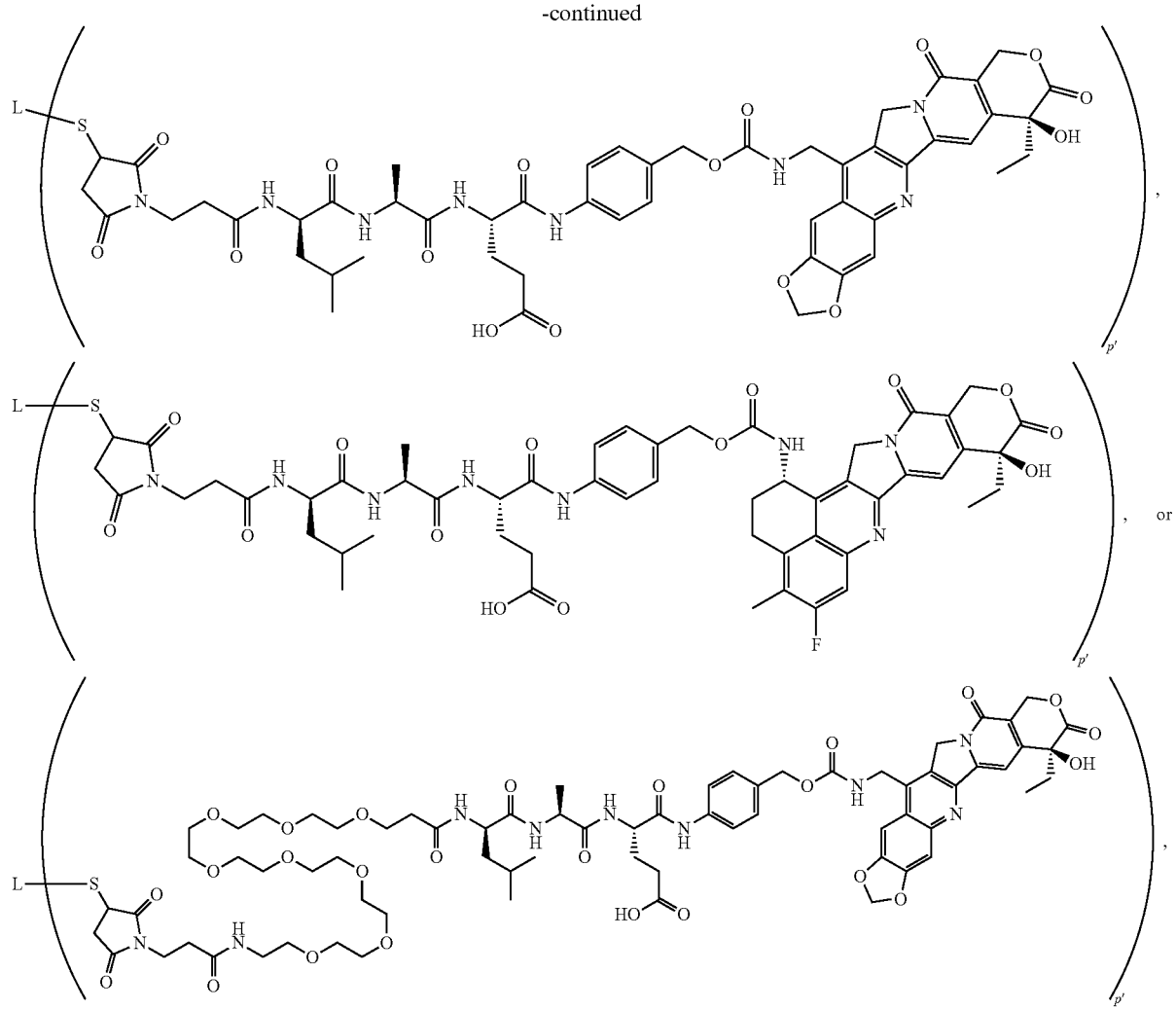

or a pharmaceutically acceptable salt thereof,
wherein L is the Ligand Unit, and subscript p' is an integer from 1 to 12.

A22. The Ligand Drug Conjugate composition of any one of embodiments A1-A21, wherein L is an antibody Ligand Unit of an intact antibody or an antigen-binding fragment thereof.

A23. The Ligand Drug Conjugate composition of embodiment A22, wherein the intact antibody is a an intact chimeric, humanized or human antibody.

A24. The Ligand Drug Conjugate composition of embodiment A22, wherein the intact antibody or fragment thereof is capable of selectively binding to a cancer cell antigen.

A25. The Ligand Drug Conjugate composition of embodiment A22, wherein the intact antibody or fragment thereof is capable of selectively binding to an immune cell antigen.

A26. The Ligand Drug Conjugate composition of embodiment A22 or embodiment A23, wherein the intact antibody or fragment thereof is capable of selectively binding CD30.

A27. The Ligand Drug Conjugate composition of embodiment A26, wherein the intact antibody or fragment thereof comprises CDR-H1, CDR-H2, CDR-H3, CDR-L1, CDR-L2, and CDR-L3 comprising the amino acid sequences of SEQ ID NOs: 1, 2, 3, 4, 5, and 6, respectively.

A28. The Ligand Drug Conjugate composition of embodiment A26 or embodiment A27, wherein the intact antibody or fragment thereof comprises a heavy chain variable region comprising the amino acid sequence of SEQ ID NO: 7 and a light chain variable region comprising the amino acid sequence of SEQ ID NO: 8.

A29. The Ligand Drug Conjugate composition of any one of embodiments A26-A28, wherein the intact antibody is cAC10.

A30. The Ligand Drug Conjugate composition of embodiment A22 or embodiment A23, wherein the intact antibody or fragment thereof is capable of selectively binding LIV1.

A31. The Ligand Drug Conjugate composition of embodiment A30, wherein the intact antibody or fragment thereof comprises CDR-H1, CDR-H2, CDR-H3, CDR-L1, CDR-L2, and CDR-L3 comprising the amino acid sequences of SEQ ID NOs: 518, 519, 520, 521, 522, and 523, respectively.

A32. The Ligand Drug Conjugate composition of embodiment A30 or embodiment A31, wherein the intact antibody or fragment thereof comprises a heavy chain variable region comprising the amino acid sequence of SEQ ID NO: 524 and a light chain variable region comprising the amino acid sequence of SEQ ID NO: 525.

A33. The Ligand Drug Conjugate composition of any one of embodiments A30-A32, wherein the intact antibody is ladiratuzumab.

A34. The Ligand Drug Conjugate composition of embodiment A22 or embodiment A23, wherein the intact antibody or fragment thereof is capable of selectively binding TROP2.

A35. The Ligand Drug Conjugate composition of embodiment A34, wherein the intact antibody is sacituzumab or datopotamab.

A36. The Ligand Drug Conjugate composition of embodiment A22 or embodiment A23, wherein the intact antibody or fragment thereof is capable of selectively binding ALPP.

A37. The Ligand Drug Conjugate composition of embodiment A22 or embodiment A23, wherein the intact antibody or fragment thereof is capable of selectively binding IL1RAP.

A38. The Ligand Drug Conjugate composition of embodiment A37, wherein the intact antibody or fragment thereof comprises CDR-H1, CDR-H2, CDR-H3, CDR-L1, CDR-L2, and CDR-L3 comprising the amino acid sequences of SEQ ID NOs: 96, 97, 98, 99, 100, and 101, respectively.

A39. The Ligand Drug Conjugate composition of embodiment A37 or embodiment A38, wherein the intact antibody or fragment thereof comprises a heavy chain variable region comprising the amino acid sequence of SEQ ID NO: 102 and a light chain variable region comprising the amino acid sequence of SEQ ID NO: 103.

A40. The Ligand Drug Conjugate composition of any one of embodiments A37-A39, wherein the intact antibody is nidanilimab.

A41. The Ligand Drug Conjugate composition of embodiment A22 or embodiment A23, wherein the intact antibody or fragment thereof is capable of selectively binding ASCT2.

A42. The Ligand Drug Conjugate composition of embodiment A41, wherein the intact antibody or fragment thereof comprises CDR-H1, CDR-H2, CDR-H3, CDR-L1, CDR-L2, and CDR-L3 comprising the amino acid sequences of SEQ ID NOs: 794, 795, 796, 797, 798, and 799, respectively.

A43. The Ligand Drug Conjugate composition of embodiment A41 or embodiment A42, wherein the intact antibody or fragment thereof comprises a heavy chain variable region comprising the amino acid sequence of SEQ ID NO: 801 and a light chain variable region comprising the amino acid sequence of SEQ ID NO: 802.

A44. The Ligand Drug Conjugate composition of embodiment A41, wherein the intact antibody or fragment thereof comprises a heavy chain variable region comprising the amino acid sequence of SEQ ID NO: 790 and a light chain variable region comprising the amino acid sequence of SEQ ID NO: 791.

A45. The Ligand Drug Conjugate composition of embodiment A41, wherein the intact antibody or fragment thereof comprises a heavy chain variable region comprising the amino acid sequence of SEQ ID NO: 792 and a light chain variable region comprising the amino acid sequence of SEQ ID NO: 793.

A46. The Ligand Drug Conjugate composition of any one of embodiments A26-A45, wherein subscript q is 1 and the Ligand Drug Conjugate compounds in the Ligand Drug Conjugate composition predominately have drug linker moieties of Formula 1H-MMAE:

(Formula 1H-MMAE)

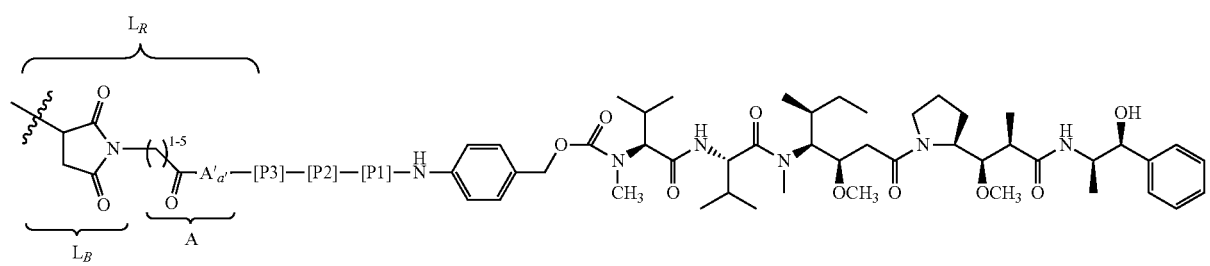

or a pharmaceutical acceptable salt thereof, and optionally having a minority of Ligand Drug Conjugate compounds in which one or more of the drug linker moieties in each of such compounds has its the succinimide ring in hydrolyzed form and wherein:
subscript a' is 0, and A' is absent; and
the wavy line indicates the site of covalent binding to a sulfur atom of the Ligand Unit.

A47. The Ligand Drug Conjugate compound composition of any one of embodiments A26-A45, wherein the composition comprises Ligand Drug Conjugate compounds having the structure of

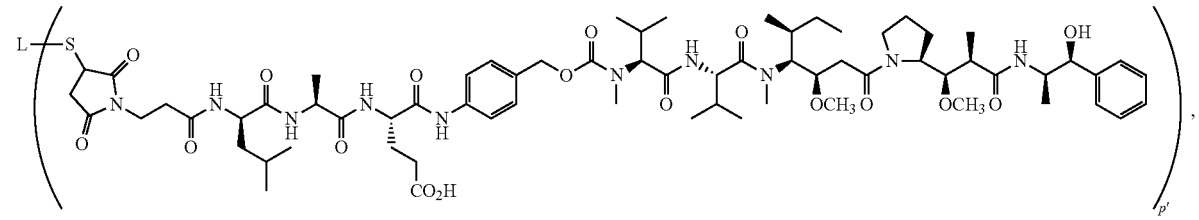

-continued

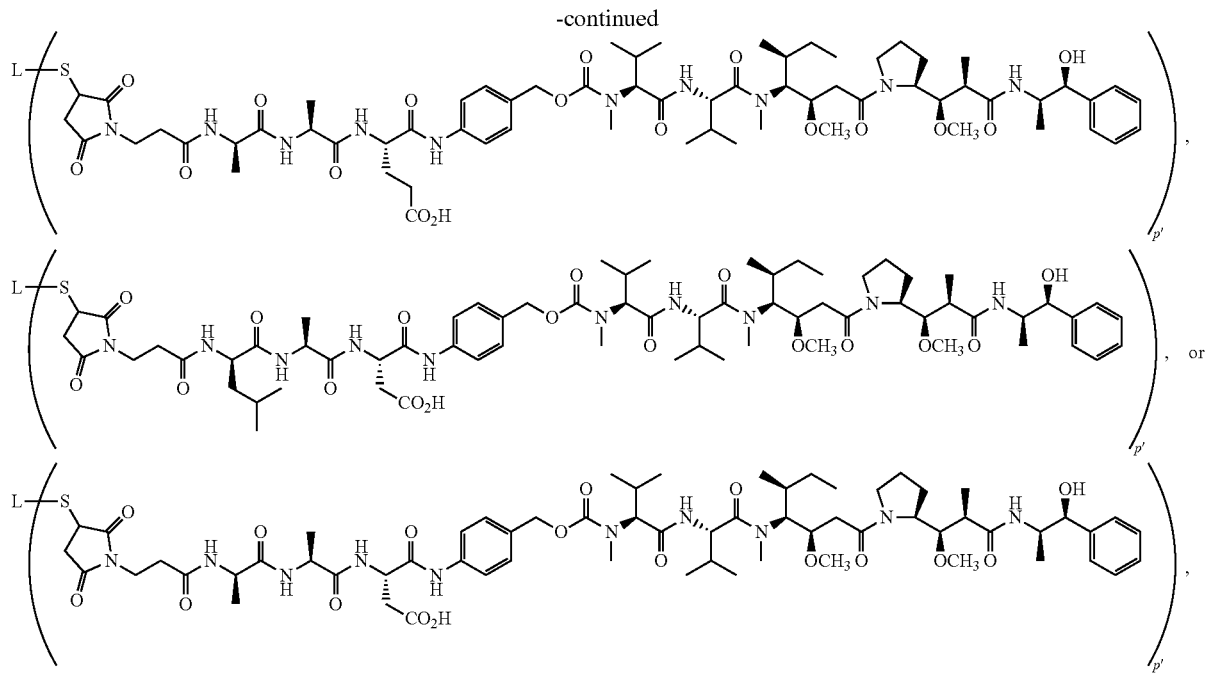

or a pharmaceutically acceptable salt thereof,
wherein L is the Ligand Unit, and subscript p' is an integer from 1 to 12.

A48. The Ligand Drug Conjugate composition of any one of embodiments A1-A48, wherein subscript p ranges from about 2 to about 12, or from about 2 to about 10, or from about 2 to about 8, or subscript p is about 2, about 4 or about 8.

A49. A pharmaceutically acceptable formulation, wherein the formulation comprises an effective amount of a Ligand Drug Conjugate composition of any one of embodiments A1-A48 and at least one pharmaceutically acceptable excipient.

A50. The pharmaceutically acceptable formulation of embodiment A49, wherein the least one pharmaceutically acceptable excipient is a liquid carrier that provides a liquid formulation, wherein the liquid formulation is suitable for lyophilization or administration to a subject in need thereof.

A51. The pharmaceutically acceptable formulation of embodiment A49, wherein the formulation is a lyophilized solid or a liquid formulation of embodiment A26, wherein the at least one excipient of the solid formulation is a lyoprotectant.

A52. A method of treating cancer comprising administering to a subject in need thereof a therapeutically effective amount of a Ligand Drug Conjugate composition of any one of embodiments A1-A48 or a pharmaceutically acceptable formulation of any one of embodiments A49-A51.

A53. A Drug Linker compound of Formula AIA:

 (AIA)

or a salt thereof, wherein
D is a Drug Unit;
$L_B'$ is a ligand covalent binding precursor moiety;
A is a first optional Stretcher Unit;
subscript a is 0 or 1, indicating the absence or presence of A, respectively;
B is an optional Branching Unit;
subscript b is 0 or 1, indicating the absence or presence of B, respectively;
$L_O$ is a secondary linker moiety, wherein the secondary linker has the formula of;

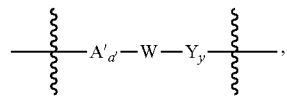

wherein the wavy line adjacent to Y indicates the site of covalent attachment of $L_O$ to the Drug Unit and the wavy line adjacent to A' indicates the site of covalent attachment of $L_O$ to the remainder of the Drug Linker compound;
A' is a second optional Stretcher Unit, which when present and in the absence of B becomes a subunit of A;
subscript a' is 0 or 1, indicating the absence or presence of A', respectively,
W is a Peptide Cleavable Unit, wherein the Peptide Cleavable Unit comprises a tripeptide having the sequence -P3-P2-P1-, wherein P1, P2, and P3 are each an amino acid, wherein:
  a first one of the amino acids P1, P2, or P3 is negatively charged;
  a second one of the amino acids P1, P2, or P3 has an aliphatic side chain with hydrophobicity no greater than that of leucine; and
  a third one of the amino acids P1, P2, or P3 has hydrophobicity lower than that of leucine,
wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3, provided that -P3-P2-P1- is not -Glu-Val-Cit- or -Asp-Val-Cit-;

each Y when present is a self-immolative Spacer Unit;

subscript y is 0, 1 or 2 indicating the absence or presence of 1 or 2 of Y, respectively; and subscript q is an integer ranging from 1 to 3, and provided that subscript q is 1 when subscript b is 0 and subscript q is 2 or 3 when subscript b is 1.

A54. The Drug Linker compound of embodiment A53, wherein the Drug Linker compound has the structure of Formula AIH:

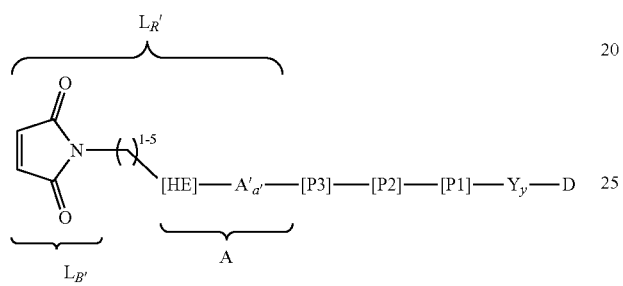

(Formula AIH)

or salt thereof, wherein:

HE is a Hydrolysis Enhancing Unit; and

A' is a subunit, when present, of the indicated first Stretcher Unit (A); subscript a' is 0 or 1, indicating the absence or presence of A', respectively.

A55. The Drug Linker compound of A54 wherein HE is —C(=O).

A56. The Drug Linker compound of any one of embodiments A53-A55, wherein —$Y_y$-D has the structure of

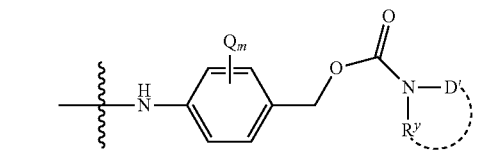

wherein —N($R^y$)D' represents D, wherein D' is the remainder of D;

the wavy line indicates the site of covalent attachment to P1;

the dotted line indicates optional cyclization of $R^y$ to D';

$R^y$ is optionally substituted $C_1$-$C_6$ alkyl in absence of cyclization to D' or optionally substituted $C_1$-$C_6$ alkylene when cyclized to D';

each Q is independently selected from the group consisting of —$C_1$-$C_8$ alkyl, —O—($C_1$-$C_8$ alkyl), halogen, nitro and cyano; and subscript m is 0, 1 or 2.

A57. The Drug Linker compound of any one of embodiments A53-A56, wherein D incorporates the structure of a tubulin disrupting agent, a DNA minor groove binder, a DNA damaging agent, or a DNA replication inhibitor.

A58. The Drug Linker compound of any one of embodiments A53-A56, wherein D incorporates the structure of a tubulysin.

A59. The Drug Linker compound of any one of embodiments A53-A56, wherein D incorporates the structure of a camptothecin.

A60. The Drug Linker compound of any one of embodiments A53-A56, wherein D incorporates the structure of an auristatin.

A61. The Drug Linker compound of any one of embodiments A53-A56, wherein D incorporates the structure of an anthracycline.

A62. The Drug Linker compound of any one of embodiments A53-A56, wherein D incorporates the structure of a camptothecin having the structure selected from the group consisting of

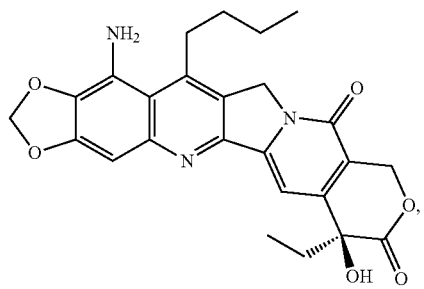

CPT1

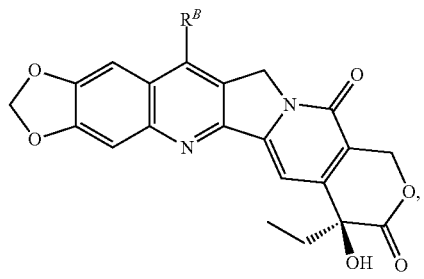

CPT2

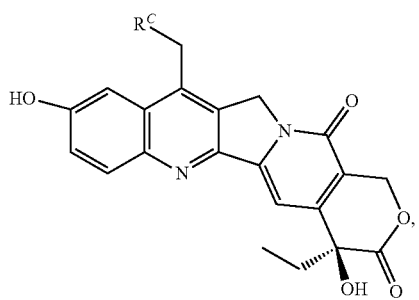

CPT3

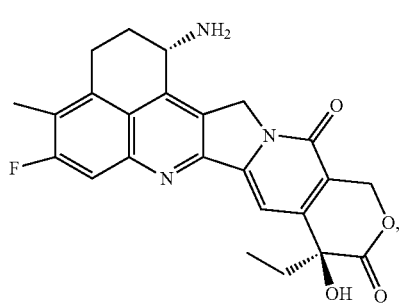

CPT4

-continued

CPT5

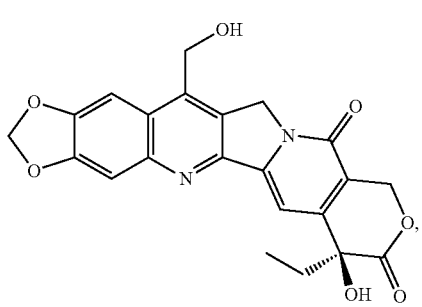

CPT6

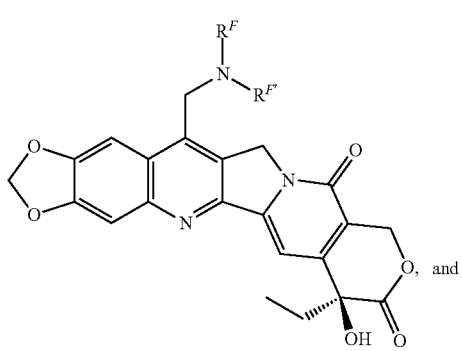

CPT7

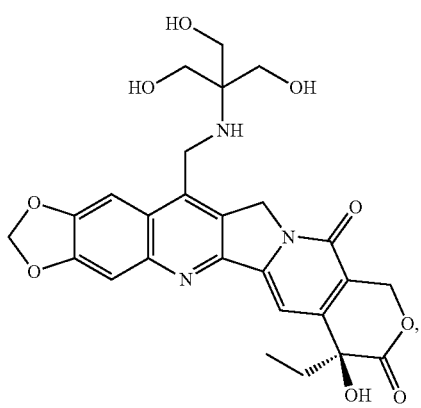

wherein
R$^B$ is selected from the group consisting of H, C$_1$-C$_8$ alkyl, C$_1$-C$_8$ haloalkyl, C$_3$-C$_8$ cycloalkyl, (C$_3$-C$_8$ cycloalkyl)-C$_1$-C$_4$ alkyl, phenyl, and phenyl-C$_1$-C$_4$ alkyl;
R$^C$ is selected from the group consisting of C$_1$-C$_6$ alkyl and C$_3$-C$_6$ cycloalkyl; and
each R$^F$ and R$^{F'}$ is independently selected from the group consisting of —H, C$_1$-C$_8$ alkyl, C$_1$-C$_8$ hydroxyalkyl, C$_1$-C$_8$ aminoalkyl, (C$_1$-C$_4$ alkylamino)-C$_1$-C$_8$ alkyl-, N,N-(C$_1$-C$_4$ hydroxyalkyl)(C$_1$-C$_4$ alkyl)amino-C$_1$-C$_8$ alkyl-, N,N-di(C$_1$-C$_4$ alkyl)amino-C$_1$-C$_8$ alkyl-, N—(C$_1$-C$_4$ hydroxyalkyl)-C$_1$-C$_8$ aminoalkyl, C$_1$-C$_8$ alkyl-C(O)—, C$_1$-C$_8$ hydoxyalkyl-C(O)—, C$_1$-C$_8$ aminoalkyl-C(O)—, C$_3$-C$_{10}$ cycloalkyl, (C$_3$-C$_{10}$ cycloalkyl)-C$_1$-C$_4$ alkyl-, C$_3$-C$_{10}$ heterocycloalkyl, (C$_3$-C$_{10}$ heterocycloalkyl)-C$_1$-C$_4$ alkyl-, phenyl, phenyl-C$_1$-C$_4$ alkyl-, diphenyl-C$_1$-C$_4$ alkyl-, heteroaryl, and heteroaryl-C$_1$-C$_4$ alkyl-, or
R$^F$ and R$^{F'}$ are combined with the nitrogen atom to which each is attached to form a 5-, 6- or 7-membered ring having 0 to 3 substituents selected from the group consisting of halogen, C$_1$-C$_4$ alkyl, —OH, —OC$_1$-C$_4$ alkyl, —NH$_2$, —NH—C$_1$-C$_4$ alkyl, —N(C$_1$-C$_4$ alkyl)$_2$; and wherein the cycloalkyl, heterocycloalkyl, phenyl and heteroaryl portions of R$^B$, R$^C$, R$^F$ and R$^{F'}$ are substituted with from 0 to 3 substituents selected from the group consisting of halogen, C$_1$-C$_4$ alkyl, —OH, —OC$_1$-C$_4$ alkyl, —NH$_2$, —NHC$_1$-C$_4$ alkyl, and —N(C$_1$-C$_4$ alkyl)$_2$.

A63. The Drug Linker compound of any one of embodiments A53-A56, wherein D has a formula selected from the group consisting of

D$_G$

 and

D$_H$

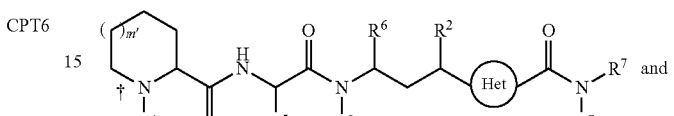

wherein the dagger represents the point of attachment of D to the remainder of the Drug Linker compound and the circle represents an 5-membered or 6-membered nitrogen heteroarylene wherein the indicated required substituents to that heteroarylene are in a 1,3- or meta-relationship to each other with optional substitution at the remaining positions;
R$^2$ is X$^A$-R$^{2A}$, wherein X$^A$ is —O—, —S—, —N(R$^{2B}$)—, —CH$_2$—, —(C=O)N(R$^{2B}$)— or —O(C=O)N(R$^{2B}$)— wherein R$^{2B}$ is hydrogen or optionally substituted alkyl, R$^{2A}$ is hydrogen, optionally substituted alkyl, optionally substituted aryl, or —C(=O)R$^C$, wherein R$^C$ is hydrogen, optionally substituted alkyl, or optionally substituted aryl or R$^2$ is an O-linked substituent;
R$^3$ is hydrogen or optionally substituted alkyl;
R$^4$, R$^{4A}$, R$^{4B}$, R$^5$ and R$^6$ are optionally substituted alkyl, independently selected,
one R$^7$ is hydrogen or optionally substituted alkyl and the other R$^7$ is optionally substituted arylalkyl or optionally substituted heteroarylalkyl, and
subscript m' is 0 or 1.

A64. The Drug Linker compound of any one of embodiments A53-A56, wherein D is a cytotoxic drug wherein the cytotoxic drug is a secondary amine-containing auristatin compound wherein the nitrogen atom of the secondary amine is the site of covalent attachment to the drug linker moiety and the secondary amine-containing auristatin compound has the structure of Formula D$_{F/E-3}$:

D$_{F/E-3}$

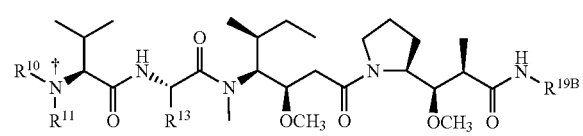

wherein the dagger indicates the site of covalent attachment of the nitrogen atom that provides the carbamate functional group;

one of $R^{10}$ and $R^{11}$ is hydrogen and the other is methyl; $R^{13}$ is isopropyl or —$CH_2$—$CH(CH_3)_2$; and
$R^{19B}$ is —$CH(CH_3)$—$CH(OH)$-Ph, —$CH(CO_2H)$—$CH(OH)$—$CH_3$, —$CH(CO_2H)$—$CH_2Ph$, —$CH(CH_2Ph)$-2-thiazolyl, —$CH(CH_2Ph)$-2-pyridyl, —$CH(CH_2$-p-Cl-Ph), —$CH(CO_2Me)$-$CH_2Ph$, —$CH(CO_2Me)$-$CH_2CH_2SCH_3$, —$CH(CH_2CH_2SCH_3)C(=O)NH$-quinol-3-yl, —$CH(CH_2Ph)C(=O)NH$-p-Cl-Ph, or $R^{19B}$ has the structure of

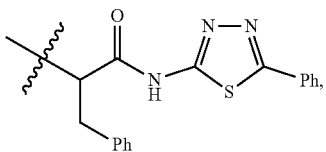 [SMILES: *C(Cc1ccccc1)C(=O)Nc1nnc(-c2ccccc2)s1]

wherein the wavy line indicates covalent attachment to the remainder of the auristatin compound.

A65. The Drug Linker compound of embodiment A64, wherein the secondary amine-containing auristatin compound is monomethylauristatin E (MMAE) or monomethylauristatin F (MMAF).

A66. The Drug Linker compound of any one of embodiments A53-A65, or a salt thereof, wherein the Peptide Cleavable Unit is a tripeptide having the sequence -P3-P2-P1-, wherein P1, P2, and P3 are each an amino acid, wherein:
the P3 amino acid of the tripeptide is in the D-amino acid configuration;

one of the P2 and P1 amino acids has an aliphatic side chain with hydrophobicity lower than that of leucine; and the other of the P2 and P1 amino acids is negatively charged.

A67. The Drug Linker compound of any one of embodiments A53-A66 wherein the P3 amino acid is D-Leu or D-Ala.

A68. The Drug Linker compound of any one of embodiments A53-A67 wherein one of the P2 or P1 amino acid has an aliphatic side chain with hydrophobicity no greater than that of valine, and the other of the P2 or P1 amino acid is negatively charged at plasma physiological pH.

A69. The Drug Linker compound of any one of embodiments A53-A68 wherein the P2 amino acid has an aliphatic side chain with hydrophobicity no greater than that of valine, and the P1 amino acid is negatively charged at plasma physiological pH.

A70. The Drug Linker compound of any one of embodiments A53-A69 wherein -P2-P1- is -Ala-Glu- or -Ala-Asp-.

A71. The Drug Linker compound of any one of embodiments A53-A70 wherein -P3-P2-P1- is -D-Leu-Ala-Asp-, -D-Leu-Ala-Glu-, -D-Ala-Ala-Asp-, or -D-Ala-Ala-Glu-.

A72. The Drug Linker compound any one of embodiments A53-A68 wherein the P3 amino acid is D-Leu or D-Ala, the P2 amino acid is Ala, Glu, or Asp, and the P1 amino acid is Ala, Glu, or Asp.

A73. The Drug Linker compound of embodiment A53, wherein the Drug Linker compound has the structure of:

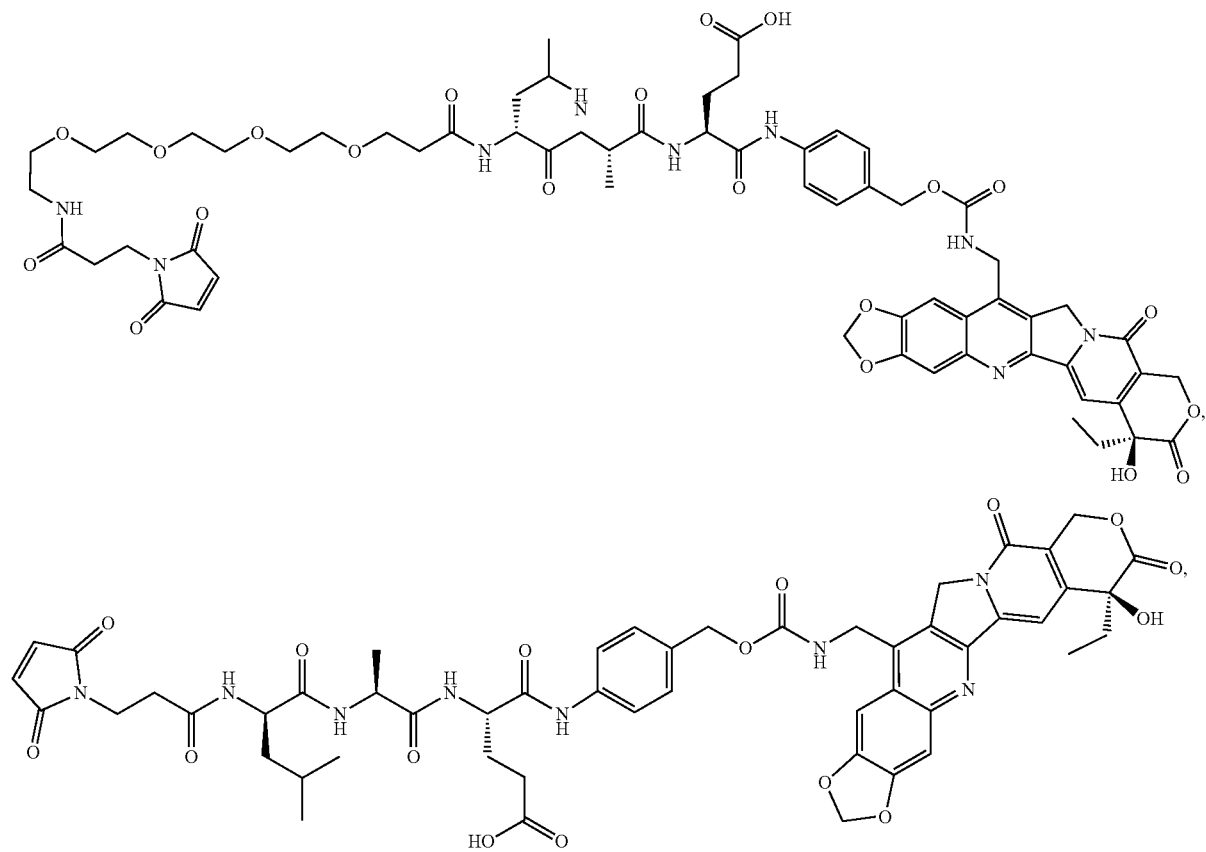

-continued
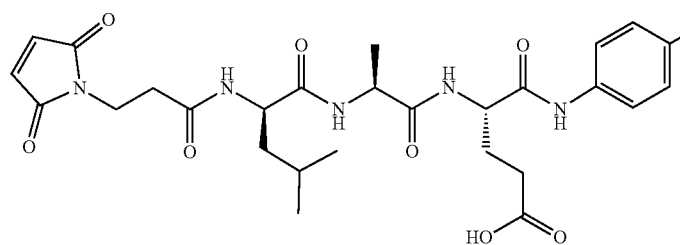
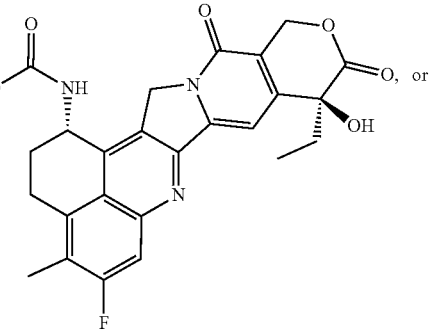
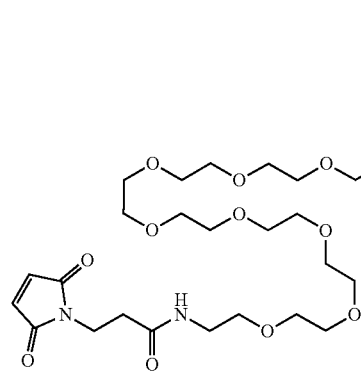
or a salt thereof.
A74. A method of preparing a compound having the structure of
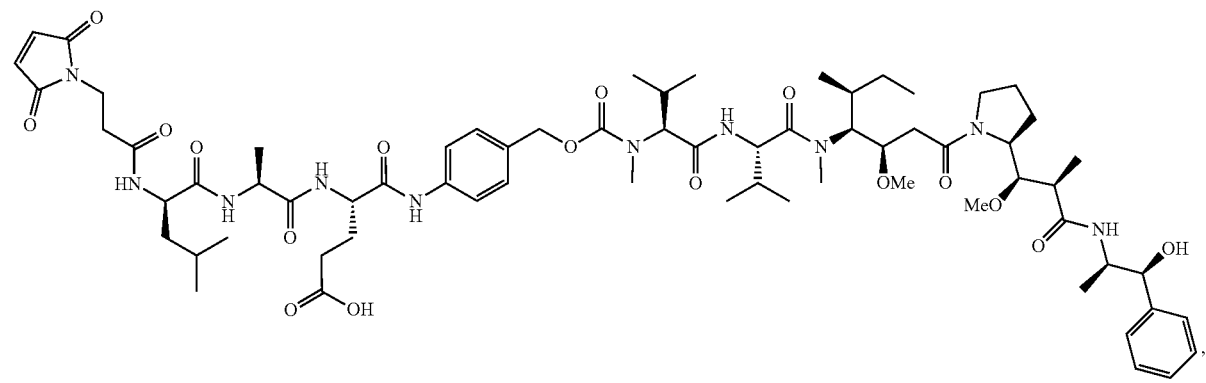 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCC(=O)O)NC(=O)[C@H](C)NC(=O)[C@@H](CC(C)C)NC(=O)CCN2C(=O)C=CC2=O)cc1)C(C)C]
or a salt thereof, comprising
a) reacting
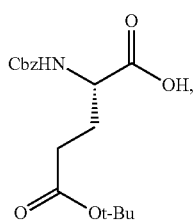 [SMILES: CC(C)(C)OC(=O)CC[C@H](NC(=O)OCc1ccccc1)C(=O)O]
or a salt thereof, with 4-aminobenzyl alcohol followed by reduction to form
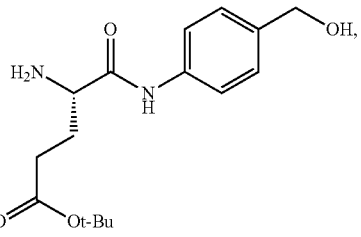
or a salt thereof, 473
b) reacting the
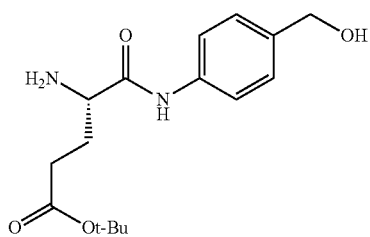 [SMILES: CC(C)(C)OC(=O)CC[C@H](N)C(=O)Nc1ccc(CO)cc1]
or salt thereof with
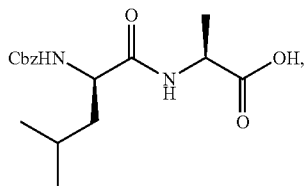
or a salt thereof, followed by reduction to form
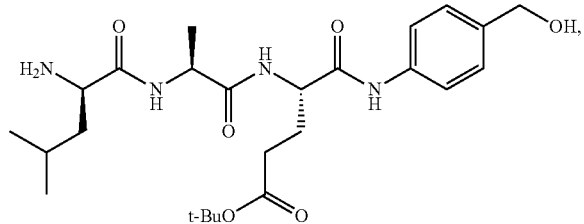 [SMILES: CC(C)C[C@@H](N)C(=O)N[C@@H](C)C(=O)N[C@@H](CCC(=O)OC(C)(C)C)C(=O)Nc1ccc(CO)cc1]
or a salt thereof;
474
c) reacting the
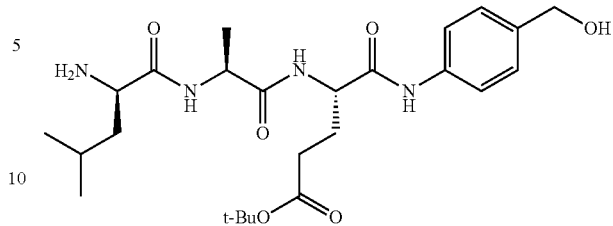
or salt thereof with 3-maleimidopropionic acid to form
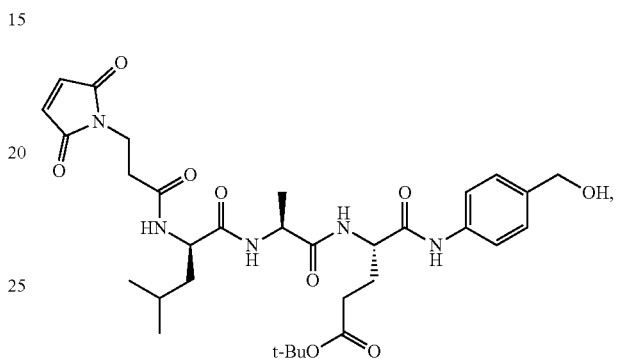
or a salt thereof; and
d) converting the
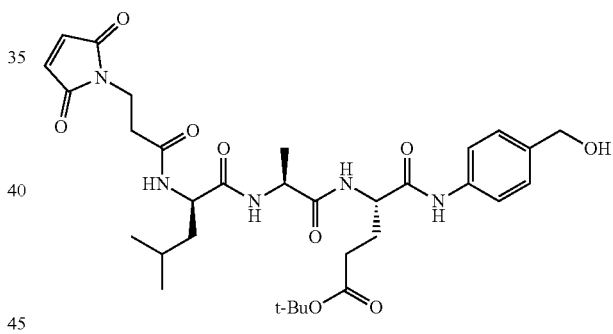
or salt thereof to the compound
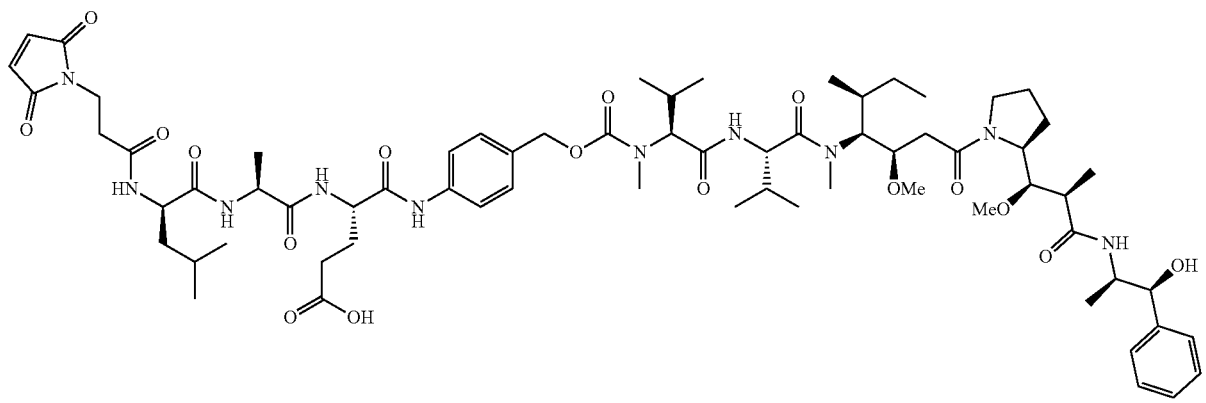 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCC(=O)O)NC(=O)[C@H](C)NC(=O)[C@@H](CC(C)C)NC(=O)CCN2C(=O)C=CC2=O)cc1)C(C)C]
or salt thereof.

B1. A Ligand Drug Conjugate composition represented by Formula B1:

or a pharmaceutically acceptable salt thereof, wherein
L is a Ligand Unit;
LU is a Linker Unit;
D' represents from 1 to 4 Drug Units (D) in each drug linker moiety of formula -LU-D'; and
subscript p is a number from 1 to 12, from 1 to 10 or from 1 to 8 or is about 4 or about 8,
wherein the Ligand Unit is from an antibody or an antigen-binding fragment of an antibody, wherein the antibody or the antigen-binding fragment is capable of selective binding to an antigen of tumor tissue for subsequent release of the Drug Unit(s) as a free drug,
wherein the drug linker moiety of formula -LU-D' in each of the Ligand Drug Conjugate compounds of the composition has the structure of Formula B1A:

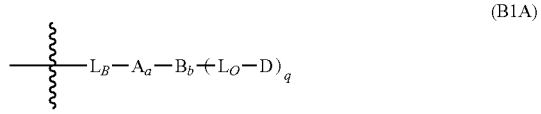

or a salt thereof,
wherein the wavy line indicates covalent attachment to L;
D is the Drug Unit, wherein the Drug Unit is a tubulysin;
$L_B$ is a ligand covalent binding moiety;
A is a first optional Stretcher Unit;
subscript a is 0 or 1, indicating the absence or presence of A, respectively;
B is an optional Branching Unit;
subscript b is 0 or 1, indicating the absence or presence of B, respectively;
$L_O$ is a secondary linker moiety, wherein the secondary linker has the formula of;

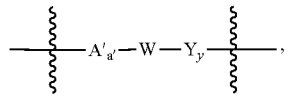

wherein the wavy line adjacent to Y indicates the site of covalent attachment of $L_O$ to the Drug Unit and the wavy line adjacent to A' indicates the site of covalent attachment of $L_O$ to the remainder of the drug linker moiety;
A' is a second optional Stretcher Unit, which when present and in the absence of B becomes a subunit of A,
subscript a' is 0 or 1, indicating the absence or presence of A', respectively,
W is a Peptide Cleavable Unit, wherein the Peptide Cleavable Unit comprises a tripeptide having the sequence -P3-P2-P1-, wherein P1, P2, and P3 are each an amino acid, wherein:
  a first one of the amino acids P1, P2, or P3 is negatively charged;
  a second one of the amino acids P1, P2, or P3 has an aliphatic side chain with hydrophobicity no greater than that of leucine; and
  a third one of the amino acids P1, P2, or P3 has hydrophobicity lower than that of leucine, wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
provided that -P3-P2-P1- is not -Glu-Val-Cit- or -Asp-Val-Cit-;
each Y when present is a self-immolative Spacer Unit;
subscript y is 0, 1 or 2 indicating the absence or presence of 1 or 2 of Y, respectively; and
subscript q is an integer ranging from 1 to 4,
provided that subscript q is 1 when subscript b is 0 and subscript q is 2, 3 or 4 when subscript b is 1; and
wherein the Ligand Drug Conjugate compounds of the composition have the structure of Formula B1 in which subscript p is replaced by subscript p', wherein subscript p' is an integer from 1 to 12, 1 to 10 or 1 to 8 or is 4 or 8.

B2. The Ligand Drug Conjugate composition of embodiment B1, wherein the Ligand Drug Conjugate compounds in the Ligand Drug Conjugate composition predominately have drug linker moieties of Formula 1H:

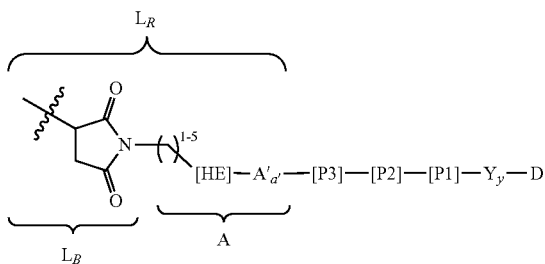

or pharmaceutically acceptable salts thereof, and optionally having a minority of Ligand Drug Conjugate compounds in which one or more of the drug linker moieties in each of such compounds has its succinimide ring in hydrolyzed form and wherein
HE is a Hydrolysis Enhancing Unit;
A' is a subunit, when present, of the indicated first Stretcher Unit (A); subscript a' is 0 or 1, indicating the absence or presence of A', respectively; and
the wavy line indicates the site of covalent attachment to a sulfur atom of the Ligand Unit.

B3. The Ligand Drug Conjugate composition of embodiment B2, wherein HE is —C(=O).

B4. The Ligand Drug Conjugate composition of any one of embodiments B1-B3, wherein —$Y_y$-D has the structure of:

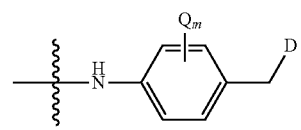

wherein each Q is independently selected from the group consisting of —$C_1$-$C_8$ alkyl, —O—($C_1$-$C_8$ alkyl), halogen, nitro and cyano; and
subscript m is 0, 1 or 2.

B5. The Ligand Drug Conjugate composition of any one of embodiments B1-B4, wherein D has a formula selected from the group consisting of

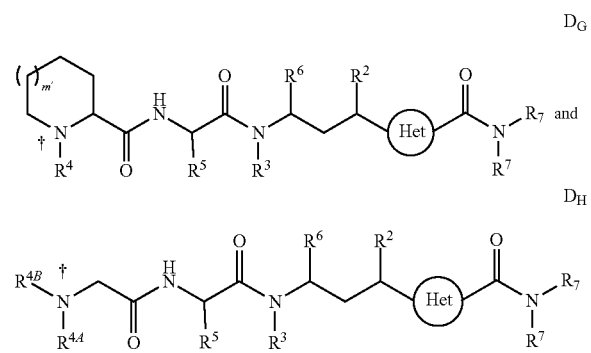

wherein the dagger represents the point of attachment of D to the drug linker moiety and the circle represents an 5-membered or 6-membered nitrogen heteroarylene wherein the indicated required substituents to that heteroarylene are in a 1,3- or meta-relationship to each other with optional substitution at the remaining positions;

$R^2$ is $X^A$-$R^{2A}$, wherein $X^A$ is —O—, —S—, —N($R^{2B}$)—, —CH$_2$—, —(C=O)N($R^{2B}$)— or —O(C=O)N($R^{2B}$)— wherein $R^{2B}$ is hydrogen or optionally substituted alkyl, $R^{2A}$ is hydrogen, optionally substituted alkyl, optionally substituted aryl, or —C(=O)$R^C$, wherein $R^C$ is hydrogen, optionally substituted alkyl, or optionally substituted aryl or $R^2$ is an O-linked substituent;

$R^3$ is hydrogen or optionally substituted alkyl;

$R^4$, $R^{4A}$, $R^{4B}$, $R^5$ and $R^6$ are optionally substituted alkyl, independently selected, one $R^7$ is hydrogen or optionally substituted alkyl and the other $R^7$ is optionally substituted arylalkyl or optionally substituted heteroarylalkyl, and subscript m' is 0 or 1.

B6. The Ligand Drug Conjugate composition of embodiment B5, wherein $R^4$ is methyl or $R^{4A}$ and $R^{4B}$ are methyl.

B7. The Ligand Drug Conjugate composition of embodiment B5 or embodiment B6, wherein the 5-membered heteroarylene is represented by the structure

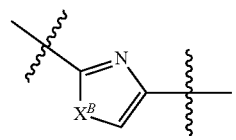

wherein $X^B$ is O, S, or N—$R^B$ wherein $R^B$ is hydrogen or lower alkyl.

B8. The Ligand Drug Conjugate composition of any one of embodiments B5-B-7, wherein the 5-membered heteroarylene is a divalent thiazole moiety.

B9. The Ligand Drug Conjugate composition of any one of embodiments B5-B-8, wherein subscript m' is 1.

B10. The Ligand Drug Conjugate composition of any one of embodiments B5-B-9, wherein D has a formula selected from the group consisting of

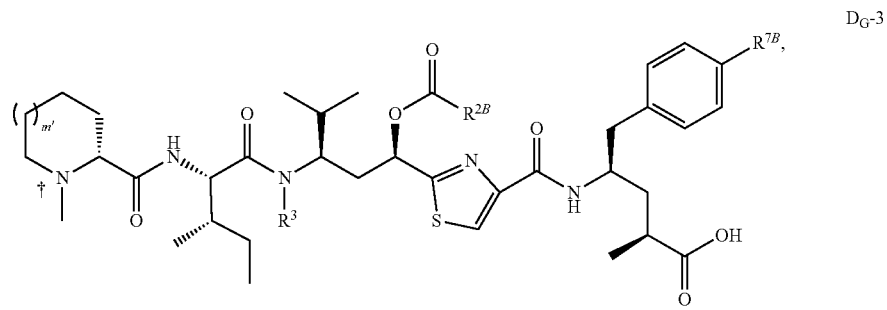

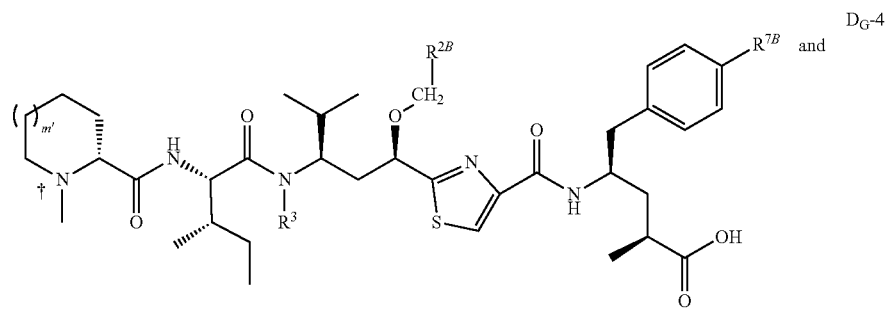

-continued

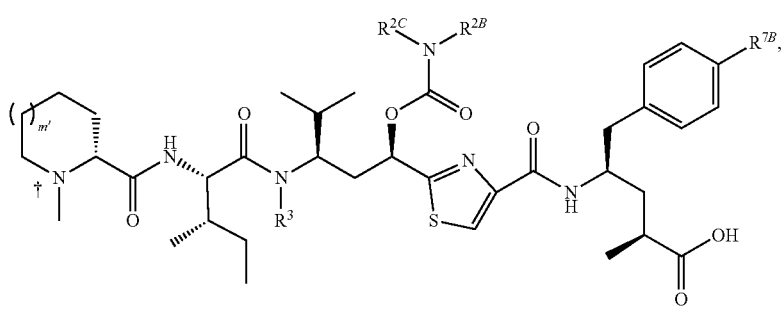

D<sub>G</sub>-5 wherein $R^{7B}$ is hydrogen or —OH, $R^3$ is lower alkyl, and $R^{2B}$ and $R^{2C}$ are independently hydrogen or lower alkyl.

B11. The Ligand Drug Conjugate composition of embodiment B1, wherein subscript q is 1 and the Ligand Drug Conjugate compounds in the Ligand Drug Conjugate composition predominately have drug linker moieties of:

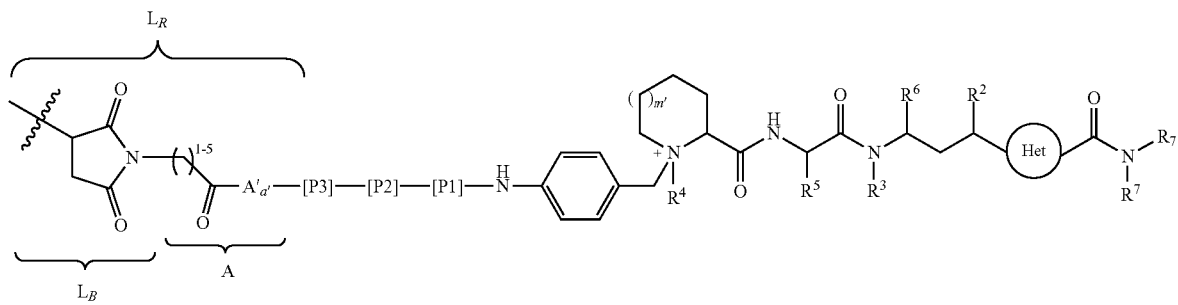

or a pharmaceutical acceptable salt thereof, and optionally having a minority of Ligand Drug Conjugate compounds in which one or more of the drug linker moieties in each of such compounds has the succinimide ring in hydrolyzed form, and wherein:
subscript a' is 0, and A' is absent; and
the wavy line indicates the site of covalent attachment to a sulfur atom of the Ligand Unit.

B12. The Ligand Drug Conjugate composition of embodiment B1, wherein subscript q is 1 and the Ligand Drug Conjugate compounds in the Ligand Drug Conjugate composition predominately have drug linker moieties of:

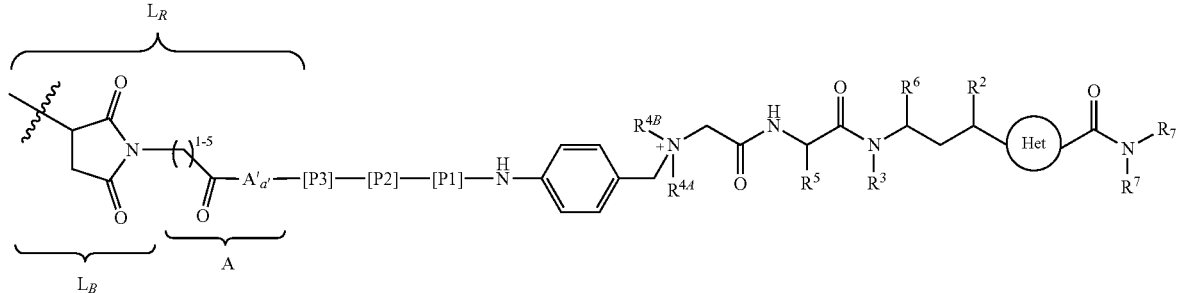

or a pharmaceutical acceptable salt thereof, and optionally having a minority of Ligand Drug Conjugate compounds in which one or more of the drug linker moieties in each of such compounds has the succinimide ring in hydrolyzed form, and wherein:
subscript a' is 0, and A' is absent; and
the wavy line indicates the site of covalent attachment to a sulfur atom of the Ligand Unit.

B13. The Ligand Drug Conjugate composition of any one of embodiments B1-B12, or a pharmaceutically acceptable salt thereof, wherein the Peptide Cleavable Unit is a tripeptide having the sequence -P3-P2-P1-, wherein P1, P2, and P3 are each an amino acid, wherein:

the P3 amino acid of the tripeptide is in the D-amino acid configuration;
one of the P2 and P1 amino acids has an aliphatic side chain with hydrophobicity lower than that of leucine; and
the other of the P2 and P1 amino acids is negatively charged.

B14. The Ligand Drug Conjugate composition of any one of embodiments B1-B13, or a pharmaceutically acceptable salt thereof, wherein the P3 amino acid is D-Leu or D-Ala.

B15. The Ligand Drug Conjugate composition of any one of embodiments B1-B14, or a pharmaceutically acceptable salt thereof, wherein one of the P2 or P1 amino acid has an aliphatic side chain with hydrophobicity no greater than that of valine, and the other of the P2 or P1 amino acid is negatively charged at plasma physiological pH.

B16. The Ligand Drug Conjugate composition of any one of embodiments B1-B15, or a pharmaceutically acceptable salt thereof, wherein the P2 amino acid has an aliphatic side chain with hydrophobicity no greater than that of valine, and the P1 amino acid is negatively charged at plasma physiological pH.

B17. The Ligand Drug Conjugate composition of any one of embodiments B1-B16, or a pharmaceutically acceptable salt thereof, wherein -P2-P1- is -Ala-Glu- or -Ala-Asp-.

B18. The Ligand Drug Conjugate composition of any one of embodiments B1-B17, or a pharmaceutically acceptable salt thereof, wherein -P3-P2-P1- is -D-Leu-Ala-Asp-, -D-Leu-Ala-Glu-, -D-Ala-Ala-Asp-, or -D-Ala-Ala-Glu-.

B19. The Ligand Drug Conjugate composition of any one of embodiments B1-B15, or a pharmaceutically acceptable salt thereof, wherein the P3 amino acid is D-Leu or D-Ala, the P2 amino acid is Ala, Glu, or Asp, and the P1 amino acid is Ala, Glu, or Asp.

B20. The Ligand Drug Conjugate compound composition of embodiment B1, wherein the composition comprises Ligand Drug Conjugate compounds having the structure of

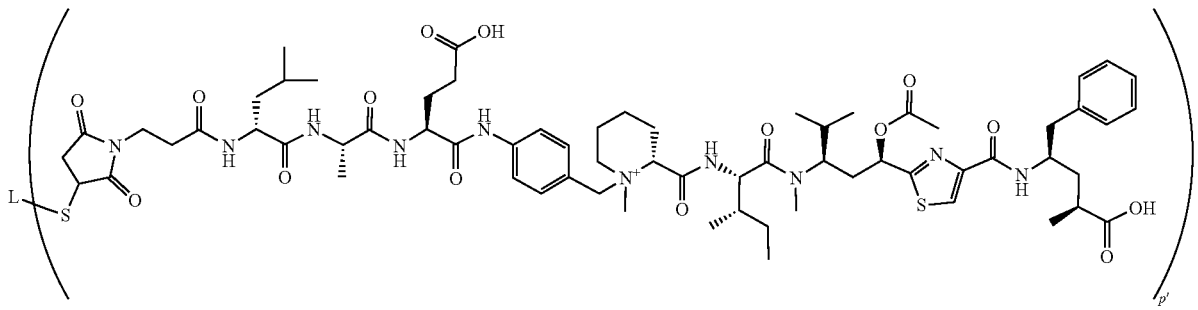

or a pharmaceutically acceptable salt thereof,
wherein L is the Ligand Unit, and subscript p' is an integer from 1 to 12.

B21. The Ligand Drug Conjugate composition of any one of embodiments B1-B20, wherein L is an antibody Ligand Unit of an intact antibody or an antigen-binding fragment thereof.

B22. The Ligand Drug Conjugate composition of embodiment B21, wherein the intact antibody is an intact chimeric, humanized or human antibody.

B23. The Ligand Drug Conjugate composition of embodiment B21, wherein the intact antibody or fragment thereof is capable of selectively binding to a cancer cell antigen.

B24. The Ligand Drug Conjugate composition of embodiment B21, wherein the intact antibody or fragment thereof is capable of selectively binding to an immune cell antigen.

B25. The Ligand Drug Conjugate composition of embodiment B21 or embodiment B22, wherein the intact antibody or fragment thereof is capable of selectively binding CD30.

B26. The Ligand Drug Conjugate composition of embodiment B25, wherein the intact antibody or fragment thereof comprises CDR-H1, CDR-H2, CDR-H3, CDR-L1, CDR-L2, and CDR-L3 comprising the amino acid sequences of SEQ ID NOs: 1, 2, 3, 4, 5, and 6, respectively.

B27. The Ligand Drug Conjugate composition of embodiment B25 or embodiment B26, wherein the intact antibody or fragment thereof comprises a heavy chain variable region comprising the amino acid sequence of SEQ ID NO: 7 and a light chain variable region comprising the amino acid sequence of SEQ ID NO: 8.

B28. The Ligand Drug Conjugate composition of any one of embodiments B25-B27, wherein the intact antibody is cAC10.

B29. The Ligand Drug Conjugate composition of embodiment B21 or embodiment B22, wherein the intact antibody or fragment thereof is capable of selectively binding LIV1.

B30. The Ligand Drug Conjugate composition of embodiment B29, wherein the intact antibody or fragment thereof comprises CDR-H1, CDR-H2, CDR-H3, CDR-L1, CDR-L2, and CDR-L3 comprising the amino acid sequences of SEQ ID NOs: 518, 519, 520, 521, 522, and 523, respectively.

B31. The Ligand Drug Conjugate composition of embodiment B29 or embodiment B30, wherein the intact antibody or fragment thereof comprises a heavy chain variable region comprising the amino acid sequence of SEQ ID NO: 524 and a light chain variable region comprising the amino acid sequence of SEQ ID NO: 525.

B32. The Ligand Drug Conjugate composition of any one of embodiments B29-B31, wherein the intact antibody is ladiratuzumab.

B33. The Ligand Drug Conjugate composition of embodiment B21 or embodiment B22, wherein the intact antibody or fragment thereof is capable of selectively binding TROP2.

B34. The Ligand Drug Conjugate composition of embodiment B33, wherein the intact antibody is sacituzumab or datopotamab.

B35. The Ligand Drug Conjugate composition of embodiment B21 or embodiment B22, wherein the intact antibody or fragment thereof is capable of selectively binding ALPP.

B36. The Ligand Drug Conjugate composition of embodiment B21 or embodiment B22, wherein the intact antibody is capable of selectively binding IL1RAP.

B37. The Ligand Drug Conjugate composition of embodiment B36, wherein the intact antibody or fragment thereof comprises CDR-H1, CDR-H2, CDR-H3, CDR-L1, CDR-L2, and CDR-L3 comprising the amino acid sequences of SEQ ID NOs: 96, 97, 98, 99, 100, and 101, respectively.

B38. The Ligand Drug Conjugate composition of embodiment B36 or embodiment B37, wherein the intact antibody or fragment thereof comprises a heavy chain variable region comprising the amino acid sequence of SEQ ID NO: 102 and a light chain variable region comprising the amino acid sequence of SEQ ID NO: 103.

B39. The Ligand Drug Conjugate composition of any one of embodiments B36-B38, wherein the intact antibody is nidanilimab.

B40. The Ligand Drug Conjugate composition of embodiment B21 or embodiment B22, wherein the intact antibody is capable of selectively binding ASCT2.

B41. The Ligand Drug Conjugate composition of embodiment B40, wherein the intact antibody or fragment thereof comprises CDR-H1, CDR-H2, CDR-H3, CDR-L1, CDR-L2, and CDR-L3 comprising the amino acid sequences of SEQ ID NOs: 794, 795, 796, 797, 798, and 799, respectively.

B42. The Ligand Drug Conjugate composition of embodiment B40 or embodiment B41, wherein the intact antibody or fragment thereof comprises a heavy chain variable region comprising the amino acid sequence of SEQ ID NO: 801 and a light chain variable region comprising the amino acid sequence of SEQ ID NO: 802.

B43. The Ligand Drug Conjugate composition of embodiment B40, wherein the intact antibody or fragment thereof comprises a heavy chain variable region comprising the amino acid sequence of SEQ ID NO: 790 and a light chain variable region comprising the amino acid sequence of SEQ ID NO: 791.

B44. The Ligand Drug Conjugate composition of embodiment B40, wherein the intact antibody or fragment thereof comprises a heavy chain variable region comprising the amino acid sequence of SEQ ID NO: 792 and a light chain variable region comprising the amino acid sequence of SEQ ID NO: 793.

B45. The Ligand Drug Conjugate composition of any one of embodiments B1-B44, wherein subscript p ranges from about 2 to about 12, or from about 2 to about 10, or from about 2 to about 8, or subscript p is about 2, about 4 or about 8.

B46. A pharmaceutically acceptable formulation, wherein the formulation comprises an effective amount of a Ligand Drug Conjugate composition of any one of embodiments B1-B45 and at least one pharmaceutically acceptable excipient.

B47. The pharmaceutically acceptable formulation of embodiment B46 wherein the least one pharmaceutically acceptable excipient is a liquid carrier that provides a liquid formulation, wherein the liquid formulation is suitable for lyophilization or administration to a subject in need thereof.

B48. The pharmaceutically acceptable formulation of embodiment B46, wherein the formulation is a lyophilized solid or a liquid formulation of embodiment B47, wherein the at least one excipient of the solid formulation is a lyoprotectant.

B49. A method of treating cancer comprising administering to a subject in need thereof a therapeutically effective amount of a Ligand Drug Conjugate composition of any one of embodiments B1-B45 or a pharmaceutically acceptable formulation of any one of embodiments B46-B48.

B50. A Drug Linker compound of Formula BIA:

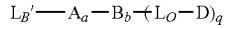

(BIA)

or a salt thereof, wherein

D is a Drug Unit, wherein the Drug Unit is a tubulysin;

$L_B'$ is a ligand covalent binding precursor moiety;

A is a first optional Stretcher Unit;

subscript a is 0 or 1, indicating the absence or presence of A, respectively;

B is an optional Branching Unit;

subscript b is 0 or 1, indicating the absence or presence of B, respectively;

$L_O$ is a secondary linker moiety, wherein the secondary linker has the formula of;

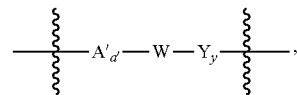

wherein the wavy line adjacent to Y indicates the site of covalent attachment of $L_O$ to the Drug Unit and the wavy line adjacent to A' indicates the site of covalent attachment of $L_O$ to the remainder of the Drug Linker compound;

A' is a second optional Stretcher Unit, which when present and in the absence of B becomes a subunit of A;

subscript a' is 0 or 1, indicating the absence or presence of A', respectively,

W is a Peptide Cleavable Unit, wherein the Peptide Cleavable Unit comprises a tripeptide having the sequence -P3-P2-P1-, wherein P1, P2, and P3 are each an amino acid, wherein:

a first one of the amino acids P1, P2, or P3 is negatively charged;

a second one of the amino acids P1, P2, or P3 has an aliphatic side chain with hydrophobicity no greater than that of leucine; and a third one of the amino acids P1, P2, or P3 has hydrophobicity lower than that of leucine, wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3, provided that -P3-P2-P1- is not -Glu-Val-Cit- or -Asp-Val-Cit-;

each Y when present is a self-immolative Spacer Unit;

subscript y is 0, 1 or 2 indicating the absence or presence of 1 or 2 of Y, respectively; and subscript q is an integer ranging from 1 to 4, and provided that subscript q is 1 when subscript b is 0 and subscript q is 2, 3 or 4 when subscript b is 1.

B51. The Drug Linker compound of embodiment B50, wherein the Drug Linker compound has the structure of Formula BIH:

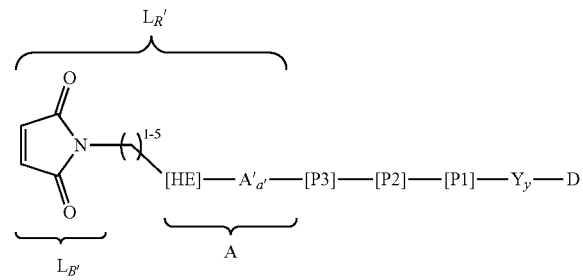

(Formula BIH)

or salt thereof, wherein:

HE is a Hydrolysis Enhancing Unit; and

A' is a subunit, when present, of the indicated first Stretcher Unit (A); subscript a' is 0 or 1, indicating the absence or presence of A', respectively.

B52. The Drug Linker compound of embodiment B51 wherein HE is —C(=O).

B53. The Drug Linker compound of any one of embodiments B50-B52, wherein —$Y_y$-D has the structure of.

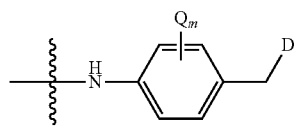

wherein each Q is independently selected from the group consisting of —$C_1$-$C_8$ alkyl, —O—($C_1$-$C_8$ alkyl), halogen, nitro and cyano; and subscript m is 0, 1 or 2.

B54. The Drug Linker compound of any one of embodiments B50-B53, wherein D has a formula selected from the group consisting of

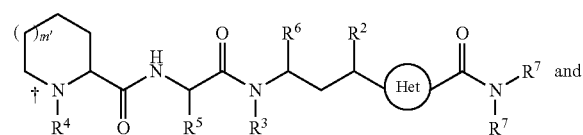

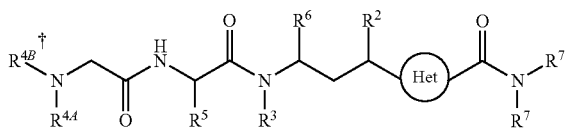

wherein the dagger represents the point of attachment of D to the drug linker moiety and the circle represents an 5-membered or 6-membered nitrogen heteroarylene wherein the indicated required substituents to that heteroarylene are in a 1,3- or meta-relationship to each other with optional substitution at the remaining positions;

$R^2$ is $X^A$—$R^{2A}$, wherein $X^A$ is —O—, —S—, —N($R^{2B}$)—, —$CH_2$—, —(C=O)N($R^{2B}$)— or —O(C=O)N($R^{2B}$)— wherein $R^{2B}$ is hydrogen or optionally substituted alkyl, $R^{2A}$ is hydrogen, optionally substituted alkyl, optionally substituted aryl, or —C(=O)$R^C$, wherein $R^C$ is hydrogen, optionally substituted alkyl, or optionally substituted aryl or $R^2$ is an O-linked substituent;

$R^3$ is hydrogen or optionally substituted alkyl;

$R^4$, $R^{4A}$, $R^{4B}$, $R^5$ and $R^6$ are optionally substituted alkyl, independently selected, one $R^7$ is hydrogen or optionally substituted alkyl and the other $R^7$ is optionally substituted arylalkyl or optionally substituted heteroarylalkyl, and subscript m' is 0 or 1.

B55. The Drug Linker compound of embodiment B54, wherein $R^4$ is methyl or $R^{4A}$ and $R^{4B}$ are methyl.

B56. The Drug Linker compound of embodiment B54 or embodiment B55, wherein the 5-membered heteroarylene is represented by the structure

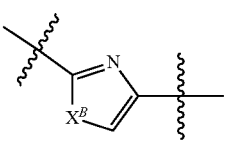

wherein $X^B$ is O, S, or N—$R^B$ wherein $R^B$ is hydrogen or lower alkyl.

B57. The Drug Linker compound of any one of embodiments B54-B56, wherein the 5-membered heteroarylene is a divalent thiazole moiety.

B58. The Drug Linker compound of any one of embodiments B54-B57, wherein subscript m' is 1.

B59. The Drug Linker compound of any one of embodiments B54-B58, wherein D has a formula selected from the group consisting of

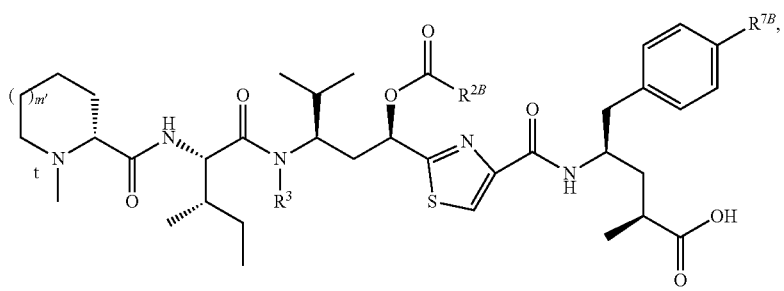

D_{G-3}

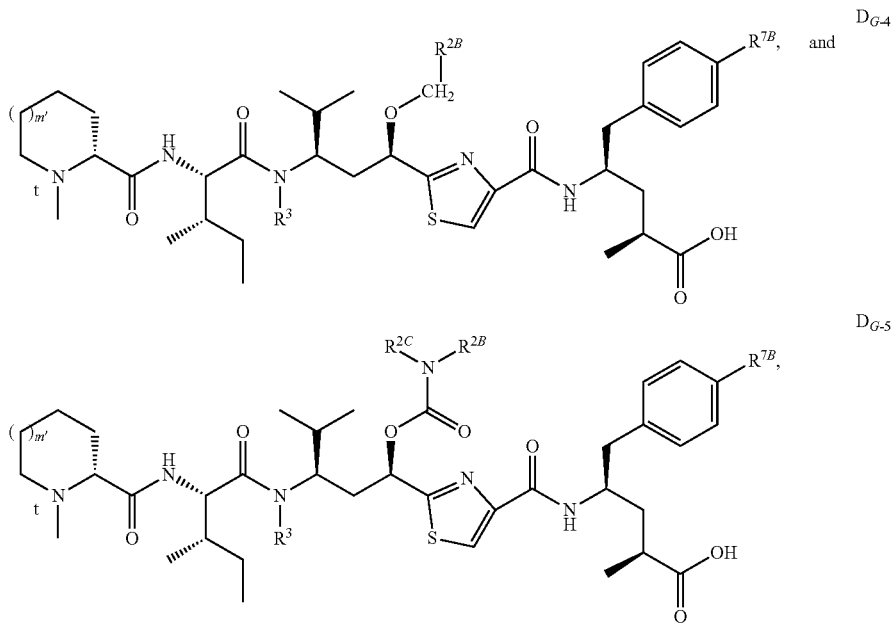

D_{G-4}, and

D_{G-5}, wherein $R^{7B}$ is hydrogen or —OH, $R^3$ is lower alkyl, and $R^{2B}$ and $R^{2C}$ are independently hydrogen or lower alkyl.

B60. The Drug Linker compound of embodiment B50, wherein Drug Linker compound has the structure:

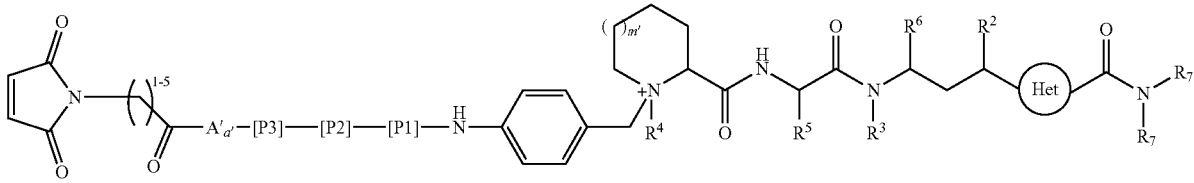

or a salt thereof, wherein
subscript a' is 0, and A' is absent.

B61. The Drug Linker compound of embodiment B50, wherein Drug Linker compound has the structure:

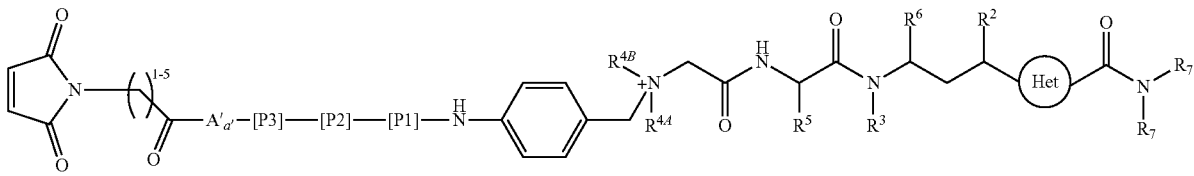

or a salt thereof, wherein
subscript a' is 0, and A' is absent.

B62. The Drug Linker compound of any one of embodiments B50-B61, or a pharmaceutically acceptable salt thereof, wherein the Peptide Cleavable Unit is a tripeptide having the sequence -P3-P2-P1-, wherein P1, P2, and P3 are each an amino acid, wherein:

the P3 amino acid of the tripeptide is in the D-amino acid configuration;
one of the P2 and P1 amino acids has an aliphatic side chain with hydrophobicity lower than that of leucine; and
the other of the P2 and P1 amino acids is negatively charged.

B63. The Drug Linker compound of any one of embodiments B50-B62 wherein the P3 amino acid is D-Leu or D-Ala.

B64. The Drug Linker compound of any one of embodiments B50-B63 wherein one of the P2 or P1 amino acid has an aliphatic side chain with hydrophobicity no greater than that of valine, and the other of the P2 or P1 amino acid is negatively charged at plasma physiological pH.

B65. The Drug Linker compound of any one of embodiments B50-B64 wherein the P2 amino acid has an aliphatic side chain with hydrophobicity no greater than that of valine, and the P1 amino acid is negatively charged at plasma physiological pH.

B66. The Drug Linker compound of any one of embodiments B50-B65 wherein -P2-P1- is -Ala-Glu- or -Ala-Asp-.

B67. The Drug Linker compound of any one of embodiments B50-B66 wherein -P3-P2-P1- is -D-Leu-Ala-Asp-, -D-Leu-Ala-Glu-, -D-Ala-Ala-Asp-, or -D-Ala-Ala-Glu-.

B68. The Drug Linker compound any one of embodiments B50-B64 wherein the P3 amino acid is D-Leu or D-Ala, the P2 amino acid is Ala, Glu, or Asp, and the P1 amino acid is Ala, Glu, or Asp.

B69. The Drug Linker compound of embodiment B50, wherein the Drug Linker compound has the structure of:

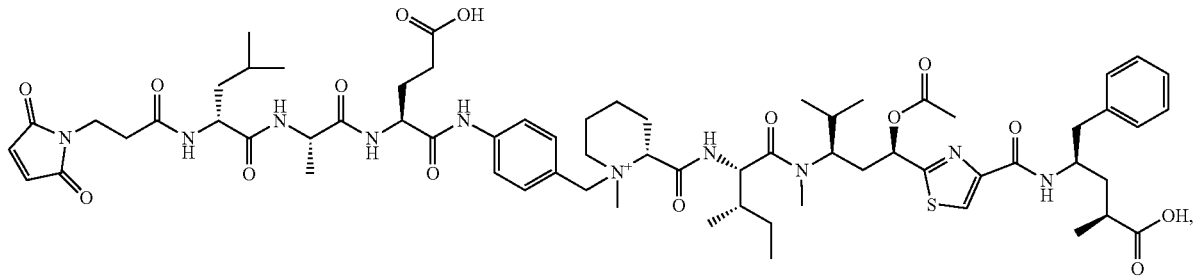

or a salt thereof.

C1. An antibody-drug conjugate comprising an antigen binding protein or fragment thereof that binds GPNMB, wherein the antibody-drug conjugate is represented by the structure:

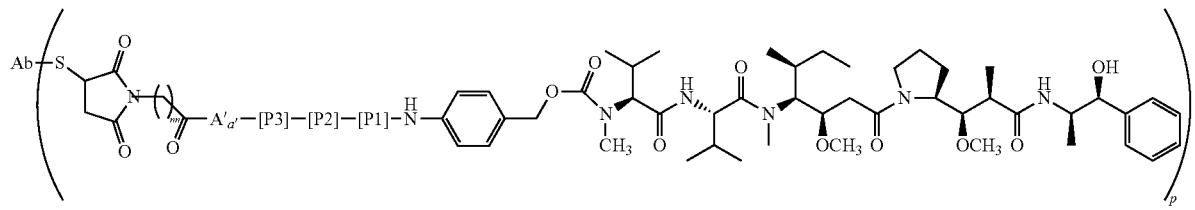

or a pharmaceutically acceptable salt thereof, wherein:
Ab is the antigen binding protein or fragment thereof and p denotes a number from 1 to 12;
subscript nn is a number from 1 to 5;
subscript a' is 0, and A' is absent;
P1, P2, and P3 are each an amino acid, wherein:
a first one of the amino acids P1, P2, or P3 is negatively charged;
a second one of the amino acids P1, P2, or P3 has an aliphatic side chain with hydrophobicity no greater than that of leucine; and
a third one of the amino acids P1, P2, or P3 has hydrophobicity lower than that of leucine,
wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
provided that -P3-P2-P1- is not -Glu-Val-Cit- or -Asp-Val-Cit-.

C2. The antibody-drug conjugate of embodiment C1, wherein subscript nn is 2.

C3. The antibody-drug conjugate of embodiment C1 or C2, wherein:
the P3 amino acid of the tripeptide is in the D-amino acid configuration;
one of the P2 and P1 amino acids has an aliphatic side chain with hydrophobicity lower than that of leucine; and
the other of the P2 and P1 amino acids is negatively charged.

C4. The antibody-drug conjugate of any one of embodiments C1-C3, wherein the P3 amino acid is D-Leu or D-Ala.

C5. The antibody-drug conjugate of any one of embodiments C1-C4, wherein the P3 amino acid is D-Leu or D-Ala, the P2 amino acid is Ala, Glu, or Asp, and the P1 amino acid is Ala, Glu, or Asp.

C6. The antibody-drug conjugate of any one of embodiments C1-C5, wherein -P3-P2-P1- is -D-Leu-Ala-Asp-, -D-Leu-Ala-Glu-, -D-Ala-Ala-Asp-, or -D-Ala-Ala-Glu-.

C7. The antibody-drug conjugate of any one of embodiments C1-C6, wherein -P3-P2-P1- is -D-Leu-Ala-Glu-.

C8. The antibody-drug conjugate of any one of embodiments C1-C7, wherein the antibody-drug conjugate is represented by the structure:

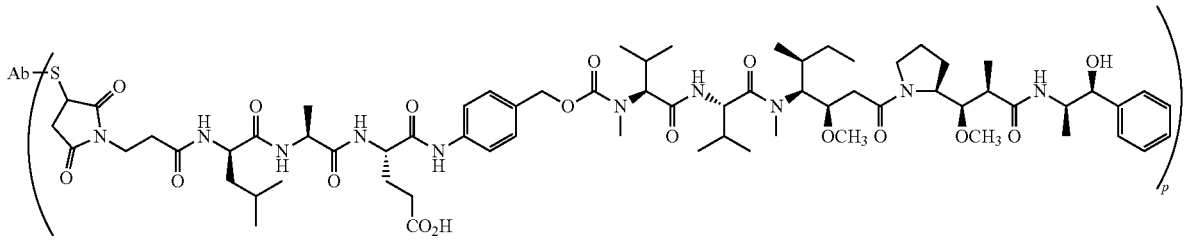

or a pharmaceutically acceptable salt thereof,
wherein Ab is the antigen binding protein or fragment thereof and p denotes a number from 1 to 12.
C9. The antibody-drug conjugate of any one of embodiments C1-C8, wherein the antigen binding protein or fragment comprises the following 6 HVRs:
   an HVR-H1 comprising the amino acid sequence of SEQ ID NO: 894;
   an HVR-H2 comprising the amino acid sequence of SEQ ID NO: 895;
   an HVR-H3 comprising the amino acid sequence of SEQ ID NO: 896;
   an HVR-L1 comprising the amino acid sequence of SEQ ID NO: 897;
   an HVR-L2 comprising the amino acid sequence of SEQ ID NO: 898; and
   an HVR-L3 comprising the amino acid sequence of SEQ ID NO: 899.
C10. The antibody-drug conjugate of any one of embodiments C1-C9 wherein the antigen binding protein or fragment comprises a VH and a VL, wherein the VH has at least 80%, 85%, 90%, 95% or 99% amino acid sequence identity to the amino acid sequence of SEQ ID NO: 892 and the VL has at least 80%, 85%, 90%, 95% or 99% amino acid sequence identity to the amino acid sequence of SEQ ID NO: 893.
C11. The antibody-drug conjugate of any one of embodiments C1-C10 wherein the antigen binding protein or fragment comprises a VH and a VL, wherein the VH comprises the amino acid sequence of SEQ ID NO: 892 and the VL comprises the amino acid sequence of SEQ ID NO: 893.
C12. The antibody-drug conjugate of any one of embodiments C1-C11 wherein the antigen binding protein or fragment comprises an HC comprising the amino acid sequence of SEQ ID NO: 890 and an LC comprising the amino acid sequence of SEQ ID NO: 891.
C13. The antibody-drug conjugate of any of embodiments C1-C12, wherein the antigen binding protein or fragment is a monoclonal antibody or fragment thereof.

C14. The antibody-drug conjugate of any of embodiments C1-C13, wherein the antigen binding protein or fragment is a chimeric antibody or fragment thereof.
C15. The antibody-drug conjugate of any of embodiments C1-C14, wherein the antigen binding protein or fragment is a humanized antibody or fragment thereof.
$C_{16}$. The antibody-drug conjugate of any of embodiments C1-C15, wherein the fragment is selected from a Fab, Fab', Fv, scFv or (Fab')$_2$ fragment.
C17. A pharmaceutical composition comprising the antibody-drug conjugate of any of embodiments C1-C16 and a pharmaceutically acceptable carrier.
C18. A method of treating a GPNMB-expressing cancer in an individual comprising administering to an individual in need thereof an effective amount of the antibody-drug conjugate of any one of embodiments C1-C16, or the pharmaceutical composition of embodiment C17.
C19. The method of embodiment C18, wherein the GPNMB-expressing cancer is melanoma, lung cancer, breast cancer, head and neck cancer, ovarian cancer, sarcoma, mesothelioma, or cervical cancer.
D1. An antibody-drug conjugate comprising an antigen binding protein or fragment thereof that binds CD228, wherein the antibody-drug conjugate is represented by the structure:

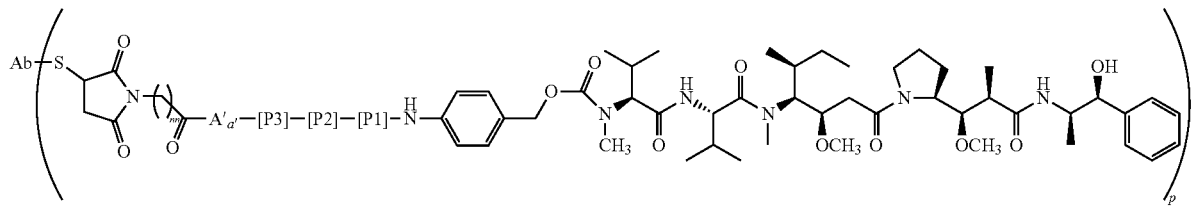

or a pharmaceutically acceptable salt thereof, wherein:
Ab is the antigen binding protein or fragment thereof and p denotes a number from 1 to 12;
subscript nn is a number from 1 to 5;
subscript a' is 0, and A' is absent;
P1, P2, and P3 are each an amino acid, wherein:
   a first one of the amino acids P1, P2, or P3 is negatively charged;
   a second one of the amino acids P1, P2, or P3 has an aliphatic side chain with hydrophobicity no greater than that of leucine; and
   a third one of the amino acids P1, P2, or P3 has hydrophobicity lower than that of leucine,
   wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3, provided that -P3-P2-P1- is not -Glu-Val-Cit- or -Asp-Val-Cit-.

D2. The antibody-drug conjugate of embodiment D1, wherein subscript nn is 2.

D3. The antibody-drug conjugate of embodiment D1 or D2, wherein:
the P3 amino acid of the tripeptide is in the D-amino acid configuration;
one of the P2 and P1 amino acids has an aliphatic side chain with hydrophobicity lower than that of leucine; and
the other of the P2 and P1 amino acids is negatively charged.

D4. The antibody-drug conjugate of any one of embodiments D1-D3, wherein the P3 amino acid is D-Leu or D-Ala.

D5. The antibody-drug conjugate of any one of embodiments D1-D4, wherein the P3 amino acid is D-Leu or D-Ala, the P2 amino acid is Ala, Glu, or Asp, and the P1 amino acid is Ala, Glu, or Asp.

D6. The antibody-drug conjugate of any one of embodiments D1-D5, wherein -P3-P2-P1- is -D-Leu-Ala-Asp-, -D-Leu-Ala-Glu-, -D-Ala-Ala-Asp-, or -D-Ala-Ala-Glu-.

D7. The antibody-drug conjugate of any one of embodiments D1-D6, wherein -P3-P2-P1- is -D-Leu-Ala-Glu-.

D8. The antibody-drug conjugate of any one of embodiments D1-D7, wherein the antibody-drug conjugate is represented by the structure:

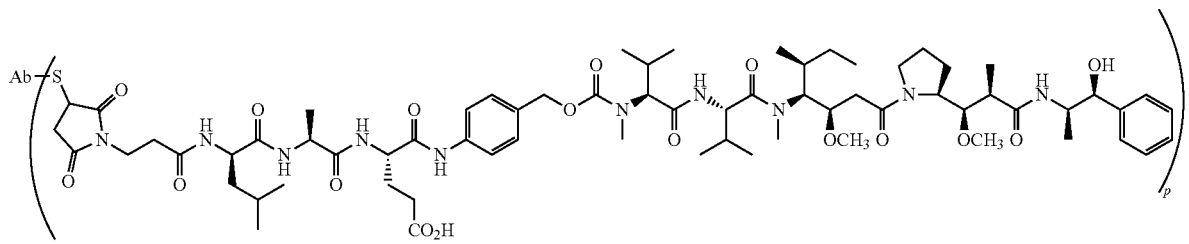

or a pharmaceutically acceptable salt thereof,
wherein Ab is the antigen binding protein or fragment thereof and p denotes a number from 1 to 12.

D9. The antibody-drug conjugate of any one of embodiments D1-D8, wherein the antigen binding protein or fragment comprises the following 6 HVRs:
an HVR-H1 comprising the amino acid sequence of SEQ ID NO: 900;
an HVR-H2 comprising the amino acid sequence of SEQ ID NO: 901;
an HVR-H3 comprising the amino acid sequence of SEQ ID NO: 902;
an HVR-L1 comprising the amino acid sequence of SEQ ID NO: 903;
an HVR-L2 comprising the amino acid sequence of SEQ ID NO: 904; and
an HVR-L3 comprising the amino acid sequence of SEQ ID NO: 905.

D10. The antibody-drug conjugate of any one of embodiments D1-D9 wherein the antigen binding protein or fragment comprises a VH and a VL, wherein the VH has at least 80%, 85%, 90%, 95% or 99% amino acid sequence identity to the amino acid sequence of SEQ ID NO: 906 and the VL has at least 80%, 85%, 90%, 95% or 99% amino acid sequence identity to the amino acid sequence of SEQ ID NO: 907.

D11. The antibody-drug conjugate of any one of embodiments D1-D10 wherein the antigen binding protein or fragment comprises a VH and a VL, wherein the VH comprises the amino acid sequence of SEQ ID NO: 906 and the VL comprises the amino acid sequence of SEQ ID NO: 907.

D12. The antibody-drug conjugate of any one of embodiments D1-D11 wherein the antigen binding protein or fragment comprises an HC comprising the amino acid sequence of SEQ ID NO: 908 and an LC comprising the amino acid sequence of SEQ ID NO: 909.

D13. The antibody-drug conjugate of any of embodiments D1-D12, wherein the antigen binding protein or fragment is a monoclonal antibody or fragment thereof.

D14. The antibody-drug conjugate of any of embodiments D1-D13, wherein the antigen binding protein or fragment is a chimeric antibody or fragment thereof.

D15. The antibody-drug conjugate of any of embodiments D1-D14, wherein the antigen binding protein or fragment is a humanized antibody or fragment thereof.

D16. The antibody-drug conjugate of any of embodiments D1-D15, wherein the fragment is selected from a Fab, Fab', Fv, scFv or (Fab')$_2$ fragment.

D17. A pharmaceutical composition comprising the antibody-drug conjugate of any of embodiments D1-D16 and a pharmaceutically acceptable carrier.

D18. A method of treating a CD228-expressing cancer in an individual comprising administering to an individual in need thereof an effective amount of the antibody-drug conjugate of any one of embodiments D1-D16, or the pharmaceutical composition of embodiment D17.

D19. The method of embodiment D18, wherein the CD228-expressing cancer is chronic leukemia, lymphoma, multiple myeloma, B type acute lymphoblastic leukemia, chronic myelocytic leukemia, chronic lymphocytic leukemia, non-Hodgkin lymphoma and Hodgkin lymphoma, B cell lymphoma, or diffuse large B-cell lymphoma.

E1. An antibody-drug conjugate comprising an antigen binding protein or fragment thereof that binds αvβ6, wherein the antibody-drug conjugate is represented by the structure:

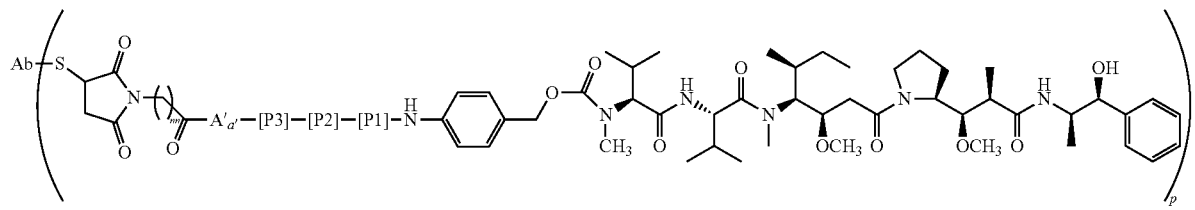

or a pharmaceutically acceptable salt thereof, wherein:
Ab is the antigen binding protein or fragment thereof and p denotes a number from 1 to 12;

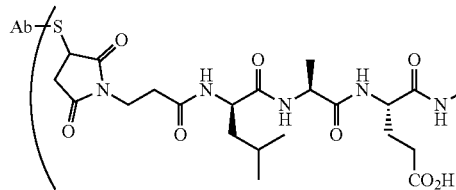
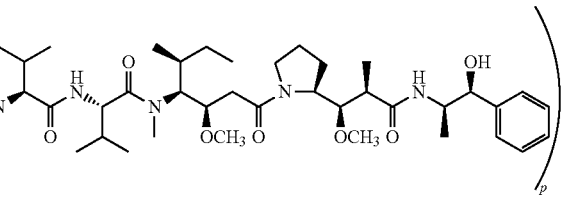

subscript nn is a number from 1 to 5;
subscript a' is 0, and A' is absent;
P1, P2, and P3 are each an amino acid, wherein:
- a first one of the amino acids P1, P2, or P3 is negatively charged;
- a second one of the amino acids P1, P2, or P3 has an aliphatic side chain with hydrophobicity no greater than that of leucine; and
- a third one of the amino acids P1, P2, or P3 has hydrophobicity lower than that of leucine,
- wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
- provided that -P3-P2-P1- is not -Glu-Val-Cit- or -Asp-Val-Cit-.

E2. The antibody-drug conjugate of embodiment E1, wherein subscript nn is 2.

E3. The antibody-drug conjugate of embodiment E1 or E2, wherein:
- the P3 amino acid of the tripeptide is in the D-amino acid configuration;
- one of the P2 and P1 amino acids has an aliphatic side chain with hydrophobicity lower than that of leucine; and
- the other of the P2 and P1 amino acids is negatively charged.

E4. The antibody-drug conjugate of any one of embodiments E1-E3, wherein the P3 amino acid is D-Leu or D-Ala.

E5. The antibody-drug conjugate of any one of embodiments E1-E4, wherein the P3 amino acid is D-Leu or D-Ala, the P2 amino acid is Ala, Glu, or Asp, and the P1 amino acid is Ala, Glu, or Asp.

E6. The antibody-drug conjugate of any one of embodiments E1-E5, wherein -P3-P2-P1- is -D-Leu-Ala-Asp-, -D-Leu-Ala-Glu-, -D-Ala-Ala-Asp-, or -D-Ala-Ala-Glu-.

E7. The antibody-drug conjugate of any one of embodiments E1-E6, wherein -P3-P2-P1- is -D-Leu-Ala-Glu-.

E8. The antibody-drug conjugate of any one of embodiments E1-E7, wherein the antibody-drug conjugate is represented by the structure:

or a pharmaceutically acceptable salt thereof,
wherein Ab is the antigen binding protein or fragment thereof and p denotes a number from 1 to 12.

E9. The antibody-drug conjugate of any one of embodiments E1-E8, wherein the antigen binding protein or fragment comprises the following 6 HVRs:
- an HVR-H1 comprising the amino acid sequence of SEQ ID NO: 914;
- an HVR-H2 comprising the amino acid sequence of SEQ ID NO: 915;
- an HVR-H3 comprising the amino acid sequence of SEQ ID NO: 916;
- an HVR-L1 comprising the amino acid sequence of SEQ ID NO: 917;
- an HVR-L2 comprising the amino acid sequence of SEQ ID NO: 918; and
- an HVR-L3 comprising the amino acid sequence of SEQ ID NO: 919.

E10. The antibody-drug conjugate of any one of embodiments E1-E9 wherein the antigen binding protein or fragment comprises a VH and a VL, wherein the VH has at least 80%, 85%, 90%, 95% or 99% amino acid sequence identity to the amino acid sequence of SEQ ID NO: 912 and the VL has at least 80%, 85%, 90%, 95% or 99% amino acid sequence identity to the amino acid sequence of SEQ ID NO: 913.

E11. The antibody-drug conjugate of any one of embodiments E1-E10 wherein the antigen binding protein or fragment comprises a VH and a VL, wherein the VH comprises the amino acid sequence of SEQ ID NO: 912 and the VL comprises the amino acid sequence of SEQ ID NO: 913.

E12. The antibody-drug conjugate of any one of embodiments E1-E11 wherein the antigen binding protein or fragment comprises an HC comprising the amino acid sequence of SEQ ID NO: 910 and an LC comprising the amino acid sequence of SEQ ID NO: 911.

E13. The antibody-drug conjugate of any of embodiments E1-E12, wherein the antigen binding protein or fragment is a monoclonal antibody or fragment thereof.

E14. The antibody-drug conjugate of any of embodiments E1-E13, wherein the antigen binding protein or fragment is a chimeric antibody or fragment thereof.
E15. The antibody-drug conjugate of any of embodiments E1-E14, wherein the antigen binding protein or fragment is a humanized antibody or fragment thereof.
E16. The antibody-drug conjugate of any of embodiments E1-E15, wherein the fragment is selected from a Fab, Fab', Fv, scFv or (Fab')$_2$ fragment.
E17. A pharmaceutical composition comprising the antibody-drug conjugate of any of embodiments E1-E16 and a pharmaceutically acceptable carrier.
E18. A method of treating a αvβ6-expressing cancer in an individual comprising administering to an individual in need thereof an effective amount of the antibody-drug conjugate of any one of embodiments E1-E16, or the pharmaceutical composition of embodiment E17.
E19. The method of embodiment E18, wherein the αvβ6-expressing cancer is non-small cell lung cancer (NSCLC), head and neck cancer, esophageal cancer, breast cancer, ovarian cancer, bladder cancer, skin cancer (SCC), ovarian cancer, cervical cancer, gastric cancer, or pancreatic cancer.
F1. An antibody-drug conjugate comprising an antigen binding protein or fragment thereof that binds CD30, wherein the antibody-drug conjugate is represented by the structure:

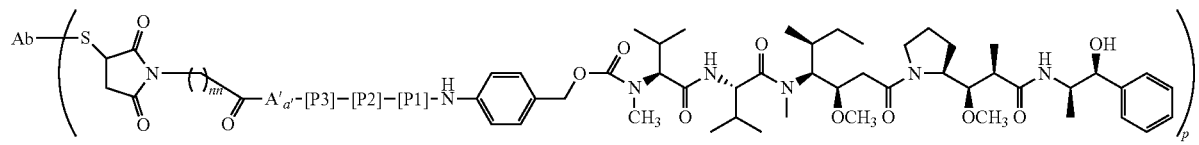

or a pharmaceutically acceptable salt thereof, wherein:
Ab is the antigen binding protein or fragment thereof and p denotes a number from 1 to 12;
subscript nn is a number from 1 to 5;
subscript a' is 0, and A' is absent;
P1, P2, and P3 are each an amino acid, wherein:
  a first one of the amino acids P1, P2, or P3 is negatively charged;
  a second one of the amino acids P1, P2, or P3 has an aliphatic side chain with hydrophobicity no greater than that of leucine; and
  a third one of the amino acids P1, P2, or P3 has hydrophobicity lower than that of leucine,
  wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
  provided that -P3-P2-P1- is not -Glu-Val-Cit- or -Asp-Val-Cit-.

F2. The antibody-drug conjugate of embodiment F1, wherein subscript nn is 2.
F3. The antibody-drug conjugate of embodiment F1 or F2, wherein:
  the P3 amino acid of the tripeptide is in the D-amino acid configuration;
  one of the P2 and P1 amino acids has an aliphatic side chain with hydrophobicity lower than that of leucine; and
  the other of the P2 and P1 amino acids is negatively charged.
F4. The antibody-drug conjugate of any one of embodiments F1-F3, wherein the P3 amino acid is D-Leu or D-Ala.
F5. The antibody-drug conjugate of any one of embodiments F1-F4, wherein the P3 amino acid is D-Leu or D-Ala, the P2 amino acid is Ala, Glu, or Asp, and the P1 amino acid is Ala, Glu, or Asp.
F6. The antibody-drug conjugate of any one of embodiments F1-F5, wherein -P3-P2-P1- is -D-Leu-Ala-Asp-, -D-Leu-Ala-Glu-, -D-Ala-Ala-Asp-, or -D-Ala-Ala-Glu-.
F7. The antibody-drug conjugate of any one of embodiments F1-F6, wherein -P3-P2-P1- is -D-Leu-Ala-Glu-.
F8. The antibody-drug conjugate of any one of embodiments F1-F7, wherein the antibody-drug conjugate is represented by the structure:

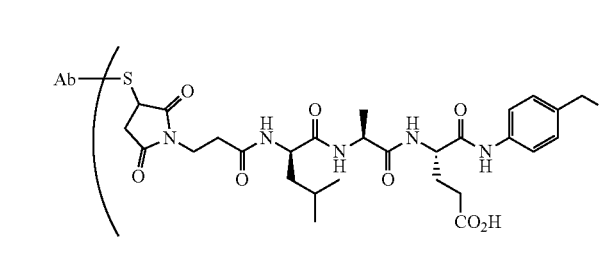

or a pharmaceutically acceptable salt thereof,
wherein Ab is the antigen binding protein or fragment thereof and p denotes a number from 1 to 12.
F9. The antibody-drug conjugate of any one of embodiments F1-F8, wherein the antigen binding protein or fragment comprises the following 6 HVRs:
  an HVR-H1 comprising the amino acid sequence of SEQ ID NO: 920;
  an HVR-H2 comprising the amino acid sequence of SEQ ID NO: 921;

an HVR-H3 comprising the amino acid sequence of SEQ ID NO: 922;
an HVR-L1 comprising the amino acid sequence of SEQ ID NO: 923;
an HVR-L2 comprising the amino acid sequence of SEQ ID NO: 924; and
an HVR-L3 comprising the amino acid sequence of SEQ ID NO: 925.

F10. The antibody-drug conjugate of any one of embodiments F1-F9 wherein the antigen binding protein or fragment comprises a VH and a VL, wherein the VH has at least 80%, 85%, 90%, 95% or 99% amino acid sequence identity to the amino acid sequence of SEQ ID NO: 926 and the VL has at least 80%, 85%, 90%, 95% or 99% amino acid sequence identity to the amino acid sequence of SEQ ID NO: 927.

F11. The antibody-drug conjugate of any one of embodiments F1-F10 wherein the antigen binding protein or fragment comprises a VH and a VL, wherein the VH comprises the amino acid sequence of SEQ ID NO: 926 and the VL comprises the amino acid sequence of SEQ ID NO: 927.

F12. The antibody-drug conjugate of any one of embodiments F1-F11 wherein the antigen binding protein or fragment comprises an HC comprising the amino acid sequence of SEQ ID NO: 928 or SEQ ID NO: 929 and an LC comprising the amino acid sequence of SEQ ID NO: 930.

F13. The antibody-drug conjugate of any of embodiments F1-F12, wherein the antigen binding protein or fragment is a monoclonal antibody or fragment thereof.

F14. The antibody-drug conjugate of any of embodiments F1-F13, wherein the antigen binding protein or fragment is a chimeric antibody or fragment thereof.

F15. The antibody-drug conjugate of any of embodiments F1-F14, wherein the antigen binding protein or fragment is a humanized antibody or fragment thereof.

F16. The antibody-drug conjugate of any of embodiments F1-F15, wherein the fragment is selected from a Fab, Fab', Fv, scFv or (Fab')$_2$ fragment.

F17. A pharmaceutical composition comprising the antibody-drug conjugate of any of embodiments F1-F16 and a pharmaceutically acceptable carrier.

F18. A method of treating a CD30-expressing disease or condition in an individual comprising administering to an individual in need thereof an effective amount of the antibody-drug conjugate of any one of embodiments F1-F16, or the pharmaceutical composition of embodiment F17.

F19. The method of embodiment F18, wherein the CD30-expressing disease or condition is cancer.

F20. The method of embodiment F19, wherein the cancer is Hodgkin's disease or a non-Hodgkin's lymphoma.

F21. The method of embodiment F18, wherein the CD30-expressing disease or condition is an autoimmune disease.

F22. The method of embodiment F18, wherein the CD30-expressing disease or condition is an infectious disease.

G1. An antibody-drug conjugate comprising an antigen binding protein or fragment thereof that binds LIV1, wherein the antibody-drug conjugate is represented by the structure:

or a pharmaceutically acceptable salt thereof, wherein:
Ab is the antigen binding protein or fragment thereof and p denotes a number from 1 to 12;
subscript nn is a number from 1 to 5;
subscript a' is 0, and A' is absent;
P1, P2, and P3 are each an amino acid, wherein:
a first one of the amino acids P1, P2, or P3 is negatively charged;
a second one of the amino acids P1, P2, or P3 has an aliphatic side chain with hydrophobicity no greater than that of leucine; and
a third one of the amino acids P1, P2, or P3 has hydrophobicity lower than that of leucine,
wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
provided that -P3-P2-P1- is not -Glu-Val-Cit- or -Asp-Val-Cit-.

G2. The antibody-drug conjugate of embodiment G1, wherein subscript nn is 2.

G3. The antibody-drug conjugate of embodiment G1 or G2, wherein:
the P3 amino acid of the tripeptide is in the D-amino acid configuration;
one of the P2 and P1 amino acids has an aliphatic side chain with hydrophobicity lower than that of leucine; and
the other of the P2 and P1 amino acids is negatively charged.

G4. The antibody-drug conjugate of any one of embodiments G1-G3, wherein the P3 amino acid is D-Leu or D-Ala.

G5. The antibody-drug conjugate of any one of embodiments G1-G4, wherein the P3 amino acid is D-Leu or D-Ala, the P2 amino acid is Ala, Glu, or Asp, and the P1 amino acid is Ala, Glu, or Asp.

G6. The antibody-drug conjugate of any one of embodiments G1-G5, wherein -P3-P2-P1- is -D-Leu-Ala-Asp-, -D-Leu-Ala-Glu-, -D-Ala-Ala-Asp-, or -D-Ala-Ala-Glu-.

G7. The antibody-drug conjugate of any one of embodiments G1-G6, wherein -P3-P2-P1- is -D-Leu-Ala-Glu-.

G8. The antibody-drug conjugate of any one of embodiments G1-G7, wherein the antibody-drug conjugate is represented by the structure:

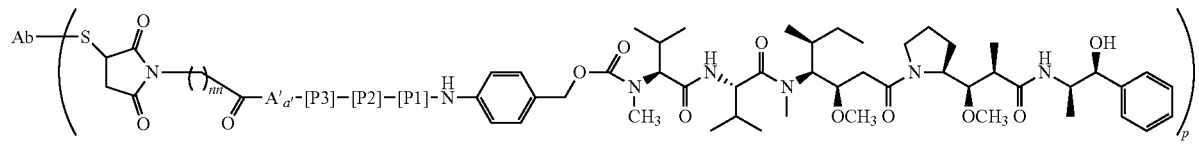

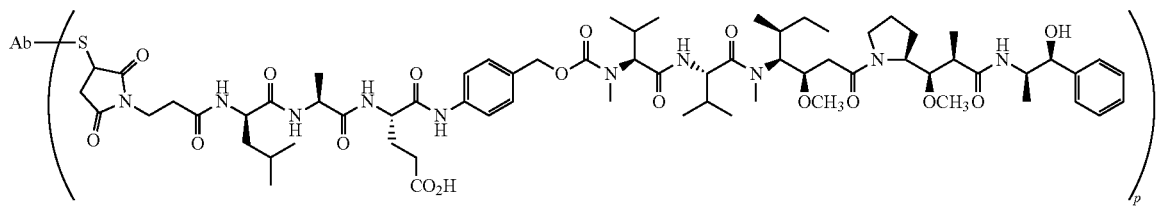

or a pharmaceutically acceptable salt thereof,
wherein Ab is the antigen binding protein or fragment thereof and p denotes a number from 1 to 12.

G9. The antibody-drug conjugate of any one of embodiments GI-G8, wherein the antigen binding protein or fragment comprises the following 6 HVRs:
- an HVR-H1 comprising the amino acid sequence of SEQ ID NO: 936;
- an HVR-H2 comprising the amino acid sequence of SEQ ID NO: 937;
- an HVR-H3 comprising the amino acid sequence of SEQ ID NO: 938;
- an HVR-L1 comprising the amino acid sequence of SEQ ID NO: 939;
- an HVR-L2 comprising the amino acid sequence of SEQ ID NO: 940; and
- an HVR-L3 comprising the amino acid sequence of SEQ ID NO: 941.

G10. The antibody-drug conjugate of any one of embodiments G1-G9 wherein the antigen binding protein or fragment comprises a VH and a VL, wherein the VH has at least 80%, 85%, 90%, 95% or 99% amino acid sequence identity to the amino acid sequence of SEQ ID NO: 934 and the VL has at least 80%, 85%, 90%, 95% or 99% amino acid sequence identity to the amino acid sequence of SEQ ID NO: 935.

G11. The antibody-drug conjugate of any one of embodiments GI-G10 wherein the antigen binding protein or fragment comprises a VH and a VL, wherein the VH comprises the amino acid sequence of SEQ ID NO: 934 and the VL comprises the amino acid sequence of SEQ ID NO: 935.

G12. The antibody-drug conjugate of any one of embodiments G1-G11 wherein the antigen binding protein or fragment comprises an HC comprising the amino acid sequence of SEQ ID NO: 932 and an LC comprising the amino acid sequence of SEQ ID NO: 933.

G13. The antibody-drug conjugate of any of embodiments GT-G12, wherein the antigen binding protein or fragment is a monoclonal antibody or fragment thereof.

G14. The antibody-drug conjugate of any of embodiments GT-G13, wherein the antigen binding protein or fragment is a chimeric antibody or fragment thereof.

G15. The antibody-drug conjugate of any of embodiments G1-G14, wherein the antigen binding protein or fragment is a humanized antibody or fragment thereof.

G16. The antibody-drug conjugate of any of embodiments G1-G15, wherein the fragment is selected from a Fab, Fab', Fv, scFv or (Fab')₂ fragment.

G17. A pharmaceutical composition comprising the antibody-drug conjugate of any of embodiments G1-G16 and a pharmaceutically acceptable carrier.

G18. A method of treating a LIV1-expressing cancer in an individual comprising administering to an individual in need thereof an effective amount of the antibody-drug conjugate of any one of embodiments GT-G16, or the pharmaceutical composition of embodiment G17.

G19. The method of embodiment G18, wherein the LIV1-expressing cancer is breast cancer, prostate cancer, ovarian cancer, endometrial cancer, cervical, liver, gastric, kidney, and squamous cell carcinomas, skin cancers, small lung cell carcinoma, or lung carcinoid.

G20. The method of embodiment G19, wherein the breast cancer is HER2 positive breast cancer, hormone responsive breast cancer, or triple negative breast cancer.

G21. The method of embodiment G19, wherein the squamous cell carcinoma is bladder, lung, or head and neck cancer.

G22. The method of embodiment G19, wherein the skin cancer is melanoma.

G23. The antibody-drug conjugate of embodiment G1, wherein the antigen binding protein or fragment specifically binds to SEQ ID NO: 942.

G24. The antibody-drug conjugate of embodiment GI, wherein the antigen binding protein or fragment specifically competes for binding with a second antibody that comprises the amino acid sequence of SEQ ID NO: 934 and the VL comprises the amino acid sequence of SEQ ID NO: 935 binds to SEQ ID NO:942.

H1. An antibody-drug conjugate comprising an antigen binding protein or fragment thereof that binds CD19, wherein the antibody-drug conjugate is represented by the structure:

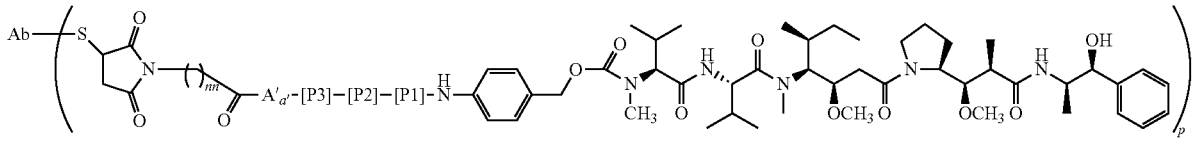

or a pharmaceutically acceptable salt thereof, wherein:
Ab is the antigen binding protein or fragment thereof and p denotes a number from 1 to 12;
subscript nn is a number from 1 to 5;
subscript a' is 0, and A' is absent;
P1, P2, and P3 are each an amino acid, wherein:
  a first one of the amino acids P1, P2, or P3 is negatively charged;
  a second one of the amino acids P1, P2, or P3 has an aliphatic side chain with hydrophobicity no greater than that of leucine; and a third one of the amino acids P1, P2, or P3 has hydrophobicity lower than that of leucine,
wherein the first one of the amino acids P1, P2, or P3 corresponds to any one of P1, P2, or P3, the second one of the amino acids P1, P2, or P3 corresponds to one of the two remaining amino acids P1, P2, or P3, and the third one of the amino acids P1, P2, or P3 corresponds to the last remaining amino acids P1, P2, or P3,
provided that -P3-P2-P1- is not -Glu-Val-Cit- or -Asp-Val-Cit-.

H2. The antibody-drug conjugate of embodiment H1, wherein subscript nn is 2.

H3. The antibody-drug conjugate of embodiment H1 or H2, wherein:
the P3 amino acid of the tripeptide is in the D-amino acid configuration;
one of the P2 and P1 amino acids has an aliphatic side chain with hydrophobicity lower than that of leucine; and
the other of the P2 and P1 amino acids is negatively charged.

H4. The antibody-drug conjugate of any one of embodiments H1-H3, wherein the P3 amino acid is D-Leu or D-Ala.

H5. The antibody-drug conjugate of any one of embodiments H1-H4, wherein the P3 amino acid is D-Leu or D-Ala, the P2 amino acid is Ala, Glu, or Asp, and the P1 amino acid is Ala, Glu, or Asp.

H6. The antibody-drug conjugate of any one of embodiments H1-H5, wherein -P3-P2-P1- is -D-Leu-Ala-Asp-, -D-Leu-Ala-Glu-, -D-Ala-Ala-Asp-, or -D-Ala-Ala-Glu-.

H7. The antibody-drug conjugate of any one of embodiments H1-H6, wherein -P3-P2-P1- is -D-Leu-Ala-Glu-.

H8. The antibody-drug conjugate of any one of embodiments H1-H7, wherein the antibody-drug conjugate is represented by the structure:

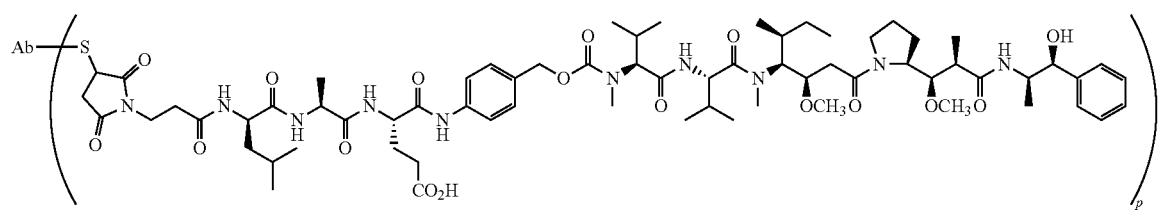

or a pharmaceutically acceptable salt thereof,
wherein Ab is the antigen binding protein or fragment thereof and p denotes a number from 1 to 12.

H9. The antibody-drug conjugate of any one of embodiments H1-H8, wherein the antigen binding protein or fragment comprises the following 6 HVRs:
an HVR-H1 comprising the amino acid sequence of SEQ ID NO: 944;
an HVR-H2 comprising the amino acid sequence of SEQ ID NO: 945;
an HVR-H3 comprising the amino acid sequence of SEQ ID NO: 946;
an HVR-L1 comprising the amino acid sequence of SEQ ID NO: 948;
an HVR-L2 comprising the amino acid sequence of SEQ ID NO: 949; and
an HVR-L3 comprising the amino acid sequence of SEQ ID NO: 950.

H10. The antibody-drug conjugate of any one of embodiments H1-H9 wherein the antigen binding protein or fragment comprises a VH and a VL, wherein the VH has at least 80%, 85%, 90%, 95% or 99% amino acid sequence identity to the amino acid sequence of SEQ ID NO: 943 and the VL has at least 80%, 85%, 90%, 95% or 99% amino acid sequence identity to the amino acid sequence of SEQ ID NO: 947.

H11. The antibody-drug conjugate of any one of embodiments H1-H10 wherein the antigen binding protein or fragment comprises a VH and a VL, wherein the VH comprises the amino acid sequence of SEQ ID NO: 943 and the VL comprises the amino acid sequence of SEQ ID NO: 947.

H12. The antibody-drug conjugate of any one of embodiments H1-H11 wherein the antigen binding protein or fragment comprises an HC comprising the amino acid sequence of SEQ ID NO: 951 and an LC comprising the amino acid sequence of SEQ ID NO: 952.

H13. The antibody-drug conjugate of any of embodiments H1-H12, wherein the antigen binding protein or fragment is a monoclonal antibody or fragment thereof.

H14. The antibody-drug conjugate of any of embodiments H1-H13, wherein the antigen binding protein or fragment is a chimeric antibody or fragment thereof.

H15. The antibody-drug conjugate of any of embodiments H1-H14, wherein the antigen binding protein or fragment is a humanized antibody or fragment thereof.

H16. The antibody-drug conjugate of any of embodiments H1-H15, wherein the fragment is selected from a Fab, Fab', Fv, scFv or (Fab')$_2$ fragment.

H17. A pharmaceutical composition comprising the antibody-drug conjugate of any of embodiments H1-H16 and a pharmaceutically acceptable carrier.

H18. A method of treating a CD19-expressing cancer in an individual comprising administering to an individual in need thereof an effective amount of the antibody-drug conjugate of any one of embodiments H1-H16, or the pharmaceutical composition of embodiment H17.

H19. The method of embodiment H18, wherein the CD19-expressing cancer is chronic leukemia, lymphoma, multiple myeloma, B type acute lymphoblastic leukemia, chronic myelocytic leukemia, chronic lymphocytic leukemia, non-Hodgkin lymphoma and Hodgkin lymphoma, B cell lymphoma, or diffuse large B-cell lymphoma.

EXAMPLES

Examples 1-19

General Information. The following information is applicable to the synthetic procedures and experiments described in Examples 1-19 unless indicated otherwise. All commercially available anhydrous solvents were used without further purification. The UPLC-MS system used for characterizing the tripeptide-based Drug Linker compounds consisted of a Waters SQ mass detector interfaced to an Acquity Ultra Performance LC equipped with an Acquity UPLC BEH C18, 130 Å, 1.7 µm, 2.1×50 mm, reverse phase column or Waters Cortecs UPLC C18, 90 Å, 1.6 µm, 2.1×50 mm. The acidic mobile phase (0.1% formic acid) consisted of a gradient of 3% acetonitrile/97% water to 100% acetonitrile (flow rate=0.5 mL/min). UPLC-MS system 2 consisted of a Waters Xevo G2 ToF mass spectrometer interfaced to a Waters Acquity H-Class Ultra Performance LC equipped with an Acquity UPLC BEH C18 2.1×50 mm, 1.7 µm reverse phase column. Preparative HPLC was carried out on a Waters 2545 Binary Gradient Module with a Waters 2998 Photodiode Array Detector or a Teledyne ISCO ACCQPrep HP150. The tripeptide-based Drug Linker compounds were purified over a C12 Phenomenex Synergi™ 4 µm Max-RP 80 Å, LC column 250 mm of appropriate diameter eluting with 0.1% trifluoroacetic acid in water (solvent A) and 0.1% trifluoroacetic acid in acetonitrile (solvent B). The purification methods generally consisted of linear gradients of solvent A to solvent B, ramping from 90% aqueous solvent A to 10% solvent A. The flow rate was set according to the column requirements with monitoring at 220 nm. NMR spectral data were collected on a Varian Mercury 400 MHz spectrometer. Chemical shifts (δ) are given in ppm relative to TMS. Coupling constants (J) are reported in hertz.

In vitro cytotoxicity. The cytotoxicity of a tripeptide-based Antibody Drug Conjugate was measured by a cell proliferation assay employing the protocol described in Promega Corp. Technical Bulletin TB288; and Mendoza et al., 2002, *Cancer Res.* 62:5485-5488), the methods of which are specifically incorporated by reference herein. Briefly, an aliquot of 40 µl of cell culture containing about 400 cells in medium is deposited in each well of a 384-well, opaque-walled plate. A 10 µL aliquot of free drug or Ligand-Drug Conjugate is added to the experimental wells and incubated for 96 h and are then equilibrated to room temperature for approximately 30 minutes whereupon a volume of CellTiter-Glo™ reagent equal to the volume of cell culture medium present in each well is added. The contents are mixed for 2 minutes on an orbital shaker to induce cell lysis and the plate is incubated at room temperature for 10 minutes to stabilize the luminescence signal for recordation.

Fluorescence assay. To a 384 well plate was added a mixture of tumor or normal tissue homogenate and citrate buffer (100 mM, pH 4.5; 9 µL) followed by a fluorescently labelled library compound (1 µL; dissolved in 50% MeCN). The reaction was incubated at 37° C. and fluorescence (330 nm excitation, 450 nm emission) was detected several times over a 6-hr. period. The fluorescence fold change was determined by dividing the fluorescence value at each time point with the background fluorescence when no homogenate was added.

Conjugation. Antibody was partially reduced using the appropriate equivalents of TCEP according to the procedure, which is specifically incorporated by reference herein, of US 2005/0238649. Briefly, the antibody in phosphate buffered saline with 2 mM EDTA, pH 7.4, was treated with 2.1 eq. TCEP and then incubated at 37° C. for about 45 minutes. The thiol/Ab value was checked by reacting the reduced antibody with compound 1 and using hydrophobic interaction chromatography to determine the loading.

The tripeptide-based auristatin Drug-Linker compounds were conjugated to the partially reduced antibody using the method, which is specifically incorporated by reference herein, of US 2005/0238649. Briefly, Drug-Linker compound (50% excess) in DMSO, was added to the reduced antibody in PBS with EDTA along with additional DMSO for a total reaction co-solvent of 10-20%. After 30 minutes at ambient temperature, an excess of QuadraSil MP™ was added to the mixture to quench all unreacted maleimide groups. The resulting Antibody Drug Conjugate was then purified, and buffer exchanged by desalting using Sephadex G25 resin into PBS buffer and kept at −80° C. until further use. The protein concentration of the resulting ADC composition was determined at 280 nm. The drug-antibody ratio (DAR) of the conjugate was determined by hydrophobic interaction chromatography (HIC).

In vivo cytotoxicity. Cancer cells were implanted into mice. After the tumor reached a volume of 100 mm³, ADC prepared from reduced antibody and tripeptide-based Drug linker compound was administered via an intraperitoneal injection. Tumor size was then measured twice a week until the end of the study.

Tissue Homogenization. Normal tissue or tumor tissue from mouse xenografts were suspended in buffer (50 mM Tris, 150 mM KCl, pH 7.0) and added to a tube containing Matrix D lysing beads (mpbio). The tissue was homogenized with a Precellys™ 24 homogenizer. The homogenized sample was centrifuged at 1000×g for 10 min and the resulting supernatant was collected then frozen at −80° C. until further use.

Toxicity Determinations. Each tripeptide-based Drug Linker compound was reacted with a reduced non-binding antibody to provide a non-binding control ADC and injected i.v. into female Sprague Dawley rats at various concentrations. Animals were euthanized on day 4 or 28 post dose.

Example 1: Preparation of p-Azido-Benzyl Alcohol (Az-PABA)

To a round bottomed flask was added p-amino-benzyl alcohol (100 mol %) suspended in 5 M HCl (5 mL per g PABA). The flask was cooled to 4° C. followed by the dropwise addition of aqueous $NaNO_2$ (150 mol %; 20 mL per gram PABA). $NaN_3$ was then added and the reaction was warmed to room temperature and incubated for 16 h. The reaction was diluted in saturated $NaHCO_3$ and extracted with EtOAc. The extract was dried with $MgSO_4$ and concentrated. The product was purified using an EtOAc/hexanes gradient (6%-42% EtOAc) with a SNAP-KP-Sil Biotage column yielding the title compound as an orange material (90% yield). $^1$H-NMR ($d_6$-DMSO) δ 7.38-7.35 (C=CH, d, 2H), 7.11-7.07 (C=CH, d, 2H), 5.25-5.22 (OH, m, 1H), 4.50-4.46 ($CH_2$, d, 2H)

Example 2: Preparation of p-Azido-Benzyl Bromide

To a round bottomed flask was added Az-PABA (100 mol %) dissolved in chloroform under a nitrogen atmosphere. To the solution was added $PBr_3$ (120 mol %) dropwise. The reaction was incubated for 2 h at which point it was diluted with $CHCl_3$ and washed with 1 M HCl followed by brine. The extract was dried with $MgSO_4$ and concentrated. The product was purified using an EtOAc/hexanes gradient (6%-42% EtOAc) with a SNAP-KP-Sil Biotage column to provide the title compound in 75% yield.

Example 3: Preparation of methyl (2-(7-hydroxy-2-oxo-2H-chromen-4-yl)acetyl)glycinate (HO-Coum-Gly-OMe)

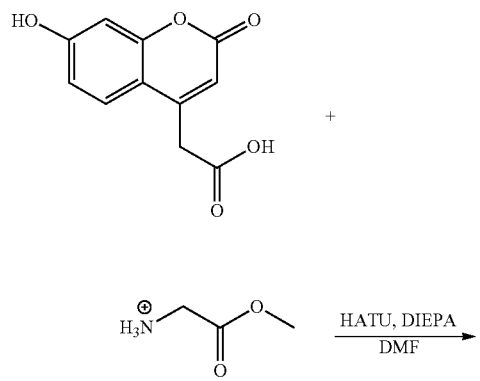

To a scintillation vial was added H-Gly-OMe (300 mol %) dissolved in DMF and DIPEA (350 mol %). To this vial was added 2-(6-hydroxy-2-oxo-2H-chromen-4-yl)acetic acid (100 mol %). DMF was then added until both reagents were fully dissolved. HATU (110 mol %) was then added followed by DIPEA (110 mol %) and the reaction was stirred for 45 min. At that time, the reaction was diluted in EtOAc and washed with 200 mM HCl. The aqueous layer was back extracted 3× with EtOAc. The combined organics were washed with brine, dried with MgSO₄, and concentrated to provide the title compound, which was purified in 80% yield from boiling isopropyl alcohol.

Example 4: Preparation of methyl (2-(7-((4-azidobenzyl)oxy)-2-oxo-2H-chromen-4-yl)acetyl)glycinate (Az-PABE-Coum-Gly-OMe)

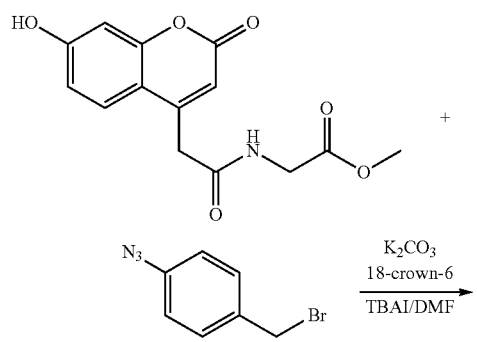

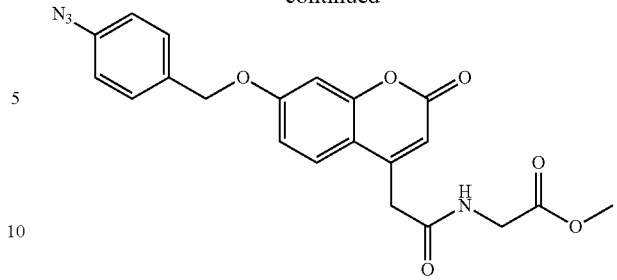

To a round bottomed flask was added HO-Coum-Gly-OMe (300 mol %), K₂CO₃ (150 mol %), and 18-crown-6 ether (200 mol %) suspended in DMF. After 15 min of vigorous stirring, Az-PAB-Br (100 mol %), prepared according to example 2, was added slowly in 4 separate aliquots. To the resulting solution was added tetrabutylammonium iodide (15 mol %), which was then stirred for 16 h. At that point the reaction was diluted into EtOAc and washed with 200 mM HCl and brine. The separated organic layer was dried with MgSO₄ and concentrated to provide the title compound as crude material that was used without further purification.

Example 5: Preparation of (2-(7-((4-azidobenzyl)oxy)-2-oxo-2H-chromen-4-yl)acetyl)glycine (Az-PABE-Coum-Gly-OH)

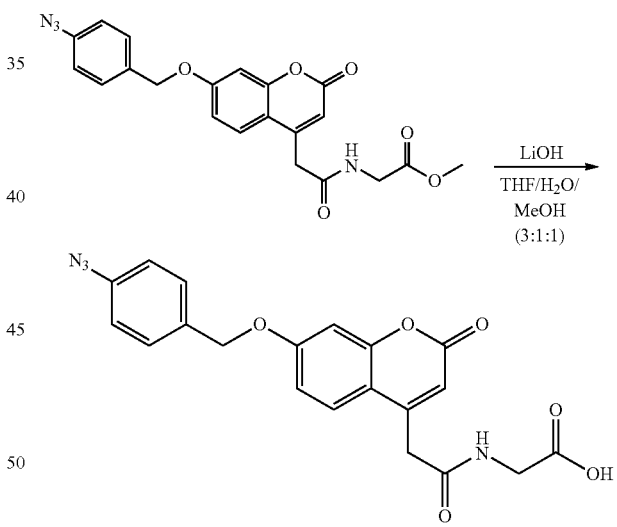

To a round bottomed flask was added crude Az-PABE-Coum-Gly-OMe (100 mol %) in THF (20 mL per 500 mg). To the vial was added MeOH (6 mL per 500 mg) and H₂O (6 mL per 500 mg). At that time LiOH (200 mol %) was added and the reaction was stirred for 1 h whereupon the reaction was diluted with EtOAc and washed twice with 200 mM HCl. The separated organic layer was dried with MgSO₄ and concentrated to provide the title compound in 88% yield. $^1$H-NMR (d₇-DMF) δ 8.80 (NH, t, 1H), 8.03-8.01 (C=CH, d, 1H), 7.80-7.77 (C=CH, d, 2H), 7.38-7.36 (C=CH, d, 2H), 7.25 (C=CH, s, 1H), 7.24-7.20 (C=CH, d, 1H), 6.58 (C=CH, s, 1H), 5.47 (CH₂, s, 2H), 4.14 (CH₂, d, 2H), 4.08 (CH₂, s, 2H).

Example 6: Preparation of P1-PABE-Coum-Gly-OH where P1=Fmoc-Leu-OH, Fmoc-D-Leu-OH, Fmoc-Ala-OH, Fmoc-Met-OH, Fmoc-Pro-OH, Fmoc-Cit-OH, Fmoc-Nal-OH, Fmoc-Tyr(All)-OH, Fmoc-Phe-OH, Fmoc-Lys(Mtt)-OH, Fmoc-Thr(Trt)-OH, Fmoc-Glu(O-2-PhiPr)-OH, wherein Cit is citrulline, and Nal is alanine in which its methyl side chain is substituted by napthth-1-yl

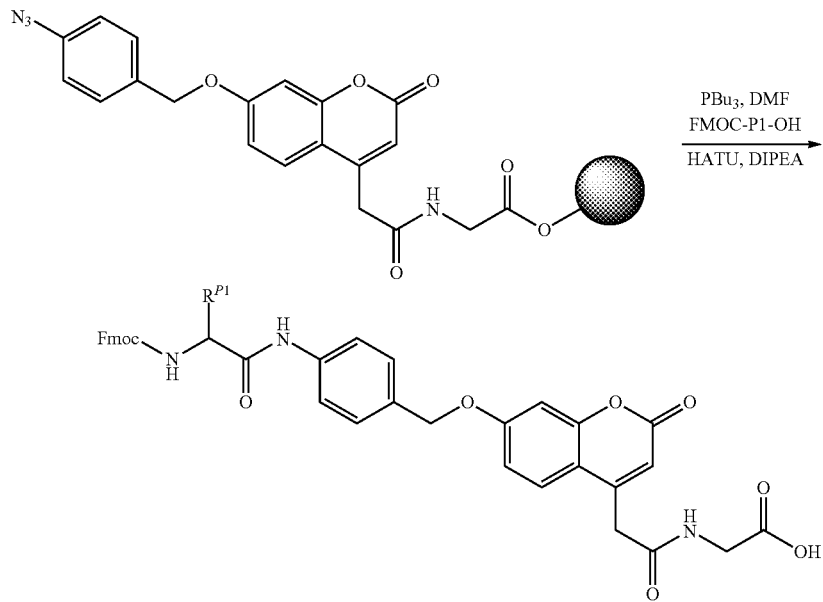

To resin (2-chloro-trityl chloride or rink acid; 100 mol %) swollen in dry DCM was added Az-PABE-Coum-Gly-OH (300 mol %) and DIPEA (310 mol %) dissolved in dry DCM. After mixing for 2 h, the solution was expelled and resin was washed with DCM. To an open round-bottomed flask was added Az-PABE-Coum-Gly-O-linked resin swollen in DMF followed by the addition of PBu$_3$ (250 mol %) and DIPEA (250 mol %). After mixing for 2 h, the solution was expelled and resin was washed with DMF, DCM, and Et$_2$O and dried overnight under vacuum. To a vial was added Fmoc-P1-OH (600 mol %) and HATU (600 mol %) dissolved in DMF, followed by DIPEA (800 mol %). The mixture was vortexed for 1 min and then added to the previously synthesized PBu$_3$ activated Az-PABE-Coum-Gly-O-linked resin (rink acid resin for Fmoc-Lys(Trt)-OH, Fmoc-Thr(Trt)-OH, and Fmoc-Glu(O-2-PhiPr), 2-chloro-trityl resin for all other amino acids) swollen in DMF. After mixing for 2 h, the solution was expelled and resin was washed with DMF and DCM. Fmoc-P1-PABE-Coum-Gly-OH was cleaved from resin using 0.2% TFA in DCM (for rink acid resin) or 5% TFA in DCM (for 2-chloro trityl resin) and purified by RP-HPLC.

Example 7: Preparation and Screening of a Tripeptide Library

Dipeptide-based Conjugates that have previously been developed were designed to be cleavable by Cathepsin B, which is a lysosomal protease that is upregulated in cancer cells compared to normal cells of the same species. Exemplary comparator dipeptide-based Conjugates have drug linker moieties in which the Drug Unit is a residue of MMAE with one of the following structures.

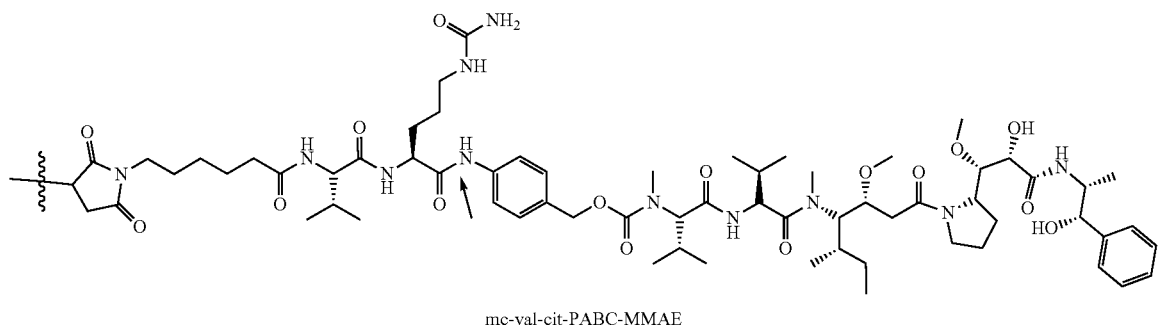

mc-val-cit-PABC-MMAE

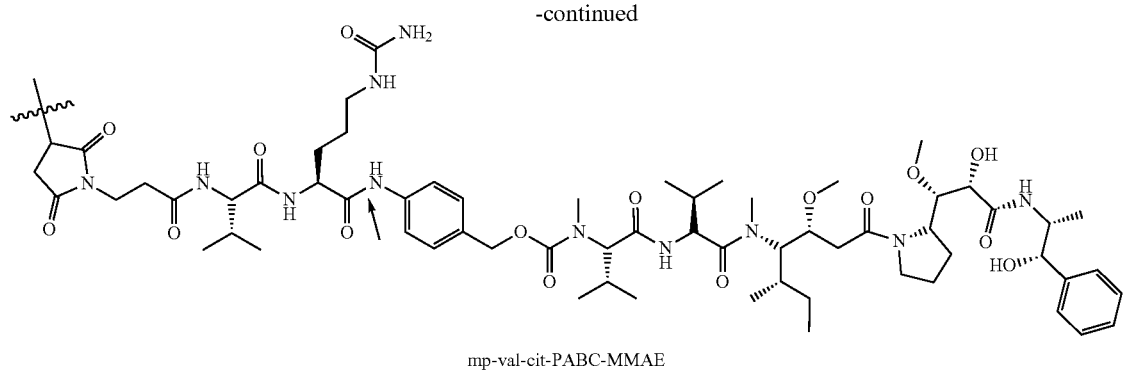

mp-val-cit-PABC-MMAE wherein the wavy line indicates the site of covalent attachment to a sulfur atom from the Ligand Unit and the arrow indicates the presumed site of proteolytic cleavage. Although more specific for Cathepsin B, other lysosomal proteases remain capable of that bond cleavage. To discover peptide sequences more specific for proteases upregulated in cancer tissue in comparison to proteases of normal tissue in which unwanted cytotoxicity towards normal cells in that tissue are associated with an adverse event when an effective amount of a comparator Conjugate have the shown dipeptide-based drug linker moieties, a library of fluorescent-quenched tripeptide-containing compounds was synthesized. Members of that library are models for Conjugate drug linker moieties in which a fluorescent tag replaces the Drug Unit and are collectively represented by the following structure:

P1 position is occupied by Met(O). When Met is in the P2 or P3 position, a mixture of tripeptides containing Met and Met(O) were obtained.

The library members were synthesized on cellulose support according to the method by Hilpert, K. et al. in "Peptide arrays on cellulose support: SPOT synthesis, a time and cost efficient method for synthesis of large numbers of peptides in a parallel and addressable fashion", *Nature Protocols* (2007) 2(6): 1333-1349, the method of which is specifically incorporated by reference herein, with one important modification. That modification uses laser-perforated cellulose paper so that synthesis of each library member occurs with a clearly defined circular disc. After SPOT synthesis, each circular area, which separately contains a discrete library member, is punched out by a multichannel pipette into individual wells of a microtiter plate. The microtiter plate is

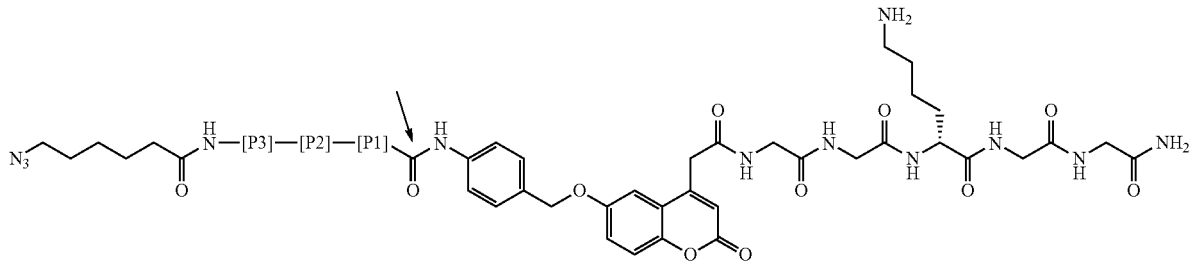

In the above structure, the conjugated coumarin moiety is non-fluorescent. Upon proteolytic cleavage of the indicated amide bond, a free coumarin-containing compound is released, which is now fluorescent. The Gly-Gly-D-Lys-Gly moiety of the free coumarin-containing compound is an artifact of the method in which the library was constructed, which is subsequently described herein. The azide provides a handle for attachment to a Ligand Unit by dipolar cycloaddition of the azide with a suitable alkyne moiety introduced onto the Ligand Unit.

The library was constructed using the non-aromatic hydrophobic amino acids Ala, Leu, Pro and D-Leu, the charged amino acids Glu and Lys, the uncharged hydrophilic amino acids Thr, Met and citrulline, and the hydrophobic aromatic amino acids Phe, Tyr (initially as the alloc-protected amino acid) and Nal (naphthyl-1-yl alanine). Thus, the library contains 1,728 distinct members. When Met is in the P1 position, the methyl sulfide group of its side chain undergoes spontaneous oxidation to the sulfoxide so that the then placed into an ammonia chamber to cleave the tripeptide containing model compounds from the cellulose discs. The cleaved compounds were then transferred to a fresh microtiter plate after solubilizing each into 50% aqueous acetonitrile. The contents of the wells were then assessed for susceptibility to proteolysis by tumor tissue homogenate in comparison to a comparator peptide-based drug linker compound having the dipeptide val-cit, which is replaced by the -[P1]-[P2]-[P3]- tripeptides in the library of drug linker compounds, by measuring the fluorescence found in each of the wells of the library after contacting with tumor or normal tissue homogenate and dividing it by the fluorescence found for tumor or normal tissue homogenate cleavage of the comparator dipeptide-containing drug linker compound.

The working assumption is that a ratio of tumor tissue to normal tissue proteolysis greater than that obtained for the comparator drug linker compound, which indicates more rapid cleavage in tumor tissue or slower cleavage in normal tissue of the library drug linker compound compared to the dipeptide-containing drug linker compound, will translate to greater selectivity for tumor tissue proteolysis in comparison to proteolysis by normal tissue homogenate of the same species, wherein cytotoxicity towards normal cells of the tissue by a comparator Conjugate having that compound as a dipeptide-based drug linker moiety responsible for an adverse event associated with administration of an effective amount of the comparator Conjugate to a subject in need thereof. The skilled person will understand that such a correlation may not hold for every library member and that the increase in proteolysis observed for the tripeptide-containing drug linker compound is not simply due to the tripeptide being a superior recognition site for Cathepsin B but instead is due at least in part to improved reactivity towards other proteases that are also upregulated in tumor tissue.

FMOC chemistry was used to prepare the Gly-D-Lys-Gly-Gly moiety, covalently attached to the cellulose solid support, in which the cellulose hydroxyl groups of the laser-perforated cellulose paper were first modified as glycine esters. The FMOC group was then removed to provide a free amine, which was confirmed by a pH sensitive indicator. The next amino acid was added, and the process was repeated. For compatibility with a 96-well microtiter plate, the laser perforated discs were 6 mm in diameter to which are added 1 µL aliquots of the FMOC protected amino acid solutions.

FMOC-P1-PABE-Coum-Gly-OH, prepared according to Example 6, was then attached to the free amino group of the $NH_2$-Gly-Lys-Gly-Gly- (SEQ ID NO: 953) residue. The key step in the reaction sequence in Example 6 is reduction of the resin-bound azide intermediate, which provides an iminophosphorane intermediate that is stable enough towards self-immolation in order for the coupling reaction with the first incoming FMOC-amino acid to occur. The P2 and P3 amino acids were then added by standard FMOC chemistry followed by acylation of the free amino group of the deprotected P3 residue to provide the resin-bound library compound, which was cleaved from the resin using an ammonia gas chamber. In Scheme 1, $R^1$, $R^{P2}$ and $R^{P3}$ are the amino acid side chains of the P1, P2 and P3 amino acid residues, respectively, and X represents the other amino acids in the $NH_2$-Gly-Gly-D-Lys-Gly-Gly- pentapeptide that tethers the fluorescently labelled tripeptide to the cellulose solid support.

Scheme 1. Preparation of Fluorescently labelled library compounds

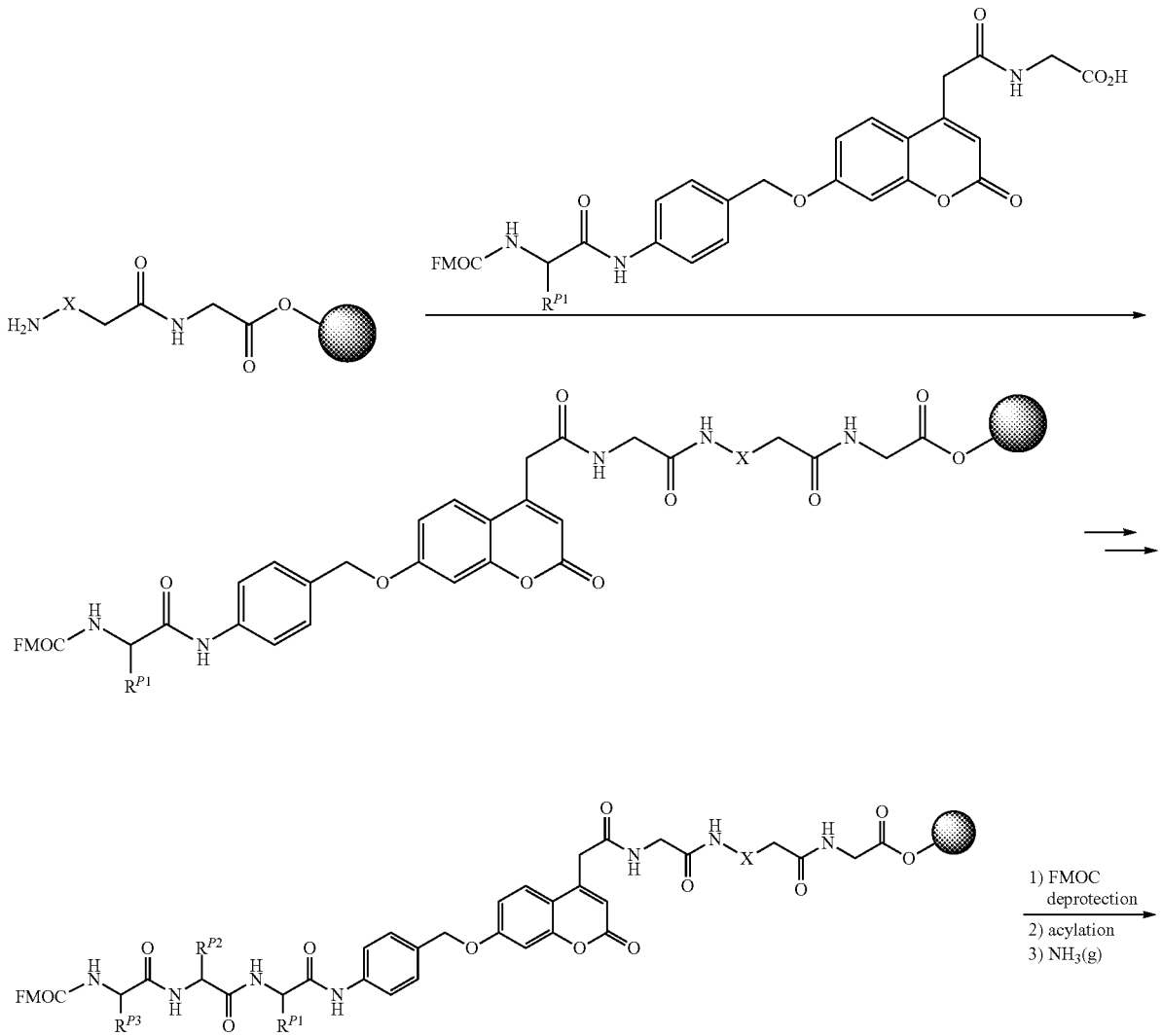

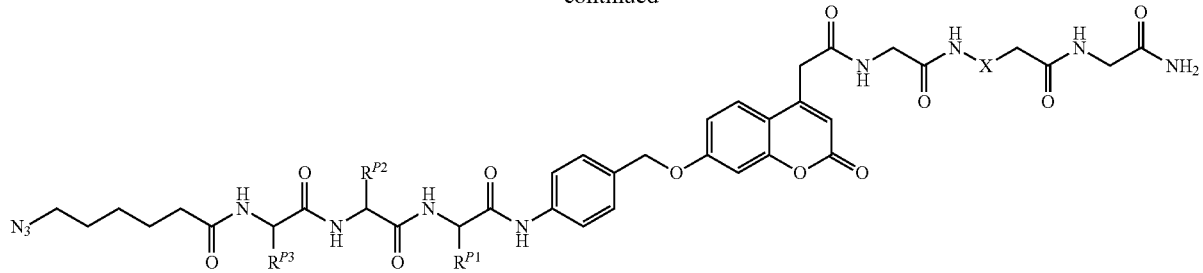

The results of Table 1A are for the top 20 tripeptide sequences in which the normalized fluorescence ratio from proteolysis by tumor vs normal tissue homogenate is greater than 2.5.

The normalized fluorescence value for tumor homogenate proteolysis is an averaged value for tumor tissue homogenates derived from four mouse xenograft models. Calculation of those normalized values are described following Table 1A.

The normalized normal tissue fluorescence values are from proteolysis by normal human bone marrow. Human bone marrow was chosen as the normal tissue because it is the site of an adverse event (neutropenia) that has been associated with administering to a human subject in need thereof an effective amount of an Antibody Drug Conjugate having drug linker moieties derived from the Drug Linker compound mc-val-cit-PABC-MMAE.

TABLE 1A

Ranking of Tripeptide Library Members by Fluorescence Ratio

| Tripeptide* | Normalized Normal Tissue | Normalized Tumor Tissue | Tumor/Normal |
|---|---|---|---|
| Pro-Ala-Glu | 0.78 | 2.48 | 3.16 |
| DLeu-Leu-Glu | 1.12 | 3.45 | 3.09 |
| Pro-Ala-Cit | 1.07 | 3.03 | 2.84 |
| Pro-Glu-Cit | 0.85 | 2.35 | 2.77 |
| DLeu-Leu-Cit | 1.37 | 3.70 | 2.70 |
| Pro-Cit-Glu | 0.85 | 2.27 | 2.68 |
| Pro-Cit-Cit | 0.95 | 2.54 | 2.67 |
| Cit-Glu-Cit | 1.21 | 3.16 | 2.61 |
| Pro-Lys-Glu | 0.72 | 1.88 | 2.59 |
| DLeu-Leu-Met(O) | 0.66 | 1.70 | 2.58 |
| Pro-Glu-Glu | 0.73 | 1.87 | 2.58 |
| Pro-Glu-Lys | 0.72 | 1.85 | 2.57 |
| Glu-Glu-Cit | 1.22 | 3.14 | 2.57 |
| DLeu-Phe-Glu | 0.89 | 2.27 | 2.55 |
| DLeu-Leu-Lys | 0.87 | 2.20 | 2.54 |
| Glu-Ala-Glu | 1.05 | 2.66 | 2.53 |
| Ala-Cit-Cit | 1.02 | 2.58 | 2.53 |
| Thr-Cit-Cit | 0.89 | 2.26 | 2.53 |
| Cit-Glu-Glu | 0.97 | 2.44 | 2.53 |
| Cit-Cit-Cit | 1.12 | 2.82 | 2.52 |

*Abbreviations: Cit = citrulline, Met(O) = methionine sulfoxide

A normalized fluorescence value is calculated by dividing the fluorescence value at the final time point (275-315 min) from addition of a tissue homogenate by the fluorescence value when no tissue homogenate was added. That value was then normalized for each peptide in each homogenate by dividing it by the average value for that homogenate. For instance, if one tripeptide had a 2-fold increase when compared to that peptide with no homogenate and the average fold increase with that homogenate was also 2-fold, then the normalized value for that tripeptide in that homogenate was 1. The normalized tumor tissue values of Table 1 were then determined by averaging the normalized fluorescence value for each peptide across all 4 cancer homogenates that were tested. Those tumor homogenates were derived from xenograft models for HPAF-II (Nude mouse), Ramos (SCID mouse), SK-Mel-5 (Nude mouse) and SU-DHL-4 (SCID mouse). The normalized normal tissue values of Table 1 were similarly calculated using homogenized bone marrow. The Tumor/Normal ratios of Table 1A were determined by dividing the normalized tumor tissue values by the normalized normal tissue values.

Given the majority of the tripeptides of Table 1A had an unnatural amino acid or proline in the P3 position and that the P2 position was more variable, three tripeptide sequences were selected that only varied in the P1 position to determine how the position closest to the self-immolative PABC Spacer Unit would alter in vivo selectivity for Ligand Drug Conjugates derived from the Drug Linker compounds containing those tripeptide sequences. Those tripeptides are D-Leu-Leu-Cit, D-Leu-Leu-Met(O) and D-Leu-Leu-Lys.

A new sort was preformed based on tripeptides of Table 1A that exhibited a normalized fluorescence for normal tissue homogenate of less than or equal to 0.7 while having a fluorescence ratio of at least 1.5. The top ten tripeptides from that sort are shown in Table 1B. The top three tripeptide sequences of Table 1B, which are D-Leu-Leu-Met(O), Pro-Nal-Lys, and D-Leu-Ala-Glu, were then selected to determine in vivo selectivity for Ligand Drug Conjugates derived from the Drug Linker compounds containing those tripeptide sequences.

TABLE 1B

Ranking of tripeptide library members by propensity for normal tissue proteolysis

| Tripeptide* | Normalized Normal | Normalized Tumor | Tumor/Normal |
|---|---|---|---|
| D-Leu-Leu-Met(O) | 0.66 | 1.70 | 2.58 |
| Pro-Nal-Lys | 0.65 | 1.33 | 2.05 |
| D-Leu-Ala-Glu | 0.69 | 1.30 | 1.87 |
| Pro-Glu-Ala | 0.70 | 1.28 | 1.84 |
| Lys-Glu-Met(O) | 0.70 | 1.16 | 1.66 |
| DLeu-Ala-Lys | 0.68 | 1.16 | 1.70 |
| Leu-Nal-Lys | 0.62 | 1.13 | 1.84 |
| DLeu-Cit-Glu | 0.64 | 1.07 | 1.67 |
| DLeu-Glu-Lys | 0.62 | 1.06 | 1.71 |
| Glu-Ala-Met(O) | 0.65 | 1.06 | 1.63 |

*Abbreviations: Cit = citrulline, Met(O) = methionine sulfoxide, Nal = naphtha-1-yl alanine.

The 5 distinct tripeptide sequences chosen from Tables 1A and 1B were incorporated into Ligand Drug Conjugates in which the Ligand Unit is from an antibody that selectively binds to an internalizable antigen preferentially displayed by cells from a human pancreatic adenocarcinoma cell line and which corresponds in structure to a comparator Conjugate having a non-binding control antibody as the "Ligand Unit" and a dipeptide Cleavable Unit in which the drug linker moieties are mc-val-cit-PABC-MMAE. Those Ligand Drug Conjugates have an average drug loading of 4.

Part B. Preparation of Drug Linker Compounds.

Drug Linker compounds in which MMAE is the Drug Unit and which were used for preparing the selected subset of Ligand Drug Conjugates discussed in Part A, are represented by the following structure.

Briefly, to synthesize MMAE on resin, FMOC-Norephedrine and pyridinium p-toluenesulfonate (PPTS) were dissolved in dichloroethane, added to DHP HM functionalized resin, and incubated at 70° C. for 8 h. After deprotection, FMOC-Dap was subsequently activated with HATU and DIPEA and then added to the norepinephrine-resin material. The reaction sequence was repeated with FMOC-N-MeVal-Val-Dil, which after deprotection, provided resin-bound MMAE.

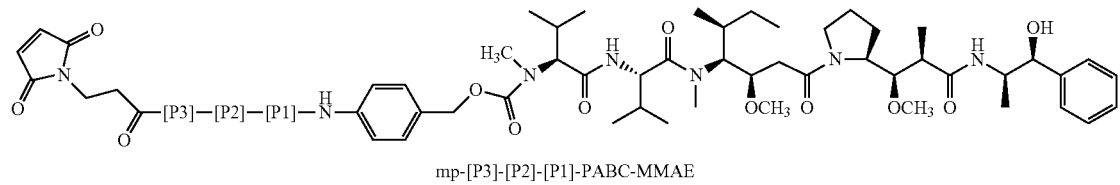

mp-[P3]-[P2]-[P1]-PABC-MMAE

Example 8: Preparation of Resin-Bound MMAE

Resin-bound MMAE was prepared using DHP HM functionalized resin according to the procedure of Scheme 2A.

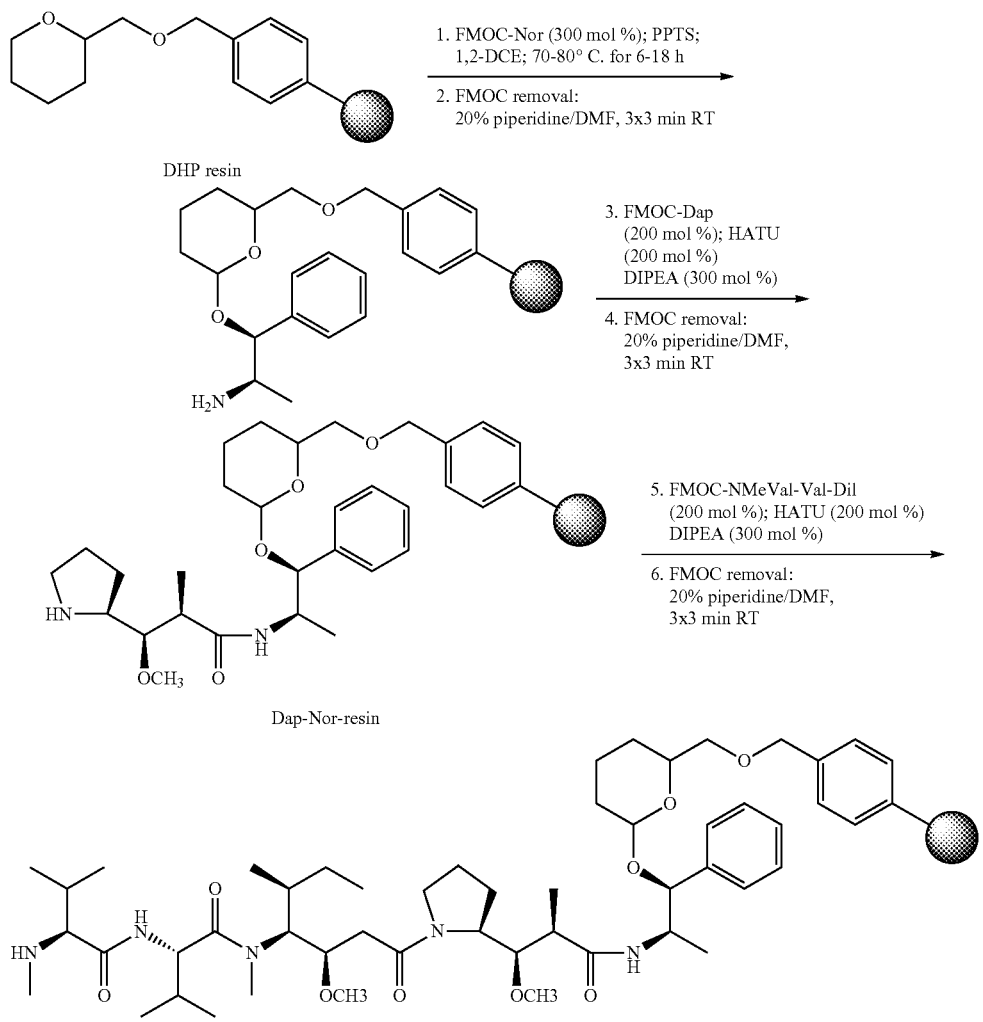

Example 9: Alternative Preparation of Resin Bound MMAE
An alternative preparation for resin-bound MMAE is shown in Scheme 2B starting from resin bound Dap-Nor of Scheme 2A.
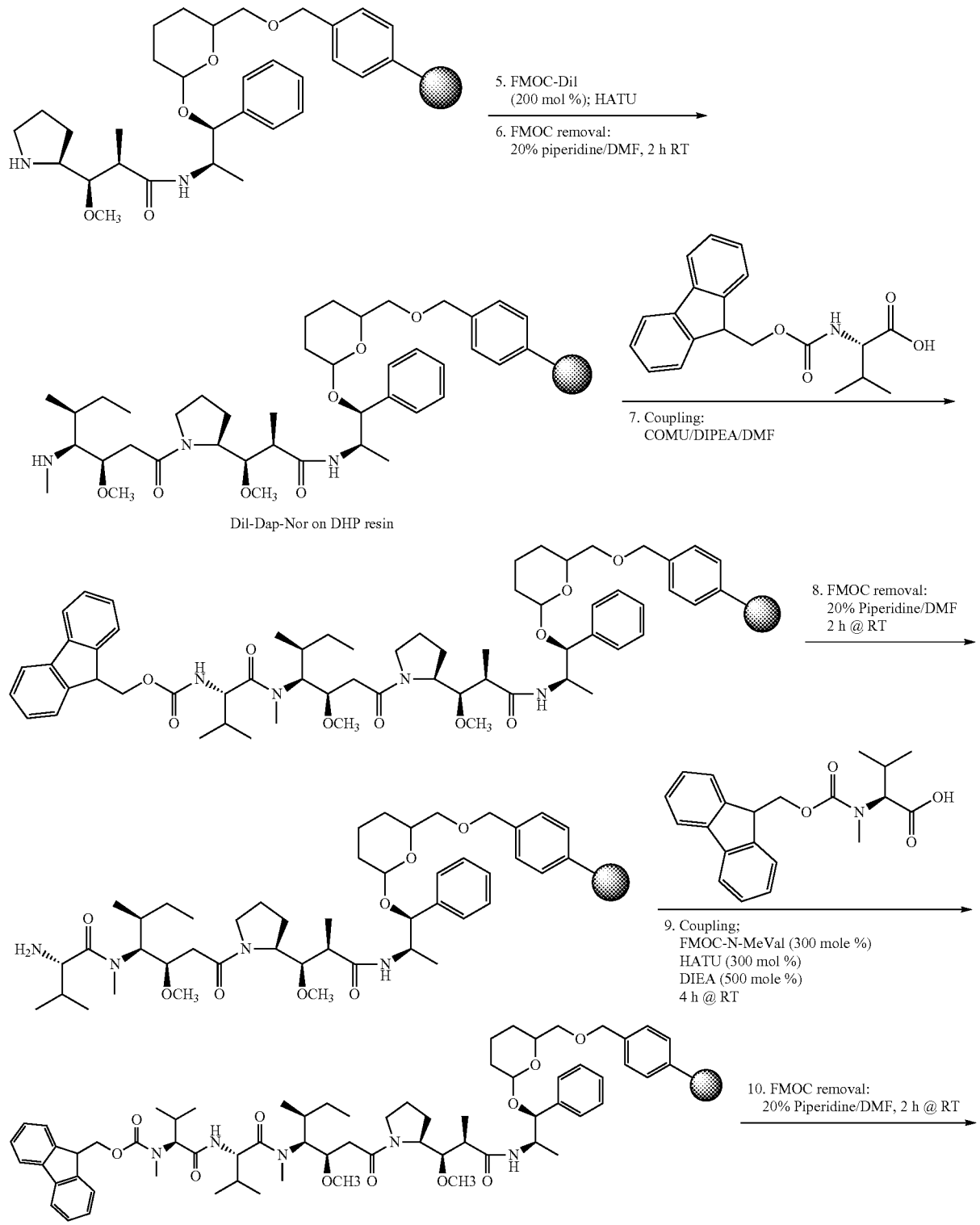
Scheme 2B. Stepwise elaboration of resin-bound Dap-Nor to MMAE -continued

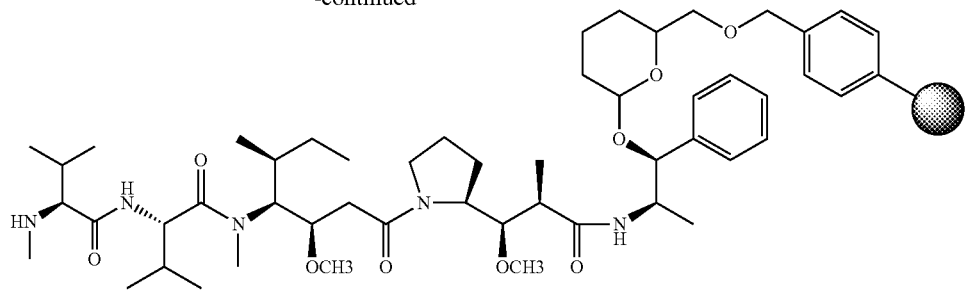

The reaction sequence of Scheme 2B is also useful for preparing radiolabeled MMAE using FMOC-protected [$^{14}$C]-valine in step 7. Completion of the Drug Linker compound from resin bound MMAE is shown in Scheme 3.

Example 10: Preparation of Tripeptide Based MMAE Drug Linker Compounds

Tripeptide-based Drug Linker compounds in which the Drug Unit is derived from MMAE and having tripeptide sequences selected from Tables 1A and 1B were prepared from resin-bound MMAE according to the procedures of Scheme 3 or from MMAE in solution phase according to the procedures of Scheme 3A.

Scheme 3. Preparation of tripeptide-based Drug Linker compounds from resin-bound MMAE

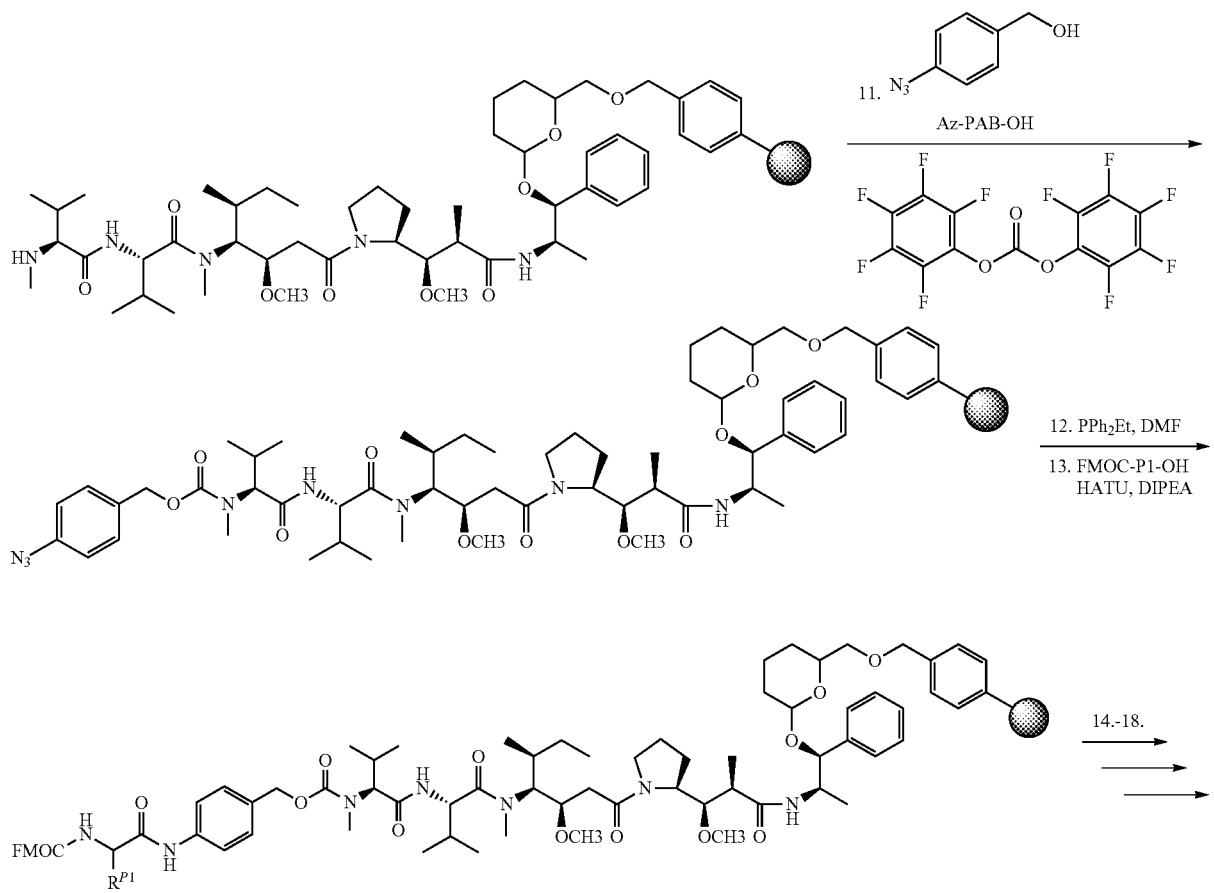

-continued

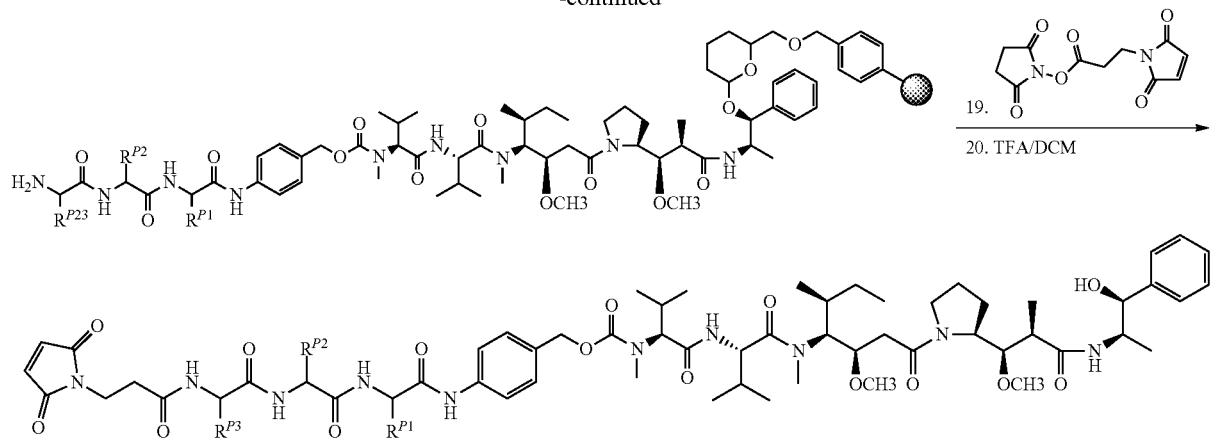

Briefly, Az-PAB-OH, prepared by reaction of NaN$_3$ with the diazonium salt from p-aminobenzyl alcohol and NaNO$_2$ in 5M HCl, was reacted with bis(pentafluorophenyl) carbonate and added to MMAE on resin. The azido group of Az-PABC-MMAE was then reduced to the iminophosphorane with PPh$_2$Et, followed by addition of FMOC-P1. After deprotection, amino acids P2 and P3 were then added through conventional FMOC peptide chemistry followed by reaction of the activated ester 3-(Maleimido)propionic acid N-hydroxysuccinimide ester with the deprotected amine of the terminal P3 amino acid. After cleavage from resin using TFA in DCM, the Drug Linker compound so obtained was purified by reverse phase HPLC.

Scheme 3A. Preparation of tripeptide-based Drug Linker compounds in solution phase

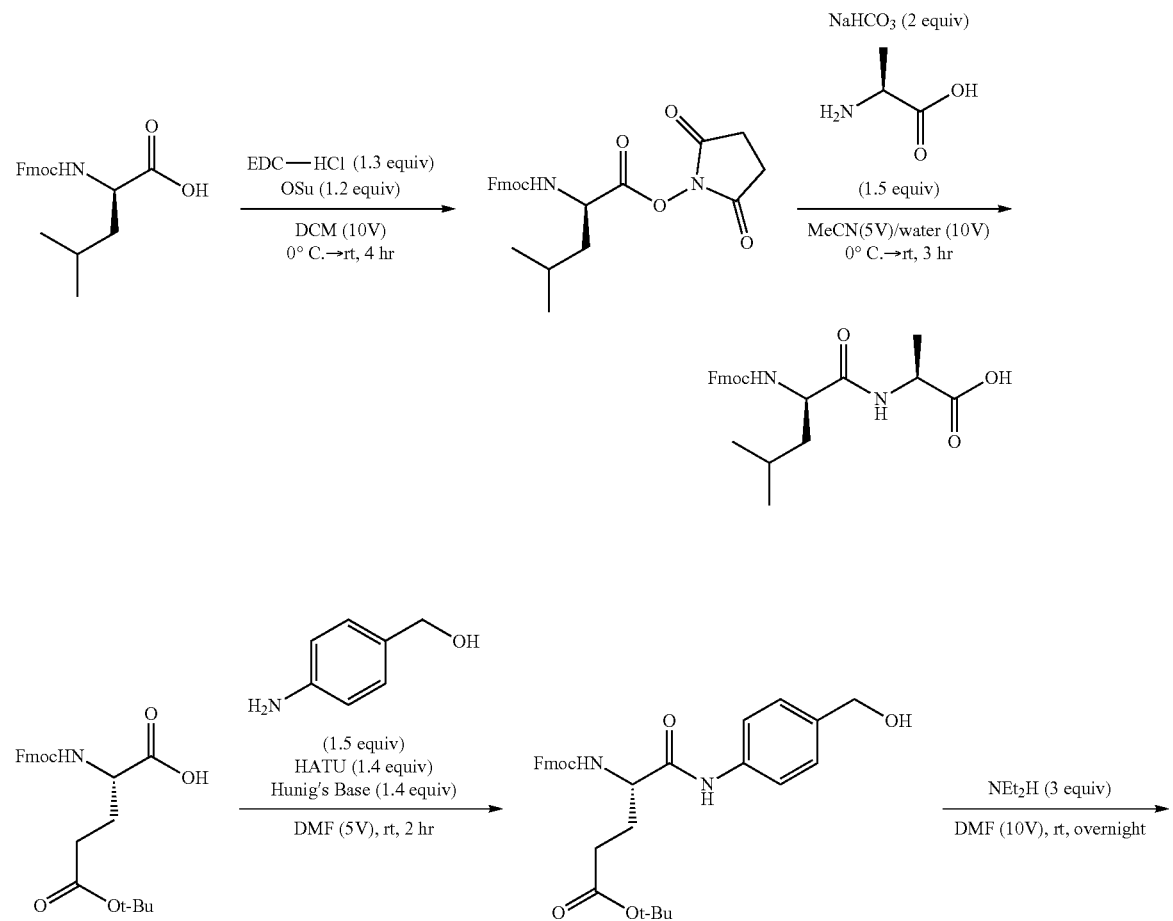

-continued
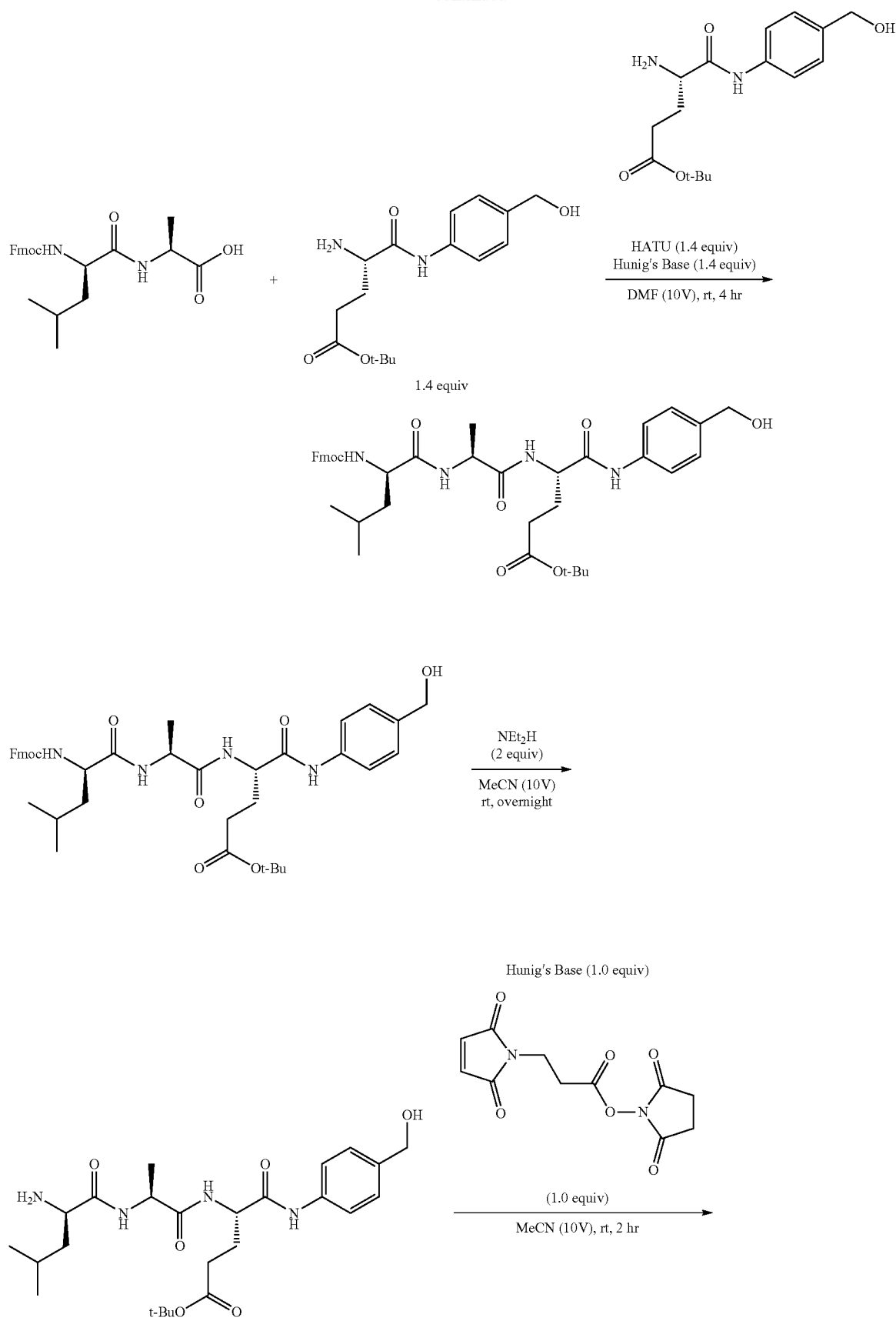

-continued
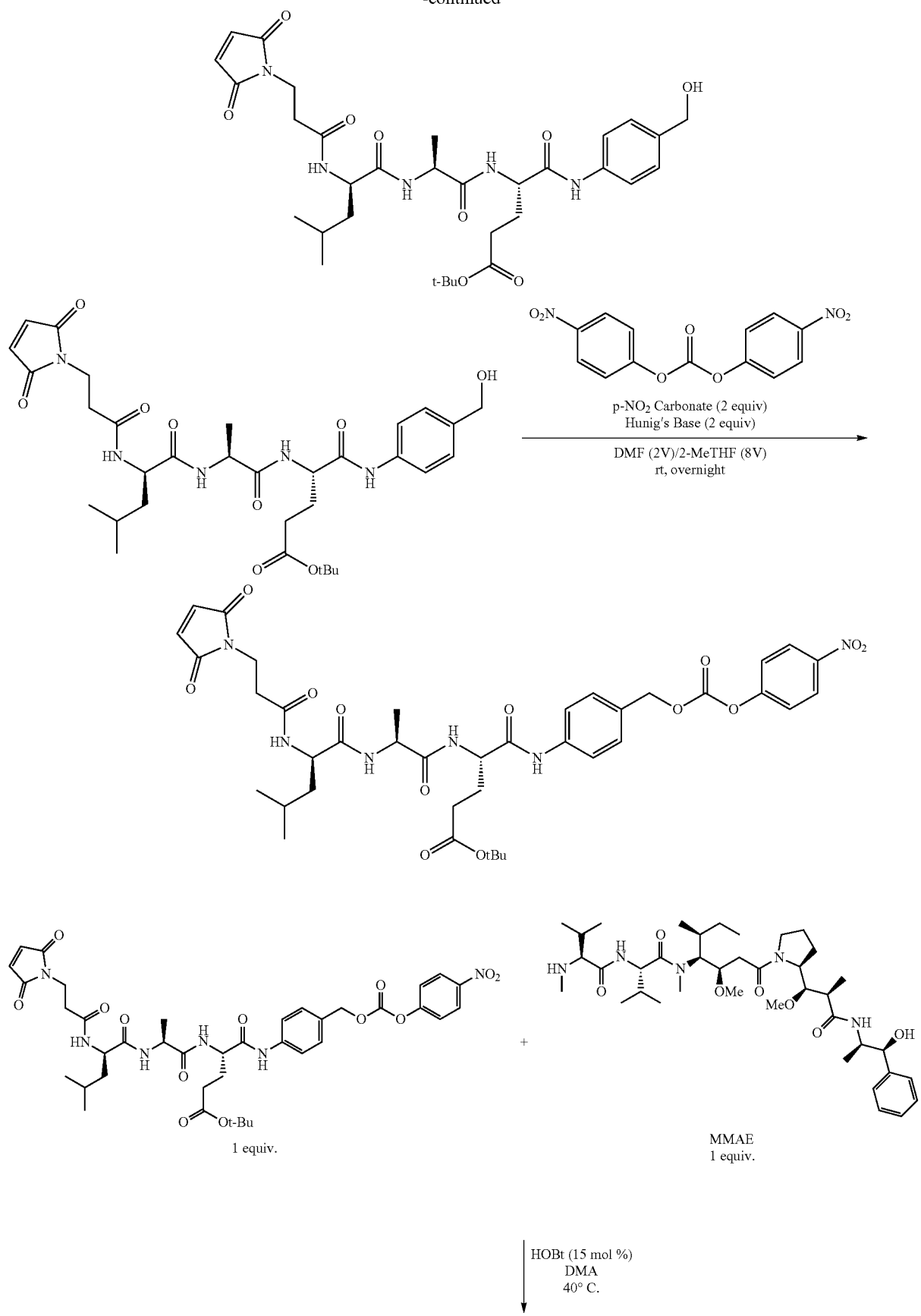

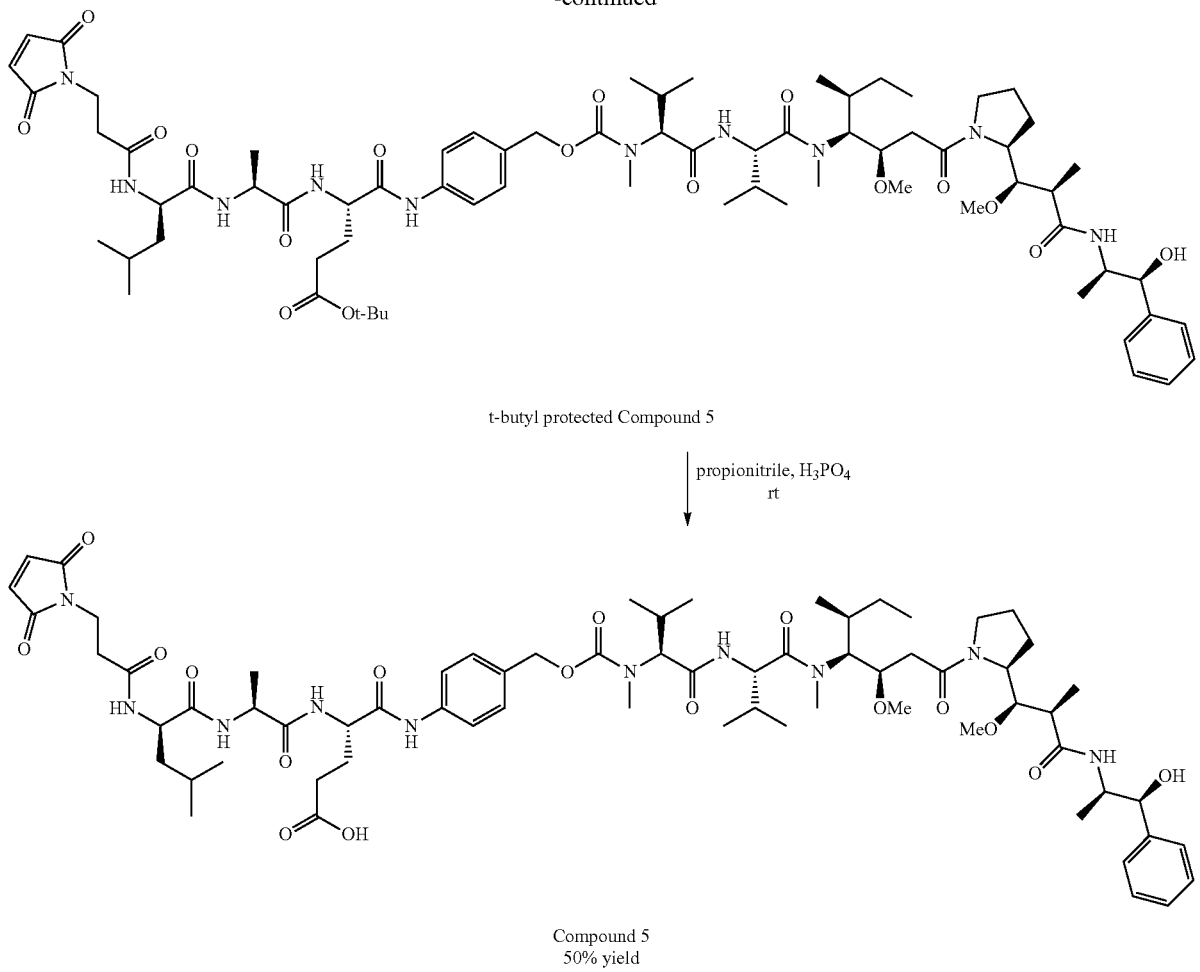

t-butyl protected Compound 5 propionitrile, H₃PO₄
rt

Compound 5
50% yield

Briefly, (((9H-fluoren-9-yl)methoxy)carbonyl)-D-leucine (1.00 equiv, 50.00 g, 141 mmol) was charged to a 2 L round bottomed flask (RBF) equipped with a magnetic stirbar. Dichloromethane (DCM) (500 ml) was added to the vessel and cooled to 0° C. with stirring followed by addition of ethylcarbodiimide hydrochloride (EDC-HCl) (1.30 eq, 35.26 g, 184 mmol) and N-hydroxysuccinimide (1.20 eq, 19.54 g, 170 mmol) was charged to the reaction. The reaction was stirred at 0° C. for 30 minutes then allowed to warm to rt (room temperature) and stirred at 4 hrs. Upon completion of the reaction water was added to the reaction (500 ml), the organic layer was separated, washed with brine (500 ml) and separated. The DCM solution was evaporated under reduced pressure to give 2,5-dioxopyrrolidin-1-yl (((9H-fluoren-9-yl)methoxy)carbonyl)-D-leucinate as a white foam (65.00 g, 144 mmol, 102% yield). This material was used without further purification.

In the next step, 2,5-dioxopyrrolidin-1-yl (((9H-fluoren-9-yl)methoxy)carbonyl)-D-leucinate (1.00 equiv, 30.0 g, 66.6 mmol) and alanine (1.5 equiv, 8.90 g, 99.9 mmol) were charged to a 1000 ml RBF with a magnetic stirbar. Acetonitrile (150 ml) and water (300 ml) were charged to the vessel and cooled to 0° C. Hunig's base was charged to the reaction in one portion (2.0 equiv, 17.2 g, 133.2 ml). The reaction was stirred at 0° C. for 1 hr then allowed to warm to rt and stirred overnight. Upon completion the solvent was swapped by rotary evaporation to ethyl acetate (EtOAc). The pH was adjusted to pH=2 by addition of 1M HCl. The organic layer was separated and washed with brine. The reaction mixture was concentrated by rotary evaporation to give a white solid (31.29 g). The solid was dissolved in EtOAc (120 ml) in a 1000 ml RBF equipped with a magnetic stirbar. The solid was precipitated by dropwise addition of Heptane (600 ml) over 1 hour. The slurry was stirred overnight. The solid was filtered and washed with Heptane (300 ml) to give a fine white solid. The solid was dried in a vacuum oven overnight at 45° C. to give (((9H-fluoren-9-yl)methoxy)carbonyl)-D-leucyl-L-alanine as a white solid (24.01 g, 85% yield)

(S)-2-((((9H-fluoren-9-yl)methoxy)carbonyl)amino)-5-(tert-butoxy)-5-oxopentanoic acid (50.0 g, 1.00 equiv, 117.5 mmol), (4-aminophenyl)methanol (21.7 g, 1.5 equiv, 176.3 mmol), and HATU (62.9 g, 1.4 equiv, 164.5 mmol) were charged to a 2000 ml RBF equipped with a magnetic stir bar. Dimethyl formamide (DMF) (250 ml) was charged to the vessel and stirred until the solids dissolve. Hunig's base (21.26 g, 1.4 equiv, 164.5 mmol) was charged to the reaction in one portion. The reaction was stirred at rt for two hours. Upon completion water (750 ml) was added by dropwise addition over 30 minutes. The slurry was stirred for an additional 1 hr at rt. The slurry was filtered and washed with water (500 ml) to give an orange solid. The solid was redissolved in DCM (500 ml) and washed with water (500 ml). To this solution in a 2000 ml RBF was added a magnetic stirbar. Diethylamine (25.64 g, 3.0 equiv, 350.54 mmol) was charged to the reaction and stirred at rt overnight (reaction precipitated overnight). Upon completion, Heptane (620 ml) was added to the reaction over 1 hr. The slurry was stirred for 1 hr. The slurry was filtered and washed with Hepante (620 ml) to give a pink solid. The solid was dried in the vacuum oven at 45° C. overnight to give tert-butyl (S)-4-amino-5-((4-(hydroxymethyl)phenyl)amino)-5-oxopentanoate as a brown solid (35.2 g, 98% yield).

(((9H-Fluoren-9-yl)methoxy)carbonyl)-D-leucyl-L-alanine (8.1 g, 1.00 equiv, 19.08 mmol), tert-butyl (S)-4-amino-5-((4-(hydroxymethyl)phenyl)amino)-5-oxopentanoate (8.82 g, 1.5 equiv, 28.62 mmol), and HATU (10.21 g, 1.4 equiv, 26.71 mmol) was charged to a 500 ml RBF. DMF (80 ml) and Hunig's base was charged to the vessel and stirred at rt for 2 hours. Upon completion the reaction was precipitated with dropwise addition of water (160 ml) over 1 hour to give a solid that sticks to the stirbar. The liquid was decanted and the solid was washed with water (80 ml). The solid was reslurried with DCM (80 ml) with heat cycling to get a red solution. The solution was precipitated with dropwise addition of Heptane (80 ml) over 30 minutes. The solid was filtered to give a yellow solid that was washed with heptane (80 ml). The solid was dried in a vacuum oven at 45° C. overnight to give Fmoc-protected tripeptide of D-Leu-Ala-Glu linked to 4-aminobenzyl alcohol a yellow solid (12 g, 88% yield).

For Fmoc-deprotection this tripeptide (1.00 equiv, 26.8 g, 37.49 mmol) was charged to a 400 ml EasyMax Reactor. MeCN (10 V, 270 ml) was charged to the vessel and stirred at 25° C. at 200 rpm (red solution). Diethylamine was added to the reaction in one portion (2.0 equiv, 5.48 g, 74.98 mmol). The reaction was stirred at rt overnight and upon completion the solvent was swapped to 10 V EtOAc by rotary evaporation. The slurry was heated to reflux to give a red solution. The slurry was cooled to 15° C. and stirred overnight. The slurry was filtered and washed with MTBE (3×10 V, 3×270 ml) to give a light brown solid. The solid was dried in a vacuum oven at 40° C. to give tert-butyl (S)-4-((S)-2-((R)-2-amino-4-methylpentanamido)propanamido)-5-((4-(hydroxymethyl)phenyl)amino)-5-oxopentanoate as a pink solid (14.47 g, 78% yield).

Tert-Butyl (S)-4-((S)-2-((R)-2-amino-4-methylpentanamido)propanamido)-5-((4-(hydroxymethyl)phenyl)amino)-5-oxopentanoate (1.00 equiv, 9.51 g, 19.31 mmol) and 2,5-dioxopyrrolidin-1-yl 3-(2,5-dioxo-2,5-dihydro-1H-pyrrol-1-yl)propanoate (1.0 equiv, 5.14 g, 19.31 mmol) were charged to a 200 ml EasyMax Reactor. MeCN (10 V, 100 ml) was added to the reactor and stirred at 25° C. at 200 rpm. Hunig's base (1.0 equiv, 2.50 g, 19.31 mmol) was added to the reaction in one portion. The reaction was stirred at 25° C. at 200 rpm for one hour (red solution). Upon completion solvent was swapped to 10V EtOAc by rotary evaporation. The product was precipitated with addition of heptane (10 V, 100 ml) over 30 minutes. The slurry was filtered and washed with MTBE (2×10 V, 2×100 ml). The solid was dried in a vacuum oven overnight at 40° C. to give tert-butyl (S)-4-((S)-2-((R)-2-(3-(2,5-dioxo-2,5-dihydro-1H-pyrrol-1-yl)propanamido)-4-methylpentanamido)propanamido)-5-((4-(hydroxymethyl)phenyl)amino)-5-oxopentanoate as a light brown solid (12.38 g, 99% yield)

Tert-butyl (S)-4-((S)-2-((R)-2-(3-(2,5-dioxo-2,5-dihydro-1H-pyrrol-1-yl)propanamido)-4-methylpentanamido)propanamido)-5-((4-(hydroxymethyl)phenyl)amino)-5-oxopentanoate (2.7 g, 1.00 equiv, 4.19 mmol) and 4-nitrophenyl carbonate (2.55 g, 2.0 equiv, 8.39 mmol) was charged to a 100 ml RBF equipped with a magnetic stirbar. DMF (2V, 5 ml) and 2-MeTHF (8V, 20 ml) were charged to the reaction with stirring at rt. Hunig's base was charged to the vessel and stirred at rt for overnight. Upon completion, the reaction was diluted with 10V 2-MeTHF. The organic layer was successively washed with 20V 5% LiCl, 20V water, and then 10% NaCl. The organic solution was added dropwise to 10V MTBE/10V Heptane over 15 minutes. The slurry was aged for 1 hour with stirring at rt. The slurry was filtered and washed with three times with 5V MTBE/5V heptane. The solid was dried in a vacuum oven at 35° C. overnight to give a pale yellow solid (2.06 g, 61% yield).

The p-nitro carbonate activated tripeptide (1 equiv, 10 mg, 0.01 mmol), MMAE (1.1 equiv, 9.7 mg, 0.01 mmol) and HOBt (0.15 equiv, 29 μl of 10 mg/ml solution in DMA) was charged to a 1 dr vial equipped with a magnetic stir bar. DMA (10 Vol, 200 μl) was charged and the reaction stirred at 40° C. Upon completion, the reaction was cooled to room temperature. Water was added dropwise, until an amorphous solid formed. The solvent was decanted and the solid redissolved in 10 V DCM. Th organic solution was washed twice with 20 V HCl (0.5 M) and concentration under vacuum to afford tert-butyl protected compound 5.

The tert-butyl protected compound 5 (1.0 g, 1.00 equiv, 0.72 mmol) was dissolved in 10 mL of propionitrile. 10 mL $H_3PO_4$ was added to the rxn mixture slowly at rt. Reaction mixture was stirred for 2 h. Upon completion 15 mL water and 10 mL Propionitrile were added. The organic layer was separated and the aqueous layer was extracted with 10 mL Propionitrile. The combined organic layer was washed one more time with 30 mL water. The reaction was concentrated and purified by reverse-phase prep-HPLC to afford Compound 5.

UPLC-MS data for MMAE and MMAF Drug Linker compounds prepared according to the reaction sequences of Scheme 2A, Scheme 3, and Scheme 3A, wherein several compounds have tripeptide sequences selected from Tables 1A and 1B, are shown in Tables 2 and 2A.

UPLC-MS was performed on a Waters single quad detector mass spectrometer interfaced to a Waters Acquity™ UPLC system using the UPLC method (Methods A-D) shown below, wherein Solvent A is 0.1% aqueous formic acid and Solvent B—acetonitrile with 0.1% formic acid.

| Method A: Column - Waters Acquity UPLC BEH C18, 130 Å, 1.7 μm, 2.1 × 50 mm, reversed-phase column | | | |
|---|---|---|---|
| Time (min) | Flow (mL/min) | A % | B % |
| Initial | 0.5 | 97 | 3 |
| 1.0 | 0.5 | 40 | 60 |
| 1.5 | 0.5 | 5 | 95 |

| Method B: Column - Waters CORTECS UPLC C18, 90 Å, 1.6 μm, 2.1 × 50 mm, reversed- phase column | | | |
|---|---|---|---|
| Time (min) | Flow (mL/min) | A % | B % |
| Initial | 0.5 | 97 | 3 |
| 1.7 | 0.5 | 40 | 60 |
| 2.0 | 0.5 | 5 | 95 |
| 3.5 | 0.5 | 5 | 95 |
| 3.8 | 0.5 | 97 | 3 |
| 4.0 | 0.5 | 97 | 3 |

| Method C: Column - Waters CORTECS UPLC C18, 90 Å, 1.6 µm, 2.1 × 50 mm, reversed-phase column | | | |
|---|---|---|---|
| Time (min) | Flow (mL/min) | A % | B % |
| Initial | 0.5 | 97 | 3 |
| 1.5 | 0.5 | 5 | 95 |

| Method D: Column - Waters Acquity UPLC BEH C18, 130 Å, 1.7 µm, 2.1 × 50 mm, reversed-phase column | | | |
|---|---|---|---|
| Time (min) | Flow (mL/min) | A % | B % |
| Initial | 0.5 | 97 | 3 |
| 1.7 | 0.5 | 40 | 60 |
| 2.0 | 0.5 | 5 | 95 |
| 3.5 | 0.5 | 5 | 95 |
| 3.8 | 0.5 | 97 | 3 |
| 4.0 | 0.5 | 97 | 3 |

| Method E: Column - Waters CORTECS UPLC C8, 90 Å, 1.6 µm, 2.1 × 50 mm, reversed-phase column | | | |
|---|---|---|---|
| Time (min) | Flow (mL/min) | A % | B % |
| Initial | 0.5 | 97 | 3 |
| 1.7 | 0.5 | 40 | 60 |
| 2.0 | 0.5 | 5 | 95 |
| 3.5 | 0.5 | 5 | 95 |
| 3.8 | 0.5 | 97 | 3 |
| 4.0 | 0.5 | 97 | 3 |

TABLE 2

UPLC-MS data for Selected MMAE Drug Linker compounds

| Compound # | Tripeptide* Sequence | Molecular Formula | MS Calc. $(M + H)^+$ | MS found | Retention Time (min.) | Method |
|---|---|---|---|---|---|---|
| 2 | Pro-Nal-Lys | $C_{78}H_{109}N_{11}O_{15}$ | 1440.8 | 1441 | 1.31 | A |
| 3 | D-Leu-Leu-Lys | $C_{72}H_{113}N_{11}O_{15}$ | 1372.8 | 1373 | 1.22 | A |
| 4 | D-Leu-Leu-Met(O) | $C_{71}H_{110}N_{10}O_{16}S$ | 1391.8 | 1392 | 1.5 | A |
| 5 | D-Leu-Ala-Glu | $C_{68}H_{102}N_{10}O_{17}$ | 1331.7 | 1332 | 1.43 | A |
| 6 | D-Leu-Leu-Cit | $C_{72}H_{112}N_{12}O_{16}$ | 1401.8 | 1402 | 1.48 | A |
| 7 | Leu-Ala-Glu | $C_{68}H_{102}N_{10}O_{17}$ | 1330.7 | 1332.2 | 1.92 | B |
| 8 | D-Leu-Ala-Cit | $C_{69}H_{106}N_{12}O_{16}$ | 1358.8 | 1359.3 | 1.39 | A |
| 9 | Pro-Leu-Glu | $C_{70}H_{104}N_{10}O_{17}$ | 1356.8 | 1357.4 | 1.49 | A |
| 10 | Thr-Glu-Leu | $C_{69}H_{104}N_{10}O_{18}$ | 1360.8 | 1361.4 | 1.44 | A |
| 11 | D-Leu-Glu-Cit | $C_{71}H_{108}N_{12}O_{18}$ | 1416.8 | 1417.4 | 1.35 | A |
| 12 | Glu-Pro-Cit | $C_{70}H_{104}N_{12}O_{18}$ | 1400.8 | 1402.2 | 1.29 | A |
| 13 | Tyr(All)-Pro-Cit | $C_{77}H_{110}N_{12}O_{17}$ | 1474.8 | 1475.9 | 1.46 | A |
| 14 | Lys-Leu-Cit | $C_{72}H_{113}N_{13}O_{16}$ | 1415.8 | 1417.6 | 1.21 | A |
| 15 | Tyr(All)-dLeu-Glu | $C_{77}H_{110}N_{10}O_{18}$ | 1462.8 | 1463.8 | 1.41 | C |
| 16 | D-Leu-Ala-Gln | $C_{68}H_{103}N_{11}O_{16}$ | 1331.6 | 1331.4 | 2.01 | D |
| 17 | D-Leu-Ala-(Se-Met) | $C_{68}H_{104}N_{10}O_{15}Se$ | 1381.6 | 1381.4 | 2.22 | D |
| 18 | D-Leu-Glu-Ala | $C_{68}H_{102}N_{10}O_{17}$ | 1332.6 | 1332.2 | 2.08 | D |
| 19 | D-Leu-Ala-Ala | $C_{66}H_{100}N_{10}O_{15}$ | 1274.6 | 1275 | 2.13 | B |
| 20 | D-Leu-Ala-Met(O) | $C_{68}H_{104}N_{10}O_{16}S$ | 1350.7 | 1350.1 | 2.07 | B |
| 21 | D-Leu-Leu-Glu | $C_{71}H_{108}N_{10}O_{17}$ | 1374.7 | 1373.9 | 2.26 | B |
| 22 | D-Ala-Ala-Glu | $C_{65}H_{96}N_{10}O_{17}$ | 1290.5 | 1290.3 | 1.89 | D |
| 23 | Ala-Ser-Glu | $C_{65}H_{96}N_{10}O_{18}$ | 1306.5 | 1306.4 | 1.88 | B |
| 24 | D-Leu-Ala-Asp | $C_{67}H_{100}N_{10}O_{17}$ | 1318.6 | 1318.5 | 2.09 | B |
| 25 | D-Leu-Val-Gln | $C_{70}H_{107}N_{11}O_{16}$ | 1359.7 | 1359.9 | 2.1 | D |
| 26 | D-Leu-Ala-Gla | $C_{69}H_{102}N_{10}O_{19}$ | 1376.6 | 1376.5 | 2.02 | B |
| 27 | D-Leu-Ala-Lys | $C_{69}H_{107}N_{11}O_{15}$ | 1332.7 | 1331.5 | 1.74 | B |
| 28 | Ala-Ser-Asp | $C_{64}H_{94}N_{10}O_{18}$ | 1292.5 | 1292.3 | 1.83 | B |
| 29 | D-Leu-Ala-Leu | $C_{69}H_{106}N_{10}O_{15}$ | 1316.6 | 1316.5 | 2.28 | B |
| 30 | Phe-Ser-Glu | $C_{71}H_{100}N_{10}O_{18}$ | 1382.6 | 1382.2 | 2.02 | D |
| 31 | Glu-Val-Cit | $C_{70}H_{106}N_{12}O_{18}$ | 1404.7 | 1418.5 | 1.96 | B |
| 32 | D-Leu-Ser-Glu | $C_{68}H_{102}N_{10}O_{18}$ | 1348.6 | 1349.2 | 2.07 | B |
| 33 | D-Ala-Ala-Cit | $C_{66}H_{100}N_{12}O_{16}$ | 1318.6 | 1318.5 | 1.86 | B |
| 34 | Glu-Leu-Cit | $C_{71}H_{108}N_{12}O_{18}$ | 1418.7 | 1418.5 | 1.96 | B |
| 35 | D-Leu-Gly-Glu | $C_{67}H_{100}N_{10}O_{17}$ | 1318.6 | 1318.5 | 2.02 | B |
| 36 | Glu-Ala-Leu | $C_{68}H_{102}N_{10}O_{17}$ | 1332.6 | 1332.2 | 2.03 | B |
| 38 | D-Leu-Aib-Glu | $C_{69}H_{104}N_{10}O_{17}$ | 1346.7 | 1346.4 | 2.13 | D |
| 39 | D-Leu-Aib-Cit | $C_{70}H_{108}N_{12}O_{16}$ | 1374.7 | 1375.1 | 2.11 | B |
| 40 | Val-Gln-Glu | $C_{69}H_{103}N_{11}O_{18}$ | 1375.6 | 1375.5 | 1.84 | B |
| 45 | Ala-Ser-Pro | $C_{65}H_{96}N_{10}O_{16}$ | 1274.5 | 1274.6 | 1.88 | B |
| 46 | Ala-Asp-Pro | $C_{66}H_{96}N_{10}O_{17}$ | 1302.5 | 1302.6 | 1.87 | B |
| 47 | Phe-Ser-Asp | $C_{70}H_{98}N_{10}O_{18}$ | 1368.6 | 1368.4 | 1.98 | E |
| 48 | Pro-Ser-Asp | $C_{66}H_{96}N_{10}O_{18}$ | 1318.5 | 1318.3 | 1.84 | E |

TABLE 2-continued

UPLC-MS data for Selected MMAE Drug Linker compounds

| Compound # | Tripeptide* Sequence | Molecular Formula | MS Calc. (M + H)+ | MS found | Retention Time (min.) | Method |
|---|---|---|---|---|---|---|
| 49 | D-Ala-Ser-Asp | $C_{64}H_{94}N_{10}O_{18}$ | 1292.5 | 1292.3 | 1.81 | E |
| 50 | Pro-Gly-Glu | $C_{66}H_{96}N_{10}O_{17}$ | 1302.5 | 1302.1 | 1.9 | E |
| 51 | Pro-Asp-Ser | $C_{66}H_{96}N_{10}O_{18}$ | 1318.5 | 1318.2 | 1.88 | E |
| 52 | D-Ala-Asp-Ser | $C_{64}H_{94}N_{10}O_{18}$ | 1292.5 | 1292.2 | 1.83 | E |
| 53 | D-Ser-Ser-Asp | $C_{64}H_{94}N_{10}O_{19}$ | 1308.5 | 1308.9 | 1.82 | E |
| 54 | Ala-Glu-Pro | $C_{67}H_{98}N_{10}O_{17}$ | 1316.5 | 1316.4 | 1.98 | E |
| 55 | D-Ala-Ser-Glu | $C_{65}H_{96}N_{10}O_{18}$ | 1306.5 | 1306.6 | 1.94 | E |
| 56 | Asp-Gly-Pro | $C_{65}H_{94}N_{10}O_{17}$ | 1288.5 | 1289.1 | 2.01 | E |
| 57 | Phe-Gln-Glu | $C_{73}H_{103}N_{11}O_{18}$ | 1423.7 | 1423.6 | 2.07 | E |
| 58 | Val-Asn-Glu | $C_{68}H_{101}N_{11}O_{18}$ | 1361.6 | 1361.4 | 2.05 | E |
| 59 | D-Ala-Gln-Glu | $C_{67}H_{99}N_{11}O_{18}$ | 1347.6 | 1347.6 | 1.99 | E |
| 60 | D-Glu-Ser-Glu | $C_{67}H_{98}N_{10}O_{20}$ | 1364.5 | 1364.5 | 1.74 | B |
| 61 | Ser-Ser-Pro | $C_{65}H_{96}N_{10}O_{17}$ | 1290.5 | 1289.6 | 1.88 | E |
| 62 | Pro-Ser-Ser | $C_{65}H_{96}N_{10}O_{17}$ | 1290.5 | 1289.7 | 1.9 | E |
| 63 | Ser-Ser-Glu | $C_{65}H_{96}N_{10}O_{19}$ | 1322.5 | 1322.4 | 1.85 | E |
| 64 | Pro-Gly-Asp | $C_{65}H_{94}N_{10}O_{17}$ | 1288.51 | 1288.1 | 1.95 | E |
| 65 | Pro-Gln-Asp | $C_{68}H_{99}N_{11}O_{18}$ | 1359.61 | 1359.4 | 1.93 | E |
| 66 | Pro-Gln-Glu | $C_{69}H_{101}N_{11}O_{18}$ | 1373.61 | 1373.3 | 1.91 | E |
| 67 | D-Ser-Ser-Glu | $C_{65}H_{96}N_{10}O_{19}$ | 1322.51 | 1322.4 | 1.95 | E |
| 68 | Gln-Ser-Ala | $C_{65}H_{97}N_{11}O_{17}$ | 1305.51 | 1305.3 | 1.75 | E |
| 69 | Glu-Ser-Ala | $C_{65}H_{96}N_{10}O_{18}$ | 1306.51 | 1306.2 | 1.76 | E |
| 70 | Ser-Asn-Asn | $C_{65}H_{96}N_{12}O_{18}$ | 1334.51 | 1334.6 | 1.69 | E |

*Abbreviations:
Aib = α-aminoisobutyric acid,
Cit = citrulline,
Met(O) = methionine sulfoxide,
Nal = naphthal-1-yl alanine,
(Se-Met) = Selenomethionine,
Gla = gamma-carboxyglutamate,
Tyr(All) = O-allyl tyrosine

TABLE 2A

UPLC-MS data for Selected MMAF Drug Linker compound

| Compound # | Tripeptide Sequence | Molecular Formula | MS Calc. (M + H)+ | MS found | Retention Time (min.) | Method |
|---|---|---|---|---|---|---|
| 42 | D-Leu-Ala-Glu | $C_{71}H_{106}N_{10}O_{18}$ | 1389.7 | 1388.6 | 2.16 | B |

Structures of the tripeptide-based Drug Linker compounds 2-36, 38-40, and 45-70 of Table 2 and compound 42 of Table 2A, as well as the comparator dipeptide-based Drug Linker compound 1, compound 7, and compound 41 are as follows:

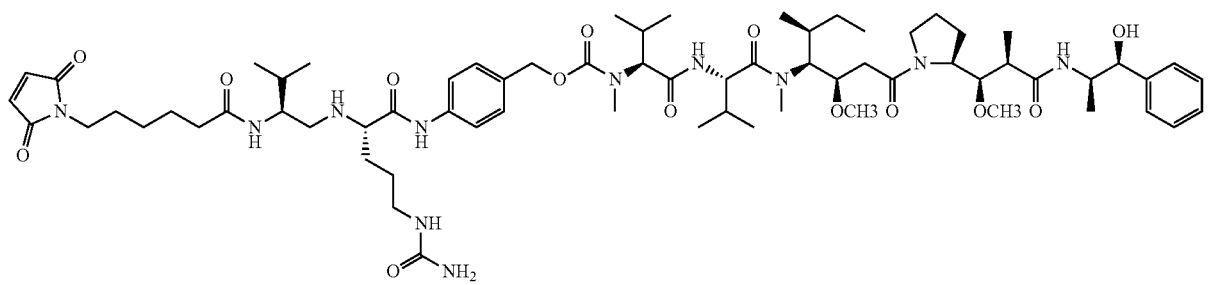

(1)

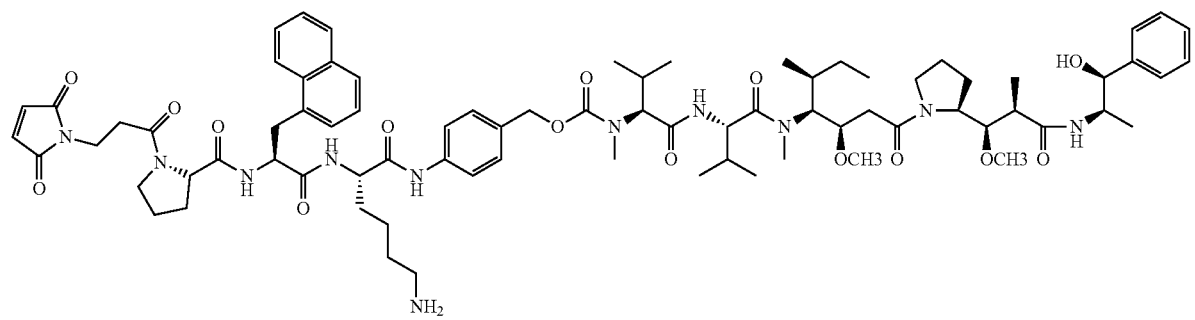
(2)
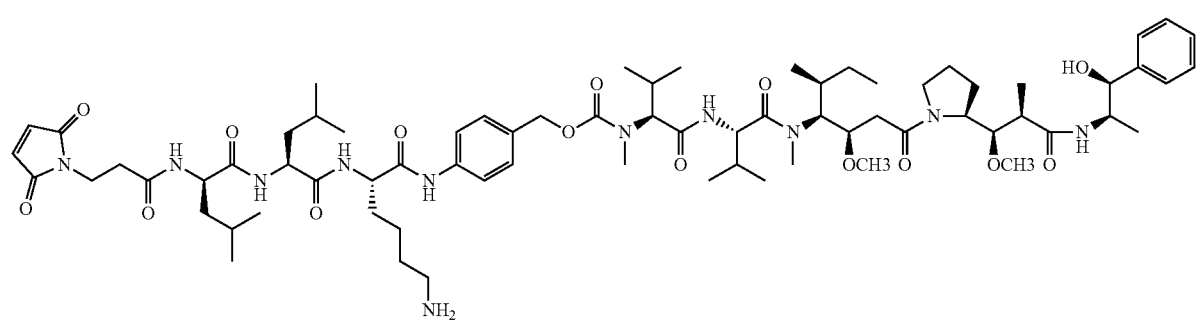
(3)
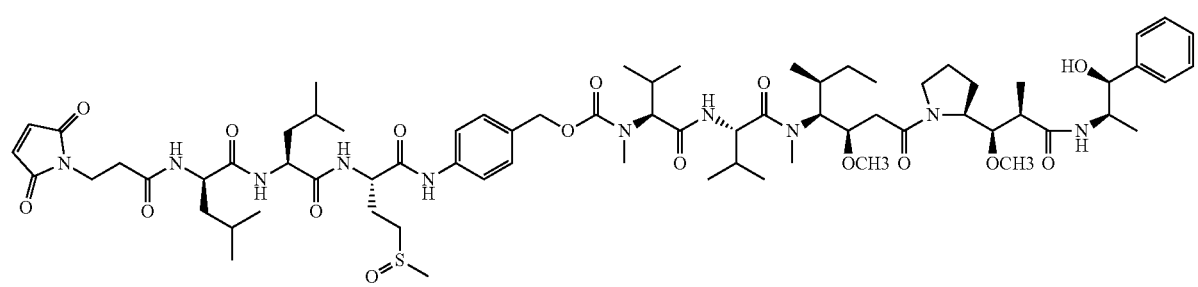
(4)
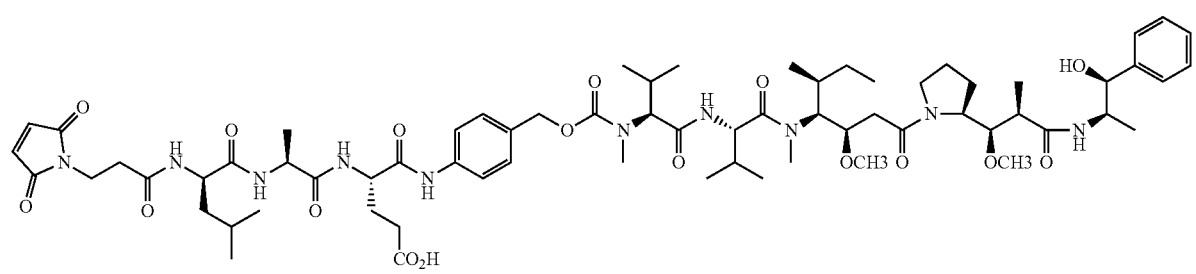
(5)
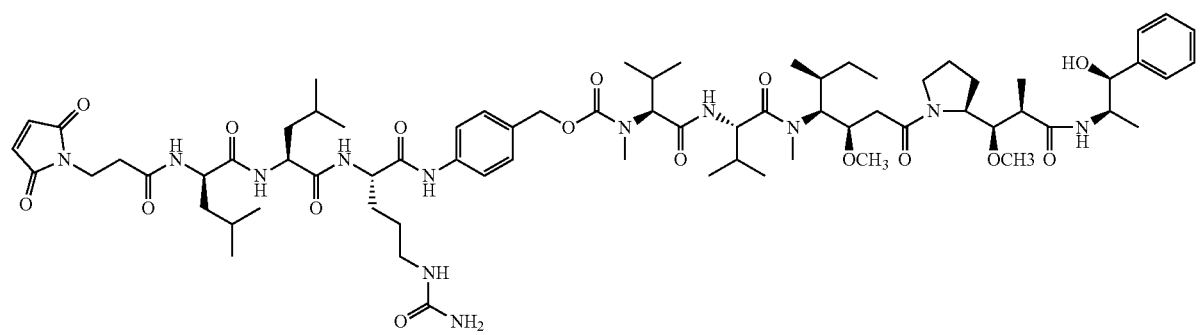
(6)

(7)
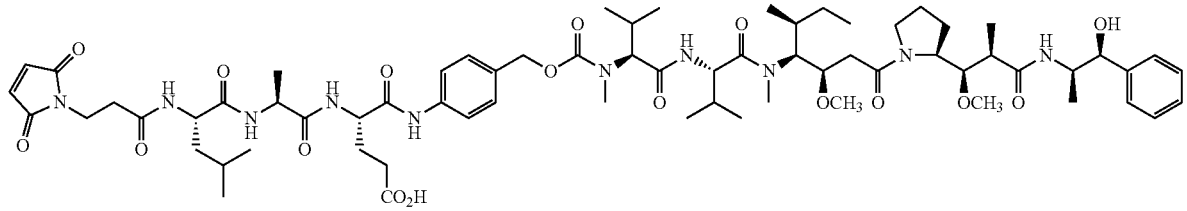
(8)
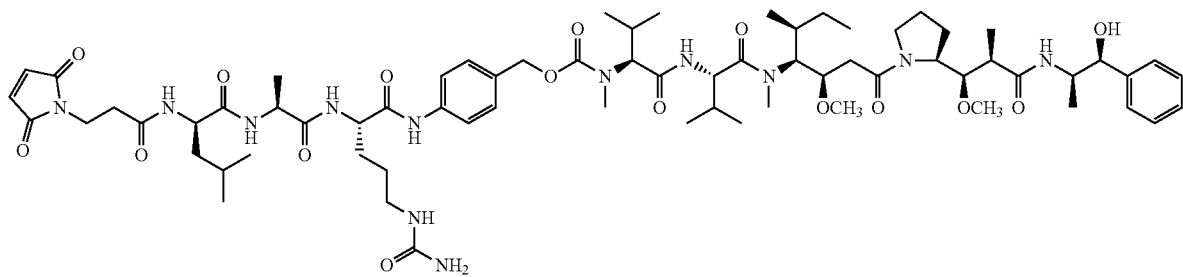
(9)
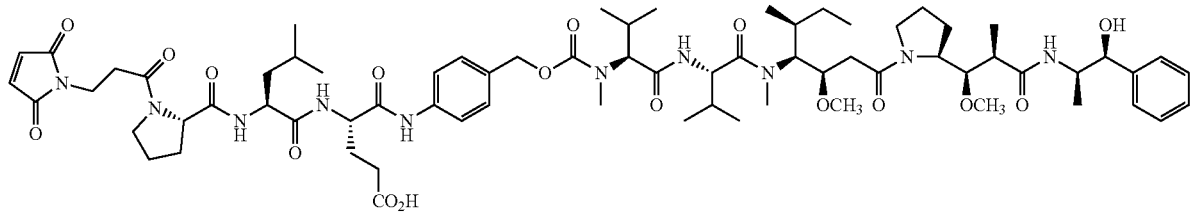
(10)
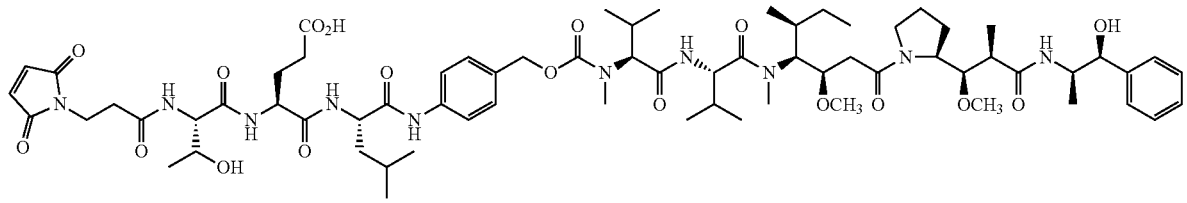
(11)
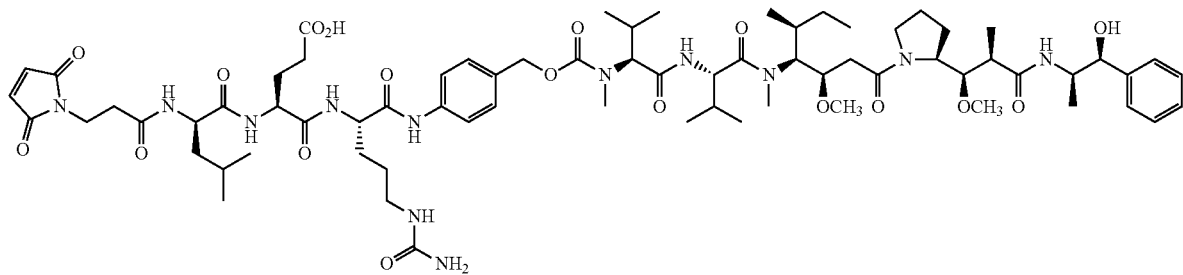
(12)
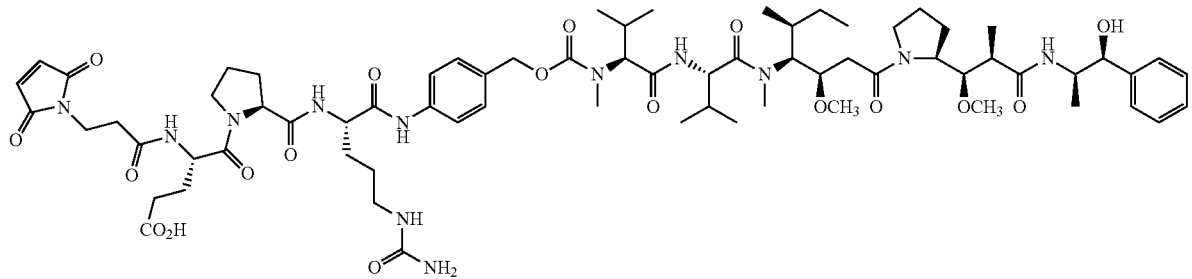

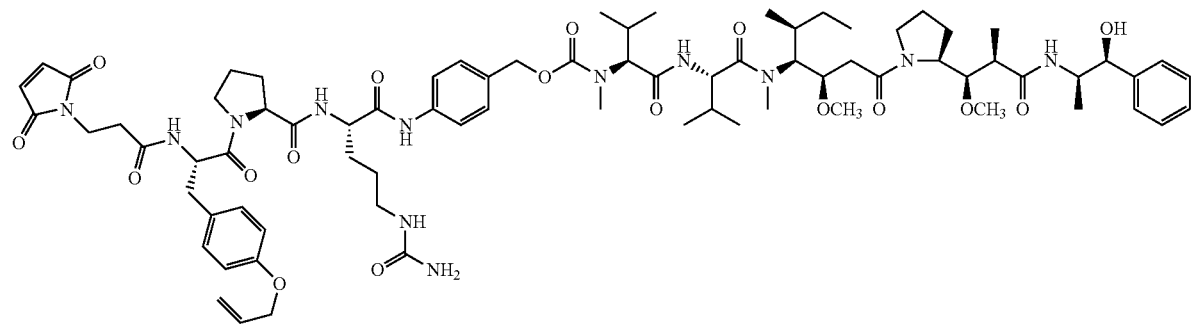
(13)
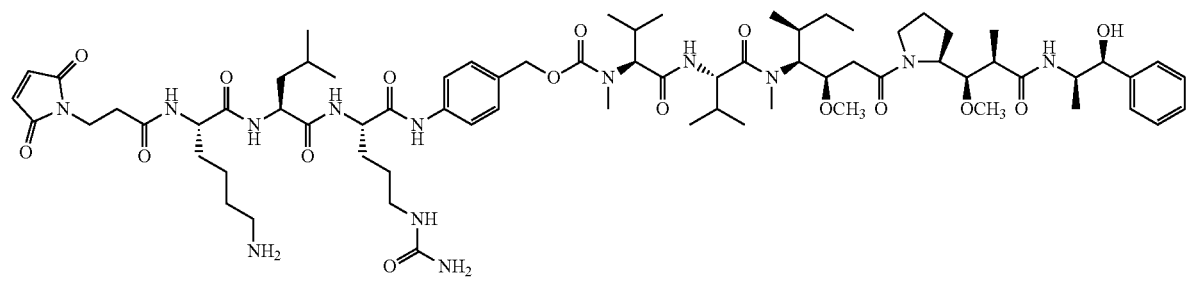
(14)
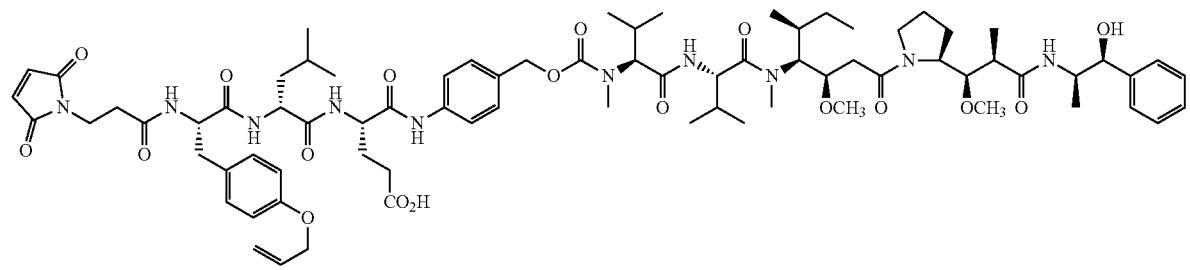
(15)
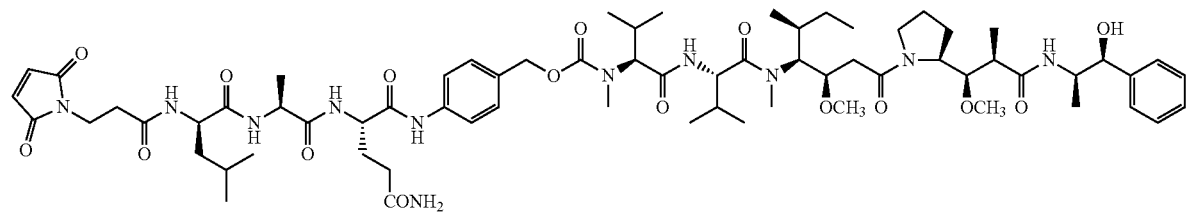
(16)
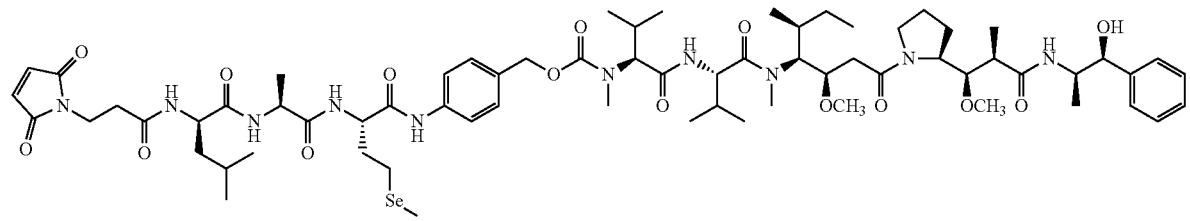
(17)

-continued
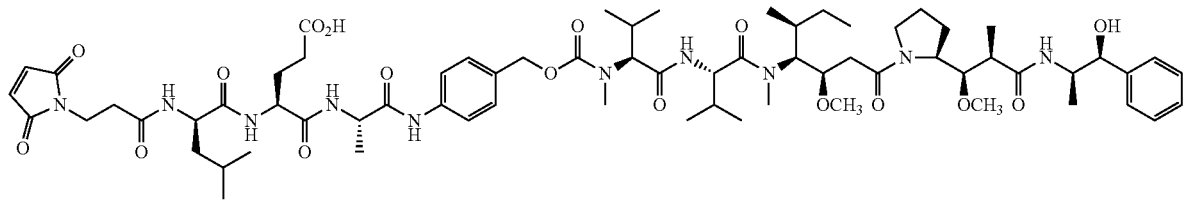
(18)
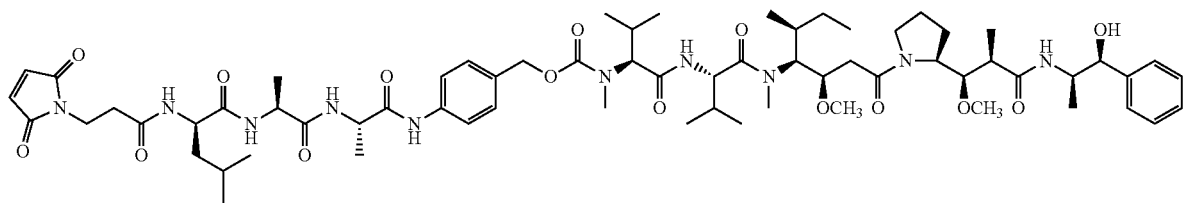
(19)
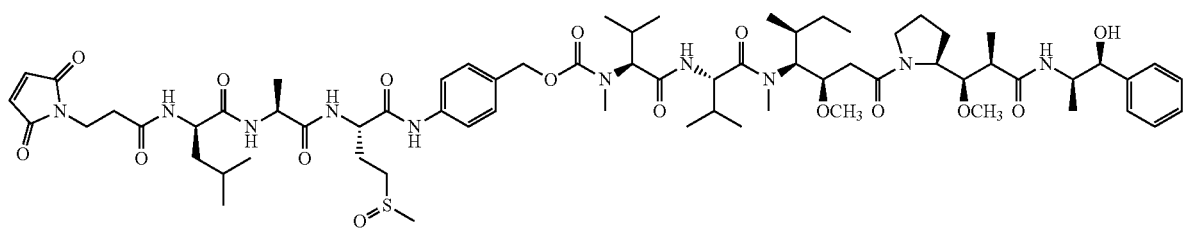
(20)
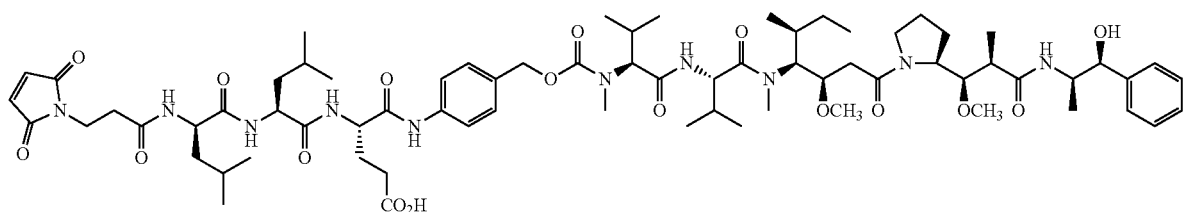
(21)
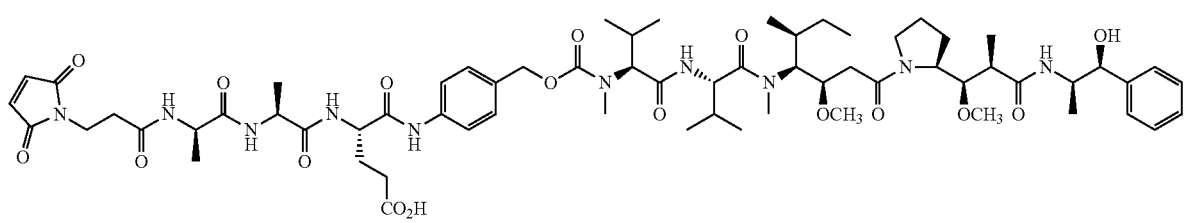
(22)
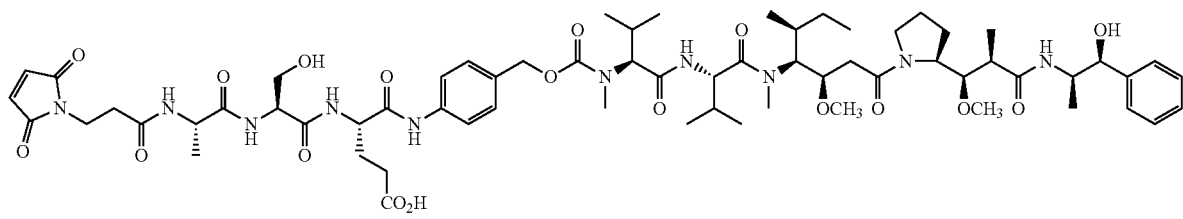
(23)

(24)
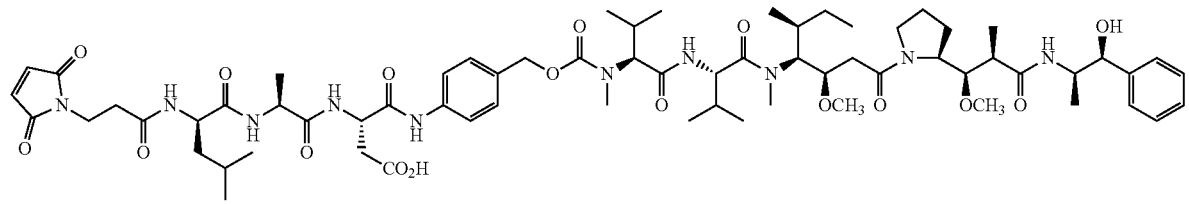
(25)
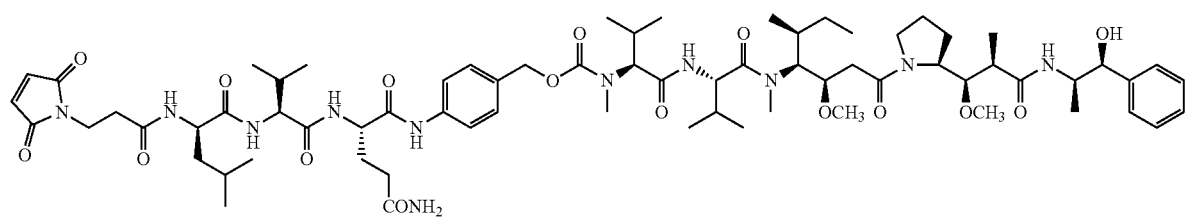
(26)
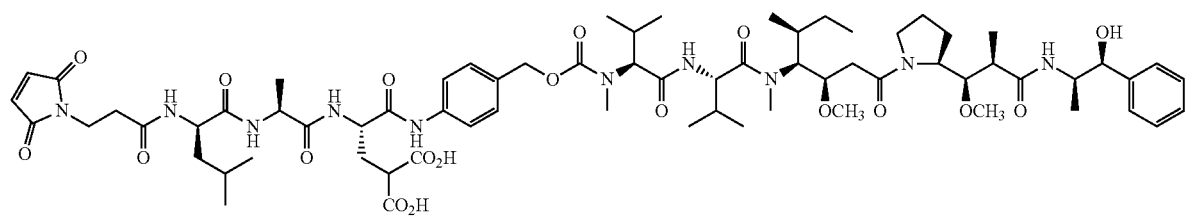
(27)
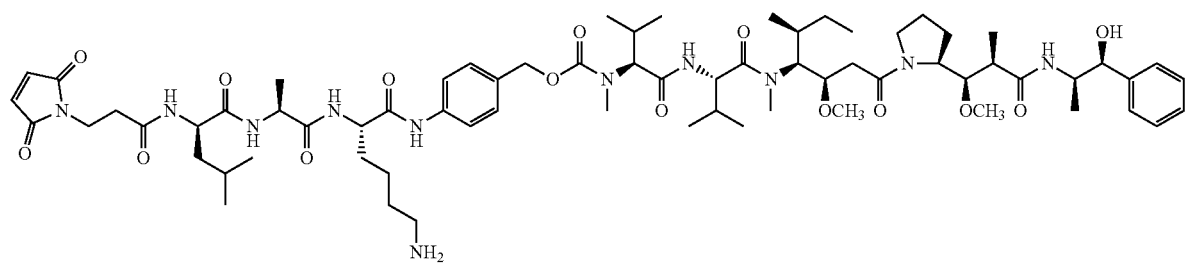
(28)
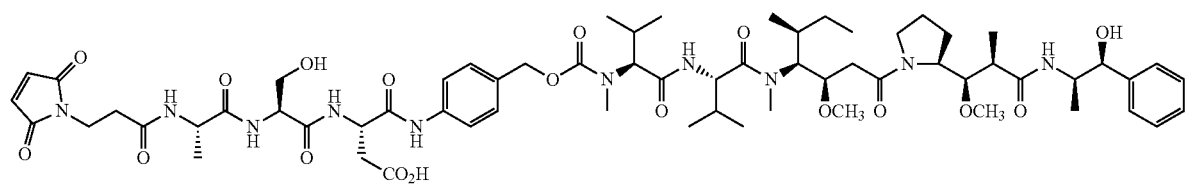
(29)
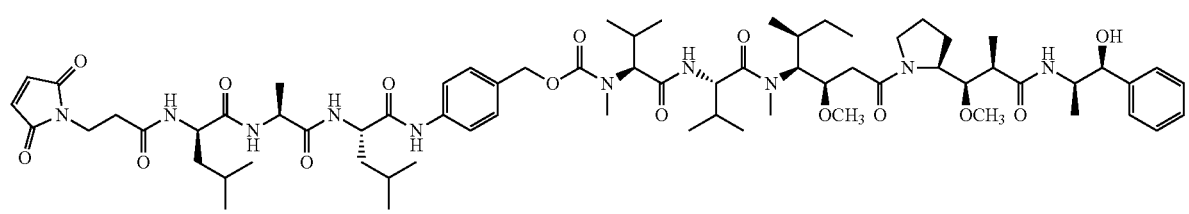

-continued
(30)
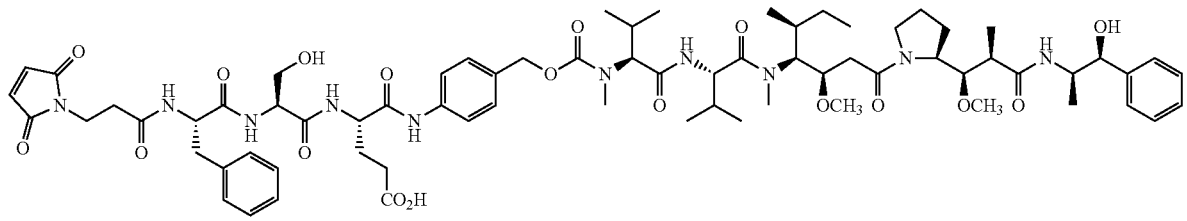
(31)
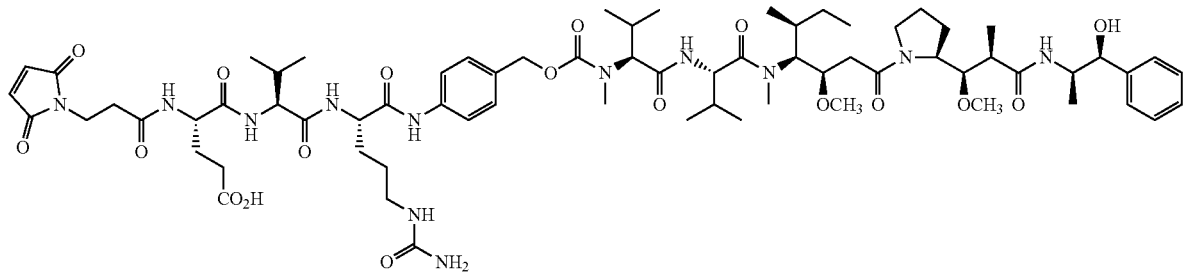
(32)
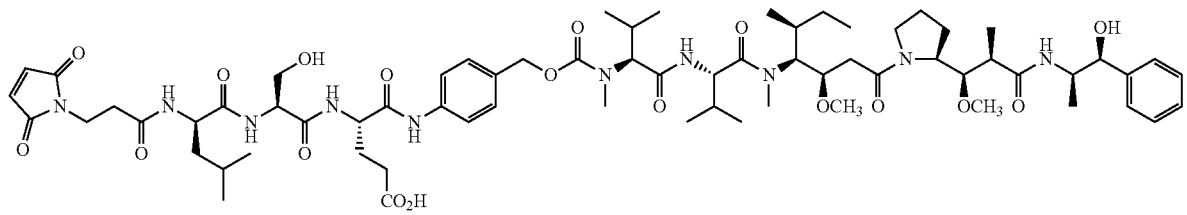
(33)
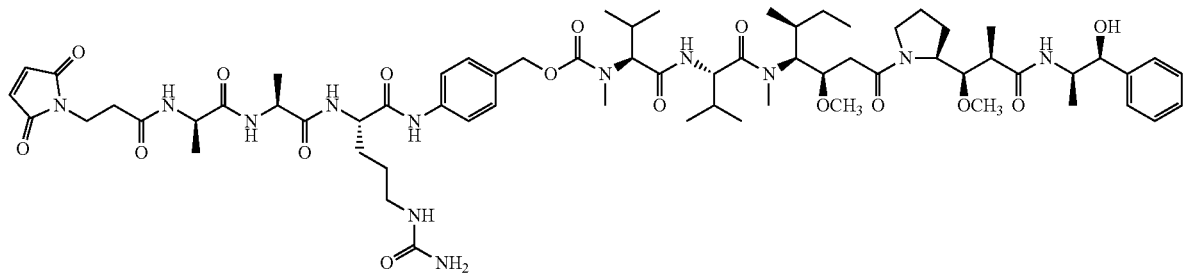
(34)
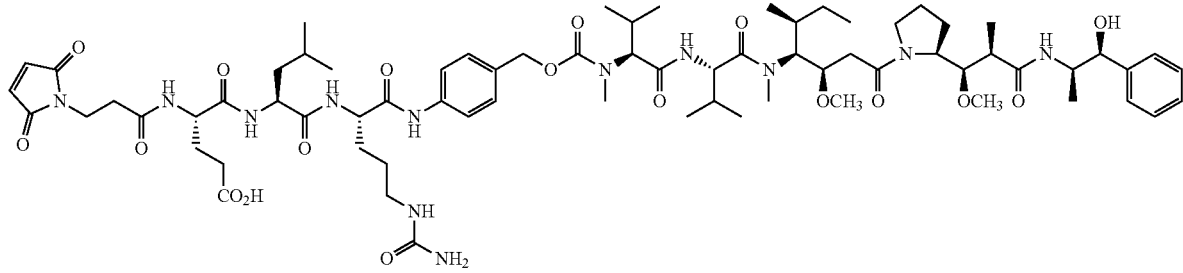
(35)
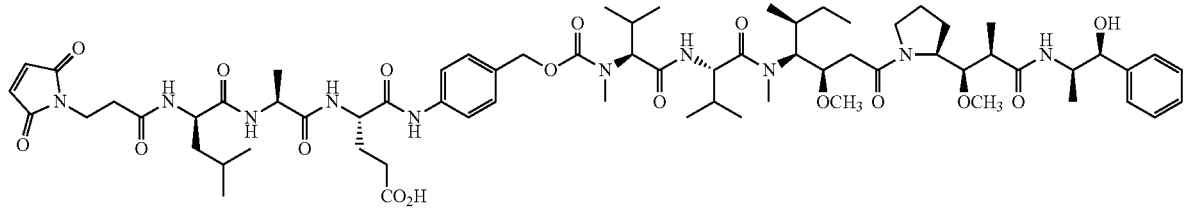

-continued
(36)
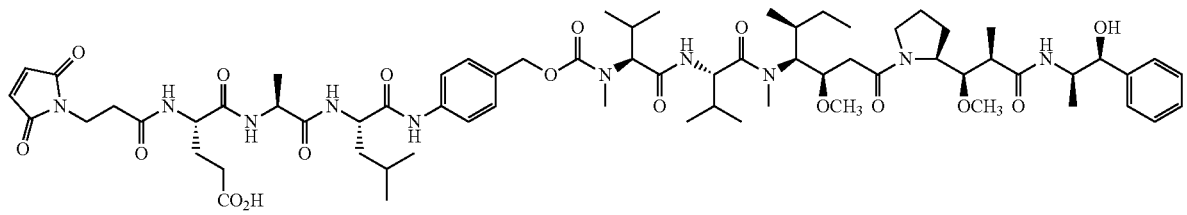
(37)
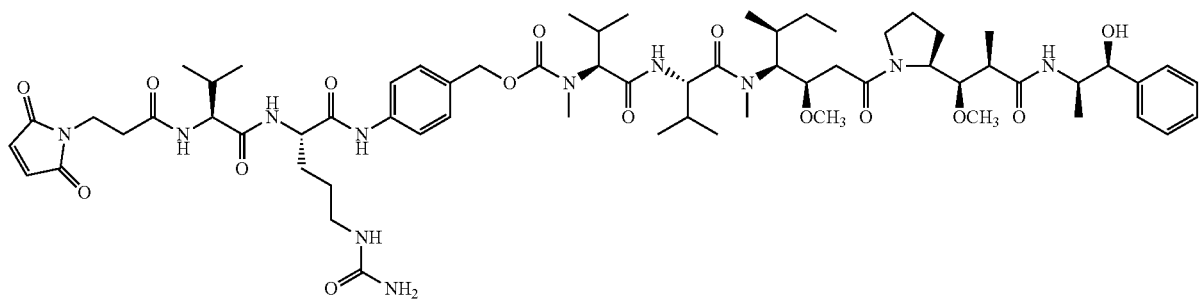
(38)
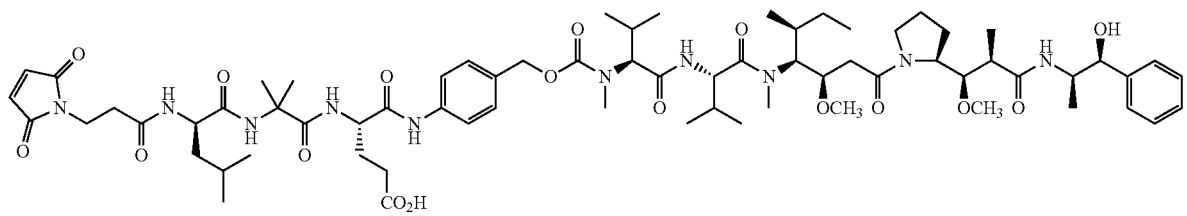
(39)
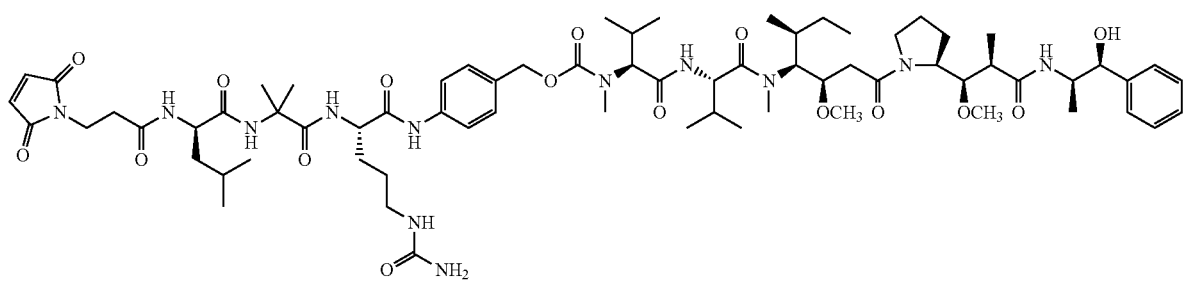
(40)
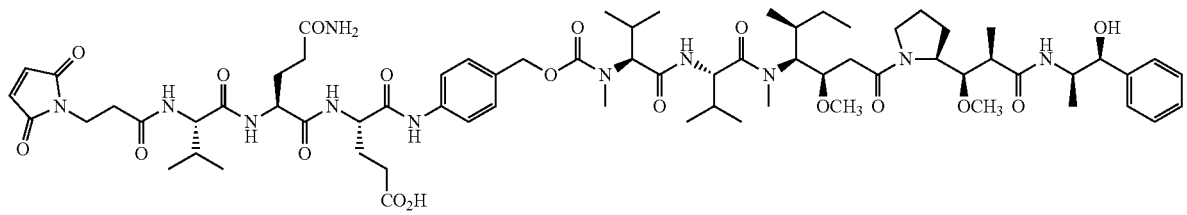
(41)
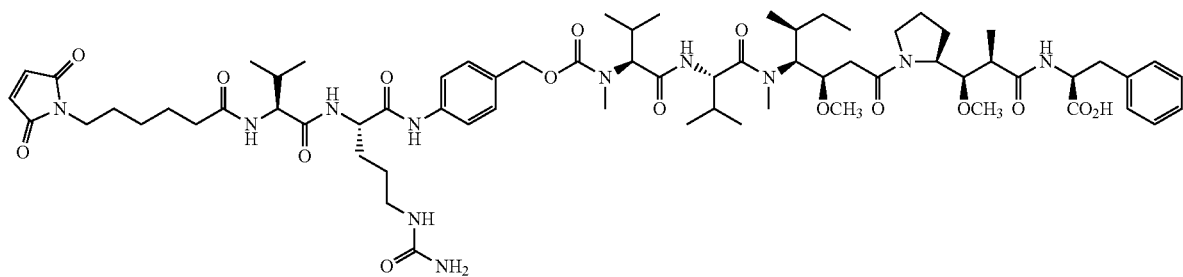

(42)
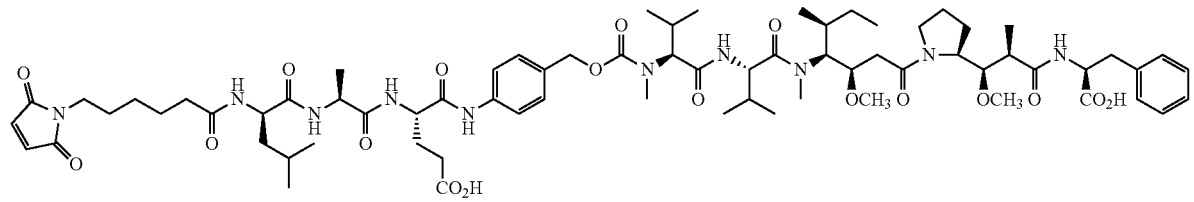
(45)
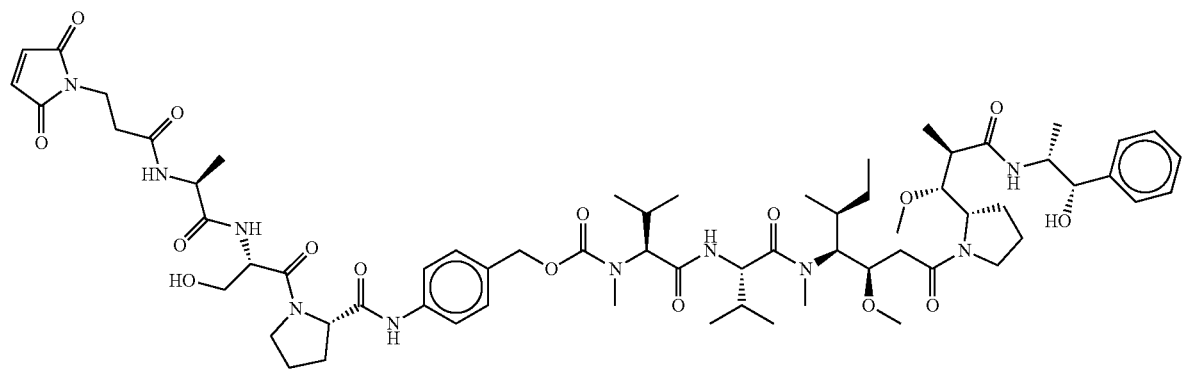
(46)
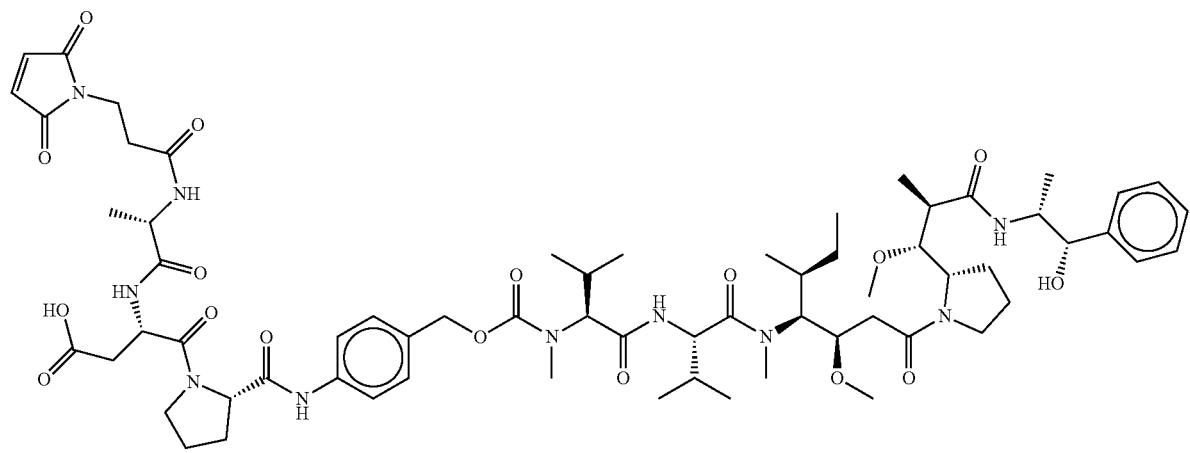
(47)
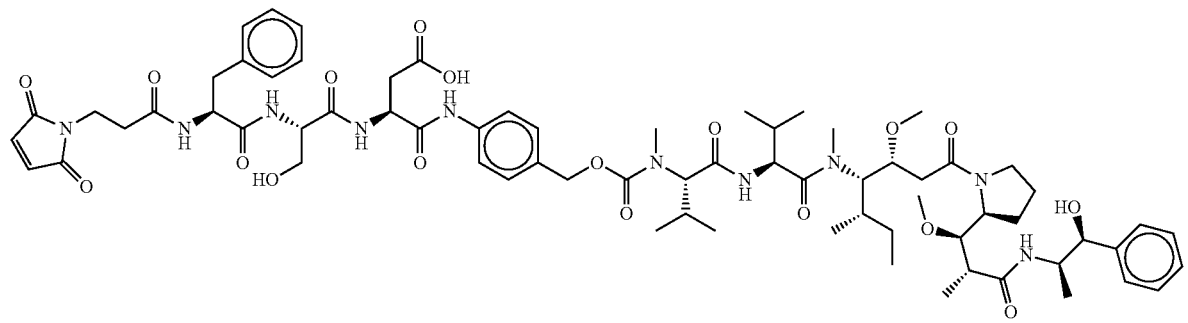

(48)
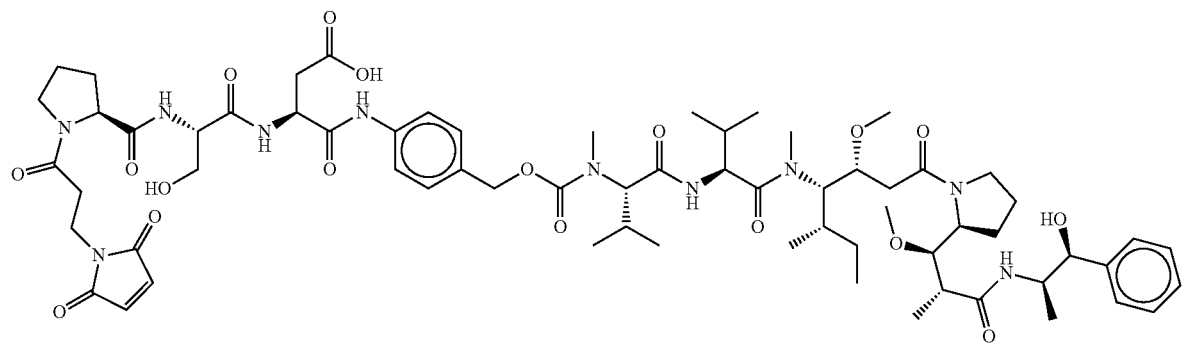
(49)
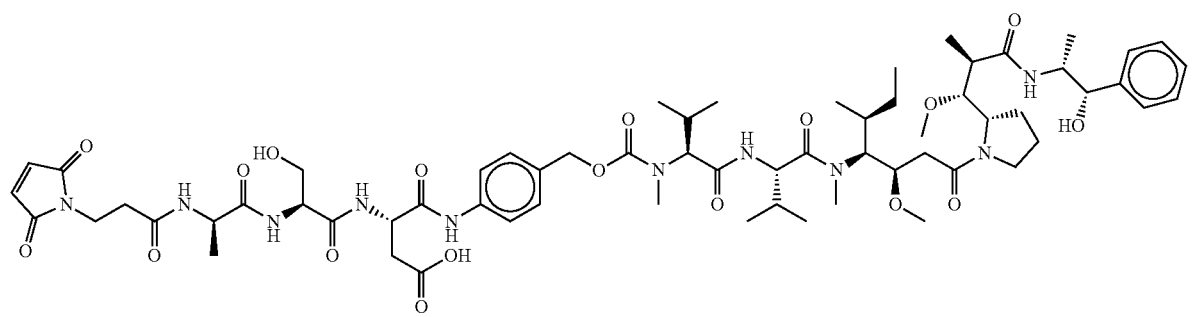
(50)
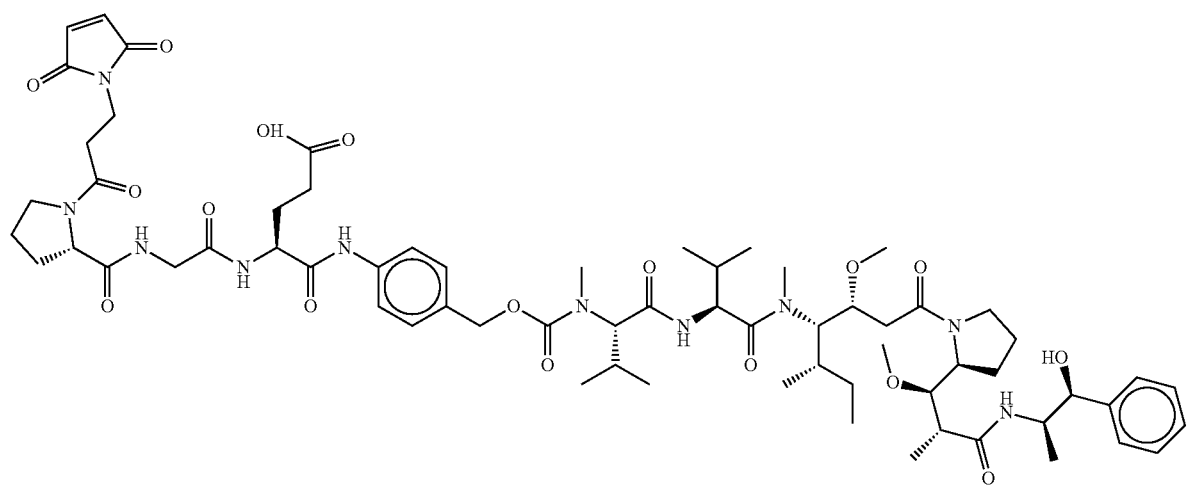
(51)
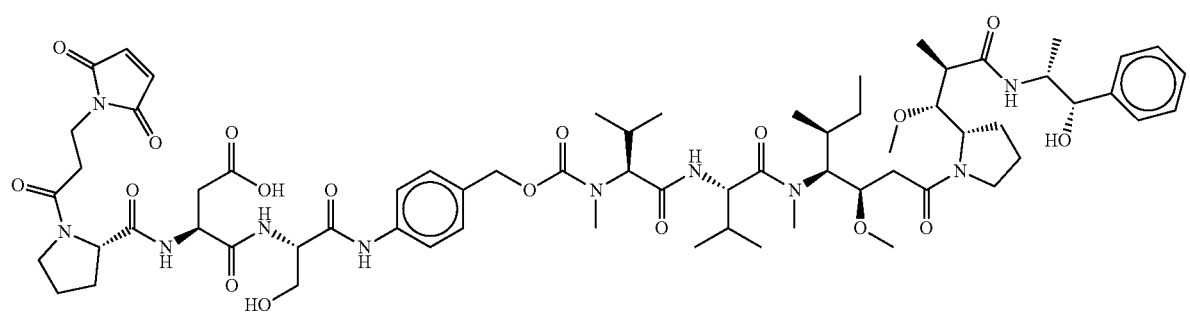

(52)
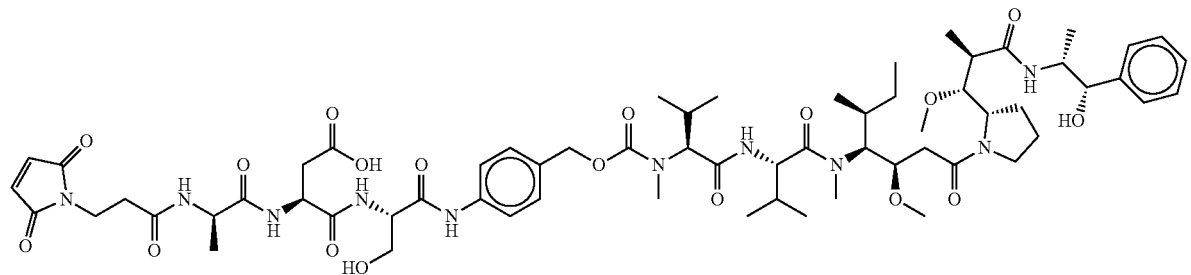
(53)
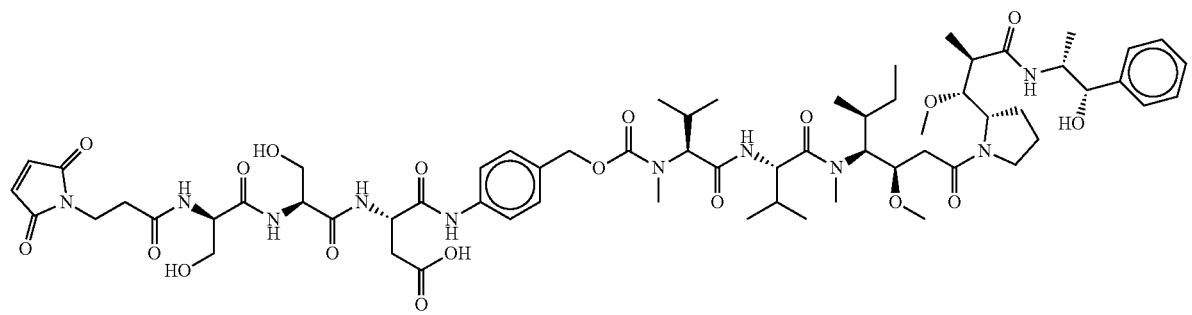
(54)
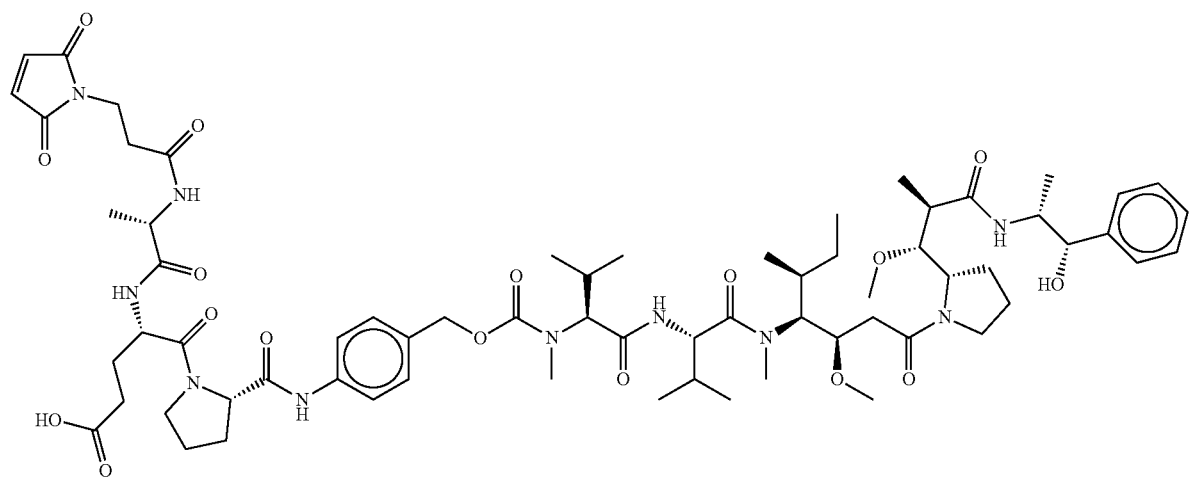
(55)
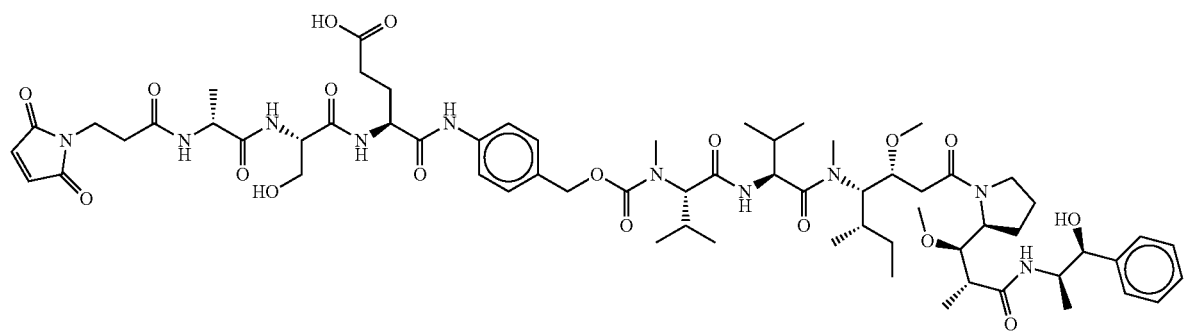

(56)
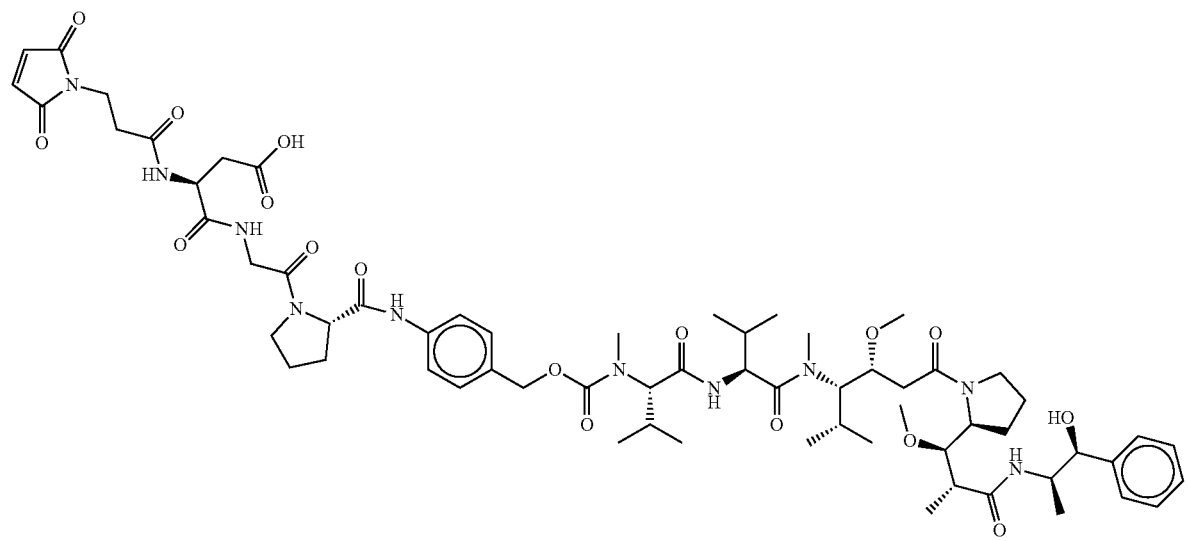
(57)
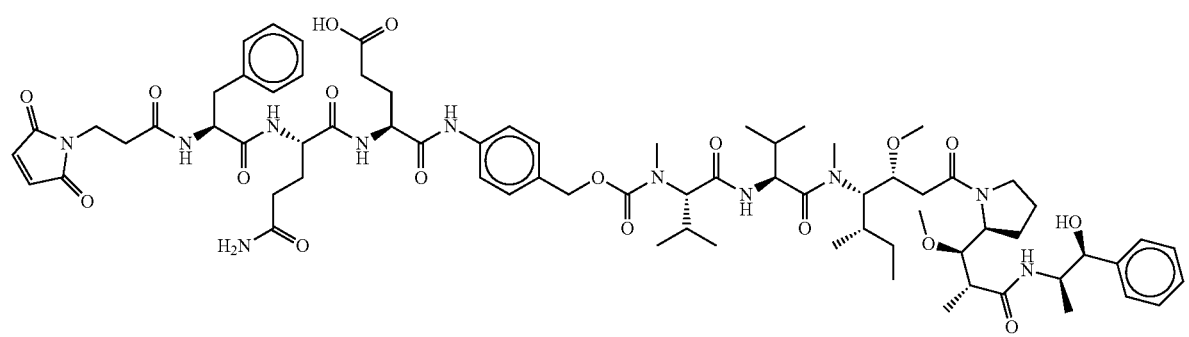
(58)
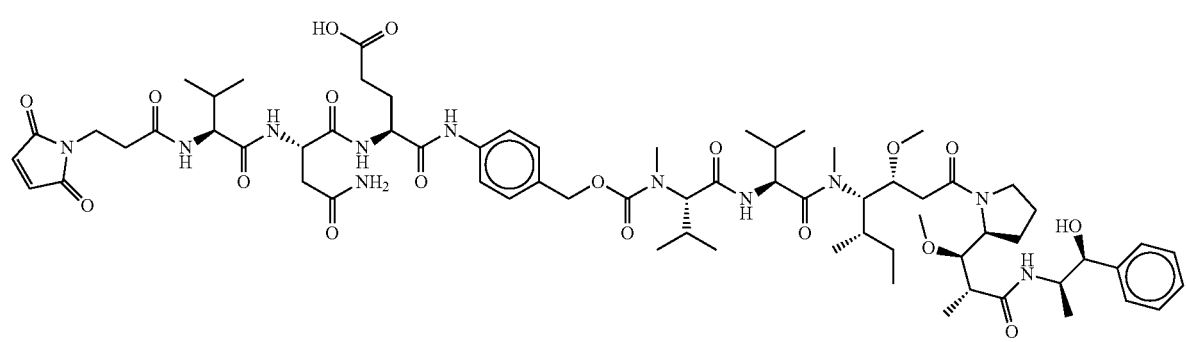
(59)
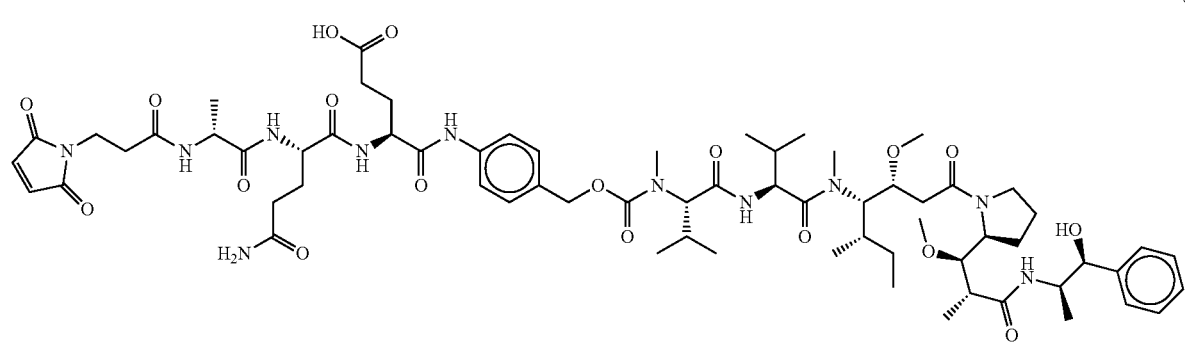

(60)
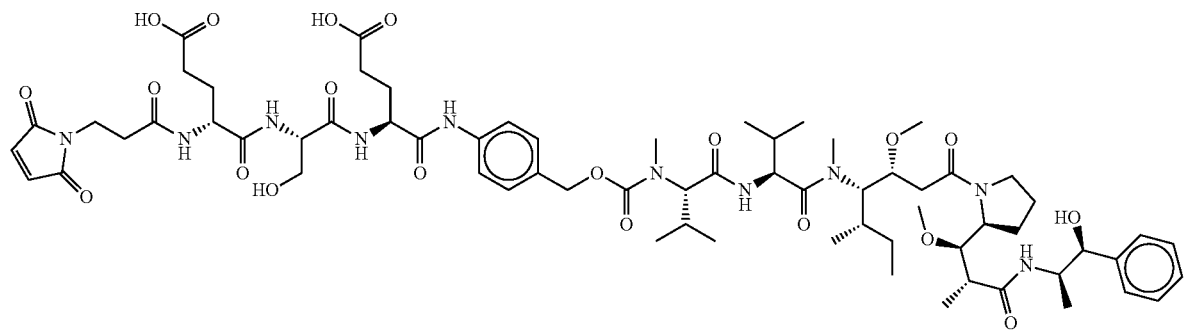
(61)
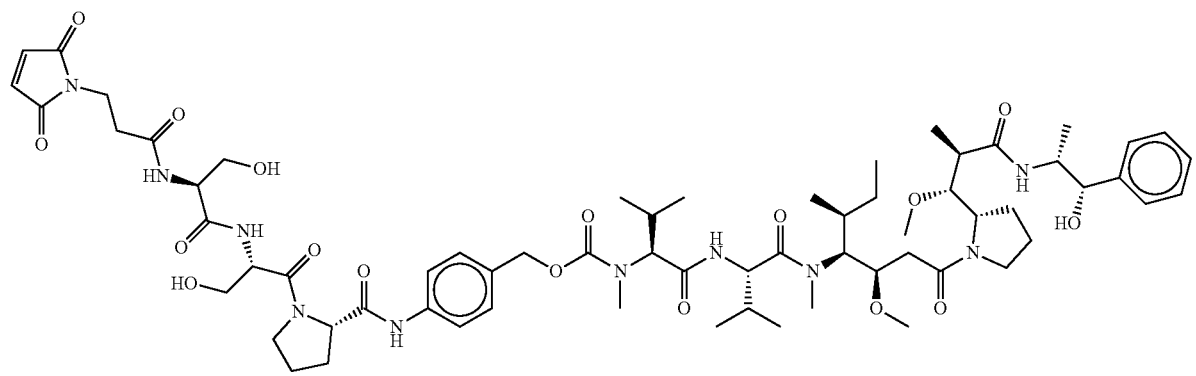
(62)
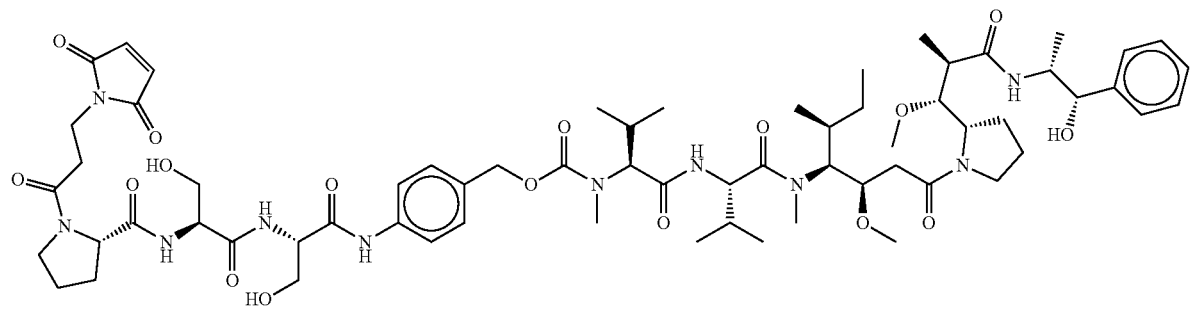
(63)
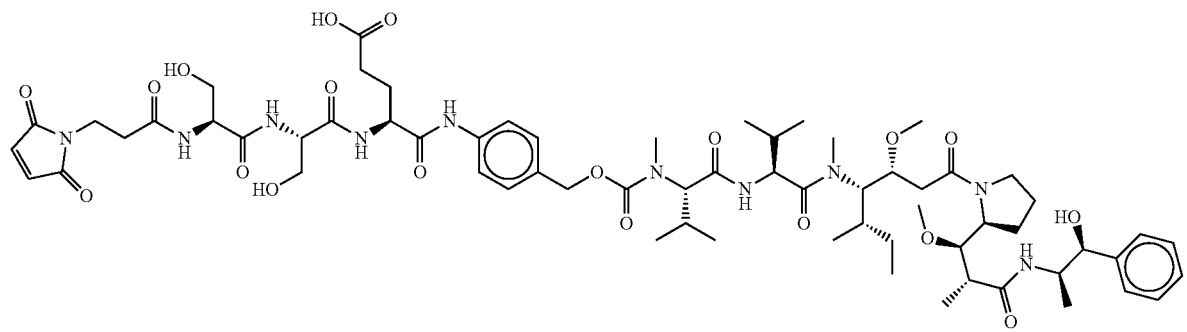

(64)
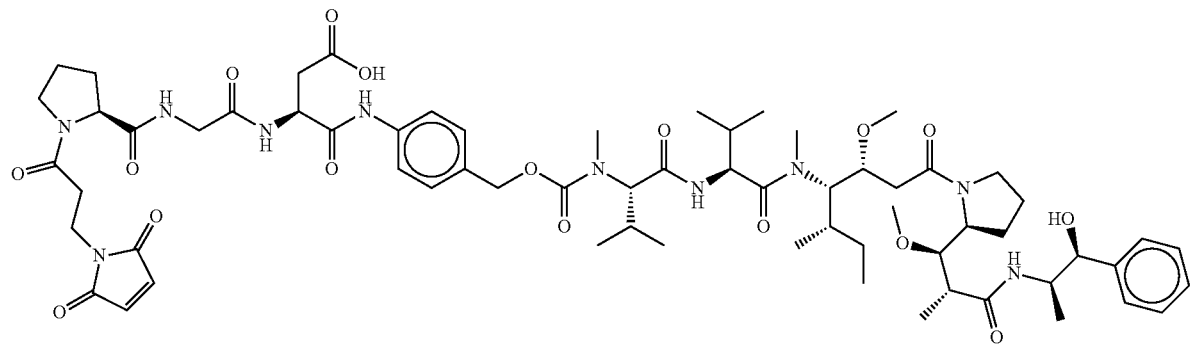
(65)
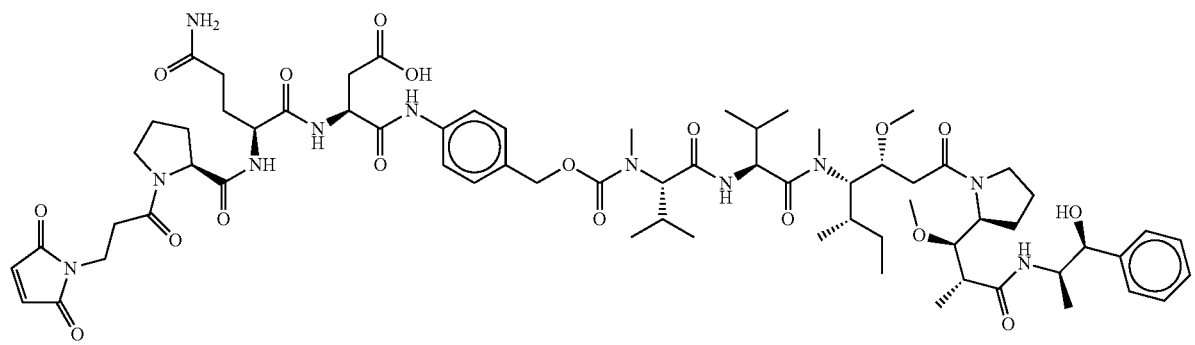
(66)
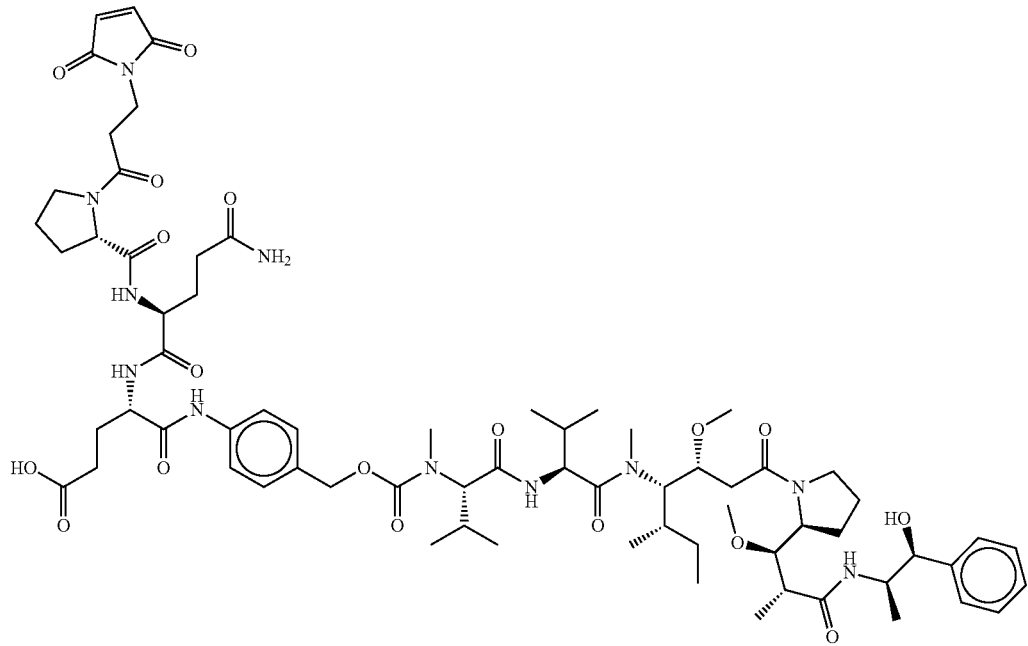

(67)
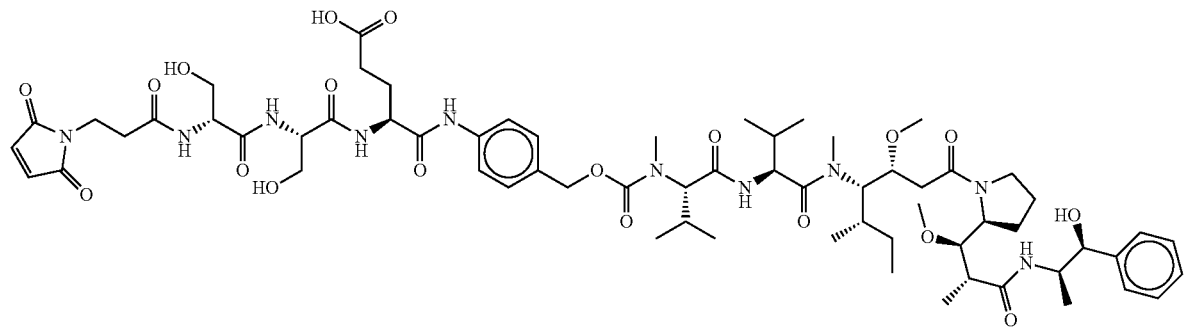
(68)
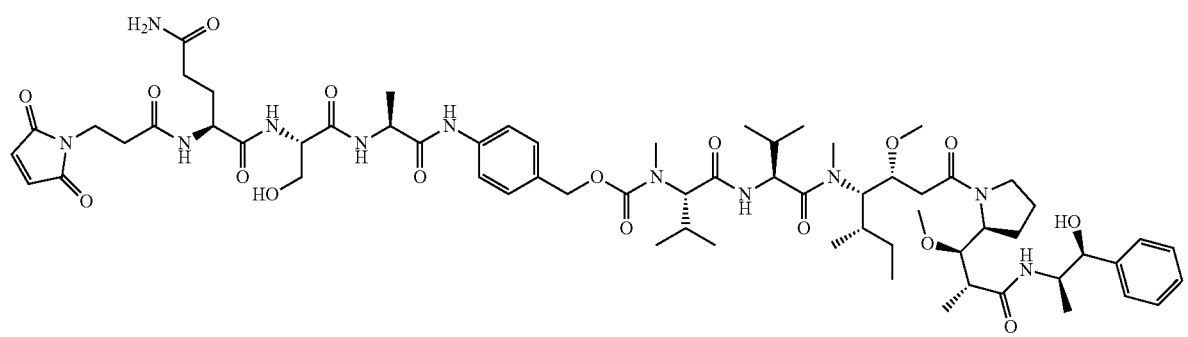
(69)
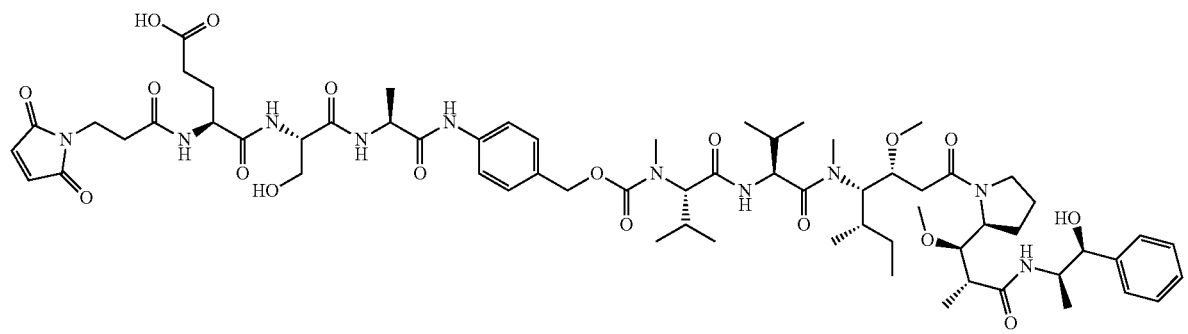
(70)
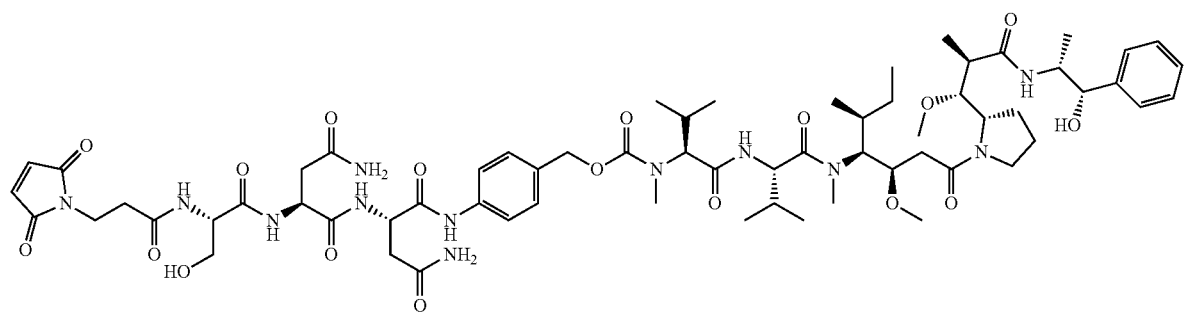

Example 11: Preparation of Tripeptide Based MMAF Drug Linker Compounds

Drug Linker compounds in which MMAF is the Drug Unit and which may be used for preparing a similar subset of Ligand Drug Conjugates discussed in Part A, are represented by the following structure and were prepared according the reaction sequence of Scheme 4 starting from commercially available L-phenylalanine-2-chlorotrityl ester polymer-bound.

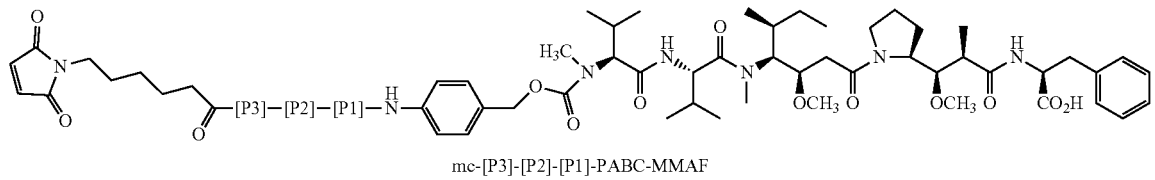

mc-[P3]-[P2]-[P1]-PABC-MMAF

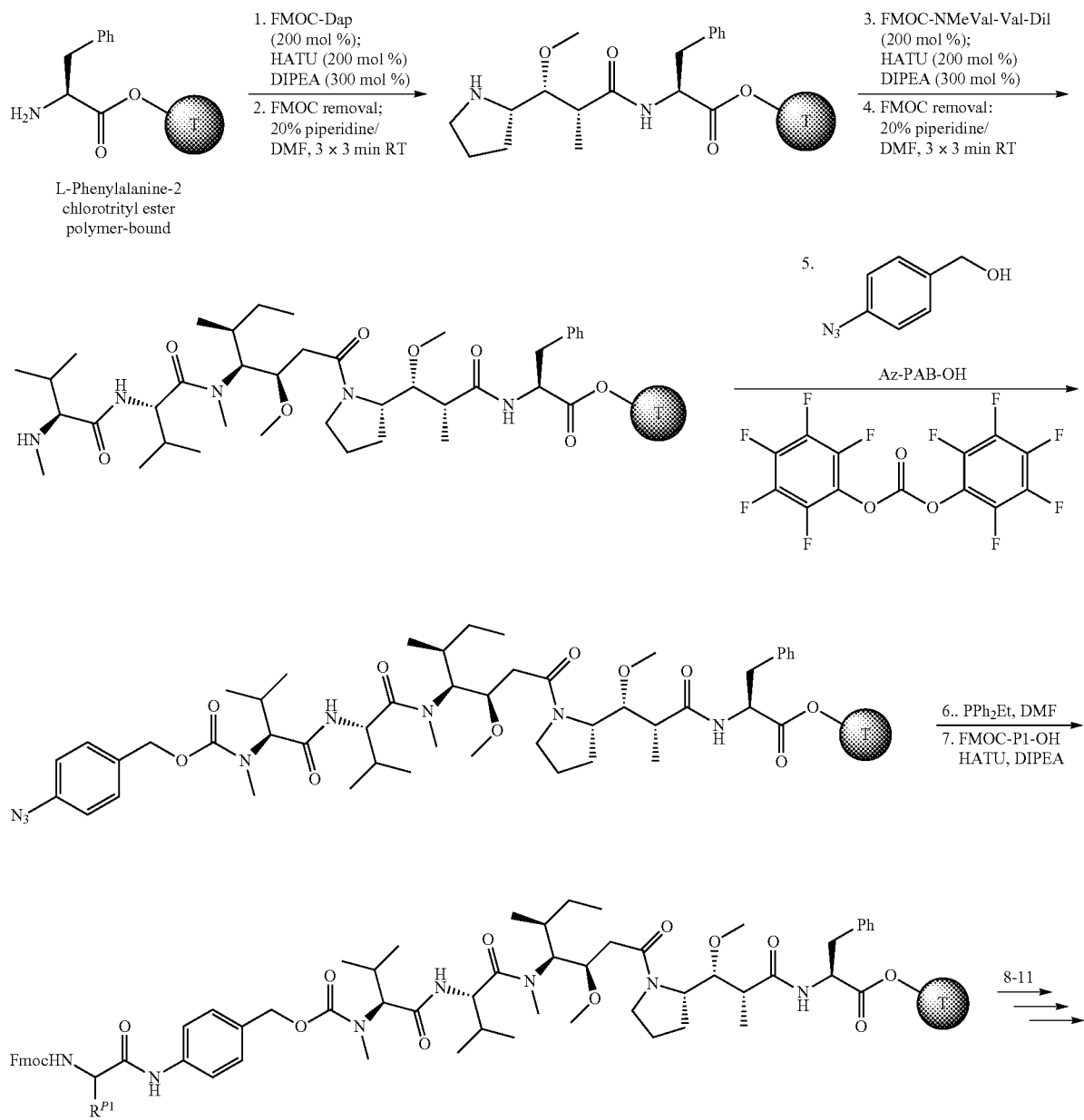

-continued

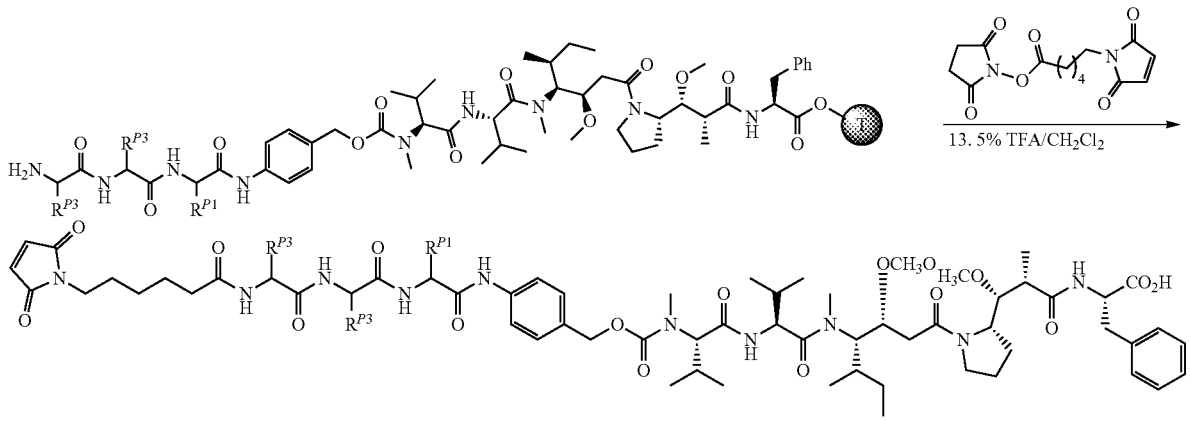

In Schemes 3 and 4, $R^1$, $R^2$ and $R^3$ are the side chains of the P1, P2 and P3 amino acid residues, respectively.

Example 12: In Vitro Cytotoxicity of Tripeptide-Based Antibody Drug Conjugates

Antibody Drug Conjugates having a drug antibody ratio (DAR) of about 4 were prepared according to the general procedures from the selected tripeptide based MMAE Drug-Linker compounds of Example 10 and a humanized antibody that selectively binds to an epithelial antigen (Ag1) that is commonly upregulated in various solid tumors including pancreatic, head and neck, lung, and esophageal tumors. Table 3 shows the $IC_{50}$ values against cells of a pancreatic adenocarcinoma cell line in which the Ag1 antigen is upregulated for the tripeptide-based ADCs (2-6) and for a dipeptide-based comparator conjugate (1) in which -val-cit- replaces the tripeptide Cleavable Unit. Table 3a shows the $IC_{50}$ values against cells of a HPAFII cell line in which the Ag1 antigen is upregulated for the tripeptide-based ADCs (8-10, 13, 16-21, 30, 31, and 38) and for a dipeptide-based comparator conjugate (1) in which -val-cit- replaces the tripeptide Cleavable Unit. Table 3b shows the $IC_{50}$ values against cells of a HPAFII cell line in which the Ag1 antigen is upregulated for the tripeptide-based ADCs (7, 15, 22-29, 32-36, 39, and 42) and for a dipeptide-based comparator conjugates (1 and 41) in which -val-cit- replaces the tripeptide Cleavable Unit. The italicized values in Tables 3, 3a, and 3b indicate the percentage of cells remaining after 96 hr incubation at the maximum concentration of drug added. For convenience the numbering for the library members of Tables 2 and 2A are retained for the corresponding Drug linker compounds that are incorporated into the ADC of Tables 3, 3a, and 3b.

TABLE 3

Cytotoxicity of ADCs against pancreatic adenocarcinoma cells

| ADC | Cytotoxicity | |
|---|---|---|
| | $IC_{50}$ | % |
| Ag1-1 | 54 | 21 |
| Ag1-2 | 36 | 21 |
| Ag1-3 | 22 | 22 |
| Ag1-4 | 35 | 21 |

TABLE 3-continued

Cytotoxicity of ADCs against pancreatic adenocarcinoma cells

| ADC | Cytotoxicity | |
|---|---|---|
| | $IC_{50}$ | % |
| Ag1-5 | 62 | 23 |
| Ag1-6 | 30 | 20 |

The results of Table 3 show that the tripeptide-based ADCs (2-6) are equipotent with the comparator dipeptide-based ADC (1) whose tolerability is to be improved by replacing its dipeptide Cleavable Unit with each of the selected tripeptide sequences.

TABLE 3a

Cytotoxicity of ADCs against HPAFII cells

| ADC | Cytotoxicity | |
|---|---|---|
| | $IC_{50}$ | % |
| Ag1-1 | 39 | 32 |
| Ag1-8 | 279 | 39 |
| Ag1-9 | 85 | 34 |
| Ag1-10 | 37 | 32 |
| Ag1-13 | 69 | 21 |
| Ag1-16 | 83 | 29 |
| Ag1-17 | 57 | 24 |
| Ag1-18 | 81 | 27 |
| Ag1-19 | 29 | 24 |
| Ag1-20 | 70 | 31 |
| Ag1-21 | 75 | 25 |
| Ag1-30 | 144 | 31 |
| Ag1-31 | 47 | 21 |
| Ag1-38 | 484 | 54 |

The results of Table 3a show that several of the tripeptide-based ADCs (e.g. 8 and 30) are less cytotoxic than the comparator dipeptide-based ADC (1), but are similarly efficacious. The results of Table 3a also show that some tripeptide-based ADCs (e.g. 38) are less cytotoxic and efficacious than the comparator dipeptide-based ADC (1), but are less toxic to rat bone marrow, which may still afford an increased therapeutic window compared to comparator dipeptide-based ADC (1).

TABLE 3b

Cytotoxicity of ADCs against HPAFII cells

| ADC | Cytotoxicity | |
|---|---|---|
| | IC$_{50}$ | % |
| Ag1-1 | 413 | 12 |
| Ag1-7 | 226 | 29 |
| Ag1-15 | 802 | 33 |
| Ag1-22 | 2210 | NA |
| Ag1-23 | 581 | 31 |
| Ag1-24 | 1239 | 32 |
| Ag1-25 | 499 | 26 |
| Ag1-26 | 1725 | 37 |
| Ag1-27 | 99 | 11 |
| Ag1-28 | 768 | 22 |
| Ag1-29 | 261 | 20 |
| Ag1-32 | 318 | 32 |
| Ag1-33 | 279 | 11 |
| Ag1-34 | 158 | 21 |
| Ag1-35 | 859 | 27 |
| Ag1-36 | 160 | 15 |
| Ag1-39 | 2352 | 40 |
| Ag1-41 | 16 | 23 |
| Ag1-42 | 56 | 30 |

The results of Table 3b show that some of the tripeptide-based ADCs (e.g. 22, 24, and, 26) may be less cytotoxic than the comparator ADC (1), but are similarly efficacious.

Example 13: In Vivo Cancer Cell Cytotoxicity of Tripeptide-Based Antibody Drug Conjugates The ADCs of Table 3 were tested in a xenograft model in which cells of the pancreatic adenocarcinoma cell line of Example 12 were implanted in nude mice. Each tripeptide-based ADC was administered at the same subcurative dose (4 mg/Kg) determined for the dipeptide-based comparator conjugate in order to clearly distinguish efficacy differences. As seen in FIG. 1A, most tripeptide-based ADCs are at least as efficacious as the dipeptide-based comparator ADC.

Figure 1B:
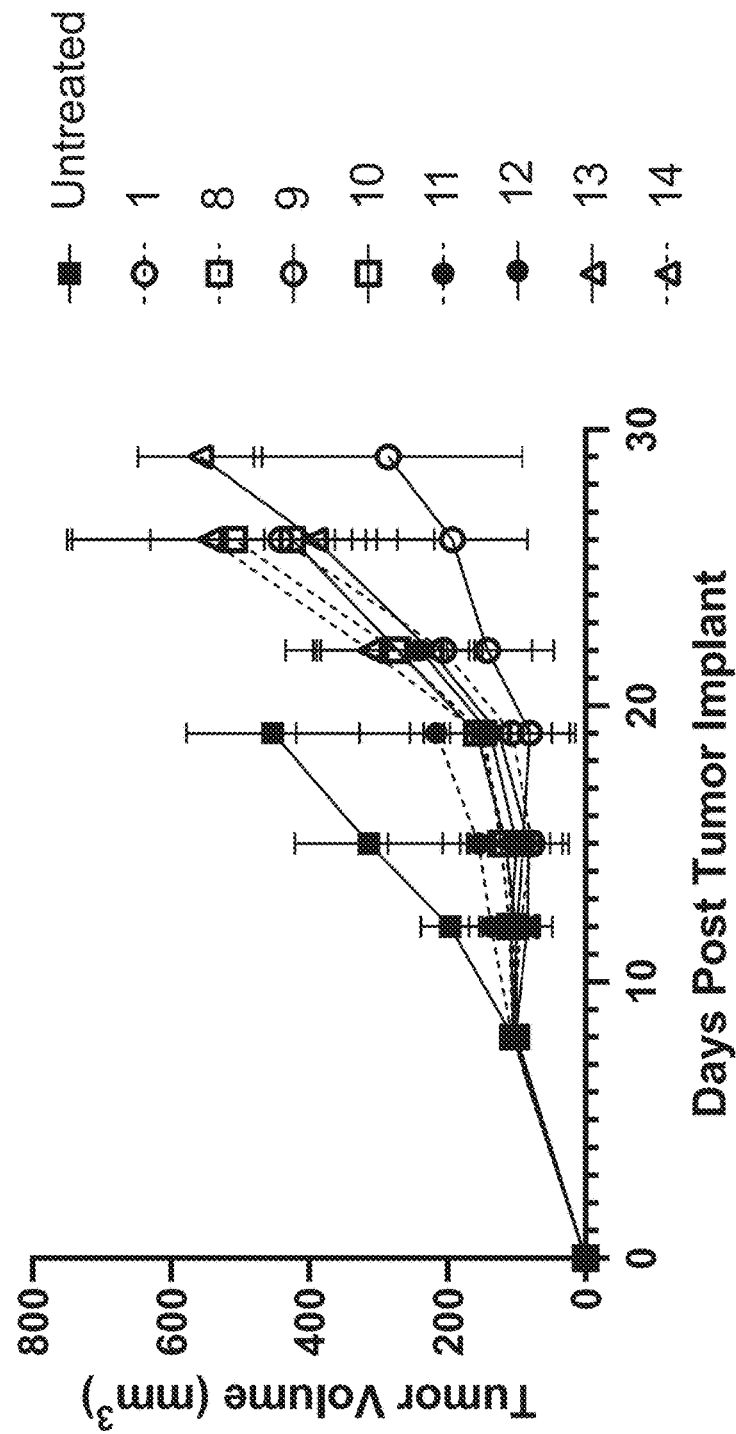
Figure 1C:
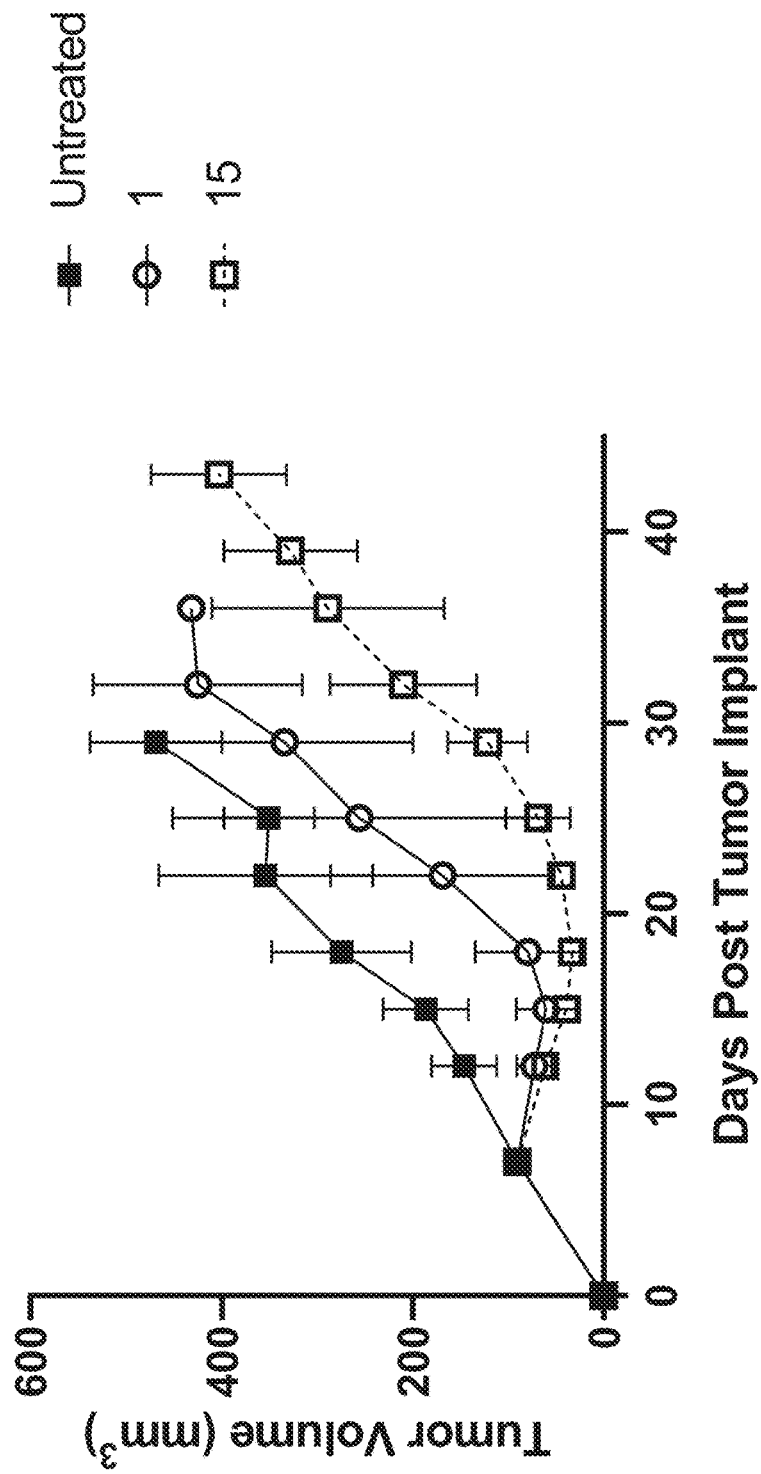
Figure 1D:
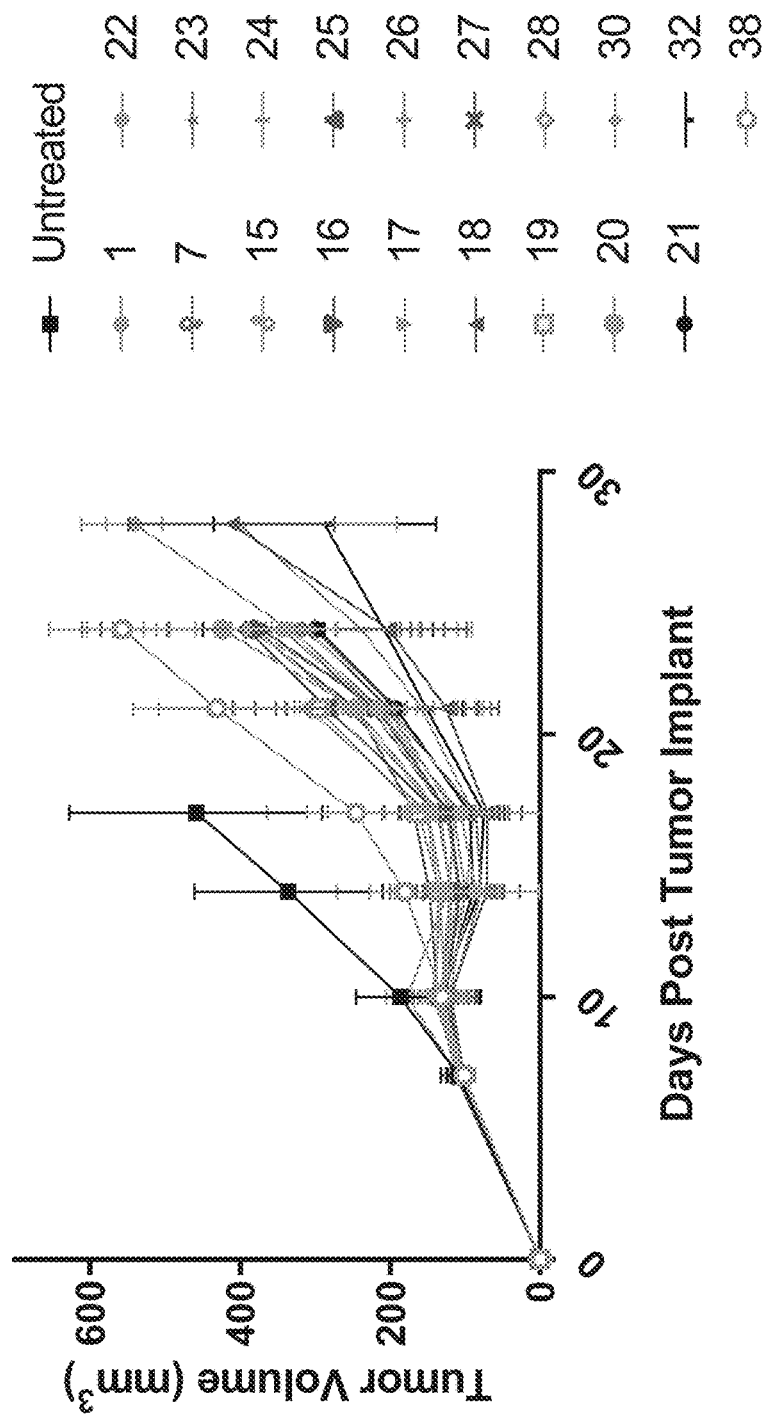

The ADCs of Table 3a were tested in a xenograft model in which cells of the HPAFII cell line of Example 12 are implanted in nude mice. Each tripeptide-based ADC is administered at the same subcurative dose (3 mg/Kg) determined for the dipeptide-based comparator conjugate in order to clearly distinguish efficacy differences. As seen in FIGS. 1B and 1D, most tripeptide-based ADCs are generally at least as efficacious as the dipeptide-based comparator ADC.

The ADCs of Table 3b were tested in a xenograft model in which cells of the HPAFII cell line of Example 12 are implanted in nude mice. Each tripeptide-based ADC was administered at the same subcurative dose (3 mg/Kg), except tripeptide-based ADC Ag1-15 and the comparator dipeptide-based ADC that were both tested at 6 mg/kg (FIG. 1C), determined for the dipeptide-based comparator conjugate in order to clearly distinguish efficacy differences. As seen in FIGS. 1C and 1D, certain tripeptide-based ADCs are at least as efficacious as the dipeptide-based comparator ADC.

Example 14: In Vivo Bone Marrow Toxicity of Tripeptide-Based Antibody Drug Conjugates Having shown that ADC efficacy has been at least retained on replacing the dipeptide with most of the selected tripeptide sequences, differences in in vivo cytotoxicity against normal bone marrow tissue was explored by replacing the antibody targeting the Ag1 antigen with a non-binding control (h00) antibody. Each of the resulting non-targeting conjugates were then administered at 10 mg/Kg to rats, whose blood were analyzed at day 5 post-administration for neutrophil and reticulocyte counts as a proxy for bone marrow toxicity compared to sham treated animals. As seen from FIG. 2A some of the tripeptide-based h00 conjugates from Tables 3, 3a, and 3b showed improved neutrophil counts in comparison to the dipeptide-based comparator conjugate (h00-1). With respect to neutrophil counts, the tripeptide-based non-binding conjugates h00-4 and h00-5 showed similar preservation of that bone marrow cell type in comparison to h00-1. However, from the non-binding conjugates analogous to the targeting ADCs of Table 3, only the D-Leu-Ala-Glu non-binding control conjugate (h00-5) corresponding to the tripeptide-based targeting ADC of Table 3 (Ag1-5) exhibited an improved reticulocyte count relative to the comparator conjugate at the tested dose. Many more non-binding conjugates analogous to the targeting ADCs of Tables 3a and 3b exhibited improved preservation of neutrophil counts in comparison to h00-1. Comparisons between FIGS. 2A and 3A seem to indicate that reticulocytes are more sensitive to the MMAE non-binding conjugates than neutrophils, which is believed to be the reason that differences between the other tripeptide-based h00 non-binding conjugates analogous to the targeting ADCs of Table 3 could not be distinguished from each other or from h00-1 at the tested dose. Many more non-binding conjugates analogous to the targeting ADCs of Tables 3a and 3b exhibited improved preservation of reticulocyte counts in comparison to h00-1.

Figure 4:
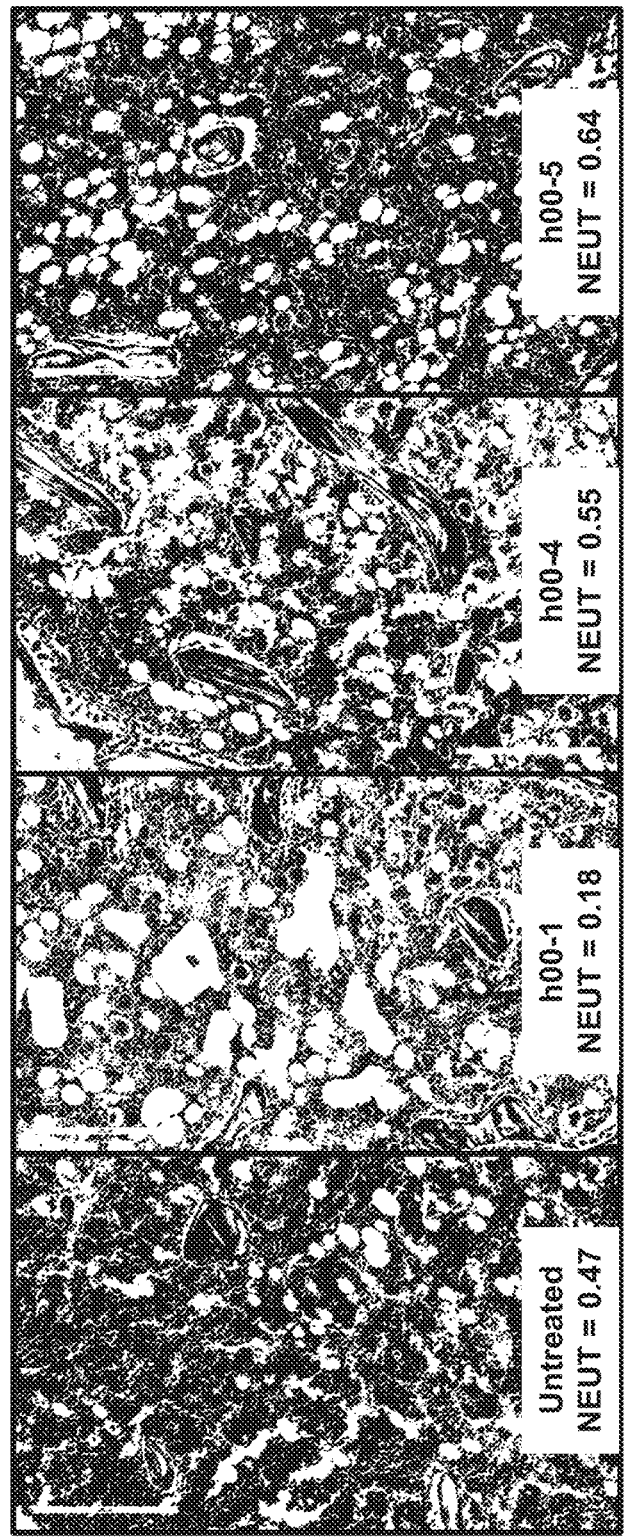
FIG. 4. Histopathology of bone marrow of rat after administration to non-tumor bearing animals at day 4 of vehicle or 10 mg/Kg of 4-loaded non-binding conjugates having varying tripeptide sequences as the Peptide Cleavable Unit with drug-linker moieties represented by the formula of mp-$P_3$-$P_2$-$P_1$-PABC-MMAE in comparison to a 4-loaded non-binding conjugate having drug-linker moieties represented by the formula of mc-val-cit-PABC-MMAE.

Histopathology of the bone marrow with IHC for mononuclear cells, which is shown in FIG. 4, confirms the preservation of mononuclear bone marrow cells by the tripeptide-based h00-4 and h00-5 conjugate compared with administration of the dipeptide-based comparator h00-1, with the result from administration of h00-5 conjugate being almost indistinguishable from sham treatment.

Figure 2A:
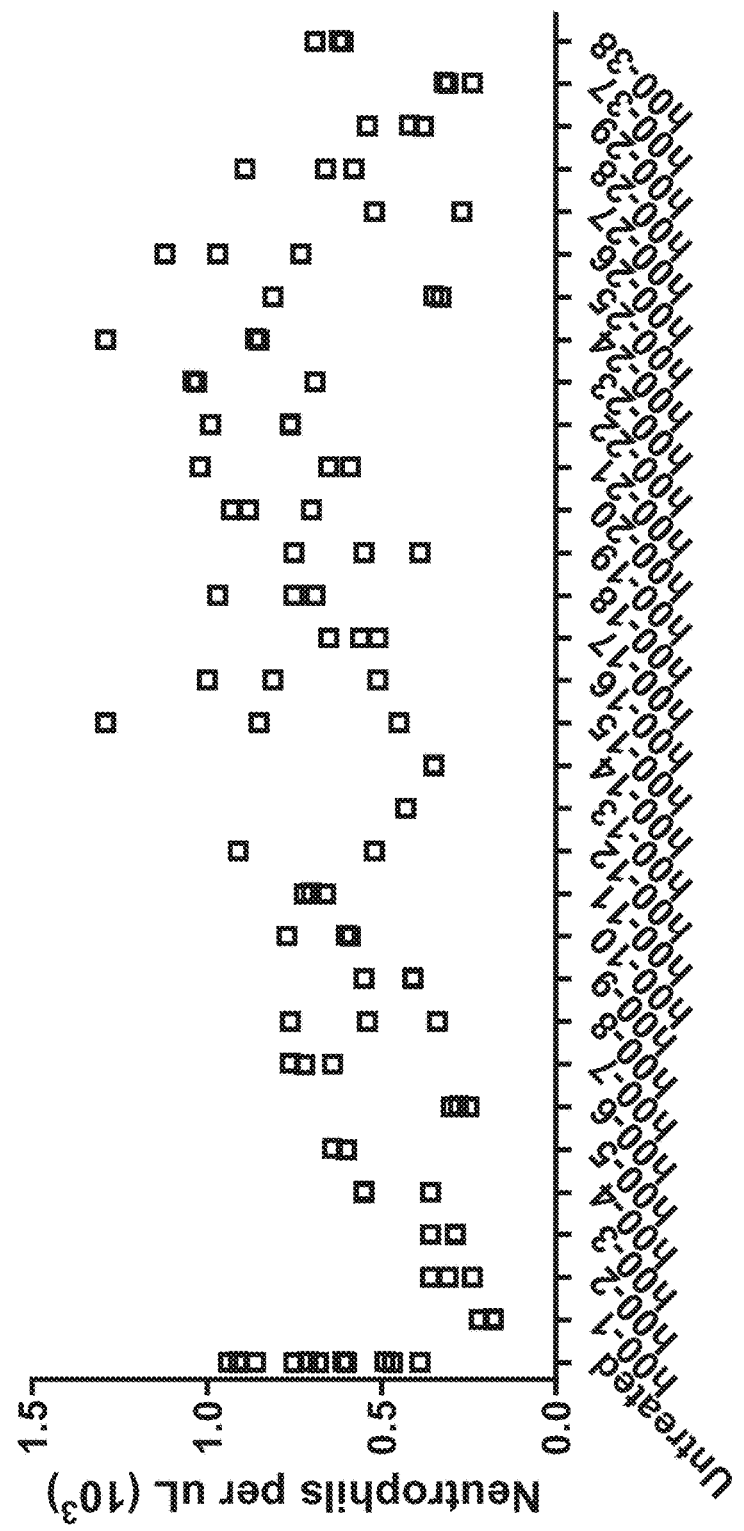
FIGS. 2A-2C. Neutrophil counts after day 4 of 10 mg/Kg administration (FIGS. 2A and 2B) or after days 8 and 22 of a highest tolerated dose (FIG. 2C) of a series of 4-loaded non-binding control conjugates having varying tripeptide sequences as the Peptide Cleavable Unit with drug-linker moieties represented by the formula of mp-$P_3$-$P_2$-$P_1$-PABC-MMAE in comparison to 4-loaded non-binding conjugates having drug-linker moieties represented by the formula of mc-val-cit-PABC-MMAE or mp-val-cit-PABC-MMAE.
Figure 2B:
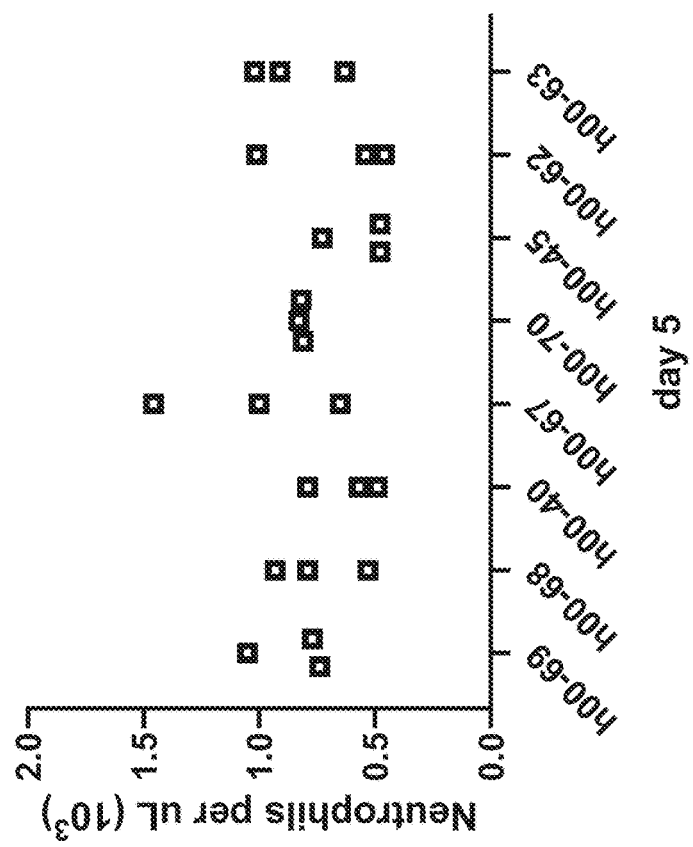
Figure 3A:
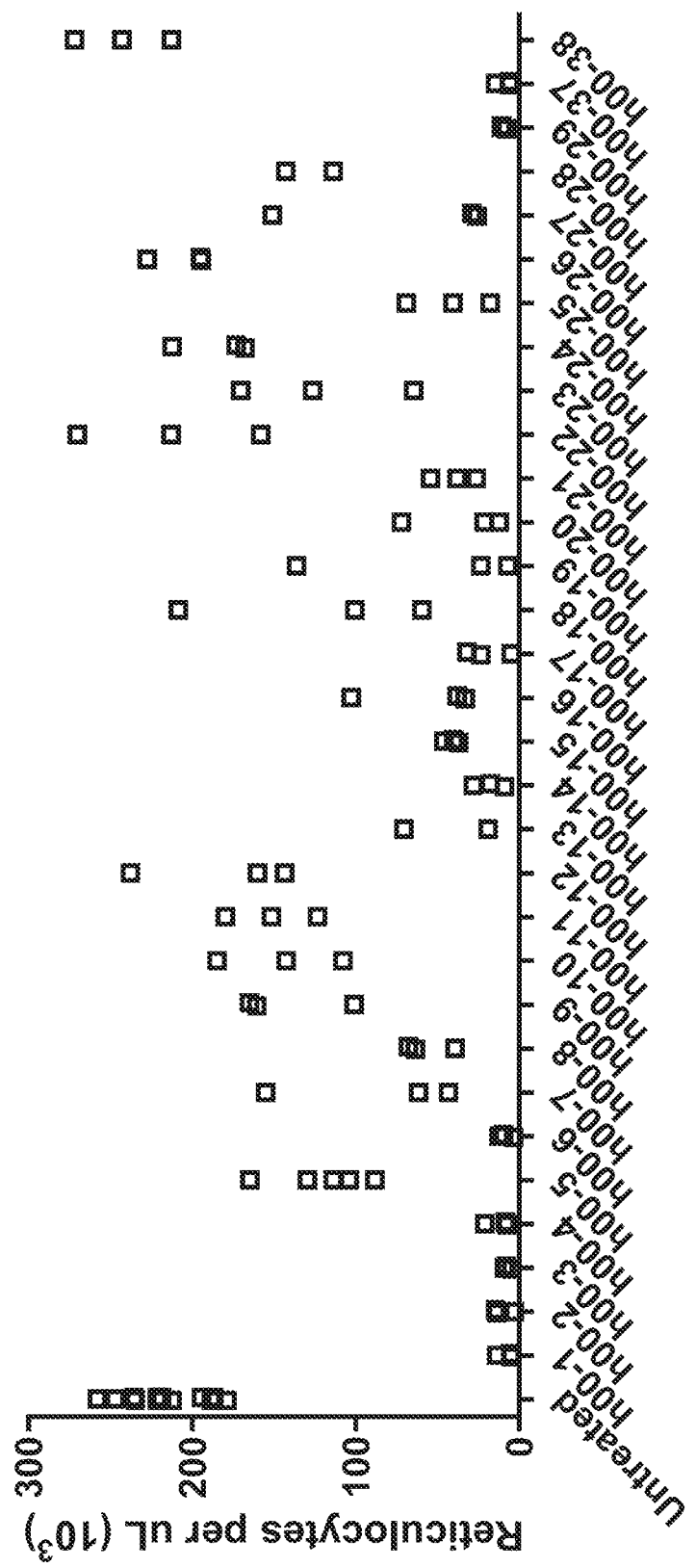
FIGS. 3A-3C. Reticulocyte counts in rat plasma after day 4 from 10 mg/Kg administration (FIGS. 3A and 3B) or after days 8 and 22 of a highest tolerated dose (FIG. 3C) to non-tumor bearing animals of a series of 4-loaded non-binding conjugates having varying tripeptide sequences as the Peptide Cleavable Unit with drug-linker moieties represented by the formula of mp-$P_3$-$P_2$-$P_1$-PABC-MMAE in comparison to 4-loaded non-binding conjugates having drug-linker moieties represented by the formula of mc-val-cit-PABC-MMAE or mp-val-cit-PABC-MMAE.
Figure 3B:
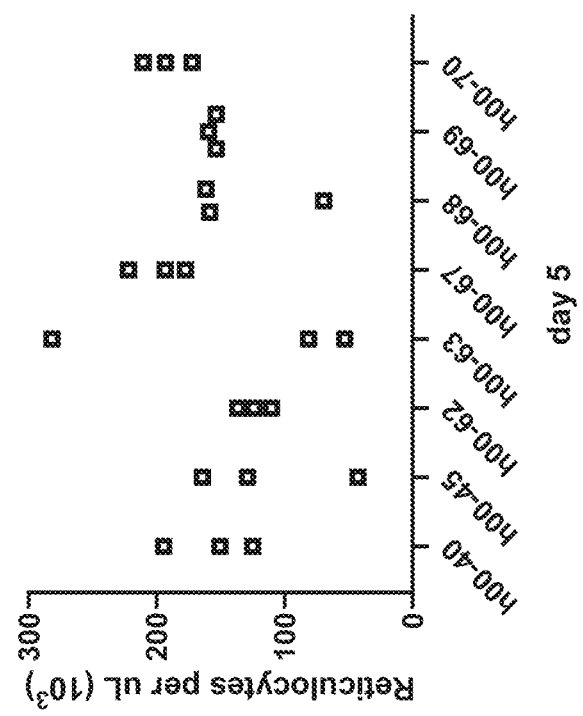

Included in FIGS. 2A and 3A is data for h00-7 in which the tripeptide sequence is Leu-Ala-Glu. That tripeptide is identical to that of h00-5 except that the stereochemical configuration of the P3 amino acid has been inverted. Both h00-5 and h00-7 appear to be less toxic to bone marrow than the other non-binding control ADCs with h00-5 being superior with respect to preserving the more sensitive reticulocytes.

Figure 2C:
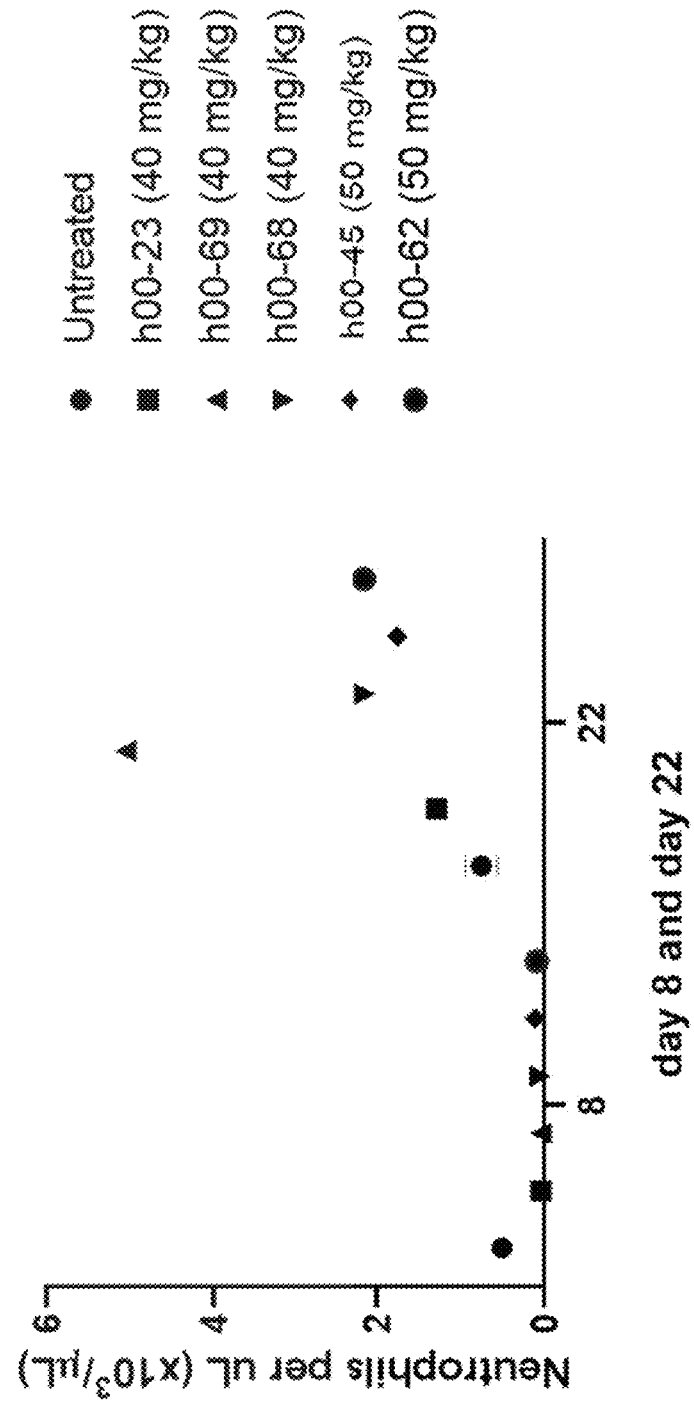
Figure 3C:
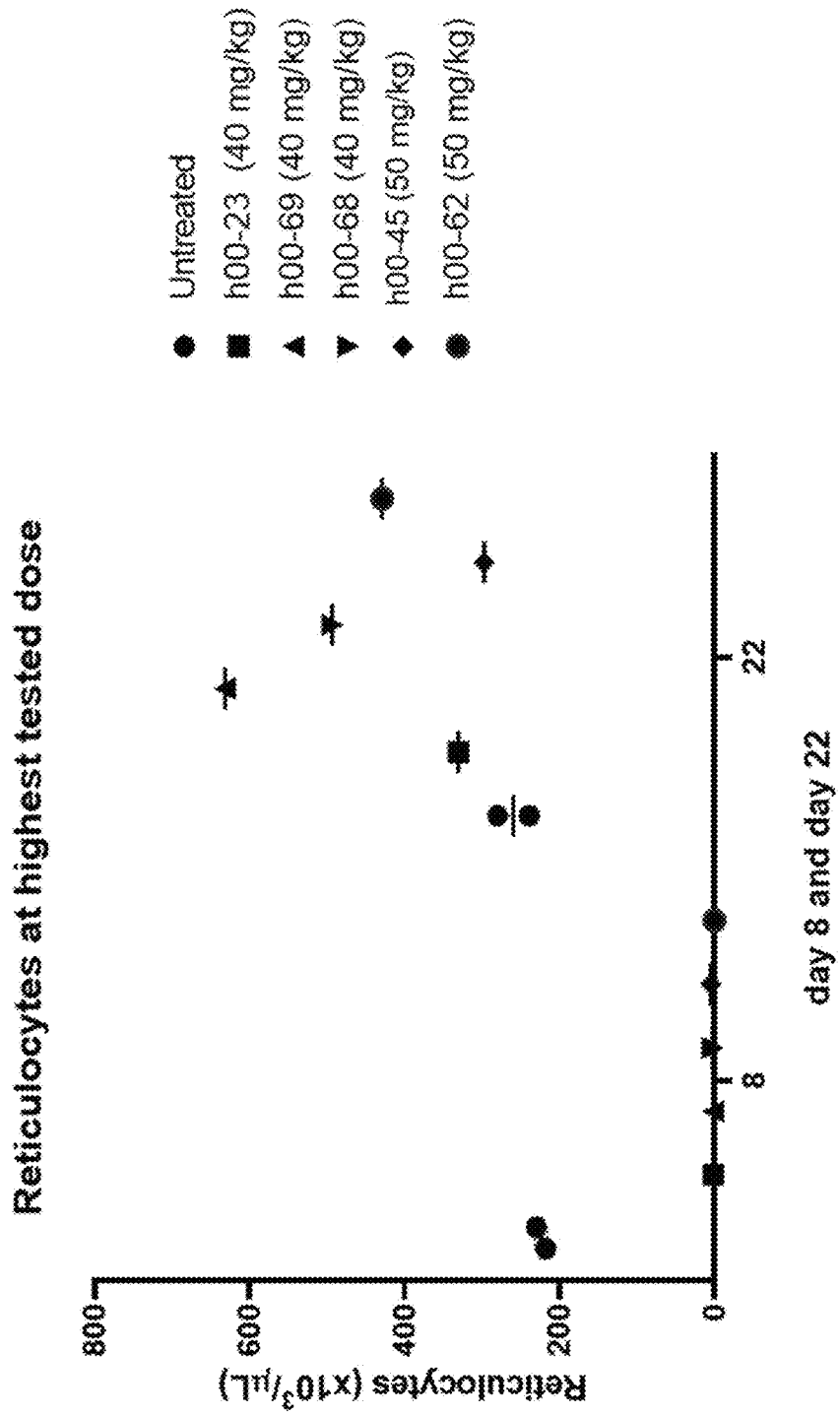

A subset of non-targeting conjugates were administered at higher doses to rats to determine the impact on bone marrow depletion. Blood from the doses rats were analyzed at day 8 and day 22 post-administration for neutrophil (FIG. 2C) and reticulocyte (FIG. 3C) counts as a proxy for bone marrow toxicity compared to sham treated animals. For h00-23, h00-68 and h00-69 the animals tolerated the ADC at 40 mg/kg single dose (n=1). For h00-45 and h00-62, animals tolerated the highest tested dose of 50 mg/kg (n=1).

Figure 14:
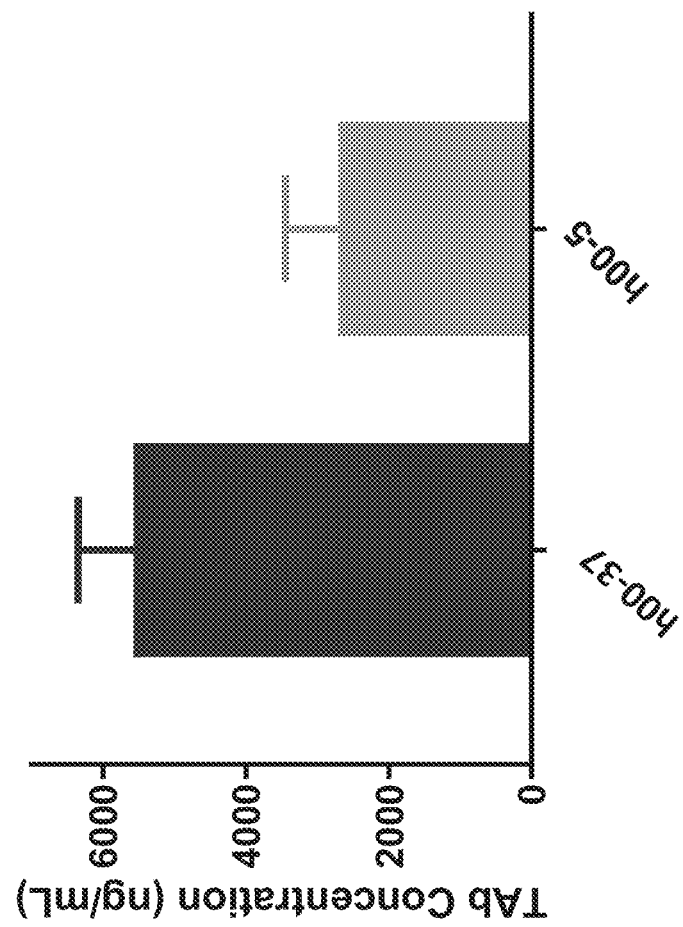
FIG. 14. Concentration of antibody in extracellular bone marrow compartment of rats administered non-targeted ADCs.

FIG. 14 shows the concentration of antibody in extracellular bone marrow compartment of rats administered non-targeted ADCs (h00-37 and h00-5).

Figure 16:
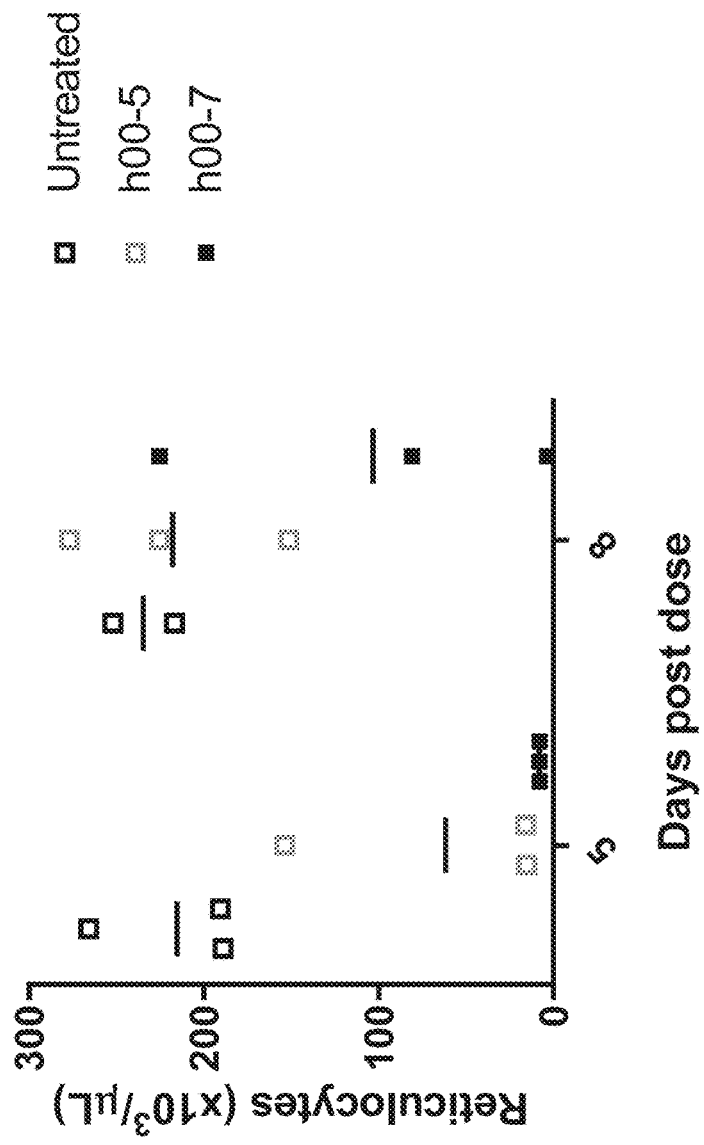
FIG. 16. Reticulocyte depletion on days 5 and 8 after dose by non-targeted tripeptide ADCs after administration in rats at 20 mg/kg.
Figure 17:
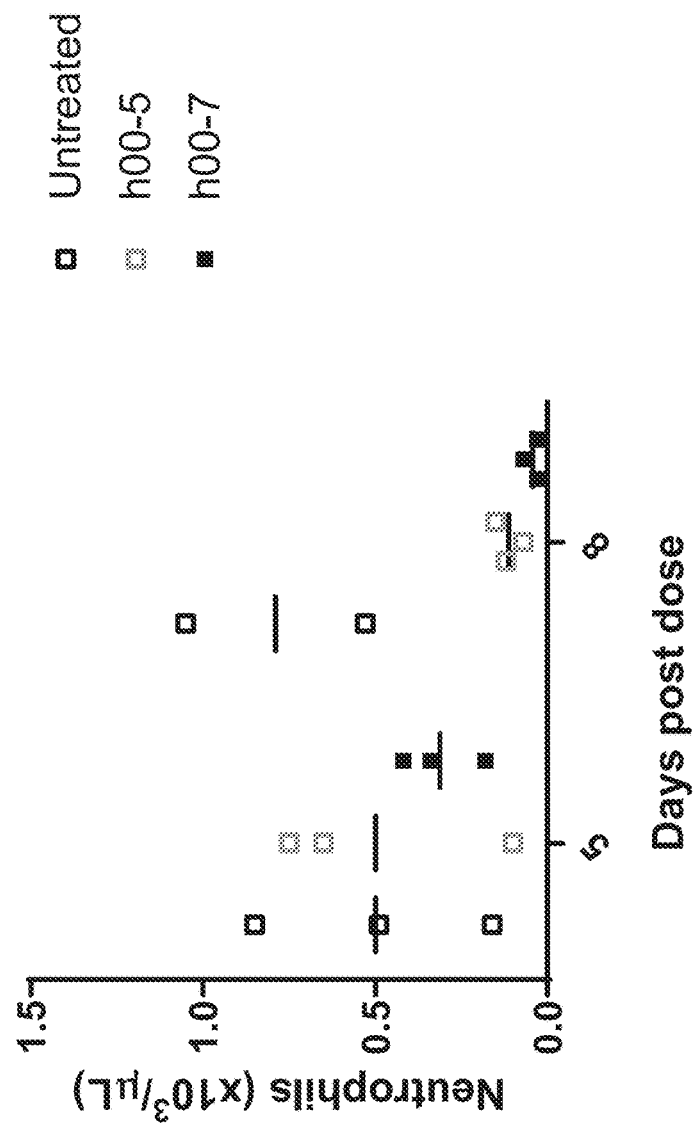
FIG. 17. Neutrophil depletion on days 5 and 8 after dose by non-targeted tripeptide ADCs after administration in rats at 20 mg/kg.

FIG. 16 shows the reticulocyte depletion on days 5 and 8 post dose by h00-5 and h00-7 after administration in rats at 20 mg/kg. FIG. 17 shows the neutrophil depletion on days 5 and 8 post dose by h00-5 and h00-7 after administration in rats at 20 mg/kg.

FIG. 18 shows the histology of bone on days 5 and 8 post dose by h00-5 and h00-7 after administration in rats at 20 mg/kg.

Example 15: In Vivo Metabolism of Tripeptide-Based ADCs

Non-specific release of free drug from an ADC is one mechanism that contributes to off-target toxicity to normal cells. To determine if the preservation of bone marrow observed for the h00-4 and h00-5 ADCs as compared to the h00-1 ADC is due to reduction in release of free MMAE from the tripeptide-based ADCs, plasma from the toxicity study of Example 14 was analyzed for that metabolite by HPLC-MS.

Figure 5A:
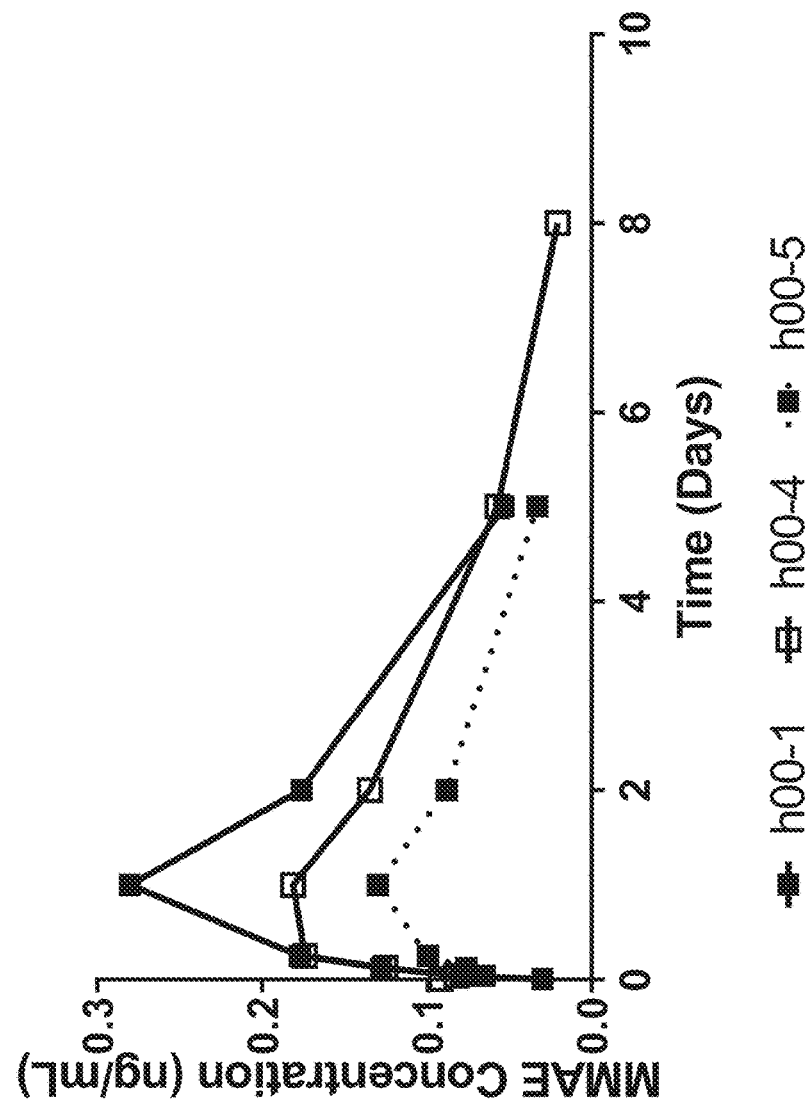
FIGS. 5A and 5B. Free MMAE in rat plasma at various time points subsequent to administration to non-tumor bearing animals of vehicle and 10 mg/Kg of 4-loaded non-binding conjugates having varying tripeptide sequences as the Peptide Cleavable Unit with drug-linker moieties represented by the formula of mp-$P_3$-$P_2$-$P_1$-PABC-MMAE in comparison to a 4-loaded non-binding conjugate having drug-linker moieties represented by the formula of mc-val-cit-PABC-MMAE.
Figure 5B:
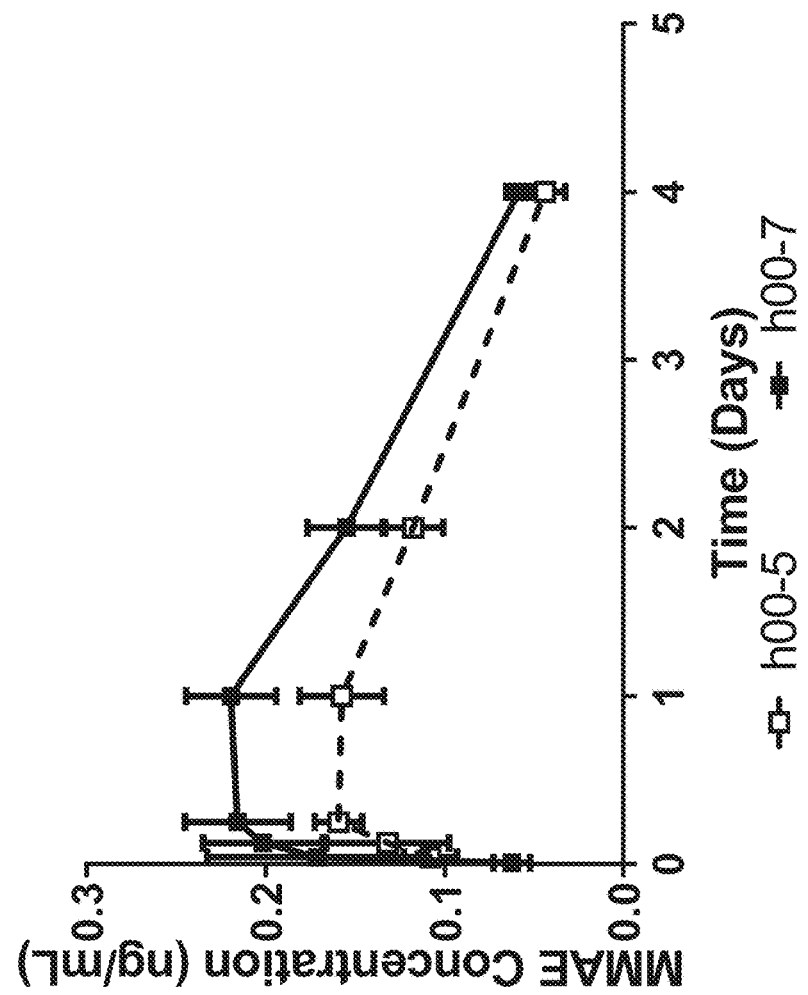

As shown in FIG. 5A, free MMAE concentration after administration of h00-4 or h00-5, remained below that found after administration of h00-1 throughout the course of the toxicity study, with the h00-5 conjugate being superior in that regard. Furthermore, FIG. 5B shows that the h00-5 conjugates, which has the P3 amino acid in the D stereochemical configuration, non-specifically releases less MMAE than h00-7, which is identical to h00-5 except the P3 amino acid is in the opposite stereochemical configuration. It thus appears that having an amino acid with the un-natural configuration at P3 confers improved stability to a tripeptide-based ADC.

Figure 15:
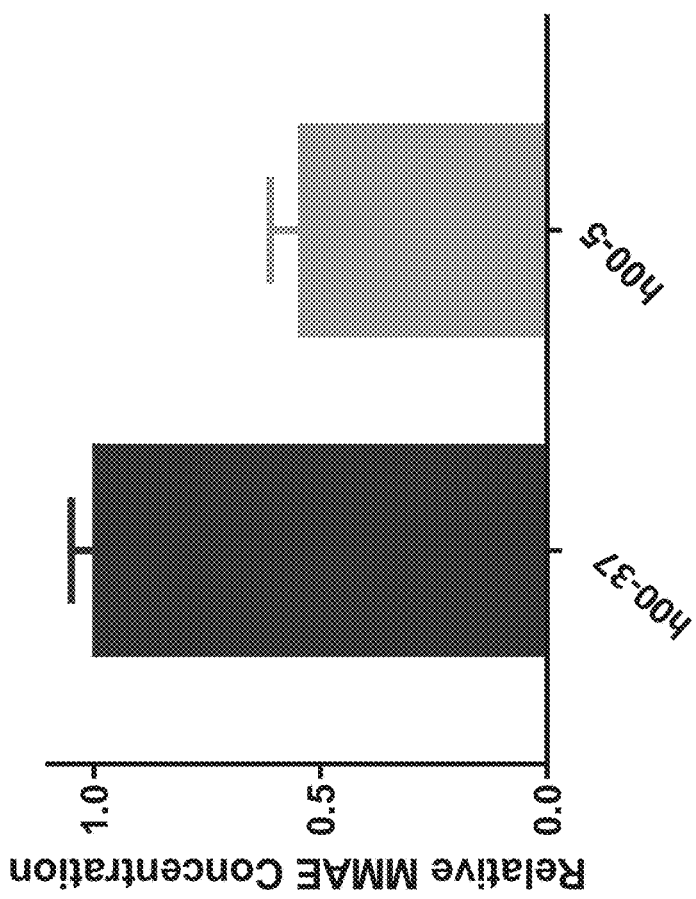
FIG. 15. Amount of free MMAE in bone marrow cells of rats administered non-targeted ADCs.

FIG. 15 shows the amount of free MMAE in bone marrow cells of rats administered non-targeted ADCs (h00-37 and h00-5).

Example 16: Neutrophil Elastase Assay of Tripeptide-Based Antibody Drug Conjugates To a mixture of 8-load ADC (5 ug), buffer (100 mM tris, 75 mM NaCl, pH 7.5; final concentration), and neutrophil elastase (100 ng) was added water to 20 uL. The reaction was incubated at 37 C for 3 h and then immediately analyzed by a QToF mass spectrometer.

Figure 6A:
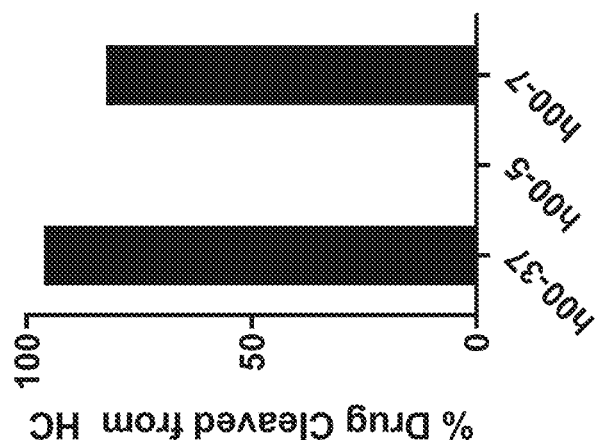
FIGS. 6A-6D. Percentage of drug cleaved from the heavy chain of 4-loaded non-targeted conjugates having varying tripeptide sequences as the Peptide Cleavable Unit with drug-linker moieties represented by the formula of mp-$P_3$-$P_2$-$P_1$-PABC-MMAE in comparison to a 4-loaded non-targeted conjugate having drug-linker moieties represented by the formula of mp-val-cit-PABC-MMAE in vitro by neutrophil elastase (FIG. 6A) or by Cathepsin B (FIGS. 6B and 6C) or in a pancreatic cancer xenograft (FIG. 6D).

As shown in FIG. 6A, percentage of drug cleaved from the heavy chain of non-targeted ADC 5 in vitro by neutrophil elastase is lower than that found for non-targeted ADC 37. Furthermore, FIG. 6A shows that the h00-5 conjugate, which has the P3 amino acid in the D stereochemical configuration, has its heavy chain cleaved by neutrophil elastase to a significantly lower extent than h00-7, which is identical to h00-5 except the P3 amino acid is in the opposite stereochemical configuration. In fact, no proteolysis of h00-5 by neutrophil elastase was observed. It thus appears that having an amino acid with the un-natural configuration at P3 confers improved stability to a tripeptide-based ADC.

Example 17: Cathepsin B Assay of Tripeptide-Based Antibody Drug Conjugates

Figure 6B:
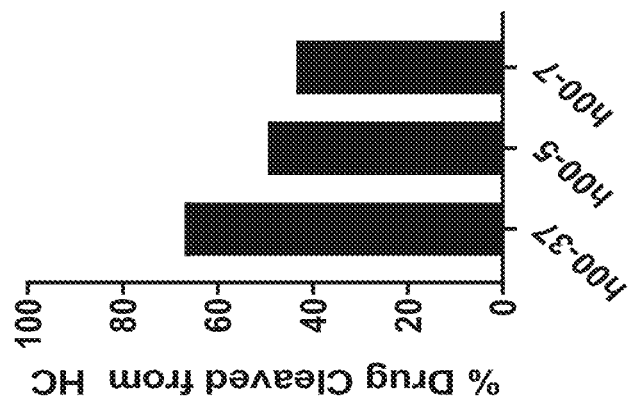
Figure 6C:
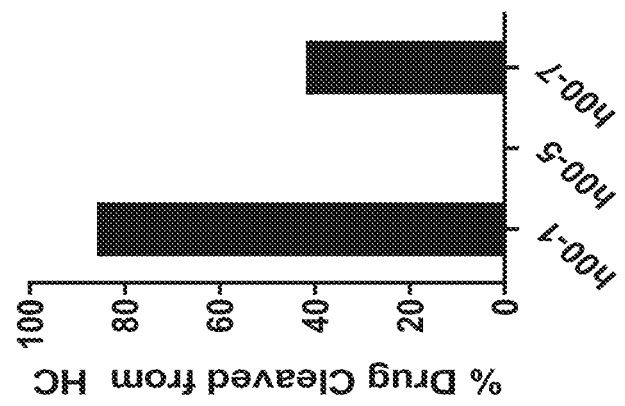

To a mixture of 8-load ADC (5 ug), buffer (50 mM citrate, 75 mM NaCL, pH 4.5; final concentration), cathepsin B (100 ng) and activating buffer (2 mM DTT/1.33 mM EDTA final concentration) was added water to 20 uL. The reaction was incubated at 37 C for 3 h and then immediately analyzed by a QToF mass spectrometer As shown in FIG. 6B (batch 1) and FIG. 6C (batch 2), percentage of drug cleaved from the heavy chain of non-targeted ADCs 5 and 7 in vitro by Cathepsin B is similar to that found for non-targeted ADC 37 suggesting that the D-Leu-Ala-Glu non-binding control conjugate (h00-5) is cleaved similarly to the Val-Cit non-binding control conjugate (h00-37) by a lysosomal protease.

Figure 6D:
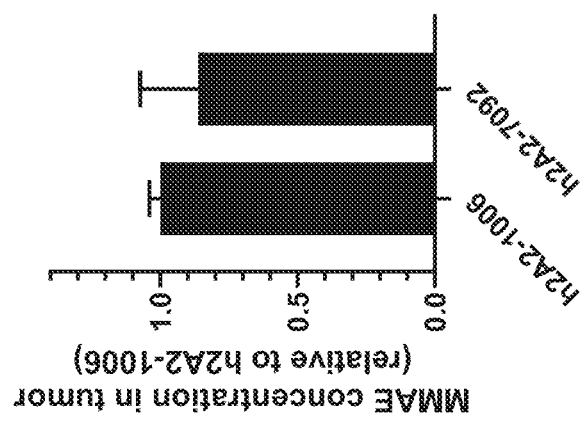

The amount of unconjugated MMAE in HPAFII tumors from an anti-tumor activity study of humanized anti-αvβ6 antibody 2A2 conjugated with me-vc-MMAE (average of 4 drugs per antibody) (h2A2-1006) or mp-dLAE-MMAE (average of 4 drugs per antibody) (h2A2-7092) was demonstrated (FIG. 6D). Tumors were excised from mice on day 3 post dose, suspended in 60%/40% MeCN/MeOH and homogenized with a Precellys™ 24 homogenizer. The samples were centrifuged at 16.1k×g for 15 minutes and the resulting supernatant was dried with N2, reconstituted in reconstitution buffer and analyzed on a Waters triple quad detector mass spectrometer.

Example 18: In Vitro Plasma Aggregation Assay of Tripeptide-Based Antibody Drug Conjugates ADCs were labeled with Alexa Fluor 488 TFP ester (Molecular Probes), desalted, buffer exchanged into PBS, pH 7.4 (Gibco), and sterile filtered. The concentration and degree of labeling of the resulting ADC-AF488 conjugate was determined by UV absorbance prior to freezing at −80° C. On the day of experiment, AF488-ADC was diluted in plasma and incubated at 37° C. At the indicated time points, aliquots were analyzed by SEC-UPLC with fluorescence detection. The resulting chromatograms were analyzed to determine % of high molecular weight species.

The aggregation appears to be lower for tripeptide MMAF than Val-Cit-MMAF. Based on the correlation observed with MMAE, the tripeptide MMAF would be less toxic.

Figure 7A:
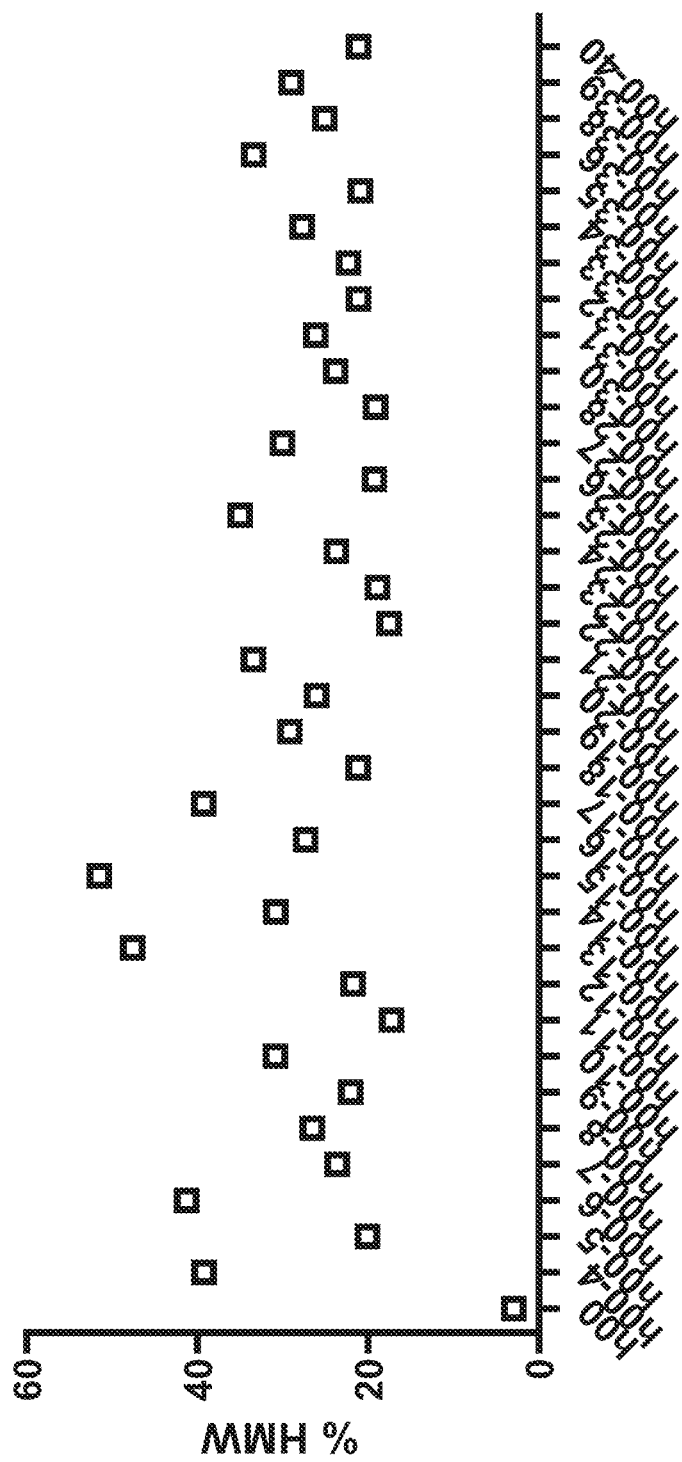
FIGS. 7A, 7B, 8, and 9. Aggregation of a series of 4-loaded non-targeted conjugates having varying tripeptide sequences as the Peptide Cleavable Unit with drug-linker moieties represented by the formula of mp-$P_3$-$P_2$-$P_1$-PABC-MMAE after a 96 h incubation in rat plasma (FIGS. 7A and 7B), cyno plasma (FIG. 8), or human plasma (FIG. 9).
Figure 7B:
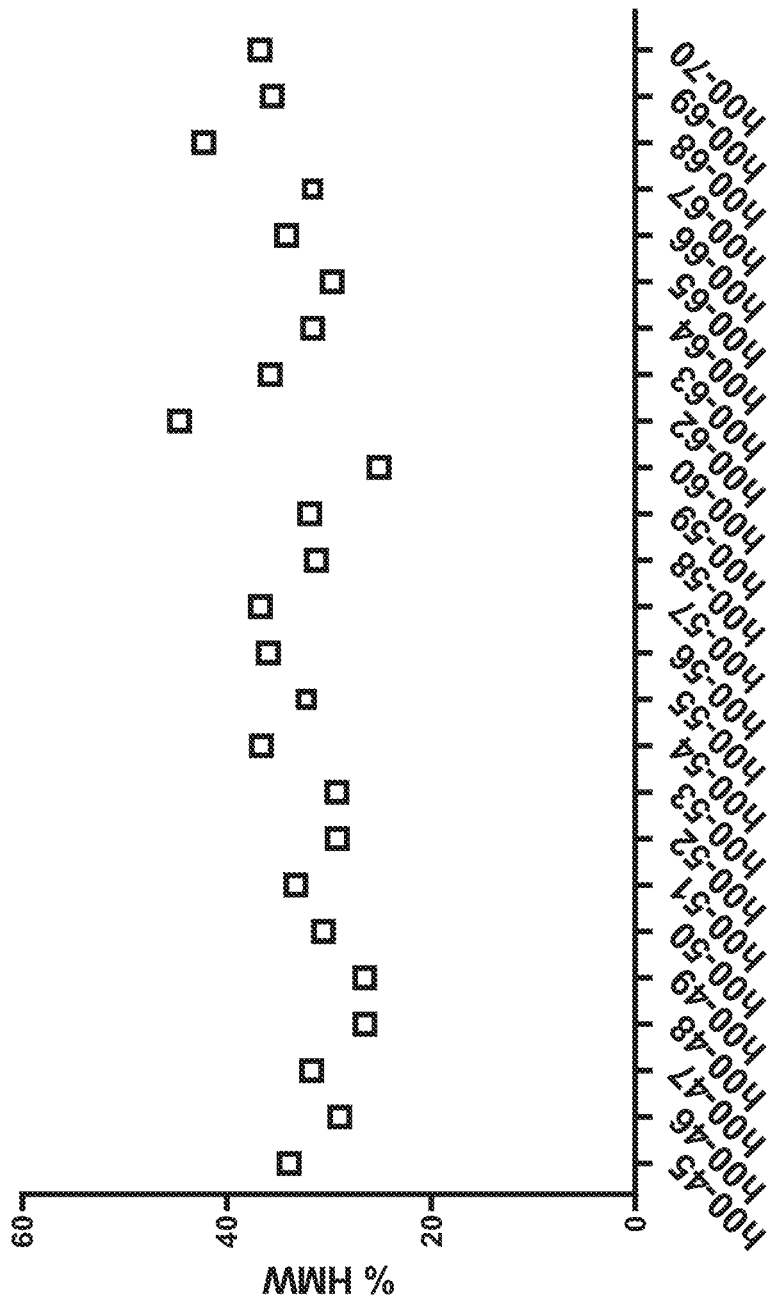

FIG. 7A and FIG. 7B show the aggregation of non-targeted ADCs after incubation in rat plasma for 96.

Figure 8:
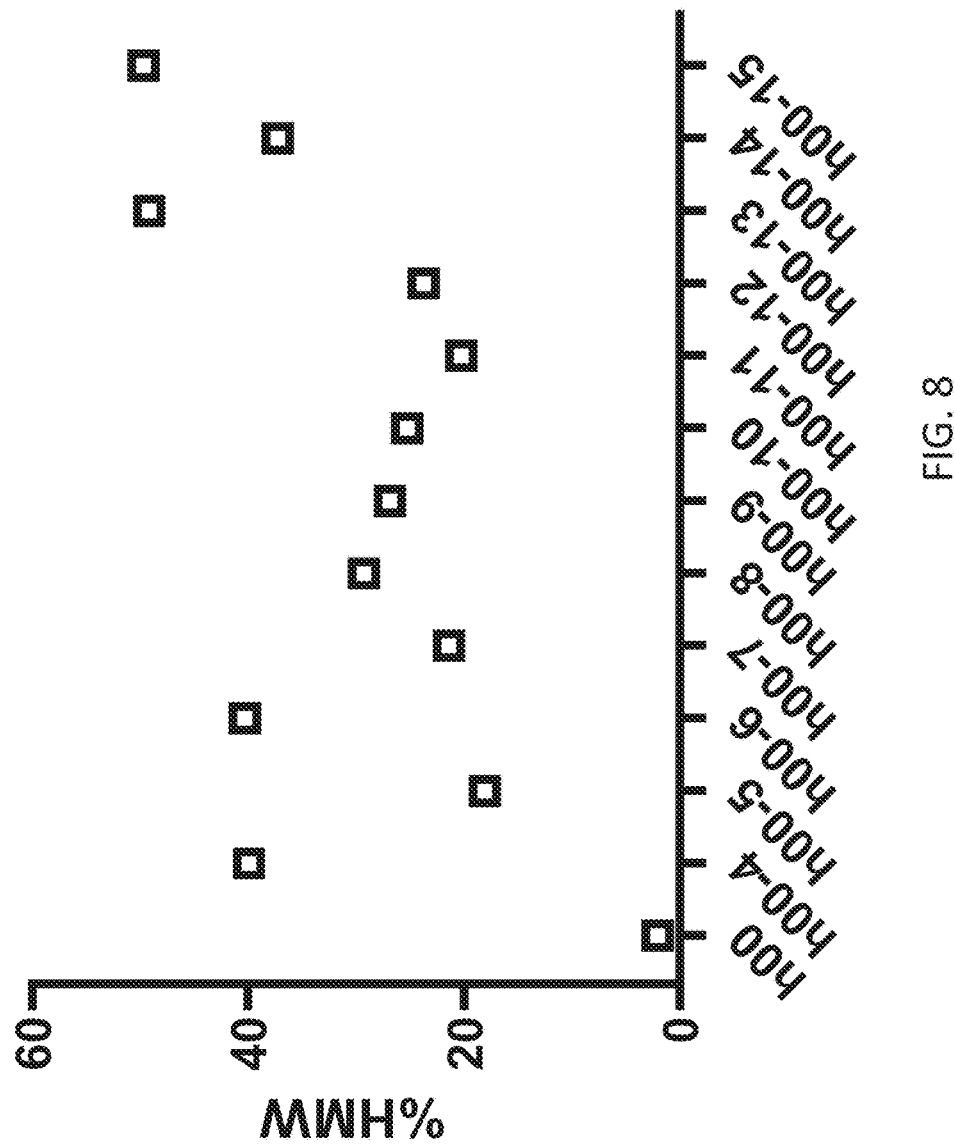

FIG. 8 shows the aggregation of non-targeted ADCs after incubation in cyno plasma for 96.

Figure 9:
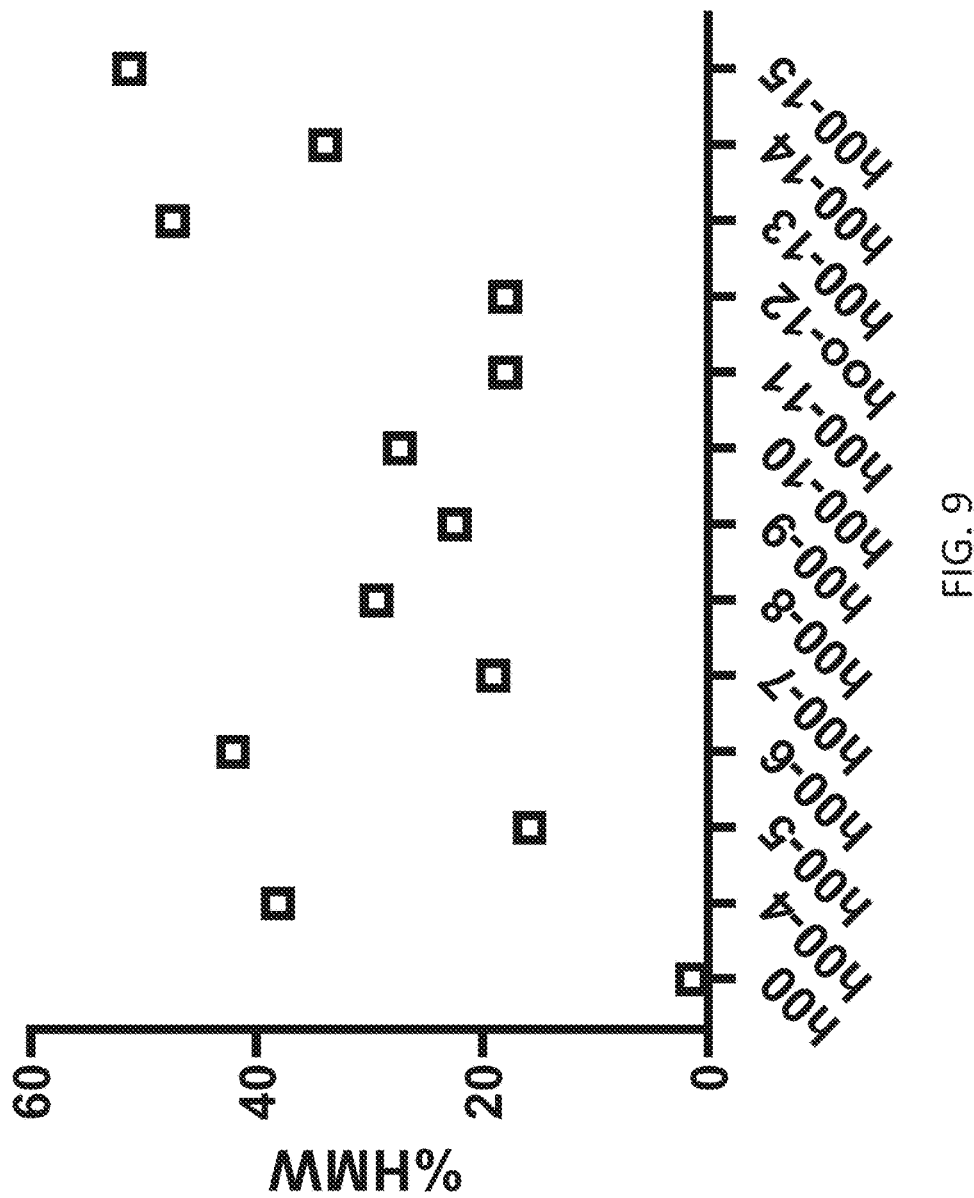

FIG. 9 shows the aggregation of non-targeted ADCs after incubation in human plasma for 96.

Figure 10:
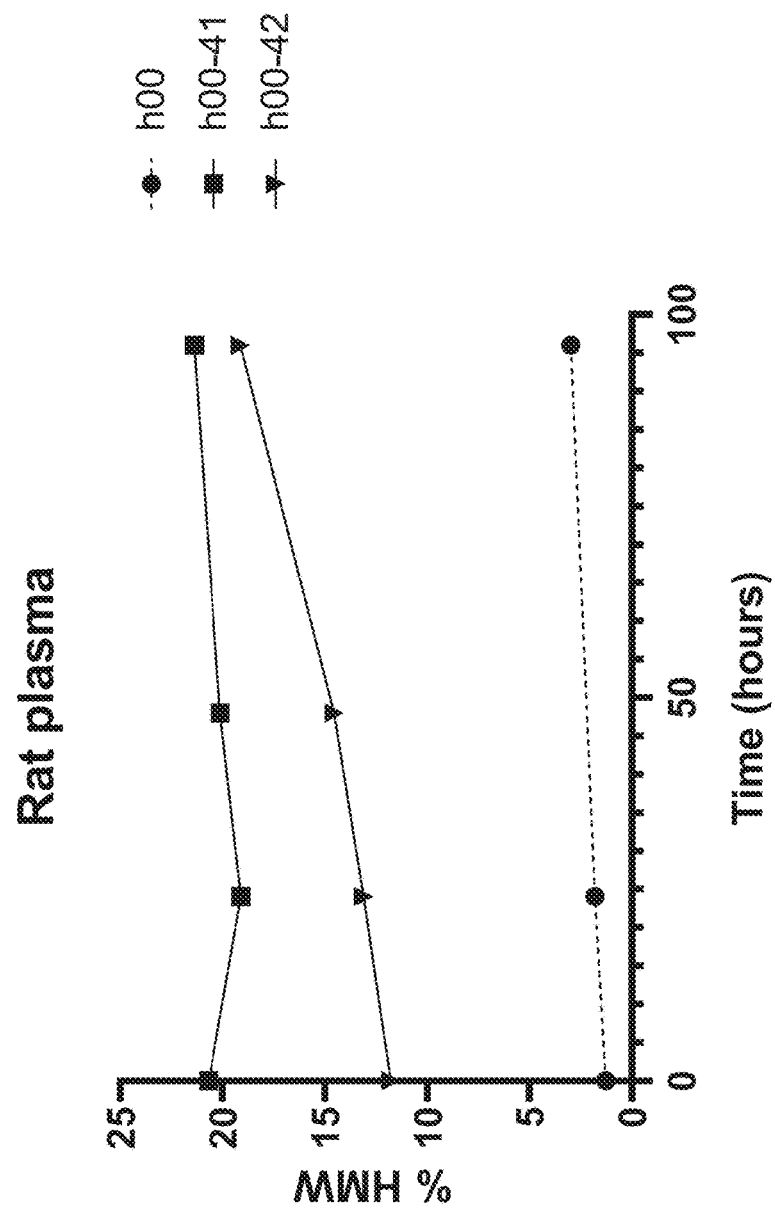
FIG. 10. Aggregation of non-targeted MMAF ADCs in rat plasma at various time points.

FIG. 10 shows the aggregation of non-targeted MMAF ADCs (h00-41 and h00-42) after incubation in rat plasma.

Figure 11:
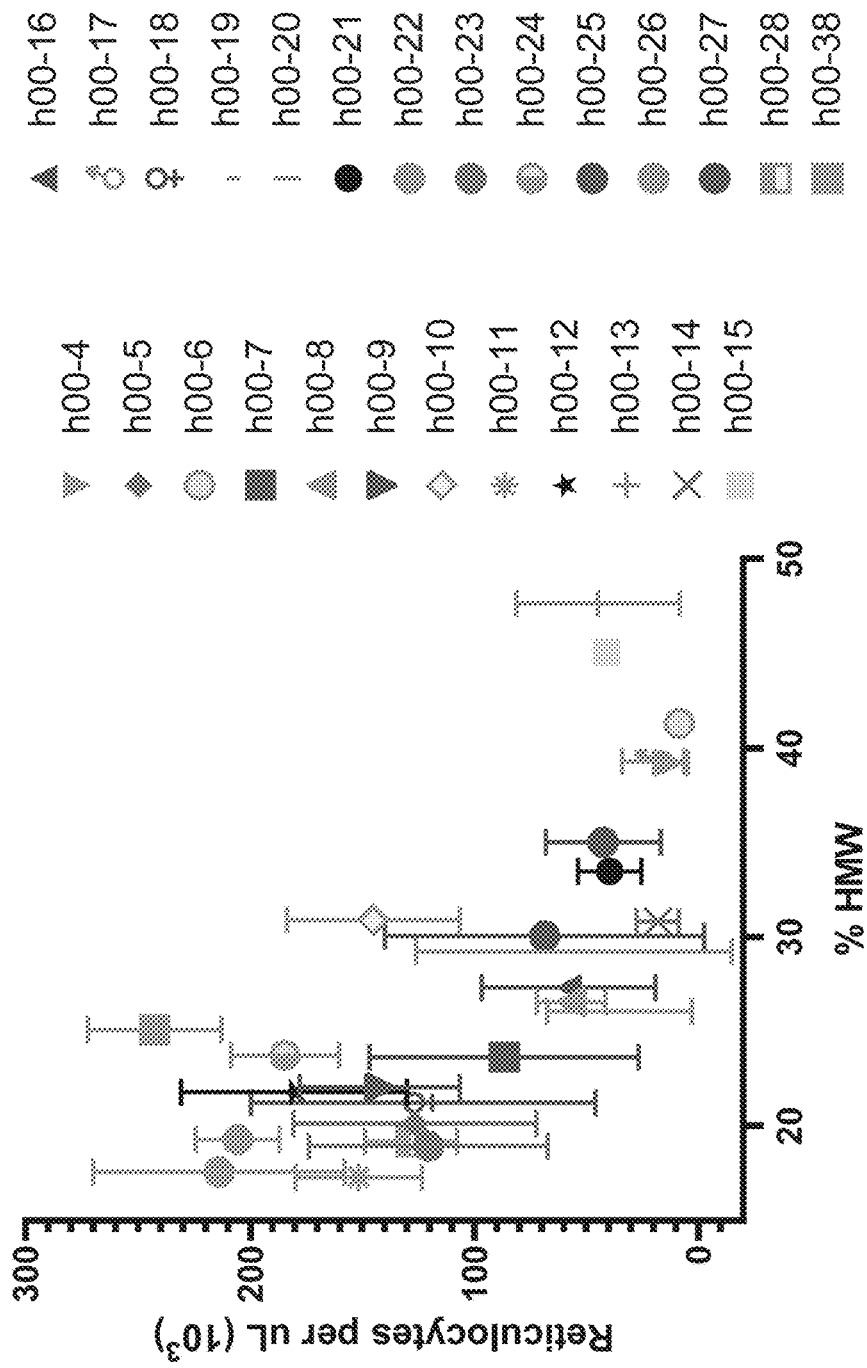
FIG. 11. Correlation of reticulocyte depletion by non-targeted ADCs in rats and ADC aggregation in rat plasma after a 96 h incubation.

FIG. 11 shows the correlation of reticulocyte depletion by non-targeted ADCs in rats and ADC aggregation in rat plasma after a 96 h incubation.

Figure 12:
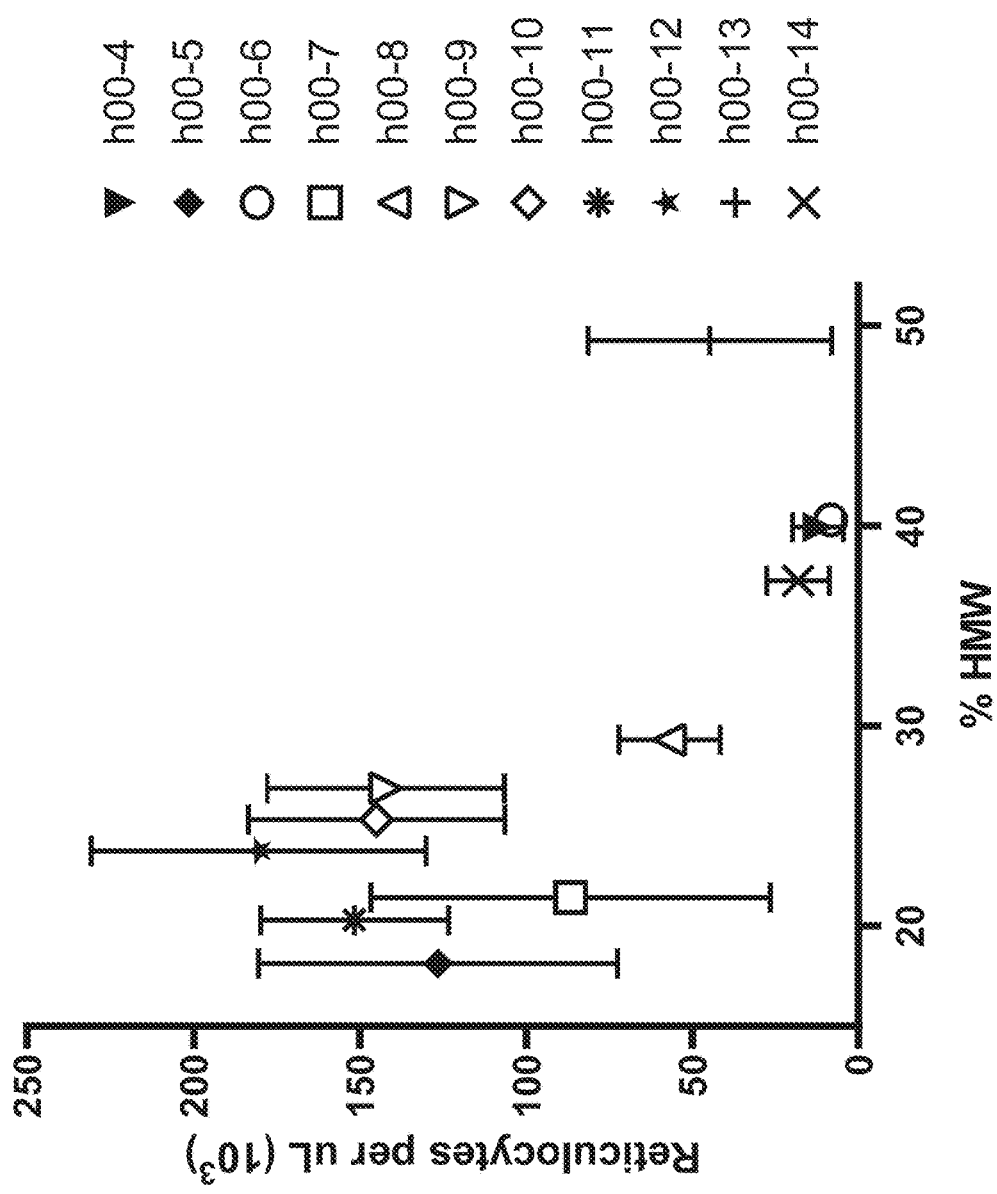
FIG. 12. Correlation of reticulocyte depletion by non-targeted ADCs in rats and ADC aggregation in cyno plasma after a 96 h incubation.

FIG. 12 shows the correlation of reticulocyte depletion by non-targeted ADCs in rats and ADC aggregation in cyno plasma after a 96 h incubation.

Figure 13:
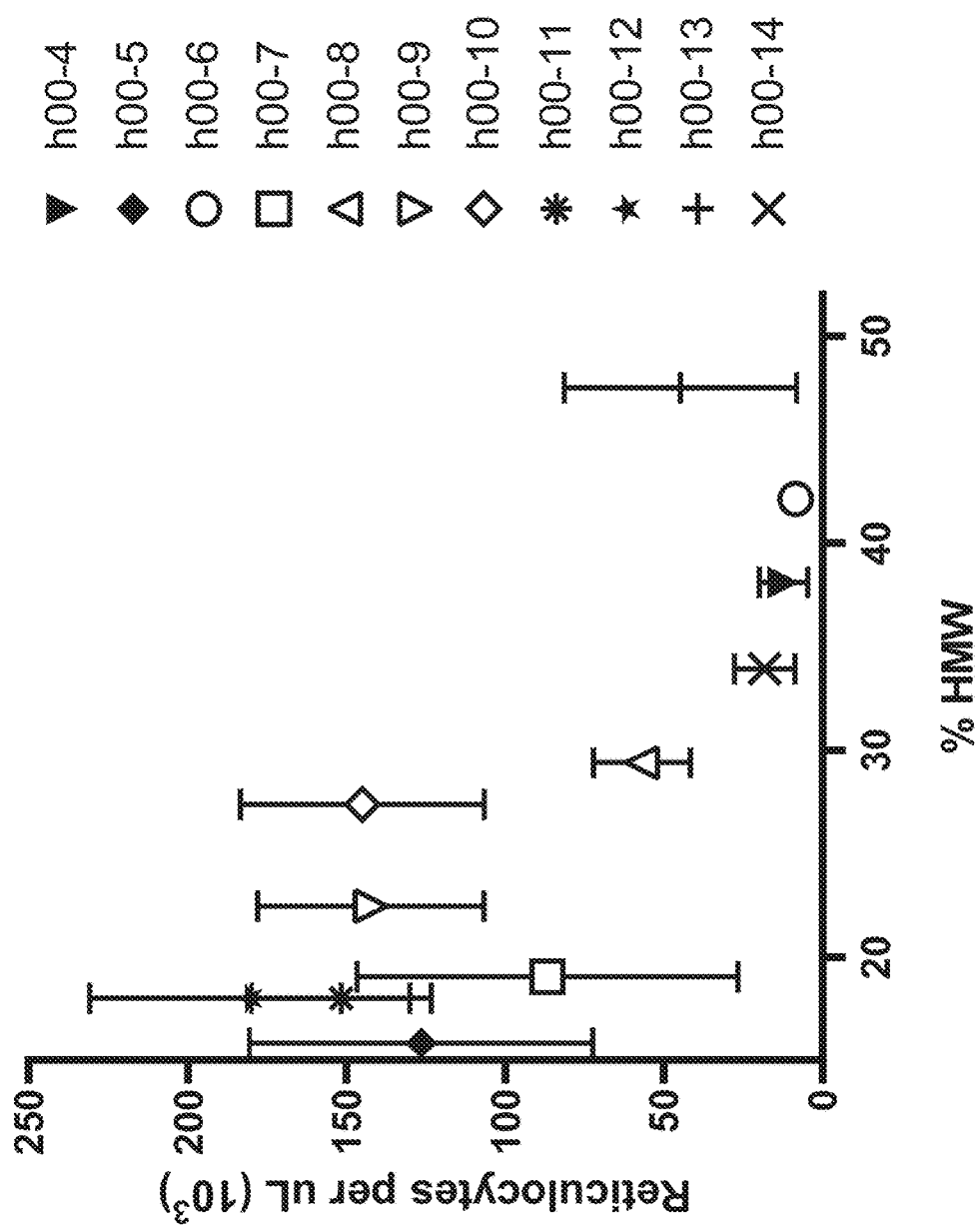
FIG. 13. Correlation of reticulocyte depletion by non-targeted ADCs in rats and ADC aggregation in human plasma after a 96 h incubation.

FIG. 13 shows the correlation of reticulocyte depletion by non-targeted ADCs in rats and ADC aggregation in human plasma after a 96 h incubation.

Figure 19:
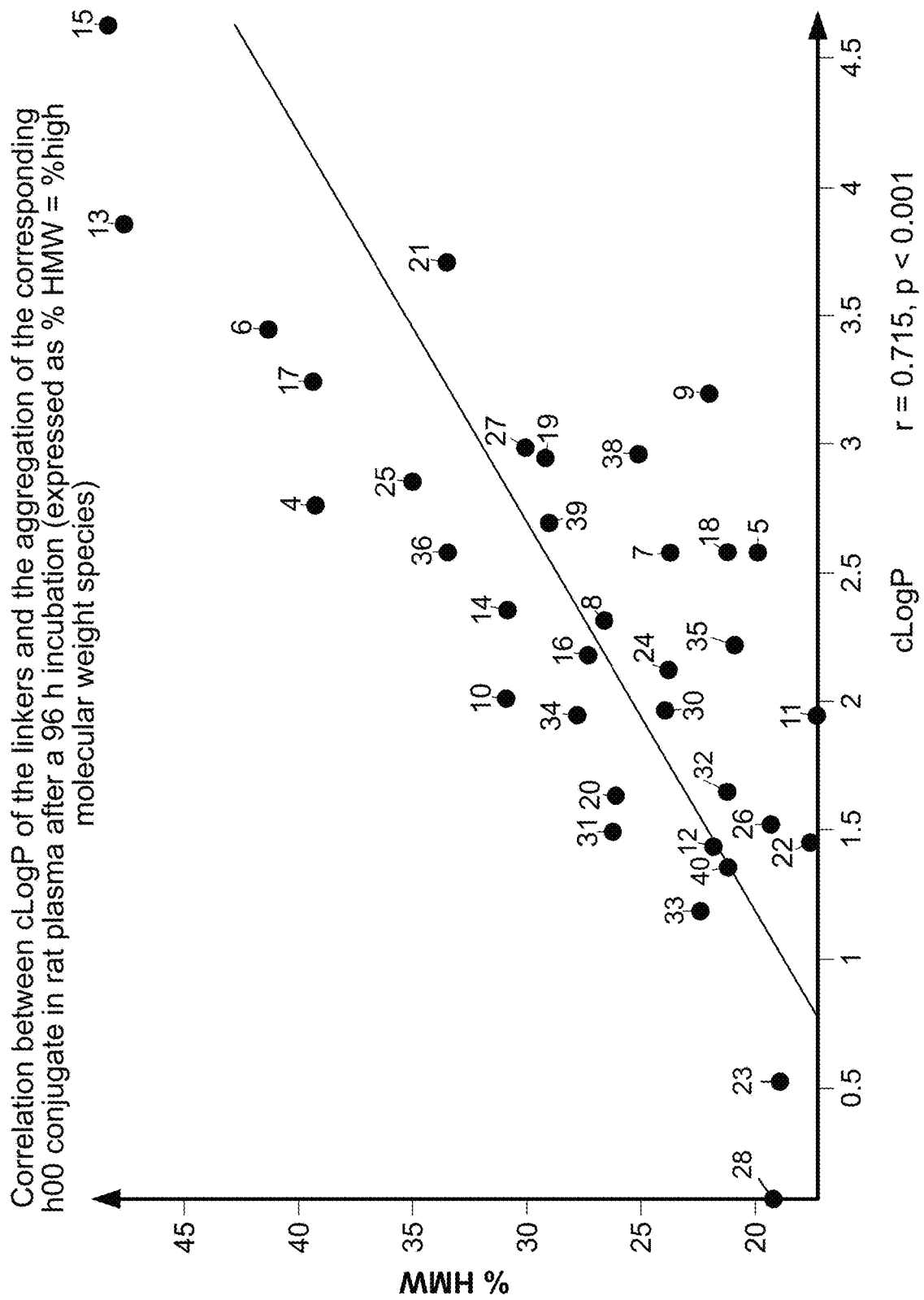
FIG. 19. Correlation between c Log P of the linkers and the aggregation of the corresponding h00 conjugate in rat plasma after a 96 h incubation (expressed as % HMW=% high molecular weight species).

In FIG. 19, wherein the correlation between c Log P of the linkers and the aggregation of the corresponding h00 conjugate in rat plasma is shown, correlation of r=0.715 indicates that presence of HMW positively correlates with the c log P (i.e., the linkers with lower c Log P values show less aggregation than those with higher c log P). Linkers with low c Log P values have low hydrophobicity, which includes linkers with polar amino acids.

Figure 20:
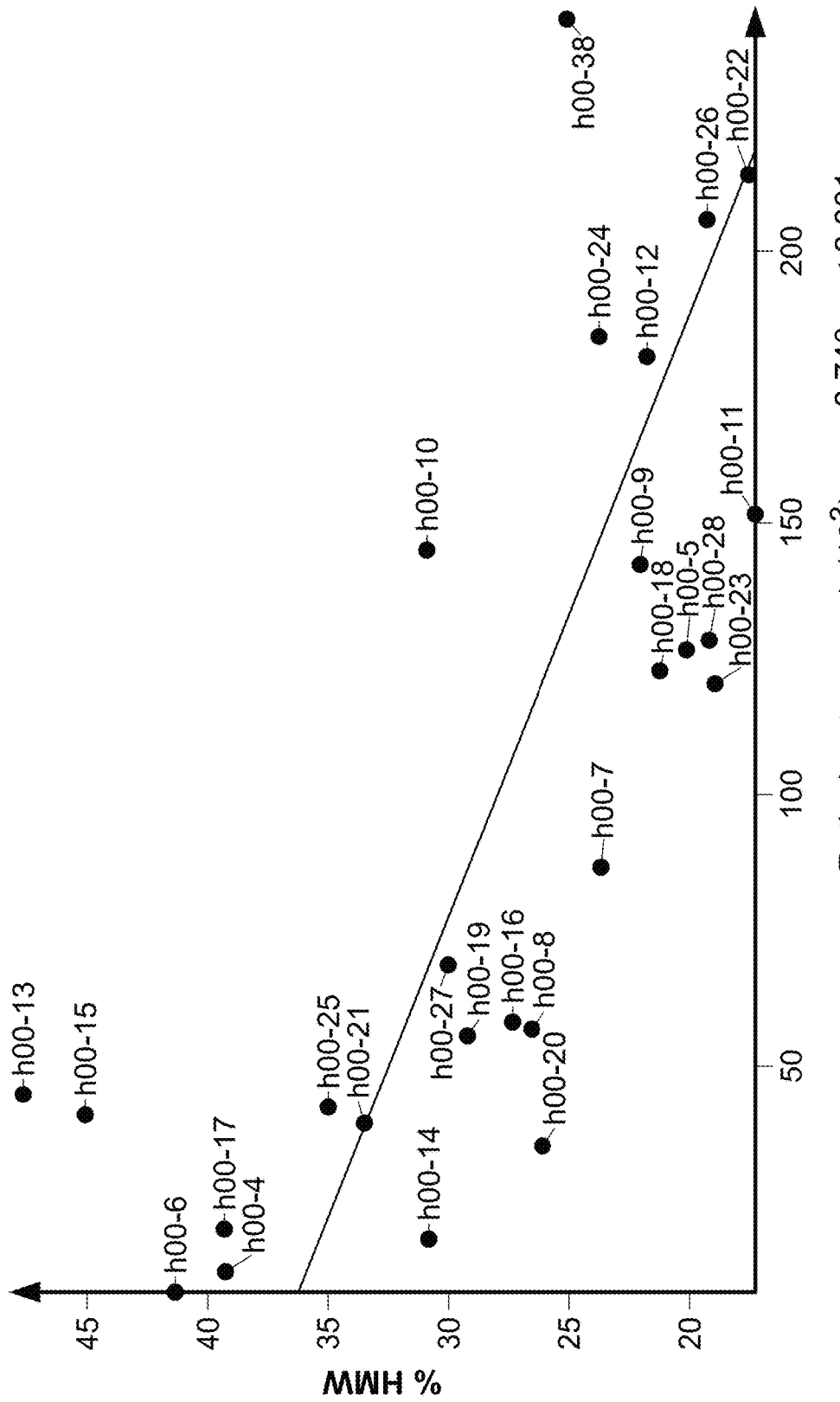
FIG. 20. Correlation between reticulocyte depletion caused by non-targeted ADCs in rats and ADC aggregation in rat plasma after a 96 h incubation (expressed as % HMW=% high molecular weight species).

In FIG. 20, wherein the correlation between reticulocyte depletion caused by non-targeted ADCs in rats and ADC aggregation in rat plasma is shown, correlation of r=−0.748 indicates that presence of HMW negatively correlates with reticulocytes (i.e. higher the % HMW, higher is the depletion of reticulocytes).

Figure 21:
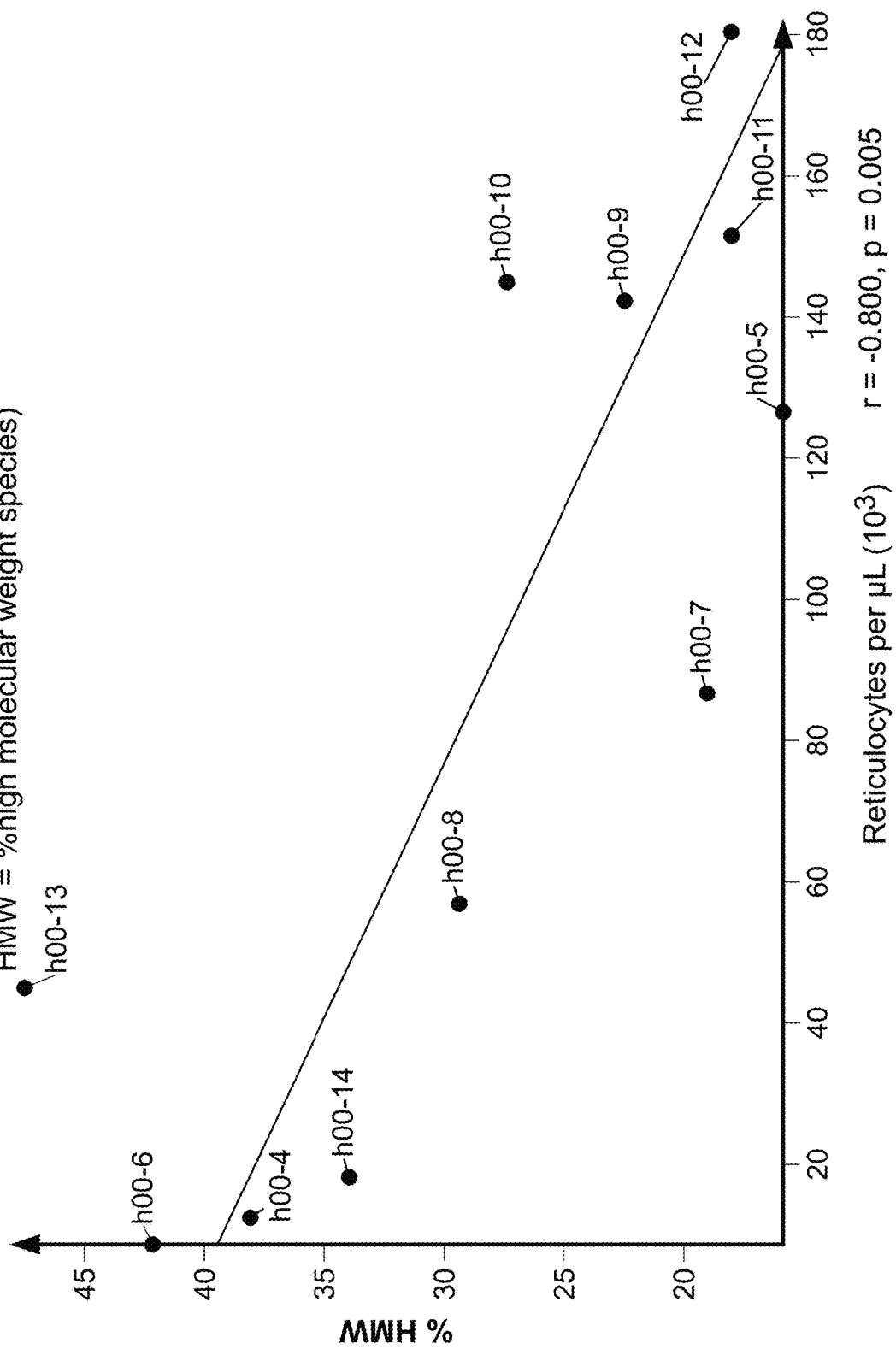
FIG. 21. Correlation between reticulocyte depletion caused by non-targeted ADCs in rats and ADC aggregation in human plasma after a 96 h incubation (expressed as % HMW=% high molecular weight species).

In FIG. 21, wherein the correlation between reticulocyte depletion caused by non-targeted ADCs in rats and ADC aggregation in human plasma is shown, correlation of r=−0.800 indicates that presence of HMW negatively correlates with reticulocytes (i.e. higher the % HMW, higher is the depletion of reticulocytes).

Figure 22:
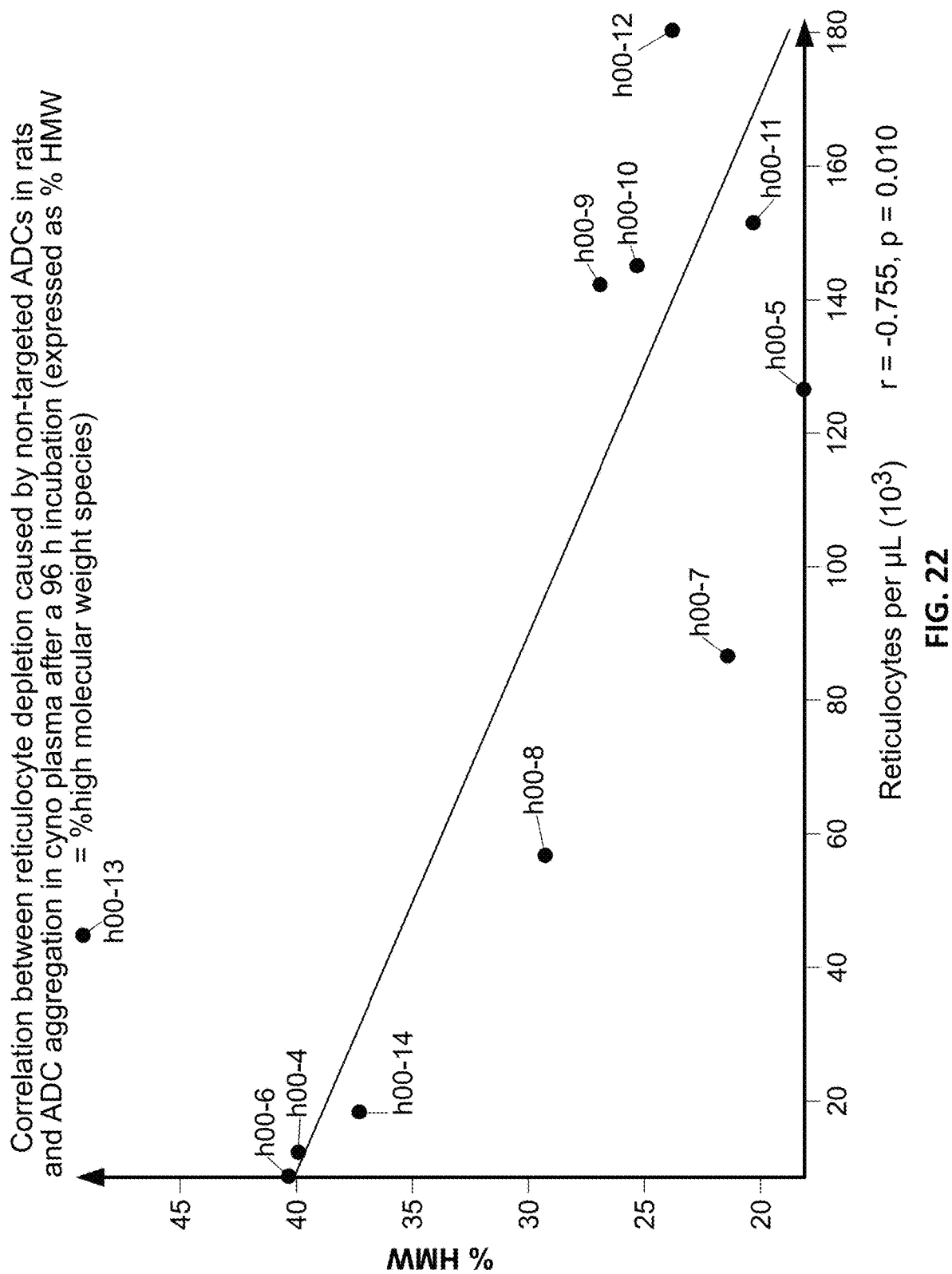
FIG. 22. Correlation between reticulocyte depletion caused by non-targeted ADCs in rats and ADC aggregation in cyno plasma after a 96 h incubation (expressed as % HMW=% high molecular weight species).

In FIG. 22, wherein the correlation between reticulocyte depletion caused by non-targeted ADCs in rats and ADC aggregation in cyno plasma is shown, correlation of r=−0.755 indicates that presence of HMW negatively cor-

Example 19: Alternative Preparation of MMAE Drug-Linker Compound

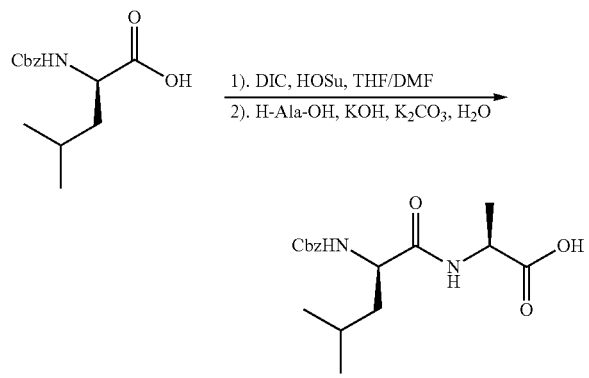

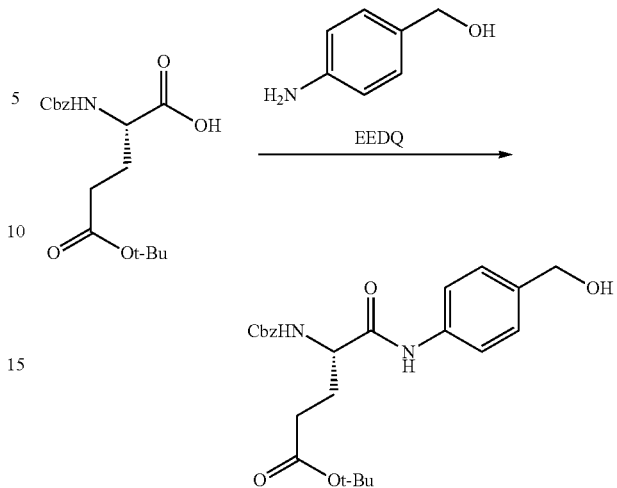

546 g (2.85 mol, 1.1 eq.) EDC×HCl were suspended in 1.7 L THF and 0.8 L DMF and a solution of 688 g (2.59 mol, 1.0 eq.) Z-D-Leu-OH and 328 g (2.85 mol, 1.1 eq.) NHS in 1.7 L THF and 0.8 L DMF was added at room temperature. The slightly exothermic reaction (IT increased initially to 30° C.) was stirred overnight at room temperature. Since after 23 h still 1.30% unreacted Z-D-LeuOH were detected in the reaction mixture, additional 25 g (0.13 mol, 0.05 eq.) of EDC×HCl were added and stirring was continued for 30 min, leaving 0.45% Z-D-Leu-OH in the mixture. The obtained thin suspension was cooled to IT=4° C. and was added to a cooled solution (IT=4° C.) of 692 g (7.77 mol, 3.0 eq.) H-Ala-OH, 291 g (5.18 mol, 2.0 eq.) potassium hydroxide and 283 g (2.05 mol, 0.79 eq.) potassium carbonate in 2.8 L deionized water. After 5 min, the temperature of the reaction mixture had increased to 19° C. By HPLC 0.04% Z-D-Leu-OSu, 91.7% Z-D-Leu-AlaOH and 1.1% Z-D-Leu-OH were detected in the reaction mixture. 6 L EtOAc were added to the reaction mixture and it was acidified to pH 1 using 2.5 L 18% HCl. The aqueous phase was discarded and the organic phase was washed twice with 1.2 L 1 N HCl, once with 1.2 L deionized water and three times with 0.6 L deionized water. 60 mL and 30 mL brine were added to the last two extraction steps with deionized water to improve phase separation. The organic phase was concentrated at 40° C. external temperature under reduced pressure (approx. 160 mbar) to about 1.5 L. Then 6.0 L EtOAc were added and the obtained solution was again concentrated to about 1.5 L. Again 6.0 L EtOAc were added and it was concentrated to give 1975 g of a clear solution. Subsequently, 4.0 L cyclohexane were added and the obtained solution was seeded with 8 g of seeding crystals. After stirring for 2 h, a thick suspension was obtained which was diluted with 2×2.3 L cyclohexane (second addition after additional 2 h). After 23 h crystallization time at room temperature, the precipitate was collected by filtration and subsequently washed with 5.0 L EtOAc/cyclohexane 1:9 and 2×4.0 L cyclohexane. After drying at 35° C. (external temperature) under reduced pressure (<5 mbar) for 24 h, 780 g (2.32 mol) of Z-D-Leu-Ala-OH were obtained as an off-white solid in 92% yield and with 99.3% HPLC-purity. Volume yield: 4.2%.

In a reactor were placed 1012 g (3.00 mol, 1.0 eq.) Z-Glu(OtBu)-OH, 443 g (3.60 mol, 1.2 eq.) 4-aminobenzyl alcohol and 890 g (3.60 mol, 1.2 eq.) EEDQ and 5.0 L EtOAc were added. Upon dissolution, the reaction temperature dropped from 23° C. to 11° C. After 2 h reaction time, 85.7% Z-Glu(OtBu)-(4-hydroxymethyl)-anilide and 1.16% Z-Glu(OtBu)-OH were found in the reaction mixture by HPLC and after 2.5 h reaction time 2.1 L deionized water were added. The pH was adjusted to 1 by addition of 700 mL 18% HCl and the layers were separated. The organic phase was washed with 3×1.0 L 1 N HCl, 3×2.0 L 5% Na2CO3/brine 9:1 and 3×2.0 L deionized water/brine 9:1 (pH of last aqueous phase: 6-7). The obtained organic layer was evaporated at 40° C. external temperature and reduced pressure (155 mbar). After approx. 3 L of distillate were removed, 5 L toluene were added and evaporation was continued, forming a thick suspension quickly. Further 4.0 L of toluene were added and the evaporation was continued until 5.8 kg of a thick suspension were obtained. It was allowed to crystallize overnight at room temperature and the residue was collected by filtration (water content before filtration: 0.03%). Filtration was slow (approx. 2 h for initial filtration) and the residue was washed with 2×4.0 L and 1×5.0 L of toluene and 1×5.0 L IPE/IPA. The desired product was obtained after drying at 35° C. under reduced pressure (<20 mbar) in 44% yield (587 g) and with 95.7% HPLC-purity (3.27% 4-aminobenzyl ethylcarbonate 4 as main impurity). The filtrate from IPE/IPA-wash was concentrated at 40° C. external temperature and reduced pressure to a brown oil and reevaporated with 2×2.0 L EtOAC to form a thick suspension, which was diluted with 400 mL EtOAc giving 1.5 kg suspension. Then 2.5 L IPE were added and crystallization was performed overnight at room temperature. The precipitate was then collected by filtration and washed with 1×1.2 L EtOAc/IPE 1:3 and 2×1.2 L IPE. The filtration of this crystallization from EtOAc/IPE 1:3 proved to be significantly faster and provided the desired product with 98.10% HPLC-purity and in 36% yield. The overall volume yield for both fractions was 10.5%. Both fractions were combined and subjected to Cbz-deprotection.

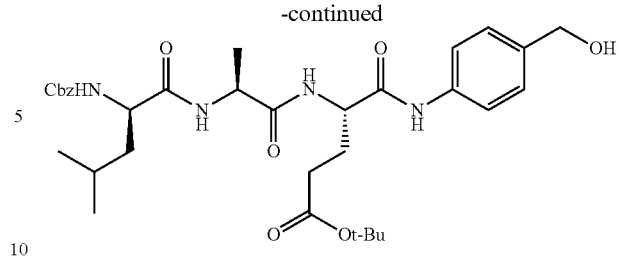

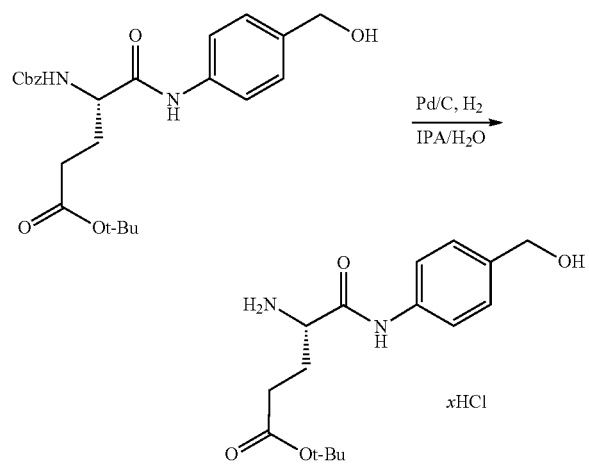

Z-Glu(OtBu)-(4-hydroxymethyl)-anilide (1057 g, 2.39 mol) was dissolved in 8.55 L IPA and 0.35 L deionized water at room temperature. Nitrogen was bubbled through the mixture to remove oxygen before a suspension of 42 g catalyst (10% Pd on carbon, 50% water; 2.1 g Pd in total) in 100 mL deionized water was added. The reaction mixture was again purged with nitrogen, and then hydrogen was bubbled through the reaction mixture using a pipette with a sintered glass filter. The reaction was monitored by HPLC and after 80 min 94.4% product and <0.1% remaining starting material were detected in the reaction mixture. The reaction mixture was again purged with nitrogen and the catalyst was filtered off using a sintered glass filter funnel (pore size approx. 5-15 μm). The filtrate was acidified using 480 mL 18% HCl to pH ~3 and was concentrated under reduced pressure at 35 C external temperature to 2.95 kg. 5.0 L IPA and seeding crystals were added and evaporation was continued until 3.9 kg of a thick suspension were obtained. This suspension was diluted with 1.0 L IPA at room temperature. After 30 min, 7.0 L IPE were added and the mixture was stirred overnight at room temperature. The precipitate was collected by filtration and was washed with 4.0 L IPA/IPE 1:2, followed by 2×4.0 L IPE then dried under vacuum to afford the desired product as HCl-salt in 96% yield (7.5% volume yield) and with 98.7% HPLC-purity.

In a double jacketed glass reactor 539 g (1.59 mol, 1.00 eq.) Z-D-Leu-Ala-OH, 588 g (1.59 mol, 1.00 eq., corrected for assay [93%]) H-Glu(OtBu)-(4-hydroxymethyl)-anilide× HCl and 226 g (1.59 mol, 1.00 eq.) Oxyma were suspended in 2.7 L ACN. The obtained thick suspension was cooled to IT=0° C. and 545 mL (3.18 mol, 2.00 eq.) DIPEA were added, whereupon the precipitate slowly dissolved (few undissolved particles remained). Since the pH of the reaction mixture was only 6-7, adjustment to pH=8 was performed using additional 29 mL (0.17 mol, 0.10 eq.) DIPEA. Then 396 g (2.07 mol, 1.30 eq.) EDC×HCl were added and the reaction was stirred at IT=0° C. and monitored by HPLC. After 4.5 h, 2.58% remaining Z-D-LEU-ALA-OH were detected in the reaction mixture and 2.7 L EtOAc and 2.7 L of a 1:1 mixture of deionized water and brine were added. After separation of the phases, the aqueous phase was discarded and the organic phase was extracted three times with 1.3 L 1 N HCl each, diluted with 2.7 L EtOAc and further extracted three times with 1.3 L each of a mixture of 5% Na₂CO₃ and brine (9:1). Then the organic layer was washed three times with 1.3 L each of a mixture of deionized water and brine (9:1) and was stored overnight at room temperature. A part (441 g) of the obtained solution was used for additional crystallization experiments and the remaining 5337 g were concentrated at 40° C. (external temperature) and 160 mbar to a weight of 2843 g. To the resulting solution, 0.7 g seeding crystals and 5.0 L EtOAc were added and it was concentrated at 40° C. (external temperature) and 150 mbar to a weight of 3640 g. The obtained thick suspension was diluted with 3.2 L IPE and stirred for 3.5 h at room temperature. Then the precipitate was filtered off (filter with 11 μm pore size, filtration time: <20 min) and washed with 2×3.4 L EtOAc/IPE 1:1 and 1×3.4 L IPE. After drying at 35° C. under reduced pressure (<20 mbar) for 16 h, 778 g Z-D-Leu-Ala-Glu(OtBu)-(4-hydroxymethyl)-anilide (84% yield, 8.1% volume yield) were obtained as slightly off-white crystals. HPLC-purity: 98.7%

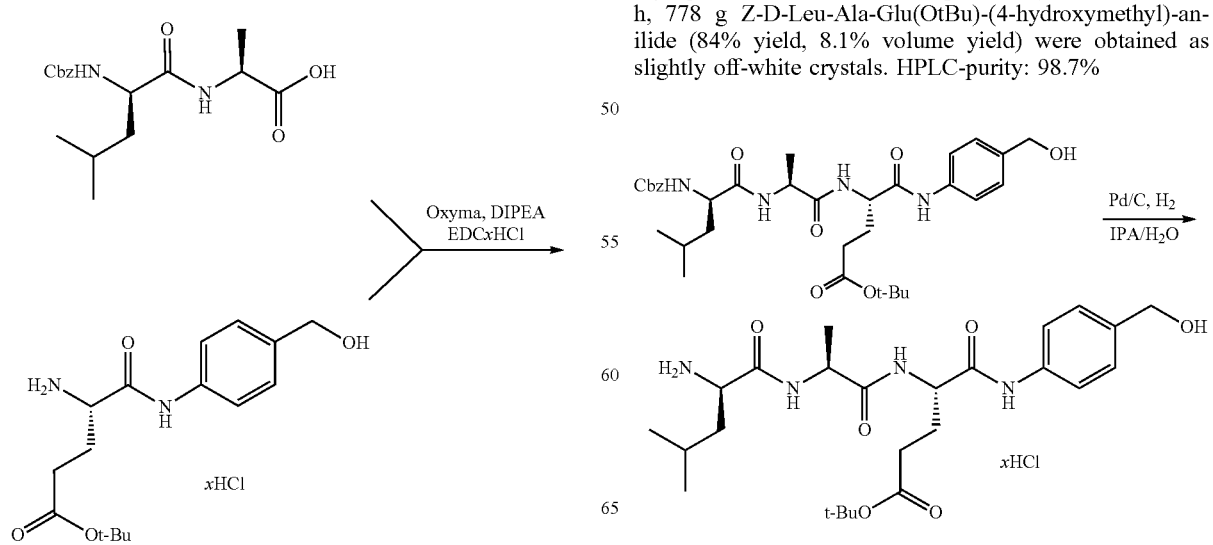

In a 10 L 4-neck flask 755 g (1.20 mol) Z-D-Leu-Ala-Glu(OtBu)-(4-hydroxymethyl)-anilide was suspended at room temperature in 6.04 L IPA and 400 mL deionized water and stirred for 1 h to give a clear solution. During this dissolution a stream of nitrogen was passed through the mixture to purge oxygen. The obtained clear solution was cooled to 4° C. before 75.5 g palladium on carbon (10% Pd on carbon, 50% water, 3.78 g Pd in total), suspended in 355 mL deionized water, were added. The reaction mixture was again purged with nitrogen for 10 min and then the hydrogenation was started by bubbling hydrogen through the reaction mixture using glass frits. The reaction was monitored by HPLC. After 60 min 0.85% remaining Z-D-Leu-Ala-Glu(OtBu)-(4-hydroxymethyl)-anilide were detected (97.3% H-D-Leu-Ala-Glu(OtBu)-(4-hydroxymethyl)-anilide×HCl). After 84 min the hydrogenation was stopped and the reaction mixture was purged with nitrogen to remove remaining hydrogen. The catalyst was filtered off using a sintered glass filter funnel (pore size approx. 5-15 μm) and was washed with 2×400 mL IPA. To the combined filtrates 218 mL (1.20 mmol, 1.00 eq.) 18% hydrochloric acid were added (pH of solution=2-3) and the obtained solution was concentrated at 40° C. (external temperature) and 80 mbar to about 4 L. Then 3.0 L IPA were added and the solution was again concentrated to about 4 L. This procedure was repeated twice. After the third addition of IPA the obtained solution was seeded with 25 mg of H-D-Leu-Ala-Glu (OtBu)-(4-hydroxymethyl)-anilide x HCl and the mixture was stored overnight at 4° C. resulting in a suspension. The next morning it was concentrated at 40° C. (external temperature) and 80 mbar to 3.21 kg. To the obtained suspension 3.4 L IPE were added over a period of 20 min and the suspension was stirred for 21 h at room temperature. Then the precipitate was filtered off (filter with 11 μm pore size, filtration time: 10 min) and washed once with 3.4 L IPA/IPE 1:1 and twice with 3.4 L IPE. The filter cake was dried under reduced pressure (<20 mbar) at 35° C. for 20 h yielding 623 g H-D-Leu-Ala-Glu(OtBu)-(4-hydroxymethyl)-anilide× HCl (84% yield, 6.4% volume yield, both corrected for assay of H-D-Leu-Ala-Glu(OtBu)-(4-hydroxymethyl)-anilide×HCl as white crystals. HPLC-purity: 99.0% Assay: 86.6% (titration with AgNO3) 85.6% (nitrogen content, elemental analysis) Palladium content: 9.1 ppm

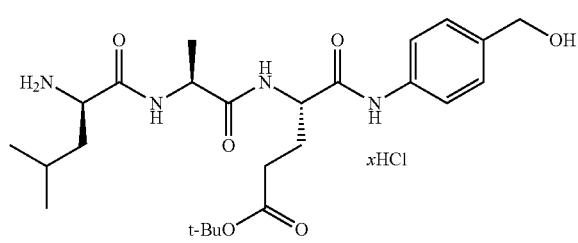

TBTU, DIPEA

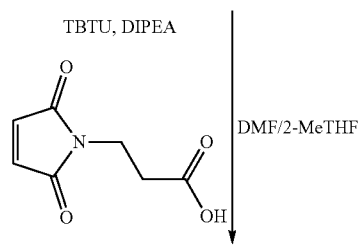

DMF/2-MeTHF

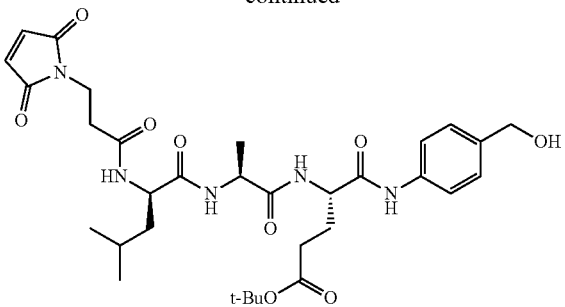

In a 10 L double-jacketed reactor 597 g (982 mmol, 1.00 eq.) H-D-Leu-Ala-Glu(OtBu)-(4-hydroxymethyl)-anilide× HCl (87% assay) and 166 g (982 mmol, 1.00 eq.) 3-maleimidopropionic acid were dissolved in 4.78 L MeTHF and 1.20 L DMF at 20° C. (jacket temperature). After cooling to 10° C. (internal temperature), 347 g (1080 mmol, 1.10 eq.) TBTU and 266 g (2062 mmol, 2.10 eq.) DIPEA were added (internal temperature rose to 13° C.). The reaction was stirred at 20° C. (jacket temperature) for 3 h, when HPLC analysis showed 94.3% 3-Maleimido-propionyl-D-Leu-Ala-Glu(OtBu)-(4-hydroxymethyl)-anilide, 2.25% H-D-Leu-Ala-Glu(OtBu)-(4-hydroxymethyl)-anilide×HCl. The reaction mixture was cooled to 5° C. and an aqueous extraction work-up was performed at 3-6° C. internal temperature (brine, deionized water, 1 N HCl, 5% NaHCO3 and MeTHF were cooled to 5° C. prior to extraction). First, the reaction mixture was extracted with a solution of 1.8 L brine and 1.8 L deionized water (complete phase separation took 7 min), followed by extraction with 6×1.8 L 1 N HCl (complete phase separation after 2-3 min). 0.8 L MeTHF were added to the first and 0.5 L MeTHF each to the following extraction steps with 1 N HCl to keep the volume of the organic layer constant (HPLC: 0.65% H-D-Leu-Ala-Glu(OtBu)-(4-hydroxymethyl)-anilide×HCl and 95.1% 3-3-Maleimido-propionyl-D-Leu-Ala-Glu(OtBu)-(4-hydroxymethyl)-anilide detected in organic phase after sixth HCl extraction step). The organic phase was then extracted with 3×1.8 L 5% NaHCO3. To keep the volume of the organic layer constant, 1.0 L MeTHF was added to the first and 0.5 L MeTHF each were added to the second and third extraction steps with 5% NaHCO3. Since the phase separation after the second extraction step with 5% NaHCO3 was very slow, 540 mL brine each were added to the second and third extraction with 5% NaHCO3 (time to complete separation of the layers: 10 min, 12 min and 11 min). The organic phase was extracted with 1×1.8 L 1N HCl and 3×1.8 L deionized water (0.5 L MeTHF were added to each extraction step, 4-5 min for complete phase separation). The obtained organic layer was filtered to remove solids (pore size approx. 5-15 μm) and was concentrated at 40° C. (external temperature) and 120 mbar. To the obtained solution (1.7 kg), 5.75 L MeTHF were added and concentration was continued to give 2.504 kg of a yellow-brownish solution. This solution was slowly added at room temperature to 4.3 L heptane over a period of 23 min, forming an off-white suspension. The flask of the solution after concentration was rinsed with 200 mL MeTHF and the rinsing solution was slowly added to the suspension. The suspension was stirred for further 4 min. Then the precipitate was filtered off (filter with 11 μm pore size, filtration time: 4 min) and was washed with 2×2.1 L MeTHF/heptane 1:2. The filter cake was dried for 87 h in a rotary evaporator at 35° C. under reduced pressure (<20 mbar), giving 563 g of a slightly off-white solid (HPLC-purity: 95.6%). 70 g of the obtained product were used for a recrystallization experiment and the rest (492 g) was further dried for 19 h at 40°

C. and <2 mbar (483 g product) and for 16 h at 50° C. and <2 mbar, yielding 480 g 3-Maleimido-propionyl-D-Leu-Ala-Glu(OtBu)-(4-hydroxymethyl)-anilide as an off-white solid (85% yield, 4.9% volume yield, both corrected for assay of 3-Maleimido-propionyl-D-Leu-Ala-Glu(OtBu)-(4-hydroxymethyl)-anilide). HPLC-purity: 95.7%

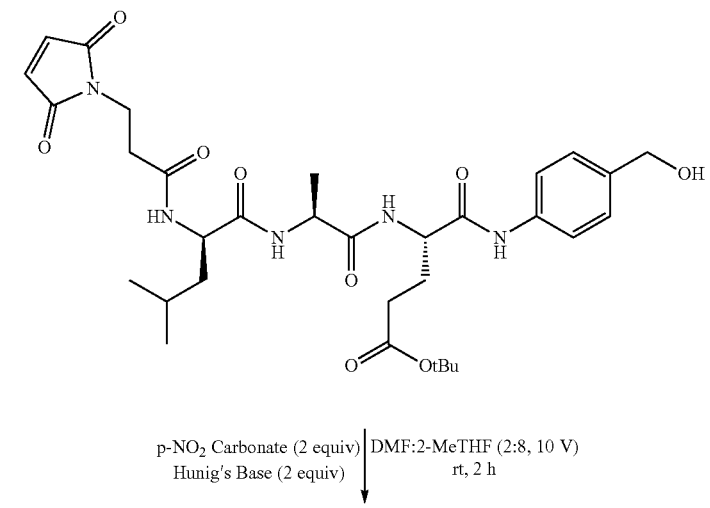

In a 1 L reactor, to a solution of 3-Maleimido-propionyl-D-Leu-Ala-Glu(OtBu)-(4-hydroxymethyl)-anilide 13.84 g (21.50 mmol, 1.0 eq) in 10V of MeTHF/DMF 8:2 was added Bis(4-nitrophenyl) carbonate 13.08 g (43.0 mmol, 2.0 eq). Mixture was stirred for 5.0 min and then DIPEA 7.5 mL (43.0 mmol, 2.0 eq) was added. Resulting mixture was stirred for 2h at 25° C. The reaction mixture was cooled to 20° C. and then diluted with MeTHF (10V) and washed with 1×140 mL 10% aq. NaCl and 2×140 mL H2O. Solvent was chased 3× with MeTHF (3×10V) down to 10V (40° C.-200 mbar). The obtained solution was then added to 40V MTBE/heptane 1:1 over 45 min. The slurry was aged for 80 minutes at RT, then filtered and washed 3× (10V MTBE/heptane 1:1). The obtained solid was dried for 18h in a vacuum oven at 30° C. to give tert-butyl (S)-4-((S)-2-((R)-2-(3-(2,5-di-oxo-2,5-dihydro-1H-pyrrol-1-yl)propanamido)-4-methyl-pentanamido)propanamido)-5-((4-((((4-nitrophenoxy)car-bonyl)oxy)methyl)phenyl)amino)-5-oxopentanoate as a white solid with 87% yield and 94.9% purity.

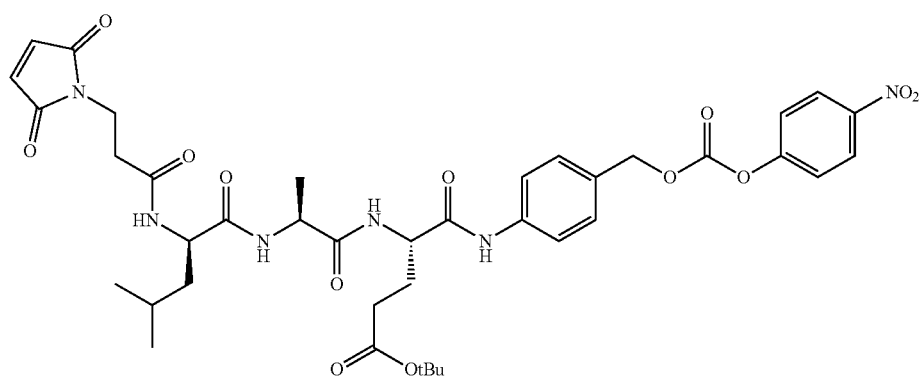

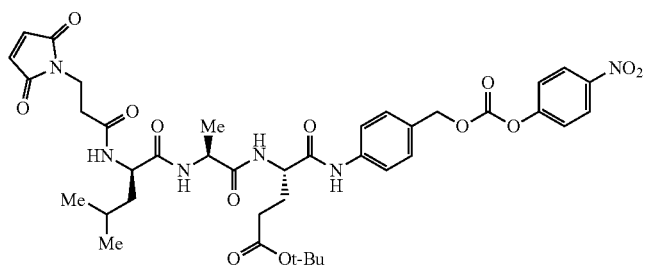

553

1 equiv.

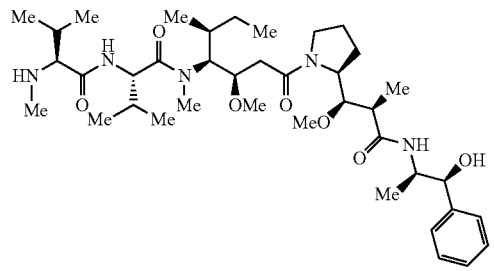

554

1.3 equiv.

NHS (15 mol %)
DMA/MTBE
40° C.

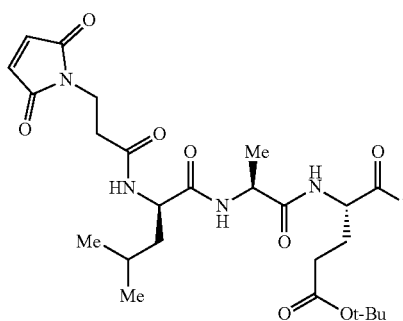

In a 2 L reactor 15.40 g (17.70 mmol, 1.00 eq.) tert-butyl (S)-4-((S)-2-((R)-2-(3-(2,5-dioxo-2,5-dihydro-1H-pyrrol-1-yl)propanamido)-4-methylpentanamido)-propanamido)-5-((4-((((4-nitrophenoxy)carbonyl)oxy)methyl)phenyl)amino)-5-oxopentanoate (93% assay), 15.40 g (23.0 mmol, 1.3 eq.) (S)-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide and 0.306 g (2.66 mmol, 0.15 eq.) NHS were dissolved in 2V DMA. To this mixture was then added 20V DMA/MTBE 7:1. Resulting mixture was stirred at 40° C. for 30h to reach to completion. Reaction mixture was then cooled down to rt and diluted with 10V of MeTHF and 20V of H$_2$O and mixed well. The two layers were separated. The aqueous was extracted again with MeTHF (1×20V). Organics were combined and washed (1×20V 0.5M HCl, 2×20V NaHCO$_3$, 2×20V H$_2$O). The organic layer was then chased with MeTHF (3×10V) and then concentrated to dryness. The residue was then dissolved in ACN/DCM 1:1 (6V). The obtained solution was then taken to the next step.

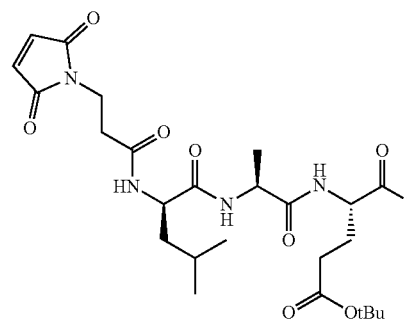

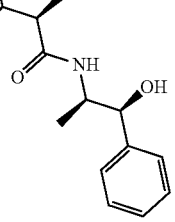

propionitrile, H$_3$PO$_4$
rt

-continued

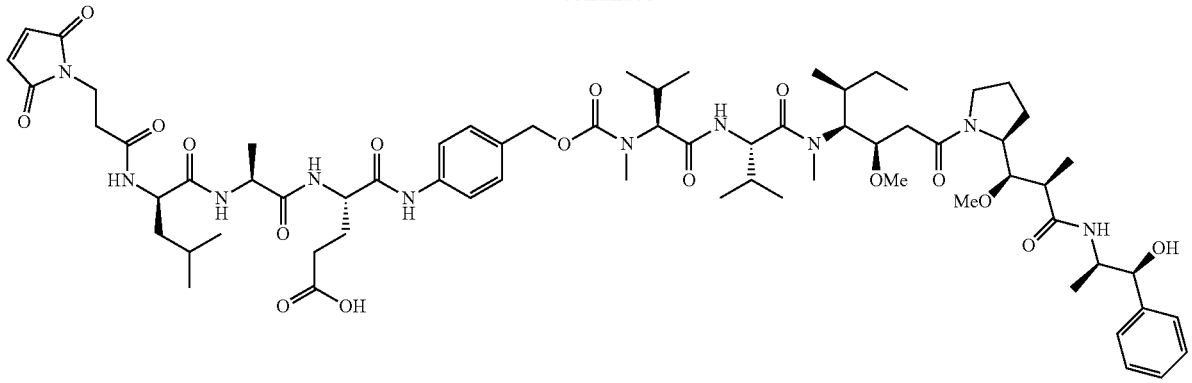

In a 2 L reactor, tert-butyl (S)-5-((4-((5S,8S,11S,12R)-11-((S)-sec-butyl)-12-(2-((S)-2-((1R,2R)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-4-((S)-2-((R)-2-(3-(2,5-dioxo-2,5-dihydro-1H-pyrrol-1-yl)propanamido)-4-methylpentanamido)propanamido)-5-oxopentanoate in DCM/ACN 1:1 (6V) was diluted with ACN (4V) and cooled to 5° C. 5V of ACN was added to $H_3PO_4$ (8V), the mixture was mixed well and cooled to 5° C. The solution of $H_3PO_4$ was slowly added to the reaction mixture while keeping the temperature below 10° C. The resulting mixture was stirred at 20° C. for 4h to reach to completion.

Reaction mixture was then cooled to 10° C. and diluted with DCM (10V) and water (15V). The reaction mixture was mixed well, and the two layers were separated. The aqueous was extracted again with 10V DCM. Organics were combined and washed with $H_2O$ until pH 5 (4×20V). The obtained organic layer was chased with DCM (3×10V) down to 10V and then dilution with 10V of DCM to obtain a solution at 50 mg/mL of the desired product with 72% yield (over two steps) and 78.0% purity.

The obtained solution of the product in DCM was then purified with normal phase column chromatography to obtain 14.4 g of the desired product as a white solid with 71% yield (over two steps+purification) and 98.6% purity.

Examples 20-26

Materials and Methods. The following materials and methods are applicable to the synthetic procedures and experiments described in Examples 20-26 unless indicated otherwise. All commercially available anhydrous solvents were used without further purification. Starting materials, reagents and solvents were purchased from commercial suppliers (SigmaAldrich and Fischer). Products were purified by flash column chromatography utilizing a Biotage Isolera One flash purification system (Charlotte, NC). UPLC-MS was performed on a Waters single quad detector mass spectrometer interfaced to a Waters Acquity UPLC system. UPLC methods are described below. Preparative HPLC was carried out on a Waters 2454 Binary Gradient Module solvent delivery system configured with a Wasters 2998 PDA detector. Products were purified with the appropriate diameter of column of a Phenomenex Max-RP 4 μm Synergi 80 Å 250 mm reverse phase column eluting with 0.05% trifluoroacetic acid in water and 0.05% trifluoroacetic acid in acetonitrile unless otherwise specified.

General Method. Column—Waters CORTECS C18 1.6 μm, 2.1×50 mm, reversed-phase column Solvent A—0.1% aqueous formic acid Solvent B—acetonitrile with 0.1% formic acid

| Time (min) | Flow (mL/min) | A % | B % | Gradient |
|---|---|---|---|---|
| Initial | 0.6 | 97 | 3 | |
| 1.70 | 0.6 | 40 | 60 | Linear |
| 2.00 | 0.6 | 5 | 95 | Linear |
| 2.50 | 0.6 | 5 | 95 | Linear |
| 2.80 | 0.6 | 97 | 3 | Linear |
| 3.00 | 0.6 | 97 | 3 | Linear |
| 2.80 | 0.6 | 97 | 3 | Linear |

List of Abbreviations

| | |
|---|---|
| AcOH | acetic acid |
| Boc | tert-butyloxycarbonyl protecting group |
| DAR | Drug Antibody Ratio (p) |
| DCM | dichloromethane |
| DIPEA | N,N-diisopropylethylamine |
| DMA | N,N-dimethyacetamide |
| DMF | N,N-dimethylformamide |
| EtOAc | ethyl acetate |
| EtOH | ethanol |
| Fmoc | 9-fluorenylmethyl carbamates |
| HATU | 1-[bis(dimethylamino)methylene]-1H-1,2,3-triazolo[4,5-b]pyridinium 3-oxid hexafluorophosphate |
| Hex | hexanes |
| HPLC | high performance liquid chromatography |
| Mal | maleimide moiety |
| MeCN | acetonitrile |
| MeOH | methanol |
| MP | 3-maleimidopropyl |
| MS | Mass spectrometry |
| OSu | N-hydroxysuccinimide |
| PABC | para-amino benzyl carbamoyl |
| PEG | polyethylene glycol |
| PPTS | pyridinium para-toluene sulfonic acid |
| pTSA | para-toluene sulfonic acid |
| Prep | preparative |
| rt | room temperature |
| RT | retention time |
| TFA | trifluoroacetic acid |
| TSTU | N,N,N',N'-tetramethyl-O-(N-succinimidyl)uronium tetrafluoroborate |
| UPLC | Ultra Performance Liquid Chromatography |

Example 20: Preparation of Camptothecin Drug-Linkers

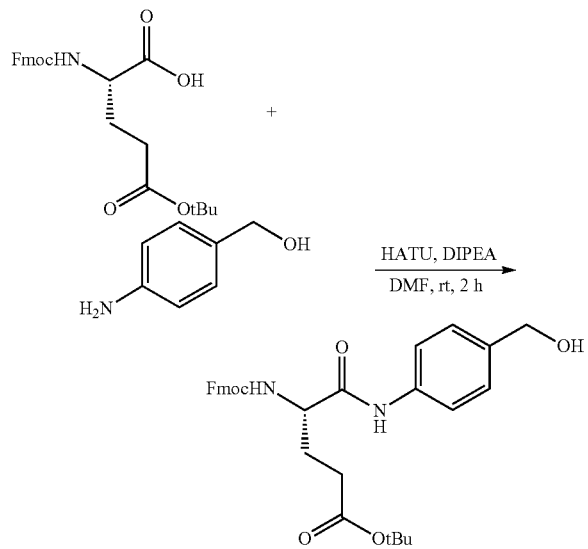

Fmoc-glutamate 5-tert-butyl ester (1.00 eq, 2.00 g, 4.701 mmmol), para-aminobenzylalcohol (1.50 eq, 868 mg, 7.051 mmol), HATU (1.40 eq, 2.516 g, 6.581 mmol) and a magnetic stir bar were added to a 200 ml RBF. DMF (10 mL) was added to the flask followed by N,N-Diisopropylethylamine (1.40 eq, 1.1 mL, 6.58 mmol). The reaction was stirred for 2 hours at room temperature. The reaction was slowly precipitated with 15 V of water and stirred for 1 hour. The slurry was filtered and washed with water to give an orange solid. The solid was dried in the vacuum oven overnight at 45° C. to give tert-butyl (4S)-4-(9H-fluoren-9-ylmethoxycarbonylamino)-5-[4-(hydroxymethyl)anilino]-5-oxo-pentanoate (2.50 g, 4.70 mmol, 100.03% yield). RT=2.12 min General Method UPLC. MS (m/z) [M+H]+ calc. for C31H35N2O6 531.25, found 531.38.

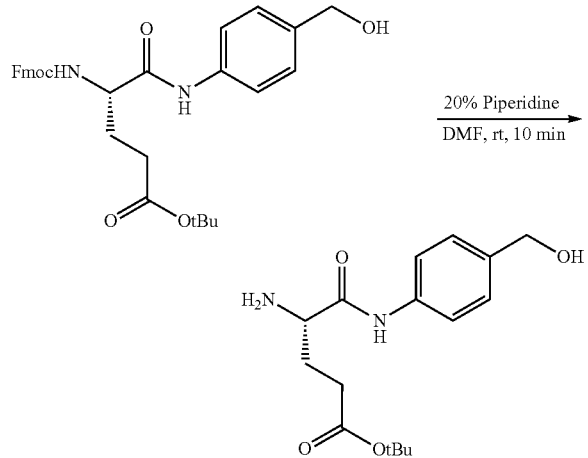

tert-butyl (4S)-4-(9H-fluoren-9-ylmethoxycarbonylamino)-5-[4-(hydroxymethyl)anilino]-5-oxo-pentanoate (1.00 eq, 0.60 g, 1.13 mmol) dissolved in 20% piperidine in DMF (3.7692 mL). The reaction was stirred for 10 minutes. Complete conversion was observed by UPLC-MS. The reaction was concentrated in vacuo and purified by prep-HPLC 30×250 mm Synergi Max-RP 5-30-95% MeCN in H2O 0.05% TFA. Fractions containing the desired product were concentrated in vacuo to afford a colorless solid tert-butyl (4S)-4-amino-5-[4-(hydroxymethyl)anilino]-5-oxo-pentanoate (0.32 g, 1.03 mmol, 90.77% yield). RT=0.79 min General Method UPLC. MS (m/z) [M+H]+ calc. for C16H24N2O4 309.18, found 309.43.

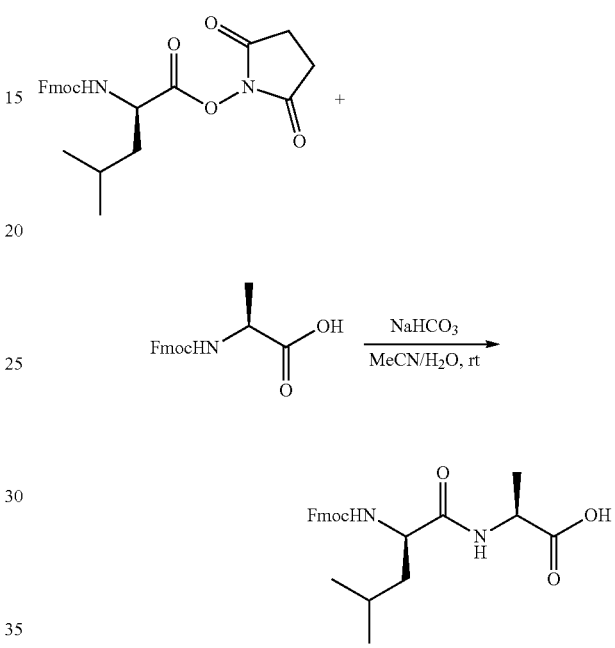

(2,5-dioxopyrrolidin-1-yl) (2R)-2-(9H-fluoren-9-ylmethoxycarbonylamino)-4-methyl-pentanoate (1.00 eq, 12.67 g, 28.1 mmol) and (2S)-2-aminopropanoic acid (1.70 eq, 4260 mg, 47.8 mmol) were dissolved in MeCN (126.7 mL). sodium bicarbonate (2.50 eq, 5907 mg, 70.3 mmol) in Water (63.4 mL) was added to the reaction. The reaction was stirred for 18 hours. The reaction was acidified with 2M HCl and concentrated in vacuo to remove MeCN. The aqueous phase was extracted with EtOAc and the combined organic phase was dried with MgSO4, filtered and concentrated in vacuo to afford the desired product as a colorless solid (2S)-2-[[(2R)-2-(9H-fluoren-9-ylmethoxycarbonylamino)-4-methyl-pentanoyl]amino]propanoic acid (7430 mg, 17.5 mmol, 62.23% yield). RT=1.89 min General Method UPLC. MS (m/z) [M+H]+ calc. for C24H29N2O5 425.21, found 425.45.

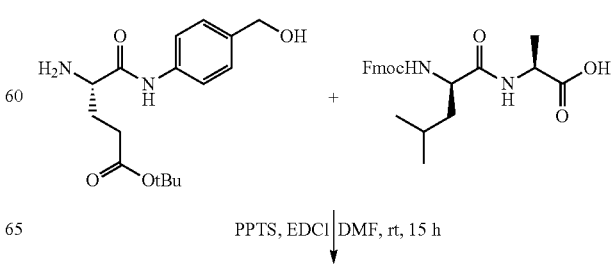

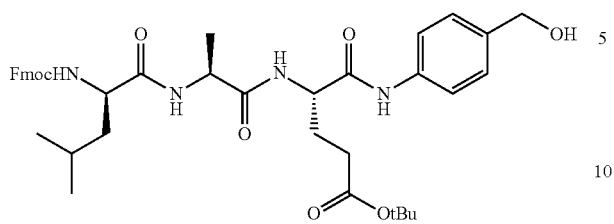

tert-butyl (4S)-4-amino-5-[4-(hydroxymethyl)anilino]-5-oxo-pentanoate (1.10 eq, 4994 mg, 16.2 mmol) dissolved in DMF (50 mL). PPTS (1.10 eq, 4070 mg, 16.2 mmol) was added followed by (2S)-2-[[(2R)-2-(9H-fluoren-9-yl-methoxycarbonylamino)-4-methyl-pentanoyl]amino]propanoic acid (1.00 eq, 6250 mg, 14.7 mmol). The reaction was cooled to 0° C. with an ice/water bath. 1-Ethyl-3-(3-dimethylaminopropyl)carbodiimide hydrochloride (1.20 eq, 3387 mg, 17.7 mmol) was added and the reaction and stirred overnight. Complete conversion was observed after 15 hours. The reaction was diluted with 1:1:1 EtOAC:THF:2MeTHF (300 mL), washed 11% K2CO3 (300 mL), washed 19% Citric acid (300 mL), washed 22% K2CO3 (300 mL), washed with 18% NaCl (300 mL). Organic layer dried MgSO$_4$, filtered and concentrated in vacuo to afford a yellow gummy solid. Purified by column chromatography 20-80% EtOAc in Hex. Fractions containing the desired product were concentrated in vacuo to afford a colorless solid tert-butyl (4S)-4-[[(2S)-2-[[(2R)-2-(9H-fluoren-9-yl-methoxycarbonylamino)-4-methyl-pentanoyl]amino]propanoyl]amino]-5-[4-(hydroxymethyl)anilino]-5-oxo-pentanoate (7416 mg, 10.4 mmol, 70.46%% yield). RT=2.13 min General Method UPLC. MS (m/z) [M+H]+ calc. for C40H51N4O8 715.37, found 715.50.

PFP Carbonate Activation

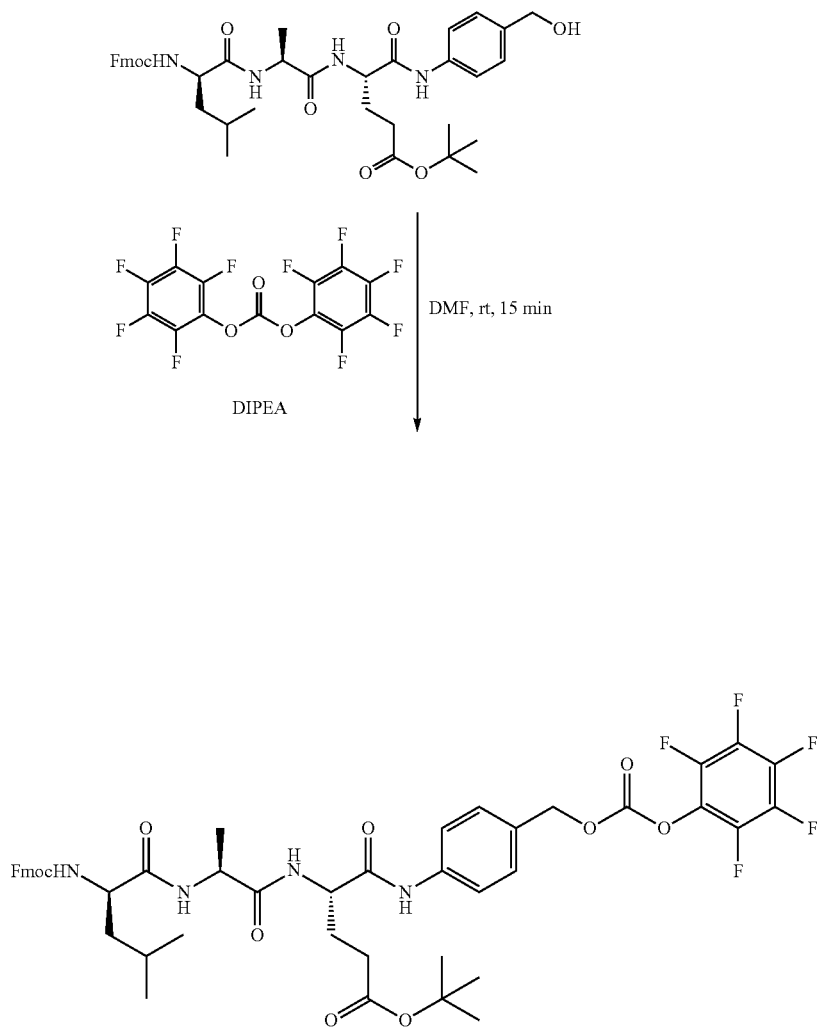

tert-butyl (4S)-4-[[(2S)-2-[[(2R)-2-(9H-fluoren-9-yl-methoxycarbonylamino)-4-methyl-pentanoyl]amino]propanoyl]amino]-5-[4-(hydroxymethyl)anilino]-5-oxo-pentanoate (1.00 eq, 1719 mg, 2.40 mmol) was dissolved in DMF (8.0157 mL). Bis(pentafluorophenyl) carbonate (2.00 eq, 1895 mg, 4.81 mmol) was added followed by N,N-Diisopropylethylamine (3.00 eq, 1.3 mL, 7.21 mmol). The reaction was stirred for 15 minutes at which point complete conversion was observed by UPLC-MS. The reaction was taken up in EtOAc (150 ml) and the organics washed with 2×150 ml 18% K2CO3 then 1×150 ml saturated brine solution. The organics were then separated and dried (MgSO4) before concentration to dryness. The crude was then purified by flash column chromatography eluting 10-80% EtOAc in hexanes. The desired fractions were concentrated to dryness in vacuo to afford a colorless solid tert-butyl (4S)-4-[[(2S)-2-[[(2R)-2-(9H-fluoren-9-yl-methoxy carbonylamino)-4-methyl-pentanoyl]amino]propanoyl]amino]-5-oxo-5-[4-[(2,3,4,5,6-pentafluorophenoxy) carbonyloxymethyl]anilino]pentanoate (1815 mg, 1.96 mmol, 81.61% yield). RT=2.38 min General Method UPLC. MS (m/z) [M+H]+ calc. for C47 H50F5N4O10 925.34, found 925.41.

Drug-Linker Formation

Preparation of AMDCPT was described in the international publication WO 2019/195665. (5S)-14-(aminomethyl)-5-ethyl-5-hydroxy-7,18,20-trioxa-11,24-diazahexacyclo[11.11.0.02,11.04,9.015,23.017,21]tetracosa-1(13),2,4(9),14,16,21,23-heptaene-6,10-dione (AMDCPT); hydrobromide (1.00 eq, 878 mg, 1.75 mmol) was dissolved in DMSO (2.9135 mL) and DMF (5.8269 mL). tert-butyl (4S)-4-[[(2S)-2-[[(2R)-2-(9H-fluoren-9-ylmethoxycarbonylamino)-4-methyl-pentanoyl]amino]propanoyl]amino]-5-oxo-5-[4-[(2,3,4,5,6-pentafluorophenoxy)carbonyloxymethyl]anilino]pentanoate (1.00 eq, 1617 mg, 1.75 mmol) was added to the reaction followed by N,N-Diisopropylethylamine (1.00 eq, 0.30 mL, 1.75 mmol). The reaction was stirred for 15 minutes at which point complete conversion was observed by UPLC-MS. Reaction was added dropwise to a 150 mL stirring water. The tan slurry was stirred for 15 minutes and collected by filtration and dried under vacuum to afford the desired product a tan solid tert-butyl (4S)-5-[4-[[(5S)-5-ethyl-5-hydroxy-6,10-dioxo-7,18,20-trioxa-11,24-diazahexacyclo[11.11.0.02,11.04,9.015,23.017,21]tetracosa-1(13),2,4(9),14,16,21,23-heptaen-14-yl]methylcarbamoyloxymethyl]anilino]-4-[[(2S)-2-[[(2R)-2-(9H-fluoren-9-ylmethoxycarbonylamino)-4-methyl-pentanoyl]amino]propanoyl]amino]-5-oxo-pentanoate (1815 mg, 1.56 mmol, 89.33%% yield). RT=2.16 min General Method UPLC. MS (m/z) [M+H]+ calc. for C63H68N7O15 1162.48, found 1162.69.

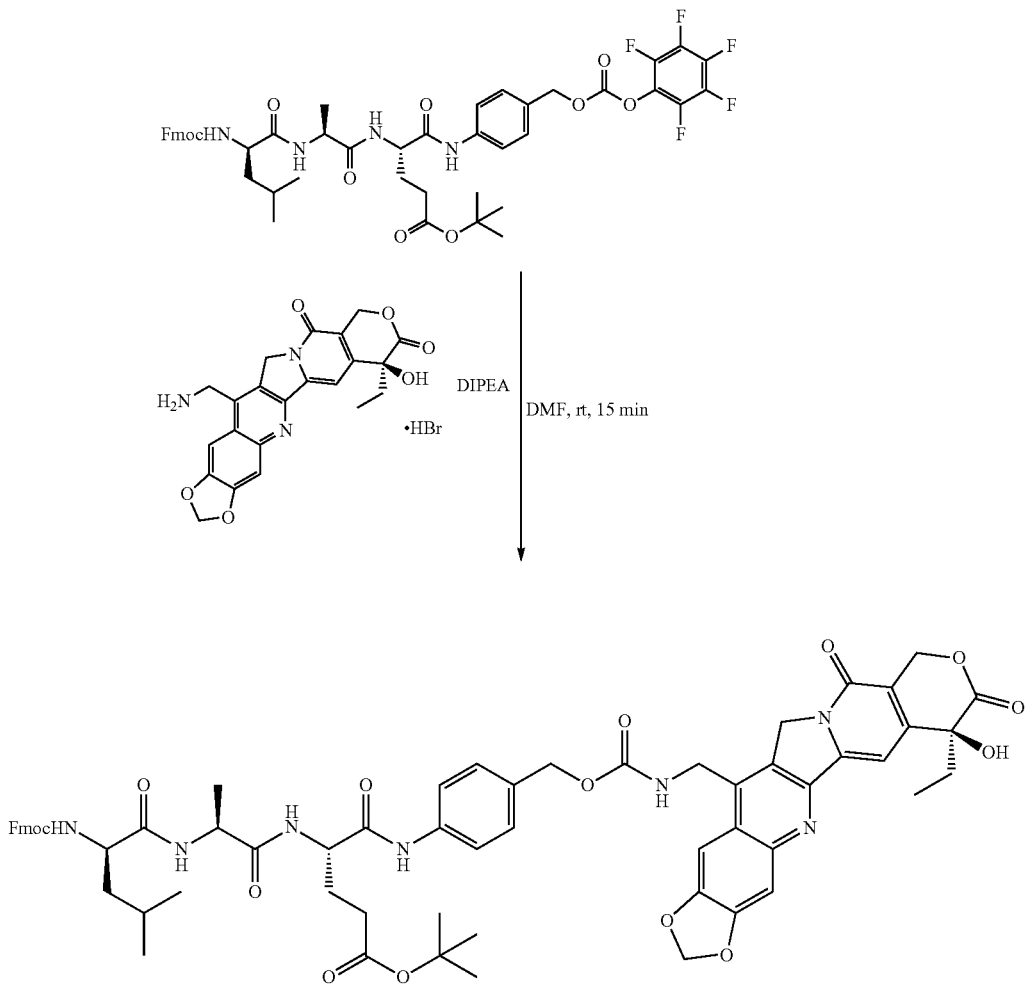

Fmoc Deprotection

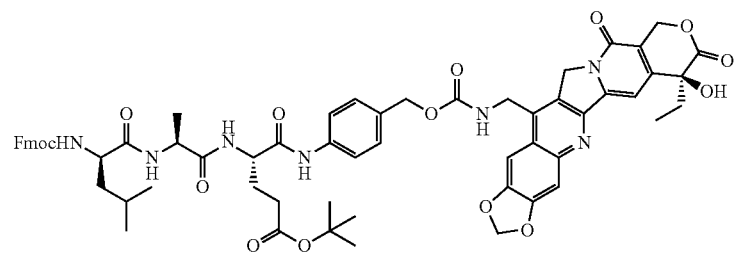

1) DBU 2) PPTS | DMF, rt, 60 min

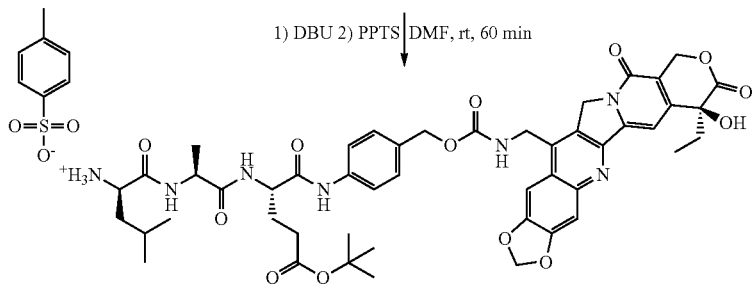

tert-butyl (4S)-5-[4-[[(5S)-5-ethyl-5-hydroxy-6,10-dioxo-7,18,20-trioxa-11,24-diazahexacyclo[11.11.0.02,11.04,9.015,23.017,21]tetracosa-1(13),2,4(9),14,16,21,23-heptaen-14-yl]methylcarbamoyloxymethyl]anilino]-4-[[(2S)-2-[[(2R)-2-(9H-fluoren-9-ylmethoxy carbonylamino)-4-methyl-pentanoyl]amino]propanoyl]amino]-5-oxo-pentanoate (1.00 eq, 727 mg, 0.625 mmol) was dissolved in DMF (2.0848 mL). 1,8-diazabicyclo[5.4.0]undec-7-ene (1.00 eq, 0.094 mL, 0.625 mmol) was added and the reaction was stirred for 60 minutes at which point complete conversion was observed. The reaction was added dropwise to a 75 mL stirring toluene. The brown precipitate was collected by filtration and dried under vacuum to afford the desired product tert-butyl (4S)-4-[[(2S)-2-[[(2R)-2-amino-4-methyl-pentanoyl]amino]propanoyl]amino]-5-[4-[[(5S)-5-ethyl-5-hydroxy-6,10-dioxo-7,18,20-trioxa-11,24-diazahexacyclo[11.11.0.02,11.04,9.015,23.017,21]tetracosa-1(13),2,4(9),14,16,21,23-heptaen-14-yl]methylcarbamoyloxymethyl]anilino]-5-oxo-pentanoate;4-methylbenzenesulfonic acid (664 mg, 0.597 mmol, 95.43% yield). RT=0.85 min General Method UPLC. MS (m/z) [M+H]+ calc. for C48H58N7O13 940.41, found 940.84.

MPOSu Coupling

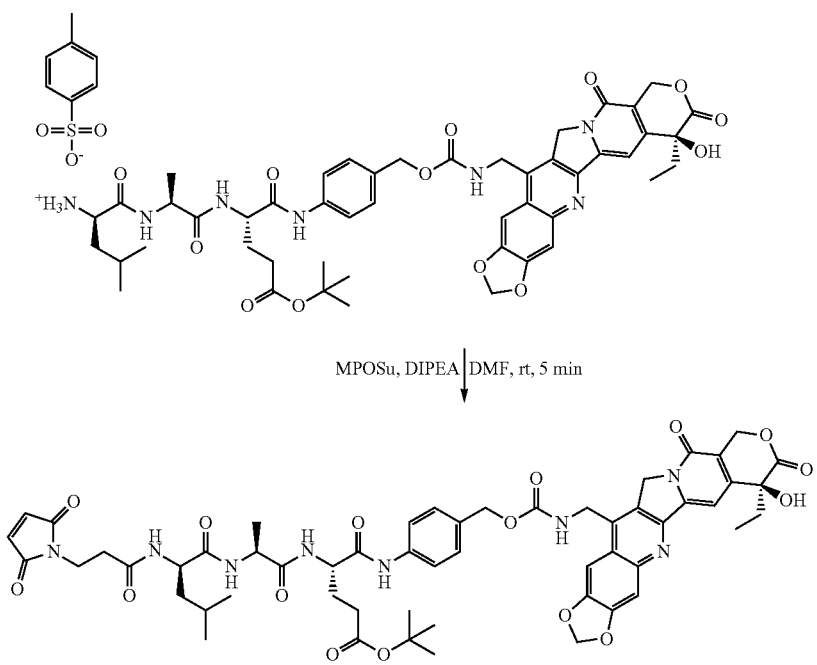

tert-butyl (4S)-4-[[(2S)-2-[[(2R)-2-amino-4-methyl-pentanoyl]amino]propanoyl]amino]-5-[4-[[[(5S)-5-ethyl-5-hydroxy-6,10-dioxo-7,18,20-trioxa-11,24-diazahexacyclo[11.11.0.0²,¹¹.0⁴,⁹.0¹⁵,²³.0¹⁷,²¹]tetracosa-1(13),2,4(9),14,16,21,23-heptaen-14-yl]methylcarbamoyloxymethyl]anilino]-5-oxo-pentanoate;4-methylbenzenesulfonic acid (1.00 eq, 664 mg, 0.597 mmol) was dissolved in DMF (3.9789 mL). 2,5-dioxopyrrolidin-1-yl 3-(2,5-dioxo-2,5-dihydro-1H-pyrrol-1-yl)propanoate (1.10 eq, 175 mg, 0.657 mmol) was added to the reaction followed by N,N-Diisopropylethylamine (1.20 eq, 0.12 mL, 0.716 mmol). The reaction was stirred for 5 minutes at which point complete conversion was observed. The reaction was acidified with AcOH (0.2 mL) and added dropwise to 75 mL stirring water. The brown precipitate was collected by filtration and dried under vacuum to afford the desired product tert-butyl (4S)-4-[[(2S)-2-[[(2R)-2-[3-(2,5-dioxopyrrol-1-yl)propanoylamino]-4-methyl-pentanoyl]amino]propanoyl]amino]-5-[4-[[[(5S)-5-ethyl-5-hydroxy-6,10-dioxo-7,18,20-trioxa-11,24-diazahexacyclo[11.11.0.0²,¹¹.0⁴,⁹.0¹⁵,²³.0¹⁷,²¹]tetracosa-1(13),2,4(9),14,16,21,23-heptaen-14-yl]methylcarbamoyloxymethyl]anilino]-5-oxo-pentanoate (519 mg, 0.476 mmol, 79.76% yield). RT=1.78 min General Method UPLC. MS (m/z) [M+H]+ calc. for $C_{55}H_{62}N_8O_{16}$ 1091.44, found 1091.58.

Tert-Butyl Ester Deprotection tert-butyl (4S)-4-[[(2S)-2-[[(2R)-2-[3-(2,5-dioxopyrrol-1-yl)propanoylamino]-4-methyl-pentanoyl]amino]propanoyl]amino]-5-[4-[[[(5S)-5-ethyl-5-hydroxy-6,10-dioxo-7,18,20-trioxa-11,24-diazahexacyclo[11.11.0.0²,¹¹.0⁴,⁹.0¹⁵,²³.0¹⁷,²¹]tetracosa-1(13),2,4(9),14,16,21,23-heptaen-14-yl]methylcarbamoyloxymethyl]anilino]-5-oxo-pentanoate (1.00 eq, 519 mg, 0.476 mmol) was dissolved in MeCN (2 mL) and Phosphoric Acid (40.0 eq, 1.2 mL, 19.0 mmol). The reaction was stirred for 60 minutes at which point complete deprotection was observed. The reaction was added dropwise to 75 mL stirring water and the tan slurry was stirred for 10 minutes. The precipitate was collected by filtration, eluted into a separate flask with 1:1 MeOH:DCM and concentrated in vacuo. Redissolved in DMSO and purified by prep-HPLC 30×250 mm MaxRP eluting 20-45-95% focused gradient MeCN in H2O 0.05% TFA. fractions containing the desired product were concentrated in vacuo to afford a yellow solid (4S)-4-[[(2S)-2-[[(2R)-2-[3-(2,5-dioxopyrrol-1-yl)propanoylamino]-4-methyl-pentanoyl]amino]propanoyl]amino]-5-[4-[[[(5S)-5-ethyl-5-hydroxy-6,10-dioxo-7,18,20-trioxa-11,24-diazahexacyclo[11.11.0.0²,¹¹.0⁴,⁹.0¹⁵,²³.0¹⁷,²¹]tetracosa-1(13),2,4(9),14,16,21,23-heptaen-14-yl]methylcarbamoyloxymethyl]anilino]-5-oxo-pentanoic acid (Compound 43, 276 mg, 0.267 mmol, 56.05% yield). RT=1.43 min General Method UPLC. MS (m/z) [M+H]+ calc. for $C_{51}H_{54}N_8O_{16}$ 1035.37, found 1035.42.

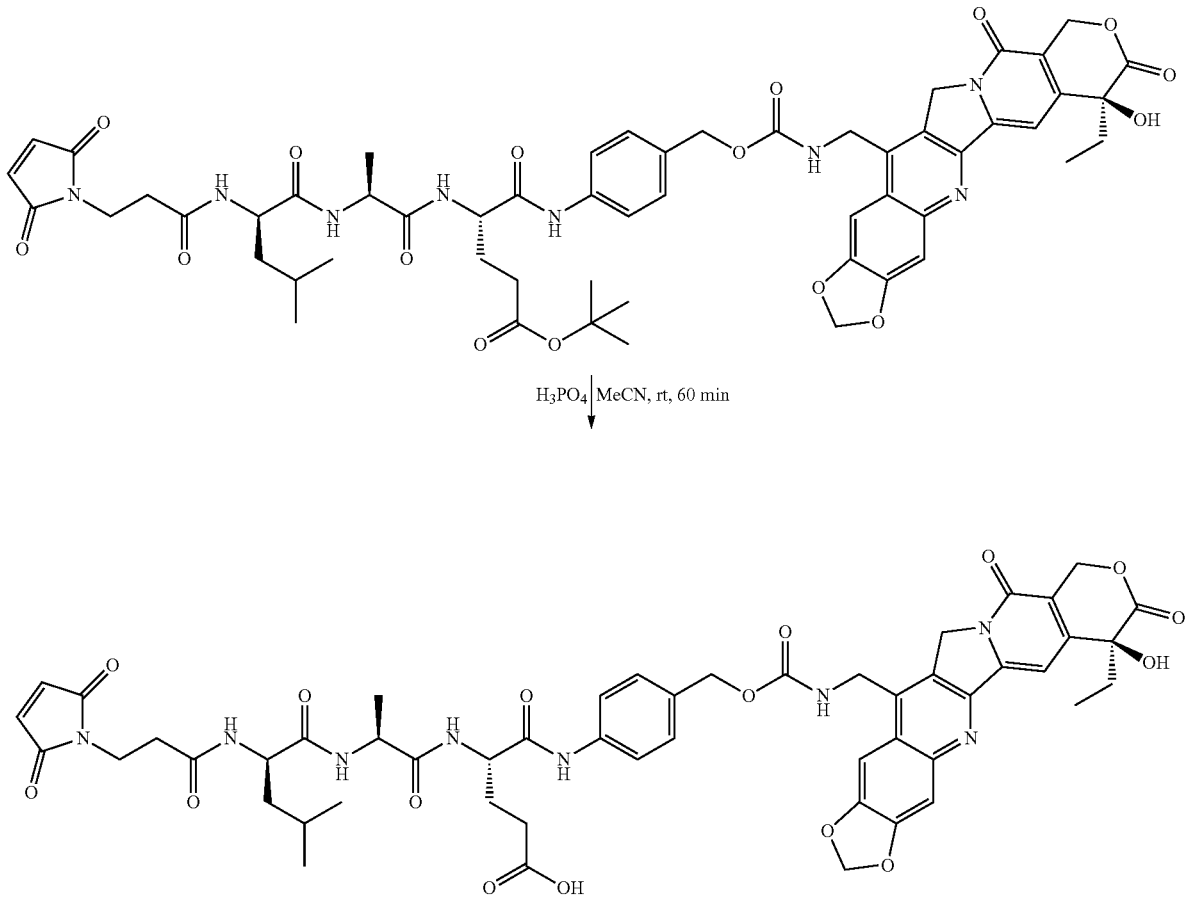

Compounds 43a, 43b, and 43c were made using similar methods. Results and characterization shown in Tables 4a and 4b. Exatecan was purchased from Advanced ChemBlock (Catalog #: 10484).

TABLE 4a

Drug Linker compounds synthesized according to the method of Example 2.2.

| Cmpd No. | $L_B$ | A | W | Y | Camptothecin (N-link) |
|---|---|---|---|---|---|
| 43 | Mal-CH$_2$CH$_2$C(O)— | — | D-Leu-Ala-Glu- | PABC | AMDCPT |
| 43a | Mal-CH$_2$CH$_2$C(O)— | —NH(CH$_2$CH$_2$O)$_4$—CH$_2$CH$_2$C(O)— | D-Leu-Ala-Glu- | PABC | AMDCPT |
| 43b | Mal-CH$_2$CH$_2$C(O)— | —NH(CH$_2$CH$_2$O)$_8$—CH$_2$CH$_2$C(O)— | D-Leu-Ala-Glu- | PABC | AMDCPT |
| 43c | Mal-CH$_2$CH$_2$C(O)— | — | D-Leu-Ala-Glu- | PABC | Exatecan |

TABLE 4b

Characterization of Drug-Linkers.

| Compound No. | Calc'd MS (m/z) [M + H]$^+$ | Observed MS (m/z) | RT |
|---|---|---|---|
| 43 | 1281.52 | 1282.97 | 1.42 |
| 43a | 1035.38 | 1035.51 | 1.43 |
| 43b | 1049.41 | 1049.58 | 1.64 |
| 43c | 1458.62 | 1458.94 | 1.43 |

Example 21: Drug Linker of AMDCPT with Val-Cit Linker

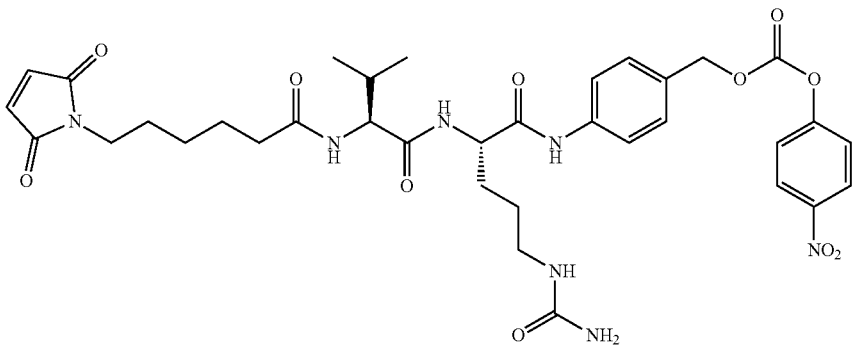 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

Preparation of Maleimidocaproyl-L-valine-L-citrulline-p-aminobenzyl alcohol p-nitrophenyl carbonate (MC-Val-Cit-PABC-PNP) was described in patent WO 2019108797.

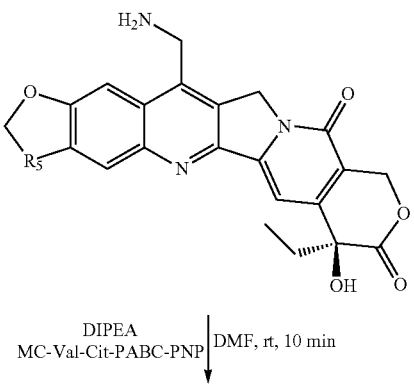

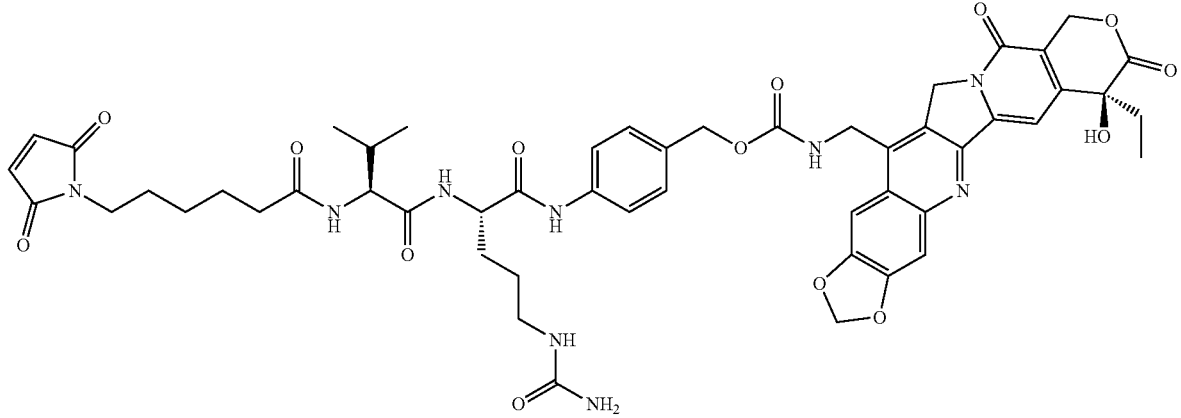

AMDCPT and MC-Val-Cit-PABA-PNP were dissolved in DMF (0.5 mL). DIPEA (4.00 eq, 0.026 mL, 0.149 mmol) was added and the reaction was stirred for 10 minutes. The reaction was acidified with AcOH and purified by Prep-HPLC 21×250 mm Synergi Max-RP 10-95% MeCN in H2O 0.05% TFA. Fractions containing the desired product were lyophilized to afford the desired product as a yellow solid 4-((S)-2-((S)-2-(6-(2,5-dioxo-2,5-dihydro-1H-pyrrol-1-yl)hexanamido)-3-methylbutanamido)-5-ureidopentanamido)benzyl (((S)-7-ethyl-7-hydroxy-8,11-dioxo-7,8,11,13-tetrahydro-1OH-dioxolo[4,5-g]pyrano[3',4':6,7]indolizino[1,2-b]quinolin-14-yl)methyl)carbamate (Compound 44, 2.40 mg, 2.35 μmol, 6.30% yield). RT=1.59 min General Method UPLC. MS (m/z) [M+H]+ calc. for $C_{51}H_{58}N_9O_{14}$ 1020.41, found 1020.09.

Example 22: Preparation of Ligand-Drug Conjugates

Fully or partially reduced ADCs were prepared in 50% propylene glycol (PG) IX PBS mixture. A half portion of the PG was added to reduced mAb, and half PG was added to the 1 mM DMSO camptothecin drug-linker stock. The PG/drug-linker mix was added to reduced mAb in 25% portions. After the addition of drug-linker was complete, excess drug-linker was removed by treating with activated charcoal (1 mg of charcoal to 1 mg of mAb). The charcoal was then removed via filtration, and the resulting ADC was buffer exchanged using a NAP5 or PD10 column, into 1×PBS pH 7.4.

Example 23: In Vitro ADC Evaluation

In vitro potency was assessed on multiple cancer cell lines. All cell lines were authenticated by STR profiling at IDEXX Bioresearch and cultured for no more than 2 months after resuscitation. Cells cultured in log-phase growth were seeded for 24 hours in 96-well plates containing 150 pi RPMI 1640 supplemented with 20% FBS. Serial dilutions of antibody-drug conjugates in cell culture media were prepared at 4× working concentrations, and 50 pL of each dilution was added to the 96-well plates. Following addition of test articles, cells were incubated with test articles for 4 days at 37 0° C. After 96 hours, growth inhibition was assessed by CellTiterGlo® (Promega, Madison, WI) and luminescence was measured on a plate reader. The $IC_{50}$ value, determined in triplicate, is defined here as the concentration that results in 50% reduction in cell growth relative to untreated controls.

In the Table 5, $IC_{50}$ values for ADCs are given in ng/mL. Cell viability was determined by CellTiter-Glo staining after 96h exposure to ADC. ND=Not Determined. The Drug-Linker compounds were conjugated to either a cAC10 or an Ag2 antibody, as indicated in the Table. Ag2 is an antibody targeting a ubiquitous and readily internalizable antigen. The cancer cell lines tested are renal carcinoma cells (786-0), melanoma cells (A2058), pancreatic cancer cells (BxPC3), (Calu1), (DEL), (DELBVR), (Karpas299), Hodgkin's lymphoma cells (L540cy), ($L_S$174T), breast cancer cells (MDA-MB-231), acute myeloid leukemia cells (MOLM-13), and B-lymphocyte cancer cells (SU-DHL4).

TABLE 5

In vitro potency ($IC_{50}$ values) of camptothecin ADCs (DAR = 8 for all ADCs).

| ADC/Drug | Description | 786-O $IC_{50}$ | A2058 $IC_{50}$ | BxPC3 $IC_{50}$ | Calu1 $IC_{50}$ | DEL $IC_{50}$ | DELBVR $IC_{50}$ |
|---|---|---|---|---|---|---|---|
| cAC10-Compound 43b | MP-PEG8-D-Leu-Ala-Glu-AMDCPT | >1000 | >1000 | >1000 | >1000 | 2 | 3.9 |
| cAC10-Compound 43 | MP-D-Leu-Ala-Glu-PABC-AMDCPT | >1000 | >1000 | >1000 | >1000 | 2 | 4 |
| Ag2-Compound 43 | MP-D-Leu-Ala-Glu-PABC-AMDCPT | >1000 | 261 | 132 | >1000 | 7 | 5 |
| Ag2-Compound 43a | MP-PEG4-D-Leu-Ala-Glu-PABC-AMDCPT | >1K | 69 | 65 | >1K | 4 | 5 |

TABLE 5-continued

In vitro potency (IC$_{50}$ values) of camptothecin ADCs (DAR = 8 for all ADCs).

| | | | | | | | |
|---|---|---|---|---|---|---|---|
| Ag2-Compound 43b | mp-PEG8-D-Leu-Ala-Glu-AMDCPT | >1000 | 98 | >1000 | >1000 | 5 | 4 |

| ADC/Drug | Description | Karpas299 IC$_{50}$ | L540cy IC$_{50}$ | Ls174T IC$_{50}$ | MDAMB231 IC$_{50}$ | MOLM-13 IC$_{50}$ | SU-DHL-4 IC$_{50}$ |
|---|---|---|---|---|---|---|---|
| cAC10-Compound 43b | MP-PEG8-D-Leu-Ala-Glu-AMDCPT | 455 | 15 | >1000 | >1000 | >1000 | >1000 |
| cAC10-Compound 43 | MP-D-Leu-Ala-Glu-PABC-AMDCPT | 49 | 11 | — | >1000 | >1000 | >1000 |
| Ag2-Compound 43 | MP-D-Leu-Ala-Glu-PABC-AMDCPT | 29 | 20 | | >1000 | 136 | 32 |
| Ag2-Compound 43a | MP-PEG4-D-Leu-Ala-Glu-PABC-AMDCPT | 9 | 10 | 41 | >1K | 41 | 14 |
| Ag2-Compound 43b | MP-PEG8-D-Leu-Ala-Glu-AMDCPT | 41 | 24 | 16.9 | 116 | 90 | 28 |

Example 24: Aggregation Study

ADC aggregation levels were determined for camptothecin drug-linkers (DAR=8). ADC aggregation was determined by Size Exclusion Chromatography (SEC). Results are shown in Table 6.

TABLE 6

Results of aggregation study.

| ADC | Description | DAR | Conc. (mg/mL) | HMW % |
|---|---|---|---|---|
| Ag2-Compound 43 | MP-D-Leu-Ala-Glu-PABC-AMDCPT | 8 | 1.07 | 5.66 |
| cAC10-Compound 43 | MP-D-Leu-Ala-Glu-PABC-AMDCPT | 8 | 1.01 | 3.96 |
| Ag2-Compound 43a | MP-PEG4-D-Leu-Ala-Glu-PABC-AMDCPT | 8 | 1.00 | 14.1 |
| Ag2-Compound 43b | MP-PEG8-D-Leu-Ala-Glu-PABC-AMDCPT | 8 | 0.98 | 4.7 |
| cAC10-Compound 43b | MP-PEG8-D-Leu-Ala-Glu-PABC-AMDCPT | 8 | 0.96 | 3.32 |
| Ag2-Compound 44 | MC-Val-Cit-PABC-AMDCPT | 8 | 1.00 | 50.1 |

Example 25: Plasma Aggregation Study

Non-binding h00 mAb was labeled with Alex Flour 488 (AF488) to a ratio of ~2-3 AF88/mAB. Camptothecin drug-linkers were conjugated to the fully reduced interchain disulfides of AF88-h in 50- propylene glycol (PG) 1×PBS mixture. The buffer was exchanged to 20 mM Glu pH 4.5 and diluted to 2 mg/mL. Test articles were diluted to 50 ug/mL in buffered rat plasma (100 mMv KPhos), pH 7.2) and incubated at 37° C. At determined time-points aliquots were sampled from the test articles, cooled to 2-8° C., and analyzed immediately by size exclusion chromatography (SEC) with fluorescence detection eluting with a neutral pH buffer, physiological ionic strength in the absence of organic solvents. The percent high molecular weight species (HMW) was analyzed representing aggregated ADC. The aggregation appears to be lower for the tripeptide D-Leu-Ala-Glu prepared camptothecin ADCs (Ex. 2.2) compared to the Val-Cit prepared camptothecin ADC (Ex. 2.3). Results are shown in Table 7.

TABLE 7

Results of plasma aggregation study.

| ADC | Description | DAR | AF488 loading | Conc. (mg/mL) | HMW % |
|---|---|---|---|---|---|
| h00-AF488-Compound 43 | MP-D-Leu-Ala-Glu-PABC-AMDCPT | 8 | 1.7 | 2.2 | 2.64 |
| h00-AF488-Compound 43a | MP-PEG4-D-Leu-Ala-Glu-PABC-AMDCPT | 8 | 1.8 | 2.12 | 3.12 |
| h00-AF488-Compound 43b | MP-PEG8-D-Leu-Ala-Glu-PABC-AMCPT | 8 | 1.8 | 2.28 | 4.58 |
| h00-AF488-Compound 43c | MP-D-Leu-Ala-Glu-PABC-Exatecan | 8 | 1.7 | 2.44 | 3.41 |
| h00-AF488-Compound 44 | MC-Val-Cit-PABC-AMDCPT | 8 | 1.7 | 2.27 | 32.01 |

Figure 23:
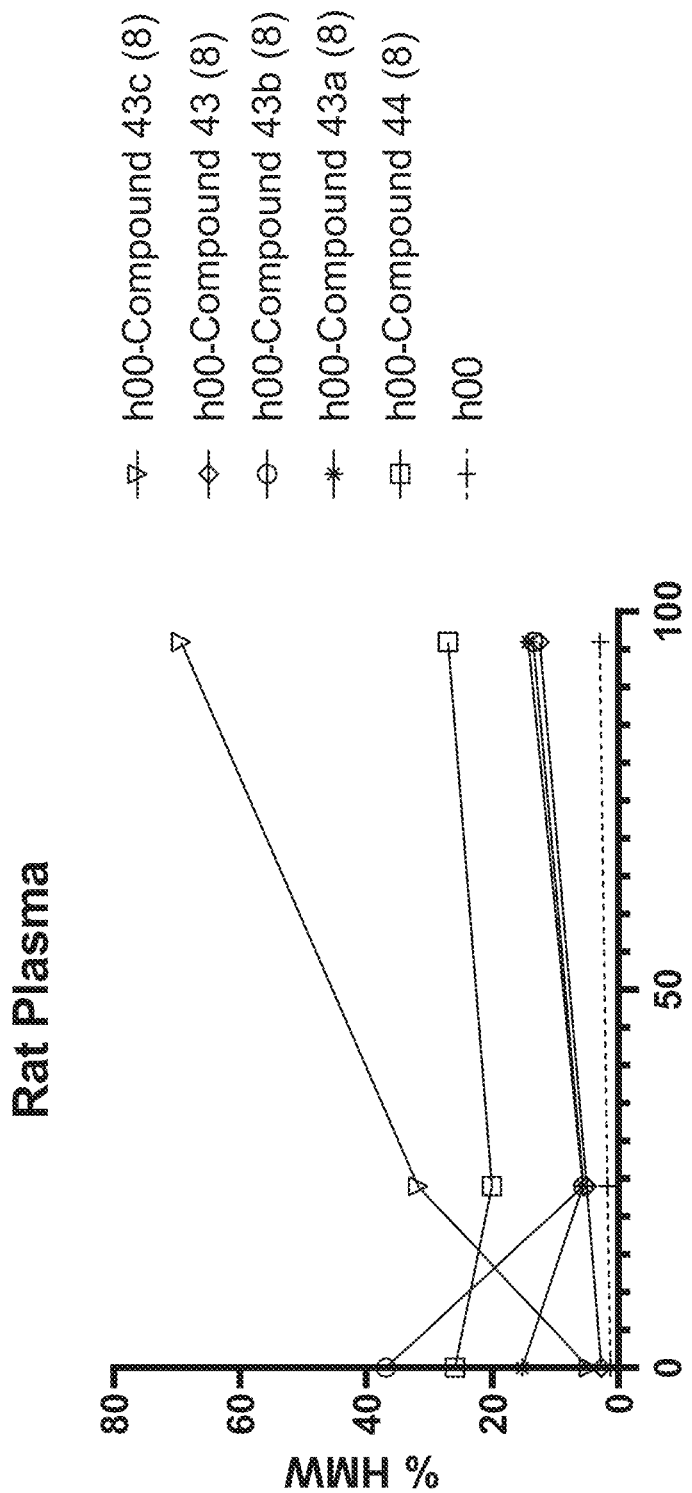
FIG. 23. Results of plasma aggregation over time for selected ADC compounds.

Plasma aggregation for the compounds was also monitored over time (FIG. 23).

Example 26: In Vivo Models

All experiments were conducted in concordance with the Animal Care and Use Committee in a facility fully accredited by the Association for Assessment and Accreditation of Laboratory Animal Care. Efficacy experiments were conducted in the L428, KMH2, Karpas/Karpas-BVR, DelBVR, and Caki-1 xenografts models. Tumor cells, as a cell suspension, were implanted sub-cutaneous in immune-compromised SCID or nude mice. Upon tumor engraftment, mice were randomized to study groups (5 mice per group) when the average tumor volume reached about 100 mm3. The ADC or controls were dosed once via intraperitoneal injection. The average number of drug-linker attached to an antibody is indicated in the parenthesis next to the ADC (also referred to herein as Drug-Antibody Ratio (DAR)

number, e.g., DAR4, DAR8, etc.). Tumor volume as a function of time was determined using the formula (L×W2)/2. Animals were euthanized when tumor volumes reached 750 mm3. Mice showing durable regressions were terminated after 10-12 weeks post implant.

Figure 24A:
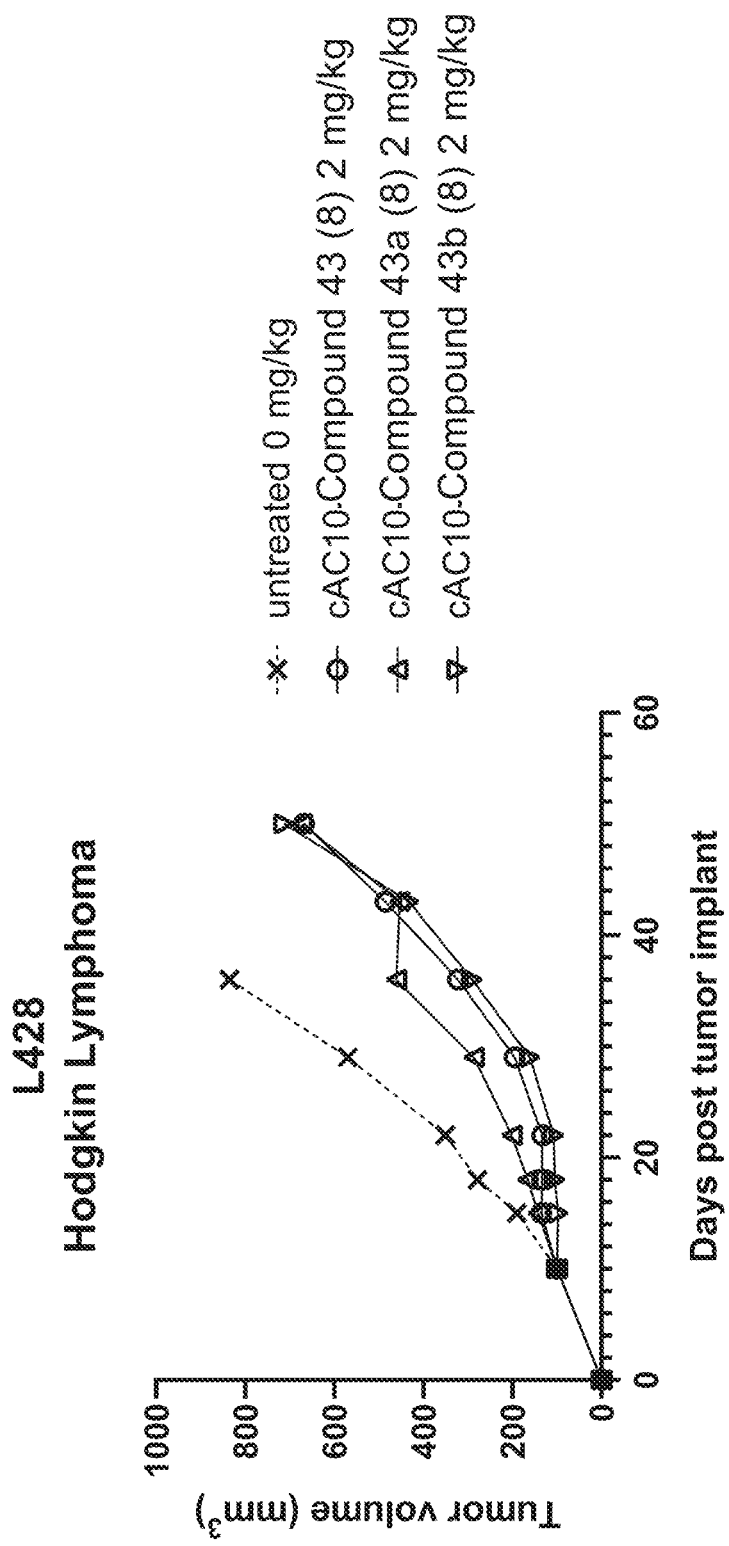
FIGS. 24A and 24B. Tumor size in mice with Hodgkin lymphoma (L428) after treatment with selected Antibody Drug Conjugate compounds.
Figure 24B:
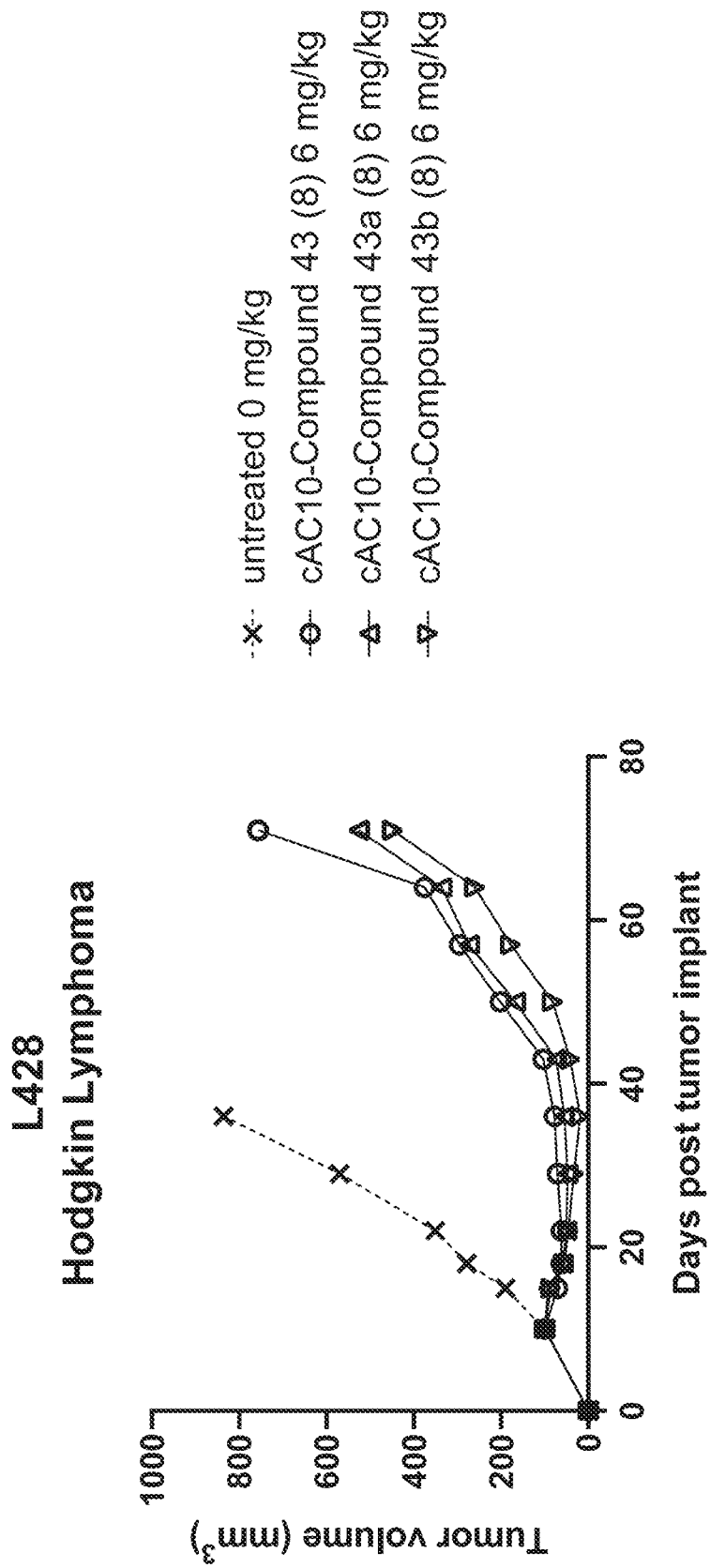

Animals were implanted with L428 cells. After 10 days, the animals were sorted into groups with an average tumor size of 100 mm3, and then treated with a single dose of camptothecin ADC cAC10-Compound 43(8), cAC10-Compound 43a(8) or cAC10-Compound 43b(8), at 2 or 6 mg/kg. Animals were evaluated for tumor size and in-life signs during the course of the study. The results are shown in FIGS. 24A and 24B.

Figure 25A:
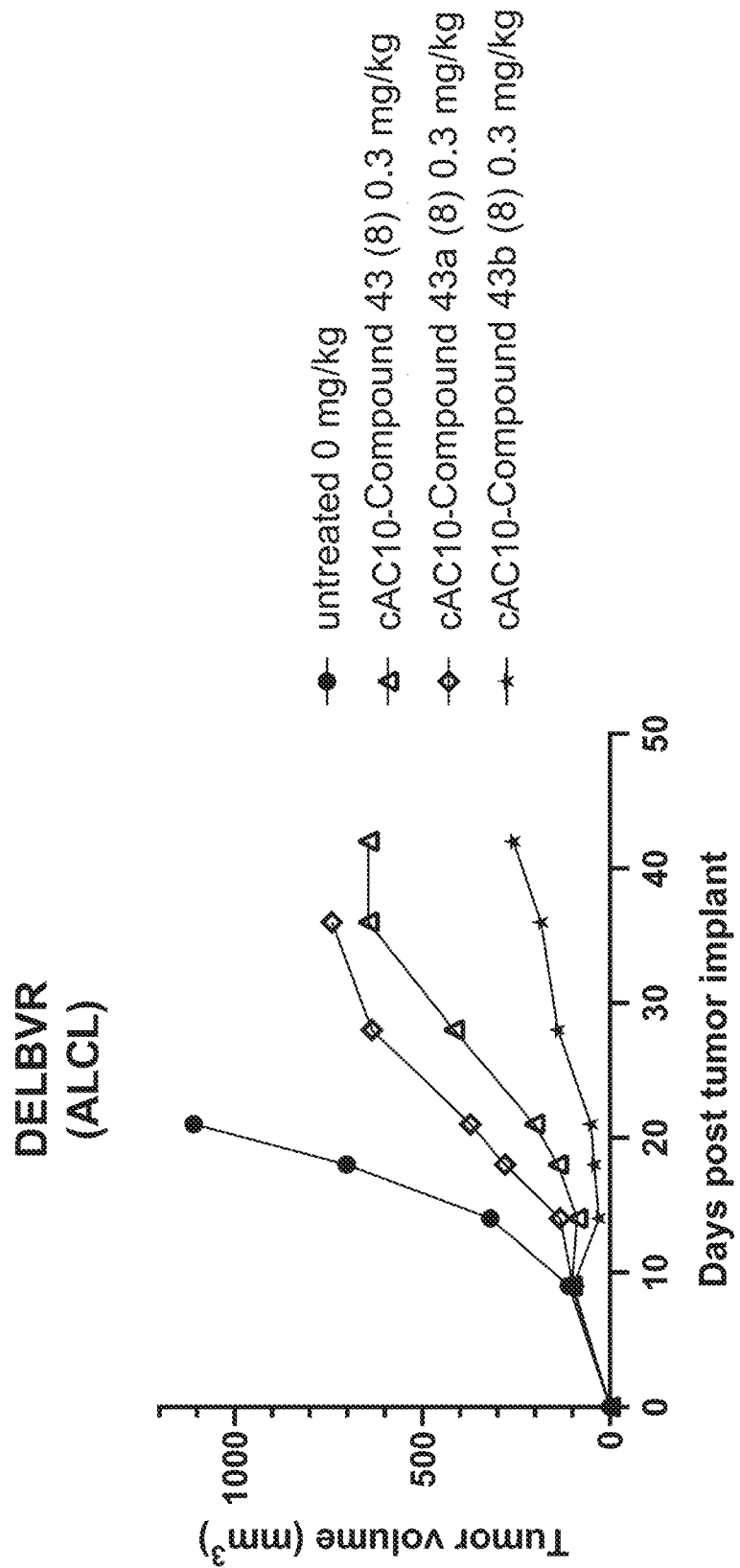
FIGS. 25A, 25B, and 25C. Tumor size in mice with DELBVR (ALCL) after treatment with selected Antibody Drug Conjugate compounds.
Figure 25B:
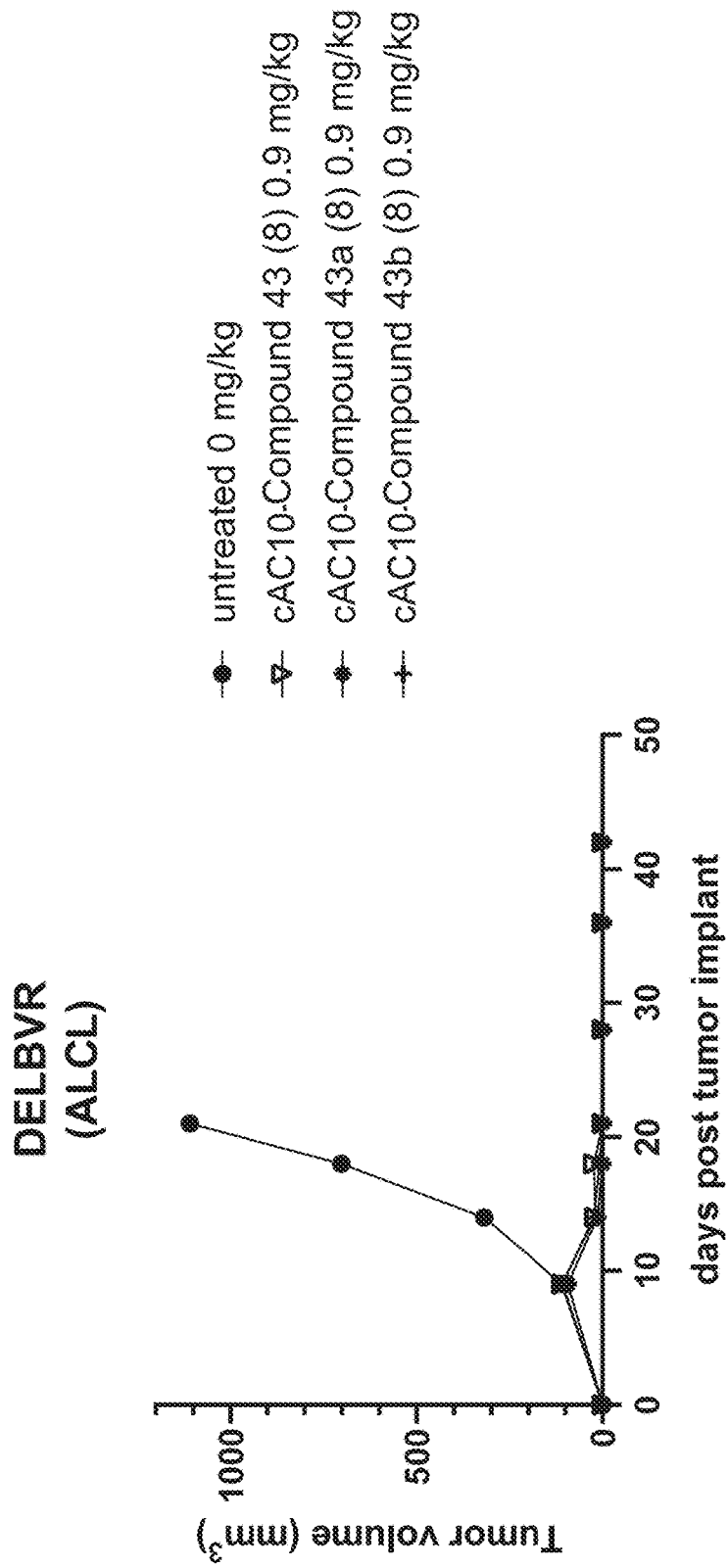
Figure 25C:
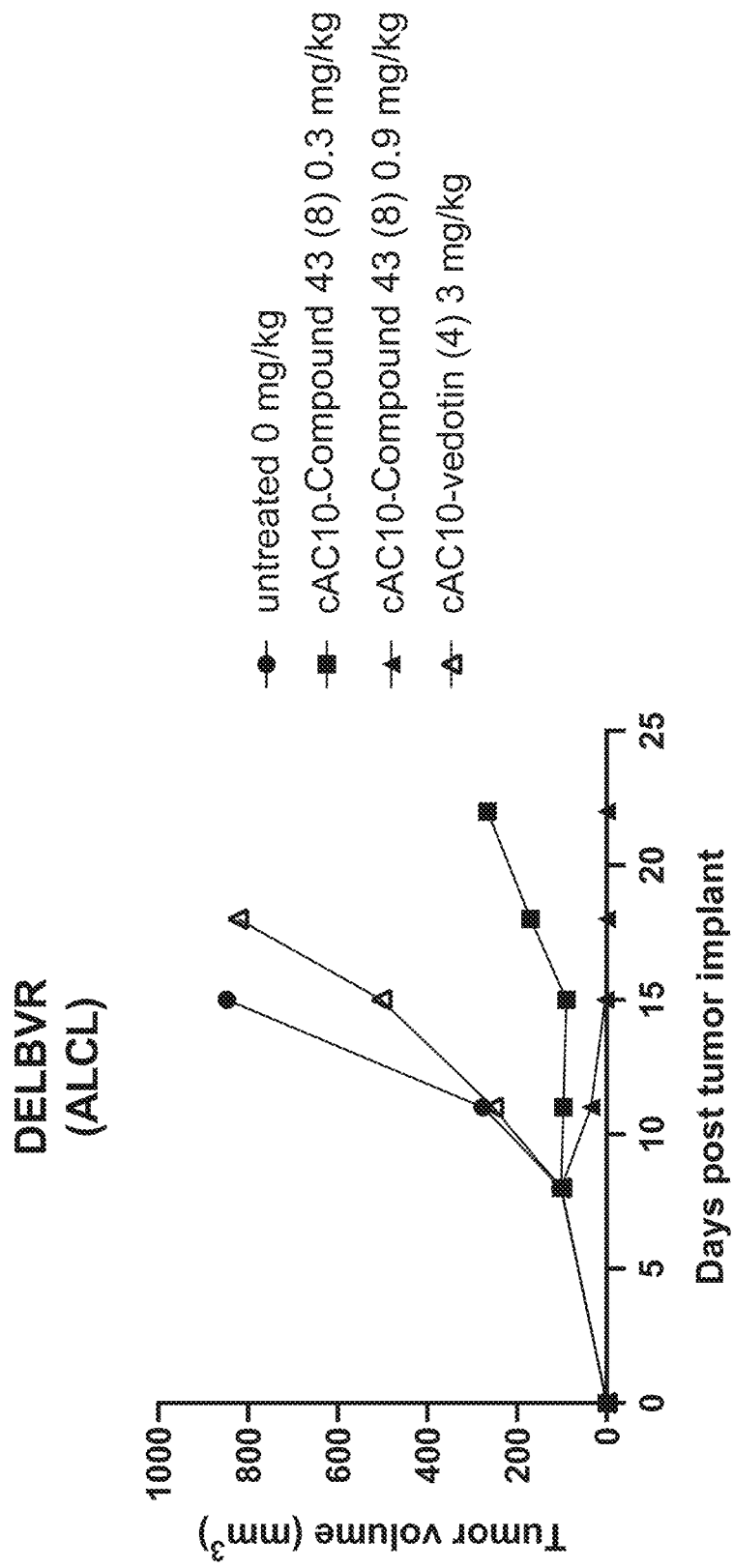

Animals were implanted with Del-brentuximab vedotin resistant (DELBVR) cells. On day 9, the animals were sorted into groups with an average tumor size of 100 mm3, and then treated with a single dose of camptothecin Compound 43(8), cAC10-Compound 43a(8) or cAC10-Compound 43b(8), at 0.3 or 0.9 mg/kg, or brentuximab vedotin 3 mg/kg. Animals were evaluated for tumor size and in-life signs during the course of the study. The results are shown in FIG. 25A-C.

Figure 26:
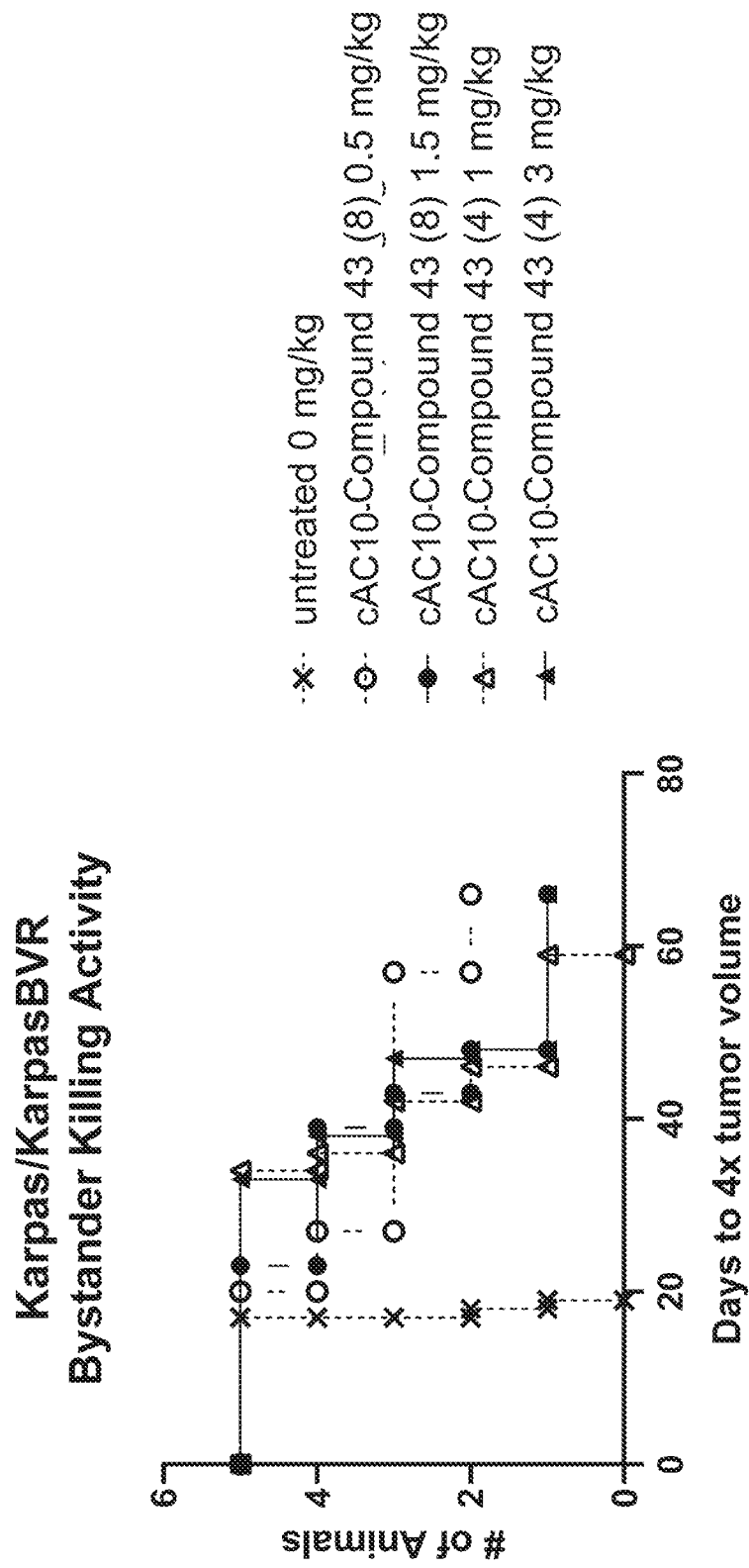
FIG. 26. Survival of mice with Karpas/KarpasBVR following treatment with selected Antibody Drug Conjugate compounds.

Animals were implanted with a 1:1 mixture of CD30+ Karpas299 and CD30-Karpas299-brentuximab vedotin resistant (Karpas299-BVR) cells. After 5 days, the animals were sorted into groups with an average tumor size of 100 mm3, and then treated with a single dose of camptothecin cAC10-Compound 43(8) at 0.5 and 1.5 mg/kg or cAC10-Compound 43(4) at 1 and 3 mg/kg. Animals were evaluated for tumor size and in-life signs during the course of the study. The results are shown in FIG. 26.

Figure 27A:
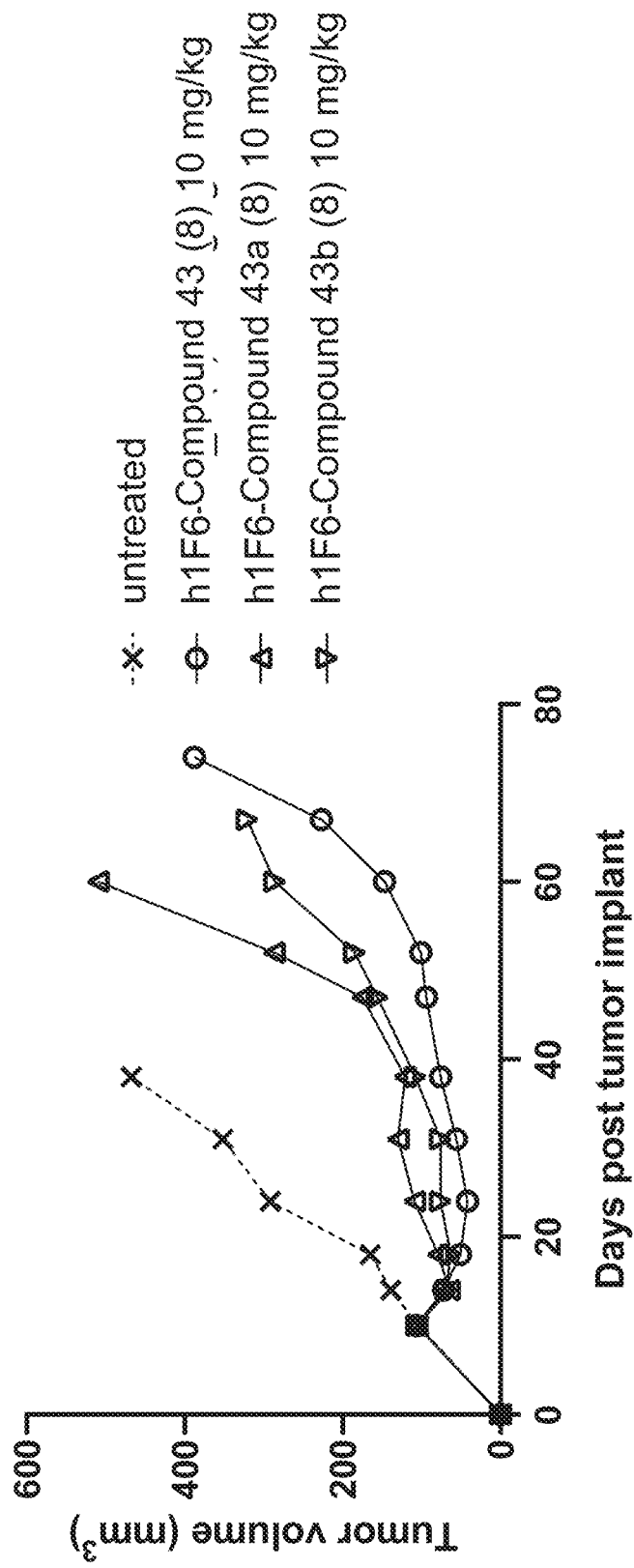
FIGS. 27A and 27B. Tumor size in mice with Caki-1 (renal cell carcinoma) following treatment with selected Antibody Drug Conjugate compounds.
Figure 27B:
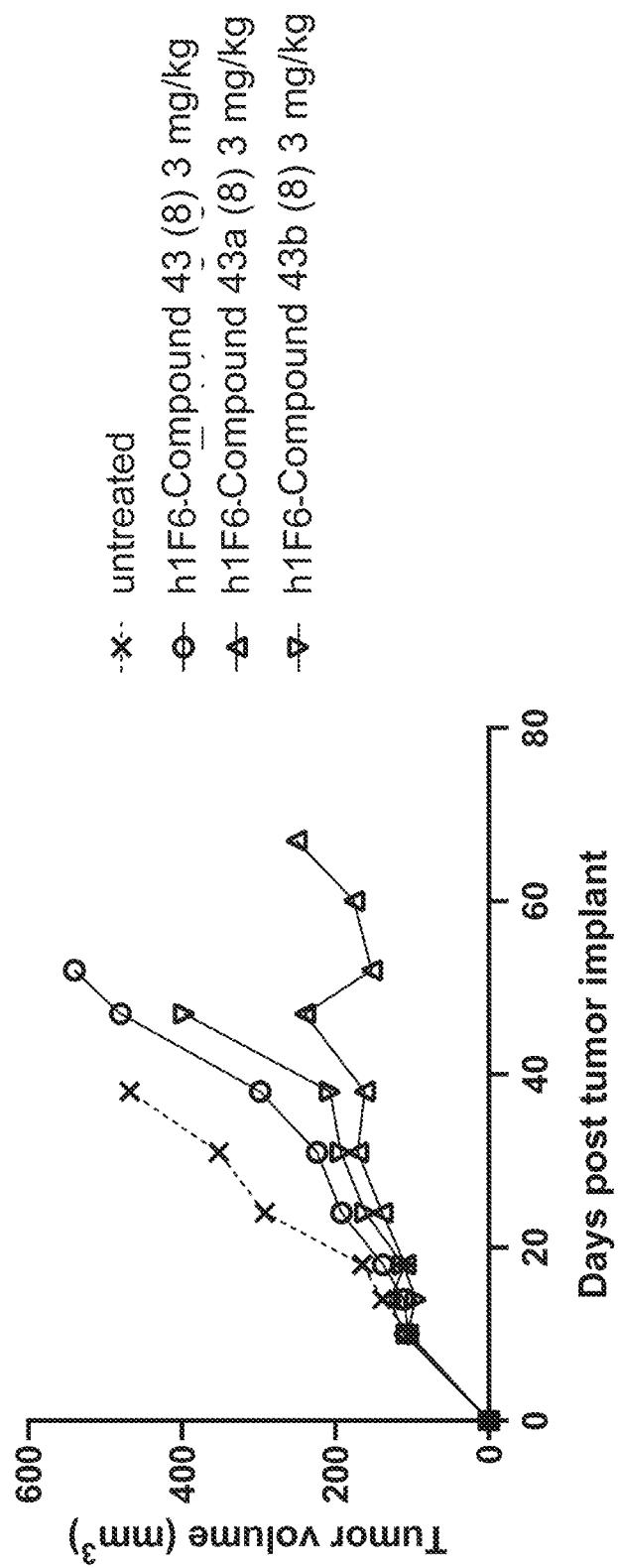

Animals were implanted with Caki-1 cells. On day 10, the animals were sorted into groups with an average tumor size of 100 mm3, and then treated with a single dose of camptothecin ADC h1F6-Compound 43(8), h1F6-Compound 43a(8) or h1F6-Compound 43b(8), at 3 or 10 mg/kg. Animals were evaluated for tumor size and in-life signs during the course of the study. The results are shown in FIGS. 27A and 27B.

Data in FIGS. 24-27 showed cAC10-Compound 43(8), cAC10-Compound 43a(8), cAC10-Compound 43b(8), h1F6-Compound 43(8), h1F6-Compound 43a(8), or h1F6-Compound 43b(8) ADCs all displayed in vivo anti-tumor activities on models tested.

Example 27: Synthesis of Tubulysin Drug-Linkers (Compound 71)

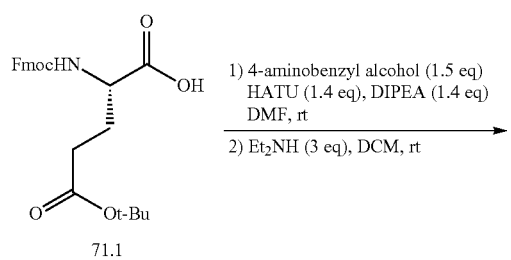

71.1

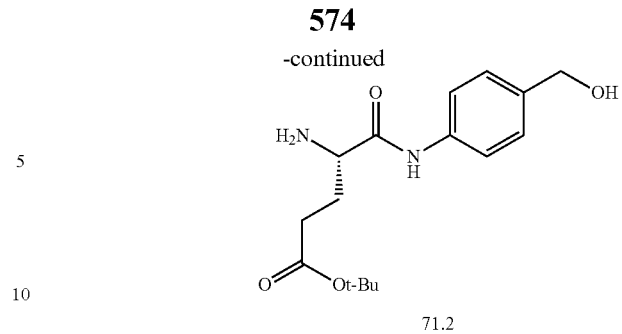

71.2

Compound 71.1 (1 mmol), (4-aminophenyl)methanol (1.5 mmol), and HATU (1.4 mmol) were charged to a 50 mL RBF equipped with a magnetic stir bar. Dimethyl formamide (DMF) (2 mL) was charged to the vessel and stirred until the solids dissolve. DIPEA (245 μL, 1.4 mmol) was charged to the reaction in one portion. The reaction was stirred at rt for two hours. Upon completion, water (6 mL) was added by dropwise addition over 30 minutes. The slurry was stirred for an additional 1 hr at rt. The slurry was filtered and washed with water to give an orange solid. The solid was redissolved in DCM (5 mL) and diethylamine (309 pL, 3.0 mmol) was added to the solution and stirred at rt overnight (reaction precipitated overnight). Upon completion, hexanes was added to the reaction and stirred for 1 hr. Following filtration, the solid was dried under vacuum overnight to compound 71.2 as a brown solid (quantitative yield).

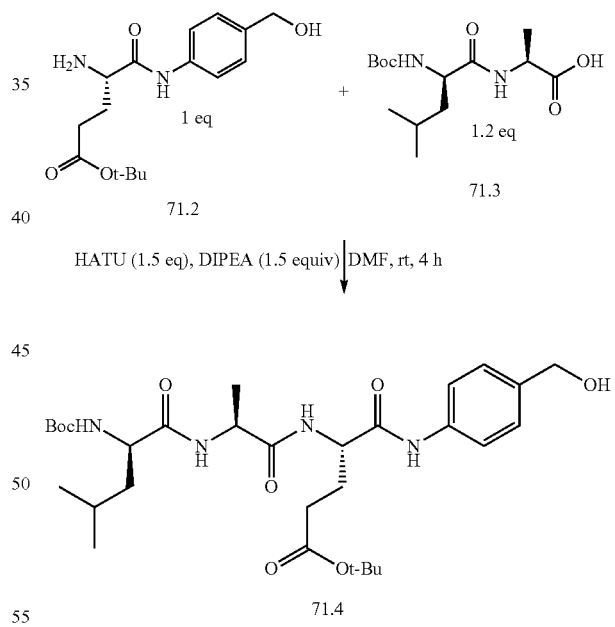

Compound 71.2 (87 mg, 0.28 mmol), compound 71.3 (102 mg, 0.34 mmol) and HATU (162 mg, 0.42 mmol) were charged to a RBF. DMF (1 mL) and DIPEA (75 μL, 0.42 mmol) was charged to the vessel and stirred at rt. After completion of reaction, water was added to the flask and transferred to a separatory funnel. The aqueous layer was extracted with dichloromethane, dried over sodium sulfate and concentrated on a rotary evaporator. The crude mixture was purified by reverse phase column chromatography to yield compound 71.4 as a white solid (63% yield).

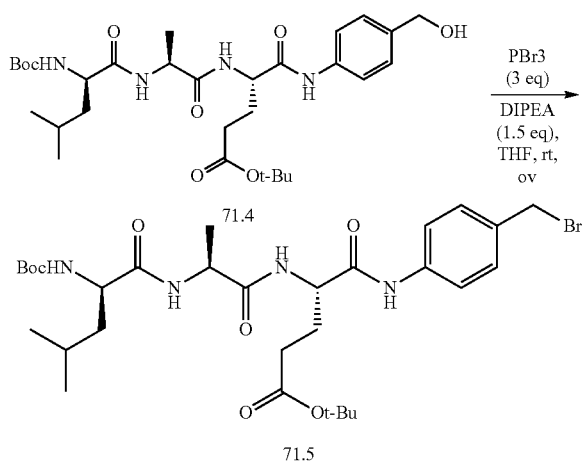

To an ice-cold solution of compound 71.4 (0.18 mmol) in THF (9 mL), was added DIPEA (47 μL) followed by dropwise addition of phosphorus tribromide (18.5 μL) over 30 minutes. The reaction was stirred at 0° C. After completion, the reaction was quenched with aqueous sodium bicarbonate and transferred to a separatory funnel. The aqueous layer was extracted with dichloromethane, dried over sodium sulfate and concentrated on a rotary evaporator. The crude mixture was purified by normal phase column chromatography using ethyl acetate and hexanes to yield 71.5 as a white solid (71% yield). Analytical UPLC-MS, m/z (ES+) calculated 656.6 [M+H]+; found 656.

A pressure vessel was charged with compound 71.5 (11.3 mg, 17.2 μmol) and compound 71.6 (12 mg, 15.6 μmol) in anhydrous 2-butanone (150 μL). The reaction was flushed with N₂, sealed, and allowed to stir at 80° C. for 12 hours. The reaction was allowed to come to room temperature and then concentrated. The crude material for carried forward without further purification. Analytical UPLC-MS: m/z (ES+) calculated 1342.7 [M]+; found 1343.

The crude solid was resolubilized in anhydrous DCM (100 μL) followed by the addition of phenylsilane (19.3 μL, 156 μmol), and Pd(PPh3)4 (5.4 mg, 4.6 μmol). LCMS indicated full removal of the allyl ester after 1 hour. The reaction was filtered to remove catalyst and the crude was carried forward. Analytical UPLC-MS: m/z (ES+) calculated 1302.7 [M]+; found 1303.

The crude solid (44 mg) was dissolved in anhydrous DCM (380 μL) and cooled to 0° C. while stirring. TFA (125 μL) was added dropwise and the reaction was allowed to warm to room temperature. LCMS showed full removal of the Boc group after 1.5 hours at which point the reaction was concentrated under reduced pressure, purified by reverse phase column chromatography to yield compound 71.7 (12.9 mg, 72% yield over 3 steps.) Analytical UPLC-MS: m/z (ES+) calculated 1046.63 [M]+; found 1047.3.

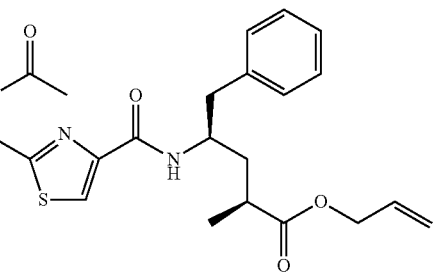

1) 71.5 (1.1 eq), 2-butanone, 80° C., 12 h
2) Pd(PPh3)4, PhSiH3, DCM, rt, 2 h
3) TFA, DCM, 0° C.-rt, 1.5 h

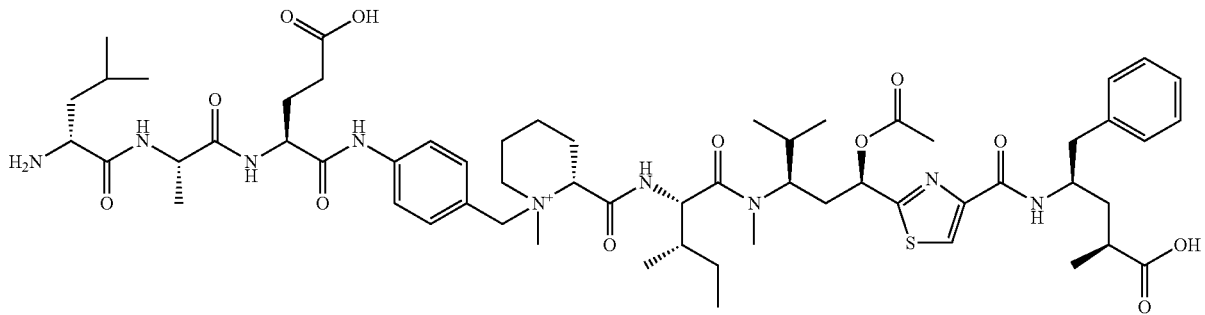

71.7

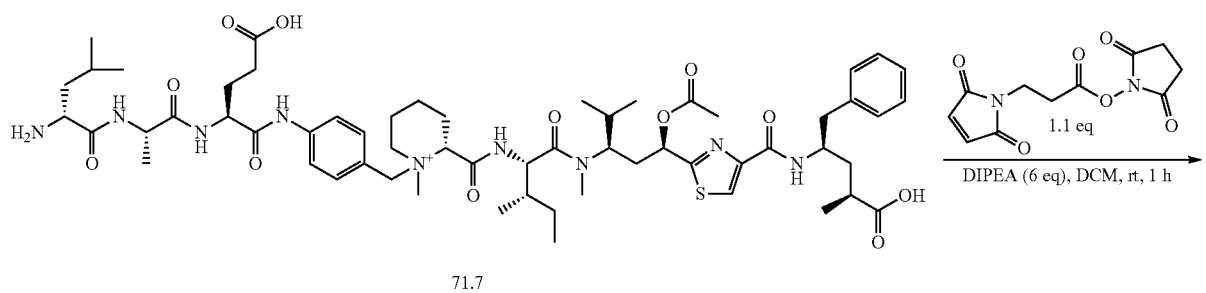

71.7

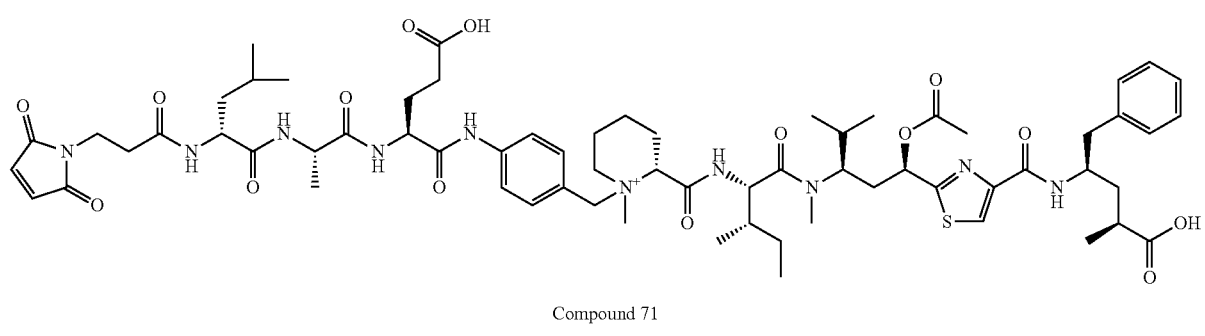

Compound 71

N-Succinimidyl 3-maleimidopropionate (3.3 mg, 12.3 µmol) was taken up in DMF (0.3 mL) and added to a flask containing compound 71.7 (12.9 mg, 11.2 µmol). N,N-diisopropylethylamine (12 µL, 67 µmol) was added and the reaction was stirred under N2 for 1 hours. The reaction was taken up in DMSO and purified by preparative LC to yield compound 71 (11 mg, 75%). Analytical UPLC-MS: m z (ES+) calculated 1298.6 [M]+; found 1298.3, RT=1.73 min.

Compound 71.6 was synthesized using methods previously described in Hamilton J. Z., et al. Improving Antibody-Tubulysin Conjugates through Linker Chemistry and Site-Specific Conjugation. *Chem Med Chem* 2020.

Figure 28:
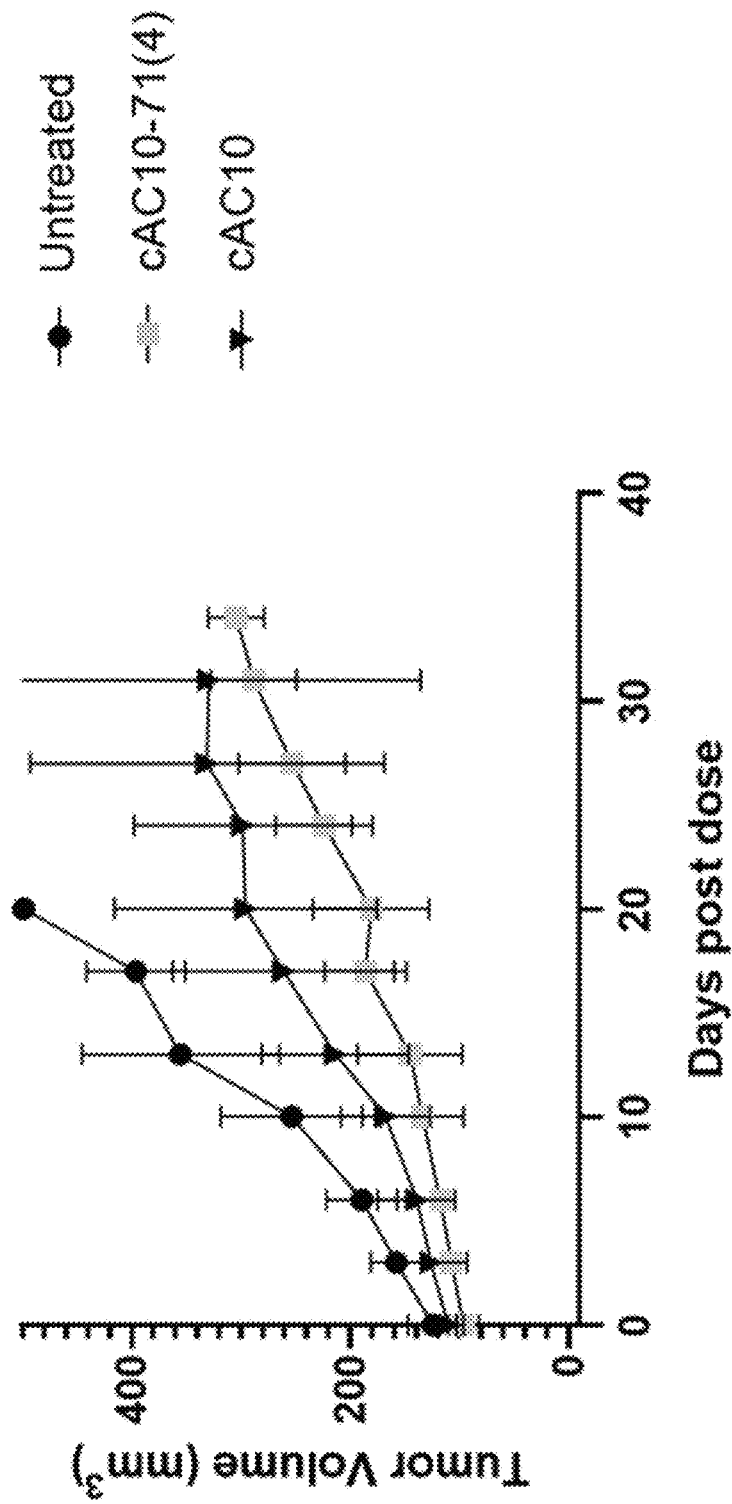
FIG. 28. Tumor volume vs days post implant in a xenograft model treated with a series of 4-loaded ADCs having the tripeptide sequence D-Leu-Ala-Glu as the Peptide Cleavable Unit with a drug-linker moiety represented by the formula of mp-D-Leu-Ala-Glu-TubM in comparison to cAC10.

Example 28: In Vivo Hodgkin's Lymphoma Cancer Cell Cytotoxicity of Tripeptide-Based Antibody Drug Conjugates Antibody Drug Conjugates having a drug antibody ratio (DAR) of about 4 were prepared according to the general procedures from compound 71 of Example 27 and the antibody cAC10. The ADCs were tested in a xenograft model in which cells of the Hodgkins lymphoma L540cy cell line are implanted in SCID mice. The ADC is administered according to the procedure in Example 13 at a 0.4 mg/kg dose. As seen in FIG. 28, the mixed 4-load antibody drug conjugate of compound 71 with a cAC10 antibody is at least as efficacious as cAC10. Example 29: Synthesis of Tubulysin Drug-Linkers (Compound 72)

Compound 72 was synthesized starting with tert-butyl ((S)-1-(((S)-1-((4-(hydroxymethyl)phenyl)amino)-1-oxo-propan-2-yl)amino)-3-methyl-1-oxobutan-2-yl)carbamate and following the same general procedure outlined above and scheme below:

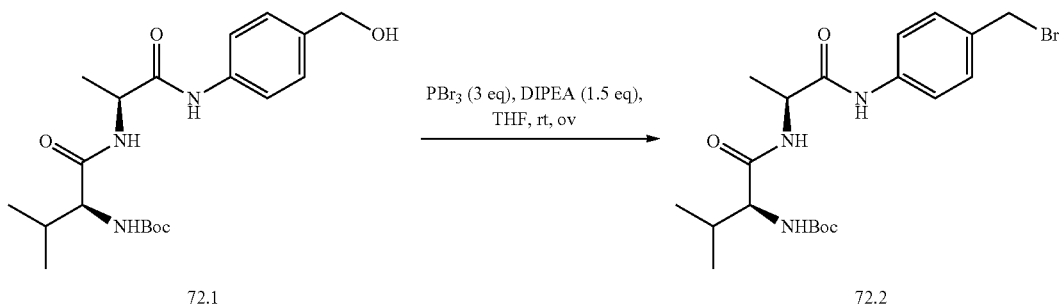

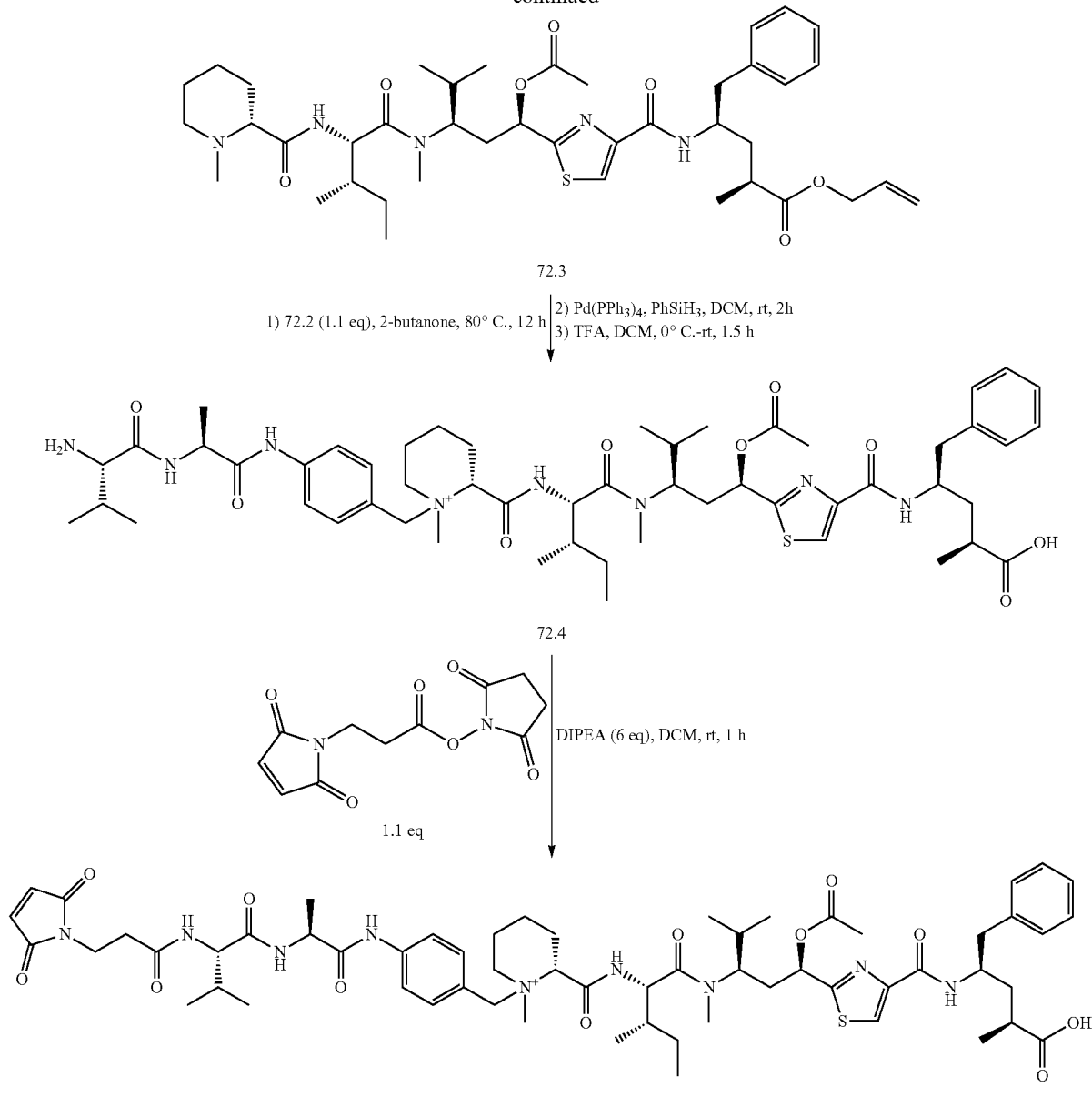

Compound 72

Compound 72.2: Analytical UPLC-MS: m/z (ES+) calculated 456.15 (M+H)+, found 456.10; Compound 72.4: Analytical UPLC-MS: m/z (ES+) calculated 1004.32 (M)+, found 1004.83; Compound 72: Analytical UPLC-MS: m/z (ES+) calculated 1155.4 (M)+, found 1155.2, RT=1.73 min.

Example 30: Anti-GPNMB In Vivo Studies

Materials

The WM266-4 cell line described in the following examples were maintained in culture according to the conditions specified by the American Type Culture Collection (ATCC), which is where the cells were obtained from.

In Vivo Activity Study

For therapy experiments in cell-line derived xenografts, $2.5 \times 10^6$ WM266-4 cells (ATCC) in 25% Matrigel HC were injected subcutaneously into 5-8 female nude (nu nu) mice (Envigo). Mice were randomly divided into study groups and dosed with test article via intraperitoneal injection once the tumors reached approximately 100 mm³. Animals were euthanized when tumor volumes reached 500-1000 mm³. Tumor volume was calculated with the formula (volume=½×length×width×width). In all xenograft studies, no weight loss or treatment-related toxicities were observed for mice treated with any of the test articles. All animal procedures were performed under a protocol approved by the Institutional Animal Care and Use Committee in a facility accredited by the Association for Assessment and Accreditation of Laboratory Animal Care.

In Vivo Anticancer Activity of hCR011 ADCs

Figure 29:
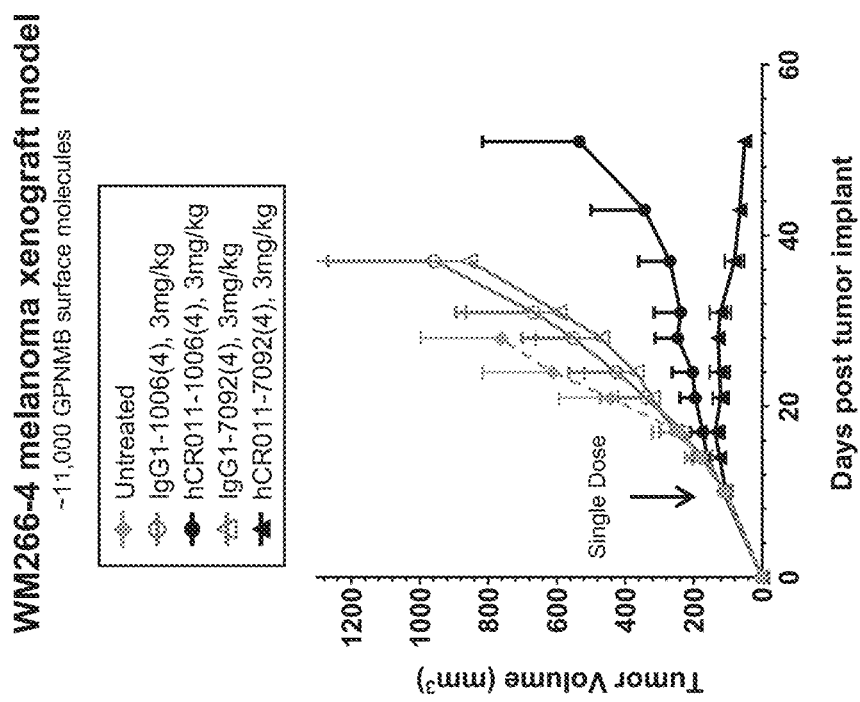
FIG. 29 shows WM266-4, a melanoma cell-derived xenograft model, tumor volumes over times in mice untreated and treated with 3 mg/kg of IgG-me-vc-PABC-MMAE (4), 3 mg/kg of hCR011-me-vc-PABC-MMAE (4), 3 mg/kg of IgG-mp-dLAE-PABC-MMAE (4), and 3 mg/kg of hCR011-mp-dLAE-PABC-MMAE (4).

The anti-tumor activity of humanized anti-GPNMB antibody hCR011 conjugated with vcMMAE (average of 4 drugs per antibody) (hCR011-1006) or dLAE-MMAE (hCR011-7092) in vivo (FIG. 29) was demonstrated. Significant tumor growth delay or tumor regression of hCR011-7092 and hCR011-1006 compared to untreated mice was observed. This is in contrast to the lack of in vivo anti-tumor activity observed when a non-specific IgG1 antibody is conjugated with vcMMAE (average of 4 drugs per antibody) (hIgG1-1006) or dLAE-MMAE (hIgG1-7092) (FIG. 29).

Example 31: Anti-CD228 In Vivo Studies

Materials

The A2058 cell line described in the following example was obtained from the American Type Culture Collection (ATCC) and maintained in culture according to the conditions specified by ATCC.

In Vivo Activity Study

For therapy experiments in cell-line derived xenografts, $2.5 \times 10^5$ cells (ATCC) in 25% Matrigel HC were injected subcutaneously into 5-8 female nude (nu nu) mice (Envigo). Mice were randomly divided into study groups and dosed with test article via intraperitoneal injection once the tumors reached approximately 100 mm³. Animals were euthanized when tumor volumes reached 500-1000 mm³. Tumor volume was calculated with the formula (volume=½×length×width×width). In all xenograft studies, no weight loss or treatment-related toxicities were observed for mice treated with any of the test articles. All animal procedures were performed under a protocol approved by the Institutional Animal Care and Use Committee in a facility accredited by the Association for Assessment and Accreditation of Laboratory Animal Care.

In Vivo Anticancer Activity of hL49 ADCs

Figure 30:
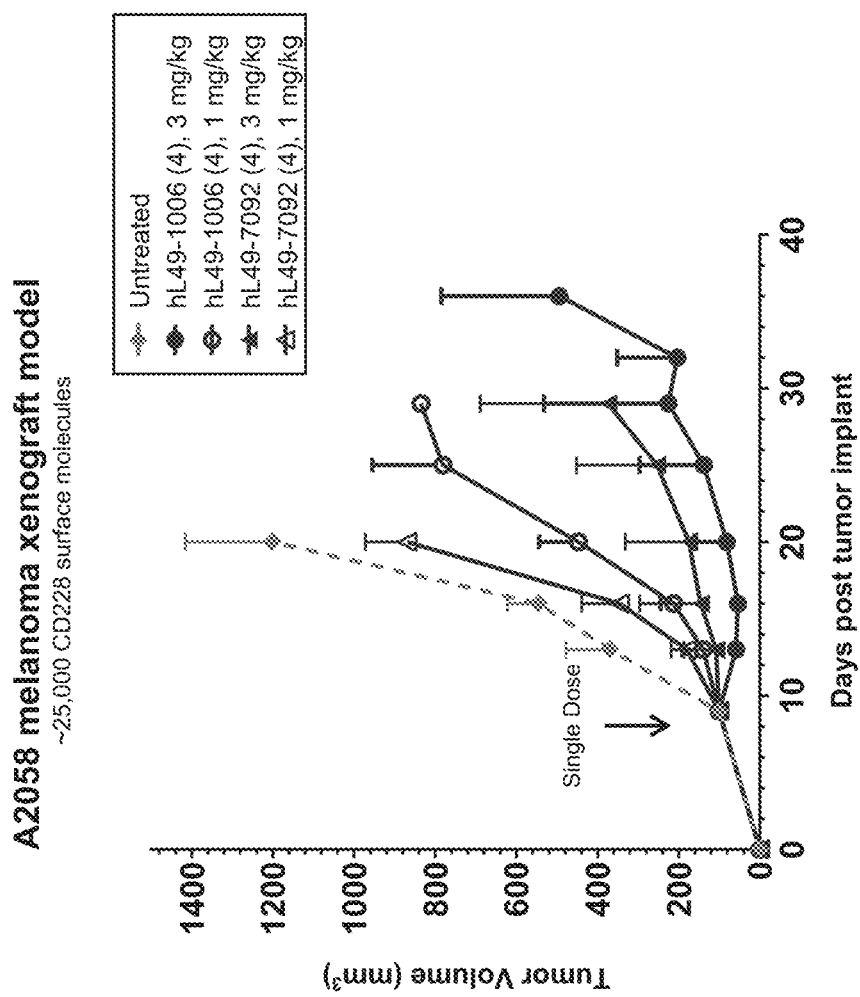
FIG. 30 shows A2058, a melanoma cell-derived xenograft model, tumor volumes over times in mice untreated and treated with 3 mg/kg of hL49-mc-vc-PABC-MMAE (4), 1 mg/kg of hL49-mc-vc-PABC-MMAE (4), 3 mg/kg of hL49-me-vc-PABC-MMAE (4), and 1 mg/kg of hL49-mp-dLAE-PABC-MMAE (4).

The anti-tumor activity of humanized anti-CD228 antibody hL49 conjugated with vcMMAE (average of 4 drugs per antibody) (hL49-1006) or dLAE-MMAE (hL49-7092) in vivo (FIG. 30) was demonstrated. Significant tumor growth delay or tumor regression of hL49-7092 and hL49-1006 compared to untreated mice was observed.

Example 32: Anti-αvβ6 In Vivo Studies

Materials

Cell lines described in the following examples were maintained in culture according to the conditions specified by the American Type Culture Collection (ATCC). Detroit 562 cell lines, HPAFII cell lines, and BxPC3 cell lines were obtained from ATCC.

In Vivo Activity Study

Figure 31:
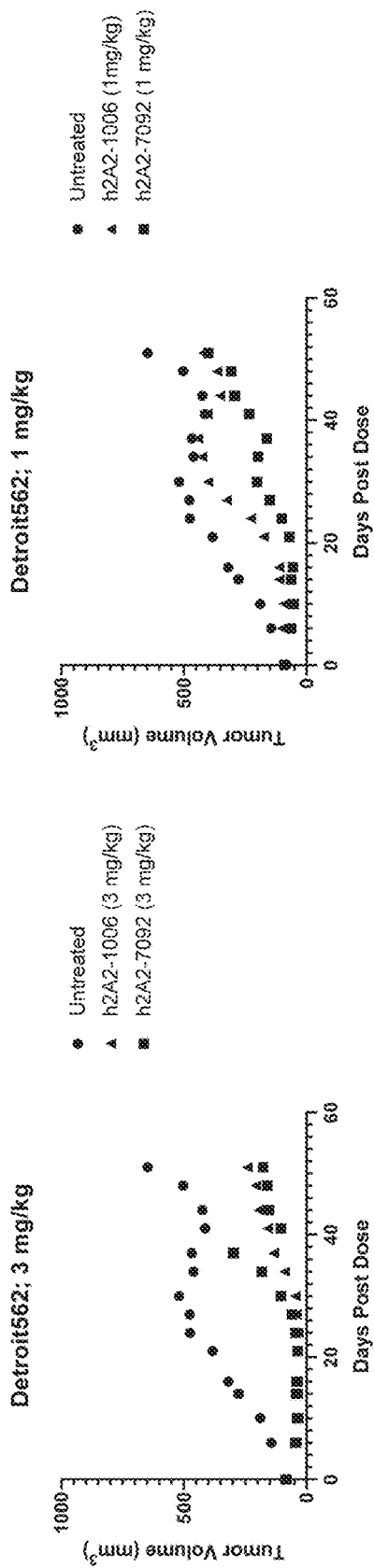
FIG. 31 shows the results of a xenograft study of the Detroit562 cell line in nude mice. The dose and schedule are indicated on the figure.
Figure 32:
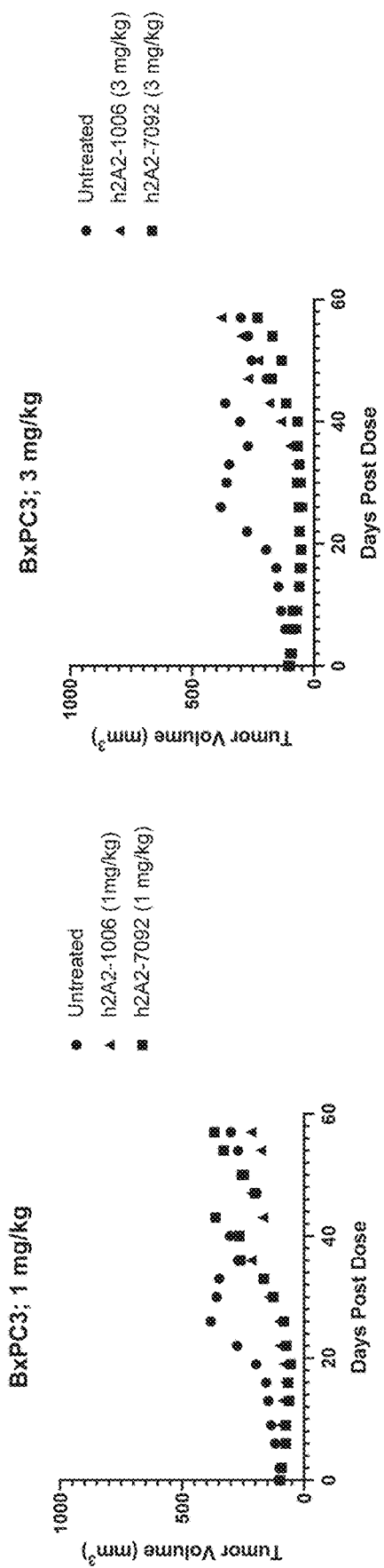
FIG. 32 shows the results of a xenograft study of the BxPC3 cell line in nude mice. The dose and schedule are indicated on the figure.
Figure 33:
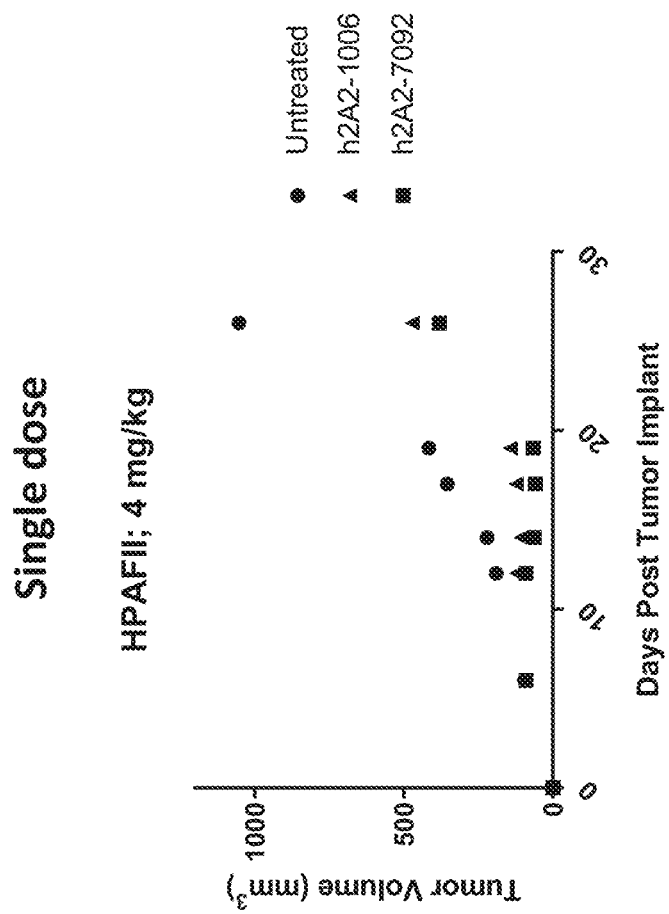
FIG. 33 shows the results of a xenograft study of the HPAFII cell line in nude mice. The dose and schedule are indicated on the figure.

For therapy experiments in cell-line derived xenografts, $5 \times 10^6$ cells (ATCC) were injected subcutaneously into the right flank of female nude (nu nu) mice (Envigo) for the BxPC3, Detroit 562, and HPAF-II studies. Mice were randomly divided into study groups (N=5 to 8) and dosed with test article via intraperitoneal injection once the tumors reached approximately 100 mm³. For the BxPC3 and Detroit 562 studies, animals were dosed two additional times one week apart. Animals were euthanized when tumor volumes reached 750-1000 mm³. Tumor volume was calculated with the formula (volume=½×length×width×width). Mice showing durable regressions were terminated around day 40-65 after implant. In all xenograft studies, no weight loss or treatment-related toxicities were observed for mice treated with any of the test articles. All animal procedures were performed under a protocol approved by the Institutional Animal Care and Use Committee in a facility accredited by the Association for Assessment and Accreditation of Laboratory Animal Care In Vivo Anticancer Activity of h2A2 ADCs The anti-tumor activity of humanized anti- anti-αvβ6 antibody 2A2 conjugated with me-vc-MMAE (average of 4 drugs per antibody) (h2A2-1006) or mp-dLAE-MMAE (h2A2-7092) in vivo (Figures. 31-33) was demonstrated. Significant tumor growth delay or tumor regression of h2A2-mp-dLAE-MMAE and h2A2-mc-vc-MMAE compared to untreated mice was observed.

Example 33: Anti-LIV1 In Vivo Studies

Materials

Cell lines described in the following examples were maintained in culture according to the conditions specified by the American Type Culture Collection (ATCC), the National Cancer Institute (NCI) or the Deutsche Sammlung von Mikroorganismen und Zellkulturen GmbH, Braunschweig, Germany (DMSZ).

In Vivo Activity Study

For therapy experiments in cell-line derived xenografts, $5 \times 10^6$ cells (ATCC) were injected subcutaneously into 5-8 female nude (nu nu) mice (Envigo) for the MCF7, PC3, and Hela-J studies. Mice were randomly divided into study groups and dosed with test article via intraperitoneal injection once the tumors reached approximately 100 mm³. Animals were euthanized when tumor volumes reached 500-1000 mm³. Tumor volume was calculated with the formula (volume=½×length×width×width). Mice showing durable regressions were terminated around day 40-65 after implant. In all xenograft studies, no weight loss or treatment-related toxicities were observed for mice treated with any of the test articles. All animal procedures were performed under a protocol approved by the Institutional Animal Care and Use Committee in a facility accredited by the Association for Assessment and Accreditation of Laboratory Animal Care.

In Vivo Anticancer Activity of hLIV22 ADCs

Figure 34B:
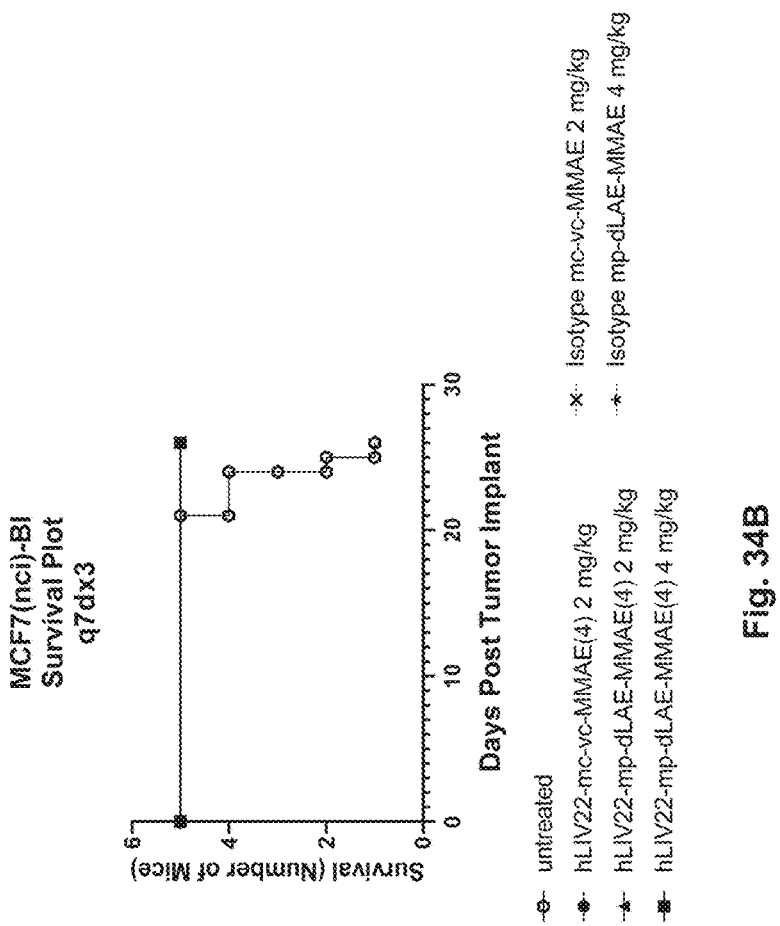
FIGS. 34A and 34B show in vivo results of mouse xenograft experiments using the breast cancer model cell line MCF7nci. The hLIV22 antibody was conjugated to either mc-vc-MMAE or mp-dLAE-MMAE and assessed.
Figure 34A:
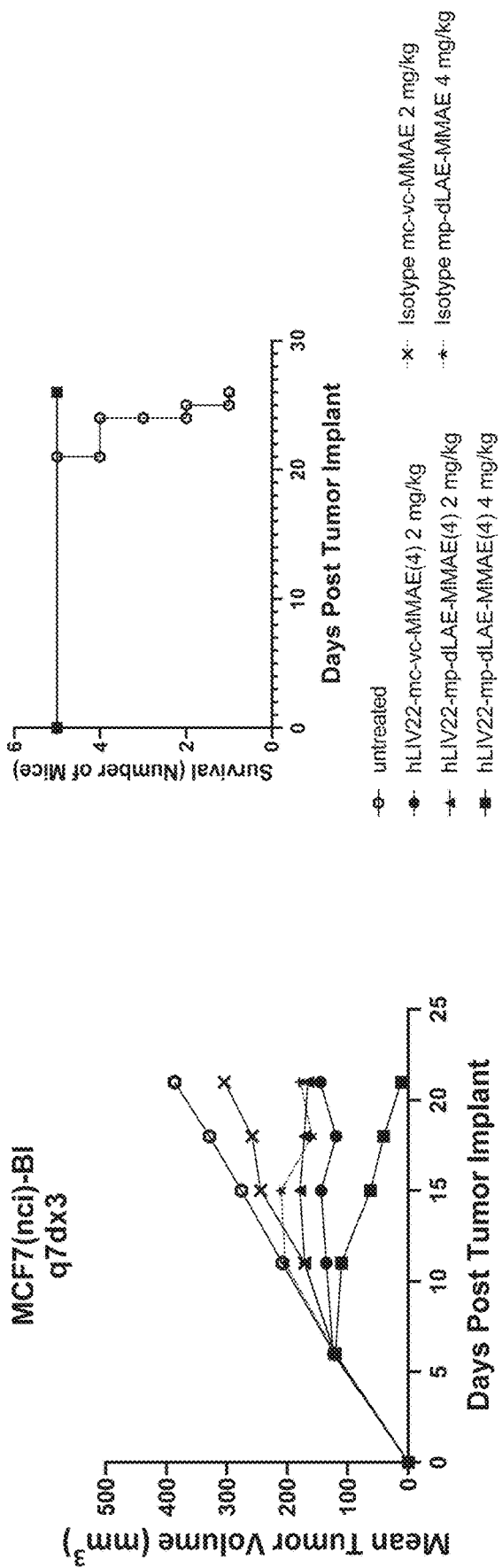
Figure 35:
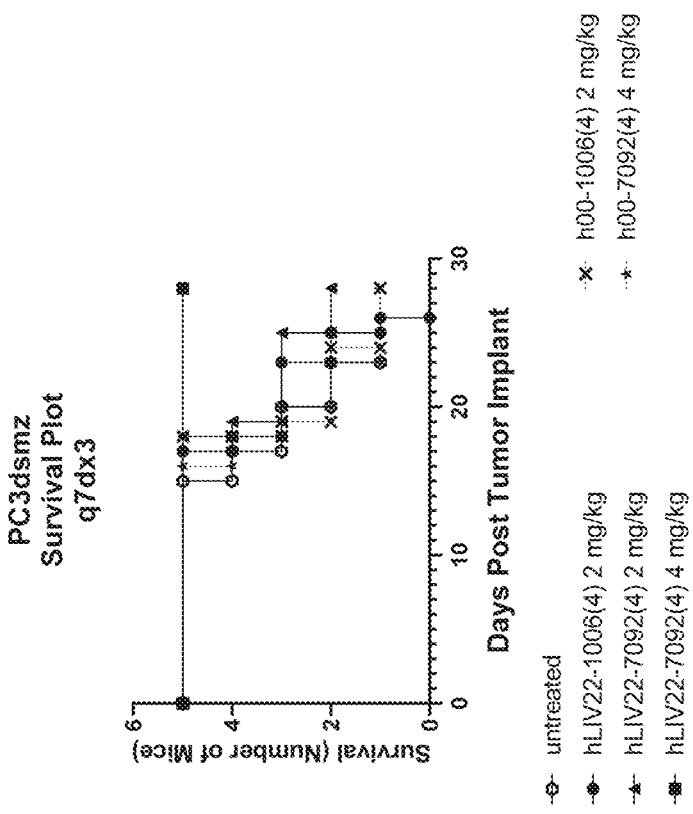
FIGS. 35A and 35B show in vivo results of mouse xenograft experiments using the prostate cancer model cell line PC3dsmz. The hLIV22 antibody was conjugated to either mc-vc-MMAE or mp-dLAE-MMAE and assessed.
Figure 35:
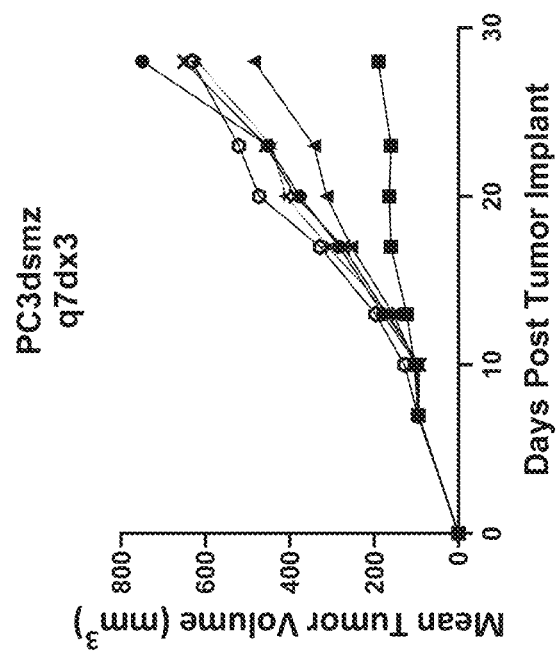
Figure 36B:
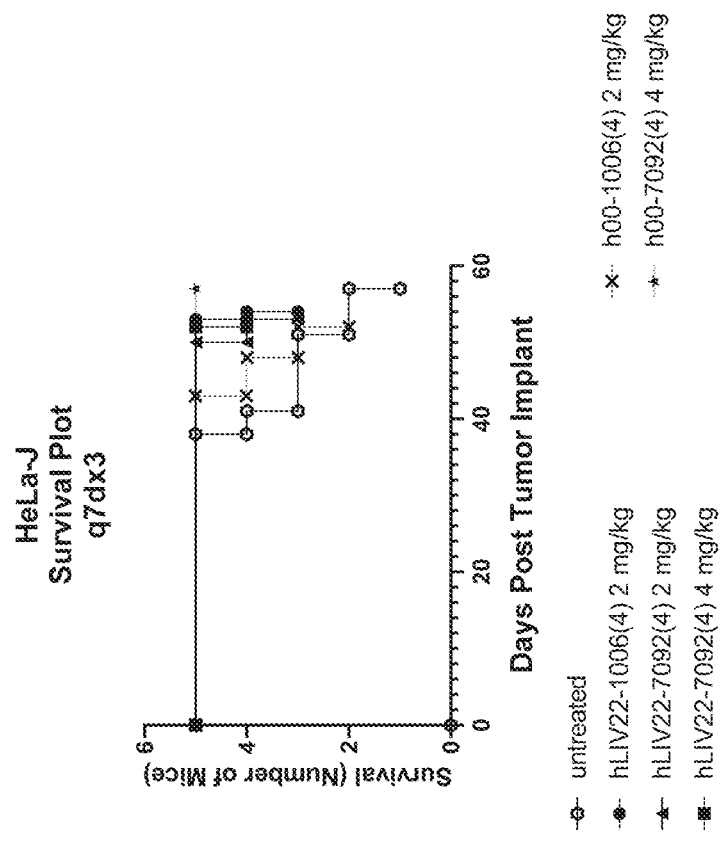
FIGS. 36A and 36B show in vivo results of mouse xenograft experiments using the cervical cancer model cell line HeLa-J. The hLIV22 antibody was conjugated to either mc-vc-MMAE or mp-dLAE-MMAE and assessed.
Figure 36A:
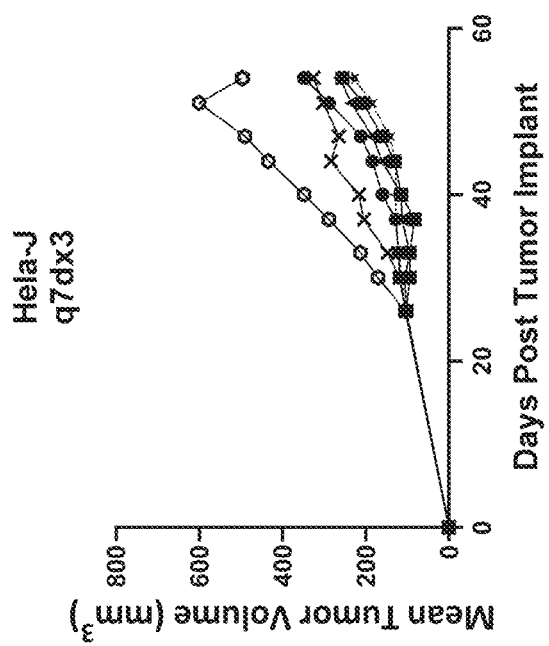

The anti-tumor activity of humanized anti-LIV1 antibody hLIV22 conjugated with vcMMAE (average of 4 drugs per antibody) (hLIV22-1006) or dLAE-MMAE (hLIV22-7092) in vivo (FIGS. 34-36) was demonstrated. Significant tumor growth delay or tumor regression of hLIV22-7092 and hLIV22-1006 compared to untreated mice was observed.

hLIV22 ADCs and Bone Marrow Toxicity hLIV22-1006 or hLIV22-7092(4) was administered to naïve cynomolgus monkeys of Chinese origin (n=5 males/5 females or n=female, respectively) as a single dose of 6 or 10 mg/kg, respectively. Serial blood samples were collected for standard hematology assessment throughout the course of the study (predose through 4-weeks post dose).

Figure 37:
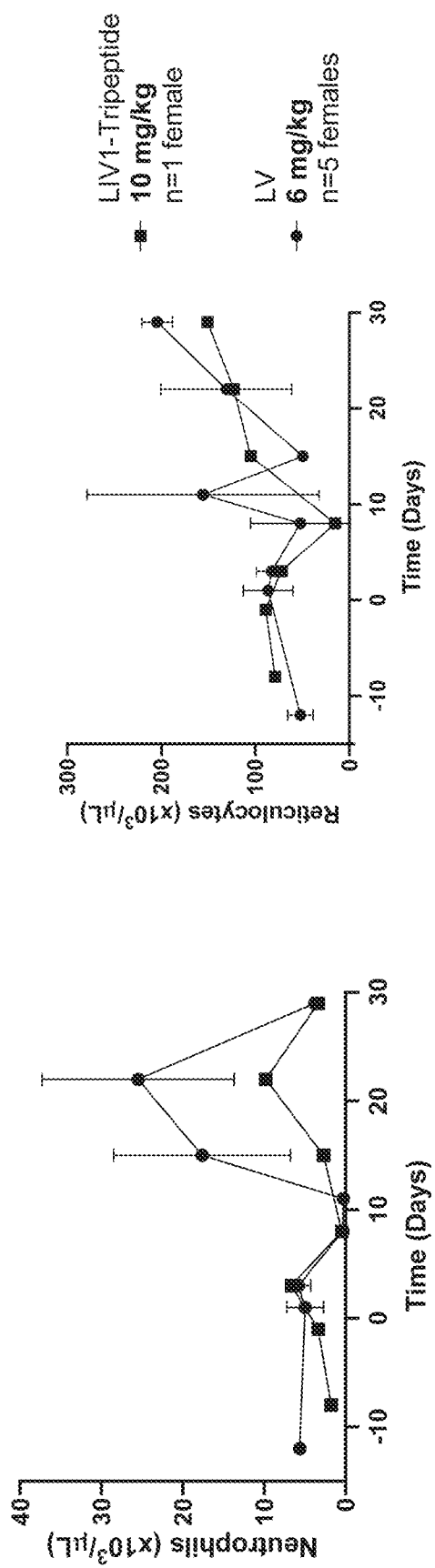
FIG. 37 shows the decrease in neutrophil and reticulocyte production upon ADC administration. The hLIV22 antibody was conjugated to either me-vc-MMAE or mp-dLAE-MMAE and assessed.

FIG. 37 shows the decrease in neutrophil and reticulocyte production when hLIV22-7092 (or LIV1-Tripeptide, or hLIV22-dLAE-MMAE) is administered at 10 mg/kg single dose, and when hLIV22-1006 (or LV, or hLIV22-vcMMAE) is administered at 6 mg/kg. The decrease in neutrophil and reticulocyte production is similar for hLIV22-7092 and hLIV22-1006 at these respective doses.

Example 34: Anti-CD19 In Vivo Studies

Materials

Cell lines described in the following examples were maintained in culture according to the conditions specified by the American Type Culture Collection (ATCC), the National Cancer Institute (NCI) or the Deutsche Sammlung von Mikroorganismen und Zellkulturen GmbH, Braunschweig, Germany (DMSZ). Raji cell lines were obtained from ATCC.

In Vivo Activity Study

For therapy experiments in cell-line derived xenografts, 5×10⁶ cells (ATCC) were injected subcutaneously into the right flank of female SCID (CB17SC sp/sp) mice (Taconic) for the Raji studies. Mice were randomly divided into study groups (N=5 to 8) and dosed with test article via intraperitoneal injection once the tumors reached approximately 100 mm³. Animals were euthanized when tumor volumes reached 750-1000 mm³. Tumor volume was calculated with the formula (volume=½× length×width×width). Mice showing durable regressions were terminated around day 40-65 after implant. In all xenograft studies, no weight loss or treatment-related toxicities were observed for mice treated with any of the test articles. All animal procedures were performed under a protocol approved by the Institutional Animal Care and Use Committee in a facility accredited by the Association for Assessment and Accreditation of Laboratory Animal Care.

In Vivo Anticancer Activity of hBU12 ADCs

Figure 38:
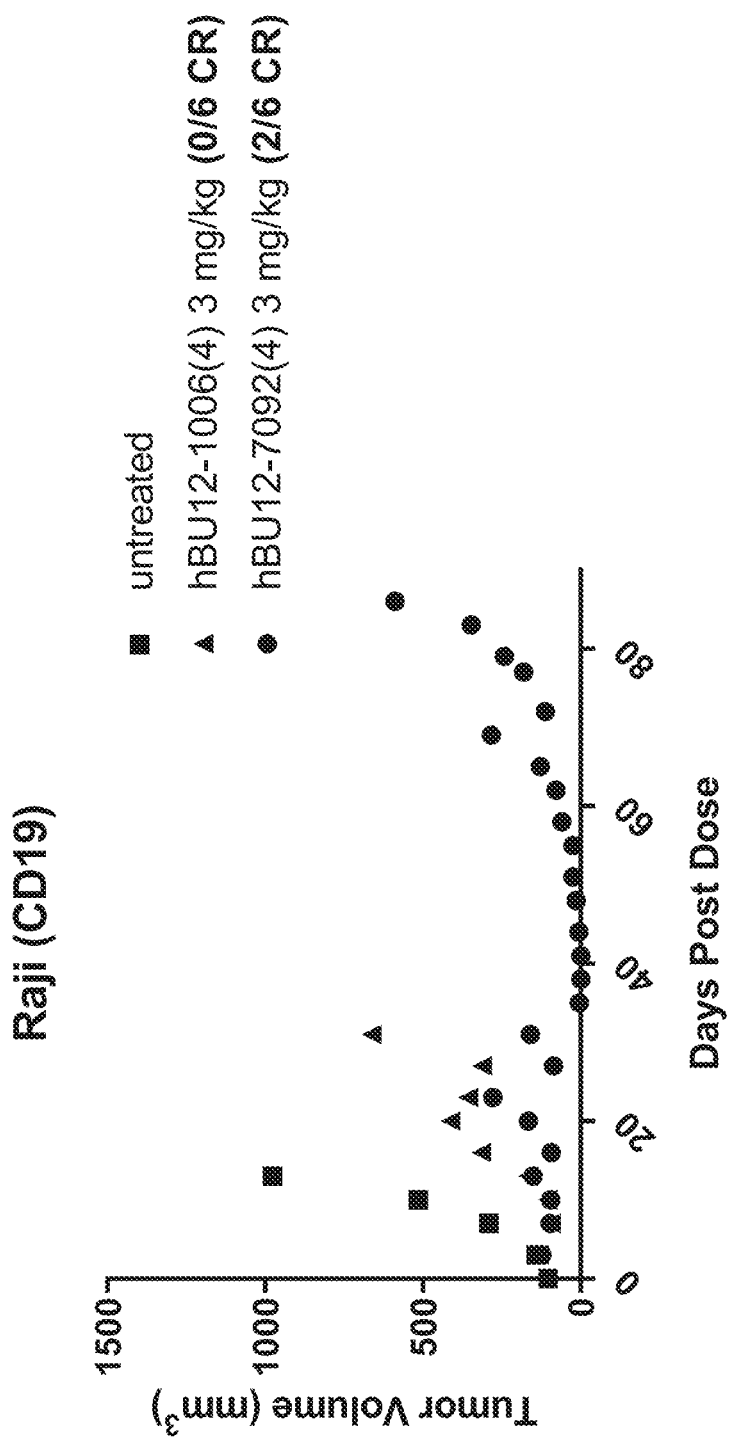
FIG. 38 shows the results of a xenograft study of the Raji cell line in SCID (CB17SC sp/sp) mice.

The anti-tumor activity of humanized anti-CD19 antibody hBU12 conjugated with vcMMAE (average of 4 drugs per antibody) (hBU12-1006(4)) or dLAE-MMAE (hBU12-7092(4)) in vivo (FIG. 38) was demonstrated. Significant tumor growth delay or tumor regression of hBU12-7092(4) and hBU12-1006(4) compared to untreated mice was observed.

Example 35: Anti-CD30 Studies

Materials

Cell lines described in the following examples were maintained in culture according to the conditions specified by the American Type Culture Collection (ATCC), the National Cancer Institute (NCI) or the Deutsche Sammlung von Mikroorganismen and Zellkulturen GmbH, Braunschweig, Germany (DMSZ). The L540cy cell line was obtained from the University of Texas. The L428, DEL, and KMH2 cell lines were obtained from DSMZ, and the Karpas cell line was obtained from Sigma Aldrich via the European collection of Authenticated Cell Cultures. The Karpas BVR and DEL BVR cell lines were produced in vitro via exposure to brentuximab vedotin. Lewis et al., "Abstract 688: Characterization and circumvention of drug resistance mechanisms in SGN-35-resistant HL and ALCL clonal cell lines" Cancer Res. (2014) 74:19 Supplement.

Example 35A

In Vitro Cytotoxicity Study

ALCL and HL cell lines (DEL, DELBVR8F9, Karpas, KMH2, L428, AND L540cy) were plated in 150 uL complete growth media in 96-well, clear-bottomed, black-walled tissue culture treated plates (Corning). Cell plates were placed at 37° C. and 5% $CO_2$ overnight to allow cells to equilibrate. The ADCs were thawed, and 4×8-point serial dilutions were prepared in RPMI-1640+10% fetal bovine serum (FBS). Fifty uL of each dilution were then added to each cell plate in triplicate. Treated cells were incubated at 37° C. and 5% $CO_2$ for 96 hours. Cell viability was assayed using CellTiter-Glo® Reagent (PROMEGA). Raw data were analyzed in Graphpad Prism (San Diego, CA) using a nonlinear, 4-parameter curve fit model [Y=Bottom+(Top−Bottom)/(1+10^((Log EC50−X)*HillSlope))].

In Vitro Cytotoxic Potency of cAC10 vcMMAE and dLAE ADCs is Similar

Figure 39:
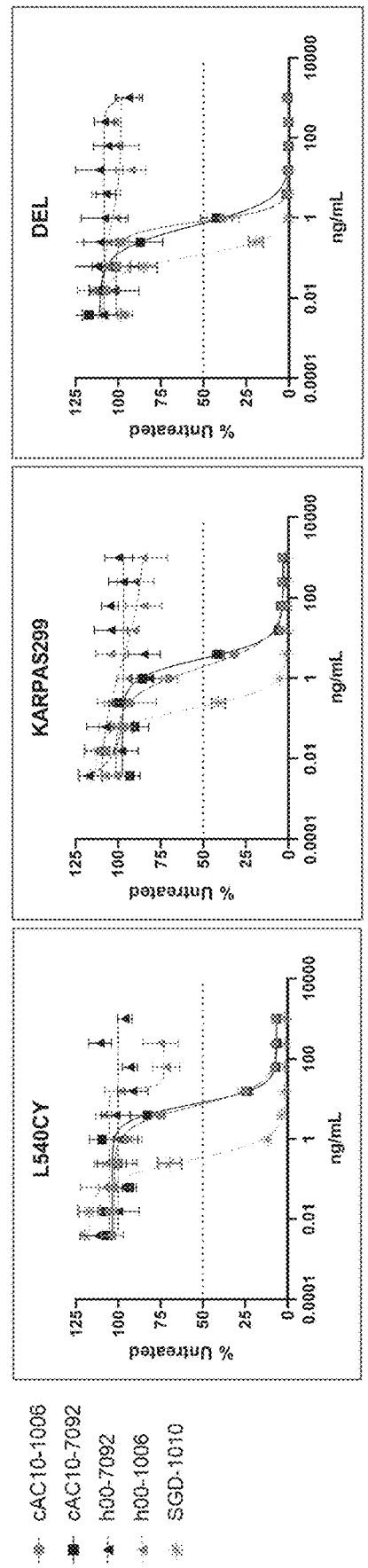
FIG. 39A-39F show in vitro potency results for cAC10-1006 and cAC10-7092 compared to conjugates containing a non-targeting antibody (h00) and free MMAE in L540cy (39A), Karpas 299 (39B), DEL (39C), KMH2 (39D), L428 (39E), and DELBVR8F9 (39F) cell lines.

The cytotoxic activity of chimeric anti-CD30 antibody cAC10 (also referred to herein as Brentuximab) conjugated with vcMMAE (average of 4 drugs per antibody) (cAC10-1006) or dLAE-MMAE (cAC10-7092) was demonstrated to be dependent on CD30 expression in vitro. Significant cell death was observed in CD30-expressing cell lines treated with cAC10-1006 and cAC10-7092 (FIG. 39A-E). In addition, anon-targeting antibody (h00) conjugated to either vcMMAE or dLAE-MMAE had minimal effect on the viability of these cells (FIG. 39A-E). Finally, viability of a cell line lacking CD30 expression, DELBVR, treated with vAC10-1006 or cAC10-7092 was comparable to cells treated with the non-targeting ADCs (FIG. 39F). As a positive control, cells were treated with free MMAE (SGN-1010), demonstrating that all cell lines are sensitive to the released drug. Taken together, as shown in FIG. 39, these data indicate that cAC10-dLAE has similar, CD30-specific potency on cancer cell lines as Brentuximab-vedotin (cAC10-1006), suggesting they may have similar efficacy in patients.

Example 35B

In Vitro Human Bone Marrow CFU-GM Assay

Human bone marrow mononuclear cell sample was obtained from ReachBio LLC and maintained in a methylcellulose media containing rhIL-3 (10 ng/mL), rhSCF (50 ng/mL) and rhGM-CSF (10 ng/mL). Human bone marrow mononuclear cells were mixed with the ADCs and added directly to the methylcellulose media containing rhIL-3, rhSCF and rhGM-CSF. The ADCs were tested in triplicate at 100, 30, 10, 3, 1, 0.1, 0.01 and 0.001 pg/mL. After incubation at 37° C., 5% CO2 for 14-16 days, the number of colonies on each plate were determined and used to determine $IC_{50}$ values.

Activity of cAC10 ADCs on Human Bone Marrow CFU-GM

Figure 40:
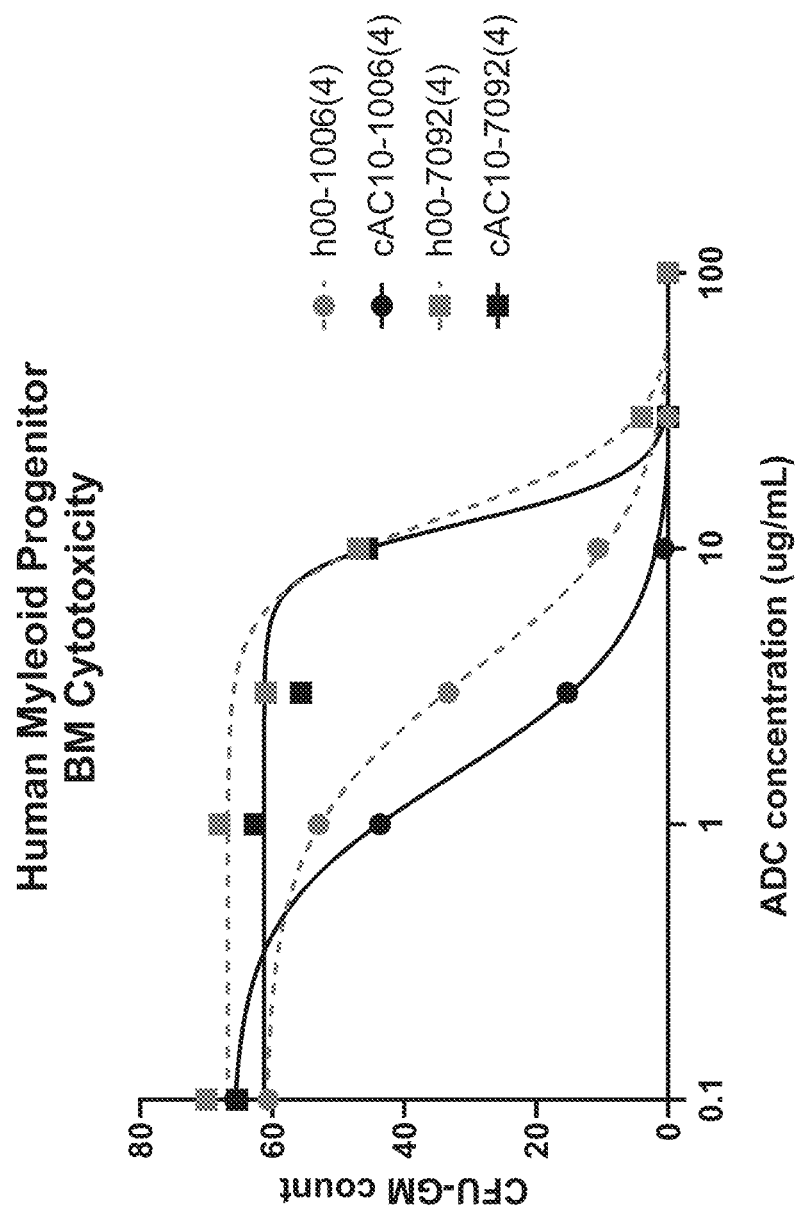
FIG. 40 shows in vitro cytotoxicity of chimeric anti-CD30 antibody cAC10 conjugated with vcMMAE (cAC10-1006) or dLAE-MMAE (cAC10-7092) on human bone marrow myeloid progenitor cells compared with conjugates containing a non-targeting antibody (h00).

The in vitro cytotoxicity of chimeric anti-CD30 antibody cAC10 conjugated with vcMMAE (cAC10-1006) or dLAE-MMAE (cAC10-7092) on human bone marrow myeloid progenitor cells was demonstrated in FIG. 40. Reduction in cytotoxicity, and a 7.5-fold increase in $IC_{50}$ value was observed with cAC10-7092 compared to cAC10-1006 (Table 8-1). The non-targeted antibody conjugated to dLAE-MMAE (h00-7092) also displayed reduced toxicity on myeloid progenitor cells compared to the non-targeted vcMMAE ADC (h00-1006), as shown in FIG. 40. This suggests the dLAE-MMAE payload may result in reduced bone marrow toxicity compared to Brentuximab-vedotin (cAC10-1006).

TABLE 8-1

Potency of cAC10-ADCs on human bone marrow monocular cells

| Test article | $IC_{50}$ (µg/ml) |
|---|---|
| h00-7092(4) | 11.5 |
| cAC10-7092(4) | 9.17 |
| h00-1006(4) | 2.18 |
| cAC10-1006(4) | 1.21 |

Example 35C

Hallmarks of Immunogenic Cell Death Assay

For experiments examining immunogenic cell death, release of HMGB1 and ATP from MIA-PaCa2 cells treated with test articles was measured after 24 hours of exposure to the ADCs. In this assay, MIA-PaCa2 cells were grown to approximately 50% confluence in 12-well tissue culture plates and then treated with 1 ug/mL of test article. After 24 hours, supernatant was collected and split for ATP and HMGB1 analysis. ATP release was measured in the collected supernatant using the CellTiter-Glo Reagent from Promega. HMGB1 release was measured in the collected supernatant using the HMGB1 express ELISA from TECAN according to the manufacturer's instructions.

Induction of Immunogenic Cell Death (ICD) by cAC10-7092

Figure 41A:
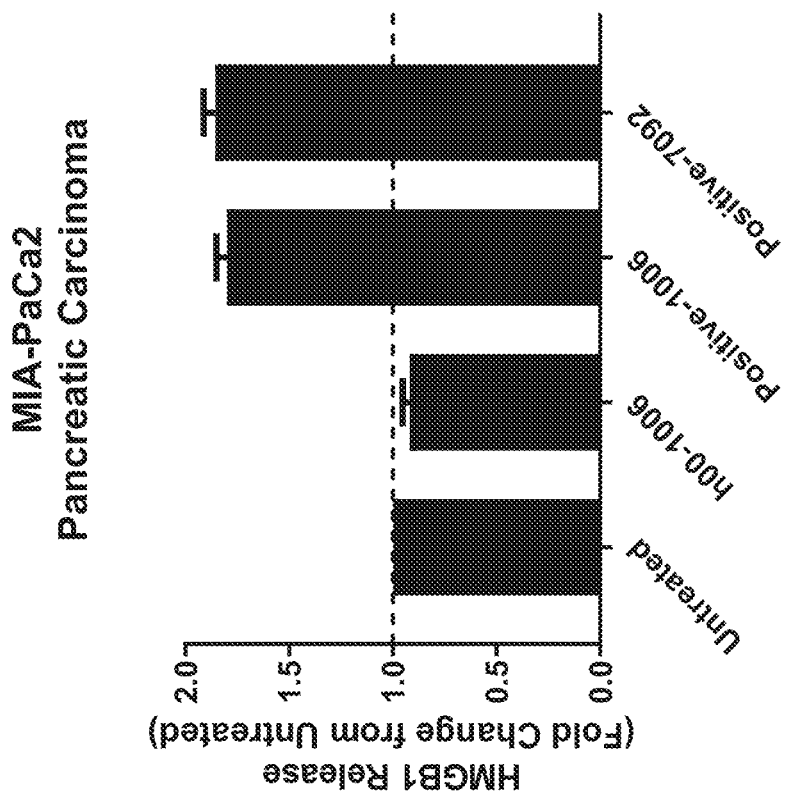
FIGS. 41A and 41B show ATP release (41A) and HMGB1 release (41B) measured in MIA-PaCa2 cells treated for 24 hours with either Receptor1-1006, Receptor1-7092, or a non-targeting antibody conjugated to 1006.
Figure 41B:
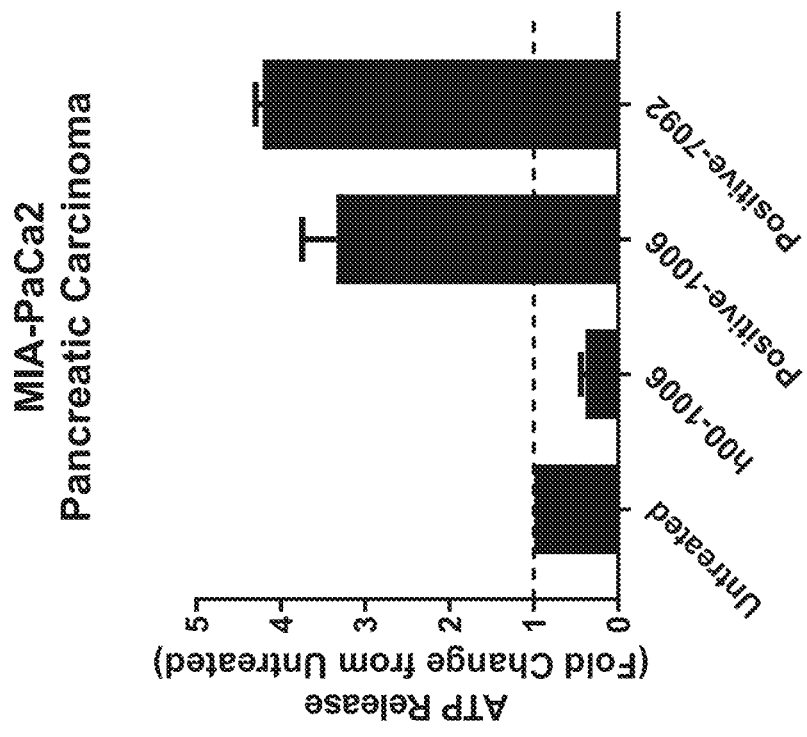
Figure 42A:
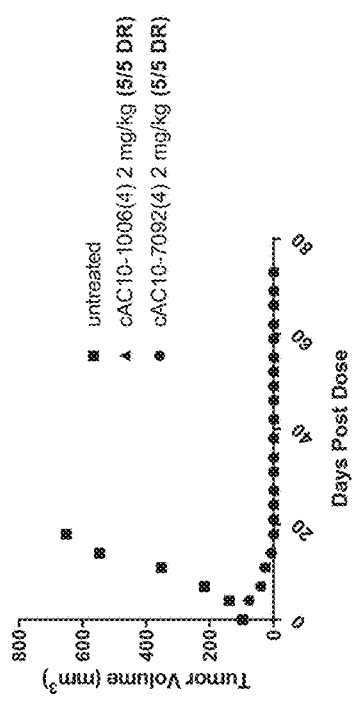
FIGS. 42A-D show the results of xenograft studies of the L540cy and L428 cell lines in SCID (CB17SC sp/sp) mice (L540cy (42A and 42B)) and NSG (NOD scid gamma) mice (L428 (42C) and KMH2 (42D)).
Figure 42B:
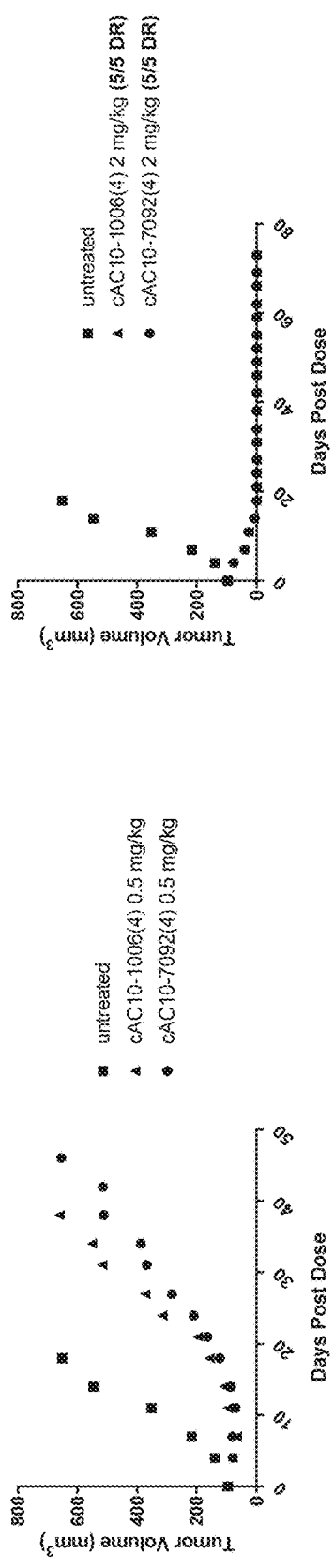
Figure 42C:
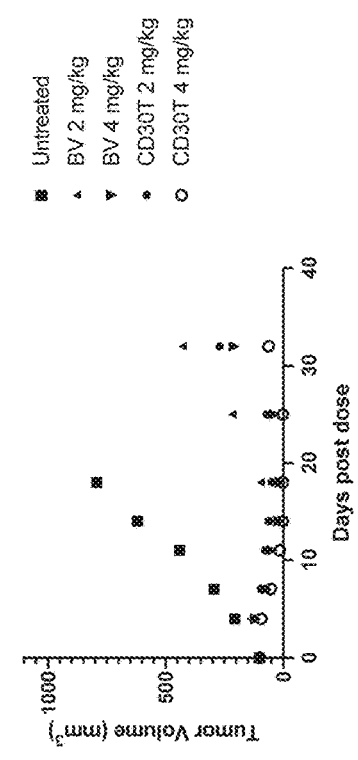
Figure 42D:
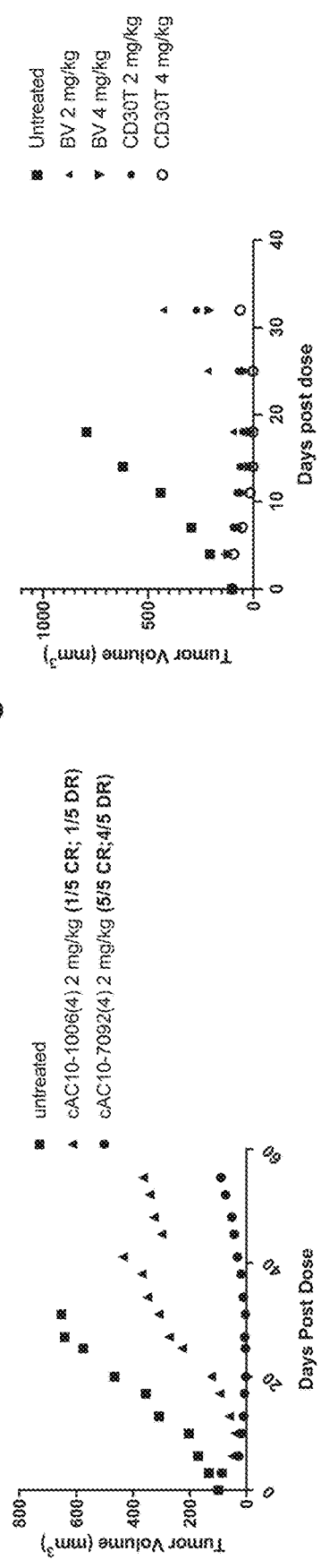

Because MIA-PaCa2 cells do not express CD30, we used an antibody targeted to an expressed surface receptor (Receptor-1 Ab) conjugated to either vcMMAE (Receptor1-1006) or dLAE-MMAE (Receptor1-7092), with an average of 4 drugs per Ab for each conjugate. Release of ATP and HMGB1, 2 DAMPs associated with Immunogenic Cell Death, was measured in MIA-PaCa2 cells treated for 24 hours with either Receptor1-1006, Receptor1-7092, or a non-targeting antibody conjugated to 1006. Receptor1-7092 increased the release of ATP by approximately 4-fold over background (FIG. 41A) and release of HMGB1 by approximately 2-fold over background (FIG. 41B). Taken together, these data indicate that both the vcMMAE and dLAE-MMAE payloads induce immunogenic cell death and may result in increased anti-tumor immune responses in patients.

Example 35D

In Vivo Anti-Tumor Activity Study

Anti tumor activity was assessed in in cell-line derived xenografts, $5\times10^6$ cells were injected subcutaneously into the right flank of female SCID (CB17SC sp sp) mice (Taconic) for the L540cy, and Karpas:Karpas BVR studies and female NSG (NOD scid gamma) mice (JAX) for the L428 and KMH2 studies. Mice were randomly divided into study groups (N=5 to 8) and dosed with test article via intraperitoneal injection once the tumors reached approximately 100 mm$^3$. Animals were euthanized when tumor volumes reached 750-1000 mm$^3$. Tumor volume was calculated with the formula (volume=½× length×width× width). Mice showing durable regressions were terminated around day 40-65 after implant. In all xenograft studies, no weight loss or treatment-related toxicities were observed for mice treated with any of the test articles. All animal procedures were performed under a protocol approved by the Institutional Animal Care and Use Committee in a facility accredited by the Association for Assessment and Accreditation of Laboratory Animal Care.

In Vivo Anticancer Activity of cAC10 ADCs

Figure 43:
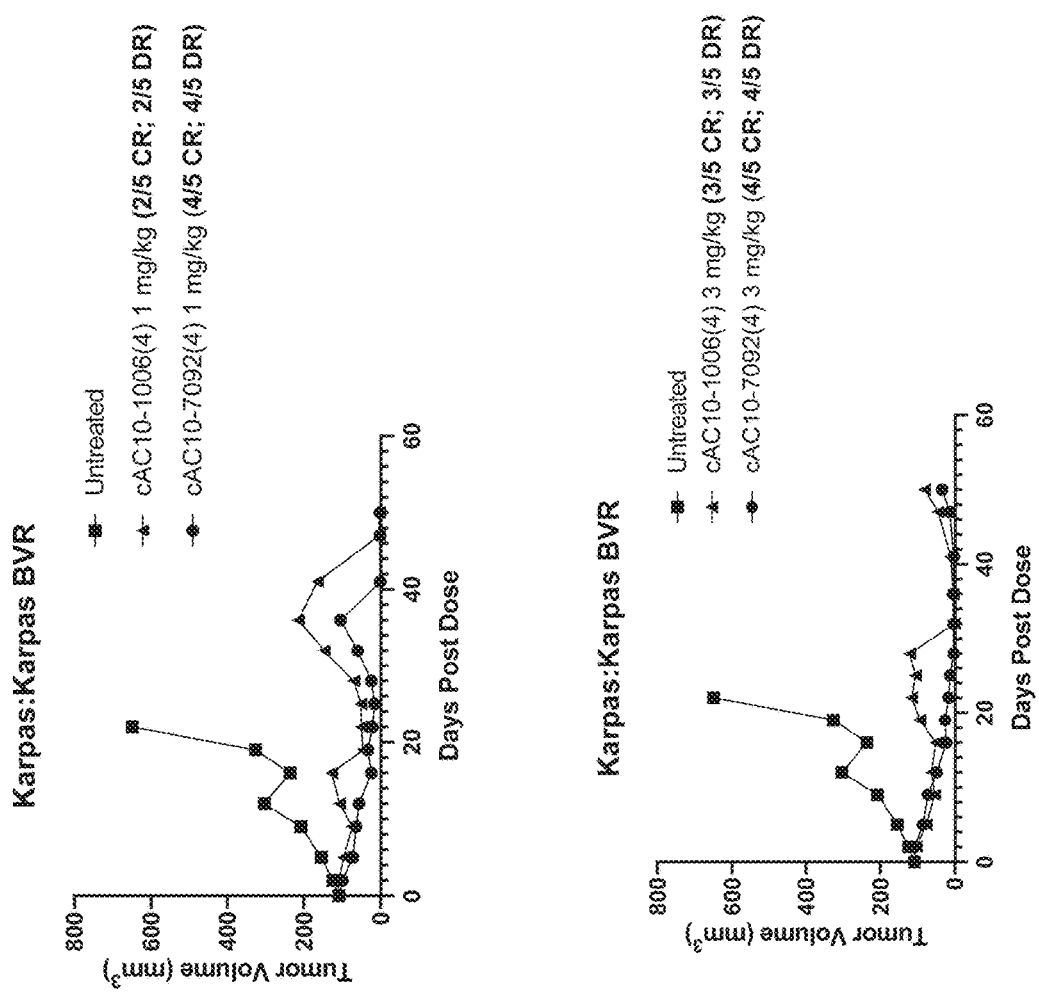
FIG. 43 shows the results of xenograft studies of the Karpas:Karpas BVR cell lines in SCID (CB17SC sp/sp) mice.

The anti-tumor activity of chimeric anti-CD30 antibody cAC10 (also referred to herein as Brentuximab) conjugated with vcMMAE (average of 4 drugs per antibody) (cAC10-1006) or dLAE-MMAE (cAC10-7092) in vivo (FIGS. 42 and 43) was demonstrated. As shown in FIG. 42, significant tumor growth delay or tumor regression of cAC10-7092 and cAC10-1006 compared to untreated mice was observed. These data indicate that cAC10-7092 is efficacious in animal models of lymphoma, with similar efficacy as Brentuximab-vedotin (cAC10-1006)

Example 35E

In Vivo Organ Toxicity Study in Rats

In the matched dose study, Sprague-Dawley rats were given a single intravenous injection of vehicle control (saline) or 10 mg/kg of test ADC. Four days after dosing a complete necropsy was performed and major organs were fixed in formalin, embedded in paraffin, sectioned onto glass slides, stained, and examined microscopically by a board-certified veterinary pathologist. The severity of microscopic findings was scored using the following scale: (0)=no effect, (1)=minimal, (2)=mild, (3)=moderate, (4)=severe. Top evaluate each ADC at the MTD, sprague-Dawley rats were given a single intravenous injection of vehicle control (saline), 15 mg/kg of h00-1006, or 30 mg/kg h00-7092. Four days after dosing a complete necropsy was performed and organs were sampled and examined as described above.

Comparative Evaluation of Tripeptide ADC In Vivo Organ Toxicity in Rats.

Since the CD30 targeted antibody, cAC10, does not cross-react with rodent CD30, a non-binding control (h00) antibody was used as a reasonable surrogate for non-targeted toxicity assessments in the rat. Studies were conducted to compare the toxicity of non-targeted ADCs conjugated with vcMMAE (h00-1006) or dLAE-MMAE (h00-7092), either at a matched dose of 10 mg/kg or each at their maximum tolerated dose of 15 mg/kg or 30 mg/kg respectively. Organs with test article-induced changes (i.e. different from vehicle control) are shown in Table 8-2 (Rat Toxicity at Matched Dose). The severity and incidence of test article-induced changes was significantly reduced following administration of 10 mg/kg h00-7092 relative to 10 mg/kg h00-1006. Additionally, the dose limiting toxicities of h00-1006 and h00-7092 were compared by dosing each ADC at its maximum tolerated dose (MTD, defined as the highest dose that can be administered without causing mortality). Organs with test article-induced changes (i.e. different from vehicle control) are shown in Table 8-3 (Rat Toxicity at MTD). The target organs, severity, and incidence of test article-induced changes was similar following administration of 30 mg/kg h00-7092 relative to 15 mg/kg h00-1006 demonstrating a single dose of h00-7092 was tolerated at twice the dose of h00-1006.

TABLE 8-2

Histopathology of non-targeted ADCs after administration at 10 mg/kg

| | Treatment: | | | | | |
|---|---|---|---|---|---|---|
| | h00-1006(4) | | | h00-7092(4) | | |
| | Dose: | | | | | |
| | 10 mg/kg | | | 10 mg/kg | | |
| | Study Day: | | | | | |
| | 5 | | | 5 | | |
| Rat ID: | A | B | C | D | E | F |
| BONE MARROW | 4 | 3 | 4 | 0 | 0 | 0 |
| EYE, CORNEA | 1 | 1 | 1 | 1 | 0 | 0 |
| LIVER | 2 | 2 | 1 | 0 | 0 | 0 |
| SMALL INTESTINE | 1 | 1 | 1 | 0 | 0 | 1 |
| THYMUS | 0 | 1 | 0 | 0 | 0 | 0 |

TABLE 8-3

Histopathology of non-targeted ADCs after administration at the maximum tolerated dose

| | Treatment: | | | | | |
|---|---|---|---|---|---|---|
| | h00-1006(4) | | | h00-7092(4) | | |
| | Dose: | | | | | |
| | 15 mg/kg | | | 30 mg/kg | | |
| | Study Day: | | | | | |
| | 5 | | | 5 | | |
| Rat ID: | G | H | I | J | K | L |
| BONE MARROW | 4 | 4 | 4 | 4 | 4 | 4 |
| EYE, CORNEA | 1 | 1 | 1 | 2 | 1 | 2 |
| LIVER | 2 | 2 | 1 | 2 | 2 | 2 |
| SMALL INTESTINE | 1 | 1 | 1 | 1 | 1 | 1 |
| THYMUS | 3 | 2 | 3 | 1 | 3 | 3 |

Example 35F

In Vitro Neurite Retraction Assay

For in vitro neurite retraction assays, 20,000-25,000 primary human neuron cells (ScienCell Research #1520) were plated per well in a 96 well plate in human neuron media (ScienCell Research #1521) and allowed to grow for 4 days. After neurite culture is established, test articles are added in either plain media or 100% serum (ATB biologics S11550H). Neuronal cultures are then imaged for 72 hours, and retraction is measured as a decrease in neurite length compared to untreated controls. Cells are fixed in 1% paraformaldehyde, washed in PBS with 0.025% Triton-X, then stained for P-tubulin.

Neurite Retraction is Reduced with dLAE-MMAE Compared to vcMMAE

Neurite cultures treated with a non-targeting antibody conjugated dLAE-MMAE (h00-7092) had reduced retraction compared to the same antibody conjugated with vcMMAE (h00-1006) (FIG. 44A-C). Addition of 50% serum, thought to increase non-specific ADC uptake, resulted in increased retraction with h00-1006 (FIG. 44D). In contrast, h00-7092 activity remains unchanged when serum is included in the assay medium (FIG. 44D). These data indicate cAC10-7092 has reduced toxicity on primary neurites and suggests that cAC10-7092 may be less likely to induce peripheral neuropathy in patients relative to Brentuximab-vedotin (cAC10-1006).

In Vivo Tolerability and Organ Toxicity Study in Non-Human Primates

A study was conducted to evaluate the toxicity of cAC10-7092(4) at repeat doses of 10 mg/kg every 3 weeks for 2 doses in the cynomolgus macaque. Animals were dosed on study days 1 and 22. Monkeys were administered a vehicle control (20 mM glutamic acid, pH 4.5) or ADC and were euthanized 1 week post-second dose. A complete necropsy was performed, and major organs were fixed in formalin, embedded in paraffin, sectioned onto glass slides, staining, and examined microscopically by a board-certified veterinary pathologist. The severity of microscopic findings was scored using the following scale: (–)=no effect, (1)=minimal, (2)=mild, (3)=moderate, (4)=severe. A second study was conducted to evaluate the impact on neutrophils in animals receiving a single dose of test article.

Example 35G

Evaluation of cAC10-7092 ADC In Vivo Tolerability and Organ Toxicity in Non-Human Primates A study was conducted to evaluate the toxicity of the cAC10-7092 at an average of 4 drugs per antibody. The cynomolgus macaques were dosed with 10 mg/kg every 3 weeks for 2 doses on Days 1 and 22 and euthanized on Day 29, test article-related anatomic pathology findings were moderate decreased mature myeloid cells in bone marrow, minimal to moderate decreased lymphocytes in lymphoid organs (lymph node, spleen, and thymus), and minimal to mild decreased/absent ovarian follicles. So the dosage of 10 mg/kg of cAC10-7092(4) dosed every three weeks for 2 doses (q3w×2) was tolerated, with mild to moderate hematological findings.

In previous studies, the highest non-severely toxic dose (HNSTD) of cAC10-1006 in cynomolgus macaques was 3 mg/kg when administered every 3 weeks, with higher doses (6 mg/kg) resulting in non-tolerated neutropenia. In contrast, the highest tested dose of 10 mg/kg q3wx2 for cAC10-7092 was tolerated, with only mild to moderate neutropenia. This suggests that treatment with cAC10-7092 may result in reduced neutropenia relative to Brentuximab-vedotin (cAC10-1006) and thus be better tolerated.

Example 36: Quaternary Salts: Mp-Tripeptide-AE and Mc-VC-AE

The general procedure for synthesis of quaternary ammonium salt based linkers of compounds 73-77 follows the scheme below:

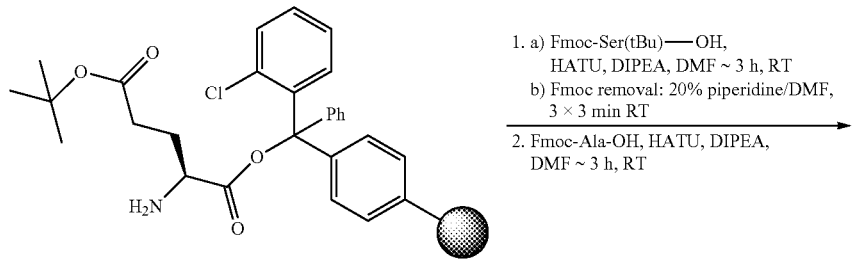

-continued
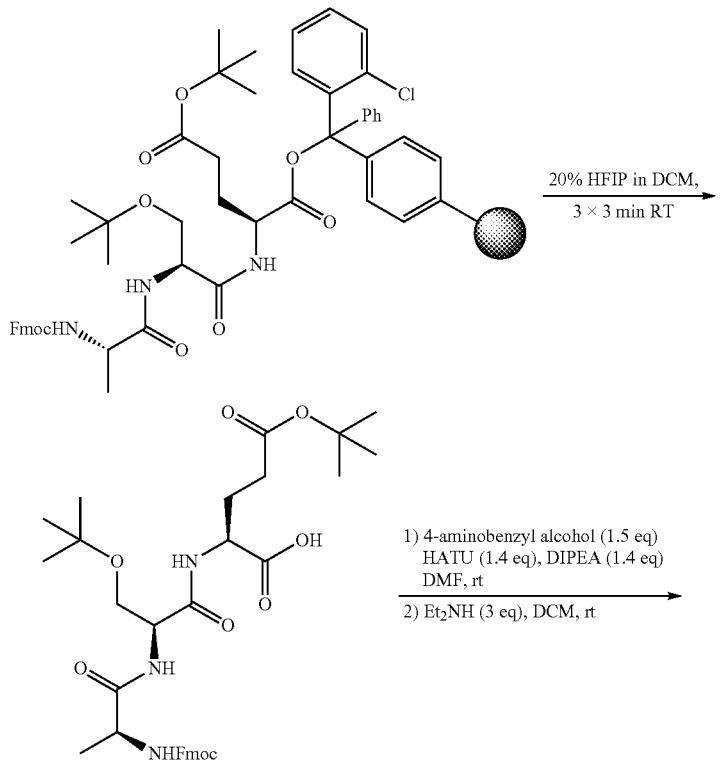
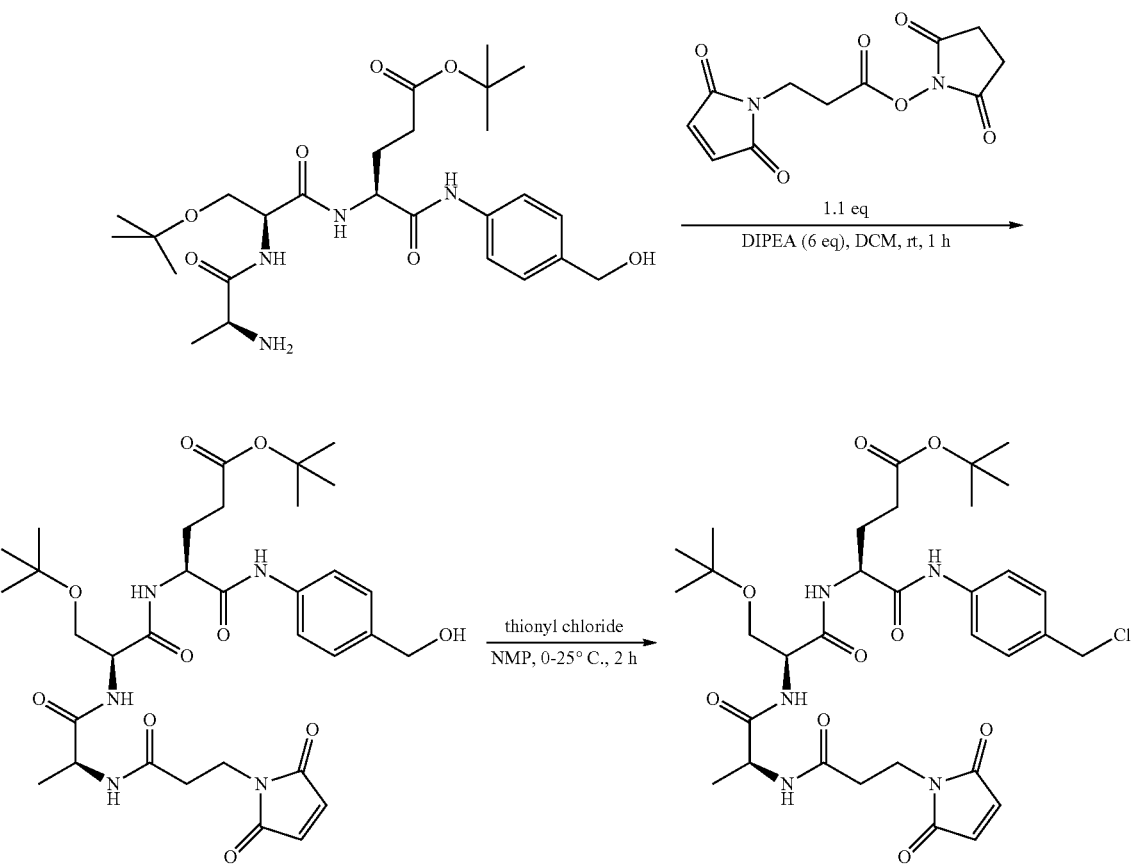

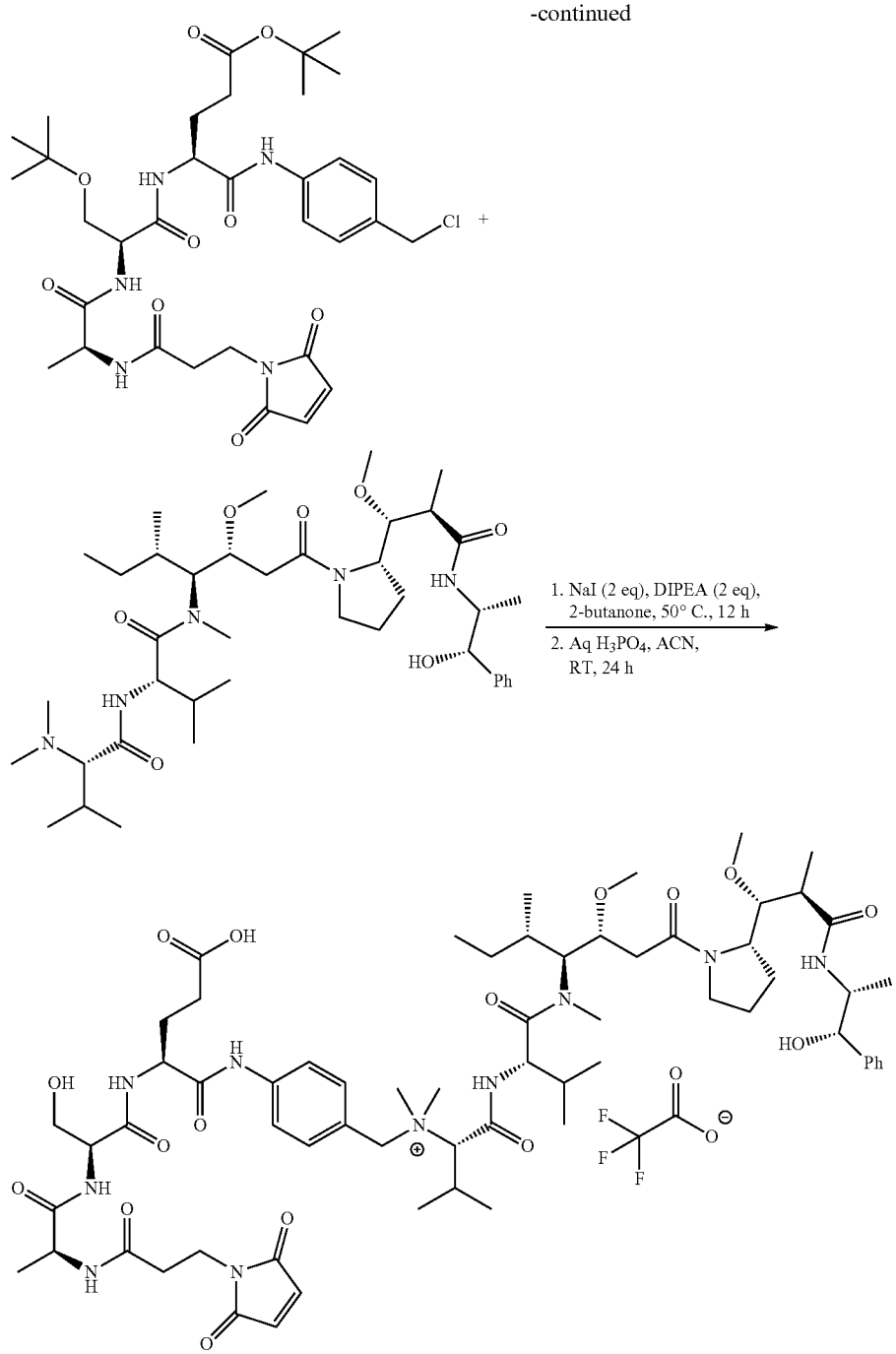

Commercially purchased H-Glu(OtBu)-2-ClTrt resin with a loading of 0.76 mmol/g was used for the synthesis. The resin (1068 mg, 0.81 mmol) was taken in a fritted syringe and swollen with dry DMF. To a vial was added HATU (3 equiv), Fmoc-Ser(tBu)-OH (3 equiv,) and DMF, followed by DIPEA (6 equiv). The solution was vortexed for 1 min and added to resin in syringe. The syringe was shaken on a vortex. Reaction was monitored by taking out an aliquot of the resin and cleaving with 5% TFA in DCM. Sample was analyzed by LC-MS. After completion, the resin was washed with DMF and the Fmoc was removed (3×3 min) with 20% piperidine in DMF and then washed with 6×DMF. At this step, half the resin (0.4 mmol) was carried forward. For the addition of the next amino acid, to a vial was added HATU (3 equiv), Fmoc-Ala-OH (3 equiv), and DMF, followed by DIPEA (6 equiv). The solution was vortexed for 1 min and added to resin in syringe. The syringe was shaken on a vortex. Reaction was monitored by taking out an aliquot of the resin and cleaving with 5% TFA in DCM. Sample was analyzed by LC-MS. After completion, the resin was washed with DMF and DCM. The product was cleaved using 20% HFIP in DCM, three times for 30 mins. After each 30 min cycle, the cleaved material was added to cold ether. The material was carried forward without further purification.

(5S,8S,11S)-11-(3-(tert-butoxy)-3-oxopropyl)-8-(tert-butoxymethyl)-1-(9H-fluoren-9-yl)-5-methyl-3,6,9-trioxo-2- oxa-4,7,10-triazadodecan-12-oic acid (0.4 mmol, crude), (4-aminophenyl)methanol (1.5 eq), and HATU (1.4 eq) were charged to a 20 mL vial equipped with a magnetic stir bar. Dimethyl formamide (DMF) (1.3 mL) was charged to the vessel and stirred until the solids dissolved. DIPEA (3 eq) was charged to the reaction in one portion. The reaction was stirred at rt for two hours. Upon completion, water (6 mL) was added by dropwise addition over 30 minutes. The slurry was stirred for an additional 1 hr at rt. The slurry was filtered and washed with water to give a solid. The solid was redissolved in DCM (5 mL) and diethylamine (124 µL, 3 eq) was added to the solution and stirred at rt. Upon completion of reaction as monitored by LC-MS, the reaction was concentrated on evaporator. The crude material was dissolved in minimum amount of DMSO and then purified by reverse phase preparative LC on a Teledyne ISCO ACCQPrep HP150 equipped with a $C_{12}$ Phenomenex Synergi™ 4 µm Max-RP 80 Å, LC column 21 mm×250 mm eluting with 0.1% trifluoroacetic acid in water (solvent A) and 0.1% trifluoroacetic acid in acetonitrile (solvent B). Tert-Butyl (S)-4-((S)-2-((S)-2-aminopropanamido)-3-(tert-butoxy)propanamido)-5-((4-(hydroxymethyl)phenyl)amino)-5-oxopentanoate was isolated as a solid (51.6 mg) Analytical UPLC-MS: m/z (ES+) calculated 523.31 [M+1]+; found=523.6, 467.5 (–tBu group), 411.4 (–2tBu groups).

N-Succinimidyl 3-maleimidopropionate (26.4 mg, 0.1 mmol) was taken up in DMF (0.3 mL) and added to a vial containing tert-butyl (S)-4-((S)-2-((S)-2-aminopropanamido)-3-(tert-butoxy)propanamido)-5-((4-(hydroxymethyl) phenyl)amino)-5-oxopentanoate (52 mg, 0.1 mmol). N,N-diisopropylethylamine (173.3 µL, 0.99 mmol) was added and the reaction was stirred under Argon for 1 hours. The reaction was taken up in DMSO and purified by preparative LC to yield tert-butyl (S)-4-((S)-3-(tert-butoxy)-2-((S)-2-(3-(2,5-dioxo-2,5-dihydro-1H-pyrrol-1-yl)propanamido)propanamido)propanamido)-5-((4-(hydroxymethyl)phenyl) amino)-5-oxopentanoate/mp-Ala-Ser(tBu)-Glu(OtBu)-PAB-OH (31.6 mg, 47%). Analytical UPLC-MS: m/z (ES+) calculated 674.34 [M+1]+; found 674.6.

A solution of mp-Ala-Ser(tBu)-Glu(OtBu)-PAB-OH (31 mg, 0.046 mmol) in N-methyl-2-pyrrolidone (NMP, 0.33 mL) was cooled to 0° C. A solution of $SOCl_2$ (6.9 µL, 0.09 mmol) in NMP (10 mL) was added dropwise. The mixture was stirred at 20° C. for 2 h. The mixture was poured into ice water and extracted with DCM. The combined DCM layer was dried over sodium sulfate, filtered, and concentrated. tert-butyl (S)-4-((S)-3-(tert-butoxy)-2-((S)-2-(3-(2,5-dioxo-2,5-dihydro-1H-pyrrol-1-yl)propanamido)propanamido)propanamido)-5-((4-(chloromethyl)phenyl)amino)-5-oxopentanoate/mp-Ala-Ser(tBu)-Glu(OtBu)-paba-Cl was obtained as a solid (19.8 mg, yield 62%). Analytical UPLC-MS: m/z (ES+) calculated 692.31 [M+1]+; found 692.8.

Auristatin E (12.4 mg, 0.017 mmol) was dissolved in 2-butanone (0.6 mL) and mp-Ala-Ser(tBu)-Glu(OtBu)-paba-Cl (17.5 mg, 0.025 mmol), sodium iodide (5 mg, 0.034 mmol) and DIPEA (6 µL, 0.034 mmol) were added to the vial. The reaction was stirred at 50° C. overnight. After reacting overnight, the reaction vial was concentrated on the evaporator and the crude material for carried forward to the next step.

To the crude material was added 1:1 mixture of aqueous phosphoric acid and acetonitrile. The deprotection of the tert-butyl group was observed to be very slow. The reaction was monitored by LC-MS. Upon completion, the reaction mixture was diluted with acetonitrile and purified by reverse phase preparative LC on a Teledyne ISCO ACCQPrep HP150 equipped with a C12 Phenomenex Synergi™ 4 µm Max-RP 80 Å, LC column 250 mm of appropriate diameter eluting with 0.1% trifluoroacetic acid in water (solvent A) and 0.1% trifluoroacetic acid in acetonitrile (solvent B). The product was obtained as a white solid (10 mg, 42.5% yield). Analytical UPLC-MS: m/z (ES+) calculated 1276.5 [M]+; found 1276.54.

TABLE 9

UPLC-MS data for Selected Quaternary Salt MMAE Drug Linker compounds

| Compound # | Tripeptide* Sequence | Molecular Formula | MS Calc. (M)+ | MS found | Retention Time (min.) | Method |
|---|---|---|---|---|---|---|
| 73 | Ser-Ser-Pro | $C_{65}H_{99}N_{10}O_{15}$ | 1260.5 | 1260.4 | 1.50 | E |
| 74 | D-Leu-Ala-Glu | $C_{68}H_{104}N_9O_{16}$ | 1303.6 | 1303.5 | 1.70 | E |
| 75 | Ala-Ser-Glu | $C_{65}H_{99}N_{10}O_{16}$ | 1276.5 | 1276.54 | 1.43 | E |
| 76 | Ala-Ser-Pro | $C_{65}H_{99}N_{10}O_{14}$ | 1244.5 | 1244.38 | 1.53 | E |
| 77 | Val-Cit | $C_{68}H_{108}N_{11}O_{13}$ | 1287.7 | 1287.3 | 1.71 | E |

Compounds 73-76:

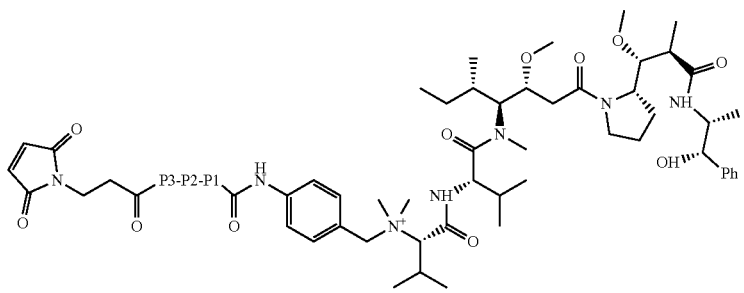

TABLE 9-continued

UPLC-MS data for Selected Quaternary Salt MMAE Drug Linker compounds

| Compound # | Tripeptide* Sequence | Molecular Formula | MS Calc. (M)+ | MS found | Retention Time (min.) | Method |
|---|---|---|---|---|---|---|

Compound 77:

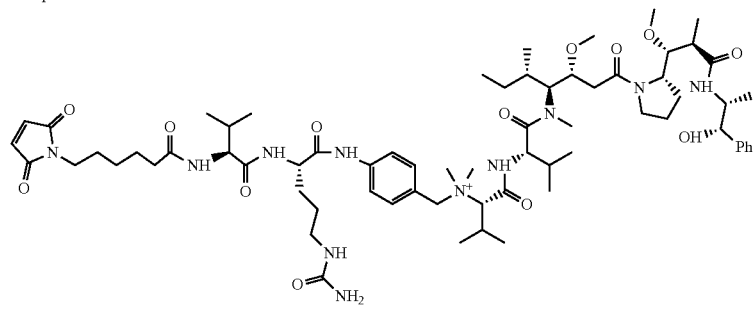

Table of Sequences

| SEQ ID NO | Description | Sequence |
|---|---|---|
| 1 | cAC10 CDR-H1 | DYYIT |
| 2 | cAC10 CDR-H2 | WIYPGSGNTKYNEKFKG |
| 3 | cAC10 CDR-H3 | YGNYWFAY |
| 4 | cAC10 CDR-L1 | KASQSVDFDGDSYMN |
| 5 | cAC10 CDR-L2 | AASNLES |
| 6 | cAC10 CDR-L3 | QQSNEDPWT |
| 7 | cAC10 VH | QIQLQQSGPEVVKPGASVKISCKASGYTFTDYYITWVKQKPGQGLEWIGWIYPGSGNTKY NEKFKGKATLTVDTSSSTAFMQLSSLTSEDTAVYFCANYGNYWFAYWGQGTQVTVSA |
| 8 | cAC10 VL | DIVLTQSPASLAVSLGQRATISCKASQSVDFDGDSYMNWYQQKPGQPPKVLIYAASNLES GIPARFSGSGSGTDFTLNIHPVEEEDAATYYCQQSNEDPWTFGGGTKLEIK |
| 9 | cAC10 HC | QIQLQQSGPEVVKPGASVKISCKASGYTFTDYYITWVKQKPGQGLEWIGWIYPGSGNTKY NEKFKGKATLTVDTSSSTAFMQLSSLTSEDTAVYFCANYGNYWFAYWGQGTQVTVSAAST KGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPGK |
| 10 | cAC10 HC v2 | QIQLQQSGPEVVKPGASVKISCKASGYTFTDYYITWVKQKPGQGLEWIGWIYPGSGNTKY NEKFKGKATLTVDTSSSTAFMQLSSLTSEDTAVYFCANYGNYWFAYWGQGTQVTVSAAST KGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPG |
| 11 | cAC10 LC | DIVLTQSPASLAVSLGQRATISCKASQSVDFDGDSYMNWYQQKPGQPPKVLIYAASNLES GIPARFSGSGSGTDFTLNIHPVEEEDAATYYCQQSNEDPWTFGGGTKLEIKR TVAAPSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 12 | h1F6 VH | QVQLVQSGAEVKKPGASVKVSCKASGYTFTNYGMNWVRQAPGQGLKWMGWINTYTGEPTY ADAFKGRVTMTRDTSISTAYMELSRLRSDDTAVYYCARDYGDYGMDYWGQGTTVTVSS |
| 13 | h1F6 VL | DIVMTQSPDSLAVSLGERATINCRASKSVSTSGYSFMHWYQQKPGQPPKLLIYLASNLES GVPDRFSGSGSGTDFTLTISSLQAEDVAVYYCQHSREVPWTFGQGTKVEIK |
| 14 | h1F6 HC | QVQLVQSGAEVKKPGASVKVSCKASGYTFTNYGMNWVRQAPGQGLKWMGWINTYTGEPTY ADAFKGRVTMTRDTSISTAYMELSRLRSDDTAVYYCARDYGDYGMDYWGQGTTVTVSSAS TKGPSVFPLAPSSKSTSGGTAALGCLVKDYFPEPVTVSWNSGALTSGVHTFPAVLQSSGL |

| SEQ ID NO | Description | Sequence |
|---|---|---|
| | | YSLSSVVTVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLTVDKSRWQQ GNVFSCSVMHEALHNHYTQKSLSLSPGK |
| 15 | h1F6 LC | DIVMTQSPDSLAVSLGERATINCRASKSVSTSGYSFMHWYQQKPGQPPKLLIYLASNLES GVPDRFSGSGSGTDFTLTISSLQAEDVAVYYCQHSREVPWTFGQGTKVEIKRTVAAPSVF IFPPSDEQLKSGTASVVCLLNNFYPREAKVQWKVDNALQSGNSQESVTEQDSKDSTYSLS STLTLSKADYEKHKVYACEVTHQGLSSPVTKSFNRGEC |
| 16 | TROP2 CDR-H1 | NYGMN |
| 17 | TROP2 CDR-H2 | WINTYTGEPTYTDDFKG |
| 18 | TROP2 CDR-H3 | GGFGSSYWYFDV |
| 19 | TROP2 CDR-L1 | KASQDVSIAVA |
| 20 | TROP2 CDR-L2 | SASYRYT |
| 21 | TROP2 CDR-L3 | QQHYITPLT |
| 22 | TROP2 VH | QVQLQQSGSELKKPGASVKVSCKASGYTFTNYGMNWVKQAPGQGLKWMGWINTYTGEPT YTDDFKGRFAFSLDTSVSTAYLQISSLKADDTAVYFCARGGFGSSYWYFDVWGQGSLVTV SS |
| 23 | TROP2 VL | DIQLTQSPSSLSASVGDRVSITCKASQDVSIAVAWYQQKPGKAPKLLIYSASYRYTGVP DRFSGSGSGTDFTLTISSLQPEDFAVYYCQQHYITPLTFGAGTKVEIK |
| 24 | TROP2 CDR-H1 | TAGMQ |
| 25 | TROP2 CDR-H2 | WINTHSGVPKYAEDFKG |
| 26 | TROP2 CDR-H3 | SGFGSSYWYFDV |
| 27 | TROP2 CDR-L1 | KASQDVSTAVA |
| 28 | TROP2 CDR-L2 | SASYRYT |
| 29 | TROP2 CDR-L3 | QQHYITPLT |
| 30 | TROP2 VH | QVQLVQSGAEVKKPGASVKVSCKASGYTFTTAGMQWVRQAPGQGLEWMGWINTHSGVPKY AEDFKGRVTISADTSTSTAYLQLSSLKSEDTAVYYCARSGFGSSYWYFDVWGQGTLVTVS S |
| 31 | TROP2 VL | DIQMTQSPSSLSASVGDRVTITCKASQDVSTAVAWYQQKPGKAPKLLIYSASYRYTGVPS RFSGSGSGTDFTLTISSLQPEDEAVYYCQQHYITPLTFGQGTKLEIK |
| 32 | MICA CDR-H1 | SQNIY |
| 33 | MICA CDR-H2 | YIEPYNVVPMYNPKFKG |
| 34 | MICA CDR-H3 | SGSSNFDY |
| 35 | MICA CDR-L1 | SASSSISSHYLN |
| 36 | MICA CDR-L2 | RTSNLAS |
| 37 | MICA CDR-L3 | QQGSSLPLT |
| 38 | MICA VH | EIQLVQSGAEVKKPGASVKVSCKASGYAFTSQNIYWVRQAPGQGLEWIGYIEPYNVVPMY NPKFKGRATLTVDKSTSTAYLELSSLRSEDTAVYYCARSGSSNFDYWGQGTLVTVSS |
| 39 | MICA VL | DIQLTQSPSSLSASVGDRVTITCSASSSISSHYLHWYQQKPGKSPKLLIYRTSNLASGVP SRFSGSGSGTDYTLTISSLQPEDFATYYCQQGSSLPLTFGQGTKVEIK |
| 40 | MICA CDR-H1 | NYAMH |
| 41 | MICA CDR-H2 | LIWYDGSNKFYGDSVKG |
| 42 | MICA CDR-H3 | EGSGHY |

-continued

Table of Sequences

| SEQ ID NO | Description | Sequence |
|---|---|---|
| 43 | MICA CDR-L1 | RASQGISSALA |
| 44 | MICA CDR-L2 | DASSLES |
| 45 | MICA CDR-L3 | QQFNSYPIT |
| 46 | MICA VH | QVQLVESGGGVVQPGRSLRLSCAASGFTFSNYAMHWVRQAPGEGLEWVALIWYDGSNKFY GDSVKGRFTISRDNSKNTLYLQMNSLSAEDTAVYYCAREGSGHYWGQGTLVTVSS |
| 47 | MICA VL | AIQLTQSPSSLSASVGDRVTITCRASQGISSALAWYQQKPGKVPKSLIYDASSLESGVPS RFSGSGSGTDFTLTISSLQPEDFATYYCQQFNSYPITFGQGTRLEIK |
| 48 | MICA CDR-H1 | NYAMS |
| 49 | MICA CDR-H2 | YISPGGDYIYYADSVKG |
| 50 | MICA CDR-H3 | DRRHYGSYAMDY |
| 51 | MICA CDR-L1 | RSSKSLLHSNLNTYLY |
| 52 | MICA CDR-L2 | RMSNLAS |
| 53 | MICA CDR-L3 | MQHLEYPFT |
| 54 | MICA VH | QVQLVESGGGLVKPGGSLRLSCAASGFTFSNYAMSWIRQAPGKGLEWVSYISPGGDYIYY ADSVKGRFTISRDNAKNSLYLQMNSLRAEDTAVYYCTTDRRHYGSYAMDYWGQGTLVTVS S |
| 55 | MICA VL | DIVMTQSPLSLPVTPGEPASISCRSSKSLLHSNLNTYLYWFLQKPGQSPQILIYRMSNLA SGVPDRFSGSGSGTAFTLKISRVEAEDVGVYYCMQHLEYPFTFGPGTKLEIK |
| 56 | MICA CDR-H1 | TYAFH |
| 57 | MICA CDR-H2 | GIVPIFGTLKYAQKFQD |
| 58 | MICA CDR-H3 | AIQLEGRPFDH |
| 59 | MICA CDR-L1 | RASQGITSYLA |
| 60 | MICA CDR-L2 | AASALQS |
| 61 | MICA CDR-L3 | QQVNRGAAIT |
| 62 | MICA VH | QVQLVQSGAEVKKPGSSVRVSCRASGGSSTTYAFHWVRQAPGQGLEWMGGIVPIFGTLKY AQKFQDRVTLTADKSTGTAYMELNSLRLDDTAVYYCARAIQLEGRPFDHWGQGTQVTVSA |
| 63 | MICA VL | DIQLTQSPSFLSASVGDRVTITCRASQGITSYLAWYQQKPGKAPKLLIYAASALQSGVPS RFSGRGSGTEFTLTISSLQPEDFATYYCQQVNRGAAITFGHGTRLDIK |
| 64 | CD24 CDR-H1 | TYAFH |
| 65 | CD24 CDR-H2 | GIVPIFGTLKYAQKFQD |
| 66 | CD24 CDR-H3 | AIQLEGRPFDH |
| 67 | CD24 CDR-L1 | RASQGITSYLA |
| 68 | CD24 CDR-L2 | AASALQS |
| 69 | CD24 CDR-L3 | QQVNRGAAIT |
| 70 | CD24 VH | QVQLVQSGAEVKKPGSSVRVSCRASGGSSTTYAFHWVRQAPGQGLEWMGGIVPIFGTLKY AQKFQDRVTLTADKSTGTAYMELNSLRLDDTAVYYCARAIQLEGRPFDHWGQGTQVTVSA |
| 71 | CD24 VL | DIQLTQSPSFLSASVGDRVTITCRASQGITSYLAWYQQKPGKAPKLLIYAASALQSGVPS RFSGRGSGTEFTLTISSLQPEDFATYYCQQVNRGAAITFGHGTRLDIK |
| 72 | ITGav CDR-H1 | RYTMH |
| 73 | ITGav CDR-H2 | VISFDGSNKYYVDSVKG |
| 74 | ITGav CDR-H3 | EARGSYAFDI |

-continued

Table of Sequences

| SEQ ID NO | Description | Sequence |
|---|---|---|
| 75 | ITGav CDR-L1 | RASQSVSSYLA |
| 76 | ITGav CDR-L2 | DASNRAT |
| 77 | ITGav CDR-L3 | QQRSNWPPFT |
| 78 | ITGav VH | QVQLVESGGGVVQPGRSRRLSCAASGFTFSRYTMHWVRQAPGKGLEWVAVISFDGSNKYY VDSVKGRFTISRDNSENTLYLQVNILRAEDTAVYYCAREARGSYAFDIWGQGTMVTVSS |
| 79 | ITGav VL | EIVLTQSPATLSLSPGERATLSCRASQSVSSYLAWYQQKPGQAPRLLIYDASNRATGIPA RFSGSGSGTDFTLTISSLEPEDFAVYYCQQRSNWPPFTFGPGTKVDIK |
| 80 | ITGav CDR-H1 | SFWMH |
| 81 | ITGav CDR-H2 | YINPRSGYTEYNEIFRD |
| 82 | ITGav CDR-H3 | FLGRGAMDY |
| 83 | ITGav CDR-L1 | RASQDISNYLA |
| 84 | ITGav CDR-L2 | YTSKIHS |
| 85 | ITGav CDR-L3 | QQGNTFPYT |
| 86 | ITGav VH | QVQLQQSGGELAKPGASVKVSCKASGYTFSSFWMHWVRQAPGQGLEWIGYINPRSGYTEY NEIFRDKATMTTDTSTSTAYMELSSLRSEDTAVYYCASFLGRGAMDYWGQGTTVTVSS |
| 87 | ITGav VL | DIQMTQSPSSLSASVGDRVTITCRASQDISNYLAWYQQKPGKAPKLLIYYTSKIHSGVPS RFSGSGSGTDYTFTISSLQPEDIATYYCQQGNTFPYTFGQGTKVEIK |
| 88 | gpA33 CDR-H1 | TSSYYWG |
| 89 | gpA33 CDR-H2 | TIYYNGSTYYSPSLKS |
| 90 | gpA33 CDR-H3 | QGYDIKINIDV |
| 91 | gpA33 CDR-L1 | RASQSVSSYLA |
| 92 | gpA33 CDR-L2 | VASNRAT |
| 93 | gpA33 CDR-L3 | QQRSNWPLT |
| 94 | gpA33 VH | QLQLQESGPGLVKPSETLSLTCTVSGGSISTSSYYWGWIRQPPGKGLEWIGTIYYNGSTY YSPSLKSRVSISVDTSKNQFSLKLSSVTAADTSVYYCARQGYDIKINIDVWGQGTTVTVS S |
| 95 | gpA33 VL | EIVLTQSPATLSLSPGERATLSCRASQSVSSYLAWYQQKPGQAPRLLIYVASNRATGIPA RFSGSGSGTDFTLTISSLEPEDFAVYYCQQRSNWPLTFGGGTKVEIK |
| 96 | IL1Rap CDR-H1 | SSWMN |
| 97 | IL1Rap CDR-H2 | RIYPGDGNTHYAQKFQG |
| 98 | IL1Rap CDR-H3 | GYLDPMDY |
| 99 | IL1Rap CDR-L1 | QASQGINNYLN |
| 100 | IL1Rap CDR-L2 | YTSGLHA |
| 101 | IL1Rap CDR-L3 | QQYSILPWT |
| 102 | IL1Rap VH | QVQLVQSGAEVKKPGSSVKVSCKASGYAFTSSWMNWVRQAPGQGLEWMGRIYPGDGNTHY AQKFQGRVTLTADKSTSTAYMELSSLRSEDTAVYYCGEGYLDPMDYWGQGTLVTVSS |
| 103 | IL1Rap VL | DIQMTQSPSSLSASVGDRVTITCQASQGINNYLNWYQQKPGKAPKLLIHYTSGLHAGVPS RFSGSGSGTDYTLTISSLEPEDVATYYCQQYSILPWTFGGGTKVEIK |

Table of Sequences

| SEQ ID NO | Description | Sequence |
|---|---|---|
| 104 | EpCAM CDR-H1 | SYGMH |
| 105 | EpCAM CDR-H2 | VISYDGSNKYYADSVKG |
| 106 | EpCAM CDR-H3 | DMG |
| 107 | EpCAM CDR-L1 | RTSQSISSYLN |
| 108 | EpCAM CDR-L2 | WASTRES |
| 109 | EpCAM CDR-L3 | QQSYDIPYT |
| 110 | EpCAM VH | EVQLLESGGGVVQPGRSLRLSCAASGFTFSSYGMHWVRQAPGKGLEWVAVISYDGSNKYYADSVKGRFTISRDNSKNTLYLQMNSLRAEDTAVYYCAKDMGWGSGWRPYYYYGMDVWGQGTTVTVSS |
| 111 | EpCAM VL | ELQMTQSPSSLSASVGDRVTITCRTSQSISSYLNWYQQKPGQPPKLLIYWASTRESGVPDRFSGSGSGTDFTLTISSLQPEDSATYYCQQSYDIPYTFGQGTKLEIK |
| 112 | EpCAM CDR-H1 | NYWMS |
| 113 | EpCAM CDR-H2 | NIKQDGSEKFYADSVKG |
| 114 | EpCAM CDR-H3 | VGPSWEQDY |
| 115 | EpCAM CDR-L1 | TGSSSNIGSYYGVH |
| 116 | EpCAM CDR-L2 | SDTNRPS |
| 117 | EpCAM CDR-L3 | QSYDKGFGHRV |
| 118 | EpCAM VH | EVQLVESGGGLVQPGGSLRLSCAASGFTFSNYWMSWVRQAPGKGLEWVANIKQDGSEKFYADSVKGRFTISRDNAKNSLYLQMNSLRAEDTAVYYCARVGPSWEQDYWGQGTLVTVSA |
| 119 | EpCAM VL | QSVLTQPPSVSGAPGQRVTISCTGSSSNIGSYYGVHWYQQLPGTAPKLLIYSDTNRPSGVPDRFSGSKSGTSASLAITGLQAEDEADYYCQSYD |
| 120 | EpCAM CDR-H1 | SYAIS |
| 121 | EpCAM CDR-H2 | GIIPIFGTANYAQKFQG |
| 122 | EpCAM CDR-H3 | GLLWNY |
| 123 | EpCAM CDR-L1 | RASQSVSSNLA |
| 124 | EpCAM CDR-L2 | GASTTAS |
| 125 | EpCAM CDR-L3 | QQYNNWPPAYT |
| 126 | EpCAM VH | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGLLWNYWGQGTLVTVSS |
| 127 | EpCAM VL | EIVMTQSPATLSVSPGERATLSCRASQSVSSNLAWYQQKPGQAPRLIIYGASTTASGIPARFSASGSGTDFTLTISSLQSEDFAVYYCQQYNNWPPAYTFGQGTKLEIK |
| 128 | EpCAM CDR-H1 | NYGMN |
| 129 | EpCAM CDR-H2 | WINTYTGEPTYGEDFKG |
| 130 | EpCAM CDR-H3 | FGNYVDY |
| 131 | EpCAM CDR-L1 | RSSKNLLHSNGITYLY |
| 132 | EpCAM CDR-L2 | QMSNLAS |
| 133 | EpCAM CDR-L3 | AQNLEIPRT |
| 134 | EpCAM VH | QVQLVQSGPEVKKPGASVKVSCKASGYTFTNYGMNWVRQAPGQGLEWMGWINTYTGEPTYGEDFKGRFAFSLDTSASTAYMELSSLRSEDTAVYFCARFGNYVDYWGQGSLVTVSS |
| 135 | EpCAM VL | DIVMTQSPLSLPVTPGEPASISCRSSKNLLHSNGITYLYWYLQKPGQSPQLLIYQMSNLASGVPDRFSSSGSGTDFTLKISRVEAEDVGVYYCAQNLEIPRTFGQGTKVEIK |

Table of Sequences

| SEQ ID NO | Description | Sequence |
|---|---|---|
| 136 | EpCAM CDR-H1 | KYGMN |
| 137 | EpCAM CDR-H2 | WINTYTEEPTYGDDFKG |
| 138 | EpCAM CDR-H3 | FGSAVDY |
| 139 | EpCAM CDR-L1 | RSSKSLLHSNGITYLY |
| 140 | EpCAM CDR-L2 | QMSNRAS |
| 141 | EpCAM CDR-L3 | AQNLELPRT |
| 142 | EpCAM VH | QIQLVQSGPEVKKPGESVKISCKASGYTFTKYGMNWVKQAPGQGLKWMGWINTYTEEPTY GDDFKGRFTFTLDTSTSTAYLEISSLRSEDTATYFCARFGSAVDYWGQGTLVTVSS |
| 143 | EpCAM VL | DIVMTQSALSNPVTLGESGSISCRSSKSLLHSNGITYLYWYLQKPGQSPQLLIYQMSNRA SGVPDRFSSSGSGTDFTLKISRVEAEDVGVYYCAQNLELPRTFGQGTKLEMKR |
| 144 | EpCAM CDR-H1 | DYSMH |
| 145 | EpCAM CDR-H2 | WINTETGEPTYADDFKG |
| 146 | EpCAM CDR-H3 | TAVY |
| 147 | EpCAM CDR-L1 | RASQEISVSLS |
| 148 | EpCAM CDR-L2 | ATSTLDS |
| 149 | EpCAM CDR-L3 | LQYASYPWT |
| 150 | EpCAM VH | QVKLQESGPELKKPGETVKISCKASGYTFTDYSMHWVKQAPGKGLKWMGWINTETGEPTY ADDFKGRFAFSLETSASTAYLQINNLKNEDTATYFCARTAVYWGQGTTVTVSS |
| 151 | EpCAM VL | DIQMTQSPSSLSASLGERVSLTCRASQEISVSLSWLQQEPDGTIKRLIYATSTLDSGVPK RFSGSRSGSDYSLTISSLESEDFVDYYCLQYASYPWTFGGGTKLEIKR |
| 152 | CD352 CDR-H1 | NYGMN |
| 153 | CD352 CDR-H2 | WINTYSGEPRYADDFKG |
| 154 | CD352 CDR-H3 | DYGRWYFDV |
| 155 | CD352 CDR-L1 | RASSSVSHMH |
| 156 | CD352 CDR-L2 | ATSNLAS |
| 157 | CD352 CDR-L3 | QQWSSTPRT |
| 158 | CD352 VH | QIQLVQSGSELKKPGASVKVSCKASGYTFTNYGMNWVRQAPGQDLKWMGWINTYSGEPRY ADDFKGRFVFSLDKSVNTAYLQISSLKAEDTAVYYCARDYGRWYFDVWGQGTTVTVSS |
| 159 | CD352 VL | QIVLSQSPATLSLSPGERATMSCRASSSVSHMHWYQQKPGQAPRPWIYATSNLASGVPAR FSGSGSGTDYTLTISSLEPEDFAVYYCQQWSSTPRTFGGGTKVEIKR |
| 160 | CS1 CDR-H1 | RYWMS |
| 161 | CS1 CDR-H2 | EINPDSSTINYAPSLKD |
| 162 | CS1 CDR-H3 | PDGNYWYFDV |
| 163 | CS1 CDR-L1 | KASQDVGIAVA |
| 164 | CS1 CDR-L2 | WASTRHT |
| 165 | CS1 CDR-L3 | QQYSSYPYT |
| 166 | CS1 VH | EVQLVESGGGLVQPGGSLRLSCAASGFDFSRYWMSWVRQAPGKGLEWIGEINPDSSTINY APSLKDKFIISRDNAKNSLYLQMNSLRAEDTAVYYCARPDGNYWYFDVWGQGTLVTVSS |
| 167 | CS1 VL | DIQMTQSPSSLSASVGDRVTITCKASQDVGIAVAWYQQKPGKVPKLLIYWASTRHTGVPD RFSGSGSGTDFTLTISSLQPEDVATYYCQQYSSYPYTFGQGTKVEIKR |
| 168 | CD38 CDR-H1 | SFAMS |

-continued

Table of Sequences

| SEQ ID NO | Description | Sequence |
|---|---|---|
| 169 | CD38 CDR-H2 | AISGSGGGTYYADSVKG |
| 170 | CD38 CDR-H3 | DKILWFGEPVFDY |
| 171 | CD38 CDR-L1 | RASQSVSSYLA |
| 172 | CD38 CDR-L2 | DASNRAT |
| 173 | CD38 CDR-L3 | QQRSNWPPT |
| 174 | CD38 VH | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS |
| 175 | CD38 VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPPTFGQGTKVEIKR |
| 176 | CD25 CDR-H1 | SYRMH |
| 177 | CD25 CDR-H2 | YINPSTGYTEYNQKFKD |
| 178 | CD25 CDR-H3 | GGGVFDY |
| 179 | CD25 CDR-L1 | SASSSISYMH |
| 180 | CD25 CDR-L2 | TTSNLAS |
| 181 | CD25 CDR-L3 | HQRSTYPLT |
| 182 | CD25 VH | QVQLVQSGAEVKKPGSSVKVSCKASGYTFTSYRMHWVRQAPGQGLEWIGYINPSTGYTEYNQKFKDKATITADESTNTAYMELSSLRSEDTAVYYCARGGGVFDYWGQGTLVTVSS |
| 183 | CD25 VL | DIQMTQSPSTLSASVGDRVTITCSASSSISYMHWYQQKPGKAPKLLIYTTSNLASGVPARFSGSGSGTEFTLTISSLQPDDFATYYCHQRSTYPLTFGQGTKVEVK |
| 184 | ADAM9 CDR-H1 | SYWM |
| 185 | ADAM9 CDR-H2 | EIIPINGHTNYNEKFKS |
| 186 | ADAM9 CDR-H3 | GGYYYYGSRDYFDY |
| 187 | ADAM9 CDR-L1 | KASQSVDYDGDSYMN |
| 188 | ADAM9 CDR-L2 | AASDLES |
| 189 | ADAM9 CDR-L3 | QQSHEDPFT |
| 190 | ADAM9 VH | QVQLQQPGAELVKPGASVKLSCKASGYTFTSYWMHWVKQRPGQGLEWIGEIIPINGHTNYNEKFKSKATLTLDKSSSTAYMQLSSLASEDSAVYYCARGGYYYYGSRDYFDYWGQGTTLTVSS |
| 191 | ADAM9 VL | DIVLTQSPASLAVSLGQRATISCKASQSVDYDGDSYMNWYQQIPGQPPKLLIYAASDLESGIPARFSGSGSGTDFTLNIHPVEEEDAATYYCQQSHEDPFTFGGGTKLEIK |
| 192 | ADAM9 CDR-H1 | SYWM |
| 193 | ADAM9 CDR-H2 | EIIPIFGHTNYNEKFKS |
| 194 | ADAM9 CDR-H3 | GGYYYYPRQGFLDY |
| 195 | ADAM9 CDR-L1 | KASQSVDYDSGDSYMN |
| 196 | ADAM9 CDR-L2 | AASDLES |
| 197 | ADAM9 CDR-L3 | QQSHEDPFT |
| 198 | ADAM9 VH | EVQLVESGGGLVKPGGSLRLSCAASGFTFSSYWMHWVRQAPGKGLEWVGETIPIFGHTNYNEKFKSRFTISLDNSKNTLYLQMGSLRAEDTAVYYCARGGYYYYPRQGFLDYWGQGTTVTVSS |
| 199 | ADAM9 VL | DIVMTQSPDSLAVSLGERATISCKASQSVDYSGDSYMNWYQQKPGQPPKLLIYAASDLESGIPARFSGSGSGTDFTLTISSLEPEDFATYYCQQSHEDPFTFGQGTKLEIK |

-continued

Table of Sequences

| SEQ ID NO | Description | Sequence |
|---|---|---|
| 200 | CD59 CDR-H1 | YGMN |
| 201 | CD59 CDR-H2 | YISSSSSTIYADSVKG |
| 202 | CD59 CDR-H3 | GPGMDV |
| 203 | CD59 CDR-L1 | KSSQSVLYSSNNKNYLA |
| 204 | CD59 CDR-L2 | WASTRES |
| 205 | CD59 CDR-L3 | QQYYSTPQLT |
| 206 | CD59 VH | QVQLQQSGGGVVQPGRSLGLSCAASFTFSSYGMNWVRQAPGKGLEWVSYISSSSSTIYAD SVKGRFTISRDNSKNTLYLQMNSLRAEDTAVYYCARGPGMDVWGQGTTVTVS |
| 207 | CD59 VL | DIVLTQSPDSLAVSLGERATINCKSSQSVLYSSNNKNYLAWYQQKPGQPPKLLIYWASTR ESGVPDRFSGSGSGTDFTPAISSLQAEDVAVYYCQQYYSTPQLTFGGGTKVDIK |
| 208 | CD19 CDR-H1 | TSGMGVG |
| 209 | CD19 CDR-H2 | HIWWDDDKRYNPALKS |
| 210 | CD19 CDR-H3 | MELWSYYFDY |
| 211 | CD19 CDR-L1 | SASSSVSYMH |
| 212 | CD19 CDR-L2 | DTSKLAS |
| 213 | CD19 CDR-L3 | FQGSVYPFT |
| 214 | CD19 VH | QVQLQESGPGLVKPSQTLSLTCTVSGGSISTSGMGVGWIRQHPGKGLEWIGHIWWDDDKR YNPALKSRVTISVDTSKNQFSLKLSSVTAADTAVYYCARMELWSYYFDYWGQGTLVTVSS |
| 215 | CD19 VL | EIVLTQSPATLSLSPGERATLSCSASSSVSYMHWYQQKPGQAPRLLIYDTSKLASGIPAR FSGSGSGTDFTLTISSLEPEDVAVYYCFQGSVYPFTFGQGTKLEIKR |
| 216 | CD70 CDR-H1 | NYGMN |
| 217 | CD70 CDR-H2 | WINTYTGEPTYADAFKG |
| 218 | CD70 CDR-H3 | DYGDYGMDY |
| 219 | CD70 CDR-L1 | RASKSVSTSGYSFMH |
| 220 | CD70 CDR-L2 | LASNLES |
| 221 | CD70 CDR-L3 | QHSREVPWT |
| 222 | CD70 VH | QVQLVQSGAEVKKPGASVKVSCKASGYTFTNYGMNWVRQAPGQGLKWMGWINTYTGEPTY ADAFKGRVTMTRDTSISTAYMELSRLRSDDTAVYYCARDYGDYGMDYWGQGTTVTVSS |
| 223 | CD70 VL | DIVMTQSPDSLAVSLGERATINCRASKSVSTSGYSFMHWYQQKPGQPPKLLIYLASNLES GVPDRFSGSGSGTDFTLTISSLQAEDVAVYYCQHSREVPWTFGQGTKVEIK |
| 224 | B7H4 CDR-H1 | SGYSWH |
| 225 | B7H4 CDR-H2 | YIHSSGSTNYNPSLKS |
| 226 | B7H4 CDR-H3 | YDDYFEY |
| 227 | B7H4 CDR-L1 | KASQNVGFNVA |
| 228 | B7H4 CDR-L2 | SASYRYS |
| 229 | B7H4 CDR-L3 | QQYNWYPFT |
| 230 | B7H4 VH | EVQLQESGPGLVKPSETLSLTCAVTGYSITSGYSWHWIRQFPGNGLEWMGYIHSSGSTNY NPSLKSRISISRDTSKNQFFLKLSSVTAADTAVYYCAGYDDYFEYWGQGTTVTVSS |
| 231 | B7H4 VL | DIQMTQSPSSLSASVGDRVTITCKASQNVGFNVAWYQQKPGKSPKALIYSASYRYSGVPS RFSGSGSGTDFTLTISSLQPEDFAEYFCQQYNWYPFTFGQGTKLEIK |

Table of Sequences

| SEQ ID NO | Description | Sequence |
|---|---|---|
| 232 | CD138 CDR-H1 | NYWIE |
| 233 | CD138 CDR-H2 | EILPGTGRTIYNEKFKG |
| 234 | CD138 CDR-H3 | RDYYGNFYYAMDY |
| 235 | CD138 CDR-IA | SASQGINNYLN |
| 236 | CD138 CDR-I2 | YTSTLQS |
| 237 | CD138 CDR-I3 | QQYSKLPRT |
| 238 | CD138 VH | QVQLQQSGSELMMPGASVKISCKATGYTFSNYWIEWVKQRPGHGLEWIGEILPGTGRTIYNEKFKGKATFTADISSNTVQMQLSSLTSEDSAVYYCARRDYYGNFYYAMDYWGQGTSVTVSS |
| 239 | CD138 VL | DIQMTQSTSSLSASLGDRVTISCSASQGINNYLNWYQQKPDGTVELLIYYTSTLQSGVPSRFSGSGSGTDYSLTISNLEPEDIGTYYCQQYSKLPRTFGGGTKLEIK |
| 240 | CD166 CDR-H1 | TYGMGVG |
| 241 | CD166 CDR-H2 | NIWWSEDKHYSPSLKS |
| 242 | CD166 CDR-H3 | IDYGNDYAFTY |
| 243 | CD166 CDR-L1 | RSSKSLLHSNGITYLY |
| 244 | CD166 CDR-L2 | QMSNLAS |
| 245 | CD166 CDR-L3 | AQNLELPYT |
| 246 | CD166 VH | QITLKESGPTLVKPTQTLTLTCTFSLSTYGMGVGWIRQPPKALEWLANIWWSEDKHYSPSLKSRLTITKDTSKNQVVLTITNVDPVDTATYYCVQIDYGNDYAFTYWGQGTLVTVSS |
| 247 | CD166 VL | DIVMTQSPLSLPVTPGEPASISCRSSKSLLHSNGITYLYWYLQKPGQSPQLLIYQMSNLASGVPDRFSGSGSGTDFTLKISRVEAEDVGVYYCAQNLELPYTFGQGTKLEIK |
| 248 | CD51 CDR-H1 | RYTMH |
| 249 | CD51 CDR-H2 | VISFDGSNKYYVDSVKG |
| 250 | CD51 CDR-H3 | EARGSYAFDI |
| 251 | CD51 CDR-L1 | RASQSVSSYLA |
| 252 | CD51 CDR-L2 | DASNRAT |
| 253 | CD51 CDR-L3 | QQRSNWPPFT |
| 254 | CD51 VH | QVQLVESGGGVVQPGRSRRLSCAASGFTFSRYTMHWVRQAPGKGLEWVAVISFDGSNKYYVDSVKGRFTISRDNSENTLYLQVNILRAEDTAVYYCAREARGSYAFDIWGQGTMVTVSS |
| 255 | CD51 VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPPFTFGPGTKVDIK |
| 256 | CD56 CDR-H1 | SFGMH |
| 257 | CD56 CDR-H2 | YISSGSFTIYYADSVKG |
| 258 | CD56 CDR-H3 | MRKGYAMDY |
| 259 | CD56 CDR-L1 | RSSQIIIHSDGNTYLE |
| 260 | CD56 CDR-L2 | KVSNRFS |
| 261 | CD56 CDR-L3 | FQGSHVPHT |
| 262 | CD56 VH | QVQLVESGGGVVQPGRSLRLSCAASGFTFSSFGMHWVRQAPGKGLEWVAYISSGSFTIYYADSVKGRFTISRDNSKNTLYLQMNSLRAEDTAVYYCARMRKGYAMDYWGQGTLVTVSS |
| 263 | CD56 VL | DVVMTQSPLSLPVTLGQPASISCRSSQIIIHSDGNTYLEWFQQRPGQSPRRLIYKVSNRFSGVPDRFSGSGSGTDFTLKISRVEAEDVGVYYCFQGSHVPHTFGQGTKVEIK |

Table of Sequences

| SEQ ID NO | Description | Sequence |
|---|---|---|
| 264 | CD74 CDR-H1 | NYGVN |
| 265 | CD74 CDR-H2 | WINPNTGEPTFDDDFKG |
| 266 | CD74 CDR-H3 | SRGKNEAWFAY |
| 267 | CD74 CDR-L1 | RSSQSLVHRNGNTYLH |
| 268 | CD74 CDR-L2 | TVSNRFS |
| 269 | CD74 CDR-L3 | SQSSHVPPT |
| 270 | CD74 VH | QVQLQQSGSELKKPGASVKVSCKASGYTFTNYGVNWIKQAPGQGLQWMGWINPNTGEPTFDDDFKGRFAFSLDTSVSTAYLQISSLKADDTAVYFCSRSRGKNEAWFAYWGQGTLVTVSS |
| 271 | CD74 VL | DIQLTQSPLSLPVTLGQPASISCRSSQSLVHRNGNTYLHWFQQRPGQSPRLLIYTVSNRFSGVPDRFSGSGSGTDFTLKISRVEAEDVGVYFCSQSSHVPPTFGAGTRLEIK |
| 272 | CEACAM5 CDR-H1 | TYWMS |
| 273 | CEACAM5 CDR-H2 | EIHPDSSTINYAPSLKD |
| 274 | CEACAM5 CDR-H3 | LYFGFPWFAY |
| 275 | CEACAM5 CDR-L1 | KASQDVGTSVA |
| 276 | CEACAM5 CDR-L2 | WTSTRHT |
| 277 | CEACAM5 CDR-L3 | QQYSLYRS |
| 278 | CEACAM5 VH | EVQLVESGGGVVQPGRSLRLSCSASGFDFTTYWMSWVRQAPGKGLEWIGEIHPDSSTINYAPSLKDRFTISRDNAKNTLFLQMDSLRPEDTGVYFCASLYFGFPWFAYWGQGTPVTVSS |
| 279 | CEACAM5 VL | DIQLTQSPSSLSASVGDRVTITCKASQDVGTSVAWYQQKPGKAPKLLIYWTSTRHTGVPSRFSGSGSGTDFTFTISSLQPEDIATYYCQQYSLYRSFGQGTKVEIK |
| 280 | CanAg CDR-H1 | YYGMN |
| 281 | CanAg CDR-H2 | WIDTTTGEPTYAQKFQG |
| 282 | CanAg CDR-H3 | RGPYNWYFDV |
| 283 | CanAg CDR-IA | RSSKSLLHSNGNTYLY |
| 284 | CanAg CDR-I2 | RMSNLVS |
| 285 | CanAg CDR-I3 | LQHLEYPFT |
| 286 | CanAg VH | QVQLVQSGAEVKKPGETVKISCKASDYTFTYYGMNWVKQAPGQGLKWMGWIDTTTGEPTYAQKFQGRIAFSLETSASTAYLQIKSLKSEDTATYFCARRGPYNWYFDVWGQGTTVTVSS |
| 287 | CanAg VL | DIVMTQSPLSVPVTPGEPVSISCRSSKSLLHSNGNTYLYWFLQRPGQSPQLLIYRMSNLVSGVPDRFSGSGSGTAFTLRISRVEAEDVGVYYCLQHLEYPFTFGPGTKLELK |
| 288 | DLL-3 CDR-H1 | NYGMN |
| 289 | DLL-3 CDR-H2 | WINTYTGEPTYADDFKG |
| 290 | DLL-3 CDR-H3 | IGDSSPSDY |
| 291 | DLL-3 CDR-L1 | KASQSVSNDVV |
| 292 | DLL-3 CDR-L2 | YASNRYT |
| 293 | DLL-3 CDR-L3 | QQDYTSPWT |

-continued

Table of Sequences

| SEQ ID NO | Description | Sequence |
|---|---|---|
| 294 | DLL-3 VH | QVQLVQSGAEVKKPGASVKVSCKASGYTFTNYGMNWVRQAPGQGLEWMGWINTYTGEPTYADDFKGRVTMTTDTSTSTAYMELRSLRSDDTAVYYCARIGDSSPSDYWGQGTLVTVSS |
| 295 | DLL-3 VL | EIVMTQSPATLSVSPGERATLSCKASQSVSNDVVWYQQKPGQAPRLLIYYASNRYTGIPARFSGSGSGTEFTLTISSLQSEDFAVYYCQQDYTSPWTFGQGTKLEIK |
| 296 | DPEP-3 CDR-H1 | SYWIE |
| 297 | DPEP-3 CDR-H2 | EILPGSGNTYYNERFKD |
| 298 | DPEP-3 CDR-H3 | RAAAYYSNPEWFAY |
| 299 | DPEP-3 CDR-L1 | TASSSVNSFYLH |
| 300 | DPEP-3 CDR-L2 | STSNLAS |
| 301 | DPEP-3 CDR-L3 | HQYHRSPYT |
| 302 | DPEP-3 VH | QVQLVQSGAEVKKPGSSVKVSCKASGGTFSSYWIEWVRQAPGQGLEWMGEILPGSGNTYYNERFKDRVTITADESTSTAYMELSSLRSEDTAVYYCARRAAAYYSNPEWFAYWGQGTLVTVSS |
| 303 | DPEP-3 VL | EIVLTQSPATLSLSPGERATLSCTASSSVNSFYLHWYQQKPGLAPRLLIYSTSNLASGIPDRFSGSGSGTDFTLTISRLEPEDFAVYYCHQYHRSPYTFGQGTKLEIK |
| 304 | EGFR CDR-H1 | SYWMQ |
| 305 | EGFR CDR-H2 | TIYPGDGDTTYTQKFQG |
| 306 | EGFR CDR-H3 | YDAPGYAMDY |
| 307 | EGFR CDR-L1 | RASQDINNYLA |
| 308 | EGFR CDR-L2 | YTSTLHP |
| 309 | EGFR CDR-L3 | LQYDNLLYT |
| 310 | EGFR VH | QVQLVQSGAEVAKPGASVKLSCKASGYTFTSYWMQWVKQRPGQGLECIGTIYPGDGDTTYTQKFQGKATLTADKSSSTAYMQLSSLRSEDSAVYYCARYDAPGYAMDYWGQGTLVTVSS |
| 311 | EGFR VL | DIQMTQSPSSLSASVGDRVTITCRASQDINNYLAWYQHKPGKGPKLLIHYTSTLHPGIPSRFSGSGSGRDYSFSISSLEPEDIATYYCLQYDNLLYTFGQGTKLEIK |
| 312 | EGFR CDR-H1 | RDFAWN |
| 313 | EGFR CDR-H2 | YISYNGNTRYQPSLKS |
| 314 | EGFR CDR-H3 | ASRGFPY |
| 315 | EGFR CDR-L1 | HSSQDINSNIG |
| 316 | EGFR CDR-L2 | HGTNLDD |
| 317 | EGFR CDR-L3 | VQYAQFPWT |
| 318 | EGFR VH | EVQLQESGPGLVKPSQTLSLTCTVSGYSISRDFAWNWIRQPPGKGLEWMGYISYNGNTRYQPSLKSRITISRDTSKNQFFLKLNSVTAADTATYYCVTASRGFPYWGQGTLVTVSS |
| 319 | EGFR VL | DIQMTQSPSSMSVSVGDRVTITCHSSQDINSNIGWLQQKPGKSFKGLIYHGTNLDDGVPSRFSGSGSGTDYTLTISSLQPEDFATYYCVQYAQFPWTFGGGTKLEIK |
| 320 | EGFR CDR-H1 | RDFAWN |
| 321 | EGFR CDR-H2 | YISYNGNTRYQPSLKS |
| 322 | EGFR CDR-H3 | ASRGFPY |

-continued

Table of Sequences

| SEQ ID NO | Description | Sequence |
|---|---|---|
| 323 | EGFR CDR-L1 | HSSQDINSNIG |
| 324 | EGFR CDR-L2 | HGTNLDD |
| 325 | EGFR CDR-L3 | VQYAQFPWT |
| 326 | EGFR VH | EVQLQESGPGLVKPSQTLSLTCTVSGYSISRDFAWNWIRQPPGKGLEWMGYISYNGNTRY QPSLKSRITISRDTSKNQFFLKLNSVTAADTATYYCVTASRGFPYWGQGTLVTVSS |
| 327 | EGFR VL | DIQMTQSPSSMSVSVGDRVTITCHSSQDINSNIGWLQQKPGKSFKGLIYHGTNLDDGVPS RFSGSGSGTDYTLTISSLQPEDFATYYCVQYAQFPWTFGGGTKLEIK |
| 328 | EGFR CDR-H1 | NYGVH |
| 329 | EGFR CDR-H2 | VIWSGGNTDYNTPFTS |
| 330 | EGFR CDR-H3 | ALTYYDYEFAY |
| 331 | EGFR CDR-L1 | RASQSIGTNIH |
| 332 | EGFR CDR-L2 | YASESIS |
| 333 | EGFR CDR-L3 | QQNNNWPTT |
| 334 | EGFR VH | QVQLKQSGPGLVQPSQSLSITCTVSGFSLTNYGVHWVRQSPGKGLEWLGVIWSGGNTDYN TPFTSRLSINKDNSKSQVFFKMNSLQSNDTAIYYCARALTYYDYEFAYWGQGTLVTVSA |
| 335 | EGFR VL | DILLTQSPVILSVSPGERVSFSCRASQSIGTNIHWYQQRTNGSPRLLIKYASESISGIPS RFSGSGSGTDFTLSINSVESEDIADYYCQQNNNWPTTFGAGTKLELK |
| 336 | FRa CDR-H1 | GYFMN |
| 337 | FRa CDR-H2 | RIHPYDGDTFYNQKFQG |
| 338 | FRa CDR-H3 | YDGSRAMDY |
| 339 | FRa CDR-L1 | KASQSVSFAGTSLMH |
| 340 | FRa CDR-L2 | RASNLEA |
| 341 | FRa CDR-L3 | QQSREYPYT |
| 342 | FRa VH | QVQLVQSGAEVVKPGASVKISCKASGYTFTGYFMNWVKQSPGQSLEWIGRIHPYDGDTFY NQKFQGKATLTVDKSSNTAHMELLSLTSEDFAVYYCTRYDGSRAMDYWGQGTTVTVSS |
| 343 | FRa VL | DIVLTQSPLSLAVSLGQPAIISCKASQSVSFAGTSLMHWYHQKPGQQPRLLIYRASNLEA GVPDRFSGSGSKTDFTLTISPVEAEDAATYYCQQSREYPYTFGGGTKLEIK |
| 344 | FRa CDR-H1 | GYGLS |
| 345 | FRa CDR-H2 | MISSGGSYTYYADSVKG |
| 346 | FRa CDR-H3 | HGDDPAWFAY |
| 347 | FRa CDR-L1 | SVSSSISSNNLH |
| 348 | FRa CDR-L2 | GTSNLAS |
| 349 | FRa CDR-L3 | QQWSSYPYMYT |
| 350 | FRa VH | EVQLVESGGGVVQPGRSLRLSCSASGFTFSGYGLSWVRQAPGKGLEWVAMISSGGSYTYY ADSVKGRFAISRDNAKNTLFLQMDSLRPEDTGVYFCARHGDDPAWFAYWGQGTPVTVSS |
| 351 | FRa VL | DIQLTQSPSSLSASVGDRVTITCSVSSSISSNNLHWYQQKPGKAPKPWIYGTSNLASGVP SRFSGSGSGTDYTFTISSLQPEDIATYYCQQWSSYPYMYTFGQGTKVEIK |
| 352 | MUC-1 CDR-H1 | NYWMN |
| 353 | MUC-1 CDR-H2 | EIRLKSNNYTTHYAESVKG |
| 354 | MUC-1 CDR-H3 | HYYFDY |
| 355 | MUC-1 CDR-L1 | RSSKSLLHSNGITYFF |

Table of Sequences

| SEQ ID NO | Description | Sequence |
|---|---|---|
| 356 | MUC-1 CDR-L2 | QMSNLAS |
| 357 | MUC-1 CDR-L3 | AQNLELPPT |
| 358 | MUC-1 VH | EVQLVESGGGLVQPGGSMRLSCVASGFPFSNYWMNWVRQAPGKGLEWVGEIRLKSNNYTTHYAESVKGRFTISRDDSKNSLYLQMNSLKTEDTAVYYCTRHYYFDYWGQGTLVTVSS |
| 359 | MUC-1 VL | DIVMTQSPLSNPVTPGEPASISCRSSKSLLHSNGITYFFWYLQKPGQSPQLLIYQMSNLASGVPDRFSGSGSGTDFTLRISRVEAEDVGVYYCAQNLELPPTFGQGTKVEIK |
| 360 | Mesothelin CDR-H1 | SYWIG |
| 361 | Mesothelin CDR-H2 | IIDPGDSRTRYSPSFQG |
| 362 | Mesothelin CDR-H3 | GQLYGGTYMDG |
| 363 | Mesothelin CDR-L1 | TGTSSDIGGYNSVS |
| 364 | Mesothelin CDR-L2 | GVNNRPS |
| 365 | Mesothelin CDR-L3 | SSYDIESATPV |
| 366 | Mesothelin VH | QVELVQSGAEVKKPGESLKISCKGSGYSFTSYWIGWVRQAPGKGLEWMGIIDPGDSRTRYSPSFQGQVTISADKSISTAYLQWSSLKASDTAMYYCARGQLYGGTYMDGWGQGTLVTVSS |
| 367 | Mesothelin VL | DIALTQPASVSGSPGQSITISCTGTSSDIGGYNSVSWYQQHPGKAPKLMIYGVNNRPSGVSNRFSGSKSGNTASLTISGLQAEDEADYYCSSYDIESATPVFGGGTKLTVL |
| 368 | ROR-1 CDR-H1 | AYNIH |
| 369 | ROR-1 CDR-H2 | SFDPYDGGSSYNQKFKD |
| 370 | ROR-1 CDR-H3 | GWYYFDY |
| 371 | ROR-1 CDR-L1 | RASKSISKYLA |
| 372 | ROR-1 CDR-L2 | SGSTLQS |
| 373 | ROR-1 CDR-L3 | QQHDESPYT |
| 374 | ROR-1 VH | QVQLQESGPGLVKPSQTLSLTCTVSGYAFTAYNIHWVRQAPGQGLEWMGSFDPYDGGSSYNQKFKDRLTISKDTSKNQVVLTMTNMDPVDTATYYCARGWYYFDYWGHGTLVTVSS |
| 375 | ROR-1 VL | DIVMTQTPLSLPVTPGEPASISCRASKSISKYLAWYQQKPGQAPRLLIYSGSTLQSGIPPRFSGSGYGTDFTLTINNIESEDAAYYFCQQHDESPYTFGEGTKVEIK |
| 376 | B7H4 CDR-H1 | GSIKSGSYYWG |
| 377 | B7H4 CDR-H2 | NIYYSGSTYYNPSLRS |
| 378 | B7H4 CDR-H3 | AREGSYPNQFDP |
| 379 | B7H4 CDR-L1 | RASQSVSSNLA |
| 380 | B7H4 CDR-L2 | GASTRAT |
| 381 | B7H4 CDR-L3 | QQYHSFPFT |
| 382 | B7H4 VH | QLQLQESGPGLVKPSETLSLTCTVSGGSIKSGSYYWGWIRQPPGKGLEWIGNIYYSGSTYYNPSLRSRVTISVDTSKNQFSLKLSSVTAADTAVYYCAREGSYPNQFDPWGQGTLVTVSS |
| 383 | B7H4 VL | EIVMTQSPATLSVSPGERATLSCRASQSVSSNLAWYQQKPGQAPRLLIYGASTRATGIPARFSGSGSGTEFTLTISSLQSEDFAVYYCQQYHSFPFTFGGGTKVEIK |
| 384 | B7-H3 CDR-H1 | SFGMH |

-continued

Table of Sequences

| SEQ ID NO | Description | Sequence |
|---|---|---|
| 385 | B7-H3 CDR-H2 | YISSDSSAIYY |
| 386 | B7-H3 CDR-H3 | GRENIYYGSRLD |
| 387 | B7-H3 CDR-L1 | KASQNVD |
| 388 | B7-H3 CDR-L2 | SASYRYSGVPD |
| 389 | B7-H3 CDR-L3 | QQYNNYPFTFGS |
| 390 | B7-H3 VH | DVQLVESGGGLVQPGGSRKLSCAASGFTFSSFGMHWVRQAPEKGLEWVAYISSDSSAIYYADTVKGRFTISRDNPKNTLFLQMTSLRSEDTAMYYCGRGRENIYYGSRLDYWGQGTTLTVSS |
| 391 | B7-H3 VL | DIAMTQSQKFMSTSVGDRVSVTCKASQNVDTNVAWYQQKPGQSPKALIYSASYRYSGVPDRFTGSGSGTDFTLTINNVQSEDLAEYFCQQYNNYPFTFGSGTKLEIK |
| 392 | B7-H3 CDR-H1 | SYWMQWVRQA |
| 393 | B7-H3 CDR-H2 | TIYPGDGDTRY |
| 394 | B7-H3 CDR-H3 | RGIPRLWYFDVM |
| 395 | B7-H3 CDR-L1 | ITCRASQDIS |
| 396 | B7-H3 CDR-L2 | YTSRLHSGVPS |
| 397 | B7-H3 CDR-L3 | QQGNTLPPFTGG |
| 398 | B7-H3 VH | DVQLVESGGGLVQPGGSRKLSCAASGFTFSSFGMHWVRQAPEKGLEWVAYISSDSSAIYYADTVKGRFTISRDNPKNTLFLQMTSLRSEDTAMYYCGRGRENIYYGSRLDYWGQGTTLTVSS |
| 399 | B7-H3 VL | DIAMTQSQKFMSTSVGDRVSVTCKASQNVDTNVAWYQQKPGQSPKALIYSASYRYSGVPDRFTGSGSGTDFTLTINNVQSEDLAEYFCQQYNNYPFTFGSGTKLEIK |
| 400 | B7-H3 CDR-H1 | SYGMSWVRQA |
| 401 | B7-H3 CDR-H2 | INSGGSNTYY |
| 402 | B7-H3 CDR-H3 | HDGGAMDYW |
| 403 | B7-H3 CDR-L1 | ITCRASESIYSYLA |
| 404 | B7-H3 CDR-L2 | NTKTLPE |
| 405 | B7-H3 CDR-L3 | HHYGTPPWTFG |
| 406 | B7-H3 VH | EVQLVESGGGLVKPGGSLRLSCAASGFTFSSYGMSWVRQAPGKGLEWVATINSGGSNTYYPDSLKGRFTISRDNAKNSLYLQMNSLRAEDTAVYYCARHDGGAMDYWGQGTTVTVSS |
| 407 | B7-H3 VL | DIQMTQSPSSLSASVGDRVTITCRASESIYSYLAWYQQKPGKAPKLLVYNTKTLPEGVPSRFSGSGSGTDFTLTISSLQPEDFATYYCQHHYGTPPWTFGQGTRLEIK |
| 408 | B7-H3 CDR-H1 | SFGMHWVRQA |
| 409 | B7-H3 CDR-H2 | ISSGSGTIYYADTVKGRFTI |
| 410 | B7-H3 CDR-H3 | HGYRYEGFDYWG |
| 411 | B7-H3 CDR-L1 | ITCKASQNVDTNVA |
| 412 | B7-H3 CDR-L2 | SASYRYSGVPS |
| 413 | B7-H3 CDR-L3 | QQYNNYPFTFGQ |
| 414 | B7-H3 VH | EVQLVESGGGLVQPGGSLRLSCAASGFTFSSFGMHWVRQAPGKGLEWVAYISSGSGTIYYADTVKGRFTISRDNAKNSLYLQMNSLRAEDTAVYYCARHGYRYEGFDYWGQGTTVTVSS |
| 415 | B7-H3 VL | DIQMTQSPSFLSASVGDRVTITCKASQNVDTNVAWYQQKPGKAPKALIYSASYRYSGVPSRFSGSGSGTDFTLTISSLQPEDFAEYFCQQYNNYPFTFGQGTKLEIK |
| 416 | B7-H3 CDR-H1 | NYVMH |

Table of Sequences

| SEQ ID NO | Description | Sequence |
|---|---|---|
| 417 | B7-H3 CDR-H2 | YINPYNDDVKYNEKFKG |
| 418 | B7-H3 CDR-H3 | WGYYGSPLYYFDY |
| 419 | B7-H3 CDR-L1 | RASSRLIYMH |
| 420 | B7-H3 CDR-L2 | ATSNLAS |
| 421 | B7-H3 CDR-L3 | QQWNSNPPT |
| 422 | B7-H3 VH | EVQLQQSGPELVKPGASVKMSCKASGYTFTNYVMHWVKQPGQGLEWIGYINPYNDDVKYNEKFKGKATQTSDKSSSTAYMELSSLTSEDSAVYYCARWGYYGSPLYYFDYWGQGTTLTVSS |
| 423 | B7-H3 VL | QIVLSQSPTILSASPGEKVTMTCRASSRLIYMHWYQQKPGSSPKPWIYATSNLASGVPARFSGSGSGTSYSLTISRVEAEDAATYYCQQWNSNPPTFGTGTKLELK |
| 424 | B7-H3 CDR-H1 | NYVMH |
| 425 | B7-H3 CDR-H2 | YINPYNDDVKYNEKFKG |
| 426 | B7-H3 CDR-H3 | WGYYGSPLYYFDY |
| 427 | B7-H3 CDR-L1 | RASSRLIYMH |
| 428 | B7-H3 CDR-L2 | ATSNLAS |
| 429 | B7-H3 CDR-L3 | QQWNSNPPT |
| 430 | B7-H3 VH | QVQLVQSGAEVKKPGSSVKVSCKASGYTFTNYVMHWVRQAPGQGLEWMGYINPYNDDVKYNEKFKGRVTITADESTSTAYMELSSLRSEDTAVYYCARWGYYGSPLYYFDYWGQGTLVTVSS |
| 431 | B7-H3 VL | EIVLTQSPATLSLSPGERATLSCRASSRLIYMHWYQQKPGQAPRPLIYATSNLASGIPARFSGSGSGTDFTLTISSLEPEDFAVYYCQQWNSNPPTFGQGTKVEIK |
| 432 | B7-H3 CDR-H1 | GYSFTSYTIH |
| 433 | B7-H3 CDR-H2 | YINPNSRNTDYAQKFQG |
| 434 | B7-H3 CDR-H3 | YSGSTPYWYFDV |
| 435 | B7-H3 CDR-L1 | RASSSVSYMN |
| 436 | B7-H3 CDR-L2 | ATSNLAS |
| 437 | B7-H3 CDR-L3 | QQWSSNPLT |
| 438 | B7-H3 VH | EVQLVQSGAEVKKPGSSVKVSCKASGYSFTSYTIHWVRQAPGQGLEWMGYINPNSRNTDYAQKFQGRVTLTADKSTSTAYMELSSLRSEDTAVYYCARYSGSTPYWYFDVWGQGTTVTVSS |
| 439 | B7-H3 VL | DIQMTQSPSSLSASVGDRVTITCKASQNVGFNVAWYQQKPGKSPKALIYSASYRYSGVPSRFSGSGSGTDFTLTISSLQPEDFAEYFCQQYNWYPFTFGQGTKLEIK |
| 440 | B7-H3 CDR-H1 | GYTFSSYWMH |
| 441 | B7-H3 CDR-H2 | LIHPDSGSTNYNEMFKN |
| 442 | B7-H3 CDR-H3 | GGRLYFD |
| 443 | B7-H3 CDR-L1 | RSSQSLVHSNGDTYLR |
| 444 | B7-H3 CDR-L2 | KVSNRFS |
| 445 | B7-H3 CDR-L3 | SQSTHVPYT |
| 446 | B7-H3 VH | EVQLVQSGAEVKKPGSSVKVSCKASGYTFSSYWMHWVRQAPGQGLEWIGLIHPDSGSTNYNEMFKNRATLTVDRSTSTAYVELSSLRSEDTAVYFCAGGGRLYFDYWGQGTTVTVSS |
| 447 | B7-H3 VL | DVVMTQSPLSLPVTPGEPASISCRSSQSLVHSNGDTYLRWYLQKPGQSPQLLIYKVSNRFSGVPDRFSGSGSGTDFTLKISRVEAEDVGVYYCSQSTHVPYTFGGGTKVEIK |

Table of Sequences

| SEQ ID NO | Description | Sequence |
|---|---|---|
| 448 | B7-H3 CDR-H1 | GYTFSSYWMH |
| 449 | B7-H3 CDR-H2 | LIHPESGSTNYNEMFKN |
| 450 | B7-H3 CDR-H3 | GGRLYFDY |
| 451 | B7-H3 CDR-L1 | RSSQSLVHSNQDTYLR |
| 452 | B7-H3 CDR-L2 | KVSNRFS |
| 453 | B7-H3 CDR-L3 | SQSTHVPYT |
| 454 | B7-H3 VH | EVQLVQSGAEVKKPGSSVKVSCKASGYTFSSYWMHWVRQAPGQGLEWIGLIHPESGSTNYNEMFKNRATLTVDRSTSTAYMELSSLRSEDTAVYYCAGGGRLYFDYWGQGTTVTVSS |
| 455 | B7-H3 VL | DIVMTQSPLSLPVTPGEPASISCRSSQSLVHSNQDTYLRWYLQKPGQSPQLLIYKVSNRFSGVPDRFSGSGSGTDFTLKKISRVEAEDVGVYYCSQSTHVPYTFGGGTKVEIK |
| 456 | B7-H3 CDR-H1 | TGYSITSGYSWH |
| 457 | B7-H3 CDR-H2 | YIHSSGSTNYNPSLKS |
| 458 | B7-H3 CDR-H3 | YDDYFEY |
| 459 | B7-H3 CDR-L1 | KASQNVGFNVAW |
| 460 | B7-H3 CDR-L2 | SASYRYS |
| 461 | B7-H3 CDR-L3 | QQYNWYPFT |
| 462 | B7-H3 VH | EVQLQESGPGLVKPSETLSLTCAVTGYSITSGYSWHWIRQFPGNGLEWMGYIHSSGSTNYNPSLKSRISISRDTSKNQFFLKLSSVTAADTAVYYCAGYDDYFEYWGQGTTVTVSS |
| 463 | B7-H3 VL | DIQMTQSPSSLSASVGDRVTITCKASQNVGGFNVAWYQQKPGKSPKALIYSASYRYSGVPSRFSGSGSGTDFTLTISSLQPEDFAEYFCQQYNWYPFTFGQGTKLEIK |
| 464 | B7-H3 CDR-H1 | NYDIN |
| 465 | B7-H3 CDR-H2 | WIGWIFPGDDSTQYNEKFKG |
| 466 | B7-H3 CDR-H3 | QTTGTWFAY |
| 467 | B7-H3 CDR-L1 | RASQSISDYLY |
| 468 | B7-H3 CDR-L2 | YASQSIS |
| 469 | B7-H3 CDR-L3 | CQNGHSFPL |
| 470 | B7-H3 VH | QVQLVQSGAEVVKPGASVKLSCKTSGYTFTNYDINWVRQRPGQGLEWIGWIFPGDDSTQYNEKFKGKATLTTDTSTSTAYMELSSLRSEDTAVYFCARQTTGTWFAYWGQGTLVTVSS |
| 471 | B7-H3 VL | EIVMTQSPATLSVSPGERVTLSCRASQSISDYLYWYQQKSHESPRLLIKYASQSISGIPARFSGSGSGSEFTLTINSVEPEDVGVYYCQNGHSFPLTFGQGTKLELK |
| 472 | B7-H3 VH | QVQLQQSGAEVKKPGSSVKVSCKASGGTFSSYAISWVRQAPGQGLEWMGGIIPILGIANYAQKFQGRVTITADESTSTAYMELSSLRSEDTAVYYCARGGSGSYHMDVWGKGTTVTVSS |
| 473 | B7-H3 VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPPRITFGQGTRLEIK |
| 474 | B7-H3 CDR-H1 | IYNVH |
| 475 | B7-H3 CDR-H2 | TIFPGNGDTSYNQKFKD |
| 476 | B7-H3 CDR-H3 | WDDGNVGFAH |
| 477 | B7-H3 CDR-L1 | RASENINNYLT |
| 478 | B7-H3 CDR-L2 | HAKTLAE |
| 479 | B7-H3 CDR-L3 | QHHYGTPPT |

Table of Sequences

| SEQ ID NO | Description | Sequence |
|---|---|---|
| 480 | B7-H3 VH | QVQLQQPGAELVKPGASVKMSCKASGYTFTIYNVHWIKQTPGQGLEWMGTIFPGNGDTSY<br>NQKFKDKATLTTDKSSKTAYMQLNSLTSEDSAVYYCARWDDGNVGFAHWGQGTLVTVSA |
| 481 | B7-H3 VL | DIQMTQSPASLSASVGETVTITCRASENINNYLTWFQQKQGKSPQLLVYHAKTLAEGVPS<br>RFSGSGSGTQFSLKINSLQPEDFGSYYCQHHYGTPPTFGGGTKLEIK |
| 482 | B7-H3 VH | EVQLVQSGAEVKKPGASVKVSCKASGYTFTIYNVHWVRQAPGQGLEWMGTIFPGNGDTS<br>YNQKFKDKVTMTTDTSTSTAYMELSSLRSEDTAVYYCARWDDGNVGFAHWGQGTLVTVSS |
| 483 | B7-H3 VL | DIQMTQSPSSLSASVGDRVTITCRASENINNYLTWFQQKQGKSPQLLIYHAKTLAEGVP<br>SRFSGSGSGTDFTLTISSLQPEDFATYYCQHHYGTPPTFGGGTKVEIK |
| 484 | B7-H3 VH | EVQLVQSGAEVKKPGASVKVSCKASGYTFTIYNVHWIRQAPGQGLEWMGTIFPGNGDTSY<br>NQKFKDRATLTTDKSTKTAYMELRSLRSDDTAVYYCARWDDGNVGFAHWGQGTLVTVSS |
| 485 | B7-H3 VL | DIQMTQSPSSLSASVGDRVTITCRASENINNYLTWFQQKPGKAPKLLVYHAKTLAEGVPS<br>RFSGSGSGTQFTLTISSLQPEDFATYYCQHHYGTPPTFGQGTKLEIK |
| 486 | HER3 H | QVQLQQWGAGLLKPSETLSLTCAVYGGSFSGYYWSWIRQPPGKGLEWIGEINHSGSTNYN<br>PSLKSRVTISVETSKNQFSLKLSSVTAADTAVYYCARDKWTWYFDLWGRGTLVTVSSAST<br>KGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKRVEPKSCDKTHTCPPCPAPELLGGPS<br>VFLFPPKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPSREEMT<br>KNQVSLTCLVKGFYPSDIAVEWESNGQPENNYKTTPPVLDSDGSFFLYSKLTVDKSRWQQ<br>GNVFSCSVMHEALHNHYTQKSLSLSPGK |
| 487 | HER3 L | DIEMTQSPDSLAVSLGERATINCRSSQSVLYSSSNRNYLAWYQQNPGQPPKLLIYWASTR<br>ESGVPDRFSGSGSGTDFTLTISSLQAEDVAVYYCQQYYSTPRTFGQGTKVEIKRTVAAPS<br>VFIFPPSDEQLKSGTASVVCLLNNFYPREAKVQWKVDNALQSGNSQESVTEQDSKDSTYS<br>LSSTLTLSKADYEKHKVYACEVTHQGLSSPVTKSFNRGEC |
| 488 | HER3 H | EVQLLESGGGLVQPGGSLRLSCAASGFTFSHYVMAWVRQAPGKGLEWVSSISSSGGWTLY<br>ADSVKGRFTISRDNSKNTLYLQMNSLRAEDTAVYYCTRGLKMATIFDYWGQGTLVTVSSA<br>STKGPSVFPLAPCSRSTSESTAALGCLVKDYFPEPVTVSWNSGALTSGVHTFPAVLQSSG<br>LYSLSSVVTVPSSNFGTQTYTCNVDHKPSNTKVDKTVERKCCVECPPCPAPPVAGPSVFL<br>FPPKPKDTLMISRTPEVTCVVVDVSHEDPEVQFNWYVDGVEVHNAKTKPREEQFNSTFRV<br>VSVLTVVHQDWLNGKEYKCKVSNKGLPAPIEKTISKTKGQPREPQVYTLPPSREEMTKNQ<br>VSLTCLVKGFYPSDIAVEWESNGQPENNYKTTPPMLDSDGSFFLYSKLTVDKSRWQQGNV<br>FSCSVMHEALHNHYTQKSLSLSPGK |
| 489 | HER3 L | QSALTQPASVSGSPGQSITISCTGTSSDVGSYNVVSWYQQHPGKAPKLIIYEVSQRPSGV<br>SNRFSGSKSGNTASLTISGLQTEDEADYYCCSYAGSSIFVIFGGGTKVTVLGQPKAAPSV<br>TLFPPSSEELQANKATLVCLVSDFYPGAVTVAWKADGSPVKVGVETTKPSKQSNNKYAAS<br>SYLSLTPEQWKSHRSYSCRVTHEGSTVEKTVAPAECS |
| 490 | HER3 H | EVQLLESGGGLVQPGGSLRLSCAASGFTFSSYAMSWVRQAPGKGLEWVSAINSQGKSTYY<br>ADSVKGRFTISRDNSKNTLYLQMNSLRAEDTAVYYCARWGDEGFDIWGQGTLVTVSSAST<br>KGPSVFPLAPSSKSTSGGTAALGCLVKDYFPEPVTVSWNSGALTSGVHTFPAVLQSSGGY<br>SLSSVVTVPSSSLGTQTYICNVNHKPSNTKVDKRVEPKSCDKTHTCPPCPAPELLGGPSV<br>FLFPPKPKDTLMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYTLPPSREEMTK<br>NQVSLTCLVKGFYPSDIAVEWESNGQPENNYKTTPPVLDSDGSFFLYSKLTVDKSRWQQG<br>NVFSCSVMHEALHNHYTQKSLSLSPGK |
| 491 | HER3 L | DIQMTQSPSSLSASVGDRVTITCRASQGISNWLAWYQQKPGKAPKLLIYGASSLQSGVPS<br>RFSGSGSGTDFTLTISSLQPEDFATYYCQQYSSFPTTFGQGTKVEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| 492 | HER3 H | QVQLVQSGAEVKKPGASVKVSCKASGYTFRSSYISWVRQAPGQGLEWMGWIYAGTGSPSY<br>NQKLQGRVTMTTDTSTSTAYMELRSLRSDDTAVYYCARHRDYYSNSLTYWGQGTLVTVSS<br>ASTKGPSVFPLAPSSKSTSGGTAALGCLVKDYFPEPVTVSWNSGALTSGVHTFPAVLQSS<br>GLYSLSSVVTVPSSSLGTQTYICNVNHKPSNTKVDKKVEPKSCDKTHTCPPCPAPELLGG<br>PSVFLFPPKPKDTLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREPQVYTLPPSRDE<br>LTKNQVSLTCLVKGFYPSDIAVEWESNGQPENNYKTTPPVLDSDGSFFLYSKLTVDKSRW<br>QQGNVFSCSVMHEALHNHYTQKSLSLSPG |
| 493 | HER3 L | DIVMTQSPDSLAVSLGERATINCKSSQSVLNSGNQKNYLTWYQQKPGQPPKLLIYWASTR<br>ESGVPDRFSGSGSGTDFTLTISSLQAEDVAVYYCQSDYSYPYTFGQGTKLEIKRTVAAPS<br>VFIFPPSDEQLKSGTASVVCLLNNFYPREAKVQWKVDNALQSGNSQESVTEQDSKDSTYS<br>LSSTLTLSKADYEKHKVYACEVTHQGLSSPVTKSFNRGEC |

Table of Sequences

| SEQ ID NO | Description | Sequence |
|---|---|---|
| 494 | PTK7 CDR-H1 | TSNMGVG |
| 495 | PTK7 CDR-H2 | HIWWDDDKYYSPSLKS |
| 496 | PTK7 CDR-H3 | SNYGYAWFAY |
| 497 | PTK7 CDR-L1 | KASQDIYPYLN |
| 498 | PTK7 CDR-L2 | RTNRLLD |
| 499 | PTK7 CDR-L3 | LQYDEFPLT |
| 500 | PTK7 VH | QITLKESGPTLVKPTQTLTLTCTFSGFSLSTSNMGVGWIRQPPGKALEWLAHIWWDDDKYYSPSLKSRLTITKDTSKNQVVLTMTNMDPVDTATYYCVRSNYGYAWFAYWGQGTLVTVSS |
| 501 | PTK7 VL | DIQMTQSPSSLSASVGDRVTITCKASQDIYPYLNWFQQKPGKAPKTLIYRTNRLLDGVPSRFSGSGSGTDFTFTISSLQPEDIATYYCLQYDEFPLTFGAGTKLEIK |
| 502 | PTK7 CDR-H1 | DYAVH |
| 503 | PTK7 CDR-H2 | VISTYNDYTYNNQDFKG |
| 504 | PTK7 CDR-H3 | GNSYFYALDY |
| 505 | PTK7 CDR-L1 | RASESVDSYGKSFMH |
| 506 | PTK7 CDR-L2 | RASNLES |
| 507 | PTK7 CDR-L3 | QQSNEDPWT |
| 508 | PTK7 VH | QVQLVQSGPEVKKPGASVKVSCKASGYTFTDYAVHWVRQAPGKRLEWIGVISTYNDYTYNNQDFKGRVTMTRDTSASTAYMELSRLRSEDTAVYYCARGNSYFYALDYWGQGTSVTVSS |
| 509 | PTK7 VL | EIVLTQSPATLSLSPGERATLSCRASESVDSYGKSFMHWYQQKPGQAPRLLIYRASNLESGIPARFSGSGSGTDFTLTISSLEPEDFAVYYCQQSNEDPWTFGGGTKLEIK |
| 510 | PTK7 CDR-H1 | RYWMS |
| 511 | PTK7 CDR-H2 | DLNPDSSAINYVDSVKG |
| 512 | PTK7 CDR-H3 | ITTLVPYTMDF |
| 513 | PTK7 CDR-L1 | ITNTDIDDDMN |
| 514 | PTK7 CDR-L2 | EGNGLRP |
| 515 | PTK7 CDR-L3 | LQSDNLPLT |
| 516 | PTK7 VH | EVQLVESGGGLVQPGGSLRLSCAASGFDFSRYWMSWVRQAPGKGLEWIGDLNPDSSAINYVDSVKGRFTISRDNAKNSLYLQMNSLRAEDTAVYYCTLITTLVPYTMDFWGQGTSVTVSS |
| 517 | PTK7 VL | ETTLTQSPAFMSATPGDKVNISCITNTDIDDDMNWYQQKPGEAAILLISEGNGLRPGIPPRFSGSGYGTDFTLTINNIESEDAAYYFCLQSDNLPLTFGSGTKLEIK |
| 518 | LIV1 CDR-H1 | DYYMH |
| 519 | LIV1 CDR-H2 | WIDPENGDTEYGPKFQG |
| 520 | LIV1 CDR-H3 | HNAHYGTWFAY |
| 521 | LIV1 CDR-L1 | RSSQSLLHSSGNTYLE |
| 522 | LIV1 CDR-L2 | KISTRFS |
| 523 | LIV1 CDR-L3 | FQGSHVPYT |
| 524 | LIV1 VH | QVQLVQSGAEVKKPGASVKVSCKASGLTIEDYYMHWVRQAPGQGLEWMGWIDPENGDTEYGPKFQGRVTMTRDTSINTAYMELSRLRSDDTAVYYCAVHNAHYGTWFAYWGQGTLVTVSS |
| 525 | LIV1 VL | DVVMTQSPLSLPVTLGQPASISCRSSQSLLHSSGNTYLEWYQQRPGQSPRPLIYKISTRFSGVPDRFSGSGSGTDFTLKISRVEAEDVGVYYCFQGSHVPYTFGGGTKVEIK |

Table of Sequences

| SEQ ID NO | Description | Sequence |
|---|---|---|
| 526 | avb6 CDR-H1 | DYNVN |
| 527 | avb6 CDR-H2 | VINPKYGTTRYNQKFKG |
| 528 | avb6 CDR-H3 | GLNAWDY |
| 529 | avb6 CDR-L1 | GASENIYGALN |
| 530 | avb6 CDR-L2 | GATNLED |
| 531 | avb6 CDR-L3 | QNVLTTPYT |
| 532 | avb6 VH | QFQLVQSGAEVKKPGASVKVSCKASGYSFTDYNVNWVRQAPGQGLEWIGVINPKYGTTRYNQKFKGRATLTVDKSTSTAYMELSSLRSEDTAVYYCTRGLNAWDYWGQGTLVTVSS |
| 533 | avb6 VL | DIQMTQSPSSLSASVGDRVTITCGASENIYGALNWYQQKPGKAPKLLIYGATNLEDGVPSRFSGSGSGRDYTFTISSLQPEDIATYYCQNVLTTPYTFGQGTKLEIK |
| 534 | avb6 CDR-H1 | GYFMN |
| 535 | avb6 CDR-H2 | LINPYNGDSFYNQKFKG |
| 536 | avb6 CDR-H3 | GLRRDFDY |
| 537 | avb6 CDR-L1 | KSSQSLLDSDGKTYLN |
| 538 | avb6 CDR-L2 | LVSELDS |
| 539 | avb6 CDR-L3 | WQGTHFPRT |
| 540 | avb6 VH | QVQLVQSGAEVKKPGASVKVSCKASGYSFSGYFMNWVRQAPGQGLEWMGLINPYNGDSFYNQKFKGRVTMTRQTSTSTVYMELSSLRSEDTAVYYCVRGLRRDFDYWGQGTLVTVSS |
| 541 | avb6 VL | DVVMTQSPLSLPVTLGQPASISCKSSQSLLDSDGKTYLNWLFQRPGQSPRRLIYLVSELDSGVPDRFSGSGSGTDFTLKISRVEAEDVGVYYCWQGTHFPRTFGGGTKLEIK |
| 542 | CD48 CDR-H1 | DFGMN |
| 543 | CD48 CDR-H2 | WINTFTGEPSYGNVFKG |
| 544 | CD48 CDR-H3 | RHGNGNVFDS |
| 545 | CD48 CDR-L1 | RASQSIGSNIH |
| 546 | CD48 CDR-L2 | YTSESIS |
| 547 | CD48 CDR-L3 | QQSNSWPLT |
| 548 | CD48 VH | QVQLVQSGSELKKPGASVKVSCKASGYTFTDFGMNWVRQAPGQGLEWMGWINTFTGEPSYGNVFKGRFVFSLDTSVSTAYLQISSLKAEDTAVYYCARRHGNGNVFDSWGQGTLVTVSS |
| 549 | CD48 VL | EIVLTQSPDFQSVTPKEKVTITCRASQSIGSNIHWYQQKPDQSPKLLIKYTSESISGVPSRFSGSGSGTDFTLTINSLEAEDAATYYCQQSNSWPLTFGGGTKVEIKR |
| 550 | PD-L1 CDR-H1 | TAAIS |
| 551 | PD-L1 CDR-H2 | GIIPIFGKAHYAQKFQG |
| 552 | PD-L1 CDR-H3 | KFHFVSGSPFGMDV |
| 553 | PD-L1 CDR-L1 | RASQSVSSYLA |
| 554 | PD-L1 CDR-L2 | DASNRAT |
| 555 | PD-L1 CDR-L3 | QQRSNWPT |
| 556 | PD-L1 VH | QVQLVQSGAEVKKPGSSVKVSCKTSGDTFSTAAISWVRQAPGQGLEWMGGIIPIFGKAHYAQKFQGRVTITADESTSTAYMELSSLRSEDTAVYFCARKFHFVSGSPFGMDVWGQGTTVTVSS |
| 557 | PD-L1 VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK |

Table of Sequences

| SEQ ID NO | Description | Sequence |
|---|---|---|
| 558 | IGF-1R CDR-H1 | SYAIS |
| 559 | IGF-1R CDR-H2 | GIIPIFGTANYAQKFQG |
| 560 | IGF-1R CDR-H3 | APLRFLEWSTQDHYYYYMDV |
| 561 | IGF-1R CDR-L1 | QGDSLRSYYAT |
| 562 | IGF-1R CDR-L2 | GENKRPS |
| 563 | IGF-1R CDR-L3 | KSRDGSGQHLV |
| 564 | IGF-1R VH | EVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARAPLRFLEWSTQDHYYYYMDVWGKGTTVTVSS |
| 565 | IGF-1R VL | SSELTQDPAVSVALGQTVRITCQGDSLRSYYATWYQQKPGQAPILVIYGENKRPSGIPDRFSGSSSGNTASLTITGAQAEDEADYYCKSRDGSGQHLVFGGGTKLTVL |
| 566 | Claudin-18.2 CDR-H1 | SYWIN |
| 567 | Claudin-18.2 CDR-H2 | NIYPSDSYTNYNQKFKD |
| 568 | Claudin-18.2 CDR-H3 | SWRGNSFDY |
| 569 | Claudin-18.2 CDR-L1 | KSSQSLLNSGNQKNYLT |
| 570 | Claudin-18.2 CDR-L2 | WASTRES |
| 571 | Claudin-18.2 CDR-L3 | QNDYSYPFT |
| 572 | Claudin-18.2 VH | QVQLQQPGAELVRPGASVKLSCKASGYTFTSYWINWVKQRPGQGLEWIGNIYPSDSYTNYNQKFKDKATLTVDKSSSTAYMQLSSPTSEDSAVYYCTRSWRGNSFDYWGQGTTLTVSS |
| 573 | Claudin-18.2 VL | DIVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPFTFGSGTKLEIK |
| 574 | Claudin-18.2 CDR-H1 | NYGMN |
| 575 | Claudin-18.2 CDR-H2 | WINTNTGEPTYAEEFKG |
| 576 | Claudin-18.2 CDR-H3 | LGFGNAMDY |
| 577 | Claudin-18.2 CDR-L1 | KSSQSLLNSGNQKNYLT |
| 578 | Claudin-18.2 CDR-L2 | WASTRES |
| 579 | Claudin-18.2 CDR-L3 | QNDYSYPLT |
| 580 | Claudin-18.2 VH | QIQLVQSGPELKKPGETVKISCKASGYTFTNYGMNWVKQAPGKGLKWMGWINTNTGEPTYAEEFKGRFAFSLETSASTAYLQINNLKNEDTATYFCARLGFGNAMDYWGQGTSVTVSS |
| 581 | Claudin-18.2 VL | DIVMTQSPSSLTVTAGEKVTMSCKSSQSLLNSGNQKNYLTWYQQKPGQPPKLLIYWASTRESGVPDRFTGSGSGTDFTLTISSVQAEDLAVYYCQNDYSYPLTFGAGTKLELK |

| SEQ ID NO | Description | Sequence |
|---|---|---|
| 582 | Nectin-4 CDR-H1 | SYNMN |
| 583 | Nectin-4 CDR-H2 | YISSSSSTIYYADSVKG |
| 584 | Nectin-4 CDR-H3 | AYYYGMDV |
| 585 | Nectin-4 CDR-L1 | RASQGISGWLA |
| 586 | Nectin-4 CDR-L2 | AASTLQS |
| 587 | Nectin-4 CDR-L3 | QQANSFPPT |
| 588 | Nectin-4 VH | EVQLVESGGGLVQPGGSLRLSCAASGFTFSSYNMNWVRQAPGKGLEWVSYISSSSSTIYYADSVKGRFTISRDNAKNSLSLQMNSLRDEDTAVYYCARAYYYGMDVWGQGTTVTVSS |
| 589 | Nectin-4 VL | DIQMTQSPSSVSASVGDRVTITCRASQGISGWLAWYQQKPGKAPKFLIYAASTLQSGVPSRFSGSGSGTDFTLTISSLQPEDFATYYCQQANSFPPTFGGGTKVEIK |
| 590 | SLTRK6 CDR-H1 | SYGMH |
| 591 | SLTRK6 CDR-H2 | VIWYDGSNQYYADSVKG |
| 592 | SLTRK6 CDR-H3 | GLTSGRYGMDV |
| 593 | SLTRK6 CDR-L1 | RSSQSLLLSHGFNYLD |
| 594 | SLTRK6 CDR-L2 | LGSSRAS |
| 595 | SLTRK6 CDR-L3 | MQPLQIPWT |
| 596 | SLTRK6 VH | QVQLVESGGGVVQPGRSLRLSCAASGFTFSSYGMHWVRQAPGKGLEWVAVIWYDGSNQYYADSVKGRFTISRDNSKNTLFLQMHSLRAEDTAVYYCARGLTSGRYGMDVWGQGTTVTVSS |
| 597 | SLTRK6 VL | DIVMTQSPLSLPVTPGEPASISCRSSQSLLLSHGFNYLDWYLQKPGQSPQLLIYLGSSRASGVPDRFSGSGSGTDFTLKISRVEAEDVGLYYCMQPLQIPWTFGQGTKVEIK |
| 598 | CD228 CDR-H1 | SGYWN |
| 599 | CD228 CDR-H2 | YISDSGITYYNPSLKS |
| 600 | CD228 CDR-H3 | RTLATYYAMDY |
| 601 | CD228 CDR-L1 | RASQSLVHSDGNTYLH |
| 602 | CD228 CDR-L2 | RVSNRFS |
| 603 | CD228 CDR-L3 | SQSTHVPPT |
| 604 | CD228 VH | QVQLQESGPGLVKPSETLSLTCTVSGDSITSGYWNWIRQPPGKGLEYIGYISDSGITYYNPSLKSRVTISRDTSKNQYSLKLSSVTAADTAVYYCARRTLATYYAMDYWGQGTLVTVSS |
| 605 | CD228 VL | DFVMTQSPLSLPVTLGQPASISCRASQSLVHSDGNTYLHWYQQRPGQSPRLLIYRVSNRFSGVPDRFSGSGSGTDFTLKISRVEAEDVGVYYCSQSTHVPPTFGQGTKLEIKR |
| 606 | CD142 (TF) CDR-H1 | NYAMS |
| 607 | CD142 (TF) CDR-H2 | SISGSGDYTYYTDSVKG |

Table of Sequences

| SEQ ID NO | Description | Sequence |
|---|---|---|
| 608 | CD142 (TF) CDR-H3 | SPWGYYLDS |
| 609 | CD142 (TF) CDR-L1 | RASQGISSRLA |
| 610 | CD142 (TF) CDR-L2 | AASSLQS |
| 611 | CD142 (TF) CDR-L3 | QQYNSYPYT |
| 612 | CD142 (TF) VH | EVQLLESGGGLVQPGGSLRLSCAASGFTFSNYAMSWVRQAPGKGLEWVSSISGSGDYTYYTDSVKGRFTISRDNSKNTLYLQMNSLRAEDTAVYYCARSPWGYYLDSWGQGTLVTVSS |
| 613 | CD142 (TF) VL | DIQMTQSPPSLSASAGDRVTITCRASQGISSRLAWYQQKPEKAPKSLIYAASSLQSGVPSRFSGSGSGTDFTLTISSLQPEDFATYYCQQYNSYPYTFGQGTKLEIK |
| 614 | STn CDR-H1 | DHAIH |
| 615 | STn CDR-H2 | YFSPGNDDIKYNEKFRG |
| 616 | STn CDR-H3 | SLSTPY |
| 617 | STn CDR-L1 | KSSQSLLNRGNHKNYLT |
| 618 | STn CDR-L2 | WASTRES |
| 619 | STn CDR-L3 | QNDYTYPYT |
| 620 | STn VH | EVQLVQSGAEVKKPGASVKVSCKASGYTFTDHAIHWVRQAPGQGLEWMGYFSPGNDDIKYNEKFRGRVTMTADKSSSTAYMELRSLRSDDTAVYFCKRSLSTPYWGQGTLVTVSS |
| 621 | STn VL | DIVMTQSPDSLAVSLGERATINCKSSQSLLNRGNHKNYLTWYQQKPGQPPKLLIYWASTRESGVPDRFSGSGSGTDFTLTISSLQAEDVAVYYCQNDYTYPYTFGQGTKVEIK |
| 622 | CD20 CDR-H1 | SYNMH |
| 623 | CD20 CDR-H2 | AIYPGNGDTSYNQKFKG |
| 624 | CD20 CDR-H3 | STYYGGDWYFNV |
| 625 | CD20 CDR-L1 | RASSSVSYIH |
| 626 | CD20 CDR-L2 | ATSNLAS |
| 627 | CD20 CDR-L3 | QQWTSNPPT |
| 628 | CD20 VH | QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSA |
| 629 | CD20 VL | QIVLSQSPAILSASPGEKVTMTCRASSSVSYIHWFQQKPGSSPKPWIYATSNLASGVPVRFSGSGSGTSYSLTISRVEAEDAATYYCQQWTSNPPTFGGGTKLEIK |
| 630 | HER2 CDR-H1 | DTYIH |
| 631 | HER2 CDR-H2 | RIYPTNGYTRYADSVKG |
| 632 | HER2 CDR-H3 | WGGDGFYAMDY |
| 633 | HER2 CDR-L1 | RASQDVNTAVA |
| 634 | HER2 CDR-L2 | SASFLYS |
| 635 | HER2 CDR-L3 | QQHYTTPPT |
| 636 | HER2 VH | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS |
| 637 | HER2 VL | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIK |

Table of Sequences

| SEQ ID NO | Description | Sequence |
|---|---|---|
| 638 | CD79b CDR-H1 | SYWIE |
| 639 | CD79b CDR-H2 | EILPGGGDTNYNEIFKG |
| 640 | CD79b CDR-H3 | RVPIRLDY |
| 641 | CD79b CDR-L1 | KASQSVDYEGDSFLN |
| 642 | CD79b CDR-L2 | AASNLES |
| 643 | CD79b CDR-L3 | QQSNEDPLT |
| 644 | CD79b VH | EVQLVESGGGLVQPGGSLRLSCAASGYTFSSYWIEWVRQAPGKGLEWIGEILPGGGDTNYNEIFKGRATFSADTSKNTAYLQMNSLRAEDTAVYYCTRRVPIRLDYWGQGTLVTVSS |
| 645 | CD79b VL | DIQLTQSPSSLSASVGDRVTITCKASQSVDYEGDSFLNWYQQKPGKAPKLLIYAASNLESGVPSRFSGSGSGTDFTLTISSLQPEDFATYYCQQSNEDPLTFGQGTKVEIK |
| 646 | NaPi2B CDR-H1 | DFAMS |
| 647 | NaPi2B CDR-H2 | TIGRVAFHTYYPDSMKG |
| 648 | NaPi2B CDR-H3 | HRGFDVGHFDF |
| 649 | NaPi2B CDR-L1 | RSSETLVHSSGNTYLE |
| 650 | NaPi2B CDR-L2 | RVSNRFS |
| 651 | NaPi2B CDR-L3 | FQGSFNPLT |
| 652 | NaPi2B VH | EVQLVESGGGLVQPGGSLRLSCAASGFSFSDFAMSWVRQAPGKGLEWVATIGRVAFHTYYPDSMKGRFTISRDNSKNTLYLQMNSLRAEDTAVYYCARHRGFDVGHFDFWGQGTLVTVSS |
| 653 | NaPi2B VL | DIQMTQSPSSLSASVGDRVTITCRSSETLVHSSGNTYLEWYQQKPGKAPKLLIYRVSNRFSGVPSRFSGSGSGTDFTLTISSLQPEDFATYYCFQGSFNPLTFGQGTKVEIK |
| 654 | Muc16 CDR-H1 | NDYAWN |
| 655 | Muc16 CDR-H2 | YISYSGYTTYNPSLKS |
| 656 | Muc16 CDR-H3 | WTSGLDY |
| 657 | Muc16 CDR-L1 | KASDLIHNWLA |
| 658 | Muc16 CDR-L2 | GATSLET |
| 659 | Muc16 CDR-L3 | QQYWTTPFT |
| 660 | Muc16 VH | EVQLVESGGGLVQPGGSLRLSCAASGYSITNDYAWNWVRQAPGKGLEWVGYISYSGYTTYNPSLKSRFTISRDTSKNTLYLQMNSLRAEDTAVYYCARWTSGLDYWGQGTLVTVSS |
| 661 | Muc16 VL | DIQMTQSPSSLSASVGDRVTITCKASDLIHNWLAWYQQKPGKAPKLLIYGATSLETGVPSRFSGSGSGTDFTLTISSLQPEDFATYYCQQYWTTPFTFGQGTKVEIK |
| 662 | STEAP1 CDR-H1 | SDYAWN |
| 663 | STEAP1 CDR-H2 | YISNSGSTSYNPSLKS |
| 664 | STEAP1 CDR-H3 | ERNYDYDDYYYAMDY |
| 665 | STEAP1 CDR-L1 | KSSQSLLYRSNQKNYLA |

-continued

Table of Sequences

| SEQ ID NO | Description | Sequence |
|---|---|---|
| 666 | STEAP1 CDR-L2 | WASTRES |
| 667 | STEAP1 CDR-L3 | QQYYNYPRT |
| 668 | STEAP1 VH | EVQLVESGGGLVQPGGSLRLSCAVSGYSITSDYAWNWVRQAPGKGLEWVGYISNSGSTSYNPSLKSRFTISRDTSKNTLYLQMNSLRAEDTAVYYCARERNYDYDDYYYAMDYWGQGTLVTVSS |
| 669 | STEAP1 VL | DIQMTQSPSSLSASVGDRVTITCKSSQSLLYRSNQKNYLAWYQQKPGKAPKLLIYWASTRESGVPSRFSGSGSGTDFTLTISSLQPEDFATYYCQQYYNYPRTFGQGTKVEIK |
| 670 | BCMA CDR-H1 | NYWMH |
| 671 | BCMA CDR-H2 | ATYRGHSDTYYNQKFKG |
| 672 | BCMA CDR-H3 | GAIYDGYDVLDN |
| 673 | BCMA CDR-L1 | SASQDISNYLN |
| 674 | BCMA CDR-L2 | YTSNLHS |
| 675 | BCMA CDR-L3 | QQYRKLPWT |
| 676 | BCMA VH | QVQLVQSGAEVKKPGSSVKVSCKASGGTFSNYWMHWVRQAPGQGLEWMGATYRGHSDTYYNQKFKGRVTITADKSTSTAYMELSSLRSEDTAVYYCARGAIYDGYDVLDNWGQGTLVTVSS |
| 677 | BCMA VL | DIQMTQSPSSLSASVGDRVTITCSASQDISNYLNWYQQKPGKAPKLLIYYTSNLHSGVPSRFSGSGSGTDFTLTISSLQPEDFATYYCQQYRKLPWTFGQGTKLEIK |
| 678 | c-Met CDR-H1 | AYTMH |
| 679 | c-Met CDR-H2 | WIKPNNGLANYAQKFQG |
| 680 | c-Met CDR-H3 | SEITTEFDY |
| 681 | c-Met CDR-L1 | KSSESVDSYANSFLH |
| 682 | c-Met CDR-L2 | RASTRES |
| 683 | c-Met CDR-L3 | QQSKEDPLT |
| 684 | c-Met VH | QVQLVQSGAEVKKPGASVKVSCKASGYIFTAYTMHWVRQAPGQGLEWMGWIKPNNGLANYAQKFQGRVTMTRDTSISTAYMELSRLRSDDTAVYYCARSEITTEFDYWGQGTLVTVSS |
| 685 | c-Met VL | DIVMTQSPDSLAVSLGERATINCKSSESVDSYANSFLHWYQQKPGQPPKLLIYRASTRESGVPDRFSGSGSGTDFTLTISSLQAEDVAVYYCQQSKEDPLTFGGGTKVEIK |
| 686 | EGFR CDR-H1 | SDFAWN |
| 687 | EGFR CDR-H2 | YISYSGNTRYQPSLKS |
| 688 | EGFR CDR-H3 | AGRGFPY |
| 689 | EGFR CDR-L1 | HSSQDINSNIG |
| 690 | EGFR CDR-L2 | HGTNLDD |
| 691 | EGFR CDR-L3 | VQYAQFPWT |
| 692 | EGFR VH | QVQLQESGPGLVKPSQTLSLTCTVSGYSISSDFAWNWIRQPPGKGLEWMGYISYSGNTRYQPSLKSRITISRDTSKNQFFLKLNSVTAADTATYYCVTAGRGFPYWGQGTLVTVSS |
| 693 | EGFR VL | DIQMTQSPSSMSVSVGDRVTITCHSSQDINSNIGWLQQKPGKSFKGLIYHGTNLDDGVPSRFSGSGSGTDYTLTISSLQPEDFATYYCVQYAQFPWTFGGGTKLEIK |
| 694 | SLAMF7 CDR-H1 | DYYMA |
| 695 | SLAMF7 CDR-H2 | SINYDGSSTYYVDSVKG |

| SEQ ID NO | Description | Sequence |
|---|---|---|
| 696 | SLAMF7 CDR-H3 | DRGYYFDY |
| 697 | SLAMF7 CDR-L1 | RSSQSLVHSNGNTYLH |
| 698 | SLAMF7 CDR-L2 | KVSNRFS |
| 699 | SLAMF7 CDR-L3 | SQSTHVPPFT |
| 700 | SLAMF7 VH | EVQLVESGGGLVQPGGSLRLSCAASGFTFSDYYMAWVRQAPGKGLEWVASINYDGSSTYYVDSVKGRFTISRDNAKNSLYLQMNSLRAEDTAVYYCARDRGYYFDYWGQGTTVTVSS |
| 701 | SLAMF7 VL | DVVMTQTPLSLSVTPGQPASISCRSSQSLVHSNGNTYLHWYLQKPGQSPQLLIYKVSNRFSGVPDRFSGSGSGTDFTLKISRVEAEDVGVYFCSQSTHVPPFTFGGGTKVEIK |
| 702 | SLITRK6 CDR-H1 | SYGMH |
| 703 | SLITRK6 CDR-H2 | VIWYDGSNQYYADSVKG |
| 704 | SLITRK6 CDR-H3 | GLTSGRYGMDV |
| 705 | SLITRK6 CDR-L1 | RSSQSLLLSHGFNYLD |
| 706 | SLITRK6 CDR-L2 | LGSSRAS |
| 707 | SLITRK6 CDR-L3 | MQPLQIPWT |
| 708 | SLITRK6 VH | QVQLVESGGGVVQPGRSLRLSCAASGFTFSSYGMHWVRQAPGKGLEWVAVIWYDGSNQYYADSVKGRFTISRDNSKNTLFLQMHSLRAEDTAVYYCARGLTSGRYGMDVWGQGTTVTVSS |
| 709 | SLITRK6 VL | DIVMTQSPLSLPVTPGEPASISCRSSQSLLLSHGFNYLDWYLQKPGQSPQLLIYLGSSRASGVPDRFSGSGSGTDFTLKISRVEAEDVGLYYCMQPLQIPWTFGQGTKVEIK |
| 710 | C4.4a CDR-H1 | NAWMS |
| 711 | C4.4a CDR-H2 | YISSSGSTIYYADSVKG |
| 712 | C4.4a CDR-H3 | EGLWAFDY |
| 713 | C4.4a CDR-L1 | TGSSSNIGAGYVVH |
| 714 | C4.4a CDR-L2 | DNNKRPS |
| 715 | C4.4a CDR-L3 | AAWDDRLNGPV |
| 716 | C4.4a VH | EVQLLESGGGLVQPGGSLRLSCAASGFTFSNAWMSWVRQAPGKGLEWVSYISSSGSTIYYADSVKGRFTISRDNSKNTLYLQMNSLRAEDTAVYYCAREGLWAFDYWGQGTLVTVSS |
| 717 | C4.4a VL | ESVLTQPPSVSGAPGQRVTISCTGSSSNIGAGYVVHWYQQLPGTAPKLLIYDNNKRPSGVPDRFSGSKSGTSASLAISGLRSEDEADYYCAAWDDRLNGPVFGGGTKLTVL |
| 718 | GCC CDR-H1 | GYYWS |
| 719 | GCC CDR-H2 | EINHRGNTNDNPSLKS |
| 720 | GCC CDR-H3 | ERGYTYGNFDH |
| 721 | GCC CDR-L1 | RASQSVSRNLA |
| 722 | GCC CDR-L2 | GASTRAT |
| 723 | GCC CDR-L3 | QQYKTWPRT |

-continued

Table of Sequences

| SEQ ID NO | Description | Sequence |
|---|---|---|
| 724 | GCC VH | QVQLQQWGAGLLKPSETLSLTCAVFGGSFSGYYWSWIRQPPGKGLEWIGEINHRGNTNDN PSLKSRVTISVDTSKNQFALKLSSVTAADTAVYYCARERGYTYGNFDHWGQGTLVTVSS |
| 725 | GCC VL | EIVMTQSPATLSVSPGERATLSCRASQSVSRNLAWYQQKPGQAPRLLIYGASTRATGIP ARFSGSGSGTEFTLTIGSLQSEDFAVYYCQQYKTWPRTFGQGTNVEIK |
| 726 | Axl CDR-H1 | SYAMN |
| 727 | Axl CDR-H2 | TTSGSGASTYYADSVKG |
| 728 | Axl CDR-H3 | IWIAFDI |
| 729 | Axl CDR-L1 | RASQSVSSSYLA |
| 730 | Axl CDR-L2 | GASSRAT |
| 731 | Axl CDR-L3 | QQYGSSPYT |
| 732 | Axl VH | EVQLLESGGGLVQPGGSLRLSCAASGFTFSSYAMNWVRQAPGKGLEWVSTTSGSGASTYY ADSVKGRFTISRDNSKNTLYLQMNSLRAEDTAVYYCAKIWIAFDIWGQGTMVTVSS |
| 733 | Axl VL | EIVLTQSPGTLSLSPGERATLSCRASQSVSSSYLAWYQQKPGQAPRLLIYGASSRATGIP DRFSGSGSGTDFTLTISRLEPEDFAVYYCQQYGSSPYTFGQGTKLEIK |
| 734 | gpNMB CDR-H1 | SFNYYWS |
| 735 | gpNMB CDR-H2 | YIYYSGSTYSNPSLKS |
| 736 | gpNMB CDR-H3 | GYNWNYFDY |
| 737 | gpNMB CDR-L1 | RASQSVDNNLV |
| 738 | gpNMB CDR-L2 | GASTRAT |
| 739 | gpNMB CDR-L3 | QQYNNWPPWT |
| 740 | gpNMB VH | QVQLQESGPGLVKPSQTLSLTCTVSGGISSFNYYWSWIRHHPGKGLEWIGYIYYSGSTY SNPSLKSRVTISVDTSKNQFSLTLSSVTAADTAVYYCARGYNWNYFDYWGQGTLVTVSS |
| 741 | gpNMB VL | EIVMTQSPATLSVSPGERATLSCRASQSVDNNLVWYQQKPGQAPRLLIYGASTRATGIPA RFSGSGSGTEFTLTISSLQSEDFAVYYCQQYNNWPPWTFGQGTKVEIK |
| 742 | Prolactin receptor CDR-H1 | TYWMH |
| 743 | Prolactin receptor CDR-H2 | EIDPSDSYSNYNQKFKD |
| 744 | Prolactin receptor CDR-H3 | NGGLGPAWFSY |
| 745 | Prolactin receptor CDR-L1 | KASQYVGTAVA |
| 746 | Prolactin receptor CDR-L2 | SASNRYT |
| 747 | Prolactin receptor CDR-L3 | QQYSSYPWT |
| 748 | Prolactin receptor VH | EVQLVQSGAEVKKPGSSVKVSCKASGYTFTTYWMHWVRQAPGQGLEWIGEIDPSDSYSNY NQKFKDRATLTVDKSTSTAYMELSSLRSEDTAVYYCARNGGLGPAWFSYWGQGTLVTVSS |
| 749 | Prolactin receptor VL | DIQMTQSPSSVSASVGDRVTITCKASQYVGTAVAWYQQKPGKSPKLLIYSASNRYTGVPS RFSDSGSGTDFTLTISSLQPEDFATYFCQQYSSYPWTFGGGTKVEIK |
| 750 | FGFR2 CDR-H1 | SYAMS |

-continued

Table of Sequences

| SEQ ID NO | Description | Sequence |
|---|---|---|
| 751 | FGFR2 CDR-H2 | AISGSGTSTYYADSVKG |
| 752 | FGFR2 CDR-H3 | VRYNWNHGDWFDP |
| 753 | FGFR2 CDR-L1 | SGSSSNIGNNYVS |
| 754 | FGFR2 CDR-L2 | ENYNRPA |
| 755 | FGFR2 CDR-L3 | SSWDDSLNYWV |
| 756 | FGFR2 VH | EVQLLESGGGLVQPGGSLRLSCAASGFTFSSYAMSWVRQAPGKGLEWVSAISGSGTSTYYADSVKGRFTISRDNSKNTLYLQMNSLRAEDTAVYYCARVRYNWNHGDWFDPWGQGTLVTVSS |
| 757 | FGFR2 VL | QSVLTQPPSASGTPGQRVTISCSGSSSNIGNNYVSWYQQLPGTAPKLLIYENYNRPAGVPDRFSGSKSGTSASLAISGLRSEDEADYYCSSWDDSLNYWVFGGGTKLTVL |
| 758 | CDCP1 CDR-H1 | SYGMS |
| 759 | CDCP1 CDR-H2 | TISSGGSYKYYVDSVKG |
| 760 | CDCP1 CDR-H3 | HPDYDGVWFAY |
| 761 | CDCP1 CDR-L1 | SVSSSVFYVH |
| 762 | CDCP1 CDR-L2 | DTSKLAS |
| 763 | CDCP1 CDR-L3 | QQWNSNPPT |
| 764 | CDCP1 VH | EVQLVESGGGLVQPGGSLRLSCAASGFTFNSYGMSWVRQAPGKGLEWVATISSGGSYKYYVDSVKGRFTISRDNAKNSLYLQMNSLRAEDTAVYYCARHPDYDGVWFAYWGQGTLVTVSS |
| 765 | CDCP1 VL | DIQMTQSPSSLSASVGDRVTITCSVSSSVFYVHWYQQKPGKAPKLLIYDTSKLASSGVPSRFSGSGSGTDFTFTISSLQPEDIATYYCQQWNSNPPTFGGGTKVEIK |
| 766 | CDCP1 CDR-H1 | SYGMS |
| 767 | CDCP1 CDR-H2 | TISSGGSYTYYPDSVKG |
| 768 | CDCP1 CDR-H3 | HPDYDGVWFAY |
| 769 | CDCP1 CDR-L1 | SVSSSVFYVH |
| 770 | CDCP1 CDR-L2 | DTSKLAS |
| 771 | CDCP1 CDR-L3 | QQWNSNPPT |
| 772 | CDCP1 VH | EVQLVESGGDLVKPGGSLKLSCAASGFTFNSYGMSWVRQTPDKRLEWVATISSGGSYTYYPDSVKGRFTISRDNAKNTLYLQMSSLKSEDTAMYYCARHPDYDGVWFAYWGQGTLVTVSA |
| 773 | CDCP1 VL | QIVLTQSPAIMASPGEKVTMTCSVSSSVFYVHWYQQKSGTSPKRWIYDTSKLASGVPARFSGSGSGTSYSLTISSMEAEDAATYYCQQWNSNPPTFGGGTKLEIK |
| 774 | CDCP1 CDR-H1 | SYYMH |
| 775 | CDCP1 CDR-H2 | IINPSGGSTSYAQKFQG |
| 776 | CDCP1 CDR-H3 | DGVLRYFDWLLDYYYY |
| 777 | CDCP1 CDR-L1 | RASQSVGSYLA |
| 778 | CDCP1 CDR-L2 | DASNRAT |
| 779 | CDCP1 CDR-L3 | QQRANVFT |
| 780 | CDCP1 VH | EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDGVLRYFDWLLDYYYYMDVWGKGTTVTVSS |
| 781 | CDCP1 VL | EIVLTQSPATLSLSPGERATLSCRASQSVGSYLAWYQQRPGQAPRLLIYDASNRATGIPARFSGSGSGTDFTLTISSLEPEDFAVYYCQQRANVFTFGQGTKVEIK |

Table of Sequences

| SEQ ID NO | Description | Sequence |
|---|---|---|
| 782 | CDCP1 CDR-H1 | SYYMH |
| 783 | CDCP1 CDR-H2 | IINPSGGSTSYAQKFQG |
| 784 | CDCP1 CDR-H3 | DAELRHFDHLLDYHYYMDV |
| 785 | CDCP1 CDR-L1 | RASQSVGSYLA |
| 786 | CDCP1 CDR-L2 | DASNRAT |
| 787 | CDCP1 CDR-L3 | QQRAQEFT |
| 788 | CDCP1 VH | EVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARDAELRHFDHLLDYHYYMDVWGQGTTVTVSS |
| 789 | CDCP1 VL | EIVMTQSPATLSLSPGERATLSCRASQSVGSYLAWYQQKPGQAPRLLIYDASNRATGIPARFSGSGSGTDFTLTISSLQPEDFAVYYCQQRAQEFTFGQGTKVEIK |
| 790 | ASCT2 VH | QVQLVQSGSELKKPGAPVKVSCKASGYTFSTFGMSWVRQAPGQGLKWMGWIHTYAGVPIYGDDFKGRFVFSLDTSVSTAYLQISSLKAEDTAVYFCARRSDNYRYFFDYWGQGTTVTVSS |
| 791 | ASCT2 VL | DIQMTQSPSSLSASLGDRVTITCRASQDIRNYLNWYQQKPGKAPKLLIYYTSRLHSGVPSRFSGSGSGTDYTLTISSLQPEDFATYFCQQGHTLPPTFGQGTKLEIK |
| 792 | ASCT2 VH | QIQLVQSGPELKKPGAPVKISCKASGYTFTTFGMSWVKQAPGQGLKWMGWIHTYAGVPIYGDDFKGRFVFSLDTSVSTAYLQISSVKAEDTATYFCARRSDNYRYFFDYWGQGTTLTVSS |
| 793 | ASCT2 VL | DIQMTQSPSSLSASLGDRVTITCRASQDIRNYLNWYQQKPGKAPKLLIYYTSRLHSGVPSRFSGSGSGTDYTLTISSLQPEDFATYFCQQGHTLPPTFGQGTKLEIK |
| 794 | ASCT2 CDR-H1 | NYYMA |
| 795 | ASCT2 CDR-H2 | SITKGGGNTYYRDSVKG |
| 796 | ASCT2 CDR-H3 | QVTIAAVSTSYFDS |
| 797 | ASCT2 CDR-L1 | KTNQKVDYYGNSYVY |
| 798 | ASCT2 CDR-L2 | LASNLAS |
| 799 | ASCT2 CDR-L3 | QQSRNLPYT |
| 800 | ASCT2 VH | EVQLVESGGGLVQSGRSIRLSCAASGFSFSNYYMAWVRQAPSKGLEWVASITKGGGNTYYRDSVKGRFTFSRDNAKSTLYLQMDSLRSEDTATYYCARQVTIAAVSTSYFDSWGQGVMVTVSS |
| 801 | ASCT2 VL | DIVLTQSPALAVSLGQRATISCKTNQKVDYYGNSYVYWYQQKPGQQPKLLIYLASNLASGIPARFSGRGSGTDFTLTIDPVEADDTATYYCQQSRNLPYTFGAGTKLELK |
| 802 | CD123 CDR-H1 | DYYMK |
| 803 | CD123 CDR-H2 | DIIPSNGATFYNQKFKG |
| 804 | CD123 CDR-H3 | SHLLRASWFAY |
| 805 | CD123 CDR-L1 | KSSQSLLNSGNQKNYLT |
| 806 | CD123 CDR-L2 | WASTRES |
| 807 | CD123 CDR-L3 | QNDYSYPYT |
| 808 | CD123 VH | QVQLVQSGAEVKKPGASVKMSCKASGYTFTDYYMKWVKQAPGQGLEWIGDIIPSNGATFYNQKFKGKATLTVDRSISTAYMHLNRLRSDDTAVYYCTRSHLLRASWFAYWGQGTLVTVSS |
| 809 | CD123 VL | DFVMTQSPDSLAVSLGERATINCKSSQSLLNSGNQKNYLTWYLQKPGQPPKLLIYWASTRESGVPDRFSGSGSGTDFTLTISSLQAEDVAVYYCQNDYSYPYTFGQGTKLEIK |
| 810 | GPC3 CDR-H1 | DYEMH |
| 811 | GPC3 CDR-H2 | WIGGIDPETGGTAYNQKFKG |
| 812 | GPC3 CDR-H3 | YYSFAY |

-continued

Table of Sequences

| SEQ ID NO | Description | Sequence |
|---|---|---|
| 813 | GPC3 CDR-L1 | RSSQSIVHSNGNTYLQ |
| 814 | GPC3 CDR-L2 | KVSNRFS |
| 815 | GPC3 CDR-L3 | FQVSHVPYT |
| 816 | GPC3 VH | EVQLVQSGAEVKKPGATVKISCKVSGYTFTDYEMHWQQAPGKGLEWMGGIDPETGGTAY NQKFKGRVTLTADKSTDTAYMELSSLRSEDTAVYYCGRYYSFAYWGQGTLVTVSS |
| 817 | GPC3 VL | DVVMTQSPLSLPVTLGQPASISCRSSQSIVHSNANTYLQWFQQRPGQSPRLLIYKVSNRF SGVPDRFSGSGSGTDFTLKISRVEAEDVGVYYCFQVSHVPYTFGQGTKLEIK |
| 818 | B6A CDR-H1 | DYNVN |
| 819 | B6A CDR-H2 | VINPKYGTTRYNQKFKG |
| 820 | B6A CDR-H3 | GLNAWDY |
| 821 | B6A CDR-L1 | GASENIYGALN |
| 822 | B6A CDR-L2 | GATNLED |
| 823 | B6A CDR-L3 | QNVLTTPYT |
| 824 | B6A VH | QFQLVQSGAEVKKPGASVKVSCKASGYSFTDYNVNWVRQAPGQGLEWIGVINPKYGTTRY NQKFKGRATLTVDKSTSTAYMELSSLRSEDTAVYYCTRGLNAWDYWGQGTLVTVSS |
| 825 | B6A VL | DIQMTQSPSSLSASVGDRVTITCGASENIYGALNWYQQKPGKAPKLLIYGATNLEDGVPS RFSGSGSGRDYTFTISSLQPEDIATYYCQNVLTTPYTFGQGTKLEIK |
| 826 | B6A CDR-H1 | GYFMN |
| 827 | B6A CDR-H2 | LINPYNGDSFYNQKFKG |
| 828 | B6A CDR-H3 | GLRRDFDY |
| 829 | B6A CDR-L1 | KSSQSLLDSDGKTYLN |
| 830 | B6A CDR-L2 | LVSELDS |
| 831 | B6A CDR-L3 | WQGTHFPRT |
| 832 | B6A VH | QVQLVQSGAEVKKPGASVKVSCKASGYSFSGYFMNWVRQAPGQGLEWMGLINPYNGDSFY NQKFKGRVTMTRQTSTSTVYMELSSLRSEDTAVYYCVRGLRRDFDYWGQGTLVTVSS |
| 833 | B6A VL | DVVMTQSPLSLPVTLGQPASISCKSSQSLLDSDGKTYLNWLFQRPGQSPRRLIYLVSELD SGVPDRFSGSGSGTDFTLKISRVEAEDVGVYYCWQGTHFPRTFGGGTKLEIK |
| 834 | PD-L1 CDR-H1 | TAAIS |
| 835 | PD-L1 CDR-H2 | GIIPIFGKAHYAQKFQG |
| 836 | PD-L1 CDR-H3 | KFHFVSGSPFGMDV |
| 837 | PD-L1 CDR-L1 | RASQSVSSYLA |
| 838 | PD-L1 CDR-L2 | DASNRAT |
| 839 | PD-L1 CDR-L3 | QQRSNWPT |
| 840 | PD-L1 VH | QVQLVQSGAEVKKPGSSVKVSCKTSGDTFSTAAISWVRQAPGQGLEWMGGIIPIFGKAHY AQKFQGRVTITADESTSTAYMELSSLRSEDTAVYFCARKFHFVSGSPFGMDVWGQGTTVT VSS |
| 841 | PD-L1 VL | EIVLTQSPATLSLSPGERATLSCRASQSVSSYLAWYQQKPGQAPRLLIYDASNRATGIPA RFSGSGSGTDFTLTISSLEPEDFAVYYCQQRSNWPTFGQGTKVEIK |
| 842 | TIGIT CDR-H1 | GTFSSYAIS |
| 843 | TIGIT CDR-H2 | SIIPIFGTANYAQKFQG |
| 844 | TIGIT CDR-H3 | ARGPSEVGAILGYVWFDP |

| SEQ ID NO | Description | Sequence |
|---|---|---|
| 845 | TIGIT CDR-L1 | RSSQSLLHSNGYNYLD |
| 846 | TIGIT CDR-L2 | LGSNRAS |
| 847 | TIGIT CDR-L3 | MQARRIPIT |
| 848 | TIGIT VH | QVQLVQSGAEVKKPGSSVKVSCKASGGTFSSYAISWVRQAPGQGLEWMGSIIPIFGTANY AQKFQGRVTITADESTSTAYMELSSLRSEDTAVYYCARGPSEVGAILGYVWFDPWGQGTL VTVSS |
| 849 | TIGIT VL | DIVMTQSPLSLPVTPGEPASISCRSSQSLLHSNGYNYLDWYLQKPGQSPQLLIYLGSNRA SGVPDRFSGSGSGTDFTLKISRVEAEDVGVYYCMQARRIPITFGGGTKVEIK |
| 850 | STN CDR-H1 | GYTFTDHAIHWV |
| 851 | STN CDR-H2 | FSPGNDDIKY |
| 852 | STN CDR-H3 | KRSLSTPY |
| 853 | STN CDR-L1 | QSLLNRGNHKNY |
| 854 | STN CDR-L2 | WASTRES |
| 855 | STN CDR-L3 | QNDYTYPYT |
| 856 | STN VH | EVQLVQSGAEVKKPGASVKVSCKASGYTFTDHAIHWVRQAPGQGLEWMGYFSPGNDDIKY NEKFRGRVTMTADKSSSTAYMELRSLRSDDTAVYFCKRSLSTPYWGQGTLVTVSS |
| 857 | STN VL | DIVMTQSPDSLAVSLGERATINCKSSQSLLNRGNHKNYLTWYQQKPGQPPKLLIYWASTR ESGVPDRFSGSGSGTDFTLTISSLQAEDVAVYYCQNDYTYPYTFGQGTKVEIK |
| 858 | CD33 CDR-H1 | NYDIN |
| 859 | CD33 CDR-H2 | WIYPGDGSTKYNEKFKA |
| 860 | CD33 CDR-H3 | GYEDAMDY |
| 861 | CD33 CDR-L1 | KASQDINSYLS |
| 862 | CD33 CDR-L2 | RANRLVD |
| 863 | CD33 CDR-L3 | LQYDEFPLT |
| 864 | CD33 VH | QVQLVQSGAE VKKPGASVKV SCKASGYTFT NYDINWVRQA PGQGLEWIGW IYPGDGSTKY NEKFKAKATL TADTSTSTAY MELRSLRSDD TAVYYCASGY EDAMDYWGQG TTVTVSS |
| 865 | CD33 VL | DIQMTQSPS SLSASVGDRVT INCKASQDINSYLSWFQQKPGKAPKTL IYRANRLVDGVPS RFSGSGSGQDYTLT ISSLQPEDFATYYCLQYDEFPLTFGGGTKVE |
| 866 | NTBA CDR-H1 | NYGMN |
| 867 | NTBA CDR-H2 | WINTYSGEPRYADDFKG |
| 868 | NTBA CDR-H3 | DYGRWYFDV |
| 869 | NTBA CDR-L1 | RASSSVSHMH |
| 870 | NTBA CDR-L2 | ATSNLAS |
| 871 | NTBA CDR-L3 | QQWSSTPRT |
| 872 | NTBA VH | QIQLVQSGSELKKPGASVKVSCKASGYTFTNYGMNWVRQAPGQDLKWMGWINTYSGEPRY ADDFKGRFVFSLDKSVNTAYLQISSLKAEDTAVYYCARDYGRWYFDVWGQGTTVTVSS |
| 873 | NTBA VL | QIVLSQSPATLSLSPGERATMSCRASSSVSHMHWYQQKPGQAPRPWIYATSNLASGVPAR FSGSGSGTDYTLTISSLEPEDFAVYYCQQWSSTPRTFGGGTKVEIK |
| 874 | BCMA CDR-H1 | DYYIH |
| 875 | BCMA CDR-H2 | YINPNSGYTNYAQKFQG |

-continued

Table of Sequences

| SEQ ID NO | Description | Sequence |
|---|---|---|
| 876 | BCMA CDR-H3 | YMWERVTGFFDF |
| 877 | BCMA CDR-L1 | LASEDISDDLA |
| 878 | BCMA CDR-L2 | TTSSLQS |
| 879 | BCMA CDR-L3 | QQTYKFPPT |
| 880 | BCMA VH | QVQLVQSGAEVKKPGASVKLSCKASGYTFTDYYIHWVRQAPGQGLEWIGYINPNSGYTNY AQKFQGRATMTADKSINTAYVELSRLRSDDTAVYFCTRYMWERVTGFFDFWGQGTMVTVS S |
| 881 | BCMA VL | DIQMTQSPSSVSASVGDRVTITCLASEDISDDLAWYQQKPGKAPKVLVYTTSSLQSGVPS RFSGSGSGTDFTLTISSLQPEDFATYFCQQTYKFPPTFGGGTKVEIK |
| 882 | TF CDR-H1 | GFTFSNYA |
| 883 | TF CDR-H2 | ISGSGDYT |
| 884 | TF CDR-H3 | ARSPWGYYLDS |
| 885 | TF CDR-L1 | QGISSR |
| 886 | TF CDR-L2 | AAS |
| 887 | TF CDR-L3 | QQYNSYPYT |
| 888 | TF VH | EVQLLESGGGLVQPGGSLRLSCAASGFTFSNYAMSWVRQAPGKGLEWVSSISGSGDYTYY TDSVKGRFTISRDNSKNTLYLQMNSLRAEDTAVYYCARSPWGYYLDSWGQGTLVTVSS |
| 889 | TF VL | DIQMTQSPPSLSASAGDRVTITCRASQGISSRLAWYQQKPEKAPKSLIYAASSLQSGVPS RFSGSGSGTDFTLTISSLQPEDFATYYCQQYNSYPYTFGQGTKLEIK |
| 890 | GPNMB HC | QVQLQESGPGLVKPSQTLSLTCTVSGGSISSFNYYWSWIRHHPGKGLEWIGYIYYSGSTY SNPSLKSRVTISVDTSKNQFSLTLSSVTAADTAVYYCARGYNWNYFDYWGQGTLVTVSSA STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSLSLSPGK |
| 891 | GPNMB LC | EIVMTQSPATLSVSPGERATLSCRASQSVDNNLVWYQQKPGQAPRLLIYGASTRATGIPA RFSGSGSGTEFTLTISSLQSEDFAVYYCQQYNNWPPWTFGQGTKVEIKRTVAAPSVFIFP PSDEQLKSGTASVVCLLNNFYPREAKVQWKVDNALQSGNSQESVTEQDSKDSTYSLSSTL TLSKADYEKHKVYACEVTHQGLSSPVTKSFNRGEC |
| 892 | GPNMB VH | QVQLQESGPGLVKPSQTLSLTCTVSGGSISSFNYYWSWIRHHPGKGLEWIGYIYYSGSTY SNPSLKSRVTISVDTSKNQFSLTLSSVTAADTAVYYCARGYNWNYFDYWGQGTLVTVSSA |
| 893 | GPNMB VL | EIVMTQSPATLSVSPGERATLSCRASQSVDNNLVWYQQKPGQAPRLLIYGASTRATGIPA RFSGSGSGTEFTLTISSLQSEDFAVYYCQQYNNWPPWTFGQGTKVEIKR |
| 894 | GPNMB HVR-H1 | SFNYYWS |
| 895 | GPNMB HVR-H2 | YIYYSGSTYSNPSLKS |
| 896 | GPNMB HVR-H3 | GYNWNYFDY |
| 897 | GPNMB HVR-L1 | RASQSVDNNLV |
| 898 | GPNMB HVR-L2 | GASTRAT |
| 899 | GPNMB HVR-L3 | QQYNNWPPWT |
| 900 | CD228 HVR-H1 | SGYWN |
| 901 | CD228 HVR-H2 | YISDSGITYYNPSLKS |
| 902 | CD228 HVR-H3 | RTLATYYAMDY |
| 903 | CD228 HVR-L1 | RASQSLVHSDGNTYLH |
| 904 | CD228 HVR-L2 | RVSNRFS |

Table of Sequences

| SEQ ID NO | Description | Sequence |
|---|---|---|
| 905 | CD228 HVR-L3 | SQSTHVPPT |
| 906 | CD228 VH | QVQLQESGPGLVKPSETLSLTCTVSGDSITSGYWNWIRQPPGKGLEYIGYISDSGITYYN PSLKSRVTISRDTSKNQYSLKLSSVTAADTAVYYCARRTLATYYAMDYWGQGTLVTVSS |
| 907 | CD228 VL | DFVMTQSPLSLPVTLGQPASISCRASQSLVHSDGNTYLHWYQQRPGQSPRLLIYRVSNRF SGVPDRFSGSGSGTDFTLKISRVEAEDVGVYYCSQSTHVPPTFGQGTKLEIK |
| 908 | CD228 HC | ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPG |
| 909 | CD228 LC | TVAAPSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 910 | h2A2 HC | QFQLVQSGAEVKKPGASVKVSCKASGYSFTDYNVNWVRQAPGQGLEWIGVINPKYGTTRY NQKFKGRATLTVDKSTSTAYMELSSLRSEDTAVYYCTRGLNAWDYWGQGTLVTVSSASTK GPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVDKSRWQQGN VFSCSVMHEALHNHYTQKSLSLSPGK |
| 911 | h2A2 LC | DIQMTQSPSSLSASVGDRVTITCGASENIYGALNWYQQKPGKAPKLLIYGATNLEDGVPS RFSGSGSGRDYTFTISSLQPEDIATYYCQNVLTTPYTFGQGTKLEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| 912 | h2A2 VH | QFQLVQSGAEVKKPGASVKVSCKASGYSFTDYNVNWVRQAPGQGLEWIGVINPKYGTTRY NQKFKGRATLTVDKSTSTAYMELSSLRSEDTAVYYCTRGLNAWDYWGQGTLVTVSS |
| 913 | h2A2 VL | DIQMTQSPSSLSASVGDRVTITCGASENIYGALNWYQQKPGKAPKLLIYGATNLEDGVPS RFSGSGSGRDYTFTISSLQPEDIATYYCQNVLTTPYTFGQGTKLEIK |
| 914 | h2A2 HVR-H1 | DYNVN |
| 915 | h2A2 HVR-H2 | VINPKYGTTRYNQKFKG |
| 916 | h2A2 HVR-H3 | GLNAWDY |
| 917 | h2A2 HVR-L1 | GASENIYGALN |
| 918 | h2A2 HVR-L2 | GATNLED |
| 919 | h2A2 HVR-L3 | QNVLTTPYT |
| 920 | cAC10 CDR-H1 | DYYIT |
| 921 | cAC10 CDR-H2 | WIYPGSGNTKYNEKFKG |
| 922 | cAC10 CDR-H3 | YGNYWFAY |
| 923 | cAC10 CDR-L1 | KASQSVDFDGDSYMN |
| 924 | cAC10 CDR-L2 | AASNLES |
| 925 | cAC10 CDR-L3 | QQSNEDPWT |
| 926 | cAC10 VH | QIQLQQSGPEVVKPGASVKISCKASGYTFTDYYITWVKQPGQGLEWIGWIYPGSGNTKY NEKFKGKATLTVDTSSSTAFMQLSSLTSEDTAVYFCANYGNYWFAYWGQGTQVTVSA |
| 927 | cAC10 VL | DIVLTQSPASLAVSLGQRATISCKASQSVDFDGDSYMNWYQQKPGQPPKVLIYAASNLES GIPARFSGSGSGTDFTLNIHPVEEEDAATYYCQQSNEDPWTFGGGTKLEIK |
| 928 | cAC10 HC | QIQLQQSGPEVVKPGASVKISCKASGYTFTDYYITWVKQPGQGLEWIGWIYPGSGNTKY NEKFKGKATLTVDTSSSTAFMQLSSLTSEDTAVYFCANYGNYWFAYWGQGTQVTVSAAST KGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN |

| SEQ ID NO | Description | Sequence |
|---|---|---|
| | | STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPGK |
| 929 | cAC10 HC v2 | QIQLQQSGPEVVKPGASVKISCKASGYTFTDYYITWVKQKPGQGLEWIGWIYPGSGNTKY NEKFKGKATLTVDTSSSTAFMQLSSLTSEDTAVYFCANYGNYWFAYWGQGTQVTVSAAST KGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPG |
| 930 | cAC10 LC | DIVLTQSPASLAVSLGQRATISCKASQSVDFDGDSYMNWYQQKPGQPPKVLIYAASNLES GIPARFSGSGSGTDFTLNIHPVEEEDAATYYCQQSNEDPWTFGGGTKLEIKR TVAAPSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 931 | <Q13433; protein | MARKLSVILI LTFALSVTNP LHELKAAAFP QTTEKISPNW ESGINVDLAI STRQYHLQQL FYRYGENNSL SVEGFRKLLQ NIGIDKIKRI HIHHDHDHHS DHEHHSDHER HSDHEHHSEH EHHSDHDHHS HHNHAASGKN KRKALCPDHD SDSSGKDPRN SQGKGAHRPE HASGRRNVKD SVSASEVTST VYNTVSEGTH FLETIETPRP GKLFPKDVSS STPPSVTSKS RVSRLAGRKT NESVSEPRKG FMYSRNTNEN PQECFNASKL LTSHGMGIQV PLNATEFNYL CPAIINQIDA RSCLIHTSEK KAEIPPKTYS LQIAWVGGFI AISIISFLSL LGVILVPLMN RVFFKFLLSF LVALAVGTLS GDAFLHLLPH SHASHHHSHS HEEPAMEMKR GPLFSHLSSQ NIEEESAYFDS TWKGLTALGG LYFMFLVEHV LTLIKQFKDK KKKNQKKPEN DDDVEIKKQL SKYESQLSTN EEKVDTDDRT EGYLRADSQE PSHFDSQQPA VLEEEEVMIA HAHPQEVYNE YVPRGCKNKC HSHFHDTLGQ SDDLIHHHHD YHHILHHHHH QNHHPHSHSQ RYSREELKDA GVATLAWMVI MGDGLHNFSD GLAIGAAFTE GLSSGLSTSV AVFCHELPHE LGDFAVLLKA GMTVKQAVLY NALSAMLAYL GMATGIFIGH YAENVSMWIF ALTAGLFMYV ALVDMVPEML HNDASDHGCS RWGYFFLQNA GMLLGFGIML LISIFEHKIV FRINF |
| 932 | hLIV22 HC + Constant | QVQLVQSGAEVKKPGASVKVSCKASGLTIEDYYMHWVRQAPGQGLEWMGWIDPENGDTEY GPKFQGRVTMTRDTSINTAYMELSRLRSDDTAVYYCAVHNAHYGTWFAYWGQGTLVTVSS ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPG |
| 933 | hLIV22 LC + Constant | DVVMTQSPLSLPVTLGQPASISCRSSQSLLHSSGNTYLEWYQQRPGQSPRPLIYKISTRF SGVPDRFSGSGSGTDFTLKISRVEAEDVGVYYCFQGSHVPYTFGGGTKVEIKRTVAAPSV FIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC |
| 934 | hLIV22 VH | QVQLVQSGAEVKKPGASVKVSCKASGLTIEDYYMHWVRQAPGQGLEWMGWIDPENGDTEY GPKFQGRVTMTRDTSINTAYMELSRLRSDDTAVYYCAVHNAHYGTWFAYWGQGTLVTVSS |
| 935 | hLIV22 VL | DVVMTQSPLSLPVTLGQPASISCRSSQSLLHSSGNTYLEWYQQRPGQSPRPLIYKISTRF SGVPDRFSGSGSGTDFTLKISRVEAEDVGVYYCFQGSHVPYTFGGGTKVEIK |
| 936 | hLIV22 HVR-H1 | DYYMH |
| 937 | hLIV22 HVR-H2 | WIDPENGDTEYGPKFQG |
| 938 | hLIV22 HVR-H3 | HNAHYGTWFAY |
| 939 | hLIV22 HVR-L1 | RSSQSLLHSSGNTYLE |
| 940 | hLIV22 HVR-L2 | KISTRFS |

Table of Sequences

| SEQ ID NO | Description | Sequence |
|---|---|---|
| 941 | hLIV22 HVR-L3 | FQGSHVPYT |
| 942 | hLIV22 epitope | KGAHRPEH |
| 943 | HBU12 VH | QVQLQESGPGLVKPSQTLSLTCTVSGGSISTSGMGVGWIRQHPGKGLEWIGHIWWDDDKR YNPALKSRVTISVDTSKNQFSLKLSSVTAADTAVYYCARMELWSYYFDYWGQGTLVTVSS |
| 944 | hBU12 HVR-H1 | TSGMGVG |
| 945 | hBU12 HVR-H2 | HIWWDDDKRYNPALKS |
| 946 | hBU12 HVR-H3 | MELWSYYFDY |
| 947 | hBU12 VL | EIVLTQSPATLSLSPGERATLSCSASSSVSYMHWYQQKPGQAPRLLIYDTSKLASGIPAR FSGSGSGTDFTLTISSLEPEDVAVYYCFQGSVYPFTFGQGTKLEIKR |
| 948 | hBU12 HVR-L1 | SASSSVSYMH |
| 949 | hBU12 HVR-L2 | DTSKLAS |
| 950 | hBU12 HVR-L3 | FQGSVYPFT |
| 951 | hBU12 HC | QVQLQESGPGLVKPSQTLSLTCTVSGGSISTSGMGVGWIRQHPGKGLEWIGHIWWDDDKR YNPALKSRVTISVDTSKNQFSLKLSSVTAADTAVYYCARMELWSYYFDYWGQGTLVTVSS ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPGK |
| 952 | HBU12 LC | EIVLTQSPATLSLSPGERATLSCSASSSVSYMHWYQQKPGQAPRLLIYDTSKLASGIPAR FSGSGSGTDFTLTISSLEPEDVAVYYCFQGSVYPFTFGQGTKLEIKRTVAAPSVFIFPPS DEQLKSGTASVVCLLNNFYPREAKVQWKVDNALQSGNSQESVTEQDSKDSTYSLSSTLTL SKADYEKHKVYACEVTHQGLSSPVTKSFNRGEC |

The following sequences correspond to SEQ IDs 943-952:

```
943A GLN VAL GLN LEU GLN GLU SER GLY PRO GLY LEU VAL LYS PRO
     SER GLN THR LEU SER LEU THR CYS THR VAL SER GLY GLY SER
     ILE SER THR SER GLY MET GLY VAL GLY TRP ILE ARG GLN HIS
     PRO GLY LYS GLY LEU GLU TRP ILE GLY HIS ILE TRP TRP ASP
     ASP ASP LYS ARG TYR ASN PRO ALA LEU LYS SER ARG VAL THR
     ILE SER VAL ASP THR SER LYS ASN GLN PHE SER LEU LYS
     LEU SER SER VAL THR ALA ALA ASP THR ALA VAL TYR TYR CYS
     ALA ARG MET GLU LEU TRP SER TYR TYR PHE ASP TYR TRP GLY
     GLN GLY THR LEU VAL THR VAL SER SER

944A THR SER GLY MET GLY VAL GLY

945A HIS ILE TRP TRP ASP ASP ASP LYS ARG TYR ASN PRO ALA LEU
     LYS SER

946A MET GLU LEU TRP SER TYR TYR PHE ASP TYR

947A GLU ILE VAL LEU THR GLN SER PRO ALA THR LEU SER LEU SER
     PRO GLY GLU ARG ALA THR LEU SER CYS SER ALA SER SER SER
     VAL SER TYR MET HIS TRP TYR GLN GLN LYS PRO GLY GLN ALA
     PRO ARG LEU LEU ILE TYR ASP THR SER LYS LEU ALA SER GLY
     ILE PRO ALA ARG PHE SER GLY SER GLY SER GLY THR ASP PHE
     THR LEU THR ILE SER SER LEU GLU PRO GLU ASP VAL ALA
     VAL TYR TYR CYS PHE GLN GLY SER VAL TYR PRO PHE THR PHE
     GLY GLN GLY THR LYS LEU GLU ILE LYS ARG

948A SER ALA SER SER SER VAL SER TYR MET HIS

949A ASP THR SER LYS LEU ALA SER
```

950A PHE GLN GLY SER VAL TYR PRO PHE THP

951A GLN VAL GLN LEU GIN GLU SER GLY PRO GLY LEU VAL LYS PRO
     SER GLN THR LEU SER LEU THR CYS THR VAL SER GLY GLY SER
     ILE SER THR SER GLY MET GLY VAL GLY TRP ILE ARG GLN HIS
     PRO GLY LYS GLY LEU GLU TRP ILE GLY HIS ILE TRP TRP ASP
     ASP ASP LYS ARG TYR ASN PRO ALA LEU LYS SER ARG VAL THR
     ILE SER VAL ASP THR SER LYS ASN GLN PHE SER LEU LYS LEU
     SER SER VAL THR ALA ALA ASP THP ALA VAL TYR TYR CYS ALA
     ARG MET GLU LEU TRR SER TYR TYR PHE ASP TYR TRR GLY GLN
     GLY THR LEU VAL THP VAL SER SER ALA SER THP LYS GLY PRO
     SER VAL PHE PRO LEU ALA PRO SER SER LYS SER THR SER GLY
     GLY THR ALA ALA LEU GLY CYS LEU VAL LYS ASP TYR PHE PRO
     GLU PRO VAL THR VAL SER TRP ASN SER GLY ALA LEU THR SER
     GLY VAL HIS THR PHE PRO ALA VAL LEU GLN SER SER GLY LEU
     TYR SER LEU SER SER VAL VAL THR VAL PRO SER SER SER LEU
     GLY THR GLN THR TYR ILE CYS ASN VAL ASN HIS LYS PRO SER
     ASN THR LYS VAL ASP LYS LYS VAL GLU PRO LYS SER CYS ASP
     LYS THR HIS THR CYS PRO PRO CYS PRO ALA PRO GLU LEU LEU
     GLY GLY PRO SER VAL PHE LEU PHE PRO PRO LYS PRO LYS ASP
     THR LEU MET ILE SER ARG THP PRO GLU VAL THR CYS VAL VAL
     VAL ASP VAL SER HIS GLU ASP PRO GLU VAL LYS PHE ASN TRP
     TYR VAL ASP GLY VAL GLU VAL HIS ASN ALA LYS THP LYS PRO
     ARG GLU GLU GLN TYR ASN SER THR TYR ARG VAL VAL SER VAL
     LEU THR VAL LEU HIS GLN ASP TRP LEU ASN GLY LYS GLU TYR
     LYS CYS LYS VAL SER ASN LYS ALA LEU PRO ALA PRO ILE GLU
     LYS THR ILE SER LYS ALA LYS GLY GLN PRO ARG GLU PRO GLN
     VAL TYR THR LEU PRO PRO SER ARG ASP GLU LEU THR LYS ASN
     GLN VAL SER LEU THR CYS LEU VAL LYS GLY PHE TYR PRO SER
     ASP ILE ALA VAL GLU TRP GLU SER ASN GLY GLN PRO GLU ASN
     ASN TYR LYS THP THP PRO PRO VAL LEU ASP SER ASP GLY SER
     PHE PHE LEU TYR SER LYS LEU THP VAL ASP LYS SER ARG TRP
     GLN GLN GLY ASN VAL PHE SER CYS SER VAL MET HIS GLU ALA
     LEU HIS ASN HIS TYR THP GLN LYS SER LEU SER LEU SER PRO
     GLY LYS

952A GLU ILE VAL LEU THR GLN SER PRO ALA THR LEU SER LEU SER
     PRO GLY GLU ARG ALA THR LEU SER CYS SER ALA SER SER SER
     VAL SER TYR MET HIS TRP TYR GLN GLN LYS PRO GLY GLN ALA
     PRO ARG LEU LEU ILE TYR ASP THR SER LYS LEU ALA SER GLY
     ILE PRO ALA ARG PHE SER GLY SER GLY SER GLY THR ASP PHE
     THR LEU THR ILE SER SER LEU GLU PRO GLU ASP VAL ALA VAL
     TYR TYR CYS PHE GLN GLY SER VAL TYR PRO PHE THR PHE GLY
     GLN GLY THR LYS LEU GLU ILE LYS ARG THR VAL ALA ALA PRO
     SER VAL PHE ILE PHE PRO PRO SER ASP GLU GLN LEU LYS SER
     GLY THP ALA SER VAL VAL CYS LEU LEU ASN ASN PHE TYR PRO
     ARG GLU ALA LYS VAL GLN TRP LYS VAL ASP ASN ALA LEU GLN
     SER GLY ASN SER GLN GLU SER VAL THR GLU GLN ASP SER LYS
     ASP SER THP TYR SER LEU SER SER THR LEU THP LEU SER LYS
     ALA ASP TYR GLU LYS HIS LYS VAL TYR ALA CYS GLU VAL THR
     HIS GLN GLY LEU SER SER PRO VAL THR LYS SER PHE ASN ARG
     GLY GLU CYS

What is claimed is:

1. An antibody-drug conjugate comprising an antigen binding protein or fragment thereof that binds CD30, wherein the antibody-drug conjugate is represented by the structure:

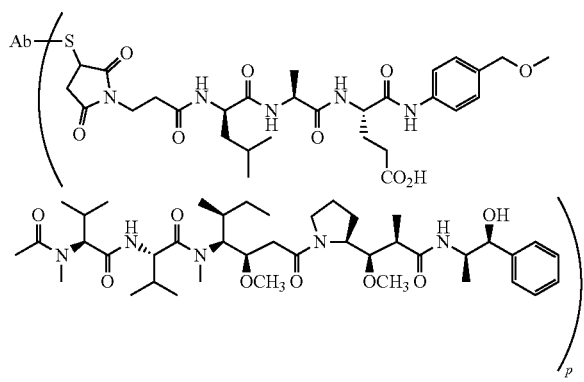

or a pharmaceutically acceptable salt thereof, wherein
Ab is the antigen binding protein or fragment thereof and p denotes a number from 1 to 12.

2. The antibody-drug conjugate of claim 1 wherein the antigen binding protein or fragment is cAC10.

3. The antibody-drug conjugate of claim 1, wherein the antigen binding protein or fragment comprises the following 6 HVRs:
an HVR-H1 comprising the amino acid sequence of SEQ ID NO: 920;
an HVR-H2 comprising the amino acid sequence of SEQ ID NO: 921;
an HVR-H3 comprising the amino acid sequence of SEQ ID NO: 922;
an HVR-L1 comprising the amino acid sequence of SEQ ID NO: 923;
an HVR-L2 comprising the amino acid sequence of SEQ ID NO: 924; and
an HVR-L3 comprising the amino acid sequence of SEQ ID NO: 925.

4. The antibody-drug conjugate of claim 3, wherein the antigen binding protein or fragment comprises a VH and a VL, wherein the VH has at least 80%, 85%, 90%, 95% or 99% amino acid sequence identity to the amino acid sequence of SEQ ID NO: 926 and the VL has at least 80%, 85%, 90%, 95% or 99% amino acid sequence identity to the amino acid sequence of SEQ ID NO: 927.

5. The antibody-drug conjugate of claim 1, wherein the antigen binding protein or fragment comprises a VH and a VL, wherein the VH comprises the amino acid sequence of SEQ ID NO: 926 and the VL comprises the amino acid sequence of SEQ ID NO: 927.

6. The antibody-drug conjugate of claim 1, wherein the antigen binding protein or fragment comprises an HC comprising the amino acid sequence of SEQ ID NO: 928 or SEQ ID NO: 929 and an LC comprising the amino acid sequence of SEQ ID NO: 930.

7. The antibody-drug conjugate of claim 1, wherein the antigen binding protein or fragment is a monoclonal antibody or fragment thereof.

8. The antibody-drug conjugate of claim 1, wherein the antigen binding protein or fragment is a chimeric antibody or fragment thereof.

9. The antibody-drug conjugate of claim 1, wherein the antigen binding protein or fragment is a humanized antibody or fragment thereof.

10. The antibody-drug conjugate of claim 1, wherein the fragment is selected from a Fab, Fab', Fv, scFv or (Fab')$_2$ fragment.

11. A pharmaceutical composition comprising the antibody-drug conjugate of claim 1 and a pharmaceutically acceptable carrier.

12. A method of treating a CD30-expressing disease or condition in an individual comprising administering to an individual in need thereof an effective amount of the antibody-drug conjugate of claim 1.

* * * * *